United States Patent
Leo

(10) Patent No.: US 10,738,268 B2
(45) Date of Patent: Aug. 11, 2020

(54) CANNABIS NANOEMULSION METHODS

(71) Applicant: Daniel Michael Leo, Baltimore, MD (US)

(72) Inventor: Daniel Michael Leo, Baltimore, MD (US)

(73) Assignee: INSECTERGY, LLC, Baltimore, MD (US)

( * ) Notice: Subject to any disclaimer, the term of this patent is extended or adjusted under 35 U.S.C. 154(b) by 72 days.

(21) Appl. No.: 16/153,724

(22) Filed: Oct. 6, 2018

(65) Prior Publication Data

US 2019/0085279 A1 Mar. 21, 2019

Related U.S. Application Data

(63) Continuation-in-part of application No. 15/841,886, filed on Dec. 14, 2017, now Pat. No. 10,219,536.
(Continued)

(51) Int. Cl.

| | |
|---|---|
| *B01F 3/00* | (2006.01) |
| *C12G 3/06* | (2006.01) |
| *A23L 2/56* | (2006.01) |
| *A23L 2/60* | (2006.01) |
| *A23L 2/46* | (2006.01) |

(Continued)

(52) U.S. Cl.
CPC .......... *C12G 3/06* (2013.01); *A23L 2/46* (2013.01); *A23L 2/56* (2013.01); *A23L 2/60* (2013.01); *B01F 3/0807* (2013.01); *A01G 22/15* (2018.02); *A01K 67/033* (2013.01); *A23V 2002/00* (2013.01); *C02F 1/28* (2013.01);
(Continued)

(58) Field of Classification Search
CPC .......... A23L 2/52; A23L 33/105; A23L 35/10; A61K 31/05
USPC ............... 426/2, 580, 590, 519, 601; 516/20
See application file for complete search history.

(56) References Cited

U.S. PATENT DOCUMENTS

| | | | |
|---|---|---|---|
| 1,028,987 A * | 6/1912 | Bettendorf | H01L 21/68 414/779 |
| 9,539,295 B2 * | 1/2017 | Bohus | A61K 36/185 |

(Continued)

FOREIGN PATENT DOCUMENTS

| | | | | |
|---|---|---|---|---|
| WO | WO-2015068052 A2 * | 5/2015 | | A61K 31/05 |
| WO | WO 2016097425 * | 6/2016 | | A23L 2/52 |
| WO | WO-2017127641 A1 * | 7/2017 | | A61M 11/02 |

OTHER PUBLICATIONS

"Cannabis Moodlifter Drink", Apr. 1, 2014 (Year: 2014).*
(Continued)

*Primary Examiner* — Nina Bhat

(57) ABSTRACT

The present disclosure relates to methods to produce *cannabis* oil nanoemulsions. *Cannabis* oil nanoemulsions may be used for the production of beverages, pharmaceuticals, drugs, and spray-dried powders. Methods to produce a *cannabis* oil nanoemulsion are described, the methods includes a two-step process to emulsifying water and *cannabis* oil with a first emulsification system to produce a microemulsion; and introducing the microemulsion to a second emulsification system to produce the nanoemulsion. A variety of emulsification systems may be used including agitators, a rotor/stator, a sawtooth blade, colloid mill, piston pump, microfluidizer processor, and ultrasonic homogenizers. Water treatment prior to emulsification is also described.

57 Claims, 116 Drawing Sheets

Related U.S. Application Data which is a continuation-in-part of application No. 15/664,490, filed on Jul. 31, 2017, now Pat. No. 10,188,086, which is a continuation-in-part of application No. 15/257,854, filed on Sep. 6, 2016, now Pat. No. 10,264,769, which is a continuation-in-part of application No. 15/242,579, filed on Aug. 21, 2016, now Pat. No. 10,188,083.

(51) Int. Cl.
| | | |
|---|---|---|
| *B01F 3/08* | (2006.01) | |
| *A01K 67/033* | (2006.01) | |
| *C02F 1/28* | (2006.01) | |
| *C02F 1/42* | (2006.01) | |
| *C02F 1/44* | (2006.01) | |
| *A01G 22/15* | (2018.01) | |

(52) U.S. Cl.
CPC .............. *C02F 1/42* (2013.01); *C02F 1/44* (2013.01); *C02F 2001/422* (2013.01); *C02F 2001/425* (2013.01)

(56) References Cited

U.S. PATENT DOCUMENTS

| | | | | |
|---|---|---|---|---|
| 9,629,886 | B2* | 4/2017 | Franklin | A61K 36/185 |
| 9,642,884 | B1* | 5/2017 | Skuratovich | C12G 3/04 |
| 10,085,965 | B2* | 10/2018 | Skuratovich | A61K 31/352 |
| 10,165,790 | B2* | 1/2019 | Franklin | A61K 36/185 |
| 10,172,379 | B2* | 1/2019 | Franklin | A61K 36/185 |
| 2007/0085058 | A1* | 4/2007 | Mora-Gutierrez | A61K 8/738 |
| | | | | 252/400.21 |
| 2013/0184354 | A1* | 7/2013 | Jackson | A61K 47/36 |
| | | | | 514/729 |
| 2014/0271940 | A1* | 9/2014 | Wurzer | A61K 36/185 |
| | | | | 424/725 |
| 2015/0182455 | A1* | 7/2015 | Llamas | A61K 31/05 |
| | | | | 514/729 |
| 2015/0352044 | A1* | 12/2015 | Benson | A61K 36/185 |
| | | | | 206/205 |
| 2016/0243177 | A1* | 8/2016 | Franklin | A23L 29/35 |
| 2016/0279073 | A1* | 9/2016 | Donsky | A61K 9/127 |
| 2017/0027543 | A1* | 2/2017 | Kiyose | A61B 8/4254 |
| 2017/0189463 | A1* | 7/2017 | Franklin | A61K 9/0056 |
| 2018/0026999 | A1* | 1/2018 | Ruvio | H04L 63/145 |
| | | | | 726/23 |
| 2018/0116240 | A1* | 5/2018 | Docherty | A23F 5/243 |
| 2018/0200315 | A1* | 7/2018 | Silver | A61K 9/107 |

OTHER PUBLICATIONS

"The Hempy Cola", Jan. 1, 2004 (Year: 2004).*
"Nano-Emulsion Production by Sonication and Microfluidization—A Comparison", Jafari et al., International Journal of Food Properties, pub Feb. 6, 2007 (Year: 2007).*
LeHerbe Cannabis Beverages "The Art and Sciene of Cannabis Beverages"; LeHerbe Cannabis Emulsion Experiment. No specific date given. White paper Dec. 1994 (Year: 1994).*
EP 141991135 , Cannabis Beverage Front Page, Machine Translation. (Year: 2014).*
EP 14199135 is equivalent to WO 2016/097425. Machine Translation and Front Page of EP 14199135. (Year: 2014).*

\* cited by examiner

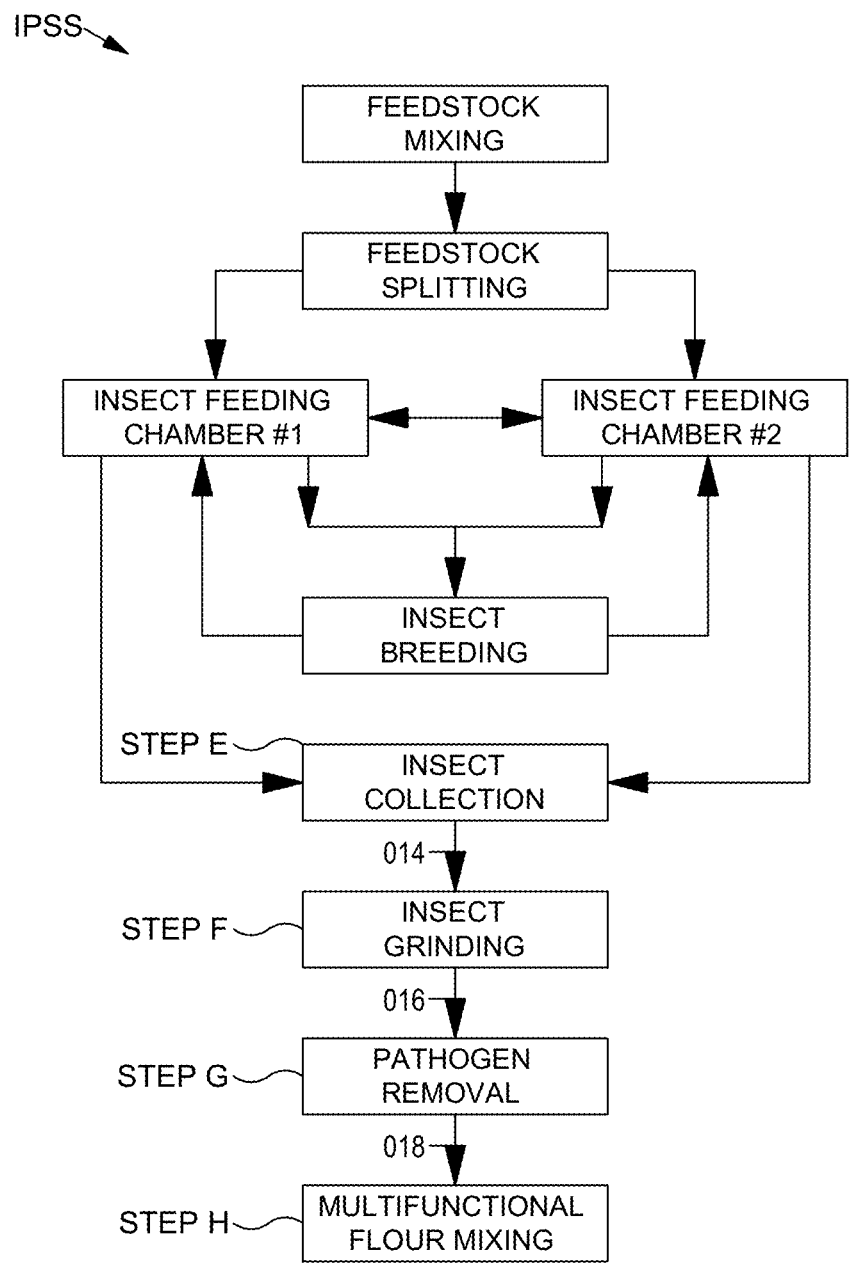

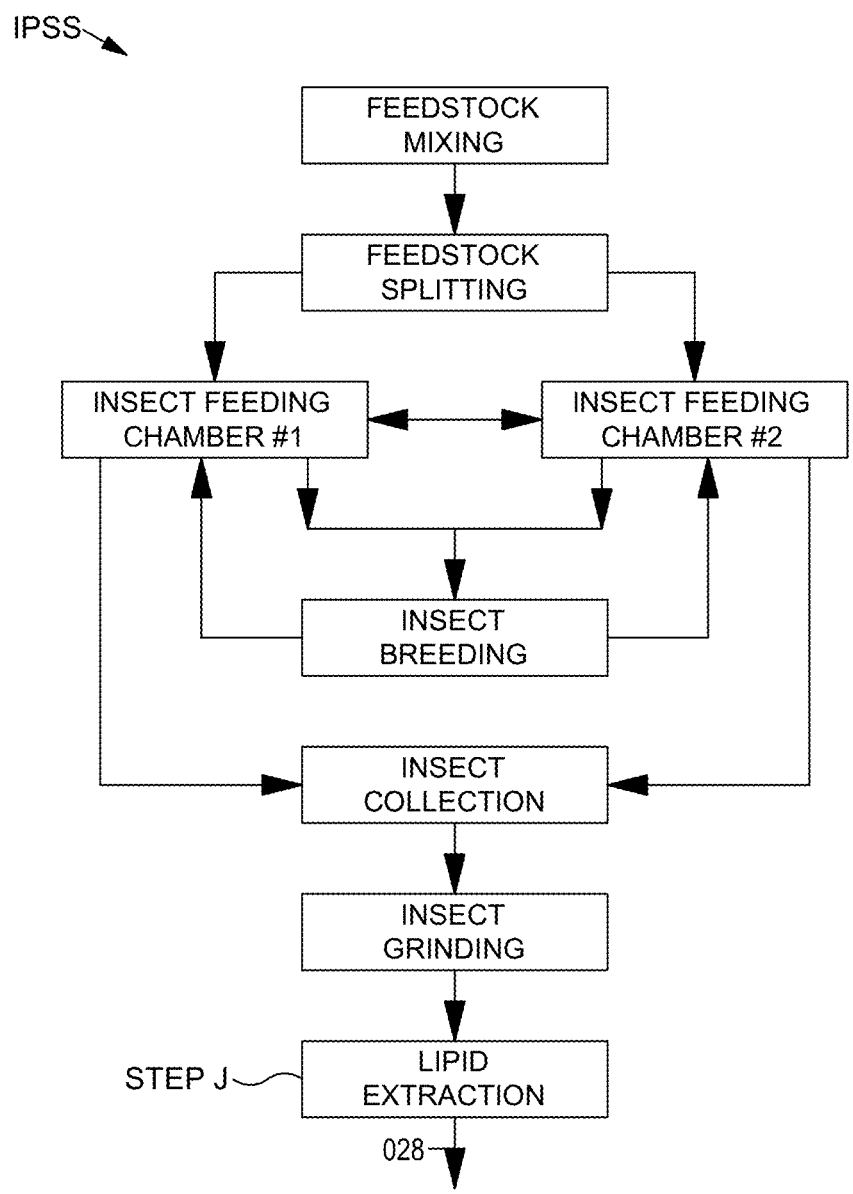

INSECT TRACEABILITY SYSTEM

INSECT GRINDING MODULE

LIPID EXTRACTION MODULE

LIPID EXTRACTION MODULE

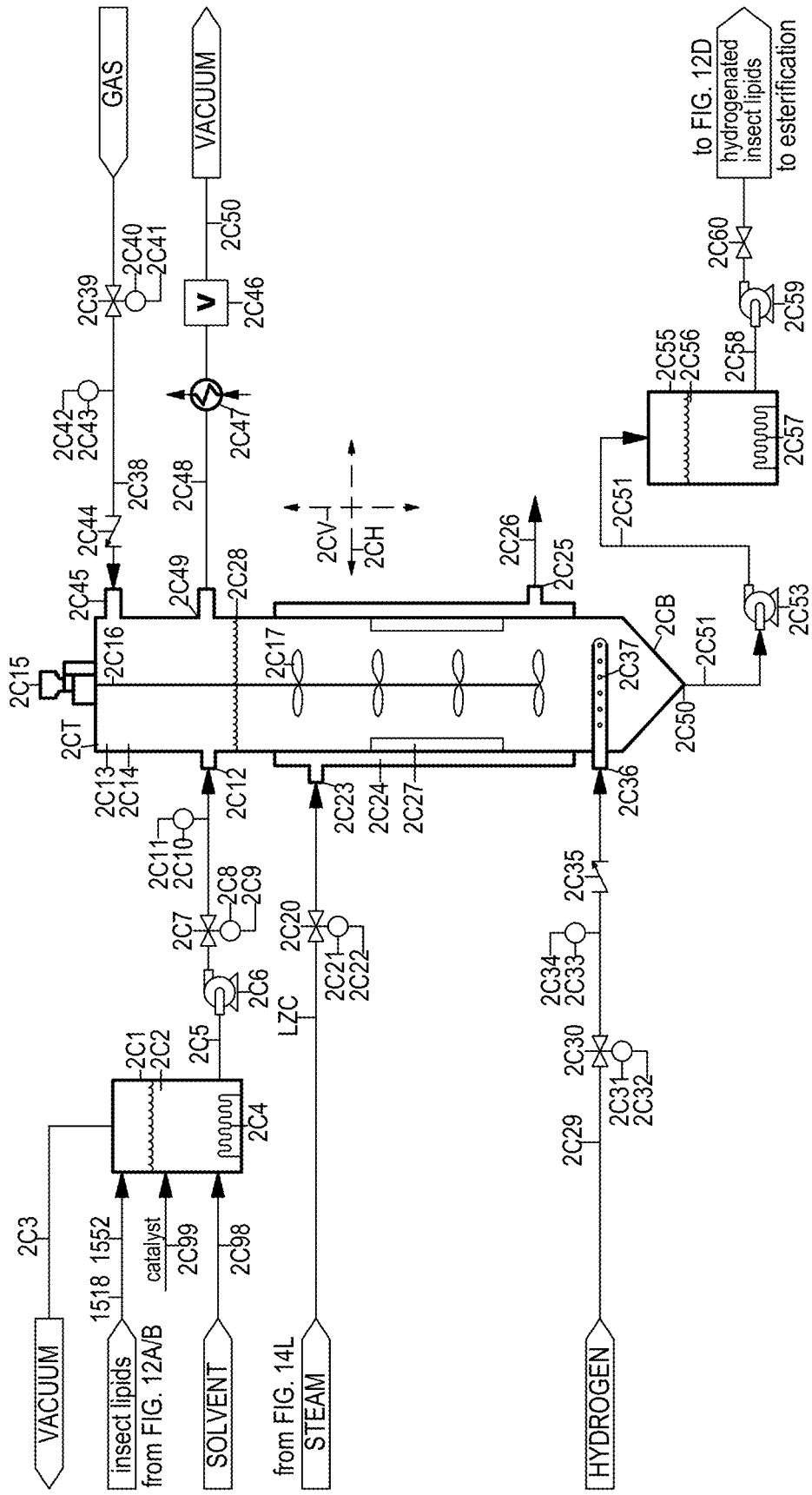

ESTERIFICATION SYSTEM

PATHOGEN REMOVAL MODULE

MULTIFUNCTIONAL FLOUR MIXING MODULE

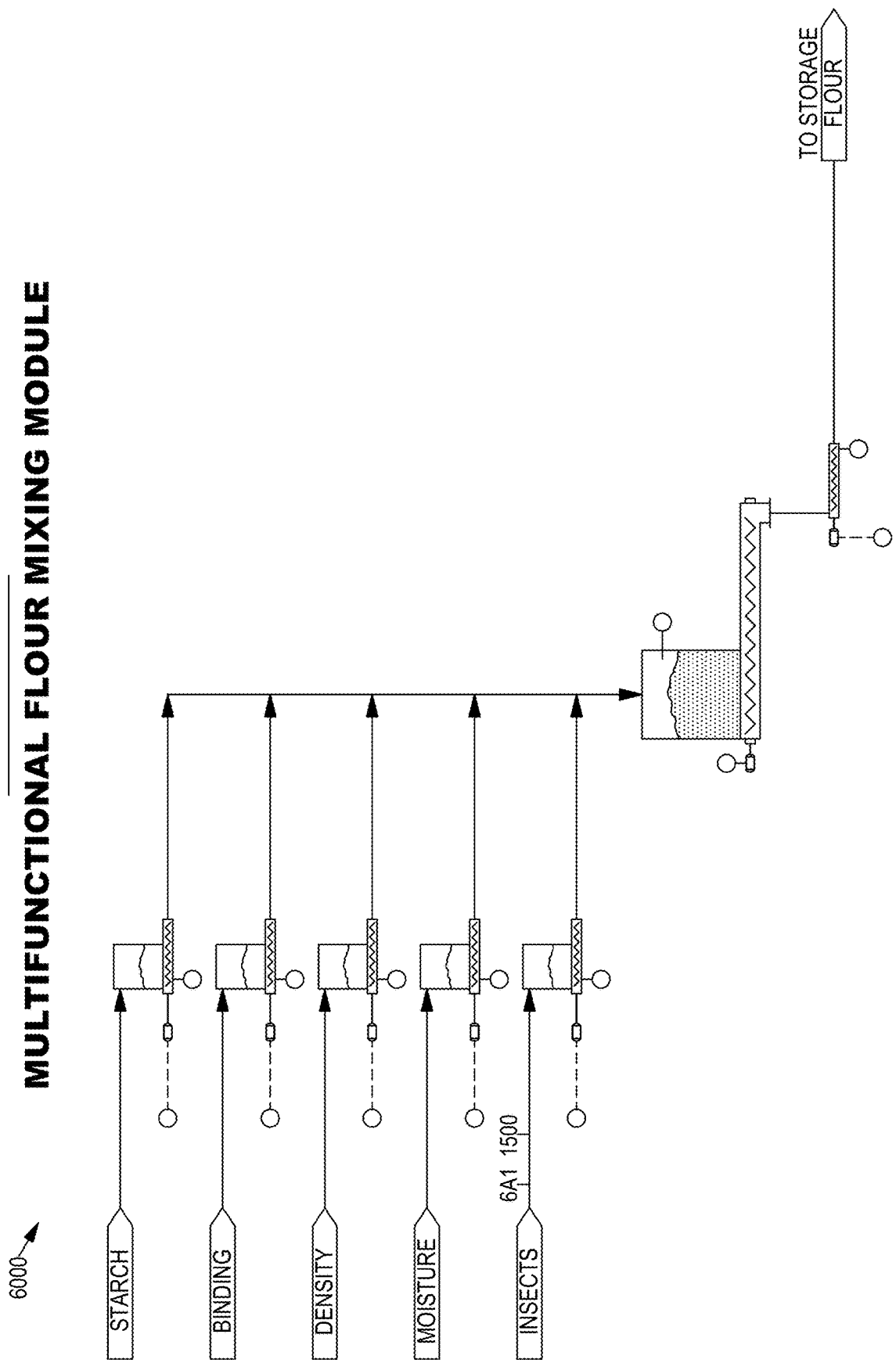

LIQUID MIXING MODULE

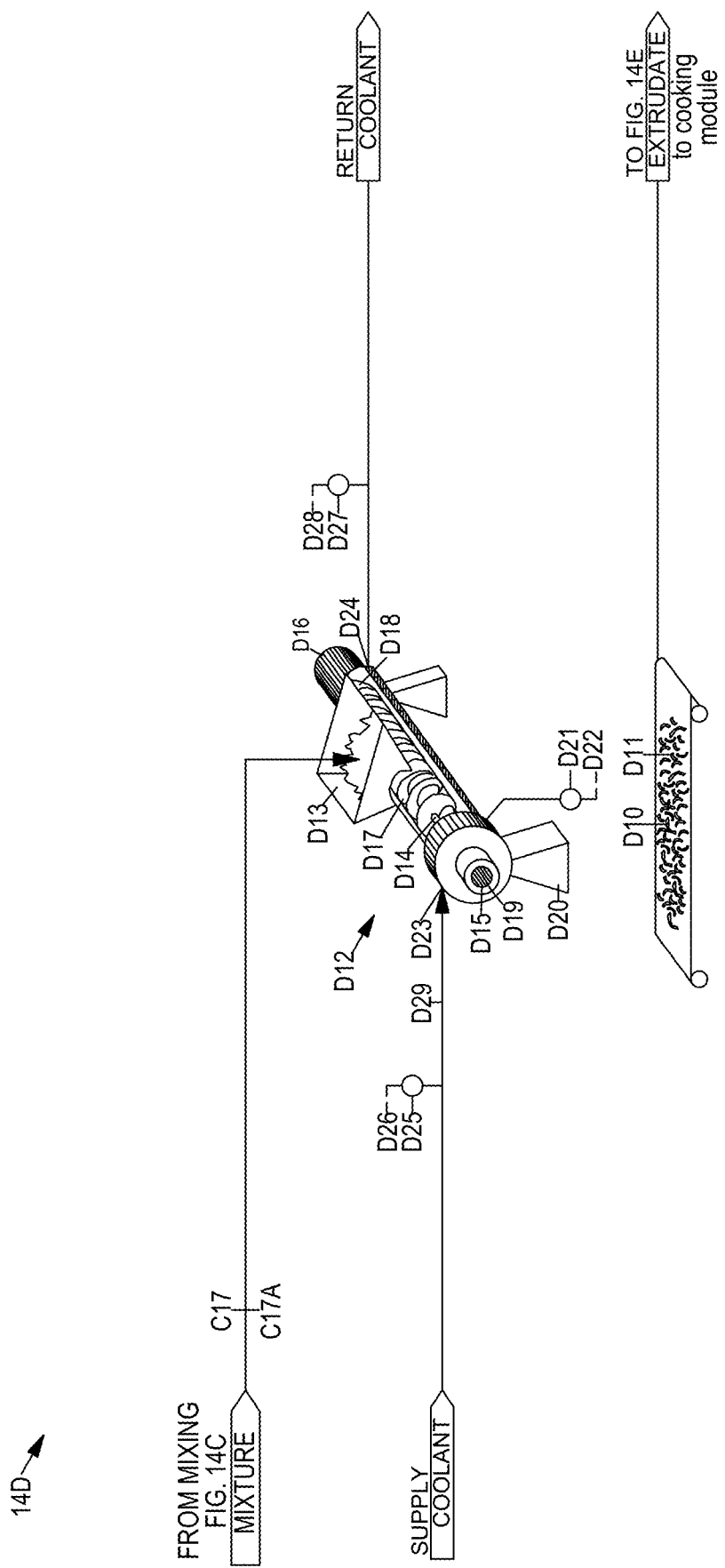

COOKING MODULE

FLAVORING MODULE

BIOCATALYST MIXING MODULE

EXOSKELETON SEPARATION MODULE

LIQUID SEPARATION MODULE
(embodiment 1, filter, candle-type)

LIQUID SEPARATION MODULE
(embodiment 2, evaporator, wiped-film type)

LIQUID SEPARATION MODULE
(embodiment 3, evaporator, spray dryer)

SPRAY DRYER, CO-CURRENT

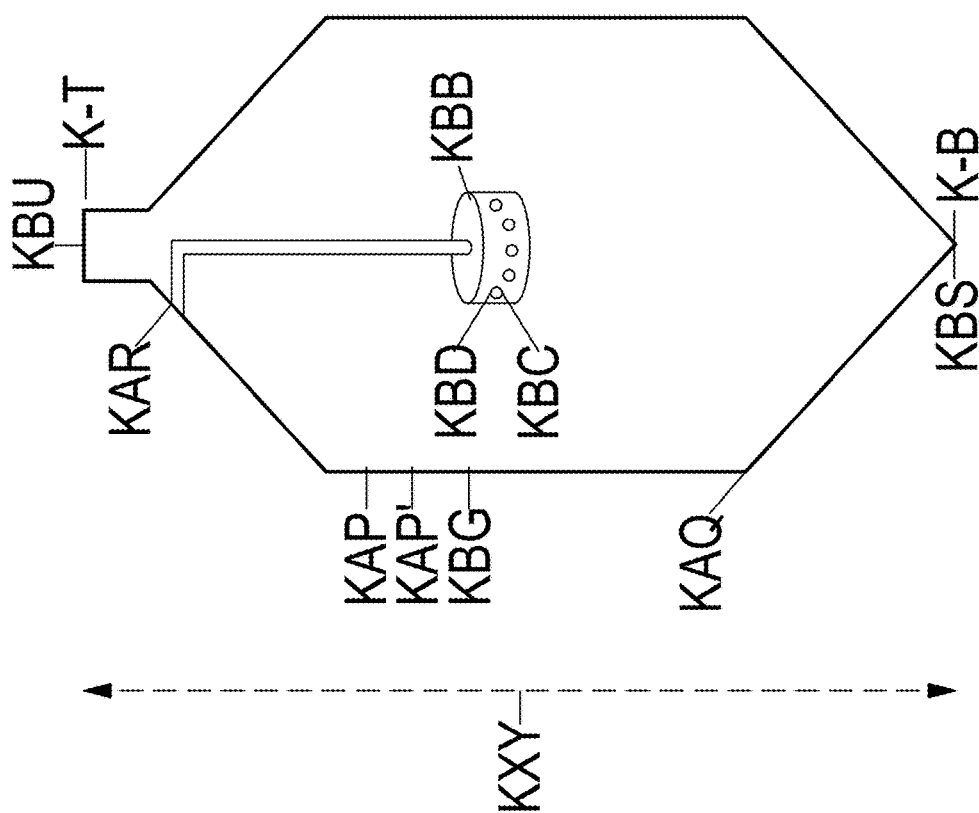

SPRAY DRYER, COUNTER-CURRENT

SPRAY DRYER, MIXED

INSECT-DERIVED BIOSENSOR

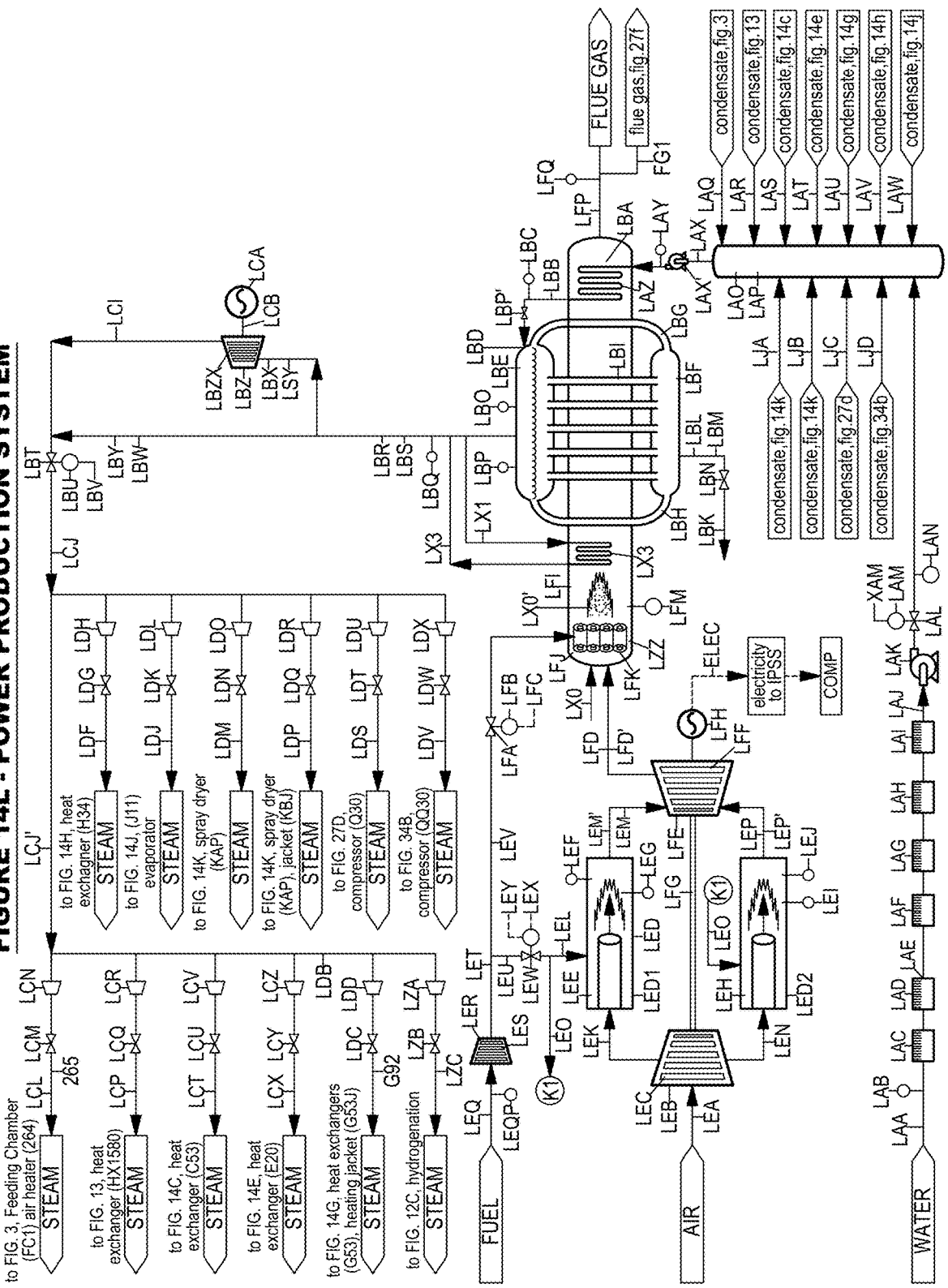

MODULAR INSECT PRODUCTION SUPERSTRUCTURE SYSTEM (IPSS)

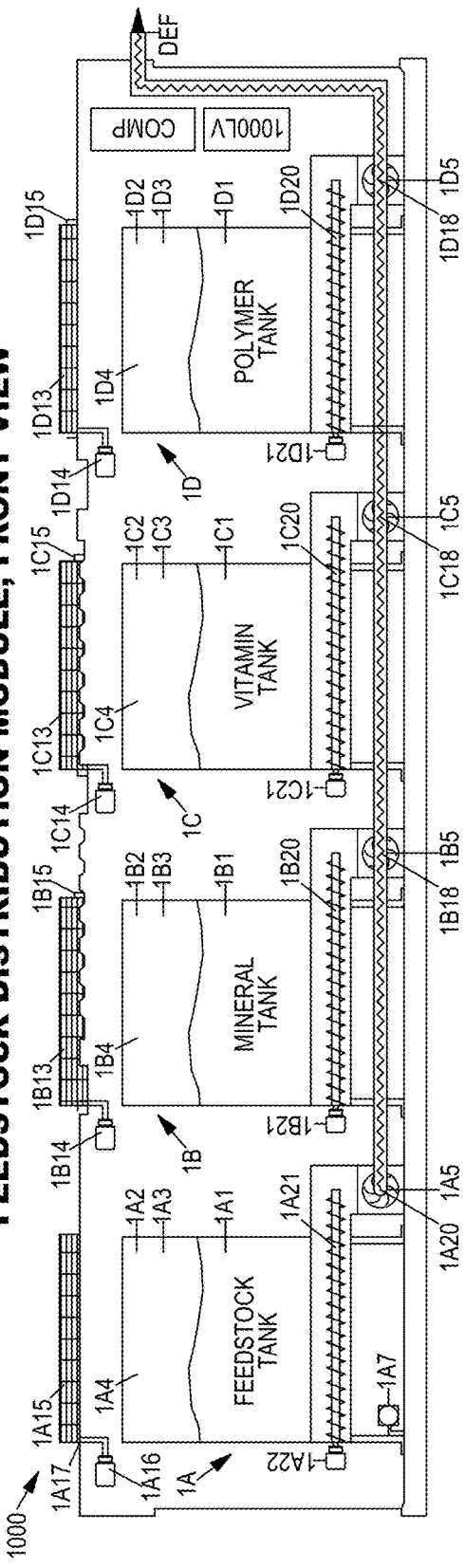
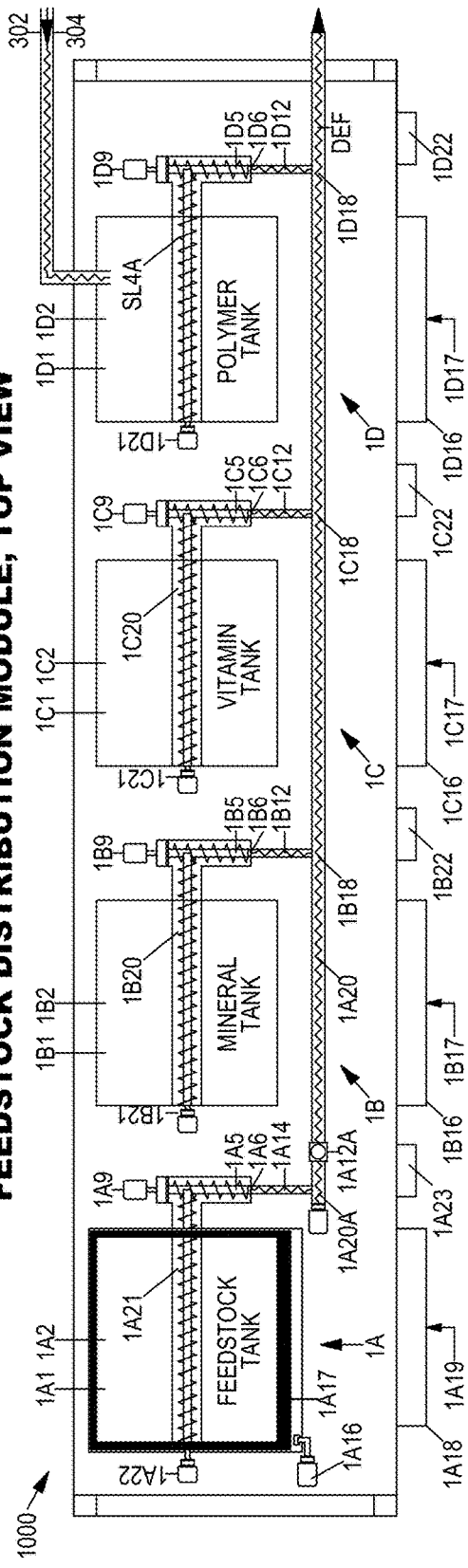

FEEDSTOCK DISTRIBUTION MODULE, SIDE VIEW

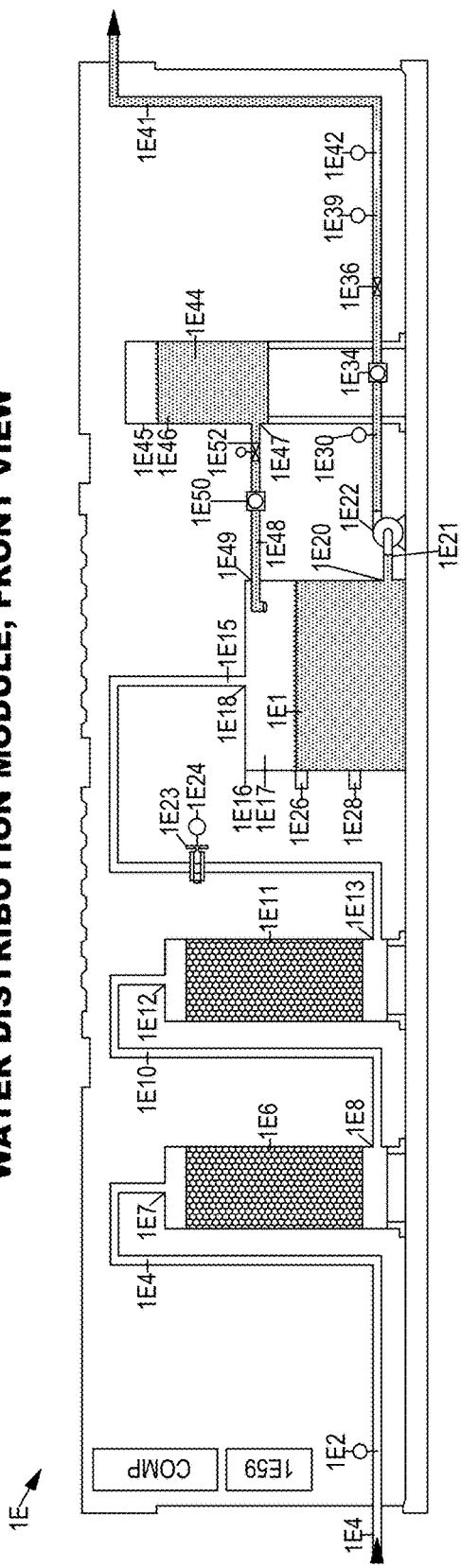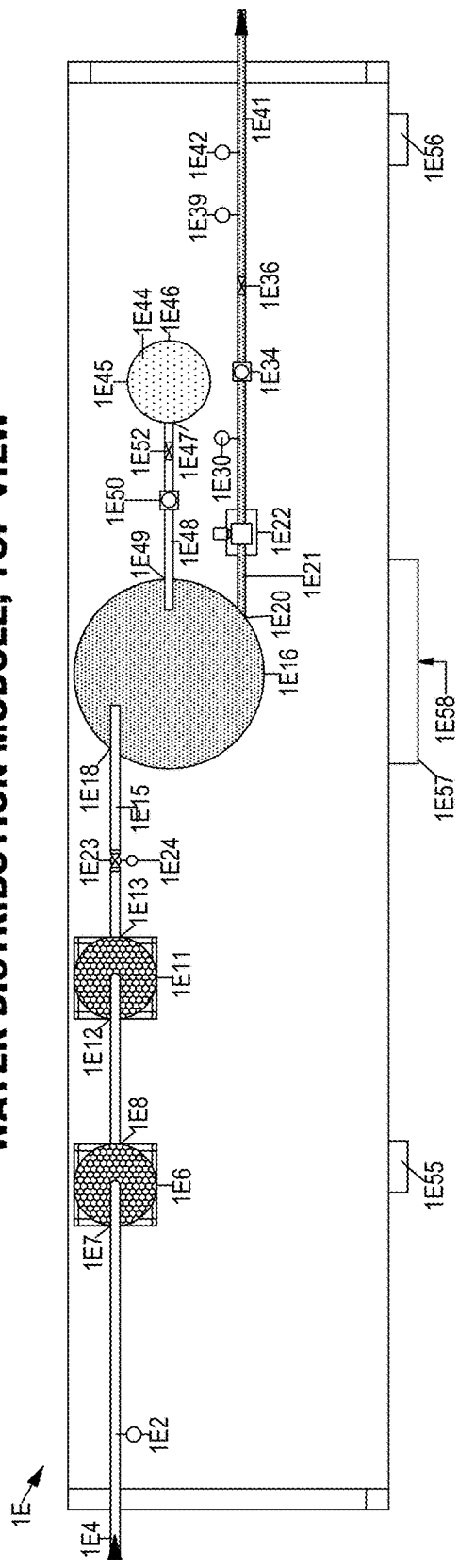

WATER DISTRIBUTION MODULE, SIDE VIEW

ENHANCED FEEDSTOCK DISTRIBUTION MODULE, FRONT VIEW

ENHANCED FEEDSTOCK DISTRIBUTION MODULE, TOP VIEW

ENHANCED FEEDSTOCK DISTRIBUTION MODULE, SIDE VIEW

INSECT FEEDING MODULE, FRONT VIEW

INSECT FEEDING MODULE, TOP VIEW

INSECT FEEDING MODULE, FRONT VIEW

INSECT FEEDING MODULE, TOP VIEW

INSECT FEEDING MODULE, FRONT VIEW

INSECT FEEDING MODULE, FRONT VIEW

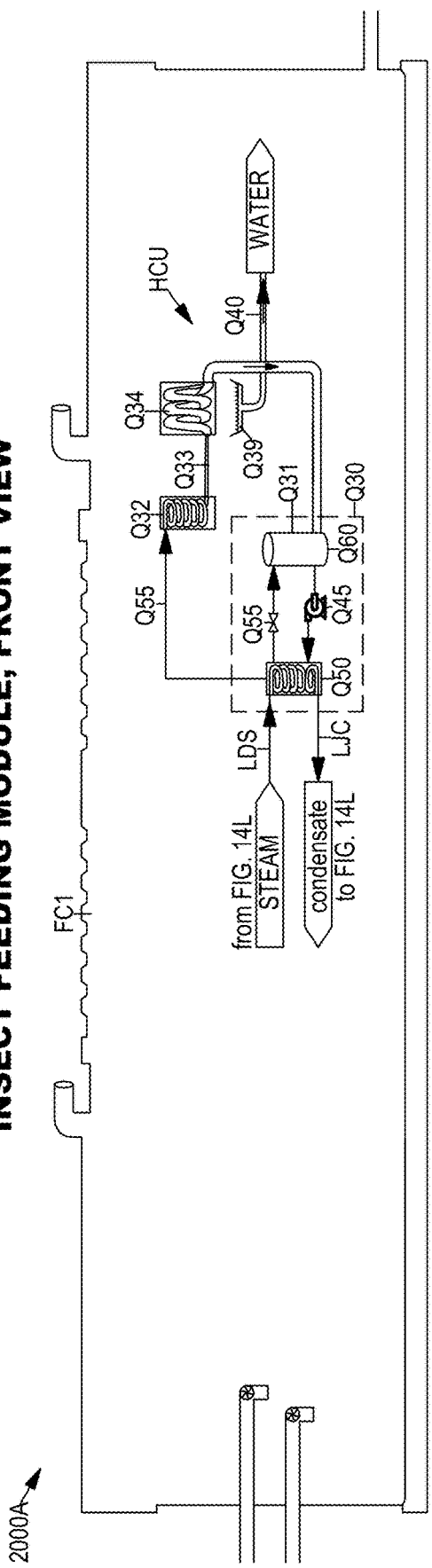
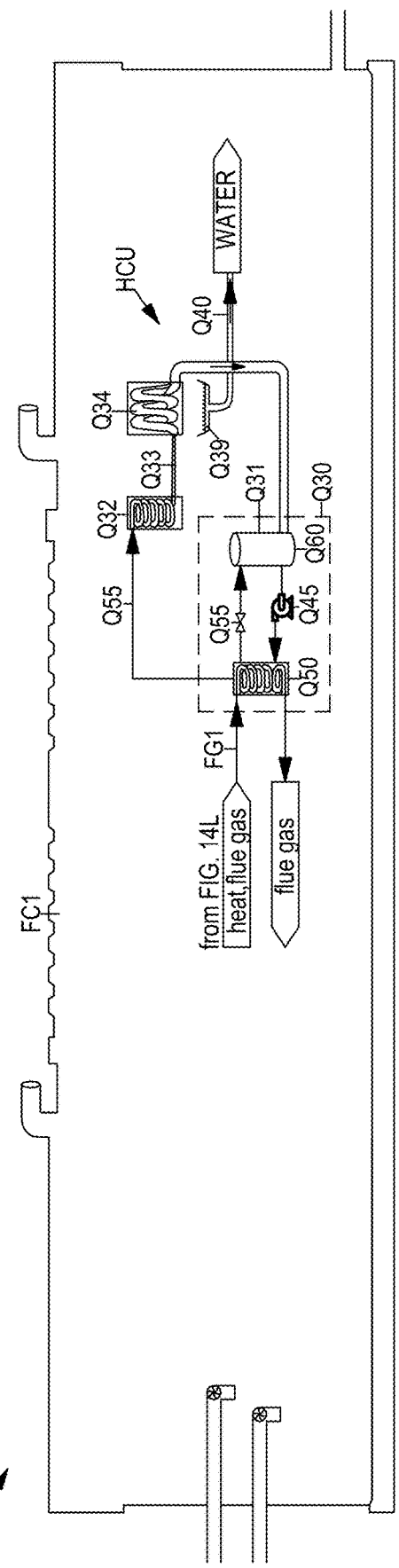

INSECT FEEDING MODULE, SIDE VIEW

INSECT EVACUATION MODULE, FRONT VIEW

INSECT EVACUATION MODULE, TOP VIEW

INSECT EVACUATION MODULE, SIDE VIEW

INSECT BREEDING MODULE, FRONT VIEW

INSECT BREEDING MODULE, TOP VIEW

INSECT BREEDING MODULE, TOP VIEW

INSECT BREEDING MODULE, TOP VIEW

INSECT BREEDING MODULE, CONVEYOR SIDE VIEW (CSV)

INSECT BREEDING MODULE, CONVEYOR SIDE VIEW (CSV)

HATCHED INSECT SEPARATION MODULE, FRONT VIEW

HATCHED INSECT SEPARATION MODULE, TOP VIEW

HATCHED INSECT SEPARATION MODULE, SIDE VIEW

FIGURE 40A

| TABLE 1 | | | |
|---|---|---|---|
| | COLUMN 1 (C1) | COLUMN 2 (C2) | COLUMN 3 (C3) |
| ROW 1 (R1) | Feedstock Mineral Enhancers | lb/ton of feed | lb/ton of feed |
| ROW 2 (R2) | potassium | 0.5 | 250 |
| ROW 3 (R3) | chloride | 0.5 | 250 |
| ROW 4 (R4) | sodium | 0.5 | 250 |
| ROW 5 (R5) | calcium | 0.5 | 250 |
| ROW 6 (R6) | phosphorous | 0.5 | 250 |
| ROW 7 (R7) | magnesium | 0.5 | 150 |
| ROW 8 (R8) | zinc | 0.5 | 150 |
| ROW 9 (R9) | iron | 0.5 | 150 |
| ROW 10 (R10) | manganese | 0.5 | 150 |
| ROW 11 (R11) | copper | 0.5 | 150 |
| ROW 12 (R12) | iodine | 0.5 | 150 |
| ROW 13 (R13) | selenium | 0.5 | 150 |
| ROW 14 (R14) | molybdenum | 0.5 | 150 |
| ROW 15 (R15) | | | |
| ROW 16 (R16) | Feedstock Vitamin Enhancers | lb/ton of feed | lb/ton of feed |
| ROW 17 (R17) | B1 | 5 | 750 |
| ROW 18 (R18) | B2 | 5 | 750 |
| ROW 19 (R19) | E | 5 | 750 |
| ROW 20 (R20) | | | |
| ROW 21 (R21) | | lb/lb of feed | lb/lb of feed |
| ROW 22 (R22) | A | 10 | 950 |
| ROW 23 (R23) | | | |
| ROW 24 (R24) | Feedstock Fiber Enhancers | lb/ton of feed | lb/ton of feed |
| ROW 25 (R25) | fiber | 15 | 100 |
| ROW 26 (R26) | | | |
| ROW 27 (R27) | Other 'Energy Insect' Enhancers | lb/ton of feed | lb/ton of feed |
| ROW 28 (R28) | niacin | 5 | 300 |
| ROW 29 (R29) | taurine | 5 | 300 |
| ROW 30 (R30) | glucuronic acid | 5 | 300 |
| ROW 31 (R31) | malic acid | 5 | 300 |
| ROW 32 (R32) | N-acetyl L tyrosine | 5 | 300 |
| ROW 33 (R33) | L-phenylalanine | 5 | 300 |
| ROW 34 (R34) | caffeine | 5 | 750 |
| ROW 35 (R35) | citicoline | 5 | 300 |

FIGURE 40B

| | COLUMN 1 (C1) | COLUMN 2 (C2) | COLUMN 3 (C3) |
|---|---|---|---|
| ROW 1 (R1) | VARIABLE | UNITS | UNITS |
| ROW 2 (R2) | Feeding Chamber Temperature | 60 deg F | 94 deg F |
| ROW 3 (R3) | Breeding Chamber Temperature | 64 deg F | 90 deg F |
| ROW 4 (R4) | Breeding Chamber Residence Time | 1 week | 5 weeks |
| ROW 5 (R5) | Feeding Chamber Humidity | 25 percent humidity | 100 percent humidity |
| ROW 6 (R6) | Breeding Chamber Humidity | 50 percent humidity | 100 percent humidity |
| ROW 7 (R7) | average insect mass | 0.2 grams | 0.907 grams |
| ROW 8 (R8) | quantity of insects per pound | 2258 insects | 500 insects |
| ROW 9 (R9) | tons of insects per cycle | 0.5 ton | 1 ton |
| ROW 10 (R10) | quantity of insects per cycle | 2,267,950 | 1,000,000 |
| ROW 11 (R11) | Cycle Time | 1 week | 5 weeks |

FIGURE 40C

| TABLE 3 | | | |
|---|---|---|---|
| | COLUMN 1 (C1) | COLUMN 2 (C2) | COLUMN 3 (C3) |
| ROW 1 (R1) | PARAMETER | UNITS | UNITS |
| ROW 2 (R2) | energy | 4.5 BTU/lb | 10.5 BTU/lb |
| ROW 3 (R3) | protein | 45 weight percent | 85 weight percent |
| ROW 4 (R4) | carbon | 15 weight percent | 55 weight percent |
| ROW 5 (R5) | oxygen | 15 weight percent | 85 weight percent |
| ROW 6 (R6) | hydrogen | 2.5 weight percent | 20 weight percent |
| ROW 7 (R7) | carbohydrates | 3.5 weight percent | 13 weight percent |
| ROW 8 (R8) | ash | 2.5 weight percent | 7.5 weight percent |
| ROW 9 (R9) | water | 2 weight percent | 10 weight percent |
| ROW 10 (R10) | total fat | 5 weight percent | 60 weight percent |
| ROW 11 (R11) | palmitoleic acid | 5 weight percent | 60 weight percent |
| ROW 12 (R12) | linoleic acid | 5 weight percent | 60 weight percent |
| ROW 13 (R13) | alpha-linoleic acid | 5 weight percent | 60 weight percent |
| ROW 14 (R14) | oleic acid | 5 weight percent | 60 weight percent |
| ROW 15 (R15) | gamma-linoleic acid | 5 weight percent | 60 weight percent |
| ROW 16 (R16) | stearic acid | 5 weight percent | 60 weight percent |
| ROW 17 (R17) | potassium | 25 ppm | 1 weight percent |
| ROW 18 (R18) | chloride | 50 ppm | 1 weight percent |
| ROW 19 (R19) | calcium | 50 ppm | 1 weight percent |
| ROW 20 (R20) | phosphorous | 50 ppm | 1 weight percent |
| ROW 21 (R21) | magnesium | 50 ppm | 1 weight percent |
| ROW 22 (R22) | zinc | 50 ppm | 1 weight percent |
| ROW 23 (R23) | iron | 25 ppm | 1500 ppm |
| ROW 24 (R24) | sodium | 1500 ppm | 5500 ppm |
| ROW 25 (R25) | manganese | 50 ppm | 1 weight percent |
| ROW 26 (R26) | copper | 50 ppm | 1 weight percent |
| ROW 27 (R27) | iodine | 50 ppm | 1 weight percent |
| ROW 28 (R28) | selenium | 50 ppm | 1 weight percent |
| ROW 29 (R29) | molybdenum | 50 ppm | 1 weight percent |
| ROW 30 (R30) | Vitamin B1 | 15 ppm | 15 weight percent |
| ROW 31 (R31) | Vitamin B2 | 15 ppm | 15 weight percent |
| ROW 32 (R32) | Vitamin B12 | 15 ppm | 15 weight percent |
| ROW 33 (R33) | Vitamin E | 15 ppm | 15 weight percent |
| ROW 34 (R34) | Vitamin A | 15 ppm | 15 weight percent |
| ROW 35 (R35) | niacin | 50 ppm | 5 weight percent |
| ROW 36 (R36) | taurine | 50 ppm | 5 weight percent |
| ROW 37 (R37) | glucuronic acid | 50 ppm | 5 weight percent |
| ROW 38 (R38) | malic acid | 50 ppm | 5 weight percent |
| ROW 39 (R39) | N-acetyl L tyrosine | 50 ppm | 5 weight percent |
| ROW 40 (R40) | L-phenylalanine | 50 ppm | 5 weight percent |
| ROW 41 (R41) | caffeine | 50 ppm | 5 weight percent |
| ROW 42 (R42) | citicoline | 50 ppm | 5 weight percent |
| ROW 43 (R43) | insect bulk density | 3.5 pounds/cubic foot | 14.999 pounds/cubic foot |
| ROW 44 (R44) | ground insect bulk density | 15 pounds/cubic foot | 50 pounds/cubic foot |

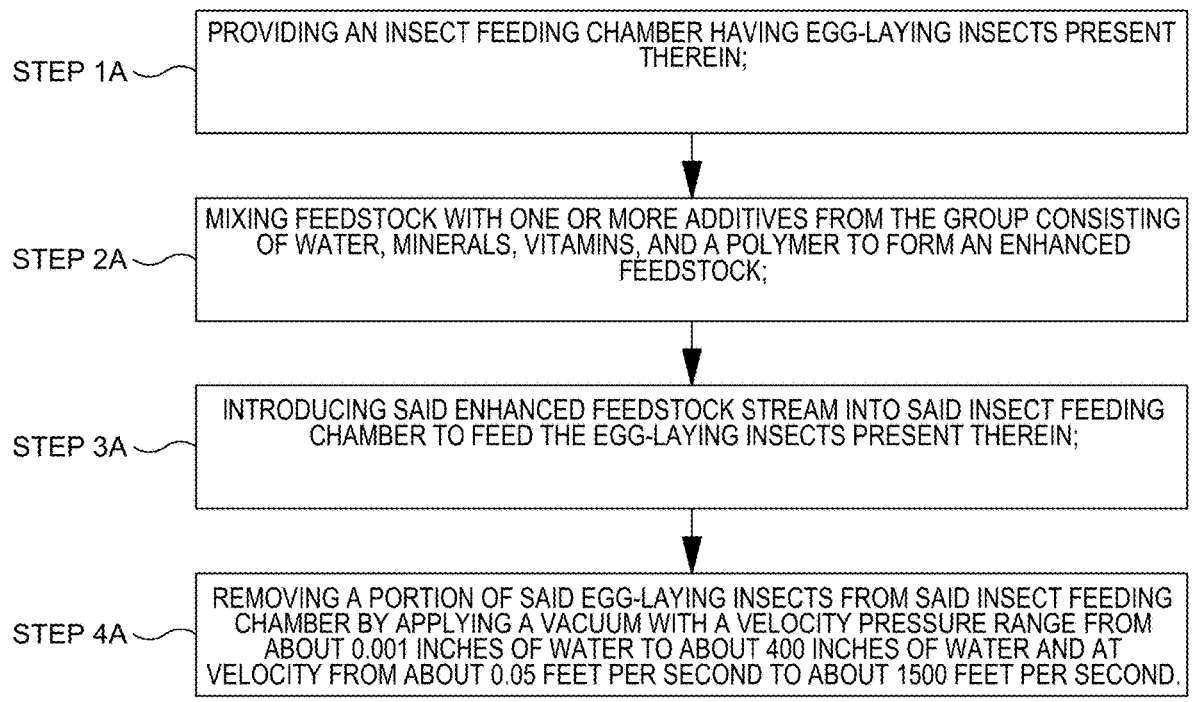

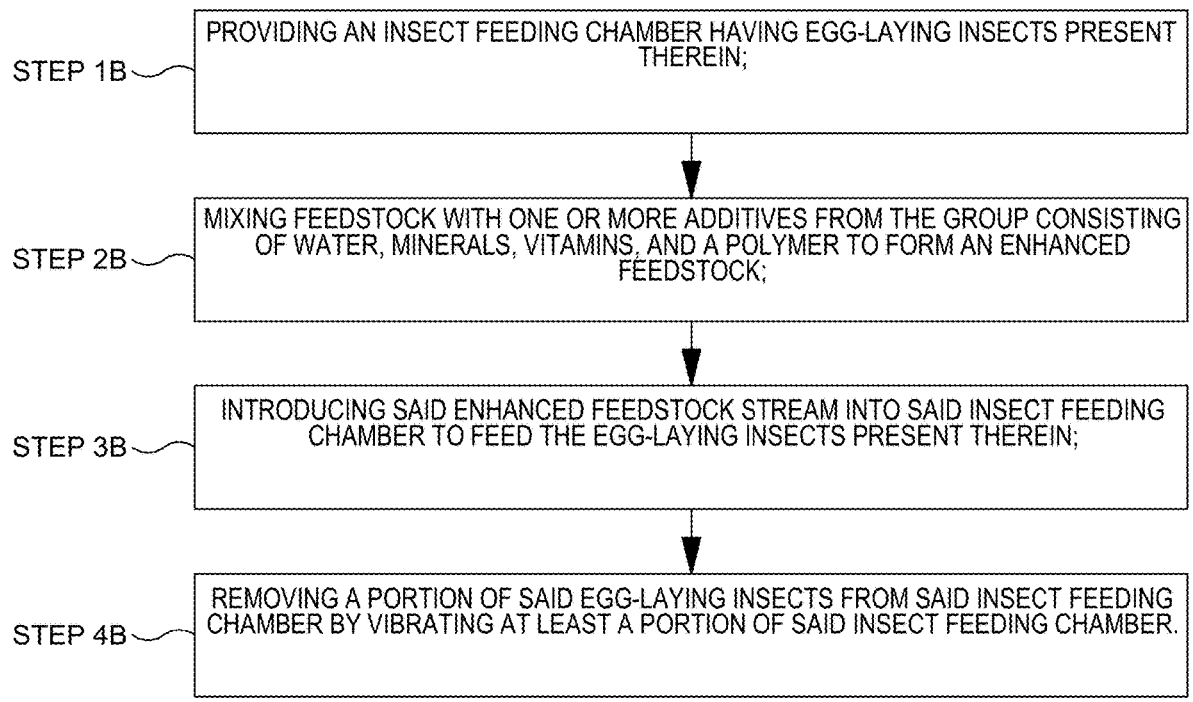

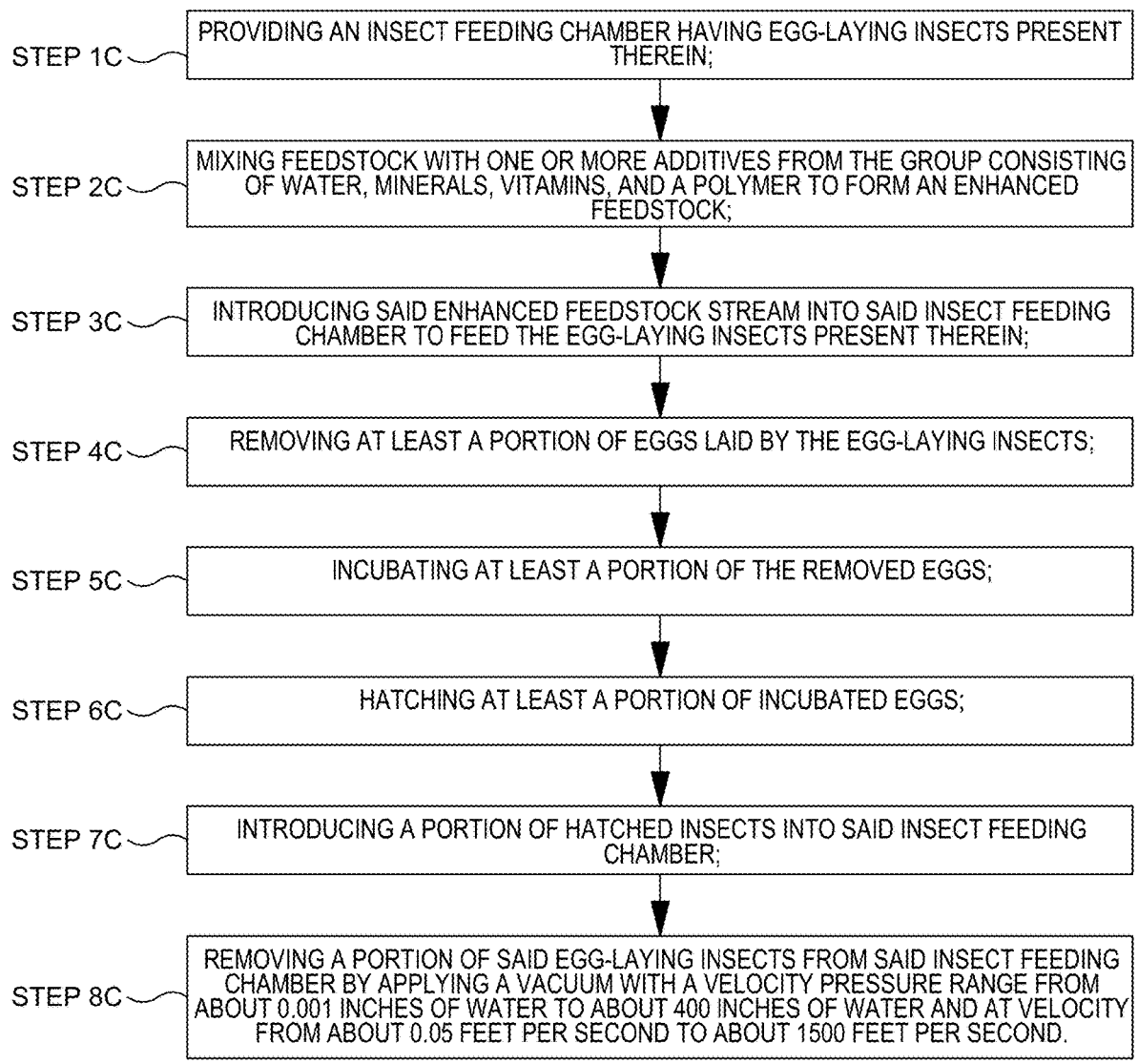

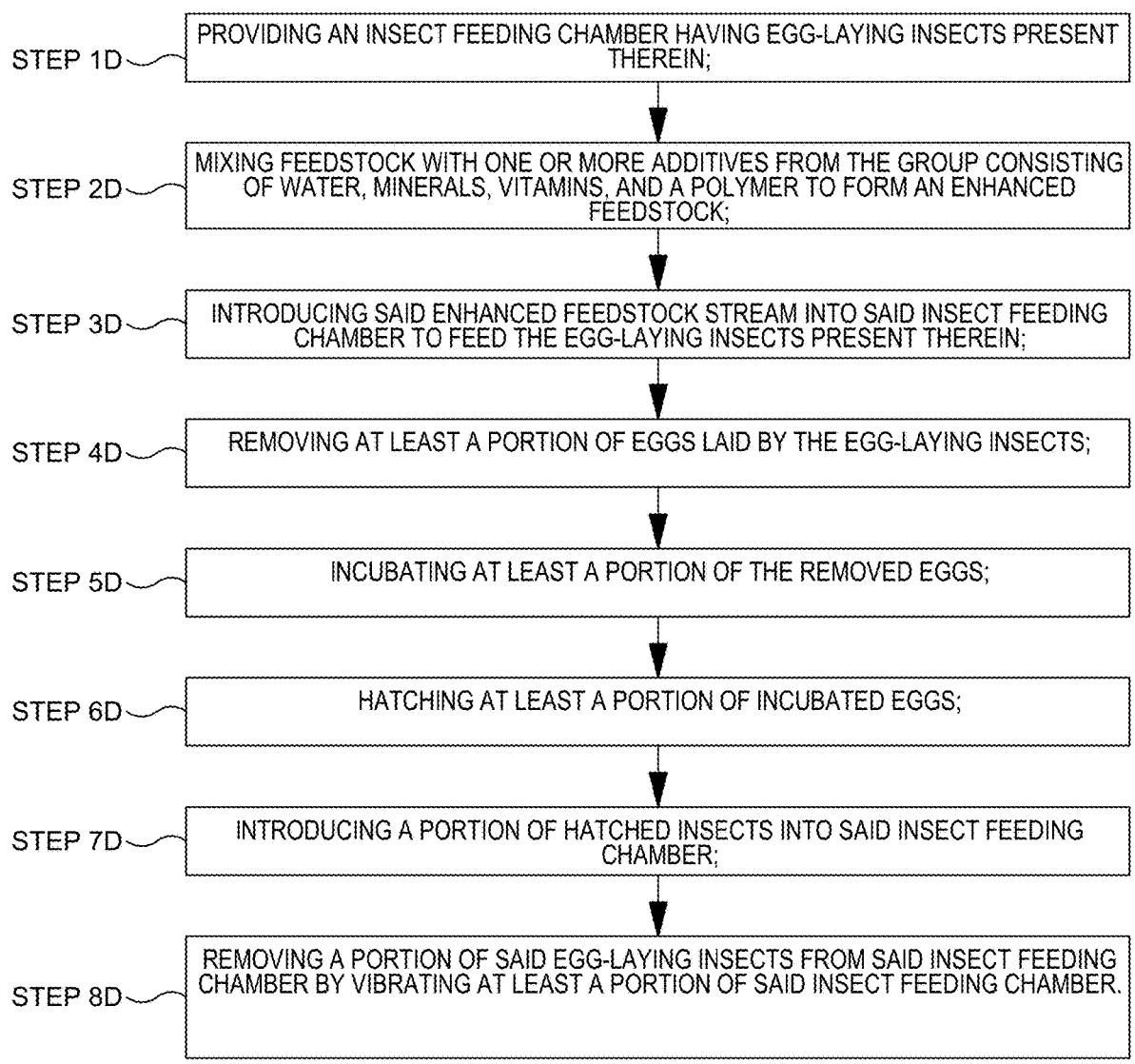

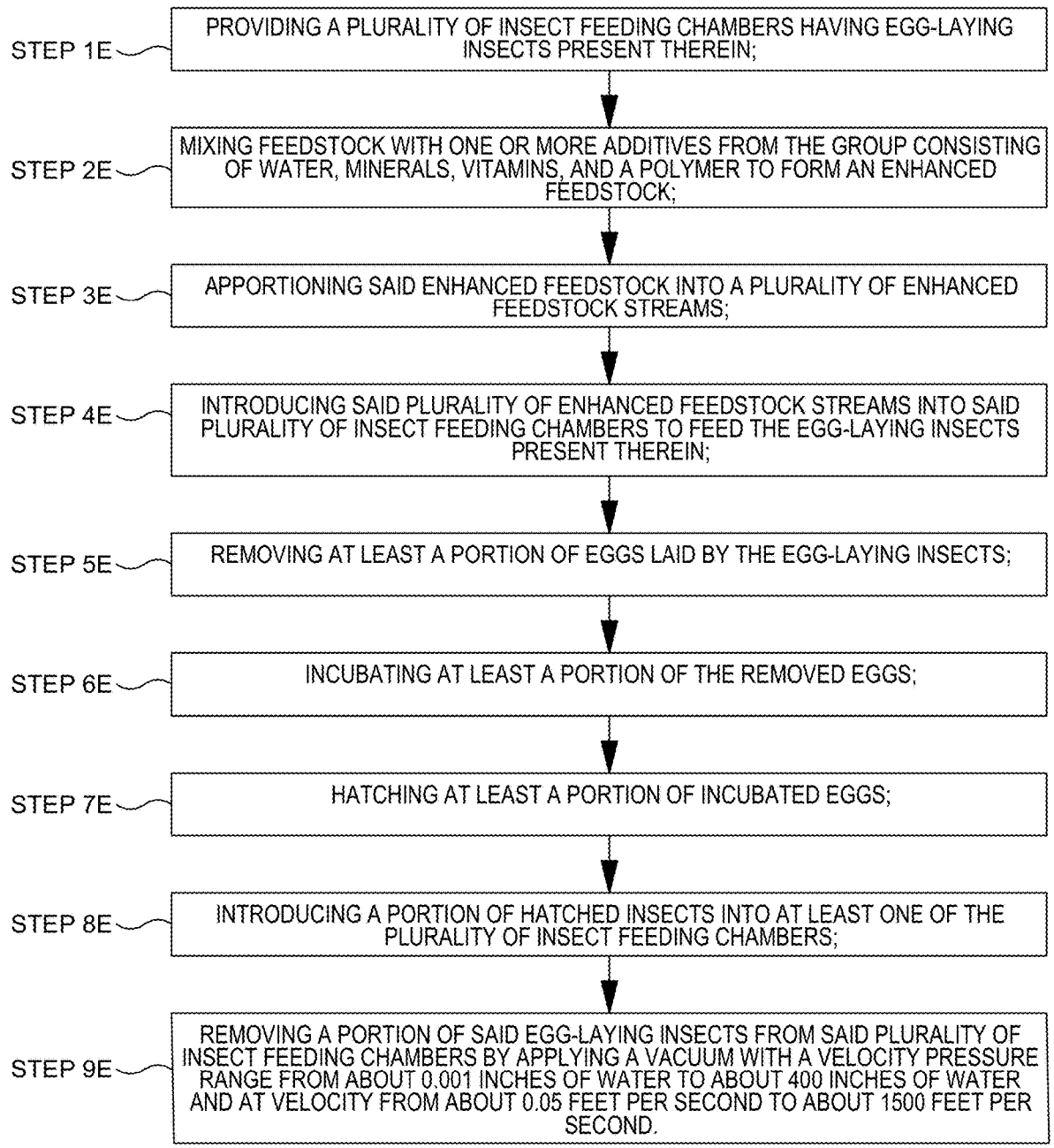

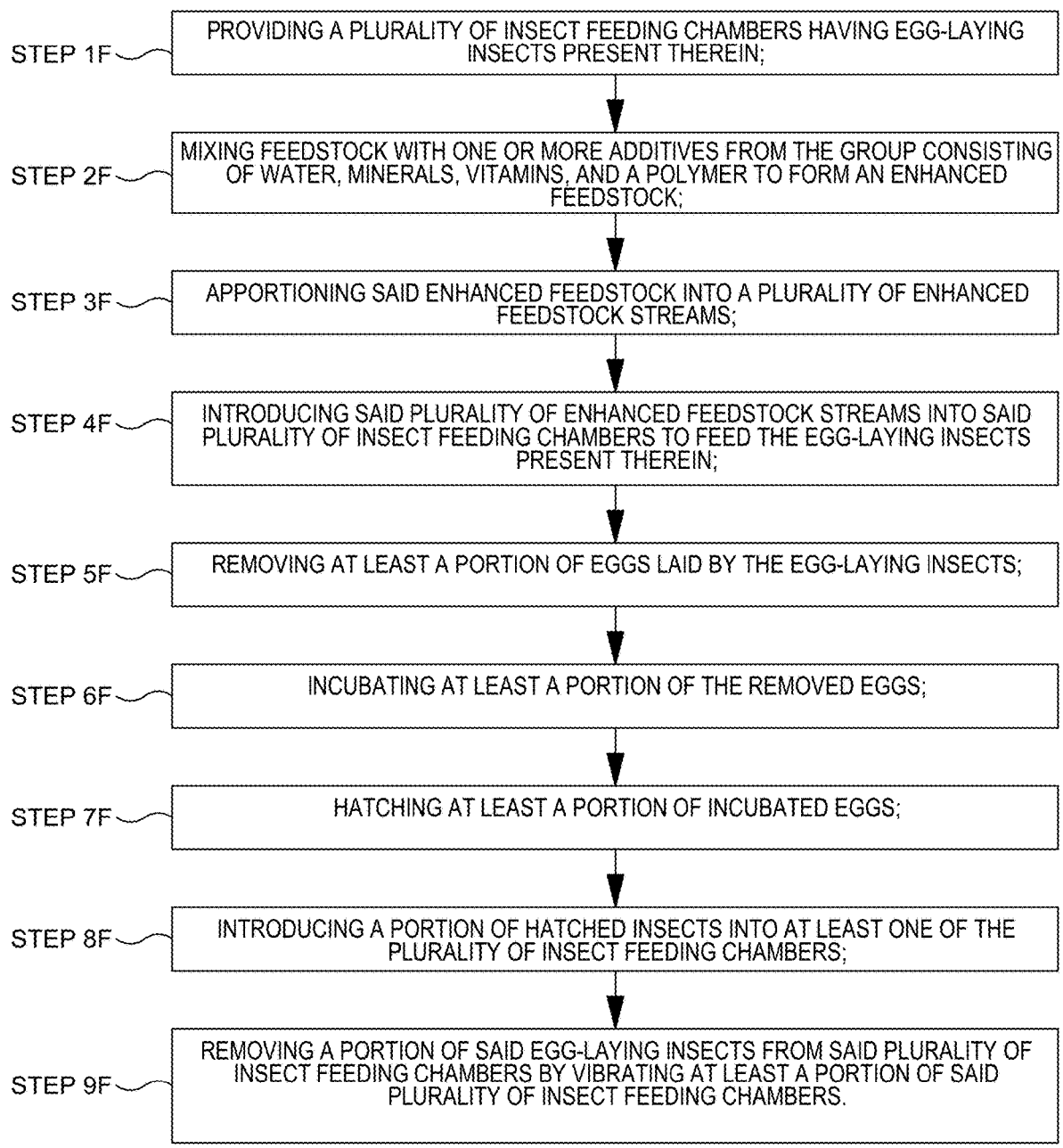

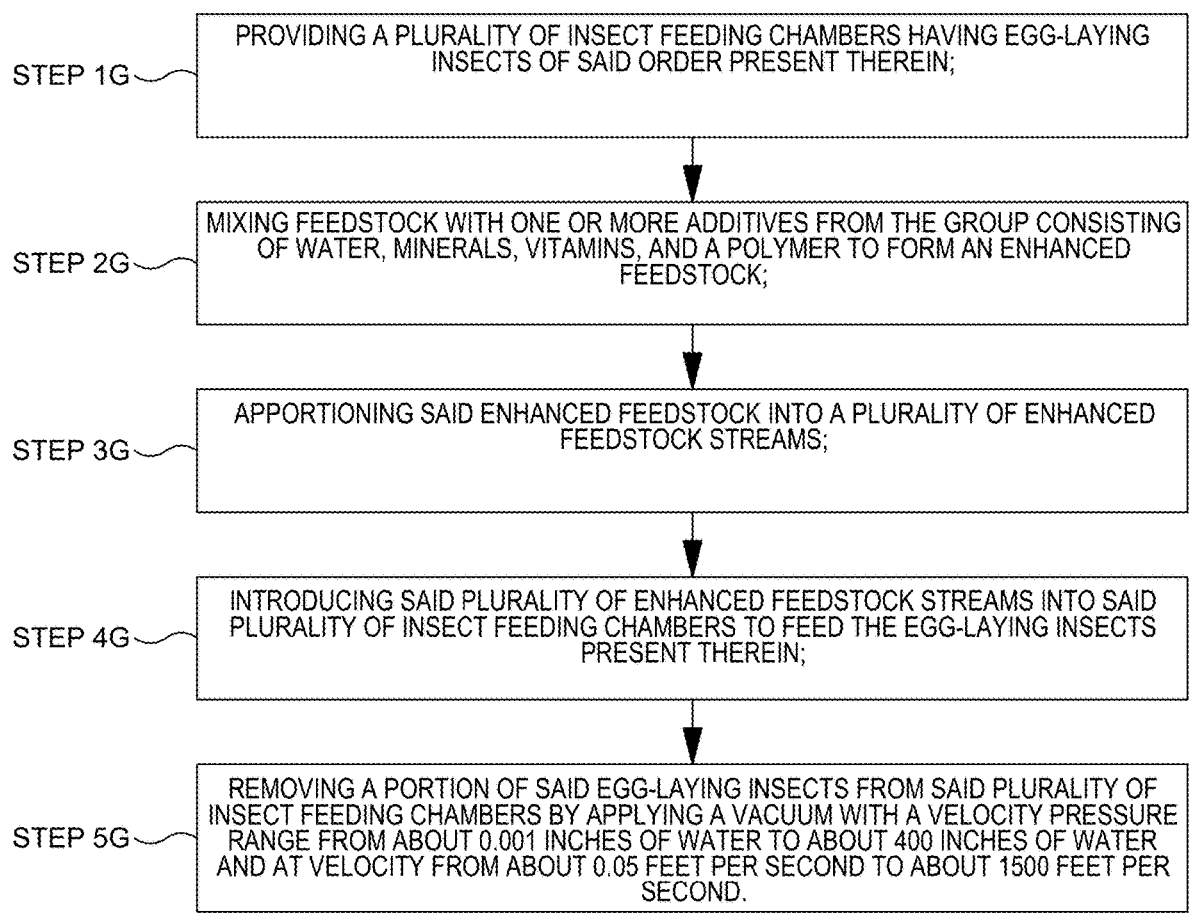

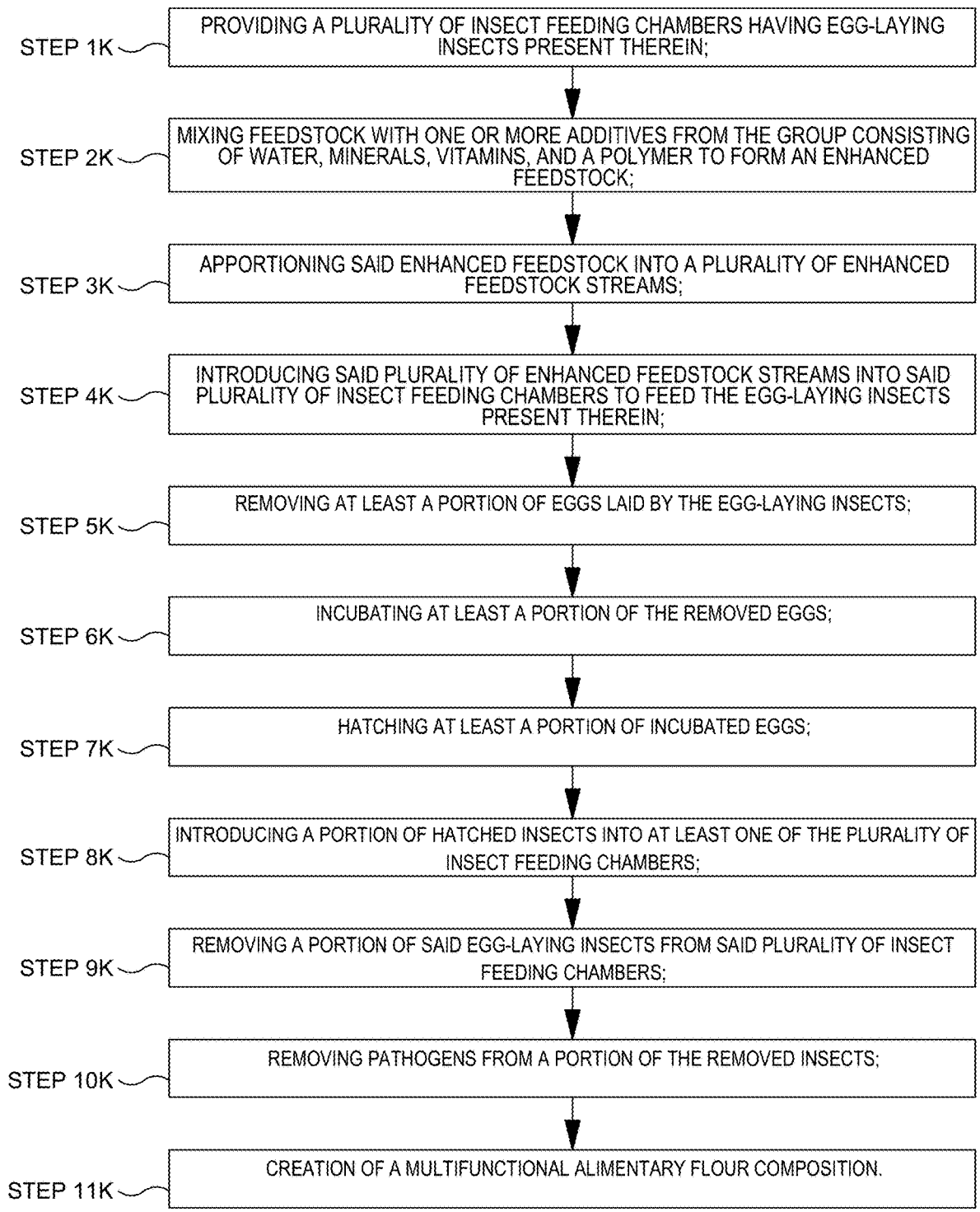

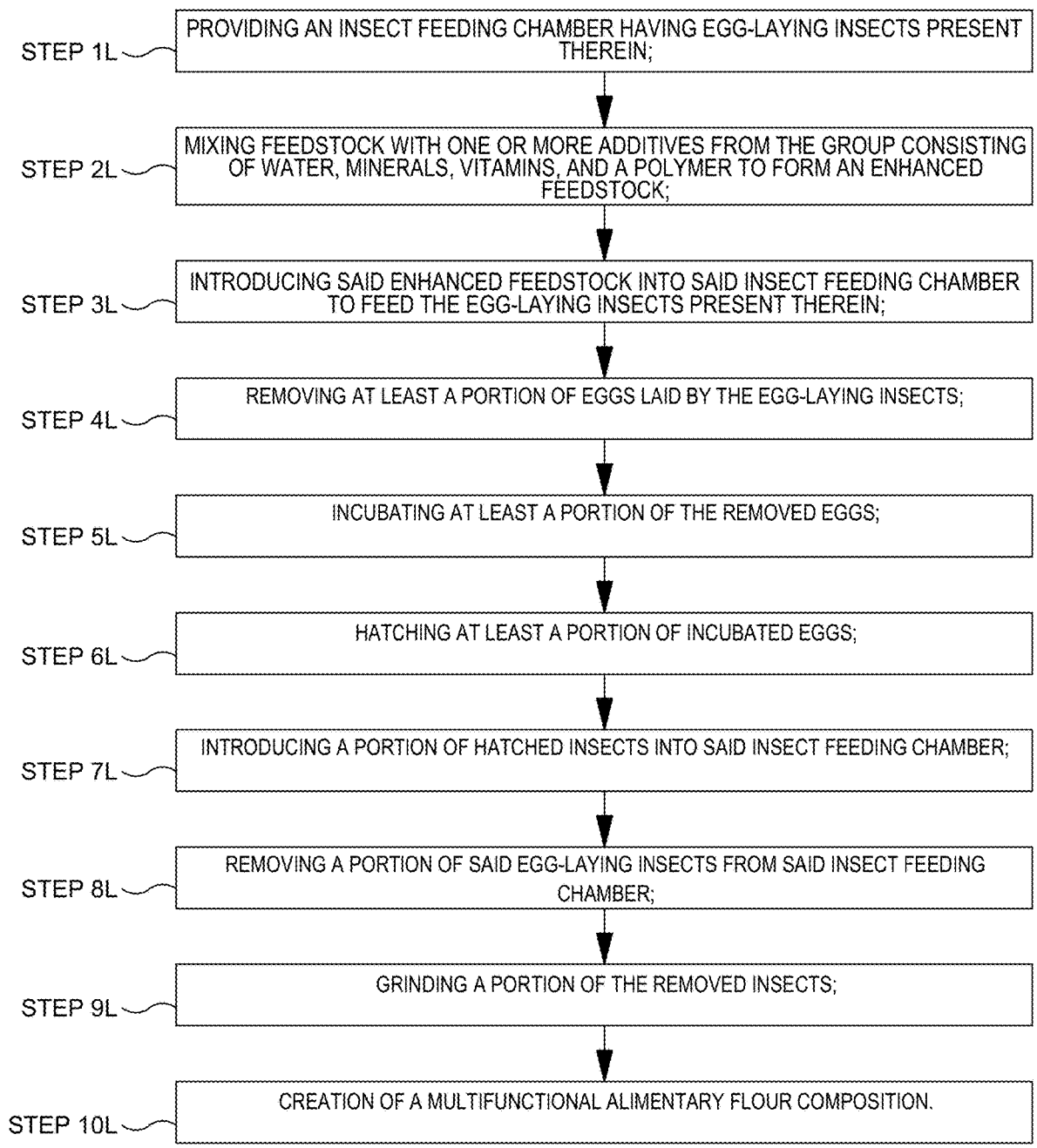

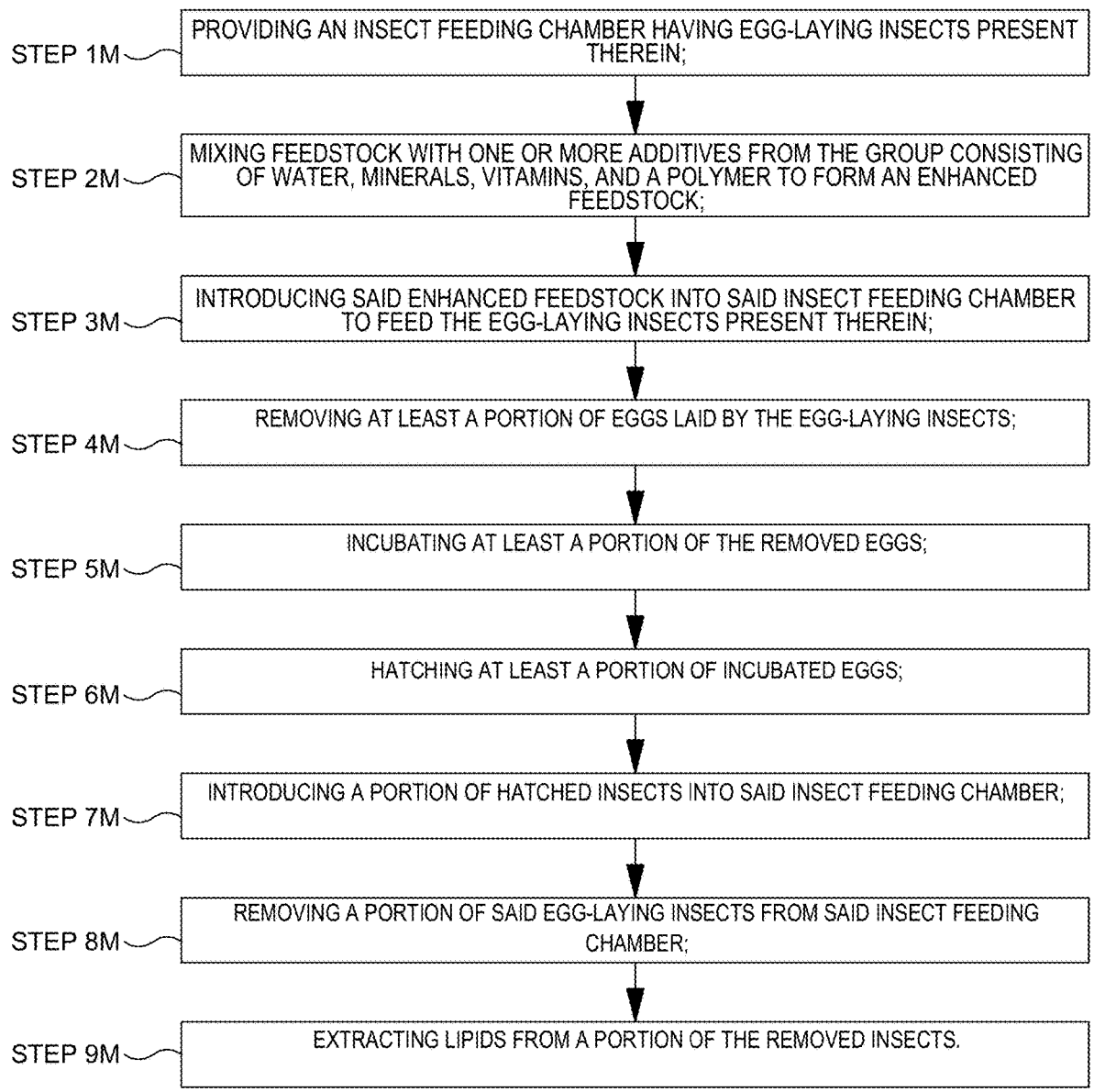

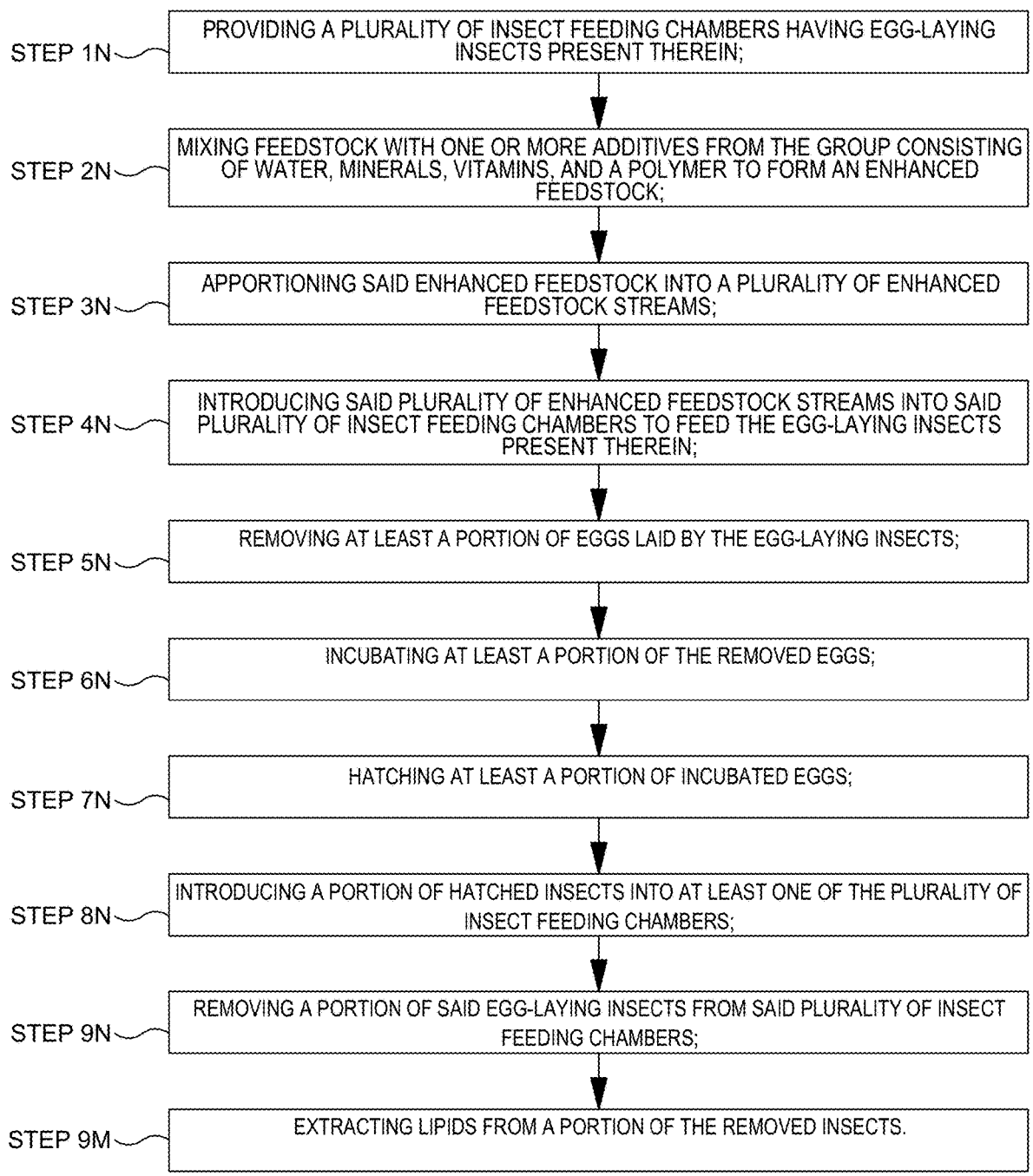

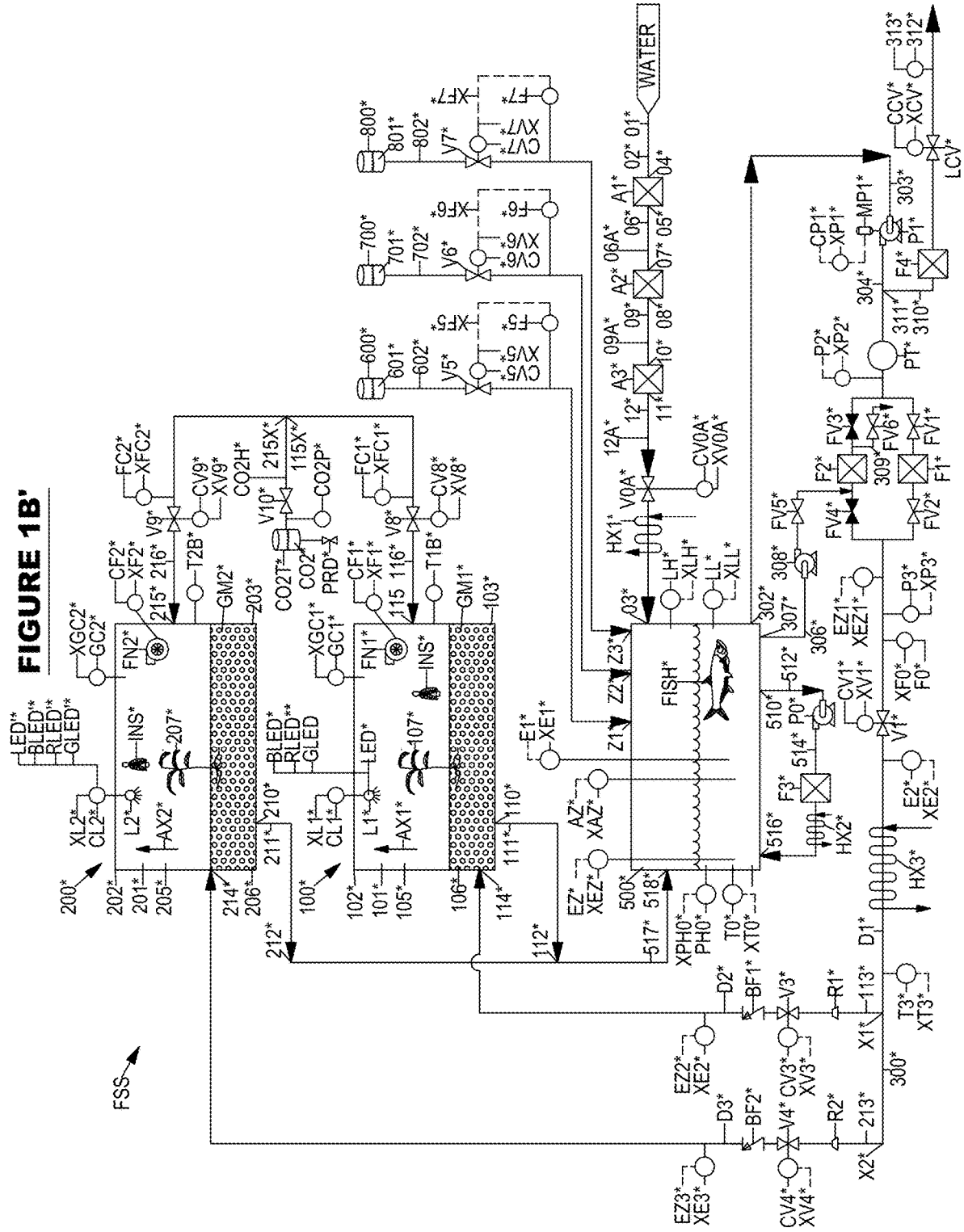

PLANT GROWING MODULE, FRONT VIEW

PLANT GROWING MODULE, TOP VIEW

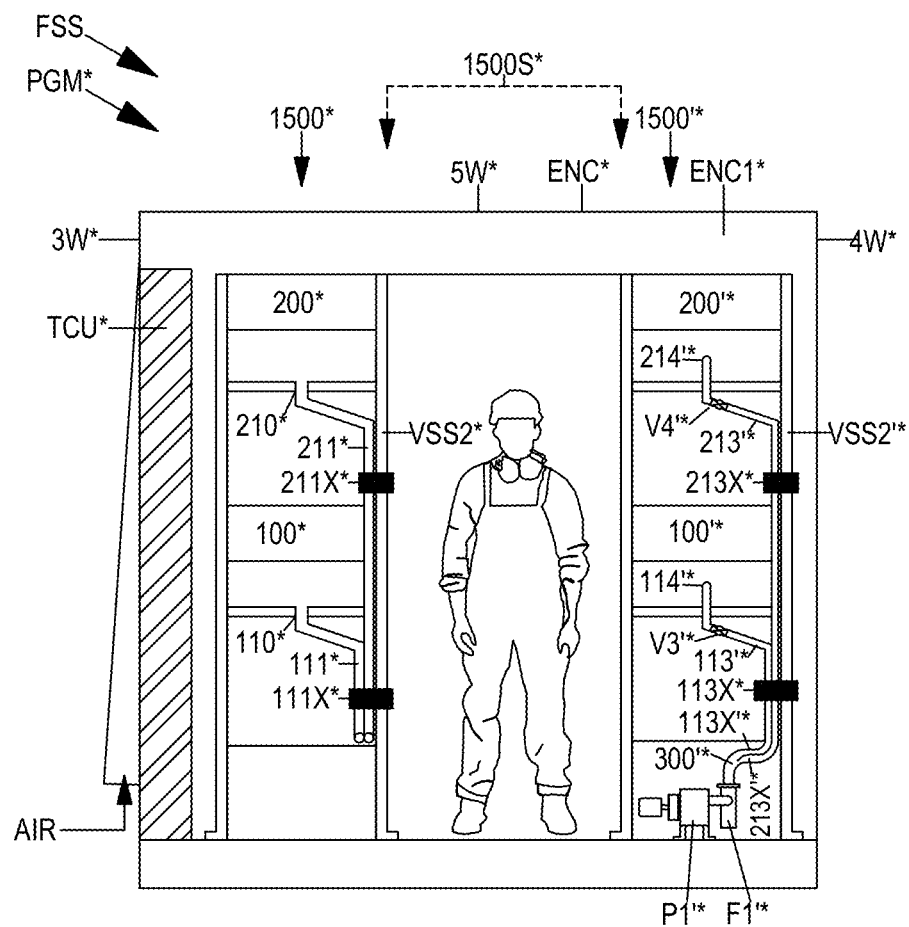

LIQUID DISTRIBUTION MODULE, FRONT VIEW

SOLUTION MIXING MODULE, TOP VIEW

LIQUID DISTRIBUTION MODULE, SIDE VIEW

CANNABIS TRIMMING

CANNABIS GRINDING

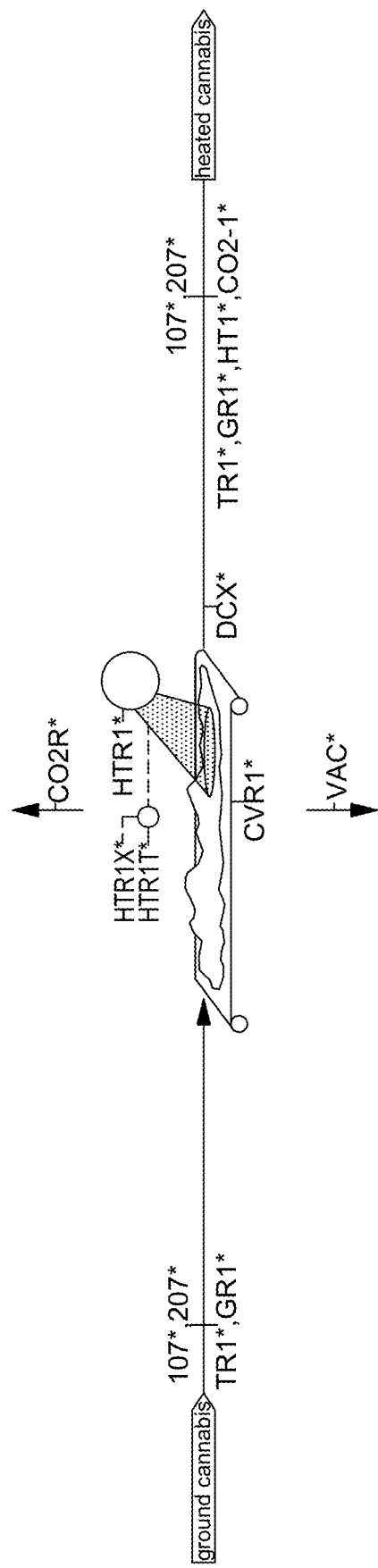

VOLATILES SEPARATION

VOLATILES SEPARATION

SOLVENT MIXING

SOLVENT SEPARATION SYSTEM

SOLVENT SEPARATION SYSTEM

SPRAY DRYER, CO-CURRENT

SPRAY DRYER, COUNTER-CURRENT

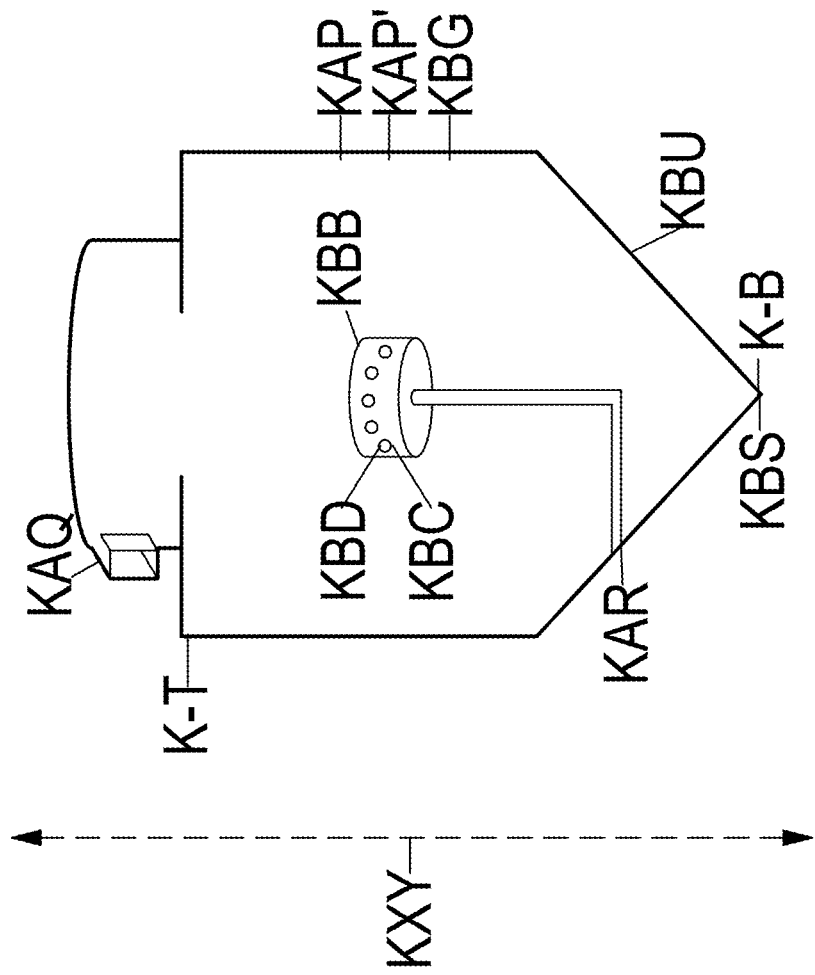

SPRAY DRYER, MIXED

POWER PRODUCTION SYSTEM

CARBON DIOXIDE RECOVERY SYSTEM

CANNABINOID EXTRACTION SYSTEM

EMULSION MIXING SYSTEM

ENCAPSULATION SYSTEM

MULTIFUNCTIONAL COMPOSITION MIXING MODULE

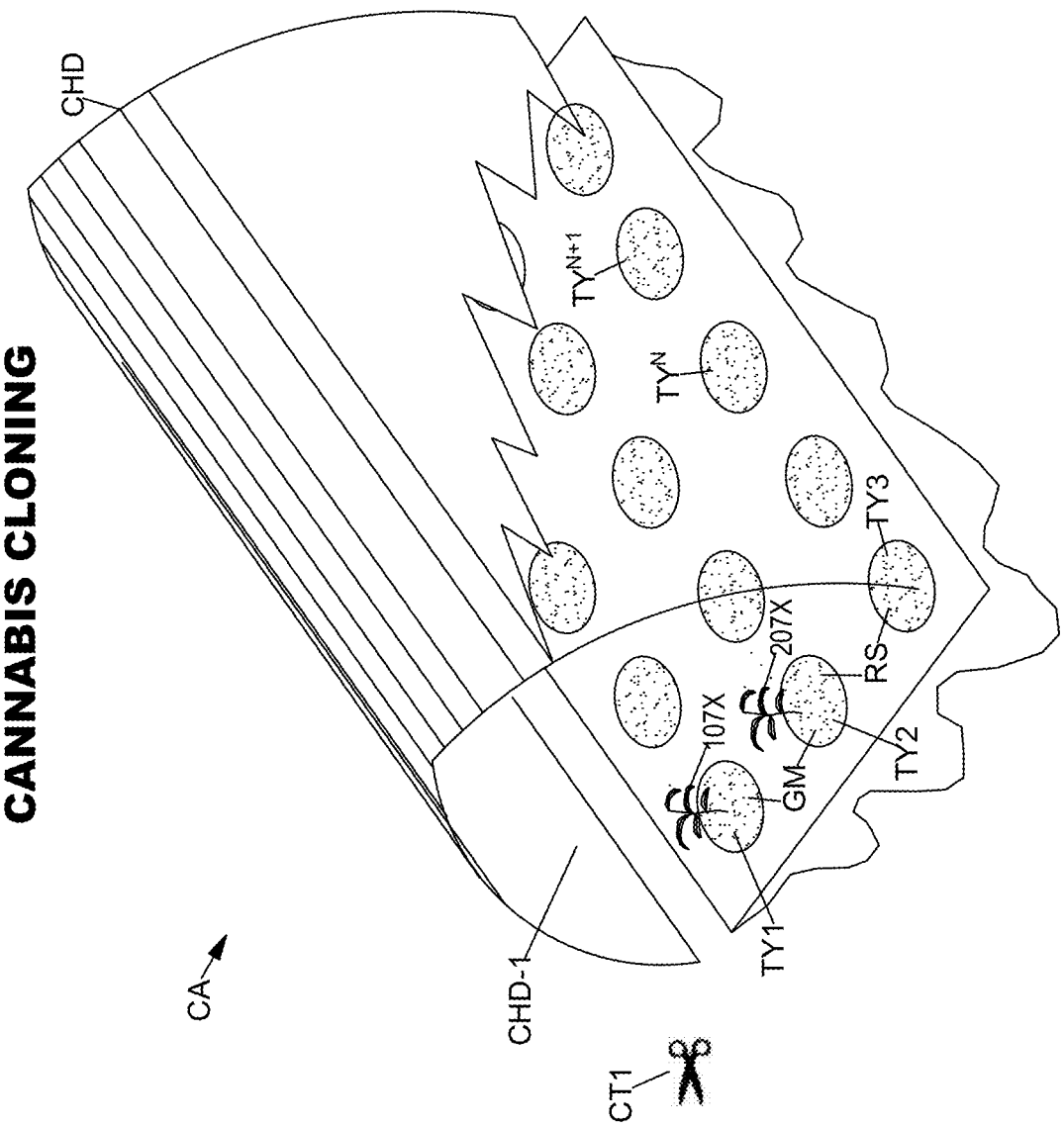

CANNABIS NANOEMULSION METHODS

RELATED APPLICATIONS

This application is a Continuation-In-Part of my co-pending patent application Ser. No. 15/841,886, filed on Dec. 14, 2017, which is a Continuation-In-Part of my co-pending patent application Ser. No. 15/664,490, filed on Jul. 31, 2017, which is a Continuation-In-Part of my co-pending patent application Ser. No. 15/257,854, filed on Sep. 6, 2016, which is a Continuation-In-Part of my co-pending patent application Ser. No. 15/242,579, filed on Aug. 21, 2016.

TECHNICAL FIELD

The present disclosure relates to the field of commercial scale production of *cannabis* and insects.

BACKGROUND

Efficient, reliable, and consistent computer operated insect rearing facilities are needed to meet the insect production demands of society. In recent years, there has been an increasing demand for insect protein for human and animal consumption. There is also promise for the extraction and use of lipids from insects for applications involving medicine, nanotechnology, consumer products, and chemical production. Large scale insect production systems must be designed responsibly to make sure that the insects are freed from hunger, thirst, discomfort, pain, injury, disease, fear and distress. These systems must be precisely sized and situated to be able to provide systematically timed and controlled computer operated methods to maintain a sufficient amount of nutrition, to prevent disease, cannibalism, and injury. A need exists for mass insect production facilities that maximize insect production on a small physical outlay while providing adequate space for high density insect rearing.

The ability to grow insects with minimal human interaction has been long regarded as desirable or needed to facilitate widespread use for human and animal or consumption or for use as an intermediate lipid-based product for the production of food and chemicals. In demographics, the world population is the total number of humans currently living. As of March 2016, it was estimated at 7.4 billion, an all-time record high. The United Nations estimates it will further increase to 11.2 billion in the year 2100. World population has experienced continuous growth since the end of the Great Famine of 1315-17 and the Black Death in 1350, when it was near 370 million.

In coming years, nuclear proliferation, food shortages, water scarcity, and diminishing petroleum reserves may result in a constraint on access to food, water, chemicals, and other resources. Famine may result causing millions of deaths over an extended number of years which will mark a clear end to the period of growth and prosperity for the human civilization, industrialization, and globalization.

The global population is expected to reach between 8.3 and 10.9 billion by 2050 which will be met with famine, malnutrition, and shortages of clean drinking water. Further, the succession of major wars, famines, and other disasters may result in large-scale population losses if no alternate source of food and chemicals is immediately put in place.

Thus, it is of paramount importance that large-scale, modular, easily manufacturable, energy efficient, reliable, computer operated insect production facilities are extensively deployed to produce insects for human and animal consumption, and for the extraction and use of lipids for applications involving medicine, nanotechnology, consumer products, and chemical production with minimal water, feedstock, and environmental impact.

There is a need for systems and methods that can clean and decontaminate water from the most-harshest of environmental conditions and provide a clean water source suitable to feed and grow insects for human, animal, and chemical production. There is a need to develop and vastly implement large-scale, systematic insect feeding and breeding facilities that can accommodate the protein and fatty acid demands of society. There is a need to re-use old containerized shipping containers to promote the implementation of widespread commercial production of insects to promote regional, rural, and urban, job opportunities that maximizes the quality of living the insects that are farmed.

A need exists for *cannabis* farming facilities that maximize plant production on a small physical outlay while providing adequate space for high-density plant growth all at an economically attractive cost. There is a need for systems and methods that can produce unique and novel foodstuffs or snack foods. There is a need for unique and novel foodstuffs or snack foods to be created from Orthoptera order of insects and produced from commercially available unit operations, including, feedstock mixing, enhanced feedstock splitting, insect feeding, insect breeding, insect collection, insect grinding, pathogen removal, multifunctional composition mixing, liquid mixing, shaping, cooking, flavoring, biocatalyst mixing, exoskeleton separation, liquid separation, and lipid extraction.

There is a need to make electrochemical biosensors made from insects for medicinal, environmental, agricultural, and food-related industrial market sectors. There is a need for insect pest management systems for *cannabis* farms. There is a need for an insect traceability system that is specifically tailored towards the unique challenges related to tracking, accountability, food safety, and state and federal government compliance of the insect industry, either for food (for humans or animals), drugs, chemicals, and medicine.

There is a need for system to hydrogenate insect oil. There is a need for systems to esterify hydrogenated insect oil to make intermediate products for the production of consumer products including, baby lotion, biomedical sensing device, blush, body cream, candles, cleanser, cologne, concealer, food, foot powder, foot spray, foundation, hand cream, hard candy, lubricant, mascara, moisturizer, nail products, nanodevice, oils, perfume, pharmaceuticals, powders, shaving cream, soap, surfactant, thickeners. There is a need for systems to process insect oil to produce intermediate products from stearic acid the intermediate product includes one or more intermediate products selected from the group consisting of glyceryl stearate, TEA-stearate, sorbitan stearate, and stearyl alcohol.

Efficient, reliable, and consistent, computer-operated *cannabis* farming systems and methods are needed to meet the *cannabis* production demands of society. In recent years, there has been an increasing demand for *cannabis* for medicinal and recreational use. Large-scale *cannabis* farming systems must be designed carefully to minimize environmental impact, reduce manual labor and human interaction, and automate the system as much as possible while maximizing plant growth. These systems must be precisely sized and situated to be able to provide systematically timed and controlled computer-operated methods to maintain a sufficient amount of water and nutrients for the *cannabis* at a precise temperature, humidity level, pH, oxygen and/or carbon dioxide level, air velocity, and light wavelength and schedule.

A need exists for an insect farm co-located at a *cannabis* farm to purposefully introduce insects into the *cannabis* plants to protect the plants allowing the insects to feed on other insect eggs, insect larva, and other insects including living organisms which may or may not contain chitin not only including spider mites, rust mites, *thrips*, jumping plant lice, white fly, knats, gnats, aphids, and insects. There is a need for computer-operated bat farms to protect *cannabis* plants within *cannabis* farms by purposefully introducing bats to the *cannabis* farm to feed on insects.

The ability to grow *cannabis* with minimal human interaction has been long regarded as desirable and needed to facilitate widespread use for human consumption and for the production of food. It is of importance that large-scale, standardized, modular, easily manufacturable, energy efficient, reliable, computer-operated *cannabis* farming systems and facilities are extensively deployed to produce *cannabis* for medicinal and recreation use with minimal water and environmental impact.

There is a need for *cannabis* farming facilities to employ systems and methods that can clean and decontaminate water from harsh and unpredictable sources and provide a clean water source suitable to feed and grow *cannabis*. There is a need to re-use old containerized shipping containers to promote the implementation of widespread commercial production of *cannabis* to promote regional, rural, and urban job opportunities that maximize the quality of living where the *cannabis* is farmed.

There is a need for a superior blend of *Cannabis sativa* L. ssp. *Sativa* and *Cannabis sativa* L. ssp. *Indica* (Lam.) that provides improved medicinal benefits, and has a high yield to meet industrial, commercial, recreational, and medicinal demand at a low price and minimal economic and environmental impact. There is a need for a new variety of plant that has a repeatable, predictable, and unique chemical composition that is based upon standardized engineered concentrations of: cannabidiol, tetrahydrocannabinol, energy, carbon, oxygen, hydrogen, ash, volatiles, nitrogen, sulfur, chlorine, sodium, potassium, iron, magnesium, phosphorous, calcium, zinc, cellulose, lignin, hemicellulose, fat, fiber, protein, while having preferred specific *Cannabis sativa* L. ssp. *Sativa* and *Cannabis sativa* L. ssp. *Indica* (Lam.) weight percentages.

SUMMARY

This Summary is provided merely to introduce certain concepts and not to identify any key or essential features of the claimed subject matter.

Paragraph A: A beverage derived by mixing:
  an alimentary multifunctional composition having a bulk density ranging from between 3.5 pounds per cubic foot to 50 pounds per cubic foot, an energy content ranging from 4,500 British Thermal Units per pound to 10,500 British Thermal Units per pound, the composition includes a *cannabis* enhancer including one or more *cannabis* enhancers selected from the group consisting of *cannabis*, dried *cannabis*, ground *cannabis*, decarboxylated *cannabis*, tetrahydrocannabinol, and combinations thereof; and
  treated water, the treated water is treated with one or more water treatment units selected from the group consisting of an adsorbent, an ion-exchange resin, a catalyst, activated carbon, a membrane, and combinations thereof.

Paragraph B: The beverage according to Paragraph A, further comprising:
  pathogens including one or more pathogens selected from the group consisting of a bacteria, a fungus, and combinations thereof and/or N-acetylglucosamine derived from insects and/or arthropods.

Paragraph C: The beverage according to Paragraph A, further derived by mixing:
  a biocatalyst including one or more biocatalysts selected from the group consisting of enzyme, casein protease, peptidase, protease A, protease, *Aspergillus oryzae, Bacillus subtilis, Bacillus licheniformis, Aspergillus niger, Aspergillus melleus,* papain, *Carica papaya,* bromelain, *Ananas comorus* stem, a fungus, a microorganism, and yeast; and/or
  an acid including one or more acids selected from the group consisting of abscic acid, acetic acid, ascorbic acid, benzoic acid, citric acid, formic acid, fumaric acid, hydrochloric acid, lactic acid, malic acid, nitric acid, organic acids, phosphoric acid, potassium hydroxide, propionic acid, salicylic acid, sulfamic acid, sulfuric acid, and tartaric acid.

Paragraph D: The beverage according to Paragraph A, further comprising:
  a sweetener including one or more sweeteners selected from the group consisting of a zero-calorie sweetener, aspartame, acesulfame potassium, saccharin, sucralose, neotame, erythritol, *stevia, stevia* leaf extract, a sugar alcohol, a polyol, sugar, honey, and combinations thereof.

Paragraph E: The beverage according to Paragraph A, wherein the beverage includes:
  a specific gravity ranging from between 0.995 to 1.2;
  a viscosity ranging from between 1 centipoise to 5 centipoise; and
  an electrical conductivity that ranges from between 750 microsiemens per centimeter to 5,000 microsiemens per centimeter.

Paragraph F: The beverage according to Paragraph E, wherein the beverage includes:
  a cannabinoid and water emulsion including:
    an average cannabinoid droplet size ranging from 10 nanometers to 100 nanometers;
    a cannabinoid including cannabidiol and/or tetrahydrocannabinol;
    a serving size ranging from 6 fluid ounces to 16 fluid ounces;
    a calorie content ranging from 0 calories per serving to 100 calories per serving; and
    a cannabinoid content ranging from 2 milligrams per serving to 100 milligrams per serving.

Paragraph G: A cannabinoid beverage including:
  (a) a cannabinoid and water emulsion including:
    (a1) an average cannabinoid droplet size ranging from 10 nanometers to 100 nanometers;
    (a2) a cannabinoid including cannabidiol and/or tetrahydrocannabinol;
    (a3) a serving size ranging from 6 fluid ounces to 16 fluid ounces;
    (a3) a calorie content ranging from 0 calories per serving to 100 calories per serving;
    (a4) a cannabinoid content ranging from 2 milligrams per serving to 100 milligrams per serving;

(b) treated water, the treated water is treated with one or more water treatment units selected from the group consisting of an adsorbent, an ion-exchange resin, a catalyst, activated carbon, a membrane, and combinations thereof; and (c) an emulsifier including one or more emulsifiers selected from the group consisting of a surfactant, a nonionic surfactant, lecithin, polyethylene (40), stearate, polysorbate, polyoxyethylene sorbitan monooleate, polyoxyethylene (20) sorbitan monooleate, polysorbate 80, polysorbate 60, polysorbate 65, ammonium salts of phosphatidic acid, sucrose acetate isobutyrate, potassium pyrophosphate, sodium acid pyrophosphate, sodium pyrophosphate, potassium polymetaphosphate, sodium metaphosphate, insoluble or sodium polyphosphates, sodium polyphosphates, insoluble polyphosphates, glassy salts of fatty acids, mono-and di-glycerides of fatty acids, mono-glycerides of fatty acids, di-glycerides of fatty acids, acetic and fatty acid esters of glycerol, lactic and fatty acid esters of glycerol, citric and fatty acid esters of glycerol, diacetyltartaric and fatty acid esters of glycerol, mixed fatty acid esters of glycerol, sucrose esters of fatty acids, polyglycerol esters of fatty acids, polyglycerol esters of interesterified ricinoleic acid, propylene glycol mono-and di-esters, propylene glycol di-esters, propylene glycol mono-esters, propylene glycol esters of fatty acids, propylene glycol esters, dioctyl sodium sulphosuccinate, sodium lactylate, sodium oleyl lactylate, sodium stearoyl lactylate, calcium lactylate, calcium oleyl lactylate, calcium stearoyl lactylate, sorbitan monostearate, maltodextrin, polyphosphates, formulated polyphosphates, gum arabic, and combinations thereof.

Paragraph H: The beverage according to Paragraph H, wherein the beverage includes:
a specific gravity ranging from between 0.995 to 1.2;
a viscosity ranging from between 1 centipoise to 5 centipoise; and
an electrical conductivity that ranges from between 750 microsiemens per centimeter to 5,000 microsiemens per centimeter.

Paragraph I: The beverage according to Paragraph H, further derived by mixing:
a biocatalyst including one or more biocatalysts selected from the group consisting of enzyme, casein protease, peptidase, protease A, protease, *Aspergillus oryzae, Bacillus subtilis, Bacillus licheniformis, Aspergillus niger, Aspergillus melleus,* papain, *Carica papaya,* bromelain, *Ananas comorus* stem, a fungus, a microorganism, and yeast; and/or an acid including one or more acids selected from the group consisting of abscic acid, acetic acid, ascorbic acid, benzoic acid, citric acid, formic acid, fumaric acid, hydrochloric acid, lactic acid, malic acid, nitric acid, organic acids, phosphoric acid, potassium hydroxide, propionic acid, salicylic acid, sulfamic acid, sulfuric acid, and tartaric acid.

Paragraph J: The beverage according to Paragraph I, further comprising:
an ingredient including one or more ingredients selected from the group consisting of malt, grain, barley, honey, and hops; and/or
a sweetener including one or more sweeteners selected from the group consisting of a zero-calorie sweetener, aspartame, acesulfame potassium, saccharin, sucralose, neotame, erythritol, *stevia, stevia* leaf extract, a sugar alcohol, a polyol, sugar, honey, and combinations thereof.

Paragraph K: An alimentary multifunctional composition having a bulk density ranging from between 3.5 pounds per cubic foot to 50 pounds per cubic foot, an energy content ranging from 4,500 British Thermal Units per pound to 10,500 British Thermal Units per pound, the composition includes:
(a) a *cannabis* enhancer including one or more *cannabis* enhancers selected from the group consisting of *cannabis*, dried *cannabis*, ground *cannabis*, decarboxylated *cannabis*;
(b) tetrahydrocannabinol;
(c) a carbon content ranging from between 15 weight percent to 55 weight percent;
(d) an oxygen content ranging from between 15 weight percent to 55 weight percent;
(e) a hydrogen content ranging from between 2.5 weight percent to 20 weight percent;
(f) an ash content ranging from between 2.5 weight percent to 7.5 weight percent; and
(g) pathogens including one or more pathogens selected from the group consisting of a bacteria, a parasite, a fungus, and combinations thereof and/or N-acetylglucosamine derived from insects.

Paragraph L: A beverage derived by mixing:
(I) the alimentary multifunctional composition according to Paragraph K; and
(II) treated water, the treated water is treated with one or more water treatment units selected from the group consisting of an adsorbent, an ion-exchange resin, a catalyst, activated carbon, a membrane, and combinations thereof.

Paragraph M: The beverage according to Paragraph L, further derived by mixing with:
a biocatalyst including one or more biocatalysts selected from the group consisting of enzyme, casein protease, peptidase, protease A, protease, *Aspergillus oryzae, Bacillus subtilis, Bacillus licheniformis, Aspergillus niger, Aspergillus melleus,* papain, *Carica papaya,* bromelain, *ananas* comorus stem, a fungus, a microorganism, and yeast.

Paragraph N: The beverage according to Paragraph L, further derived by mixing with:
an acid including one or more acids selected from the group consisting of abscic acid, acetic acid, ascorbic acid, benzoic acid, citric acid, formic acid, fumaric acid, hydrochloric acid, lactic acid, malic acid, nitric acid, organic acids, phosphoric acid, potassium hydroxide, propionic acid, salicylic acid, sulfamic acid, sulfuric acid, and tartaric acid.

Paragraph O: The beverage according to Paragraph M, further comprising ethanol or no ethanol.

Paragraph P: The beverage according to Paragraph L, wherein the beverage includes:
a specific gravity ranging from between 0.995 to 1.2;
a viscosity ranging from between 1 centipoise to 5 centipoise; and
an electrical conductivity that ranges from between 750 microsiemens per centimeter to 5,000 microsiemens per centimeter.

Paragraph Q: The beverage according to Paragraph L, further comprising:
a cannabinoid and water emulsion including:
an average cannabinoid droplet size ranging from 10 nanometers to 100 nanometers;
a cannabinoid including cannabidiol and/or tetrahydrocannabinol;

a serving size ranging from 6 fluid ounces to 16 fluid ounces;
a calorie content ranging from 0 calories per serving to 100 calories per serving; and
a cannabinoid content ranging from 2 milligrams per serving to 100 milligrams per serving.

Paragraph R: The beverage according to Paragraph L, wherein the beverage includes:
a cannabinoid and water emulsion including an average cannabinoid droplet size ranging from 10 nanometers to 75 nanometers, the cannabinoid includes cannabidiol and/or tetrahydrocannabinol.

Paragraph S: The beverage according to Paragraph R, further comprising:
an emulsifier including one or more emulsifiers selected from the group consisting of a surfactant, a nonionic surfactant, lecithin, polyethylene (40), stearate, polysorbate, polyoxyethylene sorbitan monooleate, polyoxyethylene (20) sorbitan monooleate, polysorbate 80, polysorbate 60, polysorbate 65, ammonium salts of phosphatidic acid, sucrose acetate isobutyrate, potassium pyrophosphate, sodium acid pyrophosphate, sodium pyrophosphate, potassium polymetaphosphate, sodium metaphosphate, insoluble or sodium polyphosphates, sodium polyphosphates, insoluble polyphosphates, glassy salts of fatty acids, mono-and di-glycerides of fatty acids, mono-glycerides of fatty acids, di-glycerides of fatty acids, acetic and fatty acid esters of glycerol, lactic and fatty acid esters of glycerol, citric and fatty acid esters of glycerol, diacetyltartaric and fatty acid esters of glycerol, mixed fatty acid esters of glycerol, sucrose esters of fatty acids, polyglycerol esters of fatty acids, polyglycerol esters of interesterified ricinoleic acid, propylene glycol mono-and di-esters, propylene glycol di-esters, propylene glycol mono-esters, propylene glycol esters of fatty acids, propylene glycol esters, dioctyl sodium sulphosuccinate, sodium lactylate, sodium oleyl lactylate, sodium stearoyl lactylate, calcium lactylate, calcium oleyl lactylate, calcium stearoyl lactylate, sorbitan monostearate, maltodextrin, polyphosphates, formulated polyphosphates, gum arabic, and combinations thereof.

Paragraph T: A foodstuff derived by mixing:
(I) the alimentary multifunctional composition according to Paragraph L; and
(II) one or more materials selected from the group consisting of a fiber-starch material, a binding agent, a density improving textural supplement, a moisture improving textural supplement, and mixtures thereof;
wherein:
(i) the fiber-starch material is selected from the group consisting of cereal-grain-based materials, grass-based materials, nut-based materials, powdered fruit materials, root-based materials, tuber-based materials, vegetable-based materials, and mixtures thereof;
(ii) the binding agent is selected from the group consisting of agar, agave, alginin, arrowroot, carrageenan, collagen, cornstarch, egg whites, finely ground seeds, furcellaran, gelatin, guar gum, honey, katakuri starch, locust bean gum, pectin, potato starch, proteins, *psyllium* husks, sago, sugars, syrups, tapioca, vegetable gums, xanthan gum, and mixtures thereof;
(iii) the density improving textural supplement is selected from the group consisting of extracted arrowroot starch, extracted corn starch, extracted lentil starch, extracted potato starch, extracted tapioca starch, and mixtures thereof;
(iv) the moisture improving textural supplement is selected from the group consisting of almonds, brazil nuts, cacao, cashews, chestnuts, coconut, filberts, hazelnuts, indian nuts, macadamia nuts, nut butters, nut oils, nut powders, peanuts, pecans, pili nuts, pine nuts, pinon nuts, pistachios, soy nuts, sunflower seeds, tiger nuts, walnuts, vanilla, and mixtures thereof;
(v) the foodstuff includes one or more selected from the group consisting of ada, bagels, baked goods, biscuits, bitterballen, bonda, breads, cakes, candies, cereals, chips, chocolate bars, chocolate, coffee, cokodok, confectionery, cookies, cooking batter, corn starch mixtures, crackers, crêpes, croissants, croquettes, croutons, dolma, dough, doughnuts, energy bars, flapjacks, french fries, frozen custard, frozen desserts, frying cakes, fudge, gelatin mixes, granola bars, gulha, hardtack, ice cream, khandvi, khanom buang, krumpets, meze, mixed flours, muffins, multi-grain snacks, nachos, nian gao, noodles, nougat, onion rings, pakora, pancakes, panforte, pastas, pastries, pie crust, pita chips, pizza, poffertjes, pretzels, pudding, rice krispie treats, sesame sticks, smoothies, snacks, specialty milk, tele-bhaja, tempura, toffee, tortillas, totopo, turkish delights, and waffles.

VOLUME I: INSECT PRODUCTION SUPERSTRUCTURE SYSTEM (IPSS), DESCRIPTION OF THE DRAWINGS

Reference will now be made in detail to various embodiments of the disclosure. Each embodiment is provided by way of explanation of the disclosure, not limitation of the disclosure. In fact, it will be apparent to those skilled in the art that modifications and variations can be made in the disclosure without departing from the teaching and scope thereof. For instance, features illustrated or described as part of one embodiment to yield a still further embodiment derived from the teaching of the disclosure. Thus, it is intended that the disclosure or content of the claims cover such derivative modifications and variations to come within the scope of the disclosure or claimed embodiments described herein and their equivalents.

Additional objects and advantages of the disclosure will be set forth in part in the description which follows, and in part will be obvious from the description, or may be learned by practice of the claims. The objects and advantages of the disclosure will be attained by means of the instrumentalities and combinations and variations particularly pointed out in the appended claims.

The accompanying figures show schematic process flowcharts of preferred embodiments and variations thereof. A full and enabling disclosure of the content of the accompanying claims, including the best mode thereof to one of ordinary skill in the art, is set forth more particularly in the remainder of the specification, including reference to the accompanying figures showing how the preferred embodiments and other non-limiting variations of other embodiments described herein may be carried out in practice, in which:

FIG. 1A shows a simplistic block flow diagram of one embodiment of an Insect Production Superstructure System (IPSS) including the sequence steps of feedstock mixing (step A), feedstock splitting (step B), insect feeding (step C1, C2), insect breeding (step D), insect collection (step E), and insect grinding (step F).

FIG. 1B elaborates upon the non-limiting embodiment of FIG. 1 further including the sequence steps of pathogen removal (step G) and multifunctional composition mixing (step H).

FIG. 1C elaborates upon the non-limiting embodiment of FIG. 1 further including the sequence step of lipid extraction (step J).

FIG. 1D includes one non-limiting embodiment of an insect traceability system flow chart.

Figure 3:
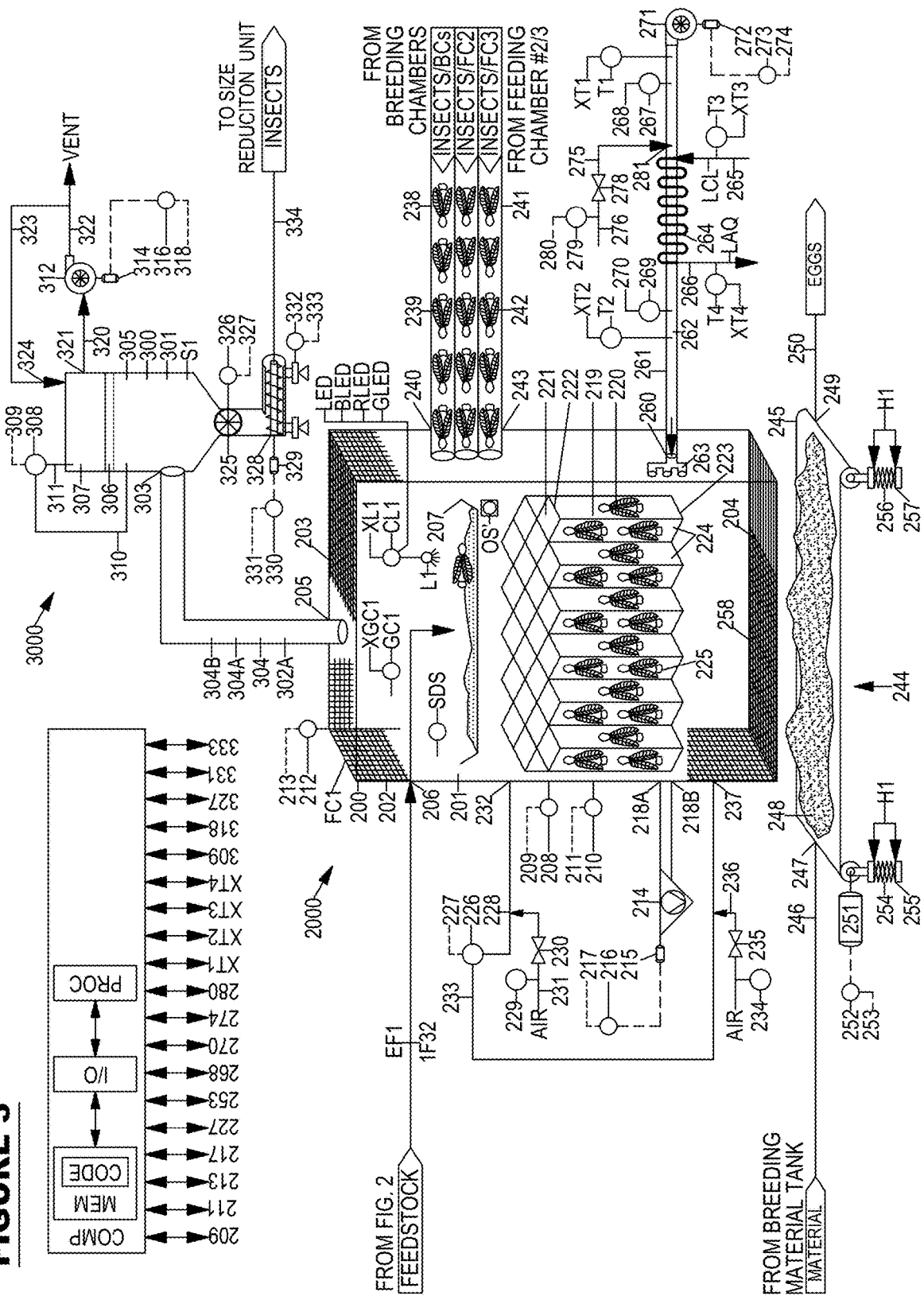
FIG. 3 shows a non-limiting embodiment of an insect feeding module (2000) integrated with an insect evacuation module (3000) operating in a first mode of operation wherein the egg transfer system (244) of the insect feeding module (2000) is at a first state in a first retracted height (H1).
Figure 5:
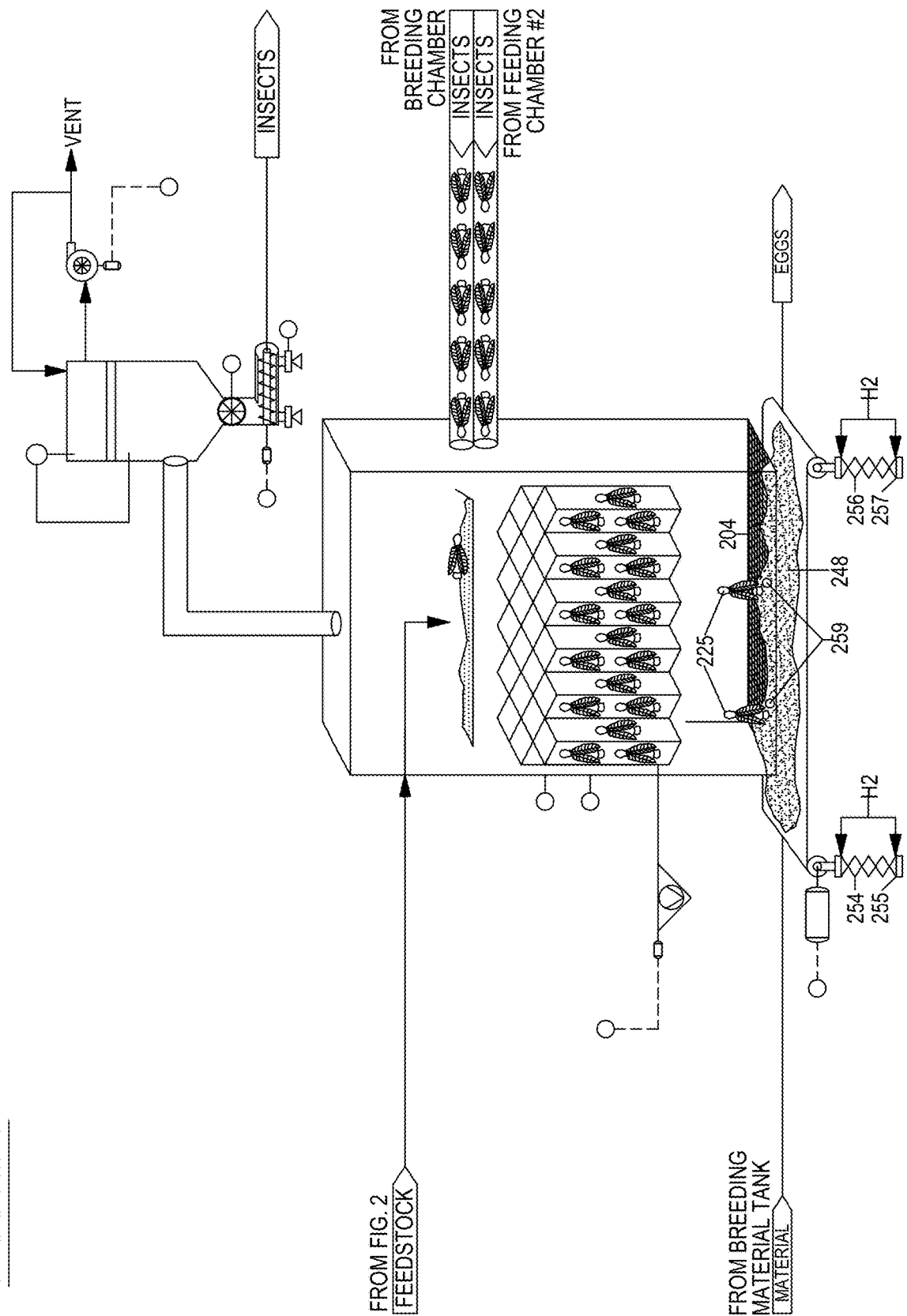

FIG. 5 elaborates upon the non-limiting embodiment of FIG. 3 but shows the insect feeding module (2000) operating in a second mode of operation wherein the egg transfer system (244) of the insect feeding module (2000) is at a second state at a second elevated height (H2) so as to permit insects (225) to lay eggs (259) within a provided breeding material (248).

Figure 6:
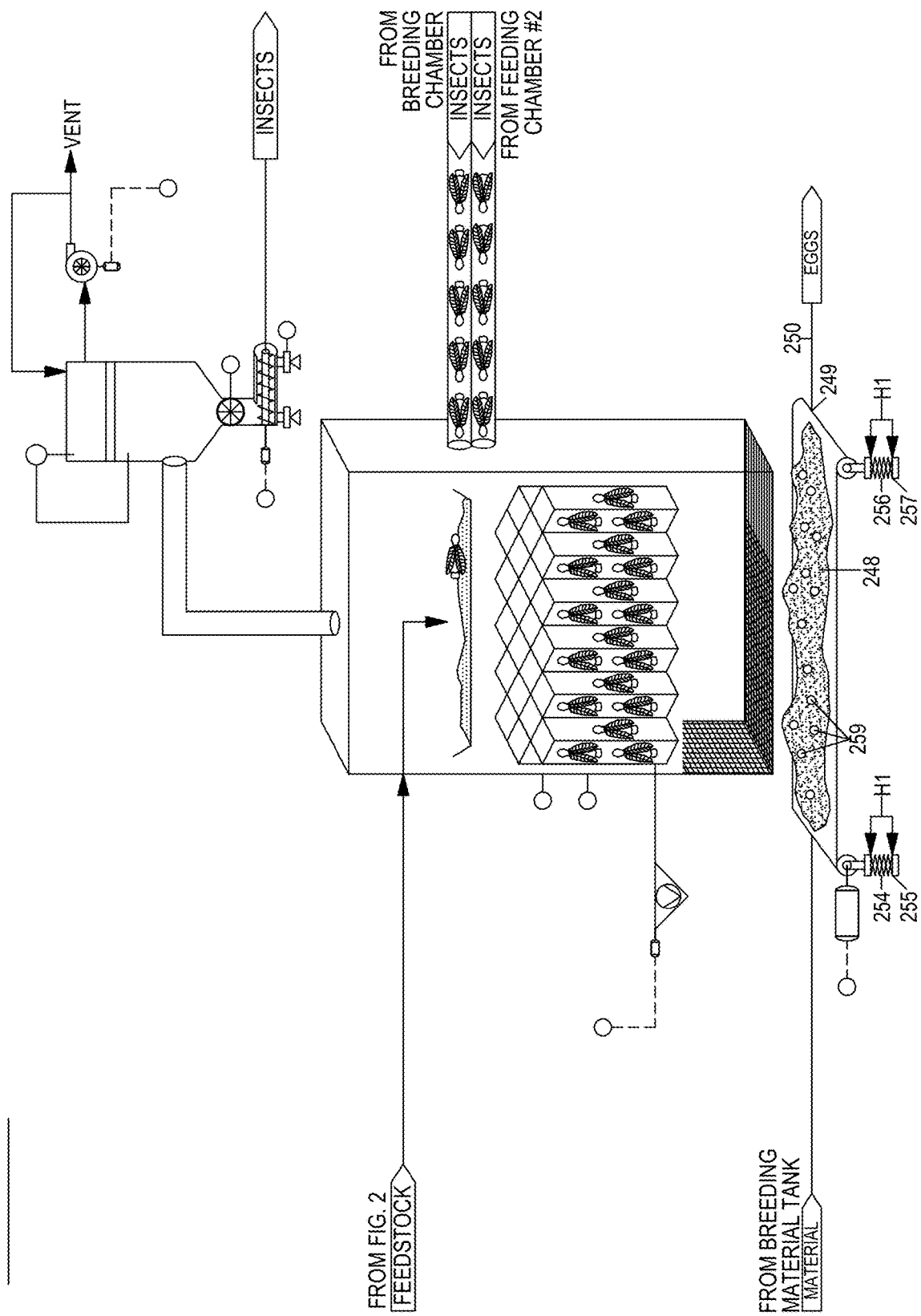

FIG. 6 elaborates upon the non-limiting embodiment of FIG. 3 but shows the insect feeding module (2000) operating in a third mode of operation wherein the egg transfer system (244) of the insect feeding module (2000) is at a first state in a first retracted height (H1) so as to discontinue insects (225) from laying eggs (259) within the provided breeding material (248).

Figure 7:
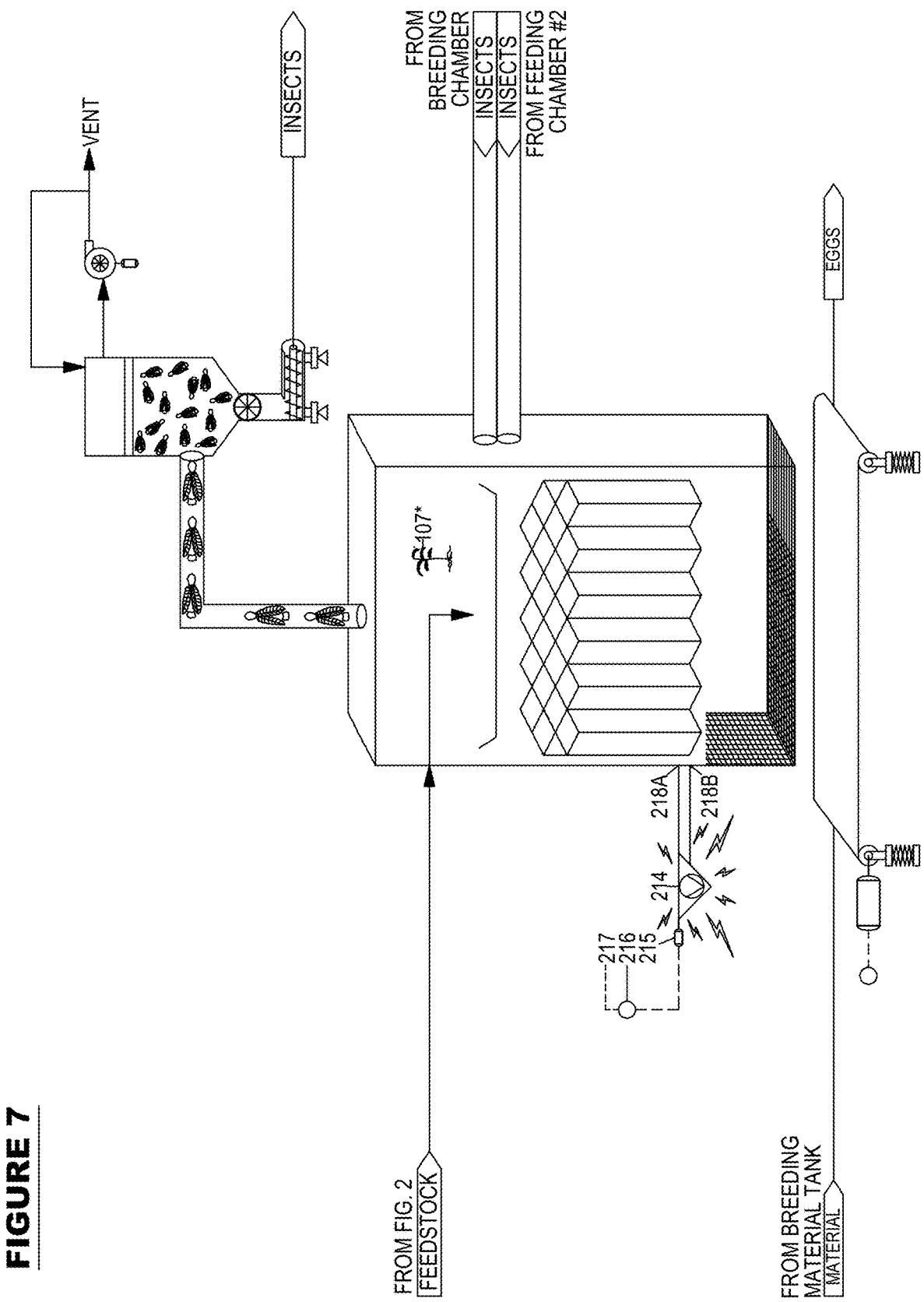

FIG. 7 elaborates upon the non-limiting embodiment of FIG. 3 but shows the insect feeding module (2000) and insect evacuation module (3000) operating in a fourth mode of operation wherein a vibration unit (214) is activated to permit the removal of insects (225) from the network (220) of cells (219) and wherein the insect evacuation module (3000) separates insects from gas while a vacuum is pulled on the insect feeding module (2000) via an insect evacuation fan (312)

Figure 8:
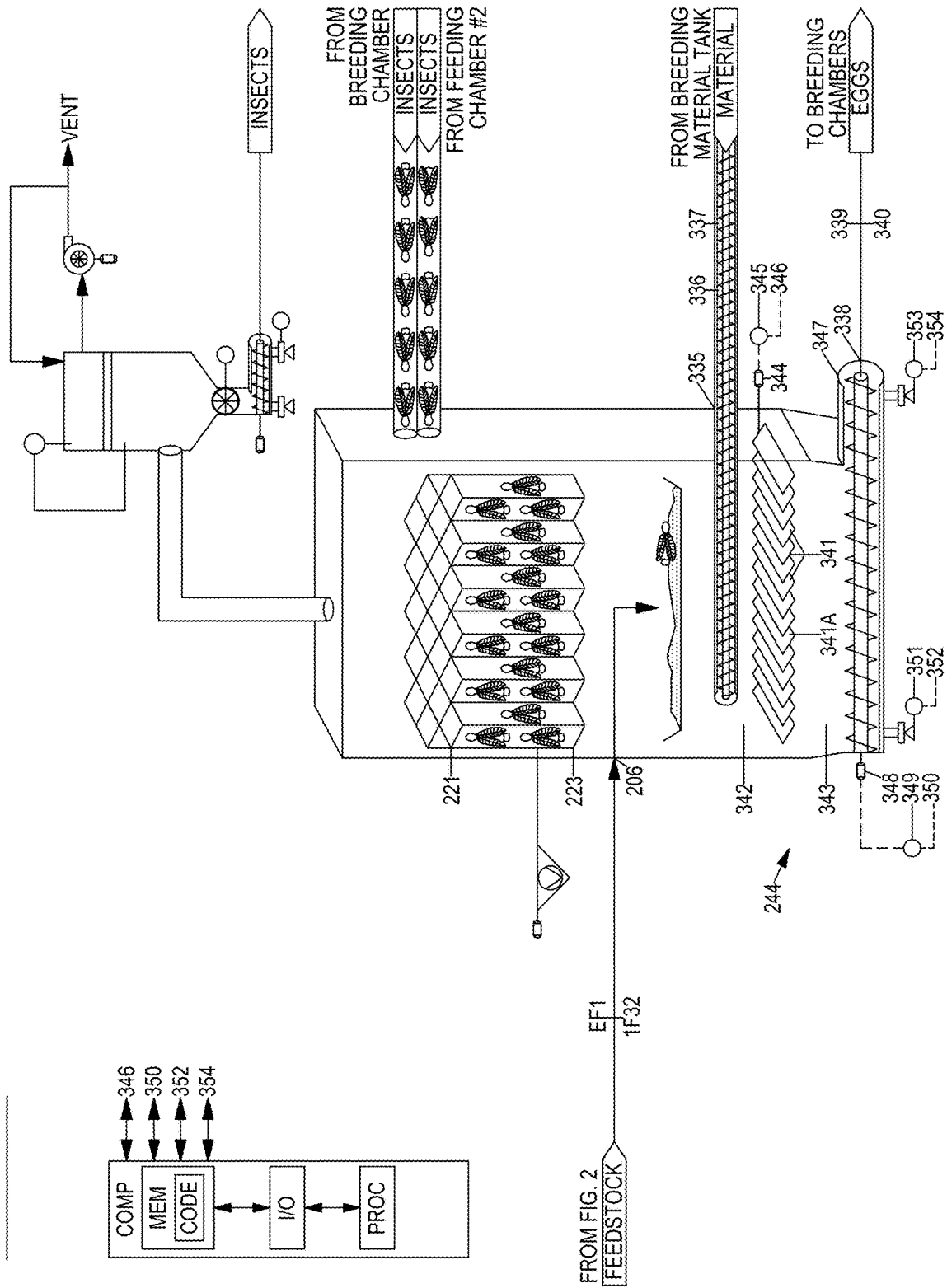

FIG. 8 shows a non-limiting embodiment of an insect feeding module (2000) integrated with an insect evacuation module (3000) operating in a first mode of operation wherein a plurality of slats (341) of an egg transfer system (244) of the insect feeding module (2000) are in first closed state (341A).

Figure 9:
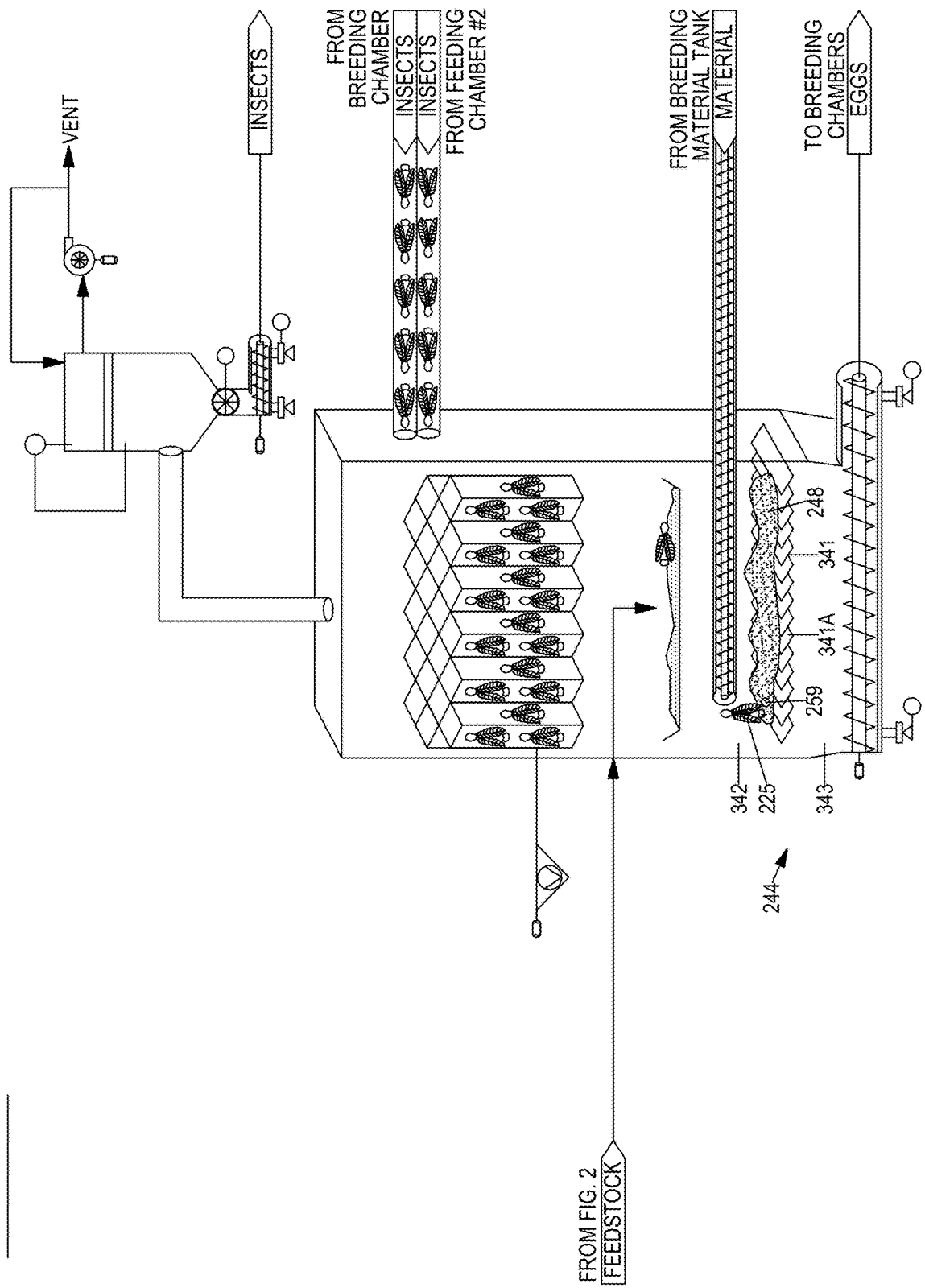

FIG. 9 elaborates upon the non-limiting embodiment of FIG. 8 and shows breeding material (248) resting upon the surface of the plurality of slats (341) of the egg transfer system (244) so as to permit insects (225) to lay eggs (259) within the breeding material (248).

Figure 10:
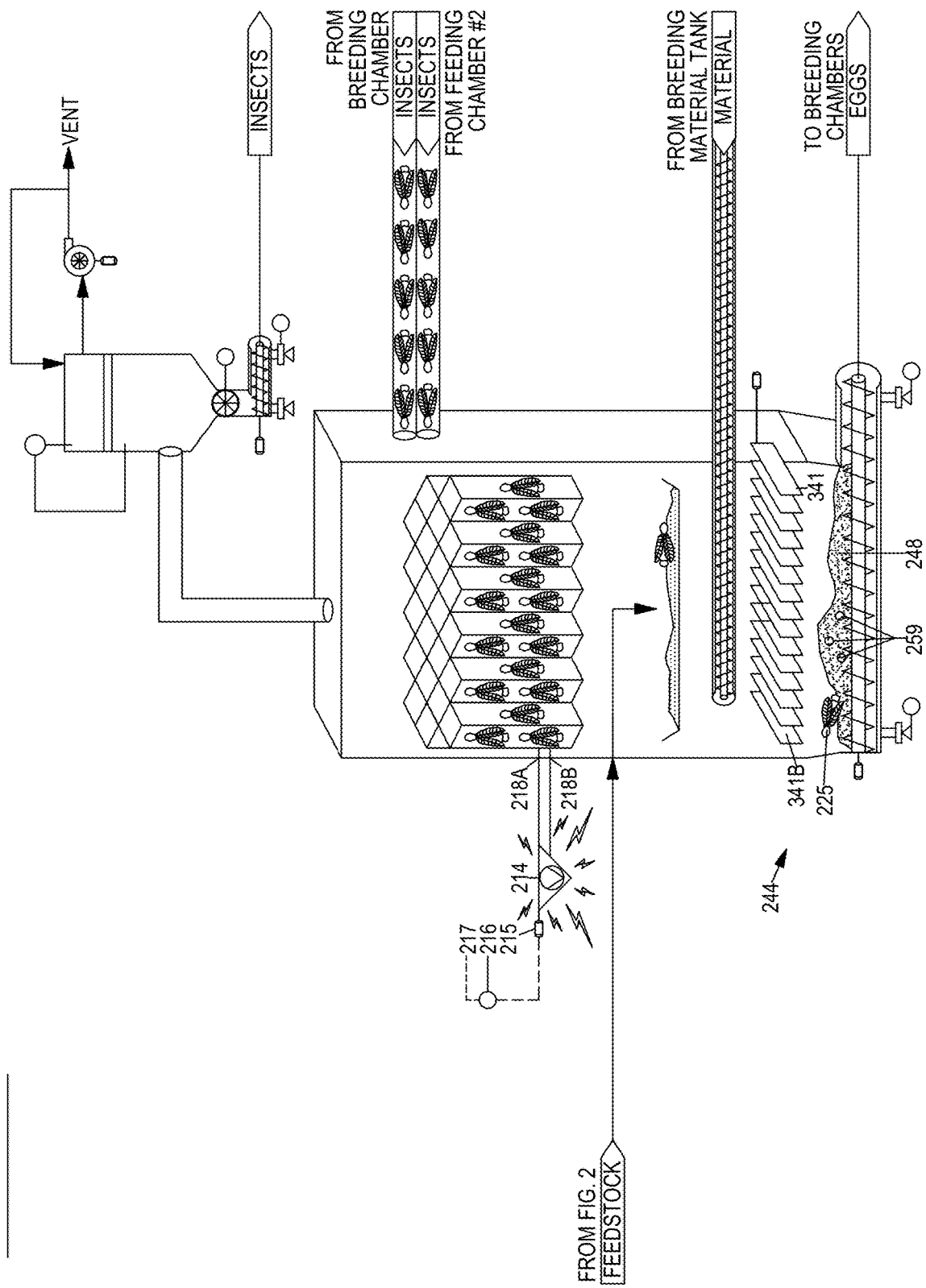

FIG. 10 elaborates upon the non-limiting embodiment FIG. 8 but shows the egg transfer system (244) in a second open state (341A) so as to permit egg-laden breeding material (248) to pass through the plurality of slats (341) while the vibration unit (214) is activated, some insects (225) may pass through the open slats (341) as well.

Figure 11:
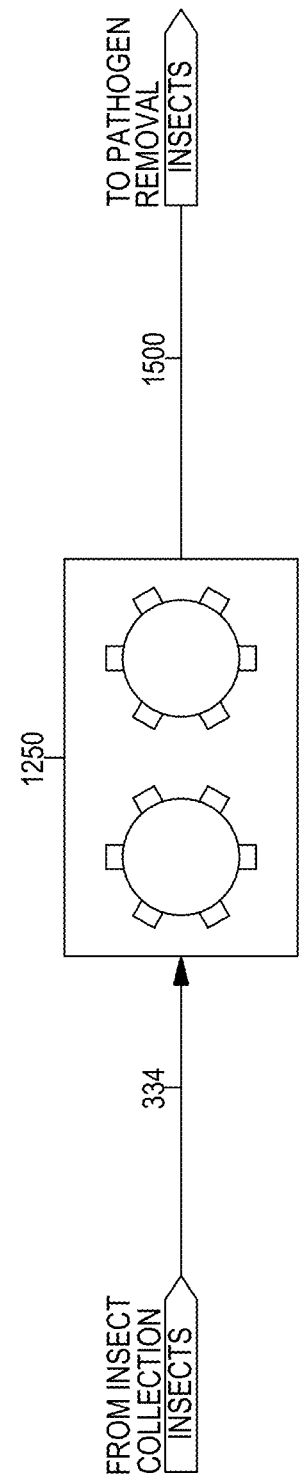

FIG. 11 shows a simplistic diagram illustrating an insect grinding module that is configured to grind at least a portion of the insects transferred from the insect evacuation module (3000).

Figure 12A:
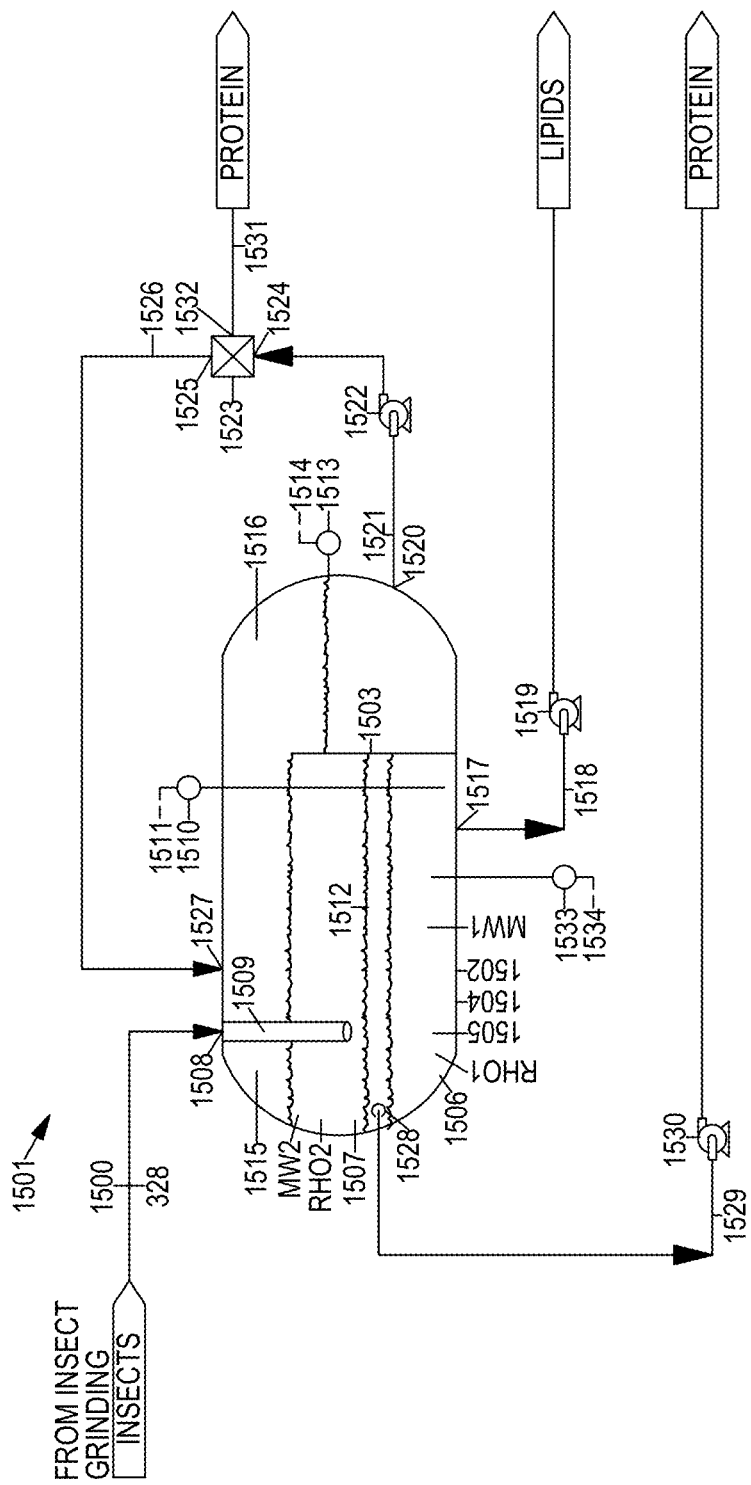

FIG. 12A shows a simplistic diagram illustrating a lipid extraction module that is configured to extract lipids from at least a portion of the insects transferred from the insect evacuation module (3000) by use of at least one solvent.

Figure 12B:
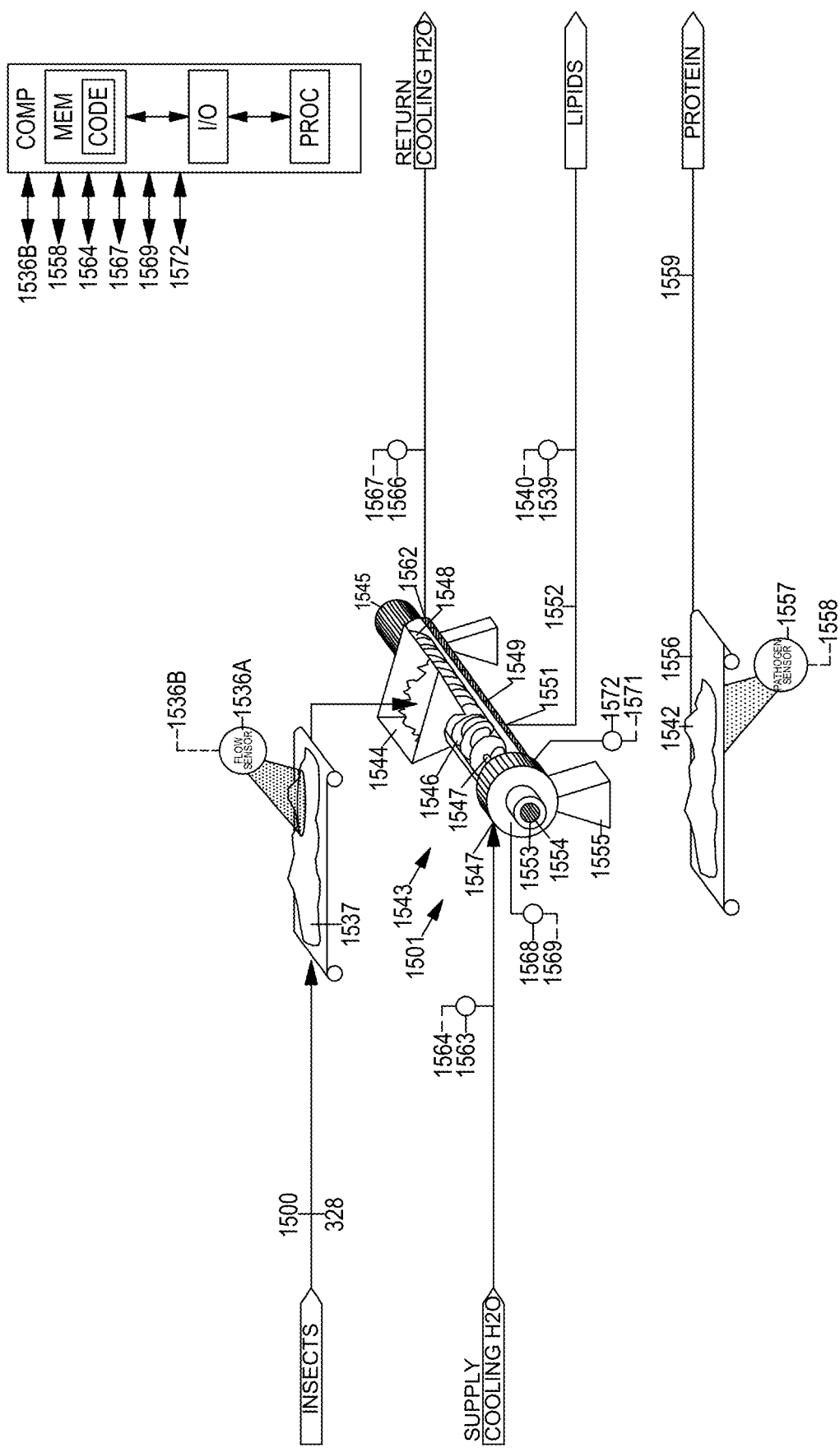

FIG. 12B shows a simplistic diagram illustrating a lipid extraction module that is configured to extract lipids from at least a portion of the insects transferred from the insect evacuation module (3000) by using of no solvent by way of an expeller press.

FIG. 12C shows one non-limiting embodiment of a hydrogenation system (12C) configured to hydrogenate the insect lipids (1518, 1552) to produce hydrogenation insect lipids (12CC).

Figure 12D:
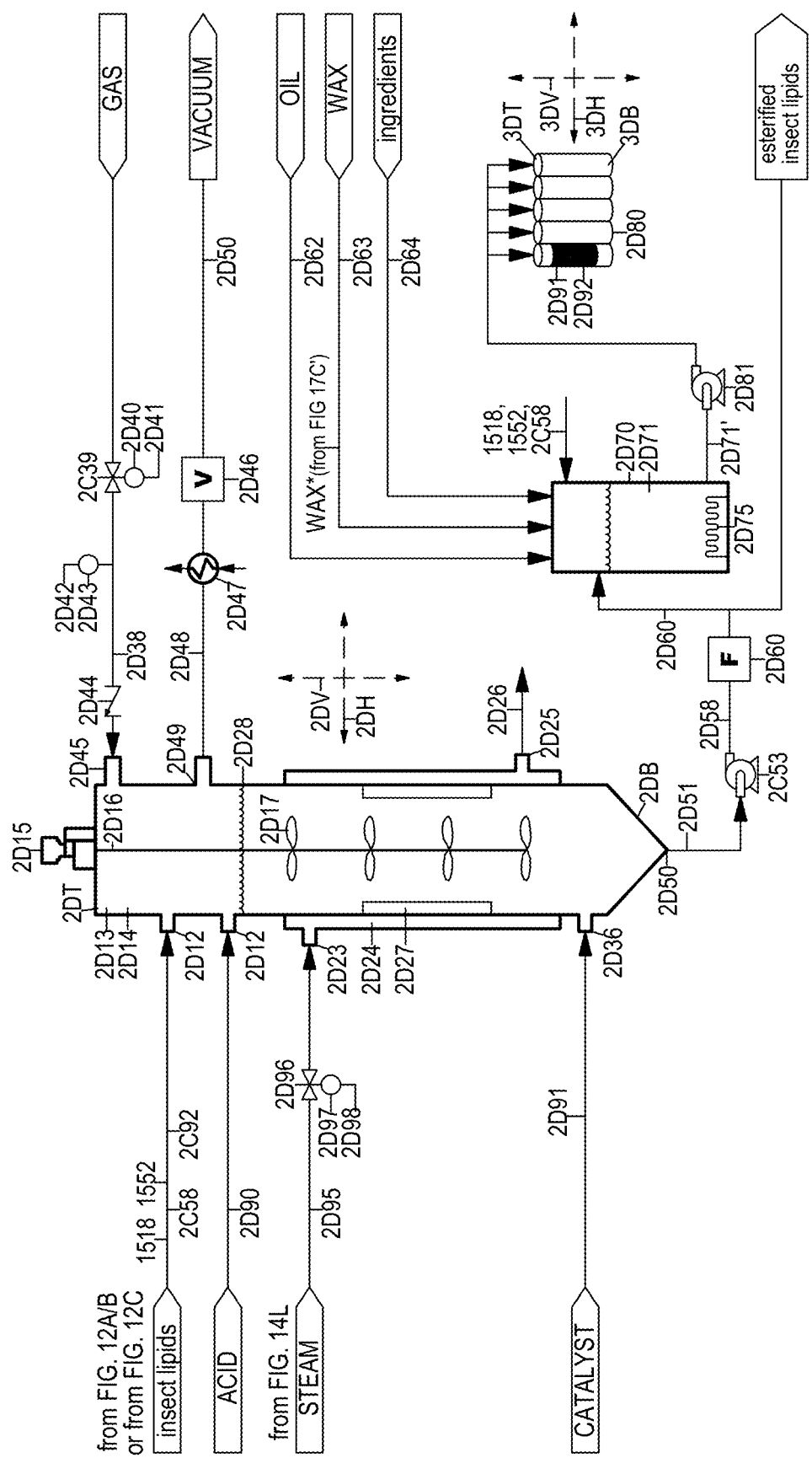

FIG. 12D shows one non-limiting embodiment of an esterification system (12D) configured to produce esterified insect lipids.

Figure 13:
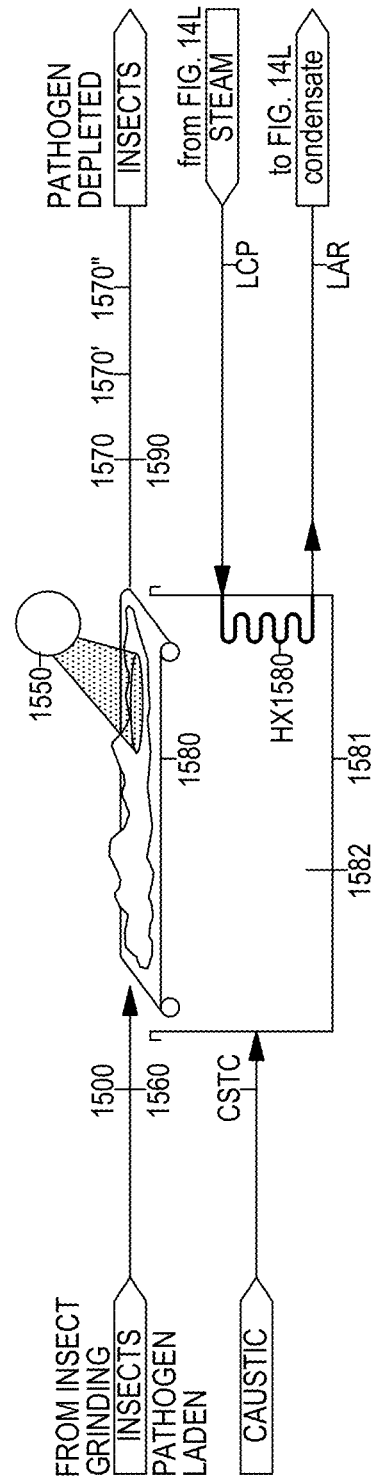

FIG. 13 shows a simplistic diagram illustrating a pathogen removal module that is configured to remove pathogens from at least a portion of the insects transferred from the insect evacuation module (3000).

Figure 14A:
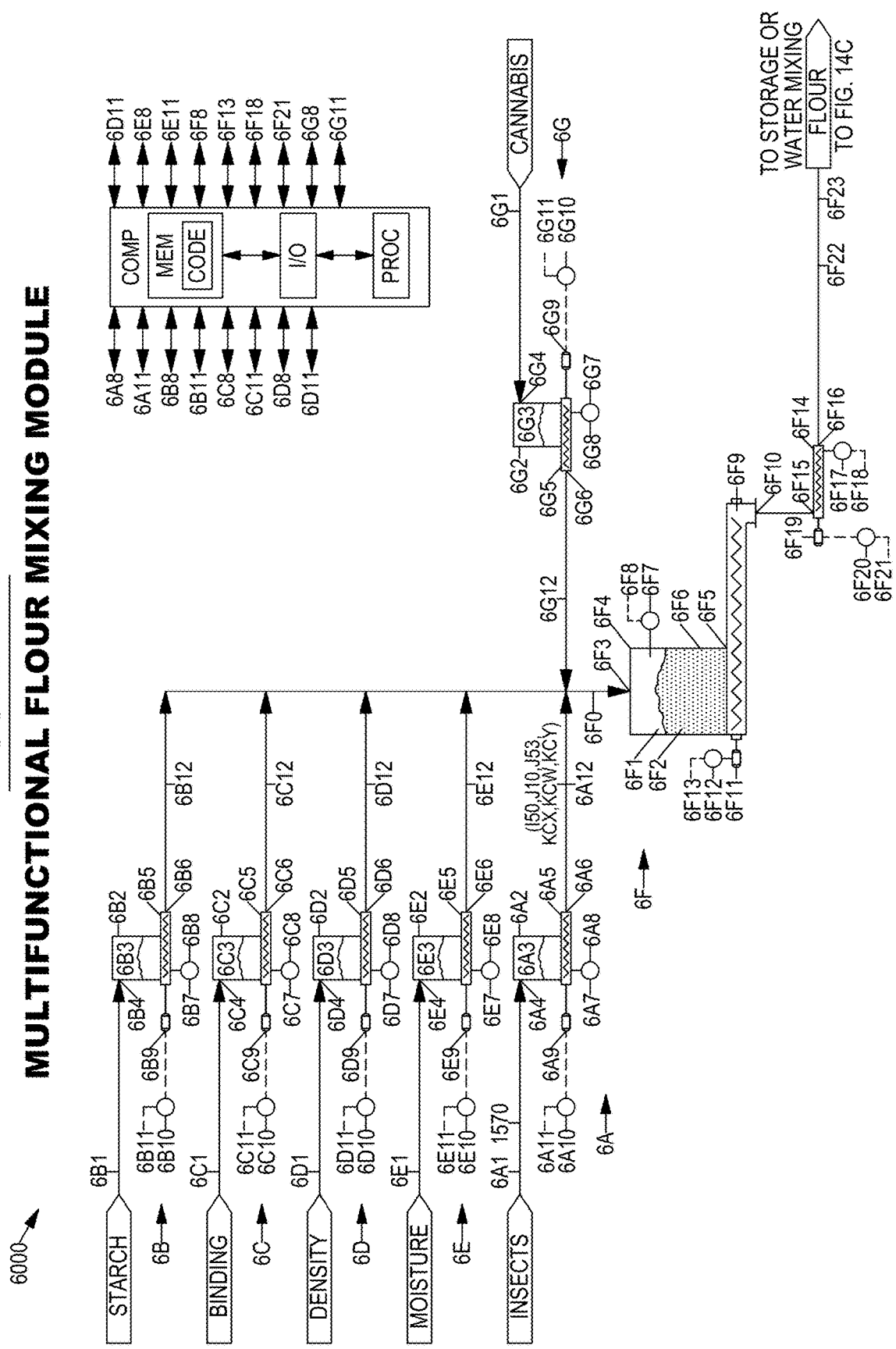

FIG. 14A shows a simplistic diagram illustrating a multifunctional composition mixing module that is configured to generate a multifunctional composition from at least a portion of the insects transferred from the pathogen removal module and including the sequence steps or sub-modules including an insect distribution module (6A), fiber-starch distribution module (6B), binding agent distribution module (6C), density improving textural supplement distribution module (6D), moisture improving textural supplement distribution module (6E), multifunctional composition mixing module (6F).

FIG. 14B shows a simplistic diagram illustrating a multifunctional composition mixing module that is configured to generate a multifunctional composition as described in FIG. 14A however instead from at least a portion of the insects transferred from the insect grinding module.

Figure 14C:
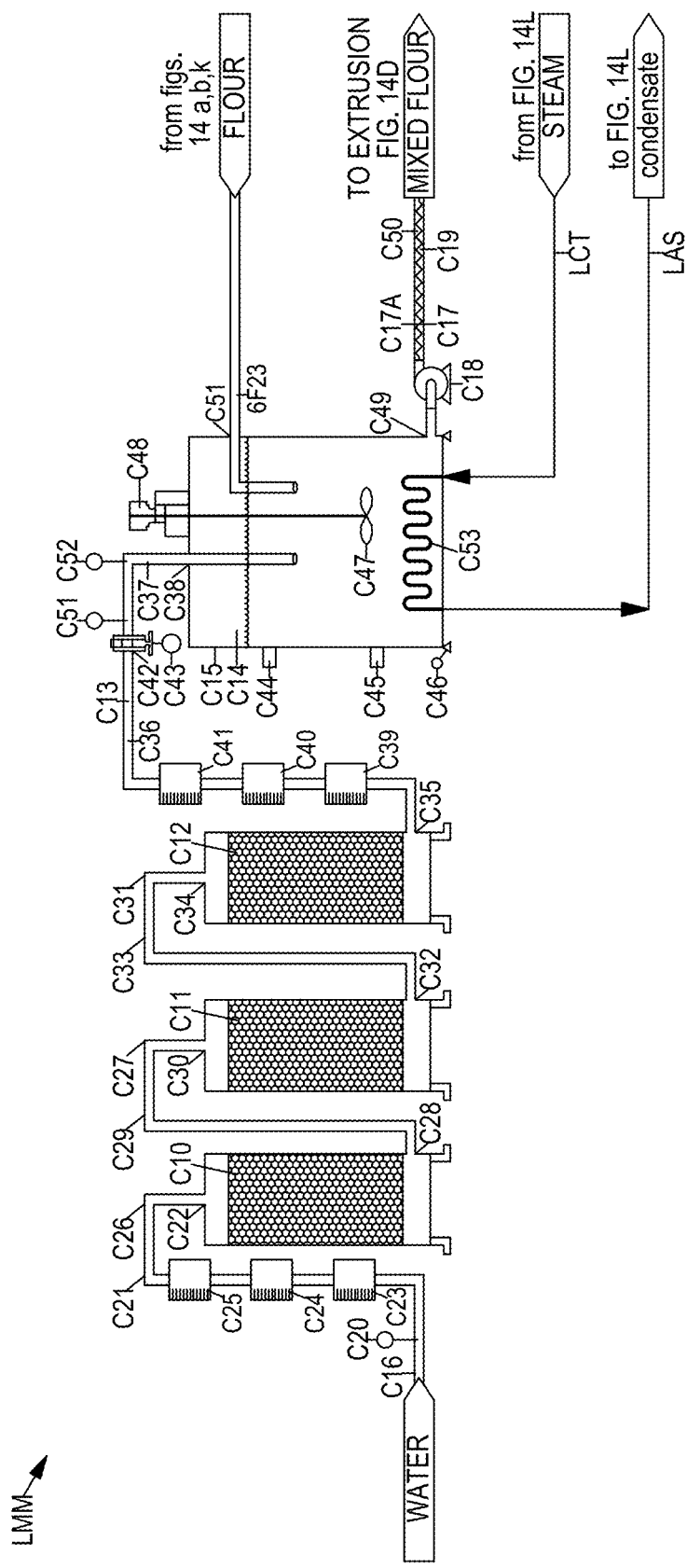

FIG. 14C shows one non-limiting embodiment of a liquid mixing module (LMM) that is configured to mix water with multifunctional composition (6F23) provided from the multifunctional composition mixing module as shown in FIG. 14A or 14B.

FIG. 14D shows one non-limiting embodiment of a shaping module (14D) that is configured to shape the multifunctional composition and water mixture (C17) to produce a shaped multifunctional composition mixture (D10).

Figure 14E:
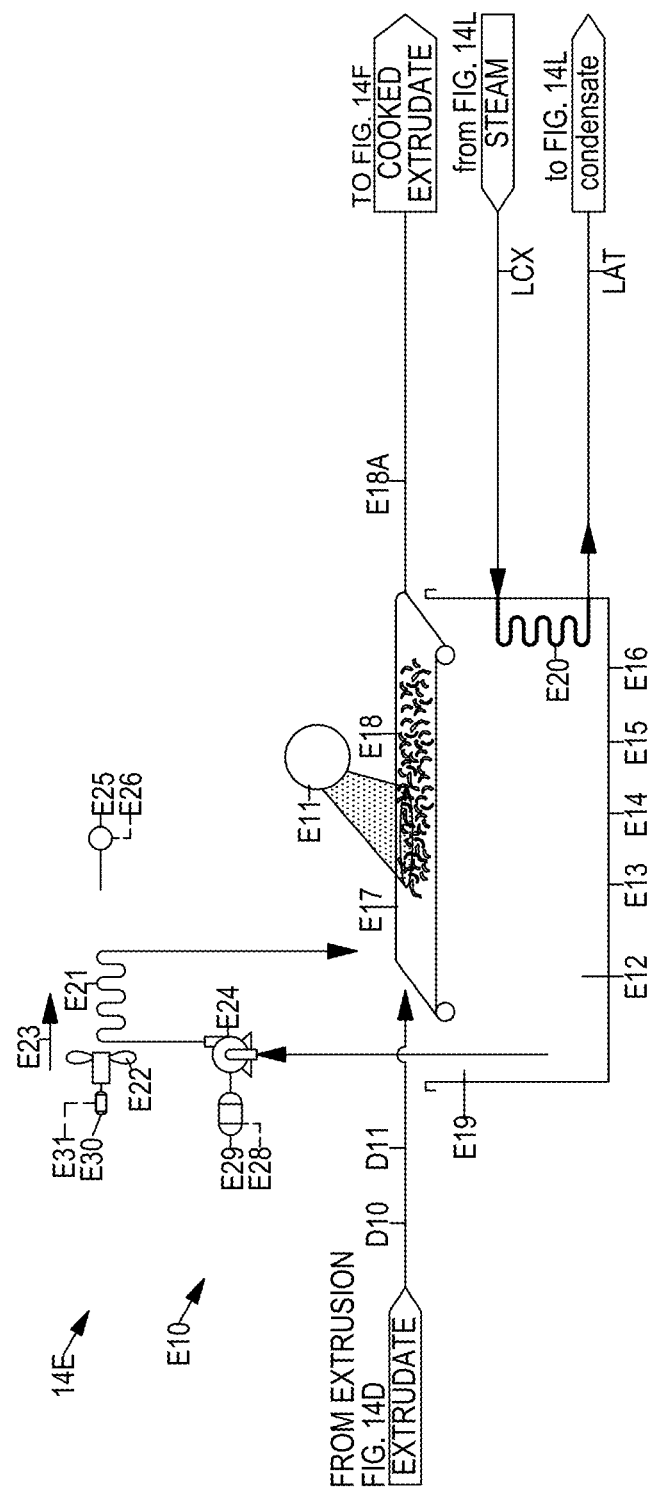

FIG. 14E shows one non-limiting embodiment of a cooking module (14E) that is configured to cook the shaped multifunctional composition mixture (D10) provided from the shaping module (14D) to form a cooked multifunctional composition mixture (E18A).

Figure 14F:
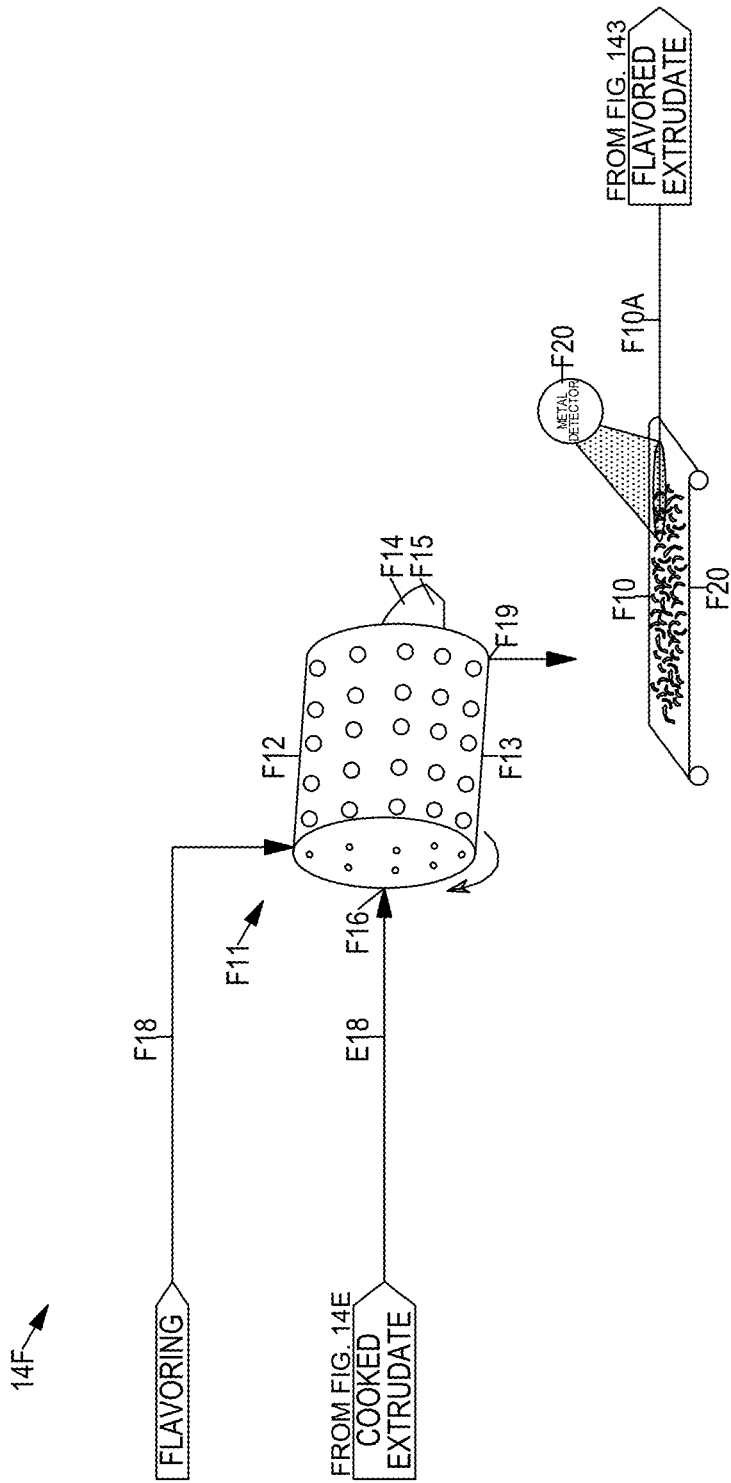

FIG. 14F shows one non-limiting embodiment of a flavoring module (14F) that is configured to flavor the cooked multifunctional composition mixture (E18A) provided from the cooking module (14E) to form a flavored multifunctional composition mixture (F10).

Figure 14G:
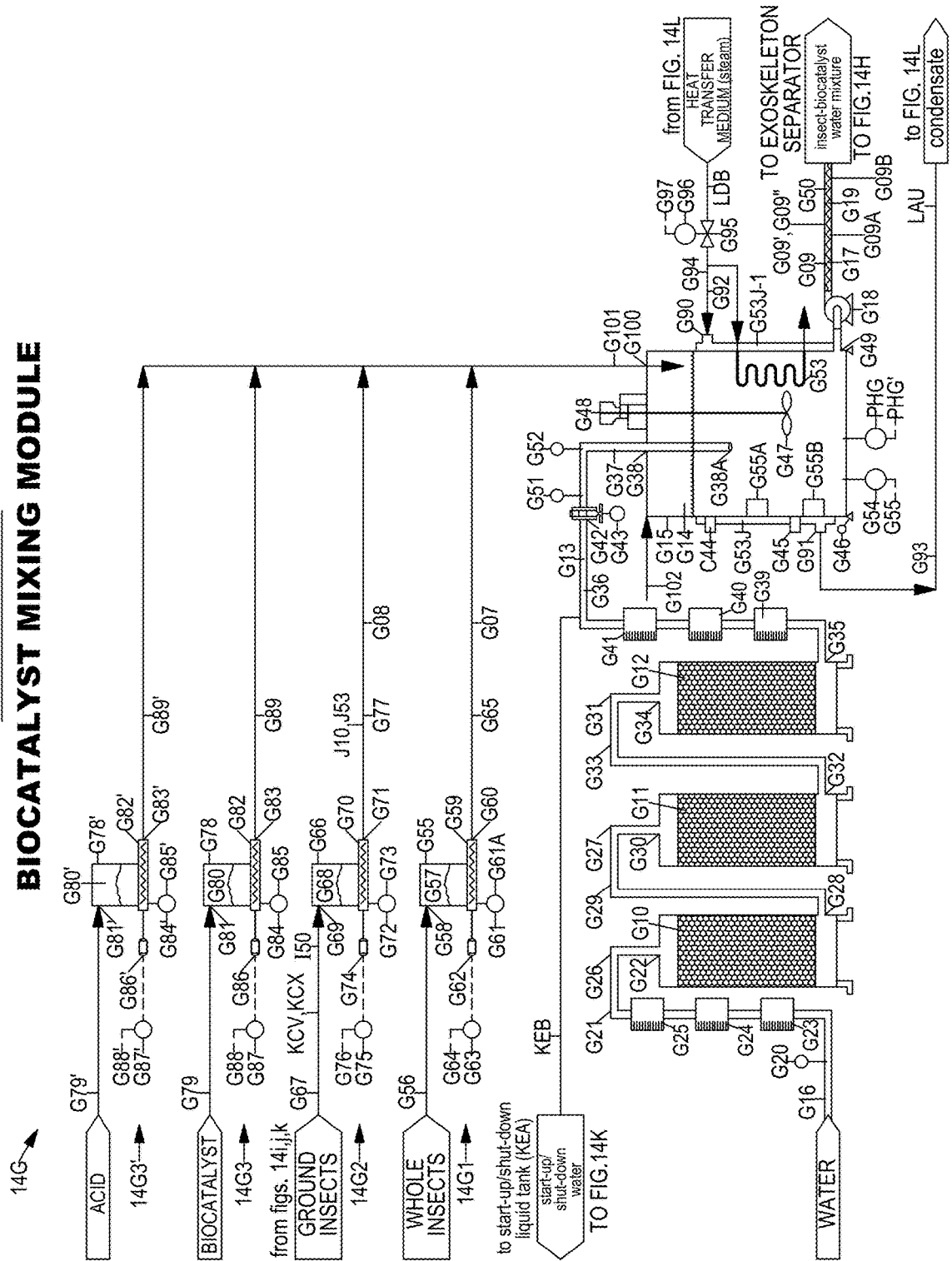

FIG. 14G shows one non-limiting embodiment of a biocatalyst mixing module (14G) that is configured to mix insects, water, biocatalyst, and optionally acid to create an insect liquid biocatalyst mixture (G09).

Figure 14H:
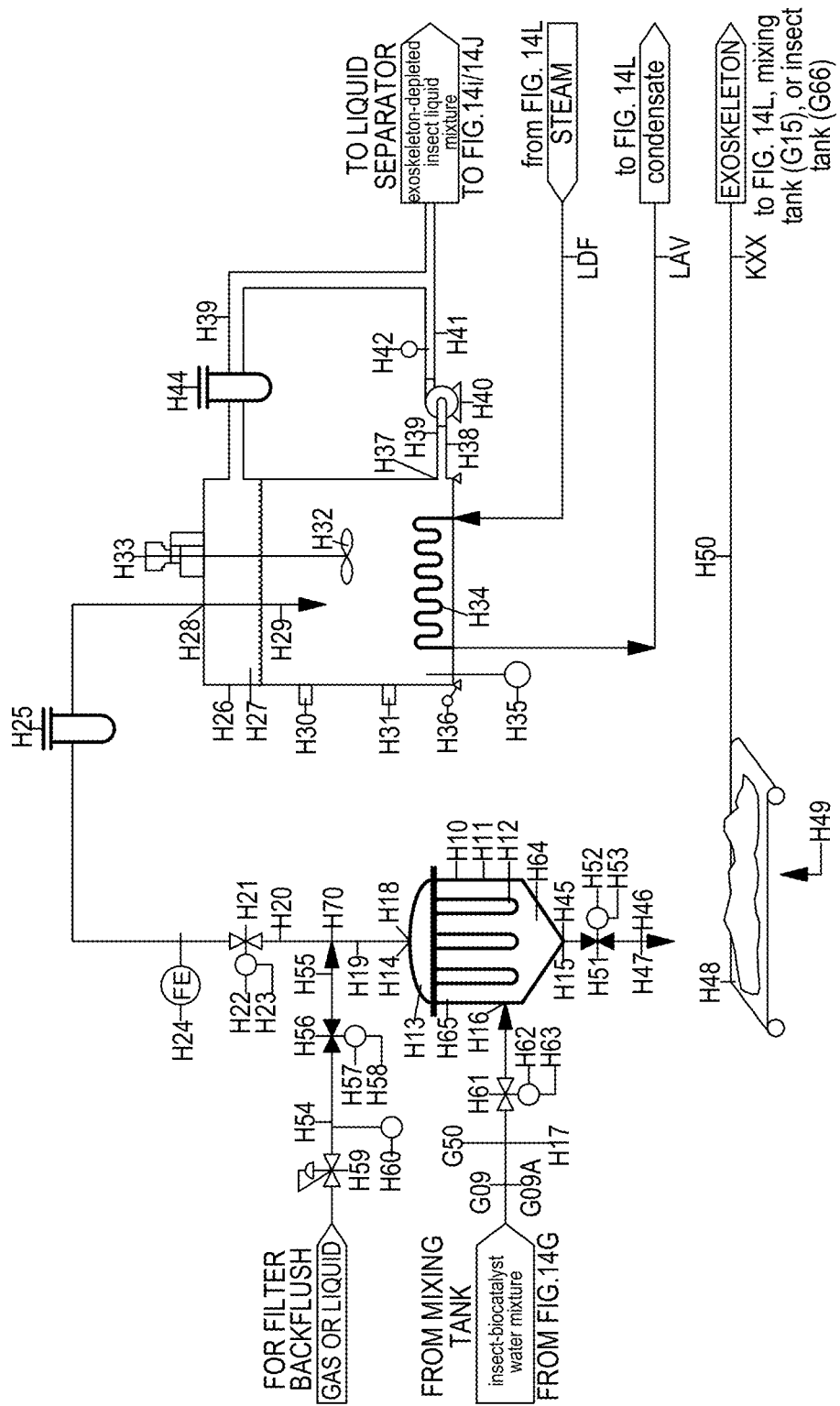
Figure 14I:
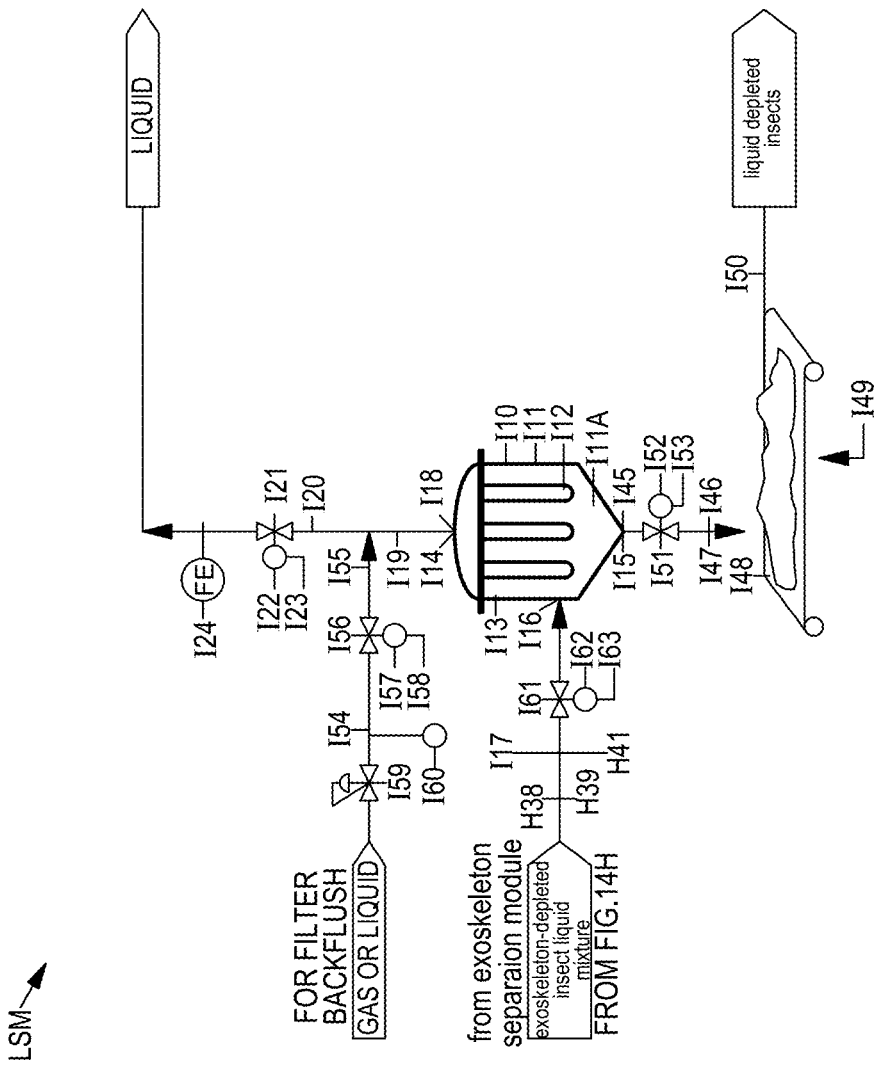

FIG. 14H shows one non-limiting embodiment of an exoskeleton separation module (14H) that is configured to remove the exoskeleton contained within the insect liquid biocatalyst mixture (G09). FIG. 14I shows one non-limiting embodiment of a liquid separation module (LSM) that is configured to remove liquid from the exoskeleton-depleted insect liquid mixture (H39) to provide an insect-depleted liquid mixture (I19) and insects (I46).

Figure 14J:
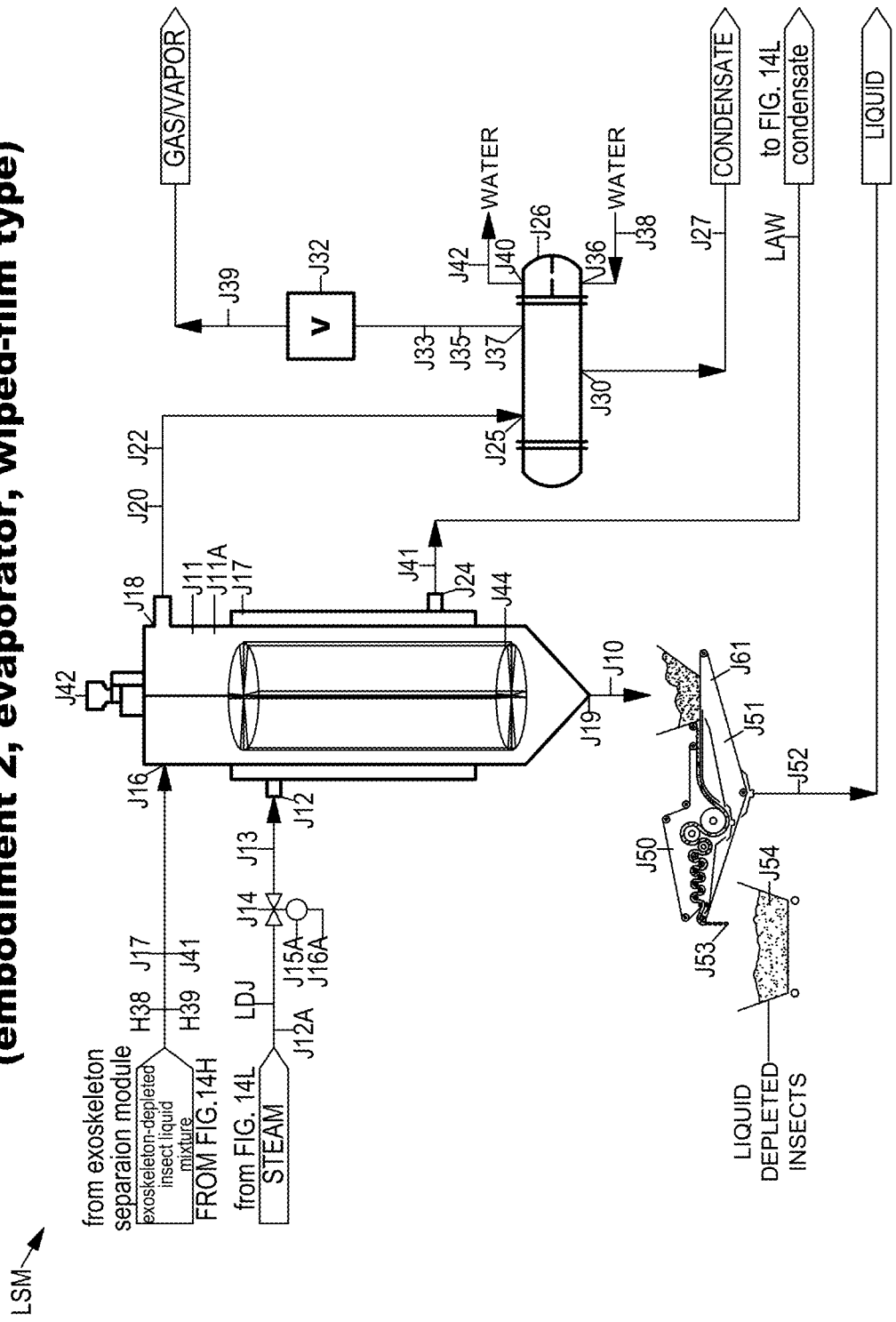

FIG. 14J shows one non-limiting embodiment of a liquid separation module (LSM) that is configured to remove liquid from the exoskeleton-depleted insect liquid mixture (H39) to produce a vaporized liquid (J22) and a stream of liquid-depleted insects (J10).

Figure 14K:
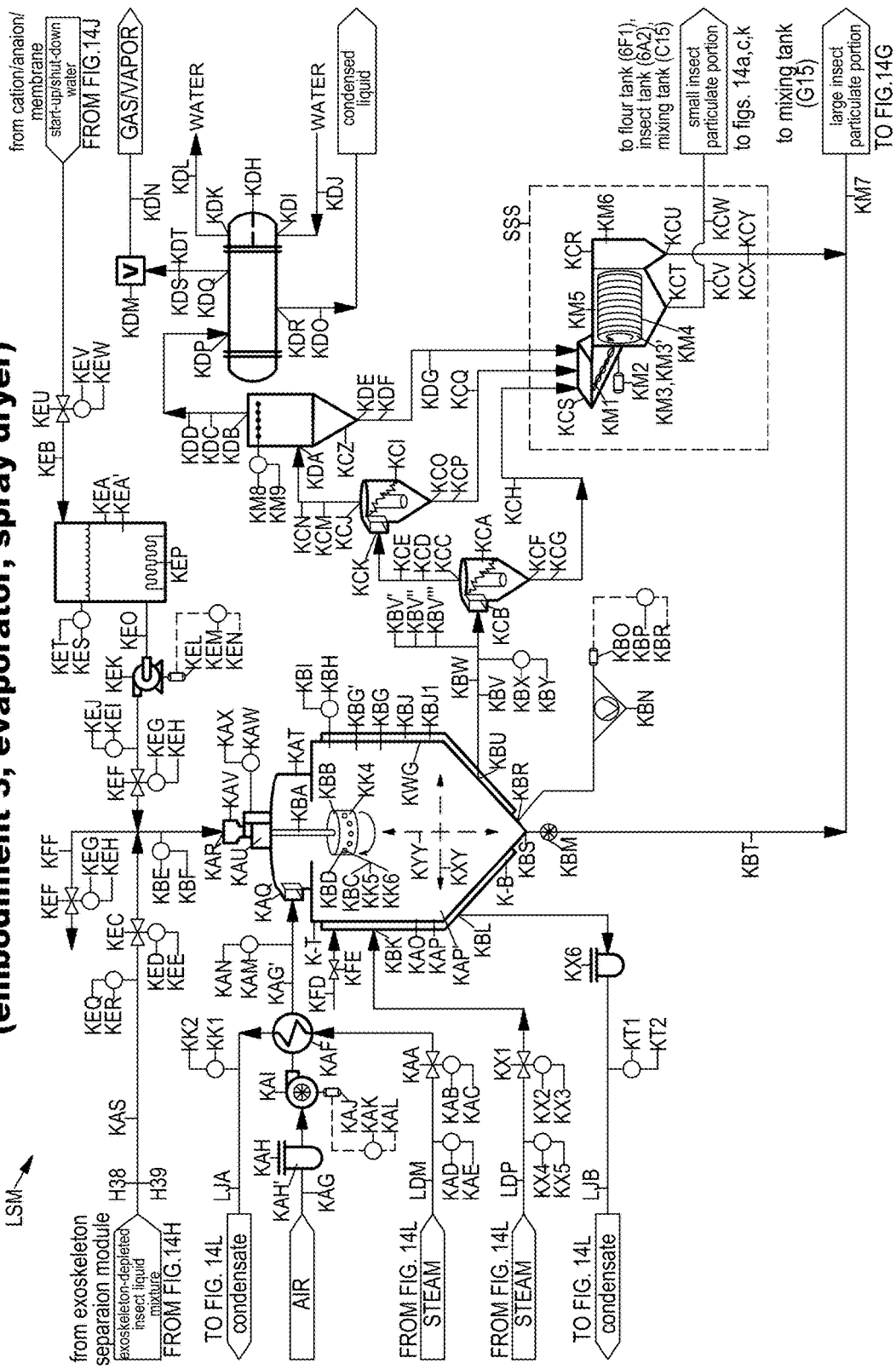

FIG. 14K shows one non-limiting embodiment of a liquid separation module (LSM) that is configured to remove liquid from an insect liquid mixture (H39) by use of a spray dryer (KAP).

Figures 1, 14K:
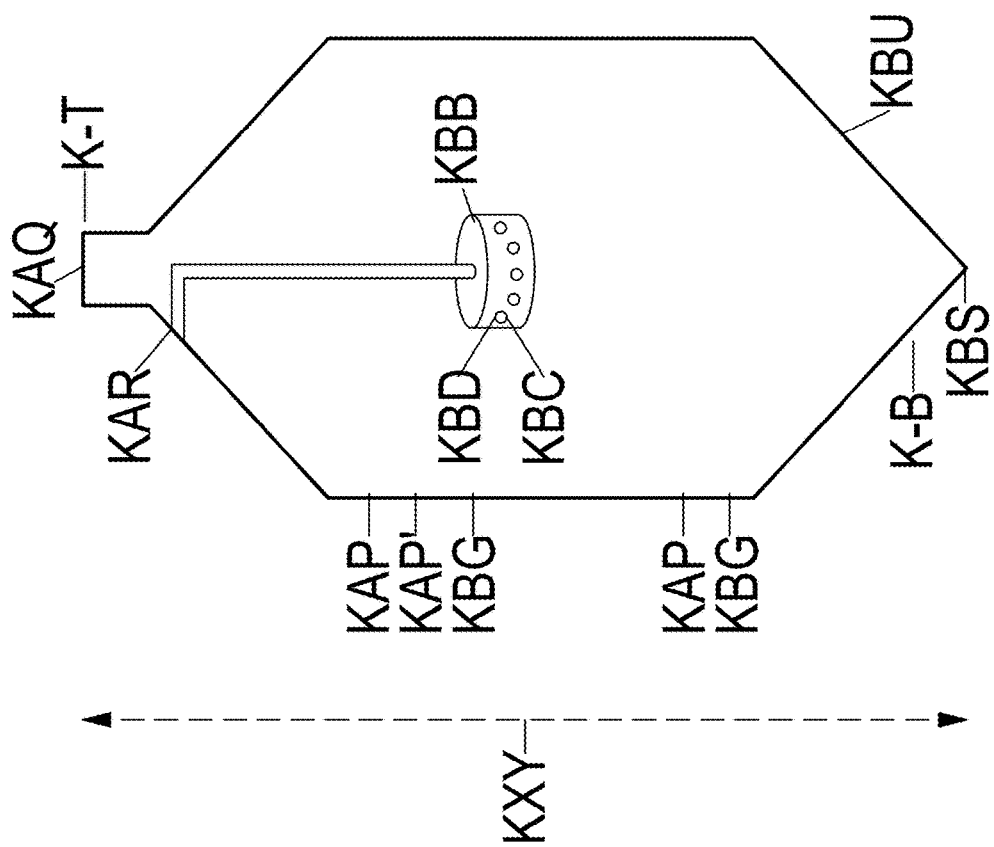
Figures 3, 14K:
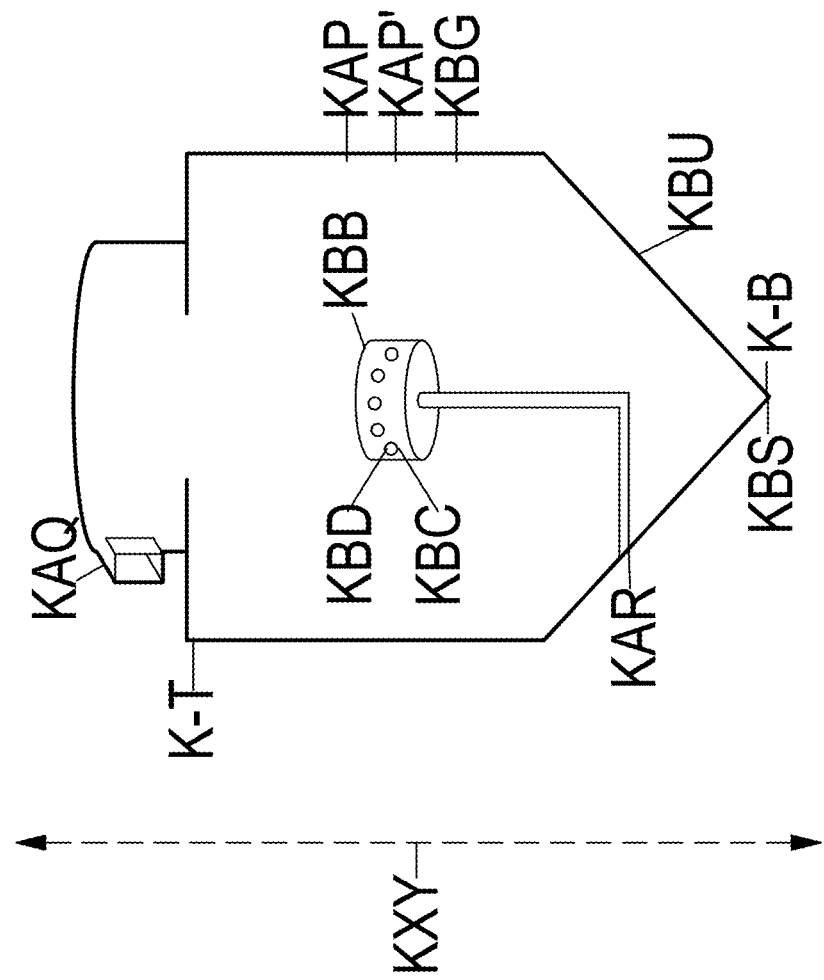
Figures 4, 14K:
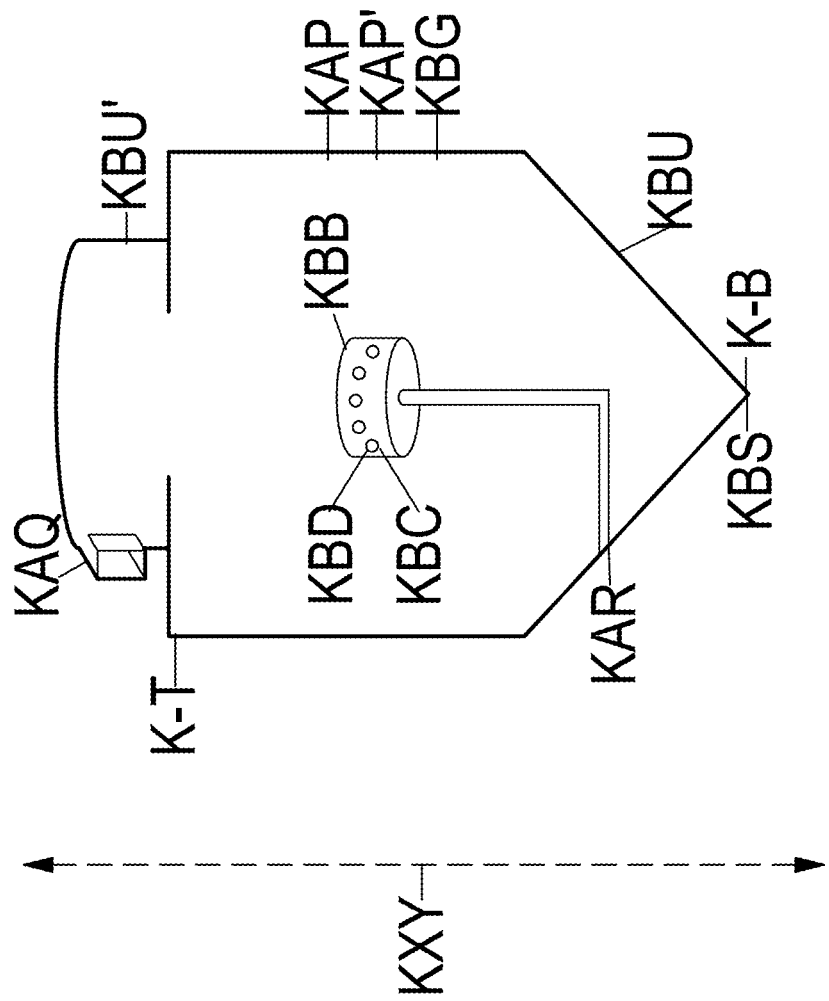
Figure 14K:
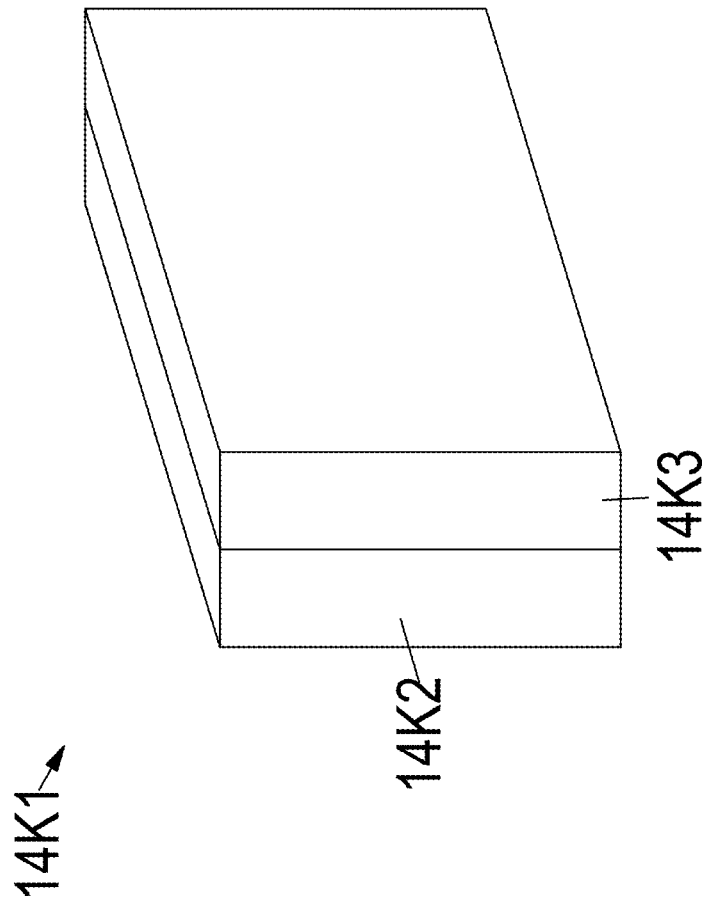

FIG. 14K-1 shows one non-limiting embodiment of a co-current type of spray dryer (KAP) that may be used with the liquid separation module (LSM) described in FIG. 14K.

Figure 2:
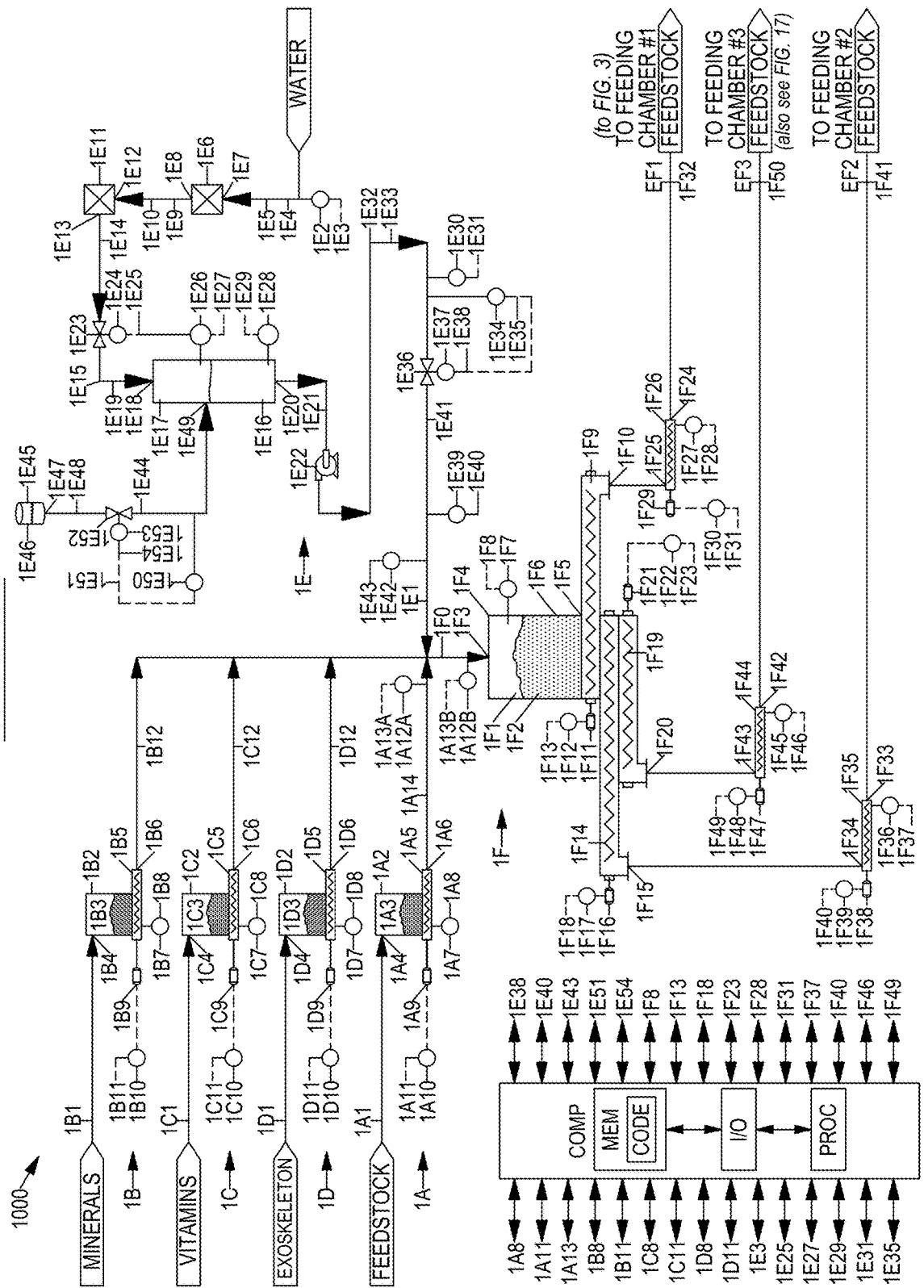
FIG. 2 shows a non-limiting embodiment of an enhanced feedstock mixing module (1000) including a feedstock distribution module (1A), mineral distribution module (1B), vitamin distribution module (1C), polymer distribution module (1D), water distribution module (1E), and an enhanced feedstock distribution module (1F).

FIG. 14K-2 shows one non-limiting embodiment of a counter-current type of spray dryer (KAP) that may be used with the liquid separation module (LSM) described in FIG. 14K.

FIG. 14K-3 shows another non-limiting embodiment of a counter-current type of spray dryer (KAP) that may be used with the liquid separation module (LSM) described in FIG. 14K.

Figure 4:
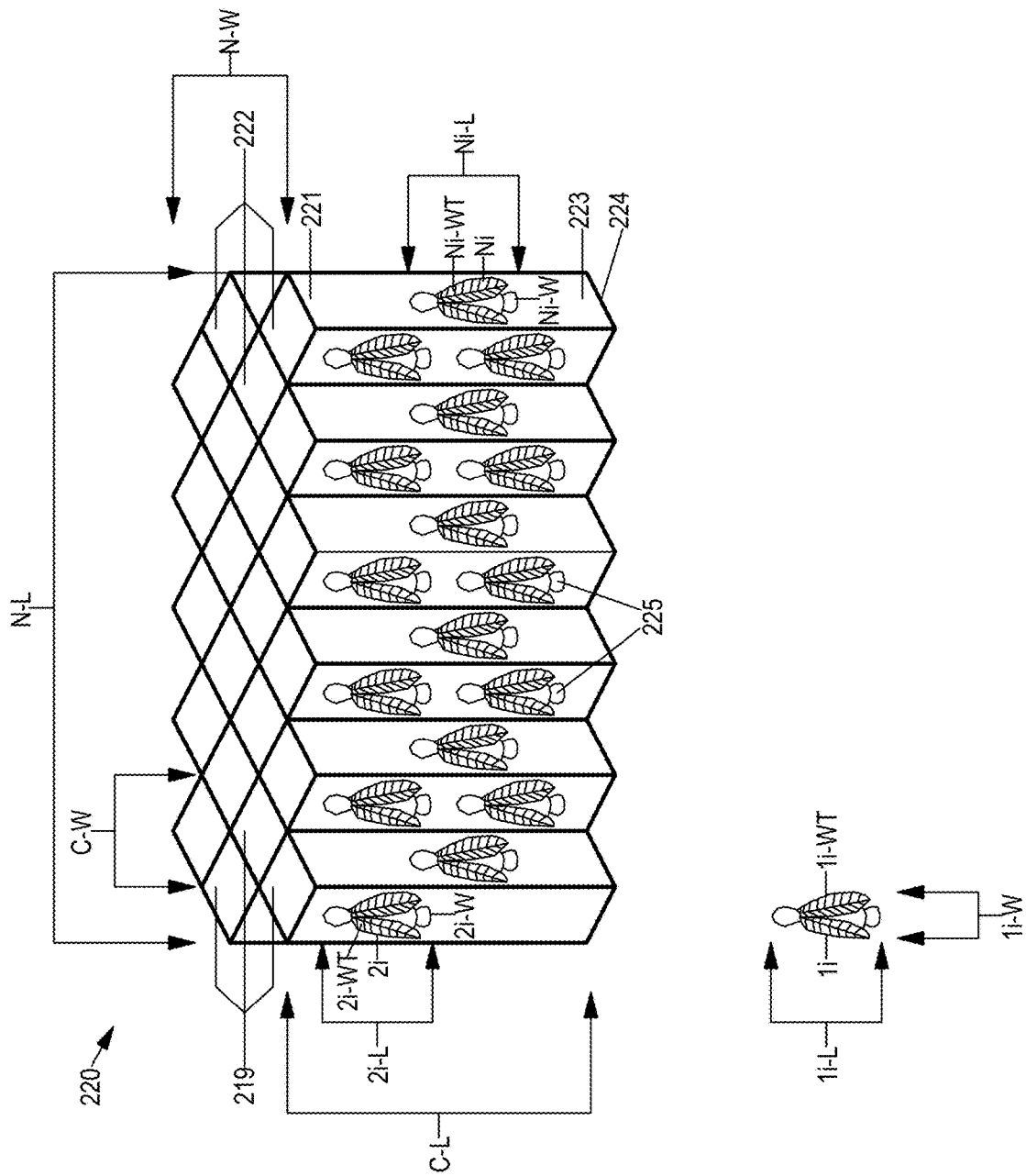
FIG. 4 shows one non-limiting embodiment of a network (220) of cells (219) for growing insects within a feeding chamber (200) of the insect feeding module (2000) shown in FIG. 3.

FIG. 14K-4 shows a non-limiting embodiment of a mixed-flow type of spray dryer (KAP) that may be used with the liquid separation module (LSM) described in FIG. 14K.

FIG. 14KK shows one non-limiting embodiment of an insect-derived-biosensor including a transducer and an insect-derived-biopolymer.

FIG. 14L shows a power production system (PPS) that is configured to generate electricity, heat, or steam for use in the Insect Production Superstructure System (IPSS).

Figure 15:
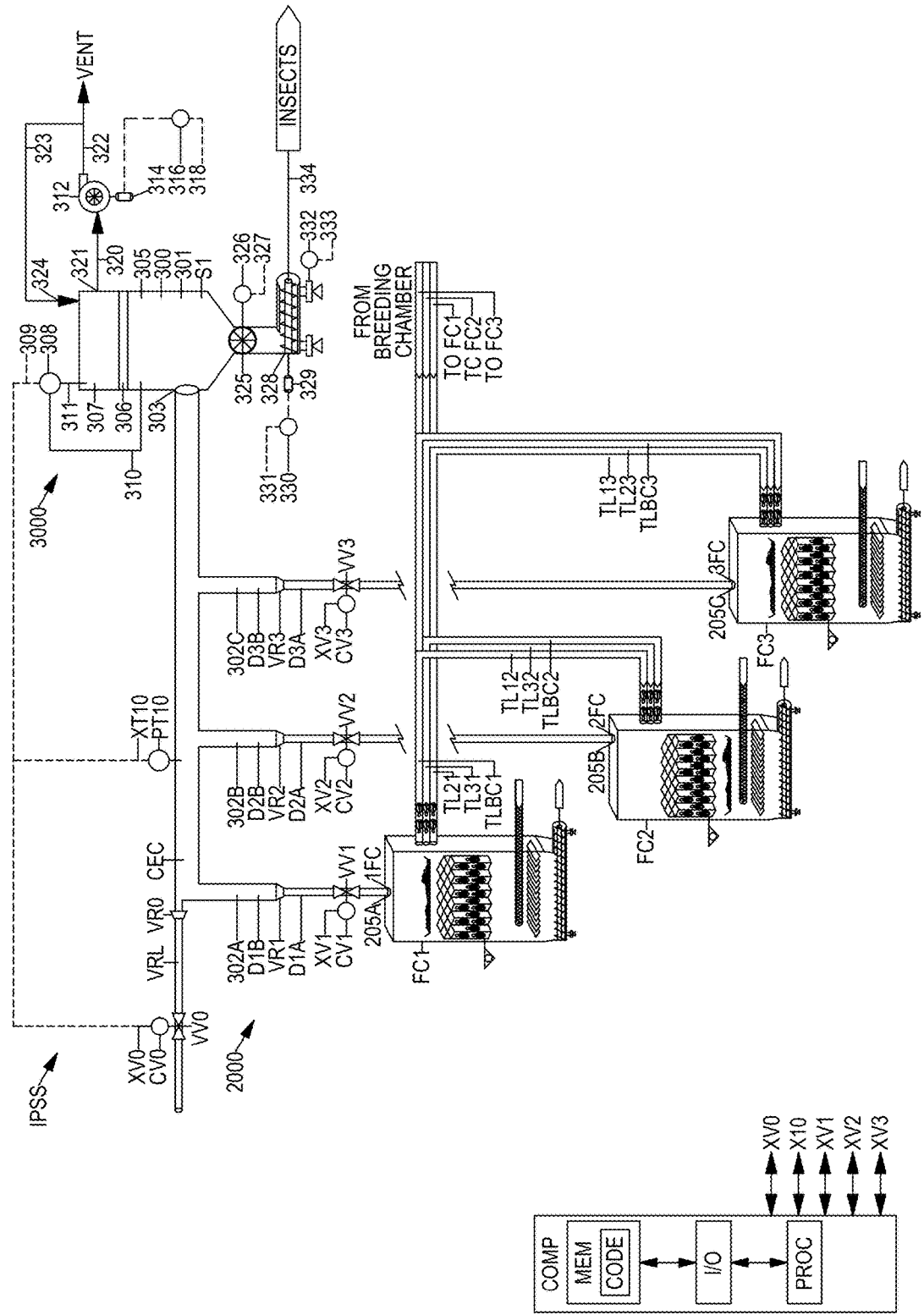

FIG. 15 shows a simplistic diagram illustrating a plurality of feeding chambers (FC1, FC2, FC3) of an insect feeding module (2000) integrated within one common separator (300) of an insect evacuation module (3000).

Figure 16:
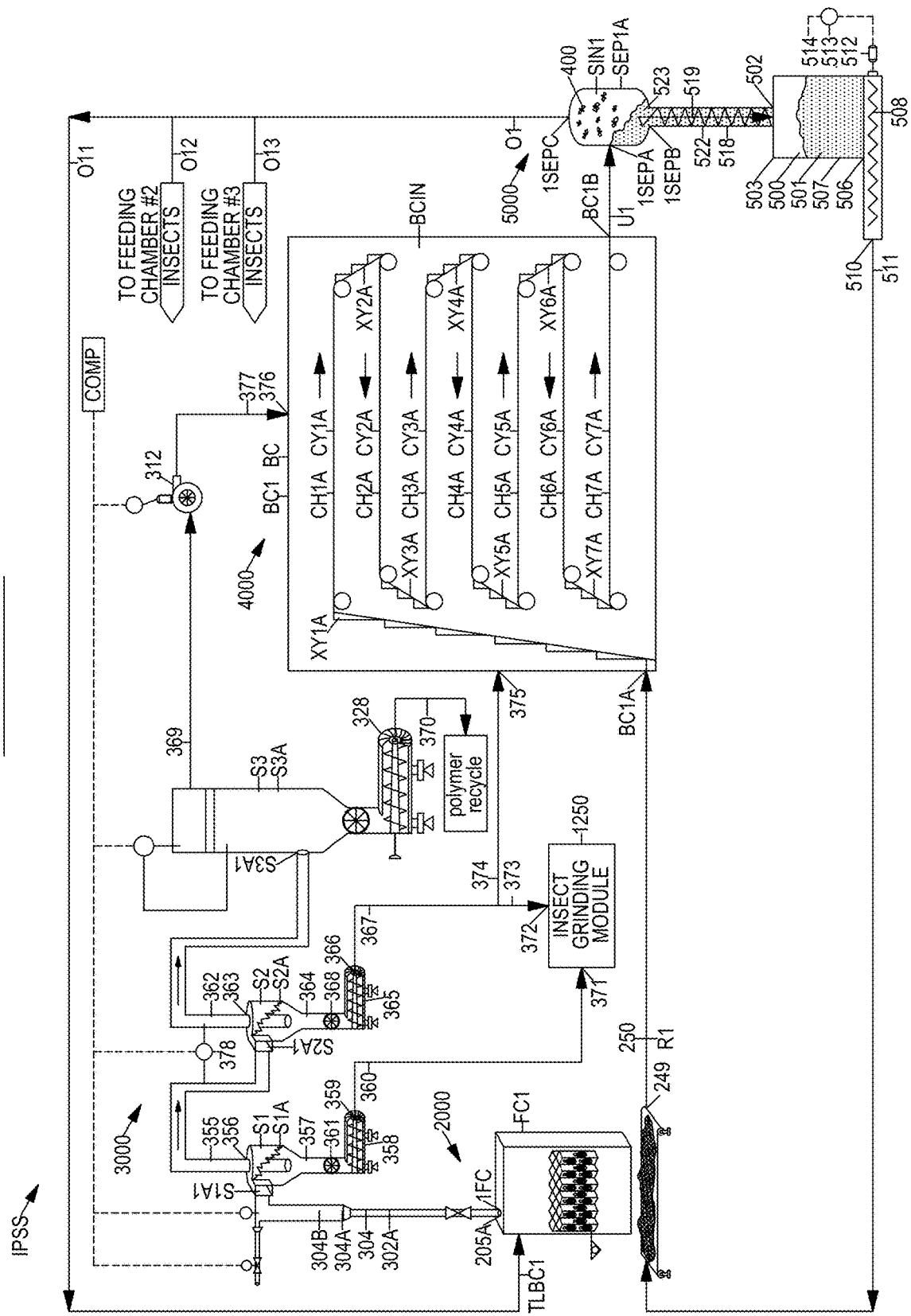

FIG. 16 shows a simplistic diagram illustrating a plurality of separators (S1, S2, S3) integrated with one common feeding chamber (FC1), and wherein the feeding chamber (FC1) and second separator (S2) are in fluid communication with one common breeding chamber (BC), and wherein the breeding chamber (BC) is in fluid communication with one common breeding material and insect separator (SEPIA), and wherein the breeding material and insect separator (SEPIA) is in fluid communication with at least one of a plurality of feeding chambers (FC1, FC2, FC3).

Figure 16A:
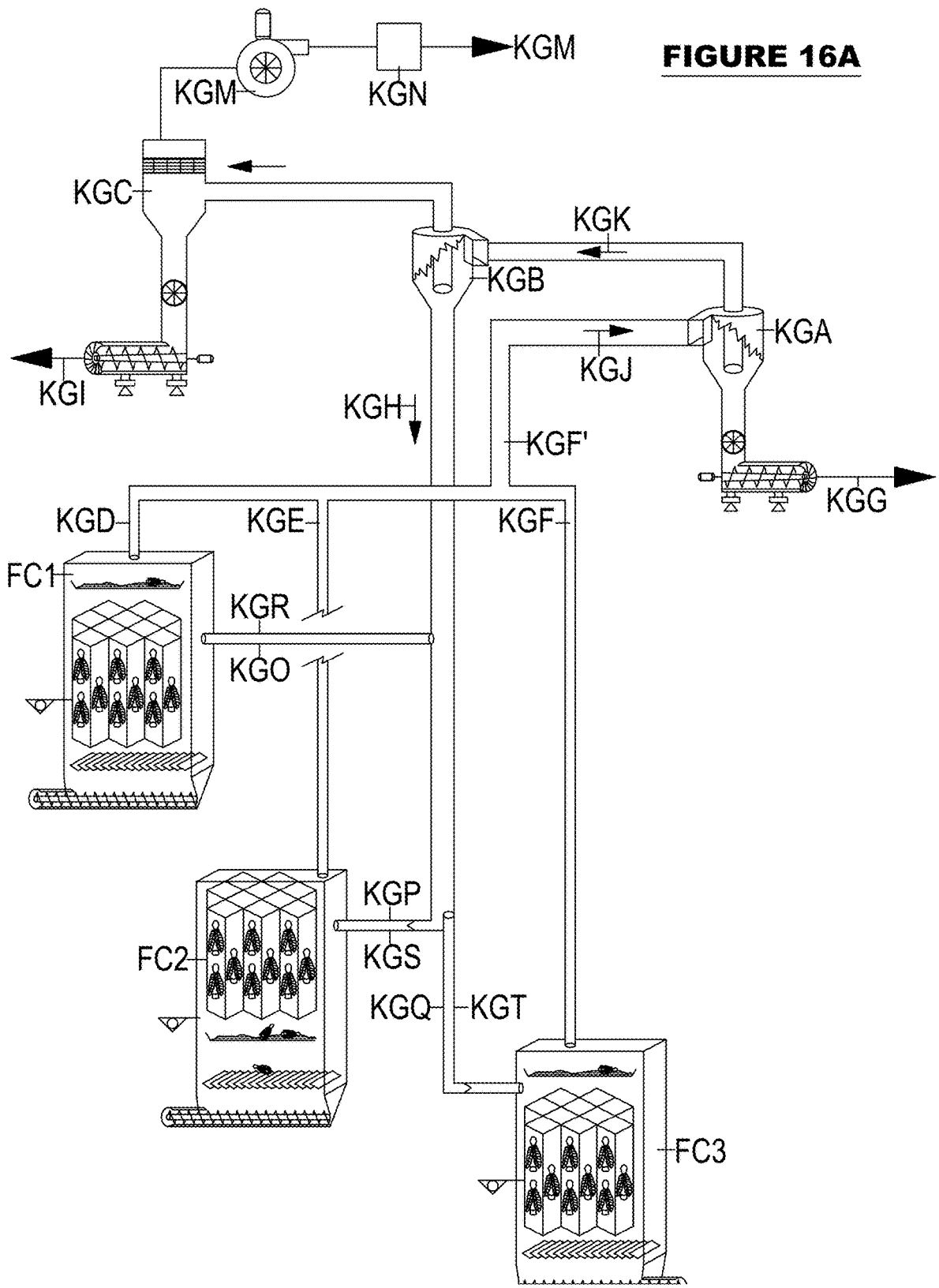

FIG. 16A shown one embodiment of a plurality of separators (KGA, KGB, KGC) that are configured to pull a vacuum on a plurality of insect feeding chambers (FC1, FC2, FC3) and separate large insects (KGG), small insects (KGH), and particulates (KGI) therefrom while returning the small insects (KGH) back to the plurality of insect feeding chambers (FC1, FC2, FC3).

Figure 17:
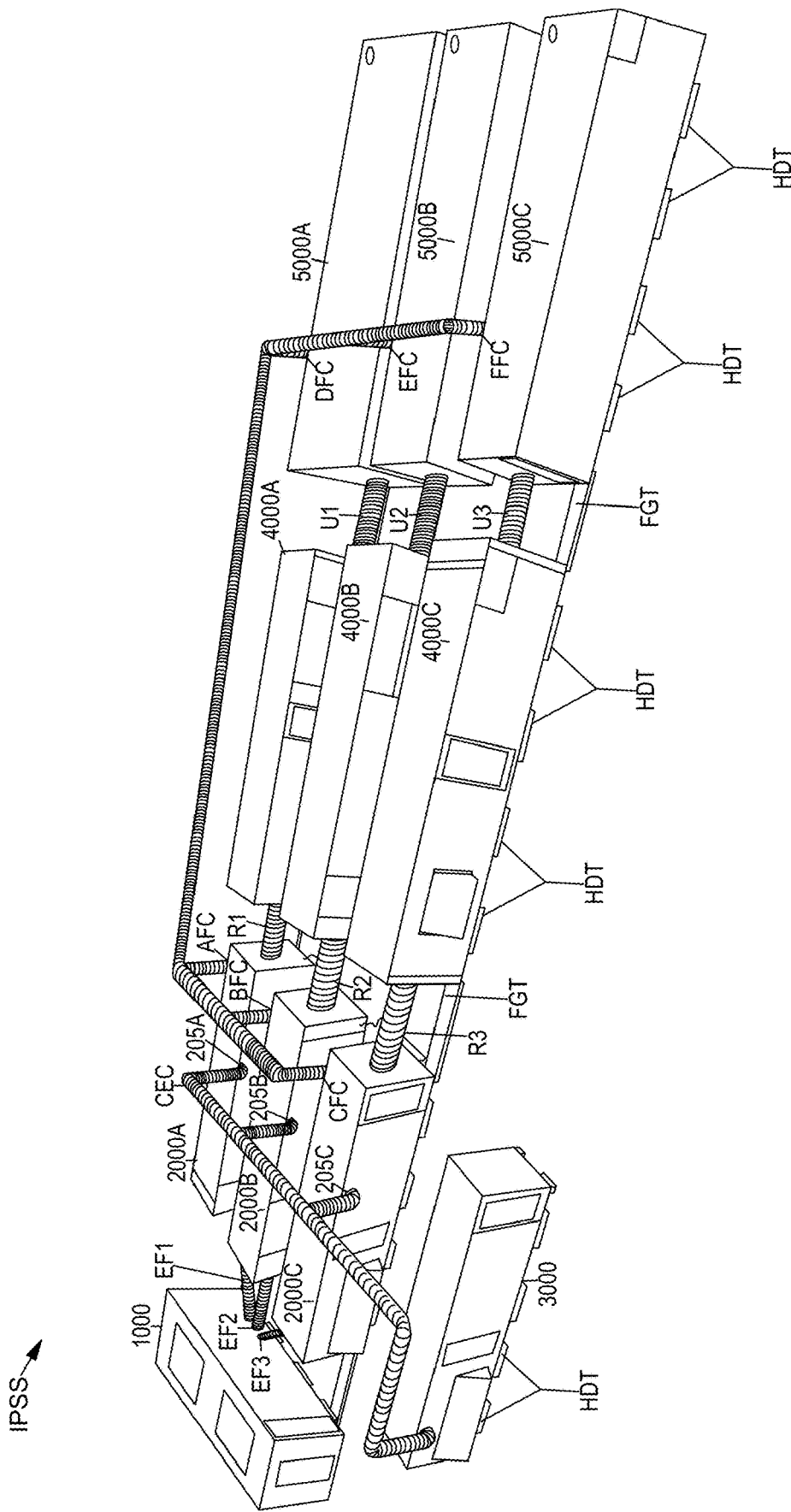

FIG. 17 shows a perspective view of one embodiment of a scalable portable modular Insect Production Superstructure System (IPSS) designed with: one enhanced feedstock mixing module (1000); three insect feeding modules (2000A, 2000B, 2000C); one insect evacuation module (3000); three insect breeding modules (4000A, 4000B, 4000C), and three insect separation modules (5000).

Figure 18:
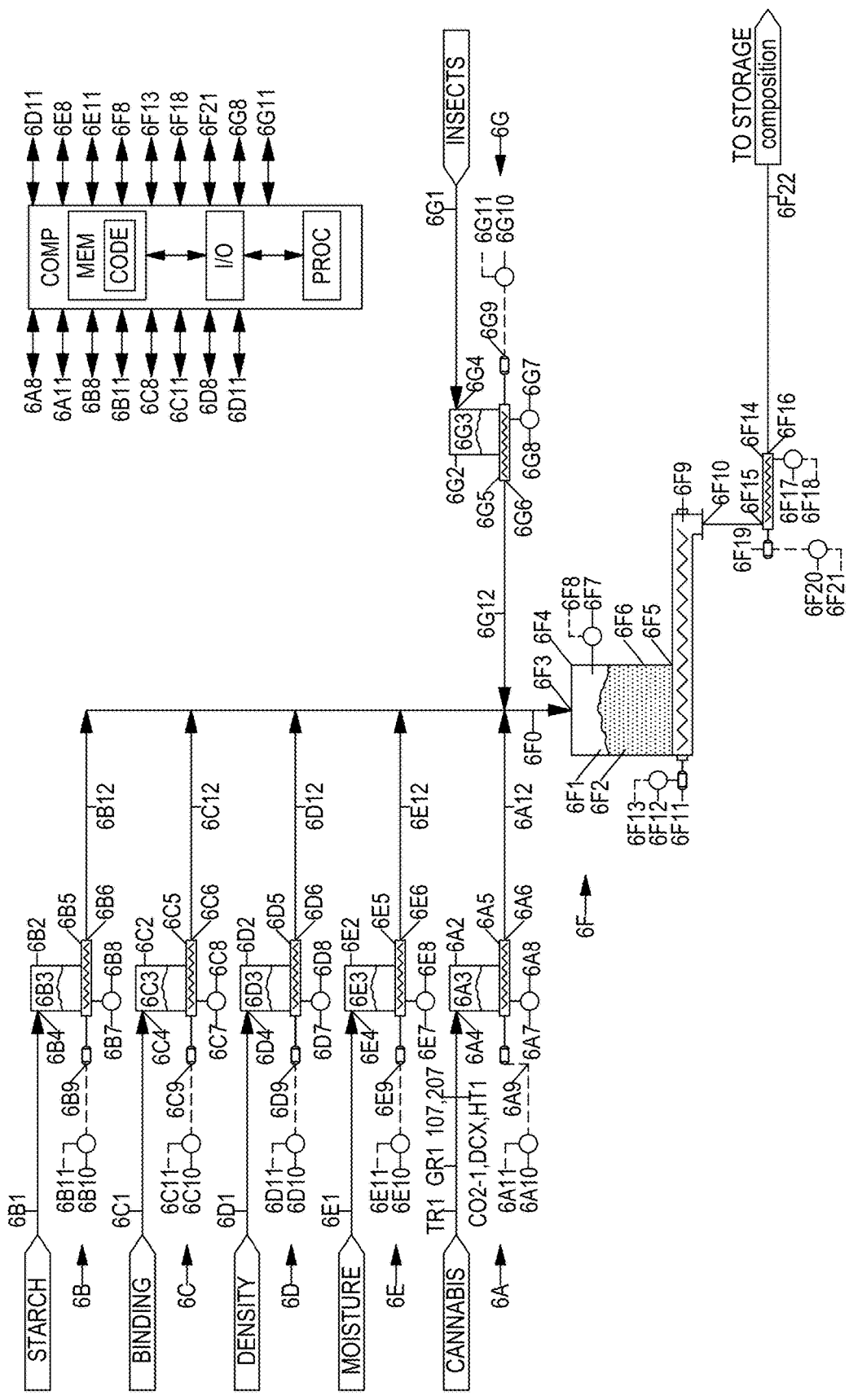

FIG. 18 shows a front view of one embodiment of an enhanced feedstock mixing module (1000) module including a feedstock distribution module (1A), mineral distribution module (1B), vitamin distribution module (1C), and a polymer distribution module (1D).

Figure 19:
Figure 20:
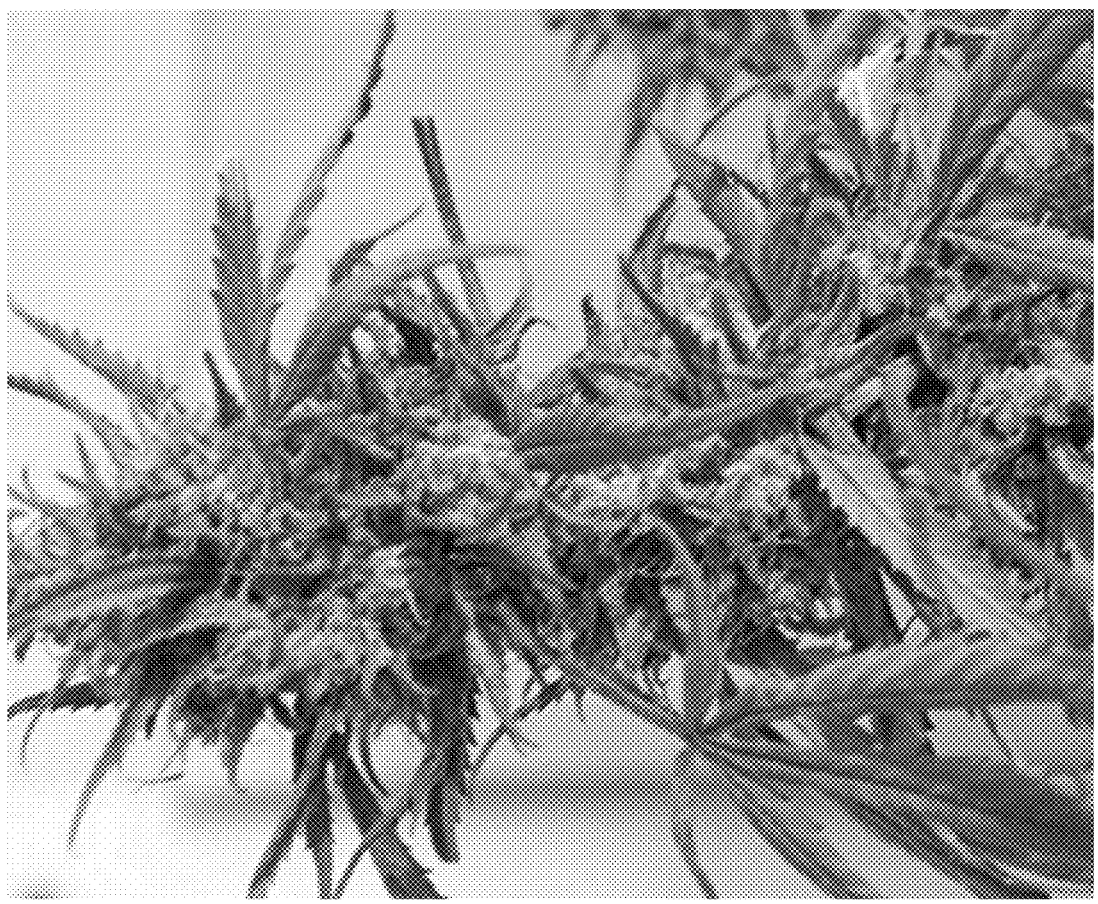

FIG. 19 shows a top view of one embodiment of an enhanced feedstock mixing module (1000) including a feedstock distribution module (1A), mineral distribution module (1B), vitamin distribution module (1C), and a polymer distribution module (1D).

Figure 20:
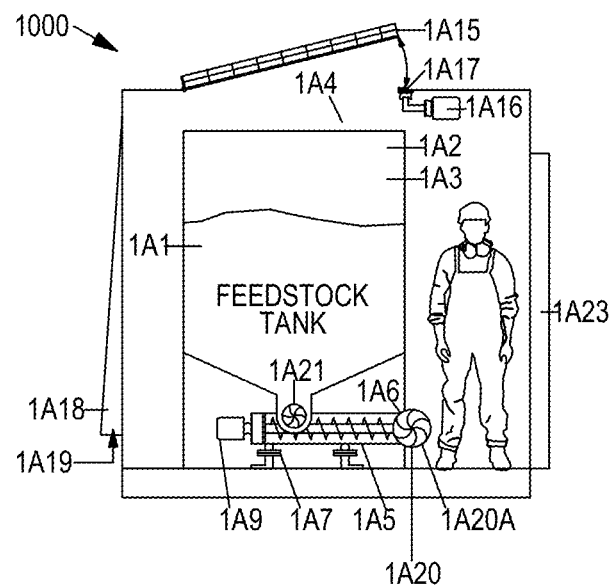

FIG. 20 shows a first side view of one embodiment of an enhanced feedstock mixing module (1000).

Figure 21:

FIG. 21 shows a front view of one embodiment of a water distribution module (1E).

Figure 22:
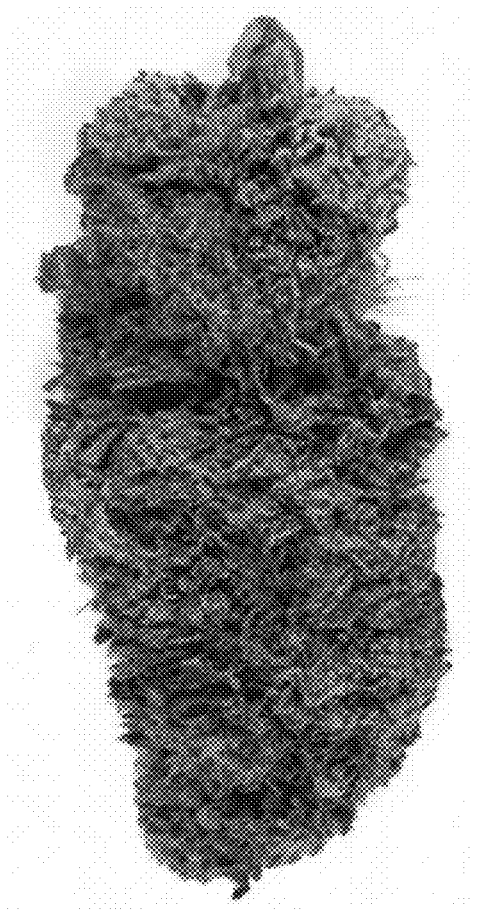

FIG. 22 shows a top view of one embodiment of a water distribution module (1E).

Figure 23:
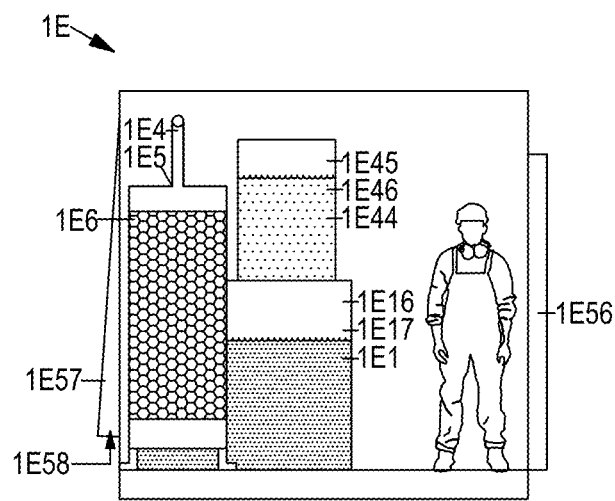

FIG. 23 shows a first side view of one embodiment of a water distribution module (1E).

Figure 24:
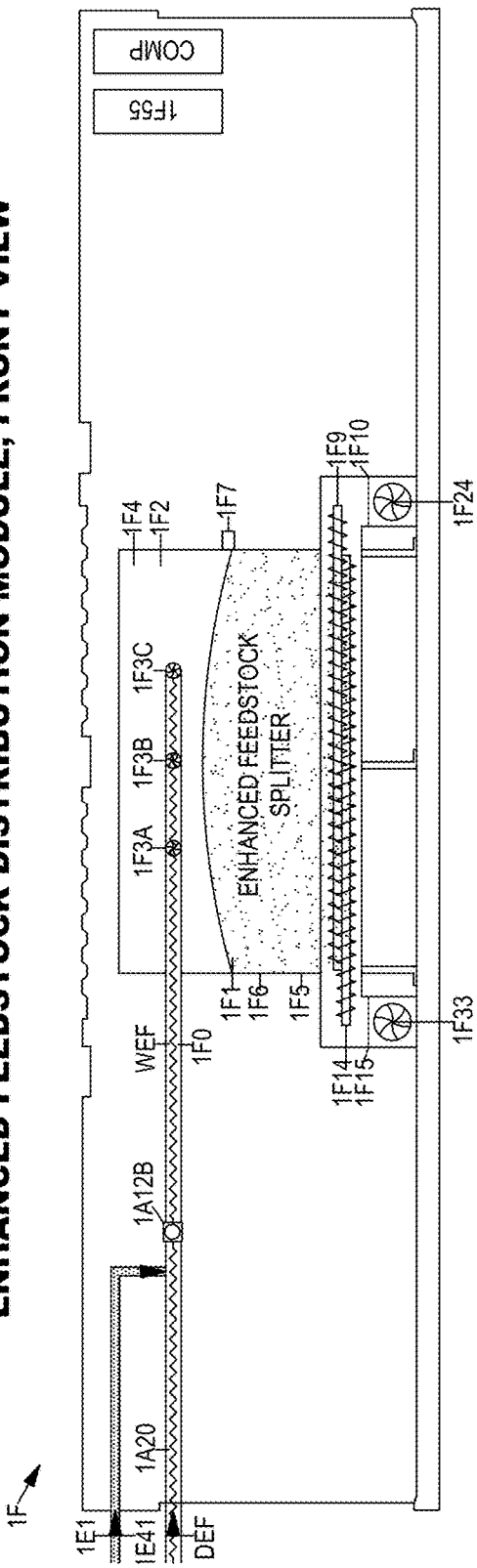

FIG. 24 shows a front view of one embodiment of an enhanced feedstock distribution module (1F).

Figure 25:
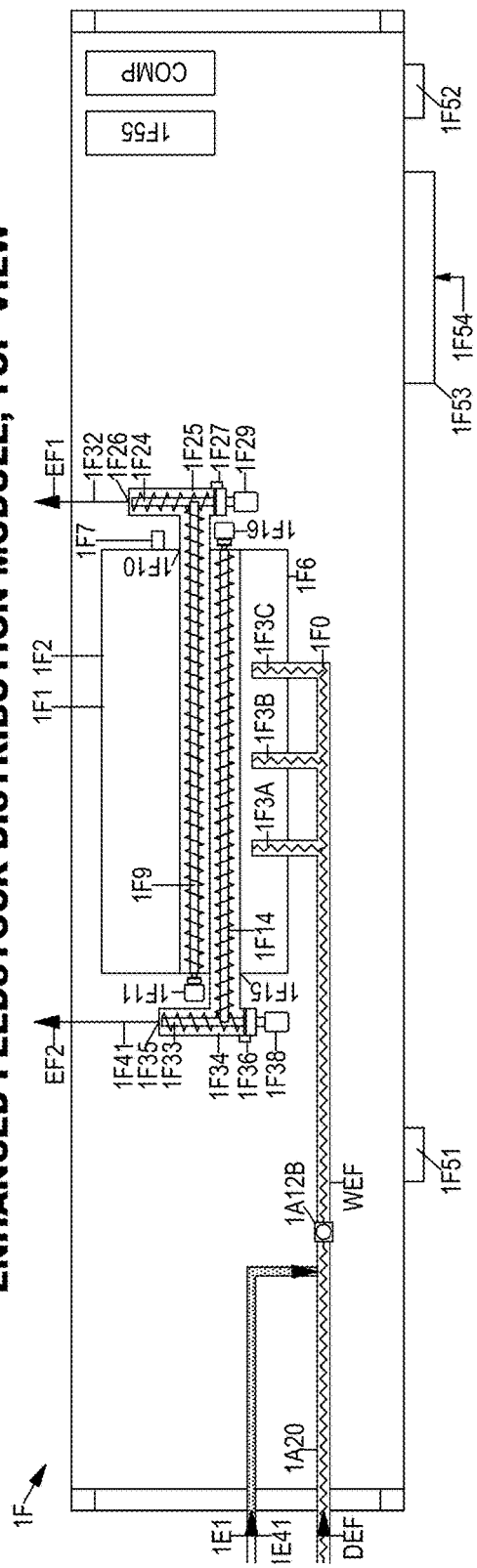

FIG. 25 shows a top view of one embodiment of an enhanced feedstock distribution module (1F).

Figure 26:
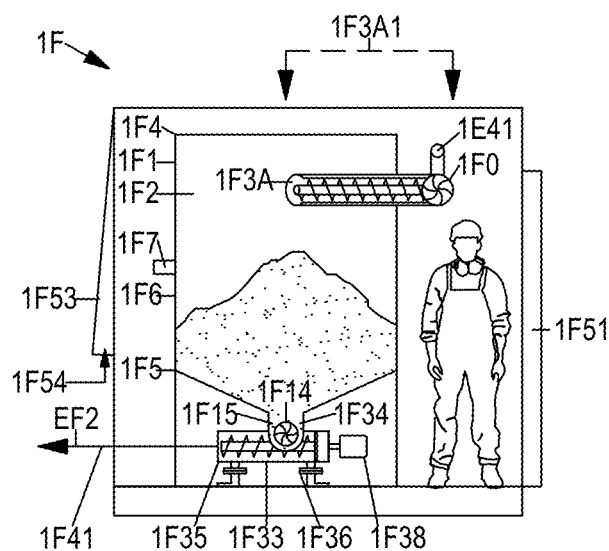

FIG. 26 shows a first side view of one embodiment of an enhanced feedstock distribution module (1F).

Figure 27A:
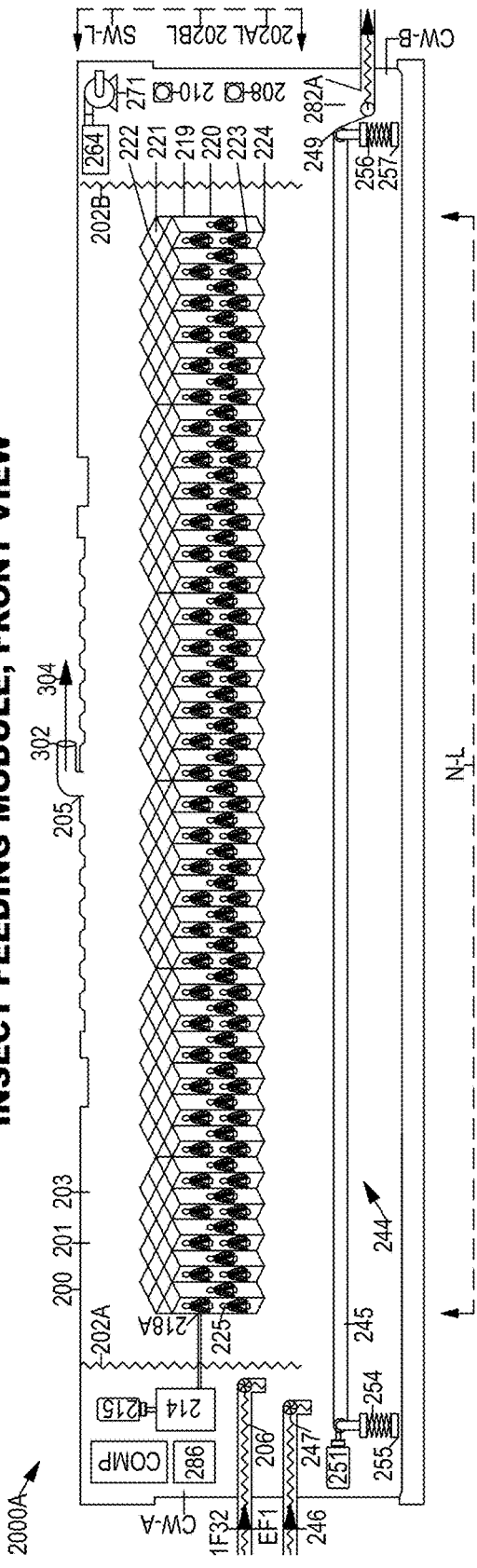

FIG. 27A shows a front view of one embodiment of an insect feeding module (2000, 2000A, 2000B, 2000C).

Figure 28A:
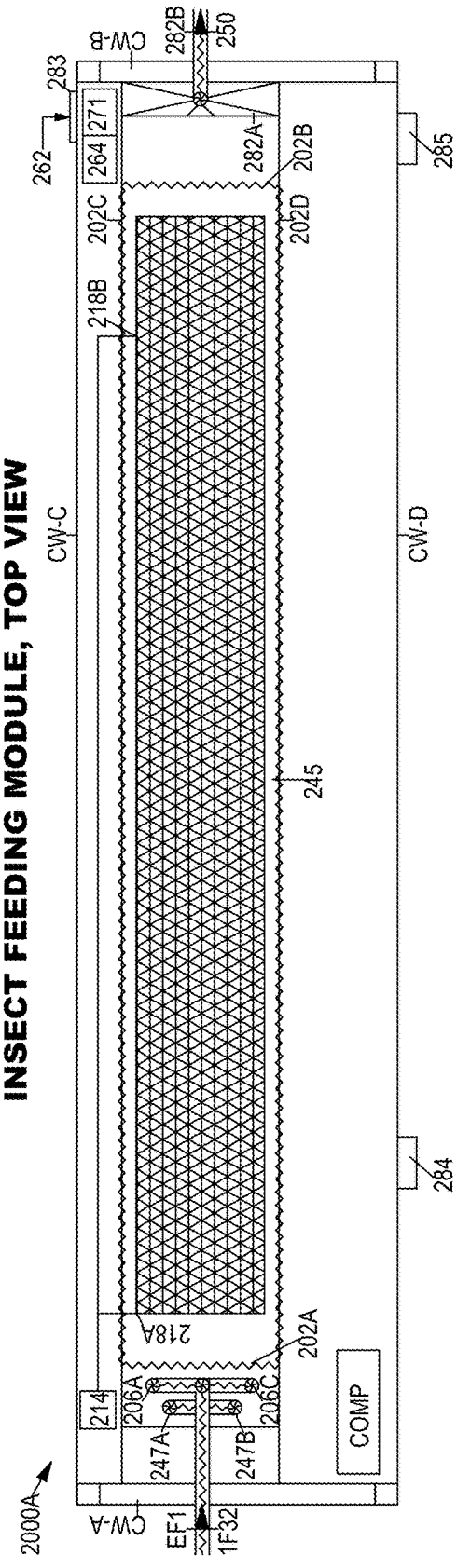

FIG. 28A shows a top view of one embodiment of an insect feeding module (2000, 2000A, 2000B, 2000C).

Figure 27B:
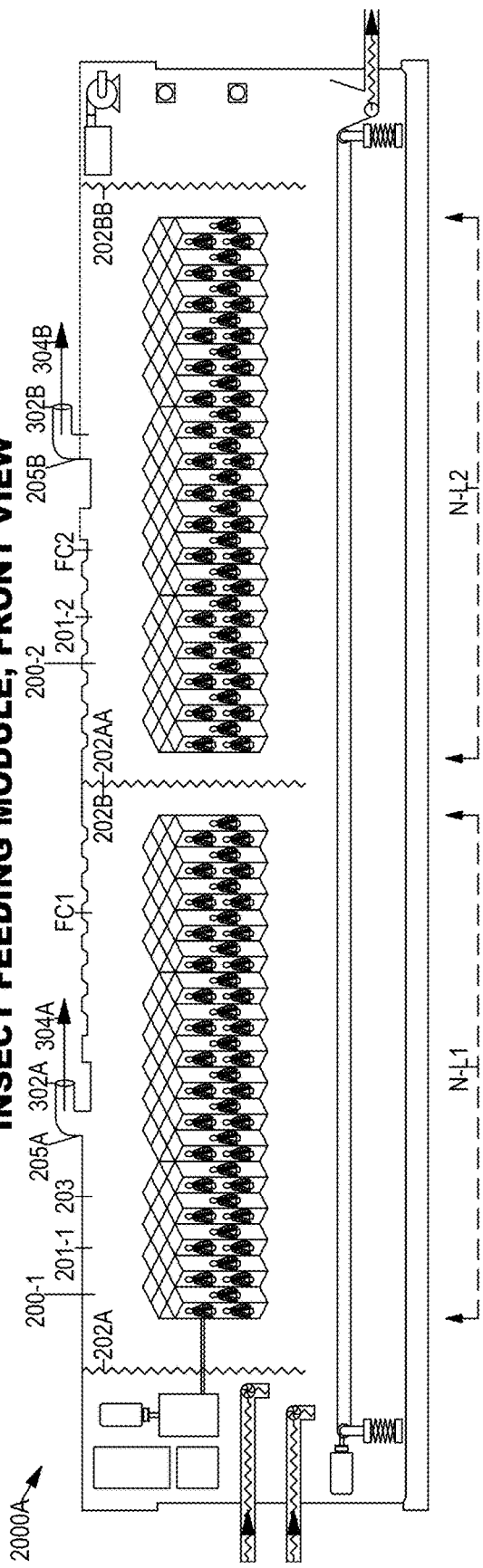

FIG. 27B shows a top view of one embodiment of an insect feeding module (2000, 2000A, 2000B, 2000C) including a plurality of feeding chambers provided in one shipping container conforming to the International Organization for Standardization (ISO) specifications.

Figure 27C:
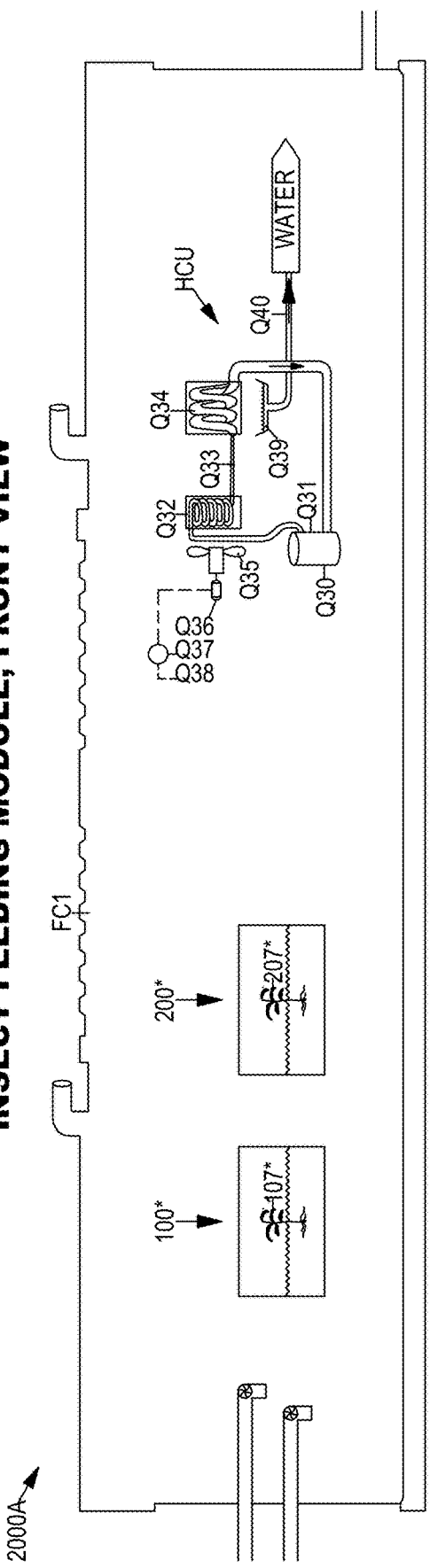

FIG. 27C shows a top view of one embodiment of an insect feeding module (2000, 24000A, 2000B, 2000C) equipped with a humidity control unit (HCU).

Figure 27D:
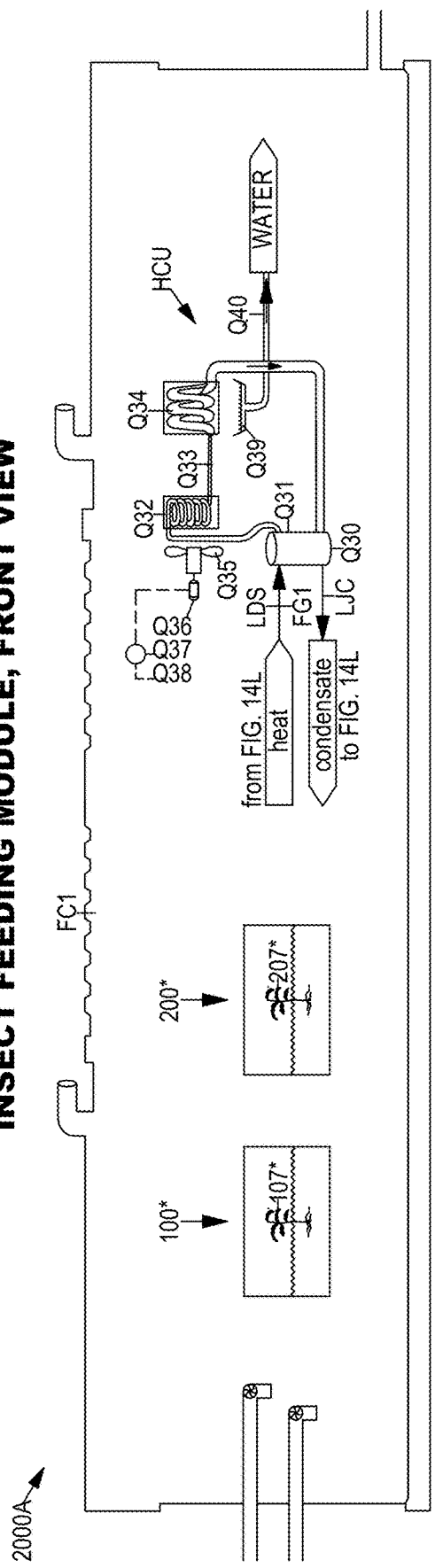

FIG. 27D shows one non-limiting embodiment where the compressor (Q30) within the humidity control unit (HCU) is that of a thermal compressor (Q30) that accepts a source of steam.

FIG. 27E shows one non-limiting embodiment where the compressor (Q30) within the humidity control unit (HCU) is that of a thermal compressor (Q30) that accepts a source of steam.

FIG. 27F elaborates upon FIG. 27E and shows one non-limiting embodiment where the compressor (Q30) within the humidity control unit (HCU) is that of a thermal compressor (Q30) that accepts a source of heat, such as flue gas (FG1).

Figure 28B:
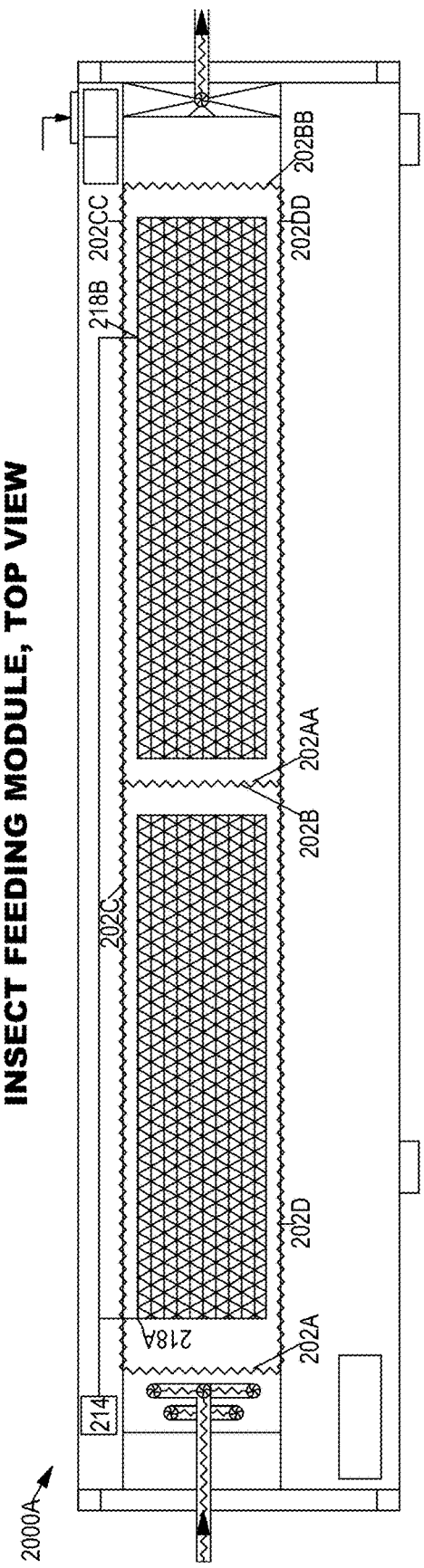

FIG. 28B shows a top view of one embodiment of an insect feeding module (2000, 2000A, 2000B, 2000C) including a plurality of feeding chambers provided in one shipping container conforming to the International Organization for Standardization (ISO) specifications.

Figure 29:
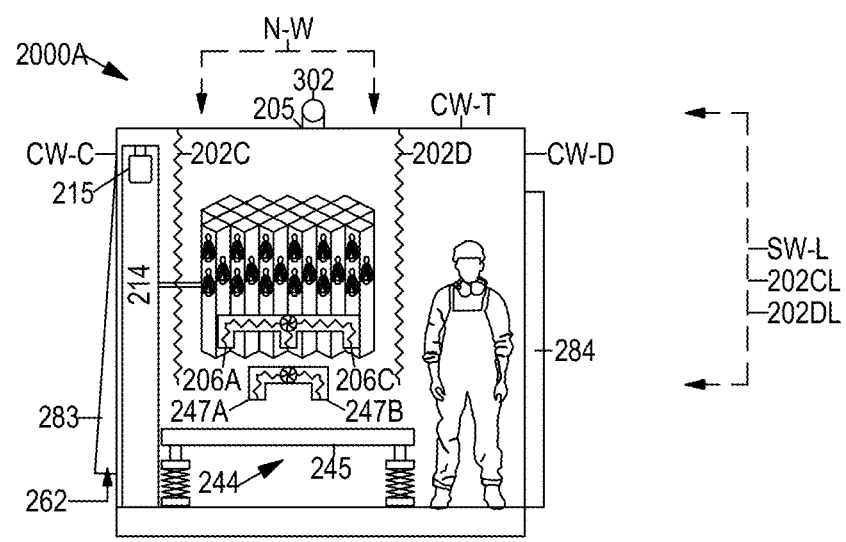

FIG. 29 shows a first side view of one embodiment of an insect feeding module (2000, 2000A, 2000B, 2000C).

Figure 30:
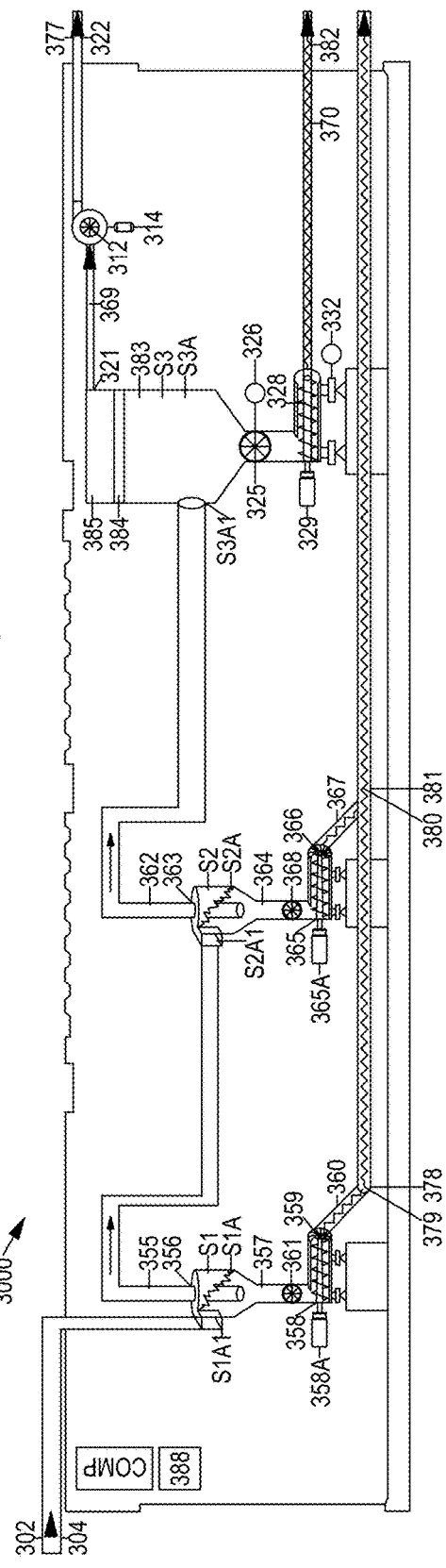

FIG. 30 shows a front view of one embodiment of an insect evacuation module (3000).

Figure 31:
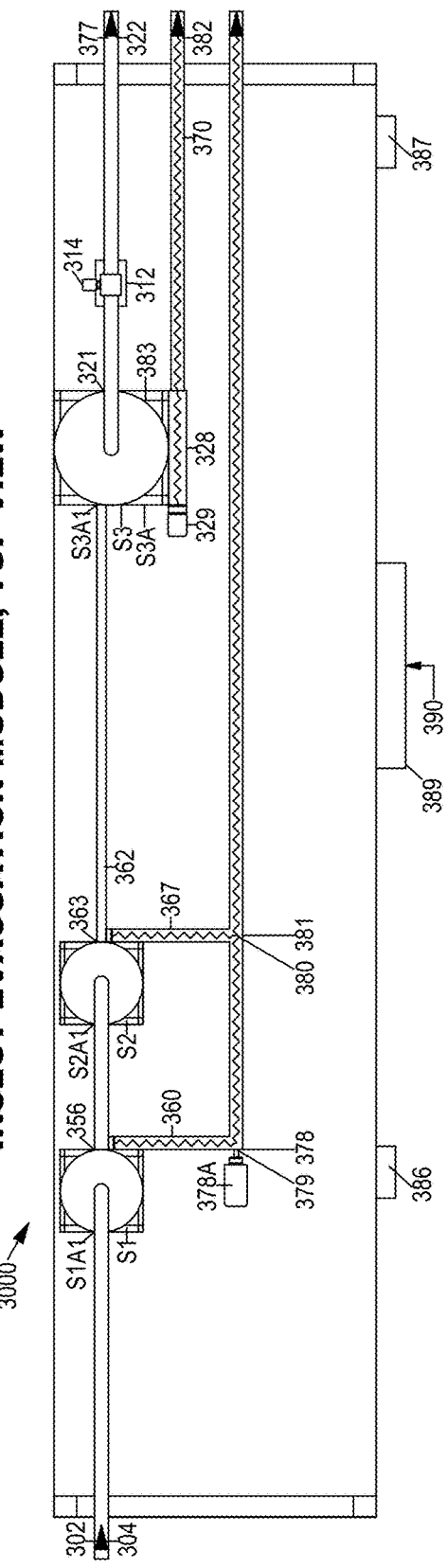

FIG. 31 shows a top view of one embodiment of an insect evacuation module (3000).

Figure 32:
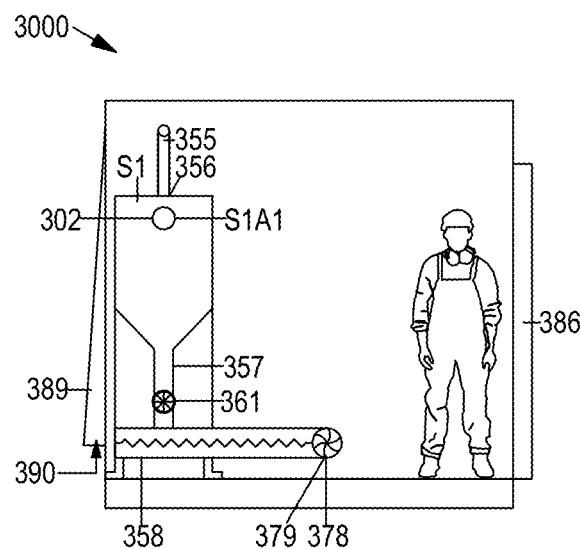

FIG. 32 shows a first side view of one embodiment of an insect evacuation module (3000).

Figure 33:
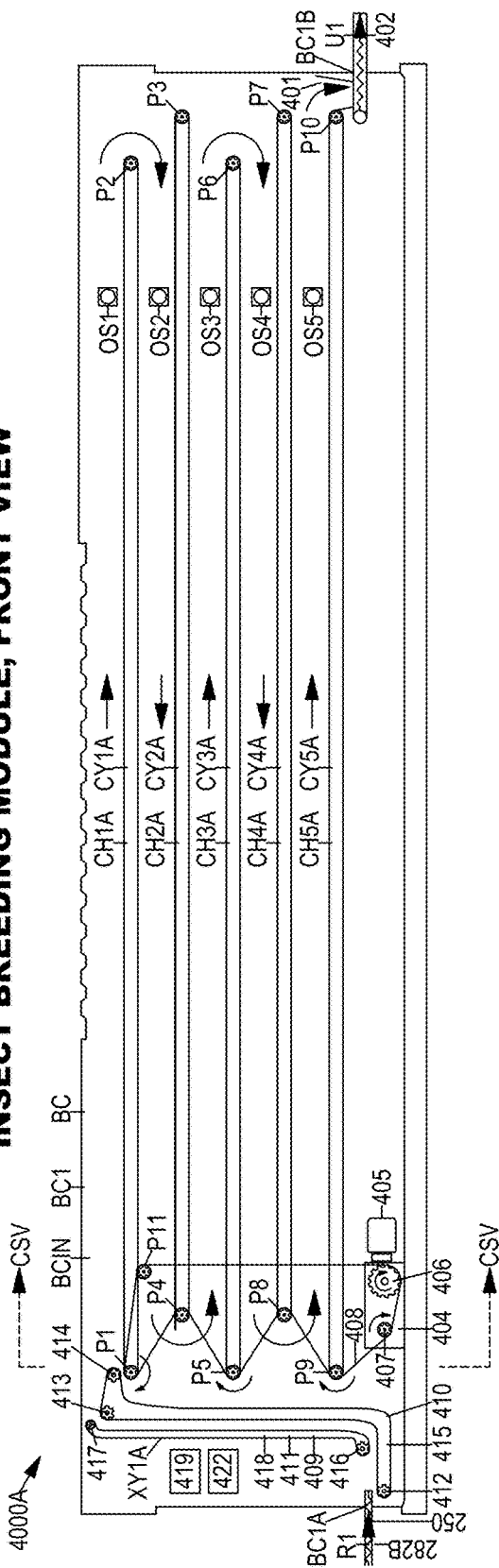

FIG. 33 shows a front view of one embodiment of an insect breeding module (4000, 4000A).

Figure 34:
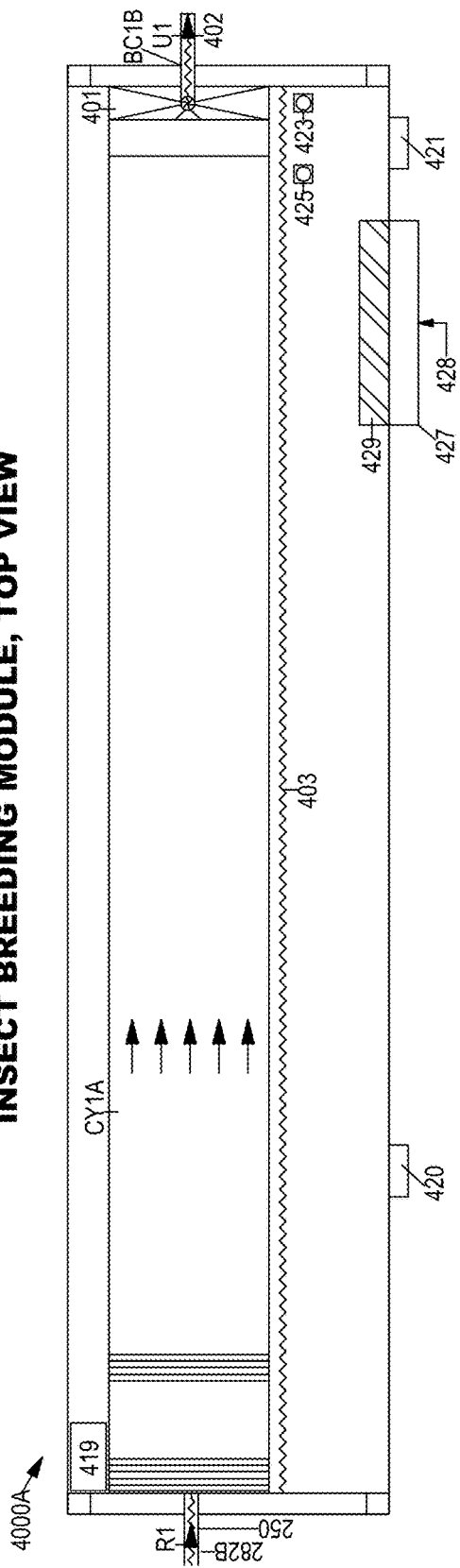

FIG. 34 shows a top view of one embodiment of an insect breeding module (4000, 4000A).

Figure 34A:
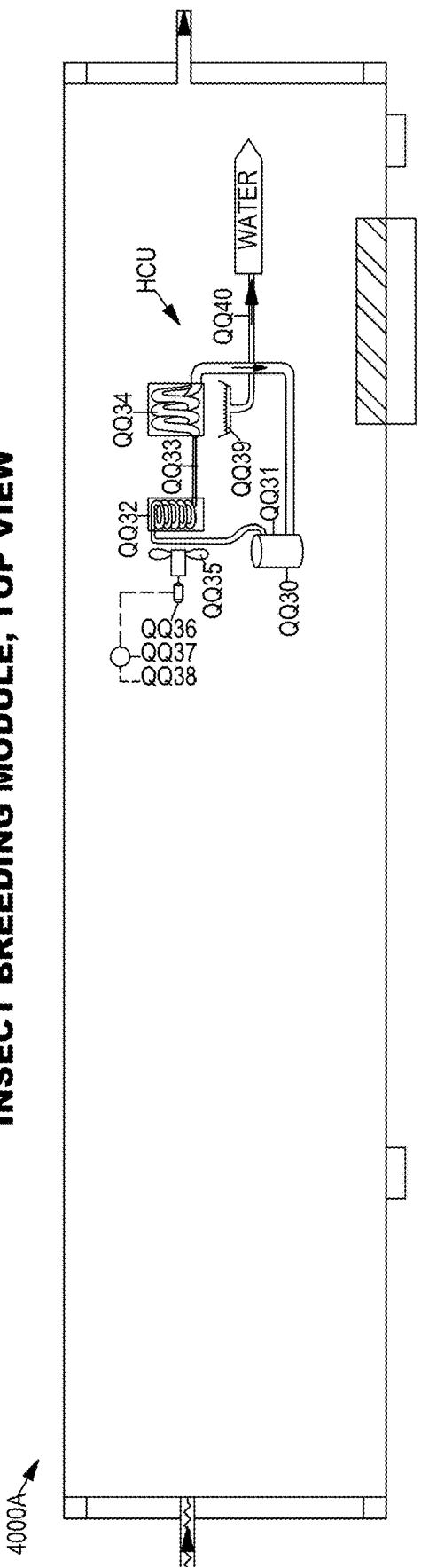

FIG. 34A shows a top view of one embodiment of an insect breeding module (4000, 4000A, 4000B, 4000C) equipped with a humidity control unit (HCU).

Figure 34B:
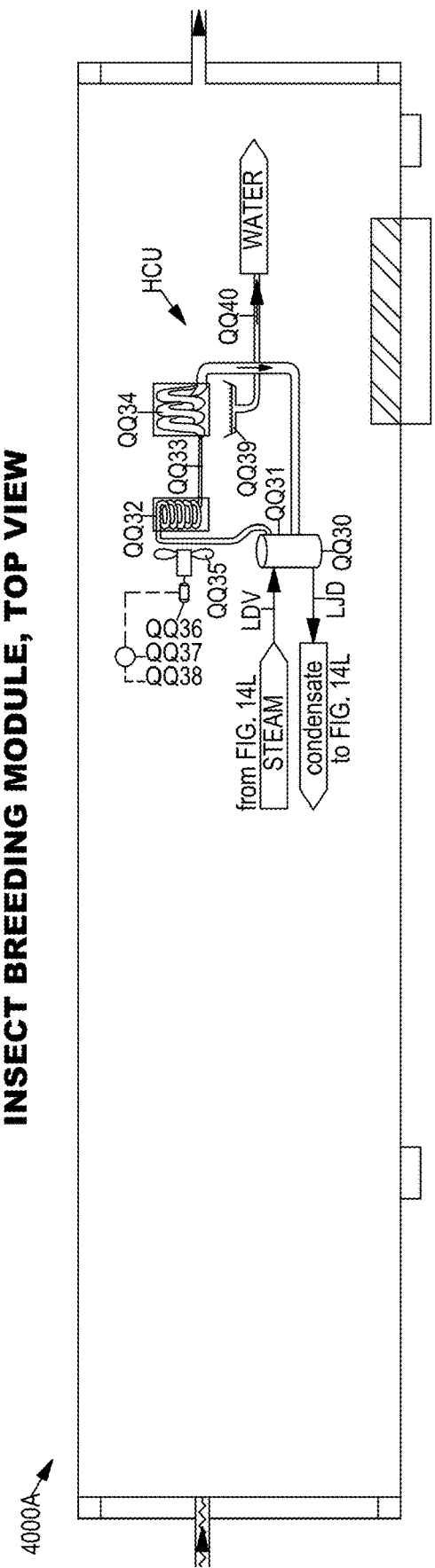

FIG. 34B shows one non-limiting embodiment where the compressor (QQ30) within the humidity control unit (HCU) is that of a thermal compressor (QQ30) that accepts a source of steam.

Figure 35:
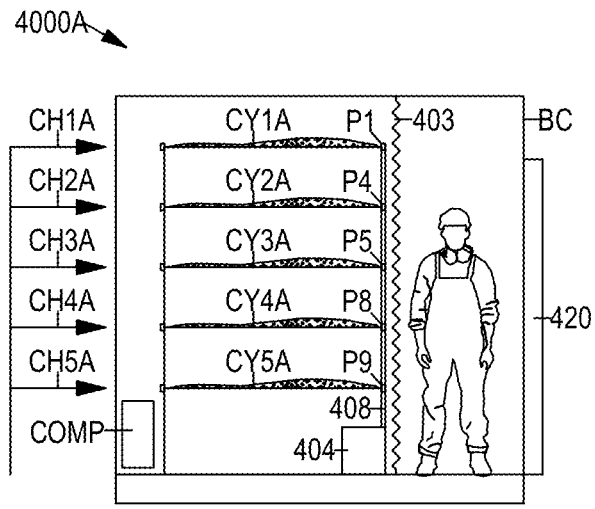

FIG. 35 shows a first side view of one embodiment of an insect breeding module (4000, 4000A) at a cutaway section of the conveyor side view (CSV).

Figure 36:
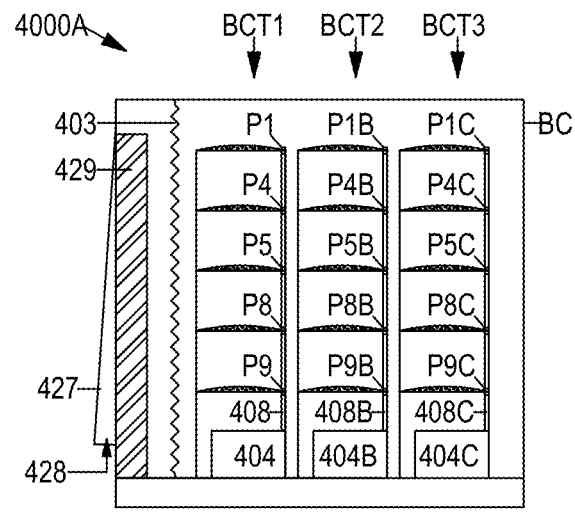

FIG. 36 shows a second side view of one embodiment of an insect breeding module (4000, 4000A) at a cutaway section of the conveyor side view (CSV).

Figure 37:
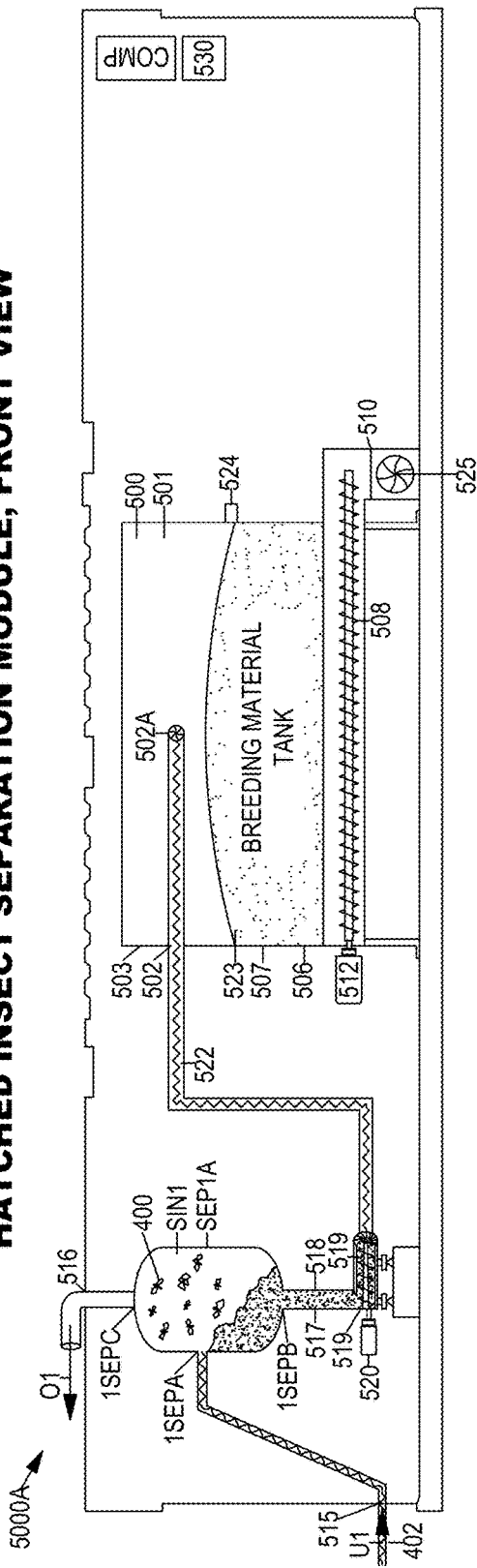

FIG. 37 shows a front view of one embodiment of a hatched insect separation module (5000, 5000A).

Figure 38:
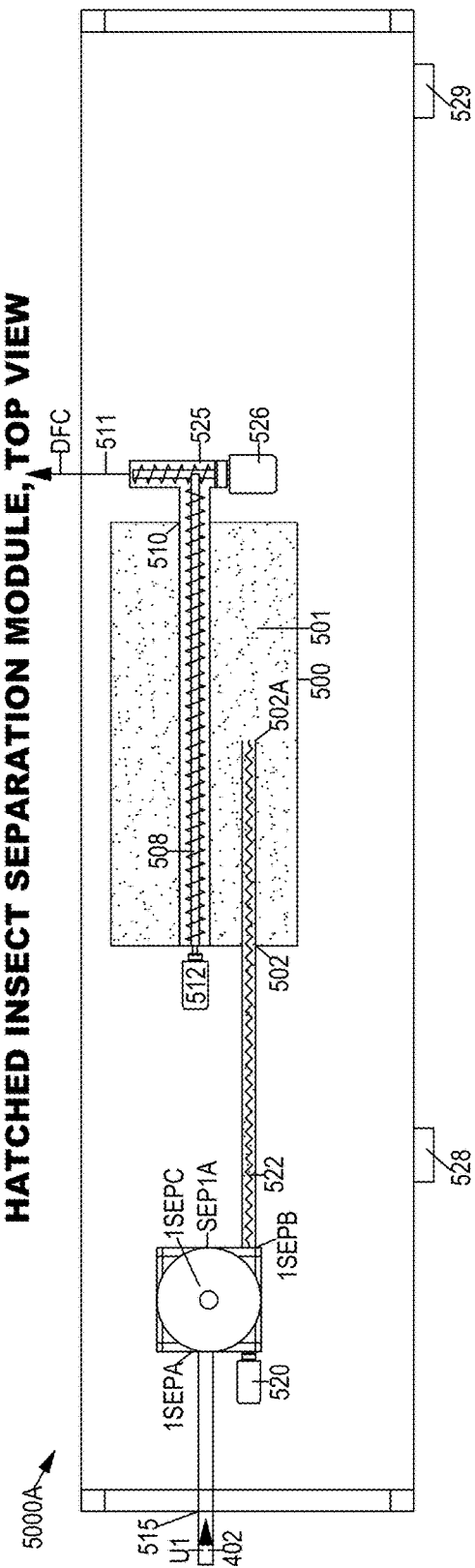

FIG. 38 shows a top view of one embodiment of a hatched insect separation module (5000, 5000A).

Figure 39:
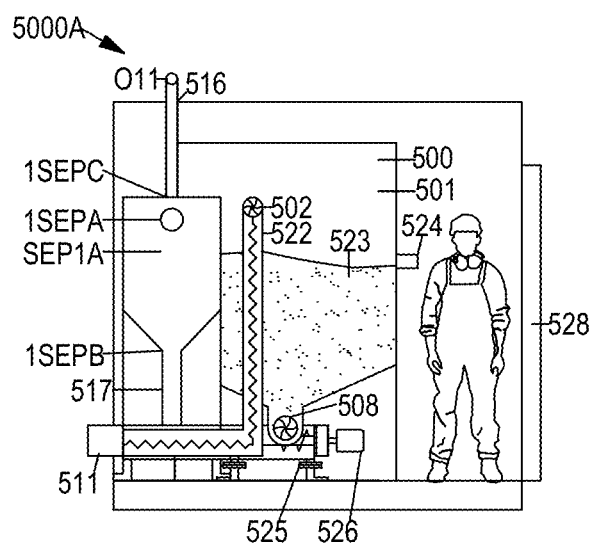

FIG. 39 shows a first side view of one embodiment of a hatched insect separation module (5000, 5000A).

FIG. 40A shows Table 1 with upper and lower ranges of feedstock mineral enhancers, feedstock vitamin enhancers, feedstock polymer enhancers, and other 'energy-insectg' enhancers.

FIG. 40B shows one non-limiting example of process conditions within an Insect Production Superstructure System (IPSS).

FIG. 40C shows nutritional requirements of insects produced in an Insect Production Superstructure System (IPSS) that are fed an enhanced feedstock.

FIG. 41A shows one non-limiting embodiment of a method for raising Orthoptera order of insects.

FIG. 41B shows one non-limiting embodiment of another method for raising Orthoptera order of insects.

FIG. 42A shows one non-limiting embodiment of a method for raising Orthoptera order of insects.

FIG. 42B shows one non-limiting embodiment of another method for raising Orthoptera order of insects.

FIG. 43A shows one non-limiting embodiment of a method for raising Orthoptera order of insects.

FIG. 43B shows one non-limiting embodiment of another method for raising Orthoptera order of insects.

FIG. 44A shows one non-limiting embodiment of a method for raising Orthoptera order of insects.

Figure 44B:
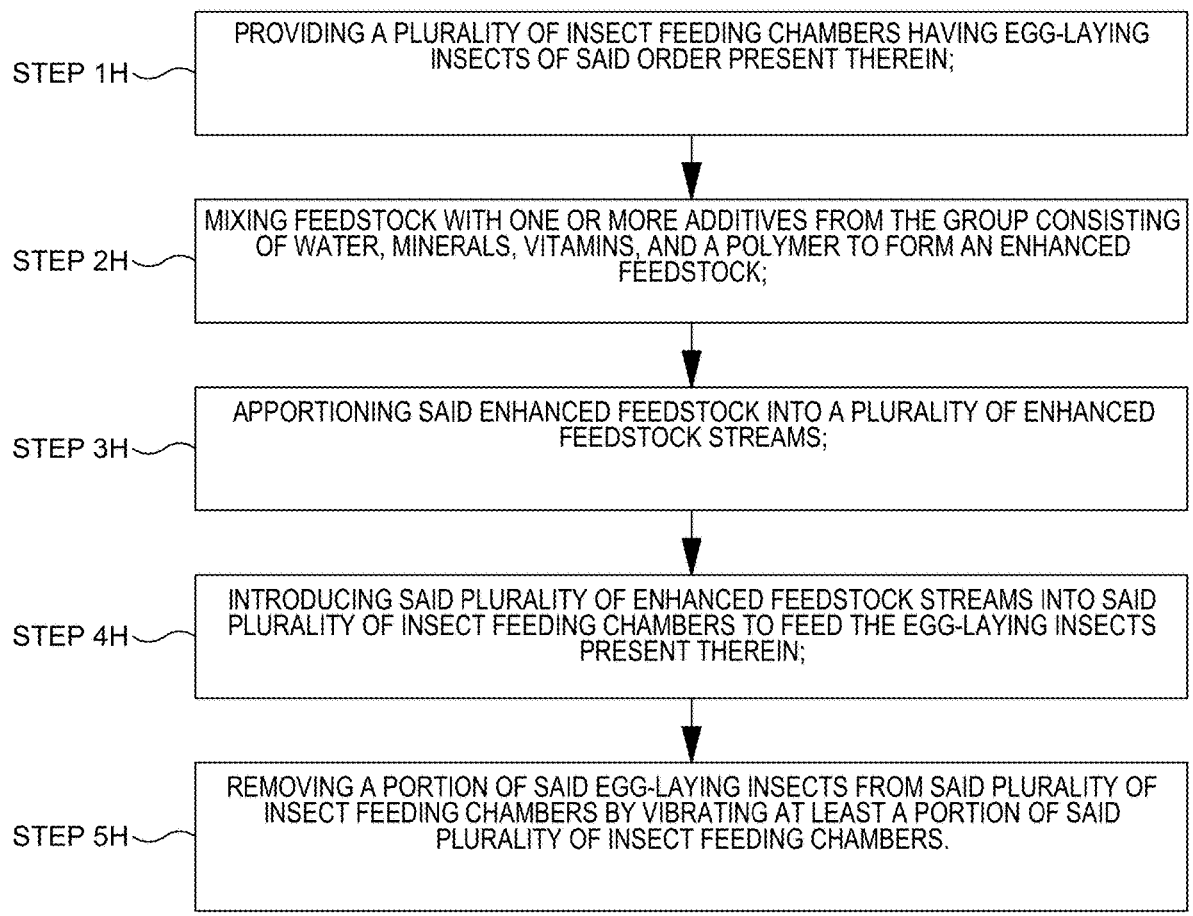

FIG. 44B shows one non-limiting embodiment of another method for raising Orthoptera order of insects.

Figure 45A:
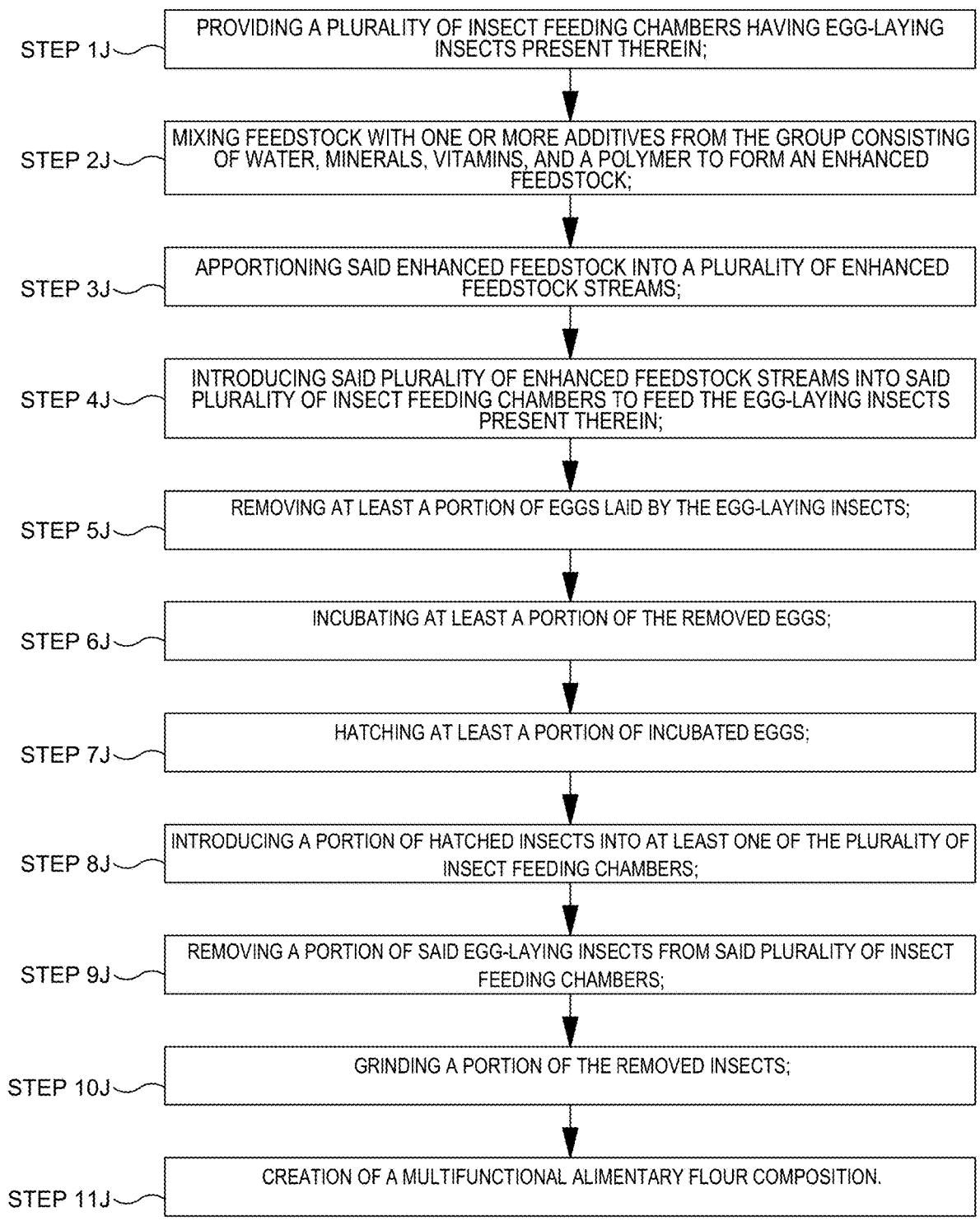

FIG. 45A shows one non-limiting embodiment of a method for raising Orthoptera order of insects to generate a multifunctional composition.

FIG. 45B shows one non-limiting embodiment of another method for raising Orthoptera order of insects to generate a multifunctional composition.

FIG. 46 shows one non-limiting embodiment of another method for raising Orthoptera order of insects to generate a multifunctional composition.

FIG. 47 shows one non-limiting embodiment of a method for raising Orthoptera order of insects for the separation of lipids contained within said insects.

Figure 1A:
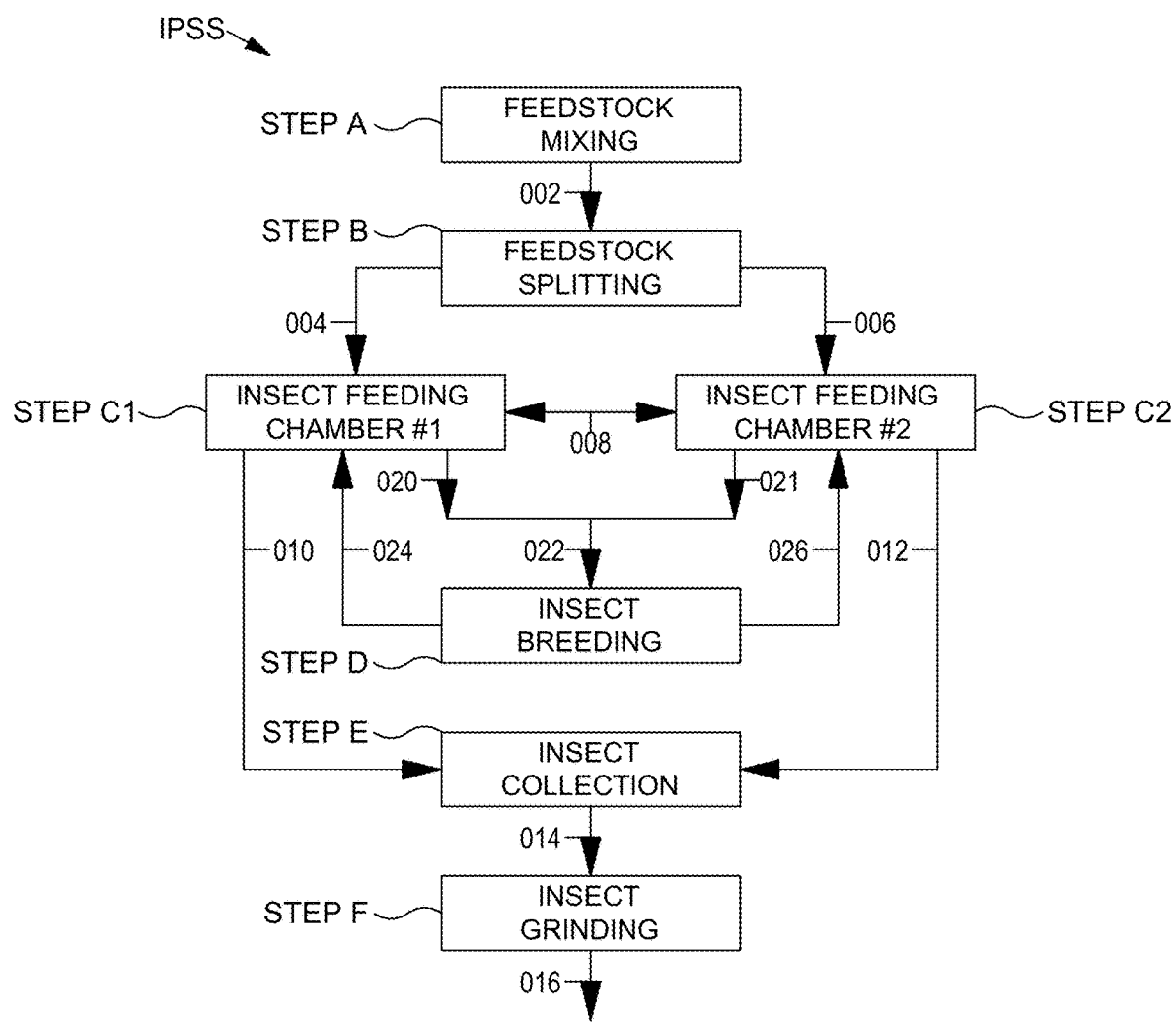

FIG. 48 shows one non-limiting embodiment of another method for raising Orthoptera order of insects for the extraction of lipids FIG. 1A' depicts one non-limiting embodiment of a farming superstructure system (FSS) including a first water treatment unit (A1*), a second water treatment unit (A2*), a third water treatment unit (A3*), a common reservoir (500*), a pump (P1*), a plurality of vertically stacked growing assemblies (100*, 200*), a fabric (104*, 204*) that partitions each growing assembly (100*, 200*) into an upper-section (105*, 205*) and a lower-section (106*, 206*), a plurality of lights (L1*, L2*) positioned within the upper-section (105*, 205*) of each growing assembly.

FIG. 1B' depicts one non-limiting embodiment of a farming superstructure system (FSS) that includes a first growing assembly (100*) having a first growing medium (GM1*) and a second growing assembly (200*) having a second growing medium (GM2*).

Figure 1D:
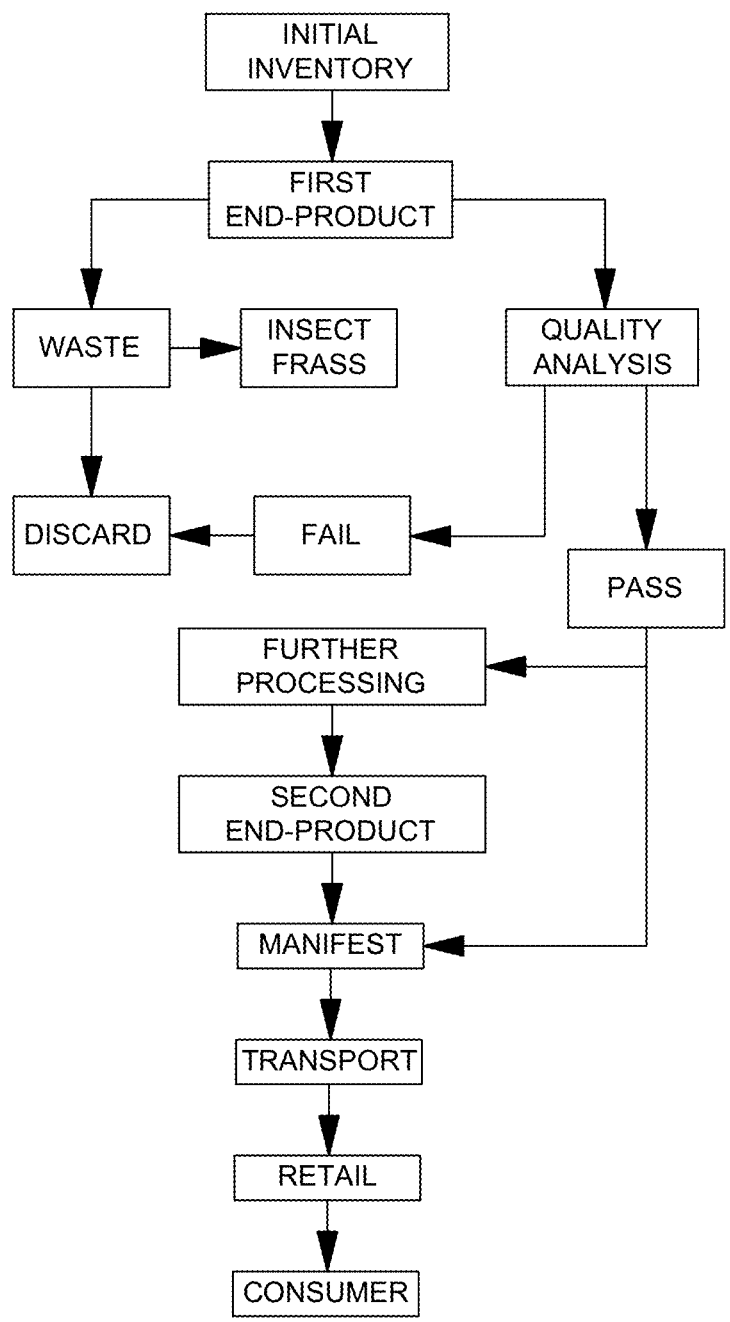
Figure 1A:
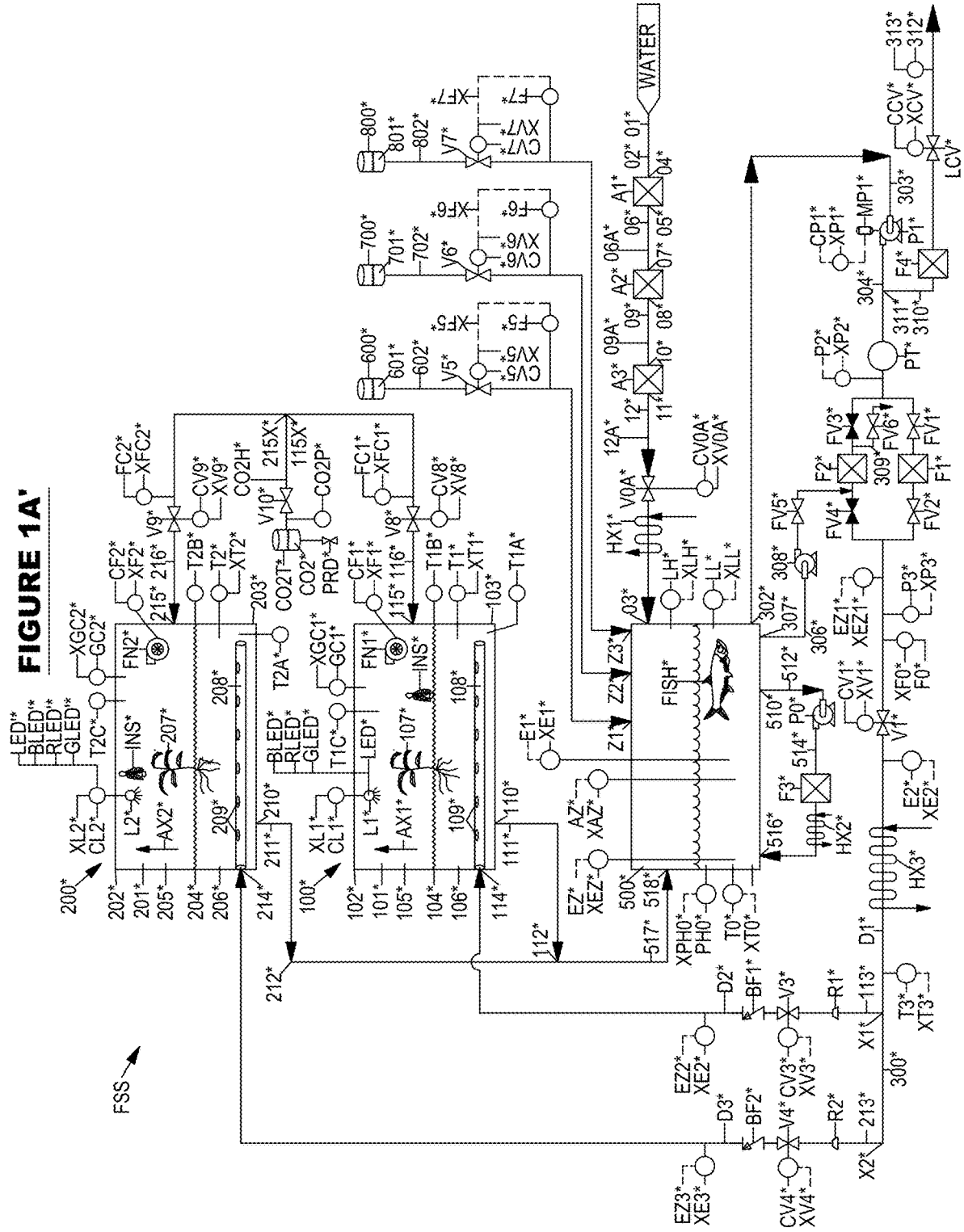
Figure 1C:
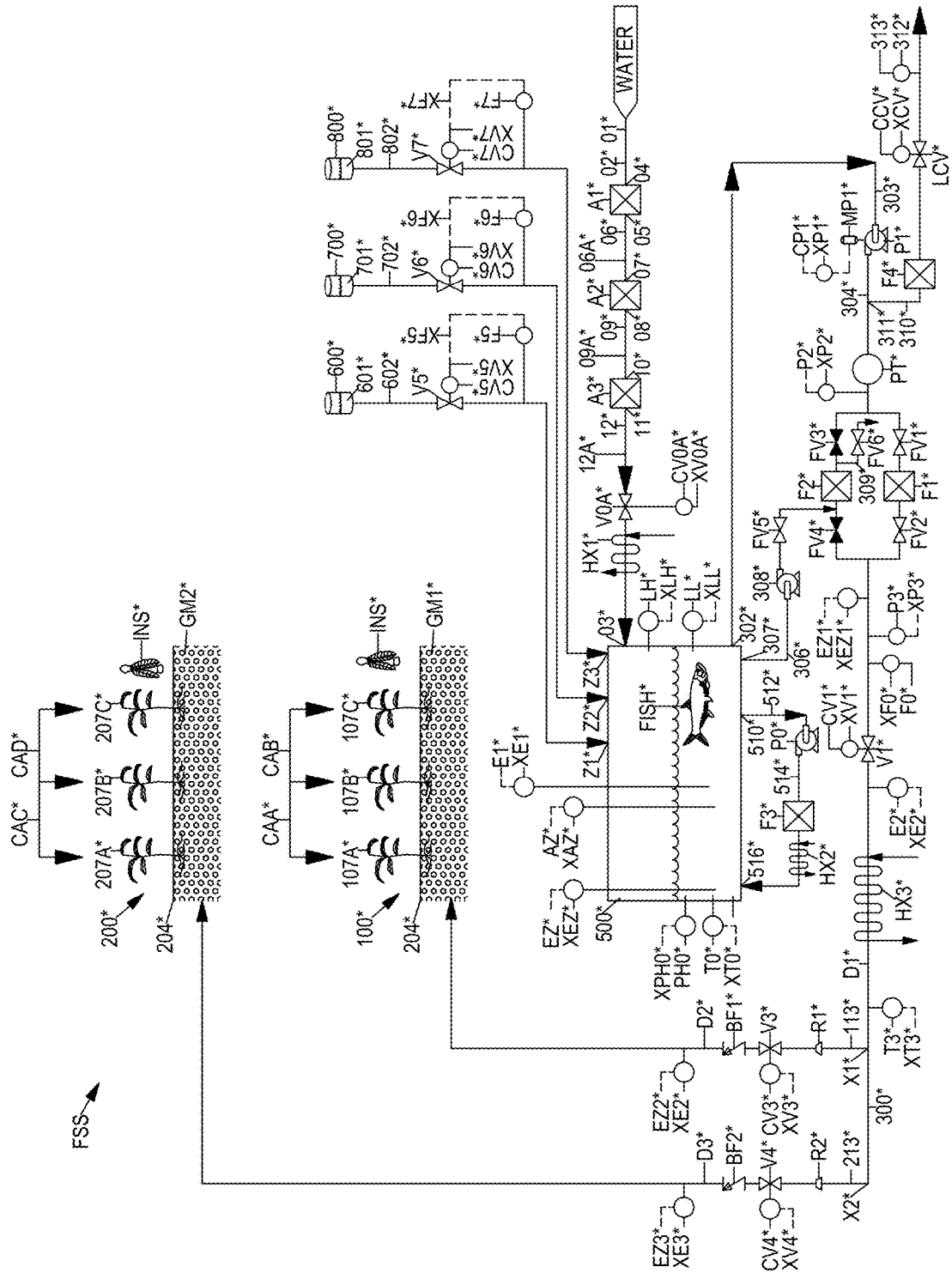
Figure 1D:
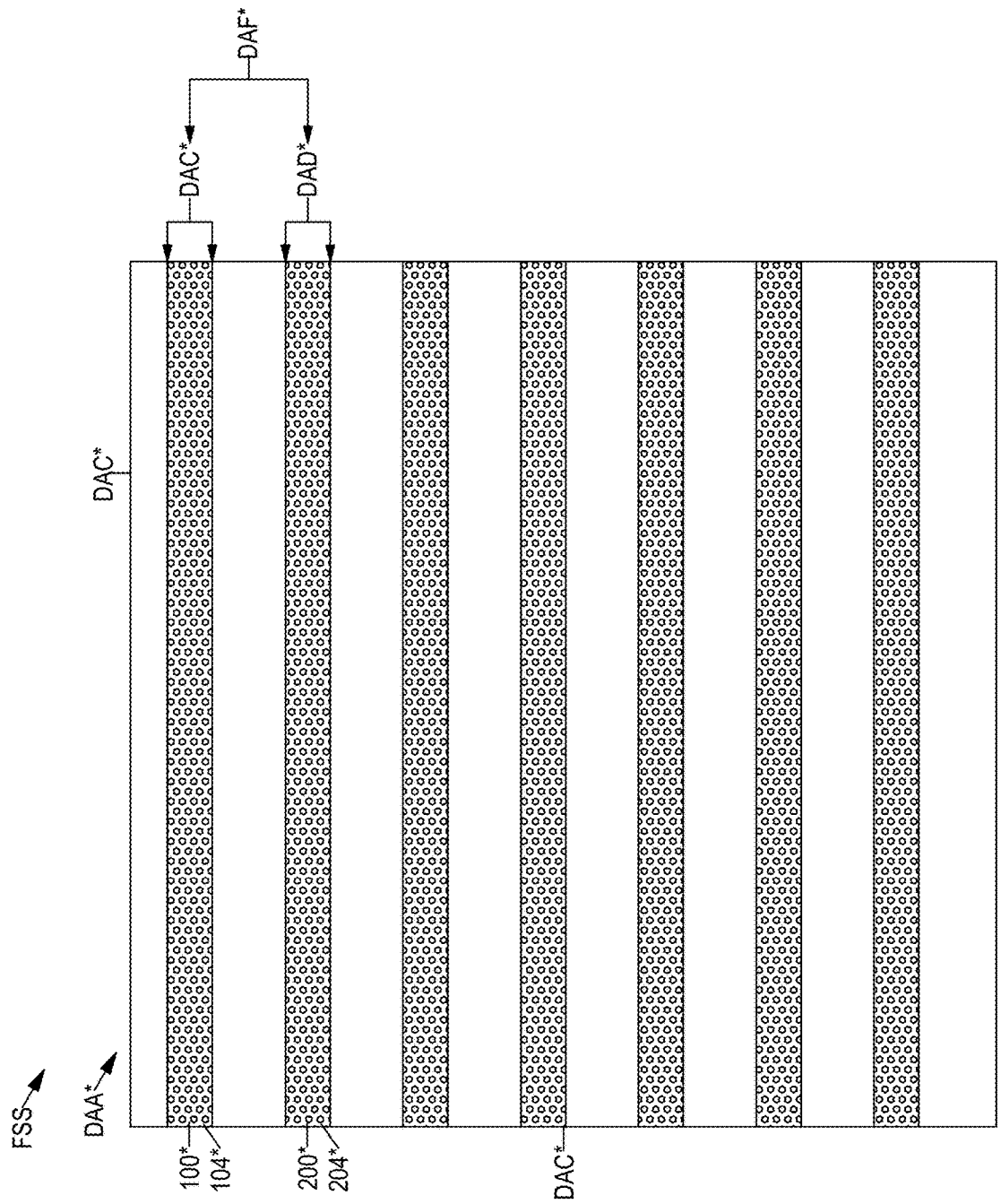
Figure 2:
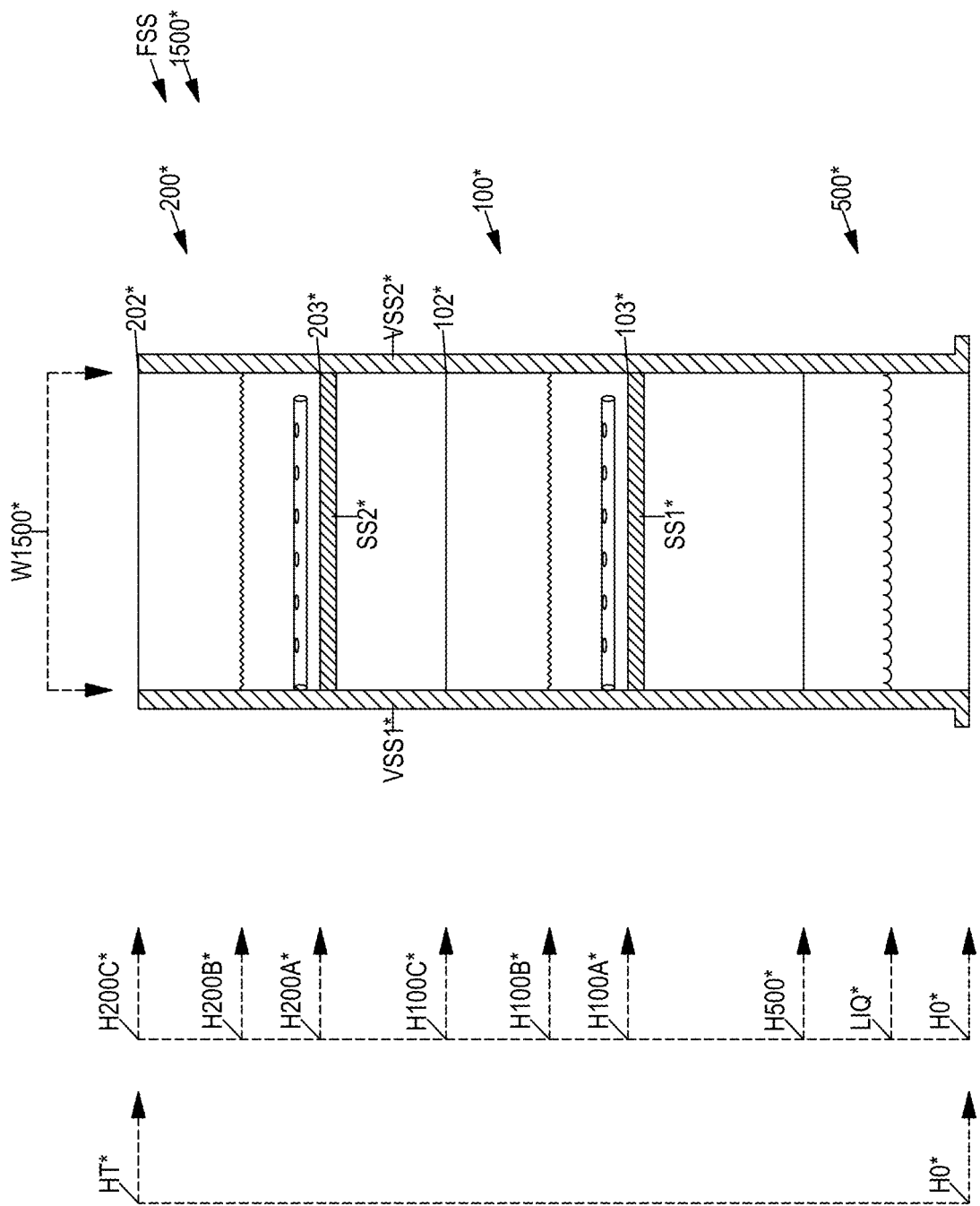
Figure 3:
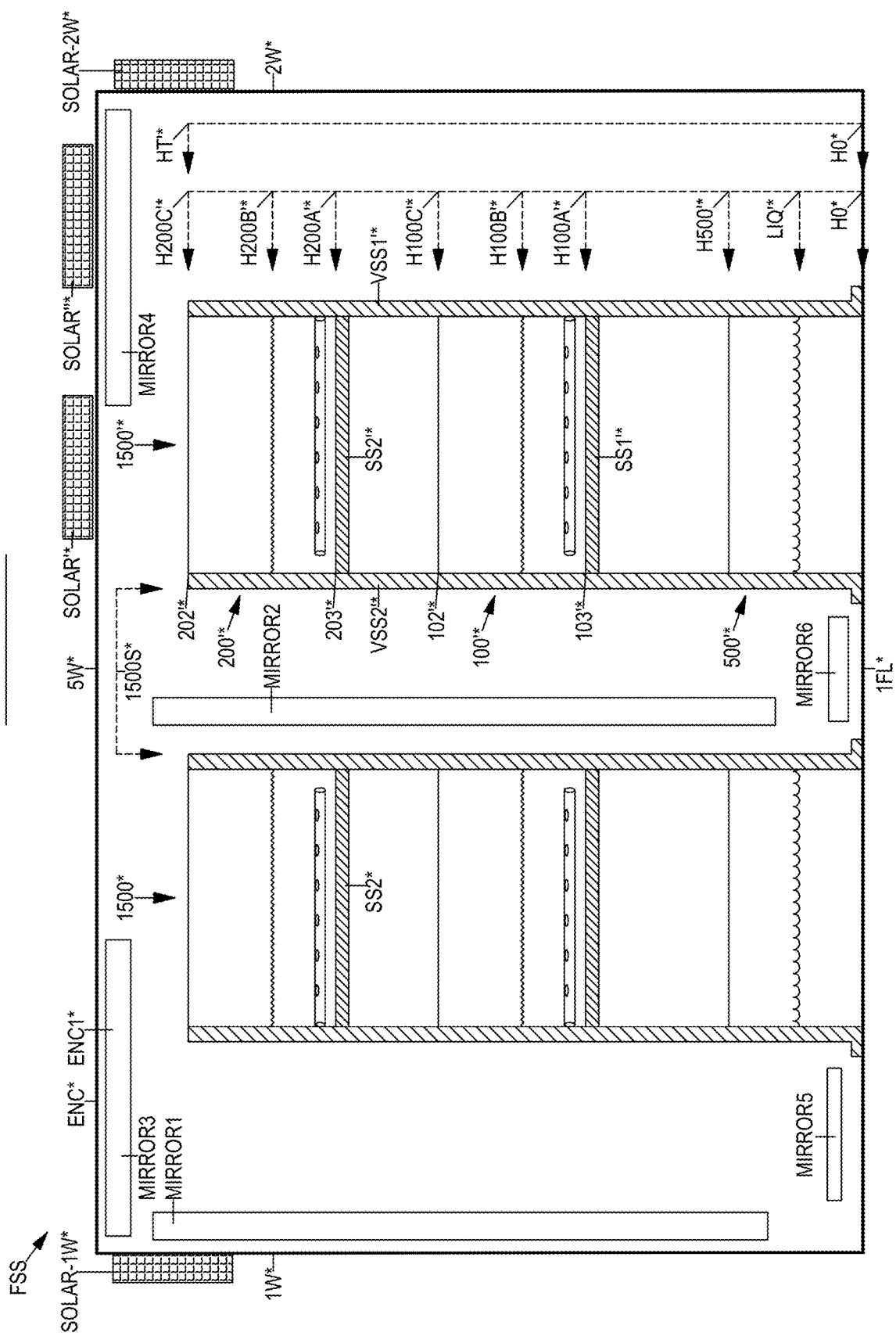

FIG. 1C' depicts one non-limiting embodiment of a farming superstructure system (FSS) that includes a first growing assembly (100*) having a first growing medium (GM1*) and a second growing assembly (200*) having a second growing medium (GM2*) and the first growing assembly (100*) and second growing assembly (200*) are grown outdoors.

FIG. 1D' depicts one non-limiting embodiment general arrangement of a farming superstructure system (FSS) top-view that includes a first growing assembly (100*) and a second growing assembly (200*) each configured to grow plants (107*, 107A*, 107B*, 107C*, 20*7, 207A*, 207B*, 207C*).

FIG. 2' depicts one non-limiting embodiment of a farming superstructure system (FSS) including a first vertically stacked system (1500*) including a plurality of vertically stacked growing assemblies (100*, 200*) integrated with a first and second vertical support structure (VSS1*, VSS2*) wherein the first growing assembly (100*) is supported by a first horizontal support structure (SS1*) and a second growing assembly (200*) is supported by a second horizontal support structure (SS2*).

FIG. 3' depicts one non-limiting embodiment of a plurality of vertically stacked systems (1500*, 1500'*) including a first vertically stacked system (1500*) and a second vertically stacked system (1500'*), the first vertically stacked system (1500*) as depicted in FIG. 2', also both vertically stacked systems (1500*, 1500'*) are contained within an enclosure (ENC*) having an interior (ENC1*).

Figure 4A:
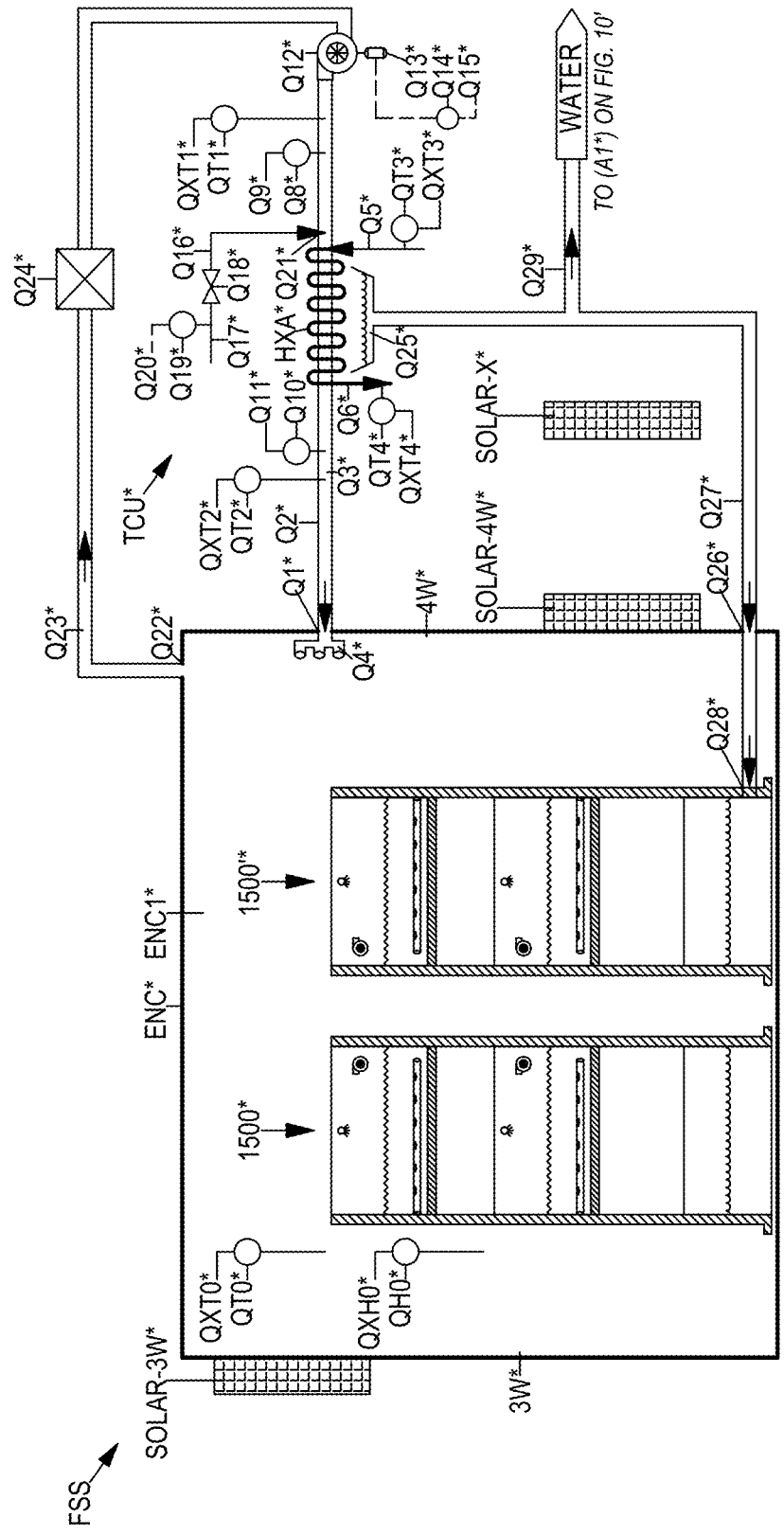

FIG. 4A' depicts one non-limiting embodiment of FIG. 3' wherein the enclosure (ENC*) is provided with a temperature control unit (TCU*) including an air heat exchanger (HXA*) that is configured to provide a temperature and/or humidity controlled air supply (Q3*) to the interior (ENC1*) of the enclosure (ENC*) which contains a plurality of vertically stacked systems (1500*, 1500'*).

Figure 4B:
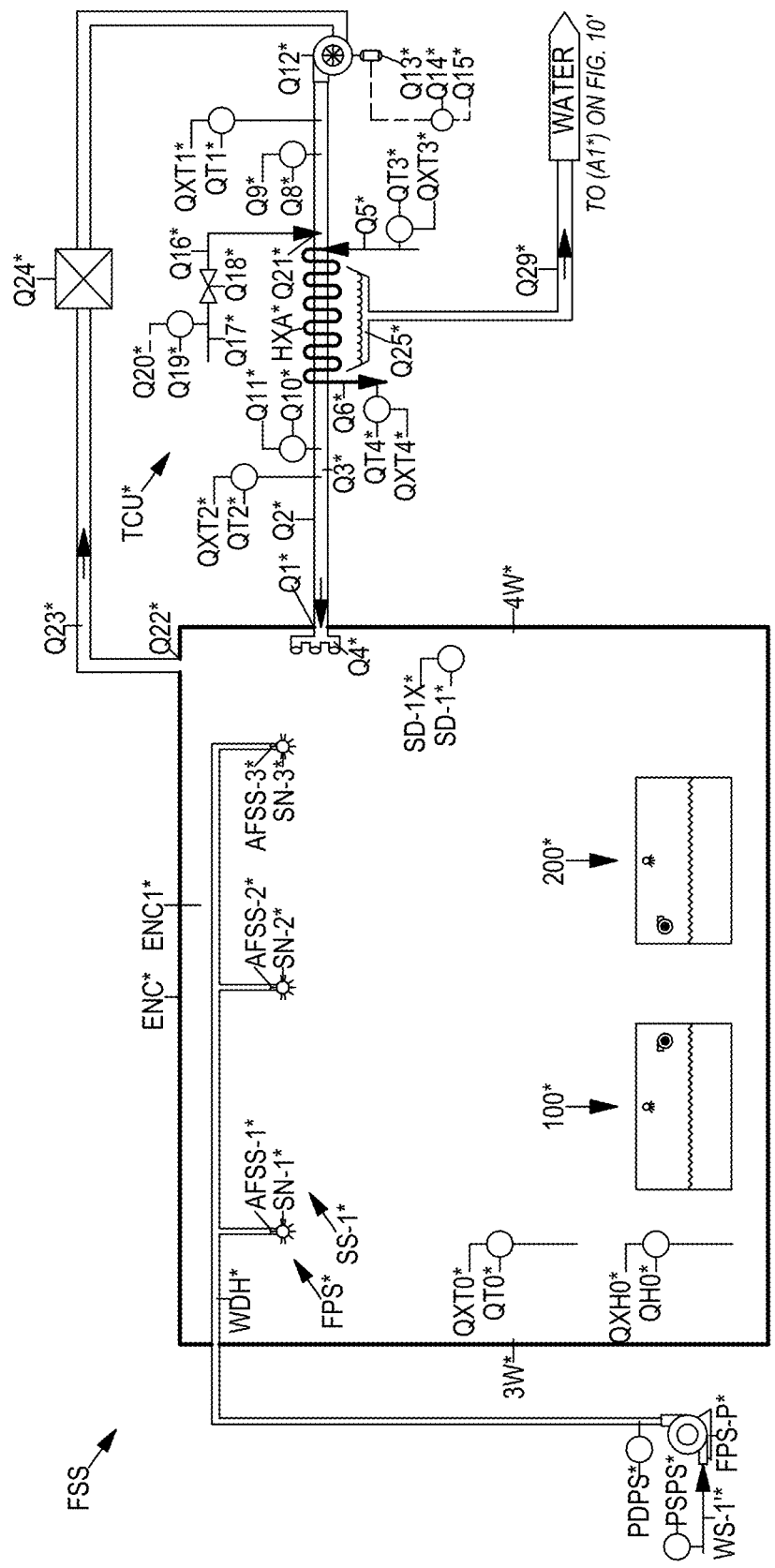

FIG. 4B' depicts one non-limiting embodiment of FIG. 1B' and FIG. 4A' wherein the enclosure (ENC*) is provided with a temperature control unit (TCU*) including an air heat exchanger (HXA*) that is configured to provide a temperature and/or humidity controlled air supply (Q3*) to the interior (ENC1*) of the enclosure (ENC*) which contains a plurality of growing assemblies (100*, 200*).

Figure 5A:
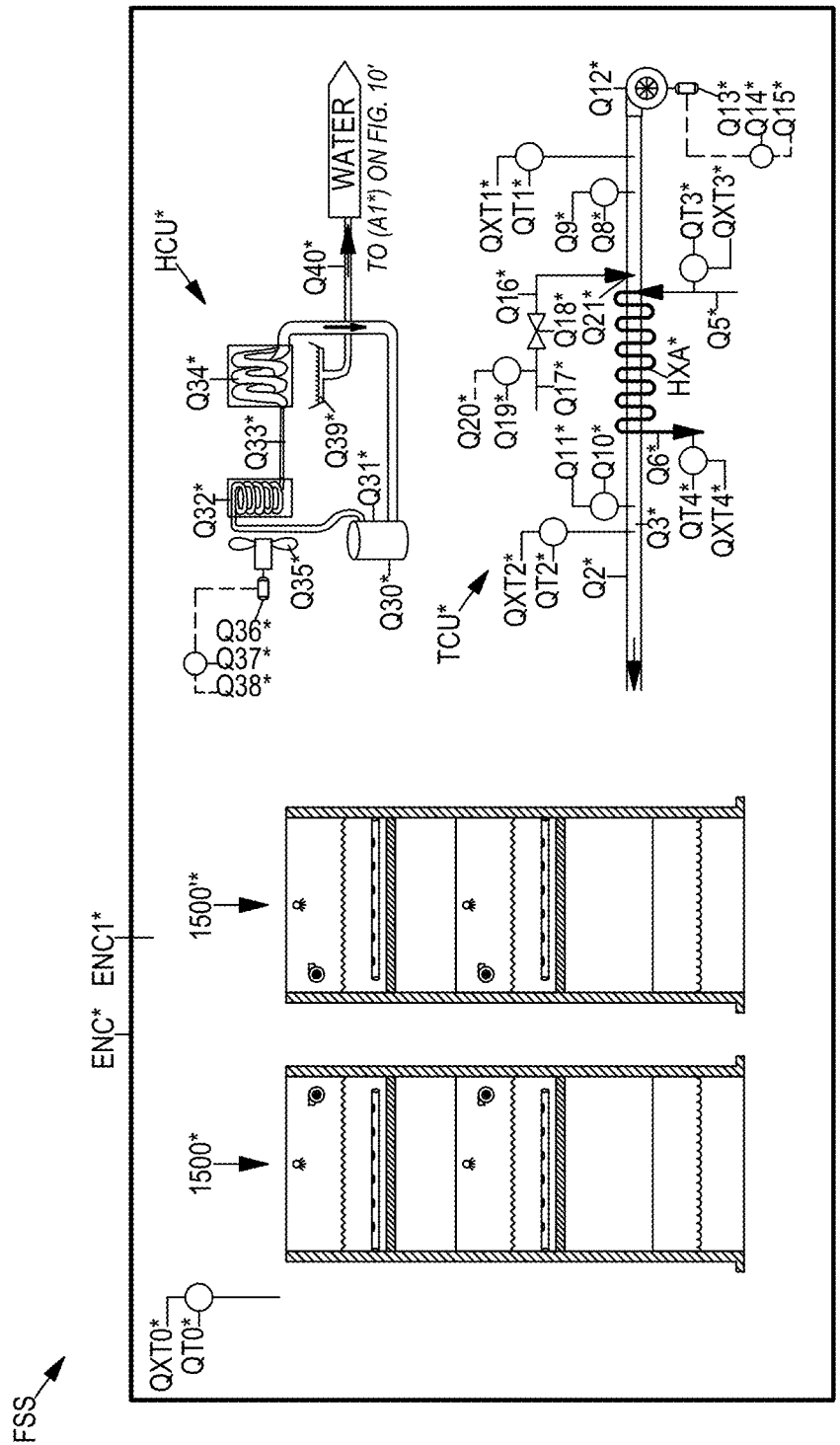

FIG. 5A' depicts one non-limiting embodiment of FIG. 4A' wherein the temperature control unit (TCU*) of FIG. 4A' is contained within the interior (ENC1*) of the enclosure (ENC*) and coupled with a humidity control unit (HCU*).

Figure 5B:
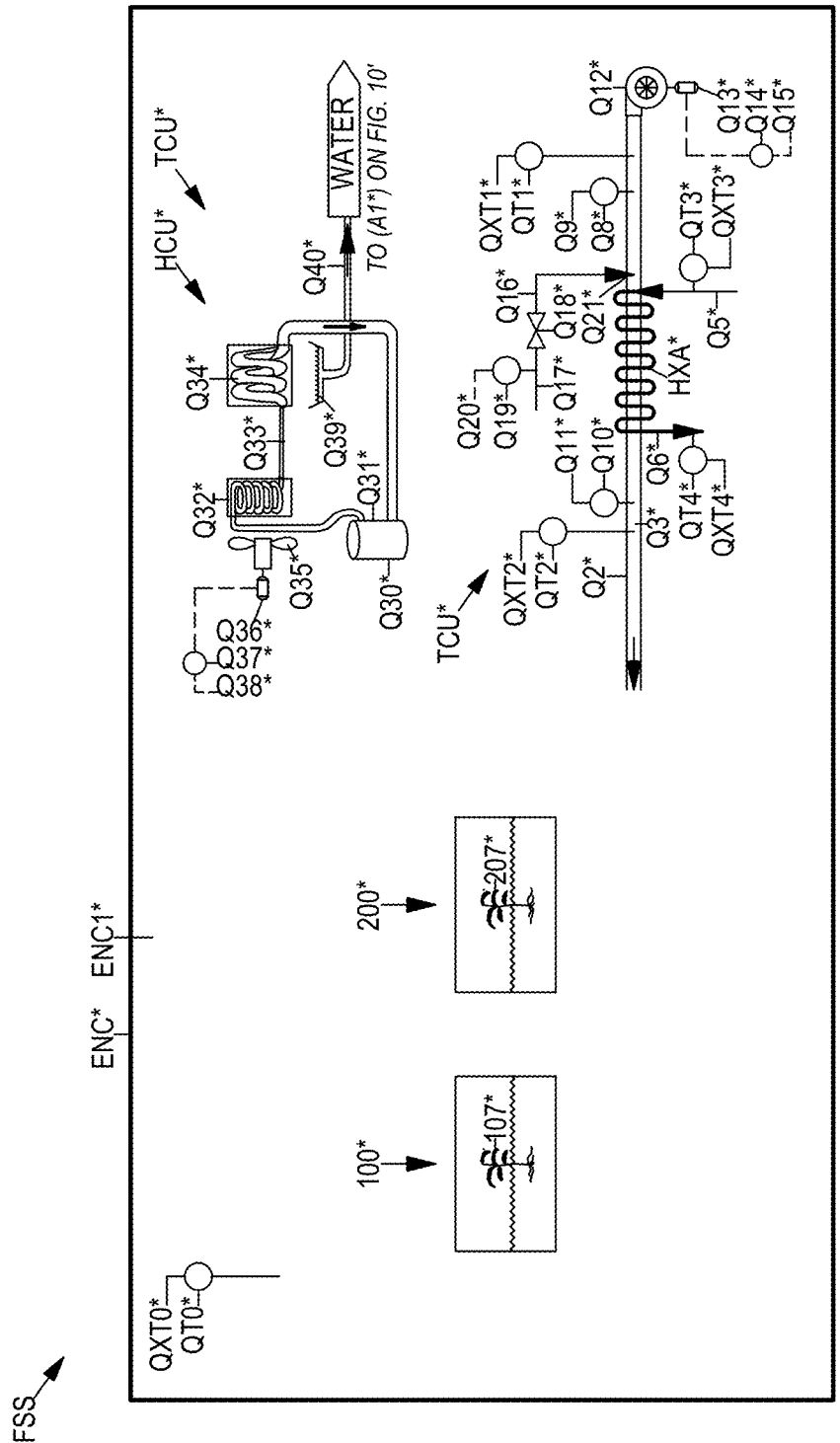

FIG. 5B' depicts one non-limiting embodiment of FIG. 4B' and FIG. 5A' wherein the temperature control unit (TCU*) of FIG. 4B' is contained within the interior (ENC1*) of the enclosure (ENC*) and coupled with a humidity control unit (HCU*).

Figure 5C:
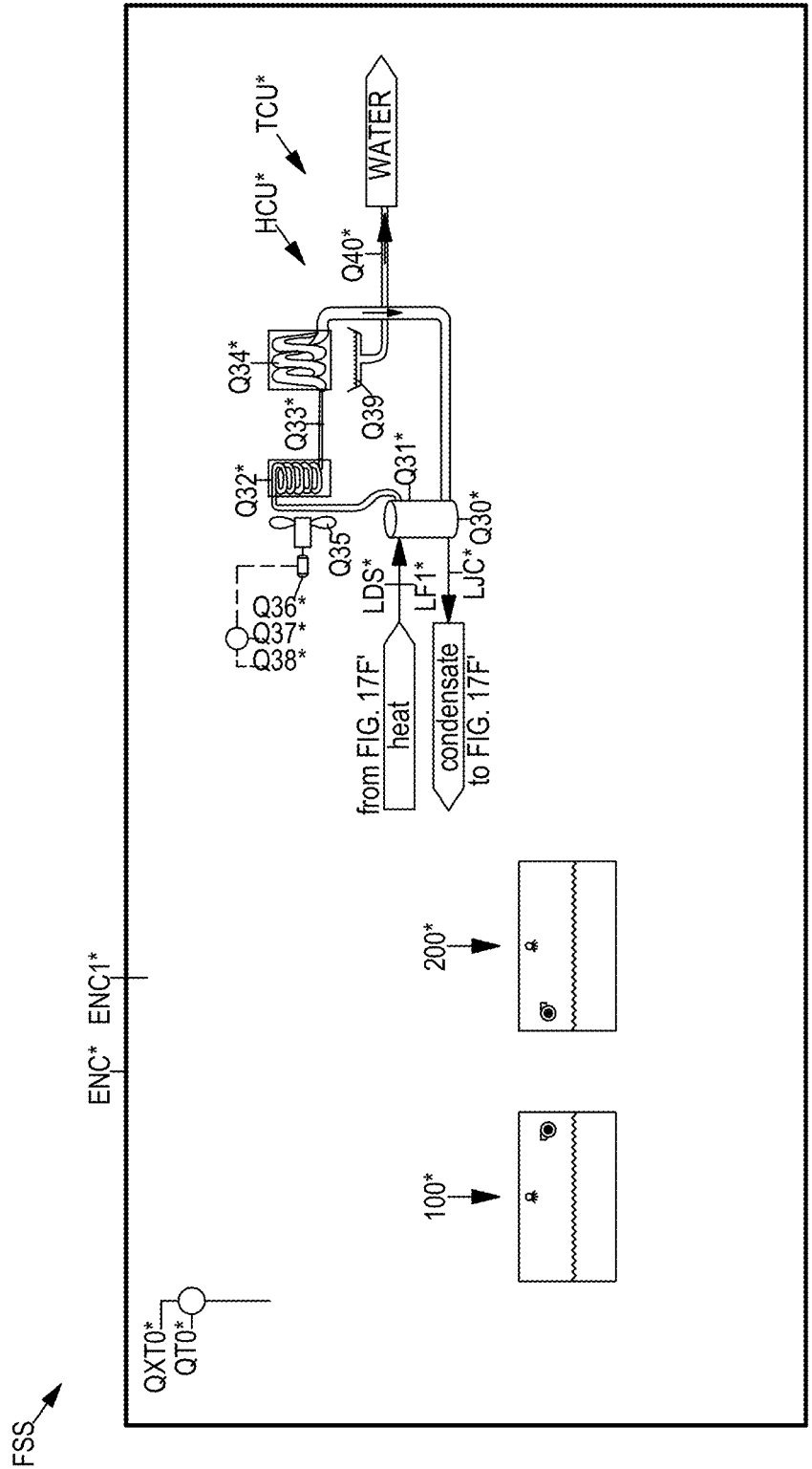

FIG. 5C' shows one non-limiting embodiment where the compressor (Q30*) within the humidity control unit (HCU*) is that of a thermal compressor (Q30*) that accepts a source of steam.

Figure 5D:
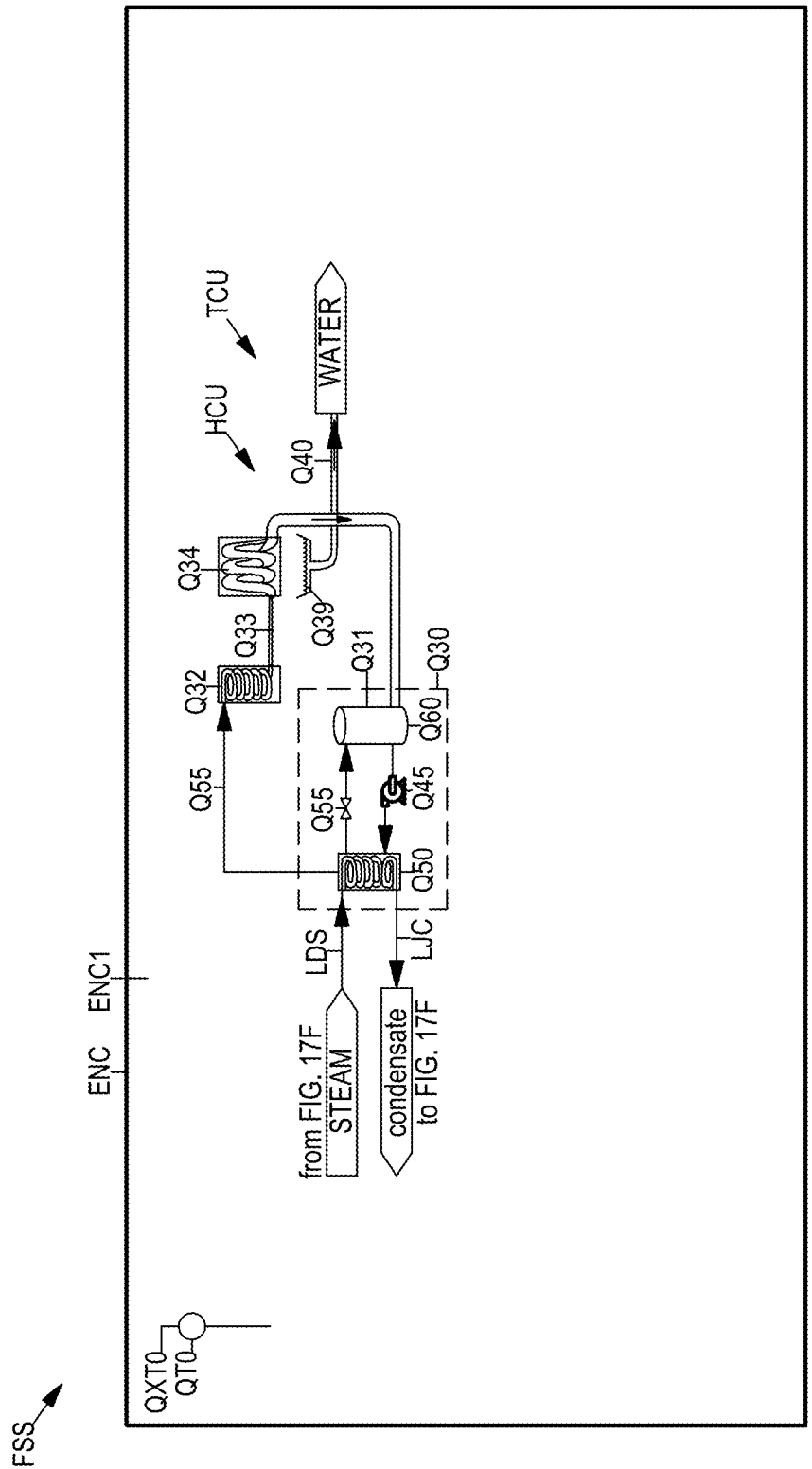

FIG. 5D' shows one non-limiting embodiment where the compressor (Q30*) within the humidity control unit (HCU*) is that of a thermal compressor (Q30*) that accepts a source of steam.

Figure 5E:
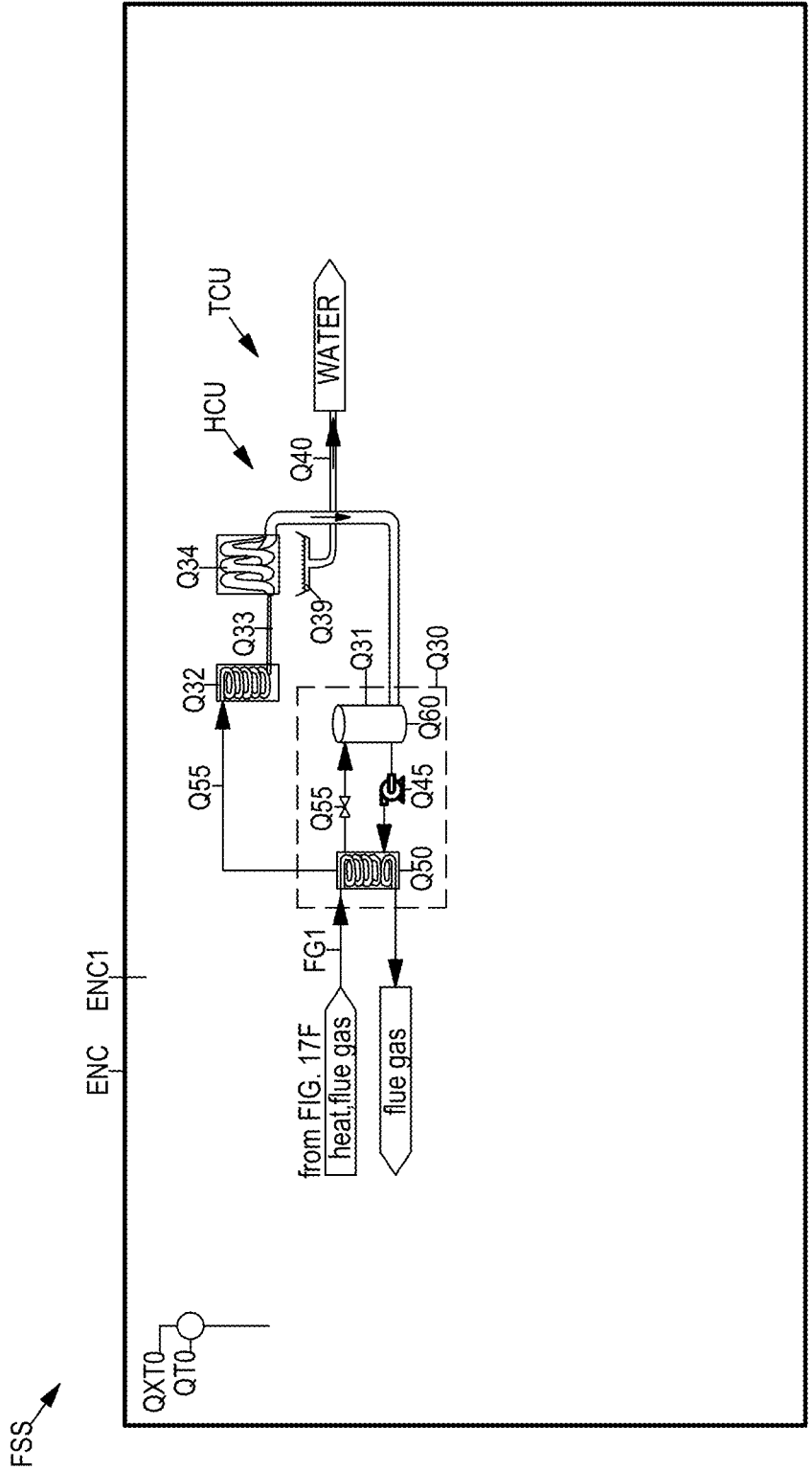
Figure 6:
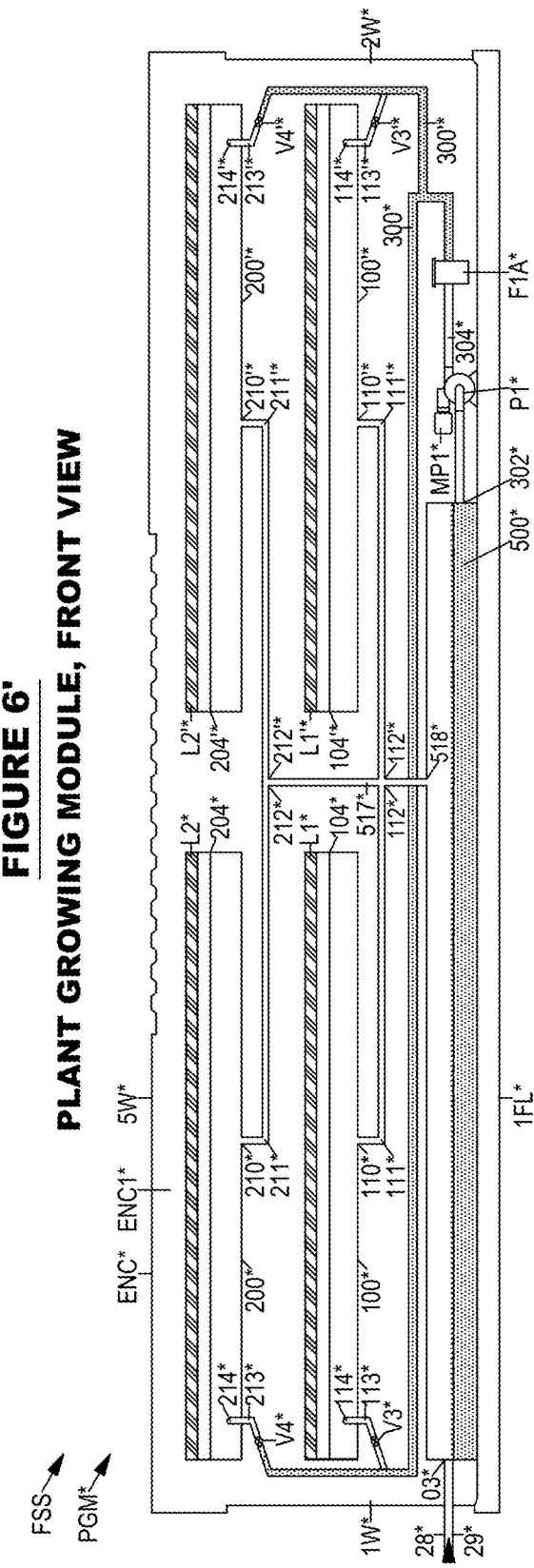
Figure 7:
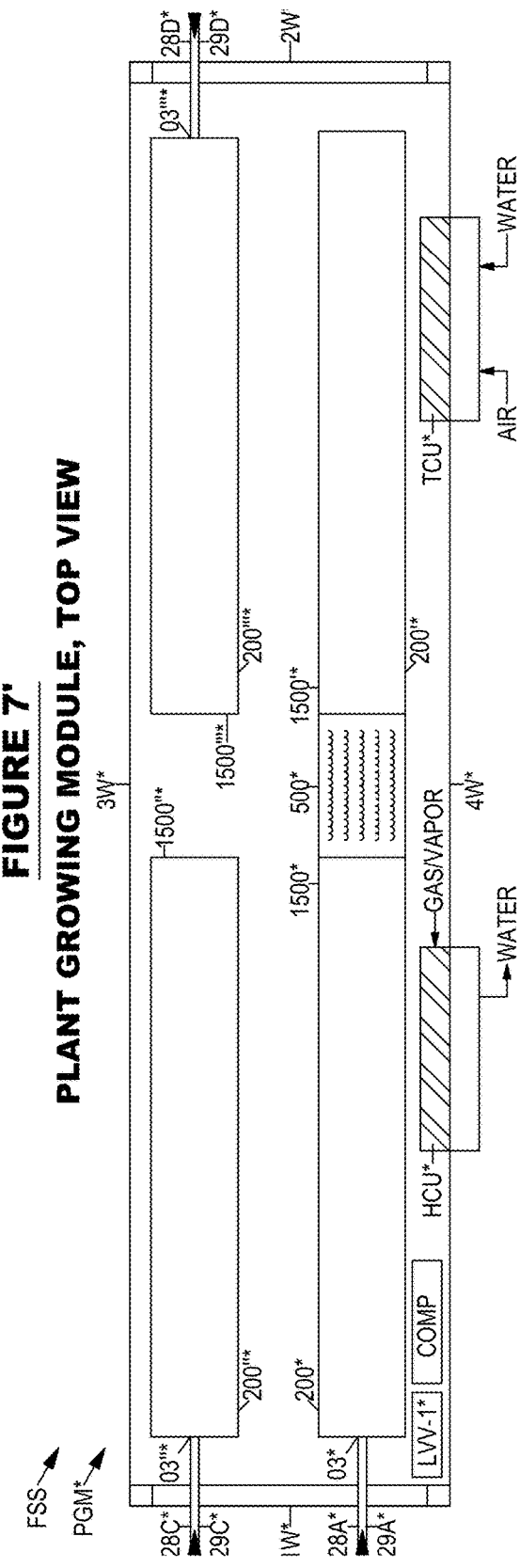
Figure 9:
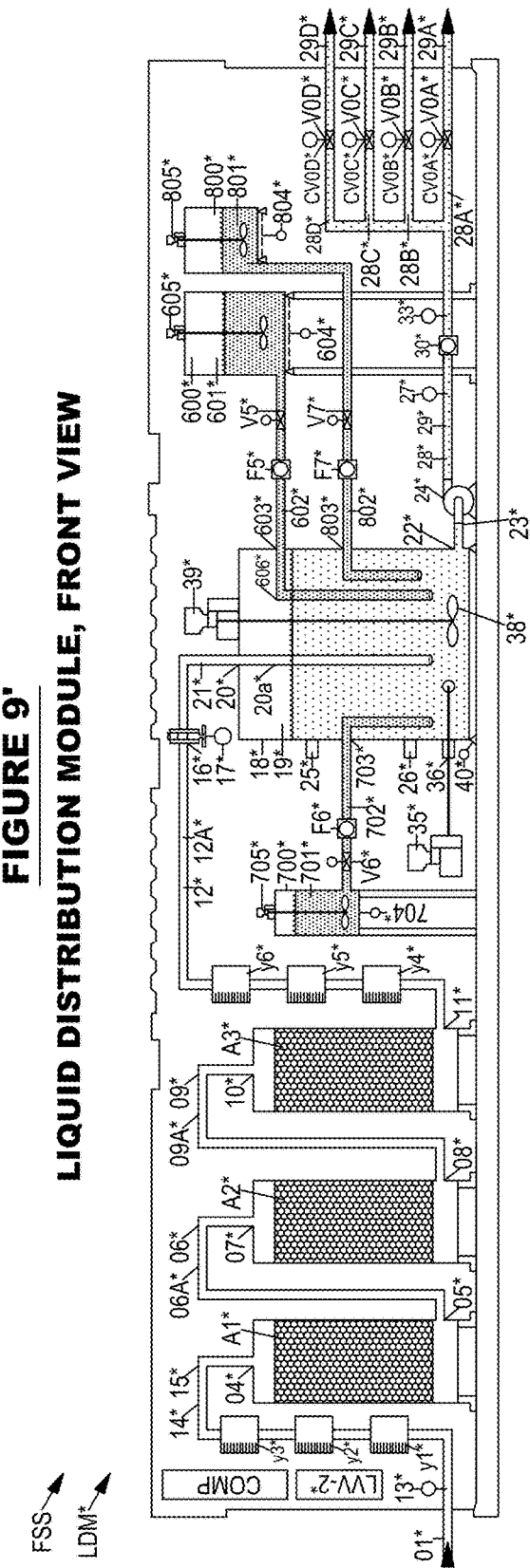
Figure 10:
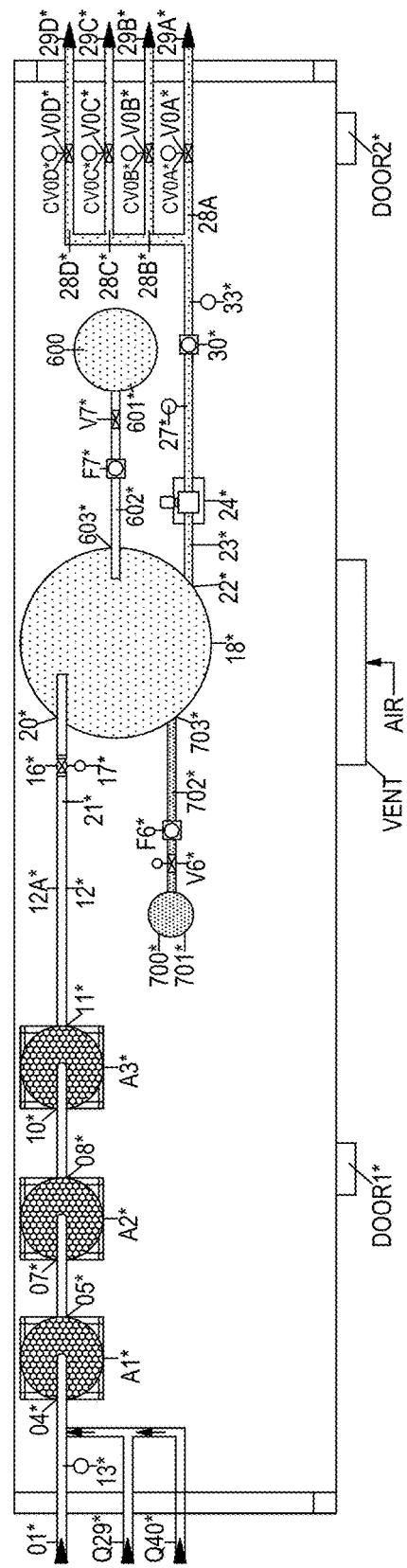
Figure 11:
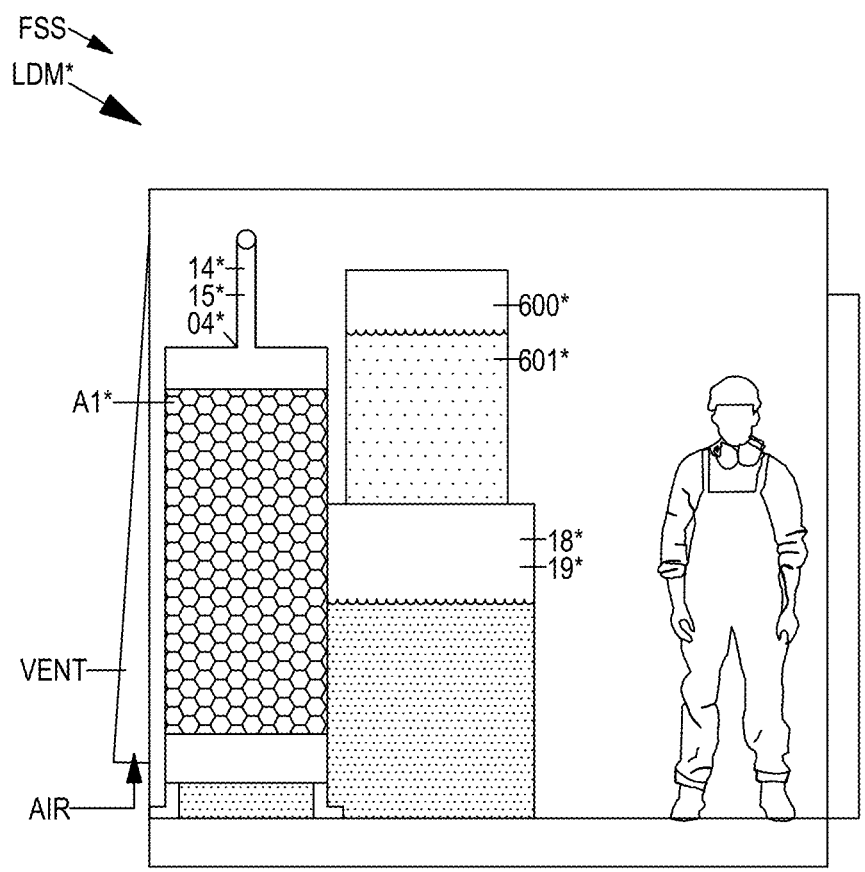

FIG. 5E' elaborates upon FIG. 5D' and shows one non-limiting embodiment where the compressor (Q30*) within the humidity control unit (HCU*) is that of a thermal compressor (Q30*) that accepts a source of heat, such as flue gas (FG1*)

FIG. 6' shows a front view of one embodiment of a plant growing module (PGM*) provided inside of a shipping container conforming to the International Organization for Standardization (ISO) specifications.

FIG. 7' shows a top view of one embodiment of a plant growing module (PGM*) provided inside of a shipping container conforming to the International Organization for Standardization (ISO) specifications.

FIG. 8' shows a first side view of one embodiment of a plant growing module (PGM*).

FIG. 9' shows a front view of one embodiment of a liquid distribution module (LDM*) provided inside of a shipping container conforming to the International Organization for Standardization (ISO) specifications and that is configured to provide a source of liquid to a plurality of plant growing modules (PGM*).

FIG. 10' shows a top view of one embodiment of a liquid distribution module (LDM*) provided inside of a shipping container conforming to the International Organization for Standardization (ISO) specifications and that is configured to provide a source of liquid to a plurality of plant growing modules (PGM*).

FIG. 11' shows a first side view of one embodiment of a liquid distribution module (LDM*).

Figure 12:
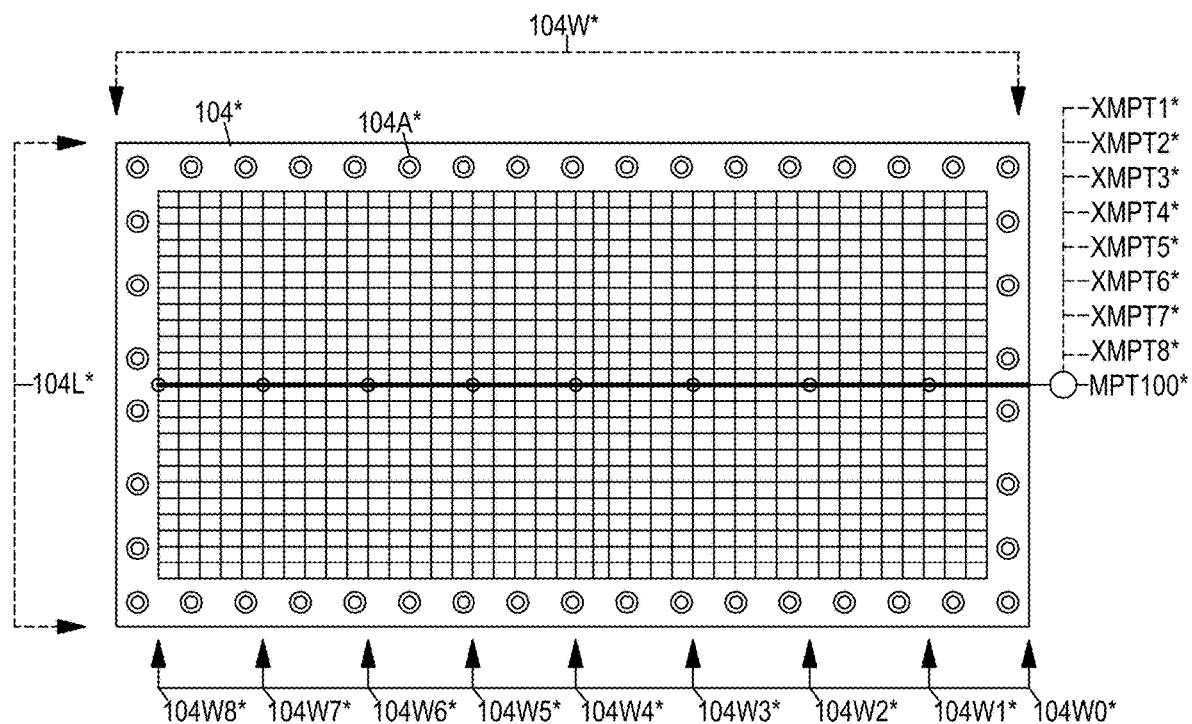
Figure 13:
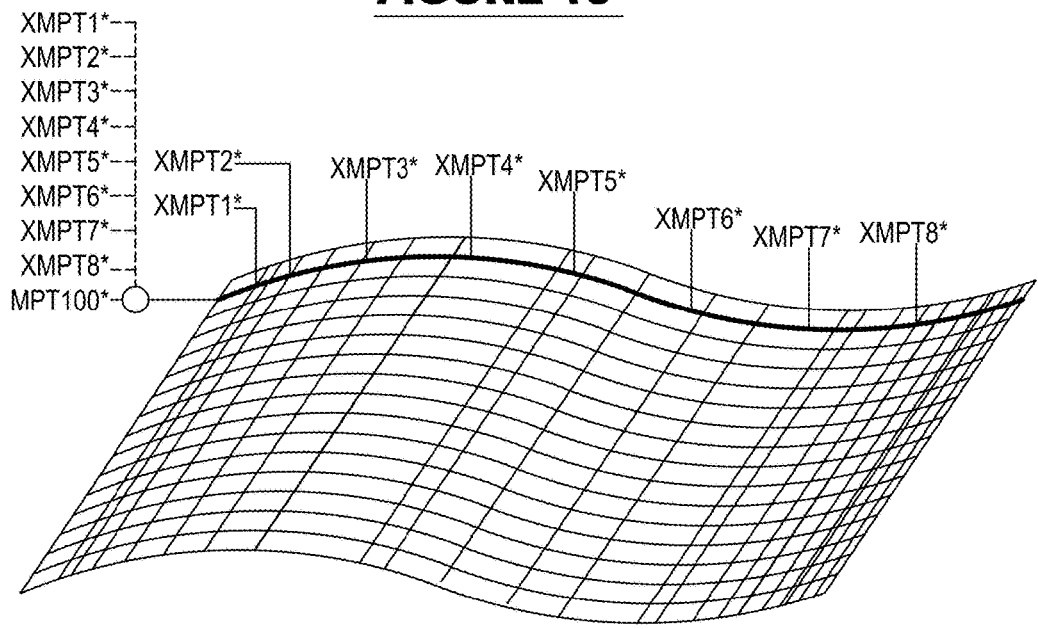

FIG. 12' shows one non-limiting embodiment of a fabric (104*) used in a growing assembly (100), the fabric (104) having a multi-point temperature sensor (MPT10*0) connected thereto for measuring temperatures at various lengths along the sensor's length.

FIG. 13' shows another one non-limiting embodiment of a fabric (104*) used in a growing assembly (100).

Figure 14:
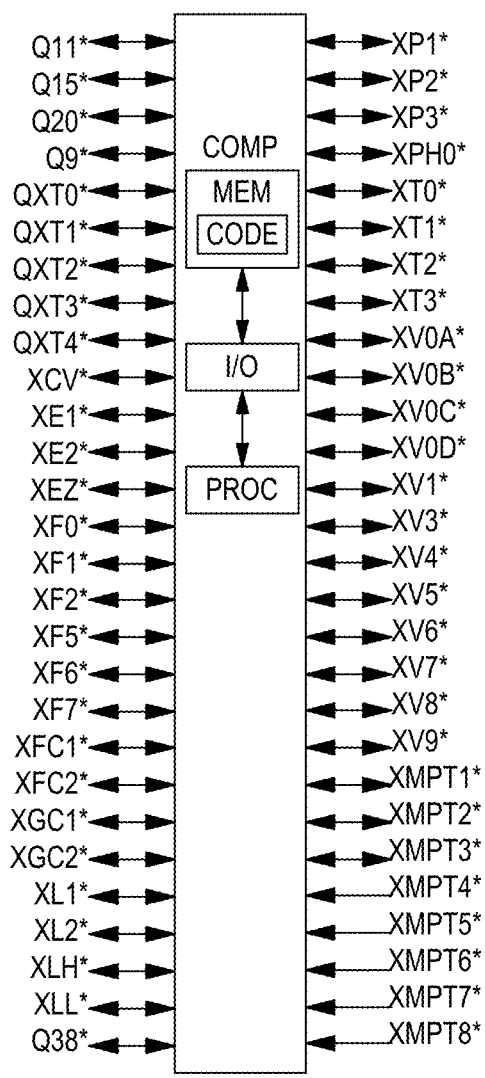
Figure 15:
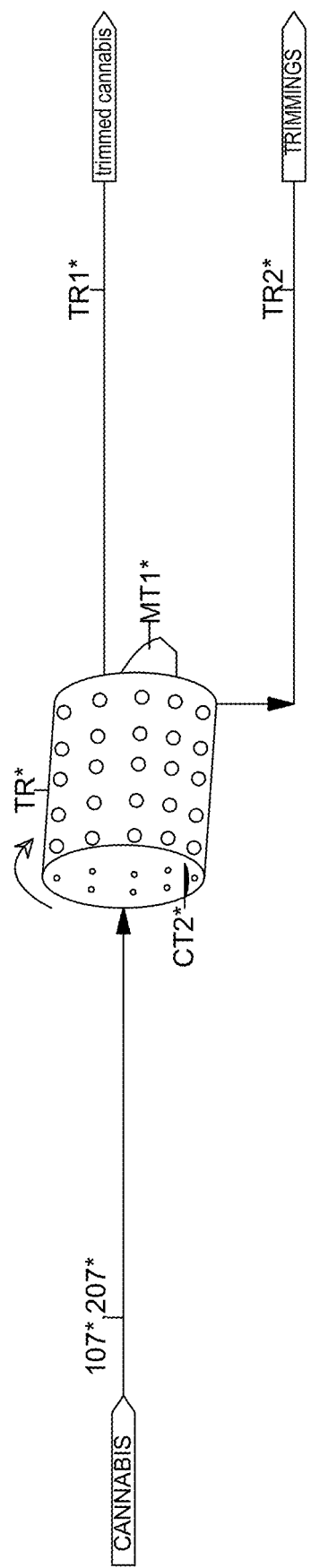
Figure 16:
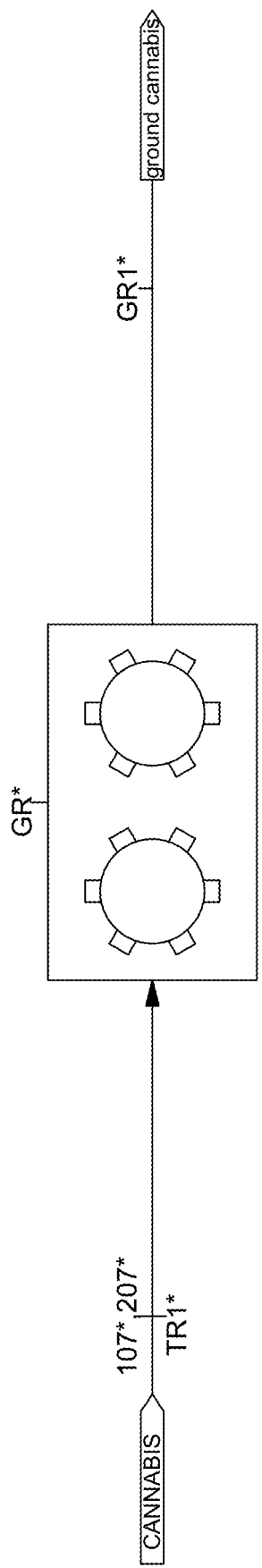

FIG. 14' depicts a computer (COMP) that is configured to input and output signals listed in FIGS. 1-17K'.

FIG. 15' shows a trimmer (TR*) that is configured to trim at least a portion of *cannabis* plants (107*, 207*) that was growing in each growing assembly (100*, 200*).

FIG. 16' shows a grinder (GR*) that is configured to grind at least a portion of *cannabis* plants (107, 207*) that was growing in each growing assembly (100*, 200*).

FIG. 17' shows a heater (HTR1*) that is configured to heat at least a portion of *cannabis* plants (107*, 207*) that was growing in each growing assembly (100*, 200*).

Figure 17A:
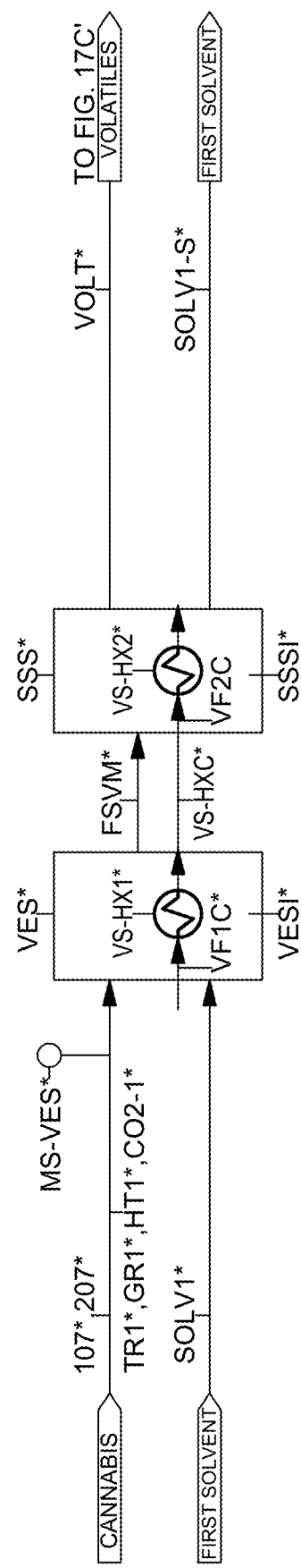

FIG. 17A' shows one non-limiting embodiment of a volatiles extraction system (VES*) that is configured to extract volatiles from *cannabis* (107*, 207*) with a first solvent (SOLV1*).

Figure 17B:
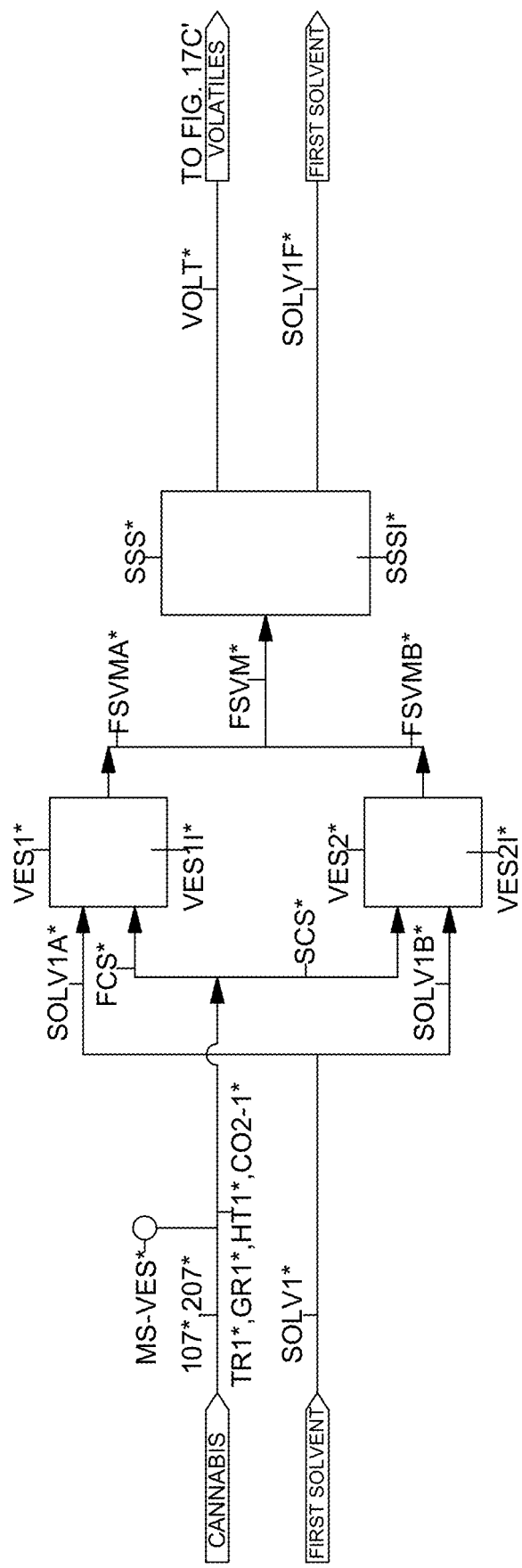

FIG. 17B' shows a plurality of volatiles extraction systems (VES1*, VES2*) equipped with one first solvent separation system (SSS*).

Figure 17C:
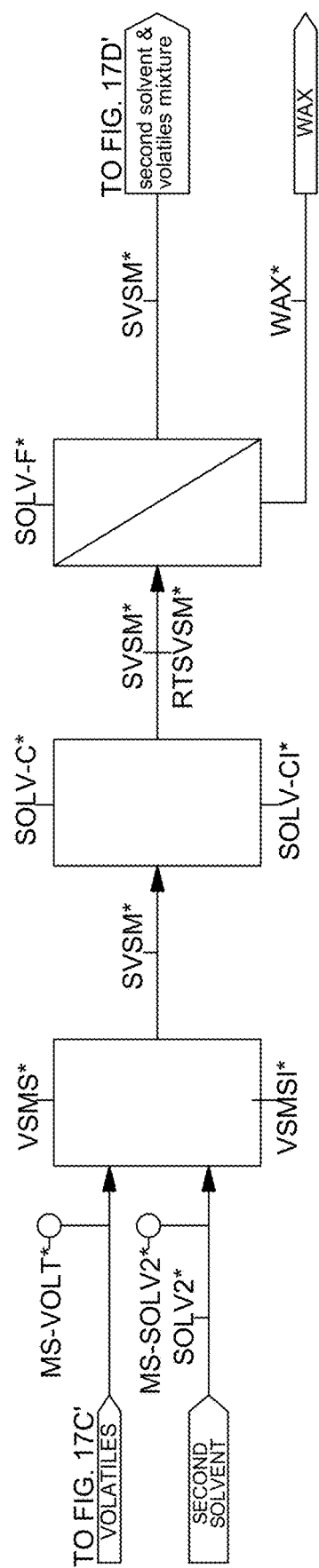

FIG. 17C' shows a volatiles and solvent mixing system (VSMS*) that is configured to mix the volatiles (VOLT*) with a second solvent (SOLV2*).

Figure 17D:
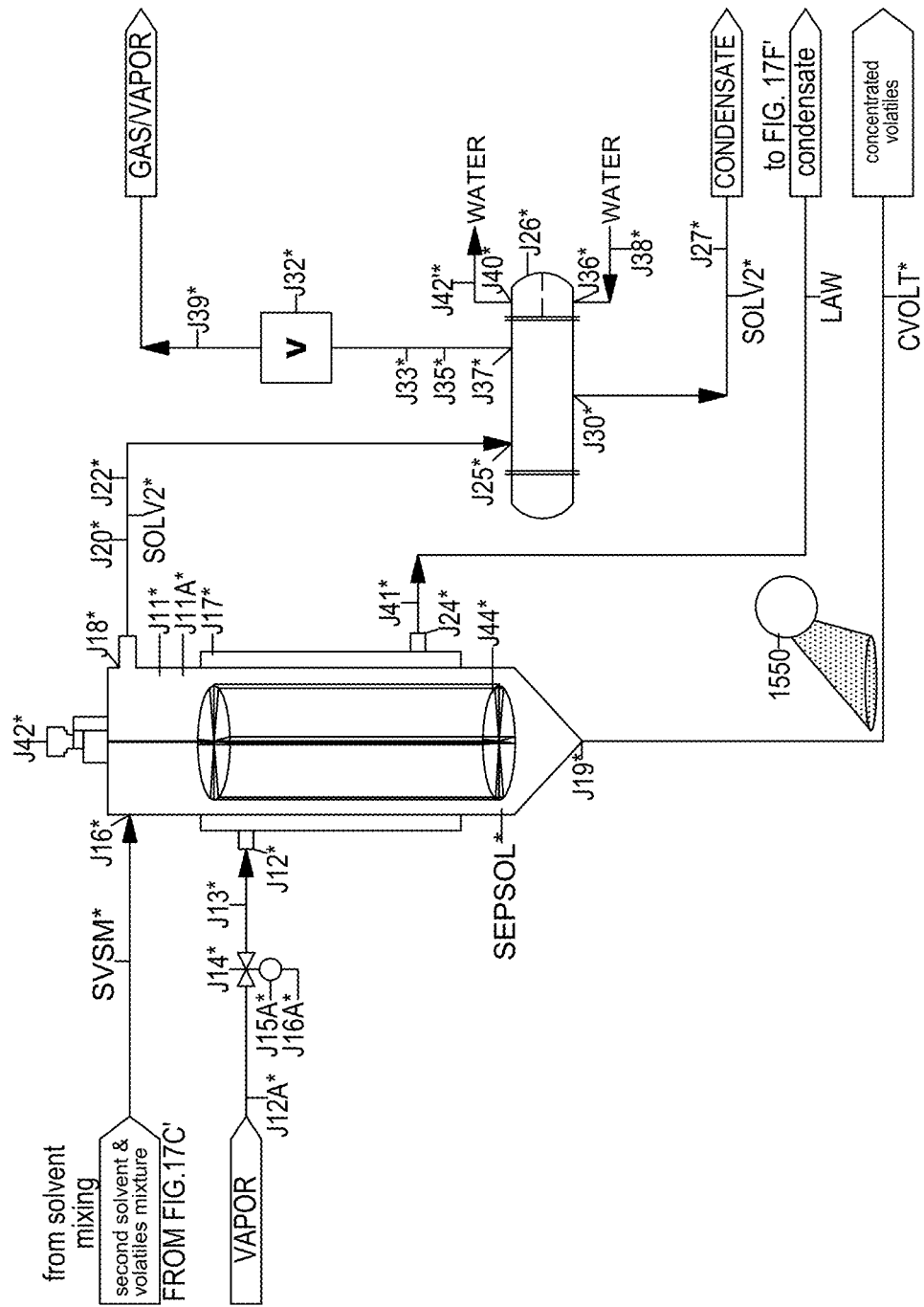

FIG. 17D' shows a second solvent separation system (SEPSOL*) that is configured to separate at least a portion of the second solvent (SOLV2*) from the second volatiles and solvent mixture (SVSM*) to produce concentrated volatiles (CVOLT*).

Figure 17E:
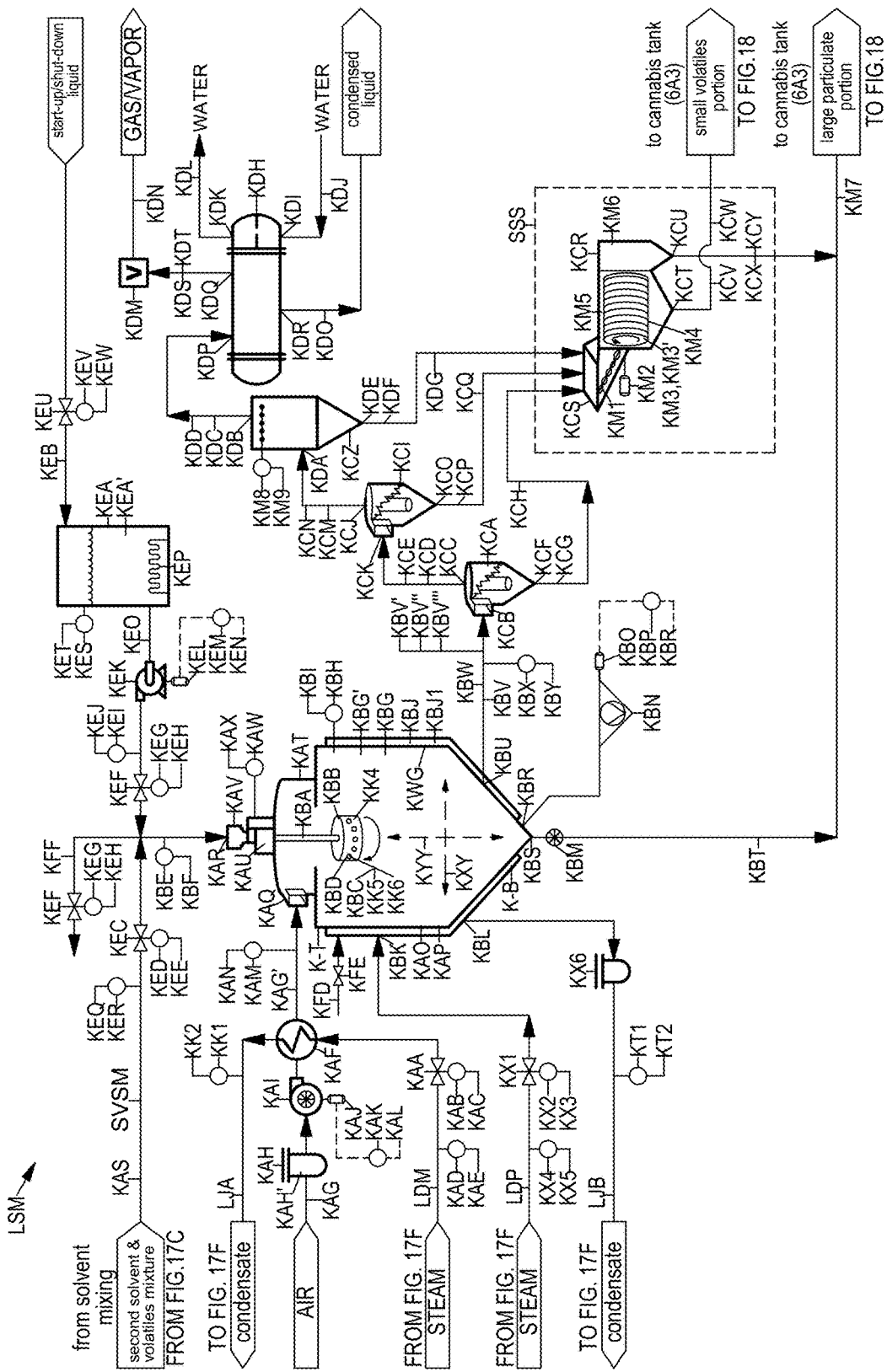
Figures 1, 17E:
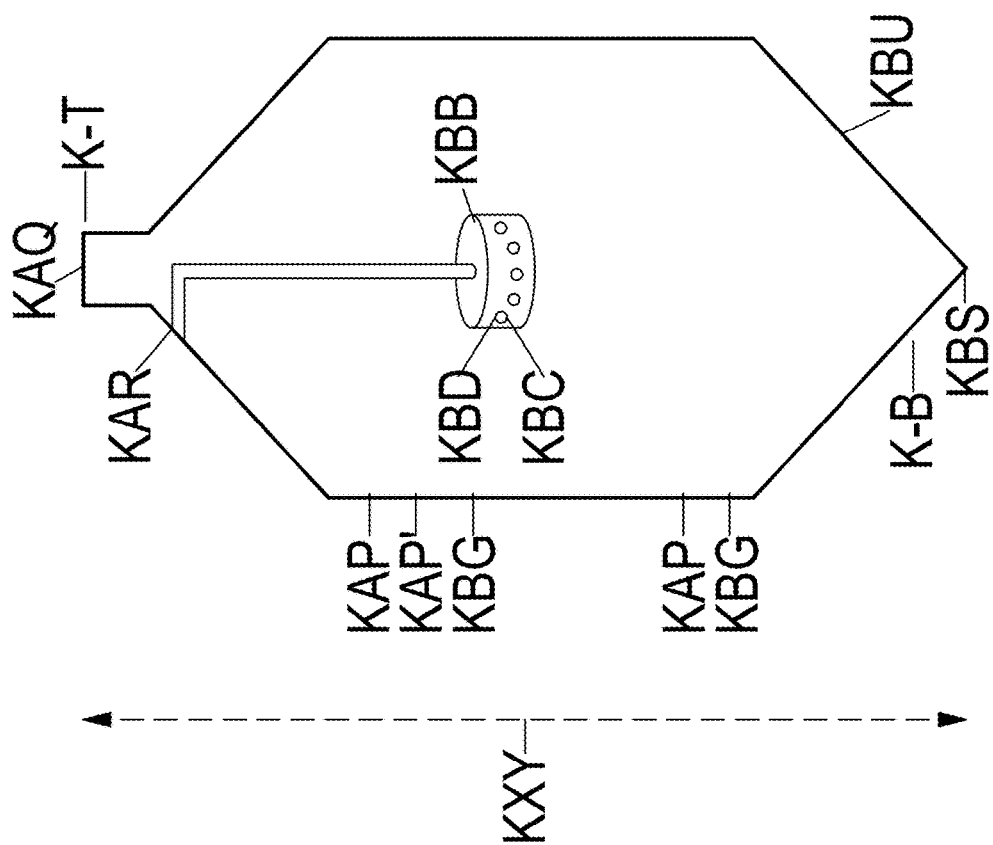
Figures 2, 17E:
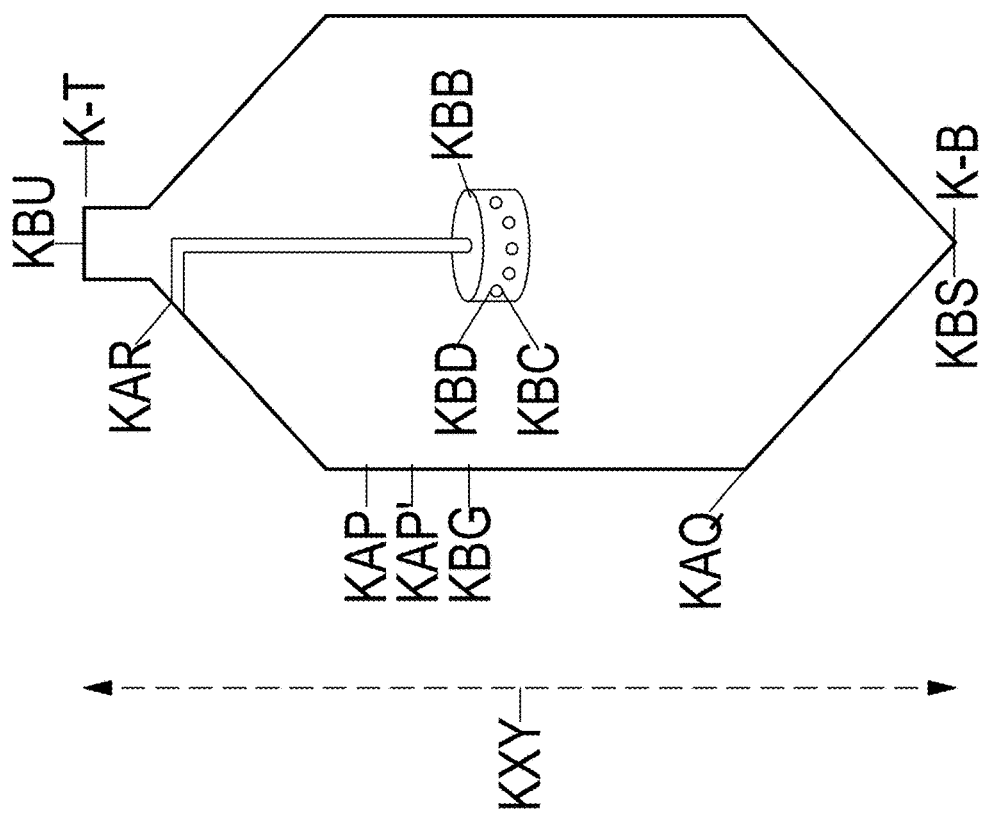
Figures 4, 17E:
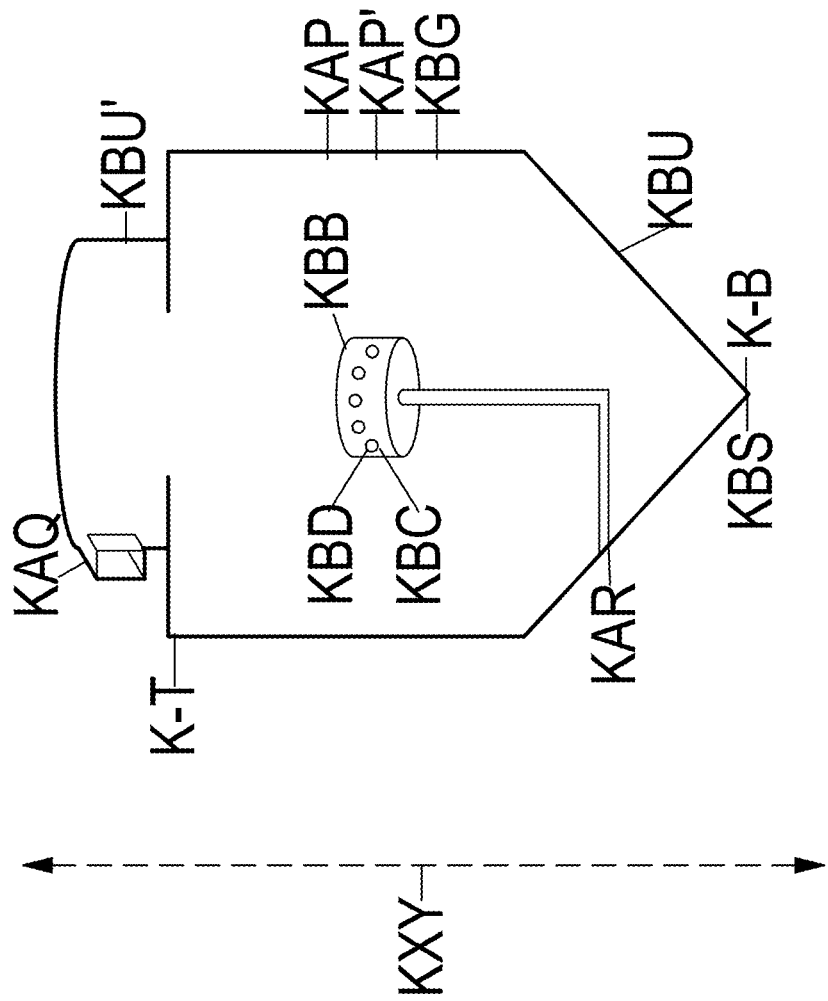

FIG. 17E' shows one non-limiting embodiment of a solvent separation system that is configured to evaporator the second solvent from the second volatiles and solvent mixture (SVSM*) by use of a spray dryer (KAP*).

FIG. 17E-1' shows one non-limiting embodiment of a co-current type of spray dryer (KAP*) that may be used with the solvent separation system described in FIG. 17E'.

FIG. 17E-2' shows one non-limiting embodiment of a counter-current type of spray dryer (KAP*) that may be used with the solvent separation system described in FIG. 17E'.

FIG. 17E-3' shows another non-limiting embodiment of a counter-current type of spray dryer (KAP*) that may be used with the solvent separation system described in FIG. 17E'.

FIG. 17E-4' shows one non-limiting embodiment of a mixed-flow type of spray dryer (KAP*) that may be used with the solvent separation system described in FIG. 17E'.

Figure 17F:
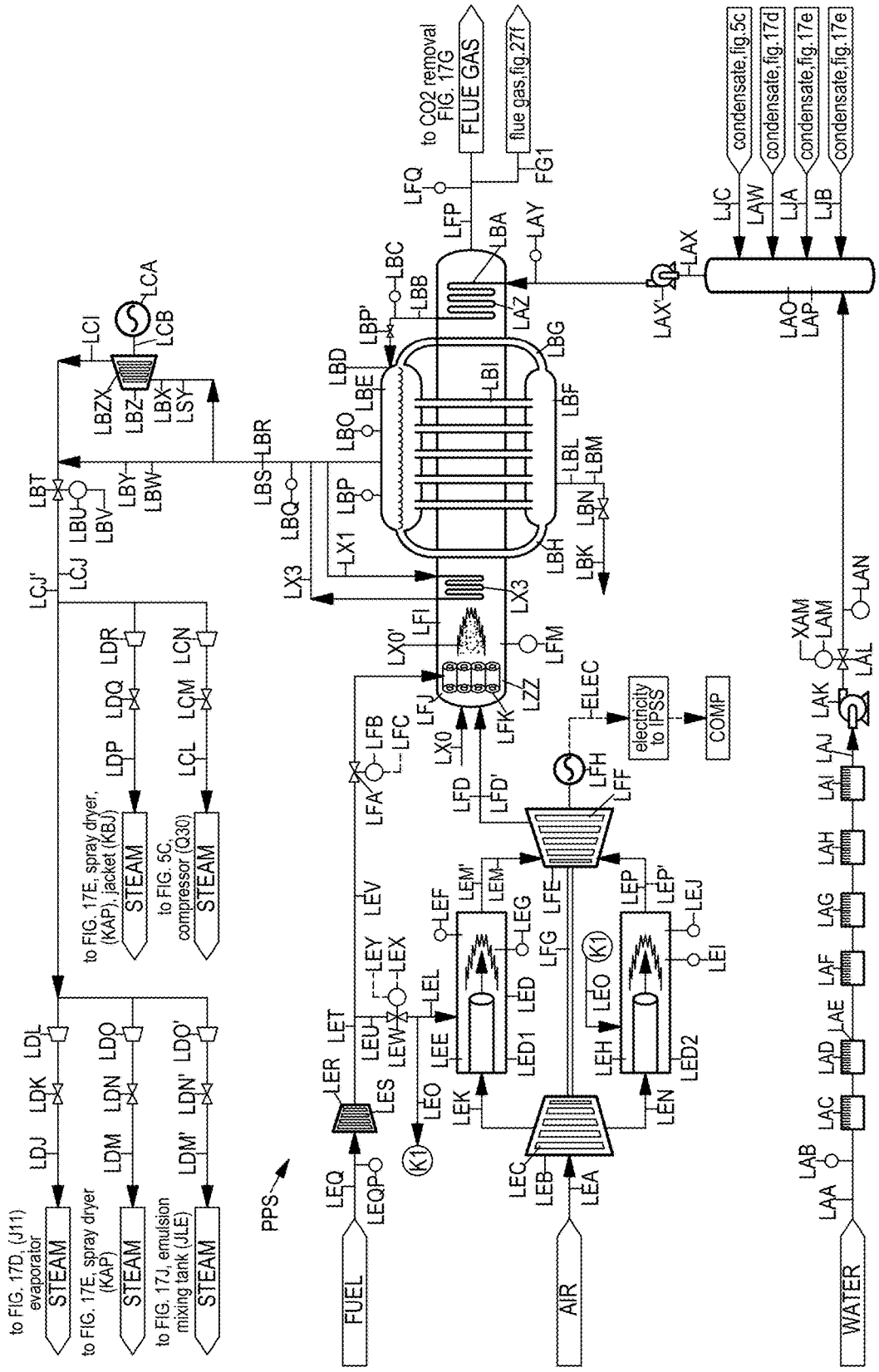

FIG. 17F' shows a power production system (PPS*) that is configured to generate electricity, heat, or steam for use in the farming superstructure system (FSS).

Figure 17G:
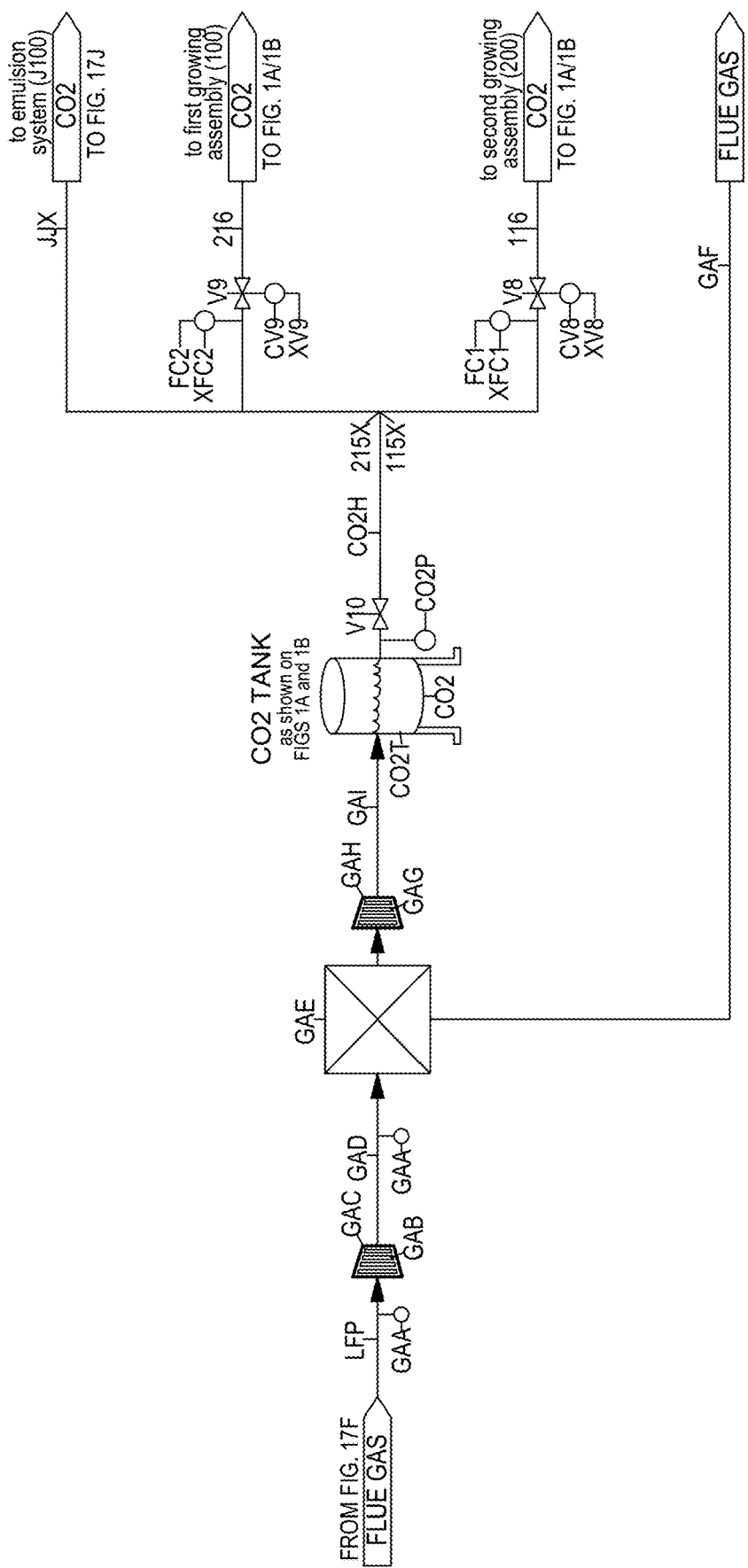

FIG. 17G' shows one non-limiting embodiment of a carbon dioxide removal system (GAE*) that is configured to remove carbon dioxide from flue gas (LFP*) for use as a source of carbon dioxide ($CO2^*$) in the farming superstructure system (FSS).

Figure 17H:
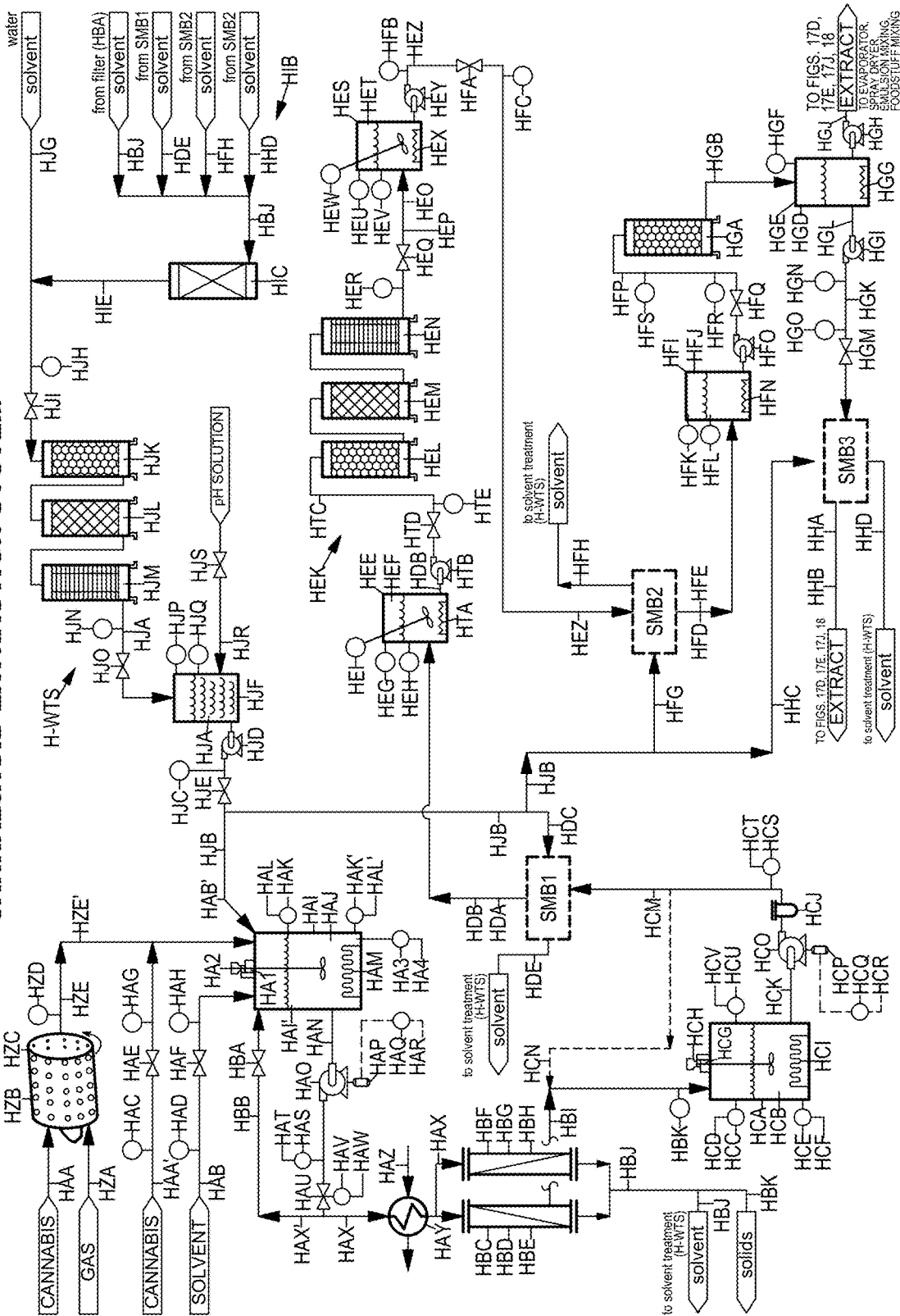

FIG. 17H' shows a cannabinoid extraction system including vessels, filters, pumps, piping connecting flow between vessels and adsorbers, valving, controllers, pressure regulators, metering equipment, flow control, and microprocessor equipment, their construction, implementation, and functionality.

Figure 17J:
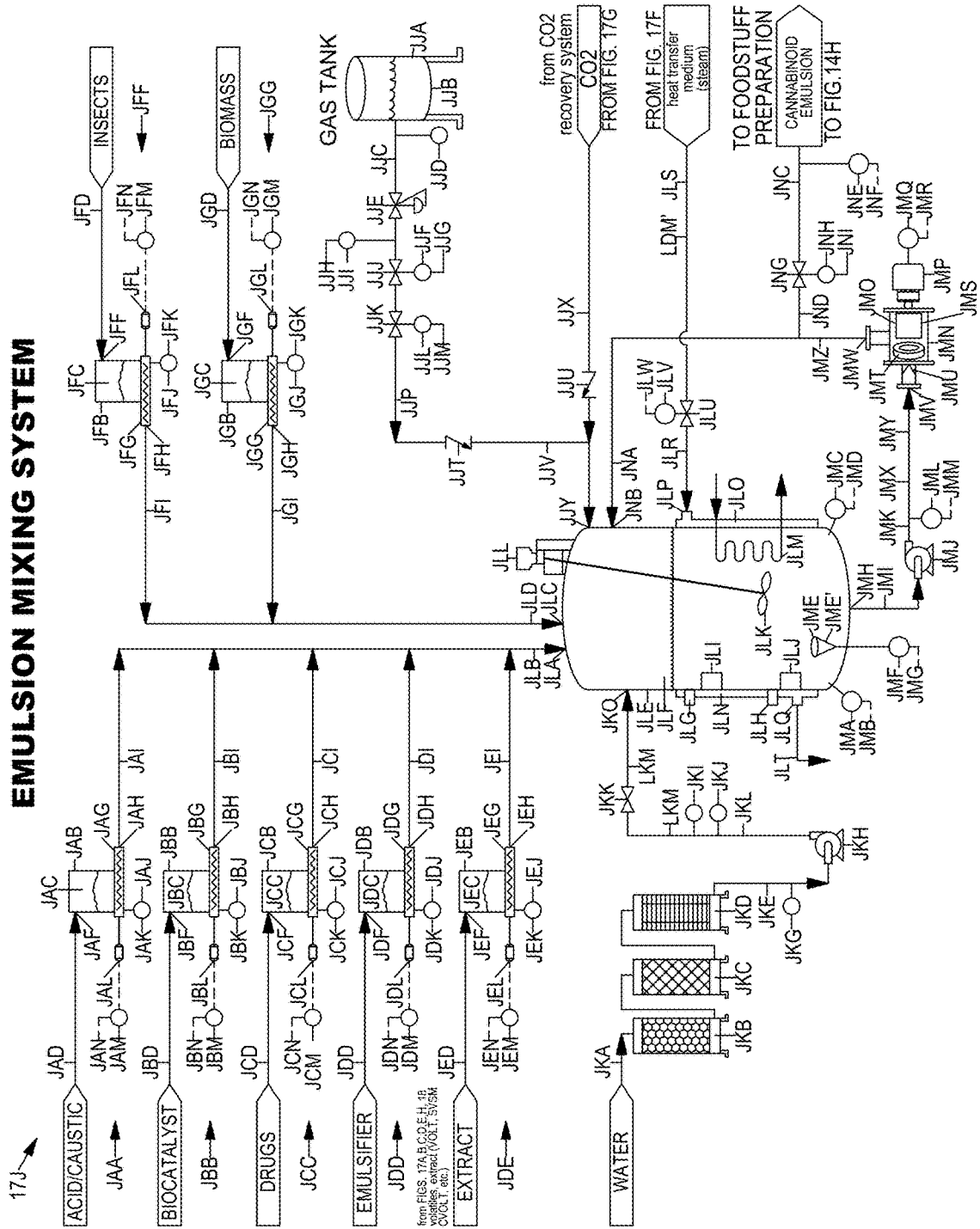

FIG. 17J' shows one non-limiting embodiment of a cannabinoid emulsion mixing system (17J*).

Figure 17K:
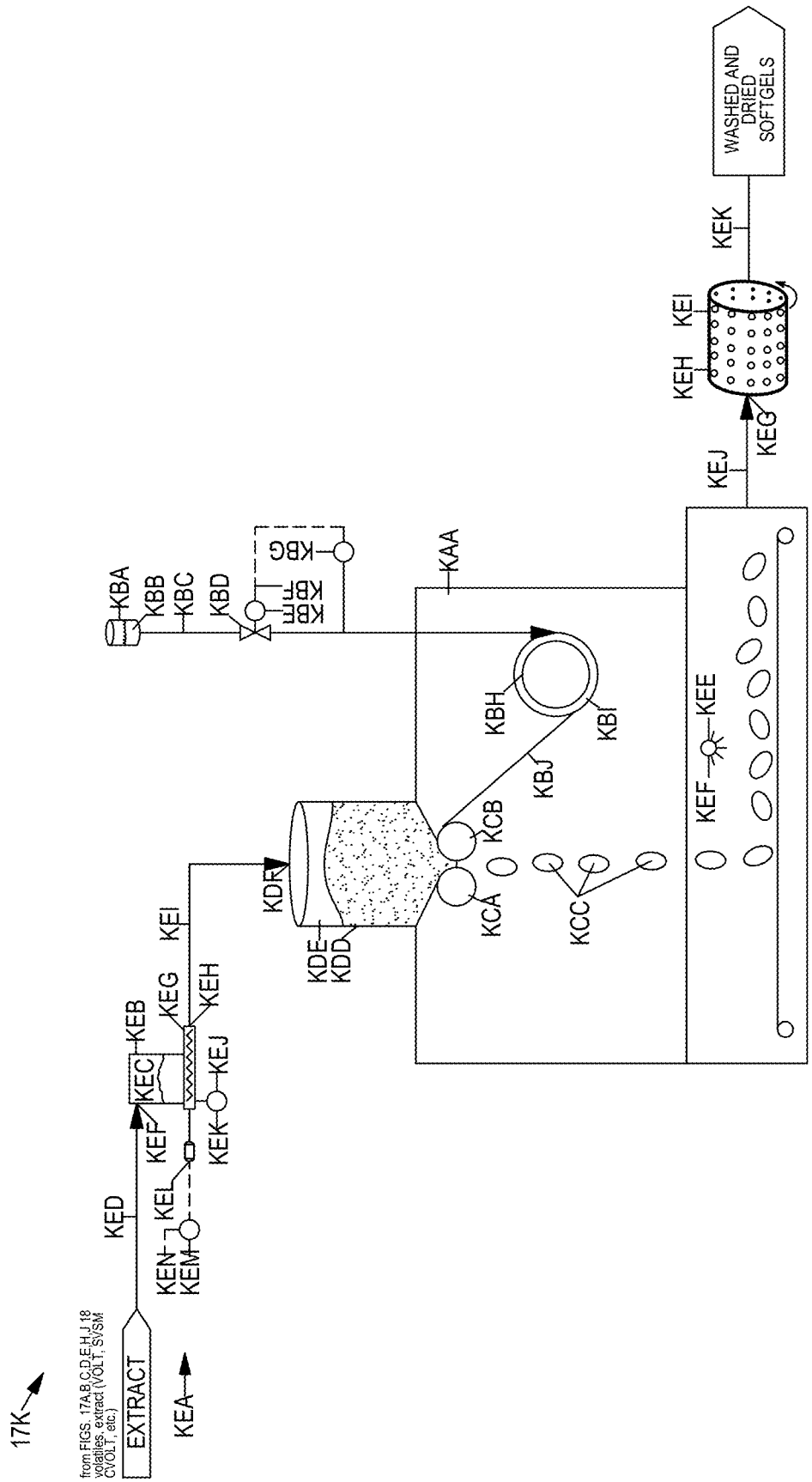

FIG. 17K' shows one non-limiting embodiment of a cannabinoid softgel encapsulation system (17K*).

FIG. 18' shows a simplistic diagram illustrating a multi-functional composition mixing module that is configured to generate a multifunctional composition from at least a portion of *Cannabis* plants (107*, 207*) that was harvested from each growing assembly (100*, 200*).

FIG. 19' illustrates a single fully-grown Beaufort Budman III plant.

FIG. 20' illustrates zoomed-in view of a budding or flowering plant.

FIG. 21' illustrates a single leaf of Beaufort Budman III.

FIG. 22' illustrates a trimmed and dried bud (reproductive structure) of Beaufort Budman III.

FIG. 23' shows a *cannabis* cloning assembly (CA*) that is configured to clone *cannabis* plants and/or Beaufort Budman III (107*, 207*) that were growing in each growing assembly (100*, 200*).

FIG. 1A:

FIG. 1A shows a simplistic block flow diagram of one embodiment of an Insect Production Superstructure System (IPSS) including the sequence steps of feedstock mixing (step A), feedstock splitting (step B), insect feeding (step C1, C2), insect breeding (step D), insect collection (step E), and insect grinding (step F).

FIG. 1A shows a plurality of sequence steps of an Insect Production Superstructure System (IPSS) including, feedstock mixing (step A), feedstock splitting (step B), insect feeding chamber #1 (step C1), insect feeding chamber #2 (step C2), insect breeding (step D), insect collection (step E), and insect grinding (step F).

Step A involves feedstock mixing where feedstock may be mixed with one or more additives from the group consisting of water, minerals, vitamins, and polymer to form an enhanced feedstock. Additionally, other enhancers may be added to the feedstock such as niacin, taurine, glucuronic acid, malic acid, N-acetyl L tyrosine, L-phenylalanine, caffeine, citicoline, or insect growth hormones. Table 1 on FIG.

40 lists the types of additives and enhancers that may be mixed with a feedstock to generate an enhanced feedstock.

Generally, a feedstock may be characterized as agriculture residue, alcohol production coproducts, animal waste, biowaste, compost, crop residues, energy crops, fermentation waste, meat, insects, fermentative process wastes, food processing residues, food waste, garbage, industrial waste, livestock waste, municipal solid waste, plant matter, poultry wastes, rice straw, sewage, spent grain, spent microorganisms, urban waste, vegetative material, or wood waste.

Mixing of feedstock with additives or enhancers is discussed below in detail. Exact proportions of feedstock, additives, and enhancers may be precisely combined to form an enhanced feedstock that is suitable to grow insects in a manner that maximizes productivity, minimizes mortality, and maximizes animal welfare. It has been my realization that the enhanced feedstock mixtures, weigh ratios, proportions, ranges cited in Table 1 of FIG. 40 are those that maximize insect production in a minimal amount of space.

It also has been my realization that the enhancers listed herein are those, when fed to insects, may then subsequently fed to humans as energy-Insects®, which are a specialized kind of edible insect that contains a dose of the stimulant caffeine, vitamins, and other functional ingredients. It has also been my realization that insects truly enjoy eating my inventive enhanced feedstock blend and it increases their quality of life. Although there is no evidence and no way of truly telling that insects have the cognitive ability to enjoy eating my proprietary enhanced feedstock blend, I certainly give them the benefit of the doubt.

It has also been my realization that mixing water with the feedstock profoundly benefits insects since it elevates their well-being by making it impossible for them not to fear from expiration from respiratory impairment from being drowned in or under a liquid. It is the totality of the features of the present application that provide the maximum benefit to society.

An enhanced feedstock transfer line (002) is discharged from feedstock mixing (step A) where it enters the feedstock splitting (step B). Step B feedstock splitting involves dividing the enhanced feedstock up into a plurality of enhanced feedstock steams. In embodiments, it may be advantageous to have a plurality of insect feeding chambers and only one feedstock mixing sequence step. This minimizes the capital intensity of the Insect Production Superstructure System (IPSS) to thus in turn permits a more lucrative return on investment (ROI). In some instances, Step B may not be required since only one feeding chamber is desired.

A first enhanced feedstock transfer line (004) and a second enhanced feedstock transfer line (006) are discharged from feedstock splitting (Step B) and are routed to insect feeding chamber #1 (step C1) and insect feeding chamber #2 (step C2). FIG. 1A discloses a plurality of feeding chamber steps (C1 and C2). Two feeding chambers are shown in FIG. 1A, however it is to be noted that only one may be utilized, or three (as depicted in FIG. 17), or more may be utilized as seen fit.

Although two feeding chambers are shown in FIG. 1A, it is to be noted that the egg-laying insects present therein may freely travel from one feeding chamber to another. This is evidenced by feeding chamber transfer line (008) which connects the insect feeding chamber #1 (step C1) with insect feeding chamber #2 (step C2). The plurality of feeding chambers and a passageways therebetween encourage egg-laying insects therein to express normal behavior by enabling mobility and relocation to a more suitable living environment. An insect may decide to up and relocate for any reason it chooses or no reason at all. In the event that one breeding chamber lacks sufficient amounts of enhanced feedstock, or is over-crowded, or contains diseased or cannibalistic insects, the insects may relocate to another feeding chamber to alleviate their discomfort, pain, injury, disease, and fear and distress.

Herein is disclosed an Insect Production Superstructure System (IPSS) that permits insects to have mobility and the opportunity to choose between different possible courses of action. Herein are disclosed advancements and better solutions that meet new requirements, unarticulated needs, or existing market needs in maximizing insect welfare, maximizing insect output on a minimal physical outlay, and benefit of large groups of people a high-value animal protein.

FIG. 1A shows a first egg-laden breeding material transfer line (020) and a second egg-laden breeding material transfer line (021) being mixed into a combined egg-laden breeding material transfer line (022) which is then in turn provided to insect breeding (step D).

Insect eggs are extracted from the plurality of breeding chambers and are provided to a breeding chamber where the eggs are incubated and hatched. Hatched insects are then provided to the plurality of insect feeding chambers (step C1 and C2) via a first feeding chamber hatched insect transfer line (024) and a second feeding chamber hatched insect transfer line (026), respectively. Thus, herein is disclosed a method to: (i) remove at least a portion of eggs laid by the egg-laying insects within the feeding chambers; (ii) incubate at least a portion of the removed eggs in a breeding chamber; (iii) hatch at least a portion of incubated eggs; and, (iv) introduce a portion of hatched insects back into the insect feeding chamber.

Generally, the innovative methods of the Insect Production Superstructure System (IPSS) and Farming Superstructure System (FSS) is more generally suited for insects including one or more selected from the group consisting of Anthocoridae, minute pirate bugs, pirate bugs, flower bugs, the genus Orius, omnivorous bugs, carnivorous bugs, Orthoptera order of insects, grasshoppers, crickets, katydids, weta, lubber, acrida, locusts, mites, spider mites, predatory mites, Neoseiulus Fallacis, genus of mites that are in the Phytoseiidae family, arthropods, beetles, cicadas, beetles, nematodes, mealworms, bats, mammals of the order Chiroptera, yellow mealworm beetles, *Tenebrio Molitor, Tetranychus Urticae*, carnivorous arthropods, omnivorous arthropods, green lacewings, insects in the family Chrysopidae, insects in the order Neuroptera, mantidflies, antlions, *Encarsia Formosa*, whitefly parasites, ladybugs, spiders, orb-weaving spiders, arachnids, members of the spider family Araneidae, praying mantis, arachnids, eight-legged arthropods, and six-legged arthropods.

In embodiments, the insects feed on insect eggs, insect larva, and other insects including living organisms which may or may not contain chitin not only including spider mites, rust mites, *thrips*, jumping plant lice, white fly, knats, gnats, aphids, and insects. In embodiments, the insects feed on *thrips* order Thysanoptera. In embodiments, the insects feed on *Tetranychus Urticae*. In embodiments, the insects feed on spider mites. In embodiments, the insects eat other insects that are found on the *cannabis* plants disclosed herein. In embodiments, the bats eat insects that are found on the *cannabis* plants disclosed herein.

Both the insect feeding chamber #1 (step C1) and insect feeding chamber #2 (step C2) are in fluid communication with insect collection (step E). The insect feeding chamber #1 (step C1) is in fluid communication with insect collection (step E) via a first feeding chamber insect transfer line (010). The insect feeding chamber #2 (step C2) is in fluid communication with insect collection (step E) via a second feeding chamber insect transfer line (012).

Insects may be collected from the insect feeding chambers in a number of ways. Some non-limiting embodiments of the present disclosure suggest removing the insects by vibrating the egg-laying insects from the feeding chamber. Some non-limiting embodiments of the present disclosure suggest removing the insects by conveying the egg-laying insects from the feeding chamber. Some non-limiting embodiments of the present disclosure suggest vacuuming the insects from the feeding chamber.

It is to be noted that all of the embodiments disclosed herein are non-limiting and as long as the insects are in fact removed from an insect feeding chamber by any conceivable means or method, the bounds of this application are deemed to have been infringed. Thus, it should be apparent, however, to those skilled in the art that many more modifications besides those already described are possible without departing from the inventive concepts herein related to removing insects from the feeding chamber. The inventive subject matter pertaining to removing insects from the feeding chambers, therefore, is not to be restricted to vibrating, conveying, vacuuming insects from the feeding chamber but instead extend to any possible means for achieving the end of removing insects from out of the interior of the feeding chamber.

In embodiments, the insect collection (step E) is in fluid communication with insect grinding (step F) via a combined collected insect transfer line (014). The insect grinding (step F) is configured to output ground insects via a ground insect transfer line (016).

FIG. 1B:

FIG. 1B elaborates upon the non-limiting embodiment of FIG. 1 further including the sequence steps of pathogen removal (step G) and multifunctional composition mixing (step H).

FIG. 1B shows a pathogen removal (step G) placed upstream of a multifunctional composition mixing (step H) step. In embodiments, the pathogen removal (step G) is configured to accept collected insects provided from the insect collection (step E) or insect grinding (step F). In embodiments, the pathogen removal (step G) is configured to accept collected insects provided from the insect collection (step E). In embodiments, the pathogen removal (step G) is configured to accept collected insects provided from the insect grinding (step F) as seen in FIG. 13 as accepting ground separated insects (1500). However, it is to be noted that grinding need not take place in order for pathogen to be removed from collected insects. As seen in the non-limiting embodiment of FIG. 1B, pathogen removal (step G) only places after insect collection (step E) and after insect grinding (step F). However, it is not necessary that grinding takes place in between insect collection (step E) and pathogen removal (step G).

Pathogen removal (step G) is optional. Until we know for sure that a death by being grinded up is not less painful than being microwaved, we will give the insects the benefit of the doubt and concede to the notion that sudden, instantaneous death will lead to less stress and suffering as opposed to being microwaved over up to about 500 seconds. Thus, it is the essence of this disclosure to intend that a person of ordinary skill in the art be on notice of my intention to entertain all possibilities to grinding insects, microwaving them, or suffocating them to death. Nonetheless, grinding can be before pathogen removal. Or pathogen removal can be before grinding. In embodiments, insects may be euthanized by hypothermia. In embodiments, insects may be euthanized by freezing them. In embodiments, insects may be euthanized by reducing the temperature to below 32 degrees Fahrenheit. In embodiments, insects may be euthanized by reducing the temperature to below 40 degrees Fahrenheit. In embodiments, insects may be euthanized by reducing the temperature to a temperature range selected from the group consisting of: 45 degrees Fahrenheit to 40 degrees Fahrenheit, 40 degrees Fahrenheit to 35 degrees Fahrenheit, 35 degrees Fahrenheit to 30 degrees Fahrenheit, 30 degrees Fahrenheit to 25 degrees Fahrenheit, 25 degrees Fahrenheit to 20 degrees Fahrenheit, 20 degrees Fahrenheit to 15 degrees Fahrenheit, 15 degrees Fahrenheit to 10 degrees Fahrenheit, 10 degrees Fahrenheit to 5 degrees Fahrenheit, 5 degrees Fahrenheit to 0 degrees Fahrenheit, 0 degrees Fahrenheit to −5 degrees Fahrenheit, −5 degrees Fahrenheit to −10 degrees Fahrenheit, −10 degrees Fahrenheit to −15 degrees Fahrenheit, and less than −15 degrees Fahrenheit.

Pathogen Removal (Step G)

The pathogen removal (step G) involves utilization of a pathogen removal unit to convert a stream of pathogen-laden insects into a stream of pathogen-depleted insects (1570). The pathogen removal (step G) removes pathogens from pathogen-laden insects to form pathogen depleted insects which has a reduced amount of pathogens relative to the pathogen-laden insects.

In embodiments, insects may be introduced to the interior (6A3) insect tank (6A2) from various locations including: from FIG. 14I and include the liquid-depleted insects (I50) that were filtered in the filter (I11); from FIG. 14J and include the liquid-depleted insects (J10, J53) that were discharged from the evaporator (J11); from FIG. 14K and include the third separated insects or fourth separated insects (KCX); from FIG. 14K and include the third separated insects or fourth separated insects (KCX); from FIG. 14K and include the small insect particulate portion (KCW) or the large insect particulate portion (KCY) that had undergone evaporation by spray drying.

In embodiments, pathogens are comprised of one or more from the group consisting of acute respiratory syndrome coronavirus, influenza A viruses, H5N1, H7N7, avian influenza, foot and mouth disease, bovine spongiform encephalopathy, Q-fever, cutaneous zoonotic leishmaniasis, Ebola, monkeypox, Rift Valley fever, Crimea Congo hemorrhagic fever, encephalopathy, West Nile fever, paramyxoviruses, viruses, bacteria, fungus, prions, and parasites. In embodiments, some of the aforesaid pathogens may be present in the insects that grow within the feeding chamber. It is possible that the water added to the enhanced feedstock contains pathogens as listed above which the insect's carry-on through to the humans and animals during consumption. Thus, it is of paramount importance to mitigate the possible threats to society that are associated with permitting pathogen-laden water to pass on to humans or animals via the pathogen-laden insects.

In embodiments, pathogens are removed from the insects by the application of heat. In embodiments, pathogens are removed by heating insects to a temperature range between about 110 degrees Fahrenheit to about 550 degrees Fahrenheit. In embodiments, pathogens are removed by heating insects to a temperature range between about 120 degrees Fahrenheit to about 170 degrees Fahrenheit. In embodiments, pathogens are removed by heating said insects to a temperature range between about 171 degrees Fahrenheit to about 250 degrees Fahrenheit. In embodiments, pathogens are removed by heating insects to a temperature range between about 350 degrees Fahrenheit to about 450 degrees Fahrenheit.

In embodiments, pathogens are removed from said insects with microwave radiation. In embodiments, the microwave radiation is in the form of variable frequency microwave radiation. In embodiments, the variable frequency microwave radiation operates at a frequency between about 2 GHz to about 8 GHz. In embodiments, the variable frequency microwave radiation operates at a frequency of about 2.45 GHz.

In embodiments, the variable frequency microwave radiation operates at a power level between about 30 Watts to about 500 Watts. In embodiments, the variable frequency microwave radiation operates at a power level between about 50 Watts to about 150 Watts. In embodiments, the variable frequency microwave radiation operates at a power level between about 100 Watts to about 200 Watts. In embodiments, pathogens are removed from said insects over a duration of time between about 0.1 seconds to about 500 seconds. In embodiments, pathogens are removed from said insects over a duration of time between about 0.5 seconds to about 15 seconds. In other embodiments, pathogens may be removed by boiling the insects in water.

FIG. 1A in no way describes every possible embodiment of the pathogen reduction disclosure because describing every possible embodiment would be impractical, if not impossible. FIG. 13 elaborates upon other possibilities related to removing pathogens from insects.

Multifunctional Composition Mixing (Step H)

The multifunctional composition mixing (step H) involves mixing the insects with fiber-starch materials, binding agents, density improving textural supplements, moisture improving textural supplements, and optionally *cannabis* enhancers, to form a multifunctional composition. The multifunctional composition may be further processed to create foodstuffs not only including ada, bagels, baked goods, beverages, biscuits, bitterballen, bonda, breads, cakes, candies, cereals, chips, chocolate bars, carbonated soft drinks, carbonated drinks, chocolate, coffee, cokodok, confectionery, cookies, cooking batter, corn starch mixtures, crackers, crêpes, croissants, croquettes, croutons, dolma, dough, doughnuts, energy bars, flapjacks, french fries, frozen custard, frozen desserts, frying cakes, fudge, gelatin mixes, granola bars, gulha, hardtack, ice cream, khandvi, khanom buang, krumpets, meze, mixed flours, muffins, multi-grain snacks, nachos, nian gao, noodles, nougat, onion rings, pakora, pancakes, panforte, pastas, pastries, pie crust, pita chips, pizza, poffertjes, pretzels, protein powders, pudding, rice krispie treats, sesame sticks, smoothies, snacks, soft drinks, sparkling drinks, specialty milk, tele-bhaja, tempura, toffee, tortillas, totopo, turkish delights, or waffles.

In embodiments, the fiber-starch materials may be comprised of singular or mixtures of cereal-grain-based materials, grass-based materials, nut-based materials, powdered fruit materials, root-based materials, tuber-based materials, or vegetable-based materials. In embodiments, the fiber-starch mass ratio ranges from between about 400 pounds of fiber-starch per ton of multifunctional composition to about 1800 pounds of fiber-starch per ton of multifunctional composition.

In embodiments, the binding agents may be comprised of singular or mixtures of agar, agave, alginin, arrowroot, aspartame, carrageenan, collagen, cornstarch, egg whites, finely ground seeds, furcellaran, gelatin, guar gum, honey, katakuri starch, locust bean gum, pectin, potato starch, proteins, *psyllium* husks, sago, sugars, *stevia*, syrups, tapioca, vegetable gums, or xanthan gum. In embodiments, the binding agent mass ratio ranges from between about 33 pounds of binding agent per ton of multifunctional composition to about 600 pounds of binding agent per ton of multifunctional composition.

In embodiments, the density improving textural supplements may be comprised of singular or mixtures of extracted arrowroot starch, extracted corn starch, extracted lentil starch, extracted potato starch, or extracted tapioca starch. In embodiments, the density improving textural supplement mass ratio ranges from between about 5 pounds of density improving textural supplement per ton of multifunctional composition to about 300 pounds of density improving textural supplement per ton of multifunctional composition.

In embodiments, the moisture improving textural supplements may be comprised of singular or mixtures of almonds, brazil nuts, cacao, cashews, chestnuts, coconut, filberts, hazelnuts, Indian nuts, macadamia nuts, nut butters, nut oils, nut powders, peanuts, pecans, pili nuts, pine nuts, pinon nuts, pistachios, soy nuts, sunflower seeds, tiger nuts, walnuts, and vanilla. In embodiments, the moisture improving textural supplement mass ratio ranges from between about 5 pounds of moisture improving textural supplement per ton of multifunctional composition to about 300 pounds of moisture improving textural supplement per ton of multifunctional composition.

In embodiments, a *cannabis* enhancer may be added to the multifunctional composition. The *cannabis* enhancer may be marijuana in a powdered, dried, ground, or decarboxylated form. In embodiments, the *cannabis* enhancer may be remnants of vaporization, such as substantially fixed carbon feedstock components. In embodiments, the *cannabis* enhancer may be comprised of volatile feedstock components and a solvent. In embodiments, the *cannabis* enhancer may be comprised of volatile feedstock components and an alcohol. The *cannabis* enhancer may be comprised of volatile feedstock components and fixed carbon feedstock components. In embodiments, *cannabis* enhancer may be comprised of volatile feedstock components. In embodiments, *cannabis* enhancer may be comprised of fixed carbon feedstock components. In embodiments, the *cannabis* enhancer contains tetrahydrocannabinol (THC) in a mixture of volatile feedstock components and fixed carbon feedstock components.

In embodiments, the multifunctional composition ranges from between about 1800 pounds of *cannabis* enhancer per ton of multifunctional composition to about 1995 pounds of *cannabis* enhancer per ton of multifunctional composition. In embodiments, the volatile feedstock component mass ratio ranges from between about 500 pounds of volatile feedstock components per ton of *cannabis* enhancer to about 2000 pounds of volatile feedstock components per ton of *cannabis* enhancer. In embodiments, the volatile feedstock component mass ratio ranges from between about 500 pounds of volatile feedstock components per ton of multifunctional composition to about 1750 pounds of volatile feedstock components per ton of multifunctional composition. In embodiments, the fixed carbon feedstock component mass ratio ranges from between about 100 pounds of fixed carbon feedstock components per ton of *cannabis* enhancer to about 1700 pounds of fixed carbon feedstock components per ton of *cannabis* enhancer. In embodiments, the fixed carbon feedstock component mass ratio ranges from between about 100 pounds of fixed carbon feedstock components per ton of multifunctional composition to about 1600 pounds of fixed carbon feedstock components per ton of multifunctional composition.

Accordingly, I wish to make my intentions clear—and at the same time put potential competitors on clear public notice. It is my intent that this portion of the specification especially relating to multifunctional composition mixing and all claims pertaining thereto receive a liberal construction and be interpreted to uphold and not destroy my rights as inventor. It is my intent that the claim terms be construed in a charitable and common-sensical manner, in a manner that encompasses the embodiments disclosed in this and other portions of the specification and drawings relating to multifunctional composition mixing without incorporating unrecited, unnecessary limitations. It is my intent that the specification relating to multifunctional composition mixing claim terms be construed as broadly as practicable while preserving the validity of the claims. It is my intent that the claim terms be construed in a manner consistent with the context of the overall claim language and this portion of the specification along with FIGS. 1B and 12A, without importing extraneous limitations from the specification or other sources into the claims, and without confining the scope of the claims to the exact representations depicted in the specification or drawings in FIGS. 1B and 12A. It is also my intent that not each and every term of the claim be systematically defined and rewritten. Claim terms and phrases should be construed only to the extent that it will provide helpful, clarifying guidance to the jury, or to the extent needed to resolve a legitimate, good faith dispute that is material to the questions of validity or infringement. Otherwise, simple claim terms and phrases should be presented to the jury without any potentially confusing and difficult-to-apply definitional construction.

FIG. 1C:

FIG. 1C elaborates upon the non-limiting embodiment of FIG. 1 further including the sequence step of lipid extraction (step J).

FIG. 1C shows lipid extraction (step J) downstream of the each of the steps insect collection (step E), insect grinding (step F), and pathogen removal (step G).

The lipid extraction (step J) is configured to produce extracted lipids (028) from insects that were previously fed an enhanced feedstock. In embodiments, the insect fat mass ratio ranges from between about 100 pounds of fat per ton of insects produced to about 1800 pounds of fat per ton of insects produced. The egg-laying insects that are present within each feeding chambers, and those that are collected, optionally ground, and optionally exposed to a pathogen removal step are intentionally engineered by feeding an enhanced feedstock to possess a wide-ranging fat content ranging from between about 5% to about 90% by weight of insects produced.

In embodiments, the feeding chamber produces insects having fatty acids including palmitic acid, linoleic acid, alpha-linoleic acid, oleic acid, gamma-linoleic acid, or stearic acid. The fatty acids of the insects that are fed the enhanced feedstock are lipids. The extraction and use of lipids has many beneficial applications in society involving medicine, nanotechnology, consumer products, and chemical production with minimal water, feedstock, and environmental impact.

Palmitoleic acid produced from palmitic acid is used to increase insulin sensitivity by suppressing inflammation, reduce inflammation associated with eczema. It is also used in cosmetic products, medical products, and can preserve and treat leather. Linoleic acid is used in oil paints and varnishes and is used in quick-drying oils. It can be used to reduce acne. It has moisture retentive properties and is used to make lotions and soaps (silky feel). It is an essential fatty acid and an emulsifier. Alpha-Linolenic acid is an essential dietary requirement linked to cardiovascular health. Oleic acid is used in hair dyes and soaps (slippery feel). It is also used as a food additive. It is used to manufacture surfactants, soaps, and plasticizers. It is an emulsifying agent in foods and pharmaceuticals. It can penetrate the skin. It can act as an herbicide, insecticide, and fungicide. It can be used in a metallic soap and with copper to clean mildew. Gamma-Linolenic acid can help prevent nerve damage. Stearic acid is used in foundation, baby lotions, oils, powders, creams, shaving cream, body and hand cream, cleansers, foot powders, sprays, moisturizers, and soaps (hardness). Stearic acid is a thickener used to make creams, oil pastels, hard candies, and candles. It is a surfactant. It can be used as a lubricant additive in plasticized PVC compounds to aid processing. It is also used to make metallic soaps.

Rubber grade stearic acid can be used as a mold release lubricant for sintering, pressing ceramic powders, and latex foam. It is also used as a thickener in greases. It can be used as a viscosity modifier for oil extraction. Stearic acid combined with castor oil is used to make softeners for textile sizing. It can be used as a yarn lubricant. Isopropyl Palmitate is in baby lotion/powder/cream, foot powders and sprays. Glyceryl stearate is in nail products, tonics and dressings, cologne/perfumes, concealers, baby lotion/powder/cream, aftershave. Sorbitan stearate is in blush. TEA-Stearate is in mascara. Stearyl alcohol is in hair conditioner, hair straighteners and relaxers, tonics and dressings (help to style hair). Oleyl alcohol is in hair straighteners and relaxers, and concealers.

Lipids extracted from insects may also be used in emerging areas of nanotechnology having uses in many areas covering chemistry, engineering, materials science, physics and biology. In coming years, science will continue to develop and increasingly appreciate sources of fatty acids derived from insects. For example, investigators are now seriously focusing on insect derived fatty acids for use in biomedical sciences, such as bio-imaging, sensing and diagnosis of pathologies at early stages, targeted drug delivery, and for use with nano-devices that interact with the plasma eukaryotic or even prokaryotic cell membranes.

Herein are disclosed systems and methods for obtaining, in mass quantities, commercial scale output of insect based lipids for use in a variety of areas throughout society. In embodiments, the lipid extraction (step J) utilizes a lipid extraction unit to extract lipids from insects.

In embodiments, the lipid extraction unit is configured to extract lipids by use of a first immiscible liquid and a second immiscible liquid. In embodiments, the first immiscible liquid has a first density and a first molecular weight, and the second immiscible liquid has a second density and a second molecular weight. In embodiments, first density is greater than the second density. In embodiments, first molecular weight is greater than the second molecular weight. In embodiments, a first immiscible liquid and lipid mixture is formed which is comprised of a lipid portion and a first immiscible liquid portion. In embodiments, second immiscible liquid and particulate mixture is formed which is comprised of a particulate portion and a second immiscible liquid portion. In embodiments, the particulate portion is comprised of one or more from the group consisting of insect legs, and wings, and protein.

FIG. 1D:

FIG. 1D includes one non-limiting embodiment of an insect traceability system flow chart. In embodiments, the present disclosure provides for an insect traceability system. In embodiments, the insect traceability system is specifically tailored towards the unique challenges related to tracking, accountability, food safety, and state and federal government compliance of the insect industry, either for food (for humans or animals), drugs, chemicals, and medicine. In embodiments, the present disclosure provides for an insect traceability system that is used to verify the history, location, or application of an item by means of documented recorded identification.

In embodiments, the insect traceability system has been developed to track inventory to end-product (whole insects, ground insects, live insects, of insect-related end-products including but not limited to fermented insects, biopolymers, lipids, chemicals, foodstuffs, hydrogenated lipids, etc.). In embodiments, the insect traceability system includes an insect end-product laboratory analytical testing component.

In embodiments, the present disclosure provides for a *cannabis*, insect, of foodstuff or beverage traceability system. In embodiments, the traceability system includes a server having tables comprising a database for receiving, processing and storing data. In embodiments, the traceability system includes a computer network providing electronic communication between the server and other computers and/or mobile devices.

In embodiments, the traceability system tracks data including: (A) times and dates insects are born fed, watered, bred, killed, suffocated, frozen, sold, leased, borrowed, processed, heated, ground, spray dried, oxidized, hydrolyzed, filtered, evaporated, pressurized, fermented, mixed with water, liquid, gas, acid, enzyme, fungus, *cannabis*, THC, a fiber-starch material, a binding agent, a density improving textural supplement, a moisture improving textural supplement, and other insects (either whole, ground, powder, slurry, particulate, frozen, heated, dehydrated, cooked, raw, ground, whole); (B) breeding material moisture, feeding/breeding chamber temperature, humidity, mass/length/width of each insect, average insect mass/length/width, genus, species; (C) entity purchased (product, insect, plant, seeds, eggs, clone, foodstuff, beverage, ingredients, compositions), end customer; insect breeding cycle time, temp, humidity, breeding material, moisture and temperature of breeding material, bacteria content of breeding material, pH); insect feedstock ingredients (composition, vendor information, MSDS).

FIG. 1D includes one non-limiting embodiment of an insect traceability system flow chart. First, the initial inventory is tracked, including: insect eggs, insects, insects at various stages of development, breeding material, water, water treatment unit (adsorbent, catalyst, ion-exchange resin, polymer, alumina, etc.), odor control system (adsorbent, sorbent, filter element), enzymes, solvents, chemicals, acid, biocatalysts.

Second, the insects are grown within the insect production system. The grown insects may be live, whole, frozen, dried, ground, pathogen-depleted, heated to form a first end-product. Various wastes are generated while making the first end-product. In embodiments, the wastes include insect frass, insect feedstock, insect enhanced feedstock, spent breeding material (that can no longer be re-used), nonregenerable adsorbent, catalyst, ion-exchange resin, polymer, alumina, or filters. In embodiments, some of the waste is discarded. In embodiments, some of the waste is sold or recycled. In embodiments, the insect frass includes solid excreta of insects. In embodiments, the insect frass includes feedstock materials. In embodiments, the insect frass includes enhanced feedstock materials. In embodiments, the insect frass includes water. In embodiments, the insect frass may be used as a fertilizer. In embodiments, the insect frass may be used as a fertilizer for the *cannabis* plants disclosed in VOLUME 2 below.

In embodiments, the insect frass may be used as a fertilizer and applied at a ratio ranging from 0.10 pounds of frass per 100 square feet, to 0.15 pounds of frass per 100 square feet, to 0.25 pounds of frass per 100 square feet, to 0.35 pounds of frass per 100 square feet, to 0.45 pounds of frass per 100 square feet, to 0.55 pounds of frass per 100 square feet, to 0.65 pounds of frass per 100 square feet, to 0.75 pounds of frass per 100 square feet, to 0.85 pounds of frass per 100 square feet, to 0.95 pounds of frass per 100 square feet, to 1 pounds of frass per 100 square feet, to 1.15 pounds of frass per 100 square feet, to 1.25 pounds of frass per 100 square feet, to 1.35 pounds of frass per 100 square feet, to 1.45 pounds of frass per 100 square feet, to 1.55 pounds of frass per 100 square feet, to 1.65 pounds of frass per 100 square feet, to 1.75 pounds of frass per 100 square feet, to 1.85 pounds of frass per 100 square feet, to 1.95 pounds of frass per 100 square feet, to 3 pounds of frass per 100 square feet, to 3 pounds of frass per 100 square feet, to 3.15 pounds of frass per 100 square feet, to 3.25 pounds of frass per 100 square feet, to 3.35 pounds of frass per 100 square feet, to 3.45 pounds of frass per 100 square feet, to 3.55 pounds of frass per 100 square feet, to 3.65 pounds of frass per 100 square feet, to 3.75 pounds of frass per 100 square feet, to 3.85 pounds of frass per 100 square feet, to 3.95 pounds of frass per 100 square feet, to 4 pounds of frass per 100 square feet, to 4 pounds of frass per 100 square feet, to 4.15 pounds of frass per 100 square feet, to 4.25 pounds of frass per 100 square feet, to 4.35 pounds of frass per 100 square feet, to 4.45 pounds of frass per 100 square feet, to 4.55 pounds of frass per 100 square feet, to 4.65 pounds of frass per 100 square feet, to 4.75 pounds of frass per 100 square feet, to 4.85 pounds of frass per 100 square feet, to 4.95 pounds of frass per 100 square feet, to 5 pounds of frass per 100 square feet.

In embodiments, the insect frass includes: a nitrogen content ranging from 1.0 weight percent to 1.5 weight percent, 1.5 weight percent to 2.0 weight percent, 2.0 weight percent to 2.5 weight percent, 2.5 weight percent to 3.0 weight percent, 3.0 weight percent to 3.5 weight percent, 3.5 weight percent to 4.0 weight percent, 4.0 weight percent to 4.5 weight percent, or 4.5 weight percent to 5.0 weight percent; a phosphorus content ranging from 1.0 weight percent to 1.5 weight percent, 1.5 weight percent to 2.0 weight percent, 2.0 weight percent to 2.5 weight percent, 2.5 weight percent to 3.0 weight percent, 3.0 weight percent to 3.5 weight percent, 3.5 weight percent to 4.0 weight percent, 4.0 weight percent to 4.5 weight percent, or 4.5 weight percent to 5.0 weight percent; a potassium content ranging from 1.0 weight percent to 1.5 weight percent, 1.5 weight percent to 2.0 weight percent, 2.0 weight percent to 2.5 weight percent, 2.5 weight percent to 3.0 weight percent, 3.0 weight percent to 3.5 weight percent, 3.5 weight percent to 4.0 weight percent, 4.0 weight percent to 4.5 weight percent, or 4.5 weight percent to 5.0 weight percent; and a total nitrogen-phosphorus-potassium content ranging from 1.0 weight percent to 1.5 weight percent, 1.5 weight percent to 2.0 weight percent, 2.0 weight percent to 2.5 weight percent, 2.5 weight percent to 3.0 weight percent, 3.0 weight percent to 3.5 weight percent, 3.5 weight percent to 4.0 weight percent, 4.0 weight percent to 4.5 weight percent, 4.5 weight percent to 5.0 weight percent, 5.0 weight percent to 5.5 weight percent, 5.5 weight percent to 6.0 weight percent, 6.0 weight percent to 6.5 weight percent, 6.5 weight percent to 7.0 weight percent, 7.0 weight percent to 7.5 weight percent, 7.5 weight percent to 8.0 weight percent, 8.0 weight percent to 8.5 weight percent, 8.5 weight percent to 9.0 weight percent, 9.0 weight percent to 9.5 weight percent, 9.5 weight percent to 10.0 weight percent, 10.0 weight percent to 10.5 weight percent, 10.5 weight percent to 11.0 weight percent, 11.0 weight percent to 11.5 weight percent, 11.5 weight percent to 12.0 weight percent, 12.0 weight percent to 12.5 weight percent, 12.5 weight percent to 13.0 weight percent, 13.0 weight percent to 13.5 weight percent, 13.5 weight percent to 14.0 weight percent, 14.0 weight percent to 14.5 weight percent, or 14.5 weight percent to 15.0 weight percent.

Quality testing takes place to ensure that recalls may be instituted if necessary. In embodiments, the quality testing includes testing the end-product prior to entering the stream of interstate commerce for: pH, chemicals, contaminants, bacteria, pathogens, yeast, mold, or allergens.

In embodiments, the insect traceability system includes a quality analysis of an that includes: a nitrate (NO3) concentration having a maximum level of 1,000 mg NO3/kg of end-product; a mycotoxin analysis including: an ochratoxin A concentration having a maximum level of 10 µg/kg of end-product; a deoxynivalenol concentration having a maximum level of 2,000 µg/kg of end-product; a zearalenone concentration having a maximum level of 275 µg/kg of end-product; a fumonisins concentration having a maximum level of 2,500 µg/kg of end-product; a metals analysis including: a lead concentration having a maximum level of 0.5 mg/kg of end-product; a cadmium concentration having a maximum level of 0.5 mg/kg of end-product; a mercury concentration having a maximum level of 0.5 mg/kg of end-product; a 3-monochloropropane-1,2-diol (3-MCPD) concentration having a maximum level of 20 µg/kg of end-product; a dioxins and polychlorinated biphenyls (PCBs) concentration having a maximum level of 3 picogram/gram; a polycyclic aromatic hydrocarbon concentration having a maximum level of 5 µg/kg of end-product; a benzo(a)pyrene concentration having a maximum level of 2 or 5 µg/kg of end-product; a total concentration of benzo(a)pyrene, benz(a)anthracene, benzo(b)fluoranthene and chrysene having a maximum level of 15 or 30 µg/kg of end-product.

In embodiments, the insect traceability system includes a quality analysis of an that includes: a standard plate count (to test for total aerobic bacterial and total mold and yeasts) having less than: 500,000 colony forming unit per gram, 400,000 colony forming units per gram, 300,000 colony forming units per gram, 200,000 colony forming units per gram, 100,000 colony forming units per gram, 50,000 colony forming units per gram, 25,000 colony forming units per gram, or 5,000 colony forming units per gram; a coliform content less than 500 colony forming units per gram, 400 colony forming units per gram, 300 colony forming units per gram, 200 colony forming units per gram, 100 colony forming units per gram, 90 colony forming units per gram, 80 colony forming units per gram, 70 colony forming units per gram, 60 colony forming units per gram, 50 colony forming units per gram, 40 colony forming units per gram, 30 colony forming units per gram, 20 colony forming units per gram, or 10 colony forming units per gram; a coliform content less than 500,000 colony forming unit per gram, 400,000 colony forming units per gram, 300,000 colony forming units per gram, 200,000 colony forming units per gram, 100,000 colony forming units per gram, 50,000 colony forming units per gram, 25,000 colony forming units per gram, or 5,000 colony forming units per gram; a spore-forming sulphite reducing anaerobe content less than 500 colony forming units per gram, 400 colony forming units per gram, 300 colony forming units per gram, 200 colony forming units per gram, 100 colony forming units per gram, 90 colony forming units per gram, 80 colony forming units per gram, 70 colony forming units per gram, 60 colony forming units per gram, 50 colony forming units per gram, 40 colony forming units per gram, 30 colony forming units per gram, 20 colony forming units per gram, or 10 colony forming units per gram; a spore-forming sulphite reducing anaerobe content less than 500,000 colony forming unit per gram, 400,000 colony forming units per gram, 300,000 colony forming units per gram, 200,000 colony forming units per gram, 100,000 colony forming units per gram, 50,000 colony forming units per gram, 25,000 colony forming units per gram, or 5,000 colony forming units per gram; a *Pseudomonas aeruginosa* content less than 500 colony forming units per gram, 400 colony forming units per gram, 300 colony forming units per gram, 200 colony forming units per gram, 100 colony forming units per gram, 90 colony forming units per gram, 80 colony forming units per gram, 70 colony forming units per gram, 60 colony forming units per gram, 50 colony forming units per gram, 40 colony forming units per gram, 30 colony forming units per gram, 20 colony forming units per gram, or 10 colony forming units per gram; a *Pseudomonas aeruginosa* content less than 500,000 colony forming unit per gram, 400,000 colony forming units per gram, 300,000 colony forming units per gram, 200,000 colony forming units per gram, 100,000 colony forming units per gram, 50,000 colony forming units per gram, 25,000 colony forming units per gram, or 5,000 colony forming units per gram; a *E. coli* content less than 500 colony forming units per gram, 400 colony forming units per gram, 300 colony forming units per gram, 200 colony forming units per gram, 100 colony forming units per gram, 90 colony forming units per gram, 80 colony forming units per gram, 70 colony forming units per gram, 60 colony forming units per gram, 50 colony forming units per gram, 40 colony forming units per gram, 30 colony forming units per gram, 20 colony forming units per gram, or 10 colony forming units per gram; a *E. coli* content less than 500,000 colony forming unit per gram, 400,000 colony forming units per gram, 300,000 colony forming units per gram, 200,000 colony forming units per gram, 100,000 colony forming units per gram, 50,000 colony forming units per gram, 25,000 colony forming units per gram, or 5,000 colony forming units per gram.

Fourth, after the initial inventory has passed product testing they may be further processed to make a second end-product from the first-end product. In embodiments, the second end-product includes insects that are tested for quality in the form of live, whole, frozen, dried, ground, pathogen-depleted, or heated insects. In embodiments, the second end-product includes a multifunctional composition, a foodstuff, lipids, lipid intermediate products, lipid consumer products, beverages, alcoholic beverages, emulsions, or consumer products. In embodiments, the second end-product includes a first end-product. In embodiments, the second end-product includes anything but a first end-product.

Fifth, a detailed transportation manifest is created prior to shipment the second end-product into the stream of commerce. In embodiments, the transportation manifest includes: origin of shipment, destination of shipment, detailed list of shipment contents shipper address, receiver address, date shipped, date received, and displaying the entire chain of custody. Sixth, the transporter name and license number is entered into the insect traceability system. Seventh, the retailer name and address is entered into the insect traceability system. Eighth, the consumer name and address is entered into the insect traceability system.

In embodiments, the insect traceability system provides a log to track insects and/or each batch of insects or each end-product. In embodiments, the insect traceability system logs insects grown in the Insect Production Superstructure System (IPSS) by used of a barcode or radio-frequency identification (RFID). In embodiments, the RFID uses electromagnetic fields to automatically identify and track tags attached to batches of insects. Each insect feeding chamber includes a tag that contains electronically-stored information such as: time and date the insects were hatched, time and date the insects were harvested, insect feed composition and ingredients, growing medium moisture, feeding chamber temperature and humidity, mass of each insect, mass increase over time of each feeding chamber, species/genus of each insect, end-customer, quality assurance records, insect water quality. In embodiments, the insect traceability system provides for an audit trail for state and federal laws, rules, and regulations and makes recalls possible.

FIG. 2:

FIG. 2 shows a non-limiting embodiment of an enhanced feedstock mixing module (1000) including a feedstock distribution module (1A), mineral distribution module (1B), vitamin distribution module (1C), polymer distribution module (1D), water distribution module (1E), and an enhanced feedstock distribution module (1F).

FIG. 2 displays a computer (COMP) that is integral to the Insect Production Superstructure System (IPSS). The computer (COMP) is configured to accept a variety of signals from process variables using a variety of sensors and/or controllers, and then apply advanced process logic control methodologies, strategies and/or sequences to realize modulation of actuators and/or valves to effectuate optimal operation of the Insect Production Superstructure Systems (IPSS) and its associated modules not only including feedstock mixing, feedstock splitting, insect feeding, insect breeding, insect collection, insect grinding, pathogen removal, multifunctional composition mixing, and lipid extraction modules. A variety of signals are sent to and from the computer (COMP) to a variety of controllers, sensors, valves, motors, actuators, and the like distributed throughout the entire Insect Production Superstructure System (IPSS).

The computer (COMP) applies the control approach and methodology for the each and every entire control loop on a continuous basis, a discrete basis, or a hybrid combination of a continuous basis and a discrete basis. Further, a computer may be applied to implement the control methodology by utilizing process variables obtained by either a continuous sensor, a discrete sensor, or a combination of a continuous sensor and a discrete sensor and hold the control action at a constant set-point at that specific control output until a later time when that control algorithm is executed. The time between successive interrogations or application of the control algorithm is applied by the control computer is defined as the control interval. The control interval for a continuous sensor is typically shorter than that of a discrete sensor and based upon commercially available mechanical, electrical, or digital continuous or discrete sensors, the control interval or control time can vary from 0.2 milliseconds, to 0.5 seconds, to 1.0 second, to 10 seconds, to 30 seconds, to 1 minute, to 5 minutes, to 10 minutes, to 30 minutes, to 1 hour, to 10 hours, or longer. The output from the control computer is transmitted to a controller device. From application of the control logic, the control computer can send a variety of signals to a variety of controllers.

In embodiments, the signals from controllers or sensors are inputted or outputted to and from a computer (COMP) by a user or operator via an input/output interface (I/O) as disclosed in FIG. 2 and many others (not only including FIGS. 3, 5, 6, 7, 8, 9, 10, 11, 12A, 12B, 13, 14A, 14B, 14C, 14D, 14E, 14F, 14G, 14H, 14I, 14J, 15, 16, 17, 18, 19, 20, 21, 22, 23, 24, 25, 26, 27A, 27B, 28A, 28B, 29-48). Program and sequencing instructions may be executed to perform particular computational functions such as automated operation of the valves, actuators, controllers, motors, or the like. In one exemplary embodiment, a computer (COMP) includes a processor (PROC) coupled to a system memory (MEM) via an input/output interface (I/O). The processor (PROC) may be any suitable processor capable of executing instructions. System memory (MEM) may be configured to store instructions and data accessible by processor (PROC). In various embodiments, system memory (MEM) may be implemented using any suitable memory technology. In all illustrated embodiments, program instructions and data implementing desired functions are shown stored within system memory (MEM) as code (CODE). In embodiments, the I/O interface (I/O) may be configured to coordinate I/O traffic between processor (PROC) and system memory (MEM). In some embodiments, the I/O interface (I/O) is configured for a user or operator to input necessary sequencing protocol into the computer (COMP) for process execution, including sequence timing and repetition of a given number of states to realize a desired sequence of steps and/or states. In embodiments, the signals operatively coupled to a controller, valve, actuator, motor, or the like, may be an input value to be entered into the computer (COMP) by the I/O interface (I/O). In embodiments, the computer (COMP) includes a small single-board computer such as a Raspberry Pi developed in the United Kingdom by the Raspberry Pi Foundation. The system is fully flexible to be tuned, configured, and optimized to provide an environment for scheduling the appropriate process parameters by programmatically controlling the opening and closing of valves at specific time intervals, or strategically and systematically opening, closing, turning on, turning off, modulating, controlling, or operating motors, valves, or actuators at specific time intervals at specific times. In embodiments, a user or operator may define control loops, cycle times, step numbers, and states which may be programmed into the computer (COMP) by an operator accessible input/output interface (I/O).

Feedstock Distribution Module (1A)

FIG. 2 displays a feedstock distribution module (1A) including a feedstock tank (1A2) that is configured to accept a feedstock (1A1). The feedstock tank (1A2) has an interior (1A3), a feedstock input (1A4), a feedstock conveyor (1A5), and a feedstock conveyor output (1A6). The feedstock tank (1A2) accepts a feedstock (1A1) to the interior (1A3) and regulates and controls an engineered amount of feedstock (1A1) downstream to be mixed to form an enhanced feedstock. The feedstock conveyor (1A5) has an integrated feedstock mass sensor (1A7) that is configured to input and output a signal (1A8) to the computer (COMP). The feedstock conveyor motor (1A9) has a controller (1A10) that is configured to input and output a signal (1A11) to the computer (COMP). The feedstock mass sensor (1A7), feedstock conveyor (1A5), and feedstock conveyor motor (1A9) are coupled so as to permit the conveyance, distribution, or output of a precise flow of feedstock (1A1) via a feedstock transfer line (1A14). A feedstock moisture sensor (1A12A)

is preferably installed on the feedstock transfer line (1A14) and is configured to input a signal (1A13A) to the computer (COMP).

In embodiments, the insect feeding chamber may operate at an enhanced feedstock to insect ratio ranging from between about 1 ton of enhanced feedstock per ton of insects produced to about 5 tons of enhanced feedstock per ton of insects produced. In embodiments, about 1 ton of enhanced feedstock can yield about 1 ton of insects. In embodiments, about 2 tons of enhanced feedstock can yield about 1 ton of insects. In embodiments, about 3 tons of enhanced feedstock can yield about 1 ton of insects. In embodiments, about 4 tons of enhanced feedstock can yield about 1 ton of insects. In embodiments, about 5 tons of enhanced feedstock can yield about 1 ton of insects.

Mineral Distribution Module (1B)

FIG. 2 displays a mineral distribution module (1B) including a mineral tank (1B2) that is configured to accept minerals (1B1). The mineral tank (1B2) has an interior (1B3), a mineral input (1B4), a mineral conveyor (1B5), and a mineral conveyor output (1B6). The mineral tank (1B2) accepts minerals (1B1) to the interior (1B3) and regulates and controls an engineered amount of minerals (1B1) downstream to be mixed to form an enhanced feedstock. The mineral conveyor (1B5) has an integrated mineral mass sensor (1B7) that is configured to input and output a signal (1B8) to the computer (COMP). The mineral conveyor motor (1B9) has a controller (1B10) that is configured to input and output a signal (1B11) to the computer (COMP). The mineral mass sensor (1B7), mineral conveyor (1B5), and mineral conveyor motor (1B9) are coupled so as to permit the conveyance, distribution, or output of a precise flow of minerals (1B1) via a mineral transfer line (1B12).

Vitamin Distribution Module (1C)

FIG. 2 displays a vitamin distribution module (1C) including a vitamin tank (1C2) that is configured to accept vitamins (1C1). The vitamin tank (1C2) has an interior (1C3), a vitamin input (1C4), a vitamin conveyor (105), and a vitamin conveyor output (106). The vitamin tank (1C2) accepts vitamins (1C1) to the interior (1C3) and regulates and controls an engineered amount of vitamins (1C1) downstream to be mixed to form an enhanced feedstock. The vitamin conveyor (105) has an integrated vitamin mass sensor (1C7) that is configured to input and output a signal (1C8) to the computer (COMP). The vitamin conveyor motor (1C9) has a controller (1C10) that is configured to input and output a signal (1C11) to the computer (COMP). The vitamin mass sensor (1C7), vitamin conveyor (105), and vitamin conveyor motor (1C9) are coupled so as to permit the conveyance, distribution, or output of a precise flow of vitamins (1C1) via a vitamin transfer line (1C12).

Polymer Distribution Module (1D)

FIG. 2 displays a polymer distribution module (1D) including a polymer tank (1D2) that is configured to accept polymer (1D1). The polymer tank (1D2) has an interior (1D3), a polymer input (1D4), a polymer conveyor (1D5), and a polymer conveyor output (1D6). The polymer tank (1D2) accepts polymer (1D1) to the interior (1D3) and regulates and controls an engineered amount of polymer (1D1) downstream to be mixed to form an enhanced feedstock. The polymer conveyor (1D5) has an integrated polymer mass sensor (1D7) that is configured to input and output a signal (1D8) to the computer (COMP). The polymer conveyor motor (1D9) has a controller (1D10) that is configured to input and output a signal (1D11) to the computer (COMP). The polymer mass sensor (1D7), polymer conveyor (1D5), and polymer conveyor motor (1D9) are coupled so as to permit the conveyance, distribution, or output of a precise flow of polymer (1D1) via a polymer transfer line (1D12). For the context of this disclosure a polymer (1D1) includes exoskeletons of insects separated from any plurality of separators (S1, S2, S3) contained within the insect evacuation module (3000). For the context of this disclosure a polymer (1D1) includes chitin having the formula of $(C_8H_{13}O_5N)_n$ which is a long-chain polymer of an N-acetylglucosamine, a derivative of glucose, and is found in many places throughout the natural world. Chitin is a polymer and a characteristic component of the cell walls of fungi, the exoskeletons of arthropods such as crustaceans (e.g., crabs, lobsters and shrimps) and insects, the radulae of mollusks, and the beaks and internal shells of cephalopods, including squid and octopuses and on the scales and other soft tissues of fish and lissamphibians. Where recycle of the exoskeletons from the insect evacuation module (3000) to the insect feeding module (2000) is not possible the polymer (1D1) includes fish scales, fungi, cephalopod shells, cephalopod beaks, Lissamphibia shells, or keratin. In its pure, unmodified form, chitin is translucent, pliable, resilient, and quite tough.

Water Distribution Module (1E)

FIG. 2 illustrates one non-limiting embodiment of a water distribution module (1E) that removes contaminants from water (1E1) prior to mixing to form an enhanced feedstock. A source of water (1E1) is routed through a water input line (1E4) and through a first water treatment unit (1E6) and a second water treatment unit (1E11) and into the interior (1E17) of a water tank (1E16) where it is then pumped via a water supply pump (1E22), though a water control valve (1E36) and then mixed with feedstock (1A1), minerals (1B1), vitamins (1C1), and polymer (1D1) to form an enhanced feedstock. In embodiments, enhancers (1E44) may be added to the interior (1E17) of the water tank (1E16). In embodiments, the enhancers (1E44) may include niacin, taurine, glucuronic acid, malic acid, N-acetyl L tyrosine, L-phenylalanine, caffeine, citicoline, insect growth hormones, or steroids, or human growth hormones.

A first water pressure sensor (1E2) is positioned on the water input line (1E4) and is configured to input a signal (1E3) to the computer (COMP). In embodiments, contaminant-laden water (1E5) is routed through the water input line (1E4) and transferred to the first water treatment unit (1E6) via a first water treatment unit input (1E7). The first water treatment unit (1E6) has a first water treatment unit input (1E7) and a first water treatment unit output (1E8) and is configured to remove contaminants from the contaminant-laden water (1E5) to form a stream of first contaminant-depleted water (1E9) that is outputted via a first contaminant-depleted water transfer line (1E10). In embodiments, a first contaminant-depleted water (1E9) is routed through the first contaminant-depleted water transfer line (1E10) and transferred to the second water treatment unit (1E11) via a second water treatment unit input (1E12). The second water treatment unit (1E11) has a second water treatment unit input (1E12) and a second water treatment unit output (1E13) and is configured to remove contaminants from the first contaminant-depleted water (1E9) to form a stream of second contaminant-depleted water (1E14) that is outputted via a second contaminant-depleted water transfer line (1E15).

The second contaminant-depleted water transfer line (1E15) is connected to the water tank (1E16) via a water input (1E18). In embodiments, the second contaminant-depleted water transfer line (1E15) has a water supply valve (1E23) interposed in between the second water treatment unit (1E11) and the water tank (1E16). In embodiments, the pressure drop across the water supply valve (1E23) may range from: between about 1 pound per square inch to about 5 pound per square inch; between about 5 pound per square inch to about 10 pound per square inch; between about 10 pound per square inch to about 15 pound per square inch; between about 15 pound per square inch to about 20 pound per square inch; between about 25 pound per square inch to about 30 pound per square inch; between about 35 pound per square inch to about 40 pound per square inch; between about 45 pound per square inch to about 50 pound per square inch; between about 55 pound per square inch to about 60 pound per square inch; between about 65 pound per square inch to about 70 pound per square inch; between about 75 pound per square inch to about 80 pound per square inch; between about 85 pound per square inch to about 90 pound per square inch; between about 95 pound per square inch to about 100 pound per square inch; between about 100 pound per square inch to about 125 pound per square inch; between about 125 pound per square inch to about 150 pound per square inch; or, between about 150 pound per square inch to about 200 pound per square inch.

The water supply valve (1E23) has a controller (1E24) that is configured to input and output a signal (1E25) to the computer (COMP). In embodiments, a source of water (1E1) may be introduced to the interior (1E17) of the water tank (1E16) via a water supply line (1E19) and water input (1E18). The first water treatment unit (1E6) and second water treatment unit (1E11) are optional because in many areas of the world the water quality is suitable for humans and animals to drink and ingest.

The water tank (1E16) is equipped with a high-water level sensor (1E26) and a low water level sensor (1E28). The high-water level sensor (1E26) is configured to input a signal (1E27) to the computer (COMP) when the level reaches a pre-determined highest most vertical height in the water tank (1E16). The low water level sensor (1E28) is configured to input a signal (1E29) to the computer (COMP) when the level reaches a pre-determined lowest most vertical height in the water tank (1E16).

A water supply pump (1E22) is connected to the water output (1E20) of the water tank (1E16) via a water discharge line (1E21). The water supply pump (1E22) is configured to transfer water (1E1) from the interior (1E17) of the water tank (1E16) to create a pressurized water supply (1E32) that is routed for mixing to form an enhanced feedstock via a pressurized water supply line (1E33).

A second water pressure sensor (1E30) is positioned on the discharge of the water supply pump (1E22) on the pressurized water supply line (1E33). The second water pressure sensor (1E30) is configured to input a signal (1E31) to the computer (COMP). A water flow sensor (1E34) is positioned on the discharge of the water supply pump (1E22) on the pressurized water supply line (1E33). The water flow sensor (1E34) is configured to input a signal (1E35) to the computer (COMP).

A water control valve (1E36) with an integrated controller (1E37) is positioned on the discharge of the water supply pump (1E22) on the pressurized water supply line (1E33). The controller (1E37) of the water control valve (1E36) is configured to input and output signal (1E38) to the computer (COMP). Water (1E1) routed through the water control valve (1E36) is then further routed towards being mixed to form an enhanced feedstock via a water transfer line (1E41). A water quality sensor (1E42) is positioned on the water transfer line (1E41) and is configured to input a signal (1E43) to the computer (COMP). A third water pressure sensor (1E39) is positioned on the water transfer line (1E41) and is configured to input a signal (1E40) to the computer (COMP).

The pressure drop across the water control valve (1E36) may range from: between about 1 pound per square inch to about 5 pound per square inch; between about 5 pound per square inch to about 10 pound per square inch; between about 10 pound per square inch to about 15 pound per square inch; between about 15 pound per square inch to about 20 pound per square inch; between about 25 pound per square inch to about 30 pound per square inch; between about 35 pound per square inch to about 40 pound per square inch; between about 45 pound per square inch to about 50 pound per square inch; between about 55 pound per square inch to about 60 pound per square inch; between about 65 pound per square inch to about 70 pound per square inch; between about 75 pound per square inch to about 80 pound per square inch; between about 85 pound per square inch to about 90 pound per square inch; between about 95 pound per square inch to about 100 pound per square inch; between about 100 pound per square inch to about 125 pound per square inch; between about 125 pound per square inch to about 150 pound per square inch; or, between about 150 pound per square inch to about 200 pound per square inch.

Enhancers (1E44) contained within the interior (1E46) of the enhancer tank (1E45) may be routed to the interior (1E17) of the water tank (1E16) via an enhancer transfer line (1E48). The enhancer transfer line (1E48) is connected at one end to the enhancer tank (1E45) via an enhancer tank output (1E47) and at another end to the water tank (1E16) via an enhancer input (1E49). A water enhancer supply valve (1E52) with an integrated controller (1E53) is positioned on the enhancer transfer line (1E48) and is configured to input and output a signal (1E54) to the computer (COMP). An enhancer flow sensor (1E50) is positioned on the enhancer transfer line (1E48) and is configured to input a signal (1E51) to the computer (COMP).

Feedstock (1A1), minerals (1B1), vitamins (1C1), polymer (1D1), and water (1E1) are mixed to form an enhanced feedstock that is routed to the interior (1F2) of the enhanced feedstock splitter (1F1) via an enhanced feedstock transfer line (1F0).

In embodiments, water may be added to the enhanced feedstock and transferred to the feeding chamber so that the insect feeding chamber operates at a water to insect ratio ranging from: between about 0.1 tons of water per ton of insects produced to about 0.2 tons of water per ton of insects produced; between about 0.2 tons of water per ton of insects produced to about 0.4 tons of water per ton of insects produced; between about 0.4 tons of water per ton of insects produced to about 0.6 tons of water per ton of insects produced; between about 0.6 tons of water per ton of insects produced to about 0.8 tons of water per ton of insects produced; between about 0.8 tons of water per ton of insects produced to about 1 ton of water per ton of insects produced; between about 1 ton of water per ton of insects produced to about 1.5 tons of water per ton of insects produced; between about 1.5 tons of water per ton of insects produced to about 2 tons of water per ton of insects produced; between about 2 tons of water per ton of insects produced to about 3 tons of water per ton of insects produced; between about 3 tons of water per ton of insects produced to about 4 tons of water per ton of insects produced; between about 4 tons of water per ton of insects produced to about 5 tons of water per ton of insects produced; between about 5 tons of water per ton of insects produced to about 6 tons of water per ton of insects produced; between about 6 tons of water per ton of insects produced to about 7 tons of water per ton of insects produced; between about 7 tons of water per ton of insects produced to about 8 tons of water per ton of insects produced; between about 8 tons of water per ton of insects produced to about 9 tons of water per ton of insects produced; between about 9 tons of water per ton of insects produced to about 10 tons of water per ton of insects produced; between about 10 tons of water per ton of insects produced to about 11 tons of water per ton of insects produced; between about 11 tons of water per ton of insects produced to about 12 tons of water per ton of insects produced; between about 12 tons of water per ton of insects produced to about 13 tons of water per ton of insects produced; between about 13 tons of water per ton of insects produced to about 14 tons of water per ton of insects produced; between about 14 tons of water per ton of insects produced to about 15 tons of water per ton of insects produced; between about 15 tons of water per ton of insects produced to about 16 tons of water per ton of insects produced; between about 16 tons of water per ton of insects produced to about 17 tons of water per ton of insects produced; between about 17 tons of water per ton of insects produced to about 18 tons of water per ton of insects produced; between about 18 tons of water per ton of insects produced to about 19 tons of water per ton of insects produced; or, between about 19 tons of water per ton of insects produced to about 20 tons of water per ton of insects produced.

In embodiments, about 0.1 tons of water yields 1 ton of insects. In embodiments, about 0.2 tons of water yields 1 ton of insects. In embodiments, about 0.4 tons of water yields 1 ton of insects. In embodiments, about 0.6 tons of water yields 1 ton of insects. In embodiments, about 0.8 tons of water yields 1 ton of insects. In embodiments, about 1 ton of water yields 1 ton of insects. In embodiments, about 2 tons of water yields 1 ton of insects. In embodiments, about 3 tons of water yields 1 ton of insects. In embodiments, about 4 tons of water yields 1 ton of insects. In embodiments, about 5 tons of water yields 1 ton of insects. In embodiments, about 6 tons of water yields 1 ton of insects. In embodiments, about 7 tons of water yields 1 ton of insects. In embodiments, about 8 tons of water yields 1 ton of insects. In embodiments, about 9 tons of water yields 1 ton of insects. In embodiments, about 10 tons of water yields 1 ton of insects. In embodiments, about 11 tons of water yields 1 ton of insects. In embodiments, about 12 tons of water yields 1 ton of insects. In embodiments, about 13 tons of water yields 1 ton of insects. In embodiments, about 14 tons of water yields 1 ton of insects. In embodiments, about 15 tons of water yields 1 ton of insects. In embodiments, about 16 tons of water yields 1 ton of insects. In embodiments, about 17 tons of water yields 1 ton of insects. In embodiments, about 18 tons of water yields 1 ton of insects. In embodiments, about 19 tons of water yields 1 ton of insects. In embodiments, about 20 tons of water yields 1 ton of insects.

Enhanced Feedstock Distribution Module (1F)

The enhanced feedstock splitter (1F1) has an interior (1F2), a splitter input (1F3), a first output (1F10), second output (1F15), and a third output (1F20). The enhanced feedstock splitter (1F1) is configured to mix the feedstock (1A1), minerals (1B1), vitamins (1C1), polymer (1D1), and water (1E1) and to split the mixed enhanced feedstock into a plurality of streams including a first enhanced feedstock stream (EF1), second enhanced feedstock stream (EF2), and a third enhanced feedstock stream (EF3). Each of the first enhanced feedstock stream (EF1), second enhanced feedstock stream (EF2), and third enhanced feedstock stream (EF3), may be transferred each to a first feeding chamber (FC1), second feeding chamber (FC2), and third feeding chamber (FC3), respectively.

An enhanced feedstock moisture sensor (1Al2B) is positioned on the enhanced feedstock transfer line (1F0) and is configured to input a signal (1A13B) to the computer (COMP). The enhanced feedstock moisture sensor (1Al2B) may be used to gauge the amount of moisture within the enhanced feedstock to increase or decrease the flow of water (1E1) passed through the water flow sensor (1E34) and water control valve (1E36).

The enhanced feedstock splitter (1F1) has a top section (1F4), bottom section (1F5), and at least one side wall (1F6). The enhanced feedstock splitter (1F1) may be cylindrical or rectangular or any other conceivable shape so long as it outputs at least one first enhanced feedstock stream. In embodiments, the enhanced feedstock splitter (1F1) has a splitter input (1F3) positioned on the top section (1F4).

In embodiments, the enhanced feedstock splitter (1F1) has a splitter first screw conveyor (1F9), splitter second screw conveyor (1F14), and splitter third screw conveyor (1F19) positioned on the bottom section (1F5). In embodiments, a first splitter level sensor (1F7) is positioned on the side wall (1F6) of the enhanced feedstock splitter (1F1) which is configured to input a signal (1F8) to the computer (COMP).

The splitter first screw conveyor (1F9) has a first output (1F10) and is configured to discharge a first enhanced feedstock stream (EF1) to a first feeding chamber (FC1). The splitter first screw conveyor (1F9) is equipped with a splitter first screw conveyor motor (1F11) and integrated controller (1F12) that is configured to input and output a signal (1F13) to the computer (COMP).

A first weigh screw (1F24) is positioned on the first output (1F10) of the splitter first screw conveyor (1F9). The first weigh screw (1F24) has a first weigh screw input (1F25) and a first weigh screw output (1F26), with an integrated mass sensor (1F27) that is configured to input a signal (1F28) to the computer (COMP). The first weigh screw (1F24) has a first weigh screw motor (1F29) with an integrated controller (1F30) that is configured to input and output a signal (1F31) to the computer (COMP). A first weighed enhanced feedstock stream (1F32) or a first enhanced feedstock stream (EF1) is discharged from the first weigh screw output (1F26).

The splitter second screw conveyor (1F14) has a first output (1F10) and is configured to discharge a second enhanced feedstock stream (EF2) to a second feeding chamber (FC2). The splitter second screw conveyor (1F14) is equipped with a splitter second screw conveyor motor (1F16) and integrated controller (1F17) that is configured to input and output a signal (1F18) to the computer (COMP). A second weigh screw (1F33) is positioned on the second output (1F15) of the splitter second screw conveyor (1F14). The second weigh screw (1F33) has a second weigh screw input (1F34) and a second weigh screw output (1F35), with an integrated mass sensor (1F26) that is configured to input a signal (1F37) to the computer (COMP). The second weigh screw (1F33) has a second weigh screw motor (1F38) with an integrated controller (1F39) that is configured to input and output a signal (1F40) to the computer (COMP). A second weighed enhanced feedstock stream (1F41) or a second enhanced feedstock stream (EF2) is discharged from the second weigh screw output (1F35).

The splitter third screw conveyor (1F19) has a first output (1F10) and is configured to third enhanced feedstock stream (EF3) to a third feeding chamber (FC3). The splitter third screw conveyor (1F19) is equipped with a splitter third screw conveyor motor (1F21) and integrated controller (1F22) that is configured to input and output a signal (1F23) to the computer (COMP). A third weigh screw (1F42) is positioned on the third output (1F20) of the splitter third screw conveyor (1F19). The third weigh screw (1F42) has a third weigh screw input (1F43) and a third weigh screw output (1F44), with an integrated mass sensor (1F45) that is configured to input a signal (1F46) to the computer (COMP). The third weigh screw (1F42) has a third weigh screw motor (1F47) with an integrated controller (1F48) that is configured to input and output a signal (1F49) to the computer (COMP). A third weighed enhanced feedstock stream (1F50) or a third enhanced feedstock stream (EF3) is discharged from the third weigh screw output (1F44).

FIG. 3:

FIG. 3 shows a non-limiting embodiment of an insect feeding module (2000) integrated with an insect evacuation module (3000) operating in a first mode of operation wherein the egg transfer system (244) of the insect feeding module (2000) is at a first state in a first retracted height (H1).

A first weighed enhanced feedstock stream (1F32), or otherwise termed a first enhanced feedstock stream (EF1), is shown in FIG. 3 to be introduced to a first feeding chamber (FC1) of an insect feeding module (2000) via an enhanced feedstock input (206). The non-limiting description of the insect feeding module (2000) shown in FIG. 3 includes a feeding chamber (200). In embodiments, the feeding chamber (200) in FIG. 3 is a first feeding chamber (FC1) in an Insect Production Superstructure System (IPSS) that includes a plurality of insect feeding chambers (FC1, FC2, FC3). The insect feeding module (2000) is shown to be in fluid communication with an insect evacuation module (3000). The feeding chamber (200) contained within an insect feeding module (2000) of FIG. 3 is shown to be in fluid communication with a separator (300) contained within an insect evacuation module (3000).

The feeding chamber (200) of is shown to have an interior (201) defined by at least one side wall (202). Each side wall (202) of the embodiment of FIG. 3 is shown to have perforations as to be comprised of a mesh, or a screen, or the like. However, it is to be noted that any such wall, perforated or not perforated, screen or an impermeable surface shall suffice. It is also to be noted that the side wall (202) when made up of a screen-type material has opening that are lesser in size than the insects contained within the interior (201) of the feeding chamber (200).

In embodiments, the feeding chamber (200) has both a top (203) and a bottom (204). In the embodiment of FIG. 3, the top and bottom are both made up of a permeable metal or plastic or wire mesh or the like. However, in some embodiments, there is no bottom (204) at all, or the bottom is made up of a plurality of slats as described below. The first weighed enhanced feedstock stream (1F32), or otherwise termed a first enhanced feedstock stream (EF1), is introduced to an enhanced feedstock distributor (207) positioned within the interior (201) of the feeding chamber (200).

The feeding chamber is equipped with a humidity sensor (208) that is configured to measure the humidity within the interior (201) and input a signal (209) to the computer (COMP). The feeding chamber is equipped with a first temperature sensor (210) that is configured to measure the temperature of a first region within the interior (201) and input a signal (211) to the computer (COMP). The feeding chamber is equipped with a second temperature sensor (212) that is configured to measure the temperature of a first region within the interior (201) and input a signal (213) to the computer (COMP).

A network (220) of cells (219) are positioned within the interior (201) of the feeding chamber and are configured to permit insects (225) to reside therein. FIG. 4 shows one non-limiting embodiment of a network (220) of cells (219) for growing insects within a feeding chamber (200) of the insect feeding module (2000) shown in FIG. 3. The network (220) of cells (219) has openings (222) positioned at a first end (221) and openings (224) positioned at a second end (223). Insects (225) may reside in the passageways between the openings (222) at the first end (221) and the openings (224) at the second end (223). The cells (219) have a cell length (C-L) and a cell width (C-W). The network (220) of cells (219) has a network length (N-L) and a network width (N-W). In embodiments, the network (220) of cells (219) has a network length (N-L) that is greater than the network width (N-W). In embodiments, the network (220) of cells (219) has a network length (N-L) that is less than the network width (N-W). The cell width (C-W) is greater than the width (li-W) of a first insect (1i) that resides within the interior (201) of the feeding chamber (200). The cell width (C-W) is greater than the average insect width (Ni-W) of a Nth insect (Ni) that collectively reside within the interior (201) of the feeding chamber (200). The cell length (C-L) is greater than the length (2i-L) of a first insect (1i) that resides within the interior (201) of the feeding chamber (200). The cell length (C-L) is greater than the average insect length (Ni-LW) of a Nth insect (Ni) that collectively reside within the interior (201) of the feeding chamber (200).

Obviously, many insects (225) may be present within the feeding chamber (200) at any given time.

This may include: a first insect (1i) having a first insect length (li-L), a first insect width (li-W), and a first insect mass (li-WT); a second insect (2i) having a second insect length (2i-L), a second insect width (2i-W), and a second insect mass (2i-WT); and a Nth insect (Ni) that has an average insect length (Ni-L), an average insect width (Ni-W), and an average insect mass (Ni-WT). The average insect length (Ni-L) is the sum of the first insect length (li-L) and the second insect length (2i-L) divided by the number of insects that being two in this particular instance and embodiment. The average insect width (Ni-W) is the sum of the first insect width (li-W) and the second insect width (2i-W) divided by the number of insects that being two in this particular instance and embodiment. It is of course obvious to one of ordinary skill in the art that more than two insects (225, li, 2i) are contained within the interior (201) of the feeding chamber (200) and that both the average insect length (Ni-L) and average insect width (Ni-W) are averaged over a plurality of insects.

In embodiments, the cell width (C-W) ranges from: between about 0.125 inches to about 0.25 inches; between about 0.25 inches to about 0.50 inches; between about 0.5 inches to about 0.75 inches; between about 0.75 inches to about 1 inch; between about 1 inch to about 1.25 inches; between about 1.25 inch to about 1.50 inches; between about 1.50 inches to about 1.75 inches; between about 1.75 inches to about 2 inches; between about 2 inches to about 2.25 inches; between about 2.25 inches to about 2.50 inches; between about 2.50 inches to about 2.75 inches; between about 2.75 inches to about 2.75 inches; between about 2.75 inches to about 3 inches; between about 3 inches to about 3.25 inches; between about 3.25 inch to about 3.50 inches; between about 3.50 inches to about 3.75 inches; between about 3.75 inches to about 4 inches; between about 4 inches to about 4.25 inches; between about 4.25 inch to about 4.50 inches; between about 4.50 inches to about 4.75 inches; and, between about 4.75 inches to about 5 inches.

In embodiments, the cell length (C-L) ranges from: between about 0.5 feet to about 1 foot; between about 1 feet to about 2 feet; between about 2 feet to about 3 feet; between about 3 feet to about 4 feet; between about 4 feet to about 5 feet; between about 5 feet to about 6 feet; between about 6 feet to about 7 feet; between about 7 feet to about 8 feet; between about 8 feet to about 9 feet; between about 9 feet to about 10 feet; between about 10 feet to about 11 feet; between about 11 feet to about 12 feet; between about 12 feet to about 13 feet; between about 13 feet to about 14 feet; between about 14 feet to about 15 feet; between about 15 feet to about 16 feet; between about 16 feet to about 17 feet; between about 17 feet to about 18 feet; between about 18 feet to about 19 feet; between about 19 feet to about 20 feet; between about 20 feet to about 21 feet; between about 21 feet to about 22 feet; between about 22 feet to about 23 feet; between about 23 feet to about 24 feet; between about 24 feet to about 25 feet; between about 25 feet to about 26 feet; between about 26 feet to about 27 feet; between about 27 feet to about 28 feet; between about 28 feet to about 29 feet; between about 29 feet to about 30 feet; between about 30 feet to about 31 feet; between about 31 feet to about 32 feet; between about 32 feet to about 33 feet; between about 33 feet to about 34 feet; between about 34 feet to about 35 feet; between about 35 feet to about 36 feet; between about 36 feet to about 37 feet; between about 37 feet to about 38 feet; between about 38 feet to about 39 feet; and, between about 39 feet to about 40 feet.

In embodiments, the average insect width (Ni-W) ranges from: between about 0.005 inches to 0.015625 inches, 0.015625 inches to about 0.03125 inches; between about 0.03125 inches to about 0.0625 inches; between about 0.0625 inches to about 0.125 inches; between about 0.125 inches to about 0.25 inches; between about 0.25 inches to about 0.50 inches; between about 0.5 inches to about 0.75 inches; between about 0.75 inches to about 1 inch; between about 1 inch to about 1.25 inches; between about 1.25 inch to about 1.50 inches; between about 1.50 inches to about 1.75 inches; between about 1.75 inches to about 2 inches; between about 2 inches to about 2.25 inches; between about 2.25 inches to about 2.50 inches; between about 2.50 inches to about 2.75 inches; between about 2.75 inches to about 2.75 inches; and, between about 2.75 inches to about 3 inches.

In embodiments, the average insect length (Ni-L) ranges from: between about 0.01 inches to 0.05 inches, 0.05 inches to 0.075 inches, 0.075 inches to 0.1 inches, 0.1 inch to 0.125 inches, 0.125 inches to about 0.25 inches; between about 0.25 inches to about 0.50 inches; between about 0.5 inches to about 0.75 inches; between about 0.75 inches to about 1 inch; between about 1 inch to about 1.25 inches; between about 1.25 inch to about 1.50 inches; between about 1.50 inches to about 1.75 inches; between about 1.75 inches to about 2 inches; between about 2 inches to about 2.25 inches; between about 2.25 inches to about 2.50 inches; between about 2.50 inches to about 2.75 inches; between about 2.75 inches to about 2.75 inches to about 3 inches; between about 3 inches to about 3.25 inches; between about 3.25 inch to about 3.50 inches; between about 3.50 inches to about 3.75 inches; between about 3.75 inches to about 4 inches; between about 4 inches to about 4.25 inches; between about 4.25 inch to about 4.50 inches; between about 4.50 inches to about 4.75 inches; between about 4.75 inches to about 5 inches; between about 5 inches to about 5.25 inches; between about 5.25 inches to about 5.5 inches; between about 5.5 inches to about 5.75 inches; between about 5.75 inches to about 6 inches; between about 6 inches to about 7 inches; between about 7 inches to about 8 inches; between about 8 inches to about 9 inches; and, between about 9 inches to about 10 inches.

Referring again to FIG. 3, a vibration unit (214) may be connected to the network (220) of cells (219) at a first vibration unit connection (218A) and a second vibration unit connection (218B). The vibration unit (214) is equipped with a vibration unit motor (215) and integrated controller (216) that is configured to input and output a signal (217) to the computer (COMP). The vibration unit (214) is used to shake or to provide oscillations to occur within the network (220) of cells (219) to dislodge insects (225) from within the passageway between the first end (221) openings (222) and the second end (223) openings (224). Alternately, the vibration unit (214) may vibrate the entire feeding chamber (200) or at least a portion of the feeding chamber (200) so as to effectuate disclosing insects (225) from their resting surface within the network (220) of cells (219) in between the first end (221) openings (222) and the second end (223) openings (224).

In embodiments, a cell network differential pressure sensor (226) may be installed to measure to pressure across the network (220) of cells (219) to ascertain some measure of the mass or volume or quantity of insects that reside in between the first end (221) openings (222) and the second end (223) openings (224).

The cell network differential pressure sensor (226) is configured to input a signal (227) to the computer (COMP). When a pre-determined differential pressure is measured across the feeding chamber (200), insects may be evacuated therefrom. In embodiments, the pre-determined differential pressure across the feeding chamber (200) ranges from: about 0.015625 inches of water to about 0.03125 inches of water; between about 0.03125 inches of water to about 0.0625 inches of water; between about 0.0625 inches of water to about 0.125 inches of water; between about 0.125 inches of water to about 0.25 inches of water; between about 0.25 inches of water to about 0.50 inches of water; between about 0.5 inches of water to about 0.75 inches of water; between about 0.75 inches of water to about 1 inch; between about 1 inch to about 1.25 inches of water; between about 1.25 inch to about 1.50 inches of water; between about 1.50 inches of water to about 1.75 inches of water; between about 1.75 inches of water to about 2 inches of water; between about 2 inches of water to about 2.25 inches of water; between about 2.25 inches of water to about 2.50 inches of water; between about 2.50 inches of water to about 2.75 inches of water; between about 2.75 inches of water to about 2.75 inches of water; between about 2.75 inches of water to about 3 inches of water; between about 3 inches of water to about 3.25 inches of water; between about 3.25 inch to about 3.50 inches of water; between about 3.50 inches of water to about 3.75 inches of water; between about 3.75 inches of water to about 4 inches of water; between about 4 inches of water to about 4.25 inches of water; between about 4.25 inch to about 4.50 inches of water; between about 4.50 inches of water to about 4.75 inches of water; between about 4.75 inches of water to about 5 inches of water; between about 5 inches of water to about 5.25 inches of water; between about 5.25 inches of water to about 5.5 inches of water; between about 5.5 inches of water to about 5.75 inches of water; between about 5.75 inches of water to about 6 inches of water; between about 6 inches of water to about 7 inches of water; between about 7 inches of water to about 8 inches of water; between about 8 inches of water to about 9 inches of water; between about 10 inches of water to about 15 inches of water; between about 15 inches of water to about 20 inches of water; between about 20 inches of water to about 25 inches of water; between about 25 inches of water to about 30 inches of water; between about 30 inches of water to about 35 inches of water; between about 35 inches of water to about 40 inches of water; between about 40 inches of water to about 45 inches of water; between about 45 inches of water to about 50 inches of water; between about 50 inches of water to about 55 inches of water; between about 55 inches of water to about 60 inches of water; between about 60 inches of water to about 65 inches of water; between about 65 inches of water to about 70 inches of water; between about 70 inches of water to about 75 inches of water; between about 75 inches of water to about 80 inches of water; between about 80 inches of water to about 85 inches of water; between about 85 inches of water to about 90 inches of water; between about 90 inches of water to about 95 inches of water; and, between about 95 inches of water to about 100 inches of water.

The cell network differential pressure sensor (226) is connected to the interior (201) of the feeding chamber (200) by a first end impulse line (228) with a first end impulse line connection (232) and a second end impulse line (233) with a second end impulse line connection (237). FIG. 3 shows the first end impulse line (228) connected to the feeding chamber (200) via a first end impulse line connection (232) that is positioned vertically above the first end (221) openings (222) of the network (220) of cells (219). FIG. 3 also shows the second end impulse line (233) connected to the feeding chamber (200) via a second end impulse line connection (237) that is positioned vertically below the second end (223) openings (224) of the network (220) of cells (219).

The first end impulse line (228) and second end impulse line (233) are preferably tubes ranging from ⅛", ¼", ⅜", ½", ¾", or 1" stainless steel, plastic, polymer, metal tubing or piping. To prevent insects (225) from crawling up the first end impulse line (228), or to prevent clogging of particulates, and thus preventing the cell network differential pressure sensor (226) from accurately measuring differential pressure across the network (220) of cells (219), a first impulse line gas supply (231) may be provided to apply a continuous purge or gas, such as air, or CO2, or the like. The first impulse line gas supply (231) is controlled and set to a pre-determined flow rate by adjusting a first air purge flow regulator (230) wherein the flow rate is detected via a first air purge flow sensor (229). Similarly, to prevent insects (225) from crawling up the second end impulse line (233), or to prevent clogging of particulates, and thus preventing the cell network differential pressure sensor (226) from accurately measuring differential pressure across the network (220) of cells (219), a second impulse line gas supply (236) may be provided to apply a continuous purge or gas, such as air, or CO2, or the like. The second impulse line gas supply (236) is controlled and set to a pre-determined flow rate by adjusting a second air purge flow regulator (235) wherein the flow rate is detected via a second air purge flow sensor (234).

In embodiments, a gas quality sensor (GC1) is configured to analyze the gas quality within the interior (201) of the feeding chamber (200). In embodiments, the gas quality sensor (GC1) is equipped to send a signal (XGC1) to the computer (COMP). In embodiments, the gas quality sensor (GC1) is comprised of one or more analyzers selected from the group consisting of Fourier-transform infrared spectroscopy, gas chromatography, mass spectrometry, and ultra-high performance liquid chromatography.

In embodiments, the interior (201) of the feeding chamber (200) is maintained at a predetermined concentration of ammonia, methane, urea, carbon dioxide. In response to the signal (XGC1) from the gas quality sensor (GC1) the computer (COMP) instructs the insect evacuation fan (312) to pull a vacuum on the interior (201) of the feeding chamber (200) is maintained at a predetermined concentration of ammonia, methane, urea, carbon dioxide.

In other embodiments, in response to the signal (XGC1) from the gas quality sensor (GC1) the computer (COMP) instructs the air supply fan (271) to delivery an air supply (262) to the interior (201) of the feeding chamber (200) to maintain the interior (201) of the feeding chamber (200) at a predetermined concentration of ammonia, methane, carbon dioxide, hydrogen sulfide.

In embodiments, the predetermined concentration of ammonia within the interior (201) of the feeding chamber (200) ranges from: 0.05 parts per million (ppm) to 0.1 ppm, 0.1 ppm to 0.2 ppm, 0.2 ppm to 0.4 ppm, 0.4 ppm to 0.8 ppm, 0.8 ppm to 1 ppm, 1 ppm to 2 ppm, 2 ppm to 3 ppm, 3 ppm to 5 ppm, 5 ppm to 6 ppm, 6 ppm to 7 ppm, 7 ppm to 8 ppm, 8 ppm to 9 ppm, 9 ppm to 10 ppm, 10 ppm to 15 ppm, 15 ppm to 25 ppm, 25 ppm to 50 ppm, and 50 ppm to 100 ppm.

In embodiments, the predetermined concentration of methane within the interior (201) of the feeding chamber (200) ranges from: 0.05 parts per million (ppm) to 0.1 ppm, 0.1 ppm to 0.2 ppm, 0.2 ppm to 0.4 ppm, 0.4 ppm to 0.8 ppm, 0.8 ppm to 1 ppm, 1 ppm to 2 ppm, 2 ppm to 3 ppm, 3 ppm to 5 ppm, 5 ppm to 6 ppm, 6 ppm to 7 ppm, 7 ppm to 8 ppm, 8 ppm to 9 ppm, 9 ppm to 10 ppm, 10 ppm to 15 ppm, 15 ppm to 25 ppm, 25 ppm to 50 ppm, and 50 ppm to 100 ppm.

In embodiments, the predetermined concentration of carbon dioxide within the interior (201) of the feeding chamber (200) ranges from: 390 parts per million (ppm) to 400 ppm, 400 ppm to 410 ppm, 410 ppm to 420 ppm, 420 ppm to 430 ppm, 430 ppm to 440 ppm, 440 ppm to 450 ppm, 450 ppm to 460 ppm, 460 ppm to 470 ppm, 470 ppm to 480 ppm, 480 ppm to 490 ppm, 490 ppm to 500 ppm, 500 ppm to 600 ppm, 600 ppm to 700 ppm, 700 ppm to 800 ppm, 800 ppm to 900 ppm, 900 ppm to 1000 ppm, 1000 ppm to 2000 ppm, 2000 ppm to 3000 ppm, 3000 ppm to 4000 ppm, 4000 ppm to 5000 ppm, 5000 ppm to 6000 ppm, 6000 ppm to 7000 ppm, 7000 ppm to 8000 ppm, 8000 ppm to 9000 ppm, and 9000 ppm to 10000 ppm.

In embodiments, the predetermined concentration of hydrogen sulfide within the interior (201) of the feeding chamber (200) ranges from: 0.05 parts per million (ppm) to 0.1 ppm, 0.1 ppm to 0.2 ppm, 0.2 ppm to 0.4 ppm, 0.4 ppm to 0.8 ppm, 0.8 ppm to 1 ppm, 1 ppm to 2 ppm, 2 ppm to 3 ppm, 3 ppm to 5 ppm, 5 ppm to 6 ppm, 6 ppm to 7 ppm, 7 ppm to 8 ppm, 8 ppm to 9 ppm, 9 ppm to 10 ppm, 10 ppm to 15 ppm, 15 ppm to 25 ppm, 25 ppm to 50 ppm, and 50 ppm to 100 ppm. In embodiments, a decibel meter (DM1) is configured to analyze noise or sound levels by measuring sound pressure level (in decibel (dB)) within the interior (201) of the feeding chamber (200). In embodiments, the gas quality sensor (GC1) is equipped to send a signal (XGC1) to the computer (COMP). In embodiments, the decibel meter (DM1) indicates a range of sound pressure in decibels (dB) including one or more decibel ranges selected from the group consisting of: 86 decibels (dB) to 88 dB, 88 dB to 90 dB, 90 dB to 92 dB, 92 dB to 94 dB, 94 dB to 96 dB, 96 dB to 98 dB, 98 dB to 100 dB, 100 dB to 102 dB, 102 dB to 104 dB, 104 dB to 106 dB, 106 dB to 108 dB, or 108 dB to 110 dB.

In embodiments, a sound damping system (SDS) is configured to reduce the noise or sound levels by reducing the sound pressure level (in decibel (dB)) within the interior (201) of the feeding chamber (200) to a predetermined decibel range selected from the group consisting of: 86 decibels (dB) to 88 dB, 88 dB to 90 dB, 90 dB to 92 dB, 92 dB to 94 dB, 94 dB to 96 dB, 96 dB to 98 dB, 98 dB to 100 dB, 100 dB to 102 dB, 102 dB to 104 dB, 104 dB to 106 dB, 106 dB to 108 dB, or 108 dB to 110 dB.

In embodiments, a sound damping system (SDS) is configured to reduce the noise or sound levels by reducing the sound pressure level (in decibel (dB)) within the interior (201) of the feeding chamber (200) by a percentage including one or more percentage ranges selected from the group consisting of: 5 percent to 10 percent, 10 percent to 15 percent, 15 percent to 20 percent, 20 percent to 25 percent, 25 percent to 30 percent, 30 percent to 35 percent, 35 percent to 40 percent, 40 percent to 45 percent, 45 percent to 50 percent, 50 percent to 55 percent, 55 percent to 60 percent, 60 percent to 65 percent, 65 percent to 70 percent, 70 percent to 75 percent, 75 percent to 80 percent, 80 percent to 85 percent, 85 percent to 90 percent, 90 percent to 95 percent, or 95 percent to 100 percent.

In embodiments, a sound damping system (SDS) includes a means of reducing the sound pressure within the interior (201) of the feeding chamber (200) including one or more selected from the group consisting of: using noise barriers to reflect or absorb the energy of the sound waves, using damping structures such as sound baffles, or using active antinoise sound generators, sound absorption damping, sound redirection damping, porous absorbers, open cell rubber foams which absorb noise by friction within the cell structure, melamine sponges which absorb noise by friction within the cell structure, resonant panels, refection, and diffusion.

In embodiments, a sound damping system (SDS) includes a means of reducing the sound pressure within the interior (201) of the feeding chamber (200) including one or more selected from the group consisting of: acoustic board, acoustic foam, acoustic quieting, noise barrier, noise mitigation, sound masking, and damping.

An air input (260) is configured to permit an air supply (262) to be transferred to the interior (201) of the feeding chamber (200) via an air supply entry conduit (261). An optional inlet gas distributor (263) may be positioned at the interface of the air input (260) so as to substantially uniformly distribute the air supply (262) over the cross-section of the interior (201) of the feeding chamber (200). In embodiments, the inlet gas distributor (263) may serve to effectuate a high velocity blast of air to the openings (222, 224) of the network (220) of cells (219) to aide in dislodging insects (225) from the cells (219) and to permit substantially complete evacuation of the egg-laying insects (225) present thing the interior (201) of the feeding chamber (200).

FIG. 3 shows an air supply fan (271) connected to the interior (201) of the feeding chamber (200) via the air supply entry conduit (261). The air supply fan (271) equipped with an air supply fan motor (272) and controller (273) is configured to input and output a signal (274) to the computer (COMP). An air heater (264) may be interposed in the air supply entry conduit (261) in between the air supply fan (271) and the feeding chamber (200).

Water (275) in the form of liquid or vapor may be introduced to the air supply entry conduit (261) via a water transfer line (276). A water input valve (278), and a water flow sensor (279) may also be installed on the water transfer line (276). The water flow sensor (279) is configured to input a signal (280) to the computer (COMP). The air supply (262) may be mixed with the water (275) in a water and gas mixing section (281) of the air supply entry conduit (261). FIG. 1 shows the water and gas mixing section (281) upstream of the air heater (264) but it may alternately also be placed downstream.

The air heater (264) may be electric, operated by natural gas, combustion, solar energy, alternative energy, or it may be a heat transfer device that uses a working heat transfer medium, such as steam or any other heat transfer medium known to persons having an ordinary skill in the art to which it pertains. FIG. 3 shows the air heater (264) to have a heat transfer medium input (265) and a heat transfer medium output (266). In embodiments, a first steam supply (LCL) is provided to the heat transfer medium input (265). In embodiments, the first steam supply (LCL) is provided from FIG. 14L.

In embodiments, heat transfer medium input (265) of the air heater (264) is equipped with a heat exchanger heat transfer medium inlet temperature (T3) that is configured to input a signal (XT3) to the computer (COMP). In embodiments, heat transfer medium output (266) of the air heater (264) is equipped with a heat exchanger heat transfer medium outlet temperature (T4) that is configured to input a signal (XT4) to the computer (COMP). In embodiments, a first condensate (LAQ) is discharged from the heat transfer medium output (266) and is provided to the condensate tank (LAP) on FIG. 14L.

A first humidity sensor (267) is positioned on the discharge of the air supply fan (271) upstream of the water and gas mixing section (281). The first humidity sensor (267) is configured to input a signal (268) to the computer (COMP). A heat exchanger inlet gas temperature sensor (T1) is positioned on the discharge of the air supply fan (271) upstream of the air heater (264). The heat exchanger inlet gas temperature sensor (T1) is configured to input a signal (XT1) to the computer (COMP).

A second humidity sensor (269) is positioned on the discharge of the air heater (264) upstream of the air input (260) to the interior (201) of the feeding chamber (200). The second humidity sensor (266) is configured to input a signal (270) to the computer (COMP). A heat exchanger outlet gas temperature sensor (T2) is positioned on the discharge of the air heater (264) upstream of the air input (260) to the interior (201) of the feeding chamber (200). The heat exchanger outlet gas temperature sensor (T2) is configured to input a signal (XT2) to the computer (COMP).

In embodiments, the air supply fan (271), air heater (264), and air supply (262), permit the computer automation while integrated with the heat exchanger inlet gas temperature sensor (T1), heat exchanger outlet gas temperature sensor (T2), and feeding chamber (200) temperature sensors (210, 212), to operate under a wide variety of automated temperature operating conditions including varying the temperature range in the feeding chamber (200) from: below 32 degrees Fahrenheit, between about 32 degrees Fahrenheit to about 40 degrees Fahrenheit; between about 40 degrees Fahrenheit to about 45 degrees Fahrenheit; between about 45 degrees Fahrenheit to about 50 degrees Fahrenheit; between about 50 degrees Fahrenheit to about 55 degrees Fahrenheit; between about 55 degrees Fahrenheit to about 60 degrees Fahrenheit; between about 60 degrees Fahrenheit to about 65 degrees Fahrenheit; between about 65 degrees Fahrenheit to about 70 degrees Fahrenheit; between about 70 degrees Fahrenheit to about 75 degrees Fahrenheit; between about 75 degrees Fahrenheit to about 80 degrees Fahrenheit; between about 80 degrees Fahrenheit to about 85 degrees Fahrenheit; between about 85 degrees Fahrenheit to about 90 degrees Fahrenheit; between about 90 degrees Fahrenheit to about 95 degrees Fahrenheit; between about 95 degrees Fahrenheit to about 100 degrees Fahrenheit; between about 100 degrees Fahrenheit to about 105 degrees Fahrenheit; between about 105 degrees Fahrenheit to about 110 degrees Fahrenheit; between about 110 degrees Fahrenheit to about 115 degrees Fahrenheit; and, between about 115 degrees Fahrenheit to about 120 degrees Fahrenheit.

In embodiments, the air supply fan (271), air heater (264), air supply (262), and water (275) permit the computer automation while integrated with the first humidity sensor (267), second humidity sensor (269), and feeding chamber (200) humidity sensor (208), to operate under a wide variety of automated operating humidity conditions including varying the humidity range in the feeding chamber (200) from: between about 5 percent humidity to about 10 percent humidity; between about 10 percent humidity to about 15 percent humidity; between about 15 percent humidity to about 20 percent humidity; between about 20 percent humidity to about 25 percent humidity; between about 25 percent humidity to about 30 percent humidity; between about 30 percent humidity to about 35 percent humidity; between about 35 percent humidity to about 40 percent humidity; between about 40 percent humidity to about 45 percent humidity; between about 45 percent humidity to about 50 percent humidity; between about 50 percent humidity to about 55 percent humidity; between about 55 percent humidity to about 60 percent humidity; between about 60 percent humidity to about 65 percent humidity; between about 65 percent humidity to about 70 percent humidity; between about 70 percent humidity to about 75 percent humidity; between about 75 percent humidity to about 80 percent humidity; between about 80 percent humidity to about 85 percent humidity; between about 85 percent humidity to about 90 percent humidity; between about 90 percent humidity to about 95 percent humidity; and, between about 95 percent humidity to about 100 percent humidity.

FIG. 3 shows the feeding chamber (200) connected to a separator (300) via a feeding chamber exit conduit (302). The insect evacuation module (3000) shown in FIG. 3 only contains a first separator (S1), however it is to be noted that more than one separator (S2, S3) may be utilized in some circumstances.

The feeding chamber exit conduit (302) is connected at a first end to the feeding chamber (200) via an insect evacuation output (205) and connected at another end to a separator (300) via an insect and gas mixture input (303). The feeding chamber exit conduit (302) is configured to transfer an insect and gas mixture (304) from the feeding chamber (200) to the separator (300).

The insect and gas mixture (304) has an insect portion (304A) and a gas portion (304B). The gas portion is mostly air, however may contain some CO2 if some CO2 is used in the first impulse line gas supply (231) or the second impulse line gas supply (236). The separator (300), showing in FIG. 3 as a first separator (S1), is also shown in a filter. However, in other embodiments, the first separator (S1) may be a filter, a cyclone, or any other conceivable means to achieve the end of separating insects from a gas.

The separator (300) of FIG. 3 is a filter and contains an interior (301), an entry section (305) and an exit section (307). A filter element (306) separates the entry section (305) from the exit section (307) so as to only permit the gas portion (304B) of the insect and gas mixture (304) to flow through the filter element (306) from the entry section (305) to the exit section (307).

The insect portion (304A) of the insect and gas mixture (304) is retained within the entry section (305) because the pores or openings in the filter element (306) are smaller than the average insect length (Ni-L) or the average insect width (Ni-W) of the insects (225, Ni) contained within the interior (201) of the feeding chamber (200) and transferred to the separator (300).

A differential pressure sensor (308) is installed on the separator (300) to measure the pressure drop across the filter element (306) in between the entry section (305) and exit section (307). The differential pressure sensor (308) is configured to input a signal (309) to the computer (COMP). The differential pressure sensor (308) has an entry section impulse line (310) in fluid communication with the entry section (305) as well as an exit section impulse line (311) in fluid communication with the exit section (307).

An insect evacuation fan (312) pulls a vacuum through the separator (300, S1) and in turn pulls a vacuum on the feeding chamber (200). The insect evacuation fan (312) is configured to pull a vacuum on the feeding chamber to remove insects (225) from within the network (220) of cells 219). Specifically, the insect evacuation fan (312) pulls a vacuum on the network (220) of cells (219) and sucks insects from the in between the openings (222) of the first end (221) and the openings (224) of the second end (223) so as to substantially completely evacuate egg-laying insects (225) from the interior (201) of the feeding chamber (200).

When a vacuum is pulled on the feeding chamber the cell network differential pressure sensor (226) sends a signal (227) to the computer (COMP) so as to quantify the quantity of mass of insects (225) present within the network (220) of cells (219) within the feeding chamber (200) interior (201).

The insect evacuation fan (312) is equipped with a fan motor (314) and a controller (316) that is configured to input and output a signal (318) to the computer (COMP). The insect evacuation fan (312) is connected to the separator (300) via an insect-depleted gas output (321). The insect-depleted gas output (321) is configured to transfer an insect-depleted gas (320) from the separator (300) to the inlet of the insect evacuation fan (312). The insect-depleted gas (320) has a reduced amount of insects in it in reference to the insect and gas mixture (304). The insect evacuation fan (312) discharges the insect-depleted gas (320) via an insect-depleted gas exhaust line (322). A portion of the insect-depleted gas (320) that passes through the insect-depleted gas exhaust line (322) may be routed back to the separator to backflush the filter element (306). Thus, the insect-depleted gas exhaust line (322) is in fluid communication with the separator (300) via an insect-depleted gas recycle line (323) and an exhaust gas recycle input (324).

The separator (300) may be equipped with a valve (325) with a controller (326) that is configured to input a signal (327) to the computer (COMP). The valve (325) is preferably a rotary style valve, but may in some embodiments be that of a ball valve, butterfly valve, knife valve, piston valve, or plug valve.

The separator (300) may also be equipped with a separated insect conveyor (328) to remove separated insects (334) from the separator (300). The separated insect conveyor (328) has a motor (329) and a controller (330) that is configured to input and output a signal (331) to the computer (COMP). The separated insect conveyor (328) may also be equipped with a mass sensor (332) for weighing the separated insects (334) by sending a signal (333) to the computer (COMP). The separated insect conveyor (328) may be any type of conveyor, but preferably is a screw auger. Other types of conveyors are compression screw conveyors, conveyor belts, a pneumatic conveyor system, a vibrating conveyor system, a flexible conveyor system, a vertical conveyor system, a spiral conveyor system, a drag chain conveyor system, or a heavy duty rear conveyor system. Any conceivable type of mechanical handling equipment may be used so long as it can move separated insects (334) from one location to another. The separated insect conveyor (328) may route the separated insects (334) to a downstream location such as to a grinder, a pathogen removal unit, breeding chamber, a lipid extraction unit, or to a multifunctional composition mixing module.

In embodiments, the insect evacuation fan (312) is configured to remove a portion of egg-laying insects from the insect feeding chamber by applying a vacuum with a velocity pressure range from: between about 0.001 inches of water to about 0.005 inches of water; between about 0.005 inches of water to about 0.01 inches of water; between about 0.01 inches of water to about 0.02 inches of water; between about 0.02 inches of water to about 0.03 inches of water; between about 0.03 inches of water to about 0.04 inches of water; between about 0.04 inches of water to about 0.05 inches of water; between about 0.05 inches of water to about 0.06 inches of water; between about 0.06 inches of water to about 0.07 inches of water; between about 0.07 inches of water to about 0.08 inches of water; between about 0.08 inches of water to about 0.09 inches of water; between about 0.09 inches of water to about 0.1 inches of water; between about 0.1 inches of water to about 0.2 inches of water; between about 0.2 inches of water to about 0.3 inches of water; between about 0.3 inches of water to about 0.4 inches of water; between about 0.4 inches of water to about 0.5 inches of water; between about 0.5 inches of water to about 0.6 inches of water; between about 0.6 inches of water to about 0.7 inches of water; between about 0.7 inches of water to about 0.8 inches of water; between about 0.8 inches of water to about 0.9 inches of water; between about 0.9 inches of water to about 1 inch of water; between about 1 inch of water to about 1.25 inches of water; between about 1.25 inches of water to about 1.5 inches of water; between about 1.5 inches of water to about 2 inches of water; between about 2 inches of water to about 3 inches of water; between about 3 inches of water to about 4 inches of water; between about 4 inches of water to about 5 inches of water; between about 5 inches of water to about 6 inches of water; between about 6 inches of water to about 7 inches of water; between about 7 inches of water to about 8 inches of water; between about 8 inches of water to about 9 inches of water; between about 9 inches of water to about 10 inches of water; between about 10 inch of water to about 15 inches of water; between about 15 inches of water to about 25 inches of water; between about 25 inches of water to about 50 inches of water; between about 50 inches of water to about 75 inches of water; between about 75 inches of water to about 100 inches of water; between about 100 inches of water to about 150 inches of water; between about 150 inches of water to about 200 inches of water; between about 200 inches of water to about 250 inches of water; between about 250 inches of water to about 300 inches of water; between about 300 inches of water to about 350 inches of water; and, between about 350 inches of water to about 400 inches of water.

FIG. 3 shows one non-limiting embodiment of an egg transfer system (244) including a conveyor (245) equipped with a first conveyor elevation unit (254) and a second conveyor elevation unit (256) that is configured to extend in a vertical direction from supports (255, 257) from a first retracted height (H1) to a second elevated height (H2).

The conveyor (245) is configured to make an egg-depleted breeding material (246) available to the interior (201) of the feeding chamber (200). This is achieved by providing a conveyor (245) having an egg-depleted breeding material (246) provided thereon and extending the conveyor (245) in a vertical direction so that the conveyor (245) and egg-depleted breeding material (246) come into contact with the screen floor (258) of the feeding chamber (200). Egg-laying insects (225) lay their eggs (259) through the screen floor (258) of the feeding chamber (200) and deposit the eggs (259) into the breeding material (248) that rests upon the conveyor (245).

In the embodiment of FIG. 3, the egg-laying insects (225) present within the interior (201) of the feeding chamber (200) will deposit the eggs (259) into the breeding material (248) and the screen floor (258) will prevent them from eating or digging up the eggs (259). More on the different states of operation is discussed below in FIGS. 5 through 10.

The conveyor (245) receives egg-depleted breeding material (246) via a conveyor input (247). The egg-depleted breeding material (246) is then made available to the insects (225) within the feeding chamber (200). This is made possible in the embodiment of FIG. 3 by activating the first conveyor elevation unit (254) and second conveyor elevation unit (256) so as to extend the conveyor (245) vertically in a direction towards the bottom of the feeding chamber (200) from a first retracted height (H1) to a second elevated height (H2).

After insects (225) have laid their eggs (259) into the breeding material (248), the first conveyor elevation unit (254) and second conveyor elevation unit (256) are returned from a first retracted height (H1) to a second elevated height (H2) so as to lower the conveyor (245) vertically in a direction away from the bottom of the feeding chamber (200).

As a result of eggs (259) being deposited into the egg-depleted breeding material (246) an egg-laden breeding material (250) is created which is discharged from the conveyor via a conveyor output (249). The egg-laden breeding material (250) has a greater amount of eggs within it in reference to the egg-depleted breeding material (246). The egg-laden breeding material (250) is then transferred to a breeding chamber as described below in detail. The conveyor (245) is equipped with a conveyor motor (251) and a controller (252) that is configured to input and output a signal (253) to the computer (COMP). The first conveyor elevation unit (254) has a first support (255) and the second conveyor elevation unit (256) has a second support (257). The breeding material (248) may be any conceivable material that is suitable for insects to deposit eggs into. In embodiments, the breeding material (248) is soil, mulch, compost, top soil, humus, clay, dirt, sand, minerals, organic matter, or a combination thereof. In embodiments, the breeding material (248) may be comprised of a gel, a damp substrate, vermiculite, leaves, grass clippings, peat moss, agricultural residue, wood chips, green waste, woodchip mulch, bark chips, straw mulch, hay, food waste, animal waste, cardboard, newspaper, carpet, foam, moss, recycled pulp, paper scraps, or feedstock, industrial waste, or any conceivable material that is suitable for an insect to lay eggs in.

FIG. 3 also shows that the feeding chamber (200) has a hatched insects input (240) that is configured to transfer hatched insects (239) from a breeding chamber to the interior (201) of the feeding chamber (200) via a breeding chamber insect transfer line (238). In embodiments where the Insect Production Superstructure System (IPSS) may have a plurality of insect feeding chambers (FC1, FC2, FC3), the first feeding chamber (FC1) is shown to have an egg-laying insects input (243) for transferring egg-laying insects (242) that were present within the second feeding chamber (FC2) or third feeding chamber (FC3) via a feeding chamber transfer line (241).

In embodiments, the feeding chamber grows insects within it over a time duration ranging from: between about 1 week to 2 weeks; between about 2 weeks to 3 weeks; between about 3 week to 4 weeks; between about 4 week to 5 weeks; between about 5 week to 6 weeks; between about 6 week to 7 weeks; between about 7 week to 8 weeks; between about 8 week to 9 weeks; between about 9 week to 10 weeks; between about 10 week to 11 weeks; between about 11 week to 12 weeks; between about 12 week to 13 weeks; between about 13 week to 14 weeks; or, between about 14 week to 15 weeks.

In embodiments, the interior (201) of the feeding chamber (200) includes a plurality of lights (L1) are configured to be controlled by the computer (COMP). In embodiments, the lights (L1) have a controller (CL1) that sends a signal (XL1) to and from the computer (COMP). In embodiments, the lights (L1, L2) may be compact fluorescent (CFL), light emitting diode (LED), incandescent lights, fluorescent lights, or halogen lights.

In embodiments, the plurality of lights (L1) operate at a wavelength ranging from 400 nm to 700 nm. In embodiment, the plurality of lights (L1) operate at a spectrum including one or more spectrum ranges selected from the group consisting of: 390 nanometers (nm) to 400 nm, 400 nm to 410 nm, 410 nm to 420 nm, 420 nm to 430 nm, 430 nm to 440 nm, 440 nm to 450 nm, 450 nm to 460 nm, 460 nm to 470 nm, 470 nm to 480 nm, 480 nm to 490 nm, 490 nm to 500 nm, 500 nm to 510 nm, 510 nm to 520 nm, 520 nm to 530 nm, 530 nm to 540 nm, 540 nm to 550 nm, 550 nm to 560 nm, 560 nm to 570 nm, 570 nm to 580 nm, 580 nm to 590 nm, 590 nm to 600 nm, 600 nm to 610 nm, 610 nm to 620 nm, 620 nm to 630 nm, 630 nm to 640 nm, 640 nm to 650 nm, 650 nm to 660 nm, 660 nm to 670 nm, 670 nm to 680 nm, 680 nm to 690 nm, or 690 nm to 700 nm.

In embodiments, the plurality of lights (L1) operate at a frequency including one or more frequencies selected from the group consisting of broad visible spectrum including: 425 terahertz (THz) to 450 THz, 450 THz to 475 THz, 475 THz to 500 THz, 500 THz to 525 THz, 525 THz to 550 THz, 550 THz to 575 THz, 575 THz to 600 THz, 600 THz to 625 THz, 625 THz to 650 THz, 650 THz to 675 THz, 675 THz to 700 THz, 700 THz to 725 THz, 725 THz to 750 THz, 750 THz to 775 THz, or 775 THz to 800 THz.

In embodiments, a plurality of lights (L1) in the interior (201) of the feeding chamber (200) include a plurality of light emitting diodes (LED). In embodiments, the plurality of light emitting diodes (LED) include blue LEDs (BLED), red LEDS (RLED), and/or green LEDS (GLED). In embodiments, the plurality of light emitting diodes (LED) in the interior (201) of the feeding chamber (200) include one or two or more from the group consisting of blue LEDs (BLED), red LEDS (RLED), and green LEDS (GLED).

In embodiments, the computer (COMP) controls the lights (L1). In embodiments, the lights (L1) illuminate each the interior (201) of the feeding chamber (200) with an illumination on-off ratio ranging from between 0.5 to 11. The illumination on-off ratio is defined as the duration of time when the lights (L1) are on and illuminate the interior (201) of the feeding chamber (200) in hours divided by the subsequent duration of time when the lights (L1) are off and are not illuminating the interior (201) of the feeding chamber (200) in hours before the lights are turned on again.

In embodiments, the lights (L1) are on and illuminate the interior (201) of the feeding chamber (200) for 18 hours and then are turned off for 6 hours. 18 divided by 6 is 3. In embodiments, an illumination on-off ratio of 3 is contemplated. In embodiments, the lights (L1) are on and illuminate the interior (201) of the feeding chamber (200) for 20 hours and then are turned off for 4 hours. 20 divided by 4 is 5. In embodiments, an illumination on-off ratio of 5 is contemplated. In embodiments, the lights (L1, L2) are on and illuminate the interior (201) of the feeding chamber (200) for 22 hours and then are turned off for 2 hours. 22 divided by 2 is 11. In embodiments, an illumination on-off ratio of 11 is contemplated. In embodiments, the lights (L1, L2) are on and illuminate the interior (201) of the feeding chamber (200) for 8 hours and then are turned off for 16 hours. 8 divided by 16 is 0.5. In embodiments, an illumination on-off ratio of 0.5 is contemplated. In embodiments, the lights (L1, L2) are on and illuminate the interior (201) of the feeding chamber (200) for 12 hours and then are turned off for 12 hours. 12 divided by 12 is 1. In embodiments, an illumination on-off ratio of 1 is contemplated. In embodiments, the is desirable to operate the interior (201) of the feeding chamber (200) at an illumination on-off ratio that is greater than 1 and less than 11. In embodiments, the is desirable to operate the interior (201) of the feeding chamber (200) at an illumination on-off ratio that is greater than 0.5 and equal to or less than 5.

In embodiments, the is illumination on-off ratio for the interior (201) of the feeding chamber (200) includes one or more illumination on-off ratios selected from the group consisting of: 0.5 to 0.75, 0.75 to 1, 1 to 1.25, 1.25 to 1.5, 1.5 to 1.75, 1.75 to 2, 2 to 2.25, 2.25 to 2.5, 2.5 to 2.75, 2.75 to 3, 3 to 3.25, 3.25 to 3.5, 3.5 to 3.75, 3.75 to 4, 4 to 4.25, 4.25 to 4.5, 4.5 to 4.75, 4.75 to 5, and 5 to 5.25.

In embodiments, a lights (L1) in the interior (201) of the feeding chamber (200) include a plurality of light emitting diodes (LED). In embodiments, the plurality of light emitting diodes (LED) include blue LEDs (BLED), red LEDS (RLED), and/or green LEDS (GLED). In embodiments, the plurality of light emitting diodes (LED) in the interior (201) of the feeding chamber (200) include one or two or more from the group consisting of blue LEDs (BLED), red LEDS (RLED), and green LEDS (GLED).

In embodiments, the blue LEDs (BLED, BLED') operate at a wavelength that ranges from 490 nanometers (nm) to 455 nm. In embodiments, the red LEDs (RLED, RLED') operate at a wavelength that ranges from 620 nm to 780 nm. In embodiments, the green LEDs (GLED, GLED') operate at a wavelength that ranges from 490 nm to 577 nm. In embodiments, the plurality of light emitting diodes (LED) are configured to be controlled by a computer (COMP) to operate at a wavelength ranging from 490 nm to 780 nm. In embodiments, the plurality of light emitting diodes (LED) are configured to be controlled by a computer (COMP) to operate at a wavelength ranging from 400 nm to 700 nm.

In embodiments, the plurality of light emitting diodes (LED) are configured to operate in the following manner:

(a) illuminating the interior (201) of the feeding chamber (200) with blue LEDs (BLED, BLED) and red LEDs (RLED, RLED); and (b) illuminating the interior (201) of the feeding chamber (200) with green LEDs (GLED, GLED);

wherein:
the blue LEDs (BLED, BLED') operate at a wavelength that ranges from 490 nanometers to 455 nanometers;
the red LEDs (RLED, RLED') operate at a wavelength that ranges from 620 nanometers to 780 nanometers;
the green LEDs (GLEDGLED') operate at a wavelength that ranges from 490 nanometers to 577 nanometers.

In embodiments, a sensor (OS') is positioned within the interior of the interior (201) of the feeding chamber (200), the senosr (OS') may be an optical sensor, digital camera, motion sensor, active infrared (AIRs) sensor, passive infrared (PIRs) sensor, microwave motion sensor, continuous wave radar motion sensor (CW), vibration motion sensor, IR sensor, ultrasonic sensor, proximity sensor, and touch sensor, mass sensor, laser sensor, or the like.

FIG. 4:

FIG. 4 shows one non-limiting embodiment of a network (220) of cells (219) for growing insects within a feeding chamber (200) of the insect feeding module (2000) shown in FIG. 3.

FIG. 5:

FIG. 5 elaborates upon the non-limiting embodiment of FIG. 3 but shows the insect feeding module (2000) operating in a second mode of operation wherein the egg transfer system (244) of the insect feeding module (2000) is at a second state at a second elevated height (H2) so as to permit insects (225) to lay eggs (259) within a provided breeding material (248).

As discussed above in FIG. 3, FIG. 5 shows the conveyor (245) configured to make breeding material (248) available to the interior (201) of the feeding chamber (200). This is achieved by providing a conveyor (245) having a breeding material (248) provided thereon and extending the conveyor (245) in a vertical direction so that the conveyor (245) and egg-depleted breeding material (246) come into contact with the screen floor (258) of the feeding chamber (200). Egg-laying insects (225) lay their eggs (259) through the screen floor (258) of the feeding chamber (200) and deposit the eggs (259) into the breeding material (248) that rests upon the conveyor (245).

In the embodiment of FIG. 5, the egg-laying insects (225) present within the interior (201) of the feeding chamber (200) will deposit the eggs (259) into the breeding material (248) and the screen floor (258) will prevent them from eating or digging up the eggs (259). The breeding material (248) is made available to the insects (225) within the feeding chamber (200). This is made possible in the embodiment of FIG. 5 by activating the first conveyor elevation unit (254) and second conveyor elevation unit (256) so as to extend the conveyor (245) vertically in a direction towards the bottom of the feeding chamber (200) from a first retracted height (H1) to a second elevated height (H2).

As a result of eggs (259) being deposited into the egg-depleted breeding material (246) an egg-laden breeding material (250) is created which is discharged from the conveyor via a conveyor output (249). The egg-laden breeding material (250) has a greater amount of eggs within it in reference to the egg-depleted breeding material (246).

FIG. 6:

FIG. 6 elaborates upon the non-limiting embodiment of FIG. 3 but shows the insect feeding module (2000) operating in a third mode of operation wherein the egg transfer system (244) of the insect feeding module (2000) is at a first state in a first retracted height (H1) so as to discontinue insects (225) from laying eggs (259) within the provided breeding material (248).

As a result of eggs (259) being deposited into the egg-depleted breeding material (246) an egg-laden breeding material (250) is created which is discharged from the conveyor via a conveyor output (249). The egg-laden breeding material (250) has a greater amount of eggs within it in reference to the egg-depleted breeding material (246).

FIG. 7:

FIG. 7 elaborates upon the non-limiting embodiment of FIG. 3 but shows the insect feeding module (2000) and insect evacuation module (3000) operating in a fourth mode of operation wherein a vibration unit (214) is activated to permit the removal of insects (225) from the network (220) of cells (219) and wherein the insect evacuation module (3000) separates insects from gas while a vacuum is pulled on the insect feeding module (2000) via an insect evacuation fan (312).

FIG. 8:

FIG. 8 shows a non-limiting embodiment of an insect feeding module (2000) integrated with an insect evacuation module (3000) operating in a first mode of operation wherein a plurality of slats (341) of an egg transfer system (244) of the insect feeding module (2000) are in first closed state (341A).

Note that in FIG. 8, the enhanced feedstock input (206) is made available to the feeding chamber (206) at a vertical height within the interior below the network (220) of cells (219).

FIG. 8 discloses another embodiment of the feeding chamber (200) without a screen floor (258). Instead, a plurality of slats (341) define the bottom of the feeding chamber (200). The plurality of slats (341) are equipped with a slat motor (344) and controller (345) configured to rotate the slats (341) upon the input or output of a signal (346) to the computer (COMP). The slat motor (344) controller (345) is operatively equipped to rotate the slats (341) into a plurality of states including a first closed state (341A) and a second open state (341B). The embodiments of FIGS. 8 and 9 show the plurality of rotatable slats (341) in the first closed state (341A).

The plurality of slats (341) define the lower section of the interior (201) of the feeding chamber (200) into an upper egg-laying section (342) and a lower egg transfer section (343). The upper egg-laying section (342) is the region within the interior (201) of the feeding chamber above the plurality of slats (341) and below the network (220) of cells (219) where the insects reside. The lower egg transfer section (343) is the region below the plurality of slats (341) and above the egg transfer system (244). The embodiment of FIG. 8 depicts the egg transfer system (244) equipped to output an egg-laden breeding material (339) via an egg-laden breeding material transfer line (340).

The embodiment of FIG. 8 also depicts the egg transfer system (244) equipped with egg-laden breeding material conveyor (347) with integral mass sensors (351, 353). Insects (225), as well as eggs (259), egg-laden breeding material (339) may also be removed via the egg transfer system (244). The egg-laden breeding material conveyor (347) has a motor (348) and a controller (349) that is configured to input and output a signal (350) to the computer (COMP). A first breeding material mass sensor (351) is operatively connected to the egg-laden breeding material conveyor (347) and is configured to input a signal (352) to the computer (COMP). A second breeding material mass sensor (353) is operatively connected to the egg-laden breeding material conveyor (347) and is configured to input a signal (354) to the computer (COMP).

In embodiments, plants (107*) are positioned within the interior (201) of the feeding chamber (200). In embodiments, the interior (ENC1) of the enclosure (ENC) of the Farming Superstructure System (FSS) (as disclosed in Volume 2) is positioned within the interior (201) of the feeding chamber (201) of the Insect Production Superstructure System (IPSS) (as disclosed on Volume 1) to permit insects (225) to be co-located within the same interior as the plants (107*).

FIG. 9:

FIG. 9 elaborates upon the non-limiting embodiment of FIG. 8 and shows breeding material (248) resting upon the surface of the plurality of slats (341) of the egg transfer system (244) so as to permit insects (225) to lay eggs (259) within the breeding material (248).

FIG. 10:

FIG. 10 elaborates upon the non-limiting embodiment FIG. 8 but shows the egg transfer system (244) in a second open state (341A) so as to permit egg-laden breeding material (248) to pass through the plurality of slats (341) while the vibration unit (214) is activated, some insects (225) may pass through the open slats (341) as well.

FIG. 11:

FIG. 11 shows a simplistic diagram illustrating an insect grinding module that is configured to grind at least a portion of the insects transferred from the insect evacuation module (3000). A grinder (1250) is shown to grind the separated insects (334) into a stream of ground separated insects (1500). The ground separated insects (1500) may be sent to the lipid extraction unit (1501) on FIG. 12A, the pathogen removal unit (1550) on FIG. 13, or the multifunctional composition mixing module (6000) on FIG. 14A.

FIG. 12A:

FIG. 12A shows a simplistic diagram illustrating a lipid extraction module that is configured to extract lipids from at least a portion of the insects transferred from the insect evacuation module (3000).

FIG. 12A discloses a lipid extraction unit (1501) for extracting insect based lipids in mass quantities for commercial scale output for use in a variety of areas throughout society. In embodiments, the lipid extraction unit (1501) includes a decanter (1502) having an interior (1505) defined by at least one side wall (1504). A weir (1503) may be positioned in the decanter (1502). In embodiments, the lipid extraction unit (1501) may be a decanter (1502) in the form of a vertical or horizontal decanter (1502). Separated insects (334) are provided to the lipid extraction unit (1501) from either the separated insect conveyor (328) via the separator or the ground separated insects (1500) via the grinder (1250). Separated insects (334) are introduced to the lipid extraction unit (1501) via a separator insect input (1508) and optionally introduced to the interior (1505) beneath the liquid level of the via a diptube (1509).

In embodiments, the lipid extraction unit (1501) is configured to extract lipids by use of a first immiscible liquid (1506) and a second immiscible liquid (1507). In embodiments, the first immiscible liquid (1506) has a first density (RHO1) and a first molecular weight (MW1), and the second immiscible liquid (1507) has a second density (RHO2), and a second molecular weight (MW2). In embodiments, first density (RHO1) is greater than the second density (RHO2). In embodiments, first molecular weight (MW1) is greater than the second molecular weight (MW2).

In embodiments, the first immiscible liquid (1506) is an organic compound, such as chloroform, with a first density (RHO1) of about 87 pounds per cubic foot, and a first molecular weight (MW1) of about 119 pound mass per pound mole. In embodiments, the second immiscible liquid (1507) is an alcohol, such as methanol, with a second density (RHO2) of about 44 pounds per cubic foot, and a second molecular weight (MW2) of about 32 pound mass per pound mole. In embodiments, the first density (RHO1) ranges from between about 70 pounds per cubic foot to about 110 pounds per cubic foot. In embodiments, the second density (RHO2) ranges from between about 25 pounds per cubic foot to about 69 pounds per cubic foot. In embodiments, the first molecular weight (MW1) ranges from between about 70 pound mass per pound mole to about 150 pound mass per pound mole. In embodiments, the second molecular weight (MW2) ranges from between about 18 pound mass per pound mole to about 69 pound mass per pound mole.

The weir (1503) separates the decanter (1502) into a first section (1515) and a second section (1516). A first level sensor (1510) is positioned within the interior (1505) to detect the level of the interface region (1512) between the first immiscible liquid (1506) and the second immiscible liquid (1507) within the first section (1515). The first level sensor (1510) is configured to output a signal (1511) to the computer (COMP). A second level sensor (1513) is positioned within the interior (1505) to detect the level of the second immiscible liquid (1507) within the second section (1516). The second level sensor (1513) is configured to output a signal (1514) to the computer (COMP).

In embodiments, a first immiscible liquid and lipid mixture (1518) is formed which is comprised of a lipid portion and a first immiscible liquid portion. In embodiments, a second immiscible liquid and particulate mixture (1521) is formed which is comprised of a particulate portion and a second immiscible liquid portion. In embodiments, the particulate portion is comprised of one or more from the group consisting of insect legs, and wings, and protein. In embodiments, the second immiscible liquid (1507) floats above first immiscible liquid (1506) in the first section (1515) of the decanter (1502). An interface region (1512) is the region in the first section (1515) of the decanter (1502) in between the upper second immiscible liquid (1507) and the lower first immiscible liquid (1506).

The decanter (1502) has a first immiscible liquid and lipid mixture output (1517) for discharging a first immiscible liquid and lipid mixture (1518) towards a lipid transfer pump (1519). The decanter (1502) also has a second immiscible liquid and particulate mixture output (1520) for discharging a second immiscible liquid and particulate mixture (1521) towards a second immiscible liquid recirculation pump (1522) and particulate filter (1523). The particulate filter (1523) has a second immiscible liquid input (1524), second immiscible liquid output (1525), and a filtered protein output (1532).

A particulate-depleted second immiscible liquid (1526) is discharged from the second immiscible liquid output (1525) of the particulate filter (1523) and returned to the decanter (1502) via a particulate-depleted liquid input (1527). A filtered protein stream (1531) is discharged from the filtered protein output (1532) of the particulate filter (1523). The decanter (1502) also has an interface layer protein take-off point (1528) configured to transfer an interface layer protein stream (1529) to an interface layer protein pump (1530). The interface layer protein stream (1529) is comprised of particulates including insect legs, and wings, and protein from the interface region (1512). A temperature sensor (1533) is operatively connected to the lipid extraction unit (1501) and is configured to input a signal (1534) to the computer (COMP).

FIG. 12B:

FIG. 12B shows a simplistic diagram illustrating a lipid extraction module that is configured to extract lipids from at least a portion of the insects transferred from the insect evacuation module (3000) by using of no solvent by way of an expeller press.

FIG. 12B shows on non-limiting embodiment wherein lipids may be removed from insects without the use of a solvent. Specifically, the lipids may be extracted from insects by use of a lipid extraction unit (1501) that incorporates the use of a is a mechanical method for extracting oil. For example, one non-limiting embodiment shows the mechanical lipid extraction unit (1501) as an expeller press (1543).

The insects are squeezed through a pressing cage (1549) by the rotating motion of a screw press (1546) under high pressure. As the insects are pressed through the pressing cage (1549) by the screw press (1546), friction causes it to heat up. In embodiments, the temperature within the expeller press (1543) can increase due to the friction caused by extraction lipids (1541) from the insects. This requires the expeller press (1543) to require a source of cooling water to cool regulate temperature and prevent overheating. Ground separated insects (1500) from the separated insect conveyor (328) or insects from any variety of feeding chambers (FC2, FC2, FC3) may be transferred to the lipid extraction unit (1501) by way of a conveyor (1535). The conveyor (1535) transfers lipid laden insects (1537) to the mechanical lipid extraction unit (1501).

The mechanical lipid extraction unit (1501) extracts lipids (1541) from the lipid laden insects (1537) to form a stream of lipid depleted insects (1538). In embodiments, the lipid depleted insects (1538) are comprised of protein (1542). The conveyor (1535) is equipped with a flow sensor (1536A) that is configured to input/output a signal (1536B) to the computer (COMP). The conveyor (1535) transfers lipid laden insects (1537) to the feed bin (1544) of the expeller press (1543).

The expeller press (1543) includes a feed bin (1544), motor (1545), and having an interior containing a screw press (1546). The screw press (1546) is equipped with a shaft (1547) and flights (1548) and is configured to extract lipids from insects by applying pressure on the insects to squeeze liquid lipids (1541) from the insects. Liquid lipids (1541) extracted from the insects is discharged from the expeller press (1543) through a pressing cage (1549) and a lipid output (1551) and a lipid transfer line (1552). A lipid composition sensor (1539) is installed on the lipid transfer line (1552) and is configured to input or output a signal (1540) to the computer (COMP). The expeller press (1543) is equipped with a stand (1555) to elevate off of the ground. The expeller press (1543) is equipped with a protein output (1553). The protein output (1553) may be an annular nozzle (1554). Lipid depleted insects (1538) are discharged from the expeller press (1543) via the protein output (1553). In embodiments, the lipid depleted insects (1538) contain protein (1542). The lipids (1541) may in embodiments be an emulsion. In embodiment, the lipids (1541) emulsion may be an emulsion of oil and water.

The lipid depleted insects (1538) are comprised of a reduced amount of lipids (1541) relative to the lipid laden insects (1537). Lipid depleted insects (1538) exiting the protein output (1553) are routed to a protein conveyor (1556). The protein conveyor (1556) is equipped with a pathogen sensor (1557) that is configured to input or output a signal (1558) to the computer (COMP). A protein transfer conduit (1559) is connected to the protein conveyor (1556) and is configured to remove lipid depleted insects (1538) containing protein (1542). The mechanical lipid extraction unit (1501) is equipped with a cooling water input (1561) and a cooling water output (1562). A cooling water input temperature sensor (1563) configured to input and output a signal (1564) to the computer (COMP) is installed on the cooling water input (1561). A cooling water output temperature sensor (1566) configured to input and output a signal (1567) to the computer (COMP) is installed on the cooling water output (1562).

In embodiments, the cooling water input temperature sensor (1563) reads a temperature ranging from between about 60 degrees Fahrenheit to about 150 degrees Fahrenheit. In embodiments, the cooling water output temperature sensor (1566) reads a temperature ranging from between about 150.999 degrees Fahrenheit to about 210 degrees Fahrenheit. In embodiments, the expeller temperature sensor (1568) reads a temperature ranging from between about 60 degrees Fahrenheit to about 210 degrees Fahrenheit.

In embodiments, the lipid extraction unit (1501) is equipped with an expeller pressure sensor (1571) that is configured to input or output a signal to the computer (COMP). In embodiments, the expeller pressure sensor (1571) reads a pressure within the expeller press (1543) ranges from: between about 0.25 PSI to about 49.99 PSI; between about 50 PSI to about 99.99 PSI; between about 100 PSI to about 149.99 PSI; between about 150 PSI to about 199.99 PSI; between about 200 PSI to about 249.99 PSI; between about 250 PSI to about 299.99 PSI; between about 300 PSI to about 349.99 PSI; between about 350 PSI to about 399.99 PSI; between about 400 PSI to about 449.99 PSI; between about 450 PSI to about 499.99 PSI; between about 500 PSI to about 549.99 PSI; between about 550 PSI to about 599.99 PSI; between about 600 PSI to about 649.99 PSI; between about 650 PSI to about 699.99 PSI; between about 700 PSI to about 749.99 PSI; between about 750 PSI to about 799.99 PSI; between about 800 PSI to about 8549.99 PSI; between about 850 PSI to about 899.99 PSI; between about 900 PSI to about 949.99 PSI; between about 950 PSI to about 999.99 PSI; between about 1,000 PSI to about 1,499.99 PSI; between about 1,500 PSI to about 1,999.99 PSI; between about 2,000 PSI to about 2,499.99 PSI; between about 2,500 PSI to about 2,999.99 PSI; between about 3,000 PSI to about 3,499.99 PSI; between about 3,500 PSI to about 3,999.99 PSI; between about 4,000 PSI to about 4,499.99 PSI; between about 4,500 PSI to about 4,999.99 PSI; between about 5,000 PSI to about 5,499.99 PSI; between about 5,500 PSI to about 5,999.99 PSI; between about 6,000 PSI to about 6,499.99 PSI; between about 6,500 PSI to about 6,999.99 PSI; between about 7,000 PSI to about 7,499.99 PSI; between about 7,500 PSI to about 7,999.99 PSI; between about 8,000 PSI to about 8,499.99 PSI; between about 8,500 PSI to about 8,999.99 PSI; between about 9,000 PSI to about 9,499.99 PSI; between about 9,500 PSI to about 9,999.99 PSI; between about 10,000 PSI to about 15,499.99 PSI; between about 15,500 PSI to about 19,999.99 PSI; between about 20,000 PSI to about 25,499.99 PSI; between about 25,500 PSI to about 29,999.99 PSI; between about 30,000 PSI to about 35,499.99 PSI; and, between about 35,500 PSI to about 40,000 PSI.

It has been my realization that in one non-limiting embodiment the best mode to operate one scale of an expeller press (1543) is so that the expeller pressure sensor (1571) reads a pressure of about 250 PSI. It has been my realization that in one non-limiting embodiment the best mode to operate one scale of an expeller press (1543) is so that the expeller pressure sensor (1571) reads a pressure of about 4,900 PSI. It has been my realization that in one non-limiting embodiment the best mode to operate one scale of an expeller press (1543) is so that the expeller pressure sensor (1571) reads a pressure of about 19,900 PSI. Nonetheless, all of the above pressures may work as intended to realize lipid extraction from insects.

FIG. 12C:

FIG. 12C shows one non-limiting embodiment of a hydrogenation system (12C) configured to hydrogenate the insect lipids (1518, 1552) to produce hydrogenation insect lipids (12CC).

In embodiments, the insect lipids (1518, 1552) include palmitic acid, linoleic acid, alpha-linoleic acid, oleic acid, gamma-linoleic acid, or stearic acid: palmitic acid (C15H31COOH) is a saturated fatty acid; linoleic acid (C17H31COOH) is a carboxylic acid, is a polyunsaturated omega-6 fatty acid; oleic acid (C17H33COOH) monounsaturated omega-9 fatty acid; stearic acid (C17H35COOH) is saturated fatty acid. In embodiments, oleic acid may be hydrogenated into stearic acid. In embodiments, linoleic acid may be hydrogenated into stearic acid as depicted in FIG. 12C.

In embodiments, the insect lipids (1518, 1552, 2C58, 2D58) have a viscosity including one or more viscosities selected from the group consisting of 5.900 centipoise (cp) to 5.950 cp, 5.950 cp to 6.000 cp, 6.000 cp to 6.050 cp, 6.050 cp to 6.100 cp, 6.100 cp to 6.150 cp, 6.150 cp to 6.175 cp, 6.175 cp to 6.200 cp, 6.200 cp to 6.225 cp, 6.225 cp to 6.250 cp, 6.250 cp to 6.275 cp, 6.275 cp to 6.300 cp, 6.300 cp to 6.325 cp, 6.325 cp to 6.350 cp, 6.350 cp to 6.375 cp, 6.375 cp to 6.400 cp, 6.400 cp to 6.425 cp, 6.425 cp to 6.450 cp, 6.450 cp to 6.475 cp, 6.475 cp to 6.500 cp, 6.500 cp to 6.525 cp, 6.525 cp to 6.550 cp, 6.550 cp to 6.575 cp, 6.575 cp to 6.600 cp, 6.600 cp to 6.625 cp, 6.625 cp to 6.650 cp, 6.650 cp to 6.675 cp, 6.675 cp to 6.700 cp, 6.700 cp to 6.725 cp, 6.725 cp to 6.750 cp, 6.750 cp to 6.775 cp, 6.775 cp to 6.800 cp, 6.800 cp to 6.825 cp, 6.825 cp to 6.850 cp, 6.850 cp to 6.875 cp, 6.875 cp to 6.900 cp, 6.900 cp to 6.925 cp, 6.925 cp to 6.950 cp, 6.950 cp to 6.975 cp, 6.975 cp to 7.000 cp, 7.000 cp to 7.025 cp, 7.025 cp to 7.050 cp, 7.050 cp to 7.075 cp, 7.075 cp to 7.100 cp, 7.100 cp to 7.125 cp, 7.125 cp to 7.150 cp, 7.150 cp to 7.175 cp, 7.175 cp to 7.200 cp, 7.200 cp to 7.225 cp, 7.225 cp to 7.250 cp, 7.250 cp to 7.275 cp, 7.275 cp to 7.300 cp, 7.300 cp to 7.325 cp, 7.325 cp to 7.350 cp, 7.350 cp to 7.375 cp, 7.375 cp to 7.400 cp, 7.400 cp to 7.425 cp, 7.425 cp to 7.450 cp, 7.450 cp to 7.475 cp, 7.475 cp to 7.500 cp, 7.500 cp to 7.525 cp, 7.525 cp to 7.550 cp, 7.550 cp to 7.575 cp, 7.575 cp to 7.600 cp, 7.600 cp to 7.625 cp, 7.625 cp to 7.650 cp, 7.650 cp to 7.675 cp, 7.675 cp to 7.700 cp, 7.700 cp to 7.725 cp, 7.725 cp to 7.750 cp, 7.750 cp to 7.775 cp, 7.775 cp to 7.800 cp, 7.800 cp to 7.825 cp, 7.825 cp to 7.850 cp, 7.850 cp to 7.875 cp, 7.875 cp to 7.900 cp, 7.900 cp to 7.925 cp, 7.925 cp to 7.950 cp, 7.950 cp to 7.975 cp, 7.975 cp to 8.000 cp, 8.000 cp to 8.025 cp, 8.025 cp to 8.050 cp, 8.050 cp to 8.075 cp, 8.075 cp to 8.100 cp, 8.100 cp to 8.125 cp, 8.125 cp to 8.150 cp, 8.150 cp to 8.175 cp, and 8.175 cp to 8.200 cp.

In embodiments, the insect lipids (1518, 1552, 2C58, 2D58) have a molecular weight including one or more molecular weights selected from the group consisting of 280.25 grams per mole (g/mol) to 280.50 g/mol, 280.50 g/mol to 280.75 g/mol, 280.75 g/mol to 281.00 g/mol, 281.00 g/mol to 281.25 g/mol, 281.25 g/mol to 281.50 g/mol, 281.50 g/mol to 281.75 g/mol, 281.75 g/mol to 282.00 g/mol, 282.00 g/mol to 282.25 g/mol, 282.25 g/mol to 282.50 g/mol, 282.50 g/mol to 282.75 g/mol, 282.75 g/mol to 283.00 g/mol, 283.00 g/mol to 283.25 g/mol, 283.25 g/mol to 283.50 g/mol, 283.50 g/mol to 283.75 g/mol, 283.75 g/mol to 284.00 g/mol, 284.00 g/mol to 284.25 g/mol, 284.25 g/mol to 284.50 g/mol, 284.50 g/mol to 284.75 g/mol, 284.75 g/mol to 285.00 g/mol, 285.00 g/mol to 285.25 g/mol, 285.25 g/mol to 285.50 g/mol, 285.50 g/mol to 285.75 g/mol, 285.75 g/mol to 286.00 g/mol, 286.00 g/mol to 286.25 g/mol, 286.25 g/mol to 286.50 g/mol, 286.50 g/mol to 286.75 g/mol, 286.75 g/mol to 287.00 g/mol, 287.00 g/mol to 287.25 g/mol, 287.25 g/mol to 287.50 g/mol, 287.50 g/mol to 287.75 g/mol, 287.75 g/mol to 288.00 g/mol, 288.00 g/mol to 288.25 g/mol, 288.25 g/mol to 288.50 g/mol, 288.50 g/mol to 288.75 g/mol, 288.75 g/mol to 289.00 g/mol, 289.00 g/mol to 289.25 g/mol, 289.25 g/mol to 289.50 g/mol, 289.50 g/mol to 289.75 g/mol, 289.75 g/mol to 290.00 g/mol, and 290.00 g/mol to 290.25 g/mol.

Insect lipids (1518) from FIG. 12A and/or insect lipids (1552) from FIG. 12B may be hydrogenated within a hydrogenation system (12C). The insect lipids (1518, 1522) are introduced to an insect lipid tank (2C1). The insect lipid tank (2C1) has an interior (2C2) which contains the insect lipids (1518, 1522). A vacuum (2C3) is configured to be pulled on the interior (2C2) of the insect lipid tank (2C1). In embodiments, a catalyst (2C99) may be added to the interior (2C2) of the insect lipid tank (2C1) which may then in turn be added to the hydrogenation system (12C). In embodiments, the catalyst (2C99) includes one or more catalysts selected from the group consisting of a precious metal, more than one precious metal, gold, silver, platinum, rhodium, palladium, iridium, molybdenum, tungsten, nickel, cobalt, manganese, copper, titanium, silicon, vanadium, copper oxide, zeolite, a sorbent, a molecular sieve, zirconia, alumina, monoclinic or stabilized or doped zirconia, alkali-earth hexaaluminates, ceria, yittria, lanthanum, magnesium aluminate, promoted alumina, silica, ortitania.

In embodiments, a solvent (2C98) may be added to the interior (2C2) of the insect lipid tank (2C1) which may then in turn be added to the hydrogenation system (12C). In embodiments, the solvent (2C98) includes one or more solvent selected from the group consisting of an alcohol, a diglyceride, an ester, ethanol, ethyl acetate, glycerin, glycerol, hexane, hydrocarbon, isopropyl alcohol, methanol, a monoglyceride, and a polyol.

A heat exchanger (2C4) is configured to heat the insect lipids (1518, 1522) within the interior (2C2) of the insect lipid tank (2C1). In embodiments, the insect lipids (1518, 1522) are heated to a temperature including one or more temperature ranges selected from the group consisting of: 50 degrees Fahrenheit to 75 degrees Fahrenheit, 75 degrees Fahrenheit to 100 degrees Fahrenheit, 100 degrees Fahrenheit to 125 degrees Fahrenheit, 125 degrees Fahrenheit to 150 degrees Fahrenheit, 150 degrees Fahrenheit to 175 degrees Fahrenheit, 175 degrees Fahrenheit to 200 degrees Fahrenheit, 200 degrees Fahrenheit to 225 degrees Fahrenheit, 225 degrees Fahrenheit to 250 degrees Fahrenheit, 250 degrees Fahrenheit to 275 degrees Fahrenheit, 275 degrees Fahrenheit to 300 degrees Fahrenheit, 300 degrees Fahrenheit to 325 degrees Fahrenheit, 325 degrees Fahrenheit to 350 degrees Fahrenheit, 350 degrees Fahrenheit to 375 degrees Fahrenheit, 375 degrees Fahrenheit to 400 degrees Fahrenheit, 400 degrees Fahrenheit to 425 degrees Fahrenheit, 425 degrees Fahrenheit to 450 degrees Fahrenheit, 450 degrees Fahrenheit to 475 degrees Fahrenheit, 475 degrees Fahrenheit to 500 degrees Fahrenheit, 500 degrees Fahrenheit to 525 degrees Fahrenheit, 525 degrees Fahrenheit to 550 degrees Fahrenheit, 550 degrees Fahrenheit to 575 degrees Fahrenheit, 575 degrees Fahrenheit to 600 degrees Fahrenheit, 600 degrees Fahrenheit to 625 degrees Fahrenheit, 625 degrees Fahrenheit to 650 degrees Fahrenheit, 650 degrees Fahrenheit to 675 degrees Fahrenheit, 675 degrees Fahrenheit to 700 degrees Fahrenheit, 700 degrees Fahrenheit to 725 degrees Fahrenheit, 725 degrees Fahrenheit to 750 degrees Fahrenheit, 750 degrees Fahrenheit to 775 degrees Fahrenheit, 775 degrees Fahrenheit to 800 degrees Fahrenheit, 800 degrees Fahrenheit to 825 degrees Fahrenheit, 825 degrees Fahrenheit to 850 degrees Fahrenheit, 850 degrees Fahrenheit to 875 degrees Fahrenheit, 875 degrees Fahrenheit to 900 degrees Fahrenheit, 900 degrees Fahrenheit to 925 degrees Fahrenheit, 925 degrees Fahrenheit to 950 degrees Fahrenheit, 950 degrees Fahrenheit to 975 degrees Fahrenheit, and 975 degrees Fahrenheit to 1000 degrees Fahrenheit.

Heated insect lipids (2C5) are transferred from the insect lipid tank (2C1) to the interior (2C14) of a hydrogenation system (2C13). The hydrogenation system (2C13) accepts the insect lipids from the insect lipid pump (2C6) via a lipid input (2C12). In embodiments, the hydrogenation system (2C13) includes a heated container configured to promote a hydrogenation reaction of lipids with a source of hydrogen gas.

Heated insect lipids (2C5) are transferred from the insect lipid tank (2C1) to an insect lipid pump (2C6). The insect lipid pump (2C6) pressurizes the insect lipids to a pressure including one or more pressure ranges selected from the group consisting of 5 pounds per square inch (PSI) to 10 PSI, 10 PSI to 20 PSI, 20 PSI to 30 PSI, 30 PSI to 40 PSI, 40 PSI to 50 PSI, 50 PSI to 60 PSI, 60 PSI to 70 PSI, 70 PSI to 80 PSI, 80 PSI to 90 PSI, 90 PSI to 100 PSI, 100 PSI to 125 PSI, 125 PSI to 150 PSI, 150 PSI to 175 PSI, 175 PSI to 200 PSI, 200 PSI to 225 PSI, 225 PSI to 250 PSI, 250 PSI to 275 PSI, 275 PSI to 300 PSI, 300 PSI to 400 PSI, 400 PSI to 500 PSI, 500 PSI to 600 PSI, 600 PSI to 700 PSI, 700 PSI to 800 PSI, 800 PSI to 900 PSI, and 900 PSI to 1,000 PSI.

The insect lipid pump (2C6) passes pressurized heated insect lipids through an insect lipid valve (2C7) prior to introducing the lipids to the interior (2C14) of the hydrogenation system (2C13). The insect lipid valve (2C7) is equipped with a controller (2C8) that is configured to input and/or output a signal (2C9) to and/or from the computer (COMP).

A sensor (2C10) is installed in between the insect lipid pump (2C6) and the lipid input (2C12) of the hydrogenation system (2C13). The sensor (2C10) is configured to measure the pressure, flow, and/or temperature of the heated insect lipids and input and/or output a signal (2C11) to the computer (COMP). In embodiments, the flow of the insect lipids through the sensor (2C10) includes one or more from the group consisting of: 0.5 gallons per minute (GPM) to 1 GPM, 1 GPM to 1.5 GPM, 1.5 GPM to 2 GPM, 2 GPM to 2.5 GPM, 2.5 GPM to 3 GPM, 3 GPM to 3.5 GPM, 3.5 GPM to 4 GPM, 4 GPM to 4.5 GPM, 4.5 GPM to 5 GPM, 5 GPM to 5.5 GPM, 5.5 GPM to 6 GPM, 6 GPM to 6.5 GPM, 6.5 GPM to 7 GPM, 7 GPM to 7.5 GPM, 7.5 GPM to 8 GPM, 8 GPM to 8.5 GPM, 8.5 GPM to 9 GPM, 9 GPM to 9.5 GPM, 9.5 GPM to 10 GPM, and 10 GPM to 10.5 GPM.

In embodiments, the hydrogenation system (2C13) includes a top (2CT) and a bottom (2CB) that are spaced apart along a vertical axis (2CV). The hydrogenation system (2C13) has a vertical axis (2CV) and a horizontal axis (2CH). In embodiments, the range of height of the hydrogenation system (2C13) is selected from one or more from the group consisting of 1 foot tall to 2 feet tall, 2 feet tall to 3 feet tall, 4 feet tall to 5 feet tall, 6 feet tall to 8 feet tall, 8 feet tall to 10 feet tall, 10 feet tall to 12 feet tall, 12 feet tall to 14 feet tall, 14 feet tall to 16 feet tall, 16 feet tall to 18 feet tall, 18 feet tall to 20 feet tall, 20 feet tall to 22 feet tall, 22 feet tall to 24 feet tall, 24 feet tall to 26 feet tall, 26 feet tall to 28 feet tall, 28 feet tall to 30 feet tall, 30 feet tall to 32 feet tall, 32 feet tall to 34 feet tall, 34 feet tall to 36 feet tall, 36 feet tall to 38 feet tall, 38 feet tall to 40 feet tall, and 40 feet tall to 50 feet tall. In embodiments, the hydrogenation system (2C13) is comprised of a material that is selected from one or more from the group consisting of glass, borosilicated glass, carbon steel, graphite, Hastelloy alloy, nickel, stainless steel, tantalum, and titanium.

In embodiments, the hydrogenation system (2C13) is equipped with a motor (2C15) that is configured to turn a shaft (2C16). In embodiments, the motor (2C15) rotates the shaft (2C16) at a revolutions per minute (rpm) including one or more rpm ranges selected from the group consisting of: 25 rpm to 50 rpm, 50 rpm to 75 rpm, 75 rpm to 100 rpm, 100 rpm to 125 rpm, 125 rpm to 150 rpm, 150 rpm to 175 rpm, 175 rpm to 200 rpm, 200 rpm to 225 rpm, 225 rpm to 250 rpm, 250 rpm to 275 rpm, 275 rpm to 300 rpm, 300 rpm to 325 rpm, 325 rpm to 350 rpm, 350 rpm to 375 rpm, 375 rpm to 400 rpm, 400 rpm to 425 rpm, 425 rpm to 450 rpm, 450 rpm to 475 rpm, 475 rpm to 500 rpm, 500 rpm to 525 rpm, 525 rpm to 550 rpm, 550 rpm to 575 rpm, 575 rpm to 600 rpm, 600 rpm to 625 rpm, 625 rpm to 650 rpm, 650 rpm to 675 rpm, 675 rpm to 700 rpm, 700 rpm to 725 rpm, 725 rpm to 750 rpm, 750 rpm to 775 rpm, 775 rpm to 800 rpm, 800 rpm to 825 rpm, 825 rpm to 850 rpm, 850 rpm to 875 rpm, 875 rpm to 900 rpm, 900 rpm to 925 rpm, 925 rpm to 950 rpm, 950 rpm to 975 rpm, 975 rpm to 1000 rpm, 1000 rpm to 1100 rpm, 1100 rpm to 1200 rpm, 1200 rpm to 1300 rpm, 1300 rpm to 1400 rpm, 1400 rpm to 1500 rpm, 1500 rpm to 2000 rpm. An impeller (2C17) or a plurality of impellers (2C17) are connected to the shaft. The impeller(s) (2C17) are configured to agitate the insect lipid mixture within the interior (2C14) of the hydrogenation system (2C13) and promote mixing between the insect lipids and a source of hydrogen gas. In embodiments, the shaft (2C16) is positioned on an angle disposed into the interior (2C14) hydrogenation system (2C13) below the liquid level (2C28) on an angle that ranges from: 3 degrees to 5 degrees, 5 degrees to 8 degrees, 8 degrees to 11 degrees, 11 degrees to 14 degrees, and 14 degrees to 20 degrees.

A source of steam (LZC) is provided to the hydrogenation system (2C13). In embodiments, the source of steam (LZC) is mixed with the insect lipids and hydrogen gas within the interior (2C14) of the hydrogenation system (2C13). In embodiments, the source of steam (LZC) is provided from the twelfth steam valve (LZB) as shown on FIG. 14L. The source of steam (LZC) is provided from a steam distribution header (LCJ) on the power production system as depicted below on FIG. 14L.

In embodiments, a steam valve (2C20) is configured to transfer the source of steam (LZC) to a steam input (2C23) of a heating jacket (2C24). The heating jacket (2C24) is in indirect thermal contact with the interior (2C14) of the hydrogenation system (2C13). Heat from the steam (LZC) is transferred through a heat transfer surface of the heating jacket (2C24) to the insect lipids and hydrogen gas within the interior (2C14) of the hydrogenation system (2C13). In embodiments, the steam valve (2C20) is equipped with a controller (2C21) that is configured to input and/or output a signal (2C22) to the computer (COMP). The heating jacket (2C24) has a heat transfer medium output (2C25) for discharging the steam condensate (2C26) from the heating jacket (2C24).

In embodiments, the interior (2C14) of the hydrogenation system (2C13) is equipped with a baffle (2C27) or a plurality of baffles (2C27). In embodiments, the baffles(s) (2C27) include flow-directing or obstructing vanes or panels that are connected to the interior (2C14) of the hydrogenation system (2C13). In embodiments, the baffles(s) (2C27) permit axial circulation within the hydrogenation system (2C13). In embodiments, the hydrogenation system (2C13) includes a cylindrical tank. In embodiments, the liquid level (2C28) within the interior (2C14) of the hydrogenation system (2C13) is maintained at a pre-determined height.

A source of hydrogen (2C29) is made available to the interior (2C14) of the hydrogenation system (2C13) via a hydrogen input (2C36). In embodiments, a hydrogen distributor (2C37) is configured to substantially uniformly distribute the source of hydrogen (2C29) to the interior (2C14) of the hydrogenation system (2C13). In embodiments, the hydrogen distributor (2C37) is configured to substantially uniformly distribute the source of hydrogen (2C29) to the interior (2C14) of the hydrogenation system (2C13) via a plurality of restrictions while bubbling up through the heated insect lipids.

In embodiments, the pressure drop of the source of hydrogen (2C29) across the hydrogen distributor (2C37) (or the plurality of restrictions) ranges from one or more pressure drop ranges selected from the group consisting of: 5 pounds per square inch (PSI) to 10 PSI, 10 PSI to 20 PSI, 20 PSI to 30 PSI, 30 PSI to 40 PSI, 40 PSI to 50 PSI, 50 PSI to 60 PSI, 60 PSI to 70 PSI, 70 PSI to 80 PSI, 80 PSI to 90 PSI, 90 PSI to 100 PSI, 100 PSI to 125 PSI, 125 PSI to 150 PSI, 150 PSI to 175 PSI, 175 PSI to 200 PSI, 200 PSI to 225 PSI, 225 PSI to 250 PSI, 250 PSI to 275 PSI, 275 PSI to 300 PSI, 300 PSI to 400 PSI, 400 PSI to 500 PSI, 500 PSI to 600 PSI, 600 PSI to 700 PSI, 700 PSI to 800 PSI, 800 PSI to 900 PSI, and 900 PSI to 1,000 PSI.

In embodiments, a hydrogen valve (2C30) is equipped to regulate the flow of the source of hydrogen (2C29) that is introduced to the interior (2C14) of the hydrogenation system (2C13). In embodiments, the hydrogen valve (2C30) is equipped with a controller (2C31) that is configured to input and/or output a signal (2C32) to and/or from the computer (COMP). In embodiments, the hydrogen valve (2C30) percent open during normal operation ranges from 10% open to 25% open, 25% open to 35% open, 35% open to 45% open, 45% open to 55% open, 55% open to 65% open, 65% open to 75% open, 75% open to 80% open. In embodiments, the pressure drop across the hydrogen valve (2C30) ranges from between 5 PSI to 10 PSI, 15 PSI to 25 PSI, 25 PSI to 35 PSI, 35 PSI to 45 PSI, 45 PSI to 55 PSI, 55 PSI to 65 PSI, 65 PSI to 75 PSI, 75 PSI to 85 PSI.

In embodiments, a sensor (2C33) is configured to analyze the hydrogen (2C29) before it is transferred to the interior (2C14) of the hydrogenation system (2C13). In embodiments, the sensor (2C33) includes a temperature sensor, a pressure sensor, a gas quality sensor, a moisture sensor, or a flow sensor. In embodiments, the sensor (2C33) is configured to input a signal (2C34) to the computer (COMP). In embodiments, the source of hydrogen (2C29) passes through a one-way valve (2C35) before it is transferred to the interior (2C14) of the hydrogenation system (2C13). In embodiments, the one-way valve (2C35) prevents flow of the insect lipid mixture within the interior (2C14) of the hydrogenation system (2C13) to flow backwards and clog up the hydrogen valve (2C30).

A source of gas (2C38) is made available to the interior (2C14) of the hydrogenation system (2C13) via a gas input (2C45). In embodiments, a gas valve (2C39) is equipped to regulate the flow of the source of gas (2C38) that is introduced to the interior (2C14) of the hydrogenation system (2C13). In embodiments, the gas valve (2C39) is equipped with a controller (2C40) that is configured to input and/or output a signal (2C41) to and/or from the computer (COMP). In embodiments, the gas valve (2C39) percent open during normal operation ranges from 10% open to 25% open, 25% open to 35% open, 35% open to 45% open, 45% open to 55% open, 55% open to 65% open, 65% open to 75% open, 75% open to 80% open. In embodiments, the pressure drop across the gas valve (2C39) ranges from between 5 PSI to 10 PSI, 15 PSI to 25 PSI, 25 PSI to 35 PSI, 35 PSI to 45 PSI, 45 PSI to 55 PSI, 55 PSI to 65 PSI, 65 PSI to 75 PSI, 75 PSI to 85 PSI.

In embodiments, a sensor (2C43) is configured to analyze the gas (2C38) before it is transferred to the interior (2C14) of the hydrogenation system (2C13). In embodiments, the sensor (2C43) includes a temperature sensor, a pressure sensor, a gas quality sensor, a moisture sensor, or a flow sensor. In embodiments, the sensor (2C43) is configured to input a signal (2C42) to the computer (COMP). In embodiments, the gas input (2C45) introduces the gas (2C38) to the interior (2C14) hydrogenation system (2C13) above the liquid level (2C28). In embodiments, the gas (2C38) includes one or more inert gases selected from the group consisting of argon, nitrogen, carbon dioxide, air, oxygen, and helium. In embodiments, the gas (2C38) forms a protective atmosphere (prevent oxidation and/or degradation of the hydrogenated lipids, improved product quality, clean good manufacturing practices as required by pharmaceutical industry, for cleaning in place, etc.) while hydrogenating the insect lipids.

In embodiments, the source of gas (2C38) passes through a one-way valve (2C44) before it is transferred to the gas input (2C45) of the hydrogenation system (2C13). In embodiments, the one-way valve (2C35) prevents flow of the insect lipid mixture within the interior (2C14) of the hydrogenation system (2C13) to flow backwards and clog up the gas valve (2C39).

In embodiments, a vacuum system (2C46) is configured to pull a vacuum on the interior (2C14) of the hydrogenation system (2C13) via a gas-vapor-mixture output (2C49). A gas-vapor-mixture (2C48) is evacuated from the interior (2C14) of the hydrogenation system (2C13) via the gas-vapor-mixture output (2C49). In embodiments, the gas-vapor-mixture (2C48) passes through a condenser (2C47) before being introduced to the vacuum system (2C46). In embodiments, at least a portion of the vapor within the gas-vapor-mixture (2C48) is condensed within the condenser (2C47). A gas (2C50) is evacuated from the vacuum system (2C46). In embodiments, the vacuum system (2C46) includes a device that removes gas molecules from interior (2C14) of the hydrogenation system (2C13) in order to leave behind a partial vacuum. In embodiments, the vacuum system (2C46) includes a rotary vane pump, diaphragm pump, liquid ring vacuum pump, piston pump, scroll pump, screw pump, Wankel pump, external vane pump, roots blower, booster pump, Toepler pump, lobe pump, venturi, eductor, or an ejector.

In embodiments, hydrogenated insect lipids (2C51) are discharged from the interior (2C14) of the hydrogenation system (2C13) via a lipid output (2C52). A hydrogenated insect lipid pump (2C53) is configured to pump hydrogenated insect lipids (2C51) from the interior (2C14) of the hydrogenation system (2C13) via the lipid output (2C52). The hydrogenated insect lipid pump (2C53) pumps and pressurizes the hydrogenated insect lipids (2C51) to form pressurized-hydrogenated-insect-lipids (2C54) which is then transferred to the interior (2C56) of a hydrogenated insect lipid tank (2C55). The hydrogenated insect lipids (2C51) are introduced to the interior (2C56) of a hydrogenated insect lipid tank (2C55). The hydrogenated insect lipid tank (2C55) has an interior (2C56) which contains the hydrogenated insect lipids (2C51). The vacuum system (2C46) is configured to pull a vacuum on the interior (2C56) of the hydrogenated insect lipid tank (2C55).

A heat exchanger (2C57) is configured to heat the hydrogenated insect lipids (2C51) within the interior (2C56) of a hydrogenated insect lipid tank (2C55). In embodiments, the hydrogenated insect lipids (2C51) are heated to a temperature including one or more temperature ranges selected from the group consisting of: 50 degrees Fahrenheit to 75 degrees Fahrenheit, 75 degrees Fahrenheit to 100 degrees Fahrenheit, 100 degrees Fahrenheit to 125 degrees Fahrenheit, 125 degrees Fahrenheit to 150 degrees Fahrenheit, 150 degrees Fahrenheit to 175 degrees Fahrenheit, 175 degrees Fahrenheit to 200 degrees Fahrenheit, 200 degrees Fahrenheit to 225 degrees Fahrenheit, 225 degrees Fahrenheit to 250 degrees Fahrenheit, 250 degrees Fahrenheit to 275 degrees Fahrenheit, 275 degrees Fahrenheit to 300 degrees Fahrenheit, 300 degrees Fahrenheit to 325 degrees Fahrenheit, 325 degrees Fahrenheit to 350 degrees Fahrenheit, 350 degrees Fahrenheit to 375 degrees Fahrenheit, 375 degrees Fahrenheit to 400 degrees Fahrenheit, 400 degrees Fahrenheit to 425 degrees Fahrenheit, 425 degrees Fahrenheit to 450 degrees Fahrenheit, 450 degrees Fahrenheit to 475 degrees Fahrenheit, 475 degrees Fahrenheit to 500 degrees Fahrenheit.

Heated hydrogenated insect lipids (2C58) are transferred from the interior (2C56) of a hydrogenated insect lipid tank (2C55) to another hydrogenated insect lipid pump (2C59) which pumps and pressurizes the heated hydrogenated insect lipids (2C58) to form pressurized-hydrogenated-insect-lipids which is then transferred to the interior (2D02) of an esterification system (2D01) as shown on FIG. 12D.

The hydrogenated insect lipid pump (2C59) passes pressurized-hydrogenated-insect-lipids through a hydrogenated insect lipid valve (2C60) prior to introducing the lipids to the interior (2D02) of an esterification system (2D01) as shown on FIG. 12D. The hydrogenated insect lipid valve (2C60) is equipped with a controller that is configured to input and/or output a signal to and/or from the computer.

FIG. 12D:

FIG. 12D shows one non-limiting embodiment of an esterification system (12D) configured to produce esterified insect lipids.

In embodiments, an ester may be produced by esterification of an ester of an alcohols and/or a polyol (ethylene glycol and glycerol) with insect lipids (1518, 1552) (as shown in FIGS. 12A and 12B) and/or hydrogenated insect lipids (2C58), as described in FIG. 12C. In embodiments, the insect lipids (1518, 1552) (as shown in FIGS. 12A and 12B) and/or hydrogenated insect lipids (2C58), as described in FIG. 12C described herein may undergo direct esterification, for example with glycerol. In embodiments, stearic acid is reacted with glycerol to produce glyceryl stearate. In embodiments, stearic acid is reacted with glycerol to produce glyceryl stearate in the presence of a catalyst.

Insect lipids (1518, 1552) and/or hydrogenated insect lipids (2C58) may be hydrogenated within the interior (2D13) of an esterification system (2D13). The insect lipids (1518, 1522, 2C58) are introduced the interior (2D13) of an esterification system (2D13). The esterification system (2D13) has an interior (2D14) which contains the insect lipids (1518, 1522, 2C58), an acid (2D90), a catalyst (2D91), and optionally a solvent as described in FIG. 12C.

In embodiment, the acid (2D90) includes one or more acids selected from the group consisting of abscic acid, acetic acid, ascorbic acid, benzoic acid, citric acid, formic acid, fumaric acid, hydrochloric acid, lactic acid, malic acid, nitric acid, organic acids, phosphoric acid, potassium hydroxide, propionic acid, salicylic acid, sulfamic acid, sulfuric acid, tartaric acid, and tosylic acid.

A vacuum (2D3) is configured to be pulled on the interior (2D13) of an esterification system (2D13). In embodiments, a catalyst (2D91) may be added to the interior (2D13) of an esterification system (2D13). In embodiments, the catalyst (2C91) includes one or more catalysts selected from the group consisting of a precious metal, more than one precious metal, gold, silver, platinum, rhodium, palladium, iridium, molybdenum, tungsten, nickel, cobalt, manganese, copper, titanium, silicon, vanadium, copper oxide, zeolite, a sorbent, a molecular sieve, zirconia, alumina, monoclinic or stabilized or doped zirconia, alkali-earth hexaaluminates, ceria, yittria, lanthanum, magnesium aluminate, promoted alumina, silica, ortitania.

In embodiments, a solvent (2D92) may be added to the interior (2D13) of an esterification system (2D13). In embodiments, the solvent (2D92) includes one or more solvent selected from the group consisting of an alcohol, a diglyceride, an ester, ethanol, ethyl acetate, glycerin, glycerol, hexane, hydrocarbon, isopropyl alcohol, methanol, a monoglyceride, and a polyol.

Insect lipids (1518, 1522, 2C58) are transferred to the interior (2D13) of an esterification system (2D13). The esterification system (2D13) accepts the insect lipids from: lipid extraction unit (1501) disclose on FIGS. 12A-B, and/or the hydrogenation system (2C13) on FIG. 12D. In embodiments, the esterification system (2D13) includes a heated container configured to promote an esterification reaction between the solvent (2D92) and the lipids (1518, 1522, 2C58) in the presence of a source of inert gas (2D38).

In embodiments, the esterification system (2D13) includes a top (2DT) and a bottom (2DB) that are spaced apart along a vertical axis (2DV). The esterification system (2D13) has a vertical axis (2DV) and a horizontal axis (2DH). In embodiments, the range of height of the esterification system (2D13) is selected from one or more from the group consisting of 1 foot tall to 2 feet tall, 2 feet tall to 3 feet tall, 4 feet tall to 5 feet tall, 6 feet tall to 8 feet tall, 8 feet tall to 10 feet tall, 10 feet tall to 12 feet tall, 12 feet tall to 14 feet tall, 14 feet tall to 16 feet tall, 16 feet tall to 18 feet tall, 18 feet tall to 20 feet tall, 20 feet tall to 22 feet tall, 22 feet tall to 24 feet tall, 24 feet tall to 26 feet tall, 26 feet tall to 28 feet tall, 28 feet tall to 30 feet tall, 30 feet tall to 32 feet tall, 32 feet tall to 34 feet tall, 34 feet tall to 36 feet tall, 36 feet tall to 38 feet tall, 38 feet tall to 40 feet tall, and 40 feet tall to 50 feet tall. In embodiments, the esterification system (2D13) is comprised of a material that is selected from one or more from the group consisting of glass, borosilicated glass, carbon steel, graphite, Hastelloy alloy, nickel, stainless steel, tantalum, and titanium.

In embodiments, the esterification system (2D13) is equipped with a motor (2D15) that is configured to turn a shaft (2D16). In embodiments, the motor (2D15) rotates the shaft (2D16) at a revolutions per minute (rpm) including one or more rpm ranges selected from the group consisting of: 25 rpm to 50 rpm, 50 rpm to 75 rpm, 75 rpm to 100 rpm, 100 rpm to 125 rpm, 125 rpm to 150 rpm, 150 rpm to 175 rpm, 175 rpm to 200 rpm, 200 rpm to 225 rpm, 225 rpm to 250 rpm, 250 rpm to 275 rpm, 275 rpm to 300 rpm, 300 rpm to 325 rpm, 325 rpm to 350 rpm, 350 rpm to 375 rpm, 375 rpm to 400 rpm, 400 rpm to 425 rpm, 425 rpm to 450 rpm, 450 rpm to 475 rpm, 475 rpm to 500 rpm, 500 rpm to 525 rpm, 525 rpm to 550 rpm, 550 rpm to 575 rpm, 575 rpm to 600 rpm, 600 rpm to 625 rpm, 625 rpm to 650 rpm, 650 rpm to 675 rpm, 675 rpm to 700 rpm, 700 rpm to 725 rpm, 725 rpm to 750 rpm, 750 rpm to 775 rpm, 775 rpm to 800 rpm, 800 rpm to 825 rpm, 825 rpm to 850 rpm, 850 rpm to 875 rpm, 875 rpm to 900 rpm, 900 rpm to 925 rpm, 925 rpm to 950 rpm, 950 rpm to 975 rpm, 975 rpm to 1000 rpm, 1000 rpm to 1100 rpm, 1100 rpm to 1200 rpm, 1200 rpm to 1300 rpm, 1300 rpm to 1400 rpm, 1400 rpm to 1500 rpm, 1500 rpm to 2000 rpm.

An impeller (2D17) or a plurality of impellers (2D17) are connected to the shaft. The impeller(s) (2D17) are configured to agitate a liquid mixture within the interior (2D14) of the esterification system (2D13) and promote mixing between the insect lipids and a source of solvent. In embodiments, the shaft (2D16) is positioned on an angle disposed into the interior (2D14) hydrogenation system (2D13) below the liquid level (2D28) on an angle that ranges from: 3 degrees to 5 degrees, 5 degrees to 8 degrees, 8 degrees to 11 degrees, 11 degrees to 14 degrees, and 14 degrees to 20 degrees.

A source of steam (2D95) is provided to the esterification system (2D13). In embodiments, the source of steam (2D95) is mixed with the liquid within the interior (2D14) of the esterification system (2D13). In embodiments, the source of steam is provided from a steam valve on FIG. 14L which is described in detail on FIG. 12C. The source of steam (2D95) is provided from a steam distribution header on the power production system as depicted below on FIG. 14L.

In embodiments, a steam valve (2D96) is configured to transfer the source of steam (2D95) to a steam input (2D23) of a heating jacket (2D24). The heating jacket (2D24) is in indirect thermal contact with the interior (2D14) of the esterification system (2D13). Heat from the steam (2D95) is transferred through a heat transfer surface of the heating jacket (2D24) to the liquid mixture within the interior (2d14) of the esterification system (2D13). In embodiments, the steam valve (2D96) is equipped with a controller (2D97) that is configured to input and/or output a signal (2D98) to the computer (COMP). The heating jacket (2D24) has a heat transfer medium output (2D25) for discharging the steam condensate (2D26) from the heating jacket (2D24).

In embodiments, the interior (2D14) of the esterification system (2D13) is equipped with a baffle (2D27) or a plurality of baffles (2D27). In embodiments, the baffles(s) (2D27) include flow-directing or obstructing vanes or panels that are connected to the interior (2D14) of the esterification system (2D13). In embodiments, the baffles(s) (2D27) permit axial circulation within the esterification system (2D13). In embodiments, the esterification system (2D13) includes a cylindrical tank. In embodiments, a liquid level (2D28) within the interior (2D14) of the esterification system (2D13) is maintained at a pre-determined height.

A source of catalyst (2D91) is made available to the interior (2D14) of the esterification system (2D13) via a catalyst input (2D36). In embodiments, the catalyst (2C99) includes one or more catalysts selected from the group consisting of a precious metal, more than one precious metal, gold, silver, platinum, rhodium, palladium, iridium, molybdenum, tungsten, nickel, cobalt, manganese, copper, titanium, silicon, vanadium, copper oxide, zeolite, a sorbent, a molecular sieve, zirconia, alumina, monoclinic or stabilized or doped zirconia, alkali-earth hexaaluminates, ceria, yittria, lanthanum, magnesium aluminate, promoted alumina, silica, ortitania.

A source of gas (2D38) is made available to the interior (2D14) of the esterification system (2D13) via a gas input (2D45). In embodiments, a gas valve (2D39) is equipped to regulate the flow of the source of gas (2D38) that is introduced to the interior (2D14) of the esterification system (2D13). In embodiments, the gas valve (2D39) is equipped with a controller (2D40) that is configured to input and/or output a signal (2D41) to and/or from the computer (COMP). In embodiments, the gas valve (2D39) percent open during normal operation ranges from 10% open to 25% open, 25% open to 35% open, 35% open to 45% open, 45% open to 55% open, 55% open to 65% open, 65% open to 75% open, 75% open to 80% open. In embodiments, the pressure drop across the gas valve (2C39) ranges from between 5 PSI to 10 PSI, 15 PSI to 25 PSI, 25 PSI to 35 PSI, 35 PSI to 45 PSI, 45 PSI to 55 PSI, 55 PSI to 65 PSI, 65 PSI to 75 PSI, 75 PSI to 85 PSI.

In embodiments, a sensor (2D43) is configured to analyze the gas (2D38) before it is transferred to the interior (2D14) of the esterification system (2D13). In embodiments, the sensor (2D43) includes a temperature sensor, a pressure sensor, a gas quality sensor, a moisture sensor, or a flow sensor. In embodiments, the sensor (2D43) is configured to input a signal (2D42) to the computer (COMP). In embodiments, the gas input (2D45) introduces the gas (2D38) to the interior (2D14) of the esterification system (2D13) above the liquid level (2C28). In embodiments, the gas (2D38) includes one or more inert gases selected from the group consisting of argon, nitrogen, carbon dioxide, air, oxygen, and helium. In embodiments, the gas (2D38) forms a protective atmosphere (prevent oxidation and/or degradation of the hydrogenated lipids, esterified lipids, improved product quality, clean good manufacturing practices as required by pharmaceutical industry, for cleaning in place, etc.) while esterifying the insect lipids.

In embodiments, the source of gas (2D38) passes through a one-way valve (2D44) before it is transferred to the gas input (2D45) of the esterification system (2D13). In embodiments, the one-way valve (2D35) prevents flow of the liquid mixture within the interior (2D14) of the esterification system (2D13) to flow backwards and clog up the gas valve (2D39).

In embodiments, a vacuum system (2D46) is configured to pull a vacuum on the interior (2D14) of the esterification system (2D13) via a gas-vapor-mixture output (2D49). A gas-vapor-mixture (2D48) is evacuated from the interior (2D14) of the esterification system (2D13) via the gas-vapor-mixture output (2D49). In embodiments, the gas-vapor-mixture (2D48) passes through a condenser (2D47) before being introduced to the vacuum system (2D46). In embodiments, at least a portion of the vapor within the gas-vapor-mixture (2D48) is condensed within the condenser (2D47). A gas (2D50) is evacuated from the vacuum system (2D6). In embodiments, the vacuum system (2D46) includes a device that removes gas molecules from interior (2D14) of the esterification system (2D13) in order to leave behind a partial vacuum. In embodiments, the vacuum system (2D46) includes a rotary vane pump, diaphragm pump, liquid ring vacuum pump, piston pump, scroll pump, screw pump, Wankel pump, external vane pump, roots blower, booster pump, Toepler pump, lobe pump, venturi, eductor, or an ejector.

In embodiments, esterified lipids (2D51) are discharged from the interior (2D14) of the esterification system (2D13)

via an output (2D52). An esterified lipid pump (2D53) is configured to pump esterified lipids (2D51) from the interior (2D14) of the esterification system (2D13) via the output (2D52). The esterified lipid pump (2D53) pumps and pressurizes the esterified lipids (2D51) to form pressurized-esterified-lipids (2D58) which are then transferred to a filter (2D60) to produce filtered lipids (2D61). In embodiments, a portion of the esterified lipids (2D51, 2D60) are introduced downstream for processing into consumer products. For example, esterified lipids (2D51) include glyceryl stearate is then mixed with a cannabinoid, the cannabinoid includes one or more selected from the group consisting of Δ9-tetrahydrocannabinol Δ9-THC, Δ8-tetrahydrocannabinol Δ8-THC, cannabichromene CBC, cannabidiol CBD, cannabigerol CBG, cannabinidiol CBND, and/or cannabinol CBN.

In embodiments, stearic acid is reacted with glycerol to produce glyceryl stearate while in an inert gas environment, the inert gas includes one or more inert gases selected from the group consisting of argon, nitrogen, carbon dioxide, air, oxygen, and helium.

In embodiments, a portion of the lipids (1518, 1552), the hydrogenated lipids (2C58), and/or esterified lipids (2D60) are mixed with oil (2D62), wax (2D63), and the other ingredients (2D64) within a mixing tank (2D70) to create a mixture (2D71). The mixture (2D71) is then heated with a heat exchanger (2D75) to produce a heated mixture (2D71') which is then pumped, poured, or transferred into a mold (2D80). In, embodiments the mold (2D80) includes a tube (2D81) to make lip balm. In embodiments, the heated mixture (2D71') is pumped into molds (2D80) via a mixture pump (2D81).

The heat exchanger (2D75) is configured to heat the mixture (2D71) within the mixing tank (2D70) to create a heated mixture (2D71') at a temperature including one or more temperature ranges selected from the group consisting of: 75 degrees Fahrenheit to 100 degrees Fahrenheit, 100 degrees Fahrenheit to 125 degrees Fahrenheit, 125 degrees Fahrenheit to 150 degrees Fahrenheit, 150 degrees Fahrenheit to 175 degrees Fahrenheit, 175 degrees Fahrenheit to 200 degrees Fahrenheit, 200 degrees Fahrenheit to 225 degrees Fahrenheit, 225 degrees Fahrenheit to 250 degrees Fahrenheit, 250 degrees Fahrenheit to 275 degrees Fahrenheit, 275 degrees Fahrenheit to 300 degrees Fahrenheit, 300 degrees Fahrenheit to 325 degrees Fahrenheit, 325 degrees Fahrenheit to 350 degrees Fahrenheit.

In embodiments, the mold (2D80) is a tube that includes an open top (3DT) and a closed bottom (3DB) that are spaced apart along a vertical axis (3DV). The mold (2D80) has a vertical axis (3DV) and a horizontal axis (3DH). In embodiments, the range of height of the mold (2D80) is selected from one or more from the group consisting of 15 millimeters to 17 millimeters, 17 millimeters to 19 millimeters, 19 millimeters to 21 millimeters, 21 millimeters to 23 millimeters, 23 millimeters to 25 millimeters, 25 millimeters to 27 millimeters, 27 millimeters to 29 millimeters, 29 millimeters to 31 millimeters, 31 millimeters to 33 millimeters, 33 millimeters to 35 millimeters, 35 millimeters to 37 millimeters, 37 millimeters to 39 millimeters, 39 millimeters to 41 millimeters, 41 millimeters to 43 millimeters, 43 millimeters to 45 millimeters, 45 millimeters to 47 millimeters, 47 millimeters to 49 millimeters, 49 millimeters to 51 millimeters, 51 millimeters to 53 millimeters, 53 millimeters to 55 millimeters, 55 millimeters to 57 millimeters, 57 millimeters to 59 millimeters, 59 millimeters to 61 millimeters, 61 millimeters to 63 millimeters, 63 millimeters to 65 millimeters, 65 millimeters to 67 millimeters, 67 millimeters to 69 millimeters, 69 millimeters to 71 millimeters, and 71 millimeters to 73 millimeters.

In embodiments, the range of diameter of the tubular mold (2D80) is selected from one or more from the group consisting of 5 millimeters to 6 millimeters, 6 millimeters to 7 millimeters, 7 millimeters to 8 millimeters, 8 millimeters to 9 millimeters, 9 millimeters to 10 millimeters, 10 millimeters to 11 millimeters, 11 millimeters to 12 millimeters, 12 millimeters to 13 millimeters, 13 millimeters to 14 millimeters, 14 millimeters to 15 millimeters, 15 millimeters to 16 millimeters, 16 millimeters to 17 millimeters, 17 millimeters to 18 millimeters, 18 millimeters to 19 millimeters, 19 millimeters to 20 millimeters, 20 millimeters to 21 millimeters, 21 millimeters to 22 millimeters, 22 millimeters to 23 millimeters, 23 millimeters to 24 millimeters, 24 millimeters to 25 millimeters, and 25 millimeters to 26 millimeters.

In embodiments, the mold (2D80) contains a volume of the mixture (2D71, 2D71') is selected from one or more from the group consisting of 0.50 milliliters to 0.75 milliliters, 0.75 milliliters to 1.00 milliliters, 1.00 milliliters to 1.25 milliliters, 1.25 milliliters to 1.50 milliliters, 1.50 milliliters to 1.75 milliliters, 1.75 milliliters to 2.00 milliliters, 2.00 milliliters to 2.25 milliliters, 2.25 milliliters to 2.50 milliliters, 2.50 milliliters to 2.75 milliliters, 2.75 milliliters to 3.00 milliliters, 3.00 milliliters to 3.25 milliliters, 3.25 milliliters to 3.50 milliliters, 3.50 milliliters to 3.75 milliliters, 3.75 milliliters to 4.00 milliliters, 4.00 milliliters to 4.25 milliliters, 4.25 milliliters to 4.50 milliliters, 4.50 milliliters to 4.75 milliliters, 4.75 milliliters to 5.00 milliliters, 5.00 milliliters to 5.25 milliliters, 5.25 milliliters to 5.50 milliliters, 5.50 milliliters to 5.75 milliliters, 5.75 milliliters to 6.00 milliliters, 6.00 milliliters to 6.25 milliliters, 6.25 milliliters to 6.50 milliliters, 6.50 milliliters to 6.75 milliliters, 6.75 milliliters to 7.00 milliliters, 7.00 milliliters to 7.25 milliliters, 7.25 milliliters to 7.50 milliliters, 7.50 milliliters to 7.75 milliliters, and 7.75 milliliters to 8.00 milliliters.

In embodiments, the mold (2D80) is a material including one or more materials selected from the group consisting of plastic. In embodiments, the mold (2D80) is transparent, white, black, green, or not transparent. In embodiments, the mold (2D80) is translucent. In embodiments, the mold (2D80) includes a label (2D91) and an adhesive (2D92) for advertising the INSECTERGY® registered trademark or Energy Insects® registered trademark.

In embodiments, the esterified lipids (2D51) is then mixed with an oil (2D62), the oil (2D62) includes one or more oils selected from the group consisting of a cannabinoid, lipids extracted from insects, almond oil, animal-based oils, apricot kernel oil, avocado oil, brazil nut oil, butter, canola oil, cashew oil, cocoa butter, coconut oil, cooking oil, coffee oil, corn oil, cottonseed oil, fish oil, grapeseed oil, hazelnut oil, hemp oil, hop oil, insect oil, lard, lard oil, macadamia nut oil, mustard oil, olive oil, palm kernel oil, palm oil, peanut oil, peppermint oil, rapeseed oil, rice oil, rice bran oil, safflower oil, semi-refined sesame oil, semi-refined sunflower oil, sesame oil, soybean oil, tallow of beef, tallow of mutton, vegetable oil, and walnut oil.

In embodiments, the esterified lipids (2D51) is then mixed with a wax (2D63), the wax (2D63) includes, *cannabis* wax (as described in VOLUME 2 below), *acacia decurrens* flower cera (*mimosa* flower wax), almond wax, avocado wax, beery wax, bees wax, *cananga odorata* flower cera (ylang ylang flower wax), candelilla wax, *Cannabis sativa* oil, castor wax, cupuacu butter, floral wax, hemp wax, hydrogenated almond oil, hydrogenated animal-based oils, hydrogenated apricot kernel oil, hydrogenated avocado oil, hydrogenated brazil nut oil, hydrogenated canola oil, hydrogenated cashew oil, hydrogenated cocoa butter, hydrogenated coconut oil, hydrogenated coffee oil, hydrogenated corn oil, hydrogenated cottonseed oil, hydrogenated grapeseed oil, hydrogenated hazelnut oil, hydrogenated hemp oil, hydrogenated hop oil, hydrogenated insect oil, hydrogenated lard oil, hydrogenated lard, hydrogenated macadamia nut oil, hydrogenated mustard oil, hydrogenated olive oil, hydrogenated palm kernel oil, hydrogenated palm oil, hydrogenated peanut oil, hydrogenated peppermint oil, hydrogenated rapeseed oil, hydrogenated rice bran oil, hydrogenated rice oil, hydrogenated safflower oil, hydrogenated semi-refined sesame oil, hydrogenated semi-refined sunflower oil, hydrogenated sesame oil, hydrogenated soybean oil, hydrogenated walnut oil, *jasminum grandiflorum* flower cera (jasmine flower wax), *Lavandula angustifolia* flower cera (lavender flower wax), mmyrica fruit wax, olive wax, *prunus Amygdalus dulcis* oil, rapeseed wax, rice bran wax rosa damascene flower cera (rose flower wax), shea butter, soybean wax, sunflow wax, vegan wax, vegetable wax, wax from Mexican shrub *Euphorbia antisyphilitica*, and wax from the berries of *Rhus verniciflua*.

In embodiments, the esterified lipids (2D51) is then mixed with one or more ingredients (2D64) selected from the group consisting of allspice berries, almond meal, anise seed, annato seed, arrowroot powder, basil, bay leaves, black pepper, buttermilk, capsaicin, caraway, cayenne, celery seed, cheese cultures, chervil, chile powder, chives, cilantro, cinnamon, citric acid, cloves, coconut shredded, coriander, corn oil, corn starch, cream of tartar, cubeb berries, cumin, curry, dextrose, dill, enzymes, fennel, fenugreek, file powder, garlic powder, ginger, grapefruit peel, green peppercorns, honey, horseradish powder, juniper berries, kaffir lime, lavender, lemon grass powder, lemon peel, lime peel, long pepper, marjoram, molasses, mustard, natural smoke flavor, nigella seeds, nutmeg, onion powder, orange peel, oregano, paprika, parsley, peppermint, poppy seed, powdered cheese, red pepper, rose petals, rosemary, saffron, sassafrass, sage, salt, savory, sesame seed, star anise, sugar, sugar maple, sumac, tamarind, tangerine peel, tarragon, thyme, tomatillo powder, tomato powder, turmeric, vanilla extract, wasabi powder, whey, and white peppercorns.

In embodiments, the esterified lipids (2D51) is then mixed with one or more ingredients (2D64) selected from the group consisting of ayahuasca, biologically active organic compound with four rings, a nootropic drug, acetate, activated charcoal, an amphetamine, ascorbic acid, aspirin, butyrate, calcium, capsaicin, carnitine, carnosine, *cassia* cinnamon, chondroitin sulfate, chromium, coenzyme q-10, cranberry, creatine, curcumin, deprenyl, dimethyltryptamine, *echinacea*, fish oil, garlic, ginger, ginkgo, *ginseng*, gluconic acid, glucosamine, green tea, hoodia, human growth hormone, 7-hydroxymitragynine, inositol, iowaska, kratom, lactic acid, lithium, lutein, magnesium, minerals, malate, melatonin, metformin, 3,4-methylenedioxymethamphetamine, milk thistle, n-acetylcysteine, niacin, niacinamide, nicotinamide riboside, omega-3 fatty acid, oxaloacetate, piracetam, psilocybin, pyruvate, resveratrol, *rhodiola*, saw palmetto, selenium, St. john's wort, steroid alternatives, steroids, testosterone, theaflavins, turmeric, valerian, vitamins, vitamin B3, vitamin C, and zinc.

In embodiments, the esterified lipids (2D51) is then mixed with one or more ingredients (2D64) selected from the group consisting of basil, bergamot, black pepper, *cassia*, cedarwood, cinnamon, citronella, clary sage, clove, coffee, cypress, *eucalyptus*, evening primrose, fennel, fir needle, frankincense, *gardenia*, geranium, ginger, grapefruit, helichrysum, hop, hyssop, jasmine, juniper berry, lavender, lemon, lemongrass, mandarin, marjoram, *melaleuca*, melissa, myrrh, neroli, orange, oregano, palo santo, patchouli, peppermint, pine, roman chamomile, rose, rosemary, sandalwood, spikenard, tea tree, thyme, turmeric, vetiver, wintergreen, and ylang ylang.

In embodiments, the esterified lipids (2D51) is then mixed with one or more ingredients (2D64) selected from the group consisting of cannabidiol, tetrahydrocannabinol, distilled THC, distilled CBD, concentrated volatiles, THC or CBD crystals, and a cannabinoid emulsion.

In embodiments, the melt point of the mixture of insect lipids and wax ranges from 75.00 degrees Fahrenheit 77.50 Fahrenheit, 77.50 degrees Fahrenheit 80.00 Fahrenheit, 80.00 degrees Fahrenheit 82.50 Fahrenheit, 82.50 degrees Fahrenheit 85.00 Fahrenheit, 85.00 degrees Fahrenheit 87.50 Fahrenheit, 87.50 degrees Fahrenheit 90.00 Fahrenheit, 90.00 degrees Fahrenheit 92.50 Fahrenheit, 92.50 degrees Fahrenheit 95.00 Fahrenheit, 95.00 degrees Fahrenheit 97.50 Fahrenheit, 97.50 degrees Fahrenheit 100.00 Fahrenheit, 100.00 degrees Fahrenheit 102.50 Fahrenheit, 102.50 degrees Fahrenheit 105.00 Fahrenheit, 105.00 degrees Fahrenheit 107.50 Fahrenheit, 107.50 degrees Fahrenheit 110.00 Fahrenheit, 110.00 degrees Fahrenheit 112.50 Fahrenheit, 112.50 degrees Fahrenheit 115.00 Fahrenheit, 115.00 degrees Fahrenheit 117.50 Fahrenheit, 117.50 degrees Fahrenheit 120.00 Fahrenheit, 120.00 degrees Fahrenheit 122.50 Fahrenheit, 122.50 degrees Fahrenheit 125.00 Fahrenheit, 125.00 degrees Fahrenheit 127.50 Fahrenheit, 127.50 degrees Fahrenheit 130.00 Fahrenheit, 130.00 degrees Fahrenheit 132.50 Fahrenheit, 132.50 degrees Fahrenheit 135.00 Fahrenheit, 135.00 degrees Fahrenheit 137.50 Fahrenheit, 137.50 degrees Fahrenheit 140.00 Fahrenheit, 140.00 degrees Fahrenheit 142.50 Fahrenheit, 142.50 degrees Fahrenheit 145.00 Fahrenheit, 145.00 degrees Fahrenheit 147.50 Fahrenheit, 147.50 degrees Fahrenheit 150.00 Fahrenheit, 150.00 degrees Fahrenheit 152.50 Fahrenheit, 152.50 degrees Fahrenheit 155.00 Fahrenheit, 155.00 degrees Fahrenheit 157.50 Fahrenheit, 157.50 degrees Fahrenheit 160.00 Fahrenheit, 160.00 degrees Fahrenheit 162.50 Fahrenheit, 162.50 degrees Fahrenheit 165.00 Fahrenheit, 165.00 degrees Fahrenheit 167.50 Fahrenheit, 167.50 degrees Fahrenheit 170.00 Fahrenheit, 170.00 degrees Fahrenheit 172.50 Fahrenheit, 172.50 degrees Fahrenheit 175.00 Fahrenheit, 175.00 degrees Fahrenheit 177.50 Fahrenheit, or 177.50 degrees Fahrenheit 180.00 Fahrenheit.

In embodiments, the kinematic viscosity of the mixture of insect lipids and wax ranges from 2.8 centipoise to 3 centipoise, 3 centipoise to 3.2 centipoise, 3.2 centipoise to 3.4 centipoise, 3.4 centipoise to 3.6 centipoise, 3.6 centipoise to 3.8 centipoise, 3.8 centipoise to 4 centipoise, 4 centipoise to 4.2 centipoise, 4.2 centipoise to 4.4, 4.4 centipoise to 4.6 centipoise, 4.6 centipoise to 4.8 centipoise, 4.8 centipoise to 5 centipoise, 5 centipoise to 5.2 centipoise, 5.2 centipoise to 5.4 centipoise, 5.4 centipoise to 5.6 centipoise, 5.6 centipoise to 5.8 centipoise, 5.8 centipoise to 6 centipoise, or 6 centipoise to 6.2 centipoise.

In embodiments, the lipids are mixed with an oil at a mixing mass ration ranging from 1 pound of insect lipids per 0.050 pounds of wax, 1 pound of insect lipids per 0.060 pounds of wax, 1 pound of insect lipids per 0.070 pounds of wax, 1 pound of insect lipids per 0.080 pounds of wax, 1 pound of insect lipids per 0.090 pounds of wax, 1 pound of insect lipids per 0.100 pounds of wax, 1 pound of insect lipids per 0.110 pounds of wax, 1 pound of insect lipids per 0.120 pounds of wax, 1 pound of insect lipids per 0.130 pounds of wax, 1 pound of insect lipids per 0.140 pounds of wax, 1 pound of insect lipids per 0.150 pounds of wax, 1 pound of insect lipids per 0.160 pounds of wax, 1 pound of insect lipids per 0.170 pounds of wax, 1 pound of insect lipids per 0.180 pounds of wax, 1 pound of insect lipids per 0.190 pounds of wax, 1 pound of insect lipids per 0.200 pounds of wax, 1 pound of insect lipids per 0.210 pounds of wax, 1 pound of insect lipids per 0.220 pounds of wax, 1 pound of insect lipids per 0.230 pounds of wax, 1 pound of insect lipids per 0.240 pounds of wax, or 1 pound of insect lipids per 0.250 pounds of wax.

In embodiments, glyceryl stearate is produced by direct esterification of glycerol with stearic acid. In embodiments, the fatty acids described herein may undergo direct esterification of glycerol. In embodiments, stearic acid is reacted with glycerol to produce glyceryl stearate. In embodiments, stearic acid is reacted with glycerol to produce glyceryl stearate in the presence of a catalyst.

In embodiments, stearic acid is reacted with glycerol to produce glyceryl stearate in the presence of a catalyst, the catalyst includes a precious metal, more than one precious metal, gold, silver, platinum, rhodium, palladium, iridium, molybdenum, tungsten, nickel, cobalt, manganese, copper, titanium, silicon, vanadium, copper oxide, zeolite, a sorbent, a molecular sieve, zirconia, alumina, monoclinic or stabilized or doped zirconia, alkali-earth hexaaluminates, ceria, yittria, lanthanum, magnesium aluminate, promoted alumina, silica, ortitania.

In embodiments, stearic acid is reacted with glycerol to produce glyceryl stearate in the presence of a catalyst in a fixed bed reactor, a fluidized bed reactor, a reactor, a continuously stirred tank reactor as shown in FIG. 12D. In embodiments, heat is added or removed from the catalyst during the esterification process with steam, cooling water, a coolant, a refrigerated coolant, and combinations thereof.

In embodiments, stearic acid is reacted with glycerol to produce glyceryl stearate in the presence of one or more ingredients selected from the group consisting of alcohol, diglycerides, esters, ethanol, ethyl acetate, glycerin, glycerol, hexane, hydrocarbon, isopropyl alcohol, methanol, monoglycerides, polyol, and a solvent.

In embodiments, glyceryl stearate is produced by direct esterification of glycerol with stearic acid and one or more acids selected from the group consisting of abscic acid, acetic acid, ascorbic acid, benzoic acid, citric acid, formic acid, fumaric acid, hydrochloric acid, lactic acid, malic acid, nitric acid, organic acids, phosphoric acid, potassium hydroxide, propionic acid, salicylic acid, sulfamic acid, sulfuric acid, and tartaric acid.

In embodiments, glyceryl stearate is produced by direct esterification of glycerol with stearic acid and a caustic material including one or more materials selected from the group consisting of an alkaline substance, sodium hydroxide, lye, caustic soda, an inorganic compound with formula NaOH, a caustic base and alkali.

In embodiments, the esterification reaction occurs at a temperature ranging from one or more temperature ranges selected from the group consisting of 50 degrees Fahrenheit to 100 degrees Fahrenheit, 100 degrees Fahrenheit to 150 degrees Fahrenheit, 150 degrees Fahrenheit to 200 degrees Fahrenheit, 200 degrees Fahrenheit to 250 degrees Fahrenheit, 250 degrees Fahrenheit to 300 degrees Fahrenheit, 300 degrees Fahrenheit to 350 degrees Fahrenheit, 350 degrees Fahrenheit to 400 degrees Fahrenheit, 400 degrees Fahrenheit to 450 degrees Fahrenheit, 450 degrees Fahrenheit to 500 degrees Fahrenheit, 500 degrees Fahrenheit to 550 degrees Fahrenheit, 550 degrees Fahrenheit to 600 degrees Fahrenheit, 600 degrees Fahrenheit to 650 degrees Fahrenheit, 650 degrees Fahrenheit to 700 degrees Fahrenheit, 700 degrees Fahrenheit to 750 degrees Fahrenheit, 750 degrees Fahrenheit to 800 degrees Fahrenheit, 800 degrees Fahrenheit to 850 degrees Fahrenheit, 850 degrees Fahrenheit to 900 degrees Fahrenheit, 900 degrees Fahrenheit to 1000 degrees Fahrenheit.

In embodiments, the esterification reaction occurs at a reaction time including one or more reaction durations selected from the group consisting of 1 second to 5 seconds, 5 seconds to 15 seconds, 15 seconds to 30 seconds, 30 seconds to 1 minute, 1 minute to 2 minutes, 2 minutes to 3 minutes, 3 minutes to 4 minutes, 4 minutes to 5 minutes, 5 minutes to 10 minutes, 10 minutes to 15 minutes, 15 minutes to 20 minutes, 20 minutes to 25 minutes, 25 minutes to 30 minutes, 30 minutes to 35 minutes, 35 minutes to 40 minutes, 40 minutes to 45 minutes, 45 minutes to 50 minutes, 50 minutes to 55 minutes, 55 minutes to 1 hours, 1 hours to 1.25 hours, 1.25 hours to 1.5 hours, 1.5 hours to 1.75 hours, 1.75 hours to 2 hours, 2 hours to 2.5 hours, 2.5 hours to 3 hours, 3 hours to 3.5 hours, 3.5 hours to 4 hours, 4 hours to 4.5 hours, 4.5 hours to 5 hours, 5 hours to 5.5 hours, 5.5 hours to 6 hours, 7 hours to 8 hours, 9 hours to 10 hours, 11 hours to 12 hours, 13 hours to 14 hours, 15 hours to 16 hours, 17 hours to 18 hours, 19 hours to 20 hours, 21 hours to 22 hours, 23 hours to 24 hours, 25 hours to 26 hours, 27 hours to 28 hours, 29 hours to 30 hours, 31 hours to 32 hours, 33 hours to 34 hours, 35 hours to 36 hours, 37 hours to 38 hours, 39 hours to 40 hours, 41 hours to 42 hours, 43 hours to 44 hours, 45 hours to 46 hours, 47 hours to 48 hours, 49 hours to 50 hours, 51 hours to 52 hours, 53 hours to 54 hours, 55 hours to 56 hours, 57 hours to 58 hours, 59 hours to 60 hours, 61 hours to 62 hours, 63 hours to 64 hours, 65 hours to 66 hours, 67 hours to 68 hours, 69 hours to 70 hours, or 71 hours to 72 hours.

In embodiments, the esterification reaction occurs at a reaction pH including one or more pH ranges selected from the group consisting of: 1 to 1.2, 1.2 to 1.4, 1.4 to 1.6, 1.6 to 1.8, 1.8 to 2, 2 to 2.2, 2.2 to 2.4, 2.4 to 2.6, 2.6 to 2.8, 2.8 to 3, 3 to 3.2, 3.2 to 3.4, 3.4 to 3.6, 3.6 to 3.8, 3.8 to 4, 4 to 4.2, 4.2 to 4.4, 4.4 to 4.6, 4.6 to 4.8, 4.8 to 5, 5 to 5.2, 5.2 to 5.4, 5.4 to 5.6, 5.6 to 5.8, 5.8 to 6, 6 to 6.2, 6.2 to 6.4, 6.4 to 6.6, 6.6 to 6.8, 6.8 to 7, 7 to 7.1, 7.1 to 7.3, 7.3 to 7.5, 7.5 to 7.7, 7.7 to 7.9, 7.9 to 8.1, 8.1 to 8.3, 8.3 to 8.5, 8.5 to 8.7, 8.7 to 8.9, 8.9 to 9.1, 9.1 to 9.3, 9.3 to 9.5, 9.5 to 9.7, 9.7 to 9.9, 9.9 to 10.1, 10.1 to 10.3, 10.3 to 10.5, 10.5 to 10.7, 10.7 to 10.9, 10.9 to 11.1, 11.1 to 11.3, 11.3 to 11.5, 11.5 to 11.7, 11.7 to 11.9, 11.9 to 12.1, 12.1 to 12.3, 12.3 to 12.5, 12.5 to 12.7, or 12.7 to 12.9.

In embodiments, the esterification reaction requires energy in the form of electricity, power, or steam which is provided by the power production systems recited and disclosed at length below. Electricity may be provided to the esterification reaction from the power production system as discussed in detail below.

In embodiments, stearic acid is reacted with glycerol to produce glyceryl stearate in the presence of a biocatalyst, the biocatalyst includes one or more biocatalysts selected from the group consisting of an enzyme, casein protease, atreptogrisin A, flavorpro, peptidase, protease A, protease, *Aspergillus oryzae, Bacillus subtilis, Bacillus licheniformis, Aspergillus niger, Aspergillus melleus, Aspergilus oryzae,* papain, *Carica papaya,* bromelain, *Ananas comorus* stem, a microorganism, yeast, a fungus. In embodiments, the glyceryl stearate is then mixed with treated water, the treated water is treated with one or more water treatment units selected from the group consisting of an adsorbent, an ion-exchange resin, a catalyst, activated carbon, a membrane, and combinations thereof. In embodiments, the glyceryl stearate is then mixed with one or more ingredients selected from the group consisting of alcohol, diglycerides, esters, ethanol, ethyl acetate, glycerin, glycerol, hexane, hydrocarbon, isopropyl alcohol, methanol, monoglycerides, and a solvent. In embodiments, the glyceryl stearate is then mixed with *cannabis* oil, wax, volatiles, a cannabinoid. In embodiments, the glyceryl stearate is then mixed with a terpene including one or more terpenes selected from the group consisting of limonene, humulene, pinene, linalool, caryophyllene, mycrene, eucalyptol, nerolidol, bisablol, FIG. 13:

FIG. 13 shows a simplistic diagram illustrating a pathogen removal module that is configured to remove pathogens from at least a portion of the insects transferred from the insect evacuation module (3000). In some embodiments, a water bath (1581) containing hot water (1582) may be used to remove pathogens from the insects. In embodiments, the temperature of the water bath (1581) includes a water bath temperature sensor (1583) that is configured to input or output a signal (1584) to the computer. In embodiment, the water bath temperature sensor (1583) indicates that the water bath (1581) operates at a temperature ranging from between: about 120 degrees Fahrenheit to about 130 degrees Fahrenheit; about 130 degrees Fahrenheit to about 140 degrees Fahrenheit; about 140 degrees Fahrenheit to about 150 degrees Fahrenheit; about 150 degrees Fahrenheit to about 160 degrees Fahrenheit; about 160 degrees Fahrenheit to about 170 degrees Fahrenheit; about 170 degrees Fahrenheit to about 180 degrees Fahrenheit; about 180 degrees Fahrenheit to about 190 degrees Fahrenheit; about 190 degrees Fahrenheit to about 200 degrees Fahrenheit; and, about 200 degrees Fahrenheit to about 212 degrees Fahrenheit.

In embodiments a heat exchanger (HX1580) heats the water (1582) within the water bath (1581). In embodiments a heat exchanger (HX1580) heats the water (1582) within the water bath (1581) to form hot water (1582). The steam for the heat exchanger is provided by the second steam supply (LCP) that is provided from FIG. 14L. In embodiments, a second condensate (LAR) is discharged from the heat exchanger (HX1580) and is provided to the condensate tank (LAP) on FIG. 14L.

In embodiments a caustic material (CSTC) may be added to the water bath (1581). In embodiments, the caustic material (CSTC) is an alkaline substance, sodium hydroxide, lye, caustic soda, an inorganic compound with formula NaOH, a caustic base and alkali. In embodiments, the hot water (1582) within the water bath (1581) contains a caustic material (CSTC).

In embodiments, the water bath (1581) containing caustic material (CSTC) operates at a temperature ranging from between: about 120 degrees Fahrenheit to about 130 degrees Fahrenheit; about 130 degrees Fahrenheit to about 140 degrees Fahrenheit; about 140 degrees Fahrenheit to about 150 degrees Fahrenheit; about 150 degrees Fahrenheit to about 160 degrees Fahrenheit; about 160 degrees Fahrenheit to about 170 degrees Fahrenheit; about 170 degrees Fahrenheit to about 180 degrees Fahrenheit; about 180 degrees Fahrenheit to about 190 degrees Fahrenheit; about 190 degrees Fahrenheit to about 200 degrees Fahrenheit; about 200 degrees Fahrenheit to about 210 degrees Fahrenheit; about 210 degrees Fahrenheit to about 215 degrees Fahrenheit; about 215 degrees Fahrenheit to about 220 degrees Fahrenheit; about 220 degrees Fahrenheit to about 225 degrees Fahrenheit; about 225 degrees Fahrenheit to about 230 degrees Fahrenheit; about 230 degrees Fahrenheit to about 235 degrees Fahrenheit; about 235 degrees Fahrenheit to about 240 degrees Fahrenheit; about 240 degrees Fahrenheit to about 245 degrees Fahrenheit; about 245 degrees Fahrenheit to about 250 degrees Fahrenheit; about 250 degrees Fahrenheit to about 255 degrees Fahrenheit; about 255 degrees Fahrenheit to about 260 degrees Fahrenheit; about 260 degrees Fahrenheit to about 265 degrees Fahrenheit; about 265 degrees Fahrenheit to about 270 degrees Fahrenheit; about 270 degrees Fahrenheit to about 275 degrees Fahrenheit; about 275 degrees Fahrenheit to about 280 degrees Fahrenheit; about 280 degrees Fahrenheit to about 285 degrees Fahrenheit; and, about 285 degrees Fahrenheit to about 300 degrees Fahrenheit.

In embodiments, the hot water (1582) within the water bath (1581) contains a caustic material (CSTC) at a water-to-caustic mass ratio ranging from between 0.43 to 19. The water-to-caustic mass ratio is defined as the weight percent of water (1582) within the water bath (1581) divided by the weight percent of caustic material (CSTC) within the water bath (1581). 30 weight percent water (1582) divided by 70 weight percent caustic material (CSTC) is a water-to-caustic mass ratio of 0.43. 35 weight percent water (1582) divided by 65 weight percent caustic material (CSTC) is a water-to-caustic mass ratio of 0.54. 40 weight percent water (1582) divided by 60 weight percent caustic material (CSTC) is a water-to-caustic mass ratio of 0.67. 45 weight percent water (1582) divided by 55 weight percent caustic material (CSTC) is a water-to-caustic mass ratio of 0.82. 50 weight percent water (1582) divided by 50 weight percent caustic material (CSTC) is a water-to-caustic mass ratio of 1.00. 55 weight percent water (1582) divided by 45 weight percent caustic material (CSTC) is a water-to-caustic mass ratio of 1.22. 60 weight percent water (1582) divided by 40 weight percent caustic material (CSTC) is a water-to-caustic mass ratio of 1.50. 65 weight percent water (1582) divided by 35 weight percent caustic material (CSTC) is a water-to-caustic mass ratio of 1.86. 70 weight percent water (1582) divided by 30 weight percent caustic material (CSTC) is a water-to-caustic mass ratio of 2.33. 75 weight percent water (1582) divided by 25 weight percent caustic material (CSTC) is a water-to-caustic mass ratio of 3.00. 80 weight percent water (1582) divided by 20 weight percent caustic material (CSTC) is a water-to-caustic mass ratio of 4.00. 85 weight percent water (1582) divided by 15 weight percent caustic material (CSTC) is a water-to-caustic mass ratio of 5.67. 90 weight percent water (1582) divided by 10 weight percent caustic material (CSTC) is a water-to-caustic mass ratio of 9.00. 95 weight percent water (1582) divided by 5 weight percent caustic material (CSTC) is a water-to-caustic mass ratio of 19.000.

In embodiments, caustic material (CSTC) mixed with the hot water (1582) within the water bath (1581) includes one of more from the group selected from: 5 weight percent caustic material (CSTC) to 10 weight percent caustic material (CSTC); 10 weight percent caustic material (CSTC) to 15 weight percent caustic material (CSTC); 15 weight percent caustic material (CSTC) to 20 weight percent caustic material (CSTC) 20 weight percent caustic material (CSTC) to 25 weight percent caustic material (CSTC); 25 weight percent caustic material (CSTC) to 30 weight percent caustic material (CSTC); 30 weight percent caustic material (CSTC) to 35 weight percent caustic material (CSTC); 35 weight percent caustic material (CSTC) to 40 weight percent caustic material (CSTC); 40 weight percent caustic material (CSTC) to 45 weight percent caustic material (CSTC); 45 weight percent caustic material (CSTC) to 50 weight percent caustic material (CSTC); 50 weight percent caustic material (CSTC) to 55 weight percent caustic material (CSTC); 55 weight percent caustic material (CSTC) to 60 weight percent caustic material (CSTC); 60 weight percent caustic material (CSTC) to 65 weight percent caustic material (CSTC); and, 65 weight percent caustic material (CSTC) to 70 weight percent caustic material (CSTC).

In embodiments, caustic material (CSTC) mixed with the hot water (1582) and insects within the water bath (1581) have a pH selected from one or more from the group consisting of: 7.1 to 7.3, 7.3 to 7.5, 7.5 to 7.7, 7.7 to 7.9, 7.9 to 8.1, 8.1 to 8.3, 8.3 to 8.5, 8.5 to 8.7, 8.7 to 8.9, 8.9 to 9.1, 9.1 to 9.3, 9.3 to 9.5, 9.5 to 9.7, 9.7 to 9.9, 9.9 to 10.1, 10.1 to 10.3, 10.3 to 10.5, 10.5 to 10.7, 10.7 to 10.9, 10.9 to 11.1, 11.1 to 11.3, 11.3 to 11.5, 11.5 to 11.7, 11.7 to 11.9, 11.9 to 12.1, 12.1 to 12.3, 12.3 to 12.5, 12.5 to 12.7, and 12.7 to 12.9.

In embodiments, the caustic material (CSTC) that is mixed with the water (1582) contacts insects and promotes a deacetylation reaction of the exoskeleton of insects. In embodiments, the caustic material (CSTC) that is mixed with the water (1582) contacts insects and promotes a deacetylation reaction of the N-acetylglucosamine portion of the insects. In embodiments, the mixture of water (1582) and caustic material (CSTC) serves to remove a function acetyl group from the N-acetylglucosamine portion of the insects.

In embodiments, the mixture of water (1582) and caustic material (CSTC) serve to remove a function acetyl group from the N-acetylglucosamine portion of the insects to form chitosan. Chitosan has the unique numerical identifier assigned by is Chemical Abstracts Service (CAS) Number of 9012-76-4.

In embodiments, the mixture of water (1582) and caustic material (CSTC) serve to remove a function acetyl group from the N-acetylglucosamine portion of the insects to form a linear polysaccharide. In embodiments, the mixture of water (1582) and caustic material (CSTC) serve to depolymerize the N-acetylglucosamine portion of the insects to form depolymerized insects. Depolymerization means to break a polymer down into or other smaller units. A caustic material (CSTC) to removes the function acetyl group from the N-acetylglucosamine portion of the insects and thus the N-acetylglucosamine portion of the insects is broken down into a smaller molecule.

Biopolymers are polymers produced by living organisms. Insects are living organisms. Chitosan is a polymer. Chitosan is a polycationic linear polysaccharide. Polysaccharides are polymers. Polysaccharides are polymeric carbohydrate molecules composed of long chains of monosaccharide units bound together by glycosidic linkages. Chitosan is a polymer that is formed from the deacetylation of insects that contain chitin. Chitin is contained within the exoskeleton of insects. Chitin is a long-chain polymer of an N-acetylglucosamine, a derivative of glucose. Polycations are polyelectrolytes. An electrolyte is a substance that produces an electrically conducting solution when dissolved in a polar solvent, such as water. Chitosan is a polyelectrolyte. A polyelectrolyte is a polymer that bears an electrolyte group. A polyelectrolyte is a positively-charged polymer. Chitosan is a is a positively-charged polymer. Heating and mixing water (1582) with a caustic material (CSTC) and insects can produce a polyelectrolyte or a polymer that bears an electrolyte group. In embodiments, linear polysaccharide includes chitosan. In embodiments, the pathogen-depleted insects (1570) may include a biopolymer (1570'), or deacetylated insects (1570").

In embodiments, the mixture of water (1582), caustic material (CSTC), and insects at a temperature ranging from 200 degrees Fahrenheit to 280 degrees Fahrenheit and at a water-to-caustic mass ratio ranging from between 0.43 to 19 to produce a polycationic linear polysaccharide or a biopolymer. In embodiments, the mixture of water (1582), caustic material (CSTC), and insects can be operated at temperature ranging from 200 degrees Fahrenheit to 280 degrees Fahrenheit and at a water-to-caustic mass ratio ranging from between 0.43 to 19 to produce a polyelectrolyte. In embodiments, the mixture of water (1582), caustic material (CSTC), and insects can be operated at temperature ranging from 200 degrees Fahrenheit to 280 degrees Fahrenheit and at a water-to-caustic mass ratio ranging from between 0.43 to 19 to produce a chitosan.

In embodiments, the mixture of water (1582), caustic material (CSTC), and insects at a temperature ranging from 200 degrees Fahrenheit to 280 degrees Fahrenheit and at a caustic concentration ranging from 5 weight percent to 70 weight percent to produce a polycationic linear polysaccharide or a biopolymer. In embodiments, the mixture of water (1582), caustic material (CSTC), and insects can be operated at temperature ranging from 200 degrees Fahrenheit to 280 degrees Fahrenheit and at a caustic concentration ranging from 5 weight percent to 70 weight percent to produce a polyelectrolyte. In embodiments, the mixture of water (1582), caustic material (CSTC), and insects can be operated at temperature ranging from 200 degrees Fahrenheit to 280 degrees Fahrenheit and at a caustic concentration ranging from 5 weight percent to 70 weight percent to produce a chitosan.

FIG. 14A:

FIG. 14A shows a simplistic diagram illustrating a multifunctional composition mixing module that is configured to generate a multifunctional composition from at least a portion of the insects transferred from the pathogen removal module and including the sequence steps or sub-modules including an insect distribution module (6A), fiber-starch distribution module (6B), binding agent distribution module (6C), density improving textural supplement distribution module (6D), moisture improving textural supplement distribution module (6E), multifunctional composition mixing module (6F).

Insect Distribution Module (6A)

FIG. 14A displays an insect distribution module (6A) including an insect tank (6A2) that is configured to accept insects (6A1). The insect tank (6A2) has an interior (6A3), an insect input (6A4), an insect conveyor (6A5), and an insect conveyor output (6A6). The insect tank (6A2) accepts insects (6A1) to the interior (6A3) and regulates and controls an engineered amount of insects (6A1) downstream to be mixed to form a multifunctional composition. The insect conveyor (6A5) has an integrated insect mass sensor (6A7) that is configured to input and output a signal (6A8) to the computer (COMP). The insect conveyor motor (6A9) has a controller (6A10) that is configured to input and output a signal (6A11) to the computer (COMP). The insect mass sensor (6A7), insect conveyor (6A5), and insect conveyor motor (6A9) are coupled so as to permit the conveyance, distribution, or output of a precise flow of insect (6A1) via an insect transfer line (6A12).

Fiber-Starch Distribution Module (6B)

FIG. 14A displays a fiber-starch distribution module (6B) including a fiber-starch tank (6B2) that is configured to accept fiber-starch (6B1). The fiber-starch tank (6B2) has an interior (6B3), a fiber-starch input (6B4), a fiber-starch conveyor (6B5), and a fiber-starch conveyor output (6B6). The fiber-starch tank (6B2) accepts fiber-starch (6B1) to the interior (6B3) and regulates and controls an engineered amount of fiber-starch (6B1) downstream to be mixed to form a multifunctional composition. The fiber-starch conveyor (6B5) has an integrated fiber-starch mass sensor (6B7) that is configured to input and output a signal (6B8) to the computer (COMP). The fiber-starch conveyor motor (6B9) has a controller (6B10) that is configured to input and output a signal (6B11) to the computer (COMP). The fiber-starch mass sensor (6B7), fiber-starch conveyor (6B5), and fiber-starch conveyor motor (6B9) are coupled so as to permit the conveyance, distribution, or output of a precise flow of fiber-starch (6B1) via a fiber-starch transfer line (6B12).

Binding Agent Distribution Module (6C)

FIG. 14A displays a binding agent distribution module (6C) including a binding agent tank (6C2) that is configured to accept a binding agent (6C1). The binding agent tank (6C2) has an interior (6C3), a binding agent input (6C4), a binding agent conveyor (6C5), and a binding agent conveyor output (6C6). The binding agent tank (6C2) accepts binding agent (6C1) to the interior (6C3) and regulates and controls an engineered amount of a binding agent (6C1) downstream to be mixed to form a multifunctional composition. The binding agent conveyor (6C5) has an integrated binding agent mass sensor (6C7) that is configured to input and output a signal (6C8) to the computer (COMP). The binding agent conveyor motor (6C9) has a controller (6C10) that is configured to input and output a signal (6C11) to the computer (COMP). The binding agent mass sensor (6C7), binding agent conveyor (6C5), and binding agent conveyor motor (6C9) are coupled so as to permit the conveyance, distribution, or output of a precise flow of binding agent (6C1) via a binding agent transfer line (6C12).

Density Improving Textural Supplement Distribution Module (6D)

FIG. 14A displays a density improving textural supplement distribution module (6D) including a density improving textural supplement tank (6D2) that is configured to accept a density improving textural supplement (6D1). The density improving textural supplement tank (6D2) has an interior (6D3), a density improving textural supplement input (6D4), a density improving textural supplement conveyor (6D5), and a density improving textural supplement conveyor output (6D6). The density improving textural supplement tank (6D2) accepts density improving textural supplement (6D1) to the interior (6D3) and regulates and controls an engineered amount of a density improving textural supplement (6D1) downstream to be mixed to form a multifunctional composition. The density improving textural supplement conveyor (6D5) has an integrated density improving textural supplement mass sensor (6D7) that is configured to input and output a signal (6D8) to the computer (COMP). The density improving textural supplement conveyor motor (6D9) has a controller (6D10) that is configured to input and output a signal (6D11) to the computer (COMP). The density improving textural supplement mass sensor (6D7), density improving textural supplement conveyor (6D5), and density improving textural supplement conveyor motor (6D9) are coupled so as to permit the conveyance, distribution, or output of a precise flow of density improving textural supplement (6D1) via a density improving textural supplement transfer line (6D12).

Moisture Improving Textural Supplement Distribution Module (6E)

FIG. 14A displays a moisture improving textural supplement distribution module (6E) including a moisture improving textural supplement tank (6E2) that is configured to accept a moisture improving textural supplement (6E1). The moisture improving textural supplement tank (6E2) has an interior (6E3), a moisture improving textural supplement input (6E4), a moisture improving textural supplement conveyor (6E5), and a moisture improving textural supplement conveyor output (6E6). The moisture improving textural supplement tank (6E2) accepts a moisture improving textural supplement (6E1) to the interior (6E3) and regulates and controls an engineered amount of a moisture improving textural supplement (6E1) downstream to be mixed to form a multifunctional composition. The moisture improving textural supplement conveyor (6E5) has an integrated moisture improving textural supplement mass sensor (6E7) that is configured to input and output a signal (6E8) to the computer (COMP). The moisture improving textural supplement conveyor motor (6E9) has a controller (6E10) that is configured to input and output a signal (6E11) to the computer (COMP). The moisture improving textural supplement mass sensor (6E7), moisture improving textural supplement conveyor (6E5), and moisture improving textural supplement conveyor motor (6E9) are coupled so as to permit the conveyance, distribution, or output of a precise flow of moisture improving textural supplement (6E1) via a moisture improving textural supplement transfer line (6E12).

*Cannabis* Enhancer Distribution Module (6G)

FIG. 14A displays a *cannabis* enhancer distribution module (6G) including a *cannabis* enhancer tank (6G2) that is configured to accept a *cannabis* enhancer (6G1). The *cannabis* enhancer tank (6G2) has an interior (6G3), a *cannabis* enhancer input (6G4), a *cannabis* enhancer conveyor (6G5), and a *cannabis* enhancer conveyor output (6G6). The *cannabis* enhancer tank (6G2) accepts a *cannabis* enhancer (6G1) to the interior (6G3) and regulates and controls an engineered amount of a *cannabis* enhancer (6G1) downstream to be mixed to form a multifunctional composition. The *cannabis* enhancer conveyor (6G5) has an integrated *cannabis* enhancer mass sensor (6G7) that is configured to input and output a signal (6G8) to the computer (COMP). The *cannabis* enhancer conveyor motor (6G9) has a controller (6G10) that is configured to input and output a signal (6G11) to the computer (COMP). The *cannabis* enhancer mass sensor (6G7), *cannabis* enhancer conveyor (6G5), and *cannabis* enhancer conveyor motor (6G9) are coupled so as to permit the conveyance, distribution, or output of a precise flow of *cannabis* enhancer (6G1) via a *cannabis* enhancer transfer line (6G12).

Multifunctional Composition Mixing Module (6F)

FIG. 14A displays a multifunctional composition mixing module (6F) including a multifunctional composition tank (6F1) that is configured to accept a mixture including insects (6A1), fiber-starch (6B1), binding agent (6C1), density improving textural supplement (6D1), moisture improving textural supplement (6E1), and *cannabis* enhancer (6G1) via a multifunctional composition transfer line (6F0). The insects (6A1) may be pathogen-depleted insects (1570) transferred from the pathogen removal unit (1550) as depicted in FIG. 14A. FIG. 14B shows the insects (6A1) as ground separated insects (1500) transferred from the grinder (1250). The multifunctional composition tank (6F1) has an interior (6F2), a multifunctional composition tank input (6F3), screw conveyor (6F9), multifunctional composition output (6F10). The multifunctional composition tank (6F1) accepts insects (6A1), fiber-starch (6B1), binding agent (6C1), density improving textural supplement (6D1), moisture improving textural supplement (6E1), and *cannabis* enhancer (6G1) to the interior (6F2) and mixes, regulates, and outputs a weighed multifunctional composition stream (6F22).

The multifunctional composition tank (6F1) has a top section (6F4), bottom section (6F5), at least one side wall (6F6), with a level sensor (6F7) positioned thereon that is configured to input and output a signal (6F8) to the computer (COMP). The screw conveyor (6F9) has a multifunctional composition conveyor motor (6F11) with a controller (6F12) that is configured to input and output a signal (6F13) to the computer (COMP). From the multifunctional composition output (6F10) of the multifunctional composition tank (6F1) is positioned a multifunctional composition weigh screw (6F14) that is equipped with a multifunctional composition weigh screw input (6F15), a multifunctional composition weigh screw output (6F16), and a mass sensor (6F17) that is configured to input and output a signal (6F18) to the computer (COMP). The multifunctional composition weigh screw (6F14) also has a weigh screw motor (6F19) with a controller (6F20) that is configured to input and output a signal (6F21) to the computer (COMP).

FIG. 14B:

FIG. 14B shows a simplistic diagram illustrating a multifunctional composition mixing module that is configured to generate a multifunctional composition as described in FIG. 14A however instead from at least a portion of the insects transferred from the insect grinding module.

FIG. 14C:

FIG. 14C shows one non-limiting embodiment of a liquid mixing module (LMM) that is configured to mix water with multifunctional composition (6F23) provided from the multifunctional composition mixing module as shown in FIG. 14A or 14B.

FIG. 14C shows one non-limiting embodiment of a liquid mixing module (LMM) that includes a first water treatment unit (C10), a second water treatment unit (C11), and a third water treatment unit (C12), that provide a third contaminant depleted water (C13) to the interior (C14) of a mixing tank (C15). The mixing tank (C15) mixes a water supply (C16) with multifunctional composition (6F23) provided from the multifunctional composition mixing module as shown in FIG. 14A or 14B to form a multifunctional composition and water mixture (C17). The multifunctional composition (6F23) introduced to the mixing tank (C15) may be a weighed multifunctional composition stream (6F22).

The multifunctional composition and water mixture (C17) is transferred from the mixing tank (C15) to the shaping module (14D) of FIG. 14D. In embodiments, the multifunctional composition and water mixture (C17) is transferred and pressurized using a pump (C18) from the mixing tank (C15) to the shaping module (14D) of FIG. 14D. In embodiments, the multifunctional composition and water mixture (C17) is transferred and pressurized using a screw auger (C19) from the mixing tank (C15) to the shaping module (14D) of FIG. 14D.

FIG. 14C depicts the first water treatment unit (C10) to include a cation, a second water treatment unit (C11) to include an anion, and a third water treatment unit (C13) to include a membrane. A first water pressure sensor (C20) is positioned on the water input conduit (C21) that is introduced to the first input (C22) to the first water treatment unit (C10). In embodiments, a filter (C23), activated carbon (C24), and/or an adsorbent (C25), are positioned on the water input conduit (C21) prior to introducing the water supply (C16) to the first water treatment unit (C10). The water supply (C16) may be considered a contaminant-laden water (C26) that includes positively charged ions, negatively charged ions, and undesirable compounds. The positively charged ions are comprised of one or more from the group consisting of calcium, magnesium, sodium, and iron. The negatively charged ions are comprised of one or more from the group consisting of iodine, chloride, and sulfate. The undesirable compounds are comprised of one or more from the group consisting of dissolved organic chemicals, viruses, bacteria, and particulates.

A first contaminant depleted water (C27) is discharged by the first water treatment unit (C10) by a first output (C28). The first contaminant depleted water (C27) may be a positively charged ion depleted water (C29). The first contaminant depleted water (C27) is then transferred to the second water treatment unit (C11) via a second input (C30). A second contaminant depleted water (C31) is discharged by the second water treatment unit (C11) by a second output (C32). The second contaminant depleted water (C31) may be a negatively charged ion depleted water (C33). The second contaminant depleted water (C31) is then transferred to the third water treatment unit (C12) via a third input (C34). A third contaminant depleted water (C13) is discharged by the third water treatment unit (C12) by a third output (C35). The third contaminant depleted water (C13) may be an undesirable compounds depleted water (C36). The third contaminant depleted water (C13) is then transferred to the interior (C14) of a mixing tank (C15) via a water supply conduit (C37) and water input (C38).

Within the interior (C14) of a mixing tank (C15), the water is mixed with multifunctional composition (6F23) provided from the multifunctional composition mixing module as shown in FIG. 14A or 14B. In embodiments, a cation (C39), an anion (C40), and a polishing unit (C41), are positioned on the water supply conduit (C37) in between the third water treatment unit (C12) and the water input (C38) of the mixing tank (C15). The polishing unit (C41) may be any type of conceivable device to improve the water quality such as an ultraviolet unit, ozone unit, microwave unit, filter, or the like.

In embodiments, water supply valve (C42) is positioned on the water supply conduit (C37) in between the third water treatment unit (C12) and the water input (C38) of the mixing tank (C15). The water supply valve (C42) is equipped with a controller (C43) that inputs or outputs a signal from a computer (COMP). In embodiments, the mixing tank (C15) is equipped with a high-level sensor (C44) and a low-level sensor (C45). The high-level sensor (C44) is used for detecting a high level and the low-level sensor (C45) is used for detecting a low level. The high-level sensor (C44) is configured to output a signal to the computer (COMP) when the high-level sensor (C44) is triggered by a high level of liquid within the mixing tank (C15). The low-level sensor (C45) is configured to output a signal to the computer (COMP) when the low-level sensor (C45) is triggered by a low level of liquid within the mixing tank (C15).

In embodiments, when the low-level sensor (C45) sends a signal to the computer (COMP), the water supply valve (C42) on the water supply conduit (C37) is opened and introduces water into the mixing tank (C15) until the high-level sensor (C44) is triggered thus sending a signal to the computer (COMP) to close the water supply valve (C42). This level control loop including the high-level sensor (C44) for detecting a high level and a low-level sensor (C45) for detecting a lower level may be coupled to the operation of the water supply valve (C42) for introducing a water supply (C16) through a first water treatment unit (C10), a second water treatment unit (C11), and a third water treatment unit (C12), to provide a third contaminant depleted water (C13) to the interior (C14) of a mixing tank (C15).

The mixing tank (C15) may be placed on a load cell (C46) for measuring the mass of the tank. The mixing tank (C15)

may be equipped with a mixer (C47) for mixing water with multifunctional composition (6F23). The multifunctional composition (6F23) is introduced to the interior (C14) of the mixing tank (C15) via an input (C51). The mixer (C47) may be of an auger or blade type that is equipped with a motor (C48). The mixing tank (C15) has a multifunctional composition and water mixture output (C49) that is connected to a discharge conduit (C50).

The discharge conduit (C50) is connected at one end to the multifunctional composition and water mixture output (C49) of the mixing tank (C15) and at another end to a supply pump (C18) or a screw auger (C19). The supply pump (C18) or a screw auger (C19) provides a pressurized source of multifunctional composition and water mixture (C17) to the downstream shaping module (14D) as shown in FIG. 14D. The multifunctional composition and water mixture (C17) may be a pressurized multifunctional composition and water mixture (C17A).

In embodiments, a flow sensor (C51) and/or a flow totalizer (C52) may be installed on the water supply conduit (C37) to determine the mass or volume of water that is sent to the interior (C14) of the mixing tank (C15). In embodiments, the mixing tank (C15) is equipped with a heat exchanger (C53) to heat the mixture of water and multifunctional composition. The heat exchanger (C53) may be electrically heated or provided with a source of steam or hot oil. In embodiments, the heat exchanger (C53) accepts a third steam supply (LCT) that is provided by FIG. 14L. In embodiments, a third condensate (LAS) is discharged from the heat exchanger (C53) and is provided to the condensate tank (LAP) on FIG. 14L.

In embodiments, the mass of water or multifunctional composition within the mixing tank (C15) can be measured via the load cell (C46). In embodiments, water can be added to the mixing tank (C15) and the mass of water is measured, following by adding the multifunctional composition to the interior (C14) of the mixing tank (C15) to know the mass of the total mixture. The contents within the mixing tank (C15) can be mixed with the mixer and optionally heated.

FIG. 14D:

FIG. 14D shows one non-limiting embodiment of a shaping module (14D) that is configured to shape the multifunctional composition and water mixture (C17) to produce a shaped multifunctional composition mixture (D10).

Many shaping technologies are available to shape the multifunctional composition and water mixture (C17) including one or more from the group consisting of extrusion, sheeting rolling, and cutting rolls. Extrusion is a process used to create a shaped multifunctional composition mixture (D10) having a fixed cross-sectional profile. The die (D15) has a fixed cross-sectional profile and is configured to accept the multifunctional composition and water mixture (C17) and press it into an extrudate (D11). The multifunctional composition and water mixture (C17) is pushed through a die of the desired cross-section to create an extrudate (D11) or a shaped multifunctional composition mixture (D10) which may then be cooked in a cooking module (14E) as shown in FIG. 14E.

In embodiments, the shaping module (14D) includes an extrusion system (D12). In embodiments, the extrusion system (D12) includes an input hopper (D13), an auger (D14), and a die (D15). The auger (D14) is driven by a motor (D16). The multifunctional composition and water mixture (C17) is transferred from the liquid mixing module (LMM) as shown in FIG. 14C and provided to the input hopper (D13) of the extrusion system (D12).

The multifunctional composition and water mixture (C17) is transferred through the die (D15) by the rotating motion of an auger (D14). As the multifunctional composition and water mixture (C17) is pressed through the die (D15) by the auger (D14), friction causes at least a portion of the extrusion system (D12) to generate heat. In embodiments, the temperature within the extrusion system (D12) can increase due to the friction caused by formation of the extrudate (D11). This requires the extrusion system (D12) to require a source of coolant, such as cooling water, to cool regulate temperature and prevent overheating. In embodiments, the auger (D14) is cooled with a coolant.

The auger (D14) is equipped with a shaft (D17) and flights (D18) and is configured to applying pressure on the multifunctional composition and water mixture (C17) sufficient to squeeze through the die (D15). The shaped multifunctional composition mixture (D10) or an extrudate (D11) is discharged from the extrusion system (D12) via a extrudate output (D19). The extrusion system (D12) is equipped with a stand (D20) to elevate it off the ground.

The shaped multifunctional composition mixture (D10) or an extrudate (D11) is discharged from the extrusion system (D12) via a extrudate output (D19) and is transferred to a conveyor (D21). The conveyor (D21) transfers the extrudate (D11) to the cooking module (14E) as shown in FIG. 14E. The conveyor (D21) may be mechanical, pneumatic, air conveyor, elevating conveyor, conveyor belt, a drag-chain conveyor, bucket elevator, or any conceivable means to transfer extrudate (D11) from the extrusion system (D12) to the cooking module (14E).

In embodiments, the extrusion system (D12) is equipped with an extrusion pressure sensor (D21) that is configured to input or output a signal (D22) to the computer (COMP). In embodiments, the extrusion pressure sensor (D21) reads a pressure within the extrusion system (D12) ranging from: between about 0.25 PSI to about 49.99 PSI; between about 50 PSI to about 99.99 PSI; between about 100 PSI to about 149.99 PSI; between about 150 PSI to about 199.99 PSI; between about 200 PSI to about 249.99 PSI; between about 250 PSI to about 299.99 PSI; between about 300 PSI to about 349.99 PSI; between about 350 PSI to about 399.99 PSI; between about 400 PSI to about 449.99 PSI; between about 450 PSI to about 499.99 PSI; between about 500 PSI to about 549.99 PSI; between about 550 PSI to about 599.99 PSI; between about 600 PSI to about 649.99 PSI; between about 650 PSI to about 699.99 PSI; between about 700 PSI to about 749.99 PSI; between about 750 PSI to about 799.99 PSI; between about 800 PSI to about 8549.99 PSI; between about 850 PSI to about 899.99 PSI; between about 900 PSI to about 949.99 PSI; between about 950 PSI to about 999.99 PSI; between about 1,000 PSI to about 1,499.99 PSI; between about 1,500 PSI to about 1,999.99 PSI; between about 2,000 PSI to about 2,499.99 PSI; between about 2,500 PSI to about 2,999.99 PSI; between about 3,000 PSI to about 3,499.99 PSI; between about 3,500 PSI to about 3,999.99 PSI; between about 4,000 PSI to about 4,499.99 PSI; between about 4,500 PSI to about 4,999.99 PSI; between about 5,000 PSI to about 5,499.99 PSI; between about 5,500 PSI to about 5,999.99 PSI; between about 6,000 PSI to about 6,499.99 PSI; between about 6,500 PSI to about 6,999.99 PSI; between about 7,000 PSI to about 7,499.99 PSI; between about 7,500 PSI to about 7,999.99 PSI; between about 8,000 PSI to about 8,499.99 PSI; between about 8,500 PSI to about 8,999.99 PSI; between about 9,000 PSI to about 9,499.99 PSI; between about 9,500 PSI to about 9,999.99 PSI; between about 10,000 PSI to about 15,499.99 PSI; between about 15,500 PSI to about 19,999.99 PSI; between about 20,000 PSI to about 25,499.99 PSI; between about 25,500 PSI to about 29,999.99 PSI; between about 30,000 PSI to about 35,499.99 PSI; and, between about 35,500 PSI to about 40,000 PSI.

It has been my realization that in one non-limiting embodiment the best mode to operate the extrusion system (D12) includes maintaining the extrusion pressure sensor (D21) at a pressure less than 250 PSI. Nonetheless, all the above pressures may work as intended to realize a shaped multifunctional composition mixture (D10).

The extrusion system (D12) may be equipped with a coolant input (D23) and a coolant output (D24). A coolant input temperature sensor (D25) is configured to input and output a signal (D26) to the computer (COMP) and measures the temperature of coolant that passes into the coolant input (D23). A coolant output temperature sensor (D27) is configured to input and output a signal (D28) to the computer (COMP) and measures the temperature of coolant that leaves the coolant output (D24). A coolant (D29) passes from the coolant input (D23) to the coolant output (D24) and accepts heat from at least a portion of the extrusion system (D12). The temperature of the coolant (D29) measured at the coolant output temperature sensor (D27) is greater than the temperature measured by the coolant input temperature sensor (D25).

In embodiments, the coolant input temperature sensor (D25) reads a temperature ranging from between about 60 degrees Fahrenheit to about 150 degrees Fahrenheit. In embodiments, the coolant output temperature sensor (D27) reads a temperature ranging from between about 150.999 degrees Fahrenheit to about 210 degrees Fahrenheit.

FIG. 14E:

FIG. 14E shows one non-limiting embodiment of a cooking module (14E) that is configured to cook the shaped multifunctional composition mixture (D10) provided from the shaping module (14D) to form a cooked multifunctional composition mixture (E18A).

FIG. 14E shows one non-limiting embodiment of a cooking module (14E) that is configured to cook the shaped multifunctional composition mixture (D10) or extrudate (D11) provided from the shaping module (14D) to form a cooked multifunctional composition mixture (E18A).

The cooking module (14E) as shown in FIG. 14E includes a cooking system (E10). The cooking system (E10) shown in FIG. 14D includes an oven (E11) or a fryer (E12). In embodiments, the fryer (E12) cooks the extrudate (D11) in an oil (E19). In embodiments, the oil (E19) are lipids extracted from insects as shown in FIGS. 12A and/or 12B. In embodiments, the oil (E19) may be comprised of one or more from the group consisting of almond oil, animal-based oils, apricot kernel oil, avocado oil, brazil nut oil, butter, canola oil, cashew oil, cocoa butter, coconut oil, cooking oil, corn oil, cottonseed oil, fish oil, grapeseed oil, hazelnut oil, hemp oil, insect oil, lard, lard oil, macadamia nut oil, mustard oil, olive oil, palm kernel oil, palm oil, peanut oil, rapeseed oil, rice oil, rice bran oil, safflower oil, semi-refined sesame oil, semi-refined sunflower oil, sesame oil, soybean oil, tallow of beef, tallow of mutton, vegetable oil, and walnut oil.

In embodiments, the cooking system (E10) has a heat exchanger (E20) that cooks the shaped multifunctional composition mixture (D10). In embodiments, the heat exchanger (E20) accepts a fourth steam supply (LCX) that is provided from FIG. 14L. In embodiments, the heat exchanger (E20) outputs a fourth condensate (LAT) and is provided to the condensate tank (LAP) on FIG. 14L. In embodiments, the fryer (E12) has a heat exchanger (E20) that heats an oil (E19) which in turn cooks the shaped multifunctional composition mixture (D10). In embodiments, the heat exchanger (E20) accepts a fourth steam supply (LCX) that is provided from FIG. 14L. In embodiments, the heat exchanger (E20) outputs a fourth condensate (LAT) and is provided to the condensate tank (LAP) on FIG. 14L. The cooking system (E10) may also include a dryer (E13), pressure cooker (E14), dehydrator (E15), freeze dryer (E16), and may operate in a batch or continuous mode.

A conveyor (E17) may be integrated with the cooking system (E10). The conveyor (E17) may be mechanical, pneumatic, air operated, an elevating conveyor, conveyor belt, drag-chain conveyor, or the like.

The cooking system (E10) cooks the extrudate (D11) provided from the shaping module (14D) to form a cooked extrudate (E18) or a cooked multifunctional composition mixture (E18A). The cooked extrudate (E18) or cooked multifunctional composition mixture (E18A) is transferred to the flavoring module (14F) as shown in FIG. 14F. In embodiments, the cooked multifunctional composition mixture (E18A) is a cooked extrudate (E18).

In embodiments, the cooking system (E10) cooks the extrudate (D11) at a temperature ranging from between: 100 degrees F. to 124.99 degrees F.; 125 degrees F. to 149.99 degrees F.; 150 degrees F. to 174.99 degrees F.; 175 degrees F. to 199.99 degrees F.; 200 degrees F. to 224.99 degrees F.; 225 degrees F. to 249.99 degrees F.; 250 degrees F. to 274.99 degrees F.; 275 degrees F. to 299.99 degrees F.; 300 degrees F. to 324.99 degrees F.; 325 degrees F. to 349.99 degrees F.; 350 degrees F. to 374.99 degrees F.; 375 degrees F. to 399.99 degrees F.; 400 degrees F. to 550 degrees F.

In embodiments, the cooking system (E10) cooks the extrudate (D11) over a time duration ranging from between: 1 second to 5 seconds, 5 seconds to 15 seconds; 15 seconds to 30 seconds; 30 seconds to 1 minute; 1 minute to 2 minutes; 2 minutes to 3 minutes; 3 minutes to 4 minutes; 4 minutes to 5 minutes; 5 minutes to 6 minutes; 6 minutes to 7 minutes; 7 minutes to 8 minutes; 8 minutes to 9 minutes; 9 minutes to 10 minutes; 11 minutes to 12 minutes; 12 minutes to 13 minutes; 13 minutes to 14 minutes; 14 minutes to 15 minutes; 15 minutes to 16 minutes; 16 minutes to 17 minutes; 17 minutes to 18 minutes; 18 minutes to 19 minutes; 19 minutes to 60 minutes.

In embodiments, an air-oil heat exchanger (E21), an oil pump (E24), temperature sensor (E25), and a computer (E26) are integrated with the cooking system (E10). Hot oil (E19) is pumped from the fryer (E12) via an oil pump (E24) to the air-oil heat exchanger (E21) where heat is removed from the oil (E19) and transferred to the air (E23) by use of a fan (E22) to heat the air (E23) that is located above the cooking system (E10).

In embodiments, the temperature sensor (E26) measures the temperature of the air (E23) above the cooking system (E10) and sends a signal (E27) to the computer (COMP). A pre-determined air temperature is entered into the computer (COMP) which may include one or more from the group consisting of 50 degrees Fahrenheit to 60 degrees Fahrenheit, 60 degrees Fahrenheit to 70 degrees Fahrenheit, 70 degrees Fahrenheit to 80 degrees Fahrenheit, and 80 degrees Fahrenheit to 90 degrees Fahrenheit.

When the temperature of the air (E23) located above the cooking system (E10) falls below the pre-determined air temperature, the computer (COMP) sends a signal (E28) to the motor (E29) of the oil pump (E24) to pump oil (E19) to the air/oil heat exchanger (E21). Also, when the temperature of the air (E23) located above the cooking system (E10) falls below the pre-determined air temperature, the computer (COMP) sends a signal (E30) to the motor (E31) of the fan (E22) to blow air (E23) across the surface of the air/oil heat exchanger (E21). This in turn transfer heat from the hot oil (E19) to the air (E23) that is located above the cooking system (E10). The air/oil heat exchanger (E21) discharged cooled oil (E33) back to the fryer (E12) where to be mixed with oil (E19) and heated using the fourth steam supply (LCX) that is provided from FIG. 14L.

FIG. 14F:

FIG. 14F shows one non-limiting embodiment of a flavoring module (14F) that is configured to flavor the cooked multifunctional composition mixture (E18A) provided from the cooking module (14E) to form a flavored multifunctional composition mixture (F10).

FIG. 14F shows one non-limiting embodiment of a flavoring module (14F) that is configured to flavor the cooked extrudate (E18) provided from the cooking module (14E) to form a flavored cooked extrudate (F10).

The flavoring module (14F) as shown in FIG. 14F includes a flavoring system (F11). The flavoring system (F11) shown in FIG. 14F includes a flavoring machine (F12) shown in the form of a tumbler (F13). The tumbler (F13) has a motor (F14) and a controller (F15) and is configured to be operated by a computer (COMP). The flavoring machine (F12) has a cooked extrudate input (F16) for receiving the cooked extrudate (E18) from the cooking module (14E).

The flavoring machine (F12) has a flavoring input (F17) for receiving flavoring (F18). The flavoring (F18) are comprised of one or more from the group consisting of allspice berries, almond meal, anise seed, annato seed, arrowroot powder, basil, bay leaves, black pepper, buttermilk, *cannabis*, capsaicin, caraway, cayenne, celery seed, cheese cultures, chervil, Chile powder, chives, cilantro, cinnamon, citric acid, cloves, coconut shredded, coriander, corn oil, corn starch, cream of tartar, cubeb berries, cumin, curry, dextrose, dill, enzymes, fennel, fenugreek, file powder, garlic powder, ginger, grapefruit peel, green peppercorns, honey, horseradish powder, juniper berries, kaffir lime, lavender, lemon grass powder, lemon peel, lime peel, long pepper, marjoram, molasses, mustard, natural smoke flavor, nigella seeds, nutmeg, onion powder, orange peel, oregano, paprika, parsley, peppermint, poppy seed, powdered cheese, red pepper, rose petals, rosemary, saffron, sassafrass, sage, salt, savory, sesame seed, star anise, sugar, sugar maple, sumac, tamarind, tangerine peel, tarragon, tetrahydrocannabinol, thyme, tomatillo powder, tomato powder, torula yeast, turmeric, vanilla extract, wasabi powder, whey, white peppercorns, yeast extract, and yeast.

In embodiments, the flavoring machine (F12) provides intimate contact between the flavoring (F18) and the cooked extrudate (E18) to form a flavored cooked extrudate (F10)

In embodiments, the flavoring machine (F12) provides intimate contact between the flavoring (F18) and the cooked multifunctional composition mixture (E18A) to form a flavored multifunctional composition mixture (F10A). In embodiments, the tumbler (F13) rotates and provides intimate contact between the flavoring (F18) and the cooked extrudate (E18) to form a flavored cooked extrudate (F10) or a flavored multifunctional composition mixture (F10A). The flavoring machine (F12) has a flavored cooked extrudate output (F19) for discharging the flavored cooked extrudate (F10) or flavored multifunctional composition mixture (F10A). In embodiments, the tumbler (F13) rotates at a revolution per minute (RPM) ranging from between: 3 RPM to 4 RPM; 4 RPM to 5 RPM; 6 RPM to 7 RPM; 7 RPM to 8 RPM; 8 RPM to 9 RPM; 9 RPM to 10 RPM; 10 RPM to 11 RPM; 11 RPM to 12 RPM; 13 RPM to 14 RPM; 14 RPM to 15 RPM; 15 RPM to 16 RPM; 16 RPM to 17 RPM; 17 RPM to 18 RPM; 18 RPM to 19 RPM; 19 RPM to 20 RPM.

In embodiments, the flavored multifunctional composition mixture (F10A) is a flavored cooked extrudate (F10). A conveyor (F20) is equipped to accept the flavored cooked extrudate (F10) from the flavored cooked extrudate output (F19). The conveyor (F20) may be mechanical, pneumatic, air operated, an elevating conveyor, conveyor belt, drag-chain conveyor, or any conceivable device to transport flavored multifunctional composition mixture (F10) away from the flavoring machine (F12). The conveyor (F20) may be equipped with a metal detector (F21). The metal detector (F21) may be an electronic instrument which detects the presence of metal within the flavored multifunctional composition mixture (F10A).

FIG. 14G:

FIG. 14G shows one non-limiting embodiment of a biocatalyst mixing module (14G) that is configured to mix insects, water, biocatalyst, and optionally acid to create an insect liquid biocatalyst mixture (G09).

FIG. 14G shows one non-limiting embodiment of a biocatalyst mixing module (14G) that includes a first water treatment unit (G10), a second water treatment unit (G11), and a third water treatment unit (G12), that provide a third contaminant depleted water (G13) to the interior (G14) of a mixing tank (G15). The mixing tank (G15) mixes a water supply (C16) with insects and biocatalyst. In embodiments, the insects introduced to the mixing tank (G15) may be ground insects or whole insects. In embodiments, the first water treatment unit (G10), a second water treatment unit (G11), and a third water treatment unit (G12) are optional. In embodiments, only one of the first water treatment unit (G10), second water treatment unit (G11), or third water treatment unit (G12) may be used. In embodiments, two of the first water treatment unit (G10), second water treatment unit (G11), or third water treatment unit (G12) may be used. In embodiments, a water supply (C16) is provided to the interior (G14) of the mixing tank (G15). In embodiments, the mixing tank (G15) as shown in FIG. 14G (of Volume 1) is the same vessel as the emulsion mixing tank (JLE) as shown in FIG. 17J' (of Volume 2).

In embodiments, the insects introduced to the mixing tank (G15) may be: (a) ground separated insects (1500) provided by the grinder (1250); (b) separated insects (334) from the separated insect conveyor (328); (c) insects (225) evacuated from the first feeding chamber (FC1) via the insect evacuation output (205); (d) insects (225) evacuated from the first feeding chamber (FC1) via the insect evacuation output (205) and feeding chamber exit conduit (302); and/or (e) insects removed from the first feeding chamber (FC1) via the conveyor output (249).

In embodiments, the insects introduced to the mixing tank (G15) may be have an insect bulk density ranging from between about 3.5 pounds per cubic foot to about 14.999 pounds per cubic foot or a ground insect bulk density ranging from between about 15 pounds per cubic foot to about 50 pounds per cubic foot.

The whole insects (G07) or ground insects (G08) introduced to the mixing tank (G15) may be a weighed. In embodiments, the whole insects (G07) introduced to the mixing tank (G15) may be have an insect bulk density ranging from between about 3.5 pounds per cubic foot to about 14.999 pounds per cubic foot. In embodiments, the ground insects (G08) have a ground insect bulk density ranging from between about 15 pounds per cubic foot to about 50 pounds per cubic foot.

The insect liquid biocatalyst mixture (G09) is transferred from the mixing tank (G15) to the exoskeleton separation module (14H) of FIG. 14H. In embodiments, the insect liquid biocatalyst mixture (G09) is transferred and pressurized using a pump (G18) from the mixing tank (G15) to the exoskeleton separation module (14H) of FIG. 14H. In embodiments, the insect liquid biocatalyst mixture (G09) is transferred and pressurized using a screw auger (G19) from the mixing tank (G15) to the exoskeleton separation module (14H) of FIG. 14H.

FIG. 14G depicts the first water treatment unit (G10) to include a cation, a second water treatment unit (G11) to include an anion, and a third water treatment unit (G13) to include a membrane. A first water pressure sensor (G20) is positioned on the water input conduit (G21) that is introduced to the first input (G22) to the first water treatment unit (G10). In embodiments, a filter (G23), activated carbon (G24), and/or an adsorbent (G25), are positioned on the water input conduit (G21) prior to introducing the water supply (G16) to the first water treatment unit (G10). The water supply (G16) may be considered a contaminant-laden water (G26) that includes positively charged ions, negatively charged ions, and undesirable compounds. The positively charged ions are comprised of one or more from the group consisting of calcium, magnesium, sodium, and iron. The negatively charged ions are comprised of one or more from the group consisting of iodine, chloride, and sulfate. The undesirable compounds are comprised of one or more from the group consisting of dissolved organic chemicals, viruses, bacteria, and particulates.

A first contaminant depleted water (G27) is discharged by the first water treatment unit (G10) by a first output (G28). The first contaminant depleted water (G27) may be a positively charged ion depleted water (G29). The first contaminant depleted water (G27) is then transferred to the second water treatment unit (G11) via a second input (G30). A second contaminant depleted water (G31) is discharged by the second water treatment unit (G11) by a second output (G32). The second contaminant depleted water (G31) may be a negatively charged ion depleted water (G33). The second contaminant depleted water (G31) is then transferred to the third water treatment unit (G12) via a third input (G34). A third contaminant depleted water (G13) is discharged by the third water treatment unit (G12) by a third output (G35). The third contaminant depleted water (G13) may be an undesirable compounds depleted water (G36). The third contaminant depleted water (G13) is then transferred to the interior (G14) of a mixing tank (G15) via a water supply conduit (G37) and water input (G38). In embodiments, a diptube (G38A) is provided to introduce water to beneath the liquid level of the contents within the interior (G14) of the mixing tank (G15).

Within the interior (G14) of a mixing tank (G15), the water is mixed with insects and biocatalyst. In embodiments, a cation (G39), an anion (G40), and a polishing unit (G41), are positioned on the water supply conduit (G37) in between the third water treatment unit (G12) and the water input (G38) of the mixing tank (G15). The polishing unit (G41) may be any type of conceivable device to improve the water quality such as an ultraviolet unit, ozone unit, microwave unit, filter, or the like.

In embodiments, water supply valve (G42) is positioned on the water supply conduit (G37) in between the third water treatment unit (G12) and the water input (G38) of the mixing tank (G15). The water supply valve (G42) is equipped with a controller (G43) that inputs or outputs a signal from a computer (COMP). In embodiments, the mixing tank (G15) is equipped with a high-level sensor (G44) and a low-level sensor (G45). The high-level sensor (G44) is used for detecting a high level and the low-level sensor (G45) is used for detecting a low level. The high-level sensor (G44) is configured to output a signal to the computer (COMP) when the high-level sensor (G44) is triggered by a high level of liquid within the mixing tank (G15). The low-level sensor (G45) is configured to output a signal to the computer (COMP) when the low-level sensor (G45) is triggered by a low level of liquid within the mixing tank (G15).

In embodiments, when the low-level sensor (G45) sends a signal to the computer (COMP), the water supply valve (G42) on the water supply conduit (G37) is opened and introduces water into the mixing tank (G15) until the high-level sensor (G44) is triggered thus sending a signal to the computer (COMP) to close the water supply valve (G42). This level control loop including the high-level sensor (G44) for detecting a high level and a low-level sensor (G45) for detecting a lower level may be coupled to the operation of the water supply valve (G42) for introducing a water supply (G16) through a first water treatment unit (G10), a second water treatment unit (G11), and a third water treatment unit (G12), to provide a third contaminant depleted water (G13) to the interior (G14) of a mixing tank (G15).

The mixing tank (GC15) may be placed on a load cell (G46) for measuring the mass of the tank. The mixing tank (G15) may be equipped with a mixer (G47) for mixing water with insects and biocatalyst. The insects and biocatalyst may be introduced to the interior (G14) of the mixing tank (G15) via an input (G51). The mixer (G47) may be of an auger or blade type that is equipped with a motor (G48). The mixing tank (G15) has an insect liquid biocatalyst mixture output (G49) that is connected to a transfer conduit (G50).

The transfer conduit (G50) is connected at one end to the insect liquid biocatalyst mixture output (G49) of the mixing tank (G15) and at another end to a supply pump (G18) or a screw auger (G19). The supply pump (G18) or a screw auger (G19) provides a pressurized insect liquid biocatalyst mixture (G09B) to the exoskeleton separation module (14H) of FIG. 14H.

In embodiments, a flow sensor (G51) and/or a flow totalizer (G52) may be installed on the water supply conduit (G37) to determine the mass or volume of water that is sent to the interior (G14) of the mixing tank (G15). In embodiments, the mixing tank (G15) is equipped with a heat exchanger (G53) to heat the mixture of water, biocatalyst, and insects. The heat exchanger (G53) may be electrically heated or provided with a heat transfer medium such as a source of steam or hot oil.

The mixing tank (G15) may have a heating jacket (G53J) to serve the purpose of the heat exchanger (G53). The mixing tank (G15) with a heating jacket (G53J) is a vessel that is designed for controlling the temperature of its contents, by using a heating jacket around the vessel through which a heat transfer medium (e.g.—steam) is circulated. The heating jacket (G53J) is a cavity external to the interior (G14) of the mixing tank (G15) that permits the uniform exchange of heat between the heat transfer medium circulating in it and the walls of the mixing tank (G15). FIG. 14G shows the heating jacket (G53J) installed over a portion of the mixing tank (G15) creating an interior (G53J-1) having an annular space within which a heat transfer medium flows.

The heating jacket (G53J) has a heat transfer medium inlet (G90) and a heat transfer medium outlet (G91). Steam (G92) is introduced to the heat transfer medium inlet (G90). Steam condensate (G93) is discharged from the heat transfer medium outlet (G91). Steam (G92) is introduced to the heat transfer medium inlet (G90) of the heating jacket (G53J) of the mixing tank (G15) via a steam inlet conduit (G94). The steam inlet conduit (G94) is connected to the heat transfer medium inlet (G90) and is configured to transfer steam to the interior (G53J-1) of the heating jacket (G53J).

In embodiments, a fifth steam supply (LDB) is provided to the heating jacket (G53J) and/or to the heat exchanger (G53) and is provided from FIG. 14L. In embodiments, the steam condensate (G93) that is discharged from the heat transfer medium outlet (G91) is transferred to the condensate tank (LAP) shown in FIG. 14L as a fifth condensate (LAU).

A steam supply valve (G95) is interposed on the steam inlet conduit (G94). The steam supply valve (G95) is equipped with a controller (G96) that inputs and outputs a signal (G97) to the computer (COMP). In embodiments, the steam supply valve (G95) is positioned to regulate the mass of heat transfer medium that leaves the heating jacket (G53J) via the discharged from the heat transfer medium outlet (G91).

In embodiments, a temperature sensor (G54) measures the temperature of the contents within the interior (G14) of the mixing tank (G15). The temperature sensor (G54) is configured to output a signal (G55) to the computer (COMP). A pre-determined setpoint for the mixing tank (G15) temperature sensor (G54) may be inputted to the computer (COMP). In response to the pre-determined setpoint, the computer (COMP) regulates the modulation of the steam supply valve (G95). The preferred modulation range of the steam supply valve (G95) ranges from 33% open to 66% open. In embodiments, the preferred modulation range of the steam supply valve (G95) ranges from: 5% open to 10% open; 10% open to 15% open; 15% open to 20% open; 20% open to 30% open; 30% open to 40% open; 40% open to 50% open; 50% open to 60% open; 60% open to 70% open.

In embodiments, the mixing tank (G15) has a plurality of baffles (G55A, G55B) that are positioned within the interior (G14). Each baffle (G55A, G55B) is configured to promote mixing and increase heat transfer and chemical reaction rate of the biocatalyst with the insects.

The pressure drop across the steam supply valve (G95) ranges from between: 1 pound per square inch (PSI) to 2 PSI; 2 pounds per square inch (PSI) to 5 PSI; 5 pounds per square inch (PSI) to 10 PSI; 10 pounds per square inch (PSI) to 20 PSI; 20 pounds per square inch (PSI) to 40 PSI; 40 pounds per square inch (PSI) to 60 PSI; 60 pounds per square inch (PSI) to 80 PSI; 80 pounds per square inch (PSI) to 100 PSI; 100 pounds per square inch (PSI) to 125 PSI; 125 pounds per square inch (PSI) to 150 PSI; 150 pounds per square inch (PSI) to 200 PSI.

The velocity of steam in the steam inlet conduit (G94) ranges from: 35 feet per second to 45 feet per second; 45 feet per second to 55 feet per second; 55 feet per second to 65 feet per second; 65 feet per second to 75 feet per second; 75 feet per second to 85 feet per second; 85 feet per second to 95 feet per second; 95 feet per second to 105 feet per second; 105 feet per second to 115 feet per second; 115 feet per second to 125 feet per second; 125 feet per second to 135 feet per second; 135 feet per second to 145 feet per second; 145 feet per second to 155 feet per second; 155 feet per second to 175 feet per second. The velocity of steam condensate discharged from the heat transfer medium outlet (G91) is less than 3 feet per second.

In embodiments, the heat transfer medium inlet (G90) is comprised of one or more from the group consisting of: a Class 150 flange, a Class 300 flange, sanitary clamp fitting, national pipe thread, or compression fitting. In embodiments, the heat transfer medium outlet (G91) is comprised of one or more from the group consisting of: a Class 150 flange, a Class 300 flange, sanitary clamp fitting, national pipe thread, or compression fitting. In embodiments, the mixing tank (G15) is comprised of stainless steel or carbon steel and may be ceramic or glass-lined. In embodiments, the heating jacket (G53J) is comprised of stainless steel or carbon steel and may be ceramic or glass-lined.

In embodiments, the temperature of the water, insect, and biocatalyst mixture within the interior (G14) of the mixing tank (G15) ranges from between: 50 degrees F. to 60 degrees F.; 60 degrees F. to 70 degrees F.; 70 degrees F. to 80 degrees F.; 80 degrees F. to 90 degrees F.; 90 degrees F. to 100 degrees F.; 100 degrees F. to 110 degrees F.; 110 degrees F. to 120 degrees F.; 120 degrees F. to 130 degrees F.; 130 degrees F. to 140 degrees F.; 140 degrees F. to 150 degrees F.; 150 degrees F. to 160 degrees F.; 160 degrees F. to 170 degrees F.; 170 degrees F. to 180 degrees F.; 180 degrees F. to 190 degrees F.; 190 degrees F. to 200 degrees F.; 200 degrees F. to 212 degrees F.

In embodiments, the water, insect, and biocatalyst mixture may mixed within the interior (G14) of the mixing tank (G15) ranges from between: 5 minutes to 10 minutes; 10 minutes to 20 minutes; 20 minutes to 30 minutes; 30 minutes to 40 minutes; 40 minutes to 50 minutes; 50 minutes to 1 hour; 1 hour to 1.5 hours; 1.5 hour to 2 hours; 2 hour to 3 hours; 3 hour to 4 hours; 4 hour to 5 hours; 5 hour to 6 hours; 6 hour to 12 hours; 12 hour to 18 hours; 18 hour to 24 hours; 1 day to 2 days; 2 days to 3 days; 3 days to 4 days; 4 days to 5 days; 5 days to 1 week.

In embodiments, the mass of water, biocatalyst, or insects within the mixing tank (G15) can be measured via the load cell (G46). In embodiments, water can be added to the mixing tank (G15) and the mass of water is measured, following by adding the insects and/or biocatalyst to the interior (G14) of the mixing tank (G15) to know the mass of the total mixture. The contents within the mixing tank (G15) can be mixed with the mixer and heated.

Whole Insect Distribution Module (14G1)

FIG. 14G displays a whole insect distribution module (14G1) including an insect tank (G55) that is configured to accept whole insects (G56). The whole insects (G56) may be: (a) separated insects (334) from the separated insect conveyor (328), (b) insects (225) evacuated from the first feeding chamber (FC1) via the insect evacuation output (205), (c) insects (225) evacuated from the first feeding chamber (FC1) via the insect evacuation output (205) and feeding chamber exit conduit (302), and/or, (d) insects removed from the first feeding chamber (FC1) via the conveyor output (249), (e) transported though interstate commerce via at least one vehicle having three or more axles and having an engine, (f) transported though interstate commerce via at least one vehicle having two axles and having an internal combustion engine or battery powered.

The insect tank (G55) has an interior (G57), an insect input (G58), an insect conveyor (G59), and an insect conveyor output (G60). The insect tank (G55) accepts whole insects (G56) to the interior (G57) and regulates and controls an engineered amount of whole insects (G56) downstream to be mixed in the mixing tank (G15). The insect conveyor (G59) has an integrated insect mass sensor (G61) that is configured to input and output a signal (G61A) to the computer (COMP). The insect conveyor motor (G62) has a controller (G63) that is configured to input and output a signal (G64) to the computer (COMP). The insect mass sensor (G61), insect conveyor (G59), and insect conveyor motor (G62) are coupled so as to permit the conveyance, distribution, or output of a precise flow of whole insects (G56) via a whole insect transfer line (G65).

Ground Insect Distribution Module (14G2)

FIG. 14G displays a ground insect distribution module (14G2) including an insect tank (G66) that is configured to accept ground insects (G67).

In embodiments, the ground insects (G67) may come from FIG. 14I and include the liquid-depleted insects (I50) that were filtered in the filter (I11). In embodiments, the ground insects (G67) may come from FIG. 14J and include the liquid-depleted insects (J10, J53) that were discharged from the evaporator (J11). In embodiments, the ground insects (G67) may come from FIG. 14K and include the third separated insects or fourth separated insects (KCX). In embodiments, the ground insects (G67) may come from FIG. 14K and include the third separated insects or fourth separated insects (KCX). In embodiments, the ground insects (G67) may come from FIG. 14K and include the small insect particulate portion (KCW) or the large insect particulate portion (KCY) that had undergone evaporation by spray drying.

The ground insects (G67) may be: (a) ground separated insects (1500) provided by the grinder (1250), or (b) insects purchased through interstate commerce, (c) transported though interstate commerce via at least one vehicle having three or more axles and having an internal combustion engine, (d) transported though interstate commerce via at least one vehicle having two axles and having an internal combustion engine or battery powered.

The insect tank (G66) has an interior (G68), an insect input (G69), an insect conveyor (G70), and an insect conveyor output (G71). The insect tank (G66) accepts ground insects (G67) to the interior (G68) and regulates and controls an engineered amount of ground insects (G67) downstream to be mixed in the mixing tank (G15). The insect conveyor (G70) has an integrated insect mass sensor (G72) that is configured to input and output a signal (G73) to the computer (COMP). The insect conveyor motor (G74) has a controller (G75) that is configured to input and output a signal (G76) to the computer (COMP). The insect mass sensor (G72), insect conveyor (G70), and insect conveyor motor (G74) are coupled so as to permit the conveyance, distribution, or output of a precise flow of ground insects (G67) via a ground insect transfer line (G77).

Biocatalyst Distribution Module (14G3)

FIG. 14G displays a biocatalyst mixing module (14G3) including a biocatalyst tank (G78) that is configured to accept at least one biocatalyst (G79). The biocatalyst (G79) may be comprised of one or more from the group consisting of an enzyme, casein protease, atreptogrisin A, flavorpro, peptidase, protease A, protease, *Aspergillus oryzae, Bacillus subtilis, Bacillus licheniformis, Aspergillus niger, Aspergillus melleus, Aspergilus oryzae*, papain, *Carica papaya*, bromelain, *Ananas comorus* stem, and yeast, and mixtures of two and three and four and more. In embodiments, mixing of the biocatalyst (G79) is optional.

In embodiments, the biocatalyst includes yeast. In embodiments, the yeast may be ale yeast, the "top-fermenting" type, *Saccharomyces cerevisiae*. In embodiments, the yeast may be lager yeast, the "bottom-fermenting" type, *Saccharomyces uvarum*, or *Saccharomyces carlsbergensis*. In embodiments, the yeast is liquid or powder. Yeasts are eukaryotic, single-celled microorganisms classified as members of the fungus kingdom.

In embodiments, the insects may be mixed with water, a biocatalyst, *cannabis*, and grain, barley, honey, and/or hops. In embodiments, the water, a biocatalyst, optionally *cannabis*, and at least one from the group consisting of grain, barley, honey, and hops may be fermented to produce ethyl alcohol. In embodiments, the water, a biocatalyst, optionally *cannabis*, and at least one from the group consisting of grain, barley, honey, and hops may be fermented to produce ethanol.

In embodiments, the water, a biocatalyst, optionally *cannabis*, and at least one from the group consisting of malt, grain, barley, honey, and hops may be fermented to produce a mixture of water and ethanol. Alcohol by volume (abbreviated as ABV, abv, or alc/vol) is a standard measure of how much ethanol is contained in a given volume of an alcoholic beverage (expressed as a volume percent). In embodiments, the mixture of water and ethanol has a range of alcohol by volume that is selected from one or more from the group consisting of 2.5 ABV to 3 ABV, 3 ABV to 3.5 ABV, 3.5 ABV to 4 ABV, 4 ABV to 4.5 ABV, 4.5 ABV to 5 ABV, 5 ABV to 5.5 ABV, 5.5 ABV to 6 ABV, 6 ABV to 6.5 ABV, 6.5 ABV to 7 ABV, 7 ABV to 7.5 ABV, 7.5 ABV to 8 ABV, 8 ABV to 8.5 ABV, 8.5 ABV to 9 ABV, 9 ABV to 9.5 ABV, 9.5 ABV to 10 ABV, 10 ABV to 10.5 ABV, 10.5 ABV to 11 ABV, 11 ABV to 11.5 ABV, 11.5 ABV to 12 ABV, and 12 ABV to 12.5 ABV.

In embodiments, the beverage has a serving size of 6 fluid ounces, 8 fluid ounces or 12 fluid ounces. In embodiments, the beverage has a serving size of 1 fluid ounce to 2 fluid ounces, 2 fluid ounces to 3 fluid ounces, 3 fluid ounces to 4 fluid ounces, 4 fluid ounces to 5 fluid ounces, 5 fluid ounces to 6 fluid ounces, 6 fluid ounces to 7 fluid ounces, 7 fluid ounces to 8 fluid ounces, 8 fluid ounces to 9 fluid ounces, 9 fluid ounces to 10 fluid ounces, 10 fluid ounces to 11 fluid ounces, 11 fluid ounces to 12 fluid ounces, 12 fluid ounces to 13 fluid ounces, 13 fluid ounces to 14 fluid ounces, 14 fluid ounces to 15 fluid ounces, 15 fluid ounces to 16 fluid ounces, 16 fluid ounces to 17 fluid ounces, 17 fluid ounces to 18 fluid ounces, 18 fluid ounces to 19 fluid ounces, 19 fluid ounces to 20 fluid ounces, 20 fluid ounces to 21 fluid ounces, 21 fluid ounces to 22 fluid ounces, 22 fluid ounces to 24 fluid ounces, 24 fluid ounces to 26 fluid ounces, 26 fluid ounces to 28 fluid ounces, 28 fluid ounces to 30 fluid ounces, 30 fluid ounces to 32 fluid ounces, 32 fluid ounces to 34 fluid ounces, 34 fluid ounces to 36 fluid ounces, 36 fluid ounces to 38 fluid ounces, or 38 fluid ounces to 40 fluid ounces.

In embodiments, each serving size of the beverage includes a cannabidiol content in milligrams per serving ranging from 0 milligrams to 0.5 milligrams, 0.5 milligrams to 1 milligrams, 1 milligrams to 1.5 milligrams, 1.5 milligrams to 2 milligrams, 2 milligrams to 2.5 milligrams, 2.5 milligrams to 3 milligrams, 3 milligrams to 3.5 milligrams, 3.5 milligrams to 4 milligrams, 4 milligrams to 4.5 milligrams, 4.5 milligrams to 5 milligrams, 5 milligrams to 5.5 milligrams, 5.5 milligrams t 6 milligrams, 6 milligrams to 6.5 milligrams, 6.5 milligrams to 7 milligrams, 7 milligrams to 7.5 milligrams, 7.5 milligrams to 8 milligrams, 8 milligrams to 8.5 milligrams, 8.5 milligrams to 9 milligrams, 9 milligrams to 9.5 milligrams, 9.5 milligrams to 10 milligrams, 10 milligrams to 11 milligrams, 11 milligrams to 12 milligrams, 12 milligrams to 13 milligrams, 13 milligrams to 14 milligrams, 14 milligrams to 15 milligrams, 15 milligrams to 16 milligrams, 16 milligrams to 17 milligrams, 17 milligrams to 18 milligrams, 18 milligrams to 19 milligrams, 19 milligrams to 20 milligrams, 20 milligrams to 25 milligrams, 25 milligrams to 30 milligrams, 30 milligrams to 35 milligrams, 35 milligrams to 40 milligrams, 40 milligrams to 45 milligrams, 45 milligrams to 50 milligrams, 50 milligrams to 60 milligrams, 60 milligrams to 70 milligrams, 70 milligrams to 80 milligrams, 80 milligrams to 90 milligrams, 90 milligrams to 100 milligrams, 100 milligrams to 125 milligrams, 125 milligrams to 150 milligrams, 150 milligrams to 175 milligrams, 175 milligrams to 200 milligrams, 200 milligrams to 250 milligrams, 250 milligrams to 300 milligrams, 300 milligrams to 350 milligrams, 350 milligrams to 400 milligrams, 400 milligrams to 450 milligrams, or 450 milligrams to 500 milligrams.

In embodiments, each serving size of the beverage includes a tetrahydrocannabinol content in milligrams per serving ranging from 0 milligrams to 0.5 milligrams, 0.5 milligrams to 1 milligrams, 1 milligrams to 1.5 milligrams, 1.5 milligrams to 2 milligrams, 2 milligrams to 2.5 milligrams, 2.5 milligrams to 3 milligrams, 3 milligrams to 3.5 milligrams, 3.5 milligrams to 4 milligrams, 4 milligrams to 4.5 milligrams, 4.5 milligrams to 5 milligrams, 5 milligrams to 5.5 milligrams, 5.5 milligrams t 6 milligrams, 6 milligrams to 6.5 milligrams, 6.5 milligrams to 7 milligrams, 7 milligrams to 7.5 milligrams, 7.5 milligrams to 8 milligrams, 8 milligrams to 8.5 milligrams, 8.5 milligrams to 9 milligrams, 9 milligrams to 9.5 milligrams, 9.5 milligrams to 10 milligrams, 10 milligrams to 11 milligrams, 11 milligrams to 12 milligrams, 12 milligrams to 13 milligrams, 13 milligrams to 14 milligrams, 14 milligrams to 15 milligrams, 15 milligrams to 16 milligrams, 16 milligrams to 17 milligrams, 17 milligrams to 18 milligrams, 18 milligrams to 19 milligrams, 19 milligrams to 20 milligrams, 20 milligrams to 25 milligrams, 25 milligrams to 30 milligrams, 30 milligrams to 35 milligrams, 35 milligrams to 40 milligrams, 40 milligrams to 45 milligrams, 45 milligrams to 50 milligrams, 50 milligrams to 60 milligrams, 60 milligrams to 70 milligrams, 70 milligrams to 80 milligrams, 80 milligrams to 90 milligrams, 90 milligrams to 100 milligrams, 100 milligrams to 125 milligrams, 125 milligrams to 150 milligrams, 150 milligrams to 175 milligrams, 175 milligrams to 200 milligrams, 200 milligrams to 250 milligrams, 250 milligrams to 300 milligrams, 300 milligrams to 350 milligrams, 350 milligrams to 400 milligrams, 400 milligrams to 450 milligrams, or 450 milligrams to 500 milligrams.

In embodiments, the beverage has zero calories per serving size. In embodiments, the beverage has a calories per serving ranging from 0 to 1, 1 to 2, 2 to 3, 3 to 4, 4 to 5, 5 to 6, 6 to 7, 7 to 8, 8 to 9, 9 to 10 to 15, 15 to 20, 20 to 25, 25 to 30, 30 to 35, 35 to 40, 40 to 45, 45 to 50, 50 to 55, 55 to 60, 60 to 65, 65 to 70, 70 to 75, 75 to 80, 80 to 85, 85 to 90, 90 to 95, 95 to 100, 100 to 110, 110 to 120, 120 to 130, 130 to 140, 140 to 150, 150 to 160, 160 to 170, 170 to 180, 180 to 190, 190 to 200, 200 to 210, 210 to 220, 220 to 230, 230 to 240, 240 to 250, 250 to 260, 260 to 270, 270 to 280, 280 to 290, 290 to 300, or 300 to 310.

In embodiments, the beverage has a sodium content (in milligrams per serving) ranging from 0 to 1, 1 to 2, 2 to 3, 3 to 4, 4 to 5, 5 to 6, 6 to 7, 7 to 8, 8 to 9, 9 to 10, 10 to 11, 11 to 12, 12 to 13, 13 to 14, 14 to 15, 15 to 16, 16 to 17, 17 to 18, 18 to 19, 19 to 20, 20 to 25, 25 to 30, 30 to 35, 35 to 40, 40 to 45, 45 to 50, 50 to 55, 55 to 60, 60 to 65, 65 to 70, 70 to 75, 75 to 80, 80 to 85, 85 to 90, 90 to 95, 95 to 100.

In embodiments, the beverage has a carbohydrate content (in grams per serving) ranging from 0 to 1, 1 to 2, 2 to 3, 3 to 4, 4 to 5, 5 to 6, 6 to 7, 7 to 8, 8 to 9, 9 to 10, 10 to 11, 11 to 12, 12 to 13, 13 to 14, 14 to 15, 15 to 16, 16 to 17, 17 to 18, 18 to 19, 19 to 20, 20 to 25, 25 to 30, 30 to 35, 35 to 40, 40 to 45, 45 to 50, 50 to 55, 55 to 60, 60 to 65, 65 to 70, 70 to 75, 75 to 80, 80 to 85, 85 to 90, 90 to 95, 95 to 100.

In embodiments, the beverage includes aspartame, sodium, sodium chloride, sucrose, sugar, dextrose, citric acid, monopotassium phosphate, and brominated vegetable oil (as a stabilizer), magnesium chloride, calcium chloride, niacinamide (vitamin B3), vitamin pyridoxine hydrochloride (B6), cyanocobalamin (vitamin B12).

In embodiments, the beverage includes a zero-calorie sweetener. In embodiments, the beverage includes low-calorie sweetener. In embodiments, the beverage includes an artificial sweetener. In embodiments, the beverage includes honey, sugar, aspartame, acesulfame potassium, saccharin, sucralose, neotame, erythritol, *stevia, stevia* leaf extract. In embodiments, the beverage includes a sugar alcohol and/or a polyol. In embodiments, the beverage includes electrolytes including sodium, potassium, magnesium, calcium. In embodiments, the beverage includes fruit juice concentrate, citric acid, white tea extract, malic acid, beta carotene, ascorbic acid (vitamin C), sodium citrate.

In embodiments, the beverage includes a coloring agent that is configured to color the beverage a color that includes one or more colors selected from the group consisting of: light green (144C), yellow (001A) or yellow green (001A), dark green (144A) with shades of yellow (001A), yellow orange (011A), orange (024A), orange red (033B), orange pink (027A), red (033A), dark purple red (046A), light red pink (039C), red pink (043C), dark pink red (045D), purple red (054A), light blue pink (055C), purple (058A), purple red (059D), blue pink (062A), light blue violet (069C), violet blue (089A), violet (075A), dark violet (079A), blue violet (083D), blue (100A), dark blue (103A), light blue (104D), light green blue (110C), green blue (111A), grey blue (115C), green blue (125C), white (155A), orange brown (169A), brown (172A), brown purple (178A), orange pink (179D) (The Royal Horticultural Society Colour Chart, 1995 Ed.).

In embodiments, the water, a biocatalyst, optionally *cannabis*, and at least one from the group consisting of malt, grain, barley, honey, and hops may be fermented at a temperature that ranges from one or more from the group consisting of 50 degrees Fahrenheit to 52 degrees Fahrenheit, 52 degrees Fahrenheit to 54 degrees Fahrenheit, 54 degrees Fahrenheit to 56 degrees Fahrenheit, 56 degrees Fahrenheit to 58 degrees Fahrenheit, 58 degrees Fahrenheit to 60 degrees Fahrenheit, 60 degrees Fahrenheit to 62 degrees Fahrenheit, 62 degrees Fahrenheit to 64 degrees Fahrenheit, 64 degrees Fahrenheit to 66 degrees Fahrenheit, 66 degrees Fahrenheit to 68 degrees Fahrenheit, 68 degrees Fahrenheit to 70 degrees Fahrenheit, 70 degrees Fahrenheit to 72 degrees Fahrenheit, 72 degrees Fahrenheit to 74 degrees Fahrenheit, 74 degrees Fahrenheit to 76 degrees Fahrenheit, 76 degrees Fahrenheit to 78 degrees Fahrenheit, 78 degrees Fahrenheit to 80 degrees Fahrenheit, 80 degrees Fahrenheit to 82 degrees Fahrenheit, 82 degrees Fahrenheit to 84 degrees Fahrenheit, 84 degrees Fahrenheit to 86 degrees Fahrenheit, 86 degrees Fahrenheit to 88 degrees Fahrenheit, 88 degrees Fahrenheit to 90 degrees Fahrenheit, 90 degrees Fahrenheit to 92 degrees Fahrenheit, and 92 degrees Fahrenheit to 94 degrees Fahrenheit.

In embodiments, the yeast within the mixture of water, yeast, optionally *cannabis*, and at least one or more from the group consisting of malt, grain, barley, honey, and hops has a range of attenuation that is selected from one or more from the group consisting of 50 percent to 52 percent, 52 percent to 54 percent, 54 percent to 56 percent, 56 percent to 58 percent, 58 percent to 60 percent, 60 percent to 62 percent, 62 percent to 64 percent, 64 percent to 66 percent, 66 percent to 68 percent, 68 percent to 70 percent, 70 percent to 72 percent, 72 percent to 74 percent, 74 percent to 76 percent, 76 percent to 78 percent, 78 percent to 80 percent, 80 percent to 82 percent, 82 percent to 84 percent, 84 percent to 86 percent, 86 percent to 88 percent, 88 percent to 90 percent, 90 percent to 92 percent, and 92 percent to 94 percent. The term attenuation is a percentage that is used to describe the percent of sugar within the malt, grain, barley, honey, or hops that is converted by the yeast into ethanol and carbon dioxide.

The biocatalyst tank (G78) has an interior (G80), a biocatalyst input (G81), a biocatalyst conveyor (G82), and a biocatalyst conveyor output (G83). The biocatalyst tank (G78) accepts biocatalyst (G79) to the interior (G80) and regulates and controls an engineered amount of biocatalyst (G79) downstream to be mixed in the mixing tank (G15). The biocatalyst conveyor (G82) has an integrated biocatalyst mass sensor (G84) that is configured to input and output a signal (G85) to the computer (COMP). The biocatalyst conveyor motor (G86) has a controller (G87) that is configured to input and output a signal (G88) to the computer (COMP). The biocatalyst mass sensor (G84), biocatalyst conveyor (G82), and biocatalyst conveyor motor (G86) are coupled so as to permit the conveyance, distribution, or output of a precise flow of biocatalyst (G79) via a biocatalyst transfer line (G89). In embodiments, the biocatalyst transfer line (G89) has a diameter that ranges from: 0.5 inches to 0.75 inches, 0.75 inches to 1 inch, 1 inch to 1.5 inches, 2 inches to 3 inches, 3 inches to 4 inches.

Acid Distribution Module (14G3')

FIG. 14G displays an acid mixing module (14G3') including an acid tank (G78') that is configured to accept at least one acid (G79'). The acid (G79') may be comprised of one or more from the group consisting of an acid, abscic acid, acetic acid, ascorbic acid, benzoic acid, citric acid, formic acid, fumaric acid, hydrochloric acid, lactic acid, malic acid, nitric acid, organic acids, phosphoric acid, potassium hydroxide, propionic acid, salicylic acid, sulfamic acid, sulfuric acid, and tartaric acid.

In embodiments, whole insects (G56) and/or ground insects (G67) have a pH that is greater than 7. In embodiments, whole insects (G56) and/or ground insects (G67) have a pH that is basic and ranges from greater than 7 to less than 8.75. In embodiments, whole insects (G56) and/or ground insects (G67) added to the interior (G14) of the mixing tank (G15) is required to lower the pH of the water, insect, biocatalyst mixture to a pH that is sufficient for the biocatalyst to digest or hydrolyze the insects. In embodiments, addition of an acid (G79') to the interior (G14) of the mixing tank (G15) is required to maintain the liquid mixture of biocatalyst, insects, and water within the mixing tank (G15) to be at a desired range from within 6.25 to 7.5.

The acid tank (G78') has an interior (G80'), an acid input (G81'), an acid conveyor (G82'), and an acid conveyor output (G83'). The acid tank (G78') accepts acid (G79') to the interior (G80') and regulates and controls an engineered amount of acid (G79') downstream to be mixed in the mixing tank (G15).

The acid conveyor (G82') has an integrated acid mass sensor (G84') that is configured to input and output a signal (G85') to the computer (COMP). The acid conveyor motor (G86') has a controller (G87') that is configured to input and output a signal (G88') to the computer (COMP). The acid mass sensor (G84'), acid conveyor (G82'), and acid conveyor motor (G86') are coupled so as to permit the conveyance, distribution, or output of a precise flow of acid (G79') via an acid transfer line (G89'). In embodiments, the acid transfer line (G89') has a diameter that ranges from: 0.5 inches to 0.75 inches, 0.75 inches to 1 inch, 1 inch to 1.5 inches, 2 inches to 3 inches, 3 inches to 4 inches.

In embodiments, the mixing tank (G15) is equipped with a pH sensor (PHG) that is configured to output a signal (PHG') to the computer (COMP). In embodiments, the pH sensor (PHG) is used in a control loop with the acid mass sensor (G84'), acid conveyor (G82'), and acid conveyor motor (G86') to permit output of a precise flow of acid (G79') to the interior (G14) of the mixing tank (G15) to maintain a predetermined pH within the mixing tank (G15).

FIG. 14G shows the whole insects (G56), ground insects (G67), biocatalyst (G79), and acid (G79') introduced to the interior (G14) of the mixing tank (G15) via an input (G100). It is not required that the whole insects (G56), ground insects (G67), biocatalyst (G79), and acid (G79') are combined into a combined stream (G101) for input (G100) to the interior (G14) of the mixing tank (G15). It is apparent to those skilled in the art to which it pertains that each whole insects (G56), ground insects (G67), biocatalyst (G79), and acid (G79') can have their own input to the interior (G14) of the mixing tank (G15) as well.

In embodiments, another alternate liquid (G102) may be added to the interior (G14) of the mixing tank (G15) to replace or be mixed with the source of water (01). In embodiments, the alternate liquid (G102) are comprised of one or more from the group consisting of alcohol, diglycerides, esters, ethanol, butanol, n-butanol, sec-butanol, isobutanol, tert-butanol, ethyl acetate, glycerin, glycerol, hexane, hydrocarbon, insect lipids, isopropyl alcohol, methanol, Monoglycerides, oil, and solvent.

In embodiments, at least a portion of the first contaminant depleted water (G27), second contaminant depleted water (G31), or third contaminant depleted water (G13) may be introduced to the start-up/shut-down liquid tank (KEA) for use as a source of start-up/shut-down water (KEB) as indicated on FIG. 14K. In embodiments, at least a portion of the first contaminant depleted water (G27), second contaminant depleted water (G31), or third contaminant depleted water (G13) may be introduced to start-up and/or shut-down the rotary atomizer (KAU) of FIG. 14K and used as start-up/shut-down water (KEB)

FIG. 14H:

FIG. 14H shows one non-limiting embodiment of an exoskeleton separation module (14H) that is configured to remove the exoskeleton contained within the insect liquid biocatalyst mixture (G09).

FIG. 14H shows the exoskeleton separation module (14H) configured to remove exoskeleton from insects that are contained within the insect liquid biocatalyst mixture (G09). In embodiments, where the biocatalyst (G79) within the biocatalyst mixing module (14G) is optional, the exoskeleton separation module (14H) is configured to remove exoskeleton from insects that are contained within an insect and liquid mixture (G09A) as depicted in FIG. 14G. In embodiments, exoskeleton is chitin. In embodiments, exoskeleton is a long-chain polymer of an N-acetylglucosamine, a derivative of glucose. In embodiments, the exoskeleton is provided to the insects to eat within the insect feeding chamber (FC). In embodiments, the exoskeleton removed in the exoskeleton separation module (14H) is provided to the polymer distribution module (1D) within the enhanced feedstock mixing module (1000) as shown in FIG. 2.

The insect liquid biocatalyst mixture (G09) or an insect and liquid mixture (G09A) is transferred from the mixing tank (G15) to the exoskeleton separation module (14H) of FIG. 14H via a transfer conduit (G50). FIG. 14H displays the exoskeleton separation module (14H) including an exoskeleton separator (H10). In embodiments, the exoskeleton separator (H10) is a filter (H11) having at least one side wall (H65). In embodiments, the filter (H11) is cylindrical. In embodiments, the filter (H11) is a candle filter (H12) that has at least one filter element (H13) contained within its interior (H64). In embodiments, the filter (H11) has a top (H14) and a bottom (H15). FIG. 14H shows a separator input (H16) positioned on the side wall (H65) of the exoskeleton separator (H10). The separator input (H16) is configured to introduce an exoskeleton-laden insect mixture (H17) to the interior (H64) of the filter (H11). In embodiments, the insect liquid biocatalyst mixture (G09) or an insect and liquid mixture (G09A) may be considered an exoskeleton-laden insect mixture (H17).

In embodiments, the biocatalyst (G79) and acid (G79') within the mixing tank (G15) hydrolyzes chitosan. In embodiments, the biocatalyst (G79) and acid (G79') hydrolyze the chitosan within the mixing tank (G15). In embodiments, the biocatalyst (G79) and acid (G79') hydrolyze deacetylated insects (1570") within the mixing tank (G15). In embodiments, the biocatalyst (G79) and acid (G79') hydrolyze the biopolymer (1570') within the mixing tank (G15).

In embodiments, introducing biocatalyst (G79), acid (G79'), and deacetylated insects (1570") to the mixing tank (G15) hydrolyzes the deacetylated insects (1570") to produce an oligosaccharide (G09'). In embodiments, introducing biocatalyst (G79), acid (G79'), and biopolymer (1570') to the mixing tank (G15) hydrolyzes the biopolymer (1570') to produce a hydrolyzed-biopolymer (G09") containing at least an oligosaccharide (G09'). In embodiments, introducing the biocatalyst (G79), acid (G79'), and insects (G07), that include deacetylated insects (1570"), to the mixing tank (G15) hydrolyzes the deacetylated insects (1570") to produce an oligosaccharide (G09'). In embodiments, introducing the biocatalyst (G79), acid (G79'), and insects (G07) that include deacetylated insects (1570") to the mixing tank (G15) hydrolyzes the deacetylated insects (1570") to produce a hydrolyzed-biopolymer (G09"). In embodiments, the insect liquid biocatalyst mixture (G09) includes an oligosaccharide (G09'). In embodiments, the insect liquid biocatalyst mixture (G09) includes a hydrolyzed-biopolymer (G09").

A supply valve (H61) equipped with a controller (H62) and configured to input and output a signal (H63) to the computer (COMP) is positioned on the transfer conduit (G50) in between the mixing tank (G15) of FIG. 14G and the separator input (H16) positioned on the side wall (H65) of the exoskeleton separator (H10).

The filter (H11) has a first output (H18) positioned on the top (H14). The first output (H18) is configured to discharge an exoskeleton-depleted insect liquid mixture (H19) via an exoskeleton-depleted mixture conduit (H20). A discharge valve (H21) equipped with a controller (H22) and configured to input and output a signal (H23) to the computer (COMP) is positioned on the exoskeleton-depleted mixture conduit (H20). The filter (H11) is configured to remove exoskeleton (H46) from either the insect liquid biocatalyst mixture (G09) or the insect and liquid mixture (G09A) to form an exoskeleton-depleted insect liquid mixture (H19). The exoskeleton-depleted insect liquid mixture (H19) has a reduced amount of exoskeleton (H46) relative to the insect liquid biocatalyst mixture (G09) or an insect and liquid mixture (G09A).

In embodiments, a flow sensor (H24) and a secondary filter (H25) are both installed on the exoskeleton-depleted mixture conduit (H20). The flow sensor (H24) can be an electronic instrument, but a manual paddle-wheel type flow sensor or a totalizer are preferred. Alternately, the flow sensor (H24) may be of a rotameter, variable-area flow meter, a bullseye type flow sensor, or a sight-glass type sensor and configured to allow one to visually observe the clarity, and lack of exoskeleton solids within the exoskeleton-depleted insect liquid mixture (H19). The secondary filter (H25) is used as an emergency filter to prevent contamination of the downstream exoskeleton-depleted insect liquid mixture tank (H26). The secondary filter (H25) is preferably installed to mitigate any risk of contamination downstream in the event that the filter element (H13) becomes ruptured and solid exoskeleton particles are transferred via the exoskeleton-depleted mixture conduit (H20) and into the interior (H27) of the exoskeleton-depleted insect liquid mixture tank (H26).

An exoskeleton-depleted insect liquid mixture tank (H26) is connected to the exoskeleton-depleted mixture conduit (H20) and configured to receive the exoskeleton-depleted insect liquid mixture (H19) from the exoskeleton separator (H10). The exoskeleton-depleted mixture conduit (H20) is connected at one end to the first output (H18) of the exoskeleton separator (H10) and at another end to the input (H28) of the exoskeleton-depleted insect liquid mixture tank (H26).

The exoskeleton-depleted insect liquid mixture tank (H26) has an input (H28) through which an exoskeleton-depleted insect liquid mixture (H19) is received to the interior (H27). A diptube (H29) may be installed on the input (H28) of the exoskeleton-depleted insect liquid mixture tank (H26) to introduce the exoskeleton-depleted insect liquid mixture (H19) to the interior (H27) beneath the liquid level. An upper level sensor (H30) and lower level sensor (H31) are installed on the exoskeleton-depleted insect liquid mixture tank (H26). A mixer (H32) with a motor (H33) may also be installed on the exoskeleton-depleted insect liquid mixture tank (H26) to provide agitation of the liquid contents within the interior (H27). A heat exchanger (H34) may be installed to heat a portion of the exoskeleton-depleted insect liquid mixture (H19) within the exoskeleton-depleted insect liquid mixture tank (H26). A temperature sensor (H35) may be installed on the exoskeleton-depleted insect liquid mixture tank (H26). A mass sensor (H36) may be installed on the exoskeleton-depleted insect liquid mixture tank (H26). In embodiments, a sixth steam supply (LDF) is made available to the heat exchanger (H34) to heat the liquid slurry within the interior (H27) of the exoskeleton-depleted insect liquid mixture tank (H26). In embodiments, the heat exchanger (H34) discharges a sixth condensate (LAV) to the condensate tank (LAP) that is shown on FIG. 14L.

The exoskeleton-depleted insect liquid mixture tank (H26) has an output (H37) that is configured to discharge an exoskeleton-depleted insect liquid mixture (H39) from the interior (H27). An exoskeleton-depleted insect liquid mixture conduit (H38) is connected to the output (H37) and configured to transfer exoskeleton-depleted insect liquid mixture (H39) away from the interior (H27) and towards the liquid separation module (LSM) shown in FIGS. 14i and 14J.

A pump (H40) is interposed on the exoskeleton-depleted insect liquid mixture conduit (H38) and configured to pressurize the exoskeleton-depleted insect liquid mixture (H39) to form a pressurized exoskeleton-depleted insect liquid mixture (H41). A pressure sensor (H42) is installed on the exoskeleton-depleted insect liquid mixture conduit (H38). In embodiments, the pump (H40) is configured to pressurize the exoskeleton-depleted insect liquid mixture (H39) to a pressure that ranges from between 10 pounds per square inch (PSI) to 20 PSI; 20 PSI to 30 PSI; 30 PSI to 40 PSI; 40 PSI to 50 PSI; 50 PSI to 60 PSI; 60 PSI to 70 PSI; 70 PSI to 80 PSI; 80 PSI to 90 PSI; 90 PSI to 100 PSI; 100 PSI to 125 PSI; 125 PSI to 150 PSI; 150 PSI to 200 PSI; 200 PSI to 300 PSI; 300 PSI to 500 PSI.

A recirculation conduit (H43) may be positioned on the exoskeleton-depleted insect liquid mixture conduit (H38) and configured to transport a portion of the pressurized exoskeleton-depleted insect liquid mixture (H41) back to the interior (H27) of the exoskeleton-depleted insect liquid mixture tank (H26). A recirculation filter (H44) may be positioned on the recirculation conduit (H43) to remove any particulates from the pressurized exoskeleton-depleted insect liquid mixture (H41) before being sent back to the interior (H27) of the exoskeleton-depleted insect liquid mixture tank (H26).

The filter (H11) has a second output (H45) positioned on the bottom (H15). Exoskeleton (H46) may be separated from the insect liquid biocatalyst mixture (G09) or an insect and liquid mixture (G09A). A separated exoskeleton transfer conduit (H47) is connected to the second output (H45) positioned on the bottom (H15) of the filter (H11). An exoskeleton conveyor (H48) is equipped to receive exoskeleton (H46) from the separated exoskeleton transfer conduit (H47).

An exoskeleton drying gas (H49) may be applied to a portion of the exoskeleton (H46) to remove liquid therefrom and form dehydrated exoskeleton (H50). In embodiments, the exoskeleton drying gas (H49) is heated to a temperature ranging from between 80 degrees F. to 90 degrees F.; 90 degrees F. to 100 degrees F.; 100 degrees F. to 110 degrees F.; 110 degrees F. to 120 degrees F.; 120 degrees F. to 140 degrees F.; 140 degrees F. to 160 degrees F.; 160 degrees F. to 180 degrees F.; 180 degrees F. to 200 degrees F.; 200 degrees F. to 250 degrees F.; 250 degrees F. to 300 degrees F.; 300 degrees F. to 400 degrees F.

An exoskeleton discharge valve (H51) equipped with a controller (H52) and configured to input and output a signal (H53) to the computer (COMP) is installed on the separated exoskeleton transfer conduit (H47).

A backflush fluid (H54) may be provided to the filter (H11) to regenerate the filter element (H13). FIG. 14H shows the backflush fluid (H54) entering the exoskeleton-depleted mixture conduit (H20) and then entering the interior (H64) of the filter (H11) via the first output (H18). In embodiments, the backflush fluid (H54) is a liquid. In embodiments, the backflush fluid (H54) is a gas.

A backflush fluid transfer conduit (H55) is connected to the exoskeleton-depleted mixture conduit (H20) via a connection (H70) in between the discharge valve (H21) and the first output (H18). A backflush fluid supply valve (H56) equipped with a controller (H57) and configured to input and output a signal (H58) to the computer (COMP) is positioned on the backflush fluid transfer conduit (H55). In embodiments, a backflush fluid pressure regulating valve (H59) with a backflush pressure sensor (H60) is positioned upstream of the backflush fluid supply valve (H56). In embodiments, the backflush fluid pressure regulating valve (H59) may be adjusted to a pressure that is less than the rupture pressure of that of the filter element (H13). It is preferred to counter currently backflush the filter element (H13) by setting the pressure of the backflush fluid pressure regulating valve (H59) to a pressure of 0.25 PSI to 0.5 PSI; 0.5 PSI to 1.5 PSI; 1.5 PSI to 3 PSI; 3 PSI to 6 PSI; 6 PSI to 9 PSI; 9 PSI to 15 PSI.

The best mode of operation for realizing a continuous filtrate stream depleted of exoskeleton and encompasses operating the filtration system in a manner which allows for periodic back flushing of the filter element cloth surface in-situ by providing a counter-current flow of backflush fluid to the filter element. The backwashing dislodges any accumulated exoskeleton, in the form of a filter cake, allowing it to sink to the bottom of the filter for removal of the system as a thick, paste-like, filter cake substance.

It is preferred to utilize differential pressure across a filter bundle as the main variable to determine when to undergo a back-flushing cycle, as opposed to using manual predetermined periodic time duration intervals, or using the reduction in flow through the filter bundles as the variable dictating when to commence filter back flushing, (synonymously termed 'filter cleaning', or 'filter backwashing', 'in-situ filter cleaning', or 'filter surface in-situ regeneration'). Filter element differential pressure between 0.25 and 15 PSI is commensurate with preferable cake thickness of 20 to 35 millimeters. In contrast, using manual predetermined periodic time duration intervals as the sole mechanism to determine when to commence filter cleaning, often results in operational impairment, in that 'cake bridging' more readily occurs. 'Cake bridging' may be described as a large mass of agglomerated exoskeleton suspended solids filling the spaces between the filter elements and thus posing a challenge to regenerate in-situ, frequently requiring process interruption for physical cleaning and removal of the heavy, gelatinous exoskeleton filter cake.

In-situ filter cleaning may be accomplished by reversing the flow of liquid or gas through the filter element thereby dislodging exoskeleton filter cake from the cloth surface thus allowing it to sink to the bottom of the interior of the filter. This affords operations the luxury of minimizing losses of valuable solvent while draining the filter cake from the system.

Filter Operating Procedure

Herein is described the preferred operating procedure for continuous filtration of exoskeleton. Filtration [step 950] cooperates with the cyclic-batch filter in-situ cleaning steps of: filter element [step 952]; filter backflush [step 954]; filter cake sedimentation [step 956]; filter cake discharge start [step 958]; filter cake discharge end [step 960]; and filtration restart preparation [step 962].

In step 950, (filtration), filtration proceeds and the filter pressure drop is monitored. As a filtration cycle progresses, solid exoskeleton particles are deposited onto the surface of the filter element and adhere to its surface until a nominal target differential pressure drop between around 0.25 to 15 PSI is attained, which is proportionate to a predetermined thickness of 20 to 35 millimeters. If the filter pressure drop is lower than the nominal target differential pressure drop, the filtering cycle continues until the nominal target differential pressure drop is reached. When a filter has reached its nominal target differential pressure drop, a filter cleaning cycle will commence, which begins with step 952 (filter bundle isolation). The sequential steps encompassing filtration and filter cleaning can be further illuminated by using FIG. 14H, which visually indicate some of the valve sequencing involved, as indicated by open and closed valve positions, illustrated by 'non-darkened-in valves' and 'darkened-in valves', respectively, wherein: supply valve (H61) is open; discharge valve (H21) is open; backflush fluid supply valve (H56) is closed; exoskeleton discharge valve (H51) is closed.

When a nominal target pressure drop across a filter is attained, the exoskeleton filter cake material must be dislodged from the filter element, and thus step 952 (filter isolation) proceeds, which involves isolating the filter by closing the supply valve (H61) and discharge valve.

Once both the supply valve (H61) and discharge valve are closed, to isolate the filter, step 954 may proceed. Step 954, (filtrate backflush), involves transferring a backflush fluid (liquid or gas) to backflush the filter. In embodiments, a typical backflush, in step 954, requires that the backflush fluid supply valve (H56) need be left open for a duration between: 5 seconds to 10 seconds; 10 seconds to 30 seconds; 30 seconds to 1 minute; 1 minute to 5 minutes; 5 minutes to 15 minutes; 15 minutes to 30 minutes; 30 minutes to 60 minutes; 60 minutes to 90 minutes.

After the backflush fluid (H54) has been introduced to the filter, and once the backflush fluid supply valve (H56) has been returned to a closed position, step 956 may commence. Step 956 (exoskeleton filter cake sedimentation) entails allowing the dislodged exoskeleton filter cake solids to sink to the bottom of the filter.

Step 958 (exoskeleton filter cake discharge start) involves opening the exoskeleton discharge valve (H51) to allow transference of an agglomerated exoskeleton particulate filter cake material from the system. The backflush fluid (H54) may be liquid or gas or a combination of both during Step 958. In embodiments, a gas may be used to dry the exoskeleton and then dislodge the dried exoskeleton from the surface of the filter element (H13).

Step 960 (filter cake discharge end) entails closing the exoskeleton discharge valve (H51) since exoskeleton have been discharged from the system. After step 960 has transpired, step 962 (filtration restart preparation) may commence which entails opening the supply valve (H61) and discharge valve (H21) to again commence filtration on the regenerated filter bundle, thus allowing step 950 to commence again, then allowing the filtration and regeneration cycle to repeat itself.

FIG. 14I:

FIG. 14I shows one non-limiting embodiment of a liquid separation module (LSM) that is configured to remove liquid from the exoskeleton-depleted insect liquid mixture (H39) to provide an insect-depleted liquid mixture (119) and insects (146).

FIG. 14I shows the liquid separation module (LSM) that is configured to remove liquid from the exoskeleton-depleted insect liquid mixture (H39) or the pressurized exoskeleton-depleted insect liquid mixture (H41). FIG. 14I shows the liquid separation module (LSM) configured to remove liquid from the exoskeleton-depleted insect liquid mixture (H39) that is provided by the exoskeleton separation module (14H). FIG. 14I shows the liquid separation module (LSM) configured to remove liquid from the pressurized exoskeleton-depleted insect liquid mixture (H41) that is provided by the exoskeleton separation module (14H). FIG. 14I shows one non-limiting embodiment of a liquid separation module (LSM) that includes a filter (I11). FIG. 14J shows one non-limiting embodiment of a liquid separation module (LSM) that includes an evaporator (J11). FIG. 14I shows an exoskeleton-depleted insect liquid mixture (H39) or a pressurized exoskeleton-depleted insect liquid mixture (H41) transferred to the liquid separation module (LSM) from the exoskeleton separation module (14H) shown in FIG. 14H. The exoskeleton-depleted insect liquid mixture (H39) or a pressurized exoskeleton-depleted insect liquid mixture (H41) is transferred from the exoskeleton-depleted insect liquid mixture tank (H26) of FIG. 14H via the exoskeleton-depleted insect liquid mixture conduit (H38).

FIG. 14I displays the liquid separation module (LSM) including a liquid separator (I10). In embodiments, the liquid separator (I10) is a filter (I11) or a membrane (I11A) having at least one side wall (165). In embodiments, the filter (I11) is cylindrical. In embodiments, the filter (I11) is a candle filter (I12) that has at least one filter element (113) contained within its interior (164). In embodiments, the filter (I11) has a top (114) and a bottom (115). FIG. 14I shows a separator input (116) positioned on the side wall (165) of the liquid separator (I10). The separator input (116) is configured to introduce an exoskeleton-depleted insect liquid mixture (H39) or a pressurized exoskeleton-depleted insect liquid mixture (H41) to the interior (164) of the filter (I11). In embodiments, the exoskeleton-depleted insect liquid mixture (H39) or pressurized exoskeleton-depleted insect liquid mixture (H41) may be considered a liquid-laden insect mixture (117).

A supply valve (161) equipped with a controller (162) and configured to input and output a signal (163) to the computer (COMP) is positioned on the exoskeleton-depleted insect liquid mixture conduit (H38) in between the exoskeleton-depleted insect liquid mixture tank (H26) of FIG. 14H and the separator input (116) positioned on the side wall (165) of the liquid separator (110) of FIG. 14I.

The filter (I11) has a first output (118) positioned on the top (114). The first output (118) is configured to discharge an insect-depleted liquid mixture (119) via an insect-depleted liquid mixture conduit (120). A discharge valve (121) equipped with a controller (122) and configured to input and output a signal (123) to the computer (COMP) is positioned on the insect-depleted liquid mixture conduit (120). The filter (I11) is configured to remove insects (146) from either the exoskeleton-depleted insect liquid mixture (H39) or pressurized exoskeleton-depleted insect liquid mixture (H41) to form an insect-depleted liquid mixture (119). The insect-depleted liquid mixture (119) has a reduced amount of insects (146) relative to the exoskeleton-depleted insect liquid mixture (H39) or pressurized exoskeleton-depleted insect liquid mixture (H41).

The filter (I11) has a second output (145) positioned on the bottom (115). Insects (146) may be separated from the exoskeleton-depleted insect liquid mixture (H39) or pressurized exoskeleton-depleted insect liquid mixture (H41). A separated insect transfer conduit (147) is connected to the second output (145) positioned on the bottom (115) of the filter (I11). An insect conveyor (148) is equipped to receive insects (146) from the separated insect transfer conduit (147).

An insect drying gas (149) may be applied to a portion of the insects (146) to remove any residual liquid therefrom and form liquid-depleted insects (I50). In embodiments, the insect drying gas (149) is heated to a temperature ranging from between 80 degrees F. to 90 degrees F.; 90 degrees F. to 100 degrees F.; 100 degrees F. to 110 degrees F.; 110 degrees F. to 120 degrees F.; 120 degrees F. to 140 degrees F.; 140 degrees F. to 160 degrees F.; 160 degrees F. to 180 degrees F.; 180 degrees F. to 200 degrees F.; 200 degrees F. to 250 degrees F.; 250 degrees F. to 300 degrees F.; 300 degrees F. to 400 degrees F. In embodiments, the liquid-depleted insects (I50) may be routed to the insect tank (G66) on FIG. 14G.

An insect discharge valve (151) equipped with a controller (152) and configured to input and output a signal (153) to the computer (COMP) is installed on the separated insect transfer conduit (147). A backflush fluid (154) may be provided to the filter (I11) to regenerate the filter element (113). FIG. 14I shows the backflush fluid (154) entering the insect-depleted liquid mixture conduit (120) and then entering the interior (164) of the filter (I11) via the first output (118). In embodiments, the backflush fluid (154) is a liquid. In embodiments, the backflush fluid (154) is a gas.

A backflush fluid transfer conduit (155) is connected to the insect-depleted liquid mixture conduit (120) via a connection (170) in between the discharge valve (121) and the first output (118). A backflush fluid supply valve (IH56) equipped with a controller (157) and configured to input and output a signal (158) to the computer (COMP) is positioned on the backflush fluid transfer conduit (155). In embodiments, a backflush fluid pressure regulating valve (159) with a backflush pressure sensor (160) is positioned upstream of the backflush fluid supply valve (156). In embodiments, the backflush fluid pressure regulating valve (159) may be adjusted to a pressure that is less than the rupture pressure of that of the filter element (113). It is preferred to counter currently backflush the filter element (113) by setting the pressure of the backflush fluid pressure regulating valve (159) to a pressure of 0.25 PSI to 0.5 PSI; 0.5 PSI to 1.5 PSI; 1.5 PSI to 3 PSI; 3 PSI to 6 PSI; 6 PSI to 9 PSI; 9 PSI to 15 PSI.

FIG. 14J:

FIG. 14J shows one non-limiting embodiment of a liquid separation module (LSM) that is configured to remove liquid from the exoskeleton-depleted insect liquid mixture (H39) to produce a vaporized liquid (J22) and a stream of liquid-depleted insects (J10).

FIG. 14J shows the liquid separation module (LSM) that is configured to remove liquid from the exoskeleton-depleted insect liquid mixture (H39) or the pressurized exoskeleton-depleted insect liquid mixture (H41) to form a stream of liquid-depleted insects (J10). FIG. 14J shows the liquid separation module (LSM) configured to remove liquid from the exoskeleton-depleted insect liquid mixture (H39) that is provided by the exoskeleton separation module (14H). FIG. 14J shows the liquid separation module (LSM) configured to remove liquid from the pressurized exoskeleton-depleted insect liquid mixture (H41) that is provided by the exoskeleton separation module (14H).

FIG. 14J shows one non-limiting embodiment of a liquid separation module (LSM) that includes an evaporator (J11). FIG. 14J shows an exoskeleton-depleted insect liquid mixture (H39) or a pressurized exoskeleton-depleted insect liquid mixture (H41) transferred to the liquid separation module (LSM) from the exoskeleton separation module (14H) shown in FIG. 14H. The exoskeleton-depleted insect liquid mixture (H39) or a pressurized exoskeleton-depleted insect liquid mixture (H41) is transferred from the exoskeleton-depleted insect liquid mixture tank (H26) of FIG. 14H via the exoskeleton-depleted insect liquid mixture conduit (H38). FIG. 14J displays the liquid separation module (LSM) including a liquid separator (J10). In embodiments, the liquid separator (I10) is an evaporator (J11) which separates liquid by vaporizing the liquid.

In embodiments, the evaporator (J11) is a wiped-film evaporator (J11A). In embodiments, the evaporator (J11) is comprised of one or more from the group consisting of a rotary evaporator, falling film tubular evaporator, rising/falling film tubular evaporator, rising film tubular evaporator, forced circulation evaporator, internal pump forced circulation evaporator, plate evaporator, evaporative cooler, multiple-effect evaporator, thermal vapor recompression evaporator, mechanical vapor recompression evaporator, flash tank, a crystallizer, and a distillation column. The evaporator (J11) shown in FIG. 14J is that of a wiped-film evaporator (J11A). The evaporator (J11) has a vapor inlet (J12), a separator input (J16), a heating jacket (J17), a first output (J18), and a second output (J19).

In embodiments, the evaporator (J11) is electrically heated. In embodiments, the vapor inlet (J12) is provided with a vapor (J12A) such as steam. In embodiments, the vapor (J12A) is a seventh steam supply (LDJ) that is provided from FIG. 14L. The vapor inlet is connected to a vapor supply conduit (J13). A vapor supply valve (J14) is positioned on the vapor supply conduit (J13). The vapor supply valve (J14) is equipped with a controller (J15A) that is configured to input and output a signal (J15B) to the computer (COMP). In embodiments, the pressure drop across the vapor supply valve (J14) ranges from between 5 PSI to 10 PSI, 15 PSI to 25 PSI, 25 PSI to 35 PSI, 35 PSI to 45 PSI, 45 PSI to 55 PSI, 55 PSI to 65 PSI, 65 PSI to 75 PSI, 75 PSI to 85 PSI. In embodiments, the vapor supply valve (J14) percent open during normal operation ranges from 10% open to 25% open, 25% open to 35% open, 35% open to 45% open, 45% open to 55% open, 55% open to 65% open, 65% open to 75% open, 75% open to 80% open.

A separated vapor transfer conduit (J20) is connected to the first output (J18) and is configured to transfer vaporized liquid (J22) from the evaporator (J11) to a condenser (J26). The condenser (J26) has a vaporized liquid input (J25) that is configured to transfer the vaporized liquid (J22) from the separated vapor transfer conduit (J20) to the condenser (J26). The condenser (J26) is configured to accept vaporized liquid (J22) from the evaporator (J11) and condense the liquid into condensate (J27). Condensate (J27) is discharged from the condenser (J26) via a condenser condensate output (J30).

The condenser is connected to a vacuum system (J32) via a gas/vapor transfer conduit (J33). Gas/vapor (J35) is evacuated from the condenser (J27) via a gas/vapor discharge (J37). The gas/vapor (J35) transferred from the condenser to the vacuum system (J32) may be comprised of one or more from the group consisting of carbon dioxide, nitrogen, air, steam, water vapor, and non-condensables. The vacuum system (J32) may be any conceivable system configured to draw a vacuum on the condenser (J26). In embodiments, the vacuum system (J32) is that of a liquid-ring vacuum pump. A portion of the gas/vapor (J35) may be in turn condensed within the vacuum system (J26). A portion of the gas/vapor (J35) may be discharged from the vacuum system (J26) via a gas/vapor transfer line (J39).

In embodiments, the vacuum system (J32) pulls a vacuum on the evaporator (J11) at a pressure ranging from 0.25 pounds per square inch absolute (PSIA) to 0.5 PSIA, 0.5 PSIA to 1 PSIA, 1 PSIA to 1.5 PSIA, 1.5 PSIA to 3 PSIA, 3 PSIA to 4.5 PSIA, 4.5 PSIA to 6 PSIA, 6 PSIA to 7.5 PSIA, 7.5 PSIA to 9 PSIA, 9 PSIA to 10.5 PSIA, 10.5 PSIA to 12 PSIA, 12 PSIA to 13.5 PSIA, 12 PSIA to 12.25 PSIA, 12.25 PSIA to 12.5 PSIA, 12.5 PSIA to 12.75PSIA, 12.75 PSIA to 13 PSIA, 13 PSIA to 13.25 PSIA, 13.25 PSIA to 13.5 PSIA, 13.5 PSIA to 13.75 PSIA, 13.75 PSIA to 14 PSIA, 14 PSIA to 14.25 PSIA, 14.25 PSIA to 14.5 PSIA, or 14.5 PSIA to 14.75 PSIA. The condenser (J26) is provided with a cooling water input (J36) and a cooling water output (J40). The cooling water input (J36) is configured to accept a cooling water supply (J38) and the cooling water output (J40) is configured to discharge a cooling water return (J42). The cooling water supply (J38) is configured to reduce the temperature of the vaporized liquid (J22) within the condenser (J26) to convert the vapor into a liquid condensate (J27).

The evaporator (J11) has an evaporator condensate output (J24) for evacuating condensate (J41) from the heating jacket (J17). The condensate (J41) discharged via the evaporator condensate output (J24) was provided to the evaporator heating jacket (J17) as the vapor (J12A) or steam. In embodiments, the evaporator condensate output (J24) discharges a seventh condensate (LAW) that is provided to the condensate tank (LAP) shown on FIG. 14L. The heating jacket (J17) accepts a source of vapor (J12A), and evaporates liquid from the exoskeleton-depleted insect liquid mixture (H39) or the pressurized exoskeleton-depleted insect liquid mixture (H41) to form vaporized liquid (J22) that is discharged from the evaporator (J11) and sent to the condenser (J26).

In embodiments, the evaporator (J11) takes the form of a wiped-film evaporator (J11A). In embodiments, the wiped-film evaporator (J11A) has a motor (J42) and a wiper (J44). In embodiments, the motor (J42) and wiper (J44) act together to wipe at least one heat transfer surface within the evaporator (J11).

The separator input (J16) is configured to introduce an exoskeleton-depleted insect liquid mixture (H39) or a pressurized exoskeleton-depleted insect liquid mixture (H41) to the evaporator (J11). In embodiments, the exoskeleton-depleted insect liquid mixture (H39) or pressurized exoskeleton-depleted insect liquid mixture (H41) may be considered a liquid-laden insect mixture (117). The evaporator vaporizes liquid from within the exoskeleton-depleted insect liquid mixture (H39) or pressurized exoskeleton-depleted insect liquid mixture (H41) to produce a vaporized liquid (J22) and a stream of liquid-depleted insects (J10).

In embodiments, the liquid-depleted insects (J10) may be transferred from the evaporator (J11) and into a subsequent liquid removal system (J50), such as a belt press (J51) or a filter press (J61). The filter press (J51) applies pressure to the liquid-depleted insects (J10) to separate additional liquid (J52) therefrom and produce a subsequent liquid-depleted insects (J53) that have a reduced amount of liquid (J52) relative to the liquid-depleted insects (J10) that are discharged from the evaporator (J11). The subsequent liquid-depleted insects (J53) are transferred from the filter press (J51) to a storage container (J54).

FIG. 14K:

FIG. 14K shows one non-limiting embodiment of a liquid separation module (LSM) that is configured to remove liquid from an insect liquid mixture (H39) by use of a spray dryer (KAP).

A plurality of separators separate at least a small insect particulate portion (KCW) and a large insect particulate portion (KCY) from an insect and gas mixture (KBV) that is discharged in the drying chamber (KBG) of a spray dryer (KAP) evaporator (KAO). The spray dryer (KAP) is type of evaporator (KAO) that evaporates liquid from an insect liquid mixture (KAS). A first separator (KCA), second separator (KCI), and a third separator (KCR) are configured to accept an insect and gas mixture (KBV) from the drying chamber (KBG) of a spray dryer (KAP). In embodiments, the first separator (KCA) is a cyclone or a filter. In embodiments, the second separator (KCI) is a cyclone or a filter. In embodiments, the third separator (KCR) is a sifter or a filter. The third separator (KCR) accepts first separated insects (KCG) from the first separator (KCA) and second separated insects (KCP) from the second separator (KCI) and separates at least a small insect particulate portion (KCW) and a large insect particulate portion (KCY) therefrom. In embodiments, the small insect particulate portion (KCW) and a large insect particulate portion (KCY) are oligosaccharides or are hydrolyzed-biopolymers, as discussed above.

The exoskeleton-depleted insect liquid mixture conduit (H38) transfers an exoskeleton-depleted insect liquid mixture (H39) or an insect liquid mixture (KAS) to a liquid input (KAR) of the spray dryer (KAP). The spray dryer (KAP) has a top (K-T) and a bottom (K-B). The spray dryer (KAP) has a vertical axis (KYY) and a horizontal axis (KXY). As shown in FIG. 14K, the liquid input (KAR) is located positioned towards the top (K-T) of the spray dryer (KAP). In embodiments, the liquid input (KAR) to the spray dryer (KAP) is positioned closer to the bottom (K-B) of the spray dryer (KAP). The pump (H40) on FIG. 14H transfers an exoskeleton-depleted insect liquid mixture (H39) or an insect liquid mixture (KAS) through the exoskeleton-depleted insect liquid mixture conduit (H38) and into the liquid input (KAR) of the spray dryer (KAP).

In embodiments, the range of height of the drying chamber (KBG) is selected from one or more from the group 6 feet tall to 8 feet tall, 8 feet tall to 10 feet tall, 10 feet tall to 12 feet tall, 12 feet tall to 14 feet tall, 14 feet tall to 16 feet tall, 16 feet tall to 18 feet tall, 18 feet tall to 20 feet tall, 20 feet tall to 22 feet tall, 22 feet tall to 24 feet tall, 24 feet tall to 26 feet tall, 26 feet tall to 28 feet tall, 28 feet tall to 30 feet tall, 30 feet tall to 32 feet tall, 32 feet tall to 34 feet tall, 34 feet tall to 36 feet tall, 36 feet tall to 38 feet tall, 38 feet tall to 40 feet tall, and 40 feet tall to 50 feet tall.

In embodiments, the exoskeleton-depleted insect liquid mixture conduit (H38) connects the pump (H40) (on FIG. 14H) to: the evaporator (J11) on FIG. 14J; the wiped film evaporator (J11) on FIG. 14J; the evaporator (KAO) on FIG. 14J; the spray dryer (KAP) evaporator (KAO) on FIG. 14J. In embodiments, the exoskeleton-depleted insect liquid mixture conduit (H38) has heat tracing on it. In embodiments the heat tracing is powered by electricity.

In embodiments, the range of diameter of the drying chamber (KBG) is selected from one or more from the group 2 feet in diameter to 4 feet in diameter, 4 feet in diameter to 6 feet in diameter, 6 feet in diameter to 8 feet in diameter, 8 feet in diameter to 10 feet in diameter, 10 feet in diameter to 12 feet in diameter, 12 feet in diameter to 14 feet in diameter, 14 feet in diameter to 16 feet in diameter, 16 feet in diameter to 18 feet in diameter, 18 feet in diameter to 20 feet in diameter, 20 feet in diameter to 22 feet in diameter, 22 feet in diameter to 24 feet in diameter, 24 feet in diameter to 26 feet in diameter, 26 feet in diameter to 28 feet in diameter, 28 feet in diameter to 30 feet in diameter, 30 feet in diameter to 32 feet in diameter, 32 feet in diameter to 34 feet in diameter, 34 feet in diameter to 36 feet in diameter, 36 feet in diameter to 38 feet in diameter, and 38 feet in diameter to 40 feet in diameter. In embodiments, the drying chamber (KBG) is comprised of a material that is selected from one or more from the group consisting of carbon steel, graphite, Hastelloy alloy, nickel, stainless steel, tantalum, and titanium.

An insect/liquid mixture flow sensor (KEQ) is positioned on the conduit (H38) prior to the spray dryer (KAP). The insect/liquid mixture flow sensor (KEQ) is configured to input or output a signal (KER) to the computer (COMP). The insect/liquid mixture flow sensor (KEQ) measures the flow of the insect liquid mixture (H39, KAS) that is introduced to the liquid input (KAR) of the spray dryer (KAP). An insect/liquid mixture valve (KEC) is positioned on the conduit (H38) prior to the spray dryer (KAP). The insect/liquid mixture valve (KEC) has a controller (KED) that is configured to input or output a signal (KEE) to the computer (COMP). The insect/liquid mixture valve (KEC) and the insect/liquid mixture flow sensor (KEQ) may be used together in a flow control loop to set the flowrate of spray dryer (KAP) to a flow rate that includes one or more from the group consisting of: 0.5 gallons per minute (GPM) to 1 GPM, 1 GPM to 1.5 GPM, 1.5 GPM to 2 GPM, 2 GPM to 2.5 GPM, 2.5 GPM to 3 GPM, 3 GPM to 3.5 GPM, 3.5 GPM to 4 GPM, 4 GPM to 4.5 GPM, 4.5 GPM to 5 GPM, 5 GPM to 5.5 GPM, 5.5 GPM to 6 GPM, 6 GPM to 6.5 GPM, 6.5 GPM to 7 GPM, 7 GPM to 7.5 GPM, 7.5 GPM to 8 GPM, 8 GPM to 8.5 GPM, 8.5 GPM to 9 GPM, 9 GPM to 9.5 GPM, 9.5 GPM to 10 GPM, and 10 GPM to 10.5 GPM.

In embodiments, the water content of the insect liquid mixture (KAS) that is transferred to the mixture input (KAR) of the spray dryer (KAP) ranges between 40 weight percent liquid and 85 weight percent liquid. In embodiments, the water content of the insect liquid mixture (KAS) that is transferred to the mixture input (KAR) of the spray dryer (KAP) ranges between 45 weight percent liquid and 80 weight percent liquid. However, other mixture rations might work such as insect to liquid ratios selected from one or more from the group consisting of 1:9, 3:17, 1:4, 1:3, 3:7, 7:13, 2:3, 9:11, 1:1, 1.22:1, 1.5:1, 1.86:1, and 2.33:1. In embodiments, the ratio of pounds of insects divided by pounds of liquid may be selected from one or more from the group consisting of 0.11, 0.18, 0.25, 0.33, 0.43, 0.54, 0.67, 0.82, 1.00, 1.22, 1.50, 1.86, and 2.33. In embodiments, insect liquid mixture (KAS) may have a ratio of pounds of liquid divided by pounds of insects that is selected from one or more from the group consisting of 9.0, 5.6, 4.0, 3.0, 2.3, 1.8, 1.5, 1.2, 1.0, 0.8, 0.6, 0.5, 0.4, and 0.3.

In embodiments, the exoskeleton-depleted insect liquid mixture (H39) or the insect liquid mixture (KAS) is pressurized. An inlet pressure sensor (KBE) is positioned on the conduit (H38) prior to the spray dryer (KAP). The inlet pressure sensor (KBE) measures the pressure of the insect liquid mixture (H39, KAS) that is introduced to the liquid input (KAR) of the spray dryer (KAP). The inlet pressure sensor (KBE) transmits a signal (KBF) to the computer (COMP).

In embodiments, the range of pressure that the inlet pressure sensor (KBE) transmits to the computer (COMP) ranges from one or more from the group consisting of: 5 pounds per square inch (PSI) to 10 PSI; 10 PSI to 15 PSI; 15 PSI to 20 PSI; 20 PSI to 25 PSI; 25 PSI to 30 PSI; 30 PSI to 35 PSI; 35 PSI to 40 PSI; 40 PSI to 45 PSI; 45 PSI to 50 PSI; 50 PSI to 55 PSI; 55 PSI to 60 PSI; 60 PSI to 65 PSI; 65 PSI to 70 PSI; 70 PSI to 75 PSI; 75 PSI to 80 PSI; 80 PSI to 85 PSI; 85 PSI to 90 PSI; 90 PSI to 95 PSI; 95 PSI to 100 PSI; 100 PSI to 125 PSI; 125 PSI to 145 PSI; 145 PSI to 170 PSI; 170 PSI to 195 PSI; 195 PSI to 200 PSI; 200 PSI to 220 PSI; 220 PSI to 250 PSI; 250 PSI to 275 PSI; 275 PSI to 300 PSI; 300 PSI to 350 PSI; 350 PSI to 402 PSI; 402 PSI to 463 PSI; 463 PSI to 532 PSI; 532 PSI to 612 PSI; 612 PSI to 704 PSI; 704 PSI to 809 PSI; 809 PSI to 930 PSI; 930 PSI to 1070 PSI; 1,070 PSI to 1,231 PSI; 1,231 PSI to 1,415 PSI; 1,415 PSI to 1,627 PSI; 1,627 PSI to 1,872 PSI; 1,872 PSI to 2,152 PSI; 2,152 PSI to 2,475 PSI; 2,475 PSI to 2,846 PSI; 2,846 PSI to 3,273 PSI; 3,273 PSI to 3,764 PSI; 3,764 PSI to 4,329 PSI; 4,329 PSI to 4,978 PSI; 4,978 PSI to 5,725 PSI; 5,725 PSI to 6,584 PSI; 6,584 PSI to 7,571 PSI; 7,571 PSI to 8,707 PSI; 8,707 PSI to 10,013 PSI; 10,013 PSI to 11,515 PSI; and 11,515 PSI to 15,000 PSI.

In embodiments, the residence time of the insect liquid mixture (KAS) and gas supply (KAG) within the spray dryer (KAP) or drying chamber (KBG) ranges from one or more from the group selected from: 0.1 seconds to 1 seconds, 1 seconds to 2 seconds, 2 seconds to 3 seconds, 3 seconds to 4 seconds, 4 seconds to 5 seconds, 5 seconds to 6 seconds, 6 seconds to 7 seconds, 7 seconds to 8 seconds, 8 seconds to 9 seconds, 9 seconds to 10 seconds, 10 seconds to 12 seconds, 12 seconds to 15 seconds, 15 seconds to 20 seconds, 20 seconds to 25 seconds, 25 seconds to 30 seconds, 30 seconds to 35 seconds, 35 seconds to 40 seconds, 40 seconds to 45 seconds, 45 seconds to 50 seconds, 50 seconds to 55 seconds, 55 seconds to 60 seconds, 60 seconds to 65 seconds, 65 seconds to 70 seconds, 70 seconds to 80 seconds, 80 seconds to 90 seconds, 90 seconds to 100 seconds, 100 seconds to 110 seconds, and 110 seconds to 120 seconds.

A gas supply (KAG) is made available to the spray dryer (KAP) via a gas input (KAQ). In embodiments, the gas supply (KAG) may include a gas. In embodiments, the gas supply (KAG) may include a carbon dioxide. In embodiments, the gas supply (KAG) may include air. In embodiments, the gas supply (KAG) may include an oxygen-containing gas which includes air, oxygen-enriched-air i.e. greater than 21 mole % O2, and substantially pure oxygen, i.e. greater than about 95 mole % oxygen (the remainder usually comprising N2 and rare gases). In embodiments, the gas supply (KAG) may include flue gas which includes a vapor or gaseous mixture containing varying amounts of nitrogen (N2), carbon dioxide (CO2), water (H2O), and oxygen (O2). Flue gas is generated from the thermochemical process of combustion. In embodiments, the gas supply (KAG) may include a combustion stream.

A filter (KAH) is made available to remove particulates from the gas supply (KAG) prior to being introduced to the gas input (KAQ) of the spray dryer (KAP). A filter (KAH) may include a sorbent (KAH') and be configured to adsorb and/or absorb at least one component that is contained within the gas supply (KAG) prior to being introduced to the gas input (KAQ) of the spray dryer (KAP). In embodiments, the filter (KAH) may be a dehumidifier. In embodiments, the filter (KAH) may remove water from the gas supply (KAG) using an adsorbent. In embodiments, the adsorbent used in the filter (KAH) be selected from one or more from the group consisting of 3 Angstrom molecular sieve, 3 Angstrom zeolite, 4 Angstrom molecular sieve, 4 Angstrom zeolite, activated alumina, activated carbon, adsorbent, alumina, carbon, catalyst, clay, desiccant, molecular sieve, polymer, resin, and silica gel. In embodiments, the filter (KAH) may include any conceivable means to remove moisture from the gas supply (KAG), such as an air conditioner, cooling tower, an adsorber, a plurality of adsorbers. In embodiments, the filter (KAH) may include a cooling tower followed by an adsorber. In embodiments, the filter (KAH) may include a cooling tower followed by a plurality of adsorbers. In embodiments, an adsorber is a packed bed of adsorbent. In embodiments, an adsorber is a moving bed of adsorbent. In embodiments, an adsorber contains an adsorbent.

A fan (KAI) is made available and is configured to introduce the gas supply (KAG) to the spray dryer (KAP). The fan (KAI) is equipped with a motor (KAJ) that has a controller (KAK) which is configured to input or output a signal (KAL) to the computer (COMP). In embodiments, the fan (KAI) operates within a range that is selected from one or more from the group consisting of: 350 standard cubic feet per minute (SCFM) to 3,500 SCFM; 700 SCFM to 7,000 SCFM; 1,050 SCFM to 10,500 SCFM; 1,400 SCFM to 14,000 SCFM; 1,750 SCFM to 17,500 SCFM; 2,100 SCFM to 21,000 SCFM; 2,450 SCFM to 24,500 SCFM; 2,800 SCFM to 28,000 SCFM; 3,150 SCFM to 31,500 SCFM; 3,500 SCFM to 35,000 SCFM; 3,850 SCFM to 38,500 SCFM; 4,200 SCFM to 42,000 SCFM; 4,550 SCFM to 45,500 SCFM; 4,900 SCFM to 49,000 SCFM; 5,250 SCFM to 52,500 SCFM; 5,600 SCFM to 56,000 SCFM; 5,950 SCFM to 59,500 SCFM; 6,300 SCFM to 63,000 SCFM; 6,650 SCFM to 66,500 SCFM; 7,000 SCFM to 70,000 SCFM; and 7,350 SCFM to 73,500 SCFM.

In embodiments, at an insect liquid mixture flow rate of 0.5 to 1 GPM, the fan (KAI) operates in a range between 350 standard cubic feet per minute (SCFM) to 3,500 SCFM. In embodiments, at an insect liquid mixture flow rate of 0.5 to 1 GPM, the fan (KAI) operates in a range between 700 SCFM to 7,000 SCFM. In embodiments, at an insect liquid mixture flow rate of 1 to 1.5 GPM, the fan (KAI) operates in a range between 1,050 SCFM to 10,500 SCFM. In embodiments, at an insect liquid mixture flow rate of 1.5 to 5 GPM, the fan (KAI) operates in a range between 1,400 SCFM to 14,000 SCFM. In embodiments, at an insect liquid mixture flow rate of 2 to 2.5 GPM, the fan (KAI) operates in a range between 1,750 SCFM to 17,500 SCFM. In embodiments, at an insect liquid mixture flow rate of 2.5 to 3 GPM, the fan (KAI) operates in a range between 2,100 SCFM to 21,000 SCFM. In embodiments, at an insect liquid mixture flow rate of 3 to 3.5 GPM, the fan (KAI) operates in a range between 2,450 SCFM to 24,500 SCFM. In embodiments, at an insect liquid mixture flow rate of 3.5 to 4 GPM, the fan (KAI) operates in a range between 2,800 SCFM to 28,000 SCFM. In embodiments, at an insect liquid mixture flow rate of 4 to 4.5 GPM, the fan (KAI) operates in a range between 3,150 SCFM to 31,500 SCFM. In embodiments, at an insect liquid mixture flow rate of 4.5 to 5 GPM, the fan (KAI) operates in a range between 3,500 SCFM to 35,000 SCFM. In embodiments, at an insect liquid mixture flow rate of 5 to 5.5 GPM, the fan (KAI) operates in a range between 3,850 SCFM to 38,500 SCFM. In embodiments, at an insect liquid mixture flow rate of 5.5 to 6 GPM, the fan (KAI) operates in a range between 4,200 SCFM to 42,000 SCFM. In embodiments, at an insect liquid mixture flow rate of 6 to 6.5 GPM, the fan (KAI) operates in a range between 4,550 SCFM to 45,500 SCFM. In embodiments, at an insect liquid mixture flow rate of 6.5 to 7 GPM, the fan (KAI) operates in a range between 4,900 SCFM to 49,000 SCFM. In embodiments, at an insect liquid mixture flow rate of 7 to 7.5 GPM, the fan (KAI) operates in a range between 5,250 SCFM to 52,500 SCFM. In embodiments, at an insect liquid mixture flow rate of 7.5 to 8 GPM, the fan (KAI) operates in a range between 5,600 SCFM to 56,000 SCFM. In embodiments, at an insect liquid mixture flow rate of 8 to 8.5 GPM, the fan (KAI) operates in a range between 5,950 SCFM to 59,500 SCFM. In embodiments, at an insect liquid mixture flow rate of 8.5 to 9 GPM, the fan (KAI) operates in a range between 6,300 SCFM to 63,000 SCFM. In embodiments, at an insect liquid mixture flow rate of 9 to 9.5 GPM, the fan (KAI) operates in a range between 6,650 SCFM to 66,500 SCFM. In embodiments, at an insect liquid mixture flow rate of 9.5 to 10 GPM, the fan (KAI) operates in a range between 7,000 SCFM to 70,000 SCFM. In embodiments, at an insect liquid mixture flow rate of 10 to 10.5 GPM, the fan (KAI) operates in a range between 7,350 SCFM to 73,500 SCFM.

An air heater (KAF) is made available to heat the gas supply (KAG) prior to being introduced to the gas input (KAQ) of the spray dryer (KAP). FIG. 14K shows the gas supply (KAG) first entering the filter (KAH), then the fan (KAI), and then the air heater (KAF). It is to be noted that combinations of the filter (KAH), fan (KAI), and air heater (KAF) shown in FIG. 14K are non-limiting. For example, the fan (KAI) may be before the filter (KAH), the fan (KAI) may be after the air heater (KAF), the filter (KAH) may be after the fan (KAI), the filter (KAH) may be after the air heater (KAF), the air heater (KAF) may be before the fan (KAI). The air heater (KAF) provides a heated gas supply (KAG) to the spray dryer (KAP).

In embodiments, the ideal range that the temperature sensor (KAM) inputs into the computer (COMP) while measuring the heated gas supply (KAG) is preferably set to 250 degrees Fahrenheit to 600 degrees Fahrenheit, but more preferably to 300 degrees Fahrenheit to 5000 degrees Fahrenheit, but more preferably to 350 degrees Fahrenheit to 450 degrees Fahrenheit. In embodiments, the heated gas supply (KAG) has a temperature selected from the group consisting of: 250 degrees Fahrenheit to 275 degrees Fahrenheit; 275 degrees Fahrenheit to 300 degrees Fahrenheit; 300 degrees Fahrenheit to 325 degrees Fahrenheit; 325 degrees Fahrenheit to 350 degrees Fahrenheit; 350 degrees Fahrenheit to 375 degrees Fahrenheit; 375 degrees Fahrenheit to 400 degrees Fahrenheit; 400 degrees Fahrenheit to 425 degrees Fahrenheit; 425 degrees Fahrenheit to 450 degrees Fahrenheit; 450 degrees Fahrenheit to 475 degrees Fahrenheit; 475 degrees Fahrenheit to 500 degrees Fahrenheit; 500 degrees Fahrenheit to 525 degrees Fahrenheit; 525 degrees Fahrenheit to 550 degrees Fahrenheit; 550 degrees Fahrenheit to 575 degrees Fahrenheit; 575 degrees Fahrenheit to 600 degrees Fahrenheit; 600 degrees Fahrenheit to 625 degrees Fahrenheit; 625 degrees Fahrenheit to 650 degrees Fahrenheit; 650 degrees Fahrenheit to 675 degrees Fahrenheit; 675 degrees Fahrenheit to 700 degrees Fahrenheit; 700 degrees Fahrenheit to 725 degrees Fahrenheit; 725 degrees Fahrenheit to 750 degrees Fahrenheit; 750 degrees Fahrenheit to 775 degrees Fahrenheit; and 775 degrees Fahrenheit to 800 degrees Fahrenheit.

The temperature sensor (KAM) is configured to input a signal (KAN) to the computer (COMP). The computer (COMP), temperature sensor (KAM), and the motor (KAJ) of the fan (KAI) may be used together in a temperature control loop to maintain a constant pre-determined temperature of heated gas to the spray dryer (KAP).

In embodiments, the heated gas supply (KAG) is created by indirect contact with steam in the air heater (KAF). In embodiments, the air heater (KAF) may be electrically heated or heated by a combustion steam or flue gas. The heated gas supply (KAG) may also be a combustion stream. In embodiments, the air heater (KAF) accepts a source of steam from a steam drum (LBE) as shown on FIG. 14L. The steam drum (LBE) provides an eighth steam supply (LDM) to the air heater (KAF), as discussed below. The eighth steam supply (LDM) may be saturated or superheated steam. A steam flow control valve (KAA) is configured to regulate the flow of the steam that passes through the air heater (KAF). The steam flow control valve (KAA) is equipped with a controller (KAB) that sends a signal (KAC) to or from the computer (COMP).

A flow sensor (KAD) is configured to measure the flow of the steam that passes through the air heater (KAF). The flow sensor (KAD) sends a signal (KAE) to the computer (COMP). The computer (COMP), steam flow control valve (KAA), and the flow sensor (KAD) may be used in a control loop to control the flow of steam that is passed through the air heater (KAF). In embodiments, the computer (COMP), steam flow control valve (KAA), flow sensor (KAD), temperature sensor (KAM), and motor (KAJ) of the fan (KAI) may be used together in a temperature control loop to maintain a constant pre-determined temperature of heated gas to the spray dryer (KAP). The steam flow control valve (KAA) may be positioned before or after the air heater (KAF). The air heater (KAF) discharges an eighth condensate (LJA) to the condensate tank (LAP) that is shown on FIG. 14L. A condensate temperature sensor (KK1) is configured to measure the temperature of the eighth condensate (LJA) that leaves the air heater (KAF). The condensate temperature sensor (KK1) sends a signal (KK2) to the computer (COMP).

In embodiments, the liquid separation module (LSM) separates liquid from the insect and liquid mixture (H39, KAS) by converting the liquid into a vapor. In embodiments, the liquid separation module (LSM) evaporates liquid from within the insect and liquid mixture (H39, KAS) by use of an evaporator (KAO). A spray dryer (KAP) is a type of evaporator (KAO).

In embodiments, the spray dryer (KAP) evaporator (KAO) operates at a temperature greater than the boiling point of the liquid within the insect and liquid mixture (H39, KAS) to vaporize the liquid portion of the insect and liquid mixture (H39, KAS) into a vapor. In embodiments, the spray dryer (KAP) is configured to mix a heated gas supply (KAG') with an insect liquid mixture (H39, KAS) under precise computer operated automated control to generate an insect and gas mixture (KBV).

In embodiments, the spray dryer (KAP) has an interior (KAP') which accepts both the heated gas supply (KAG') and the insect liquid mixture (H39, KAS). In embodiments, the spray dryer (KAP) has an interior (KAP') which accepts both the heated gas supply (KAG') via the gas input (KAQ) and the insect liquid mixture (H39, KAS) via the liquid input (KAR). In embodiments, the spray dryer (KAP) is equipped with a plurality of spray nozzles (KBC) that dispense the insect liquid mixture (H39, KAS) within the interior (KAP') of the spray dryer (KAP).

In embodiments the spray dryer (KAP) has a drying chamber (KBG) which evaporates liquid within the insect liquid mixture (H39, KAS). In embodiments, interior (KBG') of the drying chamber (KBG) is located within the interior (KAP') of the spray dryer (KAP). In embodiments the spray dryer (KAP) has an air distributor (KAT) that is configured to accept the heated gas supply (KAG') from the gas input (KAQ) and distribute it to the interior (KAP') of the drying chamber (KBG). In embodiments, the heated gas supply (KAG') is introduced to the interior (KAP') of the spray dryer (KAP) via the air distributor (KAT) using centrifugal momentum.

In embodiments, the insect liquid mixture (H39, KAS) is introduced to the interior (KAP') of the spray dryer (KAP) via a plurality of spray nozzles (KBC). In embodiments, the insect liquid mixture (H39, KAS) is introduced to the interior (KBG') of the drying chamber (KBG) via a plurality of spray nozzles (KBC). In embodiments, the insect liquid mixture (H39, KAS) is introduced to the interior (KAP') of the spray dryer (KAP) via a rotary atomizer (KAU) which may have a spray nozzle (KBC) or a plurality of spray nozzles (KBC). In embodiments, the insect liquid mixture (H39, KAS) is introduced to the interior (KBG') of the drying chamber (KBG) via a rotary atomizer (KAU). In embodiments, the rotary atomizer (KAU) dispenses insect liquid mixture (H39, KAS) or start-up liquid (KEO) into the interior (KBG') of the drying chamber (KBG) via an opening (KBD) or a plurality of openings (KBD) or a spray nozzle (KBC) or a plurality of spray nozzles (KBC).

In embodiments the pressure drop across the opening (KBD), plurality of openings (KBD), spray nozzle (KBC), or plurality of spray nozzles (KBC) includes one or more from the group consisting of: 5 pounds per square inch (PSI) to 10 PSI; 10 PSI to 15 PSI; 15 PSI to 20 PSI; 20 PSI to 25 PSI; 25 PSI to 30 PSI; 30 PSI to 35 PSI; 35 PSI to 40 PSI; 40 PSI to 45 PSI; 45 PSI to 50 PSI; 50 PSI to 55 PSI; 55 PSI to 60 PSI; 60 PSI to 65 PSI; 65 PSI to 70 PSI; 70 PSI to 75 PSI; 75 PSI to 80 PSI; 80 PSI to 85 PSI; 85 PSI to 90 PSI; 90 PSI to 95 PSI; 95 PSI to 100 PSI; 100 PSI to 125 PSI; 125 PSI to 145 PSI; 145 PSI to 170 PSI; 170 PSI to 195 PSI; 195 PSI to 200 PSI; 200 PSI to 220 PSI; 220 PSI to 250 PSI; 250 PSI to 275 PSI; 275 PSI to 300 PSI; 300 PSI to 350 PSI; 350 PSI to 402 PSI; 402 PSI to 463 PSI; 463 PSI to 532 PSI; 532 PSI to 612 PSI; 612 PSI to 704 PSI; 704 PSI to 809 PSI; 809 PSI to 930 PSI; 930 PSI to 1070 PSI; 1,070 PSI to 1,231 PSI; 1,231 PSI to 1,415 PSI; 1,415 PSI to 1,627 PSI; 1,627 PSI to 1,872 PSI; 1,872 PSI to 2,152 PSI; 2,152 PSI to 2,475 PSI; 2,475 PSI to 2,846 PSI; 2,846 PSI to 3,273 PSI; 3,273 PSI to 3,764 PSI; 3,764 PSI to 4,329 PSI; 4,329 PSI to 4,978 PSI; 4,978 PSI to 5,725 PSI; 5,725 PSI to 6,584 PSI; 6,584 PSI to 7,571 PSI; 7,571 PSI to 8,707 PSI; 8,707 PSI to 10,013 PSI; 10,013 PSI to 11,515 PSI; and 11,515 PSI to 15,000 PSI.

The rotary atomizer (KAU) has a motor (KAV) and a controller (KAW) that is configured to input or output a signal (KAX) to the computer (COMP). In embodiments, the motor (KAV) of the rotary atomizer (KAU) is connected to a shaft (KBA). In embodiments, the shaft (KBA) is connected to a disc (KBB). In embodiments, the disc (KBB) has an opening (KBD) or a plurality of openings (KBD) or spray nozzle (KBC) or a plurality of spray nozzles (KBC) installed on it. In embodiments, the motor (KAV) rotates the shaft (KBA) which in turn rotates the disc (KBB) and then distributes the insect liquid mixture (KAS) or start-up liquid (KEO) to the interior (KAP') of the spray dryer (KAP) or the interior (KBG') of the drying chamber (KBG).

In embodiments, the spray nozzle (KBC) or plurality of spray nozzles (KBC) each have an opening (KBD). In embodiments, the spray nozzle (KBC) or plurality of spray nozzles (KBC) each have a spray aperture (KK4). In embodiments, the spray nozzle (KBC) or plurality of spray nozzles (KBC) each have an orifice (KK5). In embodiments, the spray nozzle (KBC) or plurality of spray nozzles (KBC) each have an impingement surface (KK6).

In embodiments, at least a portion of the insect liquid mixture (H39, KAS) or start-up liquid (KEO) contact an impingement surface (KK6) prior to being dispensed to the interior (KAP') of the spray dryer (KAP) or the interior (KBG') of the drying chamber (KBG) via a spray aperture (KK4). In embodiments, at least a portion of the insect liquid mixture (H39, KAS) or start-up liquid (KEO) pass through an orifice (KK5) prior to being dispensed to the interior (KAP') of the spray dryer (KAP) or the interior (KBG') of the drying chamber (KBG) via a spray aperture (KK4). In embodiments, at least a portion of the insect liquid mixture (H39, KAS) or start-up liquid (KEO) pass through the spray nozzle (KBC) or plurality of spray nozzles (KBC) and contact an orifice (KK5) prior to being dispensed to the interior (KAP') of the spray dryer (KAP) or the interior (KBG') of the drying chamber (KBG).

In embodiments, the plurality of spray nozzles (KBC) have a spray pattern is a hollow cone, full cone, or a flat spray. In embodiments, the spray pattern includes is that of the whirling type. In embodiments, the whirling type spray nozzle sprays the insect liquid mixture (H39, KAS) or start-up liquid (KEO) while rotating the liquid (H39, KAS, KEO) across a portion of the spray nozzle (KBC). A whirling type spray nozzle (KBC) is one that sprays the insect liquid mixture (H39, KAS) or start-up liquid (KEO) while rotating the liquid (H39, KAS, KEO) across a portion of the spray nozzle (KBC) after a pressure drop has taken place. A whirling type spray nozzle (KBD) is one that sprays the insect liquid mixture (H39, KAS) or start-up liquid (KEO) while rotating the liquid (H39, KAS, KEO) across a portion of the spray nozzle after the liquid or slurry has passed through an orifice.

In embodiments, a whirling type spray nozzle (KBD) includes an orifice (KK5) and an impingement surface (KK6): the orifice (KK5) is configured to accept insect liquid mixture (H39, KAS) or start-up liquid (KEO) and drop the pressure from a first higher pressure to a second lower pressure, the first pressure being greater than the second pressure; an impingement surface (KK6) that is configured to accept the liquid (H39, KAS, KEO) at the second pressure at change its direction to impart rotational or centrifugal momentum.

A whirling type spray nozzle (KBD) is one that sprays a liquid (H39, KAS, KEO) under cyclone conditions. In embodiments, the spray nozzle (KBD) is comprised of ceramic, metal, brass, 316 stainless steel, 316L stainless steel, stainless steel, polytetrafluoroethylene (PTFE), or plastic, or a composite material. In embodiments, the spray nozzle (KBC) opening (KBD) ranges from 0.030 inches to 0.30 inches. In embodiments, the spray nozzle (KBC) opening (KBD) ranges from 0.03 inches to 0.16 inches. In embodiments, the spray nozzle (KBC) orifice (KK5) ranges from 0.030 inches to 0.30 inches. In embodiments, the spray nozzle (KBC) orifice (KK5) ranges from 0.03 inches to 0.16 inches.

In embodiments, the spray nozzle (KBC) has an orifice (KK5) and a spray aperture (KK4). In embodiments, the spray angle of the spray nozzle (KBC) ranges from 15° to 120°. In embodiments, the spray angle of the spray nozzle (KBC) ranges from 30° to 100°. In embodiments, the spray angle of the spray nozzle (KBC) ranges from 40° to 90°. In embodiments, the spray angle of the spray nozzle (KBC) ranges from 50° to 85°. In embodiments, the spray angle of the spray nozzle (KBC) ranges from 70° to 75°. In embodiments, the spray angle of the spray nozzle (KBC) ranges from 45° to 89°. In embodiments, the spray angle of the spray nozzle (KBC) ranges from 90° to 134°. In embodiments, the spray angle of the spray nozzle (KBC) ranges from 135° to 179°. In embodiments, the spray angle of the spray nozzle ranges (KBC) from 180° to 360°.

In embodiments, the spray nozzle (KBC) creates solid insect particulates that have a size selected from one or more from the group consisting of: 10 microns to 2,000 microns, 20 microns to 1,900 microns, 40 microns to 1,600 microns, 50 microns to 1,200 microns, 50 microns to 1,000 microns, 35 microns to 225 microns, 50 microns to 500 microns, 100 microns to 2,000 microns, and 75 microns to 1,000 microns.

In embodiments, the spray nozzle (KBC) creates solid insect particulates that have a size selected from one or more from the group consisting of: 0.001 microns to 0.002 microns; 0.002 microns to 0.004 microns; 0.004 microns to 0.008 microns; 0.008 microns to 0.016 microns; 0.016 microns to 0.032 microns; 0.032 microns to 0.064 microns; 0.064 microns to 0.122 microns; 0.128 microns to 0.251 microns; 0.256 microns to 0.512 microns; 0.512 microns to 1.0 microns; 1.0 microns to 1.5 microns; 1.5 microns to 2.3 microns; 2.3 microns to 3.5 microns; 3.5 microns to 5.2 microns; 5.2 microns to 7.8 microns; 7.8 microns to 12 microns; 12 microns to 17 microns; 17 microns to 26 microns; 26 microns to 39 microns; 39 microns to 59 microns; 59 microns to 89 microns; 89 microns to 133 microns; 133 microns to 199 microns; 199 microns to 299 microns; 299 microns to 448 microns; 448 microns to 673 microns; 673 microns to 1009 microns; 1009 microns to 1513 microns; 1513 microns to 2270 microns; 2270 microns to 3405 microns; 3405 microns to 5108 microns; and 5108 microns to 7661 microns.

In embodiments, each spray nozzle (KBC) is affixed to the disc (KAB) using one or more connectors selected from the group consisting of national pipe thread, British standard pipe thread, and welded. In embodiments, the spray nozzle (KBC) is connected to the disc (KAB) using 0.25 inch national pipe threads, 0.375 inch national pipe threads, 0.50 inch national pipe threads, 0.625 inch national pipe threads, 0.75 inch national pipe threads, 1 inch national pipe threads, 1.25 inch national pipe threads, 1.375 inch national pipe threads, 1.625 inch national pipe threads, 1.75 inch national pipe threads, 1.875 inch national pipe threads, or 2 inch national pipe threads. In embodiments, the spray nozzle (KBC) is connected to the disc (KAB) using a fitting that includes 0.25 inch pipe threads, 0.375 inch pipe threads, 0.50 inch pipe threads, 0.625 inch pipe threads, 0.75 inch pipe threads, 1 inch pipe threads, 1.25 inch pipe threads, 1.375 inch pipe threads, 1.625 inch pipe threads, 1.75 inch pipe threads, 1.875 inch pipe threads, or 2 inch pipe threads.

In embodiments, the flow through the disc (KAB) is selected from one or more from the group consisting of 30 gallons per hour to 90 gallons per hour, 90 gallons per hour to 210 gallons per hour, 210 gallons per hour to 330 gallons per hour, 330 gallons per hour to 450 gallons per hour, and 450 gallons per hour to 630 gallons per hour.

In embodiments, the disc (KAB) is has a plurality of spray nozzles (KBC), the plurality of spray nozzles (KBC) is comprised of a quantity of spray nozzles that is selected from one or more from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, and 42 spray nozzles. In embodiments, the disc (KAB) is has a plurality of spray nozzles (KBC), the quantity of spray nozzles (KBC) that are installed on the disc (KAB) is selected from one or more from the group consisting of: 1 spray nozzles to 3 spray nozzles, 3 spray nozzles to 6 spray nozzles, 6 spray nozzles to 9 spray nozzles, 9 spray nozzles to 12 spray nozzles, 12 spray nozzles to 15 spray nozzles, 15 spray nozzles to 18 spray nozzles, 18 spray nozzles to 21 spray nozzles, 21 spray nozzles to 24 spray nozzles, 24 spray nozzles to 27 spray nozzles, 27 spray nozzles to 30 spray nozzles, 30 spray nozzles to 33 spray nozzles, 33 spray nozzles to 36 spray nozzles, 36 spray nozzles to 39 spray nozzles, and 39 spray nozzles to 42 spray nozzles.

In embodiments, where 1 spray nozzles are used, the flow through each spray nozzle in gallons per hour (GPH) ranges from one of more from the group consisting of: 30 GPH to 90 GPH, 90 GPH to 210 GPH, 210 GPH to 330 GPH, 330 GPH to 450 GPH, and 450 GPH to 630 GPH. In embodiments, where 2 spray nozzles are used, the flow through each spray nozzle ranges from one of more from the group consisting of: 15 GPH to 45 GPH, 45 GPH to 105 GPH, 105 GPH to 165 GPH, 165 GPH to 225 GPH, and 225 GPH to 315 GPH. In embodiments, where 3 spray nozzles are used, the flow through each spray nozzle ranges from one of more from the group consisting of: 10 GPH to 30 GPH 30 GPH to 70 GPH 70 GPH to 110 GPH 110 GPH to 150 GPH, and 150 GPH to 210 GPH.

In embodiments, where 4 spray nozzles are used, the flow through each spray nozzle ranges from one of more from the group consisting of: 8 GPH to 23 GPH, 23 GPH to 53 GPH, 53 GPH to 83 GPH, 83 GPH to 113 GPH, and 113 GPH to 158 GPH. In embodiments, where 5 spray nozzles are used, the flow through each spray nozzle ranges from one of more from the group consisting of: 6 GPH to 18 GPH, 18 GPH to 42 GPH, 42 GPH to 66 GPH, 66 GPH to 90 GPH, and 90 GPH to 126 GPH. In embodiments, where 6 spray nozzles are used, the flow through each spray nozzle ranges from one of more from the group consisting of: 15 GPH to 35 GPH, 35 GPH to 55 GPH, 55 GPH to 75 GPH, and 75 GPH to 105 GPH.

In embodiments, where 7 spray nozzles are used, the flow through each spray nozzle ranges from one of more from the group consisting of: 12.857 GPH and 30 GPH, 30 GPH and 47.143 GPH, 47.143 GPH and 64.286 GPH, and 64.286 GPH and 90 GPH. In embodiments, where 8 spray nozzles are used, the flow through each spray nozzle ranges from one of more from the group consisting of: 11.250 GPH to 26.250 GPH, 26.250 GPH to 41.250 GPH, 41.250 GPH to 56.250 GPH, and 56.250 GPH to 78.750 GPH. In embodiments, where 9 spray nozzles are used, the flow through each spray nozzle ranges from one of more from the group consisting of: 10.000 GPH to 23.333 GPH, 23.333 GPH to 36.667 GPH, 36.667 GPH to 50.000 GPH, and 50.000 GPH to 70.000 GPH.

In embodiments, where 10 spray nozzles are used, the flow through each spray nozzle ranges from one of more from the group consisting of: 9 GPH to 21 GPH, 21 GPH to 33 GPH, 33 GPH to 45 GPH, and 45 GPH to 63 GPH. In embodiments, where 11 spray nozzles are used, the flow through each spray nozzle ranges from one of more from the group consisting of: 8.182 GPH to 19.091 GPH, 19.091 GPH to 30.000 GPH, 30.000 GPH to 40.909 GPH, and 40.909 GPH to 57.273 GPH. In embodiments, where 12 spray nozzles are used, the flow through each spray nozzle ranges from one of more from the group consisting of: 7.5 GPH to 17.5 GPH, 17.5 GPH to 27.5 GPH, 27.5 GPH to 37.5 GPH, and 37.5 GPH to 52.5 GPH.

In embodiments, where 13 spray nozzles are used, the flow through each spray nozzle ranges from one of more from the group consisting of: 6.923 GPH to 16.154 GPH, 16.154 GPH to 25.385 GPH, 25.385 GPH to 34.615 GPH, and 34.615 GPH to 48.462 GPH. In embodiments, where 14 spray nozzles are used, the flow through each spray nozzle ranges from one of more from the group consisting of: 6.429 GPH to 15.000 GPH, 15.000 GPH to 23.571 GPH, 23.571 GPH to 32.143 GPH, and 32.143 GPH to 45.000 GPH. In embodiments, where 15 spray nozzles are used, the flow through each spray nozzle ranges from one of more from the group consisting of: 6 GPH to 14 GPH, 14 GPH to 22 GPH, 22 GPH to 30 GPH, and 30 GPH to 42 GPH.

In embodiments, where 16 spray nozzles are used, the flow through each spray nozzle ranges from one of more from the group consisting of: 13.125 GPH to 20.625 GPH, 20.625 GPH to 28.125 GPH, and 28.125 GPH to 39.375 GPH. In embodiments, where 17 spray nozzles are used, the flow through each spray nozzle ranges from one of more from the group consisting of: 12.353 GPH to 19.412 GPH, 19.412 GPH to 26.471 GPH, and 26.471 GPH to 37.059 GPH. In embodiments, where 18 spray nozzles are used, the flow through each spray nozzle ranges from one of more from the group consisting of: 11.667 GPH to 18.333 GPH, 18.333 GPH to 25.000 GPH, and 25.000 GPH to 35.000 GPH.

In embodiments, where 19 spray nozzles are used, the flow through each spray nozzle ranges from one of more from the group consisting of: 11.053 GPH to 17.368 GPH, 17.368 GPH to 23.684 GPH, and 23.684 GPH to 33.158 GPH. In embodiments, where 20 spray nozzles are used, the flow through each spray nozzle ranges from one of more from the group consisting of: 10.500 GPH to 16.500 GPH, 16.500 GPH to 22.500 GPH, and 22.500 GPH to 31.500 GPH. In embodiments, where 21 spray nozzles are used, the flow through each spray nozzle ranges from one of more from the group consisting of: 10.000 GPH to 15.714 GPH, 15.714 GPH to 21.429 GPH, and 21.429 GPH to 30.000 GPH.

In embodiments, where 22 spray nozzles are used, the flow through each spray nozzle ranges from one of more from the group consisting of: 9.545 GPH to 15.000 GPH, 15.000 GPH to 20.455 GPH, and 20.455 GPH to 28.636 GPH. In embodiments, where 23 spray nozzles are used, the flow through each spray nozzle ranges from one of more from the group consisting of: 9.130 GPH to 14.348 GPH, 14.348 GPH to 19.565 GPH, and 19.565 GPH to 27.391 GPH. In embodiments, where 24 spray nozzles are used, the flow through each spray nozzle ranges from one of more from the group consisting of: 8.75 GPH to 13.75 GPH, 13.75 GPH to 18.75 GPH, and 18.75 GPH to 26.25 GPH.

In embodiments, where 25 spray nozzles are used, the flow through each spray nozzle ranges from one of more from the group consisting of: 8.40 GPH to 13.20 GPH, 13.20 GPH to 18.00 GPH, and 18.00 GPH to 25.20 GPH. In embodiments, where 26 spray nozzles are used, the flow through each spray nozzle ranges from one of more from the group consisting of: 8.077 GPH to 12.692 GPH, 12.692 GPH to 17.308 GPH, and 17.308 GPH to 24.231 GPH. In embodiments, where 27 spray nozzles are used, the flow through each spray nozzle ranges from one of more from the group consisting of: 7.778 GPH to 12.222 GPH, 12.222 GPH to 16.667 GPH, and 16.667 GPH to 23.333 GPH.

In embodiments, where 28 spray nozzles are used, the flow through each spray nozzle ranges from one of more from the group consisting of: 7.500 GPH to 11.786 GPH, 11.786 GPH to 16.071 GPH, and 16.071 GPH to 22.500 GPH. In embodiments, where 29 spray nozzles are used, the flow through each spray nozzle ranges from one of more from the group consisting of: 7.241 GPH to 11.379 GPH, 11.379 GPH to 15.517 GPH, and 15.517 GPH to 21.724 GPH. In embodiments, where 30 spray nozzles are used, the flow through each spray nozzle ranges from one of more from the group consisting of: 7 GPH to 11 GPH, 11 GPH to 15 GPH, and 15 GPH to 21 GPH.

In embodiments, where 31 spray nozzles are used, the flow through each spray nozzle ranges from one of more from the group consisting of: 6.774 GPH to 10.645 GPH, 10.645 GPH to 14.516 GPH, and 14.516 GPH to 20.323 GPH. In embodiments, where 32 spray nozzles are used, the flow through each spray nozzle ranges from one of more from the group consisting of: 6.563 GPH to 10.313 GPH, 10.313 GPH to 14.063 GPH, and 14.063 GPH to 19.688 GPH. In embodiments, where 33 spray nozzles are used, the flow through each spray nozzle ranges from one of more from the group consisting of: 6.364 GPH to 10.000 GPH, 10.000 GPH to 13.636 GPH, and 13.636 GPH to 19.091 GPH.

In embodiments, where 34 spray nozzles are used, the flow through each spray nozzle ranges from one of more from the group consisting of: 6.176 GPH to 9.706 GPH, 9.706 GPH to 13.235 GPH, and 13.235 GPH to 18.529 GPH. In embodiments, where 35 spray nozzles are used, the flow through each spray nozzle ranges from one of more from the group consisting of: 6.000 GPH to 9.429 GPH, 9.429 GPH to 12.857 GPH, and 12.857 GPH to 18.000 GPH. In embodiments, where 36 spray nozzles are used, the flow through each spray nozzle ranges from 9.167 GPH to 12.500 GPH, or 12.500 GPH to 17.500 GPH. In embodiments, where 37 spray nozzles are used, the flow through each spray nozzle ranges from 8.919 GPH to 12.162 GPH, or 12.162 GPH to 17.027 GPH. In embodiments, where 38 spray nozzles are used, the flow through each spray nozzle ranges from 8.684 GPH to 11.842 GPH, or 11.842 GPH to 16.579 GPH. In embodiments, where 39 spray nozzles are used, the flow through each spray nozzle ranges from 8.462 GPH to 11.538 GPH, or 11.538 GPH to 16.154 GPH. In embodiments, where 40 spray nozzles are used, the flow through each spray nozzle ranges from 8.250 GPH to 11.250 GPH, or 11.250 GPH to 15.750 GPH. In embodiments, where 41 spray nozzles are used, the flow through each spray nozzle ranges 8.049 GPH to 10.976 GPH, or 10.976 GPH to 15.366 GPH. In embodiments, where 42 spray nozzles are used, the flow through each spray nozzle ranges from 7.857 GPH to 10.714 GPH, or 10.714 GPH to 15.000 GPH.

In embodiments, the drying chamber (KBG) is equipped with a heating jacket (KBJ), the heating jacket (KBJ) has a heat transfer medium inlet (KBK) and a heat transfer medium outlet (KBL). FIG. 14K shows the heating jacket (KBJ) installed over a portion of the drying chamber (KBG) creating an interior (KBJ1) having an annular space within which a heat transfer medium flows. A source of steam is provided to the heat transfer medium inlet (KBK). This steam may be a ninth steam supply (LDP) that is provided from a steam drum (LBE) as indicated on FIG. 14L.

In embodiments, a steam trap (KX6) is configured to accept steam, condensate, or non-condensable gases from the interior (KBJ1) of the heating jacket (KBJ) via a heat transfer medium outlet (KBL). Steam, condensate, or non-condensable gases are passed through the valve. During normal operation, only condensate flow through the steam trap (KX6). The condensate the flows through the steam trap (KX6) is the ninth condensate (LJB) that is passed to the condensate tank (LAP) as shown on FIG. 14L.

In embodiments, the steam trap (KX6) is a valve which automatically drains the condensate from the interior (KBJ1) of the heating jacket (KBJ) while remaining tight to live steam, or if necessary, allowing steam to flow at a controlled or adjusted rate. In embodiments, the steam trap (KX6) also allows non-condensable gases to pass through it while remaining tight to steam. In embodiments, the steam trap (KX6) is a mechanical trap such as a bucket trap or a floating ball trap. In embodiments, the steam trap (KX6) is a thermostatic trap such as a balanced pressure trap or a bimetallic trap. In embodiments, the steam trap (KX6) is a thermodynamic trap which work by using the difference in velocity between steam and condensate.

In embodiments, a steam flow control valve (KX1) is provided and is configured to regulate the flow of steam that is passes through the heating jacket (KBJ). The steam flow control valve (KX1) has a controller (KX2) which is configured to input or output a signal (KX3) to the computer (COMP). FIG. 14K shows the steam flow control valve (KX1) positioned to regulate steam that enters the heat transfer medium inlet (KBK) of the heating jacket (KBJ). It is to be noted that it is also contemplated that in certain instances, the steam flow control valve (KX1) may be positioned to regulate the heat transfer fluid that is discharged from the interior (KBJ1) of the heating jacket (KBJ) via the heat transfer medium outlet (KBL).

In embodiments, a flow sensor (KX4) is provided to measure the flow of heat transfer fluid that is passes through the heating jacket (KBJ). FIG. 14K shows the flow sensor (KX4) positioned to measure the flow of steam that enters the heat transfer medium inlet (KBK) of the heating jacket (KBJ). It is to be noted that it is also contemplated that in certain instances, the flow sensor (KX4) may be positioned to measure the heat transfer fluid (steam or steam condensate) that is discharged from the interior (KBJ1) of the heating jacket (KBJ) via the heat transfer medium outlet (KBL). The flow sensor (KX4) inputs a signal (KX5) to the computer (COMP).

In embodiment, the heating jacket (KBJ) is configured to maintain the wall (KWG) within the interior (KBG') drying chamber (KBG) at a constant temperature. In embodiments, the wall temperature ranges from one or more from the group consisting of between: 110 degrees Fahrenheit to 125 degrees Fahrenheit; 125 degrees Fahrenheit to 140 degrees Fahrenheit; 140 degrees Fahrenheit to 155 degrees Fahrenheit; 155 degrees Fahrenheit to 170 degrees Fahrenheit; 170 degrees Fahrenheit to 185 degrees Fahrenheit; 185 degrees Fahrenheit to 200 degrees Fahrenheit; 200 degrees Fahrenheit to 215 degrees Fahrenheit; 215 degrees Fahrenheit to 230 degrees Fahrenheit; 230 degrees Fahrenheit to 245 degrees Fahrenheit; 250 degrees Fahrenheit to 275 degrees Fahrenheit; 275 degrees Fahrenheit to 300 degrees Fahrenheit; 300 degrees Fahrenheit to 325 degrees Fahrenheit; 325 degrees Fahrenheit to 350 degrees Fahrenheit; 350 degrees Fahrenheit to 375 degrees Fahrenheit; 375 degrees Fahrenheit to 400 degrees Fahrenheit; 400 degrees Fahrenheit to 425 degrees Fahrenheit; 425 degrees Fahrenheit to 450 degrees Fahrenheit; 450 degrees Fahrenheit to 475 degrees Fahrenheit; 475 degrees Fahrenheit to 500 degrees Fahrenheit; 500 degrees Fahrenheit to 525 degrees Fahrenheit; 525 degrees Fahrenheit to 550 degrees Fahrenheit; 550 degrees Fahrenheit to 575 degrees Fahrenheit; 575 degrees Fahrenheit to 600 degrees Fahrenheit; 600 degrees Fahrenheit to 625 degrees Fahrenheit; 625 degrees Fahrenheit to 650 degrees Fahrenheit; 650 degrees Fahrenheit to 675 degrees Fahrenheit; 675 degrees Fahrenheit to 700 degrees Fahrenheit; 700 degrees Fahrenheit to 725 degrees Fahrenheit; 725 degrees Fahrenheit to 750 degrees Fahrenheit; 750 degrees Fahrenheit to 775 degrees Fahrenheit; and 775 degrees Fahrenheit to 800 degrees Fahrenheit.

In embodiments, it is desired to operate the heating jacket (KBJ) to maintain a wall (KWG) temperature sufficient to avoid sticking, deposition, burning of insect particulates or liquid upon surface of the wall (KWG). In embodiments, the surface of the wall (KWG) transfers heat into the interior (KBG) of the drying chamber (KBG). In embodiments, it is desired to operate the heating jacket (KBJ) in a manner that is sufficient to maintain a wall (KWG) temperature that is known to now fouling of the heat surface by sticking, deposition, burning of insect particulates or liquid upon surface of the wall (KWG). Powder build-up on the wall (KWG) within the interior (KBG') surface of the drying chamber (KBG) poses problems related to start-up and shutdown as discussed below.

In embodiments, the openings (KM4) of the screen (KM3) or mesh (KM3') are selected from one or more from the group consisting of 1680 microns to 2000 microns, 1410 microns to 1680 microns, 1190 microns to 1410 microns, 1000 microns to 1190 microns, 841 microns to 1000 microns, 707 microns to 841 microns, 595 microns to 707 microns, 500 microns to 595 microns, 400 microns to 500 microns, 354 microns to 400 microns, 297 microns to 354 microns, 250 microns to 297 microns, 210 microns to 250 microns, 177 microns to 210 microns, 149 microns to 177 microns, 125 microns to 149 microns, 105 microns to 125 microns, 88 microns to 105 microns, 74 microns to 88 microns, 63 microns to 74 microns, and 53 microns to 63 microns.

In embodiments, the temperature sensor (KBY) positioned on the first transfer conduit (KBW) in between the second output (KBU) of the spray dryer (KAP) and the first input (KCB) of the first separator (KCA) that measures the temperature of the insect and gas mixture (KBV) is preferably optimized to be maintained at 120 degrees Fahrenheit to 400 degrees Fahrenheit, or between 135 degrees Fahrenheit to 300 degrees Fahrenheit, or between 140 degrees Fahrenheit to 160 degrees Fahrenheit, or between 146 degrees Fahrenheit to 154 degrees Fahrenheit. The temperature sensor (KBY) inputs a signal (KBX) to the computer (COMP).

In embodiments, the temperature sensor (KBY) positioned on the first transfer conduit (KBW) in between the second output (KBU) of the spray dryer (KAP) and the first input (KCB) of the first separator (KCA) that measures the temperature of the insect and gas mixture (KBV) is preferably optimized to be maintained at 150 degrees Fahrenheit to 250 degrees Fahrenheit, but more preferably to 135 degrees Fahrenheit to 180 degrees Fahrenheit, but more preferably to 145 degrees Fahrenheit to 155 degrees Fahrenheit.

In embodiments, the temperature of the insect and gas mixture (KBV) leaving the drying chamber (KBG) ranges from one or more from the group consisting of between: 110 degrees Fahrenheit to 125 degrees Fahrenheit; 125 degrees Fahrenheit to 140 degrees Fahrenheit; 140 degrees Fahrenheit to 155 degrees Fahrenheit; 155 degrees Fahrenheit to 170 degrees Fahrenheit; 170 degrees Fahrenheit to 185 degrees Fahrenheit; 185 degrees Fahrenheit to 200 degrees Fahrenheit; 200 degrees Fahrenheit to 215 degrees Fahrenheit; 215 degrees Fahrenheit to 230 degrees Fahrenheit; 230 degrees Fahrenheit to 245 degrees Fahrenheit; 250 degrees Fahrenheit to 275 degrees Fahrenheit; 275 degrees Fahrenheit to 300 degrees Fahrenheit; 300 degrees Fahrenheit to 325 degrees Fahrenheit; 325 degrees Fahrenheit to 350 degrees Fahrenheit; 350 degrees Fahrenheit to 375 degrees Fahrenheit; and 375 degrees Fahrenheit to 400 degrees Fahrenheit.

In embodiments, the difference in temperature between the heated gas supply (KAG') and the insect and gas mixture (KBV) ranges from between 110 degrees Fahrenheit to 125 degrees Fahrenheit; 125 degrees Fahrenheit to 140 degrees Fahrenheit; 140 degrees Fahrenheit to 155 degrees Fahrenheit; 155 degrees Fahrenheit to 170 degrees Fahrenheit; 170 degrees Fahrenheit to 185 degrees Fahrenheit; 185 degrees Fahrenheit to 200 degrees Fahrenheit; 200 degrees Fahrenheit to 215 degrees Fahrenheit; 215 degrees Fahrenheit to 230 degrees Fahrenheit; 230 degrees Fahrenheit to 245 degrees Fahrenheit; 250 degrees Fahrenheit to 275 degrees Fahrenheit; 275 degrees Fahrenheit to 300 degrees Fahrenheit; 300 degrees Fahrenheit to 325 degrees Fahrenheit; 325 degrees Fahrenheit to 350 degrees Fahrenheit; 350 degrees Fahrenheit to 375 degrees Fahrenheit; 375 degrees Fahrenheit to 400 degrees Fahrenheit; 400 degrees Fahrenheit to 425 degrees Fahrenheit; 425 degrees Fahrenheit to 450 degrees Fahrenheit; 450 degrees Fahrenheit to 475 degrees Fahrenheit; 475 degrees Fahrenheit to 500 degrees Fahrenheit.

In embodiments, a pressure sensor (KBH) is configured to measure the pressure within the interior (KBG') of the drying chamber (KBG) and output a signal (KBI) to the computer (COMP). In embodiments, the ranges of pressure within the interior (KBG') of the drying chamber (KBG) is selected from one of more from the group consisting of: 1.5 pounds per square inch absolute (PSIA) 3 PSIA, 3 PSIA to 4.5 PSIA, 4.5 PSIA to 6 PSIA, 6 PSIA to 7.5 PSIA, 7.5 PSIA to 9 PSIA, 9 PSIA to 10.5 PSIA, 10.5 PSIA to 12 PSIA, 12 PSIA to 13.5 PSIA, 12 PSIA to 12.25 PSIA, 12.25 PSIA to 12.5 PSIA, 12.5 PSIA to 12.75PSIA, 12.75 PSIA to 13 PSIA, 13 PSIA to 13.25 PSIA, 13.25 PSIA to 13.5 PSIA, 13.5 PSIA to 13.75 PSIA, 13.75 PSIA to 14 PSIA, 14 PSIA to 14.25 PSIA, 14.25 PSIA to 14.5 PSIA, 14.5 PSIA to 14.75 PSIA, 14.75 PSIA to 15 PSIA, 15 PSIA to 16.5 PSIA, 16.5 PSIA to 18 PSIA, 18 PSIA to 19.5 PSIA, 19.5 PSIA to 21 PSIA, 21 PSIA to 22.5 PSIA, 22.5 PSIA to 24 PSIA, 24 PSIA to 25.5 PSIA, 25.5 PSIA to 27 PSIA, 27 PSIA to 28.5 PSIA, 28.5 PSIA to 30 PSIA, 30 PSIA to 31.5 PSIA, 31.5 PSIA to 33PSIA, 33 PSIA to 34.5 PSIA, and 34.5 PSIA to 36 PSIA.

In embodiments, the ranges of pressure within the interior (KBG') of the drying chamber (KBG) is selected from one of more from the group consisting of: between about 0.001 inches of water to about 0.002 inches of water; between about 0.002 inches of water to about 0.003 inches of water; between about 0.003 inches of water to about 0.006 inches of water; between about 0.006 inches of water to about 0.012 inches of water; between about 0.012 inches of water to about 0.024 inches of water; between about 0.024 inches of water to about 0.050 inches of water; between about 0.050 inches of water to about 0.075 inches of water; between about 0.075 inches of water to about 0.150 inches of water; between about 0.150 inches of water to about 0.300 inches of water; between about 0.300 inches of water to about 0.450 inches of water; between about 0.450 inches of water to about 0.473 inches of water; between about 0.473 inches of water to about 0.496 inches of water; between about 0.496 inches of water to about 0.521 inches of water; between about 0.521 inches of water to about 0.547 inches of water; between about 0.547 inches of water to about 0.574 inches of water; between about 0.574 inches of water to about 0.603 inches of water; between about 0.603 inches of water to about 0.633 inches of water; between about 0.633 inches of water to about 0.665 inches of water; between about 0.665 inches of water to about 0.698 inches of water; between about 0.698 inches of water to about 0.733 inches of water; between about 0.733 inches of water to about 0.770 inches of water; between about 0.770 inches of water to about 0.808 inches of water; between about 0.808 inches of water to about 0.849 inches of water; between about 0.849 inches of water to about 0.891 inches of water; between about 0.891 inches of water to about 0.936 inches of water; between about 0.936 inches of water to about 0.982 inches of water; between about 0.982 inches of water to about 1.031 inches of water; between about 1.031 inches of water to about 1.083 inches of water; between about 1.083 inches of water to about 1.137 inches of water; between about 1.137 inches of water to about 1.194 inches of water; between about 1.194 inches of water to about 1.254 inches of water; between about 1.254 inches of water to about 1.316 inches of water; between about 1.316 inches of water to about 1.382 inches of water; between about 1.382 inches of water to about 1.451 inches of water; between about 1.451 inches of water to about 1.524 inches of water; between about 1.524 inches of water to about 2.286 inches of water; between about 2.286 inches of water to about 3.429 inches of water; between about 3.429 inches of water to about 5.143 inches of water; between about 5.143 inches of water to about 7.715 inches of water; between about 7.715 inches of water to about 11.572 inches of water; between about 11.572 inches of water to about 17.358 inches of water; between about 17.358 inches of water to about 26.037 inches of water; between about 26.037 inches of water to about 39.055 inches of water; between about 39.055 inches of water to about 58.582 inches of water; between about 58.582 inches of water to about 87.873 inches of water; between about 87.873 inches of water to about 131.810 inches of water; between about 131.810 inches of water to about 197.715 inches of water; between about 197.715 inches of water to about 296.573 inches of water; or, between about 296.573 inches of water to about 400 inches of water.

Spray dried insects (KBT) may be removed from the first output (KB S) of the drying chamber (KBG). In embodiments, the insects (KBT) removed from the first output (KB S) of the drying chamber (KBG) may be solid or may contain liquid. In embodiments, the insects (KBT) removed from the first output (KB S) of the drying chamber (KBG) are either too wet or too large, or both, to be evacuated from the second output (KBU) of the drying chamber (KBG). In embodiments, the insects (KBT) removed from the first output (KBS) of the drying chamber (KBG) are routed to the mixing tank (G15) on FIG. 14G or to the interior (6A3) insect tank (6A2) of FIG. 14K. In embodiments, the insects (KBT) removed from the first output (KB S) may be mixed with one or more stream of separated insects, such first separated insects (KCG), second separated insects (KCP), third separated insects (KCV), a fourth separated insects (KCX), or a large insect particulate portion (KCY) to form combined insects (KM7) as shown in FIG. 14K.

In embodiments, the vibrator (KBN) is connected to the spray dryer (KAP) or drying chamber (KBG) via a connection (KBR). In embodiments, the spray dryer (KAP) or drying chamber (KBG) is equipped with a vibrator (KBN). In embodiments, a vibrator (KBN) vibrates at least a portion of the spray dryer (KAP) or drying chamber (KBG) to aide in removal of the spray dried insects (KBT) from the first output (KBS). In embodiments, the vibrator (KBN) is pneumatic. In embodiments, the vibrator (KBN) operates at a vibration range that is selected from one or more from the group consisting of 3,000 vibrations per minute (VPM) to 4000 VPM, 4,000 VPM to 5,000 VPM, 5,000 VPM to 5,500 VPM, 5,500 VPM to 6,000 VPM, 6,000 VPM to 6,500 VPM, 6,500 VPM to 7,000 VPM, 7,000 VPM to 7,500 VPM, 7,500 VPM to 8,000 VPM, 8,000 VPM to 8,500 VPM, 8,500 VPM to 9,000 VPM, 9,000 VPM to 9,500 VPM, 9,500 VPM to 10,000 VPM, 10,000 VPM to 15,000 VPM, 15,000 VPM to 20,000 VPM, 20,000 VPM to 25,000 VPM, 25,000 VPM to 30,000 VPM, 30,000 VPM to 35,000 VPM, 35,000 VPM to 40,000 VPM, 40,000 VPM to 45,000 VPM, and 45,000 VPM to 50,000 VPM. In embodiments, the vibrator (KBN) has a motor (KBO) with a controller (KBP) that is configured to input or output a signal (KBQ) to the computer (COMP).

In embodiments, the small insect particulate portion (KCW) has a water content that ranges from one or more from the group selected from 0.05 weight percent of water to 0.1 weight percent of water, 0.1 weight percent of water to 0.2 weight percent of water, 0.2 weight percent of water to 0.4 weight percent of water, 0.4 weight percent of water to 0.8 weight percent of water, 0.8 weight percent of water to 1 weight percent of water, 1 weight percent of water to 2 weight percent of water, 2 weight percent of water to 3 weight percent of water, 3 weight percent of water to 4 weight percent of water, 4 weight percent of water to 5 weight percent of water, 5 weight percent of water to 6 weight percent of water, 6 weight percent of water to 7 weight percent of water, 7 weight percent of water to 8 weight percent of water, 8 weight percent of water to 9 weight percent of water, 9 weight percent of water to 10 weight percent of water, 10 weight percent of water to 11 weight percent of water, 11 weight percent of water to 12 weight percent of water, 12 weight percent of water to 13 weight percent of water, 13 weight percent of water to 14 weight percent of water, 14 weight percent of water to 15 weight percent of water, 15 weight percent of water to 16 weight percent of water, 16 weight percent of water to 17 weight percent of water, 17 weight percent of water to 18 weight percent of water, 18 weight percent of water to 19 weight percent of water, and 19 weight percent of water to 20 weight percent of water.

In embodiments, the small insect particulate portion (KCW) has a liquid content that ranges from one or more from the group selected from 0.05 weight percent of liquid to 0.1 weight percent of liquid, 0.1 weight percent of liquid to 0.2 weight percent of liquid, 0.2 weight percent of liquid to 0.4 weight percent of liquid, 0.4 weight percent of liquid to 0.8 weight percent of liquid, 0.8 weight percent of liquid to 1 weight percent of liquid, 1 weight percent of liquid to 2 weight percent of liquid, 2 weight percent of liquid to 3 weight percent of liquid, 3 weight percent of liquid to 4 weight percent of liquid, 4 weight percent of liquid to 5 weight percent of liquid, 5 weight percent of liquid to 6 weight percent of liquid, 6 weight percent of liquid to 7 weight percent of liquid, 7 weight percent of liquid to 8 weight percent of liquid, 8 weight percent of liquid to 9 weight percent of liquid, 9 weight percent of liquid to 10 weight percent of liquid, 10 weight percent of liquid to 11 weight percent of liquid, 11 weight percent of liquid to 12 weight percent of liquid, 12 weight percent of liquid to 13 weight percent of liquid, 13 weight percent of liquid to 14 weight percent of liquid, 14 weight percent of liquid to 15 weight percent of liquid, 15 weight percent of liquid to 16 weight percent of liquid, 16 weight percent of liquid to 17 weight percent of liquid, 17 weight percent of liquid to 18 weight percent of liquid, 18 weight percent of liquid to 19 weight percent of liquid, and 19 weight percent of liquid to 20 weight percent of liquid.

In embodiments, the large insect particulate portion (KCY) has a water content that ranges from one or more from the group selected from 0.05 weight percent of water to 0.1 weight percent of water, 0.1 weight percent of water to 0.2 weight percent of water, 0.2 weight percent of water to 0.4 weight percent of water, 0.4 weight percent of water to 0.8 weight percent of water, 0.8 weight percent of water to 1 weight percent of water, 1 weight percent of water to 2 weight percent of water, 2 weight percent of water to 3 weight percent of water, 3 weight percent of water to 4 weight percent of water, 4 weight percent of water to 5 weight percent of water, 5 weight percent of water to 6 weight percent of water, 6 weight percent of water to 7 weight percent of water, 7 weight percent of water to 8 weight percent of water, 8 weight percent of water to 9 weight percent of water, 9 weight percent of water to 10 weight percent of water, 10 weight percent of water to 11 weight percent of water, 11 weight percent of water to 12 weight percent of water, 12 weight percent of water to 13 weight percent of water, 13 weight percent of water to 14 weight percent of water, 14 weight percent of water to 15 weight percent of water, 15 weight percent of water to 16 weight percent of water, 16 weight percent of water to 17 weight percent of water, 17 weight percent of water to 18 weight percent of water, 18 weight percent of water to 19 weight percent of water, and 19 weight percent of water to 20 weight percent of water.

In embodiments, the large insect particulate portion (KCY) has a liquid content that ranges from one or more from the group selected from 0.05 weight percent of liquid to 0.1 weight percent of liquid, 0.1 weight percent of liquid to 0.2 weight percent of liquid, 0.2 weight percent of liquid to 0.4 weight percent of liquid, 0.4 weight percent of liquid to 0.8 weight percent of liquid, 0.8 weight percent of liquid to 1 weight percent of liquid, 1 weight percent of liquid to 2 weight percent of liquid, 2 weight percent of liquid to 3 weight percent of liquid, 3 weight percent of liquid to 4 weight percent of liquid, 4 weight percent of liquid to 5 weight percent of liquid, 5 weight percent of liquid to 6 weight percent of liquid, 6 weight percent of liquid to 7 weight percent of liquid, 7 weight percent of liquid to 8 weight percent of liquid, 8 weight percent of liquid to 9 weight percent of liquid, 9 weight percent of liquid to 10 weight percent of liquid, 10 weight percent of liquid to 11 weight percent of liquid, 11 weight percent of liquid to 12 weight percent of liquid, 12 weight percent of liquid to 13 weight percent of liquid, 13 weight percent of liquid to 14 weight percent of liquid, 14 weight percent of liquid to 15 weight percent of liquid, 15 weight percent of liquid to 16 weight percent of liquid, 16 weight percent of liquid to 17 weight percent of liquid, 17 weight percent of liquid to 18 weight percent of liquid, 18 weight percent of liquid to 19 weight percent of liquid, and 19 weight percent of liquid to 20 weight percent of liquid.

In embodiments, the insects (KBT) removed the drying chamber (KBG) have a water content that ranges from one or more from the group selected from 0.05 weight percent of water to 0.1 weight percent of water, 0.1 weight percent of water to 0.2 weight percent of water, 0.2 weight percent of water to 0.4 weight percent of water, 0.4 weight percent of water to 0.8 weight percent of water, 0.8 weight percent of water to 1 weight percent of water, 1 weight percent of water to 2 weight percent of water, 2 weight percent of water to 3 weight percent of water, 3 weight percent of water to 4 weight percent of water, 4 weight percent of water to 5 weight percent of water, 5 weight percent of water to 6 weight percent of water, 6 weight percent of water to 7 weight percent of water, 7 weight percent of water to 8 weight percent of water, 8 weight percent of water to 9 weight percent of water, 9 weight percent of water to 10 weight percent of water, 10 weight percent of water to 11 weight percent of water, 11 weight percent of water to 12 weight percent of water, 12 weight percent of water to 13 weight percent of water, 13 weight percent of water to 14 weight percent of water, 14 weight percent of water to 15 weight percent of water, 15 weight percent of water to 16 weight percent of water, 16 weight percent of water to 17 weight percent of water, 17 weight percent of water to 18 weight percent of water, 18 weight percent of water to 19 weight percent of water, and 19 weight percent of water to 20 weight percent of water.

In embodiments, the insects (KBT) removed the drying chamber (KBG) have a liquid content that ranges from one or more from the group selected from 0.05 weight percent of liquid to 0.1 weight percent of liquid, 0.1 weight percent of liquid to 0.2 weight percent of liquid, 0.2 weight percent of liquid to 0.4 weight percent of liquid, 0.4 weight percent of liquid to 0.8 weight percent of liquid, 0.8 weight percent of liquid to 1 weight percent of liquid, 1 weight percent of liquid to 2 weight percent of liquid, 2 weight percent of liquid to 3 weight percent of liquid, 3 weight percent of liquid to 4 weight percent of liquid, 4 weight percent of liquid to 5 weight percent of liquid, 5 weight percent of liquid to 6 weight percent of liquid, 6 weight percent of liquid to 7 weight percent of liquid, 7 weight percent of liquid to 8 weight percent of liquid, 8 weight percent of liquid to 9 weight percent of liquid, 9 weight percent of liquid to 10 weight percent of liquid, 10 weight percent of liquid to 11 weight percent of liquid, 11 weight percent of liquid to 12 weight percent of liquid, 12 weight percent of liquid to 13 weight percent of liquid, 13 weight percent of liquid to 14 weight percent of liquid, 14 weight percent of liquid to 15 weight percent of liquid, 15 weight percent of liquid to 16 weight percent of liquid, 16 weight percent of liquid to 17 weight percent of liquid, 17 weight percent of liquid to 18 weight percent of liquid, 18 weight percent of liquid to 19 weight percent of liquid, and 19 weight percent of liquid to 20 weight percent of liquid.

In embodiments, the spray dryer (KAP) drying chamber (KBG) is configured to mix the heated gas supply (KAG') with the insect liquid mixture (H39, KAS) to form an insect and gas mixture (KBV). The insect and gas mixture (KBV) is discharged from the spray dryer (KAP) via a second output (KBU). The insect and gas mixture (KBV) include a spray dried insect portion (KBV'), a vapor portion (KBV"), and a gas portion (KBV'"). In embodiments, the spray dried insect portion (KBV') may include solid particulates. In embodiments, the vapor portion (KBV") is steam. In embodiments, the vapor portion (KBV") may include the vapor-phase of the liquid within the insect liquid mixture (H39, KAS) which may include water. In other embodiments, the vapor portion (KBV") may include the vapor-phase of the liquid within the insect liquid mixture (H39, KAS) which may include an acid, alcohol, diglycerides, esters, ethanol, butanol, n-butanol, sec-butanol, isobutanol, tert-butanol, ethyl acetate, glycerin, glycerol, hexane, hydrocarbon, insect lipids, isopropyl alcohol, methanol, Monoglycerides, oil, and solvent. In embodiments, the gas portion (KBV'") includes whatever was within the gas supply (KAG).

The spray dryer (KAP) has a second output (KBU) that is configured to discharge an insect and gas mixture (KBV) from the interior (KBG') of the drying chamber (KBG). In embodiments, the insect and gas mixture (KBV) has a spray dried insect portion (KBV'), vapor portion (KBV"), and a gas portion (KBV'"). The second output (KBU) of the spray dryer (KAP) is connected to the first-first input (KCB) of the first separator (KCA) via a first transfer conduit (KBW). In embodiments, the first separator (KCA) is a cyclone or a filter. FIG. 14K shows the first separator (KCA) as a cyclone.

The first transfer conduit (KBW) transfers the insect and gas mixture (KBV) from the interior (KBG') of the drying chamber (KBG) to the first separator (KCA). The first separator (KCA) separates first separated insects (KCG) from the insect and gas mixture (KBV) to create a first insect depleted gas stream (KCD). The first insect depleted gas stream (KCD) is discharged from the first separator (KCA) via a first-first output (KCC).

The first separator (KCA) has: a first-first input (KCB) for receiving the insect and gas mixture (KBV) from the spray dryer (KAP), a first-first output (KCC) for evacuating the first insect depleted gas stream (KCD) towards the second separator (KCI), and a first-second output (KCF) for transferring first separated insects (KCG) towards the third separator (KCR). The first insect depleted gas stream (KCD) is transferred from the first-first output (KCC) to the second-first input (KCK) of the second separator (KCI) via a second transfer conduit (KCE).

The first insect depleted gas stream (KCD) has a reduced amount of insects relative to the insect and gas mixture (KBV). The first insect depleted gas stream (KCD) has a reduced amount of spray dried insect portion (KBV') relative to the insect and gas mixture (KBV). The second transfer conduit (KCE) is connected at one end to the first-first output (KCC) of the first separator (KCA) and at another end to the second-first input (KCK) of the second separator (KCI).

The first separated insects (KCG) that are separated from the insect and gas mixture (KBV) are discharged from the first separator (KCA) via the first-second output (KCF). The third-first input (KCS) of the third separator (KCR) is configured to receive the first separated insects (KCG) via a first dipleg (KCH). The first dipleg (KCH) is connected at one end to the first-second output (KCF) of the first separator (KCA) and at a second end to the third-first input (KCS) of the third separator (KCR). The first separated insects (KCG) includes at least a portion of the spray dried insect portion (KBV') that were separated from the insect and gas mixture (KBV).

The second separator (KCI) separates second separated insects (KCP) from the first insect depleted gas stream (KCD) to create a second insect depleted gas stream (KCM). The second insect depleted gas stream (KCM) has a reduced amount of insects relative to the first insect depleted gas stream (KCD). The second insect depleted gas stream (KCM) has a reduced amount of spray dried insect portion (KBV') relative to the first insect depleted gas stream (KCD).

In embodiments, the second separator (KCI) is a cyclone or a filter. FIG. 14K shows the second separator (KCI) as a cyclone. The second insect depleted gas stream (KCM) is discharged from the second separator (KCI) via a second-first output (KCJ).

The second separator (KCI) has: a second-first input (KCK) for receiving the first insect depleted gas stream (KCD) from the first separator (KCA), a second-first output (KCJ) for evacuating the second insect depleted gas stream (KCM) towards the fourth separator (KCZ), and a second-second output (KCO) for transferring second separated insects (KCP) towards the third separator (KCR). The second insect depleted gas stream (KCM) is transferred from the second-first output (KCJ) to the fourth-first input (KDA) of the fourth separator (KCZ) via a third transfer conduit (KCN). The third transfer conduit (KCN) is connected at one end to the second-first output (KCJ) of the second separator (KCI) and at another end to the fourth-first input (KDA) of the fourth separator (KCZ).

The second separated insects (KCP) that are separated from the first insect depleted gas stream (KCD) are discharged from the second separator (KCI) via the second-second output (KCO). The third-first input (KCS) of the third separator (KCR) is configured to receive the second separated insects (KCP) via a second dipleg (KCQ). The second dipleg (KCQ) is connected at one end to the second-second output (KCO) of the second separator (KCI) and at a second end to the third-first input (KCS) of the third separator (KCR). The second separated insects (KCP) includes at least a portion of the insects that were separated from the first insect depleted gas stream (KCD). The second separated insects (KCP) includes at least a portion of the spray dried insect portion (KBV') that were separated from the first insect depleted gas stream (KCD).

The fourth separator (KCZ) separates an additional separated insects (KDF) from the second insect depleted gas stream (KCM) to create a third insect depleted gas stream (KDC). The third insect depleted gas stream (KDC) has a reduced amount of insects relative to the second insect depleted gas stream (KCM). The third insect depleted gas stream (KDC) has a reduced amount of spray dried insect portion (KBV') relative to the second insect depleted gas stream (KCM). In embodiments, the fourth separator (KCZ) is a cyclone, filter, scrubber, or electrostatic precipitator.

FIG. 14K shows the second separator (KCI) as an electrostatic precipitator. The electrostatic precipitator has an electrode (KM8) and a power supply (KM9) and is configured to separate insects from the second insect depleted gas stream (KCM). The electrode (KM8) and a power supply (KM9) apply an electrostatic charge to the second insect depleted gas stream (KCM) as it passes through the fourth separator (KCZ).

In other embodiments, the fourth separator (KCZ) is a scrubber. The scrubber, is preferably a vertically oriented cylindrical, or rectangular, pressure vessel having a lower section, and an upper section, along with a central section that contains a quantity of packed media either comprising raschig rings, pall rings, berl saddles, intalox packing, metal structured grid packing, hollow spherical packing, high performance thermoplastic packing, structured packing, synthetic woven fabric, or ceramic packing, or the like, wherein media is supported upon a suitable support grid system commonplace to industrial chemical equipment systems. The upper section of the scrubber preferably contains a demister to enhance the removal of liquid droplets entrained in a vapor stream and to minimize carry-over losses of the sorption liquid. This demister is also positioned above the scrubber spray nozzle system, comprised of a plurality of spray nozzles, or spray balls, that introduce and substantially equally distribute the scrubbing absorption liquid to the scrubber onto the scrubber's central packing section, so it may gravity-flow down through the scrubber central section.

As the second insect depleted gas stream (KCM) passes up through the internal packing of the scrubber, excess steam within the additional separated insects (KDF) comes into intimate contact with water and/or a solvent, which are cooled prior to being introduced to the upper section of the scrubber through the scrubber spray nozzle system. Steam from within the second insect depleted gas stream (KCM) is condensed into a liquid.

The third insect depleted gas stream (KDC) is discharged from the fourth separator (KCZ) via a fourth-first input (KDA). The fourth separator (KCZ) has: fourth-first input (KDA) for receiving the second insect depleted gas stream (KCM) from the second separator (KCI), a fourth-first output (KDB) for evacuating the third insect depleted gas stream (KDC) towards the condenser (KDH), and a fourth-second output (KDE) for transferring additional separated insects (KDF) towards the third separator (KCR).

The third insect depleted gas stream (KDC) is transferred from the fourth-first output (KDB) to the gas-vapor inlet (KDP) of the condenser (KDH) via a fourth transfer conduit (KDD). The fourth transfer conduit (KDD) is connected at one end to the fourth-second output (KDE) of the fourth separator (KCZ) and at another end to the gas-vapor inlet (KDP) of the condenser (KDH). The additional separated insects (KDF) that are separated from the second insect depleted gas stream (KCM) are discharged from the fourth separator (KCZ) via the fourth-second output (KDE). In embodiments, the third-first input (KCS) of the third separator (KCR) is configured to receive at least a portion of the additional separated insects (KDF) via a fifth transfer conduit (KDG). The fifth transfer conduit (KDG) is connected at one end to the fourth-second output (KDE) of the fourth separator (KCZ) and at a second end to the third-first input (KCS) of the third separator (KCR).

The third insect depleted gas stream (KDC) includes at least a portion of the vapor portion (KBV") or gas portion (KBV''') of the insect and gas mixture (KBV) that was discharged from the drying chamber (KBG). The additional separated insects (KDF) includes at least a portion of the insects that were separated from the first insect depleted gas stream (KCD). The additional separated insects (KDF) include at least a portion of the insects that were separated from the second insect depleted gas stream (KCM). The additional separated insects (KDF) includes at least a portion of the spray dried insect portion (KBV') that were separated from the second insect depleted gas stream (KCM).

In embodiments, the additional separated insects (KDF) have a size range that is selected from one or more from the group consisting of 0.001 nanometers to 0.1 nanometers, 0.1 nanometers to 0.5 nanometers, 0.5 nanometers to 1 nanometer, 1 nanometer to 5 nanometers, 5 nanometers to 10 nanometers, 10 nanometers to 15 nanometers, 15 nanometers to 20 nanometers, 20 nanometers to 25 nanometers, 25 nanometers to 30 nanometers, 30 nanometers to 35 nanometers, 35 nanometers to 40 nanometers, 40 nanometers to 45 nanometers, 45 nanometers to 50 nanometers, 50 nanometers to 55 nanometers, 55 nanometers to 60 nanometers, 60 nanometers to 65 nanometers, 65 nanometers to 70 nanometers, 70 nanometers to 75 nanometers, 75 nanometers to 80 nanometers, 80 nanometers to 85 nanometers, 85 nanometers to 90 nanometers, 90 nanometers to 95 nanometers, 95 nanometers to 100 nanometers, 100 nanometers to 200 nanometers, 200 nanometers to 300 nanometers, 300 nanometers to 400 nanometers, 400 nanometers to 500 nanometers, 500 nanometers to 600 nanometers, 600 nanometers to 700 nanometers, 700 nanometers to 800 nanometers, and 800 nanometers to 900 nanometers.

In embodiments, the additional separated insects (KDF) have a particle size distribution (PSD) that has a lesser or smaller PSD relative to the small insect particulate portion (KCW) separated in the solid-solid separator (SSS). In embodiments, the additional separated insects (KDF) have a particle size distribution (PSD) that has a lesser or smaller PSD relative to the large insect particulate portion (KCY) separated in the solid-solid separator (SSS). In embodiments, the particle size distribution of the small insect particulate portion (KCW) is lesser or smaller than the particle size distribution of the large insect particulate portion (KCY).

In embodiments, the small insect particulate portion (KCW) have a size range that is selected from one or more from the group consisting of 1 microns to 5 microns, 5 microns to 10 microns, 10 microns to 30 microns, 30 microns to 50 microns, 50 microns to 70 microns, 70 microns to 90 microns, 90 microns to 110 microns, 110 microns to 130 microns, 130 microns to 150 microns, 150 microns to 170 microns, 170 microns to 190 microns, 190 microns to 210 microns, 210 microns to 230 microns, and 230 microns to 250 microns.

In embodiments, the large insect particulate portion (KCY) have a size range that is selected from one or more from the group consisting of 50 microns to 60 microns, 60 microns to 70 microns, 70 microns to 80 microns, 80 microns to 90 microns, 90 microns to 100 microns, 100 microns to 150 microns, 150 microns to 200 microns, 200 microns to 250 microns, 250 microns to 300 microns, 300 microns to 350 microns, 350 microns to 400 microns, 400 microns to 450 microns, 450 microns to 500 microns, 500 microns to 550 microns, 550 microns to 600 microns, 600 microns to 650 microns, 650 microns to 700 microns, 700 microns to 750 microns, 750 microns to 800 microns, 800 microns to 850 microns, 850 microns to 900 microns, 900 microns to 950 microns, and 950 microns to 1,000 microns.

As shown in FIG. 14K the third separator (KCR) accepts first separated insects (KCG) from the first separator (KCA), and second separated insects (KCP) from the second separator (KCI), and optionally a portion of the additional separated insects (KDF) from the fourth separator (KCZ), and separates at least a small insect particulate portion (KCW) and a large insect particulate portion (KCY) therefrom. In embodiments, the small insect particulate portion (KCW) and a large insect particulate portion (KCY) are oligosaccharides or are hydrolyzed-biopolymers, as discussed above.

In embodiments, the third separator (KCR) includes solid-solid separator (SSS). In embodiments, the third separator (KCR) includes a sifter as shown in FIG. 14K. In embodiments, the third separator (KCR) includes a filter. In embodiments, the third separator (KCR) has a third-first input (KCS) for receiving: first separated insects (KCG) via the first dipleg (KCH), second separated insects (KCP) via the second dipleg (KCQ), and additional separated insects (KDF) via the fifth transfer conduit (KDG). In embodiments, the third separator (KCR) has a third-first output (KCT) for discharging a third separated insects (KCV) which include a small insect particulate portion (KCW). In embodiments, the small insect particulate portion (KCW) may be transferred to the multifunctional composition tank (6F1) on FIG. 14A, mixing tank (C15) on FIG. 14C, or to the interior (6A3) insect tank (6A2) of FIG. 14K.

In embodiments, the third separator (KCR) has a third-second output (KCU) for discharging a fourth separated insects (KCX) which include a large insect particulate portion (KCY). In embodiments, the large insect particulate portion (KCY) may be transferred to the mixing tank (G15) as shown on FIG. 14G. In embodiments, the large insect particulate portion (KCY) may be transferred to the multifunctional composition tank (6F1) on FIG. 14A, mixing tank (C15) on FIG. 14C, or to the interior (6A3) insect tank (6A2) of FIG. 14K. In embodiments, the third separator (KCR) separates a small insect particulate portion (KCW) from a large insect particulate portion (KCY) using a screen (KM3) or a mesh (KM3'). The screen (KM3) or mesh (KM3') have openings (KM4) that permit the small insect particulate portion (KCW) to pass through the openings (KM4). The openings (KM4) in the screen (KM3) or mesh (KM3') are too small for the large insect particulate portion (KCY) to pass through.

In embodiments, the openings (KM4) in the screen (KM3) or mesh (KM3') include Unites States Sieve size number 18, 20, 25, 30, 35, 40, 45, 50, 60, 70, 80, 100, 120, 140, 170, 200, 230, 270, 325, or 400. In embodiments, the openings (KM4) in the screen (KM3) or mesh (KM3') have a size range that is selected from one or more from the group consisting of 37 microns to 44 microns, 44 microns to 53 microns, 53 microns to 63 microns, 63 microns to 74 microns, 74 microns to 88 microns, 88 microns to 105 microns, 105 microns to 125 microns, 125 microns to 149 microns, 149 microns to 177 microns, 177 microns to 210 microns, 210 microns to 250 microns, 250 microns to 297 microns, 297 microns to 354 microns, 354 microns to 420 microns, 420 microns to 500 microns, 500 microns to 595 microns, 595 microns to 707 microns, 707 microns to 841 microns, and 841 microns to 1,000 microns.

In embodiments, the screen (KM3) or mesh (KM3') may be cylindrical and located within a first chamber (KM5). In embodiments, the third separator (KCR) has a third-first input (KCS) that is configured to receive particulate insects that include first separated insects (KCG), second separated insects (KCP), and optionally additional separated insects (KDF). An auger (KM1) is configured to transfer the particulate insects from the third-first input (KCS) to a screen (KM3) or mesh (KM3') located within the first chamber (KM5) of the third separator (KCR). The auger (KM1) is equipped with a motor (KM2) that may be operated by the computer (COMP). The particulate insects transferred from the third-first input (KCS) are sifted using a cylindrical screen (KM3) or mesh (KM3') that is located within the first chamber (KM5).

The third-first output (KCT) is located at the bottom of the first chamber (KM5). The small insect particulate portion (KCW) may be removed from the third separator (KCR) via the third-first output (KCT) located in the first chamber (KM5). The large insect particulate portion (KCY) that are too large to pass through openings (KM4) of the screen (KM3) or a mesh (KM3') are transferred from the first chamber (KM5) to the second chamber (KM6) of the third separator (KCR). Since the openings (KM4) in the screen (KM3) or mesh (KM3') within the first chamber (KM5) are too small for the large insect particulate portion (KCY) to pass through, the large insect particulate portion (KCY) is transferred from the first chamber (KM5) to the second chamber (KM6) of the third separator (KCR). The large insect particulate portion (KCY) are removed from the second chamber (KM6) of the third separator (KCR) via the third-second output (KCU).

In embodiments, the sifter is provided by the Kason Corporation. In embodiments, sifter includes a vibratory screener or a centrifugal sifter. In embodiments, the sifter is provided by Kason Corporation and includes a VIBRO SCREEN® Circular Vibratory Screener and Separator, a CENTRI-SIFTER™ High Capacity Screener and Separator, a VIBRO-BED™ Circular Vibratory Fluid Bed Processor, or a CROSS-FLO High Capacity Static Sieve Screener and Separator.

In embodiments, the motor (KM2) of the third separator (KCR) is driven by a belt and ranges from 0.75 horsepower to 6 horsepower. In embodiments, the motor (KM2) of the third separator (KCR) is driven by a belt and ranges from 0.56 kilowatts to 4.48 kilowatts. In embodiments, the motor (KM2) of the third separator (KCR) is not driven by a belt and ranges from 0.5 horsepower to 4 horsepower. In embodiments, the motor (KM2) of the third separator (KCR) is driven by a belt and ranges from 0.37 kilowatts to 2.98 kilowatts.

The fourth separator (KCZ) is connected to the condenser (KDH) via a fourth transfer conduit (KDD). The third insect depleted gas stream (KDC) is transferred through the fourth transfer conduit (KDD) and enters the condenser (KDH). The third insect depleted gas stream (KDC) includes the vapor portion (KBV'') and gas portion (KBV''') that were transferred from the spray dryer (KAP).

The condenser (KDH) condenses the vapor portion (KBV'') which may include steam. Liquid is formed from condensing the vapor portion (KBV'') of the third insect depleted gas stream (KDC) to form process condensate (KDO). Liquid is formed from condensing steam contained within the third insect depleted gas stream (KDC) to form process condensate (KDO). The process condensate (KDO) is discharged from the condenser (KDH) via a liquid output (KDR).

The gas portion (KBV''') of the third insect depleted gas stream (KDC) is not condensed within the condenser (KDH) and is instead released from the condenser (KDH) as a via the gas output (KDQ). The non-condensables (KDT) includes the gas portion (KBV''') of the third insect depleted gas stream (KDC) and may include gas, air, nitrogen, carbon dioxide. The non-condensables (KDT) leave the gas output (KDQ) of the condenser (KDH) and are routed to a vacuum (KDM) via a gas transfer conduit (KDS).

In embodiments, the vacuum (KDM) is a vacuum pump, fan, or an eductor. A gas exhaust (KDN) is discharged from the vacuum (KDM). The gas exhaust (KDN) includes non-condensables (KDT) or the gas portion (KBV''') of the third insect depleted gas stream (KDC) is not condensed within the condenser (KDH).

The condenser (KDH) is provided with a cooling water input (KDI) and a cooling water output (KDK). The cooling water input (KDI) is configured to accept a cooling water supply (KDJ) and the cooling water output (KDK) is configured to discharge a cooling water return (KDL). The cooling water supply (KDJ) is configured to condense a portion of the vapor that enters through the gas-vapor inlet (KDP).

Evaporator Operation: The systems shown in FIGS. 14G, 14H, and 14K, specifically, the biocatalyst mixing module (14G), exoskeleton separation module (14H), and liquid separation module (LSM) can operate in a plurality of modes of operation, including:
(1) preparation of the insect liquid mixture (H39, KAS);
(2) start-up;
(3) normal operation;
(4) emergency shut-down;
(5) resuming operations after the emergency shut-down.

As seen in FIG. 14K, the liquid separation module (LSM) is equipped with a start-up/shut-down water system (KEZ). The purpose of the start-up/shut-down water system (KEZ) is to make a pressurized and optionally heated supply of water immediately available to the evaporator (KAO) whenever necessary. It is also desired to be able to mix a known flow of treated, filtered, start-up/shut-down water (KEO) in with the insect liquid mixture (H39, KAS) to be used for start-up, shut-down or maintenance purposes such as cleaning.

A start-up/shut-down water tank (KEA) is provided and is configured to accept a stream of water (KEB) from the output of the polishing unit (G41) shown in FIG. 14G. The water (KEB) transferred to the interior (KEA') of the start-up/shut-down water tank (KEA) has passed through a filter (G23), activated carbon (G24), and/or an adsorbent (G25), first water treatment unit (G10), second water treatment unit (G11), third water treatment unit (G12), and a cation (G39), an anion (G40), and a polishing unit (G41). The polishing unit (G41) may be any type of conceivable device to improve the water quality such as an ultraviolet unit, ozone unit, microwave unit, filter, or the like.

The start-up/shut-down water tank (KEA) may be equipped with a level sensor (KES) that sends a signal (KET) to the computer (COMP). A level control valve (KEU) may be used to control the amount of water (KEB) that is transferred to the interior (KEA') of the start-up/shut-down water tank (KEA). The level control valve (KEU) may be equipped with a controller (KEV) that is configured to input or output a signal (KEW) to the computer (COMP). The computer (COMP), level control valve (KEU), and level sensor (KES) may be used together in a level control loop to maintain a constant or batch supply of water to the interior (KEA') of the start-up/shut-down water tank (KEA).

In embodiments, a start-up heat exchanger (KEP) is configured to heat the water (KEB) that will be transferred to the evaporator (KAO). In embodiments, a start-up heat exchanger (KEP) is configured to heat the water (KEB) that will be transferred to the evaporator (KAO), spray dryer (KAP), rotary atomizer (KAU), spray nozzle (KBC) or plurality of spray nozzles (KBC), or openings (KBC) or plurality of openings (KBC) within the disc (KBB) of the rotary atomizer (KAU). the purpose of heating the water than will be transferred to the evaporator (KAO) is not to provide a thermal shock on the system while can result in fouled heat transfer surfaces of the outer wall (KWG) within the interior (KBG') of the drying chamber (KBG), and to prevent cloggage of either the disc (KBB), spray nozzle (KBC), plurality of spray nozzles (KBC), opening (KBD), plurality of openings (KBD), spray aperture (KK4), or orifice (KK5).

Is it desired to heat the water (KEO, KEB) that is transferred to the spray dryer (KAP) so that a seamless transition from water (KEO, KEB) to an insect and liquid mixture (H39, KAS) can be realized to attain steady-state conditions in the safest and most efficient manner as possible.

In embodiments, it is necessary to be able to heat the water (KEB) prior to adding to the evaporator (KAO) by itself, or add the water (KEB) to the evaporator (KAO) together while adding the insect liquid mixture (H39, KAS). Herein are disclosed methods to vary the flow of water (KEB) to an evaporator, such as a spray dryer, while varying either the flow of water (KEB) and/or the flow of insect liquid mixture (H39, KAS) to optimize operations and efficiency while reducing plant maintenance and cleaning.

FIG. 14K shows the start-up heat exchanger (KEP) positioned within the interior (KEA') start-up/shut-down water tank (KEA). In embodiments, the start-up heat exchanger (KEP) is located in between the start-up/shut-down water tank (KEA) and the evaporator (KAO).

In embodiments, a water pump (KEK) is provided and configured to transfer water from the start-up/shut-down water tank (KEA) and into the evaporator (KAO). The water pump (KEK) is equipped with a motor (KEL) and a controller (KEM) which is configured to input or output a signal (KEN) to the computer (COMP).

In embodiments, a water control valve (KEF) is provided to control the flow of start-up/shut-down water (KEB, KEO) transferred from the start-up/shut-down water tank (KEA) into the evaporator (KAO). The water control valve (KEF) is equipped with a controller (KEG) that is configured to input or output a signal (KEH) to the computer (COMP).

In embodiments, a water flow sensor (KEI) is provided to measure the flow of start-up/shut-down water (KEB, KEO) transferred from the start-up/shut-down water tank (KEA) into the evaporator (KAO). In embodiments, the computer (COMP), water control valve (KEF), water flow sensor (KEI), are used in a flow control loop to control the amount of water (KEB, KEO) that is provided into the evaporator (KAO).

Herein is disclosed a method to start-up a spray dryer evaporator, the method includes:
(a) providing:
(a0) providing an evaporator (KAO), spray dryer (KAP), rotary atomizer (KAU), spray nozzle (KBC) or plurality of spray nozzles (KBC), or openings (KBC) or plurality of openings (KBC) within a disc (KBB) of the rotary atomizer (KAU);
(a1) an insect/liquid mixture valve (KEC) that is configured to transfer a pressurized insect and liquid mixture (H39, KAS) to the interior (KAP') of the evaporator (KAO, KAP), the insect/liquid mixture valve (KEC) is installed on an insect liquid mixture conduit (H38);
(a2) a water valve (KEF) that is configured to transfer a pressurized source of water (KEO, KEB) to the interior (KAP') of the evaporator (KAO, KAP), the water valve (KEF) is installed on a water conduit (KEF'), the water (KEO, KEB) that is transferred through the water conduit (KEF') enters the liquid input (KAR) of the evaporator (KAP, KAO) through a common portion (KAR') of the insect liquid mixture conduit (H38);
(b) transfer water (KEO, KEB) through the water valve (KEF) and into the evaporator (KAO, KAP), while the insect/liquid mixture valve (KEC) is closed;
(c) after step (b), open the insect/liquid mixture valve (KEC) to and mix insect and liquid mixture (H39, KAS) with water in the common portion (KAR') of the insect liquid mixture conduit (H38), wherein the flow of water (KEO, KEB) is greater than the flow of insect liquid mixture (H39, KAS);
(d) after step (c), increase the flow of insect liquid mixture (H39, KAS) and decrease the flow of the water (KEO, KEB) so that the water (KEO, KEB) is equal to the flow of insect liquid mixture (H39, KAS) that enters the evaporator (KAO);
(e) after step (d), increase the flow of insect liquid mixture (H39, KAS) and decrease the flow of the water (KEO, KEB) so that the water (KEO, KEB) is less than the flow of insect liquid mixture (H39, KAS) that enters the evaporator (KAO).

Herein is disclosed a method to start-up a spray dryer, the method includes:
(a) providing:
(a1) an insect/liquid mixture valve (KEC) that is configured to transfer a pressurized insect and liquid mixture (H39, KAS) to a spray dryer (KAP) through a rotary atomizer (KAU), spray nozzle (KBC) or plurality of spray nozzles (KBC), or openings (KBC) or plurality of openings (KBC) within a disc (KBB) of the rotary atomizer (KAU), the insect/liquid mixture valve (KEC) is installed on an insect liquid mixture conduit (H38);
(a2) a water valve (KEF) that is configured to transfer a pressurized source of water (KEO, KEB) to a spray dryer (KAP) through a rotary atomizer (KAU), spray nozzle (KBC) or plurality of spray nozzles (KBC), the water valve (KEF) is installed on a water conduit (KEF'), the water (KEO, KEB) that is transferred through the water conduit (KEF') enters the liquid input (KAR) of the spray dryer (KAP) through a common portion (KAR') of the insect liquid mixture conduit (H38);
(b) transfer water (KEO, KEB) through the water valve (KEF) and into the evaporator (KAO, KAP), while the insect/liquid mixture valve (KEC) is closed;
(c) after step (b), open the insect/liquid mixture valve (KEC) to and mix insect and liquid mixture (H39, KAS) with water in the common portion (KAR') of the insect liquid mixture conduit (H38), wherein the flow of water (KEO, KEB) is greater than the flow of insect liquid mixture (H39, KAS);
(d) after step (c), increase the flow of insect liquid mixture (H39, KAS) and decrease the flow of the water (KEO, KEB) so that the water (KEO, KEB) is equal to the flow of insect liquid mixture (H39, KAS) that enters the evaporator (KAO);
(e) after step (d), increase the flow of insect liquid mixture (H39, KAS) and decrease the flow of the water (KEO, KEB) so that the water (KEO, KEB) is less than the flow of insect liquid mixture (H39, KAS) that enters the evaporator (KAO).

Herein is disclosed a method to shut-down a spray dryer evaporator, the method includes:
(a) providing:
(a0) providing an evaporator (KAO), spray dryer (KAP), rotary atomizer (KAU), spray nozzle (KBC) or plurality of spray nozzles (KBC), or openings (KBC) or plurality of openings (KBC) within a disc (KBB) of the rotary atomizer (KAU);
(a1) an insect/liquid mixture valve (KEC) that is configured to transfer a pressurized insect and liquid mixture (H39, KAS) to the interior (KAP') of the evaporator (KAO, KAP), the insect/liquid mixture valve (KEC) is installed on an insect liquid mixture conduit (H38);
(a2) a water valve (KEF) that is configured to transfer a pressurized source of water (KEO, KEB) to the interior (KAP') of the evaporator (KAO, KAP), the water valve (KEF) is installed on a water conduit (KEF'), the water (KEO, KEB) that is transferred through the water conduit (KEF') enters the liquid input (KAR) of the evaporator (KAP, KAO) through a common portion (KAR') of the insect liquid mixture conduit (H38);
(b) transfer the insect and liquid mixture (H39, KAS) through the insect/liquid mixture valve (KEC) and into the evaporator (KAO, KAP), while the water valve (KEF) is closed;
(c) after step (b), open the water valve (KEF) and mix insect and liquid mixture (H39, KAS) with water in the common portion (KAR') of the insect liquid mixture conduit (H38), wherein the flow of water (KEO, KEB) is lesser than the flow of insect liquid mixture (H39, KAS);
(d) after step (c), increase the flow of water (KEO, KEB) and decrease the flow of the insect liquid mixture (H39, KAS) so that the water (KEO, KEB) is equal to the flow of insect liquid mixture (H39, KAS) that enters the evaporator (KAO);
(e) after step (d), increase the flow of water (KEO, KEB) and decrease the flow of the insect liquid mixture (H39, KAS) so that the water (KEO, KEB) is greater than the flow of insect liquid mixture (H39, KAS) that enters the evaporator (KAO);
(f) after step (e), closing the insect/liquid mixture valve (KEC) and stopping flow of the insect liquid mixture (H39, KAS) into the evaporator (KAO).

Herein is disclosed a method to shut-down a spray dryer, the method includes:
(a) providing:
(a0) providing an evaporator (KAO), spray dryer (KAP), rotary atomizer (KAU), spray nozzle (KBC) or plurality of spray nozzles (KBC), or openings (KBC) or plurality of openings (KBC) within a disc (KBB) of the rotary atomizer (KAU);
(a1) an insect/liquid mixture valve (KEC) that is configured to transfer a pressurized insect and liquid mixture (H39, KAS) to a spray dryer (KAP) through a rotary atomizer (KAU), spray nozzle (KBC) or plurality of spray nozzles (KBC), or openings (KBC) or plurality of openings (KBC) within a disc (KBB) of the rotary atomizer (KAU), the insect/liquid mixture valve (KEC) is installed on an insect liquid mixture conduit (H38);
(a2) a water valve (KEF) that is configured to transfer a pressurized source of water (KEO, KEB) to a spray dryer (KAP) through a rotary atomizer (KAU), spray nozzle (KBC) or plurality of spray nozzles (KBC), or openings (KBC) or plurality of openings (KBC) within a disc (KBB) of the rotary atomizer (KAU), the water valve (KEF) is installed on a water conduit (KEF'), the water (KEO, KEB) that is transferred through the water conduit (KEF') enters the liquid input (KAR) of the evaporator (KAP, KAO) through a common portion (KAR') of the insect liquid mixture conduit (H38);
(b) transfer the insect and liquid mixture (H39, KAS) through the insect/liquid mixture valve (KEC) and into the spray dryer (KAP), while the water valve (KEF) is closed;
(c) after step (b), open the water valve (KEF) and mix insect and liquid mixture (H39, KAS) with water in the common portion (KAR') of the insect liquid mixture conduit (H38), wherein the flow of water (KEO, KEB) is lesser than the flow of insect liquid mixture (H39, KAS);
(d) after step (c), increase the flow of water (KEO, KEB) and decrease the flow of the insect liquid mixture (H39, KAS) so that the water (KEO, KEB) is equal to the flow of insect liquid mixture (H39, KAS) that enters the spray dryer (KAP);
(e) after step (d), increase the flow of water (KEO, KEB) and decrease the flow of the insect liquid mixture (H39, KAS) so that the water (KEO, KEB) is greater than the flow of insect liquid mixture (H39, KAS) that enters the spray dryer (KAP);
(f) after step (e), closing the insect/liquid mixture valve (KEC) and stopping flow of the insect liquid mixture (H39, KAS) into the spray dryer (KAP).

In embodiments, a gas supply (KFD) is made available to the interior (KAP') of the spray dryer (KAP). A gas supply valve (KFE) is made available to regulate the amount of gas supply (KFD) that is introduced to the interior (KAP') of the spray dryer (KAP). In embodiments, the gas supply (KFD) is made available to the interior (KAP') of the spray dryer (KAP) for maintenance purposes to back-purge and unclog a spray nozzle (KBC), plurality of spray nozzles (KBC), opening (KBD), or plurality of openings (KBD). The gas supply (KFD) may include any gas, but preferably nitrogen, carbon dioxide, compressed air, a compressed oxygen-containing gas, etc. It is preferable that the gas supply (KFD) is pressurized. In embodiments, the pressure of the gas supply may include any selected from the group consisting of 5 pounds per square inch (PSI) to 10 PSI, 10 PSI to 15 PSI, 15 PSI to 20 PSI, 20 PSI to 25 PSI, 25 PSI to 30 PSI, 30 PSI to 35 PSI, 35 PSI to 40 PSI, 40 PSI to 45 PSI, 45 PSI to 50 PSI, 50 PSI to 55 PSI, 55 PSI to 60 PSI, 60 PSI to 65 PSI, 65 PSI to 70 PSI, 70 PSI to 75 PSI, 75 PSI to 80 PSI, 80 PSI to 85 PSI, 85 PSI to 90 PSI, 90 PSI to 95 PSI, 95 PSI to 100 PSI, 100 PSI to 200 PSI, 200 PSI to 300 PSI, 300 PSI to 400 PSI, 400 PSI to 500 PSI, 500 PSI to 1,000 PSI, 1,000 PSI to 5,000 PSI, 5,000 PSI to 10,000 PSI, 10,000 PSI to 12,500 PSI, 12,500 PSI to 13,500 PSI, and 13,500 PSI to 15,000 PSI Herein is disclosed a method to shut-down a spray dryer (KAP) and unclog a spray nozzle (KBC) or opening (KBD) within the spray dryer (KAP) by reversing flow through the liquid input (KAR) of the spray dryer (KAP), the method includes:
(a) providing:
(a0) providing a spray dryer (KAP) that includes a rotary atomizer (KAU), spray nozzle (KBC) or plurality of spray nozzles (KBC), or openings (KBC) or plurality of openings (KBC) within a disc (KBB) of the rotary atomizer (KAU);
(a1) an insect/liquid mixture valve (KEC) that is configured to transfer a pressurized insect and liquid mixture (H39, KAS) to the interior (KAP') of the spray dryer (KAP), the insect/liquid mixture valve (KEC) is installed on an insect liquid mixture conduit (H38);
(a2) a water valve (KEF) that is configured to transfer a pressurized source of water (KEO, KEB) to the interior of the spray dryer (KAP), the water valve (KEF) is installed on a water conduit (KEF'), the water (KEO, KEB) that is transferred through the water conduit (KEF') enters the liquid input (KAR) of the spray dryer (KAP) through a common portion (KAR') of the insect liquid mixture conduit (H38);

(a3) a backpurge valve (KFA) that is configured to transfer a mixture of liquid and gas (KFF) backwards from the interior (KAP') of the spray dryer (KAP) through the common portion (KAR') of the insect liquid mixture conduit (H38) to unclog at least one spray nozzle (KBC) or opening (KBD);

(a4) a gas supply valve (KFE) that is configured to transfer a gas supply (KFD) to the interior (KAP') of the spray dryer (KAP), the direction of flow of the gas supply (KFD) may be routed opposite to the flow through the liquid input (KAR) to reverse flow through a common portion (KAR') of the insect liquid mixture conduit (H38) to be evacuated through the backpurge valve (KFA) as a mixture of liquid and gas (KFF) when the backpurge valve (KFA) is opened, the water valve (KEF) is closed, and the insect/liquid mixture valve (KEC) is closed;

(b) transfer the insect and liquid mixture (H39, KAS) through the insect/liquid mixture valve (KEC) and into the spray dryer (KAP), while the water valve (KEF), gas supply valve (KFE), and backpurge valve (KFA) are closed;

(c) after step (b), open the water valve (KEF) and mix insect and liquid mixture (H39, KAS) with water in the common portion (KAR') of the insect liquid mixture conduit (H38), wherein the flow of water (KEO, KEB) is lesser than the flow of insect liquid mixture (H39, KAS), while the gas supply valve (KFE) and backpurge valve (KFA) are closed;

(d) after step (c), increase the flow of water (KEO, KEB) and decrease the flow of the insect liquid mixture (H39, KAS) so that the water (KEO, KEB) is greater than the flow of insect liquid mixture (H39, KAS) that enters the evaporator (KAO), while the gas supply valve (KFE) and backpurge valve (KFA) are closed;

(e) after step (d), closing the insect/liquid mixture valve (KEC) and stopping flow of the insect liquid mixture (H39, KAS) into the spray dryer (KAP), closing the water valve (KEF) and stopping flow of the water (KEO, KAB) into the spray dryer (KAP);

(f) opening the gas supply valve (KFE) and opening the backpurge valve (KFA) and back-flowing the gas supply (KFD) from the interior (KAP') of the spray dryer (KAP) back through the liquid input (KAR) of the spray dryer (KAP) through the common portion (KAR') of the insect liquid mixture conduit (H38) to unclog at least one spray nozzle (KBC) or openings (KBD).

FIG. 14K shows a co-current spray dryer (KAP) evaporator (KAO). In FIG. 14K the liquid input (KAR) is closer to the top (K-T) than the bottom (K-B). In FIG. 14K the gas input (KAQ) is closer to the top (K-T) than the bottom (K-B). In FIG. 14K the first output (KBS) is closer to the bottom (K-B) than the top (K-T). In FIG. 14K the second output (KBU) is closer to the bottom (K-B) than the top (K-T). Here, the heated gas supply (KAG') flows in the same direction of the insect liquid mixture (H39, KAS).

FIG. 14K-1:

FIG. 14K-1 shows one non-limiting embodiment of a co-current type of spray dryer (KAP) that may be used with the liquid separation module (LSM) described in FIG. 14K.

Shown in FIGS. FIGS. 14K, 14K-1, 14K-2, 14K-3, and 14K-4, are different embodiments of a spray dryer (KAP) having a top (K-T) bottom (K-B) that are spaced apart along a vertical axis (KYY). The differences between the different types of spray dryers shown in FIGS. 14K-1, 14K-2, 14K-3, and 14K-4 are the differences in height of various inputs and outputs, specifically, the differences in relative heights of: (A) the liquid input (KAR) that introduces an insect liquid mixture (H39, KAS) to the interior (KAP') of the spray dryer (KAP); (B) the gas input (KAQ) that introduces a heated gas supply (KAG') to the interior (KAP') of the spray dryer (KAP); (C) first output (KBS) that discharges insects (KBT) from the from the interior (KAP') of the spray dryer (KAP); and (D) second output (KBU) that evacuates an insect and gas mixture (KBV) away from the interior (KAP') of the spray dryer (KAP).

In FIG. 14K-1 the liquid input (KAR) is closer to the top (K-T) than the bottom (K-B). In FIG. 14K-1 the gas input (KAQ) is closer to the top (K-T) than the bottom (K-B). In FIG. 14K-1 the first output (KBS) is closer to the bottom (K-B) than the top (K-T). In FIG. 14K-1 the second output (KBU) is closer to the bottom (K-B) than the top (K-T). FIG. 14K-1 shows a co-current spray dryer (KAP) evaporator (KAO) with the heated gas supply (KAG') flowing in the same direction of the insect liquid mixture (H39, KAS).

FIG. 14K-2:

FIG. 14K-2 shows one non-limiting embodiment of a counter-current type of spray dryer (KAP) that may be used with the liquid separation module (LSM) described in FIG. 14K.

In FIG. 14K-2 the liquid input (KAR) is closer to the top (K-T) than the bottom (K-B). In FIG. 14K-2 the gas input (KAQ) is closer to the bottom (K-B) than the top (K-T). In FIG. 14K-2 the first output (KBS) is closer to the bottom (K-B) than the top (K-T). In FIG. 14K-2 the second output (KBU) is closer to the top (K-T) than the bottom (K-B). FIG. 14K-2 shows a counter-current spray dryer (KAP) evaporator (KAO) with the heated gas supply (KAG') flowing in a direction that is opposite to the flow of the insect liquid mixture (H39, KAS). Here, the heated gas supply (KAG') flows upwards from the gas input (KAQ) to the second output (KBU), while the insect liquid mixture (H39, KAS) is sprayed in a downwards direction.

FIG. 14K-3:

FIG. 14K-3 shows another non-limiting embodiment of a counter-current type of spray dryer (KAP) that may be used with the liquid separation module (LSM) described in FIG. 14K.

In FIG. 14K-3 the liquid input (KAR) is closer to the bottom (K-B) than the top (K-T). In FIG. 14K-3 the gas input (KAQ) is closer to the top (K-T) than the bottom (K-B). In FIG. 14K-3 the first output (KBS) is closer to the bottom (K-B) than the top (K-T). In FIG. 14K-3 the second output (KBU) is closer to the bottom (K-B) than the top (K-T).

FIG. 14K-3 shows a counter-current spray dryer (KAP) evaporator (KAO) with the heated gas supply (KAG') flowing in a direction that is opposite to the flow of the insect liquid mixture (H39, KAS). Here, the heated gas supply (KAG') flows downwards from the gas input (KAQ) to the second output (KBU), while the insect liquid mixture (H39, KAS) is sprayed in an upwards direction.

FIG. 14K-4:

FIG. 14K-4 shows one non-limiting embodiment of a mixed-flow type of spray dryer (KAP) that may be used with the liquid separation module (LSM) described in FIG. 14K.

In FIG. 14K-4 the liquid input (KAR) is closer to the bottom (K-B) than the top (K-T). In FIG. 14K-4 the gas input (KAQ) is closer to the top (K-T) than the bottom (K-B). In FIG. 14K-4 the first output (KBS) is closer to the bottom (K-B) than the top (K-T). In FIG. 14K-4 the second output (KBU) is second output (KBU) is closer to the bottom (K-B) than the top (K-T), the other (KBU') is closer to the top (K-T) than the bottom (K-B).

FIG. 14K-4 shows a mixed-flow spray dryer (KAP) evaporator (KAO) with the heated gas supply (KAG') flowing in a direction that is opposite to the flow of the insect liquid mixture (H39, KAS). Here, the heated gas supply (KAG') flows both, in the same direction of the insect liquid mixture (H39, KAS), as well as opposite to the direction of the flow of the insect liquid mixture (H39, KAS). Here, the insect liquid mixture (H39, KAS) is sprayed in an upwards direction.

FIG. 14KK:

FIG. 14KK shows one non-limiting embodiment of an insect-derived-biosensor including a transducer and an insect-derived-biopolymer.

In embodiments, the biosensor is derived from the small insect particulate portion (KCW) and/or the large insect particulate portion (KCY) that has undergone evaporation by spray drying as shown in FIG. 14K. In embodiments, the biosensor is derived from the additional separated insects (KDF) that have undergone evaporation by spray drying as shown in FIG. 14K.

The biosensor (14K1), includes:

(a) a transducer (14K2); and (b) an insect-derived-biopolymer (14K3);

wherein:

the insect-derived-biopolymer interacts with a substance being tested and a biological response is converted into an electrical signal by the transducer (14K2).

In embodiments, this disclosure describes a method to produce an insect biopolymer:

(a) providing a source of insects;

(b) after step (a) mixing the insects with a caustic material and/or an oxidant and water to form an oxidized-insect-water mixture, the oxidant includes hydrogen peroxide;

(c) after step (b), mixing the oxidized-insect-water mixture with a biocatalyst and optionally an acid to form an insect-liquid-mixture, the biocatalyst includes one or more biocatalysts selected from the group consisting of an enzyme, casein protease, atreptogrisin A, flavorpro, peptidase, protease A, protease, *Aspergillus oryzae, Bacillus subtilis, Bacillus licheniformis, Aspergillus niger, Aspergillus melleus, Aspergilus oryzae, papain, Carica papaya, bromelain, Ananas comorus* stem, a fungus, a microorganism, and yeast;

(d) after step (c), spray drying the insect-liquid-mixture to create an insect and gas mixture;

(e) after step (d), separating insects from the insect and gas mixture wherein the insects include a powdered oligosaccharide;

(f) after step (e), producing a biosensor from the powdered oligosaccharide, the biosensor includes a transducer and the oligosaccharide;

wherein:

the oligosaccharide interacts with a substance being tested and a biological response is converted into an electrical signal by the transducer.

In embodiments, the insect-derived-biopolymer is an oligosaccharide which interacts with a substance being tested and a biological response is converted into an electrical signal by the transducer. In embodiments, the oligosaccharide (G09') may be used to produce a biosensor. In embodiments, the oligosaccharide (G09') is an insect-derived-biopolymer which may be used to produce the biosensor.

In embodiments, the oligosaccharide includes small insect particulate portion (KCW), the large insect particulate portion (KCY), or the additional separated insects (KDF) that have undergone evaporation by spray drying as shown in FIG. 14K which may include a size range that is selected from one or more from the group consisting of 0.001 nanometers to 0.1 nanometers, 0.1 nanometers to 0.5 nanometers, 0.5 nanometers to 1 nanometer, 1 nanometer to 5 nanometers, 5 nanometers to 10 nanometers, 10 nanometers to 15 nanometers, 15 nanometers to 20 nanometers, 20 nanometers to 25 nanometers, 25 nanometers to 30 nanometers, 30 nanometers to 35 nanometers, 35 nanometers to 40 nanometers, 40 nanometers to 45 nanometers, 45 nanometers to 50 nanometers, 50 nanometers to 55 nanometers, 55 nanometers to 60 nanometers, 60 nanometers to 65 nanometers, 65 nanometers to 70 nanometers, 70 nanometers to 75 nanometers, 75 nanometers to 80 nanometers, 80 nanometers to 85 nanometers, 85 nanometers to 90 nanometers, 90 nanometers to 95 nanometers, 95 nanometers to 100 nanometers, 100 nanometers to 200 nanometers, 200 nanometers to 300 nanometers, 300 nanometers to 400 nanometers, 400 nanometers to 500 nanometers, 500 nanometers to 600 nanometers, 600 nanometers to 700 nanometers, 700 nanometers to 800 nanometers, and 800 nanometers to 900 nanometers.

In embodiments, the biosensor (14K1) may be used for biosensor applications including environmental, agricultural, medicinal, and food industrial market sectors. In embodiments, the insect-derived-biopolymer (14K3) is an oligosaccharide. In embodiments, the insect-derived-biopolymer (14K3) is applied to the biosensor via screen printing, drop coating, and/or deposited using enzymes onto the surface of the sensor. In embodiments, the present disclosure provides for oligosaccharide printed biosensors (14K1). In embodiments, the biosensor (14K1) is an electrochemical biosensor (14K1) including an insect-derived-biopolymer (14K3). In embodiments, the biosensor (14K1) can be a tool to use for detecting pathogens, molecular diagnostics, monitoring the environment, and controlling food safety and defending the homeland of the United States of America.

Herein is disclosed an insect-derived electrochemical biosensor that is not expensive, easy to use, and extremely small-scale and miniature. In embodiments, the biosensor (14K1) can detect ammonia, pyruvate, cholesterol, lactase, glucose, can detect if a human is pregnant, can detect if a mammal is pregnant, can detect if a reptile is pregnant, can detect if an insect is pregnant, can detect if an amphibian is pregnant. In embodiments, the biosensor (14K1) transduces a process of bio-recognition into signals that can be understood via the transducer (14K2) and the insect-derived-biopolymer (14K3). In embodiments, the biosensor (14K1) can be used in clinical diagnostics due to its high sensitivity and selectivity. In embodiments, the biosensor (14K1) can be used in hospitals, urgent-care centers, or remotely-located physicians, or veterinarian centers to perform a wide variety of medical tests on a patient.

In embodiments, the biosensor (14K1) can be used to diagnose diseases such as diabetes, cardiovascular disease, optical corrections, regenerative medicine, cancer, and for therapeutic applications. In embodiments, the biosensor (14K1) can detect cancer in humans and in mammals. In embodiments, the insect-derived-biopolymer (14K3) portion of the biosensor (14K1) captures analytes. In embodiments, the transducer (14K2) portion of the biosensor (14K1) converts a binding event of the insect-derived-biopolymer (14K3) to a measurable signal variation. In embodiments, the biosensor (14K1) can recognize biomolecules including one or more biomolecules selected from the group consisting of antibodies, immunosensors, protein receptors, enzymes, whole cells, and nucleic acids. In embodiments, the biosensor (14K1) can be used for drug delivery, disease detection, prosthetic devices, environmental monitoring, water quality management, monitoring soil quality, measuring toxins in defense or military combat applications, and monitoring food quality.

In embodiments, the biosensor (14K1) has a potential including one or more potentials selected from the group consisting of −60 millivolts to −55 millivolts, −55 millivolts to −50 millivolts, −50 millivolts to −45 millivolts, −45 millivolts to −40 millivolts, −40 millivolts to −35 millivolts, −35 millivolts to −30 millivolts, −30 millivolts to −25 millivolts, −25 millivolts to −20 millivolts, −20 millivolts to −15 millivolts, −15 millivolts to −10 millivolts, −10 millivolts to −5 millivolts, −5 millivolts to 0 millivolts, 0 millivolts to 5 millivolts, 5 millivolts to 10 millivolts, 10 millivolts to 15 millivolts, 15 millivolts to 20 millivolts, 20 millivolts to 25 millivolts, 25 millivolts to 30 millivolts, 30 millivolts to 35 millivolts, 35 millivolts to 40 millivolts, 40 millivolts to 45 millivolts, 45 millivolts to 50 millivolts, 50 millivolts to 55 millivolts, 55 millivolts to 60 millivolts, 60 millivolts to 65 millivolts, 65 millivolts to 70 millivolts, and 70 millivolts to 75 millivolts.

In embodiments, the biosensor (14K1) has a voltammetry having a conduction including one or more selected from the group consisting of 1.000 $e^2/h$ to 1.250 $e^2/h$, 1.250 e $e^2/h$ to 1.500 $e^2/h$ 1.500 $e^2/h$ to 1.750 $e^2/h$, 1.750 $e^2/h$ to 2.000 $e^2/h$, 2.000 $e^2/h$ to 2.250 $e^2/h$, 2.250 $e^2/h$ to 2.500 $e^2/h$, 2.500 $e^2/h$ to 2.750 $e^2/h$, 2.750 $e^2/h$ to 3.000 $e^2/h$, 3.000 $e^2/h$ to 3.250 $e^2/h$, 3.250 $e^2/h$ to 3.500 $e^2/h$, 3.500 $e^2/h$ to 3.750 $e^2/h$, 3.750 $e^2/h$ to 4.000 $e^2/h$, 4.000 $e^2/h$ to 4.250 $e^2/h$, 4.250 $e^2/h$ to 4.500 $e^2/h$, 4.500 $e^2/h$ to 4.750 $e^2/h$, 4.750 $e^2/h$ to 5.000 $e^2/h$, 5.000 $e^2/h$ to 5.250 $e^2/h$, 5.250 $e^2/h$ to 5.500 $e^2/h$, 5.500 $e^2/h$ to 5.750 $e^2/h$, 5.750 $e^2/h$ to 6.000 $e^2/h$, 6.000 $e^2/h$ to 6.250 $e^2/h$, 6.250 $e^2/h$ to 6.500 $e^2/h$, 6.500 $e^2/h$ to 6.750 $e^2/h$, 6.750 $e^2/h$ to 7.000 $e^2/h$, 7.000 $e^2/h$ to 7.250 $e^2/h$, 7.250 $e^2/h$ to 7.500 $e^2/h$, 7.500 $e^2/h$ to 7.750 $e^2/h$, 7.750 $e^2/h$ to 8.000 $e^2/h$, and 8.000 e $e^2/h$ to 8.250 $e^2/h$. This units $e^2/h$ measure the conductance quantum of the biosensor (14K1).

In embodiments, the biosensor (14K1) has an amperometry including one or more selected from the group consisting of −0.000050 amps to −0.000045 amps, −0.000045 amps to −0.000040 amps, −0.000040 amps to −0.000035 amps, −0.000035 amps to −0.000030 amps, −0.000030 amps to −0.000025 amps, −0.000025 amps to −0.000020 amps, −0.000020 amps to −0.000015 amps, −0.000015 amps to −0.000010 amps, −0.000010 amps to −0.000005 amps, −0.000005 amps to 0.000000 amps, 0.000000 amps to 0.000005 amps, 0.000005 amps to 0.000010 amps, 0.000010 amps to 0.000015 amps, 0.000015 amps to 0.000020 amps, 0.000020 amps to 0.000025 amps, 0.000025 amps to 0.000030 amps, 0.000030 amps to 0.000035 amps, 0.000035 amps to 0.000040 amps, 0.000040 amps to 0.000045 amps, 0.000045 amps to 0.000050 amps, and 0.000050 amps to 0.000055 amps.

In embodiments, the biosensor (14K1) has a conductance including one or more selected from the group consisting of 0.01 microsiemens to 0.02 microsiemens, 0.02 microsiemens to 0.04 microsiemens, 0.04 microsiemens to 0.08 microsiemens, 0.08 microsiemens to 0.10 microsiemens, 0.10 microsiemens to 0.50 microsiemens, 0.50 microsiemens to 0.75 microsiemens, 0.75 microsiemens to 1.00 microsiemens, 1.00 microsiemens to 1.25 microsiemens, 1.25 microsiemens to 1.50 microsiemens, 1.50 microsiemens to 1.75 microsiemens, 1.75 microsiemens to 2.00 microsiemens, 2.00 microsiemens to 2.50 microsiemens, 2.50 microsiemens to 3.00 microsiemens, 3.00 microsiemens to 3.50 microsiemens, 3.50 microsiemens to 4.00 microsiemens, 4.00 microsiemens to 4.50 microsiemens, 4.50 microsiemens to 5.00 microsiemens, 5.00 microsiemens to 5.50 microsiemens, 5.50 microsiemens to 6.00 microsiemens, 6.00 microsiemens to 6.50 microsiemens, 6.50 microsiemens to 7.00 microsiemens, 7.00 microsiemens to 7.50 microsiemens, 7.50 microsiemens to 8.00 microsiemens, 8.00 microsiemens to 8.50 microsiemens, 8.50 microsiemens to 9.00 microsiemens, 9.00 microsiemens to 9.50 microsiemens, and 9.50 microsiemens to 10.00 microsiemens.

FIG. 14L:

FIG. 14L shows a power production system (PPS) that is configured to generate electricity, heat, or steam for use in the Insect Production Superstructure System (IPSS).

In embodiments, the power production system (PPS) shown in FIG. 14L can generate electricity for use in the Insect Production Superstructure System (IPSS). In embodiments, the power production system (PPS) shown in FIG. 14L can generate steam for use in the Insect Production Superstructure System (IPSS). In embodiments, the power production system (PPS) shown in FIG. 14L can generate heat for use in the Insect Production Superstructure System (IPSS). In embodiments, the power production system (PPS) includes a compressor (LEB), a combustor (LED), a turbine (LFE), a generator (LFH), a HRSG (heat recovery steam generator) (LFI), a steam drum (LBE), a steam distribution header (LCJ), and a condensate tank (LAP).

An oxygen-containing gas (LEA) is made available to a compressor (LEB). In embodiments, the oxygen-containing gas may be air, oxygen-enriched-air i.e. greater than 21 mole % O2, and substantially pure oxygen, i.e. greater than about 95 mole % oxygen (the remainder usually comprising N2 and rare gases). In embodiments, the oxygen-containing gas may be flue gas or carbon dioxide. In embodiments, flue gas includes a vapor or gaseous mixture containing varying amounts of nitrogen (N2), carbon dioxide (CO2), water (H2O), and oxygen (O2). In embodiments, flue gas is generated from the thermochemical process of combustion. In embodiments, combustion is an exothermic (releases heat) thermochemical process wherein at least the stoichiometric oxidation of a carbonaceous material takes place to generate flue gas.

In embodiments, the compressor (LEB) has a plurality of stages (LEC). In embodiments, the compressor (LEB) is an axial compressor. In embodiments, the compressor is configured to compress and pressurize the oxygen-containing gas (LEA) to form a compressed gas stream (LEK). In embodiments, the compressor is configured to compress and pressurize the oxygen-containing gas (LEA) to form a first compressed gas stream (LEK) and a second compressed gas stream (LEN). In embodiments, compressed gas stream (LEK) is provided to a combustor (LED). In embodiments, the first compressed gas stream (LEK) is provided to a first combustor (LED1). In embodiments, the second compressed gas stream (LEN) is provided to a second combustor (LED2).

In embodiments, the first combustor (LED1) has a first gas mixer (LEE). In embodiments, the second combustor (LED2) has a second gas mixer (LEH). In embodiments, the first gas mixer (LEE) or second gas mixer (LEH) is that of an annular type. In embodiments, the first combustor (LED1) or second combustor (LED2) is that of an annular type. In embodiments, the annular type gas mixer (LEE) mixes the fuel with the oxygen containing-gas within the combustor to form a fuel-and-oxygen-containing gas mixture, which is then combusted. In embodiments, the first combustor (LED1) has a first ignitor (LEF). In embodiments, the second combustor (LED2) has a second ignitor (LEI). In embodiments, the first ignitor (LEF) or second ignitor (LEI) include a torch ignitor. In embodiments, the first ignitor (LEF) or second ignitor (LEI) include a separate fuel supply to maintain a constantly burning torch. In embodiments, the first combustor (LED1) has a first flame detector (LEG). In embodiments, the second combustor (LED2) has a second flame detector (LEJ). In embodiments, the first flame detector (LEG) or second flame detector (LEJ) are selected from one or more from the group consisting of a UV flame detector, IR flame detector, UV/IR flame detector, multi-spectrum infrared flame detector, and a visual flame imaging flame detector.

In embodiments, the combustor (LED) mixes and combusts the compressed gas stream (LEK) with a first fuel (LEL) to produce a combustion stream (LEM). In embodiments, the first combustor (LED1) mixes and combusts the first compressed gas stream (LEK) with a first fuel (LEL) to produce a first combustion stream (LEM). In embodiments, the first combustion stream (LEM) is a first pressurized combustion stream (LEM'). In embodiments, the second combustor (LED2) mixes and combusts the second compressed gas stream (LEN) with a second fuel (LEO) to produce a second combustion stream (LEP). In embodiments, the second combustion stream (LEP) is a second pressurized combustion stream (LEP').

A first fuel valve (LEW) is provided to regulate the flow of the compressor fuel source (LEU) to the first combustor (LED1) and the second combustor (LED2). The first fuel valve (LEW) is equipped with a controller (LEX) that is configured to input or output a signal (LEY) to the computer (COMP). FIG. 14L shows connector (K1) to show continuity between the second fuel (LEO) that is apportioned from the compressor fuel source (LEU) and transferred to the second combustor (LED2).

The combustion stream (LEM) is transferred to a turbine (LFE). In embodiments, the first combustion stream (LEM) is combined with the second combustion stream (LEP) before being transferred to the turbine (LFE). In embodiments, the turbine (LFE) has a plurality of stages (LFF). In embodiments, the first and second combustion streams (LEM, LEP) rotate a portion of the turbine (LFE), which in turn rotates a shaft (LFG), and a generator (LFH) to produce electricity (ELEC). In embodiments, the combustion stream (LEM) rotates the turbine (LFE), which in turn rotates a shaft (LFG), and a generator (LFH) to produce electricity (ELEC).

In embodiments, the compressor (LEB) is connected to the turbine (LFE) via a shaft (LFG). In embodiments, the turbine (LFE) is connected to the generator (LFH) via a shaft (LFG). In embodiments, the turbine (LFE) rotates the shaft (LFG) which in turn drives the compressor (LEB). In embodiments, the generator (LFH) is connected to the turbine (LFE) via a shaft (LFG). In embodiments, the turbine (LFE) rotates the shaft (LFG) which in turn drives the generator (LFH) to produce electricity for use in the Insect Production Superstructure System (IPSS).

FIG. 14L shows the generator (LFH) producing electricity for use in the computer (COMP) within the Insect Production Superstructure System (IPSS). FIG. 14L shows the generator (LFH) producing electricity for use in the computer (COMP) within the farming superstructure system (FSS). In embodiments, the electricity (ELEC) may be used in the Insect Production Superstructure System (IPSS) in any number of a plurality of: sensors, motors, pumps, heat exchangers, fans, actuators, controllers, compressors, analyzers, computers, lights, heaters, vacuum pumps, etc. Any asset, including sensors, motors, pumps, heat exchangers, fans, actuators, controllers, compressors, analyzers, computers, lights, heaters, vacuum pumps, disclosed in FIGS. 1A through 48 may be powered by the electricity (ELEC) generated by the generator (LFH) or generator (LCA).

A combustion stream (LFD) is discharged from the turbine (LFE) and is routed to a HRSG (LFI). In embodiments, the combustion stream (LFD) that is discharged from the turbine (LFE) is a depressurized combustion stream (LFD'). In embodiments the depressurized combustion stream (LFD') has a pressure that is less than the pressure of the combustion stream (LEM, LEP) that is transferred to the turbine (LFE). The combustion stream (LFD) is transferred from the turbine (LFE) to the HRSG (LFI). The HRSG (LFI) is configured to remove heat from the combustion stream (LFD) by use of a heat transfer conduit (LBI) or a plurality of heat transfer conduits (LBI). At least one heat transfer conduit (LBI) generates steam through indirect heat transfer from the combustion stream (LFD).

In embodiments, the HRSG (LFI) is a fired-HRSG (LFJ). In embodiments, the fired-HRSG (LFJ) accepts a HRSG fuel source (LEV). In embodiments, the HRSG fuel source (LEV) is combusted with the combustion stream (LFD) that is transferred from the turbine (LFE) to form a combustion stream (LX0'). In embodiments, the HRSG fuel source (LEV) is combusted with an oxygen-containing gas (LX0). In the instance where the HRSG fuel source (LEV) is combusted with an oxygen-containing gas (LX0), the compressor (LEB), a combustor (LED), a turbine (LFE), a generator (LFH) are optional. Thus, saturated steam (LBR) or superheated steam (LBS) may be generated within the steam drum (LBE) by combusting an oxygen-containing gas (LX0) with the compressor fuel source (LEU) to form a combustion stream (LX0').

In embodiments, a second fuel valve (LFA) is made available to regulate the amount of the HRSG fuel source (LEV) that is introduced to the fired-HRSG (LFJ). The second fuel valve (LFA) is equipped with a controller (LFB) that is configured to input or output a signal (LFC) to the computer (COMP). In embodiments, the compressor fuel source (LEU) and HRSG fuel source (LEV) come from a common fuel source (LEQ). A compressor fuel source (LEU) provides the fuel that is used as the first fuel (LEL) and second fuel (LEO). In embodiments, the fuel source (LEQ) that is made available as the compressor fuel source (LEU) or HRSG fuel source (LEV) may include a hydrocarbon. In embodiments, the fuel source (LEQ) that is made available as the compressor fuel source (LEU) or HRSG fuel source (LEV) may be a liquid, vapor, or a gas. In embodiments, the fuel source (LEQ) that is made available as the compressor fuel source (LEU) or HRSG fuel source (LEV) may be a methane containing gas such as natural gas. In embodiments, the fuel source (LEQ) that is made available as the compressor fuel source (LEU) or HRSG fuel source (LEV) may be naphtha, natural gas, gasoline, a hydrocarbon, diesel, or oil. In embodiments, the fuel source (LEQ, LET, LEU, LEV), may include a hydrocarbon, and may be a liquid, vapor, or a gas. In embodiments, the fuel source (LEQ, LET, LEU, LEV), may be a methane containing gas such as natural gas, or otherwise may be naphtha, natural gas, gasoline, a hydrocarbon, diesel, or oil.

In embodiments, a fuel source (LEQ) is made available to a fuel compressor (LER) to form a compressed fuel (LET). In embodiments, the fuel compressor (LER) has a plurality of stages (LES). A pressure sensor (LEQP) is provided to measure the pressure of the fuel source (LEQ) that is made available to the fuel compressor (LER). In embodiments, the compressor fuel source (LEU) and HRSG fuel source (LEV) are a compressed fuel (LET). In embodiments, the HRSG fuel source (LEV) is combusted within the fired-HRSG (LFJ) using a burner (LFK) such as a duct burner. In embodiments, the fired-HRSG (LFJ) or the burner (LFK) is lined with refractory material. In embodiments, the refractory material includes a ceramic, alumina, silica, magnesia, silicon carbide, or graphite.

In embodiments, heat is removed from the HRSG (LFI) and a flue gas (LFP) is evacuated from the HRSG (LFI). In embodiments, heat is removed from the fired-HRSG (LFJ) and a flue gas (LFP) is evacuated from the fired-HRSG (LFJ). A temperature sensor (LFM) is configured to measure the temperature within the HRSG (LFI, LFJ). A temperature sensor (LFM) is configured to measure the temperature of the flue gas (LFP) that is discharged from the HRSG (LFI, LFJ).

In embodiments, at least a portion of the flue gas (LFP) is made available as flue gas (FG1) that may be transferred to the thermal compressor (Q30) on FIG. FIG. 27D or 27F. In embodiments, at least a portion of the flue gas (LFP) is made available as flue gas (FG1) that may be transferred to the generator (Q50) within the thermal compressor (Q30) on FIG. 27D or 27F.

The steam generated in the plurality of heat transfer conduits (LBI) is routed to a steam drum (LBE). In embodiments, the steam drum (LBE) generates saturated steam (LBR) or superheated steam (LBS). In embodiments, saturated steam (LBR) is discharged from the steam drum (LBE) and is routed to a superheater (LX3) through a saturated steam transfer conduit (LX1). Heat is transferred from the combustion stream (LFD, LX0') to saturated steam (LBR) within the superheater (LX3) to produce superheated steam (LBS) which is routed to a superheated steam transfer conduit (LX2).

A steam distribution header (LCJ) is configured to accept at least a portion of the saturated steam (LBR) or superheated steam (LBS). In embodiments, a first portion (LBW) of either the saturated steam (LBR) or superheated steam (LBS) is transferred through a first steam transfer conduit (LBY) and into the steam distribution header (LCJ). In embodiments, a second portion (LBX) of either the saturated steam (LBR) or superheated steam (LBS) is transferred through a second steam transfer conduit (LSY) and into steam turbine (LBZ) to generate electricity via a generator (LCA). In embodiments, the steam turbine (LBZ) has a plurality of stages (LBZX). The steam turbine (LBZ) is connected to a generator (LCA) via a shaft (LCB). Depressurized steam (LCI) is evacuated from the steam turbine (LBZ) and is routed towards the steam distribution header (LCJ).

FIG. 14L shows a steam distribution header (LCJ) that is configured to accept at least a portion of the saturated steam (LBR) or superheated steam (LBS) that are routed through either the first steam transfer conduit (LBY) or second steam transfer conduit (LSY). A pressure sensor (LBO) is provided to measure the pressure within the interior of the steam drum (LBE). A temperature sensor (LBQ) is provided to measure the temperature of the saturated steam (LBR) or superheated steam (LBS) that are discharged from the steam drum (LBE). A pressure control valve (LBT) is positioned on the steam distribution header (LCJ). In embodiments, the pressure control valve (LBT) controls the pressure within the steam drum (LBE). In embodiments, the pressure control valve (LBT) controls the pressure within first steam transfer conduit (LBY) and second steam transfer conduit (LSY). The pressure control valve (LBT) is equipped with a controller (LBU) that sends a signal (LBV) to or from the computer (COMP). In embodiments, the computer (COMP), pressure control valve (LBT), and pressure sensor (LBO) are used in a control loop to regulate the pressure within the steam drum (LBE), first steam transfer conduit (LBY), or second steam transfer conduit (LSY).

In embodiments, the steam distribution header (LCJ) provides a source of steam to a variety of locations within the Insect Production Superstructure System (IPSS). In embodiments, the velocity of steam within the steam distribution header (LCJ) ranges from one or more from the group selected from 50 feet per second (FPS) to 60 FPS, 60 FPS to 70 FPS, 70 FPS to 80 FPS, 80 FPS to 90 FPS, 90 FPS to 100 FPS, 100 FPS to 110 FPS, 110 FPS to 120 FPS, 120 FPS to 130 FPS, 130 FPS to 140 FPS, 140 FPS to 150 FPS, 150 FPS to 160 FPS, 160 FPS to 180 FPS, 180 FPS to 200 FPS, 200 FPS to 225 FPS, and 225 FPS to 250 FPS.

In embodiments, the steam distribution header (LCJ) operates at a pressure range that is selected from one or more from the group consisting of 5 pounds per square inch (PSI) 10 PSI, 10 PSI 20 PSI, 20 PSI 30 PSI, 30 PSI 40 PSI, 40 PSI 50 PSI, 50 PSI 60 PSI, 60 PSI 70 PSI, 70 PSI 80 PSI, 80 PSI 90 PSI, 90 PSI 100 PSI, 100 PSI 125 PSI, 125 PSI 150 PSI, 150 PSI 175 PSI, 175 PSI 200 PSI, 200 PSI 225 PSI, 225 PSI 250 PSI, 250 PSI 275 PSI, 275 PSI 300 PSI, 300 PSI 325 PSI, 325 PSI 350 PSI, 350 PSI 375 PSI, 375 PSI 400 PSI, 400 PSI 425 PSI, 425 PSI 450 PSI, 450 PSI 475 PSI, 475 PSI 500 PSI, 500 PSI 525 PSI, 525 PSI 550 PSI, 550 PSI 575 PSI, 575 PSI 600 PSI, 600 PSI 700 PSI, 700 PSI 800 PSI, 800 PSI 900 PSI, and 900 PSI 1,000 PSI.

In embodiments, the steam distribution header (LCJ) is insulated with insulation (LCJ'). In embodiments, the range of thickness of the insulation (LCJ') on the steam distribution header (LCJ) is selected from one or more from the group consisting of 1 inches to 1.5 inches, 1.5 inches to 2 inches, 2 inches to 2.5 inches, 2.5 inches to 3 inches, 3 inches to 3.5 inches, 3.5 inches to 4 inches, 4 inches to 4.5 inches, 4.5 inches to 5 inches, 5 inches to 5.5 inches, 5.5 inches to 6 inches, 6 inches to 6.5 inches, 6.5 inches to 7 inches, 7 inches to 7.5 inches, 7.5 inches to 8 inches, 8 inches to 8.5 inches, 8.5 inches to 9 inches, 9 inches to 9.5 inches, 9.5 inches to 10 inches, 10 inches to 11 inches, 11 inches to 12 inches, 12 inches to 13 inches, 13 inches to 14 inches, 14 inches to 15 inches, 15 inches to 16 inches, 16 inches to 17 inches, and 17 inches to 18 inches.

In embodiments, the steam distribution header (LCJ) provides a source of steam to a variety of locations including: a first steam supply (LCL) to FIG. 3, Feeding Chamber (FC1, FC2, FC3), air heater (264); a second steam supply (LCP) to FIG. 13, heat exchanger (HX1580); a third steam supply (LCT) to FIG. 14C, heat exchanger (C53); a fourth steam supply (LCX) to FIG. 14E, heat exchanger (E20); a fifth steam supply (LDB) to FIG. 14G, heating jacket (G53J) and/or to the heat exchanger (G53); a sixth steam supply (LDF) to FIG. 14H, heat exchanger (H34); a seventh steam supply (LDJ) to FIG. 14J, evaporator (J11) heating jacket (J17); an eighth steam supply (LDM) to FIG. 14K, air heater (KAF); a ninth steam supply (LDP) to FIG. 14K, drying chamber (KBG) heating jacket (KBJ); a tenth steam supply (LDS) to FIG. 27D, thermal compressor (Q30); an eleventh steam supply (LDV) to FIG. 34B, thermal compressor (QQ30).

In embodiments, a first steam valve (LCM) is configured to regulate the amount of the first steam supply (LCL) to FIG. 3, Feeding Chamber (FC1), air heater (264). A first reducer (LCN) may be positioned upstream or downstream of the first steam valve (LCM) on the steam distribution header (LCJ).

In embodiments, a second steam valve (LCQ) is configured to regulate the amount of the second steam supply (LCP) to FIG. 13, heat exchanger (HX1580). A second reducer (LCR) may be positioned upstream or downstream of the second steam valve (LCQ) on the steam distribution header (LCJ).

In embodiments, a third steam valve (LCU) is configured to regulate the amount of the third steam supply (LCT) to FIG. 14C, heat exchanger (C53). A third reducer (LCV) may be positioned upstream or downstream of the third steam valve (LCU) on the steam distribution header (LCJ).

In embodiments, a fourth steam valve (LCY) is configured to regulate the amount of the fourth steam supply (LCX) to FIG. 14E, heat exchanger (E20). A fourth reducer (LCZ) may be positioned upstream or downstream of the fourth steam valve (LCY) on the steam distribution header (LCJ).

In embodiments, a fifth steam valve (LDC) is configured to regulate the amount of the fifth steam supply (LDB) to FIG. 14G, heating jacket (G53J) and/or to the heat exchanger (G53). A fifth reducer (LDD) may be positioned upstream or downstream of the fifth steam valve (LDC) on the steam distribution header (LCJ).

In embodiments, a sixth steam valve (LDG) is configured to regulate the amount of the sixth steam supply (LDF) to FIG. 14H, heat exchanger (H34). A sixth reducer (LDH) may be positioned upstream or downstream of the sixth steam valve (LDG) on the steam distribution header (LCJ).

In embodiments, a seventh steam valve (LDK) is configured to regulate the amount of the seventh steam supply (LDJ) to FIG. 14J, evaporator (J11) heating jacket (J17). A seventh reducer (LDL) may be positioned upstream or downstream of the seventh steam valve (LDK) on the steam distribution header (LCJ).

In embodiments, an eighth steam valve (LDN) is configured to regulate the amount of the eighth steam supply (LDM) to FIG. 14K, air heater (KAF). An eighth reducer (LDO) may be positioned upstream or downstream of the eighth steam valve (LDN) on the steam distribution header (LCJ).

In embodiments, a ninth steam valve (LDQ) is configured to regulate the amount of the ninth steam supply (LDP) to FIG. 14K, drying chamber (KBG) heating jacket (KBJ). A ninth reducer (LDR) may be positioned upstream or downstream of the ninth steam valve (LDQ) on the steam distribution header (LCJ).

In embodiments, a tenth steam valve (LDT) is configured to regulate the amount of the tenth steam supply (LDS) to FIG. 27D, thermal compressor (Q30) A tenth reducer (LDU) may be positioned upstream or downstream of the tenth steam valve (LDT) on the steam distribution header (LCJ).

In embodiments, an eleventh steam valve (LDW) is configured to regulate the amount of the eleventh steam supply (LDV) to FIG. 34B, thermal compressor (QQ30) An eleventh reducer (LDX) may be positioned upstream or downstream of the eleventh steam valve (LDW) on the steam distribution header (LCJ).

In embodiments, a twelfth steam valve (LZB) is configured to regulate the amount of the twelfth steam supply (LZC) to FIG. 12C, hydrogenation system (2C13). An twelfth reducer (LZA) may be positioned upstream or downstream of the twelfth steam valve (LZB) on the steam distribution header (LCJ), In turn, a plurality of steam condensate streams are transferred from various locations within the IPSS and are returned to a condensate tank (LAP) as indicated on FIG. 14L. In embodiments, the condensate tank (LAP) accepts steam condensate streams are transferred from various locations, including: a first condensate (LAQ) from FIG. 3, Feeding Chamber (FC1, FC2, FC3), air heater (264); a second condensate (LAR) from FIG. 13, heat exchanger (HX1580); a third condensate (LAS) from FIG. 14C, heat exchanger (C53); a fourth condensate (LAT) from FIG. 14E, heat exchanger (E20); a fifth condensate (LAU) from FIG. 14G, heating jacket (G53J) and/or to the heat exchanger (G53); a sixth condensate (LAV) from FIG. 14H, heat exchanger (H34); a seventh condensate (LAW) from FIG. 14J, evaporator (J11) heating jacket (J17); an eighth condensate (LJA) from FIG. 14K, air heater (KAF); a ninth condensate (LJB) from FIG. 14K, drying chamber (KBG) heating jacket (KBJ); a tenth condensate (LJC) from FIG. 27D, thermal compressor (Q30); an eleventh condensate (LJD) from FIG. 34B, thermal compressor (QQ30).

In embodiments, at least a portion are used again to remove heat within the HRSG (LFI, LFJ): first condensate (LAQ), second condensate (LAR), third condensate (LAS), fourth condensate (LAT), fifth condensate (LAU), sixth condensate (LAV), seventh condensate (LAW), eighth condensate (LJA), ninth condensate (LJB), tenth condensate (LJC), eleventh condensate (LJD). In embodiments, feed water (LAX) (which may include condensate (LAQ, LAR, LAW, LAT, LAU, LAV, LAW, LJA, LJB, LJC, LJD)) is pumped to the from the condensate tank (LAP) to the steam drum input (LBD) of the steam drum (LBE) via a pump (LAX').

A heat exchanger (LAZ) is provided to pre-heat the feed water (LAX) as it is transferred from the condensate tank (LAP) to the steam drum (LBE). A temperature sensor (LAY) is provided to measure the temperature of the feed water (LAX) before it enters the heat exchanger (LAZ). Another temperature sensor (LBC) is provided to measure the temperature of the feed water (LAX) after is exits the heat exchanger (LAZ).

In embodiments, the steam drum (LBE) is equipped with a level sensor (LBP) that is configured to regulate the amount of feed water (LAX) that is introduced to the steam drum (LBE). In embodiments, the steam drum (LBE) is equipped with a level control valve (LBP') that is configured to regulate the amount of feed water (LAX) that is introduced to the steam drum (LBE). In embodiments, the computer (COMP), level sensor (LBP), and level control valve (LBP') may be used in a control loop to regulate the amount of feed water (LAX) that is introduced to the steam drum (LBE).

In embodiments, the steam drum (LBE) is connected to a lower steam drum (LBF) via a plurality of heat transfer conduit (LBG, LBH, LBI). In embodiments, lower steam drum (LBF) is configured to discharge a blowdown (LBK) through a valve (LBN). In embodiments, the blowdown (LBK) includes suspended solids (LBL) and/or dissolved solids (LBM). In embodiments, the suspended solids (LBL) include solids such as bacteria, silt and mud. In embodiments, the dissolved solids (LBM) may include minerals, salts, metals, cations or anions dissolved in water. In embodiments, the dissolved solids (LBM) include inorganic salts including principally calcium, magnesium, potassium, sodium, bicarbonates, chlorides, and sulfates.

In embodiments, the condensate tank (LAP) also serves the purpose as a water tank (LAO) for accepting treated water (LAJ). Thus, treated water (LAJ) is added to the condensate tank (LAP) to make-up for water losses in the system. A source of water (LAA) is made available to a series of unit operations that are configured to improve the water. In embodiments, the source of water (LAA) is passed through a filter (LAC), a packed bed (LAD) of adsorbent (LAE), a cation (LAF), an anion (LAG), a membrane (LAH), followed by another cation/anion (LAI) to result in treated water (LAJ).

The treated water (LAJ) is then provided to the condensate tank (LAP)/water tank (LAO) via a pump (LAK). In embodiments, the treated water (LAJ) that is transferred to the condensate tank (LAP)/water tank (LAO) via a pump (LAK) is passed through a valve (LAL). The valve (LAL) is equipped with a controller (LAM) that is configured to input or output a signal (XAM) to the computer (COMP). A quality sensor (LAN) is provided as a quality control of the unit operations that are configured to improve the water.

Within the interior (G14) of a mixing tank (G15), the water is mixed with insects and biocatalyst. In embodiments, a cation (G39), an anion (G40), and a polishing unit (G41), are positioned on the water supply conduit (G37) in between the third water treatment unit (G12) and the water input (G38) of the mixing tank (G15). The polishing unit (G41) may be any type of conceivable device to improve the water quality such as an ultraviolet unit, ozone unit, microwave unit, filter, or the like.

FIG. 15:

FIG. 15 shows a simplistic diagram illustrating a plurality of feeding chambers (FC1, FC2, FC3) of an insect feeding module (2000) integrated within one common separator (300) of an insect evacuation module (3000).

FIG. 15 shows an insect feeding module (2000) comprised of three separate feeding chambers (FC1, FC2, FC3) including a first feeding chamber (FC1), second feeding chamber (FC2), and a third feeding chamber (FC3). Each feeding chamber (FC1, FC2, FC3) may include the non-limiting embodiments of those previously described or those described below. It is well established that the claims of the patent serve an important public notice function to potential competitors—enabling them to not only determine what is covered, but also what is not covered—by the patent. And a number of Federal Circuit decisions have emphasized the importance of discerning the patentee's intent—as expressed in the specification—in construing the claims of the patent. The present disclosure includes several independently meritorious inventive aspects and advantages related to feeding and evacuating insects by use of at least one insect feeding module (2000) integrated at least one separator (300) of an insect evacuation module (3000) and to the notion that each feeding chamber (FC1, FC2, FC3) has a feeding chamber insect evacuation output (205A, 205B, 205C) that is connected to the separator (300) of the insect evacuation module (3000).

First Feeding Chamber (Fc1)

The first feeding chamber (FC1) has a first feeding chamber insect evacuation output (205A) or a feeding chamber 1 insect evacuation port (1FC) that is in fluid communication with the insect and gas mixture input (303) of the separator (300). A first feeding chamber exit conduit (302A) is connected at one end to the first feeding chamber (FC1) and at another and to a common entry conduit (CEC). The common entry conduit (CEC) is connected at one end to the first feeding chamber exit conduit (302A) and at another end to the insect and gas mixture input (303) of the separator (300). A feeding chamber 1 evacuation valve (VV1) in interposed in the first feeding chamber exit conduit (302A). The feeding chamber 1 evacuation valve (VV1) is equipped with a with a controller (CV1) that is configured to input and output a signal (XV1) to the computer (COMP). The first feeding chamber exit conduit (302A) has a first feeding chamber evacuation line first diameter (D1A) and a first feeding chamber evacuation line reducer (VR1) which merges into a first feeding chamber evacuation line second diameter (D1B). In embodiments, the first feeding chamber evacuation line first diameter (D1A) is greater than the first feeding chamber evacuation line second diameter (D1B). In embodiments, the first feeding chamber evacuation line first diameter (D1A) is less than the first feeding chamber evacuation line second diameter (D1B).

In embodiments, the first feeding chamber evacuation line first diameter (D1A) ranges in size from: between about 1 inch and about 2 inches; between about 2 inches and about 3 inches; between about 3 inches and about 4 inches; between about 4 inches and about 5 inches; between about 5 inches and about 6 inches; between about 6 inches and about 7 inches; between about 7 inches and about 8 inches; between about 8 inches and about 9 inches; between about 9 inches and about 10 inches; between about 10 inches and about 11 inches; between about 11 inches and about 12 inches; between about 12 inches and about 13 inches; between about 13 inches and about 14 inches; between about 14 inches and about 15 inches; between about 15 inches and about 16 inches; between about 16 inches and about 17 inches; between about 17 inches and about 18 inches; between about 18 inches and about 19 inches; between about 19 inches and about 20 inches; between about 20 inches and about 21 inches; between about 21 inches and about 22 inches; between about 22 inches and about 23 inches; between about 23 inches and about 24 inches; between about 24 inches and about 25 inches; between about 25 inches and about 26 inches; between about 26 inches and about 27 inches; between about 27 inches and about 28 inches; between about 28 inches and about 29 inches; between about 29 inches and about 30 inches; between about 30 inches and about 31 inches; between about 31 inches and about 32 inches; between about 32 inches and about 33 inches; between about 33 inches and about 34 inches; between about 34 inches and about 35 inches; between about 35 inches and about 36 inches; between about 36 inches and about 37 inches; between about 37 inches and about 38 inches; between about 38 inches and about 39 inches; or, between about 39 inches and about 40 inches; between about 38 inches and about 39 inches; between about 39 inches and about 40 inches; between about 40 inches and about 50 inches; between about 50 inches and about 60 inches; between about 60 inches and about 70 inches; between about 70 inches and about 80 inches; between about 80 inches and about 90 inches; between about 90 inches and about 100 inches; between about 100 inches and about 125 inches; between about 125 inches and about 150 inches; or, between about 150 inches and about 200 inches.

In embodiments, the first feeding chamber evacuation line second diameter (D1B) ranges in size from: between about 1 inch and about 2 inches; between about 2 inches and about 3 inches; between about 3 inches and about 4 inches; between about 4 inches and about 5 inches; between about 5 inches and about 6 inches; between about 6 inches and about 7 inches; between about 7 inches and about 8 inches; between about 8 inches and about 9 inches; between about 9 inches and about 10 inches; between about 10 inches and about 11 inches; between about 11 inches and about 12 inches; between about 12 inches and about 13 inches; between about 13 inches and about 14 inches; between about 14 inches and about 15 inches; between about 15 inches and about 16 inches; between about 16 inches and about 17 inches; between about 17 inches and about 18 inches; between about 18 inches and about 19 inches; between about 19 inches and about 20 inches; between about 20 inches and about 21 inches; between about 21 inches and about 22 inches; between about 22 inches and about 23 inches; between about 23 inches and about 24 inches; between about 24 inches and about 25 inches; between about 25 inches and about 26 inches; between about 26 inches and about 27 inches; between about 27 inches and about 28 inches; between about 28 inches and about 29 inches; between about 29 inches and about 30 inches; between about 30 inches and about 31 inches; between about 31 inches and about 32 inches; between about 32 inches and about 33 inches; between about 33 inches and about 34 inches; between about 34 inches and about 35 inches; between about 35 inches and about 36 inches; between about 36 inches and about 37 inches; between about 37 inches and about 38 inches; between about 38 inches and about 39 inches; or, between about 39 inches and about 40 inches; between about 38 inches and about 39 inches; between about 39 inches and about 40 inches; between about 40 inches and about 50 inches; between about 50 inches and about 60 inches; between about 60 inches and about 70 inches; between about 70 inches and about 80 inches; between about 80 inches and about 90 inches; between about 90 inches and about 100 inches; between about 100 inches and about 125 inches; between about 125 inches and about 150 inches; or, between about 150 inches and about 200 inches.

In embodiments, the common entry conduit (CEC) ranges in size from: between about 1 inch and about 2 inches; between about 2 inches and about 3 inches; between about 3 inches and about 4 inches; between about 4 inches and about 5 inches; between about 5 inches and about 6 inches; between about 6 inches and about 7 inches; between about 7 inches and about 8 inches; between about 8 inches and about 9 inches; between about 9 inches and about 10 inches; between about 10 inches and about 11 inches; between about 11 inches and about 12 inches; between about 12 inches and about 13 inches; between about 13 inches and about 14 inches; between about 14 inches and about 15 inches; between about 15 inches and about 16 inches; between about 16 inches and about 17 inches; between about 17 inches and about 18 inches; between about 18 inches and about 19 inches; between about 19 inches and about 20 inches; between about 20 inches and about 21 inches; between about 21 inches and about 22 inches; between about 22 inches and about 23 inches; between about 23 inches and about 24 inches; between about 24 inches and about 25 inches; between about 25 inches and about 26 inches; between about 26 inches and about 27 inches; between about 27 inches and about 28 inches; between about 28 inches and about 29 inches; between about 29 inches and about 30 inches; between about 30 inches and about 31 inches; between about 31 inches and about 32 inches; between about 32 inches and about 33 inches; between about 33 inches and about 34 inches; between about 34 inches and about 35 inches; between about 35 inches and about 36 inches; between about 36 inches and about 37 inches; between about 37 inches and about 38 inches; between about 38 inches and about 39 inches; or, between about 39 inches and about 40 inches; between about 38 inches and about 39 inches; between about 39 inches and about 40 inches; between about 40 inches and about 50 inches; between about 50 inches and about 60 inches; between about 60 inches and about 70 inches; between about 70 inches and about 80 inches; between about 80 inches and about 90 inches; between about 90 inches and about 100 inches; between about 100 inches and about 125 inches; between about 125 inches and about 150 inches; or, between about 150 inches and about 200 inches.

Second Feeding Chamber (Fc2)

The second feeding chamber (FC2) has a second feeding chamber insect evacuation output (205B) or a feeding chamber 2 insect evacuation port (2FC) that is in fluid communication with the insect and gas mixture input (303) of the separator (300). A second feeding chamber exit conduit (302B) is connected at one end to the second feeding chamber (FC2) and at another and to a common entry conduit (CEC). The common entry conduit (CEC) is connected at one end to the second feeding chamber exit conduit (302B) and at another end to the insect and gas mixture input (303) of the separator (300). A feeding chamber 2 evacuation valve (VV2) in interposed in the second feeding chamber exit conduit (302B). The feeding chamber 2 evacuation valve (VV2) is equipped with a with a controller (CV2) that is configured to input and output a signal (XV2) to the computer (COMP). The second feeding chamber exit conduit (302B) has a second feeding chamber evacuation line first diameter (D2A) and a second feeding chamber evacuation line reducer (VR2) which merges into a second feeding chamber evacuation line second diameter (D2B). In embodiments, the second feeding chamber evacuation line first diameter (D2A) is greater than the second feeding chamber evacuation line second diameter (D2B). In embodiments, the second feeding chamber evacuation line first diameter (D2A) is less than the second feeding chamber evacuation line second diameter (D2B).

In embodiments, the second feeding chamber evacuation line first diameter (D2A) ranges in size from: between about 1 inch and about 2 inches; between about 2 inches and about 3 inches; between about 3 inches and about 4 inches; between about 4 inches and about 5 inches; between about 5 inches and about 6 inches; between about 6 inches and about 7 inches; between about 7 inches and about 8 inches; between about 8 inches and about 9 inches; between about 9 inches and about 10 inches; between about 10 inches and about 11 inches; between about 11 inches and about 12 inches; between about 12 inches and about 13 inches; between about 13 inches and about 14 inches; between about 14 inches and about 15 inches; between about 15 inches and about 16 inches; between about 16 inches and about 17 inches; between about 17 inches and about 18 inches; between about 18 inches and about 19 inches; between about 19 inches and about 20 inches; between about 20 inches and about 21 inches; between about 21 inches and about 22 inches; between about 22 inches and about 23 inches; between about 23 inches and about 24 inches; between about 24 inches and about 25 inches; between about 25 inches and about 26 inches; between about 26 inches and about 27 inches; between about 27 inches and about 28 inches; between about 28 inches and about 29 inches; between about 29 inches and about 30 inches; between about 30 inches and about 31 inches; between about 31 inches and about 32 inches; between about 32 inches and about 33 inches; between about 33 inches and about 34 inches; between about 34 inches and about 35 inches; between about 35 inches and about 36 inches; between about 36 inches and about 37 inches; between about 37 inches and about 38 inches; between about 38 inches and about 39 inches; or, between about 39 inches and about 40 inches; between about 38 inches and about 39 inches; between about 39 inches and about 40 inches; between about 40 inches and about 50 inches; between about 50 inches and about 60 inches; between about 60 inches and about 70 inches; between about 70 inches and about 80 inches; between about 80 inches and about 90 inches; between about 90 inches and about 100 inches; between about 100 inches and about 125 inches; between about 125 inches and about 150 inches; or, between about 150 inches and about 200 inches.

In embodiments, the second feeding chamber evacuation line second diameter (D2B) ranges in size from: between about 1 inch and about 2 inches; between about 2 inches and about 3 inches; between about 3 inches and about 4 inches; between about 4 inches and about 5 inches; between about 5 inches and about 6 inches; between about 6 inches and about 7 inches; between about 7 inches and about 8 inches; between about 8 inches and about 9 inches; between about 9 inches and about 10 inches; between about 10 inches and about 11 inches; between about 11 inches and about 12 inches; between about 12 inches and about 13 inches; between about 13 inches and about 14 inches; between about 14 inches and about 15 inches; between about 15 inches and about 16 inches; between about 16 inches and about 17 inches; between about 17 inches and about 18 inches; between about 18 inches and about 19 inches; between about 19 inches and about 20 inches; between about 20 inches and about 21 inches; between about 21 inches and about 22 inches; between about 22 inches and about 23 inches; between about 23 inches and about 24 inches; between about 24 inches and about 25 inches; between about 25 inches and about 26 inches; between about 26 inches and about 27 inches; between about 27 inches and about 28 inches; between about 28 inches and about 29 inches; between about 29 inches and about 30 inches; between about 30 inches and about 31 inches; between about 31 inches and about 32 inches; between about 32 inches and about 33 inches; between about 33 inches and about 34 inches; between about 34 inches and about 35 inches; between about 35 inches and about 36 inches; between about 36 inches and about 37 inches; between about 37 inches and about 38 inches; between about 38 inches and about 39 inches; or, between about 39 inches and about 40 inches; between about 38 inches and about 39 inches; between about 39 inches and about 40 inches; between about 40 inches and about 50 inches; between about 50 inches and about 60 inches; between about 60 inches and about 70 inches; between about 70 inches and about 80 inches; between about 80 inches and about 90 inches; between about 90 inches and about 100 inches; between about 100 inches and about 125 inches; between about 125 inches and about 150 inches; or, between about 150 inches and about 200 inches.

Third Feeding Chamber (Fc3)

The third feeding chamber (FC3) has a third feeding chamber insect evacuation output (205C) or a feeding chamber 3 insect evacuation port (2FC) that is in fluid communication with the insect and gas mixture input (303) of the separator (300). The third feeding chamber (FC3) has a third feeding chamber insect evacuation output (205C) or a feeding chamber 3 insect evacuation port (3FC) that is in fluid communication with the insect and gas mixture input (303) of the separator (300). A third feeding chamber exit conduit (302C) is connected at one end to the third feeding chamber (FC3) and at another and to a common entry conduit (CEC). The common entry conduit (CEC) is connected at one end to the third feeding chamber exit conduit (302C) and at another end to the insect and gas mixture input (303) of the separator (300). A feeding chamber 3 evacuation valve (VV3) in interposed in the third feeding chamber exit conduit (302C). The feeding chamber 3 evacuation valve (VV3) is equipped with a with a controller (CV3) that is configured to input and output a signal (XV3) to the computer (COMP). The third feeding chamber exit conduit (302C) has a third feeding chamber evacuation line first diameter (D3A) and a third feeding chamber evacuation line reducer (VR3) which merges into a third feeding chamber evacuation line second diameter (D3B). In embodiments, the third feeding chamber evacuation line first diameter (D3A) is greater than the third feeding chamber evacuation line second diameter (D3B). In embodiments, the third feeding chamber evacuation line first diameter (D3A) is less than the third feeding chamber evacuation line second diameter (D3B).

In embodiments, the third feeding chamber evacuation line first diameter (D3A) ranges in size from: between about 1 inch and about 2 inches; between about 2 inches and about 3 inches; between about 3 inches and about 4 inches; between about 4 inches and about 5 inches; between about 5 inches and about 6 inches; between about 6 inches and about 7 inches; between about 7 inches and about 8 inches; between about 8 inches and about 9 inches; between about 9 inches and about 10 inches; between about 10 inches and about 11 inches; between about 11 inches and about 12 inches; between about 12 inches and about 13 inches; between about 13 inches and about 14 inches; between about 14 inches and about 15 inches; between about 15 inches and about 16 inches; between about 16 inches and about 17 inches; between about 17 inches and about 18 inches; between about 18 inches and about 19 inches; between about 19 inches and about 20 inches; between about 20 inches and about 21 inches; between about 21 inches and about 22 inches; between about 22 inches and about 23 inches; between about 23 inches and about 24 inches; between about 24 inches and about 25 inches; between about 25 inches and about 26 inches; between about 26 inches and about 27 inches; between about 27 inches and about 28 inches; between about 28 inches and about 29 inches; between about 29 inches and about 30 inches; between about 30 inches and about 31 inches; between about 31 inches and about 32 inches; between about 32 inches and about 33 inches; between about 33 inches and about 34 inches; between about 34 inches and about 35 inches; between about 35 inches and about 36 inches; between about 36 inches and about 37 inches; between about 37 inches and about 38 inches; between about 38 inches and about 39 inches; or, between about 39 inches and about 40 inches; between about 38 inches and about 39 inches; between about 39 inches and about 40 inches; between about 40 inches and about 50 inches; between about 50 inches and about 60 inches; between about 60 inches and about 70 inches; between about 70 inches and about 80 inches; between about 80 inches and about 90 inches; between about 90 inches and about 100 inches; between about 100 inches and about 125 inches; between about 125 inches and about 150 inches; or, between about 150 inches and about 200 inches.

In embodiments, the third feeding chamber evacuation line second diameter (D3B) ranges in size from: between about 1 inch and about 2 inches; between about 2 inches and about 3 inches; between about 3 inches and about 4 inches; between about 4 inches and about 5 inches; between about 5 inches and about 6 inches; between about 6 inches and about 7 inches; between about 7 inches and about 8 inches; between about 8 inches and about 9 inches; between about 9 inches and about 10 inches; between about 10 inches and about 11 inches; between about 11 inches and about 12 inches; between about 12 inches and about 13 inches; between about 13 inches and about 14 inches; between about 14 inches and about 15 inches; between about 15 inches and about 16 inches; between about 16 inches and about 17 inches; between about 17 inches and about 18 inches;

between about 18 inches and about 19 inches; between about 19 inches and about 20 inches; between about 20 inches and about 21 inches; between about 21 inches and about 22 inches; between about 22 inches and about 23 inches; between about 23 inches and about 24 inches; between about 24 inches and about 25 inches; between about 25 inches and about 26 inches; between about 26 inches and about 27 inches; between about 27 inches and about 28 inches; between about 28 inches and about 29 inches; between about 29 inches and about 30 inches; between about 30 inches and about 31 inches; between about 31 inches and about 32 inches; between about 32 inches and about 33 inches; between about 33 inches and about 34 inches; between about 34 inches and about 35 inches; between about 35 inches and about 36 inches; between about 36 inches and about 37 inches; between about 37 inches and about 38 inches; between about 38 inches and about 39 inches; or, between about 39 inches and about 40 inches; between about 38 inches and about 39 inches; between about 39 inches and about 40 inches; between about 40 inches and about 50 inches; between about 50 inches and about 60 inches; between about 60 inches and about 70 inches; between about 70 inches and about 80 inches; between about 80 inches and about 90 inches; between about 90 inches and about 100 inches; between about 100 inches and about 125 inches; between about 125 inches and about 150 inches; or, between about 150 inches and about 200 inches.

FIG. 15 describes an Insect Production Superstructure System (IPSS) that insect feeding module (2000) provides insects contained therein to be able to Insect Mobility Large scale insect production systems must be designed responsibly to make sure that the insects are freed from hunger, thirst, discomfort, pain, injury, disease, fear and distress. Three feeding chambers (FC1, FC2, FC3) are shown in FIG. 15 and the egg-laying insects present therein may freely travel from one feeding chamber to another.

The plurality of feeding chambers and a passageways therebetween encourage egg-laying insects therein to express normal behavior by enabling mobility and relocation to a more suitable living environment. An insect may decide to up and relocate for any reason it chooses or no reason at all. In the event that one breeding chamber lacks sufficient amounts of enhanced feedstock, or is over-crowded, or contains diseased or cannibalistic insects, the insects may relocate to another feeding chamber to alleviate their discomfort, pain, injury, disease, and fear and distress.

FIG. 15 describes a portion of an Insect Production Superstructure System (IPSS) that permits insects to have mobility and the opportunity to choose between different possible courses of action. Herein are disclosed advancements and better solutions that meet new requirements, unarticulated needs, or existing market needs in maximizing insect welfare, maximizing insect output on a minimal physical outlay, and benefit of large groups of people a high-value animal protein.

The first feeding chamber (FC1) is connected to the second feeding chamber (FC2) via a chamber 2 to chamber 1 transfer line (TL21). The first feeding chamber (FC1) is also connected to the third feeding chamber (FC3) via a chamber 3 to chamber 1 transfer line (TL31). The first feeding chamber (FC1) is also connected to the any one of a plurality of breeding chambers (BC, BC1, BC2. BC3) via a chamber 1 breeding chamber transfer line (TLBC1) which is elaborated upon more in FIGS. 16 and 17.

The second feeding chamber (FC2) is connected to the first feeding chamber (FC1) via a chamber 1 to chamber 2 transfer line (TL12). The second feeding chamber (FC2) is also connected to the third feeding chamber (FC3) via a chamber 3 to chamber 2 transfer line (TL32). The second feeding chamber (FC2) is also connected to the any one of a plurality of breeding chambers (BC, BC1, BC2. BC3) via a chamber 2 breeding chamber transfer line (TLBC2) which is elaborated upon more in FIGS. 16 and 17.

The third feeding chamber (FC3) is connected to the first feeding chamber (FC1) via a chamber 1 to chamber 3 transfer line (TL13). The third feeding chamber (FC3) is also connected to the second feeding chamber (FC2) via a chamber 2 to chamber 3 transfer line (TL23). The third feeding chamber (FC3) is also connected to the any one of a plurality of breeding chambers (BC, BC1, BC2. BC3) via a chamber 3 breeding chamber transfer line (TLBC3) which is elaborated upon more in FIGS. 16 and 17.

Insect Evacuation

The insect evacuation module (3000) is configured to pull a vacuum on each one of the plurality of insect feeding chambers at any given time to evacuate the insects contained therein. A computer (COMP) may be programmed to control the operation of the insect evacuation module (3000) to be able to systematically apply a vacuum on any one separate or individually of either of the first feeding chamber (FC1), second feeding chamber (FC2), or third feeding chamber (FC3).

The level of the vacuum by the insect evacuation fan (312) may vary. Alternatively, instead of a fan, a vacuum pump, steam jet ejector, pneumatic vacuum, eductor, or any conceivable vacuuming means to realize the end to pull a vacuum on any number of plurality of feeding chambers (FC1, FC2, FC3) at any given time may be used. At times, it is important to be able to only draw a vacuum on only one of the feeding chambers at any given time depending upon how far along in the insect growth stage any given feeding chamber (FC1, FC2, FC3) is at. For example, by measuring the pressure drop across each of the network of cells contained within any given feeding chamber (FC1, FC2, FC3), it may be determined that it is desirable to only evacuated the insects from say, for example, feeding chamber 1 (FC1) while leaving the other two feeding chambers (FC2, FC3) to remain unchanged to promote stable insect growth. To achieve this end, the computer (COMP) will send a signal (XV1) to only the feeding chamber 1 evacuation valve (VV1) on the first feeding chamber (FC1) to evacuate the contents therein.

A common insect evacuation pressure sensor (PT10) is installed on the common entry conduit (CEC), or alternatively may be installed on any plurality number of separators (S1, S1, S3). The common insect evacuation pressure sensor (PT10) is configured to input a signal (XT10) to the computer (COMP). A common insect evacuation vent line (VRL) is connected at one end to the common entry conduit (CEC) and connected at another end to a header vacuum vent valve (VV0). The header vacuum vent valve (VV0) is interposed on the common insect evacuation vent line (VRL) and is in fluid communication with both the insect evacuation fan (312) and each one of the plurality of insect feeding chambers (FC1, FC2, FC3). The header vacuum vent valve (VV0) is equipped with a controller (CV0) that is configured to input and output a signal (XV0) to the computer (COMP). At least one common insect evacuation line reducer (VR0) is interposed on the common insect evacuation vent line (VRL).

The header vacuum vent valve (VV0) is configured to be able to control the level of vacuum pulled on a feeding chamber (FC1, FC2, FC3). In the event that a deep vacuum needs to be pulled to evacuate a feeding chamber that has reached its maximum or desired insect capacity, the header vacuum vent valve (VV0) may be operatively included in a control loop while integrated with (i) the common insect evacuation pressure sensor (PT10), and (ii) the controller (316) of the fan motor (314) of the insect evacuation fan (312). For example, if a deep vacuum needs to be pulled on, say feeding chamber 1 (FC1), while leaving the other feeding chambers unchanged, the header vacuum vent valve (VV0) may remain in the closed position to permit the insect evacuation fan (312) to completely draw down the pressure in the feeding chamber 1 (FC1) to pull an insect and gas mixture having an insect portion and a gas portion through the first feeding chamber insect evacuation output (205A) and common entry conduit (CEC). If the header vacuum vent valve (VV0) is then opened, or modulated, by any given percentage, it will increase the gas portion of the insect and gas mixture flowing into the separator (300) and thus increase the pressure in the feeding chamber (FC1) since not as deep of a vacuum will be pulled on the feeding chamber (FC1). A header vacuum vent valve (VV0) may be able to aide in the separation of insects and gas within any plurality of separators (S1, S2, S3) contained within the insect evacuation module (3000) by providing a predictable and consistent inlet velocity at the inlet of any number of any give plurality of separators (S1, S2, S3).

In embodiments, the egg-laying insects may be evacuated from any plurality of feeding chambers (FC1, FC2, FC3) by applying a vacuum with a velocity pressure range from: between about 0.001 inches of water to about 0.002 inches of water; between about 0.002 inches of water to about 0.003 inches of water; between about 0.003 inches of water to about 0.006 inches of water; between about 0.006 inches of water to about 0.012 inches of water; between about 0.012 inches of water to about 0.024 inches of water; between about 0.024 inches of water to about 0.050 inches of water; between about 0.050 inches of water to about 0.075 inches of water; between about 0.075 inches of water to about 0.150 inches of water; between about 0.150 inches of water to about 0.300 inches of water; between about 0.300 inches of water to about 0.450 inches of water; between about 0.450 inches of water to about 0.473 inches of water; between about 0.473 inches of water to about 0.496 inches of water; between about 0.496 inches of water to about 0.521 inches of water; between about 0.521 inches of water to about 0.547 inches of water; between about 0.547 inches of water to about 0.574 inches of water; between about 0.574 inches of water to about 0.603 inches of water; between about 0.603 inches of water to about 0.633 inches of water; between about 0.633 inches of water to about 0.665 inches of water; between about 0.665 inches of water to about 0.698 inches of water; between about 0.698 inches of water to about 0.733 inches of water; between about 0.733 inches of water to about 0.770 inches of water; between about 0.770 inches of water to about 0.808 inches of water; between about 0.808 inches of water to about 0.849 inches of water; between about 0.849 inches of water to about 0.891 inches of water; between about 0.891 inches of water to about 0.936 inches of water; between about 0.936 inches of water to about 0.982 inches of water; between about 0.982 inches of water to about 1.031 inches of water; between about 1.031 inches of water to about 1.083 inches of water; between about 1.083 inches of water to about 1.137 inches of water; between about 1.137 inches of water to about 1.194 inches of water; between about 1.194 inches of water to about 1.254 inches of water; between about 1.254 inches of water to about 1.316 inches of water; between about 1.316 inches of water to about 1.382 inches of water; between about 1.382 inches of water to about 1.451 inches of water; between about 1.451 inches of water to about 1.524 inches of water; between about 1.524 inches of water to about 2.286 inches of water; between about 2.286 inches of water to about 3.429 inches of water; between about 3.429 inches of water to about 5.143 inches of water; between about 5.143 inches of water to about 7.715 inches of water; between about 7.715 inches of water to about 11.572 inches of water; between about 11.572 inches of water to about 17.358 inches of water; between about 17.358 inches of water to about 26.037 inches of water; between about 26.037 inches of water to about 39.055 inches of water; between about 39.055 inches of water to about 58.582 inches of water; between about 58.582 inches of water to about 87.873 inches of water; between about 87.873 inches of water to about 131.810 inches of water; between about 131.810 inches of water to about 197.715 inches of water; between about 197.715 inches of water to about 296.573 inches of water; or, between about 296.573 inches of water to about 400 inches of water.

In embodiments, the egg-laying insects may be evacuated from any plurality of feeding chambers (FC1, FC2, FC3) by applying a velocity from: between about 0.05 feet per second to between about 0.10 feet per second; 0.10 feet per second to between about 0.15 feet per second; 0.15 feet per second to between about 0.25 feet per second; 0.25 feet per second to between about 0.40 feet per second; 0.40 feet per second to between about 0.65 feet per second; 0.65 feet per second to between about 1.05 feet per second; 1.05 feet per second to between about 1.70 feet per second; 1.70 feet per second to between about 2.75 feet per second; 2.75 feet per second to between about 3.09 feet per second; 3.09 feet per second to between about 3.64 feet per second; 3.64 feet per second to between about 4.26 feet per second; 4.26 feet per second to between about 4.99 feet per second; 4.99 feet per second to between about 5.84 feet per second; 5.84 feet per second to between about 6.83 feet per second; 6.83 feet per second to between about 8.00 feet per second; 8.00 feet per second to between about 9.37 feet per second; 9.37 feet per second to between about 10.97 feet per second; 10.97 feet per second to between about 12.84 feet per second; 12.84 feet per second to between about 15.04 feet per second; 15.04 feet per second to between about 17.61 feet per second; 17.61 feet per second to between about 20.61 feet per second; 20.61 feet per second to between about 24.14 feet per second; 24.14 feet per second to between about 28.26 feet per second; 28.26 feet per second to between about 33.08 feet per second; 33.08 feet per second to between about 38.74 feet per second; 38.74 feet per second to between about 45.35 feet per second; 45.35 feet per second to between about 53.10 feet per second; 53.10 feet per second to between about 62.17 feet per second; 62.17 feet per second to between about 72.79 feet per second; 72.79 feet per second to between about 85.23 feet per second; 85.23 feet per second to between about 99.78 feet per second; 99.78 feet per second to between about 116.83 feet per second; 116.83 feet per second to between about 136.79 feet per second; 136.79 feet per second to between about 160.15 feet per second; 160.15 feet per second to between about 187.51 feet per second; 187.51 feet per second to between about 219.54 feet per second; 219.54 feet per second to between about 257.04 feet per second; 257.04 feet per second to between about 300.95 feet per second; 300.95 feet per second to between about 352.36 feet per second; 352.36 feet per second to between about 412.55 feet per second; 412.55 feet per second to between about 483.02 feet per second; 483.02 feet per second to between about 565.53 feet per second; 565.53 feet per second to between about 662.13 feet per second; 662.13 feet per second to between about 775.24 feet per second; 775.24 feet per second to between about 907.66 feet per second; 907.66 feet per second to between about 1062.71 feet per second; 1062.71 feet per second to between about 1244.24 feet per second; 1244.24 feet per second to between about 1456.78 feet per second; or, 1456.78 feet per second to between about 1500.00 feet per second.

FIG. 16:

FIG. 16 shows a simplistic diagram illustrating a plurality of separators (S1, S2, S3) integrated with one common feeding chamber (FC1), and wherein the feeding chamber (FC1) and second separator (S2) are in fluid communication with one common breeding chamber (BC), and wherein the breeding chamber (BC) is in fluid communication with one common breeding material and insect separator (SEPIA), and wherein the breeding material and insect separator (SEPIA) is in fluid communication with at least one of a plurality of feeding chambers (FC1, FC2, FC3).

FIG. 16 shows a simplistic diagram illustrating a plurality of separators (S1, S2, S3) integrated with one common feeding chamber (FC1), and wherein the feeding chamber (FC1) and second separator (S2) are in fluid communication with one common breeding chamber (BC), and wherein the breeding chamber (BC) is in fluid communication with one common breeding material and insect separator (SEPIA), and wherein the breeding material and insect separator (SEPIA) is in fluid communication with at least one of a plurality of feeding chambers (FC1, FC2, FC3).

FIG. 16 shows a portion of the Insect Production Superstructure System (IPSS) including an insect feeding module (2000), an insect evacuation module (3000), an insect breeding module (4000), and hatched insect separation module (5000). The insect feeding module (2000) is configured to feed the enhanced feedstock from the enhanced feedstock mixing module (1000) and grow insects so that egg-laying insects may in turn lay eggs. The insect evacuation module (3000) is configured to remove insects, residual enhanced feedstock, particulates including insect exoskeleton from the any of a plurality of insect feeding modules (2000, 2000A, 200B, 2000C). The insect breeding module (4000) is configured to remove eggs from the insect feeding module (2000) for incubation over a temperature and humidity controlled duration of time to form hatched-insects. The hatched insect separation module (5000) is configured to separate the hatched-insects and breeding material from the insect breeding module (4000) and then distribute the separated breeding material to any one of the plurality of the insect feeding modules (2000, 2000A, 2000B, 2000C)

FIG. 16 shows an insect feeding module (2000) including one feeding chamber (FC1) integrated with an insect evacuation module (3000) comprised of a first separator (S1), second separator (S2), and a third separator (S3). FIG. 16 shows the first separator (S1) and second separator (S2) as cyclones. FIG. 16 also shows the third separator (S3) as a filter. It is to be noted that the embodiment of FIG. 16 is non-limiting and shall not be construed to limit the disclosure in any way. Any number of separators (S1, S2, S3) may be employed and any permutation or combination of separation unit operations or devices may be used so long as insect portion (304A) is separated from a gas portion (304B) of an insect and gas mixture (304).

FIG. 16 shows the first separator (S1) as a first insect coarse separator (S1A), the second separator (S2) as a second insect fine separator (S2A), and the third separator (S3) as a particulate separator (S3A). The first insect coarse separator (S1A) is configured to remove a portion of the insect portion (304A) separated from the gas portion (304B) of an insect and gas mixture (304). The second insect fine separator (S2A) is configured to remove insects smaller than the insects separated in the first insect coarse separator (S1A). The particulate separator (S3A) is configured to remove particulates such as remnants of enhanced feedstock, or fine polymer particulate, for example, not only including pieces of portions of insect exoskeleton. The particulate separator (S3A) is in fluid communication with the polymer distribution module (1D) and is configured to transfer a portion of the separated particulate to the polymer tank (1D2) as polymer (1D1).

First Separator (S1), First Insect Coarse Separator (S1A)

The first insect coarse separator (S1A) has a first insect coarse separator input (SIAL) that is in fluid communication with the first feeding chamber insect evacuation output (205A) of the first feeding chamber (FC1) via a first feeding chamber exit conduit (302A). The first insect coarse separator (S1A) is configured to accept an insect and gas mixture (304) from the first feeding chamber (FC1), separate a portion of the insects from the gas and output a first insect-depleted gas stream (355) via a coarse separator gas and insect mixture output (356).

The first separator (S1) is equipped with a first dipleg (357), a first separator conveyor (358), and a first separator valve (361) interposed on the first dipleg (357). A first separated insect stream (360) is routed down the first dipleg (357), through the first separator valve (361) and into the first separator conveyor (358). In embodiments, the first separator conveyor (358) is a compression screw (359) which serves to instantly kill insects by compressing them. The first separated insect stream (360) may in turn be sent to a grinder (1250) within an insect grinding module via a first separated insect stream input (371). In other embodiments, the first separated insect stream (360) may be sent to a pathogen removal unit (1550) within a pathogen removal module, or to a within a lipid extraction unit (1501) lipid extraction module.

Second Separator (S2), Second Insect Fine Separator (S2A)

The second insect fine separator (S2A) has a second insect fine separator input (S2A1) that is in fluid communication with the coarse separator gas and insect mixture output (356) of the first insect coarse separator (S1A). The second insect fine separator (S2A) is configured to accept a first insect-depleted gas stream (355) from the first insect coarse separator (S1A), separate a portion of the insects from the gas and output a second insect-depleted gas stream (362) via a fine separator gas and particulate mixture output (363).

The second separator (S2) is equipped with a second dipleg (364), a second separator conveyor (365), and a second separator valve (368) interposed on the second dipleg (364). A second separated insect stream (360) is routed down the second dipleg (364), through the second separator valve (368) and into the second separator conveyor (365). In embodiments, the second separator conveyor (365) is a compression screw (366) which serves to instantly kill insects by compressing them.

In embodiments, the second separator conveyor (365) is a not a compression screw (366) but instead routes the second separated insect stream (367) to the to a breeding chamber (BC) via a breeding chamber fine separated insect portion input (375). In embodiments, the second separator conveyor (365) is a not a compression screw (366) but instead routes the second separated insect stream (367) to a plurality of other destinations such as to the grinder (1250), pathogen removal unit (1550), or lipid extraction unit (1501). The second separated insect stream (367) may be sent to a grinder (1250) within an insect grinding module via a first separated insect stream input (371). In other embodiments, the second separated insect stream (367) may be sent to a pathogen removal unit (1550) within a pathogen removal module, or to a within a lipid extraction unit (1501) lipid extraction module.

Third Separator (S3), Particulate Separator (S3A)

The particulate separator (S3A) has a particulate separator input (S3A1) that is in fluid communication with the fine separator gas and particulate mixture output (363) of the second insect fine separator (S2A). The particulate separator (S3A) is configured to accept a second insect-depleted gas stream (362) from the second insect fine separator (S2A), separate a portion of the particulates from the gas and output a particulate-depleted gas stream (369) to the insect evacuation fan (312).

The insect evacuation fan (312) is in fluid with the breeding chamber (BC) via a breeding chamber exhaust input (376) and is configured to discharge the exhaust (377) into the breeding chamber (BC). In embodiments, the separated insect conveyor (328) of the third separator (S3) particulate separator (S3A) is in fluid communication with the polymer distribution module (1D) and is configured to transfer a portion of the separated particulate stream (370) to the polymer tank (1D2) as polymer (1D1).

Insect Breeding Module (4000)

FIG. 16 shows the insect feeding module (2000) integrated with the insect breeding module (4000). The insect breeding module (4000) is configured to remove eggs from the insect feeding module (2000) for incubation over a temperature and humidity controlled duration of time to form hatched-insects.

The insect breeding module (4000) contains a breeding chamber (BC). FIG. 16 shows one breeding chamber (BC) portrayed as breeding chamber 1 (BC1). It is to be noted that FIG. 16 shows a first feeding chamber (FC1) connected to a breeding chamber 1 (BC1) via a feeding chamber 1 egg-laden breeding material transfer line (R1).

The feeding chamber 1 egg-laden breeding material transfer line (R1) is connected at one end to the first feeding chamber (FC1) via a conveyor output (249) and at another end to breeding chamber 1 (BC1) via a feeding chamber 1 breeding chamber 1 input (BC1A). The feeding chamber 1 egg-laden breeding material transfer line (R1) is configured to transfer an egg-laden breeding material (250) to the interior (BCIN) of breeding chamber 1 (BC1). In embodiments, the interior (BCIN) of the breeding chamber 1 (BC1) contains a tiered plurality of conveyors that include at least an upper and a lower conveyor wherein egg-laden breeding material (250) is transferred from conveyors spaced apart from one another in a vertical orientation to permit sufficient time to incubate the eggs contained within the egg-laden breeding material (250) to hatch insects.

FIG. 16 shows egg-laden breeding material (250) being transferred to the interior (BCIN) of the breeding chamber 1 (BC1) where it is first elevated via a first conveyor transfer unit (XY1A) to the first conveyor height (CH1A) of a first conveyor (CY1A) operating in a clockwise motion of operation.

The first conveyor (CY1A) is positioned at a vertical height above at least one other conveyor. FIG. 16 shows seven conveyors (CY1A, CY2A, CY3A, CY4A, CY5A, CY6A, CY7A) and the first conveyor (CY1A) is positioned at a vertical height above each one of a second conveyor (CY2A), third conveyor (CY3A), fourth conveyor (CY4A), fifth conveyor (CY5A), sixth conveyor (CY6A), and seventh conveyor (CY7A). The second conveyor (CY2A) is positioned at a vertical height above each one of a third conveyor (CY3A), fourth conveyor (CY4A), fifth conveyor (CY5A), sixth conveyor (CY6A), and seventh conveyor (CY7A). The third conveyor (CY3A) is positioned at a vertical height above each one of a fourth conveyor (CY4A), fifth conveyor (CY5A), sixth conveyor (CY6A), and seventh conveyor (CY7A). The fourth conveyor (CY4A) is positioned at a vertical height above each one of a fifth conveyor (CY5A), sixth conveyor (CY6A), and seventh conveyor (CY7A). The fifth conveyor (CY5A) is positioned at a vertical height above each one of a sixth conveyor (CY6A), and seventh conveyor (CY7A). The sixth conveyor (CY6A) is positioned at a vertical height above the seventh conveyor (CY7A).

The first conveyor (CY1A) is installed at a first conveyor height (CH1A) above the second conveyor (CY2A). The second conveyor (CY2A) is installed at a second conveyor height (CH2A) above the third conveyor (CY3A). The third conveyor (CY3A) is installed at a third conveyor height (CH3A) above the fourth conveyor (CY4A). The fourth conveyor (CY4A) is installed at a fourth conveyor height (CH4A) above the fifth conveyor (CY5A). The fifth conveyor (CY5A) is installed at a fifth conveyor height (CH5A) above the sixth conveyor (CY6A). The sixth conveyor (CY6A) is installed at a sixth conveyor height (CH6A) above the seventh conveyor (CY7A).

The seventh conveyor (CY7A) is installed at a seventh conveyor height (CH7A) below all other conveyors (CY1A, CY2A, CY3A, CY4A, CY5A, CY6A). FIG. 16 shows the first conveyor (CY1A), third conveyor (CY3A), fifth conveyor (CY5A), seventh conveyor (CY7A) all configured to operate in a clockwise motion of operation. FIG. 16 shows the second conveyor (CY2A), fourth conveyor (CY4A), sixth conveyor (CY6A), all configured to operate in a counter-clockwise motion of operation.

A conveyor 1 to conveyor 2 transfer unit (XY2A) is configured to transfer the egg-laden breeding material from the first conveyor (CY1A) to the second conveyor (CY2A). The conveyor 2 to conveyor 3 transfer unit (XY3A) is configured to transfer the egg-laden breeding material from the second conveyor (CY2A) to the third conveyor (CY3A). The conveyor 3 to conveyor 4 transfer unit (XY4A) is configured to transfer the egg-laden breeding material from the third conveyor (CY3A) to the fourth conveyor (CY4A). The conveyor 4 to conveyor 5 transfer unit (XY5A) is configured to transfer the egg-laden breeding material from the fourth conveyor (CY4A) to the fifth conveyor (CY5A). The conveyor 5 to conveyor 6 transfer unit (XY6A) is configured to transfer the egg-laden breeding material, and perhaps hatched insects, from the fifth conveyor (CY5A) to the sixth conveyor (CY6A). The conveyor 6 to conveyor 7 transfer unit (XY7A) is configured to transfer the egg-laden breeding material, and perhaps hatched insects, from the sixth conveyor (CY6A) to the seventh conveyor (CY7A). The seventh conveyor (CY7A) is configured to transfer the hatched insects and breeding material from the feeding chamber 1 breeding chamber output (BC1B) of the interior (BCIN) of the breeding chamber (BC) to the interior (SIN1) of the breeding material and insect separator (SEPIA) contained within the hatched insect separation module (5000).

Hatched Insect Separation Module (5000)

FIG. 16 shows the hatched insect separation module (5000) equipped with a breeding material and insect separator (SEPIA) and a breeding material tank (500). The breeding material and insect separator (SEPIA) includes an interior (SIN1), a separator input (1SEPA), a separator material output (1SEPB), and a separator insect output (1SEPC). The breeding material and insect separator (SEPIA) is connected to breeding chamber 1 (BC1) via a breeding chamber 1 hatched egg and breeding material transfer line (U1). The breeding chamber 1 hatched egg and breeding material transfer line (U1) is connected at one end to the breeding chamber 1 (BC1) via a feeding chamber 1 breeding chamber output (BC1B) and connected at another end to the breeding material and insect separator (SEPIA) via a separator input (1SEPA).

The separator input (1SEPA) is configured to accept hatched insects and breeding material from the seventh conveyor (CY7A) of breeding chamber 1 (BC1), and separate hatched insects (400) from the breeding material (523). The separator insect output (1SEPC) is configured to discharge hatched insects (400) from the interior (SIN1) of the breeding material and insect separator (SEPIA) and route the hatched insects (400) to either one of a plurality of feeding chambers (FC1, FC2, FC3) via a separator hatched insect transfer line (O1). Specifically, separator insect output (1SEPC) is configured to discharge hatched insects (400) first feeding chamber (FC1) via a separator feeding chamber 1 transfer line (O11), or to the second feeding chamber (FC2) via a separator feeding chamber 2 transfer line (O12), or to the third feeding chamber (FC3) via a separator feeding chamber 3 transfer line (O13). Hatched insects (400) transferred from the hatched insect separation module (5000) to the insect feeding module (2000) are made available to the first feeding chamber (FC1) via a separator feeding chamber 1 transfer line (O11) and a chamber 1 breeding chamber transfer line (TLBC1).

Breeding material (523) separated from the hatched insects (400) within the interior (SIN1) of the breeding material and insect separator (SEPIA) is routed to the interior (501) of a breeding material tank (500) via a separator material output (1SEPB). The breeding material (523) separated from the hatched insects (400) within the interior (SIN1) of the breeding material and insect separator (SEP1A) may be characterized as an egg-depleted material (518) since eggs were incubated to form hatched insects (400). A material transfer line (522) is connected at one end to the separator material output (1SEPB) of the breeding material and insect separator (SEPIA) and connected at another end to the breeding material input (502) of the breeding material tank (500). An egg-depleted material transfer conveyor (519) may be interposed in the material transfer line (522) in between the breeding material and insect separator (SEPIA) and the breeding material tank (500).

The breeding material tank (500) has an interior (501), a breeding material input (502), and a breeding material output (510). The breeding material tank (500) also has a top section (503), a bottom section (506), and an interior (501) defined by at least one side wall (507). A breeding material screw conveyor (508) is located at the bottom section (506) and configured to transfer breeding material to either one of a plurality of feeding chambers (FC1, FC2, FC3) via a breeding material transfer line (511). The breeding material transfer line (511) is connected at one end to any one of a plurality of feeding chambers (FC1, FC2, FC3) and connected at another end to the breeding material screw conveyor (508) via a breeding material output (510). The breeding material screw conveyor (508) is equipped with a breeding material screw conveyor motor (512), controller (513), and is configured to input and output a signal (514) to the computer (COMP).

FIG. 16A:

FIG. 16A shown one embodiment of a plurality of separators (KGA, KGB, KGC) that are configured to pull a vacuum on a plurality of insect feeding chambers (FC1, FC2, FC3) and separate large insects (KGG), small insects (KGH), and particulates (KGI) therefrom while returning the small insects (KGH) back to the plurality of insect feeding chambers (FC1, FC2, FC3).

A fan (KGM) pulls a vacuum on the first feeding chamber (FC1), second feeding chamber (FC2), and third feeding chamber (FC3) through a particulate separator (KGC), small insect separator (KGB), and a large insect separator (KGA). A large insect-small insect-particulate-gas mixture (KGJ) are evacuated from the first feeding chamber (FC1), second feeding chamber (FC2), third feeding chamber (FC3), through a first transfer conduit (KGD), second transfer conduit (KGE), third transfer conduit (KGF), respectively. The first transfer conduit (KGD), second transfer conduit (KGE), and third transfer conduit (KGF) merge into one common header (KGF') and are then connected to the large insect separator (KGA). The large insect separator (KGA) separates large insects (KGG) from the large insect-small insect-particulate-gas mixture (KGJ). A small insect-particulate-gas mixture (KGK) is evacuated from the large insect separator (KGA) and sent to the small insect separator (KGB). The small insect separator (KGB) separates small insects (KGH) from the small insect-particulate-gas mixture (KGK) and transfers the small insects (KGH) back to the first feeding chamber (FC1), second feeding chamber (FC2), and third feeding chamber (FC3).

The small insect separator (KGB) separates small insects (KGH) from the small insect-particulate-gas mixture (KGK) and transfers the a first small insect portion (KGR) back to the first feeding chamber (FC1) via a fourth transfer conduit (KGO). The small insect separator (KGB) separates small insects (KGH) from the small insect-particulate-gas mixture (KGK) and transfers the second small insect portion (KGS) back to the second feeding chamber (FC2) via a fifth transfer conduit (KGP). The small insect separator (KGB) separates small insects (KGH) from the small insect-particulate-gas mixture (KGK) and transfers a third small insect portion (KGT) back to the third feeding chamber (FC3) via a fifth transfer conduit (KGQ).

A particulate-gas mixture (KGL) is evacuated from the small insect separator (KGB) and sent to the particulate separator (KGC). The particulate separator (KGC) separates particulates (KGI) from the particulate-gas mixture (KGL). The particulates include chitin. A gas (KGM) is evacuated from the particulate separator (KGC) and is sent through a fan (KGM) and then into an odor control system (KGN). In embodiments, the odor control system (KGN) includes an adsorbent, sorbent, or a filter.

FIG. 17:

FIG. 17 shows a perspective view of one embodiment of a scalable portable modular Insect Production Superstructure System (IPSS) designed with: one enhanced feedstock mixing module (1000); three insect feeding modules (2000A, 2000B, 2000C); one insect evacuation module (3000); three insect breeding modules (4000A, 4000B, 4000C), and three insect separation modules (5000).

FIG. 17 shows a perspective view of one embodiment of a scalable portable modular Insect Production Superstructure System (IPSS) designed with: one enhanced feedstock mixing module (1000); three insect feeding modules (2000A, 2000B, 2000C); one insect evacuation module (3000); three insect breeding modules (4000A, 4000B, 4000C), and three insect separation modules (5000).

In one embodiment, each module (1000, 2000A, 2000B, 2000C, 3000, 4000A, 4000B, 4000C, 5000) container is a 40 feet high shipping container conforming to the International Organization for Standardization (ISO) specifications. In another embodiment, the container may measure 40 feet×8 feet×9.6 feet. In another embodiment, other containers of different sizes may be used.

In embodiments, each module (1000, 2000A, 2000B, 2000C, 3000, 4000A, 4000B, 4000C, 5000) may be positioned on high density plastic ties (HDT). The high density plastic ties (HDT) provide stability to the module (1000, 2000A, 2000B, 2000C, 3000, 4000A, 4000B, 4000C, 5000) of the Insect Production Superstructure System (IPSS) and may be cheaper and faster to install than traditional concrete foundations. In another embodiment, each of the module (1000, 2000A, 2000B, 2000C, 3000, 4000A, 4000B, 4000C, 5000) may be positioned on concrete foundations. Electrical cables may be contained in a plurality of fiberglass cable trays (FGT) placed between each module (1000, 2000A, 2000B, 2000C, 3000, 4000A, 4000B, 4000C, 5000).

The embodiment of FIG. 17 shows the enhanced feedstock mixing module (1000) including a feedstock distribution module (1A), mineral distribution module (1B), vitamin distribution module (1C), polymer distribution module (1D), water distribution module (1E), and enhanced feedstock distribution module (1F), However, as depicted in FIGS. 18-20 the water distribution module (1E) and enhanced feedstock distribution module (1F) may be separate from the enhanced feedstock mixing module (1000). A separate water distribution module (1E) and a separate enhanced feedstock distribution module (1F) are not shown in FIG. 17 because it these modules (1E, 1F) are designed to be housed within the enhanced feedstock mixing module (1000). A separate water distribution module (1E) is shown in FIGS. 21-23. A separate and a separate enhanced feedstock distribution module (1F) is shown in FIGS. 24-26.

In the non-limiting example of FIG. 17 for a variable-scale, modular, easily manufacturable, energy efficient, reliable, and computer operated Insect Production Superstructure Systems (IPSS) shows one enhanced feedstock mixing module (1000) in fluid communication with a first insect feeding module (2000A), second insect feeding module (2000B), and a third insect feeding module (2000C).

A first enhanced feedstock stream (EF1) is configured to pass from the enhanced feedstock mixing module (1000) to the first insect feeding module (2000A). A second enhanced feedstock stream (EF2) is configured to pass from the enhanced feedstock mixing module (1000) to the second insect feeding module (2000B). A third enhanced feedstock stream (EF3) is configured to pass from the enhanced feedstock mixing module (1000) to the third insect feeding module (2000C).

Each of the first insect feeding module (2000A), second insect feeding module (2000B), third insect feeding module (2000C), are connected to one common insect evacuation module (3000) via a common entry conduit (CEC). The common entry conduit (CEC) is connected at one end to the insect evacuation module (3000) and connected at one end to the first insect feeding module (2000A) via a first feeding chamber insect evacuation output (205A). The common entry conduit (CEC) is connected at one end to the insect evacuation module (3000) and connected at one end to the second insect feeding module (2000B) via a second feeding chamber insect evacuation output (205B). The common entry conduit (CEC) is connected at one end to the insect evacuation module (3000) and connected at one end to the third insect feeding module (2000C) via a third feeding chamber insect evacuation output (205C). Each insect feeding module (2000A, 2000B, 2000C) is connected to its own insect breeding module (4000A, 4000B, 4000C). The first insect feeding module (2000A) is connected to the first insect breeding module (4000A) via a feeding chamber 1 egg-laden breeding material transfer line (R1). The second insect feeding module (2000B) is connected to the second insect breeding module (4000B) via a feeding chamber 2 egg-laden breeding material transfer line (R2). The third insect feeding module (2000C) is connected to the third insect breeding module (4000C) via a feeding chamber 3 egg-laden breeding material transfer line (R3).

Each insect breeding module (4000A, 4000B, 4000C) is connected to its own hatched insect separation module (5000A, 5000B, 5000C). The first insect breeding module (4000A) is connected to the first hatched insect separation module (5000A) via a breeding chamber 1 hatched egg and breeding material transfer line (U1). The second insect breeding module (4000B) is connected to the second hatched insect separation module (5000B) via a breeding chamber 2 hatched egg and breeding material transfer line (U2). The third insect breeding module (4000C) is connected to the third hatched insect separation module (5000C) via a breeding chamber 3 hatched egg and breeding material transfer line (U3).

Each hatched insect separation module (5000A, 5000B, 5000C) is connected to any of the plurality of insect feeding modules (2000A, 2000B, 2000C) via a first hatched insect output (DFC), second hatched insect output (EFC), and third hatched insect output (FFC). The first hatched insect output (DFC) of the first hatched insect separation module (5000A) is in fluid communication with the first insect feeding module (2000A) via a first hatched insect input (AFC). The first hatched insect output (DFC) of the first hatched insect separation module (5000A) is in fluid communication with the second insect feeding module (2000B) via a second hatched insect input (BFC). The first hatched insect output (DFC) of the first hatched insect separation module (5000A) is in fluid communication with the third insect feeding module (2000C) via a third hatched insect input (CFC).

The second hatched insect output (EFC) of the second hatched insect separation module (5000B) is in fluid communication with the first insect feeding module (2000A) via a first hatched insect input (AFC). The second hatched insect output (EFC) of the second hatched insect separation module (5000B) is in fluid communication with the second insect feeding module (2000B) via a second hatched insect input (BFC). The second hatched insect output (EFC) of the second hatched insect separation module (5000B) is in fluid communication with the third insect feeding module (2000C) via a third hatched insect input (CFC).

The third hatched insect output (FFC) of the third hatched insect separation module (5000C) is in fluid communication with the first insect feeding module (2000A) via a first hatched insect input (AFC). The third hatched insect output (FFC) of the third hatched insect separation module (5000C) is in fluid communication with the second insect feeding module (2000B) via a second hatched insect input (BFC). The third hatched insect output (FFC) of the third hatched insect separation module (5000C) is in fluid communication with the third insect feeding module (2000C) via a third hatched insect input (CFC).

FIG. 18:

FIG. 18 shows a front view of one embodiment of an enhanced feedstock mixing module (1000) module including a feedstock distribution module (1A), mineral distribution module (1B), vitamin distribution module (1C), and a polymer distribution module (1D). The enhanced feedstock mixing module (1000) is shown to be contained within a 40 feet high shipping container conforming to the International Organization for Standardization (ISO) specifications.

The feedstock distribution module (1A) has feedstock (1A1) contained within the interior (1A3) of a feedstock tank (1A2). A feedstock mass sensor (1A7) is provided to determine the loss in mass of the feedstock tank (1A2). The feedstock tank (1A2) has a live floor screw (1A21) with a motor (1A22) is configured to transfer feedstock (1A1) from the interior (1A3) of the feedstock tank (1A2) to a feedstock conveyor (1A5) and an enhanced feedstock transport screw (1A20). A supply access door (1A15) is positioned above the feedstock input (1A4) and configured to transfer feedstock (1A1) to the interior (1A3) of the feedstock tank (1A2). A supply access door opening/closing unit (1A16) is operatively coupled to the supply access door (1A15) and a weather seal (1A17) is in contact with the supply access door (1A15) to prevent rain and other elements from entering the enhanced feedstock mixing module (1000).

The mineral distribution module (1B) has minerals (1B1) contained within the interior (1B3) of a mineral tank (1B2). A mineral mass sensor (1B7) is provided to determine the loss in mass of the mineral tank (1B2). The mineral tank (1B2) has a live floor screw (1B20) with a motor (1B21) is configured to transfer minerals (1B1) from the interior (1B3) of the mineral tank (1B2) to a mineral conveyor (1B5) and an enhanced feedstock transport screw (1A20) via an enhanced feedstock transport screw connection (1B18). A supply access door (1B13) is positioned above the mineral input (1B4) and configured to transfer minerals (1B1) to the interior (1B3) of the mineral tank (1B2). A supply access door opening/closing unit (1B14) is operatively coupled to the supply access door (1B13) and a weather seal (1B15) is in contact with the supply access door (1B13) to prevent rain and other elements from entering the enhanced feedstock mixing module (1000).

The vitamin distribution module (1C) has vitamins (1C1) contained within the interior (1C3) of a vitamin tank (1C2). A vitamin mass sensor (1C7) is provided to determine the loss in mass of the vitamin tank (1C2). The vitamin tank (1C2) has a live floor screw (1C20) with a motor (1C21) is configured to transfer vitamins (1C1) from the interior (1C3) of the vitamin tank (1C2) to a vitamin conveyor (105) and an enhanced feedstock transport screw (1A20) via an enhanced feedstock transport screw connection (1C18). A supply access door (1C13) is positioned above the vitamin input (1C4) and configured to transfer vitamins (1C1) to the interior (1C3) of the vitamin tank (1C2). A supply access door opening/closing unit (1C14) is operatively coupled to the supply access door (1C13) and a weather seal (1C15) is in contact with the supply access door (1C13) to prevent rain and other elements from entering the enhanced feedstock mixing module (1000).

The polymer distribution module (1D). includes polymer (1D1) contained within the interior (1D3) of a polymer tank (1D2). A polymer mass sensor (1D7) is provided to determine the loss in mass of the polymer tank (1D2). The polymer tank (1D2) has a live floor screw (1D20) with a motor (1D21) is configured to transfer polymer (1D1) from the interior (1D3) of the polymer tank (1D2) to a polymer conveyor (1D5) and an enhanced feedstock transport screw (1A20) via an enhanced feedstock transport screw connection (1D18). A supply access door (1D13) is positioned above the polymer input (1D4) and configured to transfer polymer (1D1) to the interior (1D3) of the polymer tank (1D2). A supply access door opening/closing unit (1C14) is operatively coupled to the supply access door (1C13) and a weather seal (1C15) is in contact with the supply access door (1C13) to prevent rain and other elements from entering the enhanced feedstock mixing module (1000).

A dry enhanced feedstock (DEF) is outputted from the enhanced feedstock mixing module (1000) via the enhanced feedstock transport screw (1A20). A feedstock moisture sensor (1A12A) is interposed on the enhanced feedstock transport screw (1A20) to measure the water content of the dry enhanced feedstock (DEF). Alternately, the feedstock moisture sensor (1A12A) may be positioned on the enhanced feedstock transport screw (1A20) after the minerals (1B1), vitamins (1C1), polymer (1D1) have been mixed with the feedstock (1A1). The enhanced feedstock mixing module (1000) may be equipped with a low voltage disconnect switch (1000LV) and a computer (COMP).

FIG. 19:

FIG. 19 shows a top view of one embodiment of an enhanced feedstock mixing module (1000) including a feedstock distribution module (1A), mineral distribution module (1B), vitamin distribution module (1C), and a polymer distribution module (1D).

Feedstock (1A1) within the feedstock tank (1A2), minerals (1B1) within the mineral tank (1B2), vitamins (1C1) within the vitamin tank (1C2), and polymer (1D1) within the polymer tank (1D2) are all mixed together in an enhanced feedstock transport screw (1A20). A live floor screw (1A21) equipped with a motor (1A22) is positioned within the feedstock tank (1A2). The live floor screw (1A21) transfers feedstock (1A1) to a feedstock conveyor (1A5). The feedstock conveyor (1A5) has a feedstock conveyor output (1A6) that is connected to a feedstock transfer line (1A14). The feedstock transfer line (1A14) is connected at one end to the feedstock conveyor output (1A6) and at another end to the enhanced feedstock transport screw (1A20) via an enhanced feedstock transport screw connection (1A20A). The feedstock distribution module (1A) is equipped with an air inlet vent (1A18) that is configured to input air (1A19) to the feedstock distribution module (1A) portion of the enhanced feedstock mixing module (1000). A feedstock module access door (1A23) is provided to access the feedstock distribution module (1A) portion of the enhanced feedstock mixing module (1000).

A live floor screw (1B20) equipped with a motor (1B21) is positioned within the mineral tank (1B2). The live floor screw (1B20) transfers minerals (1B1) to a mineral conveyor (1B5). The mineral conveyor (1B5) has a mineral conveyor output (1B6) that is connected to a mineral transfer line (1B12). The mineral transfer line (1B12) is connected at one end to the mineral conveyor output (1B6) and at another end to the enhanced feedstock transport screw (1A20) via an enhanced feedstock transport screw connection (1B18). The mineral distribution module (1B) is equipped with an air inlet vent (1B16) that is configured to input air (1B17) to the mineral distribution module (1B) portion of the enhanced feedstock mixing module (1000). A mineral module access door (1B22) is provided to access the mineral distribution module (1B) portion of the enhanced feedstock mixing module (1000).

A live floor screw (1C20) equipped with a motor (1C21) is positioned within the vitamin tank (1D2). The live floor screw (1C20) transfers vitamins (1C1) to a vitamin conveyor (105). The vitamin conveyor (105) has a vitamin conveyor output (106) that is connected to a vitamin transfer line (1C12). The vitamin transfer line (1C12) is connected at one end to the vitamin conveyor output (106) and at another end to the enhanced feedstock transport screw (1A20) via an enhanced feedstock transport screw connection (1C18). The vitamin distribution module (1C) is equipped with an air inlet vent (1C16) that is configured to input air (1C17) to the vitamin distribution module (1C) portion of the enhanced feedstock mixing module (1000). A vitamin module access door (1C22) is provided to access the vitamin distribution module (1C) portion of the enhanced feedstock mixing module (1000).

A live floor screw (1D20) equipped with a motor (1D21) is positioned within the polymer tank (1D2) to transfer polymer (1D1) to a polymer conveyor (1D5). The polymer conveyor (1D5) has a polymer conveyor output (1D6) that is connected to a polymer transfer line (1D12). The polymer transfer line (1D12) is connected at one end to the polymer conveyor output (1D6) and at another end to the enhanced feedstock transport screw (1A20) via an enhanced feedstock transport screw connection (1D18). The polymer distribution module (1D) is equipped with an air inlet vent (1D16) that is configured to input air (1D17) to the polymer distribution module (1D) portion of the enhanced feedstock mixing module (1000). A polymer module access door (1D22) is provided to access the polymer distribution module (1D) portion of the enhanced feedstock mixing module (1000). The polymer distribution module (1D) is in fluid communication with the third separator (S3) particulate separator (S3A) of the insect evacuation module (3000). The polymer tank (1D2) is configured to accept a polymer (1D1) from a portion of the separated particulate stream (370) of the separated insect conveyor (328) of the third separator (S3) particulate separator (S3A).

FIG. 20:

FIG. 20 shows a first side view of one embodiment of an enhanced feedstock mixing module (1000). Visible from the first side view of the enhanced feedstock mixing module (1000) is the supply access door (1A15) that is opened and closed by a supply access door opening/closing unit (1A16) wherein a weather seal (1A17) prevents rain and other elements from entering the enhanced feedstock mixing module (1000).

Feedstock (1A1) is contained within the interior (1A3) of the feedstock tank (1A2). Feedstock (1A1) is added to the enhanced feedstock mixing module (1000) through the supply access door (1A15) where it enters the feedstock input (1A4) and into the interior (1A3) of the feedstock tank (1A2). A live floor screw (1A21) is positioned in the interior (1A3) of the feedstock tank (1A2). The live floor screw (1A21) is configured to transfer feedstock (1A1) from the interior (1A3) of the feedstock tank (1A2) into a feedstock conveyor (1A5). The feedstock conveyor motor (1A9) drives the feedstock conveyor (1A5) to transport feedstock (1A1) through the feedstock conveyor output (1A6) and into the enhanced feedstock transport screw (1A20) via an enhanced feedstock transport screw connection (1A20A). A feedstock mass sensor (1A7) may be positioned on the feedstock conveyor (1A5) to measure the mass loss and control to a pre-determined feedstock mass flow rate into the enhanced feedstock transport screw (1A20). Also visible is the feedstock module access door (1A23) and an air inlet vent (1A18) which permits air (1A19) to enter the feedstock distribution module (1A) portion of the enhanced feedstock mixing module (1000).

FIG. 21:

FIG. 21 shows a front view of one embodiment of a water distribution module (1E). The following description for FIG. 21 also applies to FIG. 22 since the reference numerals for FIG. 20 and FIG. 21 are identical. The water distribution module (1E) is shown to be contained within a 40 feet high shipping container conforming to the International Organization for Standardization (ISO) specifications.

The water distribution module (1E) contains a first water treatment unit (1E6), second water treatment unit (1E11), water distribution module (1E) enhancer tank (1E45) and a water supply pump (1E22). A water input line (1E4) enters the water distribution module (1E) and is connected to the first water treatment unit (1E6) at a first water treatment unit input (1E7). A first water pressure sensor (1E2) is installed on the water input line (1E4). The first water treatment unit (1E6) may contain a contain an adsorbent, ion-exchange resin, catalyst, or activated carbon.

The first water treatment unit (1E6) is connected to the second water treatment unit (1E11) via a first contaminant-depleted water transfer line (1E10). The first contaminant-depleted water transfer line (1E10) is connected at one end to the first water treatment unit output (1E8) of the first water treatment unit (1E6) and connected at a second end to the second water treatment unit input (1E12) of the second water treatment unit (1E11). The second water treatment unit (1E11) may contain a contain an adsorbent, ion-exchange resin, catalyst, or activated carbon. The system as shown in FIGS. 21-23 may, for example be used to decontaminate water that contains positively charged ions and negatively charged ions and optionally undesirable compounds. The positively charged ions are comprised of one or more from the group consisting of calcium, magnesium, sodium, and iron. The negatively charged ions are comprised of one or more from the group consisting of iodine, chloride, and sulfate. The undesirable compounds are comprised of one or more from the group consisting of dissolved organic chemicals, viruses, bacteria, and particulates. In embodiments, the first water treatment unit (1E6) contains activated carbon and the second water treatment unit (1E11) contains a molecular sieve adsorbent.

In embodiments, the first water treatment unit (1E6) includes a cation configured to remove positively charged ions from water to form a positively charged ion depleted water, the positively charged ions are comprised of one or more from the group consisting of calcium, magnesium, sodium, and iron. In embodiments, the second water treatment unit (1E11) includes an anion configured to remove negatively charged ions from the positively charged ion depleted water to form a negatively charged ion depleted water, the negatively charged ions are comprised of one or more from the group consisting of iodine, chloride, and sulfate. In embodiments, the first water treatment unit (1E6) includes a cation and an anion. In embodiments, the second water treatment unit (1E11) includes a membrane configured to remove undesirable compounds from the negatively charged ion depleted water to form an undesirable compounds depleted water, the undesirable compounds are comprised of one or more from the group consisting of dissolved organic chemicals, viruses, bacteria, and particulates. In embodiments, the second water treatment unit (1E11) includes a membrane configured to remove undesirable compounds from the water to form an undesirable compounds depleted water, the undesirable compounds are comprised of one or more from the group consisting of dissolved organic chemicals, viruses, bacteria, and particulates.

The second water treatment unit (1E11) is connected to the water tank (1E16) via a second contaminant-depleted water transfer line (1E15). The second contaminant-depleted water transfer line (1E15) is connected at one end to the second water treatment unit output (1E13) of the second water treatment unit (1E11) and connected at another end to the water input (1E18) of the water tank (1E16). A water supply valve (1E23) with a controller (1E24) is interposed on the second contaminant-depleted water transfer line (1E15) in between the second water treatment unit (1E11) and water tank (1E16). The water tank (1E16) has an interior (1E17) that contains water (1E1). The water tank (1E16) is equipped with a high water level sensor (1E26) and a low water level sensor (1E28).

Enhancers (1E44) contained within the interior (1E46) of the enhancer tank (1E45) may be routed to the interior (1E17) of the water tank (1E16) through an enhancer transfer line (1E48). The enhancer transfer line (1E48) is connected at one end to the enhancer tank output (1E47) of the enhancer tank (1E45) and connected at another end to the enhancer input (1E49) of the water tank (1E16). A water enhancer supply valve (1E52) with a controller (1E53) is interposed on the enhancer transfer line (1E48) in between the enhancer tank (1E45) and the water tank (1E16). An enhancer flow sensor (1E50) is interposed on the enhancer transfer line (1E48) in between the enhancer tank (1E45) and the water tank (1E16).

A water supply pump (1E22) is connected to the water tank (1E16) via a water discharge line (1E21). The water supply pump (1E22) is configured to remove water (1E1), and enhancers (1E44), from the interior (1E17) of the water tank (1E16) for transfer downstream to be mixed with a dry enhanced feedstock (DEF) to create a wet enhanced feedstock (WEF). The water discharge line (1E21) is connected at one end to the water output (1E20) of the water tank (1E16) and connected at another end to the water supply pump (1E22).

The water supply pump (1E22) pulls a suction on the water discharge line (1E21) of the water tank (1E16) and increases the pressure of the (1E1) and outputs pressurized water via a water transfer line (1E41). The water transfer line (1E41) has a variety of instrumentation installed on it, including: a water flow sensor (1E34); a water control valve (1E36); a third water pressure sensor (1E39); and, a water quality sensor (1E42). A second water pressure sensor (1E30) is installed on the water transfer line (1E41) upstream of the water control valve (1E36) and closer to the water supply pump (1E22). In embodiments, the pressure drop across the water control valve (1E36) may range from: between about 1 pound per square inch to about 5 pound per square inch; between about 5 pound per square inch to about 10 pound per square inch; between about 10 pound per square inch to about 15 pound per square inch; between about 15 pound per square inch to about 20 pound per square inch; between about 25 pound per square inch to about 30 pound per square inch; between about 35 pound per square inch to about 40 pound per square inch; between about 45 pound per square inch to about 50 pound per square inch; between about 55 pound per square inch to about 60 pound per square inch; between about 65 pound per square inch to about 70 pound per square inch; between about 75 pound per square inch to about 80 pound per square inch; between about 85 pound per square inch to about 90 pound per square inch; between about 95 pound per square inch to about 100 pound per square inch; between about 100 pound per square inch to about 125 pound per square inch; between about 125 pound per square inch to about 150 pound per square inch; or, between about 150 pound per square inch to about 200 pound per square inch.

The water transfer line (1E41) is discharged from the water distribution module (1E) en route to the enhanced feedstock distribution module (1F) on FIGS. 24-26. The water distribution module (1E) contains a first access door (1E55) at one end and a second access door (1E56) at another end. The water distribution module (1E) also contains an air vent (1E57) for introduction of an air supply (1E58). The water distribution module (1E) also contains a low voltage disconnect switch (1E59) and a computer (COMP)

FIG. 22:

FIG. 22 shows a top view of one embodiment of a water distribution module (1E). Refer to the text in the preceding section for the description of FIG. 22.

FIG. 23:

FIG. 23 shows a first side view of one embodiment of a water distribution module (1E). Visible from the first side view of the water distribution module (1E) is the first access door (1E55) along with the air vent (1E57) for introduced on an air supply (1E58). A water input line (1E4) containing is shown entering the first water treatment unit (1E6) via a first water treatment unit input (1E7). Water (1E1) is shown contained within the interior (1E17) of the water tank (1E16). Enhancers (1E44) are shown contained within the interior (1E46) of the enhancer tank (1E45).

FIG. 24:

FIG. 24 shows a front view of one embodiment of an enhanced feedstock distribution module (1F). The enhanced feedstock distribution module (1F) is shown to be contained within a 40 feet high shipping container conforming to the International Organization for Standardization (ISO) specifications. Water (1E1) enters from the left-hand-side of the enhanced feedstock distribution module (1F) via a water transfer line (1E41). The water (1E1) is mixed with a dry enhanced feedstock (DEF) to form a wet enhanced feedstock (WEF). The dry enhanced feedstock (DEF) enters from the left-hand-side of the enhanced feedstock distribution module (1F) via an enhanced feedstock transport screw (1A20). A wet enhanced feedstock (WEF) is transported to the enhanced feedstock splitter (1F1) via an enhanced feedstock transfer line (1F0). An enhanced feedstock moisture sensor (1A12B) is installed on the enhanced feedstock transfer line (1F0). In embodiments, the wet enhanced feedstock (WEF) may be introduced to the enhanced feedstock splitter (1F1) through an enhanced feedstock transfer line (1F0) via a plurality of inputs (1F3A, 1F3B, 1F3C). Each of the first splitter input (1F3A), second splitter input (1F3B), and third splitter input (1F3C), transfer a wet enhanced feedstock (WEF) to the interior (1F2) of the enhanced feedstock splitter (1F1).

The enhanced feedstock splitter (1F1) has a top section (1F4), bottom section (1F5), and an interior (1F2) defined by at least one side wall (1F6). A first splitter level sensor (1F7) is positioned on the side wall (1F6). The enhanced feedstock splitter (1F1) is shown equipped with a splitter first screw conveyor (1F9) and a splitter second screw conveyor (1F14) both positioned at the bottom section (1F5) of the enhanced feedstock splitter (1F1). The splitter first screw conveyor (1F9) transfers enhanced feedstock from the interior (1F2) of the enhanced feedstock splitter (1F1) to a first weigh screw (1F24) via a first output (1F10). The splitter second screw conveyor (1F14) transfers enhanced feedstock from the interior (1F2) of the enhanced feedstock splitter (1F1) to a second weigh screw (1F33) via a second output (1F15). The enhanced feedstock distribution module (1F) is shown equipped with a low voltage disconnect switch (1F55) and a computer (COMP).

FIG. 25:

FIG. 25 shows a top view of one embodiment of an enhanced feedstock distribution module (1F). The enhanced feedstock distribution module (1F) is shown to be contained within a 40 feet high shipping container conforming to the International Organization for Standardization (ISO) specifications. Water (1E1) enters from the left-hand-side of the enhanced feedstock distribution module (1F) via a water transfer line (1E41). The water (1E1) is mixed with a dry enhanced feedstock (DEF) to form a wet enhanced feedstock (WEF). The dry enhanced feedstock (DEF) enters from the left-hand-side of the enhanced feedstock distribution module (1F) via an enhanced feedstock transport screw (1A20). A wet enhanced feedstock (WEF) is transported to the enhanced feedstock splitter (1F1) via an enhanced feedstock transfer line (1F0). An enhanced feedstock moisture sensor (1A12B) is installed on the enhanced feedstock transfer line (1F0). In embodiments, the wet enhanced feedstock (WEF) may be introduced to the enhanced feedstock splitter (1F1) through an enhanced feedstock transfer line (1F0) via a plurality of inputs (1F3A, 1F3B, 1F3C). Each of the first splitter input (1F3A), second splitter input (1F3B), and third splitter input (1F3C), transfer a wet enhanced feedstock (WEF) to the interior (1F2) of the enhanced feedstock splitter (1F1).

The enhanced feedstock splitter (1F1) has an interior (1F2) defined by at least one side wall (1F6). A first splitter level sensor (1F7) is positioned on the side wall (1F6). The enhanced feedstock splitter (1F1) is shown equipped with a splitter first screw conveyor (1F9) and a splitter second screw conveyor (1F14) both positioned within the interior (1F2) of the enhanced feedstock splitter (1F1).

The splitter first screw conveyor (1F9) transfers enhanced feedstock from the interior (1F2) of the enhanced feedstock splitter (1F1) to a first weigh screw (1F24) via a first output (1F10). The first weigh screw (1F24) has a first weigh screw input (1F25) and a first weigh screw output (1F26). The first weigh screw input (1F25) of the first weigh screw (1F24) accepts enhanced feedstock from the first output (1F10) of the splitter first screw conveyor (1F9). The splitter first screw conveyor (1F9) is equipped with a splitter first screw conveyor motor (1F11). The first weigh screw (1F24) is configured to discharge a first weighed enhanced feedstock stream (1F32) or a first enhanced feedstock stream (EF1) via the first weigh screw output (1F26). The first weighed enhanced feedstock stream (1F32) or the first enhanced feedstock stream (EF1) is discharged from the first weigh screw output (1F26) where it is then transferred to a first feeding chamber (FC1). The first weigh screw (1F24) is equipped with a mass sensor (1F27) and a first weigh screw motor (1F29).

The splitter second screw conveyor (1F14) transfers enhanced feedstock from the interior (1F2) of the enhanced feedstock splitter (1F1) to a second weigh screw (1F33) via a second output (1F15). The second weigh screw (1F33) has a second weigh screw input (1F34) and a second weigh screw output (1F35). The second weigh screw input (1F34) of the second weigh screw (1F33) accepts enhanced feedstock from the second output (1F15) of the splitter second screw conveyor (1F14). The splitter second screw conveyor (1F14) is equipped with a splitter second screw conveyor motor (1F16). The second weigh screw (1F33) is configured to discharge a second weighed enhanced feedstock stream (1F41) or a second enhanced feedstock stream (EF2) via the second weigh screw output (1F35). The second weighed enhanced feedstock stream (1F41) or the second enhanced feedstock stream (EF2) is discharged from the second weigh screw output (1F35) where it is then transferred to a second feeding chamber (FC2). The second weigh screw (1F33) is equipped with a mass sensor (1F36) and a second weigh screw motor (1F38).

The enhanced feedstock distribution module (1F) is shown equipped with a low voltage disconnect switch (1F55) and a computer (COMP). Also shown is a first access door (1F51), second access door (1F52), and an air vent (1F53) configured to introduce an air supply (1F54) to the enhanced feedstock distribution module (1F).

FIG. 26:

FIG. 26 shows a first side view of one embodiment of an enhanced feedstock distribution module (1F). Visible from the first side view of the enhanced feedstock transfer line (1F0) is the first access door (1F51) along with the air vent (1F53) for introduced on an air supply (1F54). The enhanced feedstock splitter (1F1) is shown to have an interior (1F2) defined by at least one side wall (1F6). A first splitter level sensor (1F7) is positioned on the side wall (1F6). The enhanced feedstock splitter (1F1) has a top section (1F4) and a bottom section (1F5). A splitter second screw conveyor (1F14) is positioned within the interior (1F2) of the enhanced feedstock splitter (1F1) at the bottom section (1F5).

A water transfer line (1E41) is shown entering the enhanced feedstock transfer line (1F0) where it mixes with enhanced feedstock and is routed to the interior (1F2) of the enhanced feedstock splitter (1F1) via an enhanced feedstock transfer line (1F0) and a first splitter input (1F3A). The first splitter input (1F3A) has an insertion distance (1F3A1) positioned within the interior (1F2) of the enhanced feedstock splitter (1F1). In embodiments, the insertion distance (1F3A1) may range from: between about 2 inches to about 4 inches; between about 4 inches to about 8 inches; between about 8 inches to about 12 inches; between about 12 inches to about 16 inches; between about 16 inches to about 20 inches; between about 20 inches to about 24 inches; between about 24 inches to about 28 inches; between about 28 inches to about 30 inches; between about 30 inches to about 34 inches; between about 34 inches to about 36 inches; between about 36 inches to about 40 inches; between about 40 inches to about 44 inches; between about 44 inches to about 46 inches; between about 46 inches to about 50 inches; or, between about 50 inches to about 60 inches.

A second output (1F15) is shown at the bottom section (1F5) of the enhanced feedstock splitter (1F1). A second weigh screw (1F33) is shown to have a second weigh screw input (1F34) and a second weigh screw output (1F35). The second weigh screw input (1F34) is connected to the second output (1F15) is shown at the bottom section (1F5) of the enhanced feedstock splitter (1F1). The second weigh screw (1F33) is equipped with a mass sensor (1F36) and a second weigh screw motor (1F38). The second weighed enhanced feedstock stream (1F41) or the second enhanced feedstock stream (EF2) is discharged from the second weigh screw output (1F35) where it is then transferred to a second feeding chamber (FC2).

FIG. 27A:

FIG. 27A shows a front view of one embodiment of an insect feeding module (2000, 2000A, 2000B, 2000C). Referring to FIGS. 27-29, the insect feeding module (2000, 2000A, 2000B, 2000C) is shown to be contained within a 40 feet high shipping container conforming to the International Organization for Standardization (ISO) specifications.

FIG. 27A shows an insect feeding module (2000, 2000A, 2000B, 2000C) containing a network (220) of cells (219) for growing insects (225). The network (220) of cells (219) has openings (222) first end (221) and openings (224) of the second end (223). A vibration unit (214) equipped with a vibration unit motor (215) is operatively connected to the network (220) of cells (219) via a first vibration unit connection (218A) and a second vibration unit connection (218B). The vibration unit (214) is configured to vibrate at least a portion of the network (220) of cells (219) to assist in removal of insects (225) contained therein.

In embodiments, the network (220) of cells (219) has a network length (N-L) that is greater than the network width (N-W). In embodiments, the network (220) of cells (219) has a network length (N-L) that is less than the network width (N-W). In one example, as in the non-limiting embodiments of FIGS. 27-29, the network width (N-W) is approximately about between about 4 feet to about 5 feet, and the network length (N-L) is approximately about between about 30 feet to about 31 feet to fit within the shipping container and allowing for access and maintenance.

In embodiments, the network length (N-L) ranges from: 0.5 feet to about 1 foot; between about 1 feet to about 2 feet; between about 2 feet to about 3 feet; between about 3 feet to about 4 feet; between about 4 feet to about 5 feet; between about 5 feet to about 6 feet; between about 6 feet to about 7 feet; between about 7 feet to about 8 feet; between about 8 feet to about 9 feet; between about 9 feet to about 10 feet; between about 10 feet to about 11 feet; between about 11 feet to about 12 feet; between about 12 feet to about 13 feet; between about 13 feet to about 14 feet; between about 14 feet to about 15 feet; between about 15 feet to about 16 feet; between about 16 feet to about 17 feet; between about 17 feet to about 18 feet; between about 18 feet to about 19 feet; between about 19 feet to about 20 feet; between about 20 feet to about 21 feet; between about 21 feet to about 22 feet; between about 22 feet to about 23 feet; between about 23 feet to about 24 feet; between about 24 feet to about 25 feet; between about 25 feet to about 26 feet; between about 26 feet to about 27 feet; between about 27 feet to about 28 feet; between about 28 feet to about 29 feet; between about 29 feet to about 30 feet; between about 30 feet to about 31 feet; between about 31 feet to about 32 feet; between about 32 feet to about 33 feet; between about 33 feet to about 34 feet; between about 34 feet to about 35 feet; between about 35 feet to about 36 feet; between about 36 feet to about 37 feet; between about 37 feet to about 38 feet; between about 38 feet to about 39 feet; and, between about 39 feet to about 40 feet.

In embodiments, the network width (N-W) ranges from: 0.5 feet to about 1 foot; between about 1 feet to about 2 feet; between about 2 feet to about 3 feet; between about 3 feet to about 4 feet; between about 4 feet to about 5 feet; between about 5 feet to about 6 feet; between about 6 feet to about 7 feet; between about 7 feet to about 8 feet; between about 8 feet to about 9 feet; between about 9 feet to about 10 feet; between about 10 feet to about 11 feet; between about 11 feet to about 12 feet; between about 12 feet to about 13 feet; between about 13 feet to about 14 feet; between about 14 feet to about 15 feet; between about 15 feet to about 16 feet; between about 16 feet to about 17 feet; between about 17 feet to about 18 feet; between about 18 feet to about 19 feet; between about 19 feet to about 20 feet; between about 20 feet to about 21 feet; between about 21 feet to about 22 feet; between about 22 feet to about 23 feet; between about 23 feet to about 24 feet; between about 24 feet to about 25 feet; between about 25 feet to about 26 feet; between about 26 feet to about 27 feet; between about 27 feet to about 28 feet; between about 28 feet to about 29 feet; between about 29 feet to about 30 feet; between about 30 feet to about 31 feet; between about 31 feet to about 32 feet; between about 32 feet to about 33 feet; between about 33 feet to about 34 feet; between about 34 feet to about 35 feet; between about 35 feet to about 36 feet; between about 36 feet to about 37 feet; between about 37 feet to about 38 feet; between about 38 feet to about 39 feet; and, between about 39 feet to about 40 feet.

In embodiments, the interior (201) of the shipping container is the interior (201) of the feeding chamber (200). The first side wall (202A) of the feeding chamber (200) is shown spaced apart from the first shipping container side wall (CW-A). The second side wall (202B) of the feeding chamber (200) is shown spaced apart from the second shipping container side wall (CW-B). The third side wall (202C) of the feeding chamber (200) is shown spaced apart from the third shipping container side wall (CW-C). The fourth side wall (202D) of the feeding chamber (200) is shown spaced apart from the fourth shipping container side wall (CW-D).

The top (203) of the feeding chamber (200) is shown to be the shipping container top wall (CW-T). The first side wall (202A), second side wall (202B), third side wall (202C), fourth side wall (202D), may be flexible, perforated, wire or screen, or the like which is positioned extending into the interior (201) of the feeding chamber (200) from the at a side wall length (SW-L). No screen floor (258) is shown in FIGS. 27-29 instead the bottom (204) of the feeding chamber (200) is open to the surface of the conveyor (255) of the egg transfer system (244).

The first side wall (202A), second side wall (202B), third side wall (202C), and fourth side wall (202D) are spaced apart from the shipping container side walls (CW-A, CW-B, CW-C, CW-D) so that the entire interior (201) of the feeding chamber (200) is positioned directly above the conveyor (245) of the egg transfer system (244). This will allow for complete removal of all the contents from within the interior (201) of the feeding chamber (200) with the use of vibration or a vacuum or both or none. In embodiments, when the first conveyor elevation unit (254) and second conveyor elevation unit (256) are extended at a second elevated height (H2) there is no gap between the terminal end of the side wall length (SW-L) of each of the first side wall (202A), second side wall (202B), third side wall (202C), and fourth side wall (202D). In embodiments, when the first conveyor elevation unit (254) and second conveyor elevation unit (256) are extended at a second elevated height (H2) there is a gap between the terminal end of the second side wall length (202BL) only.

In embodiments, when the first conveyor elevation unit (254) and second conveyor elevation unit (256) are extended at a second elevated height (H2) there is a gap between the terminal end of the first side wall length (202AL) and second side wall length (202BL). FIGS. 27-29 show non-limiting embodiments of the insect feeding module (2000, 2000A, 2000B, 2000C) contained within a shipping container and for representative and illustrative purposes only show the first conveyor elevation unit (254) and second conveyor elevation unit (256) at a first retracted height (H1). Refer to above text for modes of operation and detailed description on the feeding chamber (200) integrated with the egg transfer system (244).

A first weighed enhanced feedstock stream (1F32) or synonymously termed first enhanced feedstock stream (EF1) enters the insect feeding module (2000, 2000A) on the left-hand-side through an enhanced feedstock input (206). The enhanced feedstock input (206) transfers a wet enhanced feedstock (WEF) onto the conveyor (245) of the egg transfer system (244) through a plurality of enhanced feedstock inputs (206A, 206B, 206C) so as to be configured to evenly distribute the enhanced feedstock on the conveyor (245). In embodiments, the third side wall length (202CL) and fourth side wall length (202DL) are longer than the first side wall length (202AL) and second side wall length (202BL) so as to leave a gap in between the conveyor (245) and the terminal end of the first side wall length (202AL) and second side wall length (202BL). In embodiments, the first side wall length (202AL), second side wall length (202BL), third side wall length (202CL), fourth side wall length (202DL), range in between about 5 feet to about 6 feet so they may fit within the shipping container for interaction with the conveyor (245) of the egg transfer system (244).

In embodiments, the first side wall length (202AL), second side wall length (202BL), third side wall length (202CL), fourth side wall length (202DL), range from: 0.5 feet to about 1 foot; between about 1 feet to about 2 feet; between about 2 feet to about 3 feet; between about 3 feet to about 4 feet; between about 4 feet to about 5 feet; between about 5 feet to about 6 feet; between about 6 feet to about 7 feet; between about 7 feet to about 8 feet; between about 8 feet to about 9 feet; between about 9 feet to about 10 feet; between about 10 feet to about 11 feet; between about 11 feet to about 12 feet; between about 12 feet to about 13 feet; between about 13 feet to about 14 feet; between about 14 feet to about 15 feet; between about 15 feet to about 16 feet; between about 16 feet to about 17 feet; between about 17 feet to about 18 feet; between about 18 feet to about 19 feet; between about 19 feet to about 20 feet; between about 20 feet to about 21 feet; between about 21 feet to about 22 feet; between about 22 feet to about 23 feet; between about 23 feet to about 24 feet; between about 24 feet to about 25 feet; between about 25 feet to about 26 feet; between about 26 feet to about 27 feet; between about 27 feet to about 28 feet; between about 28 feet to about 29 feet; between about 29 feet to about 30 feet; between about 30 feet to about 31 feet; between about 31 feet to about 32 feet; between about 32 feet to about 33 feet; between about 33 feet to about 34 feet; between about 34 feet to about 35 feet; between about 35 feet to about 36 feet; between about 36 feet to about 37 feet; between about 37 feet to about 38 feet; between about 38 feet to about 39 feet; and, between about 39 feet to about 40 feet.

In embodiments, the first side wall (202A), second side wall (202B), third side wall (202C), and fourth side wall (202D) are made up of wire, screen, or mesh that is perforated with openings smaller than the average insect length (Ni-L) average insect width (Ni-W). In embodiments, the first side wall (202A), second side wall (202B), third side wall (202C), and fourth side wall (202D) are made up of a plastic, rubber, or an impermeable substance, such as a tarp, curtain, cloth, or sheet and does not have openings in it.

An egg-depleted breeding material (246) enters the insect feeding module (2000, 2000A) on the left-hand-side through a conveyor input (247). Egg-depleted breeding material (246) is transferred onto the conveyor (245) of the egg transfer system (244) through a plurality of conveyor inputs (247A, 247B) so as to be configured to evenly distribute the enhanced feedstock on the conveyor (245). The wet enhanced feedstock (WEF) and the egg-depleted breeding material (246) are mixed together on the surface of the conveyor (245) of the egg transfer system (244).

As the conveyor motor (251) drives the conveyor (245) of the egg transfer system (244). Insects (225) within the insect feeding chamber (200) eat the wet enhanced feedstock (WEF) and lay eggs in the egg-depleted breeding material (246) which are both present on the conveyor (245) of the egg transfer system (244). The conveyor output (249) discharges a mixture of wet enhanced feedstock (WEF) and egg-laden breeding material (250) towards an egg-laden breeding material conveyor (282B) for transfer to a breeding chamber (BC) within an insect breeding module (4000, 4000A, 4000B, 4000C). A conveyor transfer bin (282A) is installed in between the conveyor output (249) to funnel and direct the mixture of wet enhanced feedstock (WEF) and egg-laden breeding material (250) towards the egg-laden breeding material conveyor (282B).

An air supply fan (271) accepts an air supply (262) through an air vent (283) and passes it through an air heater (264) for delivery into the interior (201) of the feeding chamber (200). A first access door (284) and a second access door (285) are installed on the fourth shipping container side wall (CW-D). An insect evacuation output (205), that is configured to evacuate an insect and gas mixture (304) from the feeding chamber (200), is shown installed on the shipping container top wall (CW-T). The insect evacuation output (205) is connected to the feeding chamber exit conduit (302). The feeding chamber exit conduit (302) is connected to the insect and gas mixture input (303) of the separator (300) within the insect evacuation module (3000). Each insect feeding module (2000, 2000A, 2000B, 2000C) may be equipped with a low voltage disconnect switch (286) and a computer (COMP). The insect evacuation output (205) is equipped with a humidity sensor (208) and a first temperature sensor (210).

FIG. 28A:

FIG. 28A shows a top view of one embodiment of an insect feeding module (2000, 2000A, 2000B, 2000C).

FIG. 27B:

FIG. 27B shows a top view of one embodiment of an insect feeding module (2000, 2000A, 2000B, 2000C) including a plurality of feeding chambers provided in one shipping container conforming to the International Organization for Standardization (ISO) specifications.

FIGS. 27B and 28B show a front view and a side view of one non-limiting embodiment where a plurality of feeding chambers are provided in one shipping container conforming to the International Organization for Standardization (ISO) specifications. In embodiments, the shipping container of FIG. 27B and FIG. 28B are a 20 foot high. In embodiments, the shipping container of FIG. 27B and FIG. 28B are a 40 foot high.

FIG. 27B and FIG. 28B further elaborate upon FIG. 27A and FIG. 28A except including a first feeding chamber (FC1, 200-1) and a second feeding chamber (FC2, 200-2) within the same shipping container. FIG. 27B and FIG. 28B only show two feeding chambers (FC1, FC2) within one shipping container, however it is to be noted that more than two may also be used as well.

The first feeding chamber (FC1) has a first insect evacuation output (205-1) and a feeding chamber first exit conduit (302-1) that are configured to discharge a first insect and gas mixture (304-1). The second feeding chamber (FC2) has a second insect evacuation output (205-2) and a feeding chamber second exit conduit (302-2) that are configured to discharge a second insect and gas mixture (304-2). The first feeding chamber (FC1) has a first side wall (202A), second side wall (202B), third side wall (202C), and a fourth side wall (202D). The second feeding chamber (FC2) has a first side wall (202AA), second side wall (202BB), third side wall (202CC), and a fourth side wall (202DD).

As seen in FIG. 27B and FIG. 28B, the second side wall (202B) of the first feeding chamber (FC1) is the first side wall (202AA) of the second feeding chamber (FC2). The first feeding chamber (200-1) has a first network length (N-L1) and a first network width (N-W1). The second feeding chamber (200-2) has a second network length (N-L2) and a second network width (N-W2). The first feeding chamber (200-1) has a first vibration unit connection (218A). The second feeding chamber (200-2) has a second vibration unit connection (218B).

FIG. 27C:

FIG. 27C shows a top view of one embodiment of an insect feeding module (2000, 24000A, 2000B, 2000C) equipped with a humidity control unit (HCU).

FIG. 27C shows a non-limiting embodiment of a humidity control unit (HCU) positioned within the interior (201) of the feeding chamber (200). FIG. 27C also shows a humidity control unit (HCU) positioned within the interior (201) of the feeding chamber (200, FC1, FC2, FC3) that is contained within a shipping container.

In embodiments, the humidity control unit (HCU) includes a compressor (Q30), a condenser (Q32), a metering device (Q33), an evaporator (Q34), and a fan (Q35). The fan (Q35) may be equipped with a motor (Q36) and a controller (Q37) that is configured to input or output a signal (Q38) to a computer (COMP).

In embodiments, the first growing assembly (100*) and/or the second growing assembly (200*) are positioned within the interior (201) of the feeding chamber (200). In embodiments, the first growing assembly (100*) having plants (107*) is positioned within the interior (201) of the feeding chamber (200). In embodiments, the second growing assembly (200*) having plants (207*) is positioned within the interior (201) of the feeding chamber (200). In embodiments, the interior (ENC1) of the enclosure (ENC) of the Farming Superstructure System (FSS) (as disclosed in Volume 2) is positioned within the interior (201) of the feeding chamber (201) of the Insect Production Superstructure System (IPSS) (as disclosed on Volume 1) to permit insects (225) to be co-located within the same interior (201, ENC1) the plants (107*, 207*).

The compressor (Q31) is connected to the condenser (Q32), the condenser (Q32) is connected to the metering device (Q33), the metering device (Q33) is connected to an evaporator (Q34), and the evaporator (Q34) is connected to the compressor (Q31) to form a closed-loop refrigeration circuit configured to contain a refrigerant (Q31). The metering device (Q33) includes one or more from the group consisting of a restriction, orifice, valve, tube, capillary, and capillary tube. The refrigerant (Q31) is conveyed from the compressor to the condenser, from the condenser to the evaporator through the metering device, and from the evaporator to the compressor. The evaporator (Q34) is positioned to remove humidity from within the interior (201) of the feeding chamber (200, FC1, FC2, FC3) and is configured to evaporate refrigerant (Q31) within the evaporator (Q34) by removing heat from the interior (201) of the feeding chamber (200, FC1, FC2, FC3). In embodiments, a portion of the evaporator (Q34) is contained within the interior (201) of the feeding chamber 200, FC1, FC2, FC3).

In embodiments, a portion of the evaporator (Q34) is contained within the interior (201) of an enclosure, such as a shipping container, that the feeding chamber (200, FC1, FC2, FC3) is positioned within. In embodiments, the condenser (Q32) is not contained within the interior (201) of the feeding chamber (200, FC1, FC2, FC3). The fan (Q35) is configured to blow air from within the interior (201) of the feeding chamber (200, FC1, FC2, FC3) over at least a portion of the humidity control unit (HCU).

The humidity control unit (HCU) is configured to selectively operate the system in a plurality of modes of operation, the modes of operation including at least:

(1) a first mode of operation in which compression of a refrigerant (Q31) takes place within the compressor (Q30), and the refrigerant (Q31) leaves the compressor (Q30) as a superheated vapor at a temperature above the condensing point of the refrigerant (Q31);

(2) a second mode of operation in which condensation of refrigerant (Q31) takes place within the condenser (Q32), heat is rejected and the refrigerant (Q31) condenses from a superheated vapor into a liquid, and the liquid is cooled to a temperature below the boiling temperature of the refrigerant (Q31); and (3) a third mode of operation in which evaporation of the refrigerant (Q31) takes place, and the liquid phase refrigerant (Q31) boils in evaporator (Q34) to form a vapor or a superheated vapor while absorbing heat from the interior (201) of the feeding chamber (200).

The evaporator (Q34) is configured to evaporate the refrigerant (Q31) to absorb heat from the interior (201) of the feeding chamber (200). As a result, the evaporator (Q34) may condense water from the interior (201) of the feeding chamber (200). In embodiments, the evaporator (Q34) condenses water vapor from the interior (201) of the feeding chamber (200) and forms condensate (Q39).

FIG. 27D:

FIG. 27DC shows one non-limiting embodiment where the compressor (Q30) within the humidity control unit (HCU) is that of a thermal compressor (Q30) that accepts a source of steam. The thermal compressor (Q30) accepts a tenth steam supply (LDS) that is provided from FIG. 14L. Also shown is in the thermal compressor (Q30) discharging a tenth condensate (LJC) to the condensate tank (LAP) shown on FIG. 14L.

FIG. 27E:

FIG. 27E shows one non-limiting embodiment where the compressor (Q30) within the humidity control unit (HCU) is that of a thermal compressor (Q30) that accepts a source of steam. The thermal compressor (Q30) accepts a tenth steam supply (LDS) that is provided from FIG. 14L. Also shown is in the thermal compressor (Q30) discharging a tenth condensate (LJC) to the condensate tank (LAP) shown on FIG. 14L.

In embodiments, the thermal compressor (Q30) (in both FIGS. 27E and 34B) includes a generator (Q50) and an absorber (Q60). The tenth steam supply (LDS), from FIG. 14L, is transferred from the steam distribution header (LCJ) and into the generator (Q50) of the thermal compressor (Q30). In embodiments, a pump (Q45) connects the generator (Q50) to the absorber (Q60). Also, in embodiments, a metering device (Q55) connects the absorber (Q60) to the generator (Q50). The metering device (Q55) may include one or more from the group consisting of a restriction, orifice, valve, tube, capillary, and capillary tube.

Vapor-phase refrigerant is transferred from the evaporator (Q34) to the absorber (Q60). The refrigerant transferred from the evaporator (Q34) to the absorber (Q60) is then absorbed by an absorbent within the absorber (Q60). In embodiments, the refrigerant includes water or ammonia. In embodiments, the absorbent includes lithium bromine or water.

A mixture of refrigerant and absorbent is transferred from the absorber (Q60) to the generator (Q50) via the pump (Q45). Heat in the form of steam (LDS) is transferred to the mixture of refrigerant and absorbent within the generator (Q50) to vaporize the refrigerant. The vapor-phase, or superheated vapor, refrigerant is transferred from the generator (Q50) to the condenser (Q32). The absorbent is transferred back to the absorber (Q60) from the generator (Q50) through the metering device (Q55). In embodiments, the absorbent that is transferred through the metering device (Q55) takes a pressure drop. In embodiments, the generator (Q50) operates at a pressure that is greater than the pressure within the absorber (Q60).

In embodiments, the thermal compressor (Q30) may also be called an absorption chiller. In embodiments, the thermal compressor may have one stage. In embodiments, the thermal compressor may have two stages. In embodiments, electricity is required to power the pump (Q54). In embodiments, the electricity that is required to power the pump (Q54) comes from the generator (LFH) shown in FIG. 14L.

FIG. 27F:

FIG. 27F elaborates upon FIG. 27E and shows one non-limiting embodiment where the compressor (Q30) within the humidity control unit (HCU) is that of a thermal compressor (Q30) that accepts a source of heat, such as flue gas (FG1). FIG. 27F (also applies to FIG. 34B) accepts a source of heat from the flue gas (FG1) transferred from FIG. 14L.

FIG. 28B:

FIG. 28B shows a top view of one embodiment of an insect feeding module (2000, 2000A, 2000B, 2000C) including a plurality of feeding chambers provided in one shipping container conforming to the International Organization for Standardization (ISO) specifications.

FIG. 29:

FIG. 29 shows a first side view of one embodiment of an insect feeding module (2000, 2000A, 2000B, 2000C).

FIG. 30:

FIG. 30 shows a front view of one embodiment of an insect evacuation module (3000). FIG. 30 shows a front view of one embodiment of an insect evacuation module (3000). Referring to FIGS. 30-32, the insect evacuation module (3000) is shown to be contained within a 40 feet high shipping container conforming to the International Organization for Standardization (ISO) specifications.

The insect evacuation module (3000) includes a plurality of separators (S1, S2, S3) integrated with one common feeding chamber (FC1) as shown in FIGS. 27-29. FIGS. 30-32 shows the first separator (S1) as a first insect coarse separator (S1A), the second separator (S2) as a second insect fine separator (S2A), and the third separator (S3) as a particulate separator (S3A). The first insect coarse separator (S1A) is configured to remove a portion of the insect portion (304A) separated from the gas portion (304B) of an insect and gas mixture (304). The second insect fine separator (S2A) is configured to remove insects smaller than the insects separated in the first insect coarse separator (S1A). The particulate separator (S3A) is configured to remove particulates such as remnants of enhanced feedstock, or fine polymer particulate, for example, not only including pieces of portions of insect exoskeleton. The particulate separator (S3A) is in fluid communication with the polymer distribution module (1D) and is configured to transfer a portion of the separated particulate to the polymer tank (1D2) as polymer (1D1).

First Separator (S1), First Insect Coarse Separator (S1A)

The first insect coarse separator (S1A) has a first insect coarse separator input (S1A1) that is in fluid communication with the first feeding chamber insect evacuation output (205A) of the first feeding chamber (FC1) via a first feeding chamber exit conduit (302A). The first insect coarse separator (S1A) is configured to accept an insect and gas mixture (304) from the first feeding chamber (FC1), separate a portion of the insects from the gas and output a first insect-depleted gas stream (355) via a coarse separator gas and insect mixture output (356).

The first separator (S1) is equipped with a first dipleg (357), a first separator conveyor (358), and a first separator valve (361) interposed on the first dipleg (357). A first separated insect stream (360) is routed down the first dipleg (357), through the first separator valve (361) and into the first separator conveyor (358). In embodiments, the first separator conveyor (358) is a compression screw (359) which serves to instantly kill insects by compressing them. The first separated insect stream (360) may in turn be transferred to an evacuated separated insect conveyor (378) via a first separator conveyor connection (379).

The evacuated separated insect conveyor (378) has a motor (378A) that is configured to transfer the first separated insect stream (360) to a grinder (1250) within an insect grinding module via a first separated insect stream input (371). In other embodiments, the first separated insect stream (360) may be sent to a pathogen removal unit (1550) within a pathogen removal module, or to a within a lipid extraction unit (1501) lipid extraction module.

Second Separator (S2), Second Insect Fine Separator (S2A)

The second insect fine separator (S2A) has a second insect fine separator input (S2A1) that is in fluid communication with the coarse separator gas and insect mixture output (356) of the first insect coarse separator (S1A). The second insect fine separator (S2A) is configured to accept a first insect-depleted gas stream (355) from the first insect coarse separator (S1A), separate a portion of the insects from the gas and output a second insect-depleted gas stream (362) via a fine separator gas and particulate mixture output (363).

The second separator (S2) is equipped with a second dipleg (364), a second separator conveyor (365), and a second separator valve (368) interposed on the second dipleg (364). A second separated insect stream (360) is routed down the second dipleg (364), through the second separator valve (368) and into the second separator conveyor (365). In embodiments, the second separator conveyor (365) is a compression screw (366) which serves to instantly kill insects by compressing them.

In embodiments, the second separator conveyor (365) is a not a compression screw (366) but instead routes the second separated insect stream (367) to the to a breeding chamber (BC) via a breeding chamber fine separated insect portion input (375). In embodiments, the second separator conveyor (365) is a not a compression screw (366) but instead routes the second separated insect stream (367) to a plurality of other destinations such as to the grinder (1250), pathogen removal unit (1550), or lipid extraction unit (1501). The second separated insect stream (367) may in turn be transferred to an evacuated separated insect conveyor (378) via a second separator conveyor connection (380) to form a combined first and second separator insect stream (381).

The combined first and second separator insect stream (381) is a mixture of the first separated insect stream (360) and the second separated insect stream (367). The evacuated separated insect conveyor (378) has a motor (378A) that is configured to transfer the combined first and second separator insect stream (381) to a grinder (1250) within an insect grinding module via a first separated insect stream input (371). In other embodiments, the first separated insect stream (360) may be sent to a pathogen removal unit (1550) within a pathogen removal module, or to a within a lipid extraction unit (1501) lipid extraction module.

Third Separator (S3), Particulate Separator (S3A)

The particulate separator (S3A) has a particulate separator input (S3A1) that is in fluid communication with the fine separator gas and particulate mixture output (363) of the second insect fine separator (S2A). The particulate separator (S3A) is configured to accept a second insect-depleted gas stream (362) from the second insect fine separator (S2A), separate a portion of the particulates from the gas and output a particulate-depleted gas stream (369) to the insect evacuation fan (312).

The insect evacuation fan (312) is in fluid with the breeding chamber (BC) via a breeding chamber exhaust input (376) and is configured to discharge the exhaust (377) into the breeding chamber (BC). In embodiments, the separated insect conveyor (328) of the third separator (S3) particulate separator (S3A) is in fluid communication with the polymer distribution module (1D) and is configured to transfer a portion of the separated particulate stream (370) to the polymer tank (1D2) as polymer (1D1).

In embodiments, the separated insect conveyor (328) of the third separator (S3) particulate separator (S3A) is in fluid communication with the polymer distribution module (1D) and is configured to transfer a portion of the separated particulate stream (370) to the polymer tank (1D2) as a polymer (1D1). The insect evacuation module (3000) is equipped with a first access door (386), second access door (387), computer (COMP), low voltage disconnect switch (388), and an air vent (389) that is configured to accept an air supply (390).

FIG. 31:

FIG. 31 shows a top view of one embodiment of an insect evacuation module (3000).

FIG. 32:

FIG. 32 shows a first side view of one embodiment of an insect evacuation module (3000).

FIG. 33:

FIG. 33 shows a front view of one embodiment of an insect breeding module (4000, 4000A, 4000B, 4000C). Referring to FIGS. 33-36, the insect breeding module (4000, 4000A, 4000B, 4000C) is shown to be contained within a 40 feet high shipping container conforming to the International Organization for Standardization (ISO) specifications.

A feeding chamber 1 egg-laden breeding material transfer line (R1, 340) transfers egg-laden breeding material (250) via an egg-laden breeding material conveyor (282B) into the insect breeding module (4000, 4000A) from the left-hand-side. Egg-laden breeding material (250), and optionally a mixture of egg-laden breeding material (250) and a wet enhanced feedstock (WEF), are distributed onto a lower conveyor belt (415) of a first conveyor transfer unit (XY1A). The egg-laden breeding material (250) being transferred to the interior (BCIN) of the breeding chamber 1 (BC1) where it is first elevated via a first conveyor transfer unit (XY1A) to the first conveyor height (CH1A) of a first conveyor (CY1A) operating in a clockwise motion of operation.

In embodiments, the breeding chamber (BC) shown in FIGS. 33-36 represent a typical breeding chamber 1 (BC1), breeding chamber 2 (BC2), breeding chamber 3 (BC3) as shown in FIG. 17. In embodiments, the first conveyor transfer unit (XY1A) takes the form of a vertical lift conveyor (409) including a lower conveyor unit (410) and an upper conveyor unit (411). The vertical lift conveyor (409) is equipped with a lift conveyor drive unit (419) that is configured to rotate the rollers within the lower conveyor unit (410) and upper conveyor unit (411).

The lower conveyor unit (410) includes a first lower conveyor roller (412), second lower conveyor roller (413), third lower conveyor roller (414), and an endless lower conveyor belt (415) in communication with each roller (412, 423, 414) and the lift conveyor drive unit (419). The upper conveyor unit (411) includes a first upper conveyor belt roller (416), second upper conveyor roller (417), and an endless upper conveyor belt (418) in communication with each roller (416, 417) and the lift conveyor drive unit (419).

Egg-laden breeding material (250), and optionally a mixture of egg-laden breeding material (250) and a wet enhanced feedstock (WEF) are distributed onto the lower conveyor belt (415) of the lower conveyor unit (410). The breeding material and enhanced feedstock remnants are sandwiched in between the lower conveyor belt (415) of the lower conveyor unit (410) and the upper conveyor belt (418) of the upper conveyor unit (411) and is elevated to the first conveyor height (CH1A) of a first conveyor (CY1A) operating in a clockwise motion of operation.

The first conveyor (CY1A) is positioned at a vertical height above at least one other conveyor. FIGS. 33-36 shows five conveyors (CY1A, CY2A, CY3A, CY4A, CY5A) and the first conveyor (CY1A) is positioned at a vertical height above each one of a second conveyor (CY2A), third conveyor (CY3A), fourth conveyor (CY4A), and fifth conveyor (CY5A). The second conveyor (CY2A) is positioned at a vertical height above each one of a third conveyor (CY3A), fourth conveyor (CY4A), and fifth conveyor (CY5A). The third conveyor (CY3A) is positioned at a vertical height above each one of a fourth conveyor (CY4A), and fifth conveyor (CY5A). The fourth conveyor (CY4A) is positioned at a vertical height above each one of the fifth conveyor (CY5A).

The first conveyor (CY1A) is installed at a first conveyor height (CH1A) above the second conveyor (CY2A). The second conveyor (CY2A) is installed at a second conveyor height (CH2A) above the third conveyor (CY3A). The third conveyor (CY3A) is installed at a third conveyor height (CH3A) above the fourth conveyor (CY4A). The fourth conveyor (CY4A) is installed at a fourth conveyor height (CH4A) above the fifth conveyor (CY5A).

FIG. 33-36 shows the first conveyor (CY1A), third conveyor (CY3A), fifth conveyor (CY5A) all configured to operate in a clockwise motion of operation. FIG. 33-36 shows the second conveyor (CY2A) and fourth conveyor (CY4A) configured to operate in a counter-clockwise motion of operation.

The first conveyor (CY1A) rotates in a clockwise motion about a first conveyor first roller (P1) and a first conveyor second roller (P2). The second conveyor (CY2A) rotates in a counter-clockwise motion about a second conveyor first roller (P3) and a second conveyor second roller (P4). The third conveyor (CY3A) rotates in a clockwise motion about a third conveyor first roller (P5) and a third conveyor second roller (P6). The fourth conveyor (CY4A) rotates in a counter-clockwise motion about a fourth conveyor first roller (P7) and a fourth conveyor second roller (P8). The fifth conveyor (CY5A) rotates in a clockwise motion about a fifth conveyor first roller (P9) and a fifth conveyor second roller (P10).

A drive unit (404) is equipped with a motor (405) to drive a sprocket (406) and a roller (407). The drive unit (404) is operatively connected to the first conveyor first roller (P1) of the first conveyor (CY1A), second conveyor second roller (P4) of the second conveyor (CY2A), the third conveyor first roller (P5) of the third conveyor (CY3A), the fourth conveyor second roller (P8) of the fourth conveyor (CY4A), and the fifth conveyor first roller (P9) of the fifth conveyor (CY5A).

Specifically, the sprocket (406) driven by the motor (405) of the drive unit (404) drives a roller chain (408) that is configured to operate each conveyor (CY1A, CY2A, CY3A, CY4A, CY5A). The roller chain (408) is configured to interact with a roller chain support roller (P11) in between the first conveyor first roller (P1) and sprocket (406) of the drive unit (404).

The circuit including the roller chain (408), sprocket (406), and drive unit (404) turns the fifth conveyor first roller (P9), third conveyor first roller (P5), and first conveyor first roller (P1) in the clockwise motion. The circuit including the roller chain (408), sprocket (406), and drive unit (404) also turns the fourth conveyor second roller (P8) and second conveyor second roller (P4) in the counter-clockwise motion.

The first conveyor (CY1A) transfers a mixture of egg-laden breeding material (250) and remnants of an enhanced feedstock to the second conveyor (CY2A). The second conveyor (CY2A) transfers a mixture of egg-laden breeding material (250) and remnants of an enhanced feedstock, and possibly hatched insects to the third conveyor (CY3A). The third conveyor (CY3A) transfers a mixture of egg-laden breeding material (250), remnants of an enhanced feedstock, and possibly hatched insects to the fourth conveyor (CY4A). The fourth conveyor (CY4A) transfers a mixture of egg-laden breeding material (250), remnants of an enhanced feedstock, and possibly hatched insects to the fifth conveyor (CY5A). The fifth conveyor (CY5A) transfers a mixture of hatched insects, breeding material, and remnants of an enhanced feedstock to a hatched insect conveyor (402) and out of the insect breeding module (4000, 4000A, 4000B, 4000C) via a feeding chamber 1 breeding chamber output (BC1B).

A conveyor transfer bin (401) is interposed in between the fifth conveyor (CY5A) and the hatched insect conveyor (402) to funnel and direct a mixture of hatched insects, breeding material, and remnants of an enhanced feedstock from the insect breeding module (4000, 4000A, 4000B, 4000C) and into the hatched insect separation module (5000).

A conveyor side view (CSV) may be viewed in FIGS. 35-36 from the length along the insect breeding module (4000) conveyor (CY1A, CY2A, CY3A, CY4A, CY5A). The insect breeding module (4000, 4000A, 4000B, 4000C) is equipped with a first access door (420), second access door (421), low voltage disconnect switch (422), temperature sensor (423), humidity sensor (425), and an air vent (427) configured to introduce an air supply (428) to the interior (BCIN) of the breeding chamber (BC). The insect breeding module (4000, 4000A, 4000B, 4000C) may also be equipped with a temperature control unit (429) to maintain a constant temperature with the interior (BCIN) of the breeding chamber (BC).

The first conveyor (CY1A) is equipped with a first hatched insect detection sensor (OS1) to determine if insects have hatched and are active on the surface of the first conveyor (CY1A). The second conveyor (CY2A) is equipped with a second hatched insect detection sensor (OS2) to determine if insects have hatched and are active on the surface of the second conveyor (CY2A). The third conveyor (CY3A) is equipped with a third hatched insect detection sensor (OS3) to determine if insects have hatched and are active on the surface of the third conveyor (CY3A). The fourth conveyor (CY4A) is equipped with a fourth hatched insect detection sensor (OS4) to determine if insects have hatched and are active on the surface of the fourth conveyor (CY4A). The fifth conveyor (CY5A) is equipped with a fifth hatched insect detection sensor (OS5) to determine if insects have hatched and are active on the surface of the fifth conveyor (CY5A). Either of the hatched insect detection sensors (OS1, OS2, OS3, OS4, OS5) may be an optical sensor, digital camera, motion sensor, active infrared (AIRs) sensor, passive infrared (PIRs) sensor, microwave motion sensor, continuous wave radar motion sensor (CW), vibration motion sensor, IR sensor, ultrasonic sensor, proximity sensor, and touch sensor, mass sensor, laser sensor, or the like.

FIG. 34:

FIG. 34 shows a top view of one embodiment of an insect breeding module (4000, 4000A, 4000B, 4000C). A side wall (403) may be positioned in the insect breeding module (4000, 4000A, 4000B, 4000C) to permit access and maintenance as shown in FIGS. 34-35. In embodiments, the side wall (403) is made up of a plastic, rubber, or an impermeable substance, such as a tarp, curtain, cloth, or sheet and does not have openings in it. In embodiments, the side wall (403) is made up of wire, screen, or mesh that is perforated with openings smaller than the average insect length (Ni-L) average insect width (Ni-W).

FIG. 34A:

FIG. 34A shows a top view of one embodiment of an insect breeding module (4000, 4000A, 4000B, 4000C) equipped with a humidity control unit (HCU).

FIG. 34A shows a non-limiting embodiment of a humidity control unit (HCU) positioned within the interior (BCIN) of the breeding chamber (BC). FIG. 36A also shows a humidity control unit (HCU) positioned within the interior (BCIN) of the breeding chamber (BC) that is contained within a shipping container.

In embodiments, the humidity control unit (HCU) includes a compressor (QQ30), a condenser (QQ32), a metering device (QQ33), an evaporator (Q34), and a fan (Q35). The fan (Q35) may be equipped with a motor (QQ36) and a controller (QQ37) that is configured to input or output a signal (QQ38) to a computer (COMP).

The compressor (QQ31) is connected to the condenser (QQ32), the condenser (QQ32) is connected to the metering device (QQ33), the metering device (QQ33) is connected to an evaporator (QQ34), and the evaporator (QQ34) is connected to the compressor (QQ31) to form a closed-loop refrigeration circuit configured to contain a refrigerant (QQ31). The metering device (QQ33) includes one or more from the group consisting of a restriction, orifice, valve, tube, capillary, and capillary tube. The refrigerant (QQ31) is conveyed from the compressor to the condenser, from the condenser to the evaporator through the metering device, and from the evaporator to the compressor. The evaporator (QQ34) is positioned to remove humidity from within the interior (BCIN) of the breeding chamber (BC) and is configured to evaporate refrigerant (QQ31) within the evaporator (QQ34) by removing heat from the interior (BCIN) of the breeding chamber (BC). In embodiments, a portion of the evaporator (QQ34) is contained within the interior (BCIN) of the breeding chamber (BC).

In embodiments, a portion of the evaporator (QQ34) is contained within the interior (BCIN) of an enclosure, such as a shipping container, that the breeding chamber (BC) is positioned within. In embodiments, the condenser (QQ32) is not contained within the interior (BCIN) of the breeding chamber (BC). The fan (QQ35) is configured to blow air from within the interior (BCIN) of the breeding chamber (BC) over at least a portion of the humidity control unit (HCU).

The humidity control unit (HCU) is configured to selectively operate the system in a plurality of modes of operation, the modes of operation including at least:

(1) a first mode of operation in which compression of a refrigerant (QQ31) takes place within the compressor (QQ30), and the refrigerant (QQ31) leaves the compressor (QQ30) as a superheated vapor at a temperature above the condensing point of the refrigerant (QQ31);

(2) a second mode of operation in which condensation of refrigerant (QQ31) takes place within the condenser (QQ32), heat is rejected and the refrigerant (QQ31) condenses from a superheated vapor into a liquid, and the liquid is cooled to a temperature below the boiling temperature of the refrigerant (QQ31); and (3) a third mode of operation in which evaporation of the refrigerant (QQ31) takes place, and the liquid phase refrigerant (QQ31) boils in evaporator (QQ34) to form a vapor or a superheated vapor while absorbing heat from the interior (BCIN) of the breeding chamber (BC).

The evaporator (QQ34) is configured to evaporate the refrigerant (QQ31) to absorb heat from the interior (BCIN) of the breeding chamber (BC). As a result, the evaporator (QQ34) may condense water from the interior (BCIN) of the breeding chamber (BC). In embodiments, the evaporator (QQ34) condenses water vapor from the interior (BCIN) of the breeding chamber (BC) and forms condensate (QQ39).

FIG. 34B:

FIG. 34B shows one non-limiting embodiment where the compressor (QQ30) within the humidity control unit (HCU) is that of a thermal compressor (QQ30) that accepts a source of steam. The thermal compressor (QQ30) accepts an eleventh steam supply (LDV) that is provided from FIG. 14L. Also shown is the thermal compressor (QQ30) discharging an eleventh condensate (LJD) to the condensate tank (LAP) shown on FIG. 14L.

FIG. 35:

FIG. 35 shows a first side view of one embodiment of an insect breeding module (4000, 4000A) at a cutaway section of the conveyor side view (CSV). In embodiments, the breeding chamber (BC) includes a plurality of conveyors including a first conveyor (CY1A), second conveyor (CY2A), third conveyor (CY3A), fourth conveyor (CY4A), and fifth conveyor (CY5A) that are operatively rotated by a plurality of rollers including a first conveyor first roller (P1), second conveyor second roller (P4), third conveyor first roller (P5), fourth conveyor second roller (P8), and fifth conveyor first roller (P9).

FIG. 36:

FIG. 36 shows an embodiment of the insect breeding module (4000, 4000A, 4000B, 4000C) from the conveyor side view (CSV). A side wall (403) may be positioned within the insect breeding module (4000, 4000A, 4000B, 4000C) to permit a plurality of breeding trains within one since shipping container to be separated apart from the temperature control unit (429). Three separate breeding chamber conveyor trains are illustrated with a side wall (403) positioned to space-apart the breeding chamber conveyor trains (BCT1, BCT2, BCT3) from the temperature control unit (429).

A first breeding chamber conveyor train (BCT1) includes a plurality of conveyors driven by a plurality of rollers including a first conveyor first roller (P1), second conveyor second roller (P4), third conveyor first roller (P5), fourth conveyor second roller (P8), and fifth conveyor first roller (P9). A second breeding chamber conveyor train (BCT2) includes a plurality of conveyors driven by a plurality of rollers including a first conveyor first roller (P1B), second conveyor second roller (P4B), third conveyor first roller (P5B), fourth conveyor second roller (P8B), and a fifth conveyor first roller (P9B). A third breeding chamber conveyor train (BCT3) includes a plurality of conveyors driven by a plurality of rollers including a first conveyor first roller (P1C), second conveyor second roller (P4C), third conveyor first roller (P5C), fourth conveyor second roller (P8C), and fifth conveyor first roller (P9C).

FIG. 37:

FIG. 37 shows a front view of one embodiment of a hatched insect separation module (5000, 5000A, 5000B, 5000C). Referring to FIGS. 37-39, the hatched insect separation module (5000, 5000A, 5000B, 5000C) is shown to be contained within a 40 feet high shipping container conforming to the International Organization for Standardization (ISO) specifications.

FIGS. 37-39 shows the hatched insect separation module (5000) equipped with a breeding material and insect separator (SEPIA) and a breeding material tank (500). A hatched insect conveyor (402) transfers a mixture of hatched insects, breeding material, and remnants of an enhanced feedstock into a breeding material and insect separator (SEPIA) via a hatched insect and breeding material input (515).

The breeding material and insect separator (SEPIA) includes an interior (SIN1), a separator input (1SEPA), a separator material output (1SEPB), and a separator insect output (1SEPC). The breeding material and insect separator (SEPIA) is connected to breeding chamber 1 (BC1) via a breeding chamber 1 hatched egg and breeding material transfer line (U1). The breeding chamber 1 hatched egg and breeding material transfer line (U1) is connected at one end to the breeding chamber 1 (BC1) via a feeding chamber 1 breeding chamber output (BC1B) and connected at another end to the breeding material and insect separator (SEPIA) via a separator input (1SEPA).

The breeding material and insect separator (SEPIA) is equipped with a dipleg (517) to transfer an egg-depleted material (518) to an egg-depleted material transfer conveyor (519). The egg-depleted material transfer conveyor (519) is equipped with a motor (520) and is configured to transfer separated breeding material (523) to the interior (501) of the breeding material tank (500) via a material transfer line (522). The material transfer line (522) is connected at one end to the egg-depleted material transfer conveyor (519) and at another rend to the breeding material input (502) of the breeding material tank (500).

The separator input (1SEPA) is configured to accept hatched insects and breeding material from the fifth conveyor (CYSA) of breeding chamber 1 (BC1), and separate hatched insects (400) from the breeding material (523). The separator insect output (1SEPC) is configured to discharge hatched insects (400) from the interior (SIN1) of the breeding material and insect separator (SEPIA) and route the hatched insects (400) to either one of a plurality of feeding chambers (FC1, FC2, FC3) via a separator hatched insect transfer line (01). Specifically, separator insect output (1SEPC) is configured to discharge hatched insects (400) first feeding chamber (FC1), or to the second feeding chamber (FC2), or to the third feeding chamber (FC3). Hatched insects (400) transferred from the hatched insect separation module (5000) to the insect feeding module (2000) are made available to the first feeding chamber (FC1) via a first hatched insect output (DFC).

The breeding material tank (500) has an interior (501), a breeding material input (502), and a breeding material output (510). Breeding material, and remnants of an enhanced feedstock may be transferred from the breeding material and insect separator (SEPIA) interior (501) of the breeding material tank (500) through a breeding material input (502). Breeding material, and remnants of an enhanced feedstock may be substantially evenly distributed to the interior (501) of the breeding material tank (500) via a breeding material input distributor (502A).

The breeding material tank (500) also has a top section (503), a bottom section (506), and an interior (501) defined by at least one side wall (507). A breeding material screw conveyor (508) is located at the bottom section (506) and configured to transfer breeding material to either one of a plurality of feeding chambers (FC1, FC2, FC3) via a breeding material transfer line (511). The breeding material transfer line (511) is connected at one end to any one of a plurality of feeding chambers (FC1, FC2, FC3) and connected at another end to the breeding material screw conveyor (508) via a breeding material output (510). The breeding material screw conveyor (508) is equipped with a breeding material screw conveyor motor (512). The hatched insect separation module (5000) is equipped with a first access door (528), second access door (529), low voltage disconnect switch (530), and a computer (COMP).

FIG. 38:

FIG. 38 shows a top view of one embodiment of a hatched insect separation module (5000, 5000A).

FIG. 39:

FIG. 39 shows a first side view of one embodiment of a hatched insect separation module (5000, 5000A).

FIG. 40A:

FIG. 40 shows Table 1 with upper and lower ranges of feedstock mineral enhancers, feedstock vitamin enhancers, feedstock polymer enhancers, and other 'energy-Insect®' enhancers.

FIG. 40B:

FIG. 40B shows one non-limiting example of process conditions within an Insect Production Superstructure System (IPSS). Table 2 of FIG. 40B lists process conditions including the following: Feeding Chamber Temperature ranges from between about 60 degrees Fahrenheit to about 94 degrees Fahrenheit; Breeding Chamber Temperature ranges from between about 64 degrees Fahrenheit to about 90 degrees Fahrenheit; Breeding Chamber Residence Time ranges from between about 1 week to about 5 weeks; Feeding Chamber Humidity ranges from between about 25 percent humidity to about 100 percent humidity; Breeding Chamber Humidity ranges from between about 50 percent humidity to about 100 percent humidity; average insect mass ranges from between about 0.2 grams to about 0.907 grams; quantity of insects per pound ranges from between about 2268 insects to about 500 insects; tons of insects per cycle ranges from between about 0.5 ton to about 1 ton; quantity of insects per cycle ranges from between about 2,267,950 to about 1,000,000; and, duration per cycle ranges from between about 1 week to about 5 weeks. In embodiments, a cycle may be defined as the duration of time when insects are grown within the feeding chamber or plurality of feeding chambers.

FIG. 40C:

FIG. 40C shows nutritional requirements of insects produced in an Insect Production Superstructure System (IPSS) that are fed an enhanced feedstock. Table 3 of FIG. 40C lists nutritional information for insects fed an enhanced feedstock within an Insect Production Superstructure System (IPSS) including the following: energy content ranges from between about 4.5 British Thermal Units (BTU) per pound to about 10.5 BTU per pound; protein content ranges from between about 45 weight percent to about 85 weight percent; carbon content ranges from between about 15 weight percent to about 55 weight percent; oxygen content ranges from between about 15 weight percent to about 55 weight percent; hydrogen content ranges from between about 2.5 weight percent to about 20 weight percent; carbohydrate content ranges from between about 3.5 weight percent to about 13 weight percent; ash content ranges from between about 2.5 weight percent to about 7.5 weight percent; water content ranges from between about 2 weight percent to about 10 weight percent; total fat content ranges from between about 5 weight percent to about 60 weight percent; palmitic acid content ranges from between about 5 weight percent to about 60 weight percent; linoleic acid content ranges from between about 5 weight percent to about 60 weight percent; alpha-linoleic acid content ranges from between about 5 weight percent to about 60 weight percent; oleic acid content ranges from between about 5 weight percent to about 60 weight percent; gamma-linoleic acid content ranges from between about 5 weight percent to about 60 weight percent; stearic acid content ranges from between about 5 weight percent to about 60 weight percent; potassium content ranges from between about 25 ppm to about 1 weight percent; chloride content ranges from between about 50 ppm to about 1 weight percent; calcium content ranges from between about 50 ppm to about 1 weight percent; phosphorous content ranges from between about 50 ppm to about 1 weight percent; magnesium content ranges from between about 50 ppm to about 1 weight percent; zinc content ranges from between about 50 ppm to about 1 weight percent; iron content ranges from between about 25 ppm to about 1500 ppm; sodium content ranges from between about 1500 ppm to about 5500 ppm; manganese content ranges from between about 50 ppm to about 1 weight percent; copper content ranges from between about 50 ppm to about 1 weight percent; iodine content ranges from between about 50 ppm to about 1 weight percent; selenium content ranges from between about 50 ppm to about 1 weight percent; molybdenum content ranges from between about 50 ppm to about 1 weight percent; Vitamin B1 content ranges from between about 15 ppm to about 15 weight percent; Vitamin B2 content ranges from between about 15 ppm to about 15 weight percent; Vitamin B12 content ranges from between about 15 ppm to about 15 weight percent; Vitamin E content ranges from between about 15 ppm to about 15 weight percent; Vitamin A content ranges from between about 15 ppm to about 15 weight percent; niacin content ranges from between about 50 ppm to about 5 weight percent; taurine content ranges from between about 50 ppm to about 5 weight percent; glucuronic acid content ranges from between about 50 ppm to about 5 weight percent; malic acid content ranges from between about 50 ppm to about 5 weight percent; N-acetyl L tyrosine content ranges from between about 50 ppm to about 5 weight percent; L-phenylalanine content ranges from between about 50 ppm to about 5 weight percent; caffeine content ranges from between about 50 ppm to about 5 weight percent; citicoline content ranges from between about 50 ppm to about 5 weight percent; insect bulk density ranges from between about 3.5 pounds per cubic foot to about 14.999 pounds per cubic foot; ground insect bulk density ranges from between about 15 pounds per cubic foot to about 50 pounds per cubic foot.

In embodiments, the insects produced in an Insect Production Superstructure System (IPSS) also include: a bacteria content ranging from between: 0.05 colony-forming units per gram (CFU/g) to 0.100 CFU/g, 0.1 CFU/g to 0.2 CFU/g, 0.2 CFU/g to 0.4 CFU/g, 0.4 CFU/g to 0.8 CFU/g, 0.8 CFU/g to 1.6 CFU/g, 1.6 CFU/g to 3.2 CFU/g, 3.2 CFU/g to 6.4 CFU/g, 6.4 CFU/g to 12.8 CFU/g, 12.8 CFU/g to 25 CFU/g, 25 CFU/g to 50 CFU/g, 50 CFU/g to 100 CFU/g, 100 CFU/g to 200 CFU/g, 200 CFU/g to 400 CFU/g, 400 CFU/g to 800 CFU/g, 800 CFU/g to 1,600 CFU/g, 1,600 CFU/g to 3,200 CFU/g, 3,200 CFU/g to 6,400 CFU/g, 32,000 CFU/g to 320,000 CFU/g, 320,000 CFU/g to 3,200,000 CFU/g, 3,200,000 CFU/g to 32,000,000 CFU/g.

In embodiments, the insects produced in an Insect Production Superstructure System (IPSS) also include: a fungus content ranging from between: 0.05 colony-forming units per gram (CFU/g) to 0.100 CFU/g, 0.1 CFU/g to 0.2 CFU/g, 0.2 CFU/g to 0.4 CFU/g, 0.4 CFU/g to 0.8 CFU/g, 0.8 CFU/g to 1.6 CFU/g, 1.6 CFU/g to 3.2 CFU/g, 3.2 CFU/g to 6.4 CFU/g, 6.4 CFU/g to 12.8 CFU/g, 12.8 CFU/g to 25 CFU/g, 25 CFU/g to 50 CFU/g, 50 CFU/g to 100 CFU/g, 100 CFU/g to 200 CFU/g, 200 CFU/g to 400 CFU/g, 400 CFU/g to 800 CFU/g, 800 CFU/g to 1,600 CFU/g, 1,600 CFU/g to 3,200 CFU/g, 3,200 CFU/g to 6,400 CFU/g, 32,000 CFU/g to 320,000 CFU/g, 320,000 CFU/g to 3,200,000 CFU/g, 3,200,000 CFU/g to 32,000,000 CFU/g.

In embodiments, the insects produced in an Insect Production Superstructure System (IPSS) also includes: an alanine content ranging from between: 500 parts per million to 1000 parts per million, 1000 parts per million to 5000 parts per million, 5000 parts per million to 7500 parts per million, 7500 parts per million to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, or 14 weight percent to 15 weight percent.

In embodiments, the insects produced in an Insect Production Superstructure System (IPSS) also includes: an arginine content ranging from between: 500 parts per million to 1000 parts per million, 1000 parts per million to 5000 parts per million, 5000 parts per million to 7500 parts per million, 7500 parts per million to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, or 14 weight percent to 15 weight percent.

In embodiments, the insects produced in an Insect Production Superstructure System (IPSS) also includes: an aspartic acid content ranging from between: 500 parts per million to 1000 parts per million, 1000 parts per million to 5000 parts per million, 5000 parts per million to 7500 parts per million, 7500 parts per million to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, or 14 weight percent to 15 weight percent.

In embodiments, the insects produced in an Insect Production Superstructure System (IPSS) also includes: a glutamic acid content ranging from between: 500 parts per million to 1000 parts per million, 1000 parts per million to 5000 parts per million, 5000 parts per million to 7500 parts per million, 7500 parts per million to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, or 14 weight percent to 15 weight percent.

In embodiments, the insects produced in an Insect Production Superstructure System (IPSS) also includes: a glycine content ranging from between: 500 parts per million to 1000 parts per million, 1000 parts per million to 5000 parts per million, 5000 parts per million to 7500 parts per million, 7500 parts per million to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, or 14 weight percent to 15 weight percent.

In embodiments, the insects produced in an Insect Production Superstructure System (IPSS) also includes: a histidine content ranging from between: 500 parts per million to 1000 parts per million, 1000 parts per million to 5000 parts per million, 5000 parts per million to 7500 parts per million, 7500 parts per million to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, or 14 weight percent to 15 weight percent.

In embodiments, the insects produced in an Insect Production Superstructure System (IPSS) also includes: an isoleucine content ranging from between: 500 parts per million to 1000 parts per million, 1000 parts per million to 5000 parts per million, 5000 parts per million to 7500 parts per million, 7500 parts per million to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, or 14 weight percent to 15 weight percent.

In embodiments, the insects produced in an Insect Production Superstructure System (IPSS) also includes: a leucine content ranging from between: 500 parts per million to 1000 parts per million, 1000 parts per million to 5000 parts per million, 5000 parts per million to 7500 parts per million, 7500 parts per million to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, or 14 weight percent to 15 weight percent.

In embodiments, the insects produced in an Insect Production Superstructure System (IPSS) also includes: a lysine content ranging from between: 500 parts per million to 1000 parts per million, 1000 parts per million to 5000 parts per million, 5000 parts per million to 7500 parts per million, 7500 parts per million to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, or 14 weight percent to 15 weight percent.

In embodiments, the insects produced in an Insect Production Superstructure System (IPSS) also includes: a proline content ranging from between: 500 parts per million to 1000 parts per million, 1000 parts per million to 5000 parts per million, 5000 parts per million to 7500 parts per million, 7500 parts per million to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, or 14 weight percent to 15 weight percent.

In embodiments, the insects produced in an Insect Production Superstructure System (IPSS) also includes: a serine content ranging from between: 500 parts per million to 1000 parts per million, 1000 parts per million to 5000 parts per million, 5000 parts per million to 7500 parts per million, 7500 parts per million to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, or 14 weight percent to 15 weight percent.

In embodiments, the insects produced in an Insect Production Superstructure System (IPSS) also includes: a threonine content ranging from between: 500 parts per million to 1000 parts per million, 1000 parts per million to 5000 parts per million, 5000 parts per million to 7500 parts per million, 7500 parts per million to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, or 14 weight percent to 15 weight percent.

In embodiments, the insects produced in an Insect Production Superstructure System (IPSS) also includes: a tyrosine content ranging from between: 500 parts per million to 1000 parts per million, 1000 parts per million to 5000 parts per million, 5000 parts per million to 7500 parts per million, 7500 parts per million to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, or 14 weight percent to 15 weight percent.

In embodiments, the insects produced in an Insect Production Superstructure System (IPSS) also includes: a valine content ranging from between: 500 parts per million to 1000 parts per million, 1000 parts per million to 5000 parts per million, 5000 parts per million to 7500 parts per million, 7500 parts per million to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, or 14 weight percent to 15 weight percent.

In embodiments, the insects produced in an Insect Production Superstructure System (IPSS) also include: a pH ranging from between: 6.00 to 6.05, 6.05 to 6.10, 6.10 to 6.15, 6.15 to 6.20, 6.20 to 6.25, 6.25 to 6.30, 6.30 to 6.35, 6.35 to 6.40, 6.40 to 6.45, 6.45 to 6.50, 6.50 to 6.55, 6.55 to 6.60, 6.60 to 6.65, 6.65 to 6.70, 6.70 to 6.75, 6.75 to 6.80, 6.80 to 6.85, 6.85 to 6.90, 6.90 to 6.95, 6.95 to 7.00, 7.00 to 7.05, 7.05 to 7.10, 7.10 to 7.15, 7.15 to 7.20, 7.20 to 7.25, 7.25 to 7.30, 7.30 to 7.35, 7.35 to 7.40, 7.40 to 7.45, 7.45 to 7.50, 7.50 to 7.55, 7.55 to 7.60, 7.60 to 7.65, 7.65 to 7.70, 7.70 to 7.75, 7.75 to 7.80, 7.80 to 7.85, 7.85 to 7.90, 7.90 to 7.95, 7.95 to 8.00, 8.00 to 8.05, 8.05 to 8.10, 8.10 to 8.15, 8.15 to 8.20, 8.20 to 8.25, 8.25 to 8.30, 8.30 to 8.35, 8.35 to 8.40, 8.40 to 8.45, or 8.45 to 8.50.

In embodiments, the insects produced in an Insect Production Superstructure System (IPSS) also includes: a water activity (Aw) ranging from between: 0.05 to 0.1, 0.1 to 0.15, 0.15 to 0.2, 0.2 to 0.25, 0.25 to 0.3, 0.3 to 0.35, 0.35 to 0.4, 0.4 to 0.45, 0.45 to 0.5, 0.5 to 0.55, or 0.55 to 0.6.

In embodiments, the insects produced in an Insect Production Superstructure System (IPSS) also include: a carotenoid content including one or more ranges selected from the group consisting of: 5.0 µg/g to 7.5 µg/g, 7.5 µgig to 10.0 µg/g, 10.0 µgig to 12.5 µg/g, 12.5 µgig to 15.0 µg/g, 15.0 µg/g to 17.5 µg/g, 17.5 µg/g to 20.0 µg/g, 20.0 µg/g to 22.5 µg/g, 22.5 µgig to 25.0 µg/g, 25.0 µg/g to 27.5 µg/g, 27.5 µgig to 30.0 µg/g, 30.0 µgig to 32.5 µg/g, 32.5 µgig to 35.0 µg/g, 35.0 µg/g to 37.5 µg/g, 37.5 µgig to 40.0 µg/g, 40.0 µgig to 42.5 µg/g, 42.5 µgig to 45.0 µg/g, 45.0 µg/g to 47.5 µg/g, 47.5 µgig to 50.0 µg/g, 50.0 µgig to 52.5 µg/g, 52.5 µgig to 55.0 µg/g, 55.0 µg/g to 57.5 µg/g, 57.5 µgig to 60.0 µg/g, 60.0 µgig to 62.5 µg/g, 62.5 µgig to 65.0 µg/g, 65.0 µg/g to 67.5 µg/g, 67.5 µg/g to 70.0 µg/g, 70.0 µg/g to 72.5 µg/g, 72.5 µg/g to 75.0 µg/g, 75.0 µg/g to 77.5 µg/g, 77.5 µgig to 80.0 µg/g, 80.0 µgig to 82.5 µg/g, 82.5 µgig to 85.0 µg/g, 85.0 µg/g to 87.5 µg/g, 87.5 µgig to 90.0 µg/g, 90.0

μg/g to 92.5 μg/g, 92.5 μg/g to 95.0 μg/g, 95.0 μg/g to 97.5 μg/g, and 97.5 μg/g to 100.0 μg/g;

wherein:

the carotenoid includes one or more carotenoids selected from the group consisting of: antheraxanthin, astaxanthin, auroxanthin, bixin, canthaxanthin, capsanthin, capsorubin, α-carotene, β-carotene, β-carotene-5,6-epoxide, β-carotene-5,8-epoxide (mutatochrome), β-carotene-5,6,5',6'-diepoxide, δ-carotene, γ-carotene, ζ-carotene, crocetin, α-cryptoxanthin, β-cryptoxanthin, echinenone, lutein, lutein-5,6-epoxide (taraxanthin), lycopene, neoxanthin, neurosporene, phytoene, phytofluene, rubixanthin, violaxanthin, α-zeacarotene, β-zeacarotene, zeaxanthin, and zeinoxanthin.

FIG. 41A:

FIG. 41A shows one non-limiting embodiment of a method for raising Orthoptera order of insects. In embodiments, the present disclosure describes a method for raising Orthoptera order of insects, the method comprising:

(a) providing an insect feeding chamber having egg-laying insects present therein;

(b) mixing feedstock with one or more additives from the group consisting of water, minerals, vitamins, and polymer to form an enhanced feedstock;

(c) introducing said enhanced feedstock into said insect feeding chamber to feed the egg-laying insects present therein;

(d) removing a portion of said egg-laying insects from said insect feeding chamber by applying a vacuum with a velocity pressure range from about 0.001 inches of water to about 400 inches of water and at velocity from about 0.05 feet per second to about 1500 feet per second. In embodiments, the insect feeding chamber may operate at an enhanced feedstock to insect ratio ranging from between about 1 ton of enhanced feedstock per ton of insects produced to about 5 tons of enhanced feedstock per ton of insects produced. In embodiments, the feeding chamber operates at a temperature ranging from between 50 degrees Fahrenheit to about 120 degrees Fahrenheit. In embodiments, the feeding chamber operates at a pressure ranging from between 12 psia to about 16 psia.

FIG. 41B:

FIG. 41B shows one non-limiting embodiment of another method for raising Orthoptera order of insects. In embodiments, the present disclosure describes a method for raising Orthoptera order of insects, the method comprising:

(a) providing an insect feeding chamber having egg-laying insects present therein;

(b) mixing feedstock with one or more additives from the group consisting of water, minerals, vitamins, and polymer to form an enhanced feedstock;

(c) introducing said enhanced feedstock into said insect feeding chamber to feed the egg-laying insects present therein;

(d) removing a portion of said egg-laying insects from said insect feeding chamber by vibrating at least a portion of said insect feeding chamber. In embodiments, the insect feeding chamber may operate at an enhanced feedstock to insect ratio ranging from between about 1 ton of enhanced feedstock per ton of insects produced to about 5 tons of enhanced feedstock per ton of insects produced. In embodiments, the feeding chamber operates at a temperature ranging from between 50 degrees Fahrenheit to about 120 degrees Fahrenheit. In embodiments, the feeding chamber operates at a pressure ranging from between 12 psia to about 16 psia.

FIG. 42A:

FIG. 42A shows one non-limiting embodiment of a method for raising Orthoptera order of insects. In embodiments, the present disclosure describes a method for raising Orthoptera order of insects, the method comprising:

(a) providing an insect feeding chamber having egg-laying insects present therein;

(b) mixing feedstock with one or more additives from the group consisting of water, minerals, vitamins, and polymer to form an enhanced feedstock;

(c) introducing said enhanced feedstock into said insect feeding chamber to feed the egg-laying insects present therein;

(d) removing at least a portion of eggs laid by the egg-laying insects;

(e) incubating at least a portion of the removed eggs;

(f) hatching at least a portion of incubated eggs;

(g) introducing a portion of hatched insects into said insect feeding chamber;

(h) removing a portion of said egg-laying insects said insect feeding chamber by applying a vacuum with a velocity pressure range from about 0.001 inches of water to about 400 inches of water and at velocity from about 0.05 feet per second to about 1500 feet per second.

FIG. 42B:

FIG. 42B shows one non-limiting embodiment of another method for raising Orthoptera order of insects. In embodiments, the present disclosure describes a method for raising Orthoptera order of insects, the method comprising:

(a) providing an insect feeding chamber having egg-laying insects present therein;

(b) mixing feedstock with one or more additives from the group consisting of water, minerals, vitamins, and polymer to form an enhanced feedstock;

(c) introducing said enhanced feedstock into said insect feeding chamber to feed the egg-laying insects present therein;

(d) removing at least a portion of eggs laid by the egg-laying insects;

(e) incubating at least a portion of the removed eggs;

(f) hatching at least a portion of incubated eggs;

(g) introducing a portion of hatched insects into said insect feeding chamber;

(h) removing a portion of said egg-laying insects from said insect feeding chamber by vibrating at least a portion of said insect feeding chamber.

FIG. 43A:

FIG. 43A shows one non-limiting embodiment of a method for raising Orthoptera order of insects. In embodiments, the present disclosure describes a method for raising Orthoptera order of insects, the method comprising:

(a) providing a plurality of insect feeding chambers having egg-laying insects present therein;

(b) mixing feedstock with one or more additives from the group consisting of water, minerals, vitamins, and polymer to form an enhanced feedstock;

(c) apportioning said enhanced feedstock into a plurality of enhanced feedstock streams;

(d) introducing said plurality of enhanced feedstock streams into said plurality of insect feeding chambers to feed the egg-laying insects present therein;

(e) removing at least a portion of eggs laid by the egg-laying insects;

(f) incubating at least a portion of the removed eggs;

(g) hatching at least a portion of incubated eggs;

(h) introducing a portion of hatched insects into at least one of the plurality of insect feeding chambers;

(i) removing a portion of said egg-laying insects from said plurality of insect feeding chambers by applying a vacuum with a velocity pressure range from about 0.001 inches of water to about 400 inches of water and at velocity from about 0.05 feet per second to about 1500 feet per second.
FIG. 43B:

FIG. 43B shows one non-limiting embodiment of another method for raising Orthoptera order of insects. In embodiments, the present disclosure describes a method for raising Orthoptera order of insects, the method comprising:

(a) providing a plurality of insect feeding chambers having egg-laying insects present therein;

(b) mixing feedstock with one or more additives from the group consisting of water, minerals, vitamins, and polymer to form an enhanced feedstock;

(c) apportioning said enhanced feedstock into a plurality of enhanced feedstock streams;

(d) introducing said plurality of enhanced feedstock streams into said plurality of insect feeding chambers to feed the egg-laying insects present therein;

(e) removing at least a portion of eggs laid by the egg-laying insects;

(f) incubating at least a portion of the removed eggs;

(g) hatching at least a portion of incubated eggs;

(h) introducing a portion of hatched insects into at least one of the plurality of insect feeding chambers;

(i) removing a portion of said egg-laying insects from said plurality of insect feeding chambers by vibrating at least a portion of said plurality of insect feeding chambers.
FIG. 44A:

FIG. 44A shows one non-limiting embodiment of a method for raising Orthoptera order of insects. In embodiments, the present disclosure describes a method for raising Orthoptera order of insects, the method comprising:

(a) providing a plurality of insect feeding chambers having egg-laying insects of said order present therein;

(b) mixing feedstock with one or more additives from the group consisting of water, minerals, vitamins, and polymer to form an enhanced feedstock;

(c) apportioning said enhanced feedstock into a plurality of enhanced feedstock streams;

(d) introducing said plurality of enhanced feedstock streams into said plurality of insect feeding chambers to feed the egg-laying insects present therein; and, (e) removing a portion of said egg-laying insects from said plurality of insect feeding chambers by applying a vacuum with a velocity pressure range from about 0.001 inches of water to about 400 inches of water and at velocity from about 0.05 feet per second to about 1500 feet per second. In embodiments, the insect feeding chamber may operate at an enhanced feedstock to insect ratio ranging from between about 1 ton of enhanced feedstock per ton of insects produced to about 5 tons of enhanced feedstock per ton of insects produced. In embodiments, the feeding chamber operates at a temperature ranging from between 50 degrees Fahrenheit to about 120 degrees Fahrenheit. In embodiments, the feeding chamber operates at a pressure ranging from between 12 psia to about 16 psia.
FIG. 44B:

FIG. 44B shows one non-limiting embodiment of another method for raising Orthoptera order of insects. In embodiments, the present disclosure describes a method for raising Orthoptera order of insects, the method comprising:

(a) providing a plurality of insect feeding chambers having egg-laying insects of said order present therein;

(b) mixing feedstock with one or more additives from the group consisting of water, minerals, vitamins, and polymer to form an enhanced feedstock;

(c) apportioning said enhanced feedstock into a plurality of enhanced feedstock streams;

(d) introducing said plurality of enhanced feedstock streams into said plurality of insect feeding chambers to feed the egg-laying insects present therein; and, (e) removing a portion of said egg-laying insects from said plurality of insect feeding chambers by vibrating at least a portion of said plurality of insect feeding chambers.

In embodiments, the insect feeding chamber may operate at an enhanced feedstock to insect ratio ranging from between about 1 ton of enhanced feedstock per ton of insects produced to about 5 tons of enhanced feedstock per ton of insects produced. In embodiments, the feeding chamber operates at a temperature ranging from between 50 degrees Fahrenheit to about 120 degrees Fahrenheit. In embodiments, the feeding chamber operates at a pressure ranging from between 12 psia to about 16 psia.
FIG. 45A:

FIG. 45A shows one non-limiting embodiment of a method for raising Orthoptera order of insects to generate a multifunctional composition. In embodiments, the present disclosure describes a method for raising Orthoptera order of insects to generate a multifunctional composition, the method comprising:

(a) providing a plurality of insect feeding chambers having egg-laying insects present therein;

(b) mixing feedstock with one or more additives from the group consisting of water, minerals, vitamins, and polymer to form an enhanced feedstock;

(c) apportioning said enhanced feedstock into a plurality of enhanced feedstock streams;

(d) introducing said plurality of enhanced feedstock streams into said plurality of insect feeding chambers to feed the egg-laying insects present therein;

(e) removing at least a portion of eggs laid by the egg-laying insects;

(f) incubating at least a portion of the removed eggs;

(g) hatching at least a portion of incubated eggs;

(h) introducing a portion of hatched insects into at least one of the plurality of insect feeding chambers;

(i) removing a portion of said egg-laying insects from said plurality of insect feeding chambers;

(j) grinding a portion of the removed insects to form a stream of ground insects;

(k) creation of a multifunctional composition by mixing ground insects of step (j) with one or more ingredients from the group consisting of fiber-starch materials, binding agents, density improving textural supplements, moisture improving textural supplements, and *cannabis* enhancers.
FIG. 45B:

FIG. 45B shows one non-limiting embodiment of another method for raising Orthoptera order of insects to generate a multifunctional composition. In embodiments, the present disclosure describes a method for raising Orthoptera order of insects to generate a multifunctional composition, the method comprising:

(a) providing a plurality of insect feeding chambers having egg-laying insects present therein;

(b) mixing feedstock with one or more additives from the group consisting of water, minerals, vitamins, and polymer to form an enhanced feedstock;

(c) apportioning said enhanced feedstock into a plurality of enhanced feedstock streams; introducing said plurality of enhanced feedstock streams into said plurality of insect feeding chambers to feed the egg-laying insects present therein;

(d) removing at least a portion of eggs laid by the egg-laying insects;

(e) incubating at least a portion of the removed eggs;

(f) hatching at least a portion of incubated eggs;

(g) introducing a portion of hatched insects into at least one of the plurality of insect feeding chambers;

(h) removing a portion of said egg-laying insects from said plurality of insect feeding chambers;

(i) removing pathogens from a portion of the removed insects to form a stream of pathogen-depleted insects;

(j) creation of a multifunctional composition by mixing a portion of the stream of pathogen-depleted insects of step (i) with one or more ingredients from the group consisting of fiber-starch materials, binding agents, density improving textural supplements, moisture improving textural supplements, and *cannabis* enhancers.

FIG. 46:

FIG. 46 shows one non-limiting embodiment of another method for raising Orthoptera order of insects to generate a multifunctional composition. In embodiments, the present disclosure describes a method for raising Orthoptera order of insects to generate a multifunctional composition, the method comprising:

(a) providing an insect feeding chamber having egg-laying insects present therein;

(b) mixing feedstock with one or more additives from the group consisting of water, minerals, vitamins, and polymer to form an enhanced feedstock;

(c) introducing said enhanced feedstock into said insect feeding chamber to feed the egg-laying insects present therein;

(d) removing at least a portion of eggs laid by the egg-laying insects;

(e) incubating at least a portion of the removed eggs;

(f) hatching at least a portion of incubated eggs;

(g) introducing a portion of hatched insects into said insect feeding chamber;

(h) removing a portion of said egg-laying insects from said insect feeding chamber;

(i) grinding a portion of the removed insects to form a stream of ground insects;

(j) creation of a multifunctional composition by mixing ground insects of step (i) with one or more ingredients from the group consisting of fiber-starch materials, binding agents, density improving textural supplements, moisture improving textural supplements, and *cannabis* enhancers.

FIG. 47:

FIG. 47 shows one non-limiting embodiment of a method for raising Orthoptera order of insects for the separation of lipids contained within said insects. In embodiments, the present disclosure describes a method for raising Orthoptera order of insects to extract lipids contained within said insects, the method comprising:

(a) providing an insect feeding chamber having egg-laying insects present therein;

(b) mixing feedstock with one or more additives from the group consisting of water, minerals, vitamins, and polymer to form an enhanced feedstock;

(c) introducing said enhanced feedstock into said insect feeding chamber to feed the egg-laying insects present therein;

(d) removing at least a portion of eggs laid by the egg-laying insects;

(e) incubating at least a portion of the removed eggs;

(f) hatching at least a portion of incubated eggs;

(g) introducing a portion of hatched insects into said insect feeding chamber;

(h) removing a portion of said egg-laying insects from said insect feeding chamber;

(i) extracting lipids from a portion of the removed insects.

FIG. 48:

FIG. 48 shows one non-limiting embodiment of another method for raising Orthoptera order of insects for the extraction of lipids. In embodiments, the present disclosure describes a method for raising Orthoptera order of insects to generate a multifunctional composition, the method comprising:

(a) providing a plurality of insect feeding chambers having egg-laying insects present therein;

(b) mixing feedstock with one or more additives from the group consisting of water, minerals, vitamins, and polymer to form an enhanced feedstock;

(c) apportioning said enhanced feedstock into a plurality of enhanced feedstock streams; introducing said plurality of enhanced feedstock streams into said plurality of insect feeding chambers to feed the egg-laying insects present therein;

(d) removing at least a portion of eggs laid by the egg-laying insects;

(e) incubating at least a portion of the removed eggs;

(f) hatching at least a portion of incubated eggs;

(g) introducing a portion of hatched insects into at least one of the plurality of insect feeding chambers;

(h) removing a portion of said egg-laying insects from said plurality of insect feeding chambers;

(i) extracting lipids from a portion of the removed insects.

VOLUME II: FARMING SUPERSTRUCTURE SYSTEM (IPSS), DESCRIPTION OF THE DRAWINGS

The accompanying figures show schematic process flowcharts of preferred embodiments and variations thereof. A full and enabling disclosure of the content of the accompanying claims, including the best mode thereof to one of ordinary skill in the art, is set forth more particularly in the remainder of the specification, including reference to the accompanying figures showing how the preferred embodiments and other non-limiting variations of other embodiments described herein may be carried out in practice, in which:

FIG. 1A' depicts one non-limiting embodiment of a farming superstructure system (FSS) including a first water treatment unit (A1*), a second water treatment unit (A2*), a third water treatment unit (A3*), a common reservoir (500*), a pump (P1*), a plurality of vertically stacked growing assemblies (100*, 200*), a fabric (104*, 204*) that partitions each growing assembly (100*, 200*) into an upper-section (105*, 205*) and a lower-section (106*, 206*), a plurality of lights (L1*, L2*) positioned within the upper-section (105*, 205*) of each growing assembly.

FIG. 1B' depicts one non-limiting embodiment of a farming superstructure system (FSS) that includes a first growing assembly (100*) having a first growing medium (GM1*) and a second growing assembly (200*) having a second growing medium (GM2*).

FIG. 1C' depicts one non-limiting embodiment of a farming superstructure system (FSS) that includes a first growing assembly (100*) having a first growing medium (GM1*) and a second growing assembly (200*) having a second growing medium (GM2*) and the first growing assembly (100*) and second growing assembly (200*) are grown outdoors.

FIG. 1D' depicts one non-limiting embodiment general arrangement of a farming superstructure system (FSS) top-view that includes a first growing assembly (100*) and a second growing assembly (200*) each configured to grow plants (107*, 107A*, 107B*, 107C*, 20*7, 207A*, 207B*, 207C*).

FIG. 2' depicts one non-limiting embodiment of a farming superstructure system (FSS) including a first vertically stacked system (1500*) including a plurality of vertically stacked growing assemblies (100*, 200*) integrated with a first and second vertical support structure (VSS1*, VSS2*) wherein the first growing assembly (100*) is supported by a first horizontal support structure (SS1*) and a second growing assembly (200*) is supported by a second horizontal support structure (SS2*).

FIG. 3' depicts one non-limiting embodiment of a plurality of vertically stacked systems (1500*, 1500'*) including a first vertically stacked system (1500*) and a second vertically stacked system (1500'*), the first vertically stacked system (1500*) as depicted in FIG. 2', also both vertically stacked systems (1500*, 1500'*) are contained within an enclosure (ENC*) having an interior (ENC1*).

FIG. 4A' depicts one non-limiting embodiment of FIG. 3' wherein the enclosure (ENC*) is provided with a temperature control unit (TCU*) including an air heat exchanger (HXA*) that is configured to provide a temperature and/or humidity controlled air supply (Q3*) to the interior (ENC1*) of the enclosure (ENC*) which contains a plurality of vertically stacked systems (1500*, 1500'*).

FIG. 4B' depicts one non-limiting embodiment of FIG. 1B' and FIG. 4A' wherein the enclosure (ENC*) is provided with a temperature control unit (TCU*) including an air heat exchanger (HXA*) that is configured to provide a temperature and/or humidity controlled air supply (Q3*) to the interior (ENC1*) of the enclosure (ENC*) which contains a plurality of growing assemblies (100*, 200*).

FIG. 5A' depicts one non-limiting embodiment of FIG. 4A' wherein the temperature control unit (TCU*) of FIG. 4A' is contained within the interior (ENC1*) of the enclosure (ENC*) and coupled with a humidity control unit (HCU*).

FIG. 5B' depicts one non-limiting embodiment of FIG. 4B' and FIG. 5A' wherein the temperature control unit (TCU*) of FIG. 4B' is contained within the interior (ENC1*) of the enclosure (ENC*) and coupled with a humidity control unit (HCU*).

FIG. 5C' shows one non-limiting embodiment where the compressor (Q30*) within the humidity control unit (HCU*) is that of a thermal compressor (Q30*) that accepts a source of steam.

FIG. 5D' shows one non-limiting embodiment where the compressor (Q30*) within the humidity control unit (HCU*) is that of a thermal compressor (Q30*) that accepts a source of steam.

FIG. 5E' elaborates upon FIG. 5D' and shows one non-limiting embodiment where the compressor (Q30*) within the humidity control unit (HCU*) is that of a thermal compressor (Q30*) that accepts a source of heat, such as flue gas (FG1*)

FIG. 6' shows a front view of one embodiment of a plant growing module (PGM*) provided inside of a shipping container conforming to the International Organization for Standardization (ISO) specifications.

FIG. 7' shows a top view of one embodiment of a plant growing module (PGM*) provided inside of a shipping container conforming to the International Organization for Standardization (ISO) specifications.

FIG. 8' shows a first side view of one embodiment of a plant growing module (PGM*).

FIG. 9' shows a front view of one embodiment of a liquid distribution module (LDM*) provided inside of a shipping container conforming to the International Organization for Standardization (ISO) specifications and that is configured to provide a source of liquid to a plurality of plant growing modules (PGM*).

FIG. 10' shows a top view of one embodiment of a liquid distribution module (LDM*) provided inside of a shipping container conforming to the International Organization for Standardization (ISO) specifications and that is configured to provide a source of liquid to a plurality of plant growing modules (PGM*).

FIG. 11' shows a first side view of one embodiment of a liquid distribution module (LDM*).

FIG. 12' shows one non-limiting embodiment of a fabric (104*) used in a growing assembly (100), the fabric (104) having a multi-point temperature sensor (MPT10*0) connected thereto for measuring temperatures at various lengths along the sensor's length.

FIG. 13' shows another one non-limiting embodiment of a fabric (104*) used in a growing assembly (100).

FIG. 14' depicts a computer (COMP) that is configured to input and output signals listed in FIGS. 1'-17K'.

FIG. 15' shows a trimmer (TR*) that is configured to trim at least a portion of *cannabis* plants (107*, 207*) that was growing in each growing assembly (100*, 200*).

FIG. 16' shows a grinder (GR*) that is configured to grind at least a portion of *cannabis* plants (107, 207*) that was growing in each growing assembly (100*, 200*).

FIG. 17' shows a heater (HTR1*) that is configured to heat at least a portion of *cannabis* plants (107*, 207*) that was growing in each growing assembly (100*, 200*).

FIG. 17A' shows one non-limiting embodiment of a volatiles extraction system (VES*) that is configured to extract volatiles from *cannabis* (107*, 207*) with a first solvent (SOLV1*).

FIG. 17B' shows a plurality of volatiles extraction systems (VES1*, VES2*) equipped with one first solvent separation system (SSS*).

FIG. 17C' shows a volatiles and solvent mixing system (VSMS*) that is configured to mix the volatiles (VOLT*) with a second solvent (SOLV2*).

FIG. 17D' shows a second solvent separation system (SEPSOL*) that is configured to separate at least a portion of the second solvent (SOLV2*) from the second volatiles and solvent mixture (SVSM*) to produce concentrated volatiles (CVOLT*).

FIG. 17E' shows one non-limiting embodiment of a solvent separation system that is configured to evaporator the second solvent from the second volatiles and solvent mixture (SVSM*) by use of a spray dryer (KAP*).

FIG. 17E-1' shows one non-limiting embodiment of a co-current type of spray dryer (KAP*) that may be used with the solvent separation system described in FIG. 17E'.

FIG. 17E-2' shows one non-limiting embodiment of a counter-current type of spray dryer (KAP*) that may be used with the solvent separation system described in FIG. 17E'.

FIG. 17E-3' shows another non-limiting embodiment of a counter-current type of spray dryer (KAP*) that may be used with the solvent separation system described in FIG. 17E'.

FIG. 17E-4' shows one non-limiting embodiment of a mixed-flow type of spray dryer (KAP*) that may be used with the solvent separation system described in FIG. 17E'.

FIG. 17F' shows a power production system (PPS*) that is configured to generate electricity, heat, or steam for use in the farming superstructure system (FSS).

FIG. 17G' shows one non-limiting embodiment of a carbon dioxide removal system (GAE*) that is configured to remove carbon dioxide from flue gas (LFP*) for use as a source of carbon dioxide (CO2*) in the farming superstructure system (FSS).

FIG. 17H' shows a cannabinoid extraction system including vessels, filters, pumps, piping connecting flow between vessels and adsorbers, valving, controllers, pressure regulators, metering equipment, flow control, and microprocessor equipment, their construction, implementation, and functionality.

FIG. 17J' shows one non-limiting embodiment of a cannabinoid emulsion mixing system (17J*).

FIG. 17K' shows one non-limiting embodiment of a cannabinoid softgel encapsulation system (17K*).

FIG. 18' shows a simplistic diagram illustrating a multifunctional composition mixing module that is configured to generate a multifunctional composition from at least a portion of *Cannabis* plants (107*, 207*) that was harvested from each growing assembly (100*, 200*).

FIG. 19' illustrates a single fully-grown Beaufort Budman III plant.

FIG. 20' illustrates zoomed-in view of a budding or flowering plant.

FIG. 21' illustrates a single leaf of Beaufort Budman III.

FIG. 22' illustrates a trimmed and dried bud (reproductive structure) of Beaufort Budman III.

FIG. 23' shows a *cannabis* cloning assembly (CA*) that is configured to clone *cannabis* plants and/or Beaufort Budman III (107*, 207*) that were growing in each growing assembly (100*, 200*).

DETAILED DESCRIPTION

Reference will now be made in detail to various embodiments of the disclosure. Each embodiment is provided by way of explanation of the disclosure, not limitation of the disclosure. In fact, it will be apparent to those skilled in the art that modifications and variations can be made in the disclosure without departing from the teaching and scope thereof. For instance, features illustrated or described as part of one embodiment to yield a still further embodiment derived from the teaching of the disclosure. Thus, it is intended that the disclosure or content of the claims cover such derivative modifications and variations to come within the scope of the disclosure or claimed embodiments described herein and their equivalents.

Additional objects and advantages of the disclosure will be set forth in part in the description which follows, and in part will be obvious from the description, or may be learned by practice of the claims. The objects and advantages of the disclosure will be attained by means of the instrumentalities and combinations and variations particularly pointed out in the appended claims.

In embodiments, *cannabis* is grown within the insect production superstructure system (IPSS) as depicted in VOLUME 1. In embodiments, farming superstructure system (FSS) as depicted in VOLUME 2 is simultaneously includes the insect production superstructure system (IPSS) as depicted in VOLUME 1. In embodiments, insects are used within the farming superstructure system (FSS) to benefit the *cannabis* plants therein. In embodiments, insects are used within the farming superstructure system (FSS) to benefit the *cannabis* plants therein because some omnivorous or carnivorous insects eat insects that would otherwise harm the *cannabis* plants in turn protecting them. In embodiments, insects are used within the farming superstructure system (FSS) to benefit the *cannabis* plants therein and to avoid use of pesticides. In embodiments, any types of plants may be grown within the farming superstructure system (FSS). In embodiments, any types of plants may be grown within the insect production superstructure system (IPSS).

FIG. 1A'

FIG. 1A' depicts one non-limiting embodiment of a farming superstructure system (FSS) including a first water treatment unit (A1*), a second water treatment unit (A2*), a third water treatment unit (A3*), a common reservoir (500*), a pump (P1*), a plurality of vertically stacked growing assemblies (100*, 200*), a fabric (104*, 204*) that partitions each growing assembly (100*, 200*) into an upper-section (105*, 205*) and a lower-section (106*, 206*), a plurality of lights (L1*, L2*) positioned within the upper-section (105*, 205*) of each growing assembly, a carbon dioxide tank (CO2T*), a plurality of fans (FN1*, FN2*), a plurality of liquid supply conduits (113*, 213*), a liquid supply header (300*), at least one filter (F1*, F2*), a plurality of valves (V1*, V3*, V4*), a drain port (110*, 210*), and a computer (COMP).

FIG. 1A' discloses a farming superstructure system (FSS). The farming superstructure system (FSS) includes a first growing assembly (100*) and a second growing assembly (200*) in fluid communication with a common reservoir (500*). The common reservoir (500*) is provided with a water supply (01*) via a water supply conduit (02*) and a first water inlet (03*). A plurality of water treatment units (A1*, A2*, A3*), along with a contaminant depleted water valve (VOA*), and a water heat exchanger (HX1*) may be installed on the water supply conduit (02*).

A first water treatment unit (A1*) may be installed on the water supply conduit (02*). The first water treatment unit (A1*) has a first input (04*) and a first output (05*). A water supply (01*) may be provided to the first water treatment unit (A1*) via a first input (04*). Contaminants may be removed by the first water treatment unit (A1*) to produce a first contaminant depleted water (06*) that is discharged via a first output (05*). In embodiments, the first water treatment unit (A1*) includes a cation and is configured to remove positively charged ions from water to form a positively charged ion depleted water (06A*). The "positively charged ions" may include of one or more from the group consisting of calcium, magnesium, sodium, and iron. In embodiments, the first contaminant depleted water (06*) may be a positively charged ion depleted water (06A*). In embodiments, the first water treatment unit (A1*) may include a cation, an anion, a membrane, filter, activated carbon, adsorbent, or absorbent. In embodiments, an activated carbon bed may be used to remove chlorine from the water.

A second water treatment unit (A2*) may be installed on the water supply conduit (02*) after the first water treatment unit (A1*). The second water treatment unit (A2*) may include a second input (07*) and a second output (08*). The first contaminant depleted water (06*) may be provided to the second water treatment unit (A2*) via a second input (07*). The first contaminant depleted water (06*) may be provided to the second water treatment unit (A2*) from the first output (05*) of the first water treatment unit (A1*). In embodiments, the positively charged ion depleted water (06A*) may be provided to the second water treatment unit (A2*) via a second input (07*). Contaminants may be removed by the second water treatment unit (A2*) to produce a second contaminant depleted water (09*) that is discharged via a second output (08*). In embodiments, the second water treatment unit (A2*) includes an anion that is configured to remove negatively charged ions from the positively charged ion depleted water (06A*) to form a negatively charged ion depleted water (09A*). The "negatively charged ions" may include one or more from the group consisting of iodine, chloride, and sulfate. In embodiments, the second contaminant depleted water (09*) may be a negatively charged ion depleted water (09A*). In embodiments, the second water treatment unit (A2*) may include a cation, an anion, a membrane, filter, activated carbon, adsorbent, or absorbent.

A third water treatment unit (A3*) may be installed on the water supply conduit (02*) after the second water treatment unit (A2*). The third water treatment unit (A3*) may include a third input (10*) and a third output (11*). The second contaminant depleted water (09*) may be provided to the third water treatment unit (A3*) via a third input (10*). The second contaminant depleted water (09*) may be provided to the third water treatment unit (A3*) from the second output (08*) of the second water treatment unit (A2*). In embodiments, the negatively charged ion depleted water (09A*) may be provided to the third water treatment unit (A3*) via a third input (10*). Contaminants may be removed by the third water treatment unit (A3*) to produce a third contaminant depleted water (12*) that is discharged via a third output (11*). In embodiments, the third water treatment unit (A3*) includes a membrane that is configured to remove undesirable compounds from the negatively charged ion depleted water (09A*) to form an undesirable compound depleted water (12A*). The "undesirable compounds" may include one or more from the group consisting of dissolved organic chemicals, viruses, bacteria, and particulates. In embodiments, the third contaminant depleted water (12*) may be an undesirable compound depleted water (12A*). In embodiments, the third water treatment unit (A3*) may include a cation, an anion, a membrane, filter, activated carbon, adsorbent, or absorbent. In embodiments, the (10*) the undesirable compounds depleted water (12A*) has an electrical conductivity ranging from 0.10 microsiemens per centimeter to 100 microsiemens per centimeter.

In embodiments, the first water treatment unit (A1*) containing a cation may be a disposable cartridge, portable tank, cylindrical vessel, automatic unit, or a continuous unit. In embodiments, the second water treatment unit (A2*) containing an anion may be a disposable cartridge, portable tank, cylindrical vessel, automatic unit, or a continuous unit. In embodiments, the third water treatment unit (A3*) containing a membrane may have: a diameter that ranges from 1 inch to 6 inches; and a pore size ranging from 0.0001 microns to 0.5 microns.

The common reservoir (500*) is configured to accept a portion of a contaminant depleted water (06A*, 09A*, 12A*) from the at least one water treatment unit (A1*, A2*, A3*). In embodiments, the water treatment units (A1*, A2*, A3*) may be configured to remove solids from the water supply (01*). In embodiments, a contaminant depleted water valve (VOA*) is installed on the water supply conduit (02*) to regulate the amount of water transferred to the common reservoir (500*) through the water supply conduit (02*) and first water inlet (03*). The contaminant depleted water valve (VOA*) is equipped with a controller (CVOA*) which sends a signal (XVOA*) to and from a computer (COMP). In embodiments, a water heat exchanger (HX1*) is installed on the water supply conduit (02*) to control the temperature of the water transferred to the common reservoir (500*) through the water supply conduit (02*) and first water inlet (03*). In embodiments, the water heat exchanger (HX1*) increases the temperature of the water supply (01*) introduced to the common reservoir (500*). In embodiments, the water heat exchanger (HX1*) decreases the temperature of the water supply (01*) introduced to the common reservoir (500*). In embodiments, the water heat exchanger (HX1*) is positioned in between the contaminant depleted water valve (VOA*) and the water inlet (03*) of the common reservoir (500*). So, it is shown that water may be treated with a plurality of water treatment units (A1*, A2*, A3*) before being introduced to the common reservoir (500*).

In embodiments, the common reservoir (500*) is comprised of metal, plastic, fiberglass, composite materials, or combinations thereof, or any other conceivable material that may contain a liquid within its interior. In embodiments, the common reservoir (500*) is configured to accept a water supply (01*) from the water supply conduit (02*). In embodiments, the common reservoir (500*) may be configured to accept any permutation or combination of a water supply (01*) either a first contaminant depleted water (06*), second contaminant depleted water (09*), or third contaminant depleted water (12*), that is heated or cooled or not heated or cooled. In embodiments, the common reservoir (500*) may be configured to accept any permutation or combination of a water supply (01*) either a positively charged ion depleted water (06A*), negatively charged ion depleted water (09A*), or undesirable compounds depleted water (12A*) that is heated or cooled or not heated or cooled. In embodiments, the common reservoir (500*) may be configured to accept any permutation or combination of a water supply (01*) from any number of water treatment units (A1*, A2*, A3*) that includes at least a cation, an anion, a membrane, a filter, activated carbon, adsorbent, or absorbent.

In embodiments, the common reservoir (500*) is equipped with an upper level switch (LH*) for detecting a high level and a lower level switch (LL*) for detecting a lower level. The upper level switch (LH*) is configured to output a signal (XLH*) to the computer (COMP*) when the upper level switch (LH*) is triggered by a high level of liquid within the common reservoir (500*). The lower level switch (LL*) is configured to output a signal (XLL*) to the computer (COMP) when the lower level switch (LL*) is triggered by a low level of liquid within the common reservoir (500*). In embodiments, when the lower level switch (LL*) sends a signal (XLL*) to the computer (COMP), the contaminant depleted water valve (VOA*) is opened and introduces water into the common reservoir (500*) until the upper level switch (LH*) is triggered thus sending a signal (XLH*) to the computer (COMP) to close the contaminant depleted water valve (VOA*). This level control loop including the upper level switch (LH*) for detecting a high level and a lower level switch (LL*) for detecting a lower level may be coupled to the operation of the contaminant depleted water valve (VOA*) for introducing a water supply (01*) through the water supply conduit (02*) and into the common reservoir (500*) via the first water inlet (03*).

In embodiments, a pump (P1*) is configured to accept, pressurize, and transfer liquid within the common reservoir (500*) into a plurality of vertically stacked growing assemblies (100*, 200*). In embodiments, the pump (P1*) is configured to accept, pressurize, and transfer at least a portion of the undesirable compounds depleted water (12A*) transferred from the common tank (500T*) into a plurality of vertically stacked growing assemblies (100*, 200*). Each of the plurality of vertically stacked growing assemblies (100*, 200*) are positioned above the common reservoir (500*).

The first growing assembly (100*) has an interior (101*), a top (102*), a bottom (103*), and a longitudinal axis (AX1*) extending along a height direction of the first growing assembly (100*). The first growing assembly (100*) has a fabric (104*) that partitions the first growing assembly (100*) into an upper-section (105*) close to the top (102*) and a lower-section (106*) close to the bottom (103*). The fabric (104*) is used to provide structure for *Cannabis* plants (107*) to root into. For purposes of simplicity, Beaufort Budman III (107*, 207*) may be referred to and is synonymous with the term *cannabis* (107*, 207*) for purposes of this disclosure. Obviously, the farming systems and methods disclosed herein pertain to any type plant and even any type of *cannabis* plant (107*, 207*) and not only limited to growing Beaufort Budman III (107*, 207*). Growing Beaufort Budman III (107*, 207*) within the farming superstructure system (FSS) is merely a non-limiting example of any type of the *cannabis* (107*, 207*) that can be grown within the farming superstructure system (FSS). In fact, any type of plant (107*, 207*) may be grown using the farming systems and methods disclosed herein. In embodiments, any types of plants (107*, 207*) may be grown within the Farming Superstructure System FSS).

*Cannabis* plants (107*) rooted in the fabric (104*) have roots that grow downward and extend into the lower-section (106*). The first growing assembly (100*) is equipped with a plurality of lights (L1*) positioned within the upper-section (105*) above the fabric (104*). *Cannabis* (107*) rooted in the fabric (104*) grow upward extending into the upper-section (105*) towards the plurality of lights (L1*). The plurality of lights (L1*) are configured to be controlled by a computer (COMP) to operate at a wavelength ranging from 400 nm to 700 nm. In embodiments, the lights (L1*) have a controller (CL1*) that sends a signal (XL1*) to and from the computer (COMP). In embodiments, the lights (L1*, L2*) may be compact fluorescent (CFL), light emitting diode (LED), incandescent lights, fluorescent lights, or halogen lights. In embodiments, light emitting diodes are preferred.

In embodiments, a first plurality of lights (L1*) in the first growing assembly (100*) include a first plurality of light emitting diodes (LED*). In embodiments, the first plurality of light emitting diodes (LED*) include blue LEDs (BLED*), red LEDS (RLED*), and/or green LEDS (GLED*). In embodiments, the first plurality of light emitting diodes (LED*) in the first growing assembly (100*) include one or two or more from the group consisting of blue LEDs (BLED*), red LEDS (RLED*), and green LEDS (GLED*).

In embodiments, a second plurality of lights (L2*) in the second growing assembly (200*) include a second plurality of light emitting diodes (LED'*). In embodiments, the second plurality of light emitting diodes (LED'*) include blue LEDs (BLED'*), red LEDS (RLED'*), and/or green LEDS (GLED'*). In embodiments, the second plurality of light emitting diodes (LED'*) in the second growing assembly (200*) include one or two or more from the group consisting of blue LEDs (BLED'*), red LEDS (RLED'*), and green LEDS (GLED'*).

In embodiments, the blue LEDs (BLED*, BLED'*) operate at a wavelength that ranges from 490 nanometers (nm) to 455 nm. In embodiments, the red LEDs (RLED*, RLED'*) operate at a wavelength that ranges from 620 nm to 780 nm. In embodiments, the green LEDs (GLED*, GLED'*) operate at a wavelength that ranges from 490 nm to 577 nm. In embodiments, the plurality of light emitting diodes (LED) are configured to be controlled by a computer (COMP) to operate at a wavelength ranging from 490 nm to 780 nm. In embodiments, the plurality of light emitting diodes (LED) are configured to be controlled by a computer (COMP) to operate at a wavelength ranging from 400 nm to 700 nm.

In embodiments, the first plurality of light emitting diodes (LED*) and second plurality of light emitting diodes (LED"*) are configured to operate in the following manner:
  (a) illuminating plants with blue LEDs (BLED*, BLED'*) and red LEDs (RLED, RLED'*); and
  (b) illuminating the plants nanometers with green LEDs (GLED*, GLED'*);
wherein:
  the blue LEDs (BLED*, BLED'*) operate at a wavelength that ranges from 490 nanometers to 455 nanometers;
  the red LEDs (RLED*, RLED'*) operate at a wavelength that ranges from 620 nanometers to 780 nanometers;
  the green LEDs (GLED*, GLED'*) operate at a wavelength that ranges from 490 nanometers to 577 nanometers.

In embodiments, the first plurality of light emitting diodes (LED*) and second plurality of light emitting diodes (LED*) are configured to operate in the following manner:
  (a) providing:
    (a1) a first growing assembly (100*) having a first plurality of light emitting diodes (LED*), the first plurality of light emitting diodes (LED*) in the first growing assembly (100*) include blue LEDs (BLED*), red LEDS (RLED*), and green LEDS (GLED*);
    (a2) a second growing assembly (200*) having a second plurality of light emitting diodes (LED*), the second plurality of light emitting diodes (LED'*) in the second growing assembly (200*) include blue LEDs (BLED'*), red LEDS (RLED'*), and green LEDS (GLED'*);
  (b) illuminating the interiors of the first growing assembly (100*) and second growing assembly (200*) with green LEDs (GLED*, GLED'*) and optionally with blue LEDs (BLED*, BLED'*) or red LEDs (RLED*, RLED'*); and
  (c) illuminating the interiors of the first growing assembly (100*) and second growing assembly (200*) with blue LEDs (BLED*, BLED'*) and red LEDs (RLED*, RLED'*); and
wherein:
  the blue LEDs (BLED*, BLED'*) operate at a wavelength that ranges from 490 nanometers to 455 nanometers;
  the red LEDs (RLED*, RLED'*) operate at a wavelength that ranges from 620 nanometers to 780 nanometers;
  the green LEDs (GLED*, GLED'*) operate at a wavelength that ranges from 490 nanometers to 577 nanometers.

In embodiments, the disclosure provides for a farming method, including:
  (a) providing a farming superstructure system (FSS), including:
    (a1) a first water treatment unit (A1*) including a cation configured to remove positively charged ions from water to form a positively charged ion depleted water (06A*), the positively charged ions are comprised of one or more from the group consisting of calcium, magnesium, sodium, and iron;

(a2) a second water treatment unit (A2*) including an anion configured to remove negatively charged ions from the positively charged ion depleted water (06A*) to form a negatively charged ion depleted water (09A*), the negatively charged ions are comprised of one or more from the group consisting of iodine, chloride, and sulfate;

(a3) a first growing assembly (100*) having a first plurality of light emitting diodes (LED*), the first plurality of light emitting diodes (LED*) in the first growing assembly (100*) include blue LEDs (BLED*) and red LEDS (RLED*), and optionally green LEDS (GLED*);

(a4) a second growing assembly (200*) having a second plurality of light emitting diodes (LED'*), the second plurality of light emitting diodes (LED'*) in the second growing assembly (200*) include blue LEDs (BLED'*) and red LEDS (RLED'*), and optionally green LEDS (GLED'*);

(b) providing a source of water;

(c) removing positively charged ions from the water of step (b) to form a positively charged ion depleted water;

(d) removing negatively charged ions from the water after step (c) to form a negatively charged ion depleted water;

(e) mixing the negatively charged ion depleted water after step (d) with one or more from the group consisting of macro-nutrients, micro-nutrients, and a pH adjustment to form a liquid mixture;

(f) pressurizing the liquid mixture of step (e) to form a pressurized liquid mixture;

(g) splitting the pressurized liquid mixture into a plurality of pressurized liquid mixtures;

(h) transferring the plurality of pressurized liquid mixtures to each growing assembly;

(i) illuminating the interiors of the first growing assembly (100*) and second growing assembly (200*) with blue LEDs (BLED*, BLED'*) and red LEDs (RLED*, RLED'*); and (j) optionally illuminating the interiors of the first growing assembly (100*) and second growing assembly (200*) with green LEDs (GLED*, GLED'*);

wherein:

the blue LEDs (BLED*, BLED'*) operate at a wavelength that ranges from 490 nanometers to 455 nanometers;

the red LEDs (RLED*, RLED'*) operate at a wavelength that ranges from 620 nanometers to 780 nanometers;

the green LEDs (GLED*, GLED'*) operate at a wavelength that ranges from 490 nanometers to 577 nanometers;

the positively charged ions are comprised of one or more from the group consisting of calcium, magnesium, sodium, and iron;

the negatively charged ions are comprised of one or more from the group consisting of iodine, chloride, and sulfate;

the macro-nutrients are comprised of one or more from the group consisting of nitrogen, phosphorus, potassium, calcium, magnesium, and sulfur;

the micro-nutrients are comprised of one or more from the group consisting of iron, manganese, boron, molybdenum, copper, zinc, sodium, chlorine, and silicon;

the pH adjustment solution is comprised of one or more from the group consisting acid, nitric acid, phosphoric acid, potassium hydroxide, sulfuric acid, organic acids, citric acid, and acetic acid;

the blue LEDs (BLED*, BLED'*) or red LEDs (RLED*, RLED'*) illuminate the interiors of the first growing assembly (100*) and second growing assembly (200*) at an illumination on-off ratio ranging from between 0.5 and 5, the illumination on-off ratio is defined as the duration of time when the lights are on and illuminate in hours divided by the subsequent duration of time when the lights are off and are not illuminating in hours before the lights are turned on again.

In embodiments, the disclosure provides for a farming method, including:

(a) providing a farming superstructure system (FSS), including:

(a1) a first growing assembly (100*) having a first plurality of light emitting diodes (LED*), the first plurality of light emitting diodes (LED*) in the first growing assembly (100*) blue LEDs (BLED*) and red LEDS (RLED*), and optionally green LEDS (GLED*);

(a2) a second growing assembly (200*) having a second plurality of light emitting diodes (LED'*), the second plurality of light emitting diodes (LED'*) in the second growing assembly (200*) include blue LEDs (BLED'*) and red LEDS (RLED'*), and optionally green LEDS (GLED'*);

(b) illuminating the interiors of the first growing assembly (100*) and second growing assembly (200*) with blue LEDs (BLED*, BLED'*) and red LEDs (RLED*, RLED'*); and (c) optionally illuminating the interiors of the first growing assembly (100*) and second growing assembly (200*) with green LEDs (GLED*, GLED'*);

wherein:

the blue LEDs (BLED*, BLED'*) operate at a wavelength that ranges from 490 nanometers to 455 nanometers;

the red LEDs (RLED*, RLED'*) operate at a wavelength that ranges from 620 nanometers to 780 nanometers;

the green LEDs (GLED*, GLED'*) operate at a wavelength that ranges from 490 nanometers to 577 nanometers;

the blue LEDs (BLED*, BLED'*) or red LEDs (RLED*, RLED'*) illuminate the interiors of the first growing assembly (100*) and second growing assembly (200*) at an illumination on-off ratio ranging from between 0.5 and 5, the illumination on-off ratio is defined as the duration of time when the lights are on and illuminate in hours divided by the subsequent duration of time when the lights are off and are not illuminating in hours before the lights are turned on again.

In embodiments, the disclosure provides for a farming method, including:

(a) providing a farming superstructure system (FSS), including:

(a1) a first growing assembly (100*) having a first plurality of light emitting diodes (LED*), the first plurality of light emitting diodes (LED*) in the first growing assembly (100*) blue LEDs (BLED*) and red LEDS (RLED*), and optionally green LEDS (GLED*);

(a2) a second growing assembly (200*) having a second plurality of light emitting diodes (LED'*), the second plurality of light emitting diodes (LED'*) in the second growing assembly (200*) include blue LEDs (BLED'*) and red LEDS (RLED'*), and optionally green LEDS (GLED'*);

(a3) a carbon dioxide tank (CO2T*), at least one carbon dioxide valve (V8*, V9*, V10*), the at least one carbon dioxide valve (V8*, V9*, V10*) is configured to take a pressure drop of greater than 50 pounds per square inch, carbon dioxide is made available to the first growing assembly (100*) or second growing assembly (200*);

(b) illuminating the interiors of the first growing assembly (100*) and second growing assembly (200*) with blue LEDs (BLED*, BLED'*) and red LEDs (RLED*, RLED'*); and (c) optionally illuminating the interiors of the first growing assembly (100*) and second growing assembly (200) with green LEDs (GLED*, GLED'*);

(d) adjusting the carbon dioxide concentration within the first growing assembly (100*) or second growing assembly (200*) to a range between 400 parts per million and 10,000 parts per million;

wherein:

the blue LEDs (BLED*, BLED'*) operate at a wavelength that ranges from 490 nanometers to 455 nanometers;

the red LEDs (RLED*, RLED'*) operate at a wavelength that ranges from 620 nanometers to 780 nanometers;

the green LEDs (GLED*, GLED'*) operate at a wavelength that ranges from 490 nanometers to 577 nanometers;

the blue LEDs (BLED*, BLED'*) or red LEDs (RLED*, RLED'*) illuminate the interiors of the first growing assembly (100*) and second growing assembly (200*) at an illumination on-off ratio ranging from between 0.5 and 5, the illumination on-off ratio is defined as the duration of time when the lights are on and illuminate in hours divided by the subsequent duration of time when the lights are off and are not illuminating in hours before the lights are turned on again.

The second growing assembly (200*) has an interior (201*), a top (202*), a bottom (203*), and a longitudinal axis (AX2*) extending along a height direction of the first growing assembly (200*). The second growing assembly (200*) has a fabric (204*) that partitions the second growing assembly (200*) into an upper-section (205*) close to the top (202*) and a lower-section (206*) close to the bottom (203*). The fabric (204*) is used to provide structure for cannabis (207*) to root into. Cannabis (207*) rooted in the fabric (204*) have roots that grow downward and extend into the lower-section (206*). The second growing assembly (200*) is equipped with a plurality of lights (L2*) positioned within the upper-section (205*) above the fabric (204*). Cannabis (207*) rooted in the fabric (204*) grow upward extending into the upper-section (205*) towards the plurality of lights (L2*). The plurality of lights (L2*) are configured to be controlled by a computer (COMP*) to operate at a wavelength ranging from 400 nm to 700 nm. In embodiments, the lights (L2*) have a controller (CL2*) that sends a signal (XL2*) to and from the computer (COMP).

In embodiments, the farming superstructure system (FSS) is equipped with a carbon dioxide tank (CO2T*). The carbon dioxide tank (CO2T*) contains pressurized carbon dioxide (CO2*) and is equipped with a carbon dioxide pressure sensor (CO2P*). A carbon dioxide supply header (CO2H*) is connected to the carbon dioxide tank (CO2T*). A first carbon dioxide supply valve (V10*) is installed on the carbon dioxide supply header (CO2H*) and is configured to take a pressure drop of greater than 50 pounds per square inch (PSI). The first growing assembly (100*) is equipped with a CO2 input (115*) that is connected to a CO2 supply conduit (116*). The second growing assembly (200*) is also equipped with a CO2 input (215*) that is connected to a CO2 supply conduit (216*).

The CO2 supply conduit (116*) of the first growing assembly (100*) is connected to the carbon dioxide supply header (CO2H*) via a CO2 header connection (115X*). The CO2 supply conduit (116*) of the first growing assembly (100*) is configured to transfer carbon dioxide into the first interior (101*) of the first growing assembly (100*). In embodiments, a second carbon dioxide supply valve (V8*) is installed on the CO2 supply conduit (116*) of the first growing assembly (100*). The second carbon dioxide supply valve (V8*) is equipped with a controller (CV8*) that sends a signal (XV8*) to and from a computer (COMP). In embodiments, a CO2 flow sensor (FC1*) is installed on the CO2 supply conduit (116*) of the first growing assembly (100*). The CO2 flow sensor (FC1*) sends a signal (XFC1*) to the computer (COMP). In embodiments, a gas quality sensor (GC1*) is installed on the first growing assembly (100*) to monitor the concentration of carbon dioxide within the first interior (101*). The gas quality sensor (GC1*) is equipped to send a signal (XGC1*) to the computer (COMP).

The CO2 supply conduit (216*) of the second growing assembly (200*) is connected to the carbon dioxide supply header (CO2H*) via a CO2 header connection (215X*). The CO2 supply conduit (216*) of the second growing assembly (200*) is configured to transfer carbon dioxide into the second interior (201*) of the second growing assembly (100*). In embodiments, a third carbon dioxide supply valve (V9*) is installed on the CO2 supply conduit (216*) of the second growing assembly (200*). The third carbon dioxide supply valve (V9*) is equipped with a controller (CV9*) that sends a signal (XV9*) to and from a computer (COMP). In embodiments, a CO2 flow sensor (FC2*) is installed on the CO2 supply conduit (216*) of the second growing assembly (200*). The CO2 flow sensor (FC2*) sends a signal (XFC2*) to the computer (COMP). In embodiments, a gas quality sensor (GC2*) is installed on the second growing assembly (200*) to monitor the concentration of carbon dioxide within the second interior (201*). The gas quality sensor (GC2*) is equipped to send a signal (XGC2*) to the computer (COMP).

In embodiments, the carbon dioxide concentration in the upper-section (105*, 205*) of each growing assembly ranges from between 400 parts per million (ppm) to 500 ppm, 500 ppm to 600 ppm, 600 ppm to 700 ppm, 700 ppm to 800 ppm, 800 ppm to 900 ppm, 900 ppm to 1000 ppm, 1000 ppm to 1500 ppm, 1500 ppm to 2000 ppm, 2000 ppm to 2500 ppm, 2500 ppm to 3000 ppm, 3000 ppm to 3500 ppm, 3500 ppm to 4000 ppm, 4000 ppm to 4500 ppm, 4500 ppm to 5000 ppm, 5000 ppm to 5500 ppm, 5500 ppm to 6000 ppm, 6000 ppm to 6500 ppm, 6500 ppm to 7000 ppm, 7000 ppm to 7500 ppm, 7500 ppm to 8000 ppm, 8000 ppm to 8500 ppm, 8500 ppm to 9000 ppm, 9000 ppm to 9500 ppm, or 9500 ppm to 10000 ppm.

In embodiments, the gas quality sensor (GC2*) is equipped to send a signal (XGC2*) to the computer (COMP) to operate the first, second, or third carbon dioxide supply valves (V8*, V9*, V10*).

At least one fan (FN1*) is positioned in the upper-section (105*) of the first growing assembly (100*). The fan (FN1*) is configured to blow air onto the cannabis (107*). The fan (FN1*) is configured to distribute a mixture of air and CO2 onto the cannabis (107*). The fan (FN1*) is equipped with a controller (CF1*) that sends a signal (XF1*) to and from a computer (COMP).

A plurality of fans (FN2*) are positioned in the upper-section (205*) of the second growing assembly (200*). The fans (FN2*) are configured to blow air onto the cannabis (207*). In embodiments, the fans blow air and the air is comprised of a gas, vapor, and solid particulates. In embodiments, the gas within air may be oxygen, carbon dioxide, or nitrogen. In embodiments, the vapor within the air may be water vapor. In embodiments, the solid particulates within air may be dust, dirt, or pollen. The fans (FN2*) are configured to distribute a mixture of air and CO2 onto the *cannabis* (207*). The fans (FN2*) are equipped with a controller (CF2*) that sends a signal (XF2*) to and from a computer (COMP). Each of the fans (FN1*, FN2*) is configured to operate at a RPM less than 6,000 RPM. In embodiments, it is preferred to operate the fans (FN1*, FN2*) at a RPM less than 6,000 so that the velocity of air blown onto the *cannabis* ranges from 0.5 feet per second (fps) to 1 fps, 1 fps to 5 fps, 5 fps to 10 fps, 10 fps to 15 fps, 15 fps to 20 fps, 20 fps to 25 fps, 25 fps to 30 fps, 30 fps to 35 fps, 35 fps to 40 fps, 40 fps to 45 fps, or 45 fps to 50 fps.

The first growing assembly (100*) is equipped with a temperature sensor (T1*) to monitor the temperature within the first interior (101*). The temperature sensor (T1*) is configured to send a signal (XT1*) to the computer (COMP). In embodiments, the temperature sensor (T1*) may be a multi-point temperature sensor (MPT100*) that is connected to the fabric (104*) for measuring temperatures at various lengths along the sensor's length and long the length of the fabric (104*), as depicted in FIGS. 12' and 13'.

The second growing assembly (200*) is equipped with a temperature sensor (T2*) to monitor the temperature within the second interior (201*). The temperature sensor (T2*) is configured to send a signal (XT2*) to the computer (COMP). In embodiments, the temperature sensor (T2*) may be a multi-point temperature sensor (MPT100*) that is connected to the fabric (204*) for measuring temperatures at various lengths along the sensor's length and long the length of the fabric (204*), as depicted in FIGS. 12' and 13'.

In embodiments, each growing assembly (100*, 200*) is equipped with an upper temperature sensor (T1C*, T2C*) positioned within the upper-section (105*, 205*), a partition temperature sensor (T1B*, T2B*) positioned at the fabric (104*), and a lower temperature sensor (T1A*, T2A*) positioned within the lower-section (106*, 206*). Preferably the partition temperature sensor (T1B*) is a multi-point temperature sensor (MPT100*) that is integrated with the fabric (104*) as disclosed in FIGS. 12' and 13'.

In embodiments, the upper temperature sensor (T1C*, T2C*) is configured to input a signal (XT1C*, XT2C*) (not shown) to the computer (COMP). In embodiments, the partition temperature sensor (T1B*, T2B*) is configured to input a signal (XT1B*, XT2B*) (not shown) to the computer (COMP). In embodiments, the lower temperature sensor (T1A*, T2B*) is configured to input a signal (XT1A*, XT2A*) (not shown) to the computer (COMP). In embodiments, during the day-time, the upper-section (105*, 205*) has a temperature that is greater than the temperature within lower-section (106*, 206*). In embodiments, during the night-time, the upper-section (105*, 205*) has a temperature that is less than the temperature within the lower-section (106*, 206*).

A first liquid distributor (108*) is positioned in the lower-section (106*) of the first growing assembly (100*) below the fabric (104*) and equipped with a plurality of restrictions (109*) installed thereon. In embodiments, the restrictions (109*) of the first liquid distributor (108*) are spray nozzles, spray balls, or apertures. Each restriction (109*) is configured to accept pressurized liquid from the pump (P1*) and introduce the liquid into the lower-section (106*) of the first growing assembly (100*) while reducing the pressure of the liquid that passes through each restriction (109*). The first liquid distributor (108*) is connected to a first liquid supply conduit (113*) via a liquid input (114*). The first liquid distributor (108*) is configured to receive liquid from a first liquid supply conduit (113*).

A second liquid distributor (208*) is positioned in the lower-section (206*) of the second growing assembly (200*) below the fabric (204*) and equipped with a plurality of restrictions (209*) installed thereon. In embodiments, the restrictions (209*) of the second liquid distributor (208*) are spray nozzles, spray balls, or apertures. Each restriction (209*) is configured to accept pressurized liquid from the pump (P1*) and introduce the liquid into the lower-section (206*) of the second growing assembly (200*) while reducing the pressure of the liquid that passes through each restriction (209*). The second liquid distributor (208*) is connected to a second liquid supply conduit (213*) via a liquid input (214*). The second liquid distributor (208*) is configured to receive liquid from a second liquid supply conduit (213*).

The first liquid supply conduit (113*) is connected to a liquid supply header (300*) via a first connection (X1*). The second liquid supply conduit (213*) is connected to a liquid supply header (300*) via a second connection (X2*). The liquid supply header (300*) is connected to the pump discharge conduit (304*). In embodiments, the liquid supply header (300*) has a diameter (D1*) that is greater than both the first smaller diameter (D2*) of the first liquid supply conduit (113*) and the second smaller diameter (D3*) of the second liquid supply conduit (213*). A first reducer (R1*) may be positioned on the first liquid supply conduit (113*) in between the first connection (X1*) to the liquid supply header (300*) and the liquid input (114*) to the first growing assembly (100*). A second reducer (R2*) may be positioned on the second liquid supply conduit (213*) in between the second connection (X2*) to the liquid supply header (300*) and the liquid input (214*) to the second growing assembly (200*).

A first growing assembly liquid supply valve (V3*) may be positioned on the first liquid supply conduit (113*) in between the liquid supply header (300*) and the first growing assembly (100*). The first growing assembly liquid supply valve (V3*) has a controller (CV3*) that is configured to input and output a signal (XV3*) to or from the computer (COMP). A second growing assembly liquid supply valve (V4*) may be positioned on the second liquid supply conduit (213*) in between the liquid supply header (300*) and the second growing assembly (200*). The second growing assembly liquid supply valve (V4*) has a controller (CV4*) that is configured to input and output a signal (XV4*) to or from the computer (COMP).

A back-flow prevention valve (BF1*) may be positioned on the first liquid supply conduit (113*) in between the liquid supply header (300*) and the first growing assembly (100*). FIG. 1A' shows the back-flow prevention valve (BF1*) positioned in between the first growing assembly liquid supply valve (V3*) and the first growing assembly (100*). A back-flow prevention valve (BF2*) may be positioned on the second liquid supply conduit (213*) in between the liquid supply header (300*) and the second growing assembly (200*). FIG. 1A' shows the back-flow prevention valve (BF2*) positioned in between the second growing assembly liquid supply valve (V4*) and the second growing assembly (200*).

A second oxygen emitter (EZ2*) may be positioned on the first liquid supply conduit (113*) in between the liquid supply header (300*) and the first growing assembly (200*). The second oxygen emitter (EZ2*) is configured to oxygenate a portion of the liquid that flows through the first liquid supply conduit (113*). The second oxygen emitter (EZ2*) inputs signal (XEZ3*) from a computer (COMP). A third oxygen emitter (EZ3*) may be positioned on the second liquid supply conduit (213*) in between the liquid supply header (300*) and the second growing assembly (200*). The third oxygen emitter (EZ3*) is configured to oxygenate a portion of the liquid that flows through the second liquid supply conduit (213*). The third oxygen emitter (EZ3*) inputs signal (XEZ3*) from a computer (COMP).

In embodiments, the oxygen emitter is an electrolytic cell configured to produce oxygenated water. In embodiments, oxygenated water produced by the electrolytic cell may have microbubbles and nanobubbles of oxygen suspended within it. In embodiments, the oxygen emitter is an electrolytic cell which generates microbubbles and nanobubbles of oxygen in a liquid, which bubbles are too small to break the surface tension of the liquid, resulting in a liquid that is supersaturated with oxygen. "Supersaturated" means oxygen at a higher concentration than normal calculated oxygen solubility at a particular temperature and pressure. In embodiments, the very small oxygen bubbles remain suspended in the liquid, forming a solution supersaturated in oxygen. The use of supersaturated or oxygenated water for enhancing the growth of *cannabis* may be incorporated into the FSS. Electrolytic generation of microbubbles or nanobubbles of oxygen for increasing the oxygen content of flowing liquid may be incorporated into the FSS. In embodiments, the production of oxygen and hydrogen by the electrolysis of water may be used to enhance the efficiency of the FSS.

In embodiments, an electrolytic cell is comprised of an anode and a cathode. A current is applied across an anode and a cathode of the electrolytic cell which are immersed in a liquid. Hydrogen gas is produced at the cathode and oxygen gas is produced at the anode. In embodiments, the electrolytic cell tends to deactivate and have a limited life if exposed to the positively charged ions, negatively charged ions, or undesirable compounds. Therefore, a sophisticated water treatment unit is needed for the electrolytic cell to work properly deactivate by unpredictable amounts of positively charged ions, remove negatively charged ions, or undesirable components. The roots of the *cannabis* in the lower section (106*, 206*) are healthier when contacted with an oxygenated liquid. Further, oxygenated and/or supersaturated water inhibits the growth of deleterious fungi on the fabric (104*, 204*). In embodiments, the oxygen emitter may be a sparger for increasing the oxygen content of a liquid by sparging with air or oxygen. In embodiments, the oxygen emitter may be a microbubble generator that achieves a bubble size of about 0.10 millimeters to about 3 millimeters in diameter. In embodiments, the oxygen emitter may be a microbubble generator for producing microbubbles, ranging in size from 0.1 to 100 microns in diameter, by forcing air into the fluid at high pressure through an orifice.

The common reservoir (500*) is configured to accept a water supply (01*). In embodiments, the common reservoir (500*) is configured to accept a water supply (01*) that has passed through one or more water treatment units (A1*, A2*, A3*). In embodiments, the common reservoir (500*) is configured to accept a portion of the undesirable compounds depleted water (12A*).

The common reservoir (500*) is configured to accept macro-nutrients (601*) from a macro-nutrient supply tank (600*), micro-nutrients (701*) from a micro-nutrient supply tank (700*), and a pH adjustment solution (801*) from a pH adjustment solution supply tank (800*). In embodiments, the macro-nutrients (601*) include one or more from the group consisting of nitrogen, phosphorus, potassium, calcium, magnesium, and sulfur. In embodiments, the micro-nutrients (701*) include one or more from the group consisting of iron, manganese, boron, molybdenum, copper, zinc, sodium, chlorine, and silicon. In embodiments, the pH adjustment solution (801*) includes one or more from the group consisting acid, nitric acid, phosphoric acid, potassium hydroxide, sulfuric acid, organic acids, citric acid, and acetic acid.

In embodiments, the macro-nutrient supply tank (600*) is connected to the common reservoir (500*) via a macro-nutrient transfer conduit (602*) and a macro-nutrient reservoir input (Z1*). A macro-nutrient supply valve (V5*) is installed on the macro-nutrient transfer conduit (602*). The macro-nutrient supply valve (V5*) is equipped with a controller (CV5*) that inputs and outputs a signal (XV5*) to and from the computer (COMP). A macro-nutrient flow sensor (F5*) is installed on the macro-nutrient transfer conduit (602*) and configured to output a signal (XF5*) to or from a computer (COMP). Macro-nutrients (601*) may be transferred to the interior of the common reservoir (500*) via a macro-nutrient transfer conduit (602*) by operation with a macro-nutrient supply tank (600*) load cell (604*) to measure the loss-in-mass of the macro-nutrients (601*) within the macro-nutrient supply tank (600*) or the macro-nutrient transfer conduit (602*). Macro-nutrients (601*) are introduced into the interior of the common reservoir (500*) beneath the liquid level via a diptube (606*).

In embodiments, the micro-nutrient supply tank (700*) is connected to the common reservoir (500*) via a micro-nutrient transfer conduit (702*) and a micro-nutrient reservoir input (Z2*). A micro-nutrient supply valve (V6*) is installed on the micro-nutrient transfer conduit (702*). The micro-nutrient supply valve (V6*) is equipped with a controller (CV6*) that inputs and outputs a signal (XV6*) to and from the computer (COMP). A micro-nutrient flow sensor (F6*) is installed on the micro-nutrient transfer conduit (702*) and configured to output a signal (XF6*) to or from a computer (COMP). Micro-nutrients (701*) may be transferred to the interior of the common reservoir (500*) via a micro-nutrient transfer conduit (702*) by operation with a micro-nutrient supply tank (700*) load cell (704*) to measure the loss-in-mass of the micro-nutrients (701*) within the micro-nutrient supply tank (700*) or the micro-nutrient transfer conduit (702*). Macro-nutrients (601*) are introduced into the interior of the common reservoir (500*) beneath the liquid level via a diptube (606*) (not shown).

In embodiments, the pH adjustment solution supply tank (800*) is connected to the common reservoir (500*) via a pH adjustment solution transfer conduit (802*) and a pH adjustment solution reservoir input (Z3*). A pH adjustment solution supply valve (V8*) is installed on the pH adjustment solution transfer conduit (802*). The pH adjustment solution supply valve (V8*) is equipped with a controller (CV8*) that inputs and outputs a signal (XV8*) to and from the computer (COMP). A pH adjustment solution flow sensor (F7*) is installed on the pH adjustment solution transfer conduit (802*) and configured to output a signal (XF7*) to or from a computer (COMP). A pH adjustment solution (801*) may be transferred to the interior of the common reservoir (500*) via a pH adjustment solution transfer conduit (802*) by operation with a pH adjustment solution supply tank (800*) load cell (804*) to measure the loss-in-mass of the pH adjustment solution (801*) within the pH adjustment solution supply tank (800*) or the pH adjustment solution transfer conduit (802*). The pH adjustment solution (801*) are introduced into the interior of the common reservoir (500*) beneath the liquid level via a diptube (806*) (not shown).

The common reservoir (500*) is configured to accept liquid drained from each growing assembly (100*, 200*). The common reservoir (500*) is configured to accept liquid drained from the first growing assembly (100*). A drain port (110*) is installed on the lower-section (106*) of the first growing assembly (100*) and is configured to drain liquid into a common reservoir (500*) via a drain conduit (111*). In embodiments, the first growing assembly (100*) is connected to the common reservoir (500*) via a drain conduit (111*). The common reservoir (500*) is configured to accept liquid drained from the second growing assembly (200*). A drain port (210*) is installed on the lower-section (206*) of the second growing assembly (200*) and is configured to drain liquid into a common reservoir (500*) via a drain conduit (211*). In embodiments, the second growing assembly (200*) is connected to the common reservoir (500*) via a drain conduit (211*). It is preferable to drain liquid from each growing assembly at a velocity less than 3 feet per second (fps) or 0.25 fps to 0.50 fps, 0.50 fps to 0.75 fps, 0.75 fps to 1.00 fps, 1.00 fps to 1.25 fps, 1.25 fps to 1.50 fps, 1.50 fps to 1.75 fps, 1.75 fps to 2.00 fps, 2.00 fps to 2.25 fps, 2.25 fps to 2.50 fps, 2.50 fps to 2.75 fps, 2.75 fps to 3.00 fps, 3.00 fps to 3.25 fps, 3.25 fps to 3.50 fps, 3.50 fps to 3.75 fps, 3.75 fps to 4.00 fps, 4.00 fps to 4.25 fps, 4.25 fps to 4.50 fps, 4.50 fps to 4.75 fps, 4.75 fps to 5.00 fps, 5.00 fps to 5.25 fps, 5.25 fps to 5.50 fps, 5.50 fps to 5.75 fps, 5.75 fps to 6.00 fps, 6.00 fps to 6.25 fps, 6.25 fps to 6.50 fps, 6.50 fps to 6.75 fps, 6.75 fps to 7.00 fps, 7.00 fps to 7.25 fps, 7.25 fps to 7.50 fps, 7.50 fps to 7.75 fps, 7.75 fps to 8.00 fps, 8.00 fps to 8.25 fps, 8.25 fps to 8.50 fps, 8.50 fps to 8.75 fps, 8.75 fps to 9.00 fps, 9.00 fps to 9.25 fps, 9.25 fps to 9.50 fps, 9.50 fps to 9.75 fps, or 9.75 fps to 10.00 fps.

In embodiments, the drain conduit (111*) is connected at one end to the first growing assembly (100*) via a drain port (110*) and connected at another end to the common reservoir (500*) via a common drain conduit (517*). In embodiments, the drain conduit (211*) is connected at one end to the second growing assembly (200*) via a drain port (210*) and connected at another end to the common reservoir (500*) via a common drain conduit (517*). The common drain conduit (517*) is connected at one end to the common reservoir (500*) via a drain input (518*) and at another end to the first drain conduit (111*) via a first drain connection (112*). The common drain conduit (517*) is connected at one end to the common reservoir (500*) via a drain input (518*) and at another end to the second drain conduit (211*) via a second drain connection (212*). In embodiments, the common drain conduit (517*) is connected to both drain conduits (111*, 211*) from both growing assemblies (100*, 200*) and is configured to combine the liquid contents of both drain conduits (111*, 211*) prior to introducing them into the common reservoir (500*). In embodiments, as shown in FIG. 8', there is no common drain conduit (517*) and each drain conduit (111*, 211*) of the growing assemblies (100*, 200*) drains directly into the common reservoir (500*).

The interior of the common reservoir (500*) is configured to hold water, macro-nutrients (601*), micro-nutrients (701*) from a micro-nutrient supply tank (700*), and a pH adjustment solution (801*). In embodiments, the common reservoir (500*) is equipped with a reservoir pH sensor (PHO*) that is configured to input a signal (XPHO*) to a computer (COMP). In embodiments, the acidity of the water is measured by the reservoir pH sensor (PHO*) and adjusted to a desirable range from 5.15 to 6.75. In embodiments, the common reservoir (500*) is equipped with a reservoir temperature sensor (T0) that is configured to input a signal (XT0) to a computer (COMP). In embodiments, the common reservoir (500*) is equipped with a reservoir oxygen emitter (EZ*) that is configured to input a signal (XEZ*) to a computer (COMP). In embodiments, the common reservoir (500*) is equipped with a reservoir electrical conductivity sensor (E1) that is configured to input a signal (XE1*) to a computer (COMP).

In embodiments, the common reservoir (500*) is equipped with a reservoir recirculation pump (P0*) followed by a reservoir recirculation filter (F3*) to remove solids from the common reservoir (500*). In embodiments, the common reservoir (500*) is equipped with a reservoir heat exchanger (HX2*) to maintain a temperature of the liquid contents within the common reservoir (500*). In embodiments, the common reservoir (500*) is equipped with a reservoir recirculation pump (P0*) followed by a reservoir heat exchanger (HX2*) to maintain a temperature of the liquid contents within the common reservoir (500*). The common reservoir (500*) has a reservoir recirculation outlet (510*) that is connected to a reservoir recirculation pump suction conduit (512*). The reservoir recirculation pump suction conduit (512*) is connected to a reservoir recirculation pump (P0*). The reservoir recirculation pump (P0*) is connected to a reservoir recirculation pump discharge conduit (514*) that transfers liquid back to the common reservoir (500*) via a reservoir recirculation inlet (516*). In embodiments, a reservoir recirculation filter (F3*) is installed on the reservoir recirculation pump discharge conduit (514*). In embodiments, a reservoir heat exchanger (HX2*) is installed on the reservoir recirculation pump discharge conduit (514*). In embodiments, a reservoir heat exchanger (HX2*) is installed on the reservoir recirculation pump discharge conduit (514*) after the reservoir recirculation filter (F3*). In embodiments, the reservoir heat exchanger (HX2*) may increase the temperature of the liquid passing through it. In embodiments, the reservoir heat exchanger (HX2*) may decrease the temperature of the liquid passing through it.

The common reservoir (500*) is connected to a pump (P1*) via a pump suction conduit (303). The pump suction conduit (303*) is connected at one end to the common reservoir (500*) via a reservoir transfer outlet (302*) and connected at the other end to the pump (P1*). The pump (P1*) is equipped with a motor (MP1*) and a controller (CP1*) which is configured to input and output a signal (XP1*) to and from a computer (COMP). A pump discharge conduit (304*) is connected to the pump (P1*). The liquid supply header (300*) may be synonymous with the pump discharge conduit (304*) in that they both accept a portion of pressurized liquid that was provided by the pump (P1*).

In embodiments, a pressure tank (PT*) is installed on the pump discharge conduit (304*). In embodiments, the pressure tank (PT*) may be pressurized by the pump (P1*). The pressure tank (PT*) serves as a pressure storage reservoir in which a liquid is held under pressure. The pressure tank (PT*) enables the system to respond more quickly to a temporary demand, and to smooth out pulsations created by the pump (P1*). In embodiments, the pressure tank (PT*) serves as accumulator to relieve the pump (P1*) from constantly operating. In embodiments, the pressure tank (PT*) is a cylindrical tank rated for a maximum pressure of 200 PSI or 600 PSI. In embodiments, the pressure tank (PT*) is a cylindrical tank that has a length to diameter ratio ranging from 1.25 to 2.5.

A level control discharge conduit (310*) is connected to the pump discharge conduit (304*) via a connection (311*). The level control discharge conduit (310*) is configured to pump the contents of the common reservoir (500*) away from the system for any number of reasons. Clean-out, replenishing the liquid within the common reservoir (500*) or to bleed off some of the liquid contents within may be some purposes for utilizing the level control discharge conduit (310*). A filter (F4*) is installed on the level control discharge conduit (310*). A level control valve (LCV*) is installed on the level control discharge conduit (310*) and is equipped with a controller (CCV*) that sends a signal (XCV*) to or from the computer (COMP). The filter (F4*) preferably is installed upstream of the level control valve (LCV*) to that solids do not clog the level control valve (LCV*). Preferably the connection (311*) for the level control discharge conduit (310*) is connected as close as possible to the pump (P1*) on the pump discharge conduit (304*) so that if the filters (F1*, F2*) on the pump discharge conduit (304*) clog, there is still a way to drain liquid from the system. A waste treatment unit (312*) may be placed on the level control discharge conduit (310*) to destroy any organic molecules, waste, bacteria, protozoa, helminths, or viruses that may be present in the liquid. In embodiments, the waste treatment unit (312*) is an ozone unit (313*) configured to destroy organic molecules, waste, bacteria, protozoa, helminths, or viruses via oxidation.

At least one filter (F1*, F2*) may be installed on the pump discharge conduit (304). FIG. 1A' shows two filters (F1*, F2*) configured to operate in a cyclic-batch mode where when one is on-line in a first mode of normal operation, the other is off-line and undergoing a back-flush cycle in a second mode of operation. This is depicted in FIG. 1A' wherein the first filter (F1*) is on-line and filtering the liquid discharged from the pump (P1*) while the second filter (F2*) is off-line. The first filter (F1*) is shown to have a first filter inlet valve (FV1*) and a first filter outlet valve (FV2*) both of which are open in FIG. 1'. The second filter (F2*) is shown to have a second filter inlet valve (FV3*) and a second filter outlet valve (FV4*) both of which are shown in the closed position as indicted by darkened-in color of the valves (FV3*, FV4*). The second filter (F2*) is shown in the back-flush mode of operation while the first filter (F1*) is shown in the normal mode of operation. While in the back-flush mode of operation, the second filter (F2*) is shown accepting a source of liquid from the common reservoir (500*) via a filter back-flush supply conduit (306*).

The common reservoir (500*) is equipped with a filter back-flush outlet (307*) that is connected to a filter back-flush supply conduit (306*). The filter back-flush supply conduit (306*) is connected at one end to the common reservoir (500*) via a filter back-flush outlet (307*) and at another end to the filter back-flush pump (308*). The filter back-flush pump (308*) is connected to the filter back-flush discharge conduit (309*). The filter back-flush discharge conduit (309*) has a filter back-flush supply valve (FV5*) installed thereon to provide pressurized liquid from the common reservoir (500*) to the second filter (F2*) operating in the second mode of back-flush operation. The filter back-flush supply valve (FV5*) provides liquid to the second filter in between the second filter outlet valve (FV4*) and the second filter (F2*) to back-flush the second filter (F2*). A filter back-flush discharge valve (FV6*) is provided in between the second filter and the second filter inlet valve (FV3*) to flush solids that have accumulated during the first mode of normal operation.

A filter inlet pressure sensor (P2*) is installed on the pump discharge conduit (304*) before the filters (F1*, F2*). The filter inlet pressure sensor (P2*) is configured to output a signal (XP2*) to the computer (COMP). A filter discharge pressure sensor (P3*) is installed on the pump discharge conduit (304*) after the filters (F1*, F2*). The filter discharge pressure sensor (P2*) is configured to output a signal (XP3*) to the computer (COMP). Then the pressure drop across the filters (F1*, F2*) reached a threshold predetermined value, the filters (F1*, F2*) switch modes of operation from first to second and from second to first.

A first oxygen emitter (EZ1*) is installed on the pump discharge conduit (304*). In embodiments, the first oxygen emitter (EZ1*) is installed on the pump discharge conduit (304*) after the filters (F1*, F2*). The first oxygen emitter (EZ1*) is configured to output a signal (XEZ1*) to the computer (COMP). The first oxygen emitter (EZ1*) oxygenates the water passing through the pump discharge conduit (304*).

A liquid flow sensor (F0*) is installed on the pump discharge conduit (304*) after the filters (F1*, F2*). The liquid flow sensor (F0*) is configured to output a signal (XFO*) to the computer (COMP). The liquid flow sensor (F0*) measures the flow rate of water passing through the pump discharge conduit (304*).

In embodiments, the flow rate of water passing through the pump discharge conduit (304*) ranges from 0.01 gallons per minute (gpm) to 0.02 gpm, 0.02 gpm to 0.03 gpm, 0.03 gpm to 0.04 gpm, 0.04 gpm to 0.05 gpm, 0.05 gpm to 0.06 gpm, 0.05 gpm to 0.06 gpm, 0.06 gpm to 0.07 gpm, 0.07 gpm to 0.08 gpm, 0.08 gpm to 0.09 gpm, 0.09 gpm to 0.1 gpm, 0.1 gpm to 0.15 gpm, 0.15 gpm to 0.2 gpm, 0.2 gpm to 0.25 gpm, 0.25 gpm to 0.3 gpm, 0.3 gpm to 0.35 gpm, 0.35 gpm to 0.4 gpm, 0.4 gpm to 0.45 gpm, 0.45 gpm to 0.5 gpm, 0.5 gpm to 0.6 gpm, 0.6 gpm to 0.7 gpm, 0.7 gpm to 0.8 gpm, 0.8 gpm to 0.9 gpm, 0.9 gpm to 1 gpm, 1 gpm to 2 gpm, 2 gpm to 3 gpm, 3 gpm to 4 gpm, 4 gpm to 5 gpm, 5 gpm to 6 gpm, 6 gpm to 7 gpm, 7 gpm to 8 gpm, 8 gpm to 9 gpm, 9 gpm to 10 gpm, 10 gpm to 11 gpm, 11 gpm to 12 gpm, 12 gpm to 13 gpm, 13 gpm to 14 gpm, 14 gpm to 15 gpm, 15 gpm to 16 gpm, 16 gpm to 17 gpm, 17 gpm to 18 gpm, 18 gpm to 19 gpm, 19 gpm to 20 gpm, 20 gpm to 30 gpm, 30 gpm to 40 gpm, 40 gpm to 50 gpm, 50 gpm to 60 gpm, 60 gpm to 70 gpm, 70 gpm to 80 gpm, 80 gpm to 90 gpm, 90 gpm to 100 gpm, 100 gpm to 125 gpm, 125 gpm to 150 gpm, 150 gpm to 175 gpm, 175 gpm to 200 gpm, 200 gpm to 225 gpm, 225 gpm to 250 gpm, 250 gpm to 275 gpm, 275 gpm to 300 gpm, 300 gpm to 350 gpm, 350 gpm to 400 gpm, 400 gpm to 450 gpm, 450 gpm to 500 gpm, 500 gpm to 550 gpm, 550 gpm to 600 gpm, 600 gpm to 650 gpm, 650 gpm to 700 gpm, 700 gpm to 750 gpm, 750 gpm to 800 gpm, 800 gpm to 850 gpm, 850 gpm to 900 gpm, 900 gpm to 950 gpm, 950 gpm to 1000 gpm, 1000 gpm to 1500 gpm, 1500 gpm to 2000 gpm, 2000 gpm to 2500 gpm, 2500 gpm to 3000 gpm, 3000 gpm to 3500 gpm, 3500 gpm to 4000 gpm, 4000 gpm to 4500 gpm, 4500 gpm to 5000 gpm, 5000 gpm to 5500 gpm, 5500 gpm to 6000 gpm, 6000 gpm to 6500 gpm, 6500 gpm to 7000 gpm, 7000 gpm to 7500 gpm, 7500 gpm to 8000 gpm, 8000 gpm to 8500 gpm, 8500 gpm to 9000 gpm, 9000 gpm to 9500 gpm, or 9500 gpm to 10000 gpm.

In embodiments, the velocity of the water passing through the pump discharge conduit (304*) ranges from 3.00 fps to 3.25 fps, 3.25 fps to 3.50 fps, 3.50 fps to 3.75 fps, 3.75 fps to 4.00 fps, 4.00 fps to 4.25 fps, 4.25 fps to 4.50 fps, 4.50 fps to 4.75 fps, 4.75 fps to 5.00 fps, 5.00 fps to 5.25 fps, 5.25 fps to 5.50 fps, 5.50 fps to 5.75 fps, 5.75 fps to 6.00 fps, 6.00 fps to 6.25 fps, 6.25 fps to 6.50 fps, 6.50 fps to 6.75 fps, 6.75 fps to 7.00 fps, 7.00 fps to 7.25 fps, 7.25 fps to 7.50 fps, 7.50 fps to 7.75 fps, 7.75 fps to 8.00 fps, 8.00 fps to 8.25 fps, 8.25 fps to 8.50 fps, 8.50 fps to 8.75 fps, 8.75 fps to 9.00 fps, 9.00 fps to 9.25 fps, 9.25 fps to 9.50 fps, 9.50 fps to 9.75 fps, or 9.75 fps to 10.00 fps.

In embodiments, the velocity of the water passing through the pump suction conduit (303) ranges from 0.25 feet per second (fps) to 0.50 fps, 0.50 fps to 0.75 fps, 0.75 fps to 1.00 fps, 1.00 fps to 1.25 fps, 1.25 fps to 1.50 fps, 1.50 fps to 1.75 fps, 1.75 fps to 2.00 fps, 2.00 fps to 2.25 fps, 2.25 fps to 2.50 fps, 2.50 fps to 2.75 fps, or 2.75 fps to 3.00 fps.

A growing assembly liquid supply valve (V1*) is installed on the pump discharge conduit (304*). In embodiments, the growing assembly liquid supply valve (V1*) is installed on the pump discharge conduit (304*) after the filters (F1*, F2*). The growing assembly liquid supply valve (V1*) is equipped with a controller (CV1*) that sends a signal (XV1*) to or from a computer (COMP).

An electrical conductivity sensor (E2*) is installed on the pump discharge conduit (304*). In embodiments, the electrical conductivity sensor (E2*) is installed on the pump discharge conduit (304*) after the filters (F1*, F2*). The electrical conductivity sensor (E2*) is configured to output a signal (XE2*) to the computer (COMP). The electrical conductivity sensor (E2*) measures the electrical conductivity of the water passing through the pump discharge conduit (304*).

A liquid heat exchanger (HX3*) is installed on the pump discharge conduit (304*). In embodiments, the liquid heat exchanger (HX3*) is installed on the pump discharge conduit (304*) after the filters (F1*, F2*). The liquid heat exchanger (HX3*) is configured increase or decrease the temperature of the water passing through the pump discharge conduit (304*).

A liquid temperature sensor (T3*) is installed on the pump discharge conduit (304*). In embodiments, the liquid temperature sensor (T3*) is installed on the pump discharge conduit (304*) after the filters (F1*, F2*). In embodiments, the liquid temperature sensor (T3*) is installed on the pump discharge conduit (304*) after the liquid heat exchanger (HX3*). The liquid temperature sensor (T3*) is configured to input a signal (XT3*) to the computer (COMP).

In embodiments, the growing assembly liquid supply valve (V1*), first growing assembly liquid supply valve (V3*), and/or the second growing assembly liquid supply valve (V4*), may continuously be open to permit a continuous flow of liquid into the growing assemblies (100*, 200*). In embodiments, the growing assembly liquid supply valve (V1*), first growing assembly liquid supply valve (V3*), and/or second growing assembly liquid supply valve (V4*), may be opened and closed by their controllers (CV1*, CV3*, CV4*) and operated by a computer (COMP). In embodiments, the growing assembly liquid supply valve (V1*), first growing assembly liquid supply valve (V3*), and/or second growing assembly liquid supply valve (V4*), may be opened and closed by their controllers (CV1*, CV3*, CV4*) and operated by a computer (COMP) on a timer.

It is preferred to have the valves (V1*, V3*, V4*) operated in a plurality of modes of operation. In embodiments, a first mode of operation includes having the growing assembly liquid supply valve (V1*), first growing assembly liquid supply valve (V3*), second growing assembly liquid supply valve (V4*), all in an open valve position to transfer liquid from the common reservoir (500*) into the growing assemblies (100*, 200*). In embodiments, a second mode of operation includes having the growing assembly liquid supply valve (V1*) open, first growing assembly liquid supply valve (V3*) closed, and second growing assembly liquid supply valve (V4*) closed, to stop the transfer liquid to the growing assemblies (100*, 200*). In embodiments, a third mode of operation includes having the growing assembly liquid supply valve (V1*) open, first growing assembly liquid supply valve (V3*) open, second growing assembly liquid supply valve (V4*) closed, to transfer liquid to the first growing assembly (100*) and not into the second growing assembly (200*). In embodiments, a fourth mode of operation includes having the growing assembly liquid supply valve (V1*) open, first growing assembly liquid supply valve (V3*) closed, second growing assembly liquid supply valve (V4*) open, to transfer liquid to the second growing assembly (200*) and not into the first growing assembly (100*).

In embodiments, the farming superstructure system (FSS) is operated in a manner that switches from one mode of operation to another mode of operation. In embodiments, the farming superstructure system (FSS) is operated in a manner that switches on a cyclical basis from: a first mode of operation to the second mode of operation; a second mode of operation to the first mode of operation. In embodiments, the farming superstructure system (FSS) is operated in a manner that switches on a cyclical basis from: a third mode of operation to the fourth mode of operation; a fourth mode of operation to the third mode of operation. It is preferred to turn on and off at least one of the valves (V1*, V3*, V4*) in a cyclical manner to permit to prevent the roots of the *cannabis* from receiving too much mist or spray.

In embodiments, the first mode of operation lasts for 5 seconds open followed by the second mode of operation lasting for 600 seconds closed. In embodiments, the third mode of operation lasts for 5 seconds open followed by the fourth mode of operation lasting for 600 seconds closed. In embodiments, water is transferred to the first growing assembly (100*) for 5 seconds followed by not transferring water to the first growing assembly (100*) for 600 seconds. In embodiments, water is transferred to the second growing assembly (200*) for 5 seconds followed by not transferring water to the second growing assembly (200*) for 600 seconds. In embodiments, water is transferred to both the first and second growing assemblies (100*, 200*) for 5 seconds followed by not transferring water to both the first and second growing assemblies (100*, 200*) for 600 seconds. 5 divided by 600 is 0.008.

In embodiments, the first mode of operation lasts for 60 seconds open followed by the second mode of operation lasting for 180 seconds closed. In embodiments, the third mode of operation lasts for 60 seconds open followed by the fourth mode of operation lasting for 180 seconds closed. In embodiments, water is transferred to the first growing assembly (100*) for 60 seconds followed by not transferring water to the first growing assembly (100*) for 180 seconds. In embodiments, water is transferred to the second growing assembly (200*) for 60 seconds followed by not transferring water to the second growing assembly (200*) for 180 seconds. 60 divided by 180 is 0.333.

The duration of time when liquid is transferred to at least one growing assembly (100*, 200*) divided by the duration of time when liquid is not transferred to at least one growing assembly (100*, 200*) may be considered an open-close ratio. The open-close ratio may be the duration of time when at least one valve (V1*, V3*, V4*) is open in seconds divided by the subsequent duration of time when the same valve is closed in seconds before the same valve opens again. In embodiments, the open-close ratio ranges from between 0.008 to 0.33. In embodiments, the computer (COMP) opens and closes the valve (V1*, V3*, V4*) to periodically introduce the pressurized liquid mixture into to each growing assembly with an open-close ratio ranging from between 0.008 to 0.33, the open-close ratio is defined as the duration of time when the valve (V1*, V3*, V4*) is open in seconds divided by the subsequent duration of time when the same valve is closed in seconds before the same valve opens again. The computer (COMP) opens and closes the valves (V1*, V3*, V4*) to periodically introduce the pressurized liquid mixture into to each growing assembly with an open-close ratio ranging from between 0.008 to 0.33.

In embodiments, the open-close ratio varies. The open-close ratio may vary throughout the life of the *cannabis* contained within the growing assemblies (100*, 200*). The open-close ratio may vary throughout the stage of development of the *cannabis* contained within the growing assemblies (100*, 200*). Stages of development of the *cannabis* include flowering, pollination, fertilization. In embodiments, the open-close ratio is greater during flowering and less during pollination. In embodiments, the open-close ratio is greater during pollination and less during fertilization. In embodiments, the open-close ratio is greater during flowering and less during fertilization. In embodiments, the open-close ratio is less during flowering and greater during pollination. In embodiments, the open-close ratio is less during pollination and greater during fertilization. In embodiments, the open-close ratio is less during flowering and greater during fertilization.

In embodiments, the temperature is greater during flowering and less during pollination. In embodiments, the temperature is greater during pollination and less during fertilization. In embodiments, the temperature is greater during flowering and less during fertilization. In embodiments, the temperature is less during flowering and greater during pollination. In embodiments, the temperature is less during pollination and greater during fertilization. In embodiments, the temperature is less during flowering and greater during fertilization.

The open-close ratio may vary throughout a 24-hour duration of time. In embodiments, the open-close ratio is increased during the day-time and decreased during the night-time relative to one another. In embodiments, the open-close ratio varies increased during the night-time and decreased during the day-time relative to one another. Night-time is defined as the time between evening and morning. Day-time is defined as the time between morning and evening.

In embodiments, carbohydrates may be added to the common reservoir (500). The carbohydrates are comprised of one or more from the group consisting of sugar, sucrose, molasses, and plant syrups. In embodiments, enzymes may be added to the common reservoir (500). The enzymes are comprised of one or more from the group consisting of amino acids, orotidine 5'-phosphate decarboxylase, OMP decarboxylase, glucanase, beta-glucanase, cellulase, xylanase, HYGROZYME®, CANNAZYME®, MICROZYME®, and SENSIZYME®. In embodiments, vitamins may be added to the common reservoir (500*). The vitamins are comprised of one or more from the group consisting of vitamin B, vitamin C, vitamin D, and vitamin E. In embodiments, hormones may be added to the common reservoir (500*). The hormones are comprised of one or more from the group consisting of auxins, cytokinins gibberellins, abscic acid, brassinosteroids, salicylic acid, jasmonates, plant peptide hormones, polyamines, nitric oxide, strigolactones, and triacontanol. In embodiments, microorganisms may be added to the common reservoir (500*). The microorganisms are comprised of one or more from the group consisting of bacteria, diazotroph bacteria, diazotrop archaea, *Azotobacter vinelandii, Clostridium pasteurianu, fungi, Arbuscular mycorrhizal* fungi, *Glomus aggrefatum, Glomus etunicatum, glomus intraradices, Rhizophagus irregularis,* and *Glomus mosseae.*

In embodiments, an analyzer (AZ*) may be incorporated into the farming superstructure system (FSS). In embodiments, the analyzer analyzes the contents within the common reservoir (500*) of analyzes the mixture of water, macro-nutrients, micro-nutrients, and a pH adjustment solution to determine the whether any water, macro-nutrients, micro-nutrients, and a pH adjustment need to be added. A signal (XAZ*) from the analyzer may be sent to a computer (COMP). From the signal (XAZ*) obtained by the computer (COMP), the computer (COMP) may calculate and automate the introduction of water, macro-nutrients, micro-nutrients, and a pH adjustment solution introduced to the system. In embodiments, the analyzer (AZ*) may include a mass spectrometer, Fourier transform infrared spectroscopy, infrared spectroscopy, potentiometric pH meter, pH meter, electrical conductivity meter, or liquid chromatography.

FIG. 1B'

FIG. 1B' depicts one non-limiting embodiment of a farming superstructure system (FSS) that includes a first growing assembly (100*) having a first growing medium (GM1*) and a second growing assembly (200*) having a second growing medium (GM2*).

In embodiments, the first and second growing mediums (GM1*, GM2*) can be comprised of one or more from the group consisting of rockwool, perlite, amorphous volcanic glass, vermiculite, clay, clay pellets, LECA (lightweight expanded clay aggregate), coco-coir, fibrous coconut husks, soil, dirt, peat, peat moss, sand, soil, compost, manure, fir bark, foam, gel, oasis cubes, lime, gypsum, and quartz. In embodiments, a fungus may be added to the growing medium. In embodiment, the fungus may be mycorrhiza. In embodiments, the first and second growing mediums (GM1*, GM2*) can be comprised of a liquid and includes water. In embodiments, the first and second growing mediums (GM1*, GM2*) can be comprised of a liquid and includes water and includes a hydroponic system.

FIG. 1B' differs from FIG. 1A' since a fabric (104*, 204*) does not partition the growing assembly (100*, 200*) into an upper-section (105*, 205*) and a lower-section (106*, 206*). Instead, the *cannabis* (107*, 207*) are in contact with the growing medium (GM1*, GM2*), and the growing medium (GM1*, GM2*) partitions each growing assembly (100*, 200*) into an upper-section (105*, 205*) and a lower-section (106*, 206*). Liquid from with pump (P1*) is introduced into the interior (101*, 201*) of each growing assembly (100*, 200*) via a liquid input (114*, 214*) where the liquid contacts the growing medium (GM1*, GM2*). In embodiments, liquid from the pump (P1*) is the growing medium (GM1*, GM2*). In embodiments, liquid is transferred to the interior (101*, 201*) of each growing assembly (100*, 200*) via the liquid input (114*, 214*) on a periodic basis.

In embodiments, the computer (COMP) controls the lights (L1*, L2*). In embodiments, the lights (L1*, L2*) illuminate each growing assembly (100,* 200*) with an illumination on-off ratio ranging from between 0.5 to 11. The illumination on-off ratio is defined as the duration of time when the lights (L1*, L2*) are on and illuminate the

*cannabis* (107*, 207*) in hours divided by the subsequent duration of time when the lights (L1*, L2*) are off and are not illuminating the *cannabis* (107*, 207*) in hours before the lights are turned on again.

In embodiments, the lights (L1*, L2*) are on and illuminate the *cannabis* for 18 hours and then are turned off for 6 hours. 18 divided by 6 is 3. In embodiments, an illumination on-off ratio of 3 is contemplated. In embodiments, the lights (L1*, L2*) are on and illuminate the *cannabis* for 20 hours and then are turned off for 4 hours. 20 divided by 4 is 5. In embodiments, an illumination on-off ratio of 5 is contemplated. In embodiments, the lights (L1*, L2*) are on and illuminate the *cannabis* for 22 hours and then are turned off for 2 hours. 22 divided by 2 is 11. In embodiments, an illumination on-off ratio of 11 is contemplated. In embodiments, the lights (L1*, L2*) are on and illuminate the *cannabis* for 8 hours and then are turned off for 16 hours. 8 divided by 16 is 0.5. In embodiments, an illumination on-off ratio of 0.5 is contemplated. In embodiments, the lights (L1*, L2*) are on and illuminate the *cannabis* for 12 hours and then are turned off for 12 hours. 12 divided by 12 is 1. In embodiments, an illumination on-off ratio of 1 is contemplated. In embodiments, the is desirable to operate the growing assemblies at an illumination on-off ratio that is greater than 1 and less than 11. In embodiments, the is desirable to operate the growing assemblies at an illumination on-off ratio that is greater than 0.5 and equal to or less than 5.

In embodiments, each growing assembly (100*, 200*) may include a container that contains a growing medium (GM1*, GM2*) sufficient to support the roots of the *cannabis* (107*, 207*). In embodiments, the growing assembly (100*, 200*) may be a container that contains a growing medium (GM1*, GM2*).

FIG. 1C'

FIG. 1C' depicts one non-limiting embodiment of a farming superstructure system (FSS) that includes a first growing assembly (100*) having a first growing medium (GM1*) and a second growing assembly (200*) having a second growing medium (GM2*) and the first growing assembly (100*) and second growing assembly (200*) are grown outdoors.

FIG. 1C' shows a fabric (104*, 204*) that is placed upon the first growing medium (GM1*) and the second growing medium (GM2*). In embodiments, the fabric (104*, 204*) is landscape fabric that includes a textile material used to control weeds by inhibiting their exposure to sunlight. In embodiments, the fabric (104*, 204*) is placed around that *cannabis* plants (107*, 207*), covering areas where other growth is unwanted. The fabric itself can be made from plastic, rubber, synthetic or organic materials, sometimes from recycled sources. In embodiments, the fabric (104*, 204*) is woven needle punch polypropylene fabric. In embodiments, the fabric (104*, 204*) is black.

In embodiments, liquid is transferred to the first growing assembly (100*) and second growing assembly (200*) on a periodic basic through the plurality of liquid supply conduits (113*, 213*), the liquid supply header (300*), at least one filter (F1*, F2*), and at least one valve valves (V1*, V3*, V4*). In embodiments, the spacing (CAA*, CAB*, CAC*, CAD*) between each plant (107A*, 107B*, 107C*, 207A*, 207B*, 207C*) includes one or more plant spacing ranges selected from the group consisting of 1.00 foot to 1.25 feet, 1.25 feet to 1.50 feet, 1.50 feet to 1.75 feet, 1.75 feet to 2.00 feet, 2.00 feet to 2.25 feet, 2.25 feet to 2.50 feet, 2.50 feet to 2.75 feet, 2.75 feet to 3.00 feet, 3.00 feet to 3.25 feet, 3.25 feet to 3.50 feet, 3.50 feet to 3.75 feet, 3.75 feet to 4.00 feet, 4.00 feet to 4.25 feet, 4.25 feet to 4.50 feet, 4.50 feet to 4.75 feet, 4.75 feet to 5.00 feet, 5.00 feet to 5.25 feet, 5.25 feet to 5.50 feet, 5.50 feet to 5.75 feet, 5.75 feet to 6.00 feet, 6.00 feet to 6.25 feet, 6.25 feet to 6.50 feet, 6.50 feet to 6.75 feet, 6.75 feet to 7.00 feet, 7.00 feet to 7.25 feet, 7.25 feet to 7.50 feet, 7.50 feet to 7.75 feet, and 7.75 feet to 8.00 feet, 8 feet to 10 feet, 10 feet to 12 feet, 12 feet to 15 feet, 15 feet to 30 feet.

FIG. 1D'

FIG. 1D' depicts one non-limiting embodiment general arrangement of a farming superstructure system (FSS) top-view that includes a first growing assembly (100*) and a second growing assembly (200*) each configured to grow plants (107*, 107A*, 107B*, 107C*, 207*, 207A*, 207B*, 207C*).

FIG. 1D' shows a top-down-view of one-acre plot of the farming superstructure system (FSS). In embodiments, the acre (DAA*) has a length (DAB*) and a width (DAC*). The acre is a unit of land area used in the imperial and US customary systems. In embodiments, the acre is a square enclosing one acre is approximately 69.57 yards, or 208 feet 9 inches (63.61 meters) on a side. As a unit of measure, an acre has no prescribed shape; any area of 43,560 square feet is an acre. In embodiments, the acre (DAA*) has a length (DAB*) of 208 feet 9 inches. In embodiments, the acre (DAA*) has a width (DAC*) of 208 feet 9 inches.

In embodiments, the width of the fabric (104*, 204*) includes one or more fabric widths (DAD*, DAE*) selected from the group consisting of 1.00 foot to 1.25 feet, 1.25 feet to 1.50 feet, 1.50 feet to 1.75 feet, 1.75 feet to 2.00 feet, 2.00 feet to 2.25 feet, 2.25 feet to 2.50 feet, 2.50 feet to 2.75 feet, 2.75 feet to 3.00 feet, 3.00 feet to 3.25 feet, 3.25 feet to 3.50 feet, 3.50 feet to 3.75 feet, 3.75 feet to 4.00 feet, 4.00 feet to 4.25 feet, 4.25 feet to 4.50 feet, 4.50 feet to 4.75 feet, 4.75 feet to 5.00 feet, 5 feet to 6 feet, 6 feet to 8 feet, 8 feet to 10 feet, 10 feet to 12 feet, 12 feet to 14 feet, 14 feet to 16 feet, 16 feet to 20 feet.

In embodiments, the spacing (CAA*, CAB*, CAC*, CAD*) between each plant (107A*, 107B*, 107C*, 207A*, 207B*, 207C*) includes one or more plant spacing ranges selected from the group consisting of 1.00 foot to 1.25 feet, 1.25 feet to 1.50 feet, 1.50 feet to 1.75 feet, 1.75 feet to 2.00 feet, 2.00 feet to 2.25 feet, 2.25 feet to 2.50 feet, 2.50 feet to 2.75 feet, 2.75 feet to 3.00 feet, 3.00 feet to 3.25 feet, 3.25 feet to 3.50 feet, 3.50 feet to 3.75 feet, 3.75 feet to 4.00 feet, 4.00 feet to 4.25 feet, 4.25 feet to 4.50 feet, 4.50 feet to 4.75 feet, 4.75 feet to 5.00 feet, 5.00 feet to 5.25 feet, 5.25 feet to 5.50 feet, 5.50 feet to 5.75 feet, 5.75 feet to 6.00 feet, 6.00 feet to 6.25 feet, 6.25 feet to 6.50 feet, 6.50 feet to 6.75 feet, 6.75 feet to 7.00 feet, 7.00 feet to 7.25 feet, 7.25 feet to 7.50 feet, 7.50 feet to 7.75 feet, 7.75 feet to 8.00 feet, 8 feet to 9 feet, 9 feet to 10 feet, 10 feet to 11 feet, 11 feet to 12 feet, 12 feet to 13 feet, 13 feet to 14 feet, and 14 feet to 15 feet.

In embodiments, the spacing (CAA*, CAB*, CAC*, CAD*) between each growing assembly (100*, 200*) includes one or more growing assembly spacing ranges (DAF*) selected from the group consisting of 3.00 feet to 3.25 feet, 3.25 feet to 3.50 feet, 3.50 feet to 3.75 feet, 3.75 feet to 4.00 feet, 4.00 feet to 4.25 feet, 4.25 feet to 4.50 feet, 4.50 feet to 4.75 feet, 4.75 feet to 5.00 feet, 5.00 feet to 5.25 feet, 5.25 feet to 5.50 feet, 5.50 feet to 5.75 feet, 5.75 feet to 6.00 feet, 6.00 feet to 6.25 feet, 6.25 feet to 6.50 feet, 6.50 feet to 6.75 feet, 6.75 feet to 7.00 feet, 7.00 feet to 7.25 feet, 7.25 feet to 7.50 feet, 7.50 feet to 7.75 feet, 7.75 feet to 8.00 feet, 8.00 feet to 8.25 feet, 8.25 feet to 8.50 feet, 8.50 feet to 8.75 feet, 8.75 feet to 9.00 feet, 9.00 feet to 9.25 feet, 9.25 feet to 9.50 feet, 9.50 feet to 9.75 feet, 9.75 feet to 10.00 feet, 10 feet to 11 feet, 11 feet to 12 feet, 12 feet to 13 feet, 13 feet to 14 feet, and 14 feet to 15 feet.

In embodiments, the amount of growing assemblies (102*, 207*) per acre include one or more ranges of rows of plants per acre selected from the group consisting of 70 rows of plants per acre to 64 rows of plants per acre, 64 rows of plants per acre to 60 rows of plants per acre, 60 rows of plants per acre to 56 rows of plants per acre, 56 rows of plants per acre to 52 rows of plants per acre, 52 rows of plants per acre to 49 rows of plants per acre, 49 rows of plants per acre to 46 rows of plants per acre, 46 rows of plants per acre to 44 rows of plants per acre, 44 rows of plants per acre to 42 rows of plants per acre, 42 rows of plants per acre to 40 rows of plants per acre, 40 rows of plants per acre to 38 rows of plants per acre, 38 rows of plants per acre to 36 rows of plants per acre, 36 rows of plants per acre to 35 rows of plants per acre, 35 rows of plants per acre to 33 rows of plants per acre, 33 rows of plants per acre to 32 rows of plants per acre, 32 rows of plants per acre to 31 rows of plants per acre, 31 rows of plants per acre to 30 rows of plants per acre, 30 rows of plants per acre to 29 rows of plants per acre, 29 rows of plants per acre to 28 rows of plants per acre, 28 rows of plants per acre to 27 rows of plants per acre, 27 rows of plants per acre to 26 rows of plants per acre, 26 rows of plants per acre to 25 rows of plants per acre, 25 rows of plants per acre to 25 rows of plants per acre, 25 rows of plants per acre to 24 rows of plants per acre, 24 rows of plants per acre to 23 rows of plants per acre, 23 rows of plants per acre to 23 rows of plants per acre, 23 rows of plants per acre to 22 rows of plants per acre, 22 rows of plants per acre to 21 rows of plants per acre, 21 rows of plants per acre to 20 rows of plants per acre, and at most 20 rows of plants per acre. FIG. 1D' shows only 7 rows of plants per acre for simplicity but many more may be used as described and disclosed herein.

FIG. 2'

FIG. 2' depicts one non-limiting embodiment of a farming superstructure system (FSS) including a first vertically stacked system (1500*) including a plurality of vertically stacked growing assemblies (100*, 200*) integrated with a first and second vertical support structure (VSS1*, VSS2*) wherein the first growing assembly (100*) is supported by a first horizontal support structure (SS1*) and a second growing assembly (200*) is supported by a second horizontal support structure (SS2*).

The first vertically stacked system (1500*) shown in FIG. 2' has a base height (H0*) located on a floor or support surface. The first vertically stacked system (1500*) shown in FIG. 2' has a total height (HT*). In embodiments, the total height (HT*) may be dictated by the total height of the first and second vertical support structure (VSS1*, VSS2*). The common reservoir (500*) may be positioned on the base height (H0*) located on a floor or support surface. The common reservoir (500*) has a liquid level (LIQ*) that is located below the reservoir height (H500*). The reservoir height (H500*) is the height of the common reservoir (500*).

The bottom (103*) of the first growing assembly (100*) is located at a first base height (H100A*). The first base height (H100A*) is the vertical location on the first vertically stacked system (1500*) where the first growing assembly (100*) is supported by a first horizontal support structure (SS1*). The first partition height (H100B*) is the vertical location on the first vertically stacked system (1500*) of the partition (104*) of the first growing assembly (100*). The first growing assembly height (H100C*) is the vertical location on the first vertically stacked system (1500*) where the top (102*) of the first growing assembly (100*) is located.

The second base height (H200A*) is the vertical location on the first vertically stacked system (1500*) where the second growing assembly (200*) is supported by a second horizontal support structure (SS2*). The second partition height (H200B*) is the vertical location on the first vertically stacked system (1500*) of the partition (204*) of the second growing assembly (200*). The second growing assembly height (H100C*) is the vertical location on the first vertically stacked system (1500*) where the top (202*) of the second growing assembly (200*) is located.

The first vertically stacked system (1500*) has a width (W1500*). In embodiments, the width (W1500*) is greater than the difference between the first growing assembly height (H100C*) and the first base height (H100A*). In embodiments, the width (W1500*) is greater than the difference between the second growing assembly height (H200C*) and the second base height (H200A*).

FIG. 3'

FIG. 3' depicts one non-limiting embodiment of a plurality of vertically stacked systems (1500*, 1500'*) including a first vertically stacked system (1500*) and a second vertically stacked system (1500'*), the first vertically stacked system (1500*) as depicted in FIG. 2', also both vertically stacked systems (1500*, 1500'*) are contained within an enclosure (ENC*) having an interior (ENC1).

In embodiments, the interior (ENC1*) of the enclosure (ENC*) of the farming superstructure system (FSS) (disclosed in Volume 2) is also the interior (ENC1) of the enclosure (ENC) of the feeding chamber (200) of the Insect Production Superstructure System (IPSS) (disclosed in Volume 1). In embodiments, insects (INS*) live within the interior (ENC1*) of the enclosure (ENC*) of the farming superstructure system (FSS) and the insects (INS*) include one or more selected from the group consisting of Anthocoridae, minute pirate bugs, pirate bugs, flower bugs, the genus Orius, omnivorous bugs, carnivorous bugs, Orthoptera order of insects, grasshoppers, crickets, katydids, weta, lubber, acrida, locusts, mites, spider mites, predatory mites, Neoseiulus Fallacis, genus of mites that are in the Phytoseiidae family, arthropods, beetles, cicadas, beetles, nematodes, mealworms, bats, mammals of the order Chiroptera, yellow mealworm beetles, *Tenebrio Molitor, Tetranychus Urticae*, carnivorous arthropods, omnivorous arthropods, green lacewings, insects in the family Chrysopidae, insects in the order Neuroptera, mantidflies, antlions, *Encarsia Formosa*, whitefly parasites, ladybugs, spiders, orb-weaving spiders, arachnids, members of the spider family Araneidae, praying mantis, arachnids, eight-legged arthropods, and six-legged arthropods. In embodiments, insects (INS*) live within the interior (ENC1*) of the enclosure (ENC*) of the farming superstructure system (FSS) protect the plants (107*, 207*) by feeding on other insect eggs, insect larva, and other insects including living organisms which may or may not contain chitin not only including spider mites, rust mites, *thrips*, jumping plant lice, white fly, knats, gnats, aphids, and insects. In embodiments, the insects feed on *thrips* order Thysanoptera. In embodiments, the insects (INS*) within the farming superstructure system (FSS) feed on *Tetranychus Urticae*. In embodiments, the insects (INS*) within the farming superstructure system (FSS) feed on spider mites. In embodiments, the insects (INS*) within the farming superstructure system (FSS) eat other insects that are found on the *cannabis* plants disclosed herein. In embodiments, the bats eat insects that are found on the *cannabis* plants disclosed herein.

The second vertically stacked system (1500'*) shown in FIG. 3' has a base height (H0*) located on a floor or support surface. The second vertically stacked system (1500'*) shown in FIG. 3' has a total height (HT'*). In embodiments, the total height (HT'*) may be dictated by the total height of the first and second vertical support structure (VSS1'*, VSS2'*). The common reservoir (500'*) may be positioned on the base height (H0*) located on a floor or support surface. The common reservoir (500'*) has a liquid level (LIQ'*) that is located below the reservoir height (H500'*). The reservoir height (H500'*) is the height of the common reservoir (500*).

The bottom (103'*) of the first growing assembly (100'*) is located at a first base height (H100A'*). The first base height (H100A'*) is the vertical location on the second vertically stacked system (1500'*) where the first growing assembly (100'*) is supported by a first horizontal support structure (SS1'*). The first partition height (H100B'*) is the vertical location on the second vertically stacked system (1500'*) of the partition (104'*) of the first growing assembly (100'*). The first growing assembly height (H100C'*) is the vertical location on the second vertically stacked system (1500'*) where the top (102'*) of the first growing assembly (100'*) is located.

The second base height (H200A'*) is the vertical location on the second vertically stacked system (1500'*) where the second growing assembly (200'*) is supported by a second horizontal support structure (SS2'*). The second partition height (H200B'*) is the vertical location on the second vertically stacked system (1500'*) of the partition (204'*) of the second growing assembly (200'*). The second growing assembly height (H100C'*) is the vertical location on the second vertically stacked system (1500'*) where the top (202'*) of the second growing assembly (200'*) is located.

The second vertically stacked system (1500'*) has a width (W1500'*). In embodiments, the width (W1500'*) is greater than the difference between the first growing assembly height (H100C'*) and the first base height (H100A'*). In embodiments, the width (W1500'*) is greater than the difference between the second growing assembly height (H200'*) and the second base height (H200A'*).

A spacing (1500S*) exists between the first vertically stacked system (1500*) and the second vertically stacked system (1500'*). In embodiments, the spacing (1500S*) between the first vertically stacked system (1500*) and second vertically stacked system (1500'*) is less than the width (W1500*, W1500'*) of either of the first vertically stacked system (1500*) and second vertically stacked system (1500'*). In embodiments, the spacing (1500S*) between the first vertically stacked system (1500*) and second vertically stacked system (1500'*) is greater than the width (W1500*, W1500'*) of either of the first vertically stacked system (1500*) and second vertically stacked system (1500'*). In embodiments, the spacing (1500S*) between the first vertically stacked system (1500*) and second vertically stacked system (1500'*) ranges between 1 foot to 2 feet, 2 feet to 3 feet, 3 feet to 4 feet, 4 feet to 5 feet, 5 feet to 6 feet, 6 feet to 7 feet, 7 feet to 8 feet, 8 feet to 9 feet, 9 feet to 10 feet, 10 feet to 11 feet, 11 feet to 12 feet, 12 feet to 13 feet, 13 feet to 14 feet, 14 feet to 15 feet, 15 feet to 16 feet, 16 feet to 17 feet, 17 feet to 18 feet, 18 feet to 19 feet, or 19 feet to 20 feet.

FIG. 3' shows the first vertically stacked system (1500*) and a second vertically stacked system (1500'*) contained within an enclosure (ENC*) having an interior (ENC1*). In embodiments, the enclosure may be an area that is sealed off with an artificial or natural barrier. In embodiments, the enclosure may be a building, or a structure with a roof and walls. In embodiments, the enclosure may be a shipping container conforming to the International Organization for Standardization (ISO) specifications. FIG. 3' shows the enclosure (ENC*) having a first side wall (1W*), second side wall (2W*), top (5W*), and a floor (1FL*). For completeness, FIG. 4A' shows the enclosure (ENC*) of FIG. 3' with a third side wall (3W*) and a fourth side wall (4W*).

In embodiments, the top (5W*), may be comprised of one or more from the group consisting of thatch, overlapping layers, shingles, ceramic tiles, membrane, fabric, plastic, metal, concrete, cement, solar panels, wood, a membrane, tar paper, shale, tile, asphalt, polycarbonate, plastic, cement, and composite materials.

In embodiments, one or more solar panels (SOLAR*, SOLAR'*) may be positioned on top (5W*) of the enclosure (ENC*) may be used to provide electricity for the farming superstructure system (FSS). In embodiments, one or more solar panels (SOLAR-1W*, SOLAR-2W*, SOLAR-3W*, SOLAR-4W*) may be positioned on one or more walls (1W*, 2W*, 3W*, 4W*) of the enclosure (ENC*) may be used to provide electricity for the farming superstructure system (FSS). In embodiments, one or more solar panels (SOLAR-X*) not positioned on the top (5W*) one or more walls (1W*, 2W*, 3W*, 4W*) of the enclosure (ENC*) may be used to provide electricity for the farming superstructure system (FSS).

In embodiments, electricity from at least one of the solar panels (SOLAR*, SOLAR'*, (SOLAR-1W*, SOLAR-2W*, SOLAR-3W*, SOLAR-4W*, SOLAR-X*) may be used to provide electricity for one or more from the group consisting of: any motor within the farming superstructure system (FSS); any controller within the farming superstructure system (FSS); any conveyor within the farming superstructure system (FSS); a first plurality of lights (L1*) in the first growing assembly (100*); a first plurality of light emitting diodes (LED*) in the first growing assembly (100*); a second plurality of lights (L2*) in the second growing assembly (200*); a second plurality of light emitting diodes (LED'*) in the second growing assembly (200*); blue LEDs (BLED*) within the first growing assembly (100*); red LEDS (RLED*) within the first growing assembly (100*); green LEDS (GLED*) within the first growing assembly (100*); blue LEDs (BLED'*) within the second growing assembly (200*); red LEDS (RLED'*) within the second growing assembly (200*); and green LEDS (GLED'*) within the second growing assembly (200*).

In embodiments, the walls (1W*, 2W*, 3W*, 4W*) may be comprised of one or more from the group consisting of metal, concrete, cement, wood, plastic, brick, stone, composite materials, insulation, rockwool, mineral wool, fiberglass, clay, and ceramic. In embodiments, the top (5W*) and walls (1W*, 2W*, 3W*, 4W*) may form one unitary structure such as a dome, semi-spherical shape, semi-cylindrical, or a greenhouse. In embodiments, the top (5W*) and walls (1W*, 2W*, 3W*, 4W*) may be clear, translucent, transparent, or not clear.

In embodiments, a plurality of mirrors (MIRROR1, MIRROR2, MIRROR3, MIRROR4, MIRROR5, MIRROR6) are positioned within the interior (ENCL*) of the enclosure (ENC*). In embodiments, the plurality of mirrors (MIRROR1, MIRROR2, MIRROR3, MIRROR4, MIRROR5, MIRROR6) reflect light onto the plurality of plants (107*, 207*). In embodiments, the plurality of mirrors (MIRROR1, MIRROR2, MIRROR3, MIRROR4, MIRROR5, MIR-

ROR6) reflect light onto the plurality of plants (107*, 207*) wherein the light is provided by the plurality of lights (L1*, L2*). In embodiments, the plurality of mirrors (MIRROR1, MIRROR2, MIRROR3, MIRROR4, MIRROR5, MIRROR6) reflect light onto the plurality of plants (107*, 207*) wherein the light is not provided by the plurality of lights (L1*, L2*). In embodiments, the plurality of mirrors (MIRRORL MIRROR2, MIRROR3, MIRROR4, MIRROR5, MIRROR6) reflect light onto the plurality of plants (107*, 207*) wherein the light includes sunlight that is directed to the interior (ENCL*) of the enclosure (ENC*) by the plurality of mirrors (MIRRORL MIRROR2, MIRROR3, MIRROR4, MIRROR5, MIRROR6).

In embodiments, the plurality of mirrors (MIRROR3, MIRROR4) includes a plurality of mirrors (MIRROR3, MIRROR4) located above the plants to reflect light vertically down onto the plants. In embodiments, the plurality of mirrors (MIRROR1, MIRROR2) includes a plurality of mirrors (MIRROR1, MIRROR2) located on the side of the plants to reflect light down horizontally the plants. In embodiments, the plurality of mirrors (MIRROR5, MIRROR6) includes a plurality of mirrors (MIRROR5, MIRROR6) located below the plants to reflect light vertically up onto the plants.

FIG. 4A'

FIG. 4A' depicts one non-limiting embodiment of FIG. 3' wherein the enclosure (ENC*) is provided with a temperature control unit (TCU*) including an air heat exchanger (HXA*) that is configured to provide a temperature and/or humidity controlled air supply (Q3*) to the interior (ENC1*) of the enclosure (ENC*) which contains a plurality of vertically stacked systems (1500*, 1500'*).

The interior (ENC1*) of the enclosure (ENC*) has an enclosure temperature sensor (QT0*) that is configured to output a signal (QXT0*) to a computer (COMP). The interior (ENC1*) of the enclosure (ENC*) has an enclosure humidity sensor (QH0*) that is configured to output a signal (QXHO*) to a computer (COMP). An air input (Q1*) is configured to permit an air supply (Q3*) to be transferred to the interior (ENC1*) of the enclosure (ENC*) via an air supply entry conduit (Q2*). An optional inlet distributor (Q4*) may be positioned to be in fluid communication with the air supply entry conduit (Q2*) to distribute the air supply (Q3*) within the interior (ENC1*) of enclosure (ENC*). In embodiments, the air heater (HXA*) provides a heated air supply (Q3*) to the interior (ENC1*) of the enclosure (ENC*) via said air supply entry conduit (Q2*) and said air input (Q1*). In embodiments, the air heater (HXA*) provides a cooled air supply (Q3*) to the interior (ENC1*) of the enclosure (ENC*) via said air supply entry conduit (Q2*) and said air input (Q1*).

FIG. 4A' shows a temperature control unit (TCU*) including an air supply fan (Q12*) and air heater (HXA*) integrated with the interior (ENC1*) of the enclosure (ENC*). The air supply fan (Q12*) is connected to the interior (ENC1*) of the enclosure (ENC*) via the air supply entry conduit (Q2*). The air supply fan (Q12*) is equipped with an air supply fan motor (Q13*) and controller (Q14*) is configured to input and output a signal (Q15*) to the computer (COMP). An air heater (HXA*) may be interposed in the air supply entry conduit (Q2*) in between the air supply fan (Q12*) and the enclosure (ENC*). In embodiments, the air heater (HXA*) may be interposed in the air supply entry conduit (Q2*) in between the enclosure (ENC*) and the air supply fan (Q12*) and interposed on the air discharge exit conduit (Q23*).

Water (Q16*) in the form of liquid or vapor may be introduced to the air supply entry conduit (Q2*) via a water transfer conduit (Q17*). A water input valve (Q18*), and a water flow sensor (Q19*) may also be installed on the water transfer conduit (Q17*). The water flow sensor (Q19*) is configured to input a signal (Q20*) to the computer (COMP).

The air supply (Q3*) may be mixed with the water (Q16*) in a water and gas mixing section (Q21*) of the air supply entry conduit (Q2*). FIG. 4A' shows the water and gas mixing section (Q21*) upstream of the air heater (HXA*) but it may alternately also be placed downstream. The air heater (HXA*) may be electric, operated by natural gas, combustion, solar energy, fuel cell, heat pipes, or it may be a heat transfer device that uses a working heat transfer medium, such as steam, or any other heat transfer medium known to persons having an ordinary skill in the art to which it pertains.

FIG. 4A' shows the air heater (HXA*) to have a heat transfer medium input (Q5*) and a heat transfer medium output (Q6*). In embodiments, heat transfer medium input (Q5*) of the air heater (HXA*) is equipped with a heat exchanger heat transfer medium inlet temperature (QT3*) that is configured to input a signal (QXT3*) to the computer (COMP). In embodiments, heat transfer medium output (Q6*) of the air heater (HXA*) is equipped with a heat exchanger heat transfer medium outlet temperature (QT4*) that is configured to input a signal (QXT4*) to the computer (COMP).

A first humidity sensor (Q8*) is positioned on the discharge of the air supply fan (Q12*) upstream of the water and gas mixing section (Q21*). The first humidity sensor (Q8*) is configured to input a signal (Q9*) to the computer (COMP*). A heat exchanger inlet gas temperature sensor (QT1*) may be positioned on the discharge of the air supply fan (Q12*) upstream of the air heater (HXA*). The heat exchanger inlet gas temperature sensor (QT1*) is configured to input a signal (QXT1*) to the computer (COMP).

A second humidity sensor (Q10*) is positioned on the discharge of the air heater (HXA*) upstream of the air input (Q1*) to the interior (ENC1*) of the enclosure (ENC*). The second humidity sensor (Q10*) is configured to input a signal (Q11*) to the computer (COMP*). A heat exchanger outlet gas temperature sensor (QT2*) is positioned on the discharge of the air heater (HXA*) upstream of the air input (Q1*) to the interior (ENC1*) of the enclosure (ENC*). The heat exchanger outlet gas temperature sensor (QT2*) is configured to input a signal (QXT2*) to the computer (COMP).

In embodiments, the air supply fan (Q12*), air heater (HXA*), and air supply (Q2*), permit computer automation while integrated with the heat exchanger inlet gas temperature sensor (QT1*), heat exchanger outlet gas temperature sensor (QT2*), and enclosure temperature sensor (QT0*), to operate under a wide variety of automated temperature operating conditions including varying the temperature range in the interior (ENC1*) of the enclosure (ENC*) from between 30 degrees to 90 degrees Fahrenheit. In embodiments, the interior (ENC1*) of the enclosure (ENC*) may be maintained within a temperature ranging from between 65 degrees Fahrenheit to 85 degrees Fahrenheit. In embodiments, the interior (ENC1*) of the enclosure (ENC*) may be maintained within a temperature ranging from between 60 degrees Fahrenheit to 90 degrees Fahrenheit.

In embodiments, the interior (ENC1*) of the enclosure (ENC*) may be maintained at a pre-determined temperature ranging from between one or more from the group selected from 60 degrees Fahrenheit to 61 degrees Fahrenheit, 61 degrees Fahrenheit to 62 degrees Fahrenheit, 62 degrees Fahrenheit to 63 degrees Fahrenheit, 63 degrees Fahrenheit to 64 degrees Fahrenheit, 64 degrees Fahrenheit to 65 degrees Fahrenheit, 65 degrees Fahrenheit to 66 degrees Fahrenheit, 66 degrees Fahrenheit to 67 degrees Fahrenheit, 67 degrees Fahrenheit to 68 degrees Fahrenheit, 68 degrees Fahrenheit to 69 degrees Fahrenheit, 69 degrees Fahrenheit to 70 degrees Fahrenheit, 70 degrees Fahrenheit to 71 degrees Fahrenheit, 71 degrees Fahrenheit to 72 degrees Fahrenheit, 72 degrees Fahrenheit to 73 degrees Fahrenheit, 73 degrees Fahrenheit to 74 degrees Fahrenheit, 74 degrees Fahrenheit to 75 degrees Fahrenheit, 75 degrees Fahrenheit to 76 degrees Fahrenheit, 76 degrees Fahrenheit to 77 degrees Fahrenheit, 77 degrees Fahrenheit to 78 degrees Fahrenheit, 78 degrees Fahrenheit to 79 degrees Fahrenheit, 79 degrees Fahrenheit to 80 degrees Fahrenheit, 80 degrees Fahrenheit to 81 degrees Fahrenheit, 81 degrees Fahrenheit to 82 degrees Fahrenheit, 82 degrees Fahrenheit to 83 degrees Fahrenheit, 83 degrees Fahrenheit to 84 degrees Fahrenheit, 84 degrees Fahrenheit to 85 degrees Fahrenheit, 85 degrees Fahrenheit to 86 degrees Fahrenheit, 86 degrees Fahrenheit to 87 degrees Fahrenheit, 87 degrees Fahrenheit to 88 degrees Fahrenheit, 88 degrees Fahrenheit to 89 degrees Fahrenheit, 89 degrees Fahrenheit to 90 degrees Fahrenheit, 90 degrees Fahrenheit to 91 degrees Fahrenheit, 91 degrees Fahrenheit to 92 degrees Fahrenheit, 92 degrees Fahrenheit to 93 degrees Fahrenheit, 93 degrees Fahrenheit to 94 degrees Fahrenheit, and 94 degrees Fahrenheit to 95 degrees Fahrenheit.

In embodiments, the air supply fan (Q12*), air heater (HXA*), air supply (Q2*), and water (Q17*) permit the computer automation while integrated with the first humidity sensor (Q8*), second humidity sensor (Q10*), and enclosure humidity sensor (QH0*), to operate under a wide variety of automated operating humidity conditions including varying the humidity range in the growing assembly (100*, 200*) from between 5 percent humidity to 100 percent humidity. In embodiments, it is preferred to operate from between 25 percent humidity to 75 percent humidity. In embodiments, it is preferred to operate from between 40 percent humidity to 60 percent humidity. In embodiments, it is preferred to operate from between 44 percent humidity to 46 percent humidity. In embodiments, it is preferred to operate from between 36 percent humidity to 38 percent humidity, 38 percent humidity to 40 percent humidity, 40 percent humidity to 42 percent humidity, 42 percent humidity to 44 percent humidity, 44 percent humidity to 46 percent humidity, 46 percent humidity to 48 percent humidity, 48 percent humidity to 50 percent humidity, 50 percent humidity to 52 percent humidity, 52 percent humidity to 54 percent humidity, 54 percent humidity to 56 percent humidity, 56 percent humidity to 58 percent humidity, 58 percent humidity to 60 percent humidity, 60 percent humidity to 62 percent humidity, 62 percent humidity to 64 percent humidity, 64 percent humidity to 66 percent humidity, 66 percent humidity to 68 percent humidity, or 68 percent humidity to 70 percent humidity.

In embodiments, the air supply fan (Q12*) accepts an air supply (Q3*) from the interior (ENC1*) of the enclosure (ENC*) via an air discharge exit conduit (Q23*). The air discharge exit conduit (Q23*) is connected at one end to the enclosure (ENC*) via an air output (Q22*) and at another end to the air supply fan (Q12*). An air filter (Q24*) may be installed on the air discharge exit conduit (Q23*) in between the enclosure (ENC*) and the air supply fan (Q12*) to remove particles prior to entering the air supply fan (Q12*) for recycle back to the enclosure (ENC*). In embodiments, the air filter (Q24*) filters out particulates from the interior (ENC1*) of the enclosure (ENC*) and the air supply fan (Q12*) recycles the filtered air back to the interior (ENC1*) of the enclosure (ENC*). The filtered air may be cooled or heated prior to being recycled to the interior (ENC1*) of the enclosure (ENC*).

In embodiments, the air heater (HXA*) adds heat to the interior (ENC1*) of the enclosure (ENC*). In embodiments, the air heater (HXA*) removes heat from the interior (ENC1*) of the enclosure (ENC*) and as a result may condense water from the air supply (Q3*) provided from the from the interior (ENC1*) of the enclosure (ENC*). In embodiments, where the air heater (HXA*) removes heat from the interior (ENC1*) of the enclosure (ENC*) water is collected in the form of condensate (Q25*). In embodiments, the condensate (Q25*) may in turn be provided to the enclosure (ENC*) via an enclosure condensate input (Q26*) and a condensate conduit (Q27*). The condensate (Q25*) provided to the enclosure (ENC*) via an enclosure condensate input (Q26*) may be provided to at least one common reservoir (500*, 500'*) via a common tank condensate input (Q28*). In embodiments, the condensate (Q25*) may contain undesirable compounds (especially viruses and/or bacteria) and in turn may be provided to the input to the first water treatment unit (A1*) as shown in FIG. 10' as a first undesirable compounds-laden condensate (Q29*).

FIG. 4B'

FIG. 4B' depicts one non-limiting embodiment of FIG. 1B' and FIG. 4A' wherein the enclosure (ENC*) is provided with a temperature control unit (TCU*) including an air heat exchanger (HXA*) that is configured to provide a temperature and/or humidity controlled air supply (Q3*) to the interior (ENC1*) of the enclosure (ENC*) which contains a plurality of growing assemblies (100*, 200*).

In embodiments, a fire protection system (FPS*) is contained within the interior (ENC1*) of the enclosure (ENC*). In embodiments, the fire protection system (FPS*) includes a sprinkler system (SS-1*). In embodiments, the sprinkler system (SS-1*) includes a water distribution header (WDH*) connected to a plurality of spray nozzles (SN-1*, SN-2*, SN-3*). A source of pressurized water (WS-1*) is provided to the water distribution header (WDH*). In embodiments, at least a portion of the water distribution header (WDH*) is a pipe that is made of metal or polyvinyl chloride. In embodiments, at least a portion of the water distribution header (WDH*) has a diameter than includes one or more from the group consisting of: 1 inch to 2 inches, 2 inches to 3 inches, 3 inches to 4 inches, 4 inches to 5 inches, 5 inches to 6 inches, 6 inches to 8 inches, and 8 inches to 10 inches.

In embodiments, each of the plurality of spray nozzles (SN-1*, SN-2*, SN-3*) is equipped with an automatic fire sprinkler switch (AFSS-1*, AFSS-2*, AFSS-3*) that permits pressurized water (WS-1*) to pass through the plurality of spray nozzles (SN-1*, SN-2*, SN-3*) when there is a fire detected within the interior (ENC1*) of the enclosure (ENC*). In embodiments, the pressure drop of the pressurized water (WS-1*) that passes through the plurality of spray nozzles (SN-1*, SN-2*, SN-3*) ranges from: 15 PSI to 25 PSI, 25 PSI to 35 PSI, 35 PSI to 45 PSI, 45 PSI to 55 PSI, 55 PSI to 65 PSI, 65 PSI to 75 PSI, 75 PSI to 85 PSI, 85 PSI to 95 PSI, 95 PSI to 100 PSI, 100 PSI to 150 PSI, and 150 PSI to 300 PSI. In embodiments, the fire protection system (FPS*) includes a smoke detector (SD-1*) that is configured to output a signal (SD-1X*) to a computer (COMP) in the event of a fire within the interior (ENC1*) of the enclosure (ENC*).

In embodiments, the fire protection system (FPS*) is provided with a pump (FPS-P*) that is configured to provide a source of pressurized water (WS-1*) is provided to the water distribution header (WDH*). The pump (FPS-P*) is configured to accept and pressurize a source of water (WS-1'*) to form the source of pressurized water (WS-1*) that is provided to the water distribution header (WDH*) and to the plurality of spray nozzles (SN-1*, SN-2*, SN-3*). In embodiments, the pump (FPS-P*) is comprised of one of more from the group consisting of a centrifugal pump or a positive displacement pump. In embodiments, the pump is not needed to provide a source of pressurized water (WS-1*) that is provided to the water distribution header (WDH*) and to the plurality of spray nozzles (SN-1*, SN-2*, SN-3*). In embodiments, a pump discharge pressure sensor (PDPS*) and a pump suction pressure (PSPS*) are equipped to measure the pressure at the pump discharge and pump suction, respectively.

FIG. 5A'

FIG. 5A' depicts one non-limiting embodiment of FIG. 4A' wherein the temperature control unit (TCU*) of FIG. 4A' is contained within the interior (ENC1*) of the enclosure (ENC*) and coupled with a humidity control unit (HCU*), FIG. 5A' shows the temperature control unit (TCU*) of FIG. 4A' but contained within the interior (ENC1*) of the enclosure (ENC*). FIG. 5A' also shows a non-limiting embodiment of a humidity control unit (HCU*) positioned within the interior (ENC1*) of the enclosure (ENC*). A portion of the humidity control unit (HCU*) may be positioned exterior to the enclosure (ENC*) and not positioned within the interior (ENC1*). In embodiments, the humidity control unit (HCU*) may also be considered a temperature control unit (TCU*). In embodiments, the humidity control unit (HCU*) may also be considered a temperature control unit (TCU*) since it may be used to regulate the temperature within the interior (ENC1*) an enclosure (ENC*) wherein a plurality of growing assemblies (100*, 200*) are positioned within the interior (ENC1*) of the enclosure (ENC*).

In embodiments, the humidity control unit (HCU*) may include a compressor (Q30*), a condenser (Q32*), a metering device (Q33*), an evaporator (Q34*), and a fan (Q35*). The fan (Q35*) may be equipped with a motor (Q36*) and a controller (Q37*) that is configured to input or output a signal (Q38*) to a computer (COMP).

The compressor (Q31*) is connected to the condenser (Q32*), the condenser (Q32*) is connected to the metering device (Q33*), the metering device (Q33*) is connected to an evaporator (Q34*), and the evaporator (Q34*) is connected to the compressor (Q31*) to form a closed-loop refrigeration circuit configured to contain a refrigerant (Q31*). The metering device (Q33*) includes one or more from the group consisting of a restriction, orifice, valve, tube, capillary, and capillary tube. The refrigerant (Q31*) is conveyed from the compressor to the condenser, from the condenser to the evaporator through the metering device, and from the evaporator to the compressor. The evaporator (Q34*) is positioned within the interior (ENC1*) of the enclosure (ENC*) and is configured to evaporate refrigerant (Q31*) within the evaporator (Q34*) by removing heat from the interior (ENC1*) of the enclosure (ENC*). In embodiments, the evaporator (Q34*) is contained within the interior (ENC1*) of the enclosure (ENC*). In embodiments, the condenser (Q32*) is not contained within the interior (ENC1*) of the enclosure (ENC*). The fan (Q35*) is configured to blow air from within the interior (ENC1*) of the enclosure (ENC*) over at least a portion of the humidity control unit (HCU*).

The humidity control unit (HCU*) is configured to selectively operate the system in a plurality of modes of operation, the modes of operation including at least:

(1) a first mode of operation in which compression of a refrigerant (Q31*) takes place within the compressor (Q30*), and the refrigerant (Q31*) leaves the compressor (Q30*) as a superheated vapor at a temperature greater than the condensation temperature of the refrigerant (Q31*);

(2) a second mode of operation in which condensation of refrigerant (Q31*) takes place within the condenser (Q32*), heat is rejected and the refrigerant (Q31*) condenses from a superheated vapor into a liquid, and the liquid is cooled to a temperature below the boiling temperature of the refrigerant (Q31*); and (3) a third mode of operation in which evaporation of the refrigerant (Q31*) takes place, and the liquid phase refrigerant (Q31*) boils in the evaporator (Q34*) to form a vapor or a superheated vapor while absorbing heat from the interior (ENC1*) of the enclosure (ENC*).

The evaporator (Q34*) is configured to evaporate the refrigerant (Q31*) to absorb heat from the interior (ENC1*) of an enclosure (ENC*). As a result, the evaporator (Q34*) may condense water from the interior (ENC1*) of the enclosure (ENC*). In embodiments, the water condensed by the evaporator (Q34*) contains bacteria. In embodiments, the evaporator (Q34*) condenses water vapor from the interior (ENC1*) of an enclosure (ENC*) and forms condensate (Q39*). In embodiments, the condensate (Q39*) may contain undesirable compounds (especially viruses and/or bacteria) and in turn may be provided to the input to the first water treatment unit (A1*) as shown in FIG. 10' as a second undesirable compounds-laden condensate (Q40*).

FIG. 5B'

FIG. 5B' depicts one non-limiting embodiment of FIG. 4B' and FIG. 5A' wherein the temperature control unit (TCU*) of FIG. 4B' is contained within the interior (ENC1*) of the enclosure (ENC*) and coupled with a humidity control unit (HCU*).

FIG. 5C'

FIG. 5C' shows one non-limiting embodiment where the compressor (Q30*) within the humidity control unit (HCU*) is that of a thermal compressor (Q30*) that accepts a source of steam. The thermal compressor (Q30*) accepts a steam supply (LDS*) that is provided from FIG. 17F'. Also shown is in the thermal compressor (Q30*) discharging condensate (LJC*) to the condensate tank (LAP*) shown on FIG. 17F'.

FIG. 5D'

FIG. 5D' shows one non-limiting embodiment where the compressor (Q30*) within the humidity control unit (HCU*) is that of a thermal compressor (Q30*) that accepts a source of steam. The thermal compressor (Q30*) accepts a tenth steam supply (LDS*) that is provided from FIG. 17F'. Also shown is in the thermal compressor (Q30*) discharging a tenth condensate (LJC*) to the condensate tank (LAP*) shown on FIG. 17F'.

In embodiments, the thermal compressor (Q30*) includes a generator (Q50*) and an absorber (Q60*). The first steam supply (LDS*), from FIG. 17F', is transferred from the steam distribution header (LCJ*) and into the generator (Q50*) of the thermal compressor (Q30*). In embodiments, a pump (Q45*) connects the generator (Q50*) to the absorber (Q60*). Also, in embodiments, a metering device (Q55*) is positioned in between the absorber (Q60*) to the generator (Q50*). The metering device (Q55*) may include one or more from the group consisting of a restriction, orifice, valve, tube, capillary, and capillary tube.

Vapor-phase refrigerant is transferred from the evaporator (Q34*) to the absorber (Q60*). The refrigerant transferred from the evaporator (Q34*) to the absorber (Q60*) is then absorbed by an absorbent within the absorber (Q60*). In embodiments, the refrigerant includes water or ammonia. In embodiments, the absorbent includes lithium bromine or water.

A mixture of refrigerant and absorbent is transferred from the absorber (Q60*) to the generator (Q50*) via the pump (Q45*). Heat in the form of steam (LDS*) is transferred to the mixture of refrigerant and absorbent within the generator (Q50*) to vaporize the refrigerant. The vapor-phase, or superheated vapor, refrigerant is transferred from the generator (Q50*) to the condenser (Q32*). The absorbent is transferred back to the absorber (Q60*) from the generator (Q50*) through the metering device (Q55*). In embodiments, the absorbent that is transferred through the metering device (Q55*) takes a pressure drop. In embodiments, the generator (Q50*) operates at a pressure that is greater than the pressure within the absorber (Q60*).

In embodiments, the thermal compressor (Q30*) may also be called an absorption chiller. In embodiments, the thermal compressor may have one stage. In embodiments, the thermal compressor may have two stages. In embodiments, electricity is required to power the pump (Q54*). In embodiments, the electricity that is required to power the pump (Q54*) comes from the generator (LFH*) shown in FIG. 17F'.

FIG. 5E'

FIG. 5E' elaborates upon FIG. 5D' and shows one non-limiting embodiment where the compressor (Q30*) within the humidity control unit (HCU*) is that of a thermal compressor (Q30*) that accepts a source of heat, such as flue gas (FG1*).

FIG. 6'

FIG. 6' shows a front view of one embodiment of a plant growing module (PGM*) provided inside of a shipping container conforming to the International Organization for Standardization (ISO) specifications.

FIG. 6' shows a portion of the farming superstructure system (FSS) including a front view of one embodiment of a plant growing module (PGM*) provided inside of a shipping container conforming to the International Organization for Standardization (ISO) specifications.

The front view shows four growing assemblies (100*, 100'*, 200*, 200'*) including two first growing assemblies (100*, 100'*) and two second growing assembly (200*, 200'*) contained within an interior (ENC1*) of an enclosure (ENC*). FIG. 6' shows the two first growing assemblies (100*, 100'*) and two second growing assembly (200*, 200'*) each equipped with drain ports (110*, 110'*) and drain conduits (111*, 111'*) for draining liquid from each growing assembly (100*, 100'*, 200*, 200'*) into a common reservoir (500*) via a common drain conduit (517*) and drain input (518*).

FIG. 6' shows one pump (P1*) pulling liquid from one common reservoir (500*) and transferring a pressurized liquid through a filter (F1A*) into a plurality of liquid supply headers (300*, 300'*) which are in turn then provided to a plurality of first liquid supply conduits (113*, 113'*) and a plurality of second liquid supply conduit (213*, 213'*). Four liquid supply conduits (113*, 113'*, 213*, 213'*) are provided from two liquid supply headers (300*, 300'*) which is provided with pressurized water through one filter (F1A*) by one pump (P1*) pulling liquid from one common reservoir (500*).

The common reservoir (500*) of FIG. 6' is provided with a pressurized liquid (29*) through a pressurized liquid transfer conduit (28*) that enters the common reservoir (500*) via a first water inlet (03*). FIGS. 9' and 10' describe a liquid distribution module (LDM*) that provides the pressurized liquid (29*) and transfers it to the plant growing module (PGM*) via a pressurized liquid transfer conduit (28*).

As depicted in FIG. 6' and FIG. 7', one common reservoir (500*) is provided for a first vertically stacked system (1500*) and a second vertically stacked system (1500'*) that contain a total of two first growing assemblies (100*, 100'*) and two second growing assembly (200*, 200'*).

The enclosure (ENC*) of FIG. 6' is shown to have a first side wall (1W*), second side wall (2W*), top (5W*), and A floor (1FL*). For completeness, the top view of the enclosure (ENC*) of FIG. 6' is shown in FIG. 7' and is shown to have a first side wall (1W*), second side wall (2W*), third side wall (3W*), and fourth side wall (4W*).

FIG. 7'

FIG. 7' shows a top view of one embodiment of a plant growing module (PGM*) provided inside of a shipping container conforming to the International Organization for Standardization (ISO) specifications.

The enclosure (ENC*) of FIG. 7' is shown to have a low voltage shut-off switch (LVV-1*), a humidity control unit (HCU*) (as described in FIG. 5'), and a temperature control unit (TCU*) (as described in FIGS. 4A' & 4B'). FIG. 7' also shows the first vertically stacked system (1500*) and second vertically stacked system (1500'*) with one common reservoir (500*). FIG. 7' also shows a third vertically stacked system (1500"*) and a fourth vertically stacked system (1500'''*) each equipped with their own source of pressurized liquid (29C*, 29D*) provided by a plurality of pressurized liquid transfer conduits (28C*, 28D*) as described in detail in FIGS. 9' and 10'.

FIG. 8'

FIG. 8' shows a first side view of one embodiment of a plant growing module (PGM*). The enclosure (ENC*) of FIG. 8' is shown to have a humidity control unit (HCU*) (as described in FIG. 5'), and a temperature control unit (TCU*) (as described in FIGS. 4A'& 4B'). FIG. 8' shows a first vertically stacked system (1500*) on the left-hand-side and a second vertically stacked system (1500'*) on the right-hand-side.

The first vertically stacked system (1500*) is shown to have a second growing assembly (200*) located above a first growing assembly (100*). The second growing assembly (200*) has a drain port (210*) and a drain conduit (211*) that directly drains into a common reservoir (500*) located below both growing assemblies (100*, 200*). The drain conduit (211*) from the second growing assembly (200*) is secured to the second vertical support structure (VSS2*) via a support connection (211X*). In embodiments, the drain conduit (211*) from the second growing assembly (200*) may be secured to the first vertical support structure (VSS1*), or alternately to the first horizontal support structure (SS1*), or second horizontal support structure (SS2*)

The first growing assembly (100*) has a drain port (110*) and a drain conduit (111*) that directly drains into a common reservoir (500*) located below both growing assemblies (100*, 200*). The drain conduit (111*) from the first growing assembly (200*) is secured to the second vertical support structure (VSS2*) via a support connection (111X*). In embodiments, the drain conduit (111*) from the first growing assembly (100*) may be secured to the first vertical support structure (VSS1*), or alternately to the first horizontal support structure (SS1*).

The second vertically stacked system (1500'*) is shown to have a second growing assembly (200'*) located above a first growing assembly (100'*). The second growing assembly (200'*) is configured to receive liquid from the pump (P1*) via a second liquid supply conduit (213'*) and a liquid input (214'*). The second liquid supply conduit (213'*) for the second growing assembly (200'*) is secured to the second vertical support structure (VSS2'*) via a support connection (213X*). In embodiments, the second liquid supply conduit (213'*) for the second growing assembly (200'*) may be secured to the first vertical support structure (VSS1'*), or alternately to the first horizontal support structure (SS1'*), or second horizontal support structure (SS2'*).

The first growing assembly (100'*) is configured to receive liquid from the pump (P1*) via a first liquid supply conduit (113'*) and a liquid input (114'*). The first liquid supply conduit (113'*) for the first growing assembly (100'*) is secured to the second vertical support structure (VSS2'*) via a support connection (113X*). In embodiments, the first liquid supply conduit (113'*) for the first growing assembly (100'*) may be secured to the first vertical support structure (VSS1'*), or alternately to the first horizontal support structure (SS1'*). In embodiments, the spacing (1500S*) between the vertically stacked systems (1500*, 1500'*) in FIG. 8' ranges from 1 foot to 1.5 feet, 1.5 feet to 2 feet, 2 feet to 3 feet, 3 feet to 4 feet, 4 feet to 5 feet, 5 feet to 6 feet, 6 feet to 7 feet, 7 feet to 8 feet, 8 feet to 10 feet, 10 feet to 12 feet, 12 feet to 15 feet, 15 feet to 20 feet In embodiments, the spacing (1500S*) between the vertically stacked systems (1500*, 1500'*) in FIG. 8' ranges from 2.5 feet to 4.5 feet. FIG. 9'

FIG. 9' shows a front view of one embodiment of a liquid distribution module (LDM*) provided inside of a shipping container conforming to the International Organization for Standardization (ISO) specifications and that is configured to provide a source of liquid to a plurality of plant growing modules (PGM*).

FIG. 9' shows one non-limiting embodiment of a liquid distribution module (LDM*) to provide a source of liquid to a plurality of plant growing modules (PGM*). The liquid distribution module (LDM*) of FIGS. 9' and 10' include a first water treatment unit (A1*), a second water treatment unit (A2*), and a third water treatment unit (A3*), that provide a third contaminant depleted water (12*) to the interior (19*) of a solution tank (18*).

The solution tank (18*) mixes a water supply (01*) with macro-nutrients (601*), micro-nutrients (701*), and/or a pH adjustment solution (801*) to form a mixed solution prior to pumping the mixed solution to at least one common reservoir (500*) of at least one plant growing modules (PGM*). FIG. 9' depicts the first water treatment unit (A1*) to include a cation, a second water treatment unit (A2*) to include an anion, and a third water treatment unit (A3*) to include a membrane.

A first water pressure sensor (13*) is positioned on the water input conduit (14*) that is introduced to the first input (04*) to the first water treatment unit (A1*). In embodiments, a filter (y1*), activated carbon (y2*), and adsorbent (y3*), are positioned on the water input conduit (14*) prior to introducing the water supply (01*) to the first water treatment unit (A1*). The water supply (01*) may be considered a contaminant-laden water (15*) that includes positively charged ions, negatively charged ions, and undesirable compounds. A first contaminant depleted water (06*) is discharged by the first water treatment unit (A1*) by a first output (05*). The first contaminant depleted water (06*) may be a positively charged ion depleted water (06A*). The first contaminant depleted water (06*) is then transferred to the second water treatment unit (A2*) via a second input (07*). A second contaminant depleted water (09*) is discharged by the second water treatment unit (A2*) by a second output (08*). The second contaminant depleted water (09*) may be a negatively charged ion depleted water (09A*). The second contaminant depleted water (09*) is then transferred to the third water treatment unit (A3*) via a third input (10*). A third contaminant depleted water (12*) is discharged by the third water treatment unit (A3*) by a third output (11*). The third contaminant depleted water (12*) may be an undesirable compounds depleted water (12A*). The third contaminant depleted water (12*) is then transferred to the interior (19*) of a solution tank (18*) via a water supply conduit (21*) and water input (20*).

Within the interior (19*) of the solution tank (18*), the third contaminant depleted water (12*) may be mixed with macro-nutrients (601*) from a macro-nutrient supply tank (600*), micro-nutrients (701*) from a micro-nutrient supply tank (700*), and/or a pH adjustment solution (801*) from a micro-nutrient supply tank (700*). In embodiments, a cation (y4*), an anion (y5*), and a polishing unit (y6*), are positioned on the water supply conduit (21*) in between the third water treatment unit (A3*) and the water input (20*) of the solution tank (18*). The polishing unit (y6*) may be any type of conceivable device to improve the water quality such as an ultraviolet unit, ozone unit, microwave unit, or the like.

In embodiments, water supply valve (16*) is positioned on the water supply conduit (21*) in between the third water treatment unit (A3*) and the water input (20*) of the solution tank (18*). The water supply valve (16*) is equipped with a controller (17*) that inputs or outputs a signal from a computer (COMP). In embodiments, the solution tank (18*) is equipped with a high-level sensor (25*) and a low-level sensor (26*). The high-level sensor (25*) is used for detecting a high level and the low-level sensor (26*) is used for detecting a low level. The high-level sensor (25*) is configured to output a signal to the computer (COMP) when the high-level sensor (25*) is triggered by a high level of liquid within the solution tank (18*). The low-level sensor (26*) is configured to output a signal to the computer (COMP) when the low-level sensor (26*) is triggered by a low level of liquid within the solution tank (18*). In embodiments, when the low-level sensor (26*) sends a signal to the computer (COMP), the water supply valve (16*) on the water supply conduit (21*) is opened and introduces water into the solution tank (18*) until the high-level sensor (25*) is triggered thus sending a signal to the computer (COMP) to close the water supply valve (16*). This level control loop including the high-level sensor (25*) for detecting a high level and a low-level sensor (26*) for detecting a lower level may be coupled to the operation of the water supply valve (16*) for introducing a water supply (01*) through a first water treatment unit (A1*), a second water treatment unit (A2*), and a third water treatment unit (A3*), to provide a third contaminant depleted water (12*) to the interior (19*) of a solution tank (18*). The liquid distribution module (LDM*) is equipped with a low voltage shut-off switch (LVV-2*).

The interior (19*) of the solution tank (18*) is equipped with an oxygen emitter (35*) for oxygenating the water within. The oxygen emitter (35*) is connected to the interior (19*) of the solution tank (18*) via an oxygen emitter connection (36*) which protrudes the solution tank (18*). The solution tank (18*) may be placed on a load cell (40*) for measuring the mass of the tank. The solution tank (18*) may be equipped with a mixer (38*) for mixing water with macro-nutrients (601*), micro-nutrients (701*), and/or a pH adjustment solution (801*). The mixer (38*) may be of an auger or blade type that is equipped with a motor (39*).

The solution tank (18*) has a water output (22*) that is connected to a water discharge conduit (23*). The water discharge conduit (23*) is connected at one end to the water output (22*) of the solution tank (18*) and at another end to a water supply pump (24*). The water supply pump (24*) provides a source of pressurized liquid (29*) via a pressurized liquid transfer conduit (28*).

A second water pressure sensor (27*) is positioned on the pressurized liquid transfer conduit (28*). A flow sensor (30*) and a water quality sensor (33*) may be positioned on the pressurized liquid transfer conduit (28*). The water quality sensor (33*) can measure electrical conductivity or resistivity. The pressurized liquid transfer conduit (28*) can be split into a plurality of streams for providing to a plurality of plant growing modules (PGM*) having a plurality of common reservoirs (500*, 500'*, 500"*, 500'''*).

The pressurized liquid transfer conduit (28*) can be split into a plurality of streams including a first pressurized liquid transfer conduit (28A*) for sending to a common tank (500*) for the first vertically stacked system (1500*) and second vertically stacked system (1500'*) of FIG. 6', a second pressurized liquid transfer conduit (28B*) as a back-up water source to the common tank (500*) of FIG. 6', a third pressurized liquid transfer conduit (28C*) for the common tank (500"*) for the third vertically stacked system (1500"*) of FIG. 6', and a fourth pressurized liquid transfer conduit (28D*) for the common tank (500'''*) for the fourth vertically stacked system (1500'''*) of FIG. 6'.

FIG. 10'

FIG. 10' shows a top view of one embodiment of a liquid distribution module (LDM*) provided inside of a shipping container conforming to the International Organization for Standardization (ISO) specifications and that is configured to provide a source of liquid to a plurality of plant growing modules (PGM*).

FIG. 11'

FIG. 11' shows a first side view of one embodiment of a liquid distribution module (LDM*).

FIG. 12'

FIG. 12' shows one non-limiting embodiment of a fabric (104*) used in a growing assembly (100*), the fabric (104*) having a multi-point temperature sensor (MPT100*) connected thereto for measuring temperatures at various lengths along the sensor's length.

FIGS. 12' and 13' disclose a fabric (104*) that includes a multi-point temperature sensor (MPT100*). The fabric (104*) may be used in each of the growing assemblies (100*, 200*). The fabric has a width (104W*) and a length (104L*). The multi-point temperature sensor (MPT100*) is connected to the fabric (104*) and is configured to measure the temperature of the fabric (104*) along several points along the width (104W*).

FIG. 12' shows the multi-point temperature sensor (MPT100*) having 8 temperature sensor elements to measure the temperature across a first distance (104W1*), second distance (104W2*), third distance (104W*), fourth distance (104W4*), fifth distance (104W5*), sixth distance (104W6*), seventh distance (104W7*), and eighth distance (104W8*). In embodiments, each of the 8 temperature sensor elements is configured to input a signal to the computer (COMP*). The temperature element at the first distance (104W1*) sends a first signal (XMPT1*) to a computer (COMP). The temperature element at the second distance (104W2*) sends a second signal (XMPT2*) to a computer (COMP). The temperature element at the third distance (104W*) sends a third signal (XMPT3*) to a computer (COMP). The temperature element at the fourth distance (104W4*) sends a fourth signal (XMPT4*) to a computer (COMP). The temperature element at the fifth distance (104W5*) sends a fifth signal (XMPT5*) to a computer (COMP). The temperature element at the sixth distance (104W6*) sends a sixth signal (XMPT6*) to a computer (COMP). The temperature element at the seventh distance (104W7*) sends a seventh signal (XMPT7*) to a computer (COMP). The temperature element at the eighth distance (104W8*) sends an eighth signal (XMPT8*) to a computer (COMP). An average temperature of the fabric (104*) may be obtained by averaging at least two of the signals from the multi-point temperature sensor (MPT100*).

Each of the distances (104W1*, 104W2*, 104W3*, 104W4*, 104W5*, 104W6*, 104W7*, 104W8*) is measured relative to the base width (104W0*) of the fabric (104*). In embodiments, the fabric (104*) is comprised of one or more from the group consisting of plastic, polyethylene, high-density polyethylene (HDPE), low-density polyethylene (LDPE), polyethylene terephthalate (PET), polyacrylonitrile, and polypropylene.

In embodiments, the fabric (104*) is configured to have a wicking height constant characterized by a wicking height range from 0.4 inches to 1.9 inches. In embodiments, the fabric (104*) is configured to have a wicking height constant characterized by a wicking height range from 0.40 inches to 0.45 inches, 0.45 inches to 0.50 inches, 0.50 inches to 0.55 inches, 0.55 inches to 0.60 inches, 0.60 inches to 0.65 inches, 0.65 inches to 0.70 inches, 0.70 inches to 0.75 inches, 0.75 inches to 0.80 inches, 0.80 inches to 0.85 inches, 0.85 inches to 0.90 inches, 0.90 inches to 0.95 inches, 0.95 inches to 1.00 inches, 1.00 inches to 1.05 inches, 1.05 inches to 1.10 inches, 1.10 inches to 1.15 inches, 1.15 inches to 1.20 inches, 1.20 inches to 1.25 inches, 1.25 inches to 1.30 inches, 1.30 inches to 1.35 inches, 1.35 inches to 1.40 inches, 1.40 inches to 1.45 inches, 1.45 inches to 1.50 inches, 1.50 inches to 1.55 inches, 1.55 inches to 1.60 inches, 1.60 inches to 1.65 inches, 1.65 inches to 1.70 inches, 1.70 inches to 1.75 inches, 1.75 inches to 1.80 inches, 1.80 inches to 1.85 inches, or 1.85 inches to 1.90 inches.

The wicking height constant is a measurement of an ability of the fabric (104) to absorb moisture. In embodiments, the fabric (104) is configured to have an absorbance constant characterized by an absorbance range from 0.001 $lb/in^2$ to 0.005 $lb/in^2$. In embodiments, the fabric (104) is configured to have an absorbance constant characterized by an absorbance range from 0.0010 $lb/in^2$ to 0.0015 $lb/in^2$, 0.0015 $lb/in^2$ to 0.0020 $lb/in^2$, 0.0020 $lb/in^2$ to 0.0025 $lb/in^2$, 0.0025 $lb/in^2$ to 0.0030 $lb/in^2$, 0.0030 $lb/in^2$ to 0.0035 $lb/in^2$, 0.0035 $lb/in^2$ to 0.0040 $lb/in^2$, 0.0040 $lb/in^2$ to 0.0045 $lb/in^2$, or 0.0045 $lb/in^2$ to 0.0050 $lb/in^2$, or 0.0050 $lb/in^2$.

In embodiments, the absorbance constant is a measurement of moisture the fabric retains. In embodiments, the moisture that the fabric (104*) retains may be provided by a liquid, mist, spray, water, mixture of water with macro-nutrients, micro-nutrients, pH adjustment solution, carbohydrates, enzymes, vitamins, hormones.

FIG. 13'

FIG. 13' shows another one non-limiting embodiment of a fabric (104*) used in a growing assembly (100*).

FIG. 14'

FIG. 14' depicts a computer (COMP) that is configured to input and/or output signals listed in FIGS. 1-17K'. In embodiments, the computer (COMP) for the Farming Superstructure System (FSS) (disclosed in Volume 2) is the same computer (COMP) used in the Insect Production Superstructure System (IPSS) (disclosed in Volume 1). In embodiments, the computer (COMP) for the Farming Superstructure System (FSS) (disclosed in Volume 2) is not the same computer (COMP) used in the Insect Production Superstructure System (IPSS) (disclosed in Volume 1).

FIG. 15'

FIG. 15' shows a trimmer (TR*) that is configured to trim at least a portion of the *cannabis* (107*, 207*) that was growing in each growing assembly (100*, 200*).

Once the *cannabis* (107*, 207*) is harvested from each growing assembly (100*, 200*), the *cannabis* (107*, 207*) may be trimmed by use of a trimmer (TR*). In embodiments, trimming the *cannabis* (107*, 207*) is necessary to obtain a final product for medicinal or recreational use. Trimming the *cannabis* (107*, 207*) may be done for several reasons including improving appearance, taste, and tetrahydrocannabinol (THC) concentration.

*Cannabis* (107*, 207*) consists of the leaves, seeds, stems, roots, or any reproductive structures. In embodiments, the reproductive structures may be flower. In embodiments, a flower may be a reproductive structure. In embodiments, the reproductive structures may be buds. In embodiments, a bud may be a reproductive structure. In embodiments, trimming removes at least a portion of the leaves and stems from the reproductive structures. In embodiments, *cannabis* (107*, 207*) is harvested from each growing assembly (100*, 200*) by severing the plants with a cutting tool. In embodiments, the roots of the *cannabis* (107*, 207*) are not introduced to the trimmer (TR*). In embodiments, *cannabis* (107*, 207*) comprising leaves, seeds, stems, and reproductive structures (buds) are introduced to the trimmer (TR*). In embodiments, *cannabis* (107*, 207*) comprising leaves, seeds, stems, roots, and reproductive structures (buds) are introduced to the trimmer (TR*).

In embodiments, the trimmer (TR*) separates the leaves and/or stems from the buds. In embodiments, the trimmer (TR*) separates the buds from the leaves and stems. In embodiments, the trimmer (TR*) separates the buds from the leaves and stems by applying using a rotational motion provided by a motor (MT1*). In embodiments, the trimmer (TR*) imparts a rotational motion upon the *cannabis* (107*, 207*). FIG. 15' displays the trimmer (TR*) accepting a source of *cannabis* (107*, 207*) and trims leaves and/or stems from the reproductive structures (buds) to produce trimmed *cannabis* (TR1*) and trimmings (TR2*). In embodiment, the trimmer (TR*) rotates at a revolutions per minute (rpm) including one or more selected from the group consisting of 30 rpm to 35 rpm, 35 rpm to 40 rpm, 40 rpm to 45 rpm, 45 rpm to 50 rpm, 50 rpm to 55 rpm, 55 rpm to 60 rpm, 60 rpm to 65 rpm, 65 rpm to 70 rpm, 70 rpm to 75 rpm, 75 rpm to 80 rpm, 80 rpm to 85 rpm, 85 rpm to 90 rpm, 90 rpm to 95 rpm, 95 rpm to 100 rpm, 100 rpm to 105 rpm, 105 rpm to 110 rpm, 110 rpm to 115 rpm, 115 rpm to 120 rpm, 120 rpm to 125 rpm, 125 rpm to 130 rpm, 130 rpm to 135 rpm, 135 rpm to 140 rpm, 140 rpm to 145 rpm, 145 rpm to 150 rpm, 150 rpm to 155 rpm, 155 rpm to 160 rpm, 160 rpm to 165 rpm, 165 rpm to 170 rpm, 170 rpm to 175 rpm, 175 rpm to 180 rpm, 180 rpm to 185 rpm, 185 rpm to 190 rpm, 190 rpm to 195 rpm, 195 rpm to 200 rpm, 200 rpm to 205 rpm, 205 rpm to 210 rpm, 210 rpm to 215 rpm, 215 rpm to 220 rpm, and 220 rpm to 225 rpm.

In embodiments, the trimmer (TR*) moves the *cannabis* (107*, 207*) from one location to the another. In embodiments, a rotational motion *cannabis* (107*, 207*) passes the *cannabis* (107*, 207*) across a blade (CT2*), the blade is configured to separate the leaves or stems from the buds, to provide trimmed *cannabis* that is depleted of leaves or stems. In embodiments, the trimmer (TR*) moves the *cannabis* (107*, 207*) across a blade (CT2*), the blade is configured to separate the leaves or stems from the buds, to provide trimmed *cannabis* that is depleted of leaves or stems.

FIG. 16'

FIG. 16' shows a grinder (GR*) that is configured to grind at least a portion of the *cannabis* (107*, 207*) that was growing in each growing assembly (100*, 200*). FIG. 16' also shows a grinder (GR) that is configured to grind at least a portion of the trimmed *cannabis* (TR1*) that was trimmed by the trimmer (TR*) as shown in FIG. 15'.

A grinder (GR*) generates a ground *cannabis* (GR1*). The grinder may be used to grind (i) a portion of the *cannabis* (107*, 207*) harvested from each growing assembly (100*, 200*) or (ii) a portion of the trimmed *cannabis* (TR1*) that is trimmed by the trimmer (TR*) to produce ground *cannabis* (GR1*). In embodiments, grinding of the *cannabis* is required for creating food products including a multifunctional composition.

A grinder (GR*) generates a ground *cannabis* (GR1*) to a size ranging from 20 microns to 40 microns, 40 microns to 60 microns, 60 microns to 80 microns, 80 microns to 100 microns, 100 microns to 150 microns, 150 microns to 200 microns, 200 microns to 250 microns, 250 microns to 300 microns, 300 microns to 350 microns, 350 microns to 400 microns, 400 microns to 450 microns, 450 microns to 500 microns, 500 microns to 600 microns, 600 microns to 700 microns, 700 microns to 800 microns, 800 microns to 900 microns, 900 microns to 1000 microns, 1000 microns to 1250 microns, 1250 microns to 1500 microns, 1500 microns to 1750 microns, 1750 microns to 2000 microns, 2000 microns to 2250 microns, 2250 microns to 2500 microns, 2500 microns to 2750 microns, 2750 microns to 3000 microns, 3000 microns to 3500 microns, 3500 microns to 4000 microns, 4000 microns to 4500 microns, 4500 microns to 5000 microns, 5000 microns to 5500 microns, 5500 microns to 6000 microns, 6000 microns to 6500 microns, 6500 microns to 7000 microns, 7000 microns to 7500 microns, 7500 microns to 8000 microns, 8000 microns to 8500 microns, 8500 microns to 9000 microns, 9000 microns to 9500 microns, 9500 microns to 10000 microns, 10000 microns to 15000 microns, 15000 microns to 25000 microns, or 25000 microns to 35000 microns.

FIG. 17'

FIG. 17' shows a heater (HTR1*) that is configured to heat at least a portion of *Cannabis* plants (107*, 207*) that was growing in each growing assembly (100*, 200*). In embodiments, heating the *cannabis* is required for creating food products including a multifunctional composition.

FIG. 17' shows a heating unit (HTR1*) that is configured to heat at least a portion of *Cannabis* plants (107*, 207*) that was growing in each growing assembly (100*, 200*). FIG. 17' shows a heater (HTR1*) that is configured to heat at least a portion of the *cannabis* (107*, 207*) that was growing in each growing assembly (100*, 200*). FIG. 17' also shows a heater (HTR1*) that is configured to heat at least a portion of the trimmed *cannabis* (TR1*) that was trimmed by the trimmer (TR*) as shown in FIG. 15'. FIG. 17' also shows a heater (HTR1*) that is configured to heat at least a portion of the ground cannabis (GR1*) that was ground by the grinder (GR*) as shown in FIG. 16'. The heater (HTR1*) may be used to heat (i) a portion of the cannabis (107*, 207*) harvested from each growing assembly (100*, 200*), (ii) a portion of the trimmed cannabis (TR1*) that is trimmed by the trimmer (TR*), or (ii) a portion of the ground cannabis (GR1*) that is ground by the cannabis (GR1*).

The heater (HTR1*) generates a heated cannabis (HT1*). The heater (HTR1*) is configured to heat the cannabis (107*, 207*). In embodiments, the heater (HTR1*) is configured to heat the cannabis (107*, 207*) as the cannabis (107*, 207*) passes through the heater (HTR1*) via a conveyor (CVR1*).

In embodiments, heating the cannabis (107*, 207*) removes carbon dioxide (CO2R*) from the cannabis (107*, 207*) to form a carbon dioxide depleted cannabis (CO2-1*). In embodiments, the carbon dioxide depleted cannabis (CO2-1*) is synonymous with the heated cannabis (HT1*).

In embodiments, heating the cannabis (107*, 207*) decarboxylates the cannabis (107*, 207*) to produce a decarboxylated cannabis (DCX*). In embodiments, heating the cannabis (107*, 207*) decarboxylates the tetrahydrocannabinolic acid (THCA) within the cannabis (107*, 207*) to form active tetrahydrocannabinol. In embodiments, decarboxylation is a chemical reaction that removes a carboxyl group and releases carbon dioxide (CO2R*). In embodiments, heating the cannabis (107*, 207*) removes carbon dioxide form the cannabis (107*, 207*) to form a carbon dioxide depleted cannabis (CO2-1*).

The heater (HTR1*) is equipped with a heater temperature sensor (HTR1T*) that sends a signal (HTR1X*) to the computer (COMP). In embodiments, the heater (HTR1*) is operated within a temperature ranging from 185 degrees F. to 280 degrees F. In embodiments, the heater (HTR1*) is operated within a temperature ranging from 205 degrees F. to 250 degrees F. In embodiments, the heater (HTR1*) produces a heated cannabis (HT1*) that has a temperature ranging from 185 degrees F. to 280 degrees F. In embodiments, the heater (HTR1*) produces a heated cannabis (HT1*) that has a temperature ranging from 205 degrees F. to 250 degrees F.

In embodiments, the heater (HTR1*) is operated within a temperature ranging from 175 degrees Fahrenheit to 200 degrees Fahrenheit, 200 degrees Fahrenheit to 225 degrees Fahrenheit, 225 degrees Fahrenheit to 250 degrees Fahrenheit, 250 degrees Fahrenheit to 275 degrees Fahrenheit, 275 degrees Fahrenheit to 300 degrees Fahrenheit, 300 degrees Fahrenheit to 325 degrees Fahrenheit, 325 degrees Fahrenheit to 350 degrees Fahrenheit, 350 degrees Fahrenheit to 375 degrees Fahrenheit, 375 degrees Fahrenheit to 400 degrees Fahrenheit, or 400 degrees Fahrenheit to 425 degrees Fahrenheit.

In embodiments, a vacuum (VAC*) is pulled on cannabis (107*, 207*) while the heater (HTR1*) is heating the cannabis (107*, 207*) to aide in carbon dioxide removal. In embodiments, a vacuum (VAC*) is pulled on the cannabis (107*, 207*) while the heater (HTR1*) is heating the cannabis (107*, 207*) to a pressure that ranges from 0.5 inches of water to 30 inches of water. In embodiments, a vacuum (VAC*) is pulled on the cannabis (107*, 207*) while the heater (HTR1*) is heating the cannabis (107*, 207*) to a pressure that ranges from 5 inches of water to 90 inches of water. In embodiments, a vacuum (VAC*) is pulled on the cannabis (107*, 207*) while the heater (HTR1*) is heating the cannabis (107*, 207*) to a pressure that ranges from 2 pounds per square inch absolute to 14.69 pounds per square inch absolute. In embodiments, the cannabis (107*, 207*) is heated by the heater (HTR1*) for a duration of 45 minutes to 2 hours. In embodiments, the cannabis (107*, 207*) is heated by the heater (HTR1*) for a duration of 1 hour to 3 hours. In embodiments, the cannabis (107*, 207*) is heated by the heater (HTR1*) for a duration of 2 hour to 24 hours.

FIG. 17A'

FIG. 17A' shows one non-limiting embodiment of a volatiles extraction system (VES*) that is configured to extract volatiles from cannabis (107*, 207*) with a first solvent (SOLV1*). The volatiles extraction system (VES*) is configured to separate volatiles (VOLT*) from cannabis (107*, 207*). The volatiles extraction system (VES*) is configured to accept cannabis (107*, 207*), or heated cannabis (HT1*), ground cannabis (GR1*), trimmed cannabis (TR1*), and/or combinations thereof. In embodiments, the cannabis (107*, 207*), heated cannabis (HT1*), ground cannabis (GR1*), and/or trimmed cannabis (TR1*) may be weighed with a mass sensor (MS-VES*) prior to being introduced to the volatiles extraction system (VES*).

The volatiles (VOLT*) include one or more from the group consisting of oil, wax, terpenes. The volatiles (VOLT*) include cannabinoids. The terpenes include one or more from the group consisting of limonene, humulene, pinene, linalool, caryophyllene, mycrene, eucalyptol, nerolidol, bisablol, and phytol. In embodiments, the terpenes include at least one organic carbon containing chemical compound. In embodiments, the terpenes include one or more from the group consisting of limonene, humulene, pinene, linalool, caryophyllene, mycrene, eucalyptol, nerolidol, bisablol, and phytol. In embodiments, limonene includes 1-Methyl-4-(1-methylethenyl)-cyclohexene. In embodiments, humulene includes 2,6,6,9-Tetramethyl-1,4-8-cycloundecatriene. In embodiments, pinene includes (1S, 5S)-2,6,6-trimethylbicyclo[3.1.1]hept-2-ene. In embodiments, linalool includes 3,7-Dimethylocta-1,6-dien-3-ol. In embodiments, caryophyllene includes (1R,4E,9S)-4,11,11-Trimethyl-8-methylidenebicyclo[7.2.0]undec-4-ene. In embodiments, mycrene includes 7-Methyl-3-methylene-1,6-octadiene. In embodiments, eucalyptol includes 1,3,3-Trimethyl-2-oxabicyclo[2,2,2]octane. In embodiments, nerolidol includes 3,7,11-Trimethyl-1,6,10-dodecatrien-3-ol. In embodiments, bisablol includes 6-methyl-2-(4-methylcyclohex-3-en-1-yl)hept-5-en-2-ol. In embodiments, phytol includes (2E,7R,11R)-3,7,11,15-tetramethyl-2-hexadecen-1-ol.

The volatiles extraction system (VES*) extracts volatiles (VOLT*) from cannabis with use of a first solvent (SOLV1*). The first solvent (SOLV1*) includes one or more from the group consisting of acetone, alcohol, oil, butane, butter, carbon dioxide, coconut oil, ethanol, gas, gaseous carbon dioxide, hexane, isobutane, isopropanol, liquid carbon dioxide, liquid, naphtha, olive oil, pentane, propane, R134 refrigerant gas, subcritical carbon dioxide, supercritical carbon dioxide, and vapor.

The volatiles extraction system (VES*) has an interior (VESI*) that is configured to mix cannabis (107*, 207*), heated cannabis (HT1*), ground cannabis (GR1*), and/or trimmed cannabis (TR1*) with a first solvent (SOLV1*). The volatiles extraction system (VES*) is configured to accept a first solvent (SOLV1*). The first solvent (SOLV1*) is configured to contact the cannabis (107*, 207*), heated cannabis (HT1*), ground cannabis (GR1*), and/or trimmed cannabis (TR1*) within the interior (VESI*) of the volatiles extraction system (VES*).

An output of the volatiles extraction system (VES*) is a first solvent and volatiles mixture (FSVM*). The first solvent and volatiles mixture (FSVM*) is at least a mixture of volatiles (VOLT*) and the first solvent (SOLV1*). In embodiments, the first solvent and volatiles mixture (FSVM*) is a mixture of oil, wax, terpenes and first solvent (SOLV1*). In embodiments, the oil contains cannabinoids. In embodiments, the first solvent and volatiles mixture (FSVM*) is a mixture of oil, wax, and first solvent (SOLV1*). In embodiments, the first solvent and volatiles mixture (FSVM*) is a mixture of oil and first solvent (SOLV1*). The first solvent and volatiles mixture (FSVM*) is transferred from the volatiles extraction system (VES*) to the first solvent separation system (SSS*).

The first solvent separation system (SSS*) is configured to separate the volatiles (VOLT*) from the first solvent and volatiles mixture (FSVM*). The first solvent separation system (SSS*) has an interior (SSSI*). The first solvent and volatiles mixture (FSVM*) is transferred from the interior (VESI*) of the volatiles extraction system (VES*) to the interior (SSSI*) of the first solvent separation system (SSS*).

In embodiments, the interior (VESI*) of the volatiles extraction system (VES*) is in thermal contact with a first volatiles extraction heat exchanger (VS-HX1*). The first volatiles extraction heat exchanger (VS-HX1*) is configured to add and/or remove heat from the interior (VESI*) of the volatiles extraction system (VES*). The first volatiles extraction heat exchanger (VS-HX1*) is configured to add and/or remove heat from the *cannabis* within the interior (VESI*) of the volatiles extraction system (VES*). the first volatiles extraction heat exchanger (VS-HX1*) is configured to remove heat from the first solvent and volatiles mixture (FSVM*) within the interior (VESI*) of the volatiles extraction system (VES*). In embodiments, the interior (SSSI*) of the first solvent separation system (SSS*) is in thermal contact with a second volatiles extraction heat exchanger (VS-HX2*). The second volatiles extraction heat exchanger (VS-HX2) is configured to add and/or remove heat from the interior (SSSI*) of the first solvent separation system (SSS*).

The first volatiles extraction heat exchanger (VS-HX1*) includes a first heat transfer medium (VF1C*). The second volatiles extraction heat exchanger (VS-HX2*) includes a second heat transfer medium (VF2C*). In embodiments, the second coolant (VF2C*) configured to add and/or remove heat from the interior (SSSI*) of the first solvent separation system (SSS*) is the first heat transfer medium (VF1C) that was used to add and/or remove heat from the interior (VESI*) of the volatiles extraction system (VES*). In embodiments, the first heat transfer medium (VF1C*) configured to add and/or remove heat from the interior (VESI*) of the volatiles extraction system (VES*) is the second heat transfer medium (VF2C) used to add and/or remove heat from the interior (SSSI*) of the first solvent separation system (SSS*). In embodiments, the first heat transfer medium (VF1C*) and/or the second heat transfer medium (VF2C*) include a heated or cooled liquid. In embodiments, the first heat transfer medium (VF1C*) and/or the second heat transfer medium (VF2C*) include a refrigerated liquid, including water, an alcohol, ethylene glycol, ethylene alcohol, an oil, and an organic compound.

In embodiments, the first heat transfer medium (VF1C*) maintains the interior (VESI*) of the volatiles extraction system (VES*) at a temperature range including one or more ranges selected from the group consisting of: between about 32 degrees Fahrenheit to about 40 degrees Fahrenheit; between about 40 degrees Fahrenheit to about 45 degrees Fahrenheit; between about 45 degrees Fahrenheit to about 50 degrees Fahrenheit; between about 50 degrees Fahrenheit to about 55 degrees Fahrenheit; between about 55 degrees Fahrenheit to about 60 degrees Fahrenheit; between about 60 degrees Fahrenheit to about 65 degrees Fahrenheit; between about 65 degrees Fahrenheit to about 70 degrees Fahrenheit; between about 70 degrees Fahrenheit to about 75 degrees Fahrenheit; between about 75 degrees Fahrenheit to about 80 degrees Fahrenheit; between about 80 degrees Fahrenheit to about 85 degrees Fahrenheit; between about 85 degrees Fahrenheit to about 90 degrees Fahrenheit; between about 90 degrees Fahrenheit to about 95 degrees Fahrenheit; between about 95 degrees Fahrenheit to about 100 degrees Fahrenheit; between about 100 degrees Fahrenheit to about 105 degrees Fahrenheit; between about 105 degrees Fahrenheit to about 110 degrees Fahrenheit; between about 110 degrees Fahrenheit to about 115 degrees Fahrenheit; between about 115 degrees Fahrenheit to about 120 degrees Fahrenheit; between about 120 degrees Fahrenheit to about 130 degrees Fahrenheit; between about 130 degrees Fahrenheit to about 160 degrees Fahrenheit; between about 160 degrees Fahrenheit to about 190 degrees Fahrenheit.

In embodiments, the second heat transfer medium (VF2C*) maintains interior (SSSI*) of the first solvent separation system (SSS*) at a temperature range including one or more ranges selected from the group consisting of: between about 32 degrees Fahrenheit to about 40 degrees Fahrenheit; between about 40 degrees Fahrenheit to about 45 degrees Fahrenheit; between about 45 degrees Fahrenheit to about 50 degrees Fahrenheit; between about 50 degrees Fahrenheit to about 55 degrees Fahrenheit; between about 55 degrees Fahrenheit to about 60 degrees Fahrenheit; between about 60 degrees Fahrenheit to about 65 degrees Fahrenheit; between about 65 degrees Fahrenheit to about 70 degrees Fahrenheit; between about 70 degrees Fahrenheit to about 75 degrees Fahrenheit; between about 75 degrees Fahrenheit to about 80 degrees Fahrenheit; between about 80 degrees Fahrenheit to about 85 degrees Fahrenheit; between about 85 degrees Fahrenheit to about 90 degrees Fahrenheit; between about 90 degrees Fahrenheit to about 95 degrees Fahrenheit; between about 95 degrees Fahrenheit to about 100 degrees Fahrenheit; between about 100 degrees Fahrenheit to about 105 degrees Fahrenheit; between about 105 degrees Fahrenheit to about 110 degrees Fahrenheit; between about 110 degrees Fahrenheit to about 115 degrees Fahrenheit; between about 115 degrees Fahrenheit to about 120 degrees Fahrenheit; between about 120 degrees Fahrenheit to about 130 degrees Fahrenheit; between about 130 degrees Fahrenheit to about 160 degrees Fahrenheit; between about 160 degrees Fahrenheit to about 190 degrees Fahrenheit.

In embodiments, the pressure within the interior (VESI*) of the volatiles extraction system (VES*) is greater than the pressure within the interior (SSSI*) of the first solvent separation system (SSS*). In embodiments, the pressure within the interior (VESI*) of the volatiles extraction system (VES*) is less than the pressure within the interior (SSSI*) of the first solvent separation system (SSS*). In embodiments, the pressure within the interior (VESI*) of the volatiles extraction system (VES*) is equal to the pressure within the interior (SSSI*) of the first solvent separation system (SSS*).

The first solvent separation system (SSS*) outputs a volatiles (VOLT*) and a separated first solvent (SOLV1-S*). The volatiles (VOLT*) may be then mixed with a second solvent (SOLV2*) as described in FIG. 17C'. The volatiles (VOLT*) may alternately by mixed with insects which include one or more from the group consisting of Orthoptera order of insects, grasshoppers, crickets, cave crickets, Jerusalem crickets, katydids, weta, lubber, acrida, locusts, cicadas, ants, mealworms, agave worms, worms, bees, centipedes, cockroaches, dragonflies, beetles, scorpions, tarantulas, termites, insect lipids, and insect oil.

The volatiles extraction system (VES*) is configured to operate in a plurality of modes of operation. In a first mode of operation, the volatiles extraction system (VES*) separates terpenes from the *cannabis*. The first mode of operation may take place at a first temperature and a first pressure. In a second mode of operation, the volatiles extraction system (VES*) separates other volatiles (VOLT*) from the *cannabis*. The second mode of operation may take place at a second temperature and a first pressure. In embodiments, the second temperature is greater than the first temperature. In embodiments, the second pressure is greater than the first pressure.

In embodiments, the interior (VESI*) of the volatiles extraction system (VES*) is configured to operate at a pressure range including one or more ranges selected from the group consisting of: 500 PSI to 1,000 PSI, 1,000 PSI to 1,500 PSI, 1,500 PSI to 2,000 PSI, 2,000 PSI to 2,500 PSI, 2,500 PSI to 3,000 PSI, 3,500 PSI to 4,000 PSI, 4,000 PSI to 4,500 PSI, 4,500 PSI to 5,000 PSI, and 5,000 PSI to 6,000 PSI.

In embodiments, the interior (SSSI*) of the first solvent separation system (SSS*) is configured to operate at a pressure range including one or more ranges selected from the group consisting of: 500 PSI to 1,000 PSI, 1,000 PSI to 1,500 PSI, 1,500 PSI to 2,000 PSI, 2,000 PSI to 2,500 PSI, 2,500 PSI to 3,000 PSI, 3,500 PSI to 4,000 PSI, 4,000 PSI to 4,500 PSI, 4,500 PSI to 5,000 PSI, and 5,000 PSI to 6,000 PSI.

In embodiments, the difference in pressure between the interior (VESI*) of the volatiles extraction system (VES*) and the interior (SSSI*) of the first solvent separation system (SSS*) including one or more ranges selected from the group consisting of: 100 PSI to 150 PSI, 150 PSI to 250 PSI, 250 PSI to 350 PSI, 350 PSI to 500 PSI, 500 PSI to 1,000 PSI, 1,000 PSI to 1,500 PSI, 1,500 PSI to 2,000 PSI, 2,000 PSI to 2,500 PSI, 2,500 PSI to 3,000 PSI, 3,500 PSI to 4,000 PSI, 4,000 PSI to 4,500 PSI, 4,500 PSI to 5,000 PSI, and 5,000 PSI to 6,000 PSI.

FIG. 17B'

FIG. 17B' shows a plurality of volatiles extraction systems (VES1*, VES2*) equipped with one first solvent separation system (SSS*). The first volatiles extraction system (VEST*) has an interior (VES1I*) that is configured to mix *cannabis* (107*, 207*), heated *cannabis* (HT1*), ground *cannabis* (GR1*), or trimmed *cannabis* (TR1*) with a first solvent (SOLV1*). The second volatiles extraction system (VES2*) has an interior (VES1I*) that is configured to mix *cannabis* (107*, 207*), heated *cannabis* (HT1*), ground *cannabis* (GR1*), or trimmed *cannabis* (TR1*) with a first solvent (SOLV1*).

FIG. 17B' shows a first *cannabis* portion (FCS*) introduced to the first volatiles extraction system (VES1*) and a second *cannabis* portion (SCS*) introduced to the second volatiles extraction system (VES2*). The first *cannabis* portion (FCS*) may be weighed prior to being introduced to the first volatiles extraction system (VES1*). The second *cannabis* portion (SCS*) may be weighed prior to being introduced to the second volatiles extraction system (VES2*). The first *cannabis* portion (FCS*) and/or the second *cannabis* portion (SCS*) may be either *cannabis* (107*, 207*), or heated *cannabis* (HT1*), ground *cannabis* (GR1*), trimmed *cannabis* (TR1*), or combinations thereof.

A primary first solvent and volatiles mixture (FSVMA*) is discharged from the first volatiles extraction system (VES1*). A secondary first solvent and volatiles mixture (FSVMB*) is discharged from the second volatiles extraction system (VES1*). The primary first solvent and volatiles mixture (FSVMA*) and secondary first solvent and volatiles mixture (FSVMB*) are combined and introduced to the first solvent separation system (SSS*).

FIG. 17C'

FIG. 17C' shows a volatiles and solvent mixing system (VSMS*) that is configured to mix the volatiles (VOLT*) with a second solvent (SOLV2*). The volatiles (VOLT*) that are introduced to the interior (VSMSI*) of the volatiles and solvent mixing system (VSMS*) are transferred from the volatiles extraction systems (VES*, VES1*, VES2*) via the first solvent separation system (SSS*) as shown in FIGS. 17A' and 17B'.

In embodiments, the second solvent (SOLV2*) includes one or more from the group consisting of a liquid, acetone, alcohol, oil, ethanol. The second solvent (SOLV2*) can be weighed with a mass sensor (MS-SOLV2*) prior to being introduced to the interior (VSMSI*) of the volatiles and solvent mixing system (VSMS*). The volatiles (VOLT*) may also be weighed with a mass sensor (MS-VOLT*) prior to being introduced to the interior (VSMSI*) of the volatiles and solvent mixing system (VSMS*). The second solvent (SOLV2*) and volatiles (VOLT*) are mixed within the interior (VSMSI*) of the volatiles and solvent mixing system (VSMS*).

The volatiles (VOLT*) and second solvent (SOLV2*) may be are mixed at varying mass ratios. The volatiles (VOLT*) to second solvent (SOLV2*) mixing mass ratio is the pounds of volatiles (VOLT*) per pounds of second solvent (SOLV2*). In embodiments, the mixing mass ratio of volatiles (VOLT*) to the second solvent (SOLV2*) ranges from 1 pound of volatiles (VOLT*) per 1 pound of second solvent (SOLV2*), so this would be a mixing mass ratio of 1/1 or 1; In embodiments, the mixing mass ratio of volatiles (VOLT*) to the second solvent (SOLV2*) ranges from 1 pound of volatiles (VOLT*) per 2 pounds of second solvent (SOLV2*), so this would be a mixing mass ratio of ½ or 0.5; In embodiments, the mixing mass ratio of volatiles (VOLT*) to the second solvent (SOLV2*) ranges from 1 pound of volatiles (VOLT*) per 3 pounds of second solvent (SOLV2*), so this would be a mixing mass ratio of ⅓ or 0.33; In embodiments, the mixing mass ratio of volatiles (VOLT*) to the second solvent (SOLV2*) ranges from 1 pound of volatiles (VOLT*) per 4 pounds of second solvent (SOLV2*), so this would be a mixing mass ratio of ¼ or 0.25; In embodiments, the mixing mass ratio of volatiles (VOLT*) to the second solvent (SOLV2*) ranges from 1 pound of volatiles (VOLT*) per 5 pounds of second solvent (SOLV2*), so this would be a mixing mass ratio of ⅕ or 0.2; In embodiments, the mixing mass ratio of volatiles (VOLT*) to the second solvent (SOLV2*) ranges from 1 pound of volatiles (VOLT*) per 6 pounds of second solvent (SOLV2*), so this would be a mixing mass ratio of ⅙ or 0.16; In embodiments, the mixing mass ratio of volatiles (VOLT*) to the second solvent (SOLV2*) ranges from 1 pound of volatiles (VOLT*) per 7 pounds of second solvent (SOLV2*), so this would be a mixing mass ratio of 1/7 or 0.14; In embodiments, the mixing mass ratio of volatiles (VOLT*) to the second solvent (SOLV2*) ranges from 1 pound of volatiles (VOLT*) per 8 pounds of second solvent (SOLV2*), so this would be a mixing mass ratio of ⅛ or 0.125; In embodiments, the mixing mass ratio of volatiles (VOLT*) to the second solvent (SOLV2*) ranges from 1 pound of volatiles (VOLT*) per 9 pounds of second solvent (SOLV2*), so this would be a mixing mass ratio of ⅑ or 0.11; In embodiments, the mixing mass ratio of volatiles (VOLT*) to the second solvent (SOLV2*) ranges from 1 pound of volatiles (VOLT*) per 10 pounds of second solvent (SOLV2*), so this would be a mixing mass ratio of 1/10 or 0.1; In embodiments, the mixing mass ratio of volatiles (VOLT*) to the second solvent (SOLV2*) ranges from 1 pound of volatiles (VOLT*) per 12 pounds of second solvent (SOLV2*), so this would be a mixing mass ratio of 1/12 or 0.08; In embodiments, the mixing mass ratio of volatiles (VOLT*) to the second solvent (SOLV2*) ranges from 1 pound of volatiles (VOLT*) per 14 pounds of second solvent (SOLV2*), so this would be a mixing mass ratio of 1/14 or 0.07; In embodiments, the mixing mass ratio of volatiles (VOLT*) to the second solvent (SOLV2*) ranges from 1 pound of volatiles (VOLT*) per 16 pounds of second solvent (SOLV2*), so this would be a mixing mass ratio of 1/16 or 0.06; In embodiments, the mixing mass ratio of volatiles (VOLT*) to the second solvent (SOLV2*) ranges from 1 pound of volatiles (VOLT*) per 20 pounds of second solvent (SOLV2*), so this would be a mixing mass ratio of 1/20 or 0.05; In embodiments, the mixing mass ratio of volatiles (VOLT*) to the second solvent (SOLV2*) ranges from 1 pound of volatiles (VOLT*) per 60 pounds of second solvent (SOLV2*), so this would be a mixing mass ratio of 1/60 or 0.016; In embodiments, the mixing mass ratio of volatiles (VOLT*) to the second solvent (SOLV2*) ranges from 1 pound of volatiles (VOLT*) per 100 pounds of second solvent (SOLV2*), so this would be a mixing mass ratio of 1/100 or 0.01. In embodiments, the mixing mass ratio of pounds of volatiles (VOLT*) per pounds of second solvent (SOLV2*) ranges from 0.01 to 1.

A second volatiles and solvent mixture (SVSM*) is discharged from the interior (VSMSI*) of the volatiles and solvent mixing system (VSMS*). FIG. 17D' shows one non-limiting embodiment of the second solvent separation system (SEPSOL*). The second solvent separation system (SEPSOL*) is configured to separate the second solvent (SOLV2*) from the second volatiles and solvent mixture (SVSM*). The second solvent separation system (SEPSOL*) is configured to evaporate at least a portion of the second solvent (SOLV2*) from the second volatiles and solvent mixture (SVSM*) to create concentrated volatiles (CVOLT*). Concentrated volatiles (CVOLT*) have a reduced amount of second solvent (SOLV2*) relative to the second volatiles and solvent mixture (SVSM*). The second solvent separation system (SEPSOL*) is configured to separate the second solvent (SOLV2*) from the second volatiles and solvent mixture (SVSM*) to concentrate the volatiles (VOLT*). In embodiments, concentrated volatiles (CVOLT*) are mixed with terpenes that were separated out in the volatiles extraction system (VES*). In embodiments, concentrated volatiles (CVOLT*) are mixed with insects and/or insect lipids within the Insect Production Superstructure System (IPSS) as disclosed in Volume 1.

The second solvent separation system (SEPSOL*) is configured to separate the second solvent (SOLV2*) from the second volatiles and solvent mixture (SVSM*) by evaporation, rotary evaporation, distillation, crystallization, vacuum flashing, or wiped film evaporation. In embodiments, a vacuum may be pulled on the second solvent separation system (SEPSOL*) to aide in evaporation of the second solvent (SOLV2*) from the second volatiles and solvent mixture (SVSM*), as shown in FIG. 17D'.

In embodiments, the second solvent (SOLV2*) and volatiles (VOLT*) are miscible. In embodiments, the second solvent (SOLV2*) and oil within the volatiles (VOLT*) are miscible. In embodiments, the second solvent (SOLV2*) and terpenes within the volatiles (VOLT*) are miscible. In embodiments, the second solvent (SOLV2*) and wax within the volatiles (VOLT*) are miscible. In embodiments, the second solvent (SOLV2*) and wax within the volatiles (VOLT*) are immiscible.

In instances where the second solvent (SOLV2*) and wax within the volatiles (VOLT*) are immiscible, a solvent cooler (SOLV-C*) is provided to cool the second volatiles and solvent mixture (SVSM*) that is evacuated from the interior (VSMSI*) of the volatiles and solvent mixing system (VSMS*). The solvent cooler (SOLV-C*) lowers the temperature of the second volatiles and solvent mixture (SVSM*) to permit phase separation of the wax from the volatiles (VOLT*). The second volatiles and solvent mixture (SVSM*) is a reduced temperature second volatiles and solvent mixture (RTSVSM*) as it is leaves the solvent cooler (SOLV-C*).

In embodiments, the solvent cooler (SOLV-C*) operates at a temperature less than 50 degrees F. In embodiments, the solvent cooler (SOLV-C*) operates at a temperature less than 40 degrees F. In embodiments, the solvent cooler (SOLV-C*) operates at a temperature less than 30 degrees F. In embodiments, the solvent cooler (SOLV-C*) operates at a temperature less than 20 degrees F. In embodiments, the solvent cooler (SOLV-C*) operates at a temperature less than 10 degrees F. In embodiments, the solvent cooler (SOLV-C*) operates at a temperature less than 00 degrees F. In embodiments, the reduced temperature second volatiles and solvent mixture (RTSVSM*) leaves the solvent cooler (SOLV-C*) at a temperature including one or more from the group consisting of: less than 50 degrees F., less than 40 degrees F., less than 30 degrees F., less than 20 degrees F., less than 10 degrees F., and less than 0 degrees F.

In embodiments, a solvent filter (SOLV-F*) is configured to accept at least a portion of the second volatiles and solvent mixture (SVSM*). In embodiments, a solvent filter (SOLV-F*) is configured to accept at least a portion of the reduced temperature second volatiles and solvent mixture (RTSVSM*). In embodiments, the solvent filter (SOLV-F*) is configured to separate wax (WAX*) from the second volatiles and solvent mixture (SVSM*). In embodiments, the solvent filter (SOLV-F*) is configured to separate wax (WAX*) from the reduced temperature second volatiles and solvent mixture (RTSVSM*). The solvent filter (SOLV-F*) discharges a second volatiles and solvent mixture (SVSM*) which may then be routed to the second solvent separation system (SEPSOL*) of FIG. 17D'. In embodiments, the wax (WAX*) is mixed with insect lipids to make cosmetics, drugs, lip balm, and mixtures as disclosed in FIG. 12D of Volume 1.

FIG. 17D'

FIG. 17D' shows a second solvent separation system (SEPSOL*) that is configured to separate at least a portion of the second solvent (SOLV2*) from the second volatiles and solvent mixture (SVSM*) to produce concentrated volatiles (CVOLT*).

In embodiments, the second solvent separation system (SEPSOL*) includes an evaporator (J11*). FIG. 17D' shows at least a portion of the second volatiles and solvent mixture (SVSM*) transferred to the second solvent separation system (SEPSOL*) from the volatiles and solvent mixing system (VSMS*) shown in FIG. 17C'. The second volatiles and solvent mixture (SVSM*) is transferred from the volatiles and solvent mixing system (VSMS*) or from the solvent cooler (SOLV-C*) or from the solvent filter (SOLV-F*) of FIG. 17C' to the second solvent separation system (SEPSOL*) of FIG. 17D'.

FIG. 17D' displays the second solvent separation system (SEPSOL*) as an evaporator (J11*) which separates or evaporates the second solvent (SOLV2*) from the second volatiles and solvent mixture (SVSM*) to produce concentrated volatiles (CVOLT*). In embodiments, the evaporator (J11*) is a wiped-film evaporator (J11A*). In embodiments, the evaporator (J11*) is comprised of one or more from the group consisting of a rotary evaporator, falling film tubular evaporator, rising/falling film tubular evaporator, rising film tubular evaporator, forced circulation evaporator, internal pump forced circulation evaporator, plate evaporator, evaporative cooler, multiple-effect evaporator, thermal vapor recompression evaporator, mechanical vapor recompression evaporator, flash tank, a crystallizer, and a distillation column.

In embodiments, when referring to the evaporator and/or the rotary evaporator in this disclosure, the evaporator and/or rotary evaporator may include one or more selected from the group consisting of: an evaporator and/or rotary evaporator provided by: BUCHI Labortechnik AG; Eyela Tokyo Rikakikai Co. Ltd; Heidolph Instruments Gmbh & Co. KG.; IKA Works, Inc.; KNF Neuberger, Inc.; Labfirst Scientific Instruments (Shanghai) Co., Ltd.; Xi'an Yuanjian Instrument Equipment Co., Ltd.; Labtech S.R.L.; Hydrion Scientific Instruments Co., Ltd.; Shanghai HJ Lab Instruments Co., Ltd.; Stewart Equipment Co Inc.; Thermo Fisher Scientific, Fisher Clinical Services Inc; or Cole Parmer Instrument Co Ltd.

In embodiments, when referring to the rotary evaporator in this disclosure, the rotary evaporator may include one or more evaporation flask volumes selected from the group consisting of: 1 liter to 2 liters, 2 liters to 3 liters, 3 liters to 4 liters, 4 liters to 5 liters, 5 liter to 10 liters, 10 liters to 20 liters, 20 liters to 30 liters, 30 liters to 40 liters, or 40 liters to 50 liters.

The evaporator (J11*) shown in FIG. 17D' is that of a wiped-film evaporator (J11A*). The evaporator (J11*) has a vapor inlet (J12*), a separator input (J16*), a heating jacket (J17*), a first output (J18*), and a second output (J19*). In embodiments, the evaporator (J11*) is electrically heated. In embodiments, the vapor inlet (J12*) is provided with a vapor (J12A*) such as steam. The vapor inlet is connected to a vapor supply conduit (J13*). A vapor supply valve (J14*) is positioned on the vapor supply conduit (J13*). The vapor supply valve (J14*) is equipped with a controller (J15A*) that is configured to input and output a signal (J15B*) to the computer (COMP). In embodiments, the pressure drop across the vapor supply valve (J14*) ranges from between 5 PSI to 10 PSI, 15 PSI to 25 PSI, 25 PSI to 35 PSI, 35 PSI to 45 PSI, 45 PSI to 55 PSI, 55 PSI to 65 PSI, 65 PSI to 75 PSI, 75 PSI to 85 PSI. In embodiments, the vapor supply valve (J14*) percent open during normal operation ranges from 10% open to 25% open, 25% open to 35% open, 35% open to 45% open, 45% open to 55% open, 55% open to 65% open, 65% open to 75% open, 75% open to 80% open.

A separated vapor transfer conduit (J20*) is connected to the first output (J18*) and is configured to transfer vaporized solvent (J22*) from the evaporator (J11*) to a condenser (J26*). In embodiments, the vaporized solvent (J22*) is the second solvent (SOLV2*) in vapor phase. When the second solvent (SOLV2*) is evaporated or vaporized into a vaporized solvent (J22*) the concentration of the volatiles (VOLT*) within the second volatiles and solvent mixture (SVSM*) increases to form concentrated volatiles (CVOLT*).

The condenser (J26*) has a vaporized liquid input (J25*) that is configured to transfer the vaporized solvent (J22*) or vaporized second solvent (SOLV2*) from the separated vapor transfer conduit (J20*) to the condenser (J26*). The condenser (J26*) is configured to accept vaporized solvent (J22*) from the evaporator (J11*) and condense the liquid into condensate (J27*). Condensate (J27*) is discharged from the condenser (J26*) via a condenser condensate output (J30*). The condensate (J27*) is the second solvent (SOLV2*) which can then be recovered and reused in the volatiles and solvent mixing system (VSMS*).

The condenser is connected to a vacuum system (J32*) via a gas/vapor transfer conduit (J33*). Gas/vapor (J35*) is evacuated from the condenser (J27*) via a gas/vapor discharge (J37*). The gas/vapor (J35*) transferred from the condenser to the vacuum system (J32*) may be comprised of one or more from the group consisting of second solvent, carbon dioxide, nitrogen, air, steam, water vapor, and non-condensables. The vacuum system (J32*) may be any conceivable system configured to draw a vacuum on the condenser (J26*). In embodiments, the vacuum system (J32*) is that of a liquid-ring vacuum pump. A portion of the gas/vapor (J35*) may be in turn condensed within the vacuum system (J26*). A portion of the gas/vapor (J35*) may be discharged from the vacuum system (J26*) via a gas/vapor transfer line (J39*).

In embodiments, the vacuum system (J32*) pulls a vacuum on the evaporator (J11*) at a pressure ranging from 0.25 pounds per square inch absolute (PSIA) to 0.5 PSIA, 0.5 PSIA to 1 PSIA, 1 PSIA to 1.5 PSIA, 1.5 PSIA to 3 PSIA, 3 PSIA to 4.5 PSIA, 4.5 PSIA to 6 PSIA, 6 PSIA to 7.5 PSIA, 7.5 PSIA to 9 PSIA, 9 PSIA to 10.5 PSIA, 10.5 PSIA to 12 PSIA, 12 PSIA to 13.5 PSIA, 12 PSIA to 12.25 PSIA, 12.25 PSIA to 12.5 PSIA, 12.5 PSIA to 12.75PSIA, 12.75 PSIA to 13 PSIA, 13 PSIA to 13.25 PSIA, 13.25 PSIA to 13.5 PSIA, 13.5 PSIA to 13.75 PSIA, 13.75 PSIA to 14 PSIA, 14 PSIA to 14.25 PSIA, 14.25 PSIA to 14.5 PSIA, or 14.5 PSIA to 14.75 PSIA.

The condenser (J26*) is provided with a cooling water input (J36*) and a cooling water output (J40*). The cooling water input (J36*) is configured to accept a cooling water supply (J38*) and the cooling water output (J40*) is configured to discharge a cooling water return (J42'*). The cooling water supply (J38*) is configured to reduce the temperature of the vaporized solvent (J22*) within the condenser (J26*) to convert the vaporized solvent (J22*) into a liquid condensate (J27*).

The evaporator (J11*) has an evaporator condensate output (J24*) for evacuating condensate (J41*) from the heating jacket (J17*). The condensate (J41*) discharged via the evaporator condensate output (J24*) was provided to the evaporator heating jacket (J17*) as the vapor (J12A*) or steam. The heating jacket (J17*) accepts a source of vapor (J12A*), and evaporates second solvent (SOLV2*) from the second volatiles and solvent mixture (SVSM*) to form vaporized solvent (J22*) that is discharged from the evaporator (J11*) and sent to the condenser (J26*).

The heating jacket (J17*) accepts a source of vapor (J12A*), and evaporates second solvent (SOLV2*) from the second volatiles and solvent mixture (SVSM*) to form concentrates volatiles (CVOLT*) that has a reduced amount of second solvent (SOLV2*) relative to the second volatiles and solvent mixture (SVSM*).

In embodiments, the evaporator (J11*) takes the form of a wiped-film evaporator (J11A*). In embodiments, the wiped-film evaporator (J11A*) has a motor (J42*) and a wiper (J44*). In embodiments, the motor (J42*) and wiper (J44*) act together to wipe at least one heat transfer surface within the evaporator (J11*).

The separator input (J16*) is configured to introduce the second volatiles and solvent mixture (SVSM*) to the evaporator (J11*). In embodiments, the evaporator vaporizes the second solvent (SOLV2*) from within the second volatiles and solvent mixture (SVSM*) to produce a vaporized solvent (J22*) and concentrated volatiles (CVOLT*).

In embodiments, the present disclosure describes a method to separate volatiles from *cannabis*, the method includes:
  (a) providing a source of *cannabis*;
  (b) after step (a), grinding the *cannabis* to form ground *cannabis*;
  (c) after step (b), extracting volatiles from the ground *cannabis* with a first solvent to form a first solvent and volatiles mixture; and
  (d) after step (c), separating at least a portion of the volatiles from the first solvent and volatiles mixture;
wherein:
the volatiles include one or more from the group consisting of oil, wax, terpenes;
the first solvent (SOLV1*) includes one or more from the group consisting of acetone, alcohol, oil, butane, butter, carbon dioxide, coconut oil, ethanol, gas, gaseous carbon dioxide, hexane, isobutane, isopropanol, liquid carbon dioxide, liquid, naphtha, olive oil, pentane, propane, R134 refrigerant gas, subcritical carbon dioxide, supercritical carbon dioxide, vapor;
the terpenes include one or more from the group consisting of limonene, humulene, pinene, linalool, caryophyllene, mycrene, eucalyptol, nerolidol, bisablol, and phytol.

In embodiments, the present disclosure describes a method to separate volatiles from *cannabis*, the method includes:
  (a) providing Beaufort Budman III or *cannabis*;
  (b) grinding Beaufort Budman III or *cannabis* after step (a);
  (c) extracting volatiles (VOLT*) from Beaufort Budman III or *cannabis* after step (b) with a first solvent (SOLV1*) to form a first solvent and volatiles mixture (FSVM*);
  (d) separating at least a portion of the volatiles (VOLT*) from the first solvent and volatiles mixture (FSVM*);
  (e) mixing the volatiles with a second solvent (SOLV2*) after step (d) to form a second volatiles and solvent mixture (SVSM*);
  (f) cooling the second volatiles and solvent mixture (SVSM*) after step (e);
  (g) filtering the second volatiles and solvent mixture (SVSM*); and
  (h) evaporating the second solvent (SOLV2*) from the second volatiles and solvent mixture (SVSM*);
wherein:
the volatiles include one or more from the group consisting of oil, wax, terpenes;
the first solvent (SOLV1*) includes one or more from the group consisting of acetone, alcohol, oil, butane, butter, carbon dioxide, coconut oil, ethanol, gas, gaseous carbon dioxide, hexane, isobutane, isopropanol, liquid carbon dioxide, liquid, naphtha, olive oil, pentane, propane, R134 refrigerant gas, subcritical carbon dioxide, supercritical carbon dioxide, vapor;
the second solvent (SOLV2*) includes one or more from the group consisting of a liquid, acetone, alcohol, oil, ethanol;
the terpenes include one or more from the group consisting of limonene, humulene, pinene, linalool, caryophyllene, mycrene, eucalyptol, nerolidol, bisablol, and phytol.

In embodiments, the present disclosure describes a method to separate volatiles from *cannabis*, the method includes:
  (a) providing Beaufort Budman III or *cannabis*;
  (b) grinding Beaufort Budman III or *cannabis* after step (a); and
  (c) extracting volatiles (VOLT*) from Beaufort Budman III or *cannabis* after step (b) with a first solvent (SOLV1*) to form a first solvent and volatiles mixture (FSVM*);
  (d) separating at least a portion of the volatiles (VOLT*) from the first solvent and volatiles mixture (FSVM*);
  (e) mixing the volatiles with a second solvent (SOLV2*) after step (d) to form a second volatiles and solvent mixture (SVSM*);
  (f) separating at least a portion of the volatiles (VOLT*) from the second solvent (SOLV2*);
wherein:
the volatiles include one or more from the group consisting of oil, wax, terpenes;
the first solvent (SOLV1*) includes one or more from the group consisting of acetone, alcohol, oil, butane, butter, carbon dioxide, coconut oil, ethanol, gas, gaseous carbon dioxide, hexane, isobutane, isopropanol, liquid carbon dioxide, liquid, naphtha, olive oil, pentane, propane, R134 refrigerant gas, subcritical carbon dioxide, supercritical carbon dioxide, vapor;
the second solvent (SOLV2*) includes one or more from the group consisting of a liquid, acetone, alcohol, oil, ethanol;
the terpenes include one or more from the group consisting of limonene, humulene, pinene, linalool, caryophyllene, mycrene, eucalyptol, nerolidol, bisablol, and phytol.

In embodiments, the present disclosure describes a method to separate volatiles from *cannabis*, the method includes:
  (a) providing Beaufort Budman III or *cannabis*;
  (b) grinding Beaufort Budman III or *cannabis* after step (a);
  (c) extracting volatiles (VOLT*) from Beaufort Budman III or *cannabis* after step (b) with a first solvent (SOLV1*) to form a first solvent and volatiles mixture (FSVM*);
  (d) separating at least a portion of the volatiles (VOLT*) from the first solvent and volatiles mixture (FSVM*);
  (e) mixing a portion of the volatiles (VOLT*) after step (d) with insects;
wherein:
the volatiles include one or more from the group consisting of oil, wax, terpenes;
the first solvent (SOLV1*) includes one or more from the group consisting of acetone, alcohol, oil, butane, butter, carbon dioxide, coconut oil, ethanol, gas, gaseous carbon dioxide, hexane, isobutane, isopropanol, liquid carbon dioxide, liquid, naphtha, olive oil, pentane, propane, R134 refrigerant gas, subcritical carbon dioxide, supercritical carbon dioxide, vapor;
the second solvent (SOLV2*) includes one or more from the group consisting of a liquid, acetone, alcohol, oil, ethanol;
the terpenes include one or more from the group consisting of limonene, humulene, pinene, linalool, caryophyllene, mycrene, eucalyptol, nerolidol, bisablol, and phytol.

the insects are comprised of one or more from the group consisting of Orthoptera order of insects, grasshoppers, crickets, cave crickets, Jerusalem crickets, katydids, weta, lubber, acrida, locusts, cicadas, ants, mealworms, agave worms, worms, bees, centipedes, cockroaches, dragonflies, beetles, scorpions, tarantulas, termites, insect lipids, and insect oil.

In embodiments, the present disclosure describes a method to separate volatiles from *cannabis*, the method includes:
(a) providing Beaufort Budman III or *cannabis;*
(b) grinding Beaufort Budman III or *cannabis* after step (a);
(c) extracting volatiles (VOLT*) from Beaufort Budman III or *cannabis* after step (b) with a first solvent (SOLV1*) to form a first solvent and volatiles mixture (FSVM*);
(d) separating at least a portion of the volatiles (VOLT*) from the first solvent and volatiles mixture (FSVM*);
(e) mixing the volatiles (VOLT*) with a second solvent (SOLV2*) after step (d) to form a second volatiles and solvent mixture (SVSM*);
(f) separating at least a portion of the volatiles (VOLT*) from the second volatiles and solvent mixture (SVSM*);
(g) mixing a portion of the volatiles (VOLT*) after step (f) with insects;
wherein:
the volatiles include one or more from the group consisting of oil, wax, terpenes;
the first solvent (SOLV1*) includes one or more from the group consisting of acetone, alcohol, oil, butane, butter, carbon dioxide, coconut oil, ethanol, gas, gaseous carbon dioxide, hexane, isobutane, isopropanol, liquid carbon dioxide, liquid, naphtha, olive oil, pentane, propane, R134 refrigerant gas, subcritical carbon dioxide, supercritical carbon dioxide, vapor;
the second solvent (SOLV2*) includes one or more from the group consisting of a liquid, acetone, alcohol, oil, ethanol;
the terpenes include one or more from the group consisting of limonene, humulene, pinene, linalool, caryophyllene, mycrene, eucalyptol, nerolidol, bisablol, and phytol.
the insects are comprised of one or more from the group consisting of Orthoptera order of insects, grasshoppers, crickets, cave crickets, Jerusalem crickets, katydids, weta, lubber, acrida, locusts, cicadas, ants, mealworms, agave worms, worms, bees, centipedes, cockroaches, dragonflies, beetles, scorpions, tarantulas, termites, insect lipids, and insect oil.

In embodiments, the present disclosure describes a method to separate volatiles from *cannabis*, the method includes:
(a) providing Beaufort Budman III or *cannabis;*
(b) grinding Beaufort Budman III or *cannabis* after step (a); and
(c) extracting volatiles (VOLT*) from Beaufort Budman III or *cannabis* after step (b) with a first solvent (SOLV1*) to form a first solvent and volatiles mixture (FSVM*);
(d) separating at least a portion of the volatiles (VOLT*) from the first solvent and volatiles mixture (FSVM*);
(e) mixing the volatiles (VOLT*) with a second solvent (SOLV2*) after step (d) to form a second volatiles and solvent mixture (SVSM*);
(f) evaporating at least a portion of the second solvent (SOLV2*) from the second volatiles and solvent mixture (SVSM*) to create concentrated volatiles (CVOLT*) that have reduced amount of second solvent relative to the second volatiles and solvent mixture (SVSM*);
(g) mixing a portion of the volatiles (VOLT*) after step (f) with insects;
wherein:
the volatiles include one or more from the group consisting of oil, wax, terpenes;
the first solvent (SOLV1*) includes one or more from the group consisting of acetone, alcohol, oil, butane, butter, carbon dioxide, coconut oil, ethanol, gas, gaseous carbon dioxide, hexane, isobutane, isopropanol, liquid carbon dioxide, liquid, naphtha, olive oil, pentane, propane, R134 refrigerant gas, subcritical carbon dioxide, supercritical carbon dioxide, vapor;
the second solvent (SOLV2*) includes one or more from the group consisting of a liquid, acetone, alcohol, oil, ethanol;
the terpenes include one or more from the group consisting of limonene, humulene, pinene, linalool, caryophyllene, mycrene, eucalyptol, nerolidol, bisablol, and phytol.
the insects are comprised of one or more from the group consisting of Orthoptera order of insects, grasshoppers, crickets, cave crickets, Jerusalem crickets, katydids, weta, lubber, acrida, locusts, cicadas, ants, mealworms, agave worms, worms, bees, centipedes, cockroaches, dragonflies, beetles, scorpions, tarantulas, termites, insect lipids, and insect oil.

In embodiments, the present disclosure describes a method to separate volatiles from *cannabis*, the method includes:
(a) providing a farming superstructure system (FSS), including:
(a1) a first water treatment unit (A1*) including a cation configured to remove positively charged ions from water to form a positively charged ion depleted water (06A*), the positively charged ions are comprised of one or more from the group consisting of calcium, magnesium, sodium, and iron;
(a2) a second water treatment unit (A2*) including an anion configured to remove negatively charged ions from the positively charged ion depleted water (06A*) to form a negatively charged ion depleted water (09A*), the negatively charged ions are comprised of one or more from the group consisting of iodine, chloride, and sulfate;
(a3) an optional third water treatment unit (A3*) including a membrane configured to remove undesirable compounds from the negatively charged ion depleted water (09A*) to form an undesirable compounds depleted water (12A*), the undesirable compounds are comprised of one or more from the group consisting of dissolved organic chemicals, viruses, bacteria, and particulates;
(a4) an enclosure (ENC*) having an interior (ENC1*);
(a5) a plurality of growing assemblies (100*, 200*) positioned within the interior (ENC1*) of the enclosure (ENC*), each growing assembly (100*, 200*) configured to grow Beaufort Budman III (107*, 207*) or *cannabis* (107*, 207*);
(a6) a plurality of lights (L1*, L2*) configured to illuminate the interior (ENC1*) of the enclosure (ENC*);
(a7) a volatiles extraction system (VES*) that is configured to separate volatiles (VOLT*) from Beaufort Budman III (107*, 207*) or *cannabis* (107*, 207*) with use of a first solvent (SOLV1*), the volatiles extraction system (VES*) has an interior (VESI*)

that is configured to contain Beaufort Budman III (107\*, 207\*) or *cannabis* (107\*, 207\*), the volatiles extraction system (VES\*) is configured to accept a first solvent (SOLV1\*), the first solvent (SOLV1\*) is configured to contact the Beaufort Budman III (107\*, 207\*) or *cannabis* (107\*, 207\*) within the interior (VESI\*) of the volatiles extraction system (VES\*), the volatiles extraction system (VES\*) outputs a first solvent and volatiles mixture (FSVM\*);

(a8) a first solvent separation system (SSS) that is configured to separate the volatiles (VOLT) from the first solvent and volatiles mixture (FSVM), the first solvent separation system (SSS) has an interior (SSSI), the first solvent and volatiles mixture (FSVM) is transferred from the interior (VEST) of the volatiles extraction system (VES) to the interior (SSSI) of the first solvent separation system (SSS), the first solvent separation system (SSS) outputs a volatiles (VOLT) and a separated first solvent (SOLV1-S);

(a9) a volatiles and solvent mixing system (VSMS) that is configured to mix the volatiles (VOLT) with a second solvent (SOLV2), the volatiles (VOLT) that are introduced to the interior (VSMSI) of the volatiles and solvent mixing system (VSMS) are transferred from the volatiles extraction systems (VES), a second volatiles and solvent mixture (SVSM) is discharged from the interior (VSMSI) of the volatiles and solvent mixing system (VSMS);

(a10) a second solvent separation system (SEPSOL) that is configured to separate at least a portion of the second solvent (SOLV2) from the second volatiles and solvent mixture (SVSM) to produce concentrated volatiles (CVOLT);

(b) providing a source of water;
(c) removing positively charged ions and negatively charged ions and optionally undesirable compounds from the water of step (b);
(d) mixing the water after step (c) with macro-nutrients, micro-nutrients, or a pH adjustment solution to form a liquid mixture;
(e) pressurizing the liquid mixture after step (d) to form a pressurized liquid mixture;
(f) transferring the pressurized liquid mixture of step (e) to the plurality of growing assemblies; and
(g) illuminating the plurality of growing assemblies (100, 200) with the plurality of lights;
(h) growing Beaufort Budman III or *cannabis* within the plurality of growing assemblies after step (g);
(i) harvesting Beaufort Budman III or *cannabis* after growing Beaufort Budman III or *cannabis* in step (h);
(j) grinding Beaufort Budman III or *cannabis* after step (i); and
(k) extracting volatiles (VOLT\*) from Beaufort Budman III or *cannabis* after step (j) with a first solvent (SOLV1\*) to form a first solvent and volatiles mixture (FSVM\*);
(l) separating at least a portion of the volatiles (VOLT\*) from the first solvent and volatiles mixture (FSVM\*);
(m) mixing the volatiles (VOLT\*) with a second solvent (SOLV2\*) after step (l) to form a second volatiles and solvent mixture (SVSM\*);
(n) cooling the second volatiles and solvent mixture (SVSM\*) after step (m);
(o) filtering the second volatiles and solvent mixture (SVSM\*) after step (n);

(p) evaporating the second solvent (SOLV2\*) from the second volatiles and solvent mixture (SVSM);

wherein:
the volatiles include one or more from the group consisting of oil, wax, terpenes;
the first solvent (SOLV1\*) includes one or more from the group consisting of acetone, alcohol, oil, butane, butter, carbon dioxide, coconut oil, ethanol, gas, gaseous carbon dioxide, hexane, isobutane, isopropanol, liquid carbon dioxide, liquid, naphtha, olive oil, pentane, propane, R134 refrigerant gas, subcritical carbon dioxide, supercritical carbon dioxide, vapor;
the second solvent (SOLV2\*) includes one or more from the group consisting of a liquid, acetone, alcohol, oil, ethanol;
the terpenes include one or more from the group consisting of limonene, humulene, pinene, linalool, caryophyllene, mycrene, eucalyptol, nerolidol, bisablol, and phytol.

In embodiments, the present disclosure describes a method to separate volatiles from *cannabis*, the method includes:

(a) providing a farming superstructure system (FSS), including:
(a1) a cation configured to remove positively charged ions from water to form a positively charged ion depleted water (06A), the positively charged ions are comprised of one or more from the group consisting of calcium, magnesium, sodium, and iron;
(a2) an anion configured to remove negatively charged ions from the positively charged ion depleted water (06A) to form a negatively charged ion depleted water (09A), the negatively charged ions are comprised of one or more from the group consisting of iodine, chloride, and sulfate;
(a3) a membrane configured to remove undesirable compounds from the negatively charged ion depleted water (09A) to form an undesirable compounds depleted water (12A), the undesirable compounds are comprised of one or more from the group consisting of dissolved organic chemicals, viruses, bacteria, and particulates;
(a4) an enclosure (ENC) having an interior (ENC1);
(a5) a plurality of growing assemblies (100, 200) positioned within the interior (ENC1) of the enclosure (ENC), each growing assembly (100, 200) configured to grow Beaufort Budman III (107, 207) or *cannabis* (107, 207);
(a6) a plurality of lights (L1, L2) configured to illuminate the interior (ENC1) of the enclosure (ENC);
(a7) a volatiles extraction system (VES) that is configured to separate volatiles (VOLT) from Beaufort Budman III (107, 207) or *cannabis* (107, 207) with use of a first solvent (SOLV1), the volatiles extraction system (VES) has an interior (VEST) that is configured to contain Beaufort Budman III (107, 207) or *cannabis* (107, 207), the volatiles extraction system (VES) is configured to accept a first solvent (SOLV1), the first solvent (SOLV1) is configured to contact the Beaufort Budman III (107, 207) or *cannabis* (107, 207) within the interior (VEST) of the volatiles extraction system (VES), the volatiles extraction system (VES) outputs a first solvent and volatiles mixture (FSVM);
(a8) a first solvent separation system (SSS) that is configured to separate the volatiles (VOLT) from the first solvent and volatiles mixture (FSVM), the first solvent separation system (SSS) has an interior (SSSI), the first solvent and volatiles mixture (FSVM) is transferred from the interior (VEST) of the volatiles extraction system (VES) to the interior (SSSI) of the first solvent separation system (SSS), the first solvent separation system (SSS) outputs a volatiles (VOLT) and a separated first solvent (SOLV1-S);

(a9) a volatiles and solvent mixing system (VSMS) that is configured to mix the volatiles (VOLT) with a second solvent (SOLV2), the volatiles (VOLT) that are introduced to the interior (VSMSI) of the volatiles and solvent mixing system (VSMS) are transferred from the volatiles extraction systems (VES), a second volatiles and solvent mixture (SVSM) is discharged from the interior (VSMSI) of the volatiles and solvent mixing system (VSMS);

(a10) a second solvent separation system (SEPSOL) that is configured to separate at least a portion of the second solvent (SOLV2) from the second volatiles and solvent mixture (SVSM) to produce concentrated volatiles (CVOLT);

(b) providing a source of water;

(c) removing positively charged ions and negatively charged ions and optionally undesirable compounds from the water of step (b);

(d) mixing the water after step (c) with macro-nutrients, micro-nutrients, or a pH adjustment solution to form a liquid mixture;

(e) pressurizing the liquid mixture after step (d) to form a pressurized liquid mixture;

(f) transferring the pressurized liquid mixture of step (e) to the plurality of growing assemblies; and (g) illuminating the plurality of growing assemblies (100, 200) with the plurality of lights (L1, L2);

(h) growing Beaufort Budman III or *cannabis* within the plurality of growing assemblies after step (g);

(i) harvesting Beaufort Budman III or *cannabis* after growing Beaufort Budman III or *cannabis* in step (h);

(j) grinding Beaufort Budman III or *cannabis* after step (i); and (k) extracting volatiles (VOLT) from Beaufort Budman III or *cannabis* after step (j) with a first solvent (SOLV1) to form a first solvent and volatiles mixture (FSVM);

(l) separating at least a portion of the volatiles (VOLT) from the first solvent and volatiles mixture (FSVM);

(m) mixing a portion of the volatiles (VOLT) after step (l) with insects;

wherein:
the volatiles include one or more from the group consisting of oil, wax, terpenes;
the first solvent (SOLV1) includes one or more from the group consisting of acetone, alcohol, oil, butane, butter, carbon dioxide, coconut oil, ethanol, gas, gaseous carbon dioxide, hexane, isobutane, isopropanol, liquid carbon dioxide, liquid, naphtha, olive oil, pentane, propane, R134 refrigerant gas, subcritical carbon dioxide, supercritical carbon dioxide, vapor;
the second solvent (SOLV2) includes one or more from the group consisting of a liquid, acetone, alcohol, oil, ethanol;
the terpenes include one or more from the group consisting of limonene, humulene, pinene, linalool, caryophyllene, mycrene, eucalyptol, nerolidol, bisablol, and phytol.
the insects are comprised of one or more from the group consisting of Orthoptera order of insects, grasshoppers, crickets, cave crickets, Jerusalem crickets, katydids, weta, lubber, acrida, locusts, cicadas, ants, mealworms, agave worms, worms, bees, centipedes, cockroaches, dragonflies, beetles, scorpions, tarantulas, termites, insect lipids, and insect oil.

In embodiments, the present disclosure describes a method to separate volatiles from *cannabis*, the method includes:

(a) providing a farming superstructure system (FSS), including:

(a1) a first water treatment unit (A1) including a cation configured to remove positively charged ions from water to form a positively charged ion depleted water (06A), the positively charged ions are comprised of one or more from the group consisting of calcium, magnesium, sodium, and iron;

(a2) a second water treatment unit (A2) including an anion configured to remove negatively charged ions from the positively charged ion depleted water (06A) to form a negatively charged ion depleted water (09A), the negatively charged ions are comprised of one or more from the group consisting of iodine, chloride, and sulfate;

(a3) an optional third water treatment unit (A3) including a membrane configured to remove undesirable compounds from the negatively charged ion depleted water (09A) to form an undesirable compounds depleted water (12A), the undesirable compounds are comprised of one or more from the group consisting of dissolved organic chemicals, viruses, bacteria, and particulates;

(a4) an enclosure (ENC) having an interior (ENC1);

(a5) a plurality of growing assemblies (100, 200) positioned within the interior (ENC1) of the enclosure (ENC), each growing assembly (100, 200) configured to grow Beaufort Budman III (107, 207) or *cannabis* (107, 207);

(a6) a plurality of lights (L1, L2) configured to illuminate the interior (ENC1) of the enclosure (ENC);

(a7) a volatiles extraction system (VES) that is configured to separate volatiles (VOLT) from Beaufort Budman III (107, 207) or *cannabis* (107, 207) with use of a first solvent (SOLV1), the volatiles extraction system (VES) has an interior (VESI) that is configured to contain Beaufort Budman III (107, 207) or *cannabis* (107, 207), the volatiles extraction system (VES) is configured to accept a first solvent (SOLV1), the first solvent (SOLV1) is configured to contact the Beaufort Budman III (107, 207) or *cannabis* (107, 207) within the interior (VEST) of the volatiles extraction system (VES), the volatiles extraction system (VES) outputs a first solvent and volatiles mixture (FSVM);

(a8) a first solvent separation system (SSS) that is configured to separate the volatiles (VOLT) from the first solvent and volatiles mixture (FSVM), the first solvent separation system (SSS) has an interior (SSSI), the first solvent and volatiles mixture (FSVM) is transferred from the interior (VESI) of the volatiles extraction system (VES) to the interior (SSSI) of the first solvent separation system (SSS), the first solvent separation system (SSS) outputs a volatiles (VOLT) and a separated first solvent (SOLV1-S);

(a9) a volatiles and solvent mixing system (VSMS) that is configured to mix the volatiles (VOLT) with a second solvent (SOLV2), the volatiles (VOLT) that are introduced to the interior (VSMSI) of the volatiles and solvent mixing system (VSMS) are transferred from the volatiles extraction systems (VES), a second volatiles and solvent mixture (SVSM) is discharged from the interior (VSMSI) of the volatiles and solvent mixing system (VSMS);

(a10) a second solvent separation system (SEPSOL) that is configured to separate at least a portion of the second solvent (SOLV2) from the second volatiles and solvent mixture (SVSM) to produce concentrated volatiles (CVOLT);

(b) providing a source of water;
(c) removing positively charged ions and negatively charged ions and optionally undesirable compounds from the water of step (b);
(d) mixing the water after step (c) with macro-nutrients, micro-nutrients, or a pH adjustment solution to form a liquid mixture;
(e) pressurizing the liquid mixture after step (d) to form a pressurized liquid mixture;
(f) transferring the pressurized liquid mixture of step (e) to the plurality of growing assemblies; and
(g) illuminating the plurality of growing assemblies (100, 200) with the plurality of lights (L1, L2);
(h) growing Beaufort Budman III or *cannabis* within the plurality of growing assemblies after step (g);
(i) harvesting Beaufort Budman III or *cannabis* after growing Beaufort Budman III or *cannabis* in step (h);
(j) grinding Beaufort Budman III or *cannabis* after step (i); and
(k) extracting volatiles (VOLT) from Beaufort Budman III or *cannabis* after step (j) with a first solvent (SOLV1) to form a first solvent and volatiles mixture (FSVM);
(l) separating at least a portion of the volatiles (VOLT) from the first solvent and volatiles mixture (FSVM);
(m) mixing the volatiles with a second solvent (SOLV2) after step (l) to form a second volatiles and solvent mixture (SVSM); and
(n) separating at least a portion of the volatiles (VOLT) from the second volatiles and solvent mixture (SVSM);

wherein:
the volatiles include one or more from the group consisting of oil, wax, terpenes;
the first solvent (SOLV1) includes one or more from the group consisting of acetone, alcohol, oil, butane, butter, carbon dioxide, coconut oil, ethanol, gas, gaseous carbon dioxide, hexane, isobutane, isopropanol, liquid carbon dioxide, liquid, naphtha, olive oil, pentane, propane, R134 refrigerant gas, subcritical carbon dioxide, supercritical carbon dioxide, vapor;
the second solvent (SOLV2) includes one or more from the group consisting of a liquid, acetone, alcohol, oil, ethanol;
the terpenes include one or more from the group consisting of limonene, humulene, pinene, linalool, caryophyllene, mycrene, eucalyptol, nerolidol, bisablol, and phytol.

In embodiments, the present disclosure describes a method to separate volatiles from *cannabis*, the method includes:
(a) providing a farming superstructure system (FSS), including:
(a1) a first water treatment unit (A1) including a cation configured to remove positively charged ions from water to form a positively charged ion depleted water (06A), the positively charged ions are comprised of one or more from the group consisting of calcium, magnesium, sodium, and iron;
(a2) a second water treatment unit (A2) including an anion configured to remove negatively charged ions from the positively charged ion depleted water (06A) to form a negatively charged ion depleted water (09A), the negatively charged ions are comprised of one or more from the group consisting of iodine, chloride, and sulfate;
(a3) an optional third water treatment unit (A3) including a membrane configured to remove undesirable compounds from the negatively charged ion depleted water (09A) to form an undesirable compounds depleted water (12A), the undesirable compounds are comprised of one or more from the group consisting of dissolved organic chemicals, viruses, bacteria, and particulates;
(a4) an enclosure (ENC) having an interior (ENC1);
(a5) a plurality of growing assemblies (100, 200) positioned within the interior (ENC1) of the enclosure (ENC), each growing assembly (100, 200) configured to grow Beaufort Budman III (107, 207) or *cannabis* (107, 207);
(a6) a plurality of lights (L1, L2) configured to illuminate the interior (ENC1) of the enclosure (ENC);
(a7) a volatiles extraction system (VES) that is configured to separate volatiles (VOLT) from Beaufort Budman III (107, 207) or *cannabis* (107, 207) with use of a first solvent (SOLV1), the volatiles extraction system (VES) has an interior (VESI) that is configured to contain Beaufort Budman III (107, 207) or *cannabis* (107, 207), the volatiles extraction system (VES) is configured to accept a first solvent (SOLV1), the first solvent (SOLV1) is configured to contact the Beaufort Budman III (107, 207) or *cannabis* (107, 207) within the interior (VESI) of the volatiles extraction system (VES), the volatiles extraction system (VES) outputs a first solvent and volatiles mixture (FSVM);
(a8) a first solvent separation system (SSS) that is configured to separate the volatiles (VOLT) from the first solvent and volatiles mixture (FSVM), the first solvent separation system (SSS) has an interior (SSSI), the first solvent and volatiles mixture (FSVM) is transferred from the interior (VESI) of the volatiles extraction system (VES) to the interior (SSSI) of the first solvent separation system (SSS), the first solvent separation system (SSS) outputs a volatiles (VOLT) and a separated first solvent (SOLV1-S);
(a9) a volatiles and solvent mixing system (VSMS) that is configured to mix the volatiles (VOLT) with a second solvent (SOLV2), the volatiles (VOLT) that are introduced to the interior (VSMSI) of the volatiles and solvent mixing system (VSMS) are transferred from the volatiles extraction systems (VES), a second volatiles and solvent mixture (SVSM) is discharged from the interior (VSMSI) of the volatiles and solvent mixing system (VSMS);
(a10) a second solvent separation system (SEPSOL) that is configured to separate at least a portion of the second solvent (SOLV2) from the second volatiles and solvent mixture (SVSM) to produce concentrated volatiles (CVOLT);
(b) providing a source of water;
(c) removing positively charged ions and negatively charged ions and optionally undesirable compounds from the water of step (b);
(d) mixing the water after step (c) with macro-nutrients, micro-nutrients, or a pH adjustment solution to form a liquid mixture;
(e) pressurizing the liquid mixture after step (d) to form a pressurized liquid mixture;

(f) transferring the pressurized liquid mixture of step (e) to the plurality of growing assemblies; and
(g) illuminating the plurality of growing assemblies (100, 200) with the plurality of lights (L1, L2);
(h) growing Beaufort Budman III or *cannabis* within the plurality of growing assemblies after step (g);
(i) harvesting Beaufort Budman III or *cannabis* after growing Beaufort Budman III or *cannabis* in step (h);
(j) grinding Beaufort Budman III or *cannabis* after step (i); and
(k) extracting volatiles (VOLT) from Beaufort Budman III or *cannabis* after step (j) with a first solvent (SOLV1) to form a first solvent and volatiles mixture (FSVM);
(l) separating at least a portion of the volatiles (VOLT) from the first solvent and volatiles mixture (FSVM);
(m) mixing the volatiles with a second solvent (SOLV2) after step (l) to form a second volatiles and solvent mixture (SVSM); and
(n) evaporating at least a portion of the second solvent (SOLV2) from the second volatiles and solvent mixture (SVSM);
wherein:
the volatiles include one or more from the group consisting of oil, wax, terpenes;
the first solvent (SOLV1) includes one or more from the group consisting of acetone, alcohol, oil, butane, butter, carbon dioxide, coconut oil, ethanol, gas, gaseous carbon dioxide, hexane, isobutane, isopropanol, liquid carbon dioxide, liquid, naphtha, olive oil, pentane, propane, R134 refrigerant gas, subcritical carbon dioxide, supercritical carbon dioxide, vapor;
the second solvent (SOLV2) includes one or more from the group consisting of a liquid, acetone, alcohol, oil, ethanol;
the terpenes include one or more from the group consisting of limonene, humulene, pinene, linalool, caryophyllene, mycrene, eucalyptol, nerolidol, bisablol, and phytol.

In embodiments, the present disclosure describes a method to separate volatiles from *cannabis*, the method includes:
(a) providing a farming superstructure system (FSS), including:
  (a1) a first water treatment unit (A1) including a cation configured to remove positively charged ions from water to form a positively charged ion depleted water (06A), the positively charged ions are comprised of one or more from the group consisting of calcium, magnesium, sodium, and iron;
  (a2) a second water treatment unit (A2) including an anion configured to remove negatively charged ions from the positively charged ion depleted water (06A) to form a negatively charged ion depleted water (09A), the negatively charged ions are comprised of one or more from the group consisting of iodine, chloride, and sulfate;
  (a3) an optional third water treatment unit (A3) including a membrane configured to remove undesirable compounds from the negatively charged ion depleted water (09A) to form an undesirable compounds depleted water (12A), the undesirable compounds are comprised of one or more from the group consisting of dissolved organic chemicals, viruses, bacteria, and particulates;
  (a4) an enclosure (ENC) having an interior (ENC1);
  (a5) a plurality of growing assemblies (100, 200) positioned within the interior (ENC1) of the enclosure (ENC), each growing assembly (100, 200) configured to grow Beaufort Budman III (107, 207) or *cannabis* (107, 207); (a6) a plurality of lights (L1, L2) configured to illuminate the interior (ENC1) of the enclosure (ENC);
  (a7) a volatiles extraction system (VES) that is configured to separate volatiles (VOLT) from Beaufort Budman III (107, 207) or *cannabis* (107, 207) with use of a first solvent (SOLV1), the volatiles extraction system (VES) has an interior (VEST) that is configured to contain Beaufort Budman III (107, 207) or *cannabis* (107, 207), the volatiles extraction system (VES) is configured to accept a first solvent (SOLV1), the first solvent (SOLV1) is configured to contact the Beaufort Budman III (107, 207) or *cannabis* (107, 207) within the interior (VEST) of the volatiles extraction system (VES), the volatiles extraction system (VES) outputs a first solvent and volatiles mixture (FSVM);
  (a8) a first solvent separation system (SSS) that is configured to separate the volatiles (VOLT) from the first solvent and volatiles mixture (FSVM), the first solvent separation system (SSS) has an interior (SSSI), the first solvent and volatiles mixture (FSVM) is transferred from the interior (VEST) of the volatiles extraction system (VES) to the interior (SSSI) of the first solvent separation system (SSS), the first solvent separation system (SSS) outputs a volatiles (VOLT) and a separated first solvent (SOLV1-S);
  (a9) a volatiles and solvent mixing system (VSMS) that is configured to mix the volatiles (VOLT) with a second solvent (SOLV2), the volatiles (VOLT) that are introduced to the interior (VSMSI) of the volatiles and solvent mixing system (VSMS) are transferred from the volatiles extraction systems (VES), a second volatiles and solvent mixture (SVSM) is discharged from the interior (VSMSI) of the volatiles and solvent mixing system (VSMS);
  (a10) a second solvent separation system (SEPSOL) that is configured to separate at least a portion of the second solvent (SOLV2) from the second volatiles and solvent mixture (SVSM) to produce concentrated volatiles (CVOLT);
(b) providing a source of water;
(c) removing positively charged ions and negatively charged ions and optionally undesirable compounds from the water of step (b);
(d) mixing the water after step (c) with macro-nutrients, micro-nutrients, or a pH adjustment solution to form a liquid mixture;
(e) pressurizing the liquid mixture after step (d) to form a pressurized liquid mixture;
(f) transferring the pressurized liquid mixture of step (e) to the plurality of growing assemblies; and
(g) illuminating the plurality of growing assemblies (100, 200) with the plurality of lights (L1, L2);
(h) growing Beaufort Budman III or *cannabis* within the plurality of growing assemblies after step (g);
(i) harvesting Beaufort Budman III or *cannabis* after growing Beaufort Budman III or *cannabis* in step (h);
(j) grinding Beaufort Budman III or *cannabis* after step (i); and
(k) extracting volatiles (VOLT) from Beaufort Budman III or *cannabis* after step (j) with a first solvent (SOLV1) to form a first solvent and volatiles mixture (FSVM);

(l) separating at least a portion of the volatiles (VOLT) from the first solvent and volatiles mixture (FSVM);

(m) mixing the volatiles with a second solvent (SOLV2) after step (l) to form a second volatiles and solvent mixture (SVSM);

(n) separating at least a portion of the volatiles (VOLT) from the second volatiles and solvent mixture (SVSM); and (o) mixing a portion of the volatiles (VOLT) after step (n) with insects;

wherein:

the volatiles include one or more from the group consisting of oil, wax, terpenes;

the first solvent (SOLV1) includes one or more from the group consisting of acetone, alcohol, oil, butane, butter, carbon dioxide, coconut oil, ethanol, gas, gaseous carbon dioxide, hexane, isobutane, isopropanol, liquid carbon dioxide, liquid, naphtha, olive oil, pentane, propane, R134 refrigerant gas, subcritical carbon dioxide, supercritical carbon dioxide, vapor;

the second solvent (SOLV2) includes one or more from the group consisting of a liquid, acetone, alcohol, oil, ethanol;

the terpenes include one or more from the group consisting of limonene, humulene, pinene, linalool, caryophyllene, mycrene, eucalyptol, nerolidol, bisablol, and phytol.

the insects are comprised of one or more from the group consisting of Orthoptera order of insects, grasshoppers, crickets, cave crickets, Jerusalem crickets, katydids, weta, lubber, acrida, locusts, cicadas, ants, mealworms, agave worms, worms, bees, centipedes, cockroaches, dragonflies, beetles, scorpions, tarantulas, termites, insect lipids, and insect oil.

In embodiments, the present disclosure describes a method to separate volatiles from *cannabis*, the method includes:

(a) providing a farming superstructure system (FSS), including:

(a1) a first water treatment unit (A1) including a cation configured to remove positively charged ions from water to form a positively charged ion depleted water (06A), the positively charged ions are comprised of one or more from the group consisting of calcium, magnesium, sodium, and iron;

(a2) a second water treatment unit (A2) including an anion configured to remove negatively charged ions from the positively charged ion depleted water (06A) to form a negatively charged ion depleted water (09A), the negatively charged ions are comprised of one or more from the group consisting of iodine, chloride, and sulfate;

(a3) an optional third water treatment unit (A3) including a membrane configured to remove undesirable compounds from the negatively charged ion depleted water (09A) to form an undesirable compounds depleted water (12A), the undesirable compounds are comprised of one or more from the group consisting of dissolved organic chemicals, viruses, bacteria, and particulates;

(a4) an enclosure (ENC) having an interior (ENC1);

(a5) a plurality of growing assemblies (100, 200) positioned within the interior (ENC1) of the enclosure (ENC), each growing assembly (100, 200) configured to grow Beaufort Budman III (107, 207) or *cannabis* (107, 207);

(a6) a plurality of lights (L1, L2) configured to illuminate the interior (ENC1) of the enclosure (ENC);

(a7) a volatiles extraction system (VES) that is configured to separate volatiles (VOLT) from Beaufort Budman III (107, 207) or *cannabis* (107, 207) with use of a first solvent (SOLV1), the volatiles extraction system (VES) has an interior (VESI) that is configured to contain Beaufort Budman III (107, 207) or *cannabis* (107, 207), the volatiles extraction system (VES) is configured to accept a first solvent (SOLV1), the first solvent (SOLV1) is configured to contact the Beaufort Budman III (107, 207) or *cannabis* (107, 207) within the interior (VEST) of the volatiles extraction system (VES), the volatiles extraction system (VES) outputs a first solvent and volatiles mixture (FSVM);

(a8) a first solvent separation system (SSS) that is configured to separate the volatiles (VOLT) from the first solvent and volatiles mixture (FSVM), the first solvent separation system (SSS) has an interior (SSSI), the first solvent and volatiles mixture (FSVM) is transferred from the interior (VESI) of the volatiles extraction system (VES) to the interior (SSSI) of the first solvent separation system (SSS), the first solvent separation system (SSS) outputs a volatiles (VOLT) and a separated first solvent (SOLV1-S);

(a9) a volatiles and solvent mixing system (VSMS) that is configured to mix the volatiles (VOLT) with a second solvent (SOLV2), the volatiles (VOLT) that are introduced to the interior (VSMSI) of the volatiles and solvent mixing system (VSMS) are transferred from the volatiles extraction systems (VES), a second volatiles and solvent mixture (SVSM) is discharged from the interior (VSMSI) of the volatiles and solvent mixing system (VSMS);

(a10) a second solvent separation system (SEPSOL) that is configured to separate at least a portion of the second solvent (SOLV2) from the second volatiles and solvent mixture (SVSM) to produce concentrated volatiles (CVOLT);

(b) providing a source of water;

(c) removing positively charged ions and negatively charged ions and optionally undesirable compounds from the water of step (b);

(d) mixing the water after step (c) with macro-nutrients, micro-nutrients, or a pH adjustment solution to form a liquid mixture;

(e) pressurizing the liquid mixture after step (d) to form a pressurized liquid mixture;

(f) transferring the pressurized liquid mixture of step (e) to the plurality of growing assemblies; and (g) illuminating the plurality of growing assemblies (100, 200) with the plurality of lights (L1, L2);

(h) growing Beaufort Budman III or *cannabis* within the plurality of growing assemblies after step (g);

(i) harvesting Beaufort Budman III or *cannabis* after growing Beaufort Budman III or *cannabis* in step (h);

(j) grinding Beaufort Budman III or *cannabis* after step (i); and (k) extracting volatiles (VOLT) from Beaufort Budman III or *cannabis* after step (j) with a first solvent (SOLV1) to form a first solvent and volatiles mixture (FVSM);

(l) separating at least a portion of the volatiles (VOLT) from the first solvent and volatiles mixture (FVSM); and (m) mixing a portion of the volatiles (VOLT) after step (l) with insects;

wherein:
the first solvent (SOLV1) includes one or more from the group consisting of acetone, alcohol, oil, butane, butter, carbon dioxide, coconut oil, ethanol, gas, gaseous carbon dioxide, hexane, isobutane, isopropanol, liquid carbon dioxide, liquid, naphtha, olive oil, pentane, propane, R134 refrigerant gas, subcritical carbon dioxide, supercritical carbon dioxide, vapor;
the insects are comprised of one or more from the group consisting of Orthoptera order of insects, grasshoppers, crickets, cave crickets, Jerusalem crickets, katydids, weta, lubber, acrida, locusts, cicadas, ants, mealworms, agave worms, worms, bees, centipedes, cockroaches, dragonflies, beetles, scorpions, tarantulas, termites, insect lipids, and insect oil.

In embodiments, the present disclosure describes a method to separate and concentrate volatiles from *cannabis*, the method includes:
(a) providing *cannabis*;
(b) grinding *cannabis* after step (a);
(c) separating volatiles (VOLT) from *cannabis* after step (b) with a first solvent (SOLV1) to form a first solvent and volatiles mixture (FSVM);
(d) separating volatiles (VOLT) from the first solvent and volatiles mixture (FSVM);
(e) mixing the volatiles with a second solvent (SOLV2) after step (d) to form a second volatiles and solvent mixture (SVSM);
(h) separating the second solvent (SOLV2) from the second volatiles and solvent mixture (SVSM);
wherein:
the first solvent (SOLV1) includes one or more from the group consisting of butane, carbon dioxide, gas, gaseous carbon dioxide, hexane, isobutane, isopropanol, liquid carbon dioxide, naphtha, pentane, propane, R134 refrigerant gas, subcritical carbon dioxide, supercritical carbon dioxide, vapor;
the second solvent (SOLV2) includes one or more from the group consisting of a liquid, acetone, alcohol, oil, ethanol.

In embodiments, the method to separate and concentrate volatiles from *cannabis*, also includes: (e) mixing a portion of the volatiles (VOLT*) after step (d) with insects; wherein: the insects are comprised of one or more from the group consisting of Orthoptera order of insects, grasshoppers, crickets, cave crickets, Jerusalem crickets, katydids, weta, lubber, acrida, locusts, cicadas, ants, mealworms, agave worms, worms, bees, centipedes, cockroaches, dragonflies, beetles, scorpions, tarantulas, termites, insect lipids, and insect oil.

In embodiments, the method to separate and concentrate volatiles from *cannabis*, also includes: (f) cooling the second volatiles and solvent mixture (SVSM*) after step (e); and (g) filtering the second volatiles and solvent mixture (SVSM*).

In embodiments, the method to separate and concentrate volatiles from *cannabis*, also includes: in step (c), separating volatiles (VOLT*) from *cannabis* using a method that includes: (1) separating terpenes from the *cannabis* at a first temperature and a first pressure; and (2) separating oil and wax from the *cannabis* at a second temperature and a second pressure; wherein: the second temperature is greater than the first temperature; the second pressure is greater than the first pressure; the terpenes include one or more from the group consisting of limonene, humulene, pinene, linalool, caryophyllene, mycrene, eucalyptol, nerolidol, bisablol, and phytol; the volatiles include one or more from the group consisting of oil, wax, terpenes, and tetrahydrocannabinol (THC). The volatiles includes tetrahydrocannabinol (THC).

In embodiments, an analyzer (J70') is used to analyze the concentrated volatiles (CVOLT*), the analyzer (J70') includes one or more analyzers selected from the group consisting of liquid chromatography-mass spectrometry, gas chromatography-mass spectrometry (GC-MS), and inductively coupled plasma mass spectrometry (ICP-MS). In embodiments, the analyzer (J70') is used to detect for the presence of solvents, mycotoxins, microbes, moisture content, metals, pesticides, terpenes, and potency.

In embodiments, the concentrated volatiles (CVOLT*) includes: a nitrate (NO3) concentration having a maximum level of 1,000 mg NO3/kg of end-product; a mycotoxin analysis including: an ochratoxin A concentration having a maximum level of 10 µg/kg of end-product; a deoxynivalenol concentration having a maximum level of 2,000 µg/kg of end-product; a zearalenone concentration having a maximum level of 275 µg/kg of end-product; a fumonisins concentration having a maximum level of 2,500 µg/kg of end-product; a metals analysis including: a lead concentration having a maximum level of 0.5 mg/kg of end-product; a cadmium concentration having a maximum level of 0.5 mg/kg of end-product; a mercury concentration having a maximum level of 0.5 mg/kg of end-product; a 3-monochloropropane-1,2-diol (3-MCPD) concentration having a maximum level of 20 µg/kg of end-product; a dioxins and polychlorinated biphenyls (PCBs) concentration having a maximum level of 3 picogram/gram; a polycyclic aromatic hydrocarbon concentration having a maximum level of 5 µg/kg of end-product; a benzo(a)pyrene concentration having a maximum level of 2 or 5 µg/kg of end-product; a total concentration of benzo(a)pyrene, benz(a)anthracene, benzo (b)fluoranthene and chrysene having a maximum level of 15 or 30 µg/kg of end-product.

In embodiments, the insect traceability system includes a quality analysis of an that includes: a standard plate count (to test for total aerobic bacterial and total mold and yeasts) having less than: 500,000 colony forming unit per gram, 400,000 colony forming units per gram, 300,000 colony forming units per gram, 200,000 colony forming units per gram, 100,000 colony forming units per gram, 50,000 colony forming units per gram, 25,000 colony forming units per gram, or 5,000 colony forming units per gram; a coliform content less than 500 colony forming units per gram, 400 colony forming units per gram, 300 colony forming units per gram, 200 colony forming units per gram, 100 colony forming units per gram, 90 colony forming units per gram, 80 colony forming units per gram, 70 colony forming units per gram, 60 colony forming units per gram, 50 colony forming units per gram, 40 colony forming units per gram, 30 colony forming units per gram, 20 colony forming units per gram, or 10 colony forming units per gram; a coliform content less than 500,000 colony forming unit per gram, 400,000 colony forming units per gram, 300,000 colony forming units per gram, 200,000 colony forming units per gram, 100,000 colony forming units per gram, 50,000 colony forming units per gram, 25,000 colony forming units per gram, or 5,000 colony forming units per gram; a spore-forming sulphite reducing anaerobe content less than 500 colony forming units per gram, 400 colony forming units per gram, 300 colony forming units per gram, 200 colony forming units per gram, 100 colony forming units per gram, 90 colony forming units per gram, 80 colony forming units per gram, 70 colony forming units per gram, 60 colony forming units per gram, 50 colony forming units per gram, 40 colony forming units per gram, 30 colony forming units per gram, 20 colony forming units per gram, or 10 colony forming units per gram; a spore-forming sulphite reducing anaerobe content less than 500,000 colony forming unit per gram, 400,000 colony forming units per gram, 300,000 colony forming units per gram, 200,000 colony forming units per gram, 100,000 colony forming units per gram, 50,000 colony forming units per gram, 25,000 colony forming units per gram, or 5,000 colony forming units per gram; a *Pseudomonas aeruginosa* content less than 500 colony forming units per gram, 400 colony forming units per gram, 300 colony forming units per gram, 200 colony forming units per gram, 100 colony forming units per gram, 90 colony forming units per gram, 80 colony forming units per gram, 70 colony forming units per gram, 60 colony forming units per gram, 50 colony forming units per gram, 40 colony forming units per gram, 30 colony forming units per gram, 20 colony forming units per gram, or 10 colony forming units per gram; a *Pseudomonas aeruginosa* content less than 500,000 colony forming unit per gram, 400,000 colony forming units per gram, 300,000 colony forming units per gram, 200,000 colony forming units per gram, 100,000 colony forming units per gram, 50,000 colony forming units per gram, 25,000 colony forming units per gram, or 5,000 colony forming units per gram; a *E. coli* content less than 500 colony forming units per gram, 400 colony forming units per gram, 300 colony forming units per gram, 200 colony forming units per gram, 100 colony forming units per gram, 90 colony forming units per gram, 80 colony forming units per gram, 70 colony forming units per gram, 60 colony forming units per gram, 50 colony forming units per gram, 40 colony forming units per gram, 30 colony forming units per gram, 20 colony forming units per gram, or 10 colony forming units per gram; a *E. coli* content less than 500,000 colony forming unit per gram, 400,000 colony forming units per gram, 300,000 colony forming units per gram, 200,000 colony forming units per gram, 100,000 colony forming units per gram, 50,000 colony forming units per gram, 25,000 colony forming units per gram, or 5,000 colony forming units per gram.

FIG. 17E'

FIG. 17E' shows one non-limiting embodiment of a solvent separation system that is configured to evaporator the second solvent from the second volatiles and solvent mixture (SVSM) by use of a spray dryer (KAP).

A plurality of separators separate at least a small particulate portion (KCW) and a large particulate portion (KCY) from a volatiles and gas mixture (KBV) that is discharged in the drying chamber (KBG) of a spray dryer (KAP) evaporator (KAO). The spray dryer (KAP) is type of evaporator (KAO) that evaporates liquid from a second volatiles and solvent mixture (SVSM). A first separator (KCA), second separator (KCI), and a third separator (KCR) are configured to accept a volatiles and gas mixture (KBV) from the drying chamber (KBG) of a spray dryer (KAP). In embodiments, the first separator (KCA) is a cyclone or a filter. In embodiments, the second separator (KCI) is a cyclone or a filter. In embodiments, the third separator (KCR) is a sifter or a filter. The third separator (KCR) accepts first separated volatiles (KCG) from the first separator (KCA) and second separated volatiles (KCP) from the second separator (KCI) and separates at least a small particulate portion (KCW) and a large particulate portion (KCY) therefrom. In embodiments, the small particulate portion (KCW) and a large particulate portion (KCY) are crystals, solids, and contain tetrahydrocannabinol (THC).

The second volatiles and solvent mixture (SVSM) is introduced to a liquid input (KAR) of the spray dryer (KAP). The spray dryer (KAP) has a top (K-T) and a bottom (K-B). The spray dryer (KAP) has a vertical axis (KYY) and a horizontal axis (KXY). As shown in FIG. 17E', the liquid input (KAR) is located positioned towards the top (K-T) of the spray dryer (KAP). In embodiments, the liquid input (KAR) to the spray dryer (KAP) is positioned closer to the bottom (K-B) of the spray dryer (KAP).

In embodiments, the range of height of the drying chamber (KBG) is selected from one or more from the group 6 feet tall to 8 feet tall, 8 feet tall to 10 feet tall, 10 feet tall to 12 feet tall, 12 feet tall to 14 feet tall, 14 feet tall to 16 feet tall, 16 feet tall to 18 feet tall, 18 feet tall to 20 feet tall, 20 feet tall to 22 feet tall, 22 feet tall to 24 feet tall, 24 feet tall to 26 feet tall, 26 feet tall to 28 feet tall, 28 feet tall to 30 feet tall, 30 feet tall to 32 feet tall, 32 feet tall to 34 feet tall, 34 feet tall to 36 feet tall, 36 feet tall to 38 feet tall, 38 feet tall to 40 feet tall, and 40 feet tall to 50 feet tall.

In embodiments, the range of diameter of the drying chamber (KBG) is selected from one or more from the group 2 feet in diameter to 4 feet in diameter, 4 feet in diameter to 6 feet in diameter, 6 feet in diameter to 8 feet in diameter, 8 feet in diameter to 10 feet in diameter, 10 feet in diameter to 12 feet in diameter, 12 feet in diameter to 14 feet in diameter, 14 feet in diameter to 16 feet in diameter, 16 feet in diameter to 18 feet in diameter, 18 feet in diameter to 20 feet in diameter, 20 feet in diameter to 22 feet in diameter, 22 feet in diameter to 24 feet in diameter, 24 feet in diameter to 26 feet in diameter, 26 feet in diameter to 28 feet in diameter, 28 feet in diameter to 30 feet in diameter, 30 feet in diameter to 32 feet in diameter, 32 feet in diameter to 34 feet in diameter, 34 feet in diameter to 36 feet in diameter, 36 feet in diameter to 38 feet in diameter, and 38 feet in diameter to 40 feet in diameter. In embodiments, the drying chamber (KBG) is comprised of a material that is selected from one or more from the group consisting of carbon steel, graphite, Hastelloy alloy, nickel, stainless steel, tantalum, and titanium.

A flow sensor (KEQ) is made available to measure the flow to the second volatiles and solvent mixture (SVSM) prior to being introduced to the spray dryer (KAP). The flow sensor (KEQ) is configured to input or output a signal (KER) to the computer (COMP). The flow sensor (KEQ) measures the flow of the second volatiles and solvent mixture (SVSM) that is introduced to the liquid input (KAR) of the spray dryer (KAP). A valve (KEC) is positioned to regulate the flow of the second volatiles and solvent mixture (SVSM) prior to being introduced to the spray dryer (KAP). The valve (KEC) has a controller (KED) that is configured to input or output a signal (KEE) to the computer (COMP). The valve (KEC) and the flow sensor (KEQ) may be used together in a flow control loop to set the flowrate of spray dryer (KAP) to a flow rate that includes one or more from the group consisting of: 0.5 gallons per minute (GPM) to 1 GPM, 1 GPM to 1.5 GPM, 1.5 GPM to 2 GPM, 2 GPM to 2.5 GPM, 2.5 GPM to 3 GPM, 3 GPM to 3.5 GPM, 3.5 GPM to 4 GPM, 4 GPM to 4.5 GPM, 4.5 GPM to 5 GPM, 5 GPM to 5.5 GPM, 5.5 GPM to 6 GPM, 6 GPM to 6.5 GPM, 6.5 GPM to 7 GPM, 7 GPM to 7.5 GPM, 7.5 GPM to 8 GPM, 8 GPM to 8.5 GPM, 8.5 GPM to 9 GPM, 9 GPM to 9.5 GPM, 9.5 GPM to 10 GPM, and 10 GPM to 10.5 GPM.

In embodiments, the second solvent content of the second volatiles and solvent mixture (SVSM) that is transferred to the mixture input (KAR) of the spray dryer (KAP) ranges between 50 weight percent solvent and 95 weight percent solvent. In embodiments, the solvent content of the second volatiles and solvent mixture (SVSM) that is transferred to the mixture input (KAR) of the spray dryer (KAP) ranges between 60 weight percent solvent and 92 weight percent solvent.

In embodiments, the second volatiles and solvent mixture (SVSM) is pressurized. An inlet pressure sensor (KBE) is provided to measure the inlet pressure prior to the spray dryer (KAP). The inlet pressure sensor (KBE) measures the pressure of the second volatiles and solvent mixture (SVSM) that is introduced to the liquid input (KAR) of the spray dryer (KAP). The inlet pressure sensor (KBE) transmits a signal (KBF) to the computer (COMP).

In embodiments, the range of pressure that the inlet pressure sensor (KBE) transmits to the computer (COMP) ranges from one or more from the group consisting of: 5 pounds per square inch (PSI) to 10 PSI; 10 PSI to 15 PSI; 15 PSI to 20 PSI; 20 PSI to 25 PSI; 25 PSI to 30 PSI; 30 PSI to 35 PSI; 35 PSI to 40 PSI; 40 PSI to 45 PSI; 45 PSI to 50 PSI; 50 PSI to 55 PSI; 55 PSI to 60 PSI; 60 PSI to 65 PSI; 65 PSI to 70 PSI; 70 PSI to 75 PSI; 75 PSI to 80 PSI; 80 PSI to 85 PSI; 85 PSI to 90 PSI; 90 PSI to 95 PSI; 95 PSI to 100 PSI; 100 PSI to 125 PSI; 125 PSI to 145 PSI; 145 PSI to 170 PSI; 170 PSI to 195 PSI; 195 PSI to 200 PSI; 200 PSI to 220 PSI; 220 PSI to 250 PSI; 250 PSI to 275 PSI; 275 PSI to 300 PSI; 300 PSI to 350 PSI; 350 PSI to 402 PSI; 402 PSI to 463 PSI; 463 PSI to 532 PSI; 532 PSI to 612 PSI; 612 PSI to 704 PSI; 704 PSI to 809 PSI; 809 PSI to 930 PSI; 930 PSI to 1070 PSI; 1,070 PSI to 1,231 PSI; 1,231 PSI to 1,415 PSI; 1,415 PSI to 1,627 PSI; 1,627 PSI to 1,872 PSI; 1,872 PSI to 2,152 PSI; 2,152 PSI to 2,475 PSI; 2,475 PSI to 2,846 PSI; 2,846 PSI to 3,273 PSI; 3,273 PSI to 3,764 PSI; 3,764 PSI to 4,329 PSI; 4,329 PSI to 4,978 PSI; 4,978 PSI to 5,725 PSI; 5,725 PSI to 6,584 PSI; 6,584 PSI to 7,571 PSI; 7,571 PSI to 8,707 PSI; 8,707 PSI to 10,013 PSI; 10,013 PSI to 11,515 PSI; and 11,515 PSI to 15,000 PSI.

In embodiments, the residence time of the second volatiles and solvent mixture (SVSM) and gas supply (KAG) within the spray dryer (KAP) or drying chamber (KBG) ranges from one or more from the group selected from: 0.1 seconds to 1 seconds, 1 seconds to 2 seconds, 2 seconds to 3 seconds, 3 seconds to 4 seconds, 4 seconds to 5 seconds, 5 seconds to 6 seconds, 6 seconds to 7 seconds, 7 seconds to 8 seconds, 8 seconds to 9 seconds, 9 seconds to 10 seconds, 10 seconds to 12 seconds, 12 seconds to 15 seconds, 15 seconds to 20 seconds, 20 seconds to 25 seconds, 25 seconds to 30 seconds, 30 seconds to 35 seconds, 35 seconds to 40 seconds, 40 seconds to 45 seconds, 45 seconds to 50 seconds, 50 seconds to 55 seconds, 55 seconds to 60 seconds, 60 seconds to 65 seconds, 65 seconds to 70 seconds, 70 seconds to 80 seconds, 80 seconds to 90 seconds, 90 seconds to 100 seconds, 100 seconds to 110 seconds, and 110 seconds to 120 seconds.

A gas supply (KAG) is made available to the spray dryer (KAP) via a gas input (KAQ). In embodiments, the gas supply (KAG) may include a gas. In embodiments, the gas supply (KAG) may include a carbon dioxide. In embodiments, the gas supply (KAG) may include air. In embodiments, the gas supply (KAG) may include an oxygen-containing gas which includes air, oxygen-enriched-air i.e. greater than 21 mole % O2, and substantially pure oxygen, i.e. greater than about 95 mole % oxygen (the remainder usually comprising N2 and rare gases). In embodiments, the gas supply (KAG) may include flue gas which includes a vapor or gaseous mixture containing varying amounts of nitrogen (N2), carbon dioxide (CO2), water (H2O), and oxygen (O2). Flue gas is generated from the thermochemical process of combustion. In embodiments, the gas supply (KAG) may include a combustion stream.

A filter (KAH) is made available to remove particulates from the gas supply (KAG) prior to being introduced to the gas input (KAQ) of the spray dryer (KAP). A filter (KAH) may include a sorbent (KAH') and be configured to adsorb and/or absorb at least one component that is contained within the gas supply (KAG) prior to being introduced to the gas input (KAQ) of the spray dryer (KAP). In embodiments, the filter (KAH) may be a dehumidifier. In embodiments, the filter (KAH) may remove water from the gas supply (KAG) using an adsorbent. In embodiments, the adsorbent used in the filter (KAH) be selected from one or more from the group consisting of 3 Angstrom molecular sieve, 3 Angstrom zeolite, 4 Angstrom molecular sieve, 4 Angstrom zeolite, activated alumina, activated carbon, adsorbent, alumina, carbon, catalyst, clay, desiccant, molecular sieve, polymer, resin, and silica gel. In embodiments, the filter (KAH) may include any conceivable means to remove moisture from the gas supply (KAG), such as an air conditioner, cooling tower, an adsorber, a plurality of adsorbers. In embodiments, the filter (KAH) may include a cooling tower followed by an adsorber. In embodiments, the filter (KAH) may include a cooling tower followed by a plurality of adsorbers. In embodiments, an adsorber is a packed bed of adsorbent. In embodiments, an adsorber is a moving bed of adsorbent. In embodiments, an adsorber contains an adsorbent.

A fan (KAI) is made available and is configured to introduce the gas supply (KAG) to the spray dryer (KAP). The fan (KAI) is equipped with a motor (KAJ) that has a controller (KAK) which is configured to input or output a signal (KAL) to the computer (COMP). In embodiments, the fan (KAI) operates within a range that is selected from one or more from the group consisting of: 350 standard cubic feet per minute (SCFM) to 3,500 SCFM; 700 SCFM to 7,000 SCFM; 1,050 SCFM to 10,500 SCFM; 1,400 SCFM to 14,000 SCFM; 1,750 SCFM to 17,500 SCFM; 2,100 SCFM to 21,000 SCFM; 2,450 SCFM to 24,500 SCFM; 2,800 SCFM to 28,000 SCFM; 3,150 SCFM to 31,500 SCFM; 3,500 SCFM to 35,000 SCFM; 3,850 SCFM to 38,500 SCFM; 4,200 SCFM to 42,000 SCFM; 4,550 SCFM to 45,500 SCFM; 4,900 SCFM to 49,000 SCFM; 5,250 SCFM to 52,500 SCFM; 5,600 SCFM to 56,000 SCFM; 5,950 SCFM to 59,500 SCFM; 6,300 SCFM to 63,000 SCFM; 6,650 SCFM to 66,500 SCFM; 7,000 SCFM to 70,000 SCFM; and 7,350 SCFM to 73,500 SCFM.

In embodiments, at a second volatiles and solvent mixture (SVSM) flow rate of 0.5 to 1 GPM, the fan (KAI) operates in a range between 350 standard cubic feet per minute (SCFM) to 3,500 SCFM. In embodiments, at a second volatiles and solvent mixture (SVSM) flow rate of 0.5 to 1 GPM, the fan (KAI) operates in a range between 700 SCFM to 7,000 SCFM. In embodiments, at a second volatiles and solvent mixture (SVSM) flow rate of 1 to 1.5 GPM, the fan (KAI) operates in a range between 1,050 SCFM to 10,500 SCFM. In embodiments, at a second volatiles and solvent mixture (SVSM) flow rate of 1.5 to 5 GPM, the fan (KAI) operates in a range between 1,400 SCFM to 14,000 SCFM. In embodiments, at a second volatiles and solvent mixture (SVSM) flow rate of 2 to 2.5 GPM, the fan (KAI) operates in a range between 1,750 SCFM to 17,500 SCFM. In embodiments, at a second volatiles and solvent mixture (SVSM) flow rate of 2.5 to 3 GPM, the fan (KAI) operates in a range between 2,100 SCFM to 21,000 SCFM. In embodiments, at a second volatiles and solvent mixture (SVSM) flow rate of 3 to 3.5 GPM, the fan (KAI) operates in a range between 2,450 SCFM to 24,500 SCFM. In embodiments, at a second volatiles and solvent mixture (SVSM) flow rate of 3.5 to 4 GPM, the fan (KAI) operates in a range between 2,800 SCFM to 28,000 SCFM. In embodiments, at a second volatiles and solvent mixture (SVSM) flow rate of 4 to 4.5 GPM, the fan (KAI) operates in a range between 3,150 SCFM to 31,500 SCFM. In embodiments, at a second volatiles and solvent mixture (SVSM) flow rate of 4.5 to 5 GPM, the fan (KAI) operates in a range between 3,500 SCFM to 35,000 SCFM. In embodiments, at a second volatiles and solvent mixture (SVSM) flow rate of 5 to 5.5 GPM, the fan (KAI) operates in a range between 3,850 SCFM to 38,500 SCFM. In embodiments, at a second volatiles and solvent mixture (SVSM) flow rate of 5.5 to 6 GPM, the fan (KAI) operates in a range between 4,200 SCFM to 42,000 SCFM. In embodiments, at a second volatiles and solvent mixture (SVSM) flow rate of 6 to 6.5 GPM, the fan (KAI) operates in a range between 4,550 SCFM to 45,500 SCFM. In embodiments, at a second volatiles and solvent mixture (SVSM) flow rate of 6.5 to 7 GPM, the fan (KAI) operates in a range between 4,900 SCFM to 49,000 SCFM. In embodiments, at a second volatiles and solvent mixture (SVSM) flow rate of 7 to 7.5 GPM, the fan (KAI) operates in a range between 5,250 SCFM to 52,500 SCFM. In embodiments, at a second volatiles and solvent mixture (SVSM) flow rate of 7.5 to 8 GPM, the fan (KAI) operates in a range between 5,600 SCFM to 56,000 SCFM. In embodiments, at a second volatiles and solvent mixture (SVSM) flow rate of 8 to 8.5 GPM, the fan (KAI) operates in a range between 5,950 SCFM to 59,500 SCFM. In embodiments, at a second volatiles and solvent mixture (SVSM) flow rate of 8.5 to 9 GPM, the fan (KAI) operates in a range between 6,300 SCFM to 63,000 SCFM. In embodiments, at a second volatiles and solvent mixture (SVSM) flow rate of 9 to 9.5 GPM, the fan (KAI) operates in a range between 6,650 SCFM to 66,500 SCFM. In embodiments, at a second volatiles and solvent mixture (SVSM) flow rate of 9.5 to 10 GPM, the fan (KAI) operates in a range between 7,000 SCFM to 70,000 SCFM. In embodiments, at a second volatiles and solvent mixture (SVSM) flow rate of 10 to 10.5 GPM, the fan (KAI) operates in a range between 7,350 SCFM to 73,500 SCFM.

An air heater (KAF) is made available to heat the gas supply (KAG) prior to being introduced to the gas input (KAQ) of the spray dryer (KAP). FIG. 17E' shows the gas supply (KAG) first entering the filter (KAH), then the fan (KAI), and then the air heater (KAF). It is to be noted that combinations of the filter (KAH), fan (KAI), and air heater (KAF) shown in FIG. 17E' are non-limiting. For example, the fan (KAI) may be before the filter (KAH), the fan (KAI) may be after the air heater (KAF), the filter (KAH) may be after the fan (KAI), the filter (KAH) may be after the air heater (KAF), the air heater (KAF) may be before the fan (KAI). The air heater (KAF) provides a heated gas supply (KAG) to the spray dryer (KAP).

In embodiments, the ideal range that the temperature sensor (KAM) inputs into the computer (COMP) while measuring the heated gas supply (KAG) is preferably set to 250 degrees Fahrenheit to 600 degrees Fahrenheit, but more preferably to 300 degrees Fahrenheit to 5000 degrees Fahrenheit, but more preferably to 350 degrees Fahrenheit to 450 degrees Fahrenheit. In embodiments, the heated gas supply (KAG) has a temperature selected from the group consisting of: 250 degrees Fahrenheit to 275 degrees Fahrenheit; 275 degrees Fahrenheit to 300 degrees Fahrenheit; 300 degrees Fahrenheit to 325 degrees Fahrenheit; 325 degrees Fahrenheit to 350 degrees Fahrenheit; 350 degrees Fahrenheit to 375 degrees Fahrenheit; 375 degrees Fahrenheit to 400 degrees Fahrenheit; 400 degrees Fahrenheit to 425 degrees Fahrenheit; 425 degrees Fahrenheit to 450 degrees Fahrenheit; 450 degrees Fahrenheit to 475 degrees Fahrenheit; 475 degrees Fahrenheit to 500 degrees Fahrenheit; 500 degrees Fahrenheit to 525 degrees Fahrenheit; 525 degrees Fahrenheit to 550 degrees Fahrenheit; 550 degrees Fahrenheit to 575 degrees Fahrenheit; 575 degrees Fahrenheit to 600 degrees Fahrenheit; 600 degrees Fahrenheit to 625 degrees Fahrenheit; 625 degrees Fahrenheit to 650 degrees Fahrenheit; 650 degrees Fahrenheit to 675 degrees Fahrenheit; 675 degrees Fahrenheit to 700 degrees Fahrenheit; 700 degrees Fahrenheit to 725 degrees Fahrenheit; 725 degrees Fahrenheit to 750 degrees Fahrenheit; 750 degrees Fahrenheit to 775 degrees Fahrenheit; and 775 degrees Fahrenheit to 800 degrees Fahrenheit.

The temperature sensor (KAM) is configured to input a signal (KAN) to the computer (COMP). The computer (COMP), temperature sensor (KAM), and the motor (KAJ) of the fan (KAI) may be used together in a temperature control loop to maintain a constant pre-determined temperature of heated gas to the spray dryer (KAP).

In embodiments, the heated gas supply (KAG) is created by indirect contact with steam in the air heater (KAF). In embodiments, the air heater (KAF) may be electrically heated or heated by a combustion steam or flue gas. The heated gas supply (KAG) may also be a combustion stream. In embodiments, the air heater (KAF) accepts a source of steam from a steam drum (LBE) as shown on FIG. 17F'. The steam drum (LBE) provides an eighth steam supply (LDM) to the air heater (KAF), as discussed below. The eighth steam supply (LDM) may be saturated or superheated steam. A steam flow control valve (KAA) is configured to regulate the flow of the steam that passes through the air heater (KAF). The steam flow control valve (KAA) is equipped with a controller (KAB) that sends a signal (KAC) to or from the computer (COMP).

A flow sensor (KAD) is configured to measure the flow of the steam that passes through the air heater (KAF). The flow sensor (KAD) sends a signal (KAE) to the computer (COMP). The computer (COMP), steam flow control valve (KAA), and the flow sensor (KAD) may be used in a control loop to control the flow of steam that is passed through the air heater (KAF). In embodiments, the computer (COMP), steam flow control valve (KAA), flow sensor (KAD), temperature sensor (KAM), and motor (KAJ) of the fan (KAI) may be used together in a temperature control loop to maintain a constant pre-determined temperature of heated gas to the spray dryer (KAP). The steam flow control valve (KAA) may be positioned before or after the air heater (KAF). The air heater (KAF) discharges an eighth condensate (LJA) to the condensate tank (LAP) that is shown on FIG. 17F'. A condensate temperature sensor (KK1) is configured to measure the temperature of the eighth condensate (LJA) that leaves the air heater (KAF). The condensate temperature sensor (KK1) sends a signal (KK2) to the computer (COMP).

In embodiments, the solvent separation system separates liquid solvent from the second volatiles and solvent mixture (SVSM) by converting the liquid into a vapor. In embodiments, the solvent separation system evaporates liquid from within the second volatiles and solvent mixture (SVSM) by use of an evaporator (KAO). A spray dryer (KAP) is a type of evaporator (KAO).

In embodiments, the spray dryer (KAP) evaporator (KAO) operates at a temperature greater than the boiling point of the liquid solvent within the second volatiles and solvent mixture (SVSM) to vaporize the liquid portion of the second volatiles and solvent mixture (SVSM) into a vapor. In embodiments, the spray dryer (KAP) is configured to mix a heated gas supply (KAG') with a second volatiles and solvent mixture (SVSM) under precise computer operated automated control to generate a volatiles and gas mixture (KBV).

In embodiments, the spray dryer (KAP) has an interior (KAP') which accepts both the heated gas supply (KAG') and the second volatiles and solvent mixture (SVSM). In embodiments, the spray dryer (KAP) has an interior (KAP') which accepts both the heated gas supply (KAG') via the gas input (KAQ) and the second volatiles and solvent mixture (SVSM) via the liquid input (KAR). In embodiments, the spray dryer (KAP) is equipped with a plurality of spray nozzles (KBC) that dispense the second volatiles and solvent mixture (SVSM) within the interior (KAP') of the spray dryer (KAP).

In embodiments the spray dryer (KAP) has a drying chamber (KBG) which evaporates liquid within the second volatiles and solvent mixture (SVSM). In embodiments, interior (KBG') of the drying chamber (KBG) is located within the interior (KAP') of the spray dryer (KAP). In embodiments the spray dryer (KAP) has an air distributor (KAT) that is configured to accept the heated gas supply (KAG') from the gas input (KAQ) and distribute it to the interior (KAP') of the drying chamber (KBG). In embodiments, the heated gas supply (KAG') is introduced to the interior (KAP') of the spray dryer (KAP) via the air distributor (KAT) using centrifugal momentum.

In embodiments, the second volatiles and solvent mixture (SVSM) is introduced to the interior (KAP') of the spray dryer (KAP) via a plurality of spray nozzles (KBC). In embodiments, the second volatiles and solvent mixture (SVSM) is introduced to the interior (KBG') of the drying chamber (KBG) via a plurality of spray nozzles (KBC). In embodiments, the second volatiles and solvent mixture (SVSM) is introduced to the interior (KAP') of the spray dryer (KAP) via a rotary atomizer (KAU) which may have a spray nozzle (KBC) or a plurality of spray nozzles (KBC). In embodiments, the second volatiles and solvent mixture (SVSM) is introduced to the interior (KBG') of the drying chamber (KBG) via a rotary atomizer (KAU). In embodiments, the rotary atomizer (KAU) dispenses second volatiles and solvent mixture (SVSM) or start-up liquid (KEO) into the interior (KBG') of the drying chamber (KBG) via an opening (KBD) or a plurality of openings (KBD) or a spray nozzle (KBC) or a plurality of spray nozzles (KBC).

In embodiments the pressure drop across the opening (KBD), plurality of openings (KBD), spray nozzle (KBC), or plurality of spray nozzles (KBC) includes one or more from the group consisting of: 5 pounds per square inch (PSI) to 10 PSI; 10 PSI to 15 PSI; 15 PSI to 20 PSI; 20 PSI to 25 PSI; 25 PSI to 30 PSI; 30 PSI to 35 PSI; 35 PSI to 40 PSI; 40 PSI to 45 PSI; 45 PSI to 50 PSI; 50 PSI to 55 PSI; 55 PSI to 60 PSI; 60 PSI to 65 PSI; 65 PSI to 70 PSI; 70 PSI to 75 PSI; 75 PSI to 80 PSI; 80 PSI to 85 PSI; 85 PSI to 90 PSI; 90 PSI to 95 PSI; 95 PSI to 100 PSI; 100 PSI to 125 PSI; 125 PSI to 145 PSI; 145 PSI to 170 PSI; 170 PSI to 195 PSI; 195 PSI to 200 PSI; 200 PSI to 220 PSI; 220 PSI to 250 PSI; 250 PSI to 275 PSI; 275 PSI to 300 PSI; 300 PSI to 350 PSI; 350 PSI to 402 PSI; 402 PSI to 463 PSI; 463 PSI to 532 PSI; 532 PSI to 612 PSI; 612 PSI to 704 PSI; 704 PSI to 809 PSI; 809 PSI to 930 PSI; 930 PSI to 1070 PSI; 1,070 PSI to 1,231 PSI; 1,231 PSI to 1,415 PSI; 1,415 PSI to 1,627 PSI; 1,627 PSI to 1,872 PSI; 1,872 PSI to 2,152 PSI; 2,152 PSI to 2,475 PSI; 2,475 PSI to 2,846 PSI; 2,846 PSI to 3,273 PSI; 3,273 PSI to 3,764 PSI; 3,764 PSI to 4,329 PSI; 4,329 PSI to 4,978 PSI; 4,978 PSI to 5,725 PSI; 5,725 PSI to 6,584 PSI; 6,584 PSI to 7,571 PSI; 7,571 PSI to 8,707 PSI; 8,707 PSI to 10,013 PSI; 10,013 PSI to 11,515 PSI; and 11,515 PSI to 15,000 PSI.

The rotary atomizer (KAU) has a motor (KAV) and a controller (KAW) that is configured to input or output a signal (KAX) to the computer (COMP). In embodiments, the motor (KAV) of the rotary atomizer (KAU) is connected to a shaft (KBA). In embodiments, the shaft (KBA) is connected to a disc (KBB). In embodiments, the disc (KBB) has an opening (KBD) or a plurality of openings (KBD) or spray nozzle (KBC) or a plurality of spray nozzles (KBC) installed on it. In embodiments, the motor (KAV) rotates the shaft (KBA) which in turn rotates the disc (KBB) and then distributes the second volatiles and solvent mixture (SVSM) or start-up liquid (KEO) to the interior (KAP') of the spray dryer (KAP) or the interior (KBG') of the drying chamber (KBG).

In embodiments, the spray nozzle (KBC) or plurality of spray nozzles (KBC) each have an opening (KBD). In embodiments, the spray nozzle (KBC) or plurality of spray nozzles (KBC) each have a spray aperture (KK4). In embodiments, the spray nozzle (KBC) or plurality of spray nozzles (KBC) each have an orifice (KK5). In embodiments, the spray nozzle (KBC) or plurality of spray nozzles (KBC) each have an impingement surface (KK6).

In embodiments, at least a portion of the second volatiles and solvent mixture (SVSM) or start-up liquid (KEO) contact an impingement surface (KK6) prior to being dispensed to the interior (KAP') of the spray dryer (KAP) or the interior (KBG') of the drying chamber (KBG) via a spray aperture (KK4). In embodiments, at least a portion of the second volatiles and solvent mixture (SVSM) or start-up liquid (KEO) pass through an orifice (KK5) prior to being dispensed to the interior (KAP') of the spray dryer (KAP) or the interior (KBG') of the drying chamber (KBG) via a spray aperture (KK4). In embodiments, at least a portion of the second volatiles and solvent mixture (SVSM) or start-up liquid (KEO) pass through the spray nozzle (KBC) or plurality of spray nozzles (KBC) and contact an orifice (KK5) prior to being dispensed to the interior (KAP') of the spray dryer (KAP) or the interior (KBG') of the drying chamber (KBG).

In embodiments, the plurality of spray nozzles (KBC) have a spray pattern is a hollow cone, full cone, or a flat spray. In embodiments, the spray pattern includes is that of the whirling type. In embodiments, the whirling type spray nozzle sprays the second volatiles and solvent mixture (SVSM) or start-up liquid (KEO) while rotating the liquid (SVSM, KEO) across a portion of the spray nozzle (KBC). A whirling type spray nozzle (KBC) is one that sprays the second volatiles and solvent mixture (SVSM) or start-up liquid (KEO) while rotating the liquid (SVSM, KEO) across a portion of the spray nozzle (KBC) after a pressure drop has taken place. A whirling type spray nozzle (KBD) is one that sprays the second volatiles and solvent mixture (SVSM) or start-up liquid (KEO) while rotating the liquid (SVSM, KEO) across a portion of the spray nozzle after the liquid or slurry has passed through an orifice.

In embodiments, a whirling type spray nozzle (KBD) includes an orifice (KK5) and an impingement surface (KK6): the orifice (KK5) is configured to accept second volatiles and solvent mixture (SVSM) or start-up liquid (KEO) and drop the pressure from a first higher pressure to a second lower pressure, the first pressure being greater than the second pressure; an impingement surface (KK6) that is configured to accept the liquid (SVSM, KEO) at the second pressure at change its direction to impart rotational or centrifugal momentum.

A whirling type spray nozzle (KBD) is one that sprays a liquid (SVSM, KEO) under cyclone conditions. In embodiments, the spray nozzle (KBD) is comprised of ceramic, metal, brass, 316 stainless steel, 316L stainless steel, stainless steel, polytetrafluoroethylene (PTFE), or plastic, or a composite material. In embodiments, the spray nozzle (KBC) opening (KBD) ranges from 0.030 inches to 0.30 inches. In embodiments, the spray nozzle (KBC) opening (KBD) ranges from 0.03 inches to 0.16 inches. In embodiments, the spray nozzle (KBC) orifice (KK5) ranges from 0.030 inches to 0.30 inches. In embodiments, the spray nozzle (KBC) orifice (KK5) ranges from 0.03 inches to 0.16 inches.

In embodiments, the spray nozzle (KBC) has an orifice (KK5) and a spray aperture (KK4). In embodiments, the spray angle of the spray nozzle (KBC) ranges from 15° to 120°. In embodiments, the spray angle of the spray nozzle (KBC) ranges from 30° to 100°. In embodiments, the spray angle of the spray nozzle (KBC) ranges from 40° to 90°. In embodiments, the spray angle of the spray nozzle (KBC) ranges from 50° to 85°. In embodiments, the spray angle of the spray nozzle (KBC) ranges from 70° to 75°. In embodiments, the spray angle of the spray nozzle (KBC) ranges from 45° to 89°. In embodiments, the spray angle of the spray nozzle (KBC) ranges from 90° to 134°. In embodiments, the spray angle of the spray nozzle (KBC) ranges from 135° to 179°. In embodiments, the spray angle of the spray nozzle ranges (KBC) from 180° to 360°.

In embodiments, the spray nozzle (KBC) creates solid volatiles particulates that have a size selected from one or more from the group consisting of: 0.01 microns to 0.1 microns, 0.1 microns to 0.5 microns, 0.5 microns to 1 microns, 1 microns to 2 microns, 2 microns to 4 microns, 4 microns to 8 microns, 8 microns to 10 microns, 10 microns to 20 microns, 20 microns to 30 microns, 30 microns to 40 microns, 40 microns to 50 microns, 50 microns to 60 microns, 60 microns to 70 microns, 70 microns to 80 microns, 80 microns to 90 microns, 90 microns to 100 microns, and 100 microns to 200 microns.

In embodiments, the spray nozzle (KBC) creates solid volatiles particulates that have a size selected from one or more from the group consisting of: 0.001 microns to 0.002 microns; 0.002 microns to 0.004 microns; 0.004 microns to 0.008 microns; 0.008 microns to 0.016 microns; 0.016 microns to 0.032 microns; 0.032 microns to 0.064 microns; 0.064 microns to 0.122 microns; 0.128 microns to 0.251 microns; 0.256 microns to 0.512 microns; 0.512 microns to 1.0 microns; 1.0 microns to 1.5 microns; 1.5 microns to 2.3 microns; 2.3 microns to 3.5 microns; 3.5 microns to 5.2 microns; 5.2 microns to 7.8 microns; 7.8 microns to 12 microns; 12 microns to 17 microns; 17 microns to 26 microns; 26 microns to 39 microns; 39 microns to 59 microns; 59 microns to 89 microns; 89 microns to 133 microns; 133 microns to 199 microns; 199 microns to 299 microns; 299 microns to 448 microns; 448 microns to 673 microns; 673 microns to 1009 microns; 1009 microns to 1513 microns; 1513 microns to 2270 microns; 2270 microns to 3405 microns; 3405 microns to 5108 microns; and 5108 microns to 7661 microns.

In embodiments, each spray nozzle (KBC) is affixed to the disc (KAB) using one or more connectors selected from the group consisting of national pipe thread, British standard pipe thread, and welded. In embodiments, the spray nozzle (KBC) is connected to the disc (KAB) using 0.25 inch national pipe threads, 0.375 inch national pipe threads, 0.50 inch national pipe threads, 0.625 inch national pipe threads, 0.75 inch national pipe threads, 1 inch national pipe threads, 1.25 inch national pipe threads, 1.375 inch national pipe threads, 1.625 inch national pipe threads, 1.75 inch national pipe threads, 1.875 inch national pipe threads, or 2 inch national pipe threads. In embodiments, the spray nozzle (KBC) is connected to the disc (KAB) using a fitting that includes 0.25 inch pipe threads, 0.375 inch pipe threads, 0.50 inch pipe threads, 0.625 inch pipe threads, 0.75 inch pipe threads, 1 inch pipe threads, 1.25 inch pipe threads, 1.375 inch pipe threads, 1.625 inch pipe threads, 1.75 inch pipe threads, 1.875 inch pipe threads, or 2 inch pipe threads.

In embodiments, the flow through the disc (KAB) is selected from one or more from the group consisting of 30 gallons per hour to 90 gallons per hour, 90 gallons per hour to 210 gallons per hour, 210 gallons per hour to 330 gallons per hour, 330 gallons per hour to 450 gallons per hour, and 450 gallons per hour to 630 gallons per hour.

In embodiments, the disc (KAB) is has a plurality of spray nozzles (KBC), the plurality of spray nozzles (KBC) is comprised of a quantity of spray nozzles that is selected from one or more from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, and 42 spray nozzles.

In embodiments, the disc (KAB) is has a plurality of spray nozzles (KBC), the quantity of spray nozzles (KBC) that are installed on the disc (KAB) is selected from one or more from the group consisting of: 1 spray nozzles to 3 spray nozzles, 3 spray nozzles to 6 spray nozzles, 6 spray nozzles to 9 spray nozzles, 9 spray nozzles to 12 spray nozzles, 12 spray nozzles to 15 spray nozzles, 15 spray nozzles to 18 spray nozzles, 18 spray nozzles to 21 spray nozzles, 21 spray nozzles to 24 spray nozzles, 24 spray nozzles to 27 spray nozzles, 27 spray nozzles to 30 spray nozzles, 30 spray nozzles to 33 spray nozzles, 33 spray nozzles to 36 spray nozzles, 36 spray nozzles to 39 spray nozzles, and 39 spray nozzles to 42 spray nozzles.

In embodiments, where 1 spray nozzles are used, the flow through each spray nozzle in gallons per hour (GPH) ranges from one of more from the group consisting of: 30 GPH to 90 GPH, 90 GPH to 210 GPH, 210 GPH to 330 GPH, 330 GPH to 450 GPH, and 450 GPH to 630 GPH. In embodiments, where 2 spray nozzles are used, the flow through each spray nozzle ranges from one of more from the group consisting of: 15 GPH to 45 GPH, 45 GPH to 105 GPH, 105 GPH to 165 GPH, 165 GPH to 225 GPH, and 225 GPH to 315 GPH. In embodiments, where 3 spray nozzles are used, the flow through each spray nozzle ranges from one of more from the group consisting of: 10 GPH to 30 GPH 30 GPH to 70 GPH 70 GPH to 110 GPH 110 GPH to 150 GPH, and 150 GPH to 210 GPH.

In embodiments, where 4 spray nozzles are used, the flow through each spray nozzle ranges from one of more from the group consisting of: 8 GPH to 23 GPH, 23 GPH to 53 GPH, 53 GPH to 83 GPH, 83 GPH to 113 GPH, and 113 GPH to 158 GPH. In embodiments, where 5 spray nozzles are used, the flow through each spray nozzle ranges from one of more from the group consisting of: 6 GPH to 18 GPH, 18 GPH to 42 GPH, 42 GPH to 66 GPH, 66 GPH to 90 GPH, and 90 GPH to 126 GPH. In embodiments, where 6 spray nozzles are used, the flow through each spray nozzle ranges from one of more from the group consisting of: 15 GPH to 35 GPH, 35 GPH to 55 GPH, 55 GPH to 75 GPH, and 75 GPH to 105 GPH.

In embodiments, where 7 spray nozzles are used, the flow through each spray nozzle ranges from one of more from the group consisting of: 12.857 GPH and 30 GPH, 30 GPH and 47.143 GPH, 47.143 GPH and 64.286 GPH, and 64.286 GPH and 90 GPH. In embodiments, where 8 spray nozzles are used, the flow through each spray nozzle ranges from one of more from the group consisting of: 11.250 GPH to 26.250 GPH, 26.250 GPH to 41.250 GPH, 41.250 GPH to 56.250 GPH, and 56.250 GPH to 78.750 GPH. In embodiments, where 9 spray nozzles are used, the flow through each spray nozzle ranges from one of more from the group consisting of: 10.000 GPH to 23.333 GPH, 23.333 GPH to 36.667 GPH, 36.667 GPH to 50.000 GPH, and 50.000 GPH to 70.000 GPH.

In embodiments, where 10 spray nozzles are used, the flow through each spray nozzle ranges from one of more from the group consisting of: 9 GPH to 21 GPH, 21 GPH to 33 GPH, 33 GPH to 45 GPH, and 45 GPH to 63 GPH. In embodiments, where 11 spray nozzles are used, the flow through each spray nozzle ranges from one of more from the group consisting of: 8.182 GPH to 19.091 GPH, 19.091 GPH to 30.000 GPH, 30.000 GPH to 40.909 GPH, and 40.909 GPH to 57.273 GPH. In embodiments, where 12 spray nozzles are used, the flow through each spray nozzle ranges from one of more from the group consisting of: 7.5 GPH to 17.5 GPH, 17.5 GPH to 27.5 GPH, 27.5 GPH to 37.5 GPH, and 37.5 GPH to 52.5 GPH.

In embodiments, where 13 spray nozzles are used, the flow through each spray nozzle ranges from one of more from the group consisting of: 6.923 GPH to 16.154 GPH, 16.154 GPH to 25.385 GPH, 25.385 GPH to 34.615 GPH, and 34.615 GPH to 48.462 GPH. In embodiments, where 14 spray nozzles are used, the flow through each spray nozzle ranges from one of more from the group consisting of: 6.429 GPH to 15.000 GPH, 15.000 GPH to 23.571 GPH, 23.571 GPH to 32.143 GPH, and 32.143 GPH to 45.000 GPH. In embodiments, where 15 spray nozzles are used, the flow through each spray nozzle ranges from one of more from the group consisting of: 6 GPH to 14 GPH, 14 GPH to 22 GPH, 22 GPH to 30 GPH, and 30 GPH to 42 GPH.

In embodiments, where 16 spray nozzles are used, the flow through each spray nozzle ranges from one of more from the group consisting of: 13.125 GPH to 20.625 GPH, 20.625 GPH to 28.125 GPH, and 28.125 GPH to 39.375 GPH. In embodiments, where 17 spray nozzles are used, the flow through each spray nozzle ranges from one of more from the group consisting of: 12.353 GPH to 19.412 GPH, 19.412 GPH to 26.471 GPH, and 26.471 GPH to 37.059 GPH. In embodiments, where 18 spray nozzles are used, the flow through each spray nozzle ranges from one of more from the group consisting of: 11.667 GPH to 18.333 GPH, 18.333 GPH to 25.000 GPH, and 25.000 GPH to 35.000 GPH.

In embodiments, where 19 spray nozzles are used, the flow through each spray nozzle ranges from one of more from the group consisting of: 11.053 GPH to 17.368 GPH, 17.368 GPH to 23.684 GPH, and 23.684 GPH to 33.158 GPH. In embodiments, where 20 spray nozzles are used, the flow through each spray nozzle ranges from one of more from the group consisting of: 10.500 GPH to 16.500 GPH, 16.500 GPH to 22.500 GPH, and 22.500 GPH to 31.500 GPH. In embodiments, where 21 spray nozzles are used, the flow through each spray nozzle ranges from one of more from the group consisting of: 10.000 GPH to 15.714 GPH, 15.714 GPH to 21.429 GPH, and 21.429 GPH to 30.000 GPH.

In embodiments, where 22 spray nozzles are used, the flow through each spray nozzle ranges from one of more from the group consisting of: 9.545 GPH to 15.000 GPH, 15.000 GPH to 20.455 GPH, and 20.455 GPH to 28.636 GPH. In embodiments, where 23 spray nozzles are used, the flow through each spray nozzle ranges from one of more from the group consisting of: 9.130 GPH to 14.348 GPH, 14.348 GPH to 19.565 GPH, and 19.565 GPH to 27.391 GPH. In embodiments, where 24 spray nozzles are used, the flow through each spray nozzle ranges from one of more from the group consisting of: 8.75 GPH to 13.75 GPH, 13.75 GPH to 18.75 GPH, and 18.75 GPH to 26.25 GPH.

In embodiments, where 25 spray nozzles are used, the flow through each spray nozzle ranges from one of more from the group consisting of: 8.40 GPH to 13.20 GPH, 13.20 GPH to 18.00 GPH, and 18.00 GPH to 25.20 GPH. In embodiments, where 26 spray nozzles are used, the flow through each spray nozzle ranges from one of more from the group consisting of: 8.077 GPH to 12.692 GPH, 12.692 GPH to 17.308 GPH, and 17.308 GPH to 24.231 GPH. In embodiments, where 27 spray nozzles are used, the flow through each spray nozzle ranges from one of more from the group consisting of: 7.778 GPH to 12.222 GPH, 12.222 GPH to 16.667 GPH, and 16.667 GPH to 23.333 GPH.

In embodiments, where 28 spray nozzles are used, the flow through each spray nozzle ranges from one of more from the group consisting of: 7.500 GPH to 11.786 GPH, 11.786 GPH to 16.071 GPH, and 16.071 GPH to 22.500 GPH. In embodiments, where 29 spray nozzles are used, the flow through each spray nozzle ranges from one of more from the group consisting of: 7.241 GPH to 11.379 GPH, 11.379 GPH to 15.517 GPH, and 15.517 GPH to 21.724 GPH. In embodiments, where 30 spray nozzles are used, the flow through each spray nozzle ranges from one of more from the group consisting of: 7 GPH to 11 GPH, 11 GPH to 15 GPH, and 15 GPH to 21 GPH.

In embodiments, where 31 spray nozzles are used, the flow through each spray nozzle ranges from one of more from the group consisting of: 6.774 GPH to 10.645 GPH, 10.645 GPH to 14.516 GPH, and 14.516 GPH to 20.323 GPH. In embodiments, where 32 spray nozzles are used, the flow through each spray nozzle ranges from one of more from the group consisting of: 6.563 GPH to 10.313 GPH, 10.313 GPH to 14.063 GPH, and 14.063 GPH to 19.688 GPH. In embodiments, where 33 spray nozzles are used, the flow through each spray nozzle ranges from one of more from the group consisting of: 6.364 GPH to 10.000 GPH, 10.000 GPH to 13.636 GPH, and 13.636 GPH to 19.091 GPH.

In embodiments, where 34 spray nozzles are used, the flow through each spray nozzle ranges from one of more from the group consisting of: 6.176 GPH to 9.706 GPH, 9.706 GPH to 13.235 GPH, and 13.235 GPH to 18.529 GPH. In embodiments, where 35 spray nozzles are used, the flow through each spray nozzle ranges from one of more from the group consisting of: 6.000 GPH to 9.429 GPH, 9.429 GPH to 12.857 GPH, and 12.857 GPH to 18.000 GPH. In embodiments, where 36 spray nozzles are used, the flow through each spray nozzle ranges from 9.167 GPH to 12.500 GPH, or 12.500 GPH to 17.500 GPH. In embodiments, where 37 spray nozzles are used, the flow through each spray nozzle ranges from 8.919 GPH to 12.162 GPH, or 12.162 GPH to 17.027 GPH. In embodiments, where 38 spray nozzles are used, the flow through each spray nozzle ranges from 8.684 GPH to 11.842 GPH, or 11.842 GPH to 16.579 GPH. In embodiments, where 39 spray nozzles are used, the flow through each spray nozzle ranges from 8.462 GPH to 11.538

GPH, or 11.538 GPH to 16.154 GPH. In embodiments, where 40 spray nozzles are used, the flow through each spray nozzle ranges from 8.250 GPH to 11.250 GPH, or 11.250 GPH to 15.750 GPH. In embodiments, where 41 spray nozzles are used, the flow through each spray nozzle ranges 8.049 GPH to 10.976 GPH, or 10.976 GPH to 15.366 GPH. In embodiments, where 42 spray nozzles are used, the flow through each spray nozzle ranges from 7.857 GPH to 10.714 GPH, or 10.714 GPH to 15.000 GPH.

In embodiments, the drying chamber (KBG) is equipped with a heating jacket (KBJ), the heating jacket (KBJ) has a heat transfer medium inlet (KBK) and a heat transfer medium outlet (KBL). FIG. 17E' shows the heating jacket (KBJ) installed over a portion of the drying chamber (KBG) creating an interior (KBJ1) having an annular space within which a heat transfer medium flows. A source of steam is provided to the heat transfer medium inlet (KBK). This steam may be a steam supply (LDP) that is provided from a steam drum (LBE) as indicated on FIG. 17F'.

In embodiments, a steam trap (KX6) is configured to accept steam, condensate, or non-condensable gases from the interior (KBJ1) of the heating jacket (KBJ) via a heat transfer medium outlet (KBL). Steam, condensate, or non-condensable gases are passed through the valve. During normal operation, only condensate flow through the steam trap (KX6). The condensate the flows through the steam trap (KX6) is the ninth condensate (LJB) that is passed to the condensate tank (LAP) as shown on FIG. 17F'.

In embodiments, the steam trap (KX6) is a valve which automatically drains the condensate from the interior (KBJ1) of the heating jacket (KBJ) while remaining tight to live steam, or if necessary, allowing steam to flow at a controlled or adjusted rate. In embodiments, the steam trap (KX6) also allows non-condensable gases to pass through it while remaining tight to steam. In embodiments, the steam trap (KX6) is a mechanical trap such as a bucket trap or a floating ball trap. In embodiments, the steam trap (KX6) is a thermostatic trap such as a balanced pressure trap or a bimetallic trap. In embodiments, the steam trap (KX6) is a thermodynamic trap which work by using the difference in velocity between steam and condensate.

In embodiments, a steam flow control valve (KX1) is provided and is configured to regulate the flow of steam that is passes through the heating jacket (KBJ). The steam flow control valve (KX1) has a controller (KX2) which is configured to input or output a signal (KX3) to the computer (COMP). FIG. 17E' shows the steam flow control valve (KX1) positioned to regulate steam that enters the heat transfer medium inlet (KBK) of the heating jacket (KBJ). It is to be noted that it is also contemplated that in certain instances, the steam flow control valve (KX1) may be positioned to regulate the heat transfer fluid that is discharged from the interior (KBJ1) of the heating jacket (KBJ) via the heat transfer medium outlet (KBL).

In embodiments, a flow sensor (KX4) is provided to measure the flow of heat transfer fluid that is passes through the heating jacket (KBJ). FIG. 17E' shows the flow sensor (KX4) positioned to measure the flow of steam that enters the heat transfer medium inlet (KBK) of the heating jacket (KBJ). It is to be noted that it is also contemplated that in certain instances, the flow sensor (KX4) may be positioned to measure the heat transfer fluid (steam or steam condensate) that is discharged from the interior (KBJ1) of the heating jacket (KBJ) via the heat transfer medium outlet (KBL). The flow sensor (KX4) inputs a signal (KX5) to the computer (COMP).

In embodiment, the heating jacket (KBJ) is configured to maintain the wall (KWG) within the interior (KBG') drying chamber (KBG) at a constant temperature. In embodiments, the wall temperature ranges from one or more from the group consisting of between: 110 degrees Fahrenheit to 125 degrees Fahrenheit; 125 degrees Fahrenheit to 140 degrees Fahrenheit; 140 degrees Fahrenheit to 155 degrees Fahrenheit; 155 degrees Fahrenheit to 170 degrees Fahrenheit; 170 degrees Fahrenheit to 185 degrees Fahrenheit; 185 degrees Fahrenheit to 200 degrees Fahrenheit; 200 degrees Fahrenheit to 215 degrees Fahrenheit; 215 degrees Fahrenheit to 230 degrees Fahrenheit; 230 degrees Fahrenheit to 245 degrees Fahrenheit; 250 degrees Fahrenheit to 275 degrees Fahrenheit; 275 degrees Fahrenheit to 300 degrees Fahrenheit; 300 degrees Fahrenheit to 325 degrees Fahrenheit; 325 degrees Fahrenheit to 350 degrees Fahrenheit; 350 degrees Fahrenheit to 375 degrees Fahrenheit; 375 degrees Fahrenheit to 400 degrees Fahrenheit; 400 degrees Fahrenheit to 425 degrees Fahrenheit; 425 degrees Fahrenheit to 450 degrees Fahrenheit; 450 degrees Fahrenheit to 475 degrees Fahrenheit; 475 degrees Fahrenheit to 500 degrees Fahrenheit; 500 degrees Fahrenheit to 525 degrees Fahrenheit; 525 degrees Fahrenheit to 550 degrees Fahrenheit; 550 degrees Fahrenheit to 575 degrees Fahrenheit; 575 degrees Fahrenheit to 600 degrees Fahrenheit; 600 degrees Fahrenheit to 625 degrees Fahrenheit; 625 degrees Fahrenheit to 650 degrees Fahrenheit; 650 degrees Fahrenheit to 675 degrees Fahrenheit; 675 degrees Fahrenheit to 700 degrees Fahrenheit; 700 degrees Fahrenheit to 725 degrees Fahrenheit; 725 degrees Fahrenheit to 750 degrees Fahrenheit; 750 degrees Fahrenheit to 775 degrees Fahrenheit; and 775 degrees Fahrenheit to 800 degrees Fahrenheit.

In embodiments, it is desired to operate the heating jacket (KBJ) to maintain a wall (KWG) temperature sufficient to avoid sticking, deposition, burning of volatile particulates or liquid upon surface of the wall (KWG). In embodiments, the surface of the wall (KWG) transfers heat into the interior (KBG) of the drying chamber (KBG). In embodiments, it is desired to operate the heating jacket (KBJ) in a manner that is sufficient to maintain a wall (KWG) temperature that is known to now fouling of the heat surface by sticking, deposition, burning of volatile particulates or liquid upon surface of the wall (KWG). Powder build-up on the wall (KWG) within the interior (KBG') surface of the drying chamber (KBG) poses problems related to start-up and shutdown as discussed below.

In embodiments, the openings (KM4) of the screen (KM3) or mesh (KM3') are selected from one or more from the group consisting of 0.01 microns to 0.1 microns, 0.1 microns to 0.5 microns, 0.5 microns to 1 microns, 1 microns to 2 microns, 2 microns to 4 microns, 4 microns to 8 microns, 8 microns to 10 microns, 10 microns to 20 microns, 20 microns to 30 microns, 30 microns to 40 microns, 40 microns to 50 microns, 50 microns to 60 microns, 60 microns to 70 microns, 70 microns to 80 microns, 80 microns to 90 microns, 90 microns to 100 microns, and 100 microns to 200 microns.

In embodiments, the temperature sensor (KBY) positioned on the first transfer conduit (KBW) in between the second output (KBU) of the spray dryer (KAP) and the first input (KCB) of the first separator (KCA) that measures the temperature of the volatiles and gas mixture (KBV) is preferably optimized to be maintained at 120 degrees Fahrenheit to 400 degrees Fahrenheit, or between 135 degrees Fahrenheit to 300 degrees Fahrenheit, or between 140 degrees Fahrenheit to 160 degrees Fahrenheit, or between 146 degrees Fahrenheit to 154 degrees Fahrenheit. The temperature sensor (KBY) inputs a signal (KBX) to the computer (COMP).

In embodiments, the temperature sensor (KBY) positioned on the first transfer conduit (KBW) in between the second output (KBU) of the spray dryer (KAP) and the first input (KCB) of the first separator (KCA) that measures the temperature of the volatiles and gas mixture (KBV) is preferably optimized to be maintained at 150 degrees Fahrenheit to 250 degrees Fahrenheit, but more preferably to 135 degrees Fahrenheit to 180 degrees Fahrenheit, but more preferably to 145 degrees Fahrenheit to 155 degrees Fahrenheit.

In embodiments, the temperature of the volatiles and gas mixture (KBV) leaving the drying chamber (KBG) ranges from one or more from the group consisting of between: 110 degrees Fahrenheit to 125 degrees Fahrenheit; 125 degrees Fahrenheit to 140 degrees Fahrenheit; 140 degrees Fahrenheit to 155 degrees Fahrenheit; 155 degrees Fahrenheit to 170 degrees Fahrenheit; 170 degrees Fahrenheit to 185 degrees Fahrenheit; 185 degrees Fahrenheit to 200 degrees Fahrenheit; 200 degrees Fahrenheit to 215 degrees Fahrenheit; 215 degrees Fahrenheit to 230 degrees Fahrenheit; 230 degrees Fahrenheit to 245 degrees Fahrenheit; 250 degrees Fahrenheit to 275 degrees Fahrenheit; 275 degrees Fahrenheit to 300 degrees Fahrenheit; 300 degrees Fahrenheit to 325 degrees Fahrenheit; 325 degrees Fahrenheit to 350 degrees Fahrenheit; 350 degrees Fahrenheit to 375 degrees Fahrenheit; and 375 degrees Fahrenheit to 400 degrees Fahrenheit.

In embodiments, the difference in temperature between the heated gas supply (KAG') and the volatiles and gas mixture (KBV) ranges from between 110 degrees Fahrenheit to 125 degrees Fahrenheit; 125 degrees Fahrenheit to 140 degrees Fahrenheit; 140 degrees Fahrenheit to 155 degrees Fahrenheit; 155 degrees Fahrenheit to 170 degrees Fahrenheit; 170 degrees Fahrenheit to 185 degrees Fahrenheit; 185 degrees Fahrenheit to 200 degrees Fahrenheit; 200 degrees Fahrenheit to 215 degrees Fahrenheit; 215 degrees Fahrenheit to 230 degrees Fahrenheit; 230 degrees Fahrenheit to 245 degrees Fahrenheit; 250 degrees Fahrenheit to 275 degrees Fahrenheit; 275 degrees Fahrenheit to 300 degrees Fahrenheit; 300 degrees Fahrenheit to 325 degrees Fahrenheit; 325 degrees Fahrenheit to 350 degrees Fahrenheit; 350 degrees Fahrenheit to 375 degrees Fahrenheit; 375 degrees Fahrenheit to 400 degrees Fahrenheit; 400 degrees Fahrenheit to 425 degrees Fahrenheit; 425 degrees Fahrenheit to 450 degrees Fahrenheit; 450 degrees Fahrenheit to 475 degrees Fahrenheit; 475 degrees Fahrenheit to 500 degrees Fahrenheit.

In embodiments, a pressure sensor (KBH) is configured to measure the pressure within the interior (KBG') of the drying chamber (KBG) and output a signal (KBI) to the computer (COMP). In embodiments, the ranges of pressure within the interior (KBG') of the drying chamber (KBG) is selected from one of more from the group consisting of: 1.5 pounds per square inch absolute (PSIA) 3 PSIA, 3 PSIA to 4.5 PSIA, 4.5 PSIA to 6 PSIA, 6 PSIA to 7.5 PSIA, 7.5 PSIA to 9 PSIA, 9 PSIA to 10.5 PSIA, 10.5 PSIA to 12 PSIA, 12 PSIA to 13.5 PSIA, 12 PSIA to 12.25 PSIA, 12.25 PSIA to 12.5 PSIA, 12.5 PSIA to 12.75PSIA, 12.75 PSIA to 13 PSIA, 13 PSIA to 13.25 PSIA, 13.25 PSIA to 13.5 PSIA, 13.5 PSIA to 13.75 PSIA, 13.75 PSIA to 14 PSIA, 14 PSIA to 14.25 PSIA, 14.25 PSIA to 14.5 PSIA, 14.5 PSIA to 14.75 PSIA, 14.75 PSIA to 15 PSIA, 15 PSIA to 16.5 PSIA, 16.5 PSIA to 18 PSIA, 18 PSIA to 19.5 PSIA, 19.5 PSIA to 21 PSIA, 21 PSIA to 22.5 PSIA, 22.5 PSIA to 24 PSIA, 24 PSIA to 25.5 PSIA, 25.5 PSIA to 27 PSIA, 27 PSIA to 28.5 PSIA, 28.5 PSIA to 30 PSIA, 30 PSIA to 31.5 PSIA, 31.5 PSIA to 33PSIA, 33 PSIA to 34.5 PSIA, and 34.5 PSIA to 36 PSIA.

In embodiments, the ranges of pressure within the interior (KBG') of the drying chamber (KBG) is selected from one of more from the group consisting of: between about 0.001 inches of water to about 0.002 inches of water; between about 0.002 inches of water to about 0.003 inches of water; between about 0.003 inches of water to about 0.006 inches of water; between about 0.006 inches of water to about 0.012 inches of water; between about 0.012 inches of water to about 0.024 inches of water; between about 0.024 inches of water to about 0.050 inches of water; between about 0.050 inches of water to about 0.075 inches of water; between about 0.075 inches of water to about 0.150 inches of water; between about 0.150 inches of water to about 0.300 inches of water; between about 0.300 inches of water to about 0.450 inches of water; between about 0.450 inches of water to about 0.473 inches of water; between about 0.473 inches of water to about 0.496 inches of water; between about 0.496 inches of water to about 0.521 inches of water; between about 0.521 inches of water to about 0.547 inches of water; between about 0.547 inches of water to about 0.574 inches of water; between about 0.574 inches of water to about 0.603 inches of water; between about 0.603 inches of water to about 0.633 inches of water; between about 0.633 inches of water to about 0.665 inches of water; between about 0.665 inches of water to about 0.698 inches of water; between about 0.698 inches of water to about 0.733 inches of water; between about 0.733 inches of water to about 0.770 inches of water; between about 0.770 inches of water to about 0.808 inches of water; between about 0.808 inches of water to about 0.849 inches of water; between about 0.849 inches of water to about 0.891 inches of water; between about 0.891 inches of water to about 0.936 inches of water; between about 0.936 inches of water to about 0.982 inches of water; between about 0.982 inches of water to about 1.031 inches of water; between about 1.031 inches of water to about 1.083 inches of water; between about 1.083 inches of water to about 1.137 inches of water; between about 1.137 inches of water to about 1.194 inches of water; between about 1.194 inches of water to about 1.254 inches of water; between about 1.254 inches of water to about 1.316 inches of water; between about 1.316 inches of water to about 1.382 inches of water; between about 1.382 inches of water to about 1.451 inches of water; between about 1.451 inches of water to about 1.524 inches of water; between about 1.524 inches of water to about 2.286 inches of water; between about 2.286 inches of water to about 3.429 inches of water; between about 3.429 inches of water to about 5.143 inches of water; between about 5.143 inches of water to about 7.715 inches of water; between about 7.715 inches of water to about 11.572 inches of water; between about 11.572 inches of water to about 17.358 inches of water; between about 17.358 inches of water to about 26.037 inches of water; between about 26.037 inches of water to about 39.055 inches of water; between about 39.055 inches of water to about 58.582 inches of water; between about 58.582 inches of water to about 87.873 inches of water; between about 87.873 inches of water to about 131.810 inches of water; between about 131.810 inches of water to about 197.715 inches of water; between about 197.715 inches of water to about 296.573 inches of water; or, between about 296.573 inches of water to about 400 inches of water.

Spray dried volatiles (KBT) may be removed from the first output (KB S) of the drying chamber (KBG). In embodiments, the volatiles (KBT) removed from the first output (KBS) of the drying chamber (KBG) may be solid or may contain liquid. In embodiments, the volatiles (KBT) removed from the first output (KBS) of the drying chamber (KBG) are either too wet or too large, or both, to be evacuated from the second output (KBU) of the drying chamber (KBG). In embodiments, the volatiles (KBT) removed from the first output (KBS) may be mixed with one or more stream of separated volatiles, such first separated volatiles (KCG), second separated volatiles (KCP), third separated volatiles (KCV), a fourth separated volatiles (KCX), or a large particulate portion (KCY) to form combined volatiles (KM7) as shown in FIG. 17E'.

In embodiments, a vibrator (KBN) is connected to the spray dryer (KAP) or drying chamber (KBG) via a connection (KBR). In embodiments, the spray dryer (KAP) or drying chamber (KBG) is equipped with a vibrator (KBN). In embodiments, a vibrator (KBN) vibrates at least a portion of the spray dryer (KAP) or drying chamber (KBG) to aide in removal of the spray dried volatiles (KBT) from the first output (KBS). In embodiments, the vibrator (KBN) is pneumatic. In embodiments, the vibrator (KBN) operates at a vibration range that is selected from one or more from the group consisting of 3,000 vibrations per minute (VPM) to 4000 VPM, 4,000 VPM to 5,000 VPM, 5,000 VPM to 5,500 VPM, 5,500 VPM to 6,000 VPM, 6,000 VPM to 6,500 VPM, 6,500 VPM to 7,000 VPM, 7,000 VPM to 7,500 VPM, 7,500 VPM to 8,000 VPM, 8,000 VPM to 8,500 VPM, 8,500 VPM to 9,000 VPM, 9,000 VPM to 9,500 VPM, 9,500 VPM to 10,000 VPM, 10,000 VPM to 15,000 VPM, 15,000 VPM to 20,000 VPM, 20,000 VPM to 25,000 VPM, 25,000 VPM to 30,000 VPM, 30,000 VPM to 35,000 VPM, 35,000 VPM to 40,000 VPM, 40,000 VPM to 45,000 VPM, and 45,000 VPM to 50,000 VPM. In embodiments, the vibrator (KBN) has a motor (KBO) with a controller (KBP) that is configured to input or output a signal (KBQ) to the computer (COMP).

In embodiments, the small particulate portion (KCW) has a liquid content that ranges from one or more from the group selected from 0.05 weight percent of liquid to 0.1 weight percent of liquid, 0.1 weight percent of liquid to 0.2 weight percent of liquid, 0.2 weight percent of liquid to 0.4 weight percent of liquid, 0.4 weight percent of liquid to 0.8 weight percent of liquid, 0.8 weight percent of liquid to 1 weight percent of liquid, 1 weight percent of liquid to 2 weight percent of liquid, 2 weight percent of liquid to 3 weight percent of liquid, 3 weight percent of liquid to 4 weight percent of liquid, 4 weight percent of liquid to 5 weight percent of liquid, 5 weight percent of liquid to 6 weight percent of liquid, 6 weight percent of liquid to 7 weight percent of liquid, 7 weight percent of liquid to 8 weight percent of liquid, 8 weight percent of liquid to 9 weight percent of liquid, 9 weight percent of liquid to 10 weight percent of liquid, 10 weight percent of liquid to 11 weight percent of liquid, 11 weight percent of liquid to 12 weight percent of liquid, 12 weight percent of liquid to 13 weight percent of liquid, 13 weight percent of liquid to 14 weight percent of liquid, 14 weight percent of liquid to 15 weight percent of liquid, 15 weight percent of liquid to 16 weight percent of liquid, 16 weight percent of liquid to 17 weight percent of liquid, 17 weight percent of liquid to 18 weight percent of liquid, 18 weight percent of liquid to 19 weight percent of liquid, and 19 weight percent of liquid to 20 weight percent of liquid.

In embodiments, the small particulate portion (KCW) has a liquid content that ranges from one or more from the group selected from 0.05 weight percent of liquid to 0.1 weight percent of liquid, 0.1 weight percent of liquid to 0.2 weight percent of liquid, 0.2 weight percent of liquid to 0.4 weight percent of liquid, 0.4 weight percent of liquid to 0.8 weight percent of liquid, 0.8 weight percent of liquid to 1 weight percent of liquid, 1 weight percent of liquid to 2 weight percent of liquid, 2 weight percent of liquid to 3 weight percent of liquid, 3 weight percent of liquid to 4 weight percent of liquid, 4 weight percent of liquid to 5 weight percent of liquid, 5 weight percent of liquid to 6 weight percent of liquid, 6 weight percent of liquid to 7 weight percent of liquid, 7 weight percent of liquid to 8 weight percent of liquid, 8 weight percent of liquid to 9 weight percent of liquid, 9 weight percent of liquid to 10 weight percent of liquid, 10 weight percent of liquid to 11 weight percent of liquid, 11 weight percent of liquid to 12 weight percent of liquid, 12 weight percent of liquid to 13 weight percent of liquid, 13 weight percent of liquid to 14 weight percent of liquid, 14 weight percent of liquid to 15 weight percent of liquid, 15 weight percent of liquid to 16 weight percent of liquid, 16 weight percent of liquid to 17 weight percent of liquid, 17 weight percent of liquid to 18 weight percent of liquid, 18 weight percent of liquid to 19 weight percent of liquid, and 19 weight percent of liquid to 20 weight percent of liquid.

In embodiments, the large particulate portion (KCY) has a liquid content that ranges from one or more from the group selected from 0.05 weight percent of liquid to 0.1 weight percent of liquid, 0.1 weight percent of liquid to 0.2 weight percent of liquid, 0.2 weight percent of liquid to 0.4 weight percent of liquid, 0.4 weight percent of liquid to 0.8 weight percent of liquid, 0.8 weight percent of liquid to 1 weight percent of liquid, 1 weight percent of liquid to 2 weight percent of liquid, 2 weight percent of liquid to 3 weight percent of liquid, 3 weight percent of liquid to 4 weight percent of liquid, 4 weight percent of liquid to 5 weight percent of liquid, 5 weight percent of liquid to 6 weight percent of liquid, 6 weight percent of liquid to 7 weight percent of liquid, 7 weight percent of liquid to 8 weight percent of liquid, 8 weight percent of liquid to 9 weight percent of liquid, 9 weight percent of liquid to 10 weight percent of liquid, 10 weight percent of liquid to 11 weight percent of liquid, 11 weight percent of liquid to 12 weight percent of liquid, 12 weight percent of liquid to 13 weight percent of liquid, 13 weight percent of liquid to 14 weight percent of liquid, 14 weight percent of liquid to 15 weight percent of liquid, 15 weight percent of liquid to 16 weight percent of liquid, 16 weight percent of liquid to 17 weight percent of liquid, 17 weight percent of liquid to 18 weight percent of liquid, 18 weight percent of liquid to 19 weight percent of liquid, and 19 weight percent of liquid to 20 weight percent of liquid.

In embodiments, the large particulate portion (KCY) has a liquid content that ranges from one or more from the group selected from 0.05 weight percent of liquid to 0.1 weight percent of liquid, 0.1 weight percent of liquid to 0.2 weight percent of liquid, 0.2 weight percent of liquid to 0.4 weight percent of liquid, 0.4 weight percent of liquid to 0.8 weight percent of liquid, 0.8 weight percent of liquid to 1 weight percent of liquid, 1 weight percent of liquid to 2 weight percent of liquid, 2 weight percent of liquid to 3 weight percent of liquid, 3 weight percent of liquid to 4 weight percent of liquid, 4 weight percent of liquid to 5 weight percent of liquid, 5 weight percent of liquid to 6 weight percent of liquid, 6 weight percent of liquid to 7 weight percent of liquid, 7 weight percent of liquid to 8 weight percent of liquid, 8 weight percent of liquid to 9 weight percent of liquid, 9 weight percent of liquid to 10 weight percent of liquid, 10 weight percent of liquid to 11 weight percent of liquid, 11 weight percent of liquid to 12 weight percent of liquid, 12 weight percent of liquid to 13 weight percent of liquid, 13 weight percent of liquid to 14 weight percent of liquid, 14 weight percent of liquid to 15 weight percent of liquid, 15 weight percent of liquid to 16 weight percent of liquid, 16 weight percent of liquid to 17 weight percent of liquid, 17 weight percent of liquid to 18 weight percent of liquid, 18 weight percent of liquid to 19 weight percent of liquid, and 19 weight percent of liquid to 20 weight percent of liquid.

In embodiments, the volatiles (KBT) removed the drying chamber (KBG) have a liquid content that ranges from one or more from the group selected from 0.05 weight percent of liquid to 0.1 weight percent of liquid, 0.1 weight percent of liquid to 0.2 weight percent of liquid, 0.2 weight percent of liquid to 0.4 weight percent of liquid, 0.4 weight percent of liquid to 0.8 weight percent of liquid, 0.8 weight percent of liquid to 1 weight percent of liquid, 1 weight percent of liquid to 2 weight percent of liquid, 2 weight percent of liquid to 3 weight percent of liquid, 3 weight percent of liquid to 4 weight percent of liquid, 4 weight percent of liquid to 5 weight percent of liquid, 5 weight percent of liquid to 6 weight percent of liquid, 6 weight percent of liquid to 7 weight percent of liquid, 7 weight percent of liquid to 8 weight percent of liquid, 8 weight percent of liquid to 9 weight percent of liquid, 9 weight percent of liquid to 10 weight percent of liquid, 10 weight percent of liquid to 11 weight percent of liquid, 11 weight percent of liquid to 12 weight percent of liquid, 12 weight percent of liquid to 13 weight percent of liquid, 13 weight percent of liquid to 14 weight percent of liquid, 14 weight percent of liquid to 15 weight percent of liquid, 15 weight percent of liquid to 16 weight percent of liquid, 16 weight percent of liquid to 17 weight percent of liquid, 17 weight percent of liquid to 18 weight percent of liquid, 18 weight percent of liquid to 19 weight percent of liquid, and 19 weight percent of liquid to 20 weight percent of liquid.

In embodiments, the volatiles (KBT) removed the drying chamber (KBG) have a liquid content that ranges from one or more from the group selected from 0.05 weight percent of liquid to 0.1 weight percent of liquid, 0.1 weight percent of liquid to 0.2 weight percent of liquid, 0.2 weight percent of liquid to 0.4 weight percent of liquid, 0.4 weight percent of liquid to 0.8 weight percent of liquid, 0.8 weight percent of liquid to 1 weight percent of liquid, 1 weight percent of liquid to 2 weight percent of liquid, 2 weight percent of liquid to 3 weight percent of liquid, 3 weight percent of liquid to 4 weight percent of liquid, 4 weight percent of liquid to 5 weight percent of liquid, 5 weight percent of liquid to 6 weight percent of liquid, 6 weight percent of liquid to 7 weight percent of liquid, 7 weight percent of liquid to 8 weight percent of liquid, 8 weight percent of liquid to 9 weight percent of liquid, 9 weight percent of liquid to 10 weight percent of liquid, 10 weight percent of liquid to 11 weight percent of liquid, 11 weight percent of liquid to 12 weight percent of liquid, 12 weight percent of liquid to 13 weight percent of liquid, 13 weight percent of liquid to 14 weight percent of liquid, 14 weight percent of liquid to 15 weight percent of liquid, 15 weight percent of liquid to 16 weight percent of liquid, 16 weight percent of liquid to 17 weight percent of liquid, 17 weight percent of liquid to 18 weight percent of liquid, 18 weight percent of liquid to 19 weight percent of liquid, and 19 weight percent of liquid to 20 weight percent of liquid.

In embodiments, the spray dryer (KAP) drying chamber (KBG) is configured to mix the heated gas supply (KAG') with the second volatiles and solvent mixture (SVSM) to form a volatiles and gas mixture (KBV). The volatiles and gas mixture (KBV) is discharged from the spray dryer (KAP) via a second output (KBU). The volatiles and gas mixture (KBV) include a spray dried volatiles portion (KBV'), a vapor portion (KBV"), and a gas portion (KBV'"). In embodiments, the spray dried volatiles portion (KBV') may include solid particulates. In embodiments, the vapor portion (KBV") is the second solvent. In embodiments, the vapor portion (KBV") may include the vapor-phase of the liquid within the second volatiles and solvent mixture (SVSM) which may include the second solvent. In embodiments, the gas portion (KBV") includes whatever was within the gas supply (KAG).

The spray dryer (KAP) has a second output (KBU) that is configured to discharge a volatiles and gas mixture (KBV) from the interior (KBG') of the drying chamber (KBG). In embodiments, the volatiles and gas mixture (KBV) has a spray dried volatiles portion (KBV'), vapor portion (KBV"), and a gas portion (KBV'"). The second output (KBU) of the spray dryer (KAP) is connected to the first-first input (KCB) of the first separator (KCA) via a first transfer conduit (KBW). In embodiments, the first separator (KCA) is a cyclone or a filter. FIG. 17E' shows the first separator (KCA) as a cyclone.

The first transfer conduit (KBW) transfers the volatiles and gas mixture (KBV) from the interior (KBG') of the drying chamber (KBG) to the first separator (KCA). The first separator (KCA) separates first separated volatiles (KCG) from the volatiles and gas mixture (KBV) to create a first volatiles depleted gas stream (KCD). The first volatiles depleted gas stream (KCD) is discharged from the first separator (KCA) via a first-first output (KCC).

The first separator (KCA) has: a first-first input (KCB) for receiving the volatiles and gas mixture (KBV) from the spray dryer (KAP), a first-first output (KCC) for evacuating the first volatiles depleted gas stream (KCD) towards the second separator (KCI), and a first-second output (KCF) for transferring first separated volatiles (KCG) towards the third separator (KCR). The first volatiles depleted gas stream (KCD) is transferred from the first-first output (KCC) to the second-first input (KCK) of the second separator (KCI) via a second transfer conduit (KCE).

The first volatiles depleted gas stream (KCD) has a reduced amount of volatiles relative to the volatiles and gas mixture (KBV). The first volatiles depleted gas stream (KCD) has a reduced amount of spray dried volatiles portion (KBV') relative to the volatiles and gas mixture (KBV). The second transfer conduit (KCE) is connected at one end to the first-first output (KCC) of the first separator (KCA) and at another end to the second-first input (KCK) of the second separator (KCI).

The first separated volatiles (KCG) that are separated from the volatiles and gas mixture (KBV) are discharged from the first separator (KCA) via the first-second output (KCF). The third-first input (KCS) of the third separator (KCR) is configured to receive the first separated volatiles (KCG) via a first dipleg (KCH). The first dipleg (KCH) is connected at one end to the first-second output (KCF) of the first separator (KCA) and at a second end to the third-first input (KCS) of the third separator (KCR). The first separated volatiles (KCG) includes at least a portion of the spray dried volatiles portion (KBV') that were separated from the volatiles and gas mixture (KBV).

The second separator (KCI) separates second separated volatiles (KCP) from the first volatiles depleted gas stream (KCD) to create a second volatiles depleted gas stream (KCM). The second volatiles depleted gas stream (KCM) has a reduced amount of volatiles relative to the first volatiles depleted gas stream (KCD). The second volatiles depleted gas stream (KCM) has a reduced amount of spray dried volatiles portion (KBV') relative to the first volatiles depleted gas stream (KCD).

In embodiments, the second separator (KCI) is a cyclone or a filter. FIG. 17E' shows the second separator (KCI) as a cyclone. The second volatiles depleted gas stream (KCM) is discharged from the second separator (KCI) via a second-first output (KCJ).

The second separator (KCI) has: a second-first input (KCK) for receiving the first volatiles depleted gas stream (KCD) from the first separator (KCA), a second-first output (KCJ) for evacuating the second volatiles depleted gas stream (KCM) towards the fourth separator (KCZ), and a second-second output (KCO) for transferring second separated volatiles (KCP) towards the third separator (KCR). The second volatiles depleted gas stream (KCM) is transferred from the second-first output (KCJ) to the fourth-first input (KDA) of the fourth separator (KCZ) via a third transfer conduit (KCN). The third transfer conduit (KCN) is connected at one end to the second-first output (KCJ) of the second separator (KCI) and at another end to the fourth-first input (KDA) of the fourth separator (KCZ).

The second separated volatiles (KCP) that are separated from the first volatiles depleted gas stream (KCD) are discharged from the second separator (KCI) via the second-second output (KCO). The third-first input (KCS) of the third separator (KCR) is configured to receive the second separated volatiles (KCP) via a second dipleg (KCQ). The second dipleg (KCQ) is connected at one end to the second-second output (KCO) of the second separator (KCI) and at a second end to the third-first input (KCS) of the third separator (KCR). The second separated volatiles (KCP) includes at least a portion of the volatiles that were separated from the first volatiles depleted gas stream (KCD). The second separated volatiles (KCP) includes at least a portion of the spray dried volatiles portion (KBV') that were separated from the first volatiles depleted gas stream (KCD).

The fourth separator (KCZ) separates an additional separated volatiles (KDF) from the second volatiles depleted gas stream (KCM) to create a third volatiles depleted gas stream (KDC). The third volatiles depleted gas stream (KDC) has a reduced amount of volatiles relative to the second volatiles depleted gas stream (KCM). The third volatiles depleted gas stream (KDC) has a reduced amount of spray dried volatiles portion (KBV') relative to the second volatiles depleted gas stream (KCM). In embodiments, the fourth separator (KCZ) is a cyclone, filter, scrubber, or electrostatic precipitator. In embodiments, the fourth separator (KCZ) is a scrubber that uses second solvent as the scrubbing liquid.

FIG. 17E' shows the second separator (KCI) as an electrostatic precipitator. The electrostatic precipitator has an electrode (KM8) and a power supply (KM9) and is configured to separate volatiles from the second volatiles depleted gas stream (KCM). The electrode (KM8) and a power supply (KM9) apply an electrostatic charge to the second volatiles depleted gas stream (KCM) as it passes through the fourth separator (KCZ).

In other embodiments, the fourth separator (KCZ) is a scrubber. The scrubber, is preferably a vertically oriented cylindrical, or rectangular, pressure vessel having a lower section, and an upper section, along with a central section that contains a quantity of packed media either comprising raschig rings, pall rings, berl saddles, intalox packing, metal structured grid packing, hollow spherical packing, high performance thermoplastic packing, structured packing, synthetic woven fabric, or ceramic packing, or the like, wherein media is supported upon a suitable support grid system commonplace to industrial chemical equipment systems. The upper section of the scrubber preferably contains a demister to enhance the removal of liquid droplets entrained in a vapor stream and to minimize carry-over losses of the sorption liquid. In embodiments, the sorption liquid is second solvent. This demister is also positioned above the scrubber spray nozzle system, comprised of a plurality of spray nozzles, or spray balls, that introduce and substantially equally distribute the scrubbing absorption liquid to the scrubber onto the scrubber's central packing section, so it may gravity-flow down through the scrubber central section.

As the second volatiles depleted gas stream (KCM) passes up through the internal packing of the scrubber, excess vapor within the additional separated volatiles (KDF) comes into intimate contact with scrubbing liquid such as a portion of the second solvent, which are cooled prior to being introduced to the upper section of the scrubber through the scrubber spray nozzle system. Vapor from within the second volatiles depleted gas stream (KCM) is condensed into a liquid.

The third volatiles depleted gas stream (KDC) is discharged from the fourth separator (KCZ) via a fourth-first input (KDA). The fourth separator (KCZ) has: fourth-first input (KDA) for receiving the second volatiles depleted gas stream (KCM) from the second separator (KCI), a fourth-first output (KDB) for evacuating the third volatiles depleted gas stream (KDC) towards the condenser (KDH), and a fourth-second output (KDE) for transferring additional separated volatiles (KDF) towards the third separator (KCR).

The third volatiles depleted gas stream (KDC) is transferred from the fourth-first output (KDB) to the gas-vapor inlet (KDP) of the condenser (KDH) via a fourth transfer conduit (KDD). The fourth transfer conduit (KDD) is connected at one end to the fourth-second output (KDE) of the fourth separator (KCZ) and at another end to the gas-vapor inlet (KDP) of the condenser (KDH). The additional separated volatiles (KDF) that are separated from the second volatiles depleted gas stream (KCM) are discharged from the fourth separator (KCZ) via the fourth-second output (KDE). In embodiments, the third-first input (KCS) of the third separator (KCR) is configured to receive at least a portion of the additional separated volatiles (KDF) via a fifth transfer conduit (KDG). The fifth transfer conduit (KDG) is connected at one end to the fourth-second output (KDE) of the fourth separator (KCZ) and at a second end to the third-first input (KCS) of the third separator (KCR).

The third volatiles depleted gas stream (KDC) includes at least a portion of the vapor portion (KBV") or gas portion (KBV'") of the volatiles and gas mixture (KBV) that was discharged from the drying chamber (KBG). The additional separated volatiles (KDF) includes at least a portion of the volatiles that were separated from the first volatiles depleted gas stream (KCD). The additional separated volatiles (KDF) include at least a portion of the volatiles that were separated from the second volatiles depleted gas stream (KCM). The additional separated volatiles (KDF) includes at least a portion of the spray dried volatiles portion (KBV') that were separated from the second volatiles depleted gas stream (KCM).

In embodiments, the additional separated volatiles (KDF) have a size range that is selected from one or more from the group consisting of 1 nanometer to 5 nanometers, 5 nanometers to 10 nanometers, 10 nanometers to 15 nanometers, 15 nanometers to 20 nanometers, 20 nanometers to 25 nanometers, 25 nanometers to 30 nanometers, 30 nanometers to 35 nanometers, 35 nanometers to 40 nanometers, 40 nanometers to 45 nanometers, 45 nanometers to 50 nanometers, 50 nanometers to 55 nanometers, 55 nanometers to 60 nanometers, 60 nanometers to 65 nanometers, 65 nanometers to 70 nanometers, 70 nanometers to 75 nanometers, 75 nanometers to 80 nanometers, 80 nanometers to 85 nanometers, 85 nanometers to 90 nanometers, 90 nanometers to 95 nanometers, 95 nanometers to 100 nanometers, 100 nanometers to 200 nanometers, 200 nanometers to 300 nanometers, 300 nanometers to 400 nanometers, 400 nanometers to 500 nanometers, 500 nanometers to 600 nanometers, 600 nanometers to 700 nanometers, 700 nanometers to 800 nanometers, and 800 nanometers to 900 nanometers.

In embodiments, the additional separated volatiles (KDF) have a size range that is selected from one or more from the group consisting of 1 microns to 5 microns, 5 microns to 10 microns, 10 microns to 30 microns, 30 microns to 50 microns, 50 microns to 70 microns, 70 microns to 90 microns, 90 microns to 110 microns, 110 microns to 130 microns, 130 microns to 150 microns, 150 microns to 170 microns, 170 microns to 190 microns, 190 microns to 210 microns, 210 microns to 230 microns, and 230 microns to 250 microns.

In embodiments, the additional separated volatiles (KDF) have a particle size distribution (PSD) that has a lesser or smaller PSD relative to the small particulate portion (KCW) separated in the solid-solid separator (SSS). In embodiments, the additional separated volatiles (KDF) have a particle size distribution (PSD) that has a lesser or smaller PSD relative to the large particulate portion (KCY) separated in the solid-solid separator (SSS). In embodiments, the particle size distribution of the small particulate portion (KCW) is lesser or smaller than the particle size distribution of the large particulate portion (KCY).

In embodiments, the small particulate portion (KCW) have a size range that is selected from one or more from the group consisting of 1 microns to 5 microns, 5 microns to 10 microns, 10 microns to 30 microns, 30 microns to 50 microns, 50 microns to 70 microns, 70 microns to 90 microns, 90 microns to 110 microns, 110 microns to 130 microns, 130 microns to 150 microns, 150 microns to 170 microns, 170 microns to 190 microns, 190 microns to 210 microns, 210 microns to 230 microns, and 230 microns to 250 microns.

In embodiments, the large particulate portion (KCY) have a size range that is selected from one or more from the group consisting of 50 microns to 60 microns, 60 microns to 70 microns, 70 microns to 80 microns, 80 microns to 90 microns, 90 microns to 100 microns, 100 microns to 150 microns, 150 microns to 200 microns, 200 microns to 250 microns, 250 microns to 300 microns, 300 microns to 350 microns, 350 microns to 400 microns, 400 microns to 450 microns, 450 microns to 500 microns, 500 microns to 550 microns, 550 microns to 600 microns, 600 microns to 650 microns, 650 microns to 700 microns, 700 microns to 750 microns, 750 microns to 800 microns, 800 microns to 850 microns, 850 microns to 900 microns, 900 microns to 950 microns, and 950 microns to 1,000 microns.

As shown in FIG. 17E' the third separator (KCR) accepts first separated volatiles (KCG) from the first separator (KCA), and second separated volatiles (KCP) from the second separator (KCI), and optionally a portion of the additional separated volatiles (KDF) from the fourth separator (KCZ), and separates at least a small particulate portion (KCW) and a large particulate portion (KCY) therefrom.

In embodiments, the third separator (KCR) includes solid-solid separator (SSS). In embodiments, the third separator (KCR) includes a sifter as shown in FIG. 17E'. In embodiments, the third separator (KCR) includes a filter. In embodiments, the third separator (KCR) has a third-first input (KCS) for receiving: first separated volatiles (KCG) via the first dipleg (KCH), second separated volatiles (KCP) via the second dipleg (KCQ), and additional separated volatiles (KDF) via the fifth transfer conduit (KDG). In embodiments, the third separator (KCR) has a third-first output (KCT) for discharging a third separated volatiles (KCV) which include a small particulate portion (KCW). In embodiments, the small particulate portion (KCW), large particulate portion (KCY), and/or the spray dried volatiles (KBT) may be transferred to the multifunctional composition tank (6F1) on FIG. 18', or to the *cannabis* tank (6A2) on FIG. 18'.

In embodiments, the third separator (KCR) has a third-second output (KCU) for discharging a fourth separated volatiles (KCX) which include a large particulate portion (KCY). In embodiments, the large particulate portion (KCY) may be transferred to the *cannabis* tank (6A2) on FIG. 18'. In embodiments, the third separator (KCR) separates a small particulate portion (KCW) from a large particulate portion (KCY) using a screen (KM3) or a mesh (KM3'). The screen (KM3) or mesh (KM3') have openings (KM4) that permit the small particulate portion (KCW) to pass through the openings (KM4). The openings (KM4) in the screen (KM3) or mesh (KM3') are too small for the large particulate portion (KCY) to pass through.

In embodiments, the openings (KM4) in the screen (KM3) or mesh (KM3') include Unites States Sieve size number 18, 20, 25, 30, 35, 40, 45, 50, 60, 70, 80, 100, 120, 140, 170, 200, 230, 270, 325, or 400. In embodiments, the openings (KM4) in the screen (KM3) or mesh (KM3') have a size range that is selected from one or more from the group consisting of 37 microns to 44 microns, 44 microns to 53 microns, 53 microns to 63 microns, 63 microns to 74 microns, 74 microns to 88 microns, 88 microns to 105 microns, 105 microns to 125 microns, 125 microns to 149 microns, 149 microns to 177 microns, 177 microns to 210 microns, 210 microns to 250 microns, 250 microns to 297 microns, 297 microns to 354 microns, 354 microns to 420 microns, 420 microns to 500 microns, 500 microns to 595 microns, 595 microns to 707 microns, 707 microns to 841 microns, and 841 microns to 1,000 microns.

In embodiments, the screen (KM3) or mesh (KM3') may be cylindrical and located within a first chamber (KM5). In embodiments, the third separator (KCR) has a third-first input (KCS) that is configured to receive particulate volatiles that include first separated volatiles (KCG), second separated volatiles (KCP), and optionally additional separated volatiles (KDF). An auger (KM1) is configured to transfer the particulate volatiles from the third-first input (KCS) to a screen (KM3) or mesh (KM3') located within the first chamber (KM5) of the third separator (KCR). The auger (KM1) is equipped with a motor (KM2) that may be operated by the computer (COMP). The particulate volatiles transferred from the third-first input (KCS) are sifted using a cylindrical screen (KM3) or mesh (KM3') that is located within the first chamber (KM5).

The third-first output (KCT) is located at the bottom of the first chamber (KM5). The small particulate portion (KCW) may be removed from the third separator (KCR) via the third-first output (KCT) located in the first chamber (KM5). The large particulate portion (KCY) that are too large to pass through openings (KM4) of the screen (KM3) or a mesh (KM3') are transferred from the first chamber (KM5) to the second chamber (KM6) of the third separator (KCR). Since the openings (KM4) in the screen (KM3) or mesh (KM3') within the first chamber (KM5) are too small for the large particulate portion (KCY) to pass through, the large particulate portion (KCY) is transferred from the first chamber (KM5) to the second chamber (KM6) of the third separator (KCR). The large particulate portion (KCY) are removed from the second chamber (KM6) of the third separator (KCR) via the third-second output (KCU).

In embodiments, the sifter is provided by the Kason Corporation. In embodiments, sifter includes a vibratory screener or a centrifugal sifter. In embodiments, the sifter is provided by Kason Corporation and includes a VIBRO SCREEN® Circular Vibratory Screener and Separator, a CENTRI-SIFTER™ High Capacity Screener and Separator, a VIBRO-BED™ Circular Vibratory Fluid Bed Processor, or a CROSS-FLO High Capacity Static Sieve Screener and Separator.

In embodiments, the motor (KM2) of the third separator (KCR) is driven by a belt and ranges from 0.75 horsepower to 6 horsepower. In embodiments, the motor (KM2) of the third separator (KCR) is driven by a belt and ranges from 0.56 kilowatts to 4.48 kilowatts. In embodiments, the motor (KM2) of the third separator (KCR) is not driven by a belt and ranges from 0.5 horsepower to 4 horsepower. In embodiments, the motor (KM2) of the third separator (KCR) is driven by a belt and ranges from 0.37 kilowatts to 2.98 kilowatts.

The fourth separator (KCZ) is connected to the condenser (KDH) via a fourth transfer conduit (KDD). The third volatiles depleted gas stream (KDC) is transferred through the fourth transfer conduit (KDD) and enters the condenser (KDH). The third volatiles depleted gas stream (KDC) includes the vapor portion (KBV") and gas portion (KBV''') that were transferred from the spray dryer (KAP).

The condenser (KDH) condenses the vapor portion (KBV") which may include the second solvent. Liquid is formed from condensing the vapor portion (KBV") of the third volatiles depleted gas stream (KDC) to form process condensate (KDO). Liquid is formed from condensing solvent contained within the third volatiles depleted gas stream (KDC) to form process condensate (KDO). The process condensate (KDO) is discharged from the condenser (KDH) via a liquid output (KDR).

The gas portion (KBV''') of the third volatiles depleted gas stream (KDC) is not condensed within the condenser (KDH) and is instead released from the condenser (KDH) as a via the gas output (KDQ). The non-condensables (KDT) includes the gas portion (KBV''') of the third volatiles depleted gas stream (KDC) and may include gas, air, nitrogen, carbon dioxide. The non-condensables (KDT) leave the gas output (KDQ) of the condenser (KDH) and are routed to a vacuum (KDM) via a gas transfer conduit (KDS).

In embodiments, the vacuum (KDM) is a vacuum pump, fan, or an eductor. A gas exhaust (KDN) is discharged from the vacuum (KDM). The gas exhaust (KDN) includes non-condensables (KDT) or the gas portion (KBV''') of the third volatiles depleted gas stream (KDC) is not condensed within the condenser (KDH).

The condenser (KDH) is provided with a cooling water input (KDI) and a cooling water output (KDK). The cooling water input (KDI) is configured to accept a cooling water supply (KDJ) and the cooling water output (KDK) is configured to discharge a cooling water return (KDL). The cooling water supply (KDJ) is configured to condense a portion of the vapor that enters through the gas-vapor inlet (KDP).

Evaporator Operation: The system shown in FIG. 17E' can operate in a plurality of modes of operation, including:
(1) preparation of the second volatiles and solvent mixture (SVSM);
(2) start-up;
(3) normal operation;
(4) emergency shut-down;
(5) resuming operations after the emergency shut-down.

As seen in FIG. 17E', the solvent separation system is equipped with a start-up/shut-down liquid system (KEZ). The purpose of the start-up/shut-down liquid system (KEZ) is to make a pressurized and optionally heated supply of liquid immediately available to the evaporator (KAO) whenever necessary. It is preferred that second solvent (SOLV2) is used within the start-up/shut-down liquid system (KEZ), the second solvent (SOLV2) includes one or more from the group consisting of a liquid, acetone, alcohol, oil, ethanol. Water may be used in the start-up/shut-down liquid system (KEZ).

It is also desired to be able to mix a known flow of treated, filtered, start-up/shut-down water (KEO) in with the second volatiles and solvent mixture (SVSM) to be used for start-up, shut-down or maintenance purposes such as cleaning.

A start-up/shut-down liquid tank (KEA) is provided and is configured to accept a stream of liquid (KEB). The liquid (KEB) transferred to the interior (KEA') of the start-up/shut-down liquid tank (KEA) can be passed through a filter (G23), activated carbon (G24), and/or an adsorbent (G25), and a polishing unit (G41). The polishing unit (G41) may be any type of conceivable device to improve the water quality such as an ultraviolet unit, ozone unit, microwave unit, filter, or the like.

The start-up/shut-down liquid tank (KEA) may be equipped with a level sensor (KES) that sends a signal (KET) to the computer (COMP). A level control valve (KEU) may be used to control the amount of liquid (KEB) that is transferred to the interior (KEA') of the start-up/shut-down liquid tank (KEA). The level control valve (KEU) may be equipped with a controller (KEV) that is configured to input or output a signal (KEW) to the computer (COMP). The computer (COMP), level control valve (KEU), and level sensor (KES) may be used together in a level control loop to maintain a constant or batch supply of liquid to the interior (KEA') of the start-up/shut-down liquid tank (KEA).

In embodiments, a start-up heat exchanger (KEP) is configured to heat the liquid (KEB) that will be transferred to the evaporator (KAO). In embodiments, a start-up heat exchanger (KEP) is configured to heat the liquid (KEB) that will be transferred to the evaporator (KAO), spray dryer (KAP), rotary atomizer (KAU), spray nozzle (KBC) or plurality of spray nozzles (KBC), or openings (KBC) or plurality of openings (KBC) within the disc (KBB) of the rotary atomizer (KAU). The purpose of heating the liquid than will be transferred to the evaporator (KAO) is to not provide a thermal shock on the system while can result in fouled heat transfer surfaces of the outer wall (KWG) within the interior (KBG') of the drying chamber (KBG), and to prevent cloggage of either the disc (KBB), spray nozzle (KBC), plurality of spray nozzles (KBC), opening (KBD), plurality of openings (KBD), spray aperture (KK4), or orifice (KK5).

Is it desired to heat the liquid (KEO, KEB) that is transferred to the spray dryer (KAP) so that a seamless transition from liquid (KEO, KEB) to a second volatiles and solvent mixture (SVSM) can be realized to attain steady-state conditions in the safest and most efficient manner as possible.

In embodiments, it is necessary to be able to heat the liquid (KEB) prior to adding to the evaporator (KAO) by itself, or add the liquid (KEB) to the evaporator (KAO) together while adding the second volatiles and solvent mixture (SVSM). Herein are disclosed methods to vary the flow of liquid (KEB) to an evaporator, such as a spray dryer, while varying either the flow of liquid (KEB) and/or the flow of second volatiles and solvent mixture (SVSM) to optimize operations and efficiency while reducing plant maintenance and cleaning.

FIG. 17E' shows the start-up heat exchanger (KEP) positioned within the interior (KEA') start-up/shut-down liquid tank (KEA). In embodiments, the start-up heat exchanger (KEP) is located in between the start-up/shut-down liquid tank (KEA) and the evaporator (KAO).

In embodiments, a liquid pump (KEK) is provided and configured to transfer liquid from the start-up/shut-down liquid tank (KEA) and into the evaporator (KAO). The liquid pump (KEK) is equipped with a motor (KEL) and a controller (KEM) which is configured to input or output a signal (KEN) to the computer (COMP).

In embodiments, a liquid control valve (KEF) is provided to control the flow of start-up/shut-down liquid (KEB, KEO) transferred from the start-up/shut-down liquid tank (KEA) into the evaporator (KAO). The liquid control valve (KEF) is equipped with a controller (KEG) that is configured to input or output a signal (KEH) to the computer (COMP).

In embodiments, a liquid flow sensor (KEI) is provided to measure the flow of start-up/shut-down liquid (KEB, KEO) transferred from the start-up/shut-down liquid tank (KEA) into the evaporator (KAO). In embodiments, the computer (COMP), liquid control valve (KEF), liquid flow sensor (KEI), are used in a flow control loop to control the amount of liquid (KEB, KEO) that is provided into the evaporator (KAO).

FIG. 17E' shows a co-current spray dryer (KAP) evaporator (KAO). In FIG. 17E' the liquid input (KAR) is closer to the top (K-T) than the bottom (K-B). In FIG. 17E' the gas input (KAQ) is closer to the top (K-T) than the bottom (K-B). In FIG. 17E' the first output (KBS) is closer to the bottom (K-B) than the top (K-T). In FIG. 17E' the second output (KBU) is closer to the bottom (K-B) than the top (K-T). Here, the heated gas supply (KAG') flows in the same direction of the second volatiles and solvent mixture (SVSM).

FIG. 17E-1'

FIG. 17E-1' shows one non-limiting embodiment of a co-current type of spray dryer (KAP) that may be used with the solvent separation system described in FIG. 17E'.

Shown in FIGS. 17E', 17E-1', 17E-2', 17E-3', and 17E-4', are different embodiments of a spray dryer (KAP) having a top (K-T) bottom (K-B) that are spaced apart along a vertical axis (KYY). The differences between the different types of spray dryers shown in FIGS. 17E-1', 17E-2', 17E-3', and 17E-4' are the differences in height of various inputs and outputs, specifically, the differences in relative heights of: (A) the liquid input (KAR) that introduces an second volatiles and solvent mixture (SVSM) to the interior (KAP') of the spray dryer (KAP); (B) the gas input (KAQ) that introduces a heated gas supply (KAG') to the interior (KAP') of the spray dryer (KAP); (C) first output (KB S) that discharges volatiles (KBT) from the from the interior (KAP') of the spray dryer (KAP); and (D) second output (KBU) that evacuates a volatiles and gas mixture (KBV) away from the interior (KAP') of the spray dryer (KAP).

In FIG. 17E-1' the liquid input (KAR) is closer to the top (K-T) than the bottom (K-B). In FIG. 17E-1' the gas input (KAQ) is closer to the top (K-T) than the bottom (K-B). In FIG. 17E-1' the first output (KBS) is closer to the bottom (K-B) than the top (K-T). In FIG. 17E-1' the second output (KBU) is closer to the bottom (K-B) than the top (K-T). FIG. 17E-1' shows a co-current spray dryer (KAP) evaporator (KAO) with the heated gas supply (KAG') flowing in the same direction of the second volatiles and solvent mixture (SVSM).

FIG. 17E-2'

FIG. 17E-2' shows one non-limiting embodiment of a counter-current type of spray dryer (KAP) that may be used with the solvent separation system described in FIG. 17E'.

In FIG. 17E-2' the liquid input (KAR) is closer to the top (K-T) than the bottom (K-B). In FIG. 17E-2' the gas input (KAQ) is closer to the bottom (K-B) than the top (K-T). In FIG. 17E-2' the first output (KB S) is closer to the bottom (K-B) than the top (K-T). In FIG. 17E-2' the second output (KBU) is closer to the top (K-T) than the bottom (K-B). FIG. 17E-2' shows a counter-current spray dryer (KAP) evaporator (KAO) with the heated gas supply (KAG') flowing in a direction that is opposite to the flow of the second volatiles and solvent mixture (SVSM). Here, the heated gas supply (KAG') flows upwards from the gas input (KAQ) to the second output (KBU), while the second volatiles and solvent mixture (SVSM) is sprayed in a downwards direction.

FIG. 17E-3'

FIG. 17E-3' shows another non-limiting embodiment of a counter-current type of spray dryer (KAP) that may be used with the solvent separation system described in FIG. 17E'. In FIG. 17E-3' the liquid input (KAR) is closer to the bottom (K-B) than the top (K-T). In FIG. 17E-3' the gas input (KAQ) is closer to the top (K-T) than the bottom (K-B). In FIG. 17E-3' the first output (KBS) is closer to the bottom (K-B) than the top (K-T). In FIG. 17E-3' the second output (KBU) is closer to the bottom (K-B) than the top (K-T).

FIG. 17E-3' shows a counter-current spray dryer (KAP) evaporator (KAO) with the heated gas supply (KAG') flowing in a direction that is opposite to the flow of the second volatiles and solvent mixture (SVSM). Here, the heated gas supply (KAG') flows downwards from the gas input (KAQ) to the second output (KBU), while the second volatiles and solvent mixture (SVSM) is sprayed in an upwards direction.

FIG. 17E-4'

FIG. 17E-4' shows one non-limiting embodiment of a mixed-flow type of spray dryer (KAP) that may be used with the solvent separation system described in FIG. 17E'.

In FIG. 17E-4' the liquid input (KAR) is closer to the bottom (K-B) than the top (K-T). In FIG. 17E-4' the gas input (KAQ) is closer to the top (K-T) than the bottom (K-B). In FIG. 17E-4' the first output (KBS) is closer to the bottom (K-B) than the top (K-T). In FIG. 17E-4 the second output (KBU) is second output (KBU) is closer to the bottom (K-B) than the top (K-T), the other (KBU') is closer to the top (K-T) than the bottom (K-B).

FIG. 17E-4' shows a mixed-flow spray dryer (KAP) evaporator (KAO) with the heated gas supply (KAG') flowing in a direction that is opposite to the flow of the second volatiles and solvent mixture (SVSM). Here, the heated gas supply (KAG') flows both, in the same direction of the second volatiles and solvent mixture (SVSM), as well as opposite to the direction of the flow of the second volatiles and solvent mixture (SVSM). Here, the second volatiles and solvent mixture (SVSM) is sprayed in an upwards direction.

FIG. 17F'

FIG. 17F' shows a power production system (PPS) that is configured to generate electricity, heat, or steam for use in the farming superstructure system (FSS).

In embodiments, the power production system (PPS) shown in FIG. 17F' can generate electricity for use in the farming superstructure system (FSS). In embodiments, the power production system (PPS) shown in FIG. 17F' can generate steam and/or heat for use in the farming superstructure system (FSS). In embodiments, the power production system (PPS) shown in FIG. 17F' can generate heat for use in the farming superstructure system (FSS). In embodiments, the power production system (PPS) includes a compressor (LEB), a combustor (LED), a turbine (LFE), a generator (LFH), a HRSG (heat recovery steam generator) (LFI), a steam drum (LBE), a steam distribution header (LCJ), and a condensate tank (LAP).

An oxygen-containing gas (LEA) is made available to a compressor (LEB). In embodiments, the oxygen-containing gas may be air, oxygen-enriched-air i.e. greater than 21 mole % O2, and substantially pure oxygen, i.e. greater than about 95 mole % oxygen (the remainder usually comprising N2 and rare gases). In embodiments, the oxygen-containing gas may be flue gas or carbon dioxide. In embodiments, flue gas includes a vapor or gaseous mixture containing varying amounts of nitrogen (N2), carbon dioxide (CO2), water (H2O), and oxygen (O2). In embodiments, flue gas is generated from the thermochemical process of combustion. In embodiments, combustion is an exothermic (releases heat) thermochemical process wherein at least the stoichiometric oxidation of a carbonaceous material takes place to generate flue gas.

In embodiments, the compressor (LEB) has a plurality of stages (LEC). In embodiments, the compressor (LEB) is an axial compressor. In embodiments, the compressor is configured to compress and pressurize the oxygen-containing gas (LEA) to form a compressed gas stream (LEK). In embodiments, the compressor is configured to compress and pressurize the oxygen-containing gas (LEA) to form a first compressed gas stream (LEK) and a second compressed gas stream (LEN). In embodiments, compressed gas stream (LEK) is provided to a combustor (LED). In embodiments, the first compressed gas stream (LEK) is provided to a first combustor (LED1). In embodiments, the second compressed gas stream (LEN) is provided to a second combustor (LED2).

In embodiments, the first combustor (LED1) has a first gas mixer (LEE). In embodiments, the second combustor (LED2) has a second gas mixer (LEH). In embodiments, the first gas mixer (LEE) or second gas mixer (LEH) is that of an annular type. In embodiments, the first combustor (LED1) or second combustor (LED2) is that of an annular type. In embodiments, the annular type gas mixer (LEE) mixes the fuel with the oxygen containing-gas within the combustor to form a fuel-and-oxygen-containing gas mixture, which is then combusted. In embodiments, the first combustor (LED1) has a first ignitor (LEF). In embodiments, the second combustor (LED2) has a second ignitor (LEI). In embodiments, the first ignitor (LEF) or second ignitor (LEI) include a torch ignitor. In embodiments, the first ignitor (LEF) or second ignitor (LEI) include a separate fuel supply to maintain a constantly burning torch. In embodiments, the first combustor (LED1) has a first flame detector (LEG). In embodiments, the second combustor (LED2) has a second flame detector (LEJ). In embodiments, the first flame detector (LEG) or second flame detector (LEJ) are selected from one or more from the group consisting of a UV flame detector, IR flame detector, UV/IR flame detector, multi-spectrum infrared flame detector, and a visual flame imaging flame detector.

In embodiments, the combustor (LED) mixes and combusts the compressed gas stream (LEK) with a first fuel (LEL) to produce a combustion stream (LEM). In embodiments, the first combustor (LED1) mixes and combusts the first compressed gas stream (LEK) with a first fuel (LEL) to produce a first combustion stream (LEM). In embodiments, the first combustion stream (LEM) is a first pressurized combustion stream (LEM'). In embodiments, the second combustor (LED2) mixes and combusts the second compressed gas stream (LEN) with a second fuel (LEO) to produce a second combustion stream (LEP). In embodiments, the second combustion stream (LEP) is a second pressurized combustion stream (LEP').

A first fuel valve (LEW) is provided to regulate the flow of the compressor fuel source (LEU) to the first combustor (LED1) and the second combustor (LED2). The first fuel valve (LEW) is equipped with a controller (LEX) that is configured to input or output a signal (LEY) to the computer (COMP). FIG. 17F' shows connector (K1) to show continuity between the second fuel (LEO) that is apportioned from the compressor fuel source (LEU) and transferred to the second combustor (LED2).

The combustion stream (LEM) is transferred to a turbine (LFE). In embodiments, the first combustion stream (LEM) is combined with the second combustion stream (LEP) before being transferred to the turbine (LFE). In embodiments, the turbine (LFE) has a plurality of stages (LFF). In embodiments, the first and second combustion streams (LEM, LEP) rotate a portion of the turbine (LFE), which in turn rotates a shaft (LFG), and a generator (LFH) to produce electricity (ELEC). In embodiments, the combustion stream (LEM) rotates the turbine (LFE), which in turn rotates a shaft (LFG), and a generator (LFH) to produce electricity (ELEC).

In embodiments, the compressor (LEB) is connected to the turbine (LFE) via a shaft (LFG). In embodiments, the turbine (LFE) is connected to the generator (LFH) via a shaft (LFG). In embodiments, the turbine (LFE) rotates the shaft (LFG) which in turn drives the compressor (LEB). In embodiments, the generator (LFH) is connected to the turbine (LFE) via a shaft (LFG). In embodiments, the turbine (LFE) rotates the shaft (LFG) which in turn drives the generator (LFH) to produce electricity for use in the farming superstructure system (FSS).

FIG. 17F' shows the generator (LFH) producing electricity for use in the computer (COMP) within the farming superstructure system (FSS). In embodiments, the electricity (ELEC) may be used in the farming superstructure system (FSS) in any number of a plurality of: sensors, motors, pumps, heat exchangers, fans, actuators, controllers, compressors, analyzers, computers, lights, heaters, vacuum pumps, etc. Any asset, including sensors, motors, pumps, heat exchangers, fans, actuators, controllers, compressors, analyzers, computers, lights, heaters, vacuum pumps, disclosed in FIGS. 1A' through 23' may be powered by the electricity (ELEC) generated by the generator (LFH) or generator (LCA).

A combustion stream (LFD) is discharged from the turbine (LFE) and is routed to a HRSG (LFI). In embodiments, the combustion stream (LFD) that is discharged from the turbine (LFE) is a depressurized combustion stream (LFD'). In embodiments the depressurized combustion stream (LFD') has a pressure that is less than the pressure of the combustion stream (LEM, LEP) that is transferred to the turbine (LFE). The combustion stream (LFD) is transferred from the turbine (LFE) to the HRSG (LFI). The HRSG (LFI) is configured to remove heat from the combustion stream (LFD) by use of a heat transfer conduit (LBI) or a plurality of heat transfer conduits (LBI). At least one heat transfer conduit (LBI) generates steam through indirect heat transfer from the combustion stream (LFD).

In embodiments, the HRSG (LFI) is a fired-HRSG (LFJ). In embodiments, the fired-HRSG (LFJ) accepts a HRSG fuel source (LEV). In embodiments, the HRSG fuel source (LEV) is combusted with the combustion stream (LFD) that is transferred from the turbine (LFE) to form a combustion stream (LX0'). In embodiments, the HRSG fuel source (LEV) is combusted with an oxygen-containing gas (LX0). In the instance where the HRSG fuel source (LEV) is combusted with an oxygen-containing gas (LX0), the compressor (LEB), a combustor (LED), a turbine (LFE), a generator (LFH) are optional. Thus, saturated steam (LBR) or superheated steam (LBS) may be generated within the steam drum (LBE) by combusting an oxygen-containing gas (LX0) with the compressor fuel source (LEU) to form a combustion stream (LX0').

In embodiments, a second fuel valve (LFA) is made available to regulate the amount of the HRSG fuel source (LEV) that is introduced to the fired-HRSG (LFJ). The second fuel valve (LFA) is equipped with a controller (LFB) that is configured to input or output a signal (LFC) to the computer (COMP). In embodiments, the compressor fuel source (LEU) and HRSG fuel source (LEV) come from a common fuel source (LEQ). A compressor fuel source (LEU) provides the fuel that is used as the first fuel (LEL) and second fuel (LEO). In embodiments, the fuel source (LEQ) that is made available as the compressor fuel source (LEU) or HRSG fuel source (LEV) may include a hydrocarbon. In embodiments, the fuel source (LEQ) that is made available as the compressor fuel source (LEU) or HRSG fuel source (LEV) may be a liquid, vapor, or a gas. In embodiments, the fuel source (LEQ) that is made available as the compressor fuel source (LEU) or HRSG fuel source (LEV) may be a methane containing gas such as natural gas. In embodiments, the fuel source (LEQ) that is made available as the compressor fuel source (LEU) or HRSG fuel source (LEV) may be naphtha, natural gas, gasoline, a hydrocarbon, diesel, or oil. In embodiments, the fuel source (LEQ, LET, LEU, LEV), may include a hydrocarbon, and may be a liquid, vapor, or a gas. In embodiments, the fuel source (LEQ, LET, LEU, LEV), may be a methane containing gas such as natural gas, or otherwise may be naphtha, natural gas, gasoline, a hydrocarbon, diesel, or oil.

In embodiments, a fuel source (LEQ) is made available to a fuel compressor (LER) to form a compressed fuel (LET). In embodiments, the fuel compressor (LER) has a plurality of stages (LES). A pressure sensor (LEQP) is provided to measure the pressure of the fuel source (LEQ) that is made available to the fuel compressor (LER). In embodiments, the compressor fuel source (LEU) and HRSG fuel source (LEV) are a compressed fuel (LET). In embodiments, the HRSG fuel source (LEV) is combusted within the fired-HRSG (LFJ) using a burner (LFK) such as a duct burner. In embodiments, the fired-HRSG (LFJ) or the burner (LFK) is lined with refractory material. In embodiments, the refractory material includes a ceramic, alumina, silica, magnesia, silicon carbide, or graphite.

In embodiments, heat is removed from the HRSG (LFI) and a flue gas (LFP) is evacuated from the HRSG (LFI). In embodiments, heat is removed from the fired-HRSG (LFJ) and a flue gas (LFP) is evacuated from the fired-HRSG (LFJ). A temperature sensor (LFM) is configured to measure the temperature within the HRSG (LFI, LFJ). A temperature sensor (LFM) is configured to measure the temperature of the flue gas (LFP) that is discharged from the HRSG (LFI, LFJ). In embodiments, at least a portion of the flue gas (LFP) is made available as flue gas (FG1) that may be transferred to the thermal compressor (Q30) on FIG. 5C' or 5E'. In embodiments, at least a portion of the flue gas (LFP) is made available as flue gas (FG1) that may be transferred to the generator (Q50) within the thermal compressor (Q30) on FIG. 5C' or 5E'.

The steam generated in the plurality of heat transfer conduits (LBI) is routed to a steam drum (LBE). In embodiments, the steam drum (LBE) generates saturated steam (LBR) or superheated steam (LBS). In embodiments, saturated steam (LBR) is discharged from the steam drum (LBE) and is routed to a superheater (LX3) through a saturated steam transfer conduit (LX1). Heat is transferred from the combustion stream (LFD, LX0') to saturated steam (LBR) within the superheater (LX3) to produce superheated steam (LBS) which is routed to a superheated steam transfer conduit (LX2).

A steam distribution header (LCJ) is configured to accept at least a portion of the saturated steam (LBR) or superheated steam (LBS). In embodiments, a first portion (LBW) of either the saturated steam (LBR) or superheated steam (LBS) is transferred through a first steam transfer conduit (LBY) and into the steam distribution header (LCJ). In embodiments, a second portion (LBX) of either the saturated steam (LBR) or superheated steam (LBS) is transferred through a second steam transfer conduit (LSY) and into steam turbine (LBZ) to generate electricity via a generator (LCA). In embodiments, the steam turbine (LBZ) has a plurality of stages (LBZX). The steam turbine (LBZ) is connected to a generator (LCA) via a shaft (LCB). Depressurized steam (LCI) is evacuated from the steam turbine (LBZ) and is routed towards the steam distribution header (LCJ).

FIG. 17F' shows a steam distribution header (LCJ) that is configured to accept at least a portion of the saturated steam (LBR) or superheated steam (LB S) that are routed through either the first steam transfer conduit (LBY) or second steam transfer conduit (LSY). A pressure sensor (LBO) is provided to measure the pressure within the interior of the steam drum (LBE). A temperature sensor (LBQ) is provided to measure the temperature of the saturated steam (LBR) or superheated steam (LBS) that are discharged from the steam drum (LBE). A pressure control valve (LBT) is positioned on the steam distribution header (LCJ). In embodiments, the pressure control valve (LBT) controls the pressure within the steam drum (LBE). In embodiments, the pressure control valve (LBT) controls the pressure within first steam transfer conduit (LBY) and second steam transfer conduit (LSY). The pressure control valve (LBT) is equipped with a controller (LBU) that sends a signal (LBV) to or from the computer (COMP). In embodiments, the computer (COMP), pressure control valve (LBT), and pressure sensor (LBO) are used in a control loop to regulate the pressure within the steam drum (LBE), first steam transfer conduit (LBY), or second steam transfer conduit (LSY).

In embodiments, the steam distribution header (LCJ) provides a source of steam to a variety of locations within the farming superstructure system (FSS). In embodiments, the velocity of steam within the steam distribution header (LCJ) ranges from one or more from the group selected from 50 feet per second (FPS) to 60 FPS, 60 FPS to 70 FPS, 70 FPS to 80 FPS, 80 FPS to 90 FPS, 90 FPS to 100 FPS, 100 FPS to 110 FPS, 110 FPS to 120 FPS, 120 FPS to 130 FPS, 130 FPS to 140 FPS, 140 FPS to 150 FPS, 150 FPS to 160

FPS, 160 FPS to 180 FPS, 180 FPS to 200 FPS, 200 FPS to 225 FPS, and 225 FPS to 250 FPS.

In embodiments, the steam distribution header (LCJ) operates at a pressure range that is selected from one or more from the group consisting of 5 pounds per square inch (PSI) 10 PSI, 10 PSI 20 PSI, 20 PSI 30 PSI, 30 PSI 40 PSI, 40 PSI 50 PSI, 50 PSI 60 PSI, 60 PSI 70 PSI, 70 PSI 80 PSI, 80 PSI 90 PSI, 90 PSI 100 PSI, 100 PSI 125 PSI, 125 PSI 150 PSI, 150 PSI 175 PSI, 175 PSI 200 PSI, 200 PSI 225 PSI, 225 PSI 250 PSI, 250 PSI 275 PSI, 275 PSI 300 PSI, 300 PSI 325 PSI, 325 PSI 350 PSI, 350 PSI 375 PSI, 375 PSI 400 PSI, 400 PSI 425 PSI, 425 PSI 450 PSI, 450 PSI 475 PSI, 475 PSI 500 PSI, 500 PSI 525 PSI, 525 PSI 550 PSI, 550 PSI 575 PSI, 575 PSI 600 PSI, 600 PSI 700 PSI, 700 PSI 800 PSI, 800 PSI 900 PSI, and 900 PSI 1,000 PSI.

In embodiments, the steam distribution header (LCJ) is insulated with insulation (LCJ'). In embodiments, the range of thickness of the insulation (LCJ') on the steam distribution header (LCJ) is selected from one or more from the group consisting of 1 inches to 1.5 inches, 1.5 inches to 2 inches, 2 inches to 2.5 inches, 2.5 inches to 3 inches, 3 inches to 3.5 inches, 3.5 inches to 4 inches, 4 inches to 4.5 inches, 4.5 inches to 5 inches, 5 inches to 5.5 inches, 5.5 inches to 6 inches, 6 inches to 6.5 inches, 6.5 inches to 7 inches, 7 inches to 7.5 inches, 7.5 inches to 8 inches, 8 inches to 8.5 inches, 8.5 inches to 9 inches, 9 inches to 9.5 inches, 9.5 inches to 10 inches, 10 inches to 11 inches, 11 inches to 12 inches, 12 inches to 13 inches, 13 inches to 14 inches, 14 inches to 15 inches, 15 inches to 16 inches, 16 inches to 17 inches, and 17 inches to 18 inches.

In embodiments, the steam distribution header (LCJ) provides a source of steam to a variety of locations including: a first steam supply (LCL) to FIG. 5C' to the thermal compressor (Q30), a second steam supply (LCL) to FIG. 17D' to the evaporator (J11), a third steam supply (LCL) to FIG. 17E' to the spray dryer (KAP), a fourth steam supply (LCL) to FIG. 17E' to the spray dryer (KAP) heating jacket (KBJ).

In embodiments, a first steam valve (LCM) is configured to regulate the amount of the first steam supply (LCL) to FIG. 5C' to the thermal compressor (Q30). A first reducer (LCN) may be positioned upstream or downstream of the first steam valve (LCM) on the steam distribution header (LCJ).

In embodiments, a second steam valve (LDK) is configured to regulate the amount of the second steam supply (LDJ) to FIG. 17D' to the evaporator (J11). A second reducer (LDL) may be positioned upstream or downstream of the second steam valve (LDK) on the steam distribution header (LCJ).

In embodiments, a third steam valve (LDN) is configured to regulate the amount of the third steam supply (LDM) to FIG. 17E' to the spray dryer (KAP). A third reducer (LDO) may be positioned upstream or downstream of the third steam valve (LDN) on the steam distribution header (LCJ).

In embodiments, a fourth steam valve (LDQK) is configured to regulate the amount of the fourth steam supply (LDP) to FIG. 17E' to the spray dryer (KAP) heating jacket (KBJ). A fourth reducer (LDR) may be positioned upstream or downstream of the fourth steam valve (LDQ) on the steam distribution header (LCJ).

In turn, a plurality of steam condensate streams are transferred from various locations within the FSS and are returned to a condensate tank (LAP) as indicated on FIG. 17F'. In embodiments, the condensate tank (LAP) accepts steam condensate streams are transferred from various locations, including: a first condensate (LJC) from FIG. 5C' from the thermal compressor (Q30), a second condensate (LAW) from FIG. 17D' from the evaporator (J11), a third condensate (LJA) from FIG. 17E' from the spray dryer (KAP), a fourth condensate (LJB) from FIG. 17E' from the spray dryer (KAP) heating jacket (KBJ).

In embodiments, at least a portion are used again to remove heat within the HRSG (LFI, LFJ): first condensate (LJC), second condensate (LAW), third condensate (LJA), fourth condensate (LJB). In embodiments, feed water (LAX) (which may include condensate (LJC, LAW, LJA, LJB)) is pumped to the from the condensate tank (LAP) to the steam drum input (LBD) of the steam drum (LBE) via a pump (LAX').

A heat exchanger (LAZ) is provided to pre-heat the feed water (LAX) as it is transferred from the condensate tank (LAP) to the steam drum (LBE). A temperature sensor (LAY) is provided to measure the temperature of the feed water (LAX) before it enters the heat exchanger (LAZ). Another temperature sensor (LBC) is provided to measure the temperature of the feed water (LAX) after is exits the heat exchanger (LAZ).

In embodiments, the steam drum (LBE) is equipped with a level sensor (LBP) that is configured to regulate the amount of feed water (LAX) that is introduced to the steam drum (LBE). In embodiments, the steam drum (LBE) is equipped with a level control valve (LBP') that is configured to regulate the amount of feed water (LAX) that is introduced to the steam drum (LBE). In embodiments, the computer (COMP), level sensor (LBP), and level control valve (LBP') may be used in a control loop to regulate the amount of feed water (LAX) that is introduced to the steam drum (LBE).

In embodiments, the steam drum (LBE) is connected to a lower steam drum (LBF) via a plurality of heat transfer conduit (LBG, LBH, LBI). In embodiments, lower steam drum (LBF) is configured to discharge a blowdown (LBK) through a valve (LBN). In embodiments, the blowdown (LBK) includes suspended solids (LBL) and/or dissolved solids (LBM). In embodiments, the suspended solids (LBL) include solids such as bacteria, silt and mud. In embodiments, the dissolved solids (LBM) may include minerals, salts, metals, cations or anions dissolved in water. In embodiments, the dissolved solids (LBM) include inorganic salts including principally calcium, magnesium, potassium, sodium, bicarbonates, chlorides, and sulfates.

In embodiments, the condensate tank (LAP) also serves the purpose as a water tank (LAO) for accepting treated water (LAJ). Thus, treated water (LAJ) is added to the condensate tank (LAP) to make-up for water losses in the system. A source of water (LAA) is made available to a series of unit operations that are configured to improve the water. In embodiments, the source of water (LAA) is passed through a filter (LAC), a packed bed (LAD) of adsorbent (LAE), a cation (LAF), an anion (LAG), a membrane (LAH), followed by another cation/anion (LAI) to result in treated water (LAJ).

The treated water (LAJ) is then provided to the condensate tank (LAP)/water tank (LAO) via a pump (LAK). In embodiments, the treated water (LAJ) that is transferred to the condensate tank (LAP)/water tank (LAO) via a pump (LAK) is passed through a valve (LAL). The valve (LAL) is equipped with a controller (LAM) that is configured to input or output a signal (XAM) to the computer (COMP). A quality sensor (LAN) is provided as a quality control of the unit operations that are configured to improve the water. FIG. 17G'

FIG. 17G' shows one non-limiting embodiment of a carbon dioxide removal system (GAE) that is configured to remove carbon dioxide from flue gas (LFP) for use as a source of carbon dioxide ($CO_2$) in the farming superstructure system (FSS).

Flue gas (LFP) is provided from FIG. 17F' to FIG. 17G'. The flue gas (LFP) is routed to a first compressor (GAB), which may have a plurality of stages (GAC). A first pressure sensor (GAA) measures the inlet pressure to the first compressor (GAB). The first compressor (GAB) elevates the pressure of the flue gas to produce pressurized flue gas (GAD). A second pressure sensor (GAA) measures the outlet pressure to the first compressor (GAB). A carbon dioxide removal system (GAE) is provided to remove carbon dioxide ($CO_2$) from flue gas (LFP) or from the pressurized flue gas (GAD). A carbon dioxide depleted flue gas is discharged from the carbon dioxide removal system (GAE). In embodiments, the carbon dioxide ($CO_2$) that was removed from the flue gas (LFP, GAD) is provided to the carbon dioxide tank (CO2T), which is discussed in detail on FIGS. 1A' and 1B'. Alternately, the carbon dioxide ($CO_2$) that was removed from the flue gas (LFP, GAD) may be directly made available to the first growing assembly (100) or second growing assembly (200).

In embodiments, carbon dioxide removal system (GAE) may include one or more from the group consisting of a membrane, an adsorber, a pressure swing adsorber, a temperature swing adsorber, a membrane, a solvent scrubber, a scrubber, an absorber, an amine scrubber, and an amine absorber.

In embodiments, the an adsorber, fixed bed adsorber, moving bed adsorber, a pressure swing adsorber, a temperature swing adsorber, may contain an adsorbent material. In embodiments, the adsorbent material may include regenerable and non-regenerable sorbents. In embodiments, the adsorbent material may be selected from one or more from the group consisting of 3 Angstrom molecular sieve, 3 Angstrom zeolite, 4 Angstrom molecular sieve, 4 Angstrom zeolite, activated alumina, activated carbon, adsorbent, alumina, carbon, catalyst, clay, desiccant, molecular sieve, zeolites, polymer, resin, and silica gel.

In embodiments, a second compressor (GAG) is provided to compress the carbon dioxide that is discharged from the carbon dioxide removal system (GAE). The second compressor (GAG) elevates the pressure of the carbon dioxide to produce carbon dioxide (GAI). In embodiments, the second compressor (GAG) has a plurality of stages (GAH).

As shown in FIG. 17G', the carbon dioxide tank (CO2T) is in fluid communication with the plurality of growing assemblies (100, 200) as shown on FIGS. 1A' and 1B'. The carbon dioxide tank (CO2T) contains pressurized carbon dioxide ($CO_2$) and is equipped with a carbon dioxide pressure sensor (CO2P). A carbon dioxide supply header (CO2H) is connected to the carbon dioxide tank (CO2T). A first carbon dioxide supply valve (V10) is installed on the carbon dioxide supply header (CO2H) and is configured to take a pressure drop of greater than 50 pounds per square inch (PSI). In embodiments, range of the pressure drop across the first carbon dioxide supply valve (V10) is selected from one or more from the group consisting of 25 pounds per square inch (PSI) to 50 PSI, 50 PSI to 75 PSI, 75 PSI to 100 PSI, 100 PSI to 125 PSI, 125 PSI to 150 PSI, 150 PSI to 175 PSI, 175 PSI to 200 PSI, 200 PSI to 225 PSI, 225 PSI to 250 PSI, 250 PSI to 275 PSI, 275 PSI to 300 PSI, 300 PSI to 325 PSI, 325 PSI to 350 PSI, 350 PSI to 375 PSI, 375 PSI to 400 PSI, 400 PSI to 425 PSI, 425 PSI to 450 PSI, 450 PSI to 475 PSI, 475 PSI to 500 PSI, 500 PSI to 600 PSI, 600 PSI to 700 PSI, 700 PSI to 800 PSI, 800 PSI to 900 PSI, 900 PSI to 1000 PSI, 1,000 PSI to 1,250 PSI, 1,250 PSI to 1,500 PSI, 1,500 PSI to 1,750 PSI, 1,750 PSI to 2,000 PSI, 2,000 PSI to 2,250 PSI, 2,250 PSI to 2,500 PSI, 2,500 PSI to 2,750 PSI, 2,750 PSI to 3,000 PSI, 3,000 PSI to 3,250 PSI, 3,250 PSI to 3,500 PSI, 3,500 PSI to 3,750 PSI, 3,750 PSI to 4,000 PSI, 4,000 PSI to 4,500 PSI, and 4,500 PSI to 5,000 PSI.

As shown in FIGS. 1A and 1B, the carbon dioxide ($CO_2$) transferred from the carbon dioxide tank (CO2T) the first growing assembly (100) is equipped with a CO2 input (115) that is connected to a CO2 supply conduit (116). The second growing assembly (200) is also equipped with a CO2 input (215) that is connected to a CO2 supply conduit (216). The CO2 supply conduit (116) of the first growing assembly (100) is connected to the carbon dioxide supply header (CO2H) via a CO2 header connection (115X). The CO2 supply conduit (116) of the first growing assembly (100) is configured to transfer carbon dioxide into the first interior (101) of the first growing assembly (100). In embodiments, a second carbon dioxide supply valve (V8) is installed on the CO2 supply conduit (116) of the first growing assembly (100). The second carbon dioxide supply valve (V8) is equipped with a controller (CV8) that sends a signal (XV8) to and from a computer (COMP). In embodiments, a CO2 flow sensor (FC1) is installed on the CO2 supply conduit (116) of the first growing assembly (100). The CO2 flow sensor (FC1) sends a signal (XFC1) to the computer (COMP). In embodiments, a gas quality sensor (GC1) is installed on the first growing assembly (100) to monitor the concentration of carbon dioxide within the first interior (101). The gas quality sensor (GC1) is equipped to send a signal (XGC1) to the computer (COMP).

The CO2 supply conduit (216) of the second growing assembly (200) is connected to the carbon dioxide supply header (CO2H) via a CO2 header connection (215X). The CO2 supply conduit (216) of the second growing assembly (200) is configured to transfer carbon dioxide into the second interior (201) of the second growing assembly (100). In embodiments, a third carbon dioxide supply valve (V9) is installed on the CO2 supply conduit (216) of the second growing assembly (200). The third carbon dioxide supply valve (V9) is equipped with a controller (CV9) that sends a signal (XV9) to and from a computer (COMP). In embodiments, a CO2 flow sensor (FC2) is installed on the CO2 supply conduit (216) of the second growing assembly (200). The CO2 flow sensor (FC2) sends a signal (XFC2) to the computer (COMP). In embodiments, a gas quality sensor (GC2) is installed on the second growing assembly (200) to monitor the concentration of carbon dioxide within the second interior (201). The gas quality sensor (GC2) is equipped to send a signal (XGC2) to the computer (COMP).

In embodiments, the range of the carbon dioxide concentration in the plurality of growing assemblies (100, 200) is selected from one or more from the group consisting of 390 part per million (PPM) to 400 PPM, 400 PPM to 410 PPM, 410 PPM to 420 PPM, 420 PPM to 430 PPM, 430 PPM to 440 PPM, 440 PPM to 450 PPM, 450 PPM to 460 PPM, 460 PPM to 470 PPM, 470 PPM to 480 PPM, 480 PPM to 490 PPM, 490 PPM to 500 PPM, 500 PPM to 510 PPM, 510 PPM to 520 PPM, 520 PPM to 530 PPM, 530 PPM to 540 PPM, 540 PPM to 550 PPM, 550 PPM to 560 PPM, 560 PPM to 570 PPM, 570 PPM to 580 PPM, 580 PPM to 590 PPM, 590 PPM to 600 PPM, 600 PPM to 620 PPM, 620 PPM to 640 PPM, 640 PPM to 660 PPM, 660 PPM to 680 PPM, 680 PPM to 700 PPM, 700 PPM to 720 PPM, 720 PPM to 740 PPM, 740 PPM to 760 PPM, 760 PPM to 780 PPM, 780 PPM to 800 PPM, 800 PPM to 820 PPM, 820

PPM to 840 PPM, 840 PPM to 860 PPM, 860 PPM to 880 PPM, 880 PPM to 900 PPM, 900 PPM to 920 PPM, 920 PPM to 940 PPM, 940 PPM to 960 PPM, 960 PPM to 980 PPM, 980 PPM to 1000 PPM, 1,000 PPM to 1,500 PPM, 1,500 PPM to 2,000 PPM, 2,000 PPM to 2,500 PPM, 2,500 PPM to 3,000 PPM, 3,000 PPM to 3,500 PPM, 3,500 PPM to 4,000 PPM, 4,000 PPM to 4,500 PPM, 4,500 PPM to 5,000 PPM, 5,000 PPM to 5,500 PPM, 5,500 PPM to 6,000 PPM, 6,000 PPM to 6,500 PPM, 6,500 PPM to 7,000 PPM, 7,000 PPM to 7,500 PPM, 7,500 PPM to 8,000 PPM, 8,000 PPM to 8,500 PPM, 8,500 PPM to 9,000 PPM, 9,000 PPM to 9,500 PPM, 9,500 PPM to 10,000 PPM, 10,000 PPM to 11,000 PPM, 11,000 PPM to 12,000 PPM, 12,000 PPM to 13,000 PPM, 13,000 PPM to 14,000 PPM, 14,000 PPM to 15,000 PPM, 15,000 PPM to 16,000 PPM, 16,000 PPM to 17,000 PPM, 17,000 PPM to 18,000 PPM, 18,000 PPM to 19,000 PPM, 19,000 PPM to 20,000 PPM, 20,000 PPM to 21,000 PPM, 21,000 PPM to 22,000 PPM, 22,000 PPM to 23,000 PPM, 23,000 PPM to 24,000 PPM, and 24,000 PPM to 25,000 PPM.

FIG. 17H'

FIG. 17H' shows a cannabinoid extraction system including vessels, filters, pumps, piping connecting flow between vessels and adsorbers, valving, controllers, pressure regulators, metering equipment, flow control, and microprocessor equipment, their construction, implementation, and functionality.

FIG. 17H' shows one non-limiting embodiment of a solvent separation system that is configured to adsorb and desorb at least a portion of volatiles from a volatiles and solvent mixture (SVSM) by use of a plurality of adsorbers that contain an adsorbent. In embodiments, volatiles include cannabinoids. FIGS. 17H', 17J', and 17K' show non-limiting schematics of process flow diagrams illustrating configurations of a continuous cannabinoid extraction, emulsification, and softgel encapsulation system including:
  cannabis drying system;
  water treatment and pH adjustment system;
  cannabinoid extraction system;
  primary solvent filtration system;
  primary cannabinoid adsorption system;
  secondary solvent filtration system;
  secondary cannabinoid adsorption system;
  tertiary solvent filtration system;
  tertiary cannabinoid adsorption system;
  solvent recovery system;
  cannabinoid product processing (emulsion mixing system, evaporation system, spray drying system, crystallization, foodstuff preparation system, softgel encapsulation system).

Disclosed is a continuous process for the purification of cannabidiol and/or tetrahydrocannabinol extracted from cannabis using continuous simulated moving bed processes and micro and nanofiltration without the addition of organic solvents to obtain a purified cannabidiol and/or tetrahydrocannabinol product. The cannabidiol and/or tetrahydrocannabinol can be used to create foodstuffs, emulsions, drugs, beverages, alcoholic beverages or for medicinal or recreational uses, and petfoods.

In embodiments, a method for purification and separation of cannabidiol and/or tetrahydrocannabinol from cannabis and continuous purification of cannabidiol and/or tetrahydrocannabinol is disclosed. More particularly, the method relates to a process for the continuous purification of cannabidiol and/or tetrahydrocannabinol from cannabis using simulated moving bed chromatography. Most particularly, the method relates to a novel continuous process for the purification of cannabidiol and/or tetrahydrocannabinol from cannabis using a continuous simulated moving bed process using a solvent (such as water, ethanol, an alcohol, an alcohol mixture, deionized water, treated water, membrane treated water) as the mobile phase desorbent without the addition of organic solvents to obtain a purified cannabidiol and/or tetrahydrocannabinol product comprising cannabidiol and/or tetrahydrocannabinol. The cannabidiol and/or tetrahydrocannabinol can be used to create foodstuffs, emulsions, drugs, beverages, alcoholic beverages or for medicinal or recreational uses, and pet foods.

In embodiments, cannabis or Beaufort Budman III contains cannabinoids. In embodiments, cannabinoids are contained within volatiles. In embodiments, cannabinoids include cannabidiol and tetrahydrocannabinol. In embodiments, cannabinoids include 49-tetrahydrocannabinol Δ9-THC, Δ8-tetrahydrocannabinol Δ8-THC, cannabichromene CBC, cannabidiol CBD, cannabigerol CBG, cannabinidiol CBND, and/or cannabinol CBN. In embodiments, tetrahydrocannabinol has a molecular weight of 314.47 grams per mole. In embodiments, cannabidiol has a molecular weight of 314.47 grams per mole.

The cannabinoids within cannabis or Beaufort Budman III are listed below and bear the IUPAC names (6aR-trans)-6a,7,8,10a-tetrahydro-6,6,9-trimethyl-3-pentyl-6H-dibenzo[b,d]pyran-1-ol or Δ9-THC, and (6aR-trans)-6a,7,10,10a-tetrahydro-6,6,9-trimethyl-3-pentyl-6H-dibenzo[b,d]pyran-1-ol or Δ8-THC. Δ9-THC is also known under the designation of Dronabinol.

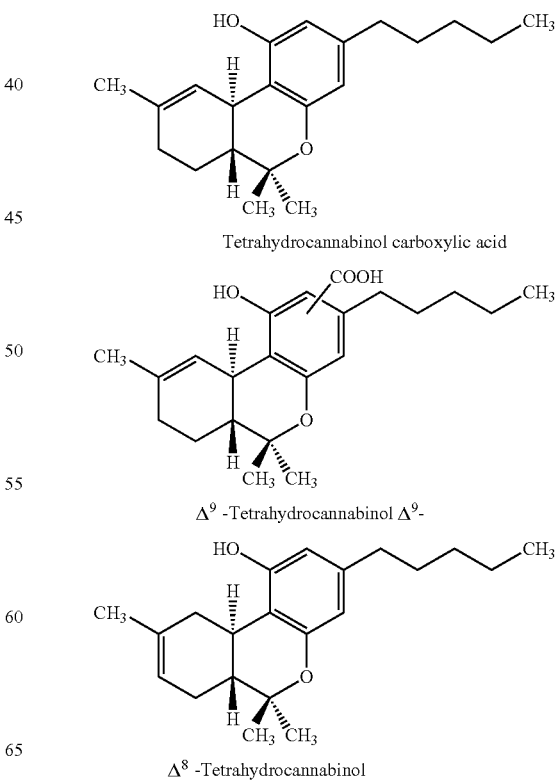

Tetrahydrocannabinol carboxylic acid

Δ⁹-Tetrahydrocannabinol Δ⁹-

Δ⁸-Tetrahydrocannabinol

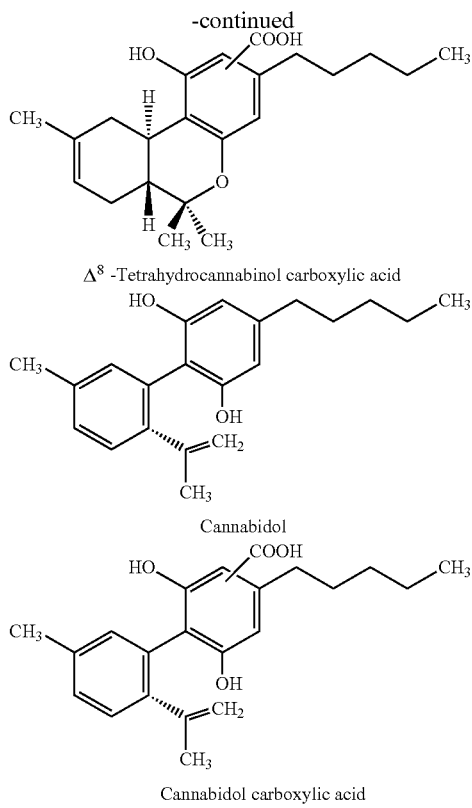

Δ⁸-Tetrahydrocannabinol carboxylic acid

Cannabidol

Cannabidol carboxylic acid

Table 17H illustrates various cannabinoids that are contained within *cannabis* or Beaufort Budman III: Δ9-tetrahydrocannabinol Δ9-THC, Δ8-tetrahydrocannabinol Δ8-THC, cannabichromene CBC, cannabidiol CBD, cannabigerol CBG, cannabinidiol CBND, and/or cannabinol CBN.

Cannabinoids can be extracted from leaves, buds, stems, and/or volatiles, of *cannabis* or Beaufort Budman III with use of a solvent, the solvent includes one or more from the group consisting of acetone, alcohol, ethanol, methanol, hexane, isobutane, isopropanol, liquid carbon dioxide, liquid, naphtha, and water. Cannabinoids can be extracted from volatiles that were separated from the *cannabis* or Beaufort Budman III by use of carbon dioxide. In embodiments, carbon dioxide extracted volatiles contain cannabinoids. In embodiments, carbon dioxide extracted volatiles contain cannabinoids including cannabidiol and/or tetrahydrocannabinol, wherein the cannabidiol content ranges from 0.00001 weight percent to 25 weight percent and the tetrahydrocannabinol content ranges from 4 weight percent to 66 weight percent.

In embodiments, cannabinoids are obtained from the leaves, buds, stems, and/or volatiles, of *cannabis* or Beaufort Budman III. In embodiments, the cannabinoids are extracted with a heated solvent and the resulting aqueous extract is passed through an adsorption resin to trap and concentrate cannabinoids. Generally, the resin can be desorbed by washing the resin with organic solvents like methanol or ethanol to release the cannabinoids. Typically, the cannabinoid product is recrystallized with a solvent such as methanol or ethanol. Typically, the cannabinoid product is recrystallized with a solvent such as methanol. Ion-exchange resins have been used in the purification process. In embodiments, the final product is typically spray-dried as shown in FIG. 17E'. In embodiments, the final product is evaporated as shown in FIG. 17D'.

As described herein, this disclosure provides for methods of supercritical fluid extraction and evaporator methods including evaporation, rotary evaporation, vacuum evaporation, distillation, crystallization, vacuum flashing, wiped film evaporation, emulsification, filtration, and spray drying. Methods for the recovery of terpenes and/or cannabidiol and/or tetrahydrocannabinol from *cannabis* using supercritical CO2, filtration technology, and water or organic solvents, such as methanol and ethanol, may also be used.

FIG. 17H' shows one non-limiting embodiment of a continuous cannabinoid extraction process. In embodiments, the *cannabis* (HAA) can be introduced to an extraction vessel (HAI). In embodiments, the *cannabis* (HAA) includes pieces or portions of harvested *cannabis*, trimmed *cannabis*, dried *cannabis*, wet *cannabis*, heated *cannabis*, or solvent extracted *cannabis*. In embodiments, the *cannabis* (HAA) can first introduced to a water removal system (HZB) to reduce its moisture content. In embodiments, the water removal system (HZB) is a dryer (HZC). In embodiments, the dryer (HZC) includes a drum dryer, a vacuum dryer, rotary dryer, steam tube dryer, indirect dryer, direct dryer, indirectly-fired dryer, directly-fired dryer, tray dryer, tunnel dryer, roller dryers, pneumatic dryer, trough dryer, bin dryer, belt dryer, freeze dryer, or a microwave using microwave radiation and/or variable frequency microwave radiation. In embodiments, the dryer (HZC) includes an indirectly-fired dryer or a directly-fired dryer that is fired with a fuel, such as natural gas, propane, gasoline, fuel oil, oil, gaseous fuel, hydrocarbon, and liquid fuel.

In embodiments, water is removed from the *cannabis* (HAA) with microwave radiation. In embodiments, the dryer (HZC) is a microwave. In embodiments, the dryer (HZC) is a variable frequency microwave. In embodiments, the microwave radiation is in the form of variable frequency microwave radiation. In embodiments, the variable frequency microwave radiation operates at a frequency between about 2 GHz to about 8 GHz. In embodiments, the variable frequency microwave radiation operates at a frequency of about 2.45 GHz. In embodiments, the variable frequency microwave radiation operates at a frequency selected from one or more from the group consisting of 2 GHz to 2.15 Ghz, 2.15 GHz to 2.25 Ghz, 2.25 GHz to 2.35 Ghz, 2.35 GHz to 2.45 Ghz, 2.45 GHz to 2.55 Ghz, 2.55 GHz to 2.65 Ghz, 2.65 GHz to 2.75 Ghz, 2.75 GHz to 2.85 Ghz, 2.85 GHz to 2.95 Ghz, 2.95 GHz to 3.05 Ghz, 3.05 GHz to 3.15 Ghz, 3.15 GHz to 3.25 Ghz, 3.25 GHz to 3.35 Ghz, 3.35 GHz to 3.45 Ghz, 3.45 GHz to 3.55 Ghz, 3.55 GHz to 3.65 Ghz, 3.65 GHz to 3.75 Ghz, 3.75 GHz to 3.85 Ghz, 3.85 GHz to 3.95 Ghz, 3.95 GHz to 4.05 Ghz, 4.05 GHz to 4.15 Ghz, 4.15 GHz to 4.25 Ghz, 4.25 GHz to 4.35 Ghz, 4.35 GHz to 4.45 Ghz, 4.45 GHz to 4.55 Ghz, 4.55 GHz to 4.65 Ghz, 4.65 GHz to 4.75 Ghz, 4.75 GHz to 4.85 Ghz, 4.85 GHz to 4.95 Ghz, 4.95 GHz to 5.05 Ghz, 5.05 GHz to 5.15 Ghz, 5.15 GHz to 5.25 Ghz, 5.25 GHz to 5.35 Ghz, 5.35 GHz to 5.45 Ghz, 5.45 GHz to 5.55 Ghz, 5.55 GHz to 5.65 Ghz, 5.65 GHz to 5.75 Ghz, 5.75 GHz to 5.85 Ghz, 5.85 GHz to 5.95 Ghz, 5.95 GHz to 6.05 Ghz, 6.05 GHz to 6.15 Ghz, 6.15 GHz to 6.25 Ghz, 6.25 GHz to 6.35 Ghz, 6.35 GHz to 6.45 Ghz, 6.45 GHz to 6.55 Ghz, 6.55 GHz to 6.65 Ghz, 6.65 GHz to 6.75 Ghz, 6.75 GHz to 6.85 Ghz, 6.85 GHz to 6.95 Ghz, 6.95 GHz to 7.05 Ghz, 7.05 GHz to 7.15 Ghz, 7.15 GHz to 7.25 Ghz, 7.25 GHz to 7.35 Ghz, 7.35 GHz to 7.45 Ghz, 7.45 GHz to 7.55 Ghz, 7.55 GHz to 7.65 Ghz, 7.65 GHz to 7.75 Ghz, 7.75 GHz to 7.85 Ghz, 7.85 GHz to 7.95 Ghz, and 7.95 GHz to 8.00 Ghz.

In embodiments, the microwave has a power output that is measured in kilowatts (kW), the power output for the microwave operates at one or more selected from the group of power ranges consisting of 10 kw to 20 kw, 20 kw to 30 kw, 30 kw to 40 kw, 40 kw to 50 kw, 50 kw to 60 kw, 60 kw to 70 kw, 70 kw to 80 kw, 80 kw to 90 kw, 90 kw to 100 kw, 100 kw to 110 kw, 110 kw to 120 kw, 120 kw to 130 kw, 130 kw to 140 kw, 140 kw to 150 kw, 150 kw to 160 kw, 160 kw to 170 kw, 170 kw to 180 kw, 180 kw to 190 kw, 190 kw to 200 kw, 200 kw to 210 kw, 210 kw to 220 kw, 220 kw to 230 kw, 230 kw to 240 kw, and 240 kw to 250 kw.

In embodiments, the microwave has a current that is measured in amps, the current for the microwave operates at one or more selected from the group of amp ranges consisting of 10 amps to 20 amps, 20 amps to 30 amps, 30 amps to 40 amps, 40 amps to 50 amps, 50 amps to 60 amps, 60 amps to 70 amps, 70 amps to 80 amps, 80 amps to 90 amps, 90 amps to 100 amps, 100 amps to 110 amps, 110 amps to 120 amps, 120 amps to 130 amps, 130 amps to 140 amps, 140 amps to 150 amps, 150 amps to 160 amps, 160 amps to 170 amps, 170 amps to 180 amps, 180 amps to 190 amps, 190 amps to 200 amps, 200 amps to 210 amps, 210 amps to 220 amps, 220 amps to 230 amps, 230 amps to 240 amps, 240 amps to 250 amps, 250 amps to 260 amps, 260 amps to 270 amps, 270 amps to 280 amps, 280 amps to 290 amps, and 290 amps to 300 amps.

In embodiments, water is removed from the *cannabis* (HAA) over a duration of time between about 0.1 seconds to about 500 seconds. In embodiments, water is removed from the *cannabis* (HAA) over a duration of time between about 0.05 minutes to 0.1 minutes, 0.1 minutes to 0.5 minutes, 0.5 minutes to 1 minutes, 1 minute to 15 minutes, 15 minute to 30 minutes, 30 minute to 60 minutes, 60 minute to 2 hours, 2 hours to 3 hours, 3 hours to 4 hours, 4 hours to 5 hours, 5 hours to 6 hours, 6 hours to 7 hours, 7 hours to 8 hours, 8 hours to 9 hours, 9 hours to 10 hours, 10 hours to 11 hours, 11 hours to 12 hours, 12 hours to 13 hours, 13 hours to 14 hours, 14 hours to 15 hours, 15 hours to 16 hours, 16 hours to 17 hours, 17 hours to 18 hours, 18 hours to 19 hours, 19 hours to 20 hours, 20 hours to 24 hours, 24 hours to 1 day, 1 day to 2 days, 2 days to 3 days, 3 days to 4 days, 4 days to 5 days, 5 days to 6 days, 6 days to 7 days, 7 days to 8 days, 8 days to 9 days, 9 days to 10 days, or 10 days to 20 days.

In embodiments, the dryer (HZC) is a vacuum dryer that operates at a pressure that is selected from one of more from the group consisting of: between about 0.001 inches of water to about 0.002 inches of water; between about 0.002 inches of water to about 0.003 inches of water; between about 0.003 inches of water to about 0.006 inches of water; between about 0.006 inches of water to about 0.012 inches of water; between about 0.012 inches of water to about 0.024 inches of water; between about 0.024 inches of water to about 0.050 inches of water; between about 0.050 inches of water to about 0.075 inches of water; between about 0.075 inches of water to about 0.150 inches of water; between about 0.150 inches of water to about 0.300 inches of water; between about 0.300 inches of water to about 0.450 inches of water; between about 0.450 inches of water to about 0.473 inches of water; between about 0.473 inches of water to about 0.496 inches of water; between about 0.496 inches of water to about 0.521 inches of water; between about 0.521 inches of water to about 0.547 inches of water; between about 0.547 inches of water to about 0.574 inches of water; between about 0.574 inches of water to about 0.603 inches of water; between about 0.603 inches of water to about 0.633 inches of water; between about 0.633 inches of water to about 0.665 inches of water; between about 0.665 inches of water to about 0.698 inches of water; between about 0.698 inches of water to about 0.733 inches of water; between about 0.733 inches of water to about 0.770 inches of water; between about 0.770 inches of water to about 0.808 inches of water; between about 0.808 inches of water to about 0.849 inches of water; between about 0.849 inches of water to about 0.891 inches of water; between about 0.891 inches of water to about 0.936 inches of water; between about 0.936 inches of water to about 0.982 inches of water; between about 0.982 inches of water to about 1.031 inches of water; between about 1.031 inches of water to about 1.083 inches of water; between about 1.083 inches of water to about 1.137 inches of water; between about 1.137 inches of water to about 1.194 inches of water; between about 1.194 inches of water to about 1.254 inches of water; between about 1.254 inches of water to about 1.316 inches of water; between about 1.316 inches of water to about 1.382 inches of water; between about 1.382 inches of water to about 1.451 inches of water; between about 1.451 inches of water to about 1.524 inches of water; between about 1.524 inches of water to about 2.286 inches of water; between about 2.286 inches of water to about 3.429 inches of water; between about 3.429 inches of water to about 5.143 inches of water; between about 5.143 inches of water to about 7.715 inches of water; between about 7.715 inches of water to about 11.572 inches of water; between about 11.572 inches of water to about 17.358 inches of water; between about 17.358 inches of water to about 26.037 inches of water; between about 26.037 inches of water to about 39.055 inches of water; between about 39.055 inches of water to about 58.582 inches of water; between about 58.582 inches of water to about 87.873 inches of water; between about 87.873 inches of water to about 131.810 inches of water; between about 131.810 inches of water to about 197.715 inches of water; between about 197.715 inches of water to about 296.573 inches of water; or, between about 296.573 inches of water to about 400 inches of water.

In embodiments, the dryer (HZC) can be operated by electricity, flue gas, solar power from at least one solar panel (SOLAR'), a fuel cell, or a combustion stream (LEM, LFD) as shown in FIG. 17F'. The dryer (HZC) can reduce the moisture of the *cannabis* (HAA) with a gas (HZA). In embodiments, the gas (HZA) includes an oxygen-containing gas which includes air, oxygen-enriched-air i.e. greater than 21 mole % $O_2$, and substantially pure oxygen, i.e. greater than about 95 mole % oxygen (the remainder usually comprising N2 and rare gases). In embodiments, the gas (HZA) may include flue gas which includes a vapor or gaseous mixture containing varying amounts of nitrogen ($N_2$), carbon dioxide ($CO_2$), water ($H_2O$), and oxygen ($O_2$). Flue gas is generated from the thermochemical process of combustion. In embodiments, the gas (HZA) may include a combustion stream.

In embodiments, a water-depleted *cannabis* (HZE) or a dried *cannabis* (HZE') is discharged from the water removal system (HZB) and has a moisture content (measured in weight percent of water) that is selected from one of more from the group consisting of: between about between about 0.300 weight percent to about 0.450 weight percent; between about 0.450 weight percent to about 0.473 weight percent; between about 0.473 weight percent to about 0.496 weight percent; between about 0.496 weight percent to about 0.521 weight percent; between about 0.521 weight percent to about 0.547 weight percent; between about 0.547 weight percent to about 0.574 weight percent; between about 0.574 weight percent to about 0.603 weight percent; between about 0.603 weight percent to about 0.633 weight percent; between about 0.633 weight percent to about 0.665 weight percent; between about 0.665 weight percent to about 0.698 weight percent; between about 0.698 weight percent to about 0.733 weight percent; between about 0.733 weight percent to about 0.770 weight percent; between about 0.770 weight percent to about 0.808 weight percent; between about 0.808 weight percent to about 0.849 weight percent; between about 0.849 weight percent to about 0.891 weight percent; between about 0.891 weight percent to about 0.936 weight percent; between about 0.936 weight percent to about 0.982 weight percent; between about 0.982 weight percent to about 1.031 weight percent; between about 1.031 weight percent to about 1.083 weight percent; between about 1.083 weight percent to about 1.137 weight percent; between about 1.137 weight percent to about 1.194 weight percent; between about 1.194 weight percent to about 1.254 weight percent; between about 1.254 weight percent to about 1.316 weight percent; between about 1.316 weight percent to about 1.382 weight percent; between about 1.382 weight percent to about 1.451 weight percent; between about 1.451 weight percent to about 1.524 weight percent; between about 1.524 weight percent to about 2.286 weight percent; between about 2.286 weight percent to about 3.429 weight percent; between about 3.429 weight percent to about 5.143 weight percent; between about 5.143 weight percent to about 7.715 weight percent; between about 7.715 weight percent to about 11.572 weight percent.

A moisture content of the water-depleted *cannabis* (HZE) or a dried *cannabis* (HZE') may be measured with a moisture sensor (HZD). In embodiments, the moisture sensor (HZD) is selected from one or more from the group consisting of a halogen moisture sensor, mass spectrometer, Fourier transform infrared spectroscopy, infrared spectroscopy, radio frequency (RF), a DC resistance circuit, frequency domain reflectometry (FDR), time domain reflectometry (TDR), time domain transmissometry (TDT), oven drying, gravimetric testing, forced air oven, vacuum oven, microwave, variable frequency microwave radiation, IR drying, toluene distillation, Karl Fischer titration, or any conceivable instantaneous contact or non-contact moisture analyzer. In embodiments, time-domain reflectometry or TDR is a measurement technique used to determine the characteristics of *cannabis* (HAA) by observing reflected waveforms. In embodiments, time-domain transmissometry (TDT) is an analogous technique that measures the transmitted (rather than reflected) impulse of *cannabis* (HAA).

In embodiments, the moisture sensor (HZD) is configured to input a signal to the computer. In embodiments, the moisture content of the water-depleted *cannabis* (HZE) may be obtained through thermo-gravimetry or the loss-on-drying principle. In embodiments, the moisture sensor (HZD) includes a mass sensor and a heat source. The starting weight is recorded by the mass sensor. The heat source applies heat to the *cannabis* (HAA). The ending weight of the water-depleted *cannabis* (HZE) or a dried *cannabis* (HZE') is then recorded via the mass sensor. The total loss in mass (the difference in mass of the water-depleted *cannabis* (HZE) and the *cannabis* (HAA)) is used to obtain the moisture content.

In embodiments, the *cannabis* (HAA') includes harvested *cannabis*, trimmed *cannabis*, dried *cannabis*, wet *cannabis*, heated *cannabis*, carbon dioxide extracted cannabidiol and/or tetrahydrocannabinol, extracted cannabidiol, cannabidiol, carbon dioxide extracted cannabidiol, terpenes, carbon dioxide extracted terpenes, and/or extracted terpenes. The *cannabis* (HAA, HAA') may come from any number of drawings disclosed within this specification and the *cannabis* (HAA') can be grown in any number of ways.

A first *cannabis* sensor (HAC) is provided to measure the pressure, temperature, moisture, purity, pH, electrical conductivity, or elemental make-up of the *cannabis* (HAA'). A first *cannabis* flow valve (HAE) is provided to determine the content of *cannabis* (HAA') that is introduced downstream to the extraction vessel (HAI). A second *cannabis* sensor (HAC) is provided to measure the pressure, temperature, moisture, purity, pH, electrical conductivity, or elemental make-up of the *cannabis* (HAA') to the extraction vessel (HAI).

A solvent (HAB, HAB') is made available to the extraction vessel (HAI). The extraction vessel (HAI) is configured to accept a *cannabis* (HAA, HAA') and a solvent (HAB, HAB'). In embodiments, the solvent (HAB) includes water, ethanol, an alcohol, an alcohol mixture, deionized water, treated water, filtered water. In embodiments, the solvent (HAB') is pressurized and comes from a solvent treatment system (H-WTS) which may or may not treat solvent (such as water) that was passed on from a solvent recovery system.

A first solvent sensor (HAD) is provided to measure the pressure, temperature, moisture, purity, pH, electrical conductivity, or elemental make-up of the solvent (HAB). A first solvent flow valve (HAF) is provided to determine the content of solvent (HAB) that is introduced downstream to the extraction vessel (HAI). A second solvent sensor (HAH) is provided to measure the pressure, temperature, moisture, purity, pH, electrical conductivity, or elemental make-up of the solvent (HAB) to the extraction vessel (HAI). In embodiments, insects are mixed with *cannabis* (HAA, HAA') prior to the extraction vessel (HAI).

In embodiments, the extraction vessel (HAI) is provided to accept at least a portion of the *cannabis* (HAA, HAA'). A solvent (HAB, HAB') is made available to the extraction vessel (HAI). The extraction vessel (HAI) is configured to accept a *cannabis* (HAA, HAA') and a solvent (HAB, HAB'). In embodiments, the extraction vessel (HAI) has an interior (HAJ). In embodiments, the interior (HAJ) of the extraction vessel (HAI) is the extraction zone (HAI') where cannabinoids are extracted from the *cannabis* (HAA, HAA') by use a solvent (HAB, HAB').

In embodiments, the extraction vessel (HAI) is a continuously stirred tank reactor having a jacketed reactor equipped with a steam supply system and at least one steam trap. In embodiments, the extraction vessel (HAI) is equipped with a level sensor (HAL) that is configured to input a signal (HAK) to the computer (COMP). In embodiments, the extraction vessel (HAI) is equipped with a pH sensor (HAL') that is configured to input a signal (HAK') to the computer (COMP). In embodiments, the extraction vessel (HAI) is equipped with an auger (HA1) that has a motor (HA2). The motor (HA2) of the auger (HA1) rotates the auger (HA1) to mix the contents within the interior (HAJ) of the extraction vessel (HAI). In embodiments, the extraction vessel (HAI) is equipped with a temperature sensor (HA3) that is configured to input a signal (HA4) to the computer (COMP). In embodiments, the extraction vessel (HAI) is equipped with a heat exchanger (HAM) to heat the contents within the interior (HAJ) of the extraction vessel (HAI). In embodiments, the extraction vessel (HAI) outputs a crude cannabinoid extract (HAN).

In embodiments, the crude cannabinoids are admixed with water or a solvent to provide a crude extract stream which comprises from one or more from the group consisting of 1 weight percent to 5 weight percent, 5 weight percent to 10 weight percent, 10 weight percent to 15 weight percent, 15 weight percent to 20 weight percent, 20 weight percent to 25 weight percent, 25 weight percent to 30 weight percent, 30 weight percent to 35 weight percent, 35 weight percent to 40 weight percent, 40 weight percent to 45 weight percent, 45 weight percent to 50 weight percent, 50 weight percent to 55 weight percent, 55 weight percent to 60 weight percent, 60 weight percent to 65 weight percent, 65 weight percent to 70 weight percent, 70 weight percent to 75 weight percent, 75 weight percent to 80 weight percent, 80 weight percent to 85 weight percent, 85 weight percent to 90 weight percent, and 90 to 100 weight percent.

Following the extraction of the cannabinoids (such as CBD, THC) from leaves, buds, stems, and/or volatiles, of *cannabis* or Beaufort Budman III, an extract stream comprising crude cannabinoids is withdrawn from the extraction zone (HAI'). In embodiments, the crude cannabinoids are admixed with water or a solvent to provide a crude cannabinoid extract (HAN).

In embodiments, the crude cannabinoid extract (HAN) discharged from the extraction vessel (HAI) is made available to a crude cannabinoid extract pump (HAO). In embodiments, the crude cannabinoid extract pump (HAO) pressurizes and pumps the crude cannabinoid extract (HAN) to form a pressurized crude cannabinoid extract (HAX, HAX'). In embodiments, the crude cannabinoid extract pump (HAO) is equipped with a motor (HAP) and a controller (HAQ) that is configured to input and/or output a signal (HAR) to the computer (COMP). A valve (HAU) may be provided to regulate the flow of the pressurized crude cannabinoid extract (HAX, HAX'). In embodiments, the valve (HAU) is equipped with a controller (HAV) that is configured to input and/or output a signal (HAW) to the computer (COMP). In embodiments, a pressure sensor (HAS) is provided to measure the pressure of the pressurized crude cannabinoid extract (HAX, HAX') that is discharged from the crude cannabinoid extract pump (HAO). In embodiments, the pressure sensor (HAS) inputs a signal (HAT) to the computer (COMP).

In embodiments, the crude cannabinoid extract pump (HAO) pressurizes the crude cannabinoid extract (HAN) to form a pressurized crude cannabinoid extract (HAX, HAX') at a pressure that includes one or more pressure ranges selected from the group consisting of 10 pounds per square inch (PSI) to 20 PSI, 20 PSI to 40 PSI, 40 PSI to 60 PSI, 60 PSI to 80 PSI, 80 PSI to 100 PSI, 100 PSI to 125 PSI, 125 PSI to 150 PSI, 150 PSI to 175 PSI, 175 PSI to 200 PSI, 200 PSI to 225 PSI, 225 PSI to 250 PSI, 250 PSI to 275 PSI, 275 PSI to 300 PSI, 300 PSI to 325 PSI, 325 PSI to 350 PSI, 350 PSI to 375 PSI, 375 PSI to 400 PSI, 400 PSI to 425 PSI, 425 PSI to 450 PSI, 450 PSI to 475 PSI, and 475 PSI to 500 PSI. In embodiments, the crude cannabinoid extract pump (HAO) pressurizes the crude cannabinoid extract (HAN) to form a pressurized crude cannabinoid extract (HAX, HAX') which is then introduced to a heat exchanger (HAY). In embodiments, the heat exchanger (HAY) is provided with a heat transfer medium (HAZ) to heat or cool the pressurized crude cannabinoid extract (HAX, HAX').

In embodiments, at least a portion of the pressurized crude cannabinoid extract (HAX') is recycled back to the interior (HAJ) of the extraction vessel (HAI) via a bypass (HBB). A crude cannabinoid extract valve (HBA) is positioned on the bypass (HBB) to permit recycled pressurized crude cannabinoid extract (HAX') to flow back into the interior (HAJ) of the extraction vessel (HAI).

In embodiments, at least a portion of the pressurized crude cannabinoid extract (HAX) is introduced to a first filter (HBC) and a second filter (HBF). In embodiments, the first filter (HBC) has an interior (HBD) and at least one filter element (HBE). In embodiments, the second filter (HBF) has an interior (HBG) and at least one filter element (HBH). In embodiments, the first filtered crude cannabinoid extract (HBI') is discharged from the first filter (HBC) and a second filtered crude cannabinoid extract (HBI") is discharged from the second filter (HBF). In embodiments, the first filtered crude cannabinoid extract (HBI') and the second filtered crude cannabinoid extract (HBI") are combined to form a filtered crude cannabinoid extract (HBI) that has less solids in it relative to the pressurized crude cannabinoid extract (HAX). In embodiments, the first filter (HBC) and the second filter (HBF) also discharge solids (HBK) and solvent (HBJ). In embodiments, the solvent (HBJ) discharged from the first filter (HBC) and the second filter (HBF) is routed to the solvent treatment system (H-WTS) as discussed below.

In embodiments, the crude cannabinoid extract (HAN) is passed to the filter (HBC, HBF) to remove any solid particles to provide a filtered crude cannabinoid extract (HBI). In embodiments, the filtration is carried at a microfiltration temperature ranging from one or more from the group consisting of 70 degrees F. to 100 degrees F., 100 deg F. to 110 deg F., 110 deg F. to 120 deg F., 120 deg F. to 130 deg F., 130 deg F. to 140 deg F., 140 deg F. to 150 deg F., 150 deg F. to 160 deg F., 160 deg F. to 170 deg F., 170 deg F. to 180 deg F., 180 deg F. to 190 deg F., 190 deg F. to 200 deg F., 200 deg F. to 210 deg F., 210 deg F. to 212 deg F.

In embodiments, the filtration is carried out in a filter (HBC, HBF) has a pore size that ranges from rom one or more from the group consisting of 0.03 microns to 0.05 microns, 0.05 microns to 0.07 microns, 0.07 microns to 0.09 microns, 0.09 microns to 0.11 microns, 0.11 microns to 0.13 microns, 0.13 microns to 0.15 microns, 0.15 microns to 0.17 microns, 0.17 microns to 0.19 microns, 0.19 microns to 0.21 microns, 0.21 microns to 0.23 microns, 0.23 microns to 0.25 microns, 0.25 microns to 0.27 microns, 0.27 microns to 0.29 microns, 0.29 microns to 0.31 microns, 0.31 microns to 0.33 microns, 0.33 microns to 0.35 microns, 0.35 microns to 0.37 microns, 0.37 microns to 0.39 microns, 0.39 microns to 0.41 microns, 0.41 microns to 0.43 microns, 0.43 microns to 0.45 microns, 0.45 microns to 0.47 microns, 0.47 microns to 0.49 microns, 0.49 microns to 0.51 microns, 0.51 microns to 0.61 microns, 0.61 microns to 0.71 microns, 0.71 microns to 0.81 microns, 0.81 microns to 0.91 microns, 0.91 microns to 1.01 microns, 1.01 microns to 1.5 microns, 1.5 microns to 2 microns, 2 microns to 2.5 microns, 2.5 microns to 3 microns, 3 microns to 3.5 microns, 3.5 microns to 4 microns, 4 microns to 4.5 microns, 4.5 microns to 5 microns, 5 microns to 5.5 microns, 5.5 microns to 6 microns, 6 microns to 6.5 microns, 6.5 microns to 7 microns, 7 microns to 7.5 microns, 7.5 microns to 8 microns, 8 microns to 8.5 microns, 8.5 microns to 9 microns, 9 microns to 9.5 microns, and 9.5 microns to 10 microns, or at least 10 microns.

In embodiments, the filtration is carried out in a filter (HBC, HBF) that includes one or more filter types selected from the group consisting of a candle filter, a centrifuge cloth filter, filter press cloth filter, filter bag, vertical belt press cloth filter, basket filter, rotary vacuum filter, rotary filter, drum filter, leaf filter, plate filter, batch filter, and a continuous filter.

In embodiments, any of the pumps in this patent specification have a pump discharge velocity that is selected from one or more pump velocity ranges consisting of: 0.65 feet per second to 0.75 feet per second, 0.75 feet per second to 0.85 feet per second, 0.85 feet per second to 0.95 feet per second, 0.95 feet per second to 1.05 feet per second, 1.05 feet per second to 1.15 feet per second, 1.15 feet per second to 1.25 feet per second, 1.25 feet per second to 1.35 feet per second, 1.35 feet per second to 1.45 feet per second, 1.45 feet per second to 1.55 feet per second, 1.55 feet per second to 1.65 feet per second, 1.65 feet per second to 1.75 feet per second, 1.75 feet per second to 1.85 feet per second, 1.85 feet per second to 1.95 feet per second, 1.95 feet per second to 2.05 feet per second, 2.05 feet per second to 2.15 feet per second, 2.15 feet per second to 2.25 feet per second, 2.25 feet per second to 2.35 feet per second, 2.35 feet per second to 2.45 feet per second, 2.45 feet per second to 2.55 feet per second, 2.55 feet per second to 2.65 feet per second, 2.65 feet per second to 2.75 feet per second, 2.75 feet per second to 2.85 feet per second, 2.85 feet per second to 2.95 feet per second, 2.95 feet per second to 3.05 feet per second, 3.05 feet per second to 3.15 feet per second, 3.15 feet per second to 3.25 feet per second, 3.25 feet per second to 3.35 feet per second, 3.35 feet per second to 3.45 feet per second, 3.45 feet per second to 3.55 feet per second, 3.55 feet per second to 3.65 feet per second, 3.65 feet per second to 3.75 feet per second, 3.75 feet per second to 3.85 feet per second, 3.85 feet per second to 3.95 feet per second, 3.95 feet per second to 4.05 feet per second, 4.05 feet per second to 4.15 feet per second, 4.15 feet per second to 4.25 feet per second, 4.25 feet per second to 4.35 feet per second, 4.35 feet per second to 4.45 feet per second, 4.45 feet per second to 4.55 feet per second, 4.55 feet per second to 4.65 feet per second, 4.65 feet per second to 4.75 feet per second, 4.75 feet per second to 4.85 feet per second, 4.85 feet per second to 4.90 feet per second, and 4.90 feet per second to 5.00 feet per second. This is true especially for all pumps on FIGS. 1'-18'.

In embodiments, any of the pumps in this patent specification have a pump discharge velocity that is selected from one or more pump velocity ranges consisting of: 5.00 feet per second to 5.10 feet per second, 5.10 feet per second to 5.20 feet per second, 5.20 feet per second to 5.30 feet per second, 5.30 feet per second to 5.40 feet per second, 5.40 feet per second to 5.50 feet per second, 5.50 feet per second to 5.60 feet per second, 5.60 feet per second to 5.70 feet per second, 5.70 feet per second to 5.80 feet per second, 5.80 feet per second to 5.90 feet per second, 5.90 feet per second to 6.00 feet per second, 6.00 feet per second to 6.10 feet per second, 6.10 feet per second to 6.20 feet per second, 6.20 feet per second to 6.30 feet per second, 6.30 feet per second to 6.40 feet per second, 6.40 feet per second to 6.50 feet per second, 6.50 feet per second to 6.60 feet per second, 6.60 feet per second to 6.70 feet per second, 6.70 feet per second to 6.80 feet per second, 6.80 feet per second to 6.90 feet per second, 6.90 feet per second to 7.00 feet per second, 7.00 feet per second to 7.10 feet per second, 7.10 feet per second to 7.20 feet per second, 7.20 feet per second to 7.30 feet per second, 7.30 feet per second to 7.40 feet per second, 7.40 feet per second to 7.50 feet per second, 7.50 feet per second to 7.60 feet per second, 7.60 feet per second to 7.70 feet per second, 7.70 feet per second to 7.80 feet per second, 7.80 feet per second to 7.90 feet per second, 7.90 feet per second to 8.00 feet per second, 8.00 feet per second to 8.10 feet per second, 8.10 feet per second to 8.20 feet per second, 8.20 feet per second to 8.30 feet per second, 8.30 feet per second to 8.40 feet per second, 8.40 feet per second to 8.50 feet per second, 8.50 feet per second to 8.60 feet per second, 8.60 feet per second to 8.70 feet per second, 8.70 feet per second to 8.80 feet per second, 8.80 feet per second to 8.90 feet per second, 8.90 feet per second to 9.00 feet per second, 9.00 feet per second to 9.10 feet per second, 9.10 feet per second to 9.20 feet per second, 9.20 feet per second to 9.30 feet per second, 9.30 feet per second to 9.40 feet per second, 9.40 feet per second to 9.50 feet per second, 9.50 feet per second to 9.60 feet per second, 9.60 feet per second to 9.70 feet per second, 9.70 feet per second to 9.80 feet per second, 9.80 feet per second to 9.90 feet per second, 9.90 feet per second to 10.00 feet per second, and 10.00 feet per second to 20.00 feet per second. This is true especially for all pumps on FIGS. 1'-18'.

In embodiments, the filter (HBC, HBF) is comprised of one or more from the group consisting of membrane, hollow, nanofiltration, microfiltration, microfilter, nanofilter, metal, ceramic, cloth, particulate filter, candle filter, ceramic fiber, filter cartridge, fiber, and mesh. In embodiments, the filter is configured to have a face velocity during depressurization ranging from 0.5 feet per minute to 50 feet per minute. In embodiments, the filter is configured to have a face velocity during filtration ranging from: 5 feet per minute to 10 feet per minute, 10 feet per minute to 15 feet per minute, 15 feet per minute to 20 feet per minute, 20 feet per minute to 25 feet per minute, 25 feet per minute to 30 feet per minute, 30 feet per minute to 35 feet per minute, 35 feet per minute to 40 feet per minute, 40 feet per minute to 45 feet per minute, 45 feet per minute to 50 feet per minute, 50 feet per minute to 55 feet per minute, 55 feet per minute to 60 feet per minute, 60 feet per minute to 65 feet per minute, 65 feet per minute to 70 feet per minute, 70 feet per minute to 75 feet per minute, 75 feet per minute to 80 feet per minute, 80 feet per minute to 85 feet per minute, 85 feet per minute to 90 feet per minute, 90 feet per minute to 95 feet per minute, 95 feet per minute to 100 feet per minute, 100 feet per minute to 125 feet per minute, 125 feet per minute to 150 feet per minute, 150 feet per minute to 175 feet per minute, 175 feet per minute to 200 feet per minute, 200 feet per minute to 225 feet per minute, 225 feet per minute to 250 feet per minute, 250 feet per minute to 275 feet per minute, 275 feet per minute to 300 feet per minute, 300 feet per minute to 325 feet per minute, 325 feet per minute to 350 feet per minute, 350 feet per minute to 375 feet per minute, 375 feet per minute to 400 feet per minute, 400 feet per minute to 425 feet per minute, 425 feet per minute to 450 feet per minute, 450 feet per minute to 475 feet per minute, 475 feet per minute to 500 feet per minute, 500 feet per minute to 525 feet per minute, 525 feet per minute to 550 feet per minute, 550 feet per minute to 575 feet per minute, 575 feet per minute to 600 feet per minute, 600 feet per minute to 625 feet per minute, 625 feet per minute to 650 feet per minute, 650 feet per minute to 675 feet per minute, 675 feet per minute to 700 feet per minute, 700 feet per minute to 725 feet per minute, 725 feet per minute to 750 feet per minute, 750 feet per minute to 775 feet per minute, 775 feet per minute to 800 feet per minute, 800 feet per minute to 825 feet per minute, 825 feet per minute to 850 feet per minute, 850 feet per minute to 875 feet per minute, 875 feet per minute to 900 feet per minute, 900 feet per minute to 925 feet per minute, 925 feet per minute to 950 feet per minute, 950 feet per minute to 975 feet per minute, and 975 feet per minute to 1,000 feet per minute.

In embodiments, the crude cannabinoids are admixed with water or a solvent to provide a crude extract which comprises from one or more from the group consisting of 20.5 weight percent to 21 weight percent, 21 weight percent to 21.5 weight percent, 21.5 weight percent to 22 weight percent, 22 weight percent to 22.5 weight percent, 22.5 weight percent to 23 weight percent, 23 weight percent to 23.5 weight percent, 23.5 weight percent to 24 weight percent, 24 weight percent to 24.5 weight percent, 24.5 weight percent to 25 weight percent, 25 weight percent to 25.5 weight percent, 25.5 weight percent to 26 weight percent, 26 weight percent to 26.5 weight percent, 26.5 weight percent to 27 weight percent, 27 weight percent to 27.5 weight percent, 27.5 weight percent to 28 weight percent, 28 weight percent to 28.5 weight percent, 28.5 weight percent to 29 weight percent, 29 weight percent to 29.5 weight percent, 29.5 weight percent to 30 weight percent, 30 weight percent to 30.5 weight percent, 30.5 weight percent to 31 weight percent, 31 weight percent to 31.5 weight percent, 31.5 weight percent to 32 weight percent, 32 weight percent to 32.5 weight percent, 32.5 weight percent to 33 weight percent, 33 weight percent to 33.5 weight percent, 33.5 weight percent to 34 weight percent, 34 weight percent to 34.5 weight percent, 34.5 weight percent to 35 weight percent, 35 weight percent to 35.5 weight percent, 35.5 weight percent to 36 weight percent, 36 weight percent to 36.5 weight percent, 36.5 weight percent to 37 weight percent, 37 weight percent to 37.5 weight percent, 37.5 weight percent to 38 weight percent, 38 weight percent to 38.5 weight percent, 38.5 weight percent to 39 weight percent, 39 weight percent to 39.5 weight percent, and 39.5 weight percent to 40 weight percent.

In embodiments, the concentration of solids within the crude cannabinoid extract is selected from one or more from the group consisting of: 6.500 weight percent to 6.625 weight percent, 6.625 weight percent to 6.750 weight percent, 6.750 weight percent to 6.875 weight percent, 6.875 weight percent to 7.000 weight percent, 7.000 weight percent to 7.125 weight percent, 7.125 weight percent to 7.250 weight percent, 7.250 weight percent to 7.375 weight percent, 7.375 weight percent to 7.500 weight percent, 7.500 weight percent to 7.625 weight percent, 7.625 weight percent to 7.750 weight percent, 7.750 weight percent to 7.875 weight percent, 7.875 weight percent to 8.000 weight percent, 8.000 weight percent to 8.125 weight percent, 8.125 weight percent to 8.250 weight percent, 8.250 weight percent to 8.375 weight percent, 8.375 weight percent to 8.500 weight percent, 8.500 weight percent to 8.625 weight percent, 8.625 weight percent to 8.750 weight percent, 8.750 weight percent to 8.875 weight percent, 8.875 weight percent to 9.000 weight percent, 9.000 weight percent to 9.125 weight percent, 9.125 weight percent to 9.250 weight percent, 9.250 weight percent to 9.375 weight percent, 9.375 weight percent to 9.500 weight percent, 9.500 weight percent to 9.625 weight percent, 9.625 weight percent to 9.750 weight percent, 9.750 weight percent to 9.875 weight percent, 9.875 weight percent to 10.000 weight percent, 10.000 weight percent to 10.125 weight percent, 10.125 weight percent to 10.250 weight percent, 10.250 weight percent to 10.375 weight percent, 10.375 weight percent to 10.500 weight percent, 10.500 weight percent to 10.625 weight percent, 10.625 weight percent to 10.750 weight percent, 10.750 weight percent to 10.875 weight percent, 10.875 weight percent to 11.000 weight percent, 11.000 weight percent to 11.125 weight percent, 11.125 weight percent to 11.250 weight percent, 11.250 weight percent to 11.375 weight percent, 11.375 weight percent to 11.500 weight percent, 11.500 weight percent to 11.625 weight percent, 11.625 weight percent to 11.750 weight percent, 11.750 weight percent to 11.875 weight percent, 11.875 weight percent to 12.000 weight percent, 12.000 weight percent to 12.125 weight percent, 12.125 weight percent to 12.250 weight percent, 12.250 weight percent to 12.375 weight percent, 12.375 weight percent to 12.500 weight percent, 12.500 weight percent to 12.625 weight percent, 12.625 weight percent to 12.750 weight percent, 12.750 weight percent to 12.875 weight percent, 12.875 weight percent to 13.000 weight percent, 13.000 weight percent to 13.125 weight percent, 13.125 weight percent to 13.250 weight percent, 13.250 weight percent to 13.375 weight percent, 13.375 weight percent to 13.500 weight percent, 13.500 weight percent to 13.625 weight percent, 13.625 weight percent to 13.750 weight percent, 13.750 weight percent to 13.875 weight percent, 13.875 weight percent to 14.000 weight percent, 14.000 weight percent to 14.125 weight percent, 14.125 weight percent to 14.250 weight percent, 14.250 weight percent to 14.375 weight percent, 14.375 weight percent to 14.500 weight percent, 14.500 weight percent to 14.625 weight percent, 14.625 weight percent to 14.750 weight percent, 14.750 weight percent to 14.875 weight percent, 14.875 weight percent to 15.000 weight percent, 15.000 weight percent to 15.125 weight percent, 15.125 weight percent to 15.250 weight percent, 15.250 weight percent to 15.375 weight percent, 15.375 weight percent to 15.500 weight percent, 15.500 weight percent to 15.625 weight percent, 15.625 weight percent to 15.750 weight percent, 15.750 weight percent to 15.875 weight percent, 15.875 weight percent to 16.000 weight percent, 16.000 weight percent to 16.125 weight percent, 16.125 weight percent to 16.250 weight percent, 16.250 weight percent to 16.375 weight percent, 16.375 weight percent to 16.500 weight percent, 16.500 weight percent to 16.625 weight percent, 16.625 weight percent to 16.750 weight percent, 16.750 weight percent to 16.875 weight percent, 16.875 weight percent to 17.000 weight percent, 17.000 weight percent to 17.125 weight percent, 17.125 weight percent to 17.250 weight percent, 17.250 weight percent to 17.375 weight percent, 17.375 weight percent to 17.500 weight percent, 17.500 weight percent to 17.625 weight percent, 17.625 weight percent to 17.750 weight percent, 17.750 weight percent to 17.875 weight percent, 17.875 weight percent to 18.000 weight percent, 8.000 weight percent to 18.125 weight percent, 18.125 weight percent to 18.250 weight percent, 18.250 weight percent to 18.375 weight percent, 18.375 weight percent to 18.500 weight percent, 18.500 weight percent to 18.625 weight percent, 18.625 weight percent to 18.750 weight percent, 18.750 weight percent to 18.875 weight percent, 18.875 weight percent to 19.000 weight percent, 19.000 weight percent to 19.125 weight percent, 19.125 weight percent to 19.250 weight percent, 19.250 weight percent to 19.375 weight percent, 19.375 weight percent to 19.500 weight percent, 19.500 weight percent to 19.625 weight percent, 19.625 weight percent to 19.750 weight percent, 19.750 weight percent to 19.875 weight percent, and 19.875 weight percent to 20.000 weight percent.

In embodiments, the filtered crude cannabinoid extract (HBI, HBI', HBI") is passed from the first filter (HBC) and/or the second filter (HBF) and into a crude cannabinoid extract vessel (HCA). In embodiments, crude cannabinoid extract vessel (HCA) is configured to accept the filtered crude cannabinoid extract (HBI, HBI', HBI").

In embodiments, the crude cannabinoid extract vessel (HCA) is a continuously stirred tank reactor having a jacketed reactor equipped with a steam supply system and at least one steam trap. In embodiments, the crude cannabinoid extract vessel (HCA) is equipped with a level sensor (HCC) that is configured to input a signal (HCD) to the computer (COMP). In embodiments, the crude cannabinoid extract vessel (HCA) is equipped with a pH sensor (HCE) that is configured to input a signal (HCF) to the computer (COMP). In embodiments, the crude cannabinoid extract vessel (HCA) is equipped with an auger (HCG) that has a motor (HCH). The motor (HCH) of the auger (HCG) rotates the auger (HCG) to mix the contents within the interior (HCB) of the crude cannabinoid extract vessel (HCA). In embodiments, the crude cannabinoid extract vessel (HCA) is equipped with a temperature sensor that is configured to input a signal to the computer (COMP). In embodiments, the crude cannabinoid extract vessel (HCA) is equipped with a heat exchanger (HCl) to heat the contents within the interior (HCB) of the crude cannabinoid extract vessel (HCA). In embodiments, the crude cannabinoid extract vessel (HCA) outputs a filtered crude cannabinoid extract (HCK).

A filtered crude cannabinoid extract (HCK) is discharged from the interior (HCB) of the crude cannabinoid extract vessel (HCA) and is transferred to a crude cannabinoid extract pump (HCO). The crude cannabinoid extract pump (HCO) is equipped with a motor (HCP) and a controller (HCQ) that is configured to input and/or output a signal (HCR) to the computer (COMP). The crude cannabinoid extract pump (HCO) pumps and pressurizes the filtered crude cannabinoid extract (HCK) to form a filtered and pressurized crude cannabinoid extract (HCM). In embodiments, the filtered and pressurized crude cannabinoid extract (HCM) is used as a backflush supply (HCN) to regenerate in-situ the first filter (HBC) and/or the second filter (HBF). In embodiments, a filter (HCJ) is provided to polish the filtered and pressurized crude cannabinoid extract (HCM) to remove any additional solids that are present. In embodiments, a pressure sensor (HCS) is provided to measure the pressure of the filtered and pressurized crude cannabinoid extract (HCM). In embodiments, the pressure sensor (HCS) is configured to input a signal (HCT) to the computer (COMP).

In embodiments, the crude cannabinoid extract pump (HCO) pressurizes the filtered crude cannabinoid extract (HCK) to form a filtered and pressurized crude cannabinoid extract (HCM) at a pressure that includes one or more pressure ranges selected from the group consisting of 10 pounds per square inch (PSI) to 20 PSI, 20 PSI to 40 PSI, 40 PSI to 60 PSI, 60 PSI to 80 PSI, 80 PSI to 100 PSI, 100 PSI to 125 PSI, 125 PSI to 150 PSI, 150 PSI to 175 PSI, 175 PSI to 200 PSI, 200 PSI to 225 PSI, 225 PSI to 250 PSI, 250 PSI to 275 PSI, 275 PSI to 300 PSI, 300 PSI to 325 PSI, 325 PSI to 350 PSI, 350 PSI to 375 PSI, 375 PSI to 400 PSI, 400 PSI to 425 PSI, 425 PSI to 450 PSI, 450 PSI to 475 PSI, and 475 PSI to 500 PSI.

In embodiments, the filtered and pressurized crude cannabinoid extract (HCM) is transferred from the crude cannabinoid extract pump (HCO) and into a first adsorber system (SMB1). In embodiments, the first adsorber system (SMB1) is configured to input a filtered and pressurized crude cannabinoid extract (HCM) and a first desorbent (HDC). In embodiments, the first adsorber system (SMB1) is configured to output a first extract (HDA) and a first raffinate (HDE). In embodiments, the first extract (HDA) can also be called a primary extract (HDB). In embodiments, the first adsorber system (SMB1) includes an adsorber or plurality of adsorbers containing an adsorbent.

In embodiments, the first adsorber system (SMB1) includes a plurality of adsorbers containing adsorbent is provided and may be called the stationary phase. In embodiments, the adsorbent positioned within the adsorber or plurality of adsorbers may be called the stationary phase. The bed of adsorbent that is contained within the adsorber does not move so therefore it is stationary. The plurality of beds of adsorbent that are contained within the plurality of adsorbers does not move so therefore it is stationary. In embodiments, at least a portion of *cannabis* is dissolved in a solvent (e.g.—the filtered and pressurized crude cannabinoid extract (HCM)) and may be called the mobile phase.

In embodiments, a first adsorber system (SMB1) operates as a simulated moving bed chromatography (SMB chromatography) which is a continuous process. This is implemented by arranging several preparative columns connected in series and periodically changing the valve setting so that a movement of the solid phase in the opposite direction of the flow of the liquid phase is simulated. In embodiments, the system is continuously fed with a feed mixture (e.g.—the filtered and pressurized crude cannabinoid extract (HCM)) comprising the compounds to be separated and an eluent (e.g.—the first desorbent (HDC) which is a liquid, water, treated water, or a solvent) while a raffinate and an extract are continuously withdrawn from the system.

In embodiments, the first adsorber system (SMB1) periodically switches the feed, eluent, extract and raffinate ports in the same direction. The basic premise of a simulated moving bed adsorber system is that the inlet and outlet ports are switched periodically in the direction of the fluid flow. This simulates the countercurrent movement of the phase in the process. Chromatography is a technique used to separate mixtures. In embodiments, the mixture may include cannabinoids and a solvent. In embodiments, the mixture may include a filtered and pressurized crude cannabinoid extract (HCM). In embodiments, the mixture may include cannabinoids from a first solvent and volatiles mixture (FSVM). In embodiments, the mixture may include cannabinoids from a second volatiles and solvent mixture (SVSM).

In embodiments, cannabinoids (e.g.—tetrahydrocannabinol, $\Delta$9-tetrahydrocannabinol $\Delta$9-THC, $\Delta$8-tetrahydrocannabinol $\Delta$8-THC, cannabichromene CBC, cannabidiol CBD, cannabigerol CBG, cannabinidiol CBND, and/or cannabinol CBN) are dissolved in a liquid solvent. The mixture of cannabinoids and the solvent may be called the mobile phase. The mobile phase is passed through an adsorber containing an adsorbent, the adsorbent within the adsorber may be called a stationary phase. In embodiments, a moving bed adsorber may be used in which the stationary phase would then move.

The mixture of cannabinoids and solvent are introduced into the adsorber and various constituents of the mixture travel at different speeds, causing them to separate. The separation is based on differential partitioning between the mobile and stationary phases. More than one adsorber may be used so there may be various stationary phases. Subtle differences in each of the cannabinoids' partition coefficient result in differential retention on the stationary phase and thus affect the separation. For example, some cannabinoids are more hydrophilic than others and are mode readily soluble in a solvent such as lipids and alcohol. These compounds in turn have a relatively larger partition coefficient than the cannabinoids that are less hydrophilic.

In embodiments, a relatively less hydrophilic cannabinoid has a greater partition coefficient than a cannabinoid that is more hydrophilic. In embodiments, a relatively more hydrophobic cannabinoid has a greater partition coefficient than a cannabinoid that is less hydrophilic. In other embodiments, a relatively less hydrophilic cannabinoid has a greater partition coefficient than a cannabinoid that is more hydrophilic. In other embodiments, a relatively more hydrophilic cannabinoid has a lesser partition coefficient than a cannabinoid that is lesser hydrophilic.

In embodiments, tetrahydrocannabinol has a partition coefficient of 6.99. In embodiments, $\Delta$9-tetrahydrocannabinol $\Delta$9-THC has a partition coefficient of 6.99. In embodiments, cannabidiol has a partition coefficient of 5.79. In embodiments, tetrahydrocannabinol has a partition coefficient that is greater than cannabidiol. In embodiments, tetrahydrocannabinol is more hydrophobic than cannabidiol. In embodiments, cannabidiol is more hydrophilic than tetrahydrocannabinol.

Since tetrahydrocannabinol has a partition coefficient that is greater than cannabidiol, it will stay in the bed longer than the cannabidiol. In embodiments, the tetrahydrocannabinol will stay in the adsorber bed longer than the cannabidiol. In embodiments, the cannabidiol will stay in the adsorber bed longer than the tetrahydrocannabinol. In embodiments, the tetrahydrocannabinol will elute before the cannabidiol. In embodiments, the cannabidiol will elute before the tetrahydrocannabinol.

In embodiments, the first, second, and/or third adsorber systems (SMB1, SMB2, SMB3), are simulated moving bed processing systems and are cyclic steady state processes configured to obtain pure components (e.g.—concentrated volatiles, an emulsion, etc.) are production rates that include one or more selected from the group consisting of 0.0015 tons per day to 0.003 tons per day, 0.003 tons per day to 0.0045 tons per day, 0.0045 tons per day to 0.006 tons per day, 0.006 tons per day to 0.0075 tons per day, 0.0075 tons per day to 0.009 tons per day, 0.009 tons per day to 0.0105 tons per day, 0.0105 tons per day to 0.012 tons per day, 0.012 tons per day to 0.0135 tons per day, 0.0135 tons per day to 0.015 tons per day, 0.015 tons per day to 0.03 tons per day, 0.03 tons per day to 0.033 tons per day, 0.033 tons per day to 0.036 tons per day, 0.036 tons per day to 0.039 tons per day, 0.039 tons per day to 0.042 tons per day, 0.042 tons per day to 0.045 tons per day, 0.045 tons per day to 0.048 tons per day, 0.048 tons per day to 0.051 tons per day, 0.051 tons per day to 0.054 tons per day, 0.054 tons per day to 0.057 tons per day, 0.057 tons per day to 0.06 tons per day, 0.06 tons per day to 0.063 tons per day, 0.063 tons per day to 0.066 tons per day, 0.066 tons per day to 0.132 tons per day, 0.132 tons per day to 0.198 tons per day, 0.198 tons per day to 0.264 tons per day, 0.264 tons per day to 0.33 tons per day, 0.33 tons per day to 0.396 tons per day, 0.396 tons per day to 0.462 tons per day, 0.462 tons per day to 0.528 tons per day, 0.528 tons per day to 0.594 tons per day, 0.594 tons per day to 0.66 tons per day, 0.66 tons per day to 0.726 tons per day, 0.726 tons per day to 0.792 tons per day, 0.792 tons per day to 1.584 tons per day, 1.584 tons per day to 3.168 tons per day, 3.168 tons per day to 6.336 tons per day, 6.336 tons per day to 12.672 tons per day, 12.672 tons per day to 25.344 tons per day, 25.344 tons per day to 50.688 tons per day, 50.688 tons per day to 101.376 tons per day.

In embodiments, the extract is the more highly adsorbed component. In embodiments, the more highly adsorbed components are cannabinoids (such as tetrahydrocannabinol, Δ9-tetrahydrocannabinol Δ9-THC, Δ8-tetrahydrocannabinol Δ8-THC, cannabichromene CBC, cannabidiol CBD, cannabigerol CBG, cannabinidiol CBND, and/or cannabinol CBN). In embodiments, the extract is desorbed with a desorbent to collect as the final product. Desorption may take place under pressure swing desorption, thermal swing desorption, or passing a heated and/or cooled desorbent liquid do desorb the extract from the adsorption sites within the adsorber. In embodiments, the desorption may take place under pressure swing desorption, thermal swing desorption, or passing a first heated desorbent liquid then a second cooled desorbent liquid do desorb the extract from the adsorption sites within the adsorber.

In embodiments, the raffinate includes poorly adsorbed components. The poorly adsorbed components adsorb less to the adsorption sites or the adsorbent within the adsorber or plurality of adsorbers in relation to the highly adsorbed components. In embodiments, the raffinate includes a liquid, first solvent, second solvent, water, alcohol, lipid. In embodiments, the raffinate includes a solvent, the solvent includes one or more from the group consisting of acetone, alcohol, ethanol, hexane, isobutane, isopropanol, liquid carbon dioxide, liquid, naphtha, and water. In embodiments, a mixture of cannabinoids and a solvent are provided to the simulated bed adsorber system. In embodiments, the cannabinoids are the extract and the solvent is the raffinate. In embodiments, the extract is more highly adsorbed components. In embodiments, the more highly adsorbed components are cannabinoids.

In embodiments, the raffinate includes cannabinoids. In embodiments, the raffinate includes cannabidiol. In embodiments, the raffinate includes THC. In embodiments, the raffinate includes a mixture of cannabinoids and water. In embodiments, the raffinate includes a mixture of cannabidiol and water. In embodiments, the raffinate includes a mixture of THC and water. In embodiments, the raffinate includes a mixture of cannabinoids and ethanol. In embodiments, the raffinate includes a mixture of cannabidiol and ethanol. In embodiments, the raffinate includes a mixture of THC and ethanol. In embodiments, the raffinate includes a mixture of cannabinoids and ethanol and water. In embodiments, the raffinate includes a mixture of cannabidiol and ethanol and water. In embodiments, the raffinate includes a mixture of THC and ethanol and water. In embodiments, the raffinate includes a mixture of cannabinoids and methanol. In embodiments, the raffinate includes a mixture of cannabidiol and methanol. In embodiments, the raffinate includes a mixture of THC and methanol.

In embodiments, the raffinate includes a mixture of cannabinoids and methanol and water. In embodiments, the raffinate includes a mixture of cannabidiol and methanol and water. In embodiments, the raffinate includes a mixture of THC and methanol and water.

In embodiments, the raffinate includes cannabinoids and ethanol at a cannabinoid-to-ethanol-raffinate-ratio selected from the group consisting of: 0.0001 pounds of cannabinoids to per pound of ethanol to 0.0002 pounds of cannabinoids to per pound of ethanol, 0.0002 pounds of cannabinoids to per pound of ethanol to 0.0004 pounds of cannabinoids to per pound of ethanol, 0.0004 pounds of cannabinoids to per pound of ethanol to 0.0008 pounds of cannabinoids to per pound of ethanol, 0.0008 pounds of cannabinoids to per pound of ethanol to 0.0016 pounds of cannabinoids to per pound of ethanol, 0.0016 pounds of cannabinoids to per pound of ethanol to 0.0032 pounds of cannabinoids to per pound of ethanol, 0.0032 pounds of cannabinoids to per pound of ethanol to 0.0064 pounds of cannabinoids to per pound of ethanol, 0.0064 pounds of cannabinoids to per pound of ethanol to 0.0128 pounds of cannabinoids to per pound of ethanol, 0.0128 pounds of cannabinoids to per pound of ethanol to 0.0256 pounds of cannabinoids to per pound of ethanol, 0.0256 pounds of cannabinoids to per pound of ethanol to 0.0512 pounds of cannabinoids to per pound of ethanol, 0.0512 pounds of cannabinoids to per pound of ethanol to 0.06 pounds of cannabinoids to per pound of ethanol, 0.06 pounds of cannabinoids to per pound of ethanol to 0.07 pounds of cannabinoids to per pound of ethanol, 0.07 pounds of cannabinoids to per pound of ethanol to 0.08 pounds of cannabinoids to per pound of ethanol, 0.08 pounds of cannabinoids to per pound of ethanol to 0.09 pounds of cannabinoids to per pound of ethanol, 0.09 pounds of cannabinoids to per pound of ethanol to 0.1 pounds of cannabinoids to per pound of ethanol, 0.1 pounds of cannabinoids to per pound of ethanol to 0.233 pounds of cannabinoids to per pound of ethanol, 0.233 pounds of cannabinoids to per pound of ethanol to 0.366 pounds of cannabinoids to per pound of ethanol, 0.366 pounds of cannabinoids to per pound of ethanol to 0.499 pounds of cannabinoids to per pound of ethanol, and 0.499 pounds of cannabinoids to per pound of ethanol to 0.632 pounds of cannabinoids to per pound of ethanol; wherein: the cannabinoid-to-ethanol-ratio is defined as the weight percent of the raffinate mixture including the pounds of cannabinoids divided by the pounds of ethanol.

In embodiments, the raffinate includes cannabinoids and methanol at a cannabinoid-to-methanol-raffinate-ratio selected from the group consisting of: 0.0001 pounds of cannabinoids to per pound of methanol to 0.0002 pounds of cannabinoids to per pound of methanol, 0.0002 pounds of cannabinoids to per pound of methanol to 0.0004 pounds of cannabinoids to per pound of methanol, 0.0004 pounds of cannabinoids to per pound of methanol to 0.0008 pounds of cannabinoids to per pound of methanol, 0.0008 pounds of cannabinoids to per pound of methanol to 0.0016 pounds of cannabinoids to per pound of methanol, 0.0016 pounds of cannabinoids to per pound of methanol to 0.0032 pounds of cannabinoids to per pound of methanol, 0.0032 pounds of cannabinoids to per pound of methanol to 0.0064 pounds of cannabinoids to per pound of methanol, 0.0064 pounds of cannabinoids to per pound of methanol to 0.0128 pounds of cannabinoids to per pound of methanol, 0.0128 pounds of cannabinoids to per pound of methanol to 0.0256 pounds of cannabinoids to per pound of methanol, 0.0256 pounds of cannabinoids to per pound of methanol to 0.0512 pounds of cannabinoids to per pound of methanol, 0.0512 pounds of cannabinoids to per pound of methanol to 0.06 pounds of cannabinoids to per pound of methanol, 0.06 pounds of cannabinoids to per pound of methanol to 0.07 pounds of cannabinoids to per pound of methanol, 0.07 pounds of cannabinoids to per pound of methanol to 0.08 pounds of cannabinoids to per pound of methanol, 0.08 pounds of cannabinoids to per pound of methanol to 0.09 pounds of cannabinoids to per pound of methanol, 0.09 pounds of cannabinoids to per pound of methanol to 0.1 pounds of cannabinoids to per pound of methanol, 0.1 pounds of cannabinoids to per pound of methanol to 0.233 pounds of cannabinoids to per pound of methanol, 0.233 pounds of cannabinoids to per pound of methanol to 0.366 pounds of cannabinoids to per pound of methanol, 0.366 pounds of cannabinoids to per pound of methanol to 0.499 pounds of cannabinoids to per pound of methanol, and 0.499 pounds of cannabinoids to per pound of methanol to 0.632 pounds of cannabinoids to per pound of methanol; wherein: the cannabinoid-to-methanol-ratio is defined as the weight percent of the raffinate mixture including the pounds of cannabinoids divided by the pounds of methanol.

In embodiments, the raffinate includes cannabinoids and water at a cannabinoid-to-water-raffinate-ratio selected from the group consisting of: 0.0001 pounds of cannabinoids to per pound of water to 0.0002 pounds of cannabinoids to per pound of water, 0.0002 pounds of cannabinoids to per pound of water to 0.0004 pounds of cannabinoids to per pound of water, 0.0004 pounds of cannabinoids to per pound of water to 0.0008 pounds of cannabinoids to per pound of water, 0.0008 pounds of cannabinoids to per pound of water to 0.0016 pounds of cannabinoids to per pound of water, 0.0016 pounds of cannabinoids to per pound of water to 0.0032 pounds of cannabinoids to per pound of water, 0.0032 pounds of cannabinoids to per pound of water to 0.0064 pounds of cannabinoids to per pound of water, 0.0064 pounds of cannabinoids to per pound of water to 0.0128 pounds of cannabinoids to per pound of water, 0.0128 pounds of cannabinoids to per pound of water to 0.0256 pounds of cannabinoids to per pound of water, 0.0256 pounds of cannabinoids to per pound of water to 0.0512 pounds of cannabinoids to per pound of water, 0.0512 pounds of cannabinoids to per pound of water to 0.06 pounds of cannabinoids to per pound of water, 0.06 pounds of cannabinoids to per pound of water to 0.07 pounds of cannabinoids to per pound of water, 0.07 pounds of cannabinoids to per pound of water to 0.08 pounds of cannabinoids to per pound of water, 0.08 pounds of cannabinoids to per pound of water to 0.09 pounds of cannabinoids to per pound of water, 0.09 pounds of cannabinoids to per pound of water to 0.1 pounds of cannabinoids to per pound of water, 0.1 pounds of cannabinoids to per pound of water to 0.233 pounds of cannabinoids to per pound of water, 0.233 pounds of cannabinoids to per pound of water to 0.366 pounds of cannabinoids to per pound of water, 0.366 pounds of cannabinoids to per pound of water to 0.499 pounds of cannabinoids to per pound of water, and 0.499 pounds of cannabinoids to per pound of water to 0.632 pounds of cannabinoids to per pound of water; wherein: the cannabinoid-to-water-ratio is defined as the weight percent of the raffinate mixture including the pounds of cannabinoids divided by the pounds of water.

In embodiments, the raffinate includes THC and ethanol at a THC-to-ethanol-raffinate-ratio selected from the group consisting of: 0.0001 pounds of THC to per pound of ethanol to 0.0002 pounds of THC to per pound of ethanol, 0.0002 pounds of THC to per pound of ethanol to 0.0004 pounds of THC to per pound of ethanol, 0.0004 pounds of THC to per pound of ethanol to 0.0008 pounds of THC to per pound of ethanol, 0.0008 pounds of THC to per pound of ethanol to 0.0016 pounds of THC to per pound of ethanol, 0.0016 pounds of THC to per pound of ethanol to 0.0032 pounds of THC to per pound of ethanol, 0.0032 pounds of THC to per pound of ethanol to 0.0064 pounds of THC to per pound of ethanol, 0.0064 pounds of THC to per pound of ethanol to 0.0128 pounds of THC to per pound of ethanol, 0.0128 pounds of THC to per pound of ethanol to 0.0256 pounds of THC to per pound of ethanol, 0.0256 pounds of THC to per pound of ethanol to 0.0512 pounds of THC to per pound of ethanol, 0.0512 pounds of THC to per pound of ethanol to 0.06 pounds of THC to per pound of ethanol, 0.06 pounds of THC to per pound of ethanol to 0.07 pounds of THC to per pound of ethanol, 0.07 pounds of THC to per pound of ethanol to 0.08 pounds of THC to per pound of ethanol, 0.08 pounds of THC to per pound of ethanol to 0.09 pounds of THC to per pound of ethanol, 0.09 pounds of THC to per pound of ethanol to 0.1 pounds of THC to per pound of ethanol, 0.1 pounds of THC to per pound of ethanol to 0.233 pounds of THC to per pound of ethanol, 0.233 pounds of THC to per pound of ethanol to 0.366 pounds of THC to per pound of ethanol, 0.366 pounds of THC to per pound of ethanol to 0.499 pounds of THC to per pound of ethanol, and 0.499 pounds of THC to per pound of ethanol to 0.632 pounds of THC to per pound of ethanol; wherein: the THC-to-ethanol-ratio is defined as the weight percent of the raffinate mixture including the pounds of THC divided by the pounds of ethanol.

In embodiments, the raffinate includes THC and methanol at a THC-to-methanol-raffinate-ratio selected from the group consisting of: 0.0001 pounds of THC to per pound of methanol to 0.0002 pounds of THC to per pound of methanol, 0.0002 pounds of THC to per pound of methanol to 0.0004 pounds of THC to per pound of methanol, 0.0004 pounds of THC to per pound of methanol to 0.0008 pounds of THC to per pound of methanol, 0.0008 pounds of THC to per pound of methanol to 0.0016 pounds of THC to per pound of methanol, 0.0016 pounds of THC to per pound of methanol to 0.0032 pounds of THC to per pound of methanol, 0.0032 pounds of THC to per pound of methanol to 0.0064 pounds of THC to per pound of methanol, 0.0064 pounds of THC to per pound of methanol to 0.0128 pounds of THC to per pound of methanol, 0.0128 pounds of THC to per pound of methanol to 0.0256 pounds of THC to per pound of methanol, 0.0256 pounds of THC to per pound of methanol to 0.0512 pounds of THC to per pound of methanol, 0.0512 pounds of THC to per pound of methanol to 0.06 pounds of THC to per pound of methanol, 0.06 pounds of THC to per pound of methanol to 0.07 pounds of THC to per pound of methanol, 0.07 pounds of THC to per pound of methanol to 0.08 pounds of THC to per pound of methanol, 0.08 pounds of THC to per pound of methanol to 0.09 pounds of THC to per pound of methanol, 0.09 pounds of THC to per pound of methanol to 0.1 pounds of THC to per pound of methanol, 0.1 pounds of THC to per pound of methanol to 0.233 pounds of THC to per pound of methanol, 0.233 pounds of THC to per pound of methanol to 0.366 pounds of THC to per pound of methanol, 0.366 pounds of THC to per pound of methanol to 0.499 pounds of THC to per pound of methanol, and 0.499 pounds of THC to per pound of methanol to 0.632 pounds of THC to per pound of methanol; wherein: the THC-to-methanol-ratio is defined as the weight percent of the raffinate mixture including the pounds of THC divided by the pounds of methanol.

In embodiments, the raffinate includes THC and water at a THC-to-water-raffinate-ratio selected from the group consisting of: 0.0001 pounds of THC to per pound of water to 0.0002 pounds of THC to per pound of water, 0.0002 pounds of THC to per pound of water to 0.0004 pounds of THC to per pound of water, 0.0004 pounds of THC to per pound of water to 0.0008 pounds of THC to per pound of water, 0.0008 pounds of THC to per pound of water to 0.0016 pounds of THC to per pound of water, 0.0016 pounds of THC to per pound of water to 0.0032 pounds of THC to per pound of water, 0.0032 pounds of THC to per pound of water to 0.0064 pounds of THC to per pound of water, 0.0064 pounds of THC to per pound of water to 0.0128 pounds of THC to per pound of water, 0.0128 pounds of THC to per pound of water to 0.0256 pounds of THC to per pound of water, 0.0256 pounds of THC to per pound of water to 0.0512 pounds of THC to per pound of water, 0.0512 pounds of THC to per pound of water to 0.06 pounds of THC to per pound of water, 0.06 pounds of THC to per pound of water to 0.07 pounds of THC to per pound of water, 0.07 pounds of THC to per pound of water to 0.08 pounds of THC to per pound of water, 0.08 pounds of THC to per pound of water to 0.09 pounds of THC to per pound of water, 0.09 pounds of THC to per pound of water to 0.1 pounds of THC to per pound of water, 0.1 pounds of THC to per pound of water to 0.233 pounds of THC to per pound of water, 0.233 pounds of THC to per pound of water to 0.366 pounds of THC to per pound of water, 0.366 pounds of THC to per pound of water to 0.499 pounds of THC to per pound of water, and 0.499 pounds of THC to per pound of water to 0.632 pounds of THC to per pound of water; wherein: the THC-to-water-ratio is defined as the weight percent of the raffinate mixture including the pounds of THC divided by the pounds of water.

In embodiments, the raffinate includes CBD and ethanol at a CBD-to-ethanol-raffinate-ratio selected from the group consisting of: 0.0001 pounds of CBD to per pound of ethanol to 0.0002 pounds of CBD to per pound of ethanol, 0.0002 pounds of CBD to per pound of ethanol to 0.0004 pounds of CBD to per pound of ethanol, 0.0004 pounds of CBD to per pound of ethanol to 0.0008 pounds of CBD to per pound of ethanol, 0.0008 pounds of CBD to per pound of ethanol to 0.0016 pounds of CBD to per pound of ethanol, 0.0016 pounds of CBD to per pound of ethanol to 0.0032 pounds of CBD to per pound of ethanol, 0.0032 pounds of CBD to per pound of ethanol to 0.0064 pounds of CBD to per pound of ethanol, 0.0064 pounds of CBD to per pound of ethanol to 0.0128 pounds of CBD to per pound of ethanol, 0.0128 pounds of CBD to per pound of ethanol to 0.0256 pounds of CBD to per pound of ethanol, 0.0256 pounds of CBD to per pound of ethanol to 0.0512 pounds of CBD to per pound of ethanol, 0.0512 pounds of CBD to per pound of ethanol to 0.06 pounds of CBD to per pound of ethanol, 0.06 pounds of CBD to per pound of ethanol to 0.07 pounds of CBD to per pound of ethanol, 0.07 pounds of CBD to per pound of ethanol to 0.08 pounds of CBD to per pound of ethanol, 0.08 pounds of CBD to per pound of ethanol to 0.09 pounds of CBD to per pound of ethanol, 0.09 pounds of CBD to per pound of ethanol to 0.1 pounds of CBD to per pound of ethanol, 0.1 pounds of CBD to per pound of ethanol to 0.233 pounds of CBD to per pound of ethanol, 0.233 pounds of CBD to per pound of ethanol to 0.366 pounds of CBD to per pound of ethanol, 0.366 pounds of CBD to per pound of ethanol to 0.499 pounds of CBD to per pound of ethanol, and 0.499 pounds of CBD to per pound of ethanol to 0.632 pounds of CBD to per pound of ethanol; wherein: the CBD-to-ethanol-ratio is defined as the weight percent of the raffinate mixture including the pounds of CBD divided by the pounds of ethanol.

In embodiments, the raffinate includes CBD and methanol at a CBD-to-methanol-raffinate-ratio selected from the group consisting of: 0.0001 pounds of CBD to per pound of methanol to 0.0002 pounds of CBD to per pound of methanol, 0.0002 pounds of CBD to per pound of methanol to 0.0004 pounds of CBD to per pound of methanol, 0.0004 pounds of CBD to per pound of methanol to 0.0008 pounds of CBD to per pound of methanol, 0.0008 pounds of CBD to per pound of methanol to 0.0016 pounds of CBD to per pound of methanol, 0.0016 pounds of CBD to per pound of methanol to 0.0032 pounds of CBD to per pound of methanol, 0.0032 pounds of CBD to per pound of methanol to 0.0064 pounds of CBD to per pound of methanol, 0.0064 pounds of CBD to per pound of methanol to 0.0128 pounds of CBD to per pound of methanol, 0.0128 pounds of CBD to per pound of methanol to 0.0256 pounds of CBD to per pound of methanol, 0.0256 pounds of CBD to per pound of methanol to 0.0512 pounds of CBD to per pound of methanol, 0.0512 pounds of CBD to per pound of methanol to 0.06 pounds of CBD to per pound of methanol, 0.06 pounds of CBD to per pound of methanol to 0.07 pounds of CBD to per pound of methanol, 0.07 pounds of CBD to per pound of methanol to 0.08 pounds of CBD to per pound of methanol, 0.08 pounds of CBD to per pound of methanol to 0.09 pounds of CBD to per pound of methanol, 0.09 pounds of CBD to per pound of methanol to 0.1 pounds of CBD to per pound of methanol, 0.1 pounds of CBD to per pound of methanol to 0.233 pounds of CBD to per pound of methanol, 0.233 pounds of CBD to per pound of methanol to 0.366 pounds of CBD to per pound of methanol, 0.366 pounds of CBD to per pound of methanol to 0.499 pounds of CBD to per pound of methanol, and 0.499 pounds of CBD to per pound of methanol to 0.632 pounds of CBD to per pound of methanol; wherein: the CBD-to-methanol-ratio is defined as the weight percent of the raffinate mixture including the pounds of CBD divided by the pounds of methanol.

In embodiments, the raffinate includes CBD and water at a CBD-to-water-raffinate-ratio selected from the group consisting of: 0.0001 pounds of CBD to per pound of water to 0.0002 pounds of CBD to per pound of water, 0.0002 pounds of CBD to per pound of water to 0.0004 pounds of CBD to per pound of water, 0.0004 pounds of CBD to per pound of water to 0.0008 pounds of CBD to per pound of water, 0.0008 pounds of CBD to per pound of water to 0.0016 pounds of CBD to per pound of water, 0.0016 pounds of CBD to per pound of water to 0.0032 pounds of CBD to per pound of water, 0.0032 pounds of CBD to per pound of water to 0.0064 pounds of CBD to per pound of water, 0.0064 pounds of CBD to per pound of water to 0.0128 pounds of CBD to per pound of water, 0.0128 pounds of CBD to per pound of water to 0.0256 pounds of CBD to per pound of water, 0.0256 pounds of CBD to per pound of water to 0.0512 pounds of CBD to per pound of water, 0.0512 pounds of CBD to per pound of water to 0.06 pounds of CBD to per pound of water, 0.06 pounds of CBD to per pound of water to 0.07 pounds of CBD to per pound of water, 0.07 pounds of CBD to per pound of water to 0.08 pounds of CBD to per pound of water, 0.08 pounds of CBD to per pound of water to 0.09 pounds of CBD to per pound of water, 0.09 pounds of CBD to per pound of water to 0.1 pounds of CBD to per pound of water, 0.1 pounds of CBD to per pound of water to 0.233 pounds of CBD to per pound of water, 0.233 pounds of CBD to per pound of water to 0.366 pounds of CBD to per pound of water, 0.366 pounds of CBD to per pound of water to 0.499 pounds of CBD to per pound of water, and 0.499 pounds of CBD to per pound of water to 0.632 pounds of CBD to per pound of water; wherein: the CBD-to-water-ratio is defined as the weight percent of the raffinate mixture including the pounds of CBD divided by the pounds of water.

Desorbent (Eluent)

In embodiments, the eluent is the first desorbent (HDC). In embodiments, the eluent is in a supercritical state. In embodiments, the eluent is not in a supercritical state. In embodiments, the eluent is a liquid. In embodiments, the eluent can be an aqueous alcohol. In embodiments, the aqueous alcohol can comprise water and one or more short chain alcohols. In embodiments, the short chain alcohol can have from 1 to 6 carbon atoms. In embodiments, the examples of suitable alcohols include methanol, ethanol, n-propanol, i-propanol, n-butanol, i-butanol, s-butanol and t-butanol. In some aspects of the present invention, methanol and ethanol can be used. In another aspect, methanol can be used. In embodiments, the eluent can be methyl tertiary butyl ether. In embodiments, the eluent is a mixture of methanol, tetrahydrofuran, and water. In embodiments, the eluent is water. In embodiments, the eluent is treated water. In embodiments, the eluent ranges from between 80 deg F. to 90 deg F., 9 deg F. to 100 deg F., 100 deg F. to 110 deg F., 110 deg F. to 120 deg F., 120 deg F. to 130 deg F., 130 deg F. to 140 deg F., 140 deg F. to 150 deg F., 150 deg F. to 160 deg F., 160 deg F. to 170 deg F., 170 deg F. to 180 deg F., 180 deg F. to 190 deg F., 190 deg F. to 200 deg F., 200 deg F. to 210 deg F., 210 deg F. to 212 deg F.

In embodiments, the weight percent of ethanol in the eluent includes one or more concentration ranges selected from the group consisting of: 15 weight percent to 20 weight percent, 20 weight percent to 25 weight percent, 25 weight percent to 30 weight percent, 30 weight percent to 35 weight percent, 35 weight percent to 40 weight percent, 40 weight percent to 45 weight percent, 45 weight percent to 50 weight percent, 50 weight percent to 55 weight percent, 55 weight percent to 60 weight percent, 60 weight percent to 65 weight percent, 65 weight percent to 70 weight percent, 70 weight percent to 75 weight percent, 75 weight percent to 80 weight percent, 80 weight percent to 85 weight percent, 85 weight percent to 90 weight percent, 90 to 95 weight percent, 95 weight percent to 99 weight percent, and 99 weight percent to 100 weight percent, and 100 weight percent.

In embodiments, the weight percent of methanol in the eluent includes one or more concentration ranges selected from the group consisting of: 15 weight percent to 20 weight percent, 20 weight percent to 25 weight percent, 25 weight percent to 30 weight percent, 30 weight percent to 35 weight percent, 35 weight percent to 40 weight percent, 40 weight percent to 45 weight percent, 45 weight percent to 50 weight percent, 50 weight percent to 55 weight percent, 55 weight percent to 60 weight percent, 60 weight percent to 65 weight percent, 65 weight percent to 70 weight percent, 70 weight percent to 75 weight percent, 75 weight percent to 80 weight percent, 80 weight percent to 85 weight percent, 85 weight percent to 90 weight percent, 90 to 95 weight percent, 95 weight percent to 99 weight percent, and 99 weight percent to 100 weight percent, and 100 weight percent.

In embodiments the weight percent of tetrahydofuran in the eluent includes one or more concentration ranges selected from the group consisting of: 0 weight percent to 1 weight percent, 1 weight percent to 5 weight percent, 5 weight percent to 10 weight percent, 10 weight percent to 15 weight percent, 15 weight percent to 20 weight percent, 20 weight percent to 25 weight percent, 25 weight percent to 30 weight percent, 30 weight percent to 35 weight percent, 35 weight percent to 40 weight percent, 40 weight percent to 45 weight percent, 45 weight percent to 50 weight percent, 50 weight percent to 55 weight percent, 55 weight percent to 60 weight percent, 60 weight percent to 65 weight percent, 65 weight percent to 70 weight percent, 70 weight percent to 75 weight percent, 75 weight percent to 80 weight percent, 80 weight percent to 85 weight percent, 85 weight percent to 90 weight percent, 90 weight percent to 95 weight percent, 95 weight percent to 99 weight percent, and 99 to 100 weight percent to percent, and 100 weight percent.

In embodiments, the weight percent of water in the eluent includes one or more concentration ranges selected from the group consisting of: 0 weight percent to 1 weight percent, 1 weight percent to 5 weight percent, 5 weight percent to 10 weight percent, 10 weight percent to 15 weight percent, 15 weight percent to 20 weight percent, 20 weight percent to 25 weight percent, 25 weight percent to 30 weight percent, 30 weight percent to 35 weight percent, 35 weight percent to 40 weight percent, 40 weight percent to 45 weight percent, 45 weight percent to 50 weight percent, 50 weight percent to 55 weight percent, 55 weight percent to 60 weight percent, 60 weight percent to 65 weight percent, 65 weight percent to 70 weight percent, 70 weight percent to 75 weight percent, 75 weight percent to 80 weight percent, 80 weight percent to 85 weight percent, 85 weight percent to 90 weight percent, 90 weight percent to 95 weight percent, 95 weight percent to 99 weight percent, and 99 weight percent to 100 weight percent, and 100 weight percent.

The process of the present invention relates to the purification of terpenes and/or cannabidiol and/or tetrahydrocannabinol directly from extracts of plant material in a process which uses novel chromatographic scheme. More specifically, Applicant has developed a sequence of purification steps and a novel simulated moving bed separation process (SMB) series of adsorbent/desorbent combinations and SMB configurations to bring about the enrichment and purification of terpenes and/or cannabidiol and/or tetrahydrocannabinol, to provide a purified terpenes and/or cannabidiol and/or tetrahydrocannabinol product and without using any potentially toxic organic solvent.

In embodiments, the adsorbent used in the simulated moving bed system employed is a combination of styrene-divinyl benzene copolymer, ion exchange and hydrophobic interaction based stationary phase adsorbents and a mobile phase comprising water in a combination of normal and reverse phase simulated moving bed separation zones to provide an enriched extract comprising major terpenes and/or cannabidiol and/or tetrahydrocannabinol.

In embodiments, the terpenes that are extracted from the SMB process have a purity that includes one or more from the group consisting of 30 percent purity to 40 percent purity, 40 percent purity to 50 percent purity, 50 percent purity to 60 percent purity, 60 percent purity to 70 percent purity, 70 percent purity to 80 percent purity, 80 percent purity to 82 percent purity, 82 percent purity to 84 percent purity, 84 percent purity to 86 percent purity, 86 percent purity to 88 percent purity, 88 percent purity to 90 percent purity, 90 percent purity to 92 percent purity, 92 percent purity to 92.5 percent purity, 92.5 percent purity to 93 percent purity, 93 percent purity to 93.5 percent purity, 93.5 percent purity to 94 percent purity, 94 percent purity to 94.5 percent purity, 94.5 percent purity to 94.75 percent purity, 94.75 percent purity to 95 percent purity, 95 percent purity to 95.25 percent purity, 95.25 percent purity to 95.5 percent purity, 95.5 percent purity to 95.75 percent purity, 95.75 percent purity to 96 percent purity, 96 percent purity to 96.25 percent purity, 96.25 percent purity to 96.5 percent purity, 96.5 percent purity to 96.75 percent purity, 96.75 percent purity to 97 percent purity, 97 percent purity to 97.25 percent purity, 97.25 percent purity to 97.5 percent purity, 97.5 percent purity to 97.75 percent purity, 97.75 percent purity to 98 percent purity, 98 percent purity to 98.25 percent purity, 98.25 percent purity to 98.5 percent purity, 98.5 percent purity to 98.75 percent purity, 98.75 percent purity to 99 percent purity, 99 percent purity to 99.25 percent purity, 99.25 percent purity to 99.5 percent purity, 99.5 percent purity to 99.75 percent purity, and 99.75 percent purity to 100 percent purity.

In embodiments, the cannabidiol that are extracted from the SMB process have a purity that includes one or more from the group consisting of 30 percent purity to 40 percent purity, 40 percent purity to 50 percent purity, 50 percent purity to 60 percent purity, 60 percent purity to 70 percent purity, 70 percent purity to 80 percent purity, 80 percent purity to 82 percent purity, 82 percent purity to 84 percent purity, 84 percent purity to 86 percent purity, 86 percent purity to 88 percent purity, 88 percent purity to 90 percent purity, 90 percent purity to 92 percent purity, 92 percent purity to 92.5 percent purity, 92.5 percent purity to 93 percent purity, 93 percent purity to 93.5 percent purity, 93.5 percent purity to 94 percent purity, 94 percent purity to 94.5 percent purity, 94.5 percent purity to 94.75 percent purity, 94.75 percent purity to 95 percent purity, 95 percent purity to 95.25 percent purity, 95.25 percent purity to 95.5 percent purity, 95.5 percent purity to 95.75 percent purity, 95.75 percent purity to 96 percent purity, 96 percent purity to 96.25 percent purity, 96.25 percent purity to 96.5 percent purity, 96.5 percent purity to 96.75 percent purity, 96.75 percent purity to 97 percent purity, 97 percent purity to 97.25 percent purity, 97.25 percent purity to 97.5 percent purity, 97.5 percent purity to 97.75 percent purity, 97.75 percent purity to 98 percent purity, 98 percent purity to 98.25 percent purity, 98.25 percent purity to 98.5 percent purity, 98.5 percent purity to 98.75 percent purity, 98.75 percent purity to 99 percent purity, 99 percent purity to 99.25 percent purity, 99.25 percent purity to 99.5 percent purity, 99.5 percent purity to 99.75 percent purity, and 99.75 percent purity to 100 percent purity.

In embodiments, the tetrahydrocannabinol that are extracted from the SMB process have a purity that includes one or more from the group consisting of 30 percent purity to 40 percent purity, 40 percent purity to 50 percent purity, 50 percent purity to 60 percent purity, 60 percent purity to 70 percent purity, 70 percent purity to 80 percent purity, 80 percent purity to 82 percent purity, 82 percent purity to 84 percent purity, 84 percent purity to 86 percent purity, 86 percent purity to 88 percent purity, 88 percent purity to 90 percent purity, 90 percent purity to 92 percent purity, 92 percent purity to 92.5 percent purity, 92.5 percent purity to 93 percent purity, 93 percent purity to 93.5 percent purity, 93.5 percent purity to 94 percent purity, 94 percent purity to 94.5 percent purity, 94.5 percent purity to 94.75 percent purity, 94.75 percent purity to 95 percent purity, 95 percent purity to 95.25 percent purity, 95.25 percent purity to 95.5 percent purity, 95.5 percent purity to 95.75 percent purity, 95.75 percent purity to 96 percent purity, 96 percent purity to 96.25 percent purity, 96.25 percent purity to 96.5 percent purity, 96.5 percent purity to 96.75 percent purity, 96.75 percent purity to 97 percent purity, 97 percent purity to 97.25 percent purity, 97.25 percent purity to 97.5 percent purity, 97.5 percent purity to 97.75 percent purity, 97.75 percent purity to 98 percent purity, 98 percent purity to 98.25 percent purity, 98.25 percent purity to 98.5 percent purity, 98.5 percent purity to 98.75 percent purity, 98.75 percent purity to 99 percent purity, 99 percent purity to 99.25 percent purity, 99.25 percent purity to 99.5 percent purity, 99.5 percent purity to 99.75 percent purity, and 99.75 percent purity to 100 percent purity.

In embodiments, the cannabinoids (Δ9-tetrahydrocannabinol Δ9-THC, Δ8-tetrahydrocannabinol Δ8-THC, cannabichromene CBC, cannabidiol CBD, cannabigerol CBG, cannabinidiol CBND, and/or cannabinol CBN, cannabidiol, tetrahydrocannabinol) that are extracted from the SMB process have a purity that includes one or more from the group consisting of 30 percent purity to 40 percent purity, 40 percent purity to 50 percent purity, 50 percent purity to 60 percent purity, 60 percent purity to 70 percent purity, 70 percent purity to 80 percent purity, 80 percent purity to 82 percent purity, 82 percent purity to 84 percent purity, 84 percent purity to 86 percent purity, 86 percent purity to 88 percent purity, 88 percent purity to 90 percent purity, 90 percent purity to 92 percent purity, 92 percent purity to 92.5 percent purity, 92.5 percent purity to 93 percent purity, 93 percent purity to 93.5 percent purity, 93.5 percent purity to 94 percent purity, 94 percent purity to 94.5 percent purity, 94.5 percent purity to 94.75 percent purity, 94.75 percent purity to 95 percent purity, 95 percent purity to 95.25 percent purity, 95.25 percent purity to 95.5 percent purity, 95.5 percent purity to 95.75 percent purity, 95.75 percent purity to 96 percent purity, 96 percent purity to 96.25 percent purity, 96.25 percent purity to 96.5 percent purity, 96.5 percent purity to 96.75 percent purity, 96.75 percent purity to 97 percent purity, 97 percent purity to 97.25 percent purity, 97.25 percent purity to 97.5 percent purity, 97.5 percent purity to 97.75 percent purity, 97.75 percent purity to 98 percent purity, 98 percent purity to 98.25 percent purity, 98.25 percent purity to 98.5 percent purity, 98.5 percent purity to 98.75 percent purity, 98.75 percent purity to 99 percent purity, 99 percent purity to 99.25 percent purity, 99.25 percent purity to 99.5 percent purity, 99.5 percent purity to 99.75 percent purity, and 99.75 percent purity to 100 percent purity.

In embodiments, a continuous process for the purification of cannabidiol and/or tetrahydrocannabinol from a crude cannabinoid extract to provide a purified cannabidiol and/or tetrahydrocannabinol product. The crude cannabinoid extract comprises cannabinoids which may include cannabidiol and/or tetrahydrocannabinol.

In embodiments, reversed-phase chromatography employs a polar (aqueous) mobile phase. As a result, hydrophobic molecules in the polar mobile phase tend to adsorb to the hydrophobic stationary phase, and hydrophilic molecules in the mobile phase will pass through an adsorber column and are eluted first.

The SMB system may be operated such that the adsorbent beds are operated individually or in parallel using a single rotary valve and associated control system. A column may comprise one or several beds containing chromatographic media. Feed tanks, filters, piping connecting flow between columns and/or beds where so connected, pumps, valving, pressure regulators, metering equipment, flow control and microprocessor equipment, their construction and function, and integration with the entire Farming Superstructure System (FSS) are all disclosed here.

Stationary Phase

In embodiments, the stationary phase adsorbent for use in the first swing bed simulated moving bed (SMB) chromatography zone is an aromatic non-polar copolymer of styrene-divinyl benzene adsorbent resin with an effective particle size of 0.25 mm and effective surface area of 590 square meters per gram (M2/g). Examples of suitable styrene-divinyl benzene adsorbent resins can be selected from the AMBERLITE XAD resin series (Available from Dow Chemical Company, Midland, Mich.), DIAION HP-20 (Available from Mitsubishi Chemical Company, Tokyo, Japan), or Stratosphere PL-PS/DVB (Available from Sigma-Aldrich, St. Louis, Mo.). In embodiments, the styrene-divinyl benzene adsorbent resin matrix provides an aromatic non-polar surface with selectivity for hydrophobic areas of molecules. In first swing bed simulated moving bed zone the cannabinoids are retained on the resin and are subsequently recovered in a first swing bed extract. Impurities such as wax, terpenes, and other undesirable cannabinoids are rejected into a first swing bed raffinate stream. In first swing bed simulated moving bed zone the cannabinoids are retained on the resin and are subsequently recovered in a first swing bed extract. In first swing bed simulated moving bed zone cannabidiol is retained on the resin and are subsequently recovered in a first swing bed extract. Impurities other cannabinoids are rejected into a first swing bed raffinate stream. In first swing bed simulated moving bed zone tetrahydrocannabinol is retained on the resin and are subsequently recovered in a first swing bed extract. Impurities other cannabinoids are rejected into a first swing bed raffinate stream. The stationary phase adsorbents may be disposed in a single adsorbent bed or may be disposed in within a single column or series of single columns containing multiple adsorbent bed zones.

In embodiments, the stationary phase adsorbent is comprised of one or more selected from the group consisting of silica gel, alumina, silica, cellulose powder, a polymer, polymeric beads, a macroporous adsorption resin, DOW XAD 418, molecular sieves, a polar macroporous adsorption resin, floridin, diatomite, zeolites, a catalyst, a resin, an ion-exchange resin, ion-exchange polymer, clay, ceramic material, activated carbon, a cation-exchange resin, an anion-exchange resin, bentonite, perlite, fly ash, chitin, charcoal, a solid substance, magnesia, titanium oxide, glass, fluorinated carbon, silicate, kaolin, a hollow substance, a porous substance.

In embodiments, the adsorbent includes Orpheus non-polar silica-based stationary phase adsorbent (available from Orochem Technologies Inc., Naperville, Ill., USA). In embodiments, the adsorbent includes C8, C18, or Polar C18 adsorbent (available from Orochem Technologies Inc., Naperville, Ill., USA).

In embodiments, the adsorber or the plurality of adsorbers are comprised of one or more corrosion resistant materials selected from the group consisting of stainless steel, corrosion resistant alloys, metals having a fluoropolymer coating, and mixtures thereof. In embodiments, the valve used to connect each of the adsorbers is a rotary valve. In embodiments, the adsorber or the plurality of adsorbers are non-rotating and are disposed in an asymmetrical manner about the axis of rotation of the rotary valve. In embodiments, the rotary valve is actuated by either hydraulics, electricity, or electromechanical actuation.

In embodiments, the adsorbent is comprised of one or more selected from the group consisting of a strongly acidic ion-exchange resin, a strongly basic ion-exchange resin, a weakly acidic ion-exchange resin and a weakly basic ion-exchange resin. In embodiments, the strongly acidic ion-exchange resin includes sulfonic acid groups, e.g. sodium polystyrene sulfonate or PolyAMPS, or poly(2-acrylamido-2-methyl-1-propanesulfonic acid)® (Trademark of The Lubrizol Corporation), is an organic polymer.

In embodiments, the strongly basic ion-exchange resin includes quaternary amino groups, for example, trimethylammonium groups, e.g. PolyAPTAC, or poly (acrylamido-N-propyltrimethylammonium chloride)® (Trademark of The Lubrizol Corporation), is an organic polymer. In embodiments, the weakly acidic ion-exchange resin includes carboxylic acid groups. In embodiments, the weakly basic ion-exchange resin includes primary, secondary, and/or tertiary amino groups, e.g. polyethylene amine.

In embodiments, the adsorbent is comprised of one or more selected from the group consisting of a powder, spheres, spherical pellets, rods, moldings, and monoliths. In embodiments, the adsorbent has pores. In embodiments, the range of size of the pores of the adsorbent are comprised of one or more selected from the group consisting of: 0.1 nanometers to 1 nanometer, 1 nanometer to 2 nanometers, 2 nanometers to 5 nanometers, 5 nanometers to 15 nanometers, 15 nanometers to 25 nanometers, 25 nanometers to 35 nanometers, 35 nanometers to 40 nanometers, 45 nanometers to 50 nanometers, 50 nanometers to 100 nanometers, 100 nanometers to 150 nanometers, 150 nanometers to 200 nanometers, 200 nanometers to 1000 nanometers, and greater than 1000 nanometers.

In embodiments, the plurality of adsorbers are considered a simulated moving bed (SMB). In embodiments, the plurality of adsorbers are considered a simulated moving bed (SMB) and operate via chromatography. In embodiments, the SMB adsorption technique is a continuous. In embodiments, the plurality of adsorbers include more than one adsorber. In embodiments, the plurality of adsorbers include two adsorbers. In embodiments, the plurality of adsorbers include three adsorbers. In embodiments, the plurality of adsorbers include four adsorbers. In embodiments, the plurality of adsorbers include five adsorbers. In embodiments, the plurality of adsorbers include six adsorbers. In embodiments, the plurality of adsorbers include seven adsorbers. In embodiments, the plurality of adsorbers include eight adsorbers. In embodiments, the plurality of adsorbers include nine adsorbers. In embodiments, the plurality of adsorbers include ten adsorbers. In embodiments, the plurality of adsorbers include eleven adsorbers. In embodiments, the plurality of adsorbers include twelve adsorbers. In embodiments, the plurality of adsorbers include thirteen adsorbers. In embodiments, the plurality of adsorbers include fourteen adsorbers. In embodiments, the plurality of adsorbers include fifteen adsorbers. In embodiments, the plurality of adsorbers include sixteen adsorbers. In embodiments, the plurality of adsorbers include seventeen adsorbers. In embodiments, the plurality of adsorbers include eighteen adsorbers. In embodiments, the plurality of adsorbers include nineteen adsorbers. In embodiments, the plurality of adsorbers include twenty adsorbers. In embodiments, the plurality of adsorbers include twenty one adsorbers. In embodiments, the plurality of adsorbers include twenty two adsorbers. In embodiments, the plurality of adsorbers include twenty three adsorbers. In embodiments, the plurality of adsorbers include twenty four adsorbers. In embodiments, the plurality of adsorbers include twenty five adsorbers. In embodiments, the plurality of adsorbers include twenty six adsorbers. In embodiments, the plurality of adsorbers include twenty seven adsorbers. In embodiments, the plurality of adsorbers include twenty eight adsorbers. In embodiments, the plurality of adsorbers include twenty nine adsorbers. In embodiments, the plurality of adsorbers include thirty adsorbers. In embodiments, the plurality of adsorbers include thirty one adsorbers. In embodiments, the plurality of adsorbers include thirty two adsorbers. In embodiments, the plurality of adsorbers include thirty three adsorbers. In embodiments, the plurality of adsorbers include thirty four adsorbers. In embodiments, the plurality of adsorbers include thirty five adsorbers. In embodiments, the plurality of adsorbers include thirty six adsorbers. In embodiments, the plurality of adsorbers include thirty seven adsorbers. In embodiments, the plurality of adsorbers include thirty eight adsorbers. In embodiments, the plurality of adsorbers include thirty nine adsorbers. In embodiments, the plurality of adsorbers include forty adsorbers. In embodiments, the plurality of adsorbers include fifty adsorbers. In embodiments, the plurality of adsorbers include sixty adsorbers. In embodiments, the plurality of adsorbers include seventy adsorbers. In embodiments, the plurality of adsorbers include eighty adsorbers. In embodiments, the plurality of adsorbers include ninety adsorbers. In embodiments, the plurality of adsorbers include one hundred adsorbers.

In embodiments, the adsorbers operate at a pressure that is selected from one or more from the group consisting of between: 10 pounds per square inch (PSI) to 20 PSI, 20 PSI to 40 PSI, 40 PSI to 60 PSI, 60 PSI to 80 PSI, 80 PSI to 100 PSI, 100 PSI to 125 PSI, 125 PSI to 150 PSI, 150 PSI to 175 PSI, 175 PSI to 200 PSI, 200 PSI to 225 PSI, 225 PSI to 250 PSI, 250 PSI to 275 PSI, 275 PSI to 300 PSI, 300 PSI to 325 PSI, 325 PSI to 350 PSI, 350 PSI to 375 PSI, 375 PSI to 400 PSI, 400 PSI to 425 PSI, 425 PSI to 450 PSI, 450 PSI to 475 PSI, and 475 PSI to 500 PSI.

In embodiments, an analyzer is used to analyze the purified cannabidiol and/or tetrahydrocannabinol product. In embodiments, the analyzer is comprised of one or more analyzers selected from the group consisting of Fourier-transform infrared spectroscopy, gas chromatography, high-performance liquid chromatography, liquid chromatograph, liquid chromatography-mass spectrometry, mass spectrometry, and ultra-high performance liquid chromatography.

In embodiments, the adsorbent is comprised of one or more selected from the group consisting of a strongly acidic cation exchange resin include such as AMBERLITE IR-118 (Available from Dow Chemical Company, Midland, Mich.), or DIAION PK216LH (Available from Mitsubishi Chemical Company, Tokyo, Japan). Suitable examples of the weakly basic anion exchange resin include AMBERLITE IRA-70RF (Available from Dow Chemical Company, Midland, Mich.) or RELITE RAM2 (Available from Mitsubishi Chemical Company, Tokyo, Japan).

In embodiments, the first extract (HDA) or the primary extract (HDB) is transferred from the first adsorber system (SMB1) and into a primary extract vessel (HEE). In embodiments, the first raffinate (HDE) is transferred from the first adsorber system (SMB1) into the solvent treatment system (H-WTS) as discussed below.

In embodiments, the primary extract vessel (HEE) has an interior (HEF). In embodiments, the primary extract vessel (HEE) is a continuously stirred tank reactor having a jacketed reactor equipped with a steam supply system and at least one steam trap. In embodiments, the primary extract vessel (HEE) is equipped with a level sensor (HEG) that is configured to input a signal to the computer (COMP). In embodiments, the primary extract vessel (HEE) is equipped with a pH sensor (HEH) that is configured to input a signal to the computer (COMP). In embodiments, the primary extract vessel (HEE) is equipped with an auger (HEI) that has a motor. The motor of the auger (HEI) rotates the auger (HEI) to mix the contents within the interior (HEF) of the primary extract vessel (HEE). In embodiments, the primary extract vessel (HEE) is equipped with a temperature sensor that is configured to input a signal to the computer (COMP). In embodiments, the primary extract vessel (HEE) is equipped with a heat exchanger (HTA) to heat the contents within the interior (HEF) of the primary extract vessel (HEE). In embodiments, the primary extract vessel (HEE) outputs a primary extract (HDB).

A primary extract pump (HTB) is configured to accept the primary extract (HDB) from the interior (HEF) of the primary extract vessel (HEE). The primary extract pump (HTB) pumps and pressurizes the primary extract (HDB) to produce a pressurized primary extract (HTC). A valve (HTD) and a pressure sensor (HTE) are installed on the discharged of the primary extract pump (HTB). In embodiments, the primary extract pump (HTB) pressurizes the primary extract (HDB) to form a pressurized primary extract (HTC) at a pressure that includes one or more pressure ranges selected from the group consisting of 10 pounds per square inch (PSI) to 20 PSI, 20 PSI to 40 PSI, 40 PSI to 60 PSI, 60 PSI to 80 PSI, 80 PSI to 100 PSI, 100 PSI to 125 PSI, 125 PSI to 150 PSI, 150 PSI to 175 PSI, 175 PSI to 200 PSI, 200 PSI to 225 PSI, 225 PSI to 250 PSI, 250 PSI to 275 PSI, 275 PSI to 300 PSI, 300 PSI to 325 PSI, 325 PSI to 350 PSI, 350 PSI to 375 PSI, 375 PSI to 400 PSI, 400 PSI to 425 PSI, 425 PSI to 450 PSI, 450 PSI to 475 PSI, and 475 PSI to 500 PSI.

In embodiments, the pressurized primary extract (HTC) is transferred from the primary extract pump (HTB) and into at least one filter (HEL, HEM, HEN). In embodiments, the pressurized primary extract (HTC) is transferred from the primary extract pump (HTB) and a primary extract filter system (HEK) that includes a first primary extract first filter (HEL), a first primary extract second filter (HEM), and a first primary extract third filter (HEN).

In embodiments, the first primary extract first filter (HEL) includes one or more selected from the group consisting of a cation, an anion, a membrane, a filter, activated carbon, an adsorbent, an absorbent, an ultraviolet unit, an ozone unit, or a microwave unit. In embodiments, the first primary extract second filter (HEM) includes one or more selected from the group consisting of a cation, an anion, a membrane, a filter, activated carbon, an adsorbent, an absorbent, an ultraviolet unit, an ozone unit, or a microwave unit. In embodiments, the first primary extract third filter (HEN) includes one or more selected from the group consisting of a cation, an anion, a membrane, a filter, activated carbon, an adsorbent, an absorbent, an ultraviolet unit, an ozone unit, or a microwave unit. In embodiments, the adsorbent includes one or more selected from the group consisting of 3 Angstrom molecular sieve, 3 Angstrom zeolite, 4 Angstrom molecular sieve, 4 Angstrom zeolite, activated alumina, activated carbon, adsorbent, alumina, carbon, catalyst, clay, desiccant, molecular sieve, polymer, resin, and silica gel.

In embodiments, the cation is configured to remove positively charged ions from the pressurized primary extract (HTC), the positively charged ions are comprised of one or more from the group consisting of calcium, magnesium, sodium, and iron. In embodiments, the anion is configured to remove negatively charged ions from the pressurized primary extract (HTC), the negatively charged ions are comprised of one or more from the group consisting of iodine, chloride, and sulfate. In embodiments, the membrane is configured to remove undesirable compounds from the pressurized primary extract (HTC), the undesirable compounds are comprised of one or more from the group consisting of dissolved organic chemicals, viruses, bacteria, and particulates. In embodiments, the membrane has a diameter that ranges from 1 inch to 6 inches and a pore size ranging from 0.0001 microns to 0.5 microns.

In embodiments, a filtered primary extract (HEO) is discharged from the primary extract filter system (HEK). In embodiments, the filtered primary extract (HEO) discharged from the primary extract filter system (HEK) is a pressurized filtered primary extract (HEP). In embodiments, a valve (HEQ) is configured to regulate the flow of the pressurized filtered primary extract (HEP) that leaves the primary extract filter system (HEK). In embodiments, a pressure sensor (HER) is configured to measure the pressure of the pressurized filtered primary extract (HEP).

In embodiments, the pressurized filtered primary extract (HEP) is passed from the primary extract filter system (HEK) and into a filtered primary extract vessel (HES). In embodiments, filtered primary extract vessel (HES) is configured to accept the filtered primary extract (HEO). In embodiments, the filtered primary extract vessel (HES) is a continuously stirred tank reactor having a jacketed reactor equipped with a steam supply system and at least one steam trap. In embodiments, the filtered primary extract vessel (HES) is equipped with a level sensor (HEU) that is configured to input a signal to the computer (COMP). In embodiments, the filtered primary extract vessel (HES) is equipped with a pH sensor (HEV) that is configured to input a signal to the computer (COMP). In embodiments, the filtered primary extract vessel (HES) is equipped with an auger (HEW) that has a motor. The motor of the auger (HEW) rotates the auger (HEW) to mix the contents within the interior (HET) of the filtered primary extract vessel (HES). In embodiments, the filtered primary extract vessel (HES) is equipped with a temperature sensor that is configured to input a signal to the computer (COMP). In embodiments, the filtered primary extract vessel (HES) is equipped with a heat exchanger (HEX) to heat the contents within the interior (HET) of the filtered primary extract vessel (HES). In embodiments, the filtered primary extract vessel (HES) outputs a filtered primary extract.

In embodiments, a filtered primary extract is discharged from the interior (HET) of the filtered primary extract vessel (HES). In embodiments, a filtered primary extract is discharged from the interior (HET) of the filtered primary extract vessel (HES) and introduced to a filtered primary extract pump (HEY). The filtered primary extract pump (HEY) pumps and pressurizes the filtered primary extract to form a pressurized filtered primary extract (HEZ). In embodiments, a valve (HFA) is configured to regulate the flow of the pressurized filtered primary extract (HEZ) that leaves the filtered primary extract vessel (HES). In embodiments, a pressure sensor (HFB) is configured to measure the pressure of the pressurized filtered primary extract (HEZ) discharged from the filtered primary extract pump (HEY). In embodiments, a flow sensor (HFC) is configured to measure the flow of the pressurized filtered primary extract (HEZ) discharged from the filtered primary extract pump (HEY).

In embodiments, the pressurized filtered primary extract (HEZ) is transferred from the filtered primary extract pump (HEY) and into a second adsorber system (SMB2). In embodiments, the second adsorber system (SMB2) is configured to input a pressurized filtered primary extract (HEZ) and a second desorbent (HFG). In embodiments, the second adsorber system (SMB2) is configured to output a second extract (HFD) and a second raffinate (HFH). In embodiments, the second extract (HFD) can also be called a secondary extract (HFE). In embodiments, the second adsorber system (SMB2) includes an adsorber or a plurality of adsorbers each containing an adsorbent. In embodiments, the second desorbent (HFG) is pressurized and comes from a water treatment system (H-WTS) which may or may not treat solvent (such as water) that was passed on from a solvent recovery system. In embodiments, the second raffinate (HFH) is routed to the solvent treatment system (H-WTS) as discussed below.

In embodiments, the second adsorber system (SMB2) includes a plurality of adsorbers containing adsorbent is provided and may be called the stationary phase. In embodiments, the adsorbent positioned within the adsorber or plurality of adsorbers may be called the stationary phase. The bed of adsorbent that is contained within the adsorber does not move so therefore it is stationary. The plurality of beds of adsorbent that are contained within the plurality of adsorbers does not move so therefore it is stationary.

In embodiments, the second adsorber system (SMB2) periodically switches the feed, eluent, extract and raffinate ports in the same direction. The basic premise of a simulated moving bed adsorber system is that the inlet and outlet ports are switched periodically in the direction of the fluid flow. This simulates the countercurrent movement of the phase in the process. Chromatography is a technique used to separate mixtures. In embodiments, the mixture may include cannabinoids and a solvent.

In embodiments, the raffinate includes cannabinoids. In embodiments, the raffinate includes cannabidiol. In embodiments, the raffinate includes THC. In embodiments, the raffinate includes a mixture of cannabinoids and water. In embodiments, the raffinate includes a mixture of cannabidiol and water. In embodiments, the raffinate includes a mixture of THC and water. In embodiments, the raffinate includes a mixture of cannabinoids and ethanol. In embodiments, the raffinate includes a mixture of cannabidiol and ethanol. In embodiments, the raffinate includes a mixture of THC and ethanol. In embodiments, the raffinate includes a mixture of cannabinoids and ethanol and water. In embodiments, the raffinate includes a mixture of cannabidiol and ethanol and water. In embodiments, the raffinate includes a mixture of THC and ethanol and water. In embodiments, the raffinate includes a mixture of cannabinoids and methanol. In embodiments, the raffinate includes a mixture of cannabidiol and methanol. In embodiments, the raffinate includes a mixture of THC and methanol.

In embodiments, the raffinate includes a mixture of cannabinoids and methanol and water. In embodiments, the raffinate includes a mixture of cannabidiol and methanol and water. In embodiments, the raffinate includes a mixture of THC and methanol and water.

In embodiments, the second extract (HFD) or the secondary extract (HFE) is transferred from the second adsorber system (SMB2) and into a secondary extract vessel (HFI). In embodiments, the second raffinate (HFH) is transferred from the second adsorber system (SMB2) into the solvent treatment system (H-WTS) as discussed below.

In embodiments, the secondary extract vessel (HFI) has an interior (HFJ). In embodiments, the secondary extract vessel (HFI) is a continuously stirred tank reactor having a jacketed reactor equipped with a steam supply system and at least one steam trap. In embodiments, the secondary extract vessel (HFI) is equipped with a level sensor (HFK) that is configured to input a signal to the computer (COMP). In embodiments, the secondary extract vessel (HFI) is equipped with a pH sensor (HFL) that is configured to input a signal to the computer (COMP). In embodiments, the secondary extract vessel (HFI) is equipped with an auger that has a motor. The motor of the auger rotates the auger to mix the contents within the interior (HFJ) of the secondary extract vessel (HFI). In embodiments, the secondary extract vessel (HFI) is equipped with a temperature sensor that is configured to input a signal to the computer (COMP). In embodiments, the secondary extract vessel (HFI) is equipped with a heat exchanger (HFN) to heat the contents within the interior (HFJ) of the secondary extract vessel (HFI). In embodiments, the secondary extract vessel (HFI) outputs a secondary extract.

A secondary extract pump (HFO) is configured to accept the second extract from the interior (HFJ) of the secondary extract vessel (HFI). The secondary extract pump (HFO) pumps and pressurizes the secondary extract to produce a pressurized secondary extract (HFP). A valve (HFQ) and a pressure sensor (HFR) are installed on the discharged of the secondary extract pump (HFO). In embodiments, the secondary extract pump (HFO) pressurizes the secondary extract to form a pressurized secondary extract (HFP) at a pressure that includes one or more pressure ranges selected from the group consisting of 10 pounds per square inch (PSI) to 20 PSI, 20 PSI to 40 PSI, 40 PSI to 60 PSI, 60 PSI to 80 PSI, 80 PSI to 100 PSI, 100 PSI to 125 PSI, 125 PSI to 150 PSI, 150 PSI to 175 PSI, 175 PSI to 200 PSI, 200 PSI to 225 PSI, 225 PSI to 250 PSI, 250 PSI to 275 PSI, 275 PSI to 300 PSI, 300 PSI to 325 PSI, 325 PSI to 350 PSI, 350 PSI to 375 PSI, 375 PSI to 400 PSI, 400 PSI to 425 PSI, 425 PSI to 450 PSI, 450 PSI to 475 PSI, and 475 PSI to 500 PSI.

In embodiments, the pressurized secondary extract (HFP) is transferred from the secondary extract pump (HFO) and into a secondary extract filter system (HGA). In embodiments, the secondary extract filter system (HGA) includes one or more selected from the group consisting of a cation, an anion, a membrane, a filter, activated carbon, an adsorbent, an absorbent, an ultraviolet unit, an ozone unit, or a microwave unit. In embodiments, the adsorbent includes one or more selected from the group consisting of 3 Angstrom molecular sieve, 3 Angstrom zeolite, 4 Angstrom molecular sieve, 4 Angstrom zeolite, activated alumina, activated carbon, adsorbent, alumina, carbon, catalyst, clay, desiccant, molecular sieve, polymer, resin, and silica gel.

In embodiments, a filtered secondary extract (HGB) is discharged from the secondary extract filter system (HGA). In embodiments, the filtered secondary extract (HGB) is transferred to a filtered secondary extract vessel (HGD). In embodiments, the filtered secondary extract vessel (HGD) has an interior (HGE). In embodiments, the filtered secondary extract vessel (HGD) is a continuously stirred tank reactor having a jacketed reactor equipped with a steam supply system and at least one steam trap. In embodiments, the filtered secondary extract vessel (HGD) is equipped with a level sensor (HGF) that is configured to input a signal to the computer (COMP). In embodiments, the filtered secondary extract vessel (HGD) is equipped with a pH sensor that is configured to input a signal to the computer (COMP). In embodiments, the filtered secondary extract vessel (HGD) is equipped with an auger that has a motor. The motor of the auger rotates the auger to mix the contents within the interior (HGE) of the filtered secondary extract vessel (HGD). In embodiments, the filtered secondary extract vessel (HGD) is equipped with a temperature sensor that is configured to input a signal to the computer (COMP). In embodiments, the filtered secondary extract vessel (HGD) is equipped with a heat exchanger (HGG) to heat the contents within the interior (HGE) of the filtered secondary extract vessel (HGD). In embodiments, the filtered secondary extract vessel (HGD) outputs a first pressurized filtered secondary extract (HGJ) and a second pressurized filtered secondary extract (HGK).

In embodiments, the first pressurized filtered secondary extract (HGJ) is discharged from the interior (HGE) of the filtered secondary extract vessel (HGD) and transferred to a first filtered secondary extract pump (HGH). The first filtered secondary extract pump (HGH) pumps and pressurizes the filtered secondary extract to produce a first pressurized filtered secondary extract (HGJ).

In embodiments, the first pressurized filtered secondary extract (HGJ) may be transferred to FIGS. 17D', 17E', 17J', and/or FIG. 18' or any figure in this patent specification for evaporation, spray drying, emulsion mixing, encapsulation, and foodstuff mixing. In embodiments, the second pressurized filtered secondary extract (HGK) is discharged from the interior (HGE) of the filtered secondary extract vessel (HGD) and transferred to a second filtered secondary extract pump (HGI). The second filtered secondary extract pump (HGI) pumps and pressurizes the filtered secondary extract to produce a second pressurized filtered secondary extract (HGK). In embodiments, the second pressurized filtered secondary extract (HGK) may be transferred to a third adsorber system (SMB3).

In embodiments, the secondary extract (HGL) is transferred from the interior (HGE) of the filtered secondary extract vessel (HGD) and into a second filtered secondary extract pump (HGI). The second filtered secondary extract pump (HGI) pumps and pressurizes the filtered secondary extract to produce a second pressurized filtered secondary extract (HGK). In embodiments, a valve (HGM) is configured to regulate the flow of the second pressurized filtered secondary extract (HGK) that leaves the filtered secondary extract vessel (HGD). In embodiments, a pressure sensor (HFB) is configured to measure the pressure of the second pressurized filtered secondary extract (HGK) discharged from the second filtered secondary extract pump (HGI). In embodiments, a flow sensor (HFC) is configured to measure the flow of the second pressurized filtered secondary extract (HGK) discharged from the second filtered secondary extract pump (HGI).

In embodiments, the second pressurized filtered secondary extract (HGK) is transferred from the second filtered secondary extract pump (HGI) and into a third adsorber system (SMB3). In embodiments, the third adsorber system (SMB3) is configured to input a second pressurized filtered secondary extract (HGK) and a third desorbent (HHC). In embodiments, the third adsorber system (SMB3) is configured to output a third extract (HHA) and a third raffinate (HHD). In embodiments, the third extract (HHA) can also be called a tertiary extract (HHB). In embodiments, the third adsorber system (SMB3) includes an adsorber or a plurality of adsorbers each containing an adsorbent. In embodiments, the third desorbent (HHC) is pressurized and comes from a water treatment system (H-WTS) which may or may not treat solvent (such as water) that was passed on from a solvent recovery system. In embodiments, the third raffinate (HHD) is routed to the solvent treatment system (H-WTS) as discussed below.

In embodiments, the third adsorber system (SMB3) includes a plurality of adsorbers containing adsorbent is provided and may be called the stationary phase. In embodiments, the adsorbent positioned within the adsorber or plurality of adsorbers may be called the stationary phase. The bed of adsorbent that is contained within the adsorber does not move so therefore it is stationary. The plurality of beds of adsorbent that are contained within the plurality of adsorbers does not move so therefore it is stationary.

In embodiments, the third adsorber system (SMB3) periodically switches the feed, eluent, extract and raffinate ports in the same direction. The basic premise of a simulated moving bed adsorber system is that the inlet and outlet ports are switched periodically in the direction of the fluid flow. This simulates the countercurrent movement of the phase in the process. Chromatography is a technique used to separate mixtures. In embodiments, the mixture may include cannabinoids and a solvent. In embodiments, the third extract (HHA) may be transferred to FIGS. 17D', 17E', 17J', and/or FIG. 18' or any figure in this patent specification for evaporation, spray drying, emulsion mixing, encapsulation, and foodstuff mixing.

In embodiments, the first desorbent (HDC) for the first adsorber system (SMB1), second desorbent (HFG) for the second adsorber system (SMB2), third desorbent (HHC) for the third adsorber system (SMB3), are provided by a solvent treatment system (H-WTS).

In embodiments, the solvent (HBJ) from the first filter (HBC) and/or second filter (HBF), the first raffinate (HDE) from the first adsorber system (SMB1), the second raffinate (HFH) from the second adsorber system (SMB2), and the third raffinate (HHD) from the third adsorber system (SMB3), are provided by to a solvent treatment system (H-WTS). In embodiments, the solvent treatment system (H-WTS) includes a treatment unit (HIC). In embodiments, the treatment unit (HIC) includes one or more selected from the group consisting of a cation, an anion, a membrane, a filter, activated carbon, an adsorbent, an absorbent, an ultraviolet unit, an ozone unit, or a microwave unit. In embodiments, the adsorbent includes one or more selected from the group consisting of 3 Angstrom molecular sieve, 3 Angstrom zeolite, 4 Angstrom molecular sieve, 4 Angstrom zeolite, activated alumina, activated carbon, adsorbent, alumina, carbon, catalyst, clay, desiccant, molecular sieve, polymer, resin, and silica gel. In embodiments, the treatment unit (HIC) includes one or more selected from the group consisting of an evaporator, an anaerobic digestion system, a distillation column, a packed column, a reactor, liquid-liquid extraction, vacuum distillation, pressurized distillation, and reverse osmosis.

In embodiments, the first desorbent (HDC) for the first adsorber system (SMB1), second desorbent (HFG) for the second adsorber system (SMB2), third desorbent (HHC) for the third adsorber system (SMB3), are provided by a solvent treatment system (H-WTS). In embodiments, the solvent (HBJ) from the first filter (HBC) and/or second filter (HBF), the first raffinate (HDE) from the first adsorber system (SMB1), the second raffinate (HFH) from the second adsorber system (SMB2), and the third raffinate (HHD) from the third adsorber system (SMB3), are provided by to a solvent treatment system (H-WTS). In embodiments, a treated solvent (HIE) is discharged from the treatment unit (HIC) of the solvent treatment system (H-WTS). In embodiments, the treated solvent (HIE) has contaminants removed therefrom so that the solvent (water, ethanol, alcohol, oil, etc.) may be reused again in the solvent (HAB, HAB') or for the first desorbent (HDC) for the first adsorber system (SMB1), second desorbent (HFG) for the second adsorber system (SMB2), third desorbent (HHC) for the third adsorber system (SMB3).

In embodiments, the solvent (HAB') used within the extraction vessel (HAI) is water that comes from the solvent treatment system (H-WTS). In embodiments, a water supply (HJG) is made available to the solvent treatment system (H-WTS) for use as either a solvent (HAB'HAB') in the process or for use as the first desorbent (HDC) for the first adsorber system (SMB1), second desorbent (HFG) for the second adsorber system (SMB2), third desorbent (HHC) for the third adsorber system (SMB3). In embodiments, the water supply (HJG) is mixed with the treated solvent (HIE) (which may be water). In embodiments, a valve (HJI) is configured to regulate the flow of the water supply (HJG) that enters the first water treatment unit (HJK) of the solvent treatment system (H-WTS). In embodiments, a pressure sensor (HJH) is configured to measure the pressure of the water supply (HJG) that enters the first water treatment unit (HJK) of the solvent treatment system (H-WTS). In embodiments, the solvent treatment system (H-WTS) includes a first water treatment unit (HJK), second water treatment unit (HJL), and a third water treatment unit (HJM).

In embodiments, the first water treatment unit (HJK) includes one or more selected from the group consisting of a cation, an anion, a membrane, a filter, activated carbon, an adsorbent, an absorbent, an ultraviolet unit, an ozone unit, or a microwave unit. In embodiments, the second water treatment unit (HJL) includes one or more selected from the group consisting of a cation, an anion, a membrane, a filter, activated carbon, an adsorbent, an absorbent, an ultraviolet unit, an ozone unit, or a microwave unit. In embodiments, the third water treatment unit (HJM) includes one or more selected from the group consisting of a cation, an anion, a membrane, a filter, activated carbon, an adsorbent, an absorbent, an ultraviolet unit, an ozone unit, or a microwave unit. In embodiments, the adsorbent includes one or more selected from the group consisting of 3 Angstrom molecular sieve, 3 Angstrom zeolite, 4 Angstrom molecular sieve, 4 Angstrom zeolite, activated alumina, activated carbon, adsorbent, alumina, carbon, catalyst, clay, desiccant, molecular sieve, polymer, resin, and silica gel. In embodiments, the cation is configured to remove positively charged ions from the water supply (HJG), the positively charged ions are comprised of one or more from the group consisting of calcium, magnesium, sodium, and iron. In embodiments, the anion is configured to remove negatively charged ions from the water supply (HJG), the negatively charged ions are comprised of one or more from the group consisting of iodine, chloride, and sulfate. In embodiments, the membrane is configured to remove undesirable compounds from the water supply (HJG), the undesirable compounds are comprised of one or more from the group consisting of dissolved organic chemicals, viruses, bacteria, and particulates. In embodiments, the membrane has a diameter that ranges from 1 inch to 6 inches and a pore size ranging from 0.0001 microns to 0.5 microns.

In embodiments, treated water (HJA) is discharged from the first water treatment unit (HJK), second water treatment unit (HJL), and/or the third water treatment unit (HJM). In embodiments, treated water (HJA) has less positively charged ions, negatively charged ions, and undesirable compounds relative to the supply (HJG) that enters the solvent treatment system (H-WTS). In embodiments, a valve (HJI) is configured to regulate the flow of the treated water (HJA) that leaves the first water treatment unit (HJK), second water treatment unit (HJL), and/or the third water treatment unit (HJM). In embodiments, a quality sensor (HJN) is configured to measure the quality of the treated water (HJA) that leaves the first water treatment unit (HJK), second water treatment unit (HJL), and/or the third water treatment unit (HJM). For example, the quality sensor (HJN) may measure the electrical conductivity of the treated water (HJA) to determine if either of the first water treatment unit (HJK), second water treatment unit (HJL), and/or the third water treatment unit (HJM) require maintenance and/or cleaning. In embodiments, the quality sensor (HJN) measures the electrical conductivity of the treatment unit (HJM) to ensure that the electrical conductivity ranges from 0.10 microsiemens per centimeter to 100 microsiemens per centimeter.

In embodiments, the quality sensor (HJN) measures the electrical conductivity of the treatment unit (HJM) to ensure that the electrical conductivity ranges from one or more selected from the group consisting of 0.1 µS to 0.5 µS, 0.5 µS to 1.00 µS, 1.00 µS to 1.25 µS, 1.25 µS to 1.50 µS, 1.50 µS to 1.75 µS, 1.75 µS to 2.00 µS, 2.00 µS to 2.25 µS, 2.25 µS to 2.50 µS, 2.50 µS to 2.75 µS, 2.75 µS to 3.00 µS, 3.00 µS to 3.25 µS, 3.25 µS to 3.50 µS, 3.50 µS to 3.75 µS, 3.75 µS to 4.00 µS, 4.00 µS to 4.25 µS, 4.25 µS to 4.50 µS, 4.50 µS to 4.75 µS, 4.75 µS to 5.00 µS, 5.00 µS to 5.25 µS, 5.25 µS to 5.50 µS, 5.50 µS to 5.75 µS, 5.75 µS to 6.00 µS, 6.00 µS to 6.25 µS, 6.25 µS to 6.50 µS, 6.50 µS to 6.75 µS, 6.75 µS to 7.00 µS, 7.00 µS to 7.25 µS, 7.25 µS to 7.50 µS, 7.50 µS to 7.75 µS, 7.75 µS, to 8.00 µS, 8.00 µS to 8.25 µS, 8.25 µS to 8.50 µS, 8.50 µS to 8.75 µS, 8.75 µS to 9.00 µS, 9.00 µS to 9.25 µS, 9.25 µS to 9.50 µS, 9.50 µS to 9.75 µS, 9.75 µS to 10.00 µS, 10.00 µS to 12.50 µS, 12.50 µS to 15.00 µS, 15.00 µS to 17.50 µS, 17.50 µS to 20.00 µS, 20.00 µS to 22.50 µS, 22.50 µS to 25.00 µS, 25.00 µS to 27.50 µS, 27.50 µS to 30.00 µS, 30.00 µS to 32.50 µS, 32.50 µS to 35.00 µS, 35.00 µS to 37.50 µS, 37.50 µS to 40.00 µS, 40.00 µS to 42.50 µS, 42.50 µS to 45.00 µS, 45.00 µS to 47.50 µS, 47.50 µS to 50.00 µS, 50.00 µS to 52.50 µS, 52.50 µS to 55.00 µS, 55.00 µS to 57.50 µS, 57.50 µS to 60.00 µS, 60.00 µS to 62.50 µS, 62.50 µS to 65.00 µS, 65.00 µS to 67.50 µS, 67.50 µS to 70.00 µS, 70.00 µS to 72.50 µS, 72.50 µS to 75.00 µS, 75.00 µS to 77.50 µS, and 77.50 µS to 100.00 µS. In embodiments, µS means µS per centimeter.

In embodiments, the treated solvent (HIE) is transferred from the first water treatment unit (HJK), second water treatment unit (HJL), or third water treatment unit (HJM) and into a treated water vessel (HJF). In embodiments, the treated water vessel (HJF) has an interior. In embodiments, the treated water vessel (HJF) is a continuously stirred tank reactor having a jacketed reactor equipped with a steam supply system and at least one steam trap. In embodiments, the treated water vessel (HJF) is equipped with a level sensor (HJPP) that is configured to input a signal to the computer (COMP). In embodiments, the treated water vessel (HJF) is equipped with a pH sensor (HJQ) that is configured to input a signal to the computer (COMP). In embodiments, the treated water vessel (HJF) is equipped with an auger that has a motor. The motor of the auger rotates the auger to mix the contents within the interior of the treated water vessel (HJF). In embodiments, the treated water vessel (HJF) is equipped with a temperature sensor that is configured to input a signal to the computer (COMP). In embodiments, the treated water vessel (HJF) is equipped with a heat exchanger to heat the contents within the interior of the treated water vessel (HJF). In embodiments, the treated water vessel (HJF) outputs treated water (HJA).

In embodiments, the treated water (HJA) discharged from the treated water vessel (HJF) is provided to a treated water pump (HJD). In embodiments, the treated water pump (HJD) pumps and pressurizes the treated water (HJA) to form pressurized treated water (HJB). In embodiments, the pressurized treated water (HJB) provided by the treated water pump (HJD) is made available to the interior (HAJ) extraction zone (HAI') as a solvent (HAB'). In embodiments, the pressurized treated water (HJB) provided by the treated water pump (HJD) is made available for use as the first desorbent (HDC) for the first adsorber system (SMB1), second desorbent (HFG) for the second adsorber system (SMB2), third desorbent (HHC) for the third adsorber system (SMB3). In embodiments, a treated water valve (HJE) is configured to regulate the flow of the pressurized treated water (HJB) that leaves the solvent treatment system (H-WTS). In embodiments, a pressure sensor (HJH) is configured to measure the pressure of the pressurized treated water (HJB) that is discharged from the treated water pump (HJD). In embodiments, a pH adjustment solution (HJR) is made available to the treated water vessel (HJF). In embodiments, the pH adjustment solution (HJR) passes through a valve (HJS) prior to being introduced to the interior of the treated water vessel (HJF).

In embodiments, the treated water (HJA) within the treated water vessel (HJF) is preferably maintained at a pH of 6.1 to 6.8. In embodiments, the treated water (HJA) within the treated water vessel (HJF) is preferably maintained at a pH including one or more selected from the group consisting of 5.00 to 5.05, 5.05 to 5.10, 5.10 to 5.15, 5.15 to 5.20, 5.20 to 5.25, 5.25 to 5.30, 5.30 to 5.35, 5.35 to 5.40, 5.40 to 5.45, 5.45 to 5.50, 5.50 to 5.55, 5.55 to 5.60, 5.60 to 5.65, 5.65 to 5.70, 5.70 to 5.75, 5.75 to 5.80, 5.80 to 5.85, 5.85 to 5.90, 5.90 to 5.95, 5.95 to 6.00, 6.00 to 6.05, 6.05 to 6.10, 6.10 to 6.15, 6.15 to 6.20, 6.20 to 6.25, 6.25 to 6.30, 6.30 to 6.35, 6.35 to 6.40, 6.40 to 6.45, 6.45 to 6.50, 6.50 to 6.55, 6.55 to 6.60, 6.60 to 6.65, 6.65 to 6.70, 6.70 to 6.75, 6.75 to 6.80, 6.80 to 6.85, 6.85 to 6.90, and 6.90 to 6.95.

In embodiments, the pH adjustment solution (HJR) is comprised of one or more from the group consisting of acid, nitric acid, phosphoric acid, potassium hydroxide, sulfuric acid, organic acids, citric acid, and acetic acid.

FIG. 17J'

FIG. 17J' shows one non-limiting embodiment of a cannabinoid emulsion mixing system.

Cannabinoids (THC, CBD, etc.) are lipophilic and hydrophobic. Cannabinoids such as THC and CDB are lipophilic and that they tend to combine with or dissolve in each other or in other compounds such as lipids or fats. Cannabinoids such as THC and CDB are hydrophobic and they tend to repel or fail to mix with water. An emulsion is a mixture of water and cannabinoids. An emulsion can be prepared from treated water having an electrical conductivity ranging from 0.10 microsiemens per centimeter to 100 microsiemens per centimeter.

In embodiments, the emulsion mixing system shown in FIG. 17H' is specially equipped with a purge system to provide inert gases to the interior of the system to form a protective atmosphere (prevent oxidation and/or degradation of the emulsion or ingredients, improved product quality, clean good manufacturing practices as required by pharmaceutical industry, for cleaning in place, etc.) while creating the emulsion.

In embodiments, the emulsion mixing system shown in FIG. 17H' creates a nanoemulsion is thermodynamically stable. In embodiments, the emulsion produced has the following characteristics:

(i) a pH ranging from one or more selected from the group consisting of 6 to 6.25, 6.25 to 6.5, 6.5 to 6.75, 6.75 to 7, 7 to 7.05, 7.05 to 7.1, 7.1 to 7.15, 7.15 to 7.2, 7.2 to 7.25, 7.25 to 7.3, 7.3 to 7.35, 7.35 to 7.4, 7.4 to 7.45, 7.45 to 7.5, 7.5 to 7.55, 7.55 to 7.6, 7.6 to 7.65, 7.65 to 7.7, 7.7 to 7.75, 7.75 to 7.8, 7.8 to 7.85, 7.85 to 7.9, 7.9 to 7.95, 7.95 to 8, 8 to 8.05, 8.05 to 8.1, 8.1 to 8.15, 8.15 to 8.2, 8.2 to 8.25, 8.25 to 8.3, 8.3 to 8.35, 8.35 to 8.4, 8.4 to 8.45, 8.45 to 8.5, and 8.5 to 9.

(ii) a viscosity ranging from one or more selected from the group consisting of 1 centipoise (cps) to 2 cps, 2 cps to 5 cps, 5 cps to 10 cps, 10 cps to 20 cps, 20 cps to 30 cps, 30 cps to 40 cps, 40 cps to 50 cps, 50 cps to 60 cps, 60 cps to 70 cps, 70 cps to 80 cps, 80 cps to 90 cps, 90 cps to 100 cps, 100 cps to 125 cps, 125 cps to 150 cps, 150 cps to 175 cps, 175 cps to 200 cps, 200 cps to 225 cps, 225 cps to 250 cps, 250 cps to 275 cps, 275 cps to 300 cps, 300 cps to 325 cps, 325 cps to 350 cps, 350 cps to 375 cps, 375 cps to 400 cps, 400 cps to 425 cps, 425 cps to 450 cps, 450 cps to 475 cps, 475 cps to 500 cps, 500 cps to 550 cps, 550 cps to 600 cps, 600 cps to 650 cps, 650 cps to 700 cps, 700 cps to 750 cps, 750 cps to 800 cps, 800 cps to 850 cps, 850 cps to 900 cps, 900 cps to 950 cps, 950 cps to 1000 cps, 1,000 cps to 1,250 cps, 1,250 cps to 1,500 cps, 1,500 cps to 1,750 cps, 1,750 cps to 2,000 cps, 2,000 cps to 2,500 cps, 2,500 cps to 3,000 cps, 3,000 cps to 3,500 cps, 3,500 cps to 4,000 cps, 4,000 cps to 4,500 cps, 4,500 cps to 5,000 cps, 5,000 cps to 5,500 cps, 5,500 cps to 6,000 cps, 6,000 cps to 6,500 cps, 6,500 cps to 7,000 cps, 7,000 cps to 7,500 cps, 7,500 cps to 8,000 cps, 8,000 cps to 8,500 cps, 8,500 cps to 9,000 cps, 9,000 cps to 9,500 cps, 9,500 cps to 10,000 cps, 10,000 cps to 11,000 cps, 11,000 cps to 12,000 cps, 12,000 cps to 13,000 cps, 13,000 cps to 14,000 cps, 14,000 cps to 15,000 cps, 15,000 cps to 16,000 cps, 16,000 cps to 17,000 cps, 17,000 cps to 18,000 cps, 18,000 cps to 19,000 cps, 19,000 cps to 20,000 cps, 20,000 cps to 21,000 cps, 21,000 cps to 22,000 cps, 22,000 cps to 23,000 cps, 23,000 cps to 24,000 cps, 24,000 cps to 25,000 cps, and 25,000 cps to 26,000 cps.

(iii) a specific gravity ranging from one or more selected from the group consisting of 0.7 to 0.705, 0.705 to 0.71, 0.71 to 0.715, 0.715 to 0.72, 0.72 to 0.725, 0.725o 0.73, 0.73 to 0.735, 0.735 to 0.74, 0.74 to 0.745, 0.745 to 0.75, 0.75 to 0.755, 0.755 to 0.76, 0.76 to 0.765, 0.765 to 0.77, 0.77 to 0.775, 0.775 to 0.78, 0.78 to 0.785, 0.785 to 0.79, 0.79 to 0.795, 0.795 to 0.8, 0.8 to 0.805, 0.805 to 0.81, 0.81 to 0.815, 0.815 to 0.82, 0.82 to 0.825, 0.825 to 0.83, 0.83 to 0.835, 0.835 to 0.84, 0.84 to 0.845, 0.845 to 0.85, 0.85 to 0.855, 0.855 to 0.86, 0.86 to 0.865, 0.865 to 0.87, 0.87 to 0.875, 0.875 to 0.88, 0.88 to 0.885, 0.885 to 0.89, 0.89 to 0.895, 0.895 to 0.9, 0.9 to 0.905, 0.905 to 0.91, 0.91 to 0.915, 0.915 to 0.92, 0.92 to 0.925, 0.925 to 0.93, 0.93 to 0.935, 0.935 to 0.94, 0.94 to 0.945, 0.945 to 0.95, 0.95 to 0.955, 0.955 to 0.96, 0.96 to 0.965, 0.965 to 0.97, 0.97 to 0.975, 0.975 to 0.98, 0.98 to 0.985, 0.985 to 0.99, 0.99 to 0.995, 0.995 to 0.999, 0.999 to 1, 1 to 1.1, 1.1 to 1.2, and 1.2 to 1.3.

(iv) a conductivity ranging from one or more selected from the group consisting of 1.00 microsiemens (µS) to 1.25 µS, 1.25 µS to 1.50 µS, 1.50 µS to 1.75 µS, 1.75 µS to 2.00 µS, 2.00 µS to 2.25 µS, 2.25 µS to 2.50 µS, 2.50 µS to 2.75 µS, 2.75 µS to 3.00 µS, 3.00 µS to 3.25 µS, 3.25 µS to 3.50 µS, 3.50 µS to 3.75 µS, 3.75 µS to 4.00 µS, 4.00 µS to 4.25 µS, 4.25 µS to 4.50 µS, 4.50 µS to 4.75 µS, 4.75 µS to 5.00 µS, 5.00 µS to 5.25 µS, 5.25 µS to 5.50 µS, 5.50 µS to 5.75 µS, 5.75 µS to 6.00 µS, 6.00 µS to 6.25 µS, 6.25 µS to 6.50 µS, 6.50 µS to 6.75 µS, 6.75 µS to 7.00 µS, 7.00 µS to 7.25 µS, 7.25 µS to 7.50 µS, 7.50 µS to 7.75 µS, 7.75 µS to 8.00 µS, 8.00 µS to 8.25 µS, 8.25 µS to 8.50 µS, 8.50 µS to 8.75 µS, 8.75 µS to 9.00 µS, 9.00 µS to 9.25 µS, 9.25 µS to 9.50 µS, 9.50 µS to 9.75 µS, 9.75 µS to 10.00 µS, 10.00 µS to 12.50 µS, 12.50 µS to 15.00 µS, 15.00 µS to 17.50 µS, 17.50 µS to 20.00 µS, 20.00 µS to 22.50 µS, 22.50 µS to 25.00 µS, 25.00 µS to 27.50 µS, 27.50 µS to 30.00 µS, 30.00 µS to 32.50 µS, 32.50 µS to 35.00 µS, 35.00 µS to 37.50 µS, 37.50 µS to 40.00 µS, 40.00 µS to 42.50 µS, 42.50 µS to 45.00 µS, 45.00 µS to 47.50 µS, 47.50 µS to 50.00 µS, 50.00 µS to 52.50 µS, 52.50 µS to 55.00 µS, 55.00 µS to 57.50 µS, 57.50 µS to 60.00 µS, 60.00 µS to 62.50 µS, 62.50 µS to 65.00 µS, 65.00 µS to 67.50 µS, 67.500 to 70.00 µS, 70.000 to 72.50 µS, 72.500 to 75.00 µS, 75.00 µS to 77.50 µS, and 77.50 µS to 80.00 µS. In embodiments, µS means µS per centimeter.

(v) a conductivity ranging from one or more selected from the group consisting of 80 µS to 125 µS, 100 µS to 125 µS, 125 µS to 150 µS, 150 µS to 175 µS, 175 µS to 200 µS, 200 µS to 225 µS, 225 µS to 250 µS, 250 µS to 275 µS, 275 µS to 300 µS, 300 µS to 325 µS, 325 µS to 350 µS, 350 µS to 375 µS, 375 µS to 400 µS, 400 µS to 425 µS, 425 µS to 450 µS, 450 µS to 475 µS, 475 µS to 500 µS, 500 µS to 525 µS, 525 µS to 550 µS, 550 µS to 575 µS, 575 µS to 600 µS, 600 µS to 625 µS, 625 µS to 650 µS, 650 µS to 675 µS, 675 µS to 700 µS, 700 µS to 725 µS, 725 µS to 750 µS, 750 µS to 775 µS, 775 µS to 800 µS, 800 µS to 825 µS, 825 µS to 850 µS, 850 µS to 875 µS, 875 µS to 900 µS, 900 µS to 925 µS, 925 µS to 950 µS, 950 µS to 975 µS, 975 µS to 1,000 µS, 1,000 µS to 1,250 µS, 1,250 µS to 1,500 µS, 1,500 µS to 1,750 µS, 1,750 µS to 2,000 µS, 2,000 µS to 2,250 µS, 2,250 µS to 2,500 µS, 2,500 µS to 2,750 µS, 2,750 µS to 3,000 µS, 3,000 µS to 3,250 µS, 3,250 µS to 3,500 µS, 3,500 µS to 3,750 µS, 3,750 µS to 4,000 µS, 4,000 µS to 4,250 µS, 4,250 µS to 4,500 µS, 4,500 µS to 4,750 µS, 4,750 µS to 5,000 µS, 5,000 µS to 5,250 µS, 5,250 µS to 5,500 µS, 5,500 µS to 5,750 µS, 5,750 µS to 6,000 µS, 6,000 µS to 6,250 µS, 6,250 µS to 6,500 µS, 6,500 µS to 6,750 µS, 6,750 µS to 7,000 µS, 7,000 µS to 7,250 µS, 7,250 µS to 7,500 µS, 7,500 µS to 7,750 µS, and 7,750 µS to 8,000 µS In embodiments, µS means µS per centimeter (vi) a preservation that includes: freezer, 0 degrees F. to 32 degrees F., 30 months to 40 months; refrigerator, 34 degrees F. to 45 degrees F., 30 months to 40 months; elevated temperature, 76 degrees F. to 98 degrees F., 4 months to 6 months; ambient temperature, 68 degrees F. to 76 degrees F., 30 months to 40 months.

Applicant has discovered an improved process to emulsify a lipophilic and hydrophobic cannabinoid mixture or extract with water. Applicant has discovered an improved process to emulsify a lipophilic and hydrophobic cannabinoid extract with water. The simulated moving bed extraction method utilized with an emulsification procedure is a core concept of this disclosure shown in FIGS. 17G' and 17H'.

Lipophilic and hydrophobic cannabinoid mixtures do not easily disperse into water-based formulations. In embodiments, ultrasonic homogenizers can be used to produce stable nanoemulsions of cannabinoids in water or any aqueous phase. In embodiments, an emulsification system may be used for the production of *cannabis* oil-emulsions. In embodiments, the type of emulsification system varies. In embodiments, the type of emulsification system includes a homogenizer, agitator, sawtooth blade, closed rotor, rotor/stator, an ultrasonic homogenizer rotor/stator generator, colloid mill, high pressure, piston pump, a microfluidizer, and a microfluidizer processor.

Applicant has discovered a new microemulsion and nanoemulsion technology based water soluble platform to greatly enhance the bioavailability of water soluble cannabinoid (THC, CBD, etc.) powders, liquids, gels, and creams. In embodiments, the bioavailability of the cannabinoid emulsion is the proportion of the cannabinoid that enters the circulation of the human or animal when introduced into the body and so is able to have an active effect.

In embodiments, the bioavailability of the cannabinoid emulsion is the proportion of the cannabinoid that enters the circulation of the human or animal when introduced into the human or animal body and so is able to have an active effect. In embodiments, the bioavailability of the cannabinoid emulsion is selected from one or more bioavailability ranges selected from one or more from the group of bioavailability ranges consisting of: 30.00 percent to 40.00 percent, 40.00 percent to 50.00 percent, 50.00 percent to 60.00 percent, 60.00 percent to 70.00 percent, 70.00 percent to 72.50 percent, 72.50 percent to 75.00 percent, 75.00 percent to 77.50 percent, 77.50 percent to 80.00 percent, 80.00 percent to 82.50 percent, 82.50 percent to 85.00 percent, 85.00 percent to 87.50 percent, 87.50 percent to 90.00 percent, 90.00 percent to 90.50 percent, 90.50 percent to 91.00 percent, 91.00 percent to 91.50 percent, 91.50 percent to 92.00 percent, 92.00 percent to 92.50 percent, 92.50 percent to 93.00 percent, 93.00 percent to 93.50 percent, 93.50 percent to 94.00 percent, 94.00 percent to 94.50 percent, 94.50 percent to 95.00 percent, 95.00 percent to 95.50 percent, 95.50 percent to 96.00 percent, 96.00 percent to 96.50 percent, 96.50 percent to 97.00 percent, 97.00 percent to 97.50 percent, 97.50 percent to 98.00 percent, 98.00 percent to 98.50 percent, 98.50 percent to 99.00 percent, 99.00 percent to 99.50 percent, and 99.50 percent to 100.00 percent.

In embodiments, these new and advanced water soluble technology formulations transforms cannabinoid oil (THC, CBD, etc.) into microemulsions and nanoemulsions making them more absorbable when delivered orally, and much more permeable when administered topically. Applicant has discovered a method to make new water soluble powder and liquid cannabinoid drugs, foodstuffs, oils, crystals, and emulsions.

In embodiments, the emulsion is a nano-size emulsion or a nanoemulsion and has nano-size droplets. In embodiments, the emulsion is a micro-size emulsion or a microemulsion and has micro-sized droplets. In embodiments, emulsions, such as micro-sized or nano-sized emulsions, may be liquids, gels, of creams. In embodiments, emulsions, such as micro-sized or nano-sized emulsions, may be two immiscible fluids dispersed into one another. In embodiments, the emulsion contains cannabinoids and water. In embodiments, the emulsion contains cannabinoids and a solvent.

In embodiments, the emulsion contains cannabinoids, a solvent, an emulsifier, a biocatalyst, and acid. In embodiments, the emulsion contains cannabinoids, a solvent, an emulsifier, a biocatalyst, an acid/caustic, and water. In embodiments, the emulsion contains cannabinoids, a water, an emulsifier, a biocatalyst, drugs, and an acid. In embodiments, the emulsion contains cannabinoids, a water, an emulsifier, a biocatalyst, drugs, an acid/caustic, and a pH adjustment solution. In embodiments, the emulsion contains cannabinoids and water. In embodiments, the emulsion contains cannabinoids and deionized water. In embodiments, the emulsion contains cannabinoids and deionized and membrane treated water. In embodiments, the emulsion contains cannabinoids and filtered and deionized water.

In embodiments, the emulsion has an average droplet size selected from one or more from the group consisting of between: 1 nanometers to 2 nanometers, 2 nanometers to 3 nanometers, 3 nanometers to 4 nanometers, 4 nanometers to 5 nanometers, 5 nanometers to 6 nanometers, 6 nanometers to 7 nanometers, 7 nanometers to 8 nanometers, 8 nanometers to 9 nanometers, 9 nanometers to 10 nanometers, 10 nanometers to 11 nanometers, 11 nanometers to 12 nanometers, 12 nanometers to 13 nanometers, 13 nanometers to 14 nanometers, 14 nanometers to 15 nanometers, 15 nanometers to 16 nanometers, 16 nanometers to 17 nanometers, 17 nanometers to 18 nanometers, 18 nanometers to 19 nanometers, 19 nanometers to 20 nanometers, 20 nanometers to 21 nanometers, 21 nanometers to 22 nanometers, 22 nanometers to 23 nanometers, 23 nanometers to 24 nanometers, 24 nanometers to 25 nanometers, 25 nanometers to 26 nanometers, 26 nanometers to 27 nanometers, 27 nanometers to 28 nanometers, 28 nanometers to 29 nanometers, 29 nanometers to 30 nanometers, 30 nanometers to 31 nanometers, 31 nanometers to 32 nanometers, 32 nanometers to 33 nanometers, 33 nanometers to 34 nanometers, 34 nanometers to 35 nanometers, 35 nanometers to 36 nanometers, 36 nanometers to 37 nanometers, 37 nanometers to 38 nanometers, 38 nanometers to 39 nanometers, 39 nanometers to 40 nanometers, 40 nanometers to 41 nanometers, 41 nanometers to 42 nanometers, 42 nanometers to 43 nanometers, 43 nanometers to 44 nanometers, 44 nanometers to 45 nanometers, 45 nanometers to 46 nanometers, 46 nanometers to 47 nanometers, 47 nanometers to 48 nanometers, 48 nanometers to 49 nanometers, 49 nanometers to 50 nanometers, 50 nanometers to 75 nanometers, 75 nanometers to 100 nanometers, 100 nanometers to 150 nanometers, 150 nanometers to 250 nanometers, 250 nanometers to 500 nanometers, 500 nanometers to 750 nanometers, 750 nanometers to 1,000 nanometers, 1,000 nanometers to 1,500 nanometers, 1,500 nanometers to 2,000 nanometers, 2,000 nanometers to 3,000 nanometers, 3,000 nanometers to 4,000 nanometers, 4,000 nanometers to 5,000 nanometers, 5,000 nanometers to 6,000 nanometers, and 6,000 nanometers to 10,000 nanometers.

Applicant has discovered new and improved oil-in-water emulsions. In embodiments, the emulsion is prepared by mixing the cannabinoid and solvent mixture with an emulsifier. In embodiments, the emulsifier used in Applicants cannabinoid emulsion process is selected from one or more emulsifiers selected from the group consisting of a surfactant, a nonionic surfactant, lecithin, polyethylene (40), stearate, polysorbate, Polyoxyethylene sorbitan monooleate, Polyoxyethylene (20) sorbitan monooleate, polysorbate 80, polysorbate 60, polysorbate 65, ammonium salts of phosphatidic acid, sucrose acetate isobutyrate, potassium pyrophosphate, sodium acid pyrophosphate, sodium pyrophosphate, potassium polymetaphosphate, sodium metaphosphate, insoluble or sodium polyphosphates, sodium polyphosphates, insoluble polyphosphates, glassy salts of fatty acids, mono-and di-glycerides of fatty acids, mono-glycerides of fatty acids, di-glycerides of fatty acids, acetic and fatty acid esters of glycerol, lactic and fatty acid esters of glycerol, citric and fatty acid esters of glycerol, diacetyltartaric and fatty acid esters of glycerol, mixed fatty acid esters of glycerol, sucrose esters of fatty acids, polyglycerol esters of fatty acids, polyglycerol esters of interesterified ricinoleic acid, propylene glycol mono-and di-esters, propylene glycol di-esters, propylene glycol mono-esters, propylene glycol esters of fatty acids, propylene glycol esters, dioctyl sodium sulphosuccinate, sodium lactylate, sodium oleyl lactylate, sodium stearoyl lactylate, calcium lactylate, calcium oleyl lactylate, calcium stearoyl lactylate, sorbitan monostearate, maltodextrin, polyphosphates, formulated polyphosphates, and gum arabic.

In embodiment, the biocatalyst includes one or more selected from the group consisting of a microorganism, bacteria, fungi, Lactobacilli, *Lactobacillus acidophilus, Lactobacillus bulgaricus, Lactobacillus plantarum, Lactobacillus rhamnosus, Lactobacillus fermentum, Lactobacillus caucasicus, Lactobacillus helveticus, Lactobacillus lactis, Lactobacillus reuteri, Lactobacillus casei, Lactobacillus brevis, Lactobacillus gasseri, Lactobacillus paracasei, Lactobacillus salivarius, Bifidobacteria, Bifidobacterium animalis, Bifidobacterium bifidum, Bifidobacterium breve, Bifidobacterium infantis, Bifidobacterium lactis, Bifidobacterium longum, Enterococcus faecium, Streptococcus thermophilus, Bacillus laterosporus*, and *Pediococcus acidilactici*.

In embodiments, the drugs include one or more selected from the group consisting of a ayahuasca, biologically active organic compound with four rings, a nootropic drug, acetate, activated charcoal, an amphetamine, ascorbic acid, aspirin, butyrate, calcium, capsaicin, carnitine, carnosine, *cassia* cinnamon, chondroitin sulfate, chromium, coenzyme q-10, cranberry, creatine, curcumin, deprenyl, dimethyltryptamine, *echinacea*, fish oil, garlic, ginger, ginkgo, *ginseng*, gluconic acid, glucosamine, green tea, hoodia, human growth hormone, 7-hydroxymitragynine, inositol, iowaska, kratom, lactic acid, lithium, lutein, magnesium, minerals, malate, melatonin, metformin, 3,4-methylenedioxymethamphetamine, milk thistle, n-acetylcysteine, niacin, niacinamide, nicotinamide riboside, omega-3 fatty acid, oxaloacetate, piracetam, psilocybin, pyruvate, resveratrol, *rhodiola*, saw palmetto, selenium, St. john's wort, steroid alternatives, steroids, testosterone, theaflavins, turmeric, valerian, vitamins, vitamin B3, vitamin C, and zinc.

In embodiments, the drugs include one or more selected from the group consisting of basil, bergamot, black pepper, *cassia*, cedarwood, cinnamon, citronella, clary sage, clove, coffee, cypress, *eucalyptus*, evening primrose, fennel, fir needle, frankincense, *gardenia*, geranium, ginger, grapefruit, helichrysum, hop, hyssop, jasmine, juniper berry, lavender, lemon, lemongrass, mandarin, marjoram, *melaleuca*, melissa, myrrh, neroli, orange, oregano, palo santo, patchouli, peppermint, pine, roman chamomile, rose, rosemary, sandalwood, spikenard, tea tree, thyme, turmeric, vetiver, wintergreen, and ylang ylang.

In embodiments, the drugs include one or more selected from the group consisting of barley, binding agents, brown rice, buckwheat flour, buckwheat, bulgur, carrageenan, corn meal, corn, cracked wheat, cricket flour, density improving textural supplements, farro, fiber-starch materials, insect flour, insects, mealworms, millet, moisture improving textural supplements, oatmeal, popcorn, *quinoa*, rice, rye, sorghum, triticale, wheat, whole farro, whole grain barley, whole grain corn, whole oats, whole rye, whole wheat flour, wild rice, fiber-starch materials, binding agents, density improving textural supplements, and moisture improving textural supplements.

In embodiments, the emulsion may be further processed to create foodstuffs not only including ada, bagels, baked goods, biscuits, bitterballen, bonda, breads, cakes, candies, cereals, chips, chocolate bars, chocolate, coffee, cokodok, confectionery, cookies, cooking batter, corn starch mixtures, crackers, crêpes, croissants, croquettes, croutons, dolma, dough, doughnuts, energy bars, flapjacks, french fries, frozen custard, frozen desserts, frying cakes, fudge, gelatin mixes, granola bars, gulha, hardtack, ice cream, khandvi, khanom buang, krumpets, meze, mixed flours, muffins, multi-grain snacks, nachos, nian gao, noodles, nougat, onion rings, pakora, pancakes, panforte, pastas, pastries, pie crust, pita chips, pizza, poffertjes, pretzels, protein powders, pudding, rice krispie treats, sesame sticks, smoothies, snacks, specialty milk, tele-bhaja, tempura, toffee, tortillas, topo, turkish delights, or waffles.

In embodiments, the fiber-starch materials may be comprised of singular or mixtures of cereal-grain-based materials, grass-based materials, nut-based materials, powdered fruit materials, root-based materials, tuber-based materials, or vegetable-based materials. In embodiments, the binding agents may be comprised of singular or mixtures of agar, agave, alginin, aspartame, arrowroot, carrageenan, collagen, cornstarch, egg whites, finely ground seeds, furcellaran, gelatin, guar gum, honey, katakuri starch, locust bean gum, pectin, potato starch, proteins, *psyllium* husks, sago, sugars, *stevia*, syrups, tapioca, vegetable gums, or xanthan gum. In embodiments, the moisture improving textural supplements may be comprised of singular or mixtures of almonds, brazil nuts, cacao, cashews, chestnuts, coconut, filberts, hazelnuts, Indian nuts, macadamia nuts, nut butters, nut oils, nut powders, peanuts, pecans, pili nuts, pine nuts, pinon nuts, pistachios, soy nuts, sunflower seeds, tiger nuts, walnuts, and oils extracted from any one of the aforesaid nuts and nuts listed herein and combinations thereof. In embodiments, the insects may be Orthoptera order of insects including grasshoppers, crickets, cave crickets, Jerusalem crickets, katydids, weta, lubber, acrida, and locusts. However, other orders of insects, such as cicadas, ants, mealworms, agave worms, worms, bees, centipedes, cockroaches, dragonflies, beetles, scorpions, tarantulas, and termites may be used as well.

In embodiments the emulsion is created in a continuously stirred tank reactor. In embodiments the emulsion is created in a homogenizer. In embodiments, the emulsion is created using ultrasound technology. In embodiments, the emulsion is created using ultrasonic homogenizer. In embodiments, the ultrasonic homogenizer includes an ultrasonic horn (also known as acoustic horn, sonotrode, acoustic waveguide, ultrasonic probe) is a tapering metal bar commonly used for augmenting the oscillation displacement amplitude provided by an ultrasonic transducer operating at the low end of the ultrasonic frequency spectrum. In embodiments, the ultrasonic homogenizer includes one or more ultrasonic homogenizers selected from the group consisting of an ultrasonic horn, a converging ultrasonic horn, and a barbell ultrasonic horn. In embodiments, a sonotrode is a tool that creates ultrasonic vibrations and applies this vibrational energy to a gas, liquid, solid or tissue. In embodiments, a sonotrode includes of a plurality of piezoelectric transducers attached to a tapering metal rod.

In embodiments, the ultrasonic homogenizer consumes power at a power consumption level ranging from one or more power consumption levels selected from the group consisting of 0.1 kw to 0.25 kw, 0.25 kw to 0.5 kw, 0.5 kw to 1 kw, 1 kw to 2 kw, 2 kw to 3 kw, 3 kw to 4 kw, 4 kw to 5 kw, 5 kw to 6 kw, 6 kw to 7 kw, 7 kw to 8 kw, 8 kw to 9 kw, 9 kw to 10 kw, 10 kw to 11 kw, 11 kw to 12 kw, 12 kw to 13 kw, 13 kw to 14 kw, 14 kw to 15 kw, 15 kw to 16 kw, 16 kw to 17 kw, 17 kw to 18 kw, 18 kw to 19 kw, 19 kw to 20 kw, 20 kw to 25 kw, 25 kw to 30 kw, 30 kw to 35 kw, 35 kw to 40 kw, 40 kw to 45 kw, 45 kw to 50 kw, 50 kw to 55 kw, 55 kw to 60 kw, 60 kw to 65 kw, 65 kw to 70 kw, 70 kw to 75 kw, 75 kw to 80 kw, 80 kw to 85 kw, 85 kw to 90 kw, 90 kw to 95 kw, 95 kw to 100 kw, 100 kw to 300 kw, 300 kw to 500 kw, and 500 kw to 1,000 kw.

In embodiments, the weight percent of emulsifier in the final emulsion product includes at least one emulsifier weight percent range that is selected from the emulsifier weight percent ranges selected from the group consisting of: 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, 14 weight percent to 15 weight percent, 15 weight percent to 16 weight percent, 16 weight percent to 17 weight percent, 17 weight percent to 18 weight percent, 18 weight percent to 19 weight percent, 19 weight percent to 20 weight percent, 20 weight percent to 21 weight percent, 21 weight percent to 22 weight percent, 22 weight percent to 23 weight percent, 23 weight percent to 24 weight percent, 24 weight percent to 25 weight percent, 25 weight percent to 26 weight percent, 26 weight percent to 27 weight percent, 27 weight percent to 28 weight percent, 28 weight percent to 29 weight percent, 29 weight percent to 30 weight percent, 30 weight percent to 31 weight percent, 31 weight percent to 32 weight percent, 32 weight percent to 33 weight percent, 33 weight percent to 34 weight percent, 34 weight percent to 35 weight percent, 35 weight percent to 36 weight percent, 36 weight percent to 37 weight percent, 37 weight percent to 38 weight percent, 38 weight percent to 39 weight percent, 39 weight percent to 40 weight percent, 40 weight percent to 41 weight percent, 41 weight percent to 42 weight percent, 42 weight percent to 43 weight percent, 43 weight percent to 44 weight percent, 44 weight percent to 45 weight percent, 45 weight percent to 46 weight percent, 46 weight percent to 47 weight percent, 47 weight percent to 48 weight percent, 48 weight percent to 49 weight percent, 49 weight percent to 50 weight percent, 50 weight percent to 51 weight percent, 51 weight percent to 52 weight percent, 52 weight percent to 53 weight percent, 53 weight percent to 54 weight percent, 54 weight percent to 55 weight percent, 55 weight percent to 56 weight percent, 56 weight percent to 57 weight percent, 57 weight percent to 58 weight percent, 58 weight percent to 59 weight percent, 59 weight percent to 60 weight percent, 60 weight percent to 61 weight percent, 61 weight percent to 62 weight percent, 62 weight percent to 63 weight percent, 63 weight percent to 64 weight percent, 64 weight percent to 65 weight percent, and 65 weight percent to 66 weight percent.

In embodiments, the weight percent of cannabinoids in the final emulsion product includes at least one cannabinoid weight percent range that is selected from the cannabinoid weight percent ranges selected from the group consisting of: 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, 14 weight percent to 15 weight percent, 15 weight percent to 16 weight percent, 16 weight percent to 17 weight percent, 17 weight percent to 18 weight percent, 18 weight percent to 19 weight percent, 19 weight percent to 20 weight percent, 20 weight percent to 21 weight percent, 21 weight percent to 22 weight percent, 22 weight percent to 23 weight percent, 23 weight percent to 24 weight percent, 24 weight percent to 25 weight percent, 25 weight percent to 26 weight percent, 26 weight percent to 27 weight percent, 27 weight percent to 28 weight percent, 28 weight percent to 29 weight percent, 29 weight percent to 30 weight percent, 30 weight percent to 31 weight percent, 31 weight percent to 32 weight percent, 32 weight percent to 33 weight percent, 33 weight percent to 34 weight percent, 34 weight percent to 35 weight percent, 35 weight percent to 36 weight percent, 36 weight percent to 37 weight percent, 37 weight percent to 38 weight percent, 38 weight percent to 39 weight percent, 39 weight percent to 40 weight percent, 40 weight percent to 41 weight percent, 41 weight percent to 42 weight percent, 42 weight percent to 43 weight percent, 43 weight percent to 44 weight percent, 44 weight percent to 45 weight percent, 45 weight percent to 46 weight percent, 46 weight percent to 47 weight percent, 47 weight percent to 48 weight percent, 48 weight percent to 49 weight percent, 49 weight percent to 50 weight percent, 50 weight percent to 51 weight percent, 51 weight percent to 52 weight percent, 52 weight percent to 53 weight percent, 53 weight percent to 54 weight percent, 54 weight percent to 55 weight percent, 55 weight percent to 56 weight percent, 56 weight percent to 57 weight percent, 57 weight percent to 58 weight percent, 58 weight percent to 59 weight percent, 59 weight percent to 60 weight percent, 60 weight percent to 61 weight percent, 61 weight percent to 62 weight percent, 62 weight percent to 63 weight percent, 63 weight percent to 64 weight percent, 64 weight percent to 65 weight percent, and 65 weight percent to 66 weight percent.

In embodiments, the weight percent of acid in the final emulsion product includes at least one acid weight percent range that is selected from the acid weight percent ranges selected from the group consisting of: 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, 14 weight percent to 15 weight percent, 15 weight percent to 16 weight percent, 16 weight percent to 17 weight percent, 17 weight percent to 18 weight percent, 18 weight percent to 19 weight percent, 19 weight percent to 20 weight percent, 20 weight percent to 21 weight percent, 21 weight percent to 22 weight percent, 22 weight percent to 23 weight percent, 23 weight percent to 24 weight percent, 24 weight percent to 25 weight percent, 25 weight percent to 26 weight percent, 26 weight percent to 27 weight percent, 27 weight percent to 28 weight percent, 28 weight percent to 29 weight percent, 29 weight percent to 30 weight percent, 30 weight percent to 31 weight percent, 31 weight percent to 32 weight percent, 32 weight percent to 33 weight percent, 33 weight percent to 34 weight percent, 34 weight percent to 35 weight percent, 35 weight percent to 36 weight percent, 36 weight percent to 37 weight percent, 37 weight percent to 38 weight percent, 38 weight percent to 39 weight percent, 39 weight percent to 40 weight percent, 40 weight percent to 41 weight percent, 41 weight percent to 42 weight percent, 42 weight percent to 43 weight percent, 43 weight percent to 44 weight percent, 44 weight percent to 45 weight percent, 45 weight percent to 46 weight percent, 46 weight percent to 47 weight percent, 47 weight percent to 48 weight percent, 48 weight percent to 49 weight percent, 49 weight percent to 50 weight percent, 50 weight percent to 51 weight percent, 51 weight percent to 52 weight percent, 52 weight percent to 53 weight percent, 53 weight percent to 54 weight percent, 54 weight percent to 55 weight percent, 55 weight percent to 56 weight percent, 56 weight percent to 57 weight percent, 57 weight percent to 58 weight percent, 58 weight percent to 59 weight percent, 59 weight percent to 60 weight percent, 60 weight percent to 61 weight percent, 61 weight percent to 62 weight percent, 62 weight percent to 63 weight percent, 63 weight percent to 64 weight percent, 64 weight percent to 65 weight percent, and 65 weight percent to 66 weight percent.

In embodiments, the weight percent of biocatalyst in the final emulsion product includes at least one biocatalyst weight percent range that is selected from the biocatalyst weight percent ranges selected from the group consisting of: 25 parts per million to 0.1 weight percent, 0.1 weight percent to 0.5 weight percent, 0.5 weight percent to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, 14 weight percent to 15 weight percent, 15 weight percent to 16 weight percent, 16 weight percent to 17 weight percent, 17 weight percent to 18 weight percent, 18 weight percent to 19 weight percent, 19 weight percent to 20 weight percent, 20 weight percent to 21 weight percent, 21 weight percent to 22 weight percent, 22 weight percent to 23 weight percent, 23 weight percent to 24 weight percent, 24 weight percent to 25 weight percent, 25 weight percent to 26 weight percent, 26 weight percent to 27 weight percent, 27 weight percent to 28 weight percent, 28 weight percent to 29 weight percent, 29 weight percent to 30 weight percent, 30 weight percent to 31 weight percent, 31 weight percent to 32 weight percent, 32 weight percent to 33 weight percent, 33 weight percent to 34 weight percent, 34 weight percent to 35 weight percent, 35 weight percent to 36 weight percent, 36 weight percent to 37 weight percent, 37 weight percent to 38 weight percent, 38 weight percent to 39 weight percent, 39 weight percent to 40 weight percent, 40 weight percent to 41 weight percent, 41 weight percent to 42 weight percent, 42 weight percent to 43 weight percent, 43 weight percent to 44 weight percent, 44 weight percent to 45 weight percent, 45 weight percent to 46 weight percent, 46 weight percent to 47 weight percent, 47 weight percent to 48 weight percent, 48 weight percent to 49 weight percent, 49 weight percent to 50 weight percent, 50 weight percent to 51 weight percent, 51 weight percent to 52 weight percent, 52 weight percent to 53 weight percent, 53 weight percent to 54 weight percent, 54 weight percent to 55 weight percent, 55 weight percent to 56 weight percent, 56 weight percent to 57 weight percent, 57 weight percent to 58 weight percent, 58 weight percent to 59 weight percent, 59 weight percent to 60 weight percent, 60 weight percent to 61 weight percent, 61 weight percent to 62 weight percent, 62 weight percent to 63 weight percent, 63 weight percent to 64 weight percent, 64 weight percent to 65 weight percent, and 65 weight percent to 66 weight percent.

In embodiments, the weight percent of drugs in the final emulsion product includes at least one drug weight percent range that is selected from the drug weight percent ranges selected from the group consisting of: 0.001 weight percent to 0.002 weight percent, 0.002 weight percent to 0.01 weight percent, 0.01 weight percent to 0.1 weight percent, 0.1 weight percent to 0.5 weight percent, 0.5 weight percent to 0.6 weight percent, 0.6 weight percent to 0.7 weight percent, 0.7 weight percent to 0.8 weight percent, 0.8 weight percent to 0.9 weight percent, 0.9 weight percent to 1.0 weight percent, 1.0 weight percent to 1.1 weight percent, 1.1 weight percent to 1.2 weight percent, 1.2 weight percent to 1.3 weight percent, 1.3 weight percent to 1.4 weight percent, 1.4 weight percent to 1.5 weight percent, 1.5 weight percent to 1.6 weight percent, 1.6 weight percent to 1.7 weight percent, 1.7 weight percent to 1.8 weight percent, 1.8 weight percent to 1.9 weight percent, 1.9 weight percent to 2.0 weight percent, 2.0 weight percent to 2.1 weight percent, 2.1 weight percent to 2.2 weight percent, 2.2 weight percent to 2.3 weight percent, 2.3 weight percent to 2.4 weight percent, 2.4 weight percent to 2.5 weight percent, 2.5 weight percent to 2.6 weight percent, 2.6 weight percent to 2.7 weight percent, 2.7 weight percent to 2.8 weight percent, 2.8 weight percent to 2.9 weight percent, 2.9 weight percent to 3.0 weight percent, 3.0 weight percent to 3.1 weight percent, 3.1 weight percent to 3.2 weight percent, 3.2 weight percent to 3.3 weight percent, 3.3 weight percent to 3.4 weight percent, 3.4 weight percent to 3.5 weight percent, 3.5 weight percent to 3.6 weight percent, 3.6 weight percent to 3.7 weight percent, 3.7 weight percent to 3.8 weight percent, 3.8 weight percent to 3.9 weight percent, 3.9 weight percent to 4.0 weight percent, 4.0 weight percent to 4.1 weight percent, 4.1 weight percent to 4.2 weight percent, 4.2 weight percent to 4.3 weight percent, 4.3 weight percent to 4.4 weight percent, 4.4 weight percent to 4.5 weight percent, 4.5 weight percent to 4.6 weight percent, 4.6 weight percent to 4.7 weight percent, 4.7 weight percent to 4.8 weight percent, 4.8 weight percent to 4.9 weight percent, 4.9 weight percent to 5.0 weight percent, 5.0 weight percent to 5.1 weight percent, 5.1 weight percent to 5.2 weight percent, 5.2 weight percent to 5.3 weight percent, 5.3 weight percent to 5.4 weight percent, 5.4 weight percent to 5.5 weight percent, 5.5 weight percent to 5.6 weight percent, 5.6 weight percent to 5.7 weight percent, 5.7 weight percent to 5.8 weight percent, 5.8 weight percent to 5.9 weight percent, 5.9 weight percent to 6.0 weight percent, 6.0 weight percent to 6.1 weight percent, 6.1 weight percent to 6.2 weight percent, 6.2 weight percent to 6.3 weight percent, 6.3 weight percent to 6.4 weight percent, 6.4 weight percent to 6.5 weight percent, and 6.5 weight percent to 6.6 weight percent.

In embodiments, the weight percent of caustic in the final emulsion product includes at least one caustic weight percent range that is selected from the caustic weight percent ranges selected from the group consisting of: 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, 14 weight percent to 15 weight percent, 15 weight percent to 16 weight percent, 16 weight percent to 17 weight percent, 17 weight percent to 18 weight percent, 18 weight percent to 19 weight percent, 19 weight percent to 20 weight percent, 20 weight percent to 21 weight percent, 21 weight percent to 22 weight percent, 22 weight percent to 23 weight percent, 23 weight percent to 24 weight percent, 24 weight percent to 25 weight percent, 25 weight percent to 26 weight percent, 26 weight percent to 27 weight percent, 27 weight percent to 28 weight percent, 28 weight percent to 29 weight percent, 29 weight percent to 30 weight percent, 30 weight percent to 31 weight percent, 31 weight percent to 32 weight percent, and 32 weight percent to 33 weight percent.

In embodiments, the weight percent of water in the final emulsion product includes at least one caustic water percent range that is selected from the water weight percent ranges selected from the group consisting of: 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, 14 weight percent to 15 weight percent, 15 weight percent to 16 weight percent, 16 weight percent to 17 weight percent, 17 weight percent to 18 weight percent, 18 weight percent to 19 weight percent, 19 weight percent to 20 weight percent, 20 weight percent to 21 weight percent, 21 weight percent to 22 weight percent, 22 weight percent to 23 weight percent, 23 weight percent to 24 weight percent, 24 weight percent to 25 weight percent, 25 weight percent to 26 weight percent, 26 weight percent to 27 weight percent, 27 weight percent to 28 weight percent, 28 weight percent to 29 weight percent, 29 weight percent to 30 weight percent, 30 weight percent to 31 weight percent, 31 weight percent to 32 weight percent, 32 weight percent to 33 weight percent, 33 weight percent to 34 weight percent, 34 weight percent to 35 weight percent, 35 weight percent to 36 weight percent, 36 weight percent to 37 weight percent, 37 weight percent to 38 weight percent, 38 weight percent to 39 weight percent, 39 weight percent to 40 weight percent, 40 weight percent to 41 weight percent, 41 weight percent to 42 weight percent, 42 weight percent to 43 weight percent, 43 weight percent to 44 weight percent, 44 weight percent to 45 weight percent, 45 weight percent to 46 weight percent, 46 weight percent to 47 weight percent, 47 weight percent to 48 weight percent, 48 weight percent to 49 weight percent, 49 weight percent to 50 weight percent, 50 weight percent to 51 weight percent, 51 weight percent to 52 weight percent, 52 weight percent to 53 weight percent, 53 weight percent to 54 weight percent, 54 weight percent to 55 weight percent, 55 weight percent to 56 weight percent, 56 weight percent to 57 weight percent, 57 weight percent to 58 weight percent, 58 weight percent to 59 weight percent, 59 weight percent to 60 weight percent, 60 weight percent to 61 weight percent, 61 weight percent to 62 weight percent, 62 weight percent to 63 weight percent, 63 weight percent to 64 weight percent, 64 weight percent to 65 weight percent, and 65 weight percent to 66 weight percent.

In embodiments, a homogenizer may be configured to homogenize cannabinoids, solvents, water, an emulsifier, an acid/caustic, a biocatalyst, drugs, and a caustic material. In embodiments, homogenization may include any number of several processes used to make a mixture of two mutually non-soluble liquids the same throughout. In embodiments, homogenization is used to create an emulsion. In embodiments, an emulsification system may be configured to emulsify cannabinoids, solvents, water, an emulsifier, an acid/caustic, a biocatalyst, drugs, insect, and biomass. In embodiments, emulsification may include any number of several processes used to make a mixture of two mutually non-soluble liquids the same throughout. In embodiments, an emulsification system is used to create an emulsion.

In embodiments, a mixture of cannabinoids, solvents, water, an emulsifier, an acid/caustic, a biocatalyst, and drugs is introduced to an emulsification system at a pressure greater than the emulsion that is discharged from the emulsifier system. In embodiments, the pressure drop across the emulsification system is selected from one or more pressure drop ranges selected from the group consisting of 25 pounds per square inch (PSI) to 50 PSI, 50 PSI to 100 PSI, 100 PSI to 200 PSI, 200 PSI to 300 PSI, 300 PSI to 400 PSI, 400 PSI to 500 PSI, 500 PSI to 600 PSI, 600 PSI to 700 PSI, 700 PSI to 800 PSI, 800 PSI to 900 PSI, 900 PSI to 1,000 PSI, 1,000 PSI to 1,500 PSI, 1,500 PSI to 2,000 PSI, 2,000 PSI to 2,500 PSI, 2,500 PSI to 3,000 PSI, 3,000 PSI to 3,500 PSI, 3,500 PSI to 4,000 PSI, 4,000 PSI to 4,500 PSI, 4,500 PSI to 5,000 PSI, 5,000 PSI to 5,500 PSI, 5,500 PSI to 6,000 PSI, 6,000 PSI to 6,500 PSI, 6,500 PSI to 7,000 PSI, 7,000 PSI to 7,500 PSI, 7,500 PSI to 8,000 PSI, 8,000 PSI to 8,500 PSI, 8,500 PSI to 9,000 PSI, 9,000 PSI to 9,500 PSI, 9,500 PSI to 10,000 PSI, 10,000 PSI to 11,000 PSI, 11,000 PSI to 12,000 PSI, 12,000 PSI to 13,000 PSI, 13,000 PSI to 14,000 PSI, 14,000 PSI to 15,000 PSI, 15,000 PSI to 16,000 PSI, 16,000 PSI to 17,000 PSI, 17,000 PSI to 18,000 PSI, 18,000 PSI to 19,000 PSI, 19,000 PSI to 20,000 PSI, 20,000 PSI to 22,500 PSI, 22,500 PSI to 25,000 PSI, 25,000 PSI to 27,500 PSI, 27,500 PSI to 30,000 PSI, 30,000 PSI to 35,000 PSI. and 35,000 PSI to 40,000 PSI.

In embodiments the emulsion is created under inert gas conditions in the presence of a gas such as and not only including carbon dioxide, nitrogen, or argon. In embodiments, an inert gas is introduced to the emulsion mixing tank to prolong the life of the emulsion product. The gas supply system is configured to continuously maintain a positive pressure in the vapor space within the emulsion mixing tank.

FIG. 17J displays an acid-caustic distribution system (JAA) including an acid-caustic tank (JAB) that is configured to accept acid-caustic (JAD). The acid-caustic tank (JAB) has an interior (JAC), an acid-caustic input (JAF), an acid-caustic conveyor (JAG), and an acid-caustic conveyor output (JAH). The acid-caustic tank (JAB) accepts acid and/or caustic (JAD) to the interior (JAC) and regulates and controls an engineered amount of acid and/or caustic (JAD) downstream to be mixed to form an emulsion. The acid-caustic conveyor (6B5) has an integrated mass sensor (JAJ) that is configured to input and output a signal (JAK) to the computer (COMP). The acid-caustic conveyor motor (JAL) has a controller (JAM) that is configured to input and output a signal (JAN) to the computer (COMP). The mass sensor (JAJ), acid-caustic conveyor (JAG), and acid-caustic conveyor motor (JAL) are coupled so as to permit the conveyance, distribution, or output of a precise flow of acid and/or caustic (JAD) via an acid-caustic transfer line (JAI). It is to be noted that the acid-caustic may be in solid, powder, liquid, or slurry form. Transferring an engineered amount of acid and/or caustic (JAD) downstream to be mixed to form an emulsion is the premise of the disclosure and is not limited to regulating as a solid, powder, liquid, gel, slurry, or the equivalent.

FIG. 17J' displays a biocatalyst distribution system (JBA) including a biocatalyst tank (JBB) that is configured to accept a biocatalyst (JBD). The biocatalyst tank (JBB) has an interior (JBC), a biocatalyst input (JBF), a biocatalyst conveyor (JBG), and a biocatalyst conveyor output (JBH). The biocatalyst tank (JBB) accepts a biocatalyst (JBD) to the interior (JBC) and regulates and controls an engineered amount of biocatalyst (JBD) downstream to be mixed to form an emulsion. The biocatalyst conveyor (6B5) has an integrated mass sensor (JBJ) that is configured to input and output a signal (JBK) to the computer (COMP). The biocatalyst conveyor motor (JBL) has a controller (JBM) that is configured to input and output a signal (JBN) to the computer (COMP). The mass sensor (JBJ), biocatalyst conveyor (JBG), and biocatalyst conveyor motor (JBL) are coupled so as to permit the conveyance, distribution, or output of a precise flow of biocatalyst (JBD) via a biocatalyst transfer line (JBI). It is to be noted that the biocatalyst may be in solid, powder, liquid, or slurry form. Transferring an engineered amount of biocatalyst (JBD) downstream to be mixed to form an emulsion is the premise of the disclosure and is not limited to regulating as a solid, powder, liquid, gel, slurry, or the equivalent.

FIG. 17J' displays a drug distribution system (JCA) including a drug tank (JCB) that is configured to accept a drug (JCD). The drug tank (JCB) has an interior (JCC), a drug input (JCF), a drug conveyor (JCG), and a drug conveyor output (JCH). The drug tank (JCB) accepts drugs (JCD) to the interior (JCC) and regulates and controls an engineered amount of drugs (JCD) downstream to be mixed to form an emulsion. The drug conveyor (6B5) has an integrated mass sensor (JCJ) that is configured to input and output a signal (JCK) to the computer (COMP). The drug conveyor motor (JCL) has a controller (JCM) that is configured to input and output a signal (JCN) to the computer (COMP). The mass sensor (JCJ), drug conveyor (JCG), and drug conveyor motor (JCL) are coupled so as to permit the conveyance, distribution, or output of a precise flow of drugs (JCD) via a drug transfer line (JCI). It is to be noted that the drugs may be in solid, powder, liquid, or slurry form. Transferring an engineered amount of drugs (JCD) downstream to be mixed to form an emulsion is the premise of the disclosure and is not limited to regulating as a solid, powder, liquid, gel, slurry, or the equivalent.

FIG. 17J' displays an emulsifier distribution system (JDA) including an emulsifier tank (JDB) that is configured to accept an emulsifier (JDD). The emulsifier tank (JDB) has an interior (JDC), an emulsifier input (JDF), an emulsifier conveyor (JDG), and an emulsifier conveyor output (JDH). The emulsifier tank (JDB) accepts an emulsifier (JDD) to the interior (JDC) and regulates and controls an engineered amount of emulsifier (JDD) downstream to form an emulsion. The emulsifier conveyor (6B5) has an integrated mass sensor (JDJ) that is configured to input and output a signal (JDK) to the computer (COMP). The emulsifier conveyor motor (JDL) has a controller (JDM) that is configured to input and output a signal (JDN) to the computer (COMP). The mass sensor (JDJ), emulsifier conveyor (JDG), and emulsifier conveyor motor (JDL) are coupled so as to permit the conveyance, distribution, or output of a precise flow of emulsifier (JDD) via an emulsifier transfer line (JDI). It is to be noted that the emulsifier may be in solid, powder, liquid, or slurry form. Transferring an engineered amount of emulsifier (JDD) downstream to be mixed to form an emulsion is the premise of the disclosure and is not limited to regulating as a solid, powder, liquid, gel, slurry, or the equivalent.

FIG. 17J' displays an extract distribution system (JEA) including an extract tank (JEB) that is configured to accept an extract (JED). The extract tank (JEB) has an interior (JEC), an extract input (JEF), an extract conveyor (JEG), and an extract conveyor output (JEH). The extract tank (JEB) accepts an extract (JED) to the interior (JEC) and regulates and controls an engineered amount of extract (JED) downstream to be mixed to form an emulsion. The extract conveyor (6B5) has an integrated mass sensor (JEJ) that is configured to input and output a signal (JEK) to the computer (COMP). The extract conveyor motor (JEL) has a controller (JEM) that is configured to input and output a signal (JEN) to the computer (COMP). The mass sensor (JEJ), extract conveyor (JEG), and extract conveyor motor (JEL) are coupled so as to permit the conveyance, distribution, or output of a precise flow of extract (JED) via an extract transfer line (JEI). It is to be noted that the extract may be in solid, powder, liquid, or slurry form. Transferring an engineered amount of extract (JED) downstream to be mixed to form an emulsion is the premise of the disclosure and is not limited to regulating as a solid, powder, liquid, gel, slurry, or the equivalent.

In embodiments, the extract is not only including from: (VOLT) from FIG. 17A' or 17B', (SVSM) from FIG. 17C', (CVOLT) from FIG. 17D', volatiles from FIG. 17E', and/or extract from FIG. 17H'. In embodiments, the extract comes from any disclosed Figure in this patent specification.

FIG. 17J' displays an insect distribution system (JFA) including an insect tank (JFB) that is configured to accept an insect (JFD). The insect tank (JFB) has an interior (JFC), an insect input (JFF), an insect conveyor (JFG), and an insect conveyor output (JFH). The insect tank (JFB) accepts an insect (JFD) to the interior (JFC) and regulates and controls an engineered amount of insects (JFD) downstream to be mixed to form an emulsion. The insect conveyor (6B5) has an integrated mass sensor (JFJ) that is configured to input and output a signal (JFK) to the computer (COMP). The insect conveyor motor (JFL) has a controller (JFM) that is configured to input and output a signal (JFN) to the computer (COMP). The mass sensor (JFJ), insect conveyor (JFG), and insect conveyor motor (JFL) are coupled so as to permit the conveyance, distribution, or output of a precise flow of insects (JFD) via an insect transfer line (JFI). It is to be noted that the insects may be in solid, powder, liquid, or slurry form. Transferring an engineered amount of insects (JFD) downstream to be mixed to form an emulsion is the premise of the disclosure and is not limited to regulating as a solid, powder, liquid, gel, slurry, or the equivalent.

FIG. 17J' displays a biomass distribution system (JGA) including a biomass tank (JGB) that is configured to accept biomass (JGD). The biomass tank (JGB) has an interior (JGC), a biomass input (JGF), a biomass conveyor (JGG), and a biomass conveyor output (JGH). The biomass tank (JGB) accepts biomass (JGD) to the interior (JGC) and regulates and controls an engineered amount of biomass (JGD) downstream to be mixed to form an emulsion. The biomass conveyor (6B5) has an integrated mass sensor (JGJ) that is configured to input and output a signal (JGK) to the computer (COMP). The biomass conveyor motor (JGL) has a controller (JGM) that is configured to input and output a signal (JGN) to the computer (COMP). The mass sensor (JGJ), biomass conveyor (JGG), and biomass conveyor motor (JGL) are coupled so as to permit the conveyance, distribution, or output of a precise flow of biomass (JGD) via a biomass transfer line (JGI). It is to be noted that the biomass may be in solid, powder, liquid, or slurry form. Transferring an engineered amount of biomass (JGD) downstream to be mixed to form an emulsion is the premise of the disclosure and is not limited to regulating as a solid, powder, liquid, gel, slurry, or the equivalent.

In embodiments, an emulsion mixing tank (JLE) is configured to accept acid and/or caustic (JAD) via an acid-caustic transfer line (JAI), biocatalyst (JBD) via a biocatalyst transfer line (JBI), drugs (JCD) via a drug transfer line (JCI), emulsifier (JDD) via an emulsifier transfer line (JDI), extract (JED) via an extract transfer line (JEI), as a first input (JLA) through a first input (JLA). In embodiments, an emulsion mixing tank (JLE) is configured to accept insects (JFD) via an insect transfer line (JFI), and biomass (JGD) via a biomass transfer line (JGI) as a second mixture (JLD) through a second input (JLC). It is to be noted that the first input (JLA) through a first input (JLA) and the second mixture (JLD) through a second input (JLC) are non-limiting and it is true that each of the acid and/or caustic (JAD), biocatalyst (JBD), drugs (JCD), emulsifier (JDD), extract (JED), insects (JFD), and biomass (JGD) through one input or each having their own input to the emulsion mixing tank (JLE). In embodiments, the mixing tank (G15) as shown in FIG. 14G (of Volume 1) is the same vessel as the emulsion mixing tank (JLE) as shown in FIG. 17J' (of Volume 2).

In embodiments, a water supply (JKA) is made available to the emulsion mixing tank (JLE). In embodiments, a water supply (JKA) transferred to the emulsion mixing tank (JLE) is first treated in a first water treatment unit (JKB), second water treatment unit (JKC), and a third water treatment unit (JKD) to form treated water (JKE).

In embodiments, the first water treatment unit (JKB) includes one or more selected from the group consisting of a cation, an anion, a membrane, a filter, activated carbon, an adsorbent, an absorbent, an ultraviolet unit, an ozone unit, or a microwave unit. In embodiments, the second water treatment unit (JKC) includes one or more selected from the group consisting of a cation, an anion, a membrane, a filter, activated carbon, an adsorbent, an absorbent, an ultraviolet unit, an ozone unit, or a microwave unit. In embodiments, the third water treatment unit (JKD) includes one or more selected from the group consisting of a cation, an anion, a membrane, a filter, activated carbon, an adsorbent, an absorbent, an ultraviolet unit, an ozone unit, or a microwave unit. In embodiments, the adsorbent includes one or more selected from the group consisting of 3 Angstrom molecular sieve, 3 Angstrom zeolite, 4 Angstrom molecular sieve, 4 Angstrom zeolite, activated alumina, activated carbon, adsorbent, alumina, carbon, catalyst, clay, desiccant, molecular sieve, polymer, resin, and silica gel. In embodiments, the cation is configured to remove positively charged ions from the water supply (JKA), the positively charged ions are comprised of one or more from the group consisting of calcium, magnesium, sodium, and iron. In embodiments, the anion is configured to remove negatively charged ions from the water supply (JKA), the negatively charged ions are comprised of one or more from the group consisting of iodine, chloride, and sulfate. In embodiments, the membrane is configured to remove undesirable compounds from the water supply (JKA), the undesirable compounds are comprised of one or more from the group consisting of dissolved organic chemicals, viruses, bacteria, and particulates. In embodiments, the membrane has a diameter that ranges from 1 inch to 6 inches and a pore size ranging from 0.0001 microns to 0.5 microns.

In embodiments, treated water (JKE) is discharged from the first water treatment unit (JKB), second water treatment unit (JKC), and/or the third water treatment unit (JKD). In embodiments, treated water (JKE) has less positively charged ions, negatively charged ions, and undesirable compounds relative to the supply (JKA). In embodiments, a valve (HJI) is configured to regulate the flow of the treated water (HJA) that leaves the first water treatment unit (HJK), second water treatment unit (HJL), and/or the third water treatment unit (HJM). In embodiments, a quality sensor (JKG) is configured to measure the quality of the treated water (JKE) that leaves the first water treatment unit (HJK), second water treatment unit (HJL), and/or the third water treatment unit (HJM). For example, the quality sensor (JKG) may measure the electrical conductivity of the treated water (JKE) to determine if either of the first water treatment unit (HJK), second water treatment unit (HJL), and/or the third water treatment unit (HJM) require maintenance and/or cleaning. In embodiments, the quality sensor (HJN) measures the electrical conductivity of the treatment unit (HJM) to ensure that the electrical conductivity ranges from 0.10 microsiemens per centimeter to 100 microsiemens per centimeter.

In embodiments, a treated water pump (JKH) is provided and is configured to accept the treated water (JKE) from either one of the first water treatment unit (HJK), second water treatment unit (HJL), and/or the third water treatment unit (HJM). In embodiments, a valve (JKK) is configured to regulate the flow of the treated water (JKE) that leaves the treated water pump (JKH). In embodiments, a pressure sensor (HFB) is configured to measure the pressure of the treated water (JKE) that leaves the treated water pump (JKH). In embodiments, a flow sensor (HFC) is configured to measure the flow of the treated water (JKE) that leaves the treated water pump (JKH). In embodiments, the treated water (JKE) that leaves the treated water pump (JKH) has a pressure that includes one or more pressure ranges selected from the group consisting of 10 pounds per square inch (PSI) to 20 PSI, 20 PSI to 40 PSI, 40 PSI to 60 PSI, 60 PSI to 80 PSI, 80 PSI to 100 PSI, 100 PSI to 125 PSI, 125 PSI to 150 PSI, 150 PSI to 175 PSI, 175 PSI to 200 PSI, 200 PSI to 225 PSI, 225 PSI to 250 PSI, 250 PSI to 275 PSI, 275 PSI to 300 PSI, 300 PSI to 325 PSI, 325 PSI to 350 PSI, 350 PSI to 375 PSI, 375 PSI to 400 PSI, 400 PSI to 425 PSI, 425 PSI to 450 PSI, 450 PSI to 475 PSI, and 475 PSI to 500 PSI.

In embodiments, an emulsion mixing tank (JLE) is provided to mix the acid and/or caustic (JAD), biocatalyst (JBD), drugs (JCD), emulsifier (JDD), extract (JED), insects (JFD), and biomass (JGD) through one input or each having their own input to the emulsion mixing tank (JLE).

In embodiments, an emulsion mixing tank (JLE) has an interior (JLF). In embodiments, the emulsion mixing tank (JLE) has have a heating jacket (JLN) to serve the purpose of the heat exchanger (JLM). The emulsion mixing tank (JLE) with a heating jacket (JLN) is a vessel that is designed for controlling the temperature of its contents, by using a heating jacket around the vessel through which a heat transfer medium (e.g.—steam) is circulated. The heating jacket (JLN) is a cavity external to the interior (JLF) of the emulsion mixing tank (JLE) that permits the uniform exchange of heat between the heat transfer medium circulating in it and the walls of the emulsion mixing tank (JLE). FIG. 17J' shows the heating jacket (JLN) installed over a portion of the emulsion mixing tank (JLE) creating an interior (JLO) having an annular space within which a heat transfer medium flows.

The heating jacket (JLN) has a heat transfer medium inlet (JLP) and a heat transfer medium outlet (JLQ). Steam (JLR) is introduced to the heat transfer medium inlet (JLP). Steam condensate (JLT) is discharged from the heat transfer medium outlet (JLQ). Steam (JLR) is introduced to the heat transfer medium inlet (JLP) of the heating jacket (JLN) of the emulsion mixing tank (JLE) via a steam inlet conduit (JLS). The steam inlet conduit (JLS) is connected to the heat transfer medium inlet (JLP) and is configured to transfer steam (JLR) to the interior (JLO) of the heating jacket (JLN).

In embodiments, a steam supply (LDM') is provided to the heating jacket (JLN) and/or to the heat exchanger (JLM) and is provided from FIG. 17F'. In embodiments, the steam condensate (JLT) that is discharged from the heat transfer medium outlet (JLQ) is transferred to the condensate tank (LAP) shown in FIG. 17F'.

A steam supply valve (JLU) is interposed on the steam inlet conduit (JLS). The steam supply valve (JLU) is equipped with a controller (JLV) that inputs and outputs a signal (JLW) to the computer (COMP). In embodiments, the steam supply valve (JLU) is positioned to regulate the mass of heat transfer medium that leaves the heating jacket (JLN) via the discharged from the heat transfer medium outlet (JLQ).

In embodiments, a temperature sensor (JMA) measures the temperature of the contents within the interior (JLF) of the emulsion mixing tank (JLE). The temperature sensor (JMA) is configured to output a signal (JMB) to the computer (COMP). A pre-determined setpoint for the emulsion mixing tank (JLE) temperature sensor (JMA) may be inputted to the computer (COMP). In response to the pre-determined setpoint, the computer (COMP) regulates the modulation of the steam supply valve (JLU). The preferred modulation range of the steam supply valve (JLU) ranges from 33% open to 66% open. In embodiments, the preferred modulation range of the steam supply valve (JLU) ranges from: 5% open to 10% open; 10% open to 15% open; 15% open to 20% open; 20% open to 30% open; 30% open to 40% open; 40% open to 50% open; 50% open to 60% open; 60% open to 70% open.

In embodiments, the emulsion mixing tank (JLE) has a plurality of baffles (JLI, JLJ) that are positioned within the interior (JLF). Each baffle (JLI, JLJ) is configured to promote mixing and increase heat transfer and to create an emulsion.

The pressure drop across the steam supply valve (JLU) ranges from between: 1 pound per square inch (PSI) to 2 PSI; 2 pounds per square inch (PSI) to 5 PSI; 5 pounds per square inch (PSI) to 10 PSI; 10 pounds per square inch (PSI) to 20 PSI; 20 pounds per square inch (PSI) to 40 PSI; 40 pounds per square inch (PSI) to 60 PSI; 60 pounds per square inch (PSI) to 80 PSI; 80 pounds per square inch (PSI) to 100 PSI; 100 pounds per square inch (PSI) to 125 PSI; 125 pounds per square inch (PSI) to 150 PSI; 150 pounds per square inch (PSI) to 200 PSI.

The velocity of steam in the steam inlet conduit (JLR) ranges from: 35 feet per second to 45 feet per second; 45 feet per second to 55 feet per second; 55 feet per second to 65 feet per second; 65 feet per second to 75 feet per second; 75 feet per second to 85 feet per second; 85 feet per second to 95 feet per second; 95 feet per second to 105 feet per second; 105 feet per second to 115 feet per second; 115 feet per second to 125 feet per second; 125 feet per second to 135 feet per second; 135 feet per second to 145 feet per second; 145 feet per second to 155 feet per second; 155 feet per second to 175 feet per second. The velocity of steam condensate discharged from the heat transfer medium outlet (G91) is less than 3 feet per second.

In embodiments, the heat transfer medium inlet (JLP) is comprised of one or more from the group consisting of: a Class 150 flange, a Class 300 flange, sanitary clamp fitting, national pipe thread, or compression fitting. In embodiments, the heat transfer medium outlet (JLQ) is comprised of one or more from the group consisting of: a Class 150 flange, a Class 300 flange, sanitary clamp fitting, national pipe thread, or compression fitting. In embodiments, the emulsion mixing tank (JLE) is comprised of stainless steel or carbon steel and may be ceramic or glass-lined. In embodiments, the heating jacket (JLN) is comprised of stainless steel or carbon steel and may be ceramic or glass-lined.

In embodiments, the temperature of the mixture within the interior (JLF) of the emulsion mixing tank (JLE) ranges from between: 50 degrees F. to 60 degrees F.; 60 degrees F. to 70 degrees F.; 70 degrees F. to 80 degrees F.; 80 degrees F. to 90 degrees F.; 90 degrees F. to 100 degrees F.; 100 degrees F. to 110 degrees F.; 110 degrees F. to 120 degrees F.; 120 degrees F. to 130 degrees F.; 130 degrees F. to 140 degrees F.; 140 degrees F. to 150 degrees F.; 150 degrees F. to 160 degrees F.; 160 degrees F. to 170 degrees F.; 170 degrees F. to 180 degrees F.; 180 degrees F. to 190 degrees F.; 190 degrees F. to 200 degrees F.; 200 degrees F. to 212 degrees F.

In embodiments, the mixture may mixed within the interior (JLF) of the emulsion mixing tank (JLE) ranges from between: 5 minutes to 10 minutes; 10 minutes to 20 minutes; 20 minutes to 30 minutes; 30 minutes to 40 minutes; 40 minutes to 50 minutes; 50 minutes to 1 hour; 1 hour to 1.5 hours; 1.5 hour to 2 hours; 2 hour to 3 hours; 3 hour to 4 hours; 4 hour to 5 hours; 5 hour to 6 hours; 6 hour to 12 hours; 12 hour to 18 hours; 18 hour to 24 hours; 1 day to 2 days; 2 days to 3 days; 3 days to 4 days; 4 days to 5 days; 5 days to 1 week.

In embodiments, the emulsion mixing tank (JLE) is equipped with a pH sensor (JMC) that is configured to input a signal (JMD) to the computer (COMP). In embodiments, the emulsion mixing tank (JLE) is equipped with a first emulsifier system (JME). In embodiments, the first emulsifier system (JME) is an ultrasonic homogenizer (JME'). In embodiments, the ultrasonic homogenizer (JME') is equipped with a controller (JMF) that is equipped to send a signal (JMG) to and from the computer (COMP).

In embodiments, the emulsion mixing tank (JLE) has a mixture output (JMH) that discharges a mixture (JMI) from within the interior (JLF) of the emulsion mixing tank (JLE). In embodiments, the mixture (JMI) that is discharged from the interior (JLF) of the emulsion mixing tank (JLE) is an emulsion (JMX). In embodiments, the mixture (JMI) that is discharged from the interior (JLF) of the emulsion mixing tank (JLE) is transferred to a mixture pump (JMJ). In embodiments, the mixture pump (JMJ) pumps and pressurizes the mixture (JMI) that is discharged from the interior (JLF) of the emulsion mixing tank (JLE) to form a pressurized mixture (JMK). A pressure sensor (JML) is installed to measure the pressure of the pressurized mixture (JMK) and transmit a signal (JMM) to the computer (COMP). In embodiments, the pressurized mixture (JMK) is transferred to a second emulsifier system (JMN).

In embodiments, the second emulsifier system (JMN) accepts the pressurized mixture (JMK) via a mixture input (JMV). In embodiments, the second emulsifier system (JMN) has an emulsion output (JMW) for discharging an emulsion (JMX). In embodiments, the pressurized mixture (JMK) is a first emulsion (JMY) and the emulsion (JMX) discharged from the second emulsifier system (JMN) is the second emulsion (JMZ). In embodiments, at least a portion of the emulsion (JMX) discharged from the second emulsifier system (JMN) is returned to the interior (JLF) of the emulsion mixing tank (JLE) via a recycle conduit (JNA) and a recycle input (JNB). In embodiments, at least a portion of the emulsion (JMX) discharged from the second emulsifier system (JMN) is an emulsion product (JNC) or a pressurized emulsion product (JND).

A flow sensor (JNE) is configured to measure the flow rate of the emulsion product (JNC) and input a signal (JNF) to the computer (COMP). An emulsion product valve (JNG) is configured to regulate the flow of the emulsion product (JNC) and the emulsion product valve (JNG) is equipped with a controller (JNH) that inputs or outputs a signal (JNI) to the computer (COMP). In embodiments, the second emulsifier system (JMN) has an interior (JMO) and is equipped with a motor (JMP) that has a controller (JMQ) and is configured to input or output a signal (JMR) to the computer (COMP). In embodiments, the second emulsifier system (JMN) is equipped with a piston (JMS), a rotor-stator (JMT), or a valve and seat (JMU).

The emulsion mixing tank (JLE) may be equipped with a mixer (JLK) for mixing the contents of the interior (JLF) of the emulsion mixing tank (JLE). The mixer (JLK) may be of an auger or blade type that is equipped with a motor (JLL).

In embodiments, when the low-level sensor (JLH) sends a signal to the computer (COMP), the valve (JKK) on the discharge of the water pump (JKH) may be opened to introduce water into the interior (JLF) of the emulsion mixing tank (JLE) until the high-level sensor (JLG) is triggered thus sending a signal to the computer (COMP) to close the valve (JKK). This level control loop including the high-level sensor (JLG) for detecting a high level and a low-level sensor (JLH) for detecting a lower level may be coupled to the operation of the water supply valve (JKK) for introducing a treated water (JKE) through a first water treatment unit (JKB), a second water treatment unit (JKC), and a third water treatment unit (JKD) and into the interior (JLF) of the emulsion mixing tank (JLE).

In embodiments, the treated water (JKL) is transferred from the water pump (JKH) to form pressurized treated water (JKL). In embodiments, the pressurized treated water (JKL) is transferred through a water transfer conduit (JKM) and through a valve (JKK). In embodiments, as the pressurized treated water (JKL) passes through the valve (JKK) on the water transfer conduit (JKM), the pressurized treated water (JKL) is reduced in pressure to form a depressurized treated water (JKN) which is then introduced to the interior (JLF) of the emulsion mixing tank (JLE) via a water input (JKO).

In embodiments, a gas tank (JJA) is provided. In embodiments, the gas tank (JJA) contains a gas (JJB). In embodiments, the gas (JJB) is transferred from the gas tank (JJA) and is made available to the interior (JLF) of the emulsion mixing tank (JLE) as a gas supply (JJC). A pressure sensor (JJD) is installed to measure the pressure of the gas (JJB) within the gas tank (JJA). A pressure regulating valve (JJE) is provided to set a pressure of the gas supply conduit (JJP) to transfer gas (JJB) from the gas tank (JJA) into the interior (JLF) of the emulsion mixing tank (JLE).

A pressure sensor (JJI) is provided to measure the pressure within the gas supply conduit (JJP) and input a signal (JJH) to the computer (COMP). In embodiments, a first gas valve (JJJ) is provided to regulate the flow of gas (JJB) from the gas supply conduit (JJP) and into the interior (JLF) of the emulsion mixing tank (JLE). The first gas valve (JJJ) has a controller (JJF) that is equipped to input or output a signal (JJG) to the computer (COMP). In embodiments, a second gas valve (JJK) is provided to regulate the flow of gas (JJB) from the gas supply conduit (JJP) and into the interior (JLF) of the emulsion mixing tank (JLE). The second gas valve (JJK) has a controller (JJL) that is equipped to input or output a signal (JJM) to the computer (COMP). A pressure sensor (110) is provided to measure the pressure within the gas supply conduit (JJP) downstream of both the first gas valve (JJJ) and second gas valve (JJK) and input a signal (JJN) to the computer (COMP). A first one-way valve (JJT) is installed on the gas supply conduit (JJP) downstream of both of the first gas valve (JJJ) and second gas valve (JJK) and before the gas input (JJY) of the emulsion mixing tank (JLE). In embodiments, a second one-way valve (JJU) is provided to prevent back-flow of recycled carbon dioxide (JJX) from the gas input (JJY) of the emulsion mixing tank (JLE) backwards to the CO2 recovery system on FIG. 17G'.

FIG. 17K'

FIG. 17K' shows one non-limiting embodiment of a cannabinoid softgel encapsulation system (17K).

FIG. 17K' displays an extract distribution system (KEA) including an extract tank (KEB) that is configured to accept an extract (KED). The extract tank (KEB) has an interior (KEC), an extract input (KEF), an extract conveyor (KEG), and an extract conveyor output (KEH). The extract tank (KEB) accepts an extract (KED) to the interior (KEC) and regulates and controls an engineered amount of extract (KED) downstream to be mixed to form an emulsion. The extract conveyor (KB5) has an integrated mass sensor (KEJ) that is configured to input and output a signal (KEK) to the computer (COMP). The extract conveyor motor (KEL) has a controller (KEM) that is configured to input and output a signal (KEN) to the computer (COMP). The mass sensor (KEJ), extract conveyor (KEG), and extract conveyor motor (KEL) are coupled so as to permit the conveyance, distribution, or output of a precise flow of extract (KED) via an extract transfer line (KEI) into the input (KDF) of the cannabinoid softgel encapsulation system (17K). It is to be noted that the extract may be in solid, powder, crystal, liquid, or slurry form. Transferring an engineered amount of extract (KED) downstream to be mixed to form a softgel (KCC) is the premise of the disclosure and is not limited at all whatsoever.

The cannabinoid softgel encapsulation system (JKB) shown in FIG. 17K' is configured to produce cannabinoid softgels (KCC). In embodiments, a softgel (KCC) is an oral dosage form for medicine similar to capsules. In embodiments, softgels (KCC) are comprised of a gelatin based shell surrounding a liquid fill. In embodiments, the liquid fill is either an emulsion, volatiles from *cannabis* or Beaufort Budman Jr, or any number of combinations and permutations of THC and/or CBD as disclosed in this patent specification.

In embodiments, softgel shells are a combination of cannabinoids, gelatin, water, and a plasticiser such as glycerin or sorbitol. In embodiments, the plasticiser is used to increase the plasticity or decrease the viscosity of a material for the encapsulation of cannabinoids. In embodiments, the plasticiser is an emulsifier. In embodiments, softgel shells are a combination of cannabinoids, an emulsifier, medium chain triglycerides, beta caryophyllene, and a gelatin shell that includes bovine-derived gelatin, glycerin, sorbitol, and deionized water. In embodiments, medium chain triglycerides are triglycerides whose fatty acids have an aliphatic tail of 6-12 carbon atoms. In embodiments, triglycerides include esters derived from glycerol and three fatty acids (from tri- and glyceride).

In embodiments, each softgel contains cannabinoids at a cannabinoid concentration ranging from one or more cannabinoid concentrations selected from the group consisting of 5 mg to 10 mg, 10 mg to 15 mg, 15 mg to 20 mg, 20 mg to 25 mg, 25 mg to 30 mg, 30 mg to 35 mg, 35 mg to 40 mg, 40 mg to 45 mg, 45 mg to 50 mg, 50 mg to 55 mg, 55 mg to 60 mg, 60 mg to 65 mg, 65 mg to 70 mg, 70 mg to 75 mg, 75 mg to 80 mg, 80 mg to 85 mg, 85 mg to 90 mg, 90 mg to 95 mg, 95 mg to 100 mg, 100 mg to 125 mg, 125 mg to 150 mg, 150 mg to 175 mg, 175 mg to 200 mg, 200 mg to 225 mg, 225 mg to 250 mg, 250 mg to 275 mg, 275 mg to 300 mg, 300 mg to 325 mg, 325 mg to 350 mg, 350 mg to 375 mg, 375 mg to 400 mg, 400 mg to 425 mg, 425 mg to 450 mg, 450 mg to 475 mg, 475 mg to 500 mg, 500 mg to 550 mg, 550 mg to 600 mg, 600 mg to 650 mg, 650 mg to 700 mg, 700 mg to 750 mg, 750 mg to 800 mg, 800 mg to 850 mg, 850 mg to 900 mg, 900 mg to 950 mg, 950 mg to 1,000 mg, 1,000 mg to 2,000 mg, 2,000 mg to 3,000 mg, 3,000 mg to 4,000 mg, 4,000 mg to 5,000 mg, 5,000 mg to 6,000 mg, 6,000 mg to 7,000 mg, 7,000 mg to 8,000 mg, 8,000 mg to 9,000 mg, and 9,000 mg to 10,000 mg.

In embodiments, the cannabinoid softgel encapsulation system (JKB) includes a rotary die encapsulation system (KAA). In embodiments, rotary die encapsulation system (KAA) includes a gelatin tank (KBA) having an interior (KBB). In embodiments, gelatin (KBC) is contained within the interior (KBB) of the gelatin tank (KBA). In embodiments, gelatin (KBC) is discharged from the gelatin tank (KBA) and is passed through a valve (KBD). A gas supply may pressurize the gelatin tank (KBA), the gas supply system of FIG. 17J' can be used as similar to the way that the gas supply is provided to the emulsion process. The valve (KBD) has a controller (KBE) and is configured to input and output a signal (KBF) to the computer (COMP). A flow sensor (KBG) is provided to measure the amount of gelatin (KBC) transferred from the gelatin tank (KBA) and into the rotary die encapsulation system (KAA).

In embodiments, the rotary die encapsulation system (KAA) includes a roller (KBH), conveyor (KBI), and a ribbon (KBJ) of gelatin (KBC) (provided from the gelatin tank (KBA)), and a first roller (KCA) and a second roller (KCB). A softgel (KCC) is created by passing the liquid mixture from within the mixture tank (KDD) through the first roller (KCA) and a second roller (KCB) where the liquid mixture is encapsulated by the ribbon (KBJ) of gelatin (KBC).

In embodiments, the mixture tank (KDD) contains a variety of cannabinoid products from a variety of places and figures discussed in this patent specification. The mixture tank (KDD) is configured to accept at least: volatiles (VOLT) from FIG. 17A' or 17B', a volatiles and solvent mixture (SVSM) from FIG. 17C', concentrated volatiles (CVOLT) from FIG. 17D' that have undergone evaporation, volatiles from FIG. 17E', and/or extract from a variety of sources on FIG. 17H', and the emulsion from FIG. 17J', and any combination thereof, or any *cannabis* extract that is disclosed in the bounds of this disclosure. In embodiments, the extract comes from any disclosed figure or text from within this patent specification.

In embodiments, each softgel has a length and a width. In embodiments, the length of each softgel falls within a range of length that is selected from one or more length ranges consisting from the group including 0.125 inches to 0.250 inches, 0.250 inches to 0.375 inches, 0.375 inches to 0.500 inches, 0.500 inches to 0.625 inches, 0.625 inches to 0.750 inches, 0.750 inches to 0.875 inches, and 0.875 inches to 1.000 inch. In embodiments, the width of each softgel falls within a range of length that is selected from one or more width ranges consisting from the group including 0.125 inches to 0.250 inches, 0.250 inches to 0.375 inches, 0.375 inches to 0.500 inches, 0.500 inches to 0.625 inches, 0.625 inches to 0.750 inches, 0.750 inches to 0.875 inches, and 0.875 inches to 1.000 inch. In embodiments, the length is about 0.5 inches and the width is about 0.313 inches.

In embodiments, each softgel has a mass. In embodiments, the mass of each softgel falls within a range of mass that is selected from one or more mass ranges consisting from the group including 0.500 grams to 0.550 grams, 0.550 grams to 0.600 grams, 0.600 grams to 0.650 grams, 0.650 grams to 0.700 grams, 0.700 grams to 0.750 grams, 0.750 grams to 0.800 grams, 0.800 grams to 0.850 grams, 0.850 grams to 0.900 grams, 0.900 grams to 0.950 grams, and 0.950 grams to 1.000 grams.

In embodiments, the thickness of the ribbon (KBJ) of gelatin (KBC) in the rotary die encapsulation system (KAA) includes one or more selected from the group of ribbon thickness ranges consisting of 0.0050 inches to 0.0053 inches, 0.0053 inches to 0.0055 inches, 0.0055 inches to 0.0058 inches, 0.0058 inches to 0.0061 inches, 0.0061 inches to 0.0064 inches, 0.0064 inches to 0.0067 inches, 0.0067 inches to 0.0070 inches, 0.0070 inches to 0.0074 inches, 0.0074 inches to 0.0078 inches, 0.0078 inches to 0.0081 inches, 0.0081 inches to 0.0086 inches, 0.0086 inches to 0.0090 inches, 0.0090 inches to 0.0094 inches, 0.0094 inches to 0.0099 inches, 0.0099 inches to 0.0104 inches, 0.0104 inches to 0.0109 inches, 0.0109 inches to 0.0115 inches, 0.0115 inches to 0.0120 inches, 0.0120 inches to 0.0126 inches, 0.0126 inches to 0.0133 inches, 0.0133 inches to 0.0139 inches, 0.0139 inches to 0.0146 inches, 0.0146 inches to 0.0154 inches, 0.0154 inches to 0.0161 inches, 0.0161 inches to 0.0169 inches, 0.0169 inches to 0.0178 inches, 0.0178 inches to 0.0187 inches, 0.0187 inches to 0.0196 inches, 0.0196 inches to 0.0206 inches, 0.0206 inches to 0.0216 inches, 0.0216 inches to 0.0227 inches, 0.0227 inches to 0.0238 inches, 0.0238 inches to 0.0250 inches, 0.0250 inches to 0.0263 inches, 0.0263 inches to 0.0276 inches, 0.0276 inches to 0.0290 inches, 0.0290 inches to 0.0304 inches, 0.0304 inches to 0.0319 inches, 0.0319 inches to 0.0335 inches, 0.0335 inches to 0.0352 inches, 0.0352 inches to 0.0370 inches, 0.0370 inches to 0.0388 inches, 0.0388 inches to 0.0407 inches, 0.0407 inches to 0.0428 inches, 0.0428 inches to 0.0449 inches, 0.0449 inches to 0.0472 inches, 0.0472 inches to 0.0495 inches, 0.0495 inches to 0.0520 inches, 0.0520 inches to 0.0546 inches, 0.0546 inches to 0.0573 inches, 0.0573 inches to 0.0602 inches, 0.0602 inches to 0.0632 inches, and 0.0632 inches to 0.0664 inches.

In embodiments, the cannabinoid softgel encapsulation system (JKB) includes a washing system (KFA) and a drying system (FGA) that are configured to first wash the softgels (KCC) with a wash liquid (KEF) and then dry the washed softgels (KEJ) in a dryer (KEH) to produce washed and dried softgels (KEK). In embodiments, the wash liquid (KEF) includes treated water (see water treatment system on FIG. 17H'). In embodiments, the wash liquid (KEF) includes an alcohol or a liquid. In embodiments, the wash liquid (KEF) includes ethanol. In embodiments, the washing system (KFA) includes a conveyor (KEA) that is configured to accept the softgels (KCC) from the first roller (KCA) and a second roller (KCB).

In embodiments, the first roller (KCA) and a second roller (KCB) rotate to form the softgels (KEJ) at a revolutions per minute (RPM) that is selected from one or more from RPMs from the group consisting of 2 rpm to 4 rpm, 4 rpm to 6 rpm, 6 rpm to 8 rpm, 8 rpm to 10 rpm, 10 rpm to 12 rpm, 12 rpm to 14 rpm, 14 rpm to 16 rpm, 16 rpm to 18 rpm, 18 rpm to 20 rpm, 20 rpm to 22 rpm, 22 rpm to 24 rpm, 24 rpm to 26 rpm, 26 rpm to 28 rpm, 28 rpm to 30 rpm, 30 rpm to 32 rpm, 32 rpm to 34 rpm, 34 rpm to 36 rpm, 36 rpm to 38 rpm, 38 rpm to 40 rpm, 40 rpm to 42 rpm, 42 rpm to 44 rpm, 44 rpm to 46 rpm, 46 rpm to 48 rpm, 48 rpm to 50 rpm, 50 rpm to 52 rpm, 52 rpm to 54 rpm, 54 rpm to 56 rpm, 56 rpm to 58 rpm, 58 rpm to 60 rpm, 60 rpm to 62 rpm, 62 rpm to 64 rpm, 64 rpm to 66 rpm, 66 rpm to 68 rpm, 68 rpm to 70 rpm, and 70 rpm to 85 rpm.

The conveyor (KEA) is equipped with a motor (KEB) and a controller (KEC). The controller (KEC) sends a signal (KED) to and/or from the computer (COMP). In embodiments, the conveyor (KEA) is configured to convey the softgels (KCC) past a washing system (KFA). In embodiments, the washing system (KFA) is configured to wash the softgels (KCC) with a wash liquid (KEF) that is dispensed onto the softgels (KCC) through a spray nozzle (KEE) or a plurality of spray nozzles (KEE) to produce washed softgels (KEJ). In embodiments, the pressure drop across the spray nozzle (KEE) or a plurality of spray nozzles (KEE) includes one or more pressure drop ranges selected from the group consisting of 5 pounds per square inch (PSI) to 10 PSI, 10 PSI to 20 PSI, 20 PSI to 30 PSI, 30 PSI to 40 PSI, 40 PSI to 50 PSI, 50 PSI to 60 PSI, 60 PSI to 70 PSI, 70 PSI to 80 PSI, 80 PSI to 90 PSI, 90 PSI to 100 PSI, 100 PSI to 125 PSI, 125 PSI to 150 PSI, 150 PSI to 175 PSI, 175 PSI to 200 PSI, 200 PSI to 225 PSI, 225 PSI to 250 PSI, 250 PSI to 275 PSI, 275 PSI to 300 PSI, 300 PSI to 400 PSI, 400 PSI to 500 PSI, 500 PSI to 600 PSI, 600 PSI to 700 PSI, 700 PSI to 800 PSI, 800 PSI to 900 PSI, and 900 PSI to 1,000 PSI.

In embodiments, the washed softgels (KEJ) are conveyed away from the washing system (KFA) and are introduced to the input (KEG) of a drying system (FGA). In embodiments, the drying system (FGA) includes a dryer (KEH) that is configured to dry the washed softgels (KEJ) to produce washed and dried softgels (KEK). In embodiments, the dryer (KEH) is a rotary dryer (KEI) that rotates to dry the washed softgels (KEJ) and produce washed and dried softgels (KEK). In embodiments, the rotary dryer (KEI) rotates to dry the washed softgels (KEJ) and produce washed and dried softgels (KEK) at a revolutions per minute (RPM) that is selected from one or more from RPMs from the group consisting of 2 rpm to 4 rpm, 4 rpm to 6 rpm, 6 rpm to 8 rpm, 8 rpm to 10 rpm, 10 rpm to 12 rpm, 12 rpm to 14 rpm, 14 rpm to 16 rpm, 16 rpm to 18 rpm, 18 rpm to 20 rpm, 20 rpm to 22 rpm, 22 rpm to 24 rpm, 24 rpm to 26 rpm, 26 rpm to 28 rpm, 28 rpm to 30 rpm, 30 rpm to 32 rpm, 32 rpm to 34 rpm, 34 rpm to 36 rpm, 36 rpm to 38 rpm, 38 rpm to 40 rpm, 40 rpm to 42 rpm, 42 rpm to 44 rpm, 44 rpm to 46 rpm, 46 rpm to 48 rpm, 48 rpm to 50 rpm, 50 rpm to 52 rpm, 52 rpm to 54 rpm, 54 rpm to 56 rpm, 56 rpm to 58 rpm, 58 rpm to 60 rpm, 60 rpm to 62 rpm, 62 rpm to 64 rpm, 64 rpm to 66 rpm, 66 rpm to 68 rpm, 68 rpm to 70 rpm, and 70 rpm to 85 rpm.

In embodiments, the cannabinoid softgel encapsulation system (17K) produces softgels (KCC) that may be in bulk or bottled form. In embodiments, the cannabinoid softgel encapsulation system (17K) produces washed and dried softgels (KEK) that may be in bulk or bottled form. In embodiments, the softgels (KCC, KEK) have a bulk density that includes one or more bulk density ranges selected from the group consisting of 8 pounds per cubic foot to 10 pounds per cubic foot, 10 pounds per cubic foot to 12 pounds per cubic foot, 12 pounds per cubic foot to 14 pounds per cubic foot, 14 pounds per cubic foot to 16 pounds per cubic foot, 16 pounds per cubic foot to 18 pounds per cubic foot, 18 pounds per cubic foot to 20 pounds per cubic foot, 20 pounds per cubic foot to 22 pounds per cubic foot, 22 pounds per cubic foot to 24 pounds per cubic foot, 24 pounds per cubic foot to 26 pounds per cubic foot, 26 pounds per cubic foot to 28 pounds per cubic foot, 28 pounds per cubic foot to 30 pounds per cubic foot, 30 pounds per cubic foot to 32 pounds per cubic foot, 32 pounds per cubic foot to 34 pounds per cubic foot, 34 pounds per cubic foot to 36 pounds per cubic foot, 36 pounds per cubic foot to 38 pounds per cubic foot, 38 pounds per cubic foot to 40 pounds per cubic foot, 40 pounds per cubic foot to 42 pounds per cubic foot, 42 pounds per cubic foot to 44 pounds per cubic foot, 44 pounds per cubic foot to 46 pounds per cubic foot, 46 pounds per cubic foot to 48 pounds per cubic foot, 48 pounds per cubic foot to 50 pounds per cubic foot, 50 pounds per cubic foot to 52 pounds per cubic foot, 52 pounds per cubic foot to 54 pounds per cubic foot, 54 pounds per cubic foot to 56 pounds per cubic foot, 56 pounds per cubic foot to 58 pounds per cubic foot, 58 pounds per cubic foot to 60 pounds per cubic foot, 60 pounds per cubic foot to 62 pounds per cubic foot, 62 pounds per cubic foot to 64 pounds per cubic foot, 64 pounds per cubic foot to 66 pounds per cubic foot, 66 pounds per cubic foot to 68 pounds per cubic foot, 68 pounds per cubic foot to 70 pounds per cubic foot, 70 pounds per cubic foot to 72 pounds per cubic foot, 72 pounds per cubic foot to 74 pounds per cubic foot, 74 pounds per cubic foot to 76 pounds per cubic foot, 76 pounds per cubic foot to 78 pounds per cubic foot, and 78 pounds per cubic foot to 80 pounds per cubic foot.

FIG. 18'

FIG. 18' shows a simplistic diagram illustrating a multifunctional composition mixing module (6000) that is configured to generate a multifunctional composition from at least a portion of the *cannabis* (107, 207) that was harvested from each growing assembly (100, 200). In embodiments, the *cannabis* is first trimmed before being mixed with one or more from the group consisting of fiber-starch, binding agent, density improving textural supplement, moisture improving textural supplement, and insects. In embodiments, the *cannabis* is first trimmed and then grinded before being mixed with one or more from the group consisting of fiber-starch, binding agent, density improving textural supplement, moisture improving textural supplement, and insects.

FIG. 18' displays a *cannabis* distribution module (6A) including a *cannabis* tank (6A2) that is configured to accept at least a portion of the *cannabis* (107, 207) that was harvested from each growing assembly (100, 200). In embodiments, the *cannabis* is first trimmed before being introduced to the *cannabis* tank (6A). In embodiments, the *cannabis* is first trimmed and then grinded before being introduced to the *cannabis* tank (6A).

The *cannabis* tank (6A2) has an interior (6A3), a *cannabis* input (6A4), a *cannabis* conveyor (6A5), and a *cannabis* conveyor output (6A6). The *cannabis* tank (6A2) accepts *cannabis* to the interior (6A3) and regulates and controls an engineered amount of *cannabis* (6A1) downstream to be mixed to form a multifunctional composition. In embodiments, the *cannabis* tank (6A2) accepts trimmed *cannabis*

(TR1) to the interior (6A3). In embodiments, the *cannabis* tank (6A2) accepts ground *cannabis* (GR1) to the interior (6A3).

The *cannabis* conveyor (6A5) has an integrated *cannabis* mass sensor (6A7) that is configured to input and output a signal (6A8) to the computer (COMP). The *cannabis* conveyor motor (6A9) has a controller (6A10) that is configured to input and output a signal (6A11) to the computer (COMP). The *cannabis* mass sensor (6A7), *cannabis* conveyor (6A5), and *cannabis* conveyor motor (6A9) are coupled so as to permit the conveyance, distribution, or output of a precise flow of *cannabis* via a *cannabis* transfer line (6A12).

FIG. 18' displays a fiber-starch distribution module (6B) including a fiber-starch tank (6B2) that is configured to accept fiber-starch (6B1). The fiber-starch tank (6B2) has an interior (6B3), a fiber-starch input (6B4), a fiber-starch conveyor (6B5), and a fiber-starch conveyor output (6B6). The fiber-starch tank (6B2) accepts fiber-starch (6B1) to the interior (6B3) and regulates and controls an engineered amount of fiber-starch (6B1) downstream to be mixed to form a multifunctional composition. The fiber-starch conveyor (6B5) has an integrated fiber-starch mass sensor (6B7) that is configured to input and output a signal (6B8) to the computer (COMP). The fiber-starch conveyor motor (6B9) has a controller (6B10) that is configured to input and output a signal (6B11) to the computer (COMP). The fiber-starch mass sensor (6B7), fiber-starch conveyor (6B5), and fiber-starch conveyor motor (6B9) are coupled so as to permit the conveyance, distribution, or output of a precise flow of fiber-starch (6B1) via a fiber-starch transfer line (6B12).

FIG. 18' displays a binding agent distribution module (6C) including a binding agent tank (6C2) that is configured to accept a binding agent (6C1). The binding agent tank (6C2) has an interior (6C3), a binding agent input (6C4), a binding agent conveyor (6C5), and a binding agent conveyor output (6C6). The binding agent tank (6C2) accepts binding agent (6C1) to the interior (6C3) and regulates and controls an engineered amount of a binding agent (6C1) downstream to be mixed to form a multifunctional composition. The binding agent conveyor (6C5) has an integrated binding agent mass sensor (6C7) that is configured to input and output a signal (6C8) to the computer (COMP). The binding agent conveyor motor (6C9) has a controller (6C10) that is configured to input and output a signal (6C11) to the computer (COMP). The binding agent mass sensor (6C7), binding agent conveyor (6C5), and binding agent conveyor motor (6C9) are coupled so as to permit the conveyance, distribution, or output of a precise flow of binding agent (6C1) via a binding agent transfer line (6C12).

FIG. 18' displays a density improving textural supplement distribution module (6D) including a density improving textural supplement tank (6D2) that is configured to accept a density improving textural supplement (6D1). The density improving textural supplement tank (6D2) has an interior (6D3), a density improving textural supplement input (6D4), a density improving textural supplement conveyor (6D5), and a density improving textural supplement conveyor output (6D6). The density improving textural supplement tank (6D2) accepts density improving textural supplement (6D1) to the interior (6D3) and regulates and controls an engineered amount of a density improving textural supplement (6D1) downstream to be mixed to form a multifunctional composition. The density improving textural supplement conveyor (6D5) has an integrated density improving textural supplement mass sensor (6D7) that is configured to input and output a signal (6D8) to the computer (COMP). The density improving textural supplement conveyor motor (6D9) has a controller (6D10) that is configured to input and output a signal (6D11) to the computer (COMP). The density improving textural supplement mass sensor (6D7), density improving textural supplement conveyor (6D5), and density improving textural supplement conveyor motor (6D9) are coupled so as to permit the conveyance, distribution, or output of a precise flow of density improving textural supplement (6D1) via a density improving textural supplement transfer line (6D12).

FIG. 18' displays a moisture improving textural supplement distribution module (6E) including a moisture improving textural supplement tank (6E2) that is configured to accept a moisture improving textural supplement (6E1). The moisture improving textural supplement tank (6E2) has an interior (6E3), a moisture improving textural supplement input (6E4), a moisture improving textural supplement conveyor (6E5), and a moisture improving textural supplement conveyor output (6E6). The moisture improving textural supplement tank (6E2) accepts a moisture improving textural supplement (6E1) to the interior (6E3) and regulates and controls an engineered amount of a moisture improving textural supplement (6E1) downstream to be mixed to form a multifunctional composition. The moisture improving textural supplement conveyor (6E5) has an integrated moisture improving textural supplement mass sensor (6E7) that is configured to input and output a signal (6E8) to the computer (COMP). The moisture improving textural supplement conveyor motor (6E9) has a controller (6E10) that is configured to input and output a signal (6E11) to the computer (COMP). The moisture improving textural supplement mass sensor (6E7), moisture improving textural supplement conveyor (6E5), and moisture improving textural supplement conveyor motor (6E9) are coupled so as to permit the conveyance, distribution, or output of a precise flow of moisture improving textural supplement (6E1) via a moisture improving textural supplement transfer line (6E12).

FIG. 18' displays an insect distribution module (6G) including an insect tank (6G2) that is configured to accept insects (6G1). The insect tank (6G2) has an interior (6G3), an insect input (6G4), an insect conveyor (6G5), and an insect conveyor output (6G6). The insect tank (6G2) accepts insects (6G1) to the interior (6G3) and regulates and controls an engineered amount of insects (6G1) downstream to be mixed to form a multifunctional composition. The insect conveyor (6G5) has an integrated insect mass sensor (6G7) that is configured to input and output a signal (6G8) to the computer (COMP). The insect conveyor motor (6G9) has a controller (6G10) that is configured to input and output a signal (6G11) to the computer (COMP). The insect mass sensor (6G7), insect conveyor (6G5), and insect conveyor motor (6G9) are coupled so as to permit the conveyance, distribution, or output of a precise flow of insects (6G1) via an insect transfer line (6G12). In embodiments, the insects may be Orthoptera order of insects including grasshoppers, crickets, cave crickets, Jerusalem crickets, katydids, weta, lubber, acrida, and locusts. However, other orders of insects, such as cicadas, ants, mealworms, agave worms, worms, bees, centipedes, cockroaches, dragonflies, beetles, scorpions, tarantulas, and termites may be used as well.

FIG. 18' displays a multifunctional composition mixing module (6F) including a multifunctional composition tank (6F1) that is configured to accept a mixture including *cannabis*, fiber-starch (6B1), binding agent (6C1), density improving textural supplement (6D1), moisture improving textural supplement (6E1), and insects (6G1) via a multifunctional composition transfer line (6F0).

The multifunctional composition tank (6F1) has an interior (6F2), a multifunctional composition tank input (6F3), screw conveyor (6F9), multifunctional composition output (6F10). The multifunctional composition tank (6F1) accepts *cannabis*, fiber-starch (6B1), binding agent (6C1), density improving textural supplement (6D1), moisture improving textural supplement (6E1), and insects (6G1) to the interior (6F2) and mixes, regulates, and outputs a weighed multifunctional composition stream (6F22).

The multifunctional composition tank (6F1) has a top section (6F4), bottom section (6F5), at least one side wall (6F6), with a level sensor (6F7) positioned thereon that is configured to input and output a signal (6F8) to the computer (COMP). The screw conveyor (6F9) has a multifunctional composition conveyor motor (6F11) with a controller (6F12) that is configured to input and output a signal (6F13) to the computer (COMP). From the multifunctional composition output (6F10) of the multifunctional composition tank (6F1) is positioned a multifunctional composition weigh screw (6F14) that is equipped with a multifunctional composition weigh screw input (6F15), a multifunctional composition weigh screw output (6F16), and a mass sensor (6F17) that is configured to input and output a signal (6F18) to the computer (COMP). The multifunctional composition weigh screw (6F14) also has a weigh screw motor (6F19) with a controller (6F20) that is configured to input and output a signal (6F21) to the computer (COMP).

The multifunctional composition mixing module (6000) involves mixing the *cannabis* with fiber-starch materials, binding agents, density improving textural supplements, moisture improving textural supplements, and optionally insects, to form a multifunctional composition.

The multifunctional composition may be further processed to create foodstuffs not only including ada, bagels, baked goods, biscuits, bitterballen, bonda, breads, cakes, candies, cereals, chips, chocolate bars, chocolate, coffee, cokodok, confectionery, cookies, cooking batter, corn starch mixtures, crackers, crêpes, croissants, croquettes, croutons, dolma, dough, doughnuts, energy bars, flapjacks, french fries, frozen custard, frozen desserts, frying cakes, fudge, gelatin mixes, granola bars, gulha, hardtack, ice cream, khandvi, khanom buang, krumpets, meze, mixed flours, muffins, multi-grain snacks, nachos, nian gao, noodles, nougat, onion rings, pakora, pancakes, panforte, pastas, pastries, pie crust, pita chips, pizza, poffertjes, pretzels, protein powders, pudding, rice krispie treats, sesame sticks, smoothies, snacks, specialty milk, tele-bhaja, tempura, toffee, tortillas, totopo, turkish delights, or waffles.

In embodiments, the fiber-starch materials may be comprised of singular or mixtures of cereal-grain-based materials, grass-based materials, nut-based materials, powdered fruit materials, root-based materials, tuber-based materials, or vegetable-based materials. In embodiments, the fiber-starch mass ratio ranges from between about 33 pounds of fiber-starch per ton of multifunctional composition to about 600 pounds of fiber-starch per ton of multifunctional composition.

In embodiments, the binding agents may be comprised of singular or mixtures of agar, agave, alginin, arrowroot, carrageenan, collagen, cornstarch, egg whites, finely ground seeds, furcellaran, gelatin, guar gum, honey, katakuri starch, locust bean gum, pectin, potato starch, proteins, *psyllium* husks, sago, sugars, syrups, tapioca, vegetable gums, or xanthan gum. In embodiments, the binding agent mass ratio ranges from between about 5 pounds of binding agent per ton of multifunctional composition to about 300 pounds of binding agent per ton of multifunctional composition.

In embodiments, the density improving textural supplements may be comprised of singular or mixtures of extracted arrowroot starch, extracted corn starch, extracted lentil starch, extracted potato starch, or extracted tapioca starch. In embodiments, the density improving textural supplement mass ratio ranges from between about 5 pounds of density improving textural supplement per ton of multifunctional composition to about 300 pounds of density improving textural supplement per ton of multifunctional composition.

In embodiments, the moisture improving textural supplements may be comprised of singular or mixtures of almonds, brazil nuts, cacao, cashews, chestnuts, coconut, filberts, hazelnuts, Indian nuts, macadamia nuts, nut butters, nut oils, nut powders, peanuts, pecans, pili nuts, pine nuts, pinon nuts, pistachios, soy nuts, sunflower seeds, tiger nuts, and walnuts. In embodiments, the moisture improving textural supplement mass ratio ranges from between about 10 pounds of moisture improving textural supplement per ton of multifunctional composition to about 1000 pounds of moisture improving textural supplement per ton of multifunctional composition.

In embodiments, insects may be added to the multifunctional composition. In embodiments, the insect mass ratio ranges from between about 250 pounds of insects per ton of multifunctional composition to about 1500 pounds of insects per ton of multifunctional composition.

In embodiments, the *cannabis* ratio ranges from between about 25 pounds of *cannabis* per ton of multifunctional composition to about 1800 pounds of *cannabis* per ton of multifunctional composition. In embodiments, the *cannabis* ratio ranges from between about 1800 pounds of *cannabis* per ton of multifunctional composition to about 2000 pounds of *cannabis* per ton of multifunctional composition. In embodiments, the multifunctional composition includes *cannabis*, N-acetylglucosamine, bacteria, fungus, and parasites.

The multifunctional composition may be further processed to create pet foods by further mixing with animal fat, animal protein, animal skin, antibiotics, beef by-product meal, beef meal, beef, carcasses of beef, carcasses of chicken, carcasses of fish, carcasses of lamb, carcasses of pigs, chicken by-product meal, chicken meal, chicken, chicken eggs, eggs, fish meal, fish oil, fish scales, flaxseed, lamb by-product meal, lamb meal, lamb, mammal by-product meal, mammal meal, pork by-product meal, pork meal, pork, shrimp, soybean oil, or sugar. The multifunctional composition may be further processed to create pet foods by further mixing with cannabinoids including cannabidiol to alleviate arthritis in pets.

In embodiments, the pet food is fed to pets, the pets include dogs and cats. In embodiments, the pet food is fed to pets, the pets include amphibians, arachnids, arthropods, aviary birds, bats, burros, canaries, cats, centipedes, chickens, chinchillas, cockatiels, crabs, crickets, dogs, doves, ducks, falcons, ferrets, finches, freshwater fish, geese, gerbils, goats, guinea pigs, hamsters, hawks, hedgehogs, horses, invertebrates, insects, land invertebrates, lizards, llamas, lorikeets, lovebirds, mice, miniature horses, mites, worms, mynah birds, octopus, parakeets, parrots, pheasants, pigeons, pond fish, ponies, pot-bellied pigs, quail, rabbits, raccoons, rats, ring-tail possum, saltwater fish, scorpions, short-tailed possum, shrimp, snails, squirrels, sugar gliders, tarantulas, tortoises, toucans, turkeys, or turtles.

In embodiments, the pet food is fed to pets, the pets include Anthocoridae, minute pirate bugs, pirate bugs, flower bugs, the genus Orius, omnivorous bugs, carnivorous bugs, Orthoptera order of insects, grasshoppers, crickets, katydids, weta, lubber, acrida, locusts, mites, spider mites, predatory mites, Neoseiulus Fallacis, genus of mites that are in the Phytoseiidae family, arthropods, beetles, cicadas, beetles, nematodes, mealworms, bats, mammals of the order Chiroptera, yellow mealworm beetles, *Tenebrio Molitor, Tetranychus Urticae*, carnivorous arthropods, omnivorous arthropods, green lacewings, insects in the family Chrysopidae, insects in the order Neuroptera, mantidflies, antlions, *Encarsia Formosa*, whitefly parasites, ladybugs, spiders, orb-weaving spiders, arachnids, members of the spider family Araneidae, praying mantis, arachnids, eight-legged arthropods, and six-legged arthropods.

In embodiments, the pet food is shaped, cooked, flavored as disclosed herein. In embodiments, the pet food is kibble, wet, or canned. In embodiments, the pet food includes a water content ranging from between 1 weight percent of water to 2 weight percent of water, 2 weight percent of water to 3 weight percent of water, 3 weight percent of water to 4 weight percent of water, 4 weight percent of water to 5 weight percent of water, 5 weight percent of water to 6 weight percent of water, 6 weight percent of water to 7 weight percent of water, 7 weight percent of water to 8 weight percent of water, 8 weight percent of water to 9 weight percent of water, 9 weight percent of water to 10 weight percent of water, 10 weight percent of water to 11 weight percent of water, 11 weight percent of water to 12 weight percent of water, 12 weight percent of water to 13 weight percent of water, 13 weight percent of water to 14 weight percent of water, 14 weight percent of water to 15 weight percent of water, 15 weight percent of water to 16 weight percent of water, 16 weight percent of water to 17 weight percent of water, 17 weight percent of water to 18 weight percent of water, 18 weight percent of water to 19 weight percent of water, and 19 weight percent of water to 20 weight percent of water, 20 weight percent of water to 25 weight percent of water, 25 weight percent of water to 30 weight percent of water, 30 weight percent of water to 35 weight percent of water, 35 weight percent of water to 40 weight percent of water, 40 weight percent of water to 50 weight percent of water, 50 weight percent of water to 60 weight percent of water, 60 weight percent of water to 65 weight percent of water, 65 weight percent of water to 70 weight percent of water.

FIG. 19'

FIG. 19' illustrates a single fully-grown Beaufort Budman III plant.

FIG. 20'

FIG. 20' illustrates zoomed-in view of a budding or flowering plant.

FIG. 21'

FIG. 21' illustrates a single leaf of Beaufort Budman III.

FIG. 22'

FIG. 22' illustrates a trimmed and dried bud (reproductive structure) of Beaufort Budman III.

FIGS. 19'-22' illustrate the overall appearance of the Beaufort Budman III. These photographs show the colors as true as it is reasonably possible to obtain in reproductions of this type. Colors in the photographs may differ slightly from the color values cited in the detailed botanical description which accurately describe the colors of Beaufort Budman III.

This disclosure relates to a new and distinct hybrid plant named Beaufort Budman III characterized by a mixture of *Cannabis sativa* L. ssp. *Sativa* X *Cannabis sativa* L. ssp. *Indica* (Lam.);

Within the leaves, seeds, stems, roots, or any reproductive structures, Beaufort Budman III has a:

(a) a cannabidiol content ranging from 0.125 weight percent to less than 5 weight percent;
(b) a tetrahydrocannabinol ranging from 5 weight percent to 63 weight percent;
(c) an energy content ranging from between 2,500 British Thermal Units per pound to 15,000 British Thermal Units per pound;
(d) a carbon content ranging from between 20 weight percent to 65 weight percent;
(e) an oxygen content ranging from between 12 weight percent to 55 weight percent;
(f) a hydrogen content ranging from between 2 weight percent to 20 weight percent;
(g) an ash content ranging from between 2.5 weight percent to 30 weight percent;
(h) volatiles content ranging from between 30 weight percent to 90 weight percent;
(i) a nitrogen content ranging from between 1 weight percent to 10 weight percent;
(j) a sulfur content ranging from between 0.01 weight percent to 8 weight percent;
(k) a chlorine content ranging from 0.05 weight percent to 5 weight percent;
(l) a sodium content ranging from 0.02 weight percent to 15 weight percent;
(m) a potassium content ranging from 0.05 weight percent to 15 weight percent;
(n) an iron content ranging from 0.01 weight percent to 13 weight percent;
(o) a magnesium content ranging from 0.02 weight percent to 10 weight percent;
(p) a phosphorous content ranging from 0.05 weight percent to 12 weight percent;
(q) a calcium content ranging from 0.03 weight percent to 10 weight percent;
(r) a zinc content ranging from 0.01 weight percent to 5 weight percent;
(s) a cellulose content ranging from 25 weight percent to 75 weight percent;
(t) a lignin content ranging from 3 weight percent to 35 weight percent;
(u) a hemicellulose content ranging from 3 weight percent to 30 weight percent;
(v) a fat content ranging from 5 weight percent to 35 weight percent;
(w) a fiber content ranging from 5 weight percent to 75 weight percent; and
(x) a protein content ranging from 5 weight percent to 35 weight percent;
wherein:
the *Cannabis Sativa* L. ssp *indica* content ranges from 15% to 65%;
the *Cannabis Sativa* L. ssp *sativa* content ranges from 20% to 70%.

In embodiments, Beaufort Budman III also includes: a N-acetylglucosamine content ranging from between: 0.050 parts per million to 0.100 parts per million, 0.100 parts per million to 0.200 parts per million, 0.200 parts per million to 0.400 parts per million, 0.400 parts per million to 0.800 parts per million, 0.800 parts per million to 1.600 parts per million, 1.600 parts per million to 3.200 parts per million, 3.200 parts per million to 6.400 parts per million, 6.4 parts per million to 12.8 parts per million, 12.8 parts per million to 25.6 parts per million, 25 parts per million to 50 parts per million, 50 parts per million to 100 parts per million, 100 parts per million to 200 parts per million, 200 parts per million to 400 parts per million, 400 parts per million to 800 parts per million, 800 parts per million to 1600 parts per million, 1600 parts per million to 3200 parts per million, 3200 parts per million to 6400 parts per million, 6400 parts per million to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, 14 weight percent to 15 weight percent, 15 weight percent to 16 weight percent, 16 weight percent to 17 weight percent, 17 weight percent to 18 weight percent, 18 weight percent to 19 weight percent, 19 weight percent to 20 weight percent, 20 weight percent to 21 weight percent, 21 weight percent to 22 weight percent, 22 weight percent to 23 weight percent, 23 weight percent to 24 weight percent, 24 weight percent to 25 weight percent, 25 weight percent to 30 weight percent, 30 weight percent to 35 weight percent, 35 weight percent to 40 weight percent, 40 weight percent to 45 weight percent, 45 weight percent to 50 weight percent, 50 weight percent to 55 weight percent, 55 weight percent to 60 weight percent, 60 weight percent to 65 weight percent, 65 weight percent to 70 weight percent, 70 weight percent to 75 weight percent, 75 weight percent to 80 weight percent, 80 weight percent to 85 weight percent, 85 weight percent to 90 weight percent, 90 weight percent to 95 weight percent, 95 weight percent to 95.25 weight percent, 95.25 weight percent to 95.50 weight percent, 95.50 weight percent to 95.75 weight percent, 95.75 weight percent to 96.00 weight percent, 96.00 weight percent to 96.25 weight percent, 96.25 weight percent to 96.50 weight percent, 96.50 weight percent to 96.75 weight percent, 96.75 weight percent to 97.00 weight percent, 97.00 weight percent to 97.25 weight percent, 97.25 weight percent to 97.50 weight percent, 97.50 weight percent to 97.75 weight percent, 97.75 weight percent to 98.00 weight percent, 98.00 weight percent to 98.25 weight percent, 98.25 weight percent to 98.50 weight percent, 98.50 weight percent to 98.75 weight percent, 98.75 weight percent to 99.00 weight percent, 99.00 weight percent to 99.25 weight percent, 99.25 weight percent to 99.50 weight percent, 99.50 weight percent to 99.75 weight percent, and 99.75 weight percent to 99.99 weight percent.

In embodiments, Beaufort Budman III also includes: a fungus content ranging from between: 0.050 parts per million to 0.100 parts per million, 0.100 parts per million to 0.200 parts per million, 0.200 parts per million to 0.400 parts per million, 0.400 parts per million to 0.800 parts per million, 0.800 parts per million to 1.600 parts per million, 1.600 parts per million to 3.200 parts per million, 3.200 parts per million to 6.400 parts per million, 6.4 parts per million to 12.8 parts per million, 12.8 parts per million to 25.6 parts per million, 25 parts per million to 50 parts per million, 50 parts per million to 100 parts per million, 100 parts per million to 200 parts per million, 200 parts per million to 400 parts per million, 400 parts per million to 800 parts per million, 800 parts per million to 1600 parts per million, 1600 parts per million to 3200 parts per million, 3200 parts per million to 6400 parts per million, 6400 parts per million to 1 weight percent.

In embodiments, Beaufort Budman III also includes: a bacteria content ranging from between: 0.05 colony-forming units per gram (CFU/g) to 0.100 CFU/g, 0.1 CFU/g to 0.2 CFU/g, 0.2 CFU/g to 0.4 CFU/g, 0.4 CFU/g to 0.8 CFU/g, 0.8 CFU/g to 1.6 CFU/g, 1.6 CFU/g to 3.2 CFU/g, 3.2 CFU/g to 6.4 CFU/g, 6.4 CFU/g to 12.8 CFU/g, 12.8 CFU/g to 25 CFU/g, 25 CFU/g to 50 CFU/g, 50 CFU/g to 100 CFU/g, 100 CFU/g to 200 CFU/g, 200 CFU/g to 400 CFU/g, 400 CFU/g to 800 CFU/g, 800 CFU/g to 1,600 CFU/g, 1,600 CFU/g to 3,200 CFU/g, 3,200 CFU/g to 6,400 CFU/g, 32,000 CFU/g to 320,000 CFU/g, 320,000 CFU/g to 3,200,000 CFU/g, 3,200,000 CFU/g to 32,000,000 CFU/g.

In embodiments, Beaufort Budman III also includes: a fungus content ranging from between: 0.05 colony-forming units per gram (CFU/g) to 0.100 CFU/g, 0.1 CFU/g to 0.2 CFU/g, 0.2 CFU/g to 0.4 CFU/g, 0.4 CFU/g to 0.8 CFU/g, 0.8 CFU/g to 1.6 CFU/g, 1.6 CFU/g to 3.2 CFU/g, 3.2 CFU/g to 6.4 CFU/g, 6.4 CFU/g to 12.8 CFU/g, 12.8 CFU/g to 25 CFU/g, 25 CFU/g to 50 CFU/g, 50 CFU/g to 100 CFU/g, 100 CFU/g to 200 CFU/g, 200 CFU/g to 400 CFU/g, 400 CFU/g to 800 CFU/g, 800 CFU/g to 1,600 CFU/g, 1,600 CFU/g to 3,200 CFU/g, 3,200 CFU/g to 6,400 CFU/g, 32,000 CFU/g to 320,000 CFU/g, 320,000 CFU/g to 3,200,000 CFU/g, 3,200,000 CFU/g to 32,000,000 CFU/g.

In embodiments, Beaufort Budman III also includes: an alanine content ranging from between: 500 parts per million to 1000 parts per million, 1000 parts per million to 5000 parts per million, 5000 parts per million to 7500 parts per million, 7500 parts per million to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, or 14 weight percent to 15 weight percent.

In embodiments, Beaufort Budman III also includes: an arginine content ranging from between: 500 parts per million to 1000 parts per million, 1000 parts per million to 5000 parts per million, 5000 parts per million to 7500 parts per million, 7500 parts per million to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, or 14 weight percent to 15 weight percent.

In embodiments, Beaufort Budman III also includes: an aspartic acid content ranging from between: 500 parts per million to 1000 parts per million, 1000 parts per million to 5000 parts per million, 5000 parts per million to 7500 parts per million, 7500 parts per million to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, or 14 weight percent to 15 weight percent.

In embodiments, Beaufort Budman III also includes: a glutamic acid content ranging from between: 500 parts per million to 1000 parts per million, 1000 parts per million to 5000 parts per million, 5000 parts per million to 7500 parts per million, 7500 parts per million to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, or 14 weight percent to 15 weight percent.

In embodiments, Beaufort Budman III also includes: a glycine content ranging from between: 500 parts per million to 1000 parts per million, 1000 parts per million to 5000 parts per million, 5000 parts per million to 7500 parts per million, 7500 parts per million to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, or 14 weight percent to 15 weight percent.

In embodiments, Beaufort Budman III also includes: a histidine content ranging from between: 500 parts per million to 1000 parts per million, 1000 parts per million to 5000 parts per million, 5000 parts per million to 7500 parts per million, 7500 parts per million to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, or 14 weight percent to 15 weight percent.

In embodiments, Beaufort Budman III also includes: an isoleucine content ranging from between: 500 parts per million to 1000 parts per million, 1000 parts per million to 5000 parts per million, 5000 parts per million to 7500 parts per million, 7500 parts per million to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, or 14 weight percent to 15 weight percent.

In embodiments, Beaufort Budman III also includes: a Leucine content ranging from between: 500 parts per million to 1000 parts per million, 1000 parts per million to 5000 parts per million, 5000 parts per million to 7500 parts per million, 7500 parts per million to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, or 14 weight percent to 15 weight percent.

In embodiments, Beaufort Budman III also includes: a lysine content ranging from between: 500 parts per million to 1000 parts per million, 1000 parts per million to 5000 parts per million, 5000 parts per million to 7500 parts per million, 7500 parts per million to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, or 14 weight percent to 15 weight percent.

In embodiments, Beaufort Budman III also includes: a proline content ranging from between: 500 parts per million to 1000 parts per million, 1000 parts per million to 5000 parts per million, 5000 parts per million to 7500 parts per million, 7500 parts per million to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, or 14 weight percent to 15 weight percent.

In embodiments, Beaufort Budman III also includes: a serine content ranging from between: 500 parts per million to 1000 parts per million, 1000 parts per million to 5000 parts per million, 5000 parts per million to 7500 parts per million, 7500 parts per million to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, or 14 weight percent to 15 weight percent.

In embodiments, Beaufort Budman III also includes: a threonine content ranging from between: 500 parts per million to 1000 parts per million, 1000 parts per million to 5000 parts per million, 5000 parts per million to 7500 parts per million, 7500 parts per million to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, or 14 weight percent to 15 weight percent.

In embodiments, Beaufort Budman III also includes: a tyrosine content ranging from between: 500 parts per million to 1000 parts per million, 1000 parts per million to 5000 parts per million, 5000 parts per million to 7500 parts per million, 7500 parts per million to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, or 14 weight percent to 15 weight percent.

In embodiments, Beaufort Budman III also includes: a valine content ranging from between: 500 parts per million to 1000 parts per million, 1000 parts per million to 5000 parts per million, 5000 parts per million to 7500 parts per million, 7500 parts per million to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, or 14 weight percent to 15 weight percent.

In embodiments, Beaufort Budman III also includes: a pH ranging from between: 6.00 to 6.05, 6.05 to 6.10, 6.10 to 6.15, 6.15 to 6.20, 6.20 to 6.25, 6.25 to 6.30, 6.30 to 6.35, 6.35 to 6.40, 6.40 to 6.45, 6.45 to 6.50, 6.50 to 6.55, 6.55 to 6.60, 6.60 to 6.65, 6.65 to 6.70, 6.70 to 6.75, 6.75 to 6.80, 6.80 to 6.85, 6.85 to 6.90, 6.90 to 6.95, 6.95 to 7.00, 7.00 to 7.05, 7.05 to 7.10, 7.10 to 7.15, 7.15 to 7.20, 7.20 to 7.25, 7.25 to 7.30, 7.30 to 7.35, 7.35 to 7.40, 7.40 to 7.45, 7.45 to 7.50, 7.50 to 7.55, 7.55 to 7.60, 7.60 to 7.65, 7.65 to 7.70, 7.70 to 7.75, 7.75 to 7.80, 7.80 to 7.85, 7.85 to 7.90, 7.90 to 7.95, 7.95 to 8.00, 8.00 to 8.05, 8.05 to 8.10, 8.10 to 8.15, 8.15 to 8.20, 8.20 to 8.25, 8.25 to 8.30, 8.30 to 8.35, 8.35 to 8.40, 8.40 to 8.45, or 8.45 to 8.50.

In embodiments, Beaufort Budman III also includes: a water activity (Aw) ranging from between: 0.05 to 0.1, 0.1 to 0.15, 0.15 to 0.2, 0.2 to 0.25, 0.25 to 0.3, 0.3 to 0.35, 0.35 to 0.4, 0.4 to 0.45, 0.45 to 0.5, 0.5 to 0.6, or 0.6 to 0.7, 0.7 to 0.8, or 0.8 to 0.9.

The present plant was developed in the United States. In embodiments, the plant may be propagated from seed. In embodiments, the plant is asexually propagated using stem cuttings especially for large-scale production. The plant may be grown indoors, such as for example in a greenhouse, building, or other suitable indoor growing environment under controlled conditions. In embodiments, the plant is grown outdoors. The density of the plant ranges from 3.5 pounds per cubic foot to about 14.999 pounds per cubic foot or a ground bulk density ranging from between about 15 pounds per cubic foot to about 50 pounds per cubic foot.

In embodiments, the plants undergoes a deliberately stressed training method, including: (a) providing a branch of a *cannabis* plant; (b) after step (a), squeezing and/or bending the branch; (c) after step (b), allowing the plant to heal. In embodiments, after step (b) and before step (c), inspecting the plant for tears in the outside plant tissue and optionally taping the branch that was squeezed and/or bended.

Plant

Exposed Plant Structure: This is an aggressive annual, dioecious plant. The natural height at 6 months old for indoor growth is 40 inches to 120 inches, and, and for outdoor growth is 50 inches to 160 inches. A detailed list of characteristics follows:

Botanical Classification:
Mixture of *Cannabis sativa* L. ssp. *Sativa* X *Cannabis sativa* L. ssp. *Indica* (Lam.).
Percentages:
A new and distinct hybrid plant named Beaufort Budman III, as illustrated and described herein characterized by a mixture of:
 (i) *Cannabis Sativa* L. ssp *indica*, and
 (ii) *Cannabis Sativa* L. ssp *sativa*;
Within the leaves, seeds, stems, roots, or any reproductive structures, Beaufort Budman III has a:
(a) a cannabidiol content ranging from 0.125 weight percent to less than 5 weight percent;
(b) a tetrahydrocannabinol ranging from 5 weight percent to 63 weight percent;
(c) an energy content ranging from between 2,500 British Thermal Units per pound to 15,000 British Thermal Units per pound;
(d) a carbon content ranging from between 20 weight percent to 65 weight percent;
(e) an oxygen content ranging from between 12 weight percent to 55 weight percent;
(f) a hydrogen content ranging from between 2 weight percent to 20 weight percent;
(g) an ash content ranging from between 2.5 weight percent to 30 weight percent;
(h) volatiles content ranging from between 30 weight percent to 90 weight percent;
(i) a nitrogen content ranging from between 1 weight percent to 10 weight percent;
(j) a sulfur content ranging from between 0.01 weight percent to 8 weight percent;
(k) a chlorine content ranging from 0.05 weight percent to 5 weight percent;
(l) a sodium content ranging from 0.02 weight percent to 15 weight percent;
(m) a potassium content ranging from 0.05 weight percent to 15 weight percent;
(n) an iron content ranging from 0.01 weight percent to 13 weight percent;
(o) a magnesium content ranging from 0.02 weight percent to 10 weight percent;
(p) a phosphorous content ranging from 0.05 weight percent to 12 weight percent;
(q) a calcium content ranging from 0.03 weight percent to 10 weight percent;
(r) a zinc content ranging from 0.01 weight percent to 5 weight percent;
(s) a cellulose content ranging from 25 weight percent to 75 weight percent;
(t) a lignin content ranging from 3 weight percent to 35 weight percent;
(u) a hemicellulose content ranging from 3 weight percent to 30 weight percent;
(v) a fat content ranging from 5 weight percent to 35 weight percent;
(w) a fiber content ranging from 5 weight percent to 75 weight percent; and
(x) a protein content ranging from 5 weight percent to 35 weight percent;

wherein:

the *Cannabis Sativa* L. ssp *indica* content ranges from 15% to 65%;

the *Cannabis Sativa* L. ssp *sativa* content ranges from 20% to 70%.

PROPAGATION: This plant may be perpetuated by stem cuttings. Seed propagation is possible but not preferred due to lack of efficiency when compared to asexual reproduction.

TIME TO INITIATE ROOTS IN SUMMER: about 4 to 20 days.

PLANT DESCRIPTION: Annual, dioecious flowering shrub; multi-stemmed; vigorous; freely branching; removal of the terminal bud enhances lateral branch development.

In embodiments, the turgor pressure within the plants includes the force within the cell that pushes the plasma membrane against the cell wall. In embodiments, the turgor pressure within the plants includes one or more pressure ranges selected from the group consisting of: 0.5 bars to 0.6 bars, 0.6 bars to 0.7 bars, 0.7 bars to 0.8 bars, 0.8 bars to 0.9 bars, 0.9 bars to 1 bars, 1 bars to 1.1 bars, 1.1 bars to 1.2 bars, 1.2 bars to 1.3 bars, 1.3 bars to 1.4 bars, 1.4 bars to 1.5 bars, 1.5 bars to 1.6 bars, 1.6 bars to 1.7 bars, 1.7 bars to 1.8 bars, 1.8 bars to 1.9 bars, 1.9 bars to 2 bars, 2 bars to 2.1 bars, 2.1 bars to 2.2 bars, 2.2 bars to 2.3 bars, 2.3 bars to 2.4 bars, 2.4 bars to 2.5 bars, 2.5 bars to 2.6 bars, 2.6 bars to 2.7 bars, 2.7 bars to 2.8 bars, 2.8 bars to 2.9 bars, and 2.9 bars to 3 bars.

MATURE HABIT: Tap-rooted annual, with extensive fibrous root system, upright and much branched aerial portion of plant. The growth form of all cloned plants was highly manipulated by systematic removal of terminal buds, inducing a greater branching habit. Many petiole scars on stems from systematic removal of large shade leaves. In this habit, these are obviously very vigorous annual herbs.

First Year Stems:

Shape: Round. Moderate to fine pubescence.

First year stem strength: Medium to Strong.

First year stem color:

In embodiments, the young stem has a color that is comprised of one or more from the group consisting of: light green (144C), yellow (001A) or yellow green (001A), dark green (144A) with shades of yellow (001A), yellow orange (011A), orange (024A), orange red (033B), orange pink (027A), red (033A), dark purple red (046A), light red pink (039C), red pink (043C), dark pink red (045D), purple red (054A), light blue pink (055C), purple (058A), purple red (059D), blue pink (062A), light blue violet (069C), violet blue (089A), violet (075A), dark violet (079A), blue violet (083D), blue (100A), dark blue (103A), light blue (104D), light green blue (110C), green blue (111A), grey blue (115C), green blue (125C), white (155A), orange brown (169A), brown (172A), brown purple (178A), orange pink (179D) (The Royal Horticultural Society Colour Chart, 1995 Ed.).

In embodiments, the older stem has a color that is comprised of one or more from the group consisting of: light green (144C), yellow (001A) or yellow green (001A), dark green (144A) with shades of yellow (001A), yellow orange (011A), orange (024A), orange red (033B), orange pink (027A), red (033A), dark purple red (046A), light red pink (039C), red pink (043C), dark pink red (045D), purple red (054A), light blue pink (055C), purple (058A), purple red (059D), blue pink (062A), light blue violet (069C), violet blue (089A), violet (075A), dark violet (079A), blue violet (083D), blue (100A), dark blue (103A), light blue (104D), light green blue (110C), green blue (111A), grey blue (115C), green blue (125C), white (155A), orange brown (169A), brown (172A), brown purple (178A), orange pink (179D) (The Royal Horticultural Society Colour Chart, 1995 Ed.).

Stem Diameter:

In embodiments, the stem diameter at the soil line is 1.05 inches to 7.15 inches. In embodiments, the middle of plant average stem diameter is 0.2 inches to 1.5 inches.

In embodiments, the stem diameter at the soil line is 0.75 inches to 4 inches. In embodiments, the middle of plant average stem diameter is 0.2 inches to 1.5 inches.

In embodiments, the stem diameter at the soil line is 0.25 inches to 2 inches. In embodiments, the middle of plant average stem diameter is 0.1 inches to 0.75 inches.

Stem Height:

In embodiments, the stem height is 3 feet to 9 feet. In embodiments, the stem height is 3 feet to 9 feet. In embodiments, the stem height is 1.5 feet to 4.5 feet. In embodiments, the stem height is 5.5 feet to 11.25 feet. In embodiments, the stem height is 10 feet to 20 feet. In embodiments, the stem height is 11 feet to 24.5 feet. In embodiments, the stem height is 18 feet to 32 feet.

Stem Strength:

In embodiments, lateral stems are strong but benefit from being staked during flowering. In embodiments, the stem has a hollow cross-section. In embodiments, the stem is ribbed having ribs that run parallel to the stem. In embodiments, the stem is hollow.

Internode Spacing:

In embodiments, from between 1.15 inches to 2 inches at the top half of the plant. In embodiments, from between 1.15 inches to 3.15 inches at the bottom half of the plant. In embodiments, from between 0.75 inches to 5 inches at the bottom half of the plant. In embodiments, from between 0.35 inches to 3.15 inches at the bottom half of the plant. In embodiments, from between 0.35 inches to 4.15 inches at the bottom half of the plant. In embodiments, from between 1.15 inches to 7.15 inches at the bottom half of the plant. In embodiments, from between 2 inches to 9 inches at the bottom half of the plant. In embodiments, from between 2 inches to 9 inches at the bottom half of the plant.

Foliage Description:

Texture (upper and lower surfaces): Upper surface scabrid with non-visible stiff hairs; lower surface more or less densely pubescent, covered with sessile glands.

Branch strength: Strong to medium to weak.

Branch description: In embodiments, branches may be short, dense with short, broad leaflets. In embodiments, branches may be medium length, dense with long, broad or compact leaflets. In embodiments, lateral branches off the main stem may be fine and of medium strength, they contain few leaves with many bud sites extending up the branch. In embodiments, branches may be long and sparse.

Leaf rrangement: In embodiments, palmately compound (digitate) leaves with 5 to 9 serrates leaflets per leaf. In embodiments, palmately compound (digitate) leaves with 3 to 7 serrates leaflets per leaf. In embodiments, palmately compound (digitate) leaves with 7 to 11 serrates leaflets per leaf. In embodiments, palmately compound (digitate) leaves with 3 to 11 serrates leaflets per leaf. In embodiments, palmately compound (digitate) leaves with 5 to 11 serrates leaflets per leaf. In embodiments, the bottom two leaflets may be angled upwards at about a 45-degree angle towards the middle leaflet. In embodiments, the bottom two leaflets extend out from the petiole at approximately 180 degrees.

Leaf width: In embodiments, the average leaf width ranges from between 1.5 inches to 12 inches. In embodiments, the average leaf width ranges from between 1.5 inches to 3 inches. In embodiments, the average leaf width ranges from between 1.5 inches to 4 inches. In embodiments, the average leaf width ranges from between 1.5 inches to 5 inches. In embodiments, the average leaf width ranges from between 1.5 inches to 6 inches. In embodiments, the average leaf width ranges from between 1.5 inches to 7 inches. In embodiments, the average leaf width ranges from between 1.5 inches to 8 inches. In embodiments, the average leaf width ranges from between 1.5 inches to 10 inches.

Leaf length: In embodiments, the average leaf length ranges from between 1.5 inches to 12 inches. In embodiments, the average leaf length ranges from between 1.5 inches to 3 inches. In embodiments, the average leaf length ranges from between 1.5 inches to 4 inches. In embodiments, the average leaf length ranges from between 1.5 inches to 5 inches. In embodiments, the average leaf length ranges from between 1.5 inches to 6 inches. In embodiments, the average leaf length ranges from between 1.5 inches to 7 inches. In embodiments, the average leaf length ranges from between 1.5 inches to 8 inches. In embodiments, the average leaf length ranges from between 1.5 inches to 10 inches.

Leaf venation pattern: Venation of each leaf is palmately compound (digitate), with serrated leaflets. In embodiments, the lateral venation extends off the main vein to each serrated tip. In embodiments, the sublateral veins extend to the notch of each serration rather than the tip. In embodiments, each serration has a lateral vein extending to its tip from the central (primary) vein of the leaflet. In embodiments, the from each lateral vein there is usually a single spur vein (sublateral vein) extending to the notch of each serration.

Leaf venation Color: Leaf venation is very colorful with one or more from the group consisting of: light green (144C), dark green (144A), yellow (001A), yellow orange (011A), orange (024A), orange red (033B), orange pink (027A), red (033A), dark purple red (046A), light red pink (039C), red pink (043C), dark pink red (045D), purple red (054A), light blue pink (055C), purple (058A), purple red (059D), blue pink (062A), light blue violet (069C), violet blue (089A), violet (075A), dark violet (079A), blue violet (083D), blue (100A), dark blue (103A), light blue (104D), light green blue (110C), green blue (111A), grey blue (115C), green blue (125C), green (130A), dark green (132A), light green (149B), white (155A), orange brown (169A), brown (172A), brown purple (178A), orange pink (179D) (The Royal Horticultural Society Colour Chart, 1995 Ed.).

Petiole length: Average length of petiole of fan leaves 1.5 inches to 8 inches. In embodiments, Petioles are very study and appear a light brown (166C) or light green (144C) (The Royal Horticultural Society Colour Chart, 1995 Ed.). Petioles are very study.

Petiole Color: Petioles are very colorful with one or more from the group consisting of: light green (144C), dark green (144A), yellow (001A), yellow orange (011A), orange (024A), orange red (033B), orange pink (027A), red (033A), dark purple red (046A), light red pink (039C), red pink (043C), dark pink red (045D), purple red (054A), light blue pink (055C), purple (058A), purple red (059D), blue pink (062A), light blue violet (069C), violet blue (089A), violet (075A), dark violet (079A), blue violet (083D), blue (100A), dark blue (103A), light blue (104D), light green blue (110C), green blue (111A), grey blue (115C), green blue (125C), green (130A), dark green (132A), light green (149B), white (155A), orange brown (169A), brown (172A), brown purple (178A), orange pink (179D) (The Royal Horticultural Society Colour Chart, 1995 Ed.).

Color of emerging foliage (upper surface): In embodiments, the color of emerging foliage is have a color comprised of one or more from the group consisting of: light green (144C), dark green (144A), yellow (001A), yellow orange (011A), orange (024A), orange red (033B), orange pink (027A), red (033A), dark purple red (046A), light red pink (039C), red pink (043C), dark pink red (045D), purple red (054A), light blue pink (055C), purple (058A), purple red (059D), blue pink (062A), light blue violet (069C), violet blue (089A), violet (075A), dark violet (079A), blue violet (083D), blue (100A), dark blue (103A), light blue (104D), light green blue (110C), green blue (111A), grey blue (115C), green blue (125C), green (130A), dark green (132A), light green (149B), white (155A), orange brown (169A), brown (172A), brown purple (178A), orange pink (179D) (The Royal Horticultural Society Colour Chart, 1995 Ed.).

Vegetative bud (reproductive structure) description: In embodiments, the dried flower buds (reproductive structures) are a light green (144C), green (124A), or dark green (144A), small to large in nature, diffuse and airy, and coated with glandular trichomes. In embodiments, the fragrance may be quite spicy with an earthy aroma with noticeable hints of pine, clove, citrus, pepper, candy, and tropical fruit. In embodiments, the fragrance is slightly sweet, having a fruity, fresh, musky, cotton-candy, or grape-soda type smell.

Flower description: In embodiments, inflorescence (buds, or reproductive structures) may be conical, spherical, cylindrical, tubular, oblong, or rectangular. In embodiments, the flower, bud, or reproductive structures may be devoid of any petals. In embodiments, the flower, bud, or reproductive structures are comprised of a cluster of false spikes with single flowers. These flowers are often paired and enclosed by a bracteole. In embodiments, the wet flower buds have a color comprised of one or more from the group consisting of: light green (144C), dark green (144A), yellow (001A), yellow orange (011A), orange (024A), orange red (033B), orange pink (027A), red (033A), dark purple red (046A), light red pink (039C), red pink (043C), dark pink red (045D), purple red (054A), light blue pink (055C), purple (058A), purple red (059D), blue pink (062A), light blue violet (069C), violet blue (089A), violet (075A), dark violet (079A), blue violet (083D), blue (100A), dark blue (103A), light blue (104D), light green blue (110C), green blue (111A), grey blue (115C), green blue (125C), green (130A), dark green (132A), light green (149B), white (155A), orange brown (169A), brown (172A), brown purple (178A), orange pink (179D) (The Royal Horticultural Society Colour Chart, 1995 Ed.). In embodiments, the wet flower buds have many long white (155A) pistils (hairs), which may become brown (172A) a week before harvest (The Royal Horticultural Society Colour Chart, 1995 Ed.).

Seed description: In embodiments, the seeds typically brown (172A). In embodiments, the seeds are brown (172A) and have stripes that include one or more colors from the group consisting of light green (144C), dark green (144A), yellow (001A), yellow orange (011A), orange (024A), orange red (033B), orange pink (027A), red (033A), dark purple red (046A), light red pink (039C), red pink (043C), dark pink red (045D), purple red (054A), light blue pink (055C), purple (058A), purple red (059D), blue pink (062A), light blue violet (069C), violet blue (089A), violet (075A), dark violet (079A), blue violet (083D), blue (100A), dark blue (103A), light blue (104D), light green blue (110C), green blue (111A), grey blue (115C), green blue (125C), green (130A), dark green (132A), light green (149B), white (155A), orange brown (169A), brown (172A), brown purple (178A), orange pink (179D) (The Royal Horticultural Society Colour Chart, 1995 Ed.). In embodiments, the wet flower buds have many long white (155A) pistils (hairs), which may become brown (172A) a week before harvest (The Royal Horticultural Society Colour Chart, 1995 Ed.). In embodiments, the seeds are on average about 0.1 inches to 0.2 inches in diameter. In embodiments, the seeds are on average about 0.075 inches to 0.4 inches in diameter. The seeds have a high fat content ranging from 4 weight percent to 45 weight percent, with an energy content ranging up to or less than 65,000 British Thermal Units per pound.

Vegetative bud (reproductive structure) color: In embodiments, the dried flower buds are very colorful and are comprised of a vast array of different colors including one or more from the group consisting of light green (144C), green (124A), dark green (144A), yellow (001A), yellow orange (011A), orange (024A), orange red (033B), orange pink (027A), red (033A), dark purple red (046A), light red pink (039C), red pink (043C), dark pink red (045D), purple red (054A), light blue pink (055C), purple (058A), purple red (059D), blue pink (062A), light blue violet (069C), violet blue (089A), violet (075A), dark violet (079A), blue violet (083D), blue (100A), dark blue (103A), light blue (104D), light green blue (110C), green blue (111A), grey blue (115C), green blue (125C), white (155A), orange brown (169A), brown (172A), brown purple (178A), orange pink (179D), (The Royal Horticultural Society Colour Chart, 1995 Ed.).

Vegetative bud (reproductive structure) & pistils color: In embodiments, the dried flower buds (including reproductive structures) are comprised of one or more from the group consisting of: green (144C or 144A) with yellow (001A) pistils, green (144C or 144A) with yellow orange (011A) pistils, green (144C or 144A) with orange (024A) pistils, green (144C or 144A) with orange red (033B) pistils, green (144C or 144A) with orange pink (027A) pistils, green (144C or 144A) with red (033A) pistils, green (144C or 144A) with dark purple red (046A) pistils, green (144C or 144A) with light red pink (039C) pistils, green (144C or 144A) with red pink (043C) pistils, green (144C or 144A) with dark pink red (045D) pistils, green (144C or 144A) with purple red (054A) pistils, green (144C or 144A) with light blue pink (055C) pistils, green (144C or 144A) with purple (058A) pistils, green (144C or 144A) with purple red (059D) pistils, green (144C or 144A) with blue pink (062A) pistils, green (144C or 144A) with light blue violet (069C) pistils, green (144C or 144A) with violet blue (089A) pistils, green (144C or 144A) with violet (075A) pistils, green (144C or 144A) with dark violet (079A) pistils, green (144C or 144A) with blue violet (083D) pistils, green (144C or 144A) with blue (100A) pistils, green (144C or 144A) with dark blue (103A) pistils, green (144C or 144A) with light blue (104D) pistils, green (144C or 144A) with light green blue (110C) pistils, green (144C or 144A) with green blue (111A) pistils, green (144C or 144A) with grey blue (115C) pistils, green (144C or 144A) with green (124A) pistils, green (144C or 144A) with green blue (125C) pistils, green (144C or 144A) with green (130A) pistils, green (144C or 144A) with dark green (132A) pistils, green (144C or 144A) with light green (149B) pistils, green (144C or 144A) with white (155A) pistils, green (144C or 144A) with orange brown (169A) pistils, green (144C or 144A) with brown (172A) pistils, green (144C or 144A) with brown purple (178A) pistils, green (144C or 144A) with orange pink (179D) (The Royal Horticultural Society Colour Chart, 1995 Ed.).

Bud (reproductive structures) length: In embodiments, the bud spike length ranges from 0.75 inches to 10 inches. In embodiments, the bud spike length ranges from 0.75 inches to 20 inches. In embodiments, the bud spike length ranges from 0.75 inches to 30 inches. In embodiments, the bud spike length ranges from 0.75 inches to 40 inches.

Bud (reproductive structures) diameter: Flower size is approximately: 0.25 inches to 3 inches in diameter; and approximately 0.35 to 10 inches in height.

Flowering time: In embodiments, flowering time ranges from 5 weeks to 18 weeks. In embodiments, flowering time ranges from 5 weeks to 28 weeks. In embodiments, flowering time ranges from 25 weeks to 37 weeks. In embodiments, flowering time ranges from 35 weeks to 60 weeks. In embodiments, flowering time ranges from 45 weeks to 101 weeks.

Peduncles: Peduncle strength is weak to medium to strong. In embodiments, they can bend horizontally from weight of flower buds. In embodiments, the average diameter of the peduncles ranges from between 0.2 to 0.5 inches in diameter. In embodiments, the average diameter of the peduncles ranges from between 0.1 to 0.3 inches in diameter. In embodiments, the average diameter of the peduncles ranges from between 0.3 to 1 inches in diameter. In embodiments, the average diameter of the peduncles ranges from between 1 to 2 inches in diameter. In embodiments, texture is smooth with few hairs. In embodiments, texture is moderately smooth, glabrous. In embodiments, texture is coarse with many hairs. In embodiments, pedicels are short to medium length, with visible hairs. They may be scabrid with sessile glands. In embodiments, pedicels are short to medium length, scabrid with sessile glands and visible hairs.

Peduncles color: In embodiments, peduncles are very colorful with many varied colors including having one or more from the group selected from: light green (144C), dark green (144A), yellow (001A), yellow orange (011A), orange (024A), orange red (033B), orange pink (027A), red (033A), dark purple red (046A), light red pink (039C), red pink (043C), dark pink red (045D), purple red (054A), light blue pink (055C), purple (058A), purple red (059D), blue pink (062A), light blue violet (069C), violet blue (089A), violet (075A), dark violet (079A), blue violet (083D), blue (100A), dark blue (103A), light blue (104D), light green blue (110C), green blue (111A), grey blue (115C), green blue (125C), green (130A), dark green (132A), light green (149B), white (155A), orange brown (169A), brown (172A), brown purple (178A), orange pink (179D) (The Royal Horticultural Society Colour Chart, 1995 Ed.).

Pedicel color: Pedicels are very colorful with many varied colors including having one or more from the group selected from: light green (144C), dark green (144A), yellow (001A), yellow orange (011A), orange (024A), orange red (033B), orange pink (027A), red (033A), dark purple red (046A), light red pink (039C), red pink (043C), dark pink red (045D), purple red (054A), light blue pink (055C), purple (058A), purple red (059D), blue pink (062A), light blue violet (069C), violet blue (089A), violet (075A), dark violet (079A), blue violet (083D), blue (100A), dark blue (103A), light blue (104D), light green blue (110C), green blue (111A), grey blue (115C), green blue (125C), green (130A), dark green (132A), light green (149B), white (155A), orange brown (169A), brown (172A), brown purple (178A), orange pink (179D) (The Royal Horticultural Society Colour Chart, 1995 Ed.).

Seed production on this plant is difficult. Seed production can be induced using colloidal silver solution but even with this step male inflorescence production is marginal. Pollen generated from this procedure may then be collected and used to self-cross with a non-treated female. The relative proportion of male plants is medium/high.

The inflorescences (e.g.—flowers, buds, reproductive structures) of the female plant are used for medical purposes. This plant is very versatile. It can be used to treat a wide range of health disorders. It has many beneficial medicinal qualities. Some uses include: stimulant, anti-inflammatory, pain management, sleep disorders, Tourette syndrome, Parkinson's disease, spasms, post-traumatic stress disorder (PTSD), epilepsy, multiple sclerosis, digestive disorders, Beaufort Budman III prefers water having an electrical conductivity ranging from 0.10 microsiemens per centimeter to 100 microsiemens per centimeter. Other water sources with other electrical conductivity may be suitable but just not as efficient. Beaufort Budman III prefers water having an electrical conductivity ranging from 0.10 microsiemens per centimeter to 100 microsiemens per centimeter is provided by:

(a1) a first water treatment unit (A1) including a cation, (a2) a second water treatment unit (A2) including an anion, and (a3) a third water treatment unit (A3) including a membrane.

In embodiments, Beaufort Budman III is grown using a method by providing water having an electrical conductivity ranging from 0.10 microsiemens per centimeter to 100 microsiemens per centimeter, the method includes:

(a) providing:

(a1) a first water treatment unit (A1) including a cation configured to remove positively charged ions from water to form a positively charged ion depleted water (06A), the positively charged ions are comprised of one or more from the group consisting of calcium, magnesium, sodium, and iron;

(a2) a second water treatment unit (A2) including an anion configured to remove negatively charged ions from the positively charged ion depleted water (06A) to form a negatively charged ion depleted water (09A), the negatively charged ions are comprised of one or more from the group consisting of iodine, chloride, and sulfate;

(a3) a third water treatment unit (A3) including a membrane configured to remove undesirable compounds from the negatively charged ion depleted water (09A) to form an undesirable compounds depleted water (12A), the undesirable compounds are comprised of one or more from the group consisting of dissolved organic chemicals, viruses, bacteria, and particulates;

(b) providing a source of water;

(c) removing positively charged ions from the water of step (b) to form a positively charged ion depleted water;

(d) removing negatively charged ions from the water after step (c) to form a negatively charged ion depleted water;

(e) removing undesirable compounds from the water after step (d) to form an undesirable compound depleted water;

(f) mixing the undesirable compounds depleted water after step (e) with one or more from the group consisting of macro-nutrients, micro-nutrients, and a pH adjustment to form a liquid mixture;

(g) pressurizing the liquid mixture of step (f) to form a pressurized liquid mixture;

(h) splitting the pressurized liquid mixture into a plurality of pressurized liquid mixtures;

(i) transferring the plurality of pressurized liquid mixtures to each growing assembly;

wherein:

the macro-nutrients are comprised of one or more from the group consisting of nitrogen, phosphorus, potassium, calcium, magnesium, and sulfur;

the micro-nutrients are comprised of one or more from the group consisting of iron, manganese, boron, molybdenum, copper, zinc, sodium, chlorine, and silicon;

the pH adjustment solution is comprised of one or more from the group consisting acid, nitric acid, phosphoric acid, potassium hydroxide, sulfuric acid, organic acids, citric acid, and acetic acid.

This new and remarkable variety of plant prefers that lights illuminate the plant at an illumination on-off ratio ranging from between 0.5 and 5, the illumination on-off ratio is defined as the duration of time when the lights are on and illuminate the plant in hours divided by the subsequent duration of time when the lights are off and are not illuminating the plant in hours before the lights are turned on again. In embodiments, this variety of plant thrives at a carbon dioxide concentration that between 400 parts per million (ppm) to 500 ppm, 500 ppm to 600 ppm, 600 ppm to 700 ppm, 700 ppm to 800 ppm, 800 ppm to 900 ppm, 900 ppm to 1000 ppm, 1000 ppm to 1500 ppm, 1500 ppm to 2000 ppm, 2000 ppm to 2500 ppm, 2500 ppm to 3000 ppm, 3000 ppm to 3500 ppm, 3500 ppm to 4000 ppm, 4000 ppm to 4500 ppm, 4500 ppm to 5000 ppm, 5000 ppm to 5500 ppm, 5500 ppm to 6000 ppm, 6000 ppm to 6500 ppm, 6500 ppm to 7000 ppm, 7000 ppm to 7500 ppm, 7500 ppm to 8000 ppm, 8000 ppm to 8500 ppm, 8500 ppm to 9000 ppm, 9000 ppm to 9500 ppm, or 9500 ppm to 10000 ppm.

In embodiments, the Beaufort Budman III is grown in a farming superstructure system (FSS) as described here and is grown while the FSS system is operated in a manner that switches from one mode of operation to another mode of operation.

In embodiments, the farming superstructure system (FSS) is operated in a manner that switches on a cyclical basis from: a first mode of operation to the second mode of operation; a second mode of operation to the first mode of operation. In embodiments, the farming superstructure system (FSS) is operated in a manner that switches on a cyclical basis from: a third mode of operation to the fourth mode of operation; a fourth mode of operation to the third mode of operation. It is preferred to turn on and off at least one valves (V1, V3, V4) in a cyclical manner to prevent the roots of the *cannabis* from receiving too much mist or spray or liquid water or water or nutrients.

In embodiments, the first mode of operation lasts for 5 seconds open followed by the second mode of operation lasting for 600 seconds closed. In embodiments, the third mode of operation lasts for 5 seconds open followed by the fourth mode of operation lasting for 600 seconds closed. In embodiments, water is transferred to the first growing assembly (100) for 5 seconds followed by not transferring water to the first growing assembly (100) for 600 seconds. In embodiments, water is transferred to the second growing assembly (200) for 5 seconds followed by not transferring water to the second growing assembly (200) for 600 seconds. In embodiments, water is transferred to both the first and second growing assemblies (100, 200) for 5 seconds followed by not transferring water to both the first and second growing assemblies (100, 200) for 600 seconds. 5 divided by 600 is 0.008.

In embodiments, the first mode of operation lasts for 60 seconds open followed by the second mode of operation lasting for 180 seconds closed. In embodiments, the third mode of operation lasts for 60 seconds open followed by the fourth mode of operation lasting for 180 seconds closed. In embodiments, water is transferred to the first growing assembly (100) for 60 seconds followed by not transferring water to the first growing assembly (100) for 180 seconds. In embodiments, water is transferred to the second growing assembly (200) for 60 seconds followed by not transferring water to the second growing assembly (200) for 180 seconds. 60 divided by 180 is 0.333.

The duration of time when liquid is transferred to at least one growing assembly (100, 200) divided by the duration of time when liquid is not transferred to at least one growing assembly (100, 200) may be considered an open-close ratio. The open-close ratio may be the duration of time when at least one valve (V1, V3, V4) is open in seconds divided by the subsequent duration of time when the same valve is closed in seconds before the same valve opens again. In embodiments, the open-close ratio ranges from between 0.008 to 0.33. In embodiments, the computer (COMP) opens and closes the valve (V1, V3, V4) to periodically introduce the pressurized liquid mixture into to each growing assembly with an open-close ratio ranging from between 0.008 to 0.33, the open-close ratio is defined as the duration of time when the valve (V1, V3, V4) is open in seconds divided by the subsequent duration of time when the same valve is closed in seconds before the same valve opens again. The computer (COMP) opens and closes the valves (V1, V3, V4) to periodically introduce the pressurized liquid mixture into to each growing assembly with an open-close ratio ranging from between 0.008 to 0.33.

In embodiments, the open-close ratio varies. The open-close ratio may vary throughout the life of the *cannabis* contained within the growing assemblies (100, 200). The open-close ratio may vary throughout the stage of development of the *cannabis* contained within the growing assemblies (100, 200). Stages of development of the *cannabis* include flowering, pollination, fertilization. In embodiments, the open-close ratio is greater during flowering and less during pollination. In embodiments, the open-close ratio is greater during pollination and less during fertilization. In embodiments, the open-close ratio is greater during flowering and less during fertilization. In embodiments, the open-close ratio is less during flowering and greater during pollination. In embodiments, the open-close ratio is less during pollination and greater during fertilization. In embodiments, the open-close ratio is less during flowering and greater during fertilization.

The open-close ratio may vary throughout a 24-hour duration of time. In embodiments, the open-close ratio is increased during the day-time and decreased during the night-time relative to one another. In embodiments, the open-close ratio varies increased during the night-time and decreased during the day-time relative to one another. Night-time is defined as the time between evening and morning. Day-time is defined as the time between morning and evening.

In embodiments, carbohydrates may be made available to Beaufort Budman III. The carbohydrates are comprised of one or more from the group consisting of sugar, sucrose, molasses, and plant syrups.

In embodiments, enzymes may be made available to Beaufort Budman III. The enzymes are comprised of one or more from the group consisting of amino acids, orotidine 5'-phosphate decarboxylase, OMP decarboxylase, glucanase, beta-glucanase, cellulase, xylanase, HYGROZYME®, CANNAZYME®, MICROZYME®, and SENSIZYME®.

In embodiments, vitamins may be made available to Beaufort Budman III. The vitamins are comprised of one or more from the group consisting of vitamin B, vitamin C, vitamin D, and vitamin E.

In embodiments, hormones may be made available to Beaufort Budman III. The hormones are comprised of one or more from the group consisting of auxins, cytokinins gibberellins, abscic acid, brassinosteroids, salicylic acid, jasmonates, plant peptide hormones, polyamines, nitric oxide, strigolactones, and triacontanol.

In embodiments, microorganisms may be made available to Beaufort Budman III. The microorganisms are comprised of one or more from the group consisting of bacteria, diazotroph bacteria, diazotrop archaea, *Azotobacter vinelandii, Clostridium pasteurianu, fungi, arbuscular mycorrhizal fungi, Glomus aggrefatum, Glomus etunicatum, glomus intraradices, rhizophagus irregularis,* and *Glomus mosseae.*

Permits and Patent Licenses are Required for Growth of Beaufort Budman III in the United States of America and Internationally.

The claims and specification are in conformity with 37 CFR 1.163, this specification and especially claimed ranges of elements (a) through (x) and other elements of the claims contain as full and complete a disclosure as possible of the plant and the characteristics thereof that distinguish the same over related known varieties, and its antecedents, and particularly point out where and in what manner the variety of plant has been asexually reproduced. Further, in the case of this newly found plant, this specification particularly points out the location and character of the area where the plant was discovered. Applicant is based out of Baltimore, Md., 21202.

The claims and specification are in conformity with 35 U.S.C. 1 12(a), since this specification and especially claimed ranges of elements (a) through (x) and other elements of the claims contain a written description of the invention, and of the manner and process of making and using it, in such full, clear, concise, and exact terms as to enable any person skilled in the art to which it pertains, or with which it is most nearly connected, to make and use the same, and shall set forth the best mode contemplated by the inventor or joint inventor of carrying out the invention.

Complete botanical description and the characteristics which distinguish over related known varieties are herein provided. The new variety differs from parents and related (similar) cultivars of *Cannabis sativa* L. ssp. *Sativa* and *Cannabis sativa* L. ssp. *Indica* (Lam.). The new variety differs from parents and related (similar) cultivars because Beaufort Budman III has a precise and unique engineered concentrations of: cannabidiol, tetrahydrocannabinol, energy, carbon, oxygen, hydrogen, ash, volatiles, nitrogen, sulfur, chlorine, sodium, potassium, iron, magnesium, phosphorous, calcium, zinc, cellulose, lignin, hemicellulose, fat, fiber, protein, as well as specific *Cannabis sativa* L. ssp. *Sativa* and *Cannabis sativa* L. ssp. *Indica* (Lam.) contents and ratios. The new plant differs from its parents and related cultivars because it is engineered to more effectively alleviate inflammation, manage pain, treat post-traumatic stress disorder (PTSD), and digestive disorders, while also helping to prevent sleep disorders. It provides adequate stimulant to cure attention deficit disorder but does not so act as such a stimulating drug to prevent normal sleep, dietary, and exercise patterns. Because of this remarkable new plant, and combination of ingredients, individuals seeking to medicate with tetrahydrocannabinol can now use this plant as medicine while having little-to-no side effects at all whatsoever and at a very low dosage compared to its parents and related cultivars.

Applicant has specifically identified the characteristic of improved medicinal benefits through extensive trial and error and has a claim which is the result of quantifiable, experimental, and empirical data characterizing the difference between Beaufort Budman III and *Cannabis sativa* L. ssp. *Sativa* or *Cannabis sativa* L. ssp. *Indica* (Lam.) alone. Most importantly, Beaufort Budman III possesses a volatiles content ranging from between 30 weight percent to 90 weight percent, and a *Cannabis sativa* L. ssp. *Sativa* content ranges from 20 weight percent to 70 weight percent, and a *Cannabis sativa* L. ssp. *Indica* (Lam.) content ranges from 15 weight percent to 65 weight percent. Whereas the patents and cultivars possess 100 weight percent of each of *Cannabis sativa* L. ssp. *Sativa* content and a *Cannabis sativa* L. ssp. *Indica* (Lam.), applicant's research and development has resulted in a new and distinct plant that has an engineered amount of volatiles while mixing *Cannabis sativa* L. ssp. *Sativa* content and a *Cannabis sativa* L. ssp. *Indica* (Lam.) at varying ratios to achieve a preferred cannabidiol content ranging from 0.125 weight percent to 25 weight percent. Applicant has realized that the tetrahydrocannabinol content ranging from 5 weight percent to 63 weight percent is specifically tailored to maximize dosage while having a volatiles content ranging from between 30 weight percent to 90 weight percent. The combination of Beaufort Budman III having a volatiles content ranging from between 30 weight percent to 90 weight percent together with the tetrahydrocannabinol content ranging from 5 weight percent to 63 weight percent provides a remarkable new plant. Because of this, a user can use less of the plant to achieve the required dosage.

The application conforms to 37 CFR1.163(a) since the specification particularly points out that Applicant is based out of Baltimore, Md., USA in zip code 21202 which was the location that Applicant realized that he can take stem cuttings and asexually reproduce plants in a manner disclosed in this specification. This disclosure conforms to 37 CFR 1.163(a) since the specification particularly points out that Baltimore, Md., USA in zip code 21202, indoor propagation, growing, and cultivation were the location and character of the area where the plant was discovered.

Applicant has generated the ranges of claimed ranges of elements (a) through (x) were discovered through comprehensive compositional analysis, particle-induced X-ray emission analysis, elemental analysis, proximate analysis, and ultimate analysis immediately available from a variety of different laboratories in the USA. Obtaining the appropriate ranges of varying concentrations of *Cannabis sativa* L. ssp. *Sativa* and *Cannabis sativa* L. ssp. *Indica* (Lam.) were performed on a trial and error basis. The tetrahydrocannabinol concentration is provided as a measurement of Beaufort Budman III's leaves, seeds, stems, roots, or any reproductive structures on a dry basis.

The age and growing conditions of this plant shown in FIGS. 19'-22' may be: adult plant of 14 weeks, average temperature 70 degrees F. to 80 degrees F., humidity 45 to 55 percent humidity, water pH from 5.15 to 6.8, water having an electrical conductivity ranging from 0.10 microsiemens per centimeter to 100 microsiemens per centimeter, an illumination on-off ratio ranging from between 0.5 and 5 (the illumination on-off ratio is defined as the duration of time when the lights are on and illuminate the *cannabis* in hours divided by the subsequent duration of time when the lights are off and are not illuminating the *cannabis* in hours before the lights are turned on again), a carbon dioxide concentration that is greater than 400 parts per million and less than 3,000 parts per million, a LED lighting wavelength ranging from 400 nm to 700 nm, air velocity ranging from 5 feet per second to 50 feet per second.

The parents of the instant plant are known and are comprised of *Cannabis sativa* L. ssp. *Sativa* X *Cannabis sativa* L. ssp. *Indica* (Lam.). Seeds from either are commercially available from many vendors throughout the USA. Applicant devised various plant hybrids of *Cannabis sativa* L. ssp. *Sativa* X *Cannabis sativa* L. ssp. *Indica* (Lam.) to create a plant best suited to accommodate industrial, commercial, recreation and medicinal popular demand.

The idea of a superior and precisely engineered composition that embodies Beaufort Budman III as described and disclosed herein was discovered by the applicant's in his garden where the inventor was asexually reproducing and cultivating many plants, in many different containers, of many different species. Applicant's work with plants has resulted in the discovery of a cross between *Cannabis sativa* L. ssp. *Sativa* X *Cannabis sativa* L. ssp. *Indica* (Lam.) described herein. Applicant has discovered that Beaufort Budman III can be reproduced asexually, by taking cuttings of the plants of origin resulting in a remarkable new plant. The discovered female plant can be asexually reproduced by cuttings.

The invention employs a novel plant variety. Since the plant is essential to the claimed invention it must be obtainable by the following method. A method to asexually clone a plurality of Beaufort Budman III plants, the method includes:

(a) providing:
  (a0) a plurality of Beaufort Budman III (107, 207) plants;
  (a1) a cutting tool (CT1);
  (a2) a liquid, powder, or gel rooting solution (RS), the rooting solution includes one or more from the group consisting of water, carbohydrates, enzymes, vitamins, hormones, and microorganisms;
  (a3) a growing medium (GM), the growing medium includes one or more from the group consisting of rockwool, perlite, amorphous volcanic glass, vermiculite, clay, clay pellets, LECA (lightweight expanded clay aggregate), coco-coir, fibrous coconut husks, soil, dirt, peat, peat moss, sand, soil, compost, manure, fir bark, foam, gel, oasis cubes, lime, gypsum, quartz, plastic, polyethylene, high-density polyethylene (HDPE), low-density polyethylene (LDPE), polyethylene terephthalate (PET), polyacrylonitrile, and polypropylene; and
  (a4) a plurality of containers (TY1, TY2, TY3, $TY^N$, $TY^{N+1}$) configured to accept the rooting solution (RS) and the growing medium (GM), the plurality of containers are configured to be positioned within a cloning enclosure (CHD);
  (a5) the cloning enclosure (CHD) has an interior (CHD-1), the cloning enclosure (CHD) is configured to contain water vapor within the interior (CHD-1) to provide a humid environment for plants within the interior (CHD-1);
(b) introducing the rooting solution and the growing medium to the plurality of containers;
(c) using the cutting tool to sever the tips from a plurality of Beaufort Budman III plants to form a plurality of severed plants (107X, 207X);
(d) inserting the plurality of severed plants (107X, 207X) of step (c) into the plurality of containers;

(e) placing the plurality of containers within the interior of the cloning enclosure;
(f) illuminating the plants after step (e);
(g) growing the plants for 4 to 20 days or until roots are formed; and
(h) optionally venting the interior of the cloning enclosure;
wherein:
the carbohydrates are comprised of one or more from the group consisting of sugar, sucrose, molasses, and plant syrups;
the enzymes are comprised of one or more from the group consisting of amino acids, orotidine 5'-phosphate decarboxylase, OMP decarboxylase, glucanase, beta-glucanase, cellulase, xylanase, HYGROZYME®, CANNAZYME®, MICROZYME®, and SENSIZYME®;
the vitamins are comprised of one or more from the group consisting of vitamin B, vitamin C, vitamin D, and vitamin E;
the hormones are comprised of one or more from the group consisting of auxins, cytokinins gibberellins, abscic acid, brassinosteroids, salicylic acid, jasmonates, plant peptide hormones, polyamines, nitric oxide, strigolactones, and triacontanol;
the microorganisms are comprised of one or more from the group consisting of bacteria, diazotroph bacteria, diazotrop archaea, *Azotobacter vinelandii*, *Clostridium pasteurianu*, fungi, *Arbuscular mycorrhizal* fungi, mycorrhiza, *Glomus aggrefatum*, *Glomus etunicatum*, *Glomus intraradices*, *Rhizophagus irregularis*, and *Glomus mosseae*.

TABLE 1

USDA Plants Growth Habit Code: FB;
Vigor: 5;
Productivity: Good;
Flowering timing: 5 weeks to 18 weeks;
Flowering score: 7.5;
Branches: strong to medium to weak;
(a) a cannabidiol content ranging from 0.125 weight percent to less than 25 weight percent;
(b) a tetrahydrocannabinol ranging from 5 weight percent to 63 weight percent;
(c) an energy content ranging from between 2,500 British Thermal Units per pound to 15,000 British Thermal Units per pound;
(d) a carbon content ranging from between 20 weight percent to 65 weight percent;
(e) an oxygen content ranging from between 12 weight percent to 55 weight percent;
(f) a hydrogen content ranging from between 2 weight percent to 20 weight percent;
(g) an ash content ranging from between 2.5 weight percent to 30 weight percent;
(h) volatiles content ranging from between 30 weight percent to 90 weight percent;
(i) a nitrogen content ranging from between 1 weight percent to 10 weight percent;
(j) a sulfur content ranging from between 0.01 weight percent to 8 weight percent;
(k) a chlorine content ranging from 0.05 weight percent to 5 weight percent;
(l) a sodium content ranging from 0.02 weight percent to 15 weight percent;
(m) a potassium content ranging from 0.05 weight percent to 15 weight percent;
(n) an iron content ranging from 0.01 weight percent to 13 weight percent;
(o) a magnesium content ranging from 0.02 weight percent to 10 weight percent;
(p) a phosphorous content ranging from 0.05 weight percent to 12 weight percent;
(q) a calcium content ranging from 0.03 weight percent to 10 weight percent;

TABLE 1-continued (r) a zinc content ranging from 0.01 weight percent to 5 weight percent;
(s) a cellulose content ranging from 25 weight percent to 75 weight percent;
(t) a lignin content ranging from 3 weight percent to 35 weight percent;
(u) a hemicellulose content ranging from 3 weight percent to 30 weight percent;
(v) a fat content ranging from 5 weight percent to 35 weight percent;
(w) a fiber content ranging from 5 weight percent to 75 weight percent; and
(x) a protein content ranging from 5 weight percent to 35 weight percent;
wherein:
the *Cannabis Sativa* L. ssp *indica* content ranges from 15% to 65%;
the *Cannabis Sativa* L. ssp *sativa* content ranges from 20% to 70%;

Comparison to Parents:
The parents of Beaufort Budman III were Beaufort Budman I and Beaufort Budman II.

Beaufort Budman I

USDA Plants Growth Habit Code: FB;
Vigor: 5;
Productivity: Good;
Flowering timing: 5 weeks to 18 weeks;
Flowering score: 7.5;
Branches: strong to medium to weak;
(a) a cannabidiol content ranging from 0.1 weight percent to less than 28 weight percent;
(b) a tetrahydrocannabinol ranging from 3 weight percent to 65 weight percent;
(c) an energy content ranging from between 2,400 British Thermal Units per pound to 15,500 British Thermal Units per pound;
(d) a carbon content ranging from between 18 weight percent to 66 weight percent;
(e) an oxygen content ranging from between 10 weight percent to 60 weight percent;
(f) a hydrogen content ranging from between 1 weight percent to 25 weight percent;
(g) an ash content ranging from between 2 weight percent to 35 weight percent;
(h) volatiles content ranging from between 25 weight percent to 95 weight percent;
(i) a nitrogen content ranging from between 0.5 weight percent to 12 weight percent;
(j) a sulfur content ranging from between 0.005 weight percent to 10 weight percent;
(k) a chlorine content ranging from 0.01 weight percent to 7 weight percent;
(l) a sodium content ranging from 0.01 weight percent to 16 weight percent;
(m) a potassium content ranging from 0.04 weight percent to 16 weight percent;
(n) an iron content ranging from 0.008 weight percent to 15 weight percent;
(o) a magnesium content ranging from 0.01 weight percent to 12 weight percent;
(p) a phosphorous content ranging from 0.01 weight percent to 14 weight percent;
(q) a calcium content ranging from 0.02 weight percent to 12 weight percent;
(r) a zinc content ranging from 0.005 weight percent to 6 weight percent;
(s) a cellulose content ranging from 20 weight percent to 78 weight percent;
(t) a lignin content ranging from 2 weight percent to 38 weight percent;
(u) a hemicellulose content ranging from 2 weight percent to 32 weight percent;
(v) a fat content ranging from 4 weight percent to 38 weight percent;
(w) a fiber content ranging from 4 weight percent to 77 weight percent; and -continued (x) a protein content ranging from 4
weight percent to 38 weight percent;
wherein:
the *Cannabis Sativa* L. ssp *indica* content ranges from 10% to 70%;
the *Cannabis Sativa* L. ssp *sativa* content ranges from 15% to 75%;
Beaufort Budman II USDA Plants Growth Habit Code: FB;
Vigor: 5;
Productivity: Good;
Flowering timing: 5 weeks to 18 weeks;
Flowering score: 7.5;
Branches: strong to medium to weak;
(a) a cannabidiol content ranging from 0.15
weight percent to less than 24 weight percent;
(b) a tetrahydrocannabinol ranging from 8
weight percent to 60 weight percent;
(c) an energy content ranging from between 3,000
British Thermal Units per pound to 14,500
British Thermal Units per pound;
(d) a carbon content ranging from between
22 weight percent to 60 weight percent;
(e) an oxygen content ranging from between
15 weight percent to 50 weight percent;
(f) a hydrogen content ranging from between
3 weight percent to 18 weight percent;
(g) an ash content ranging from between
3 weight percent to 28 weight percent;
(h) volatiles content ranging from between
35 weight percent to 85 weight percent;
(i) a nitrogen content ranging from between
1.5 weight percent to 9.5 weight percent;
(j) a sulfur content ranging from between
0.015 weight percent to 7.5 weight percent;
(k) a chlorine content ranging from 0.08
weight percent to 4.5 weight percent;
(l) a sodium content ranging from 0.03
weight percent to 14 weight percent;
(m) a potassium content ranging from
0.06 weight percent to 14 weight percent;
(n) an iron content ranging from 0.02
weight percent to 12 weight percent;
(o) a magnesium content ranging from
0.03 weight percent to 9 weight percent;
(p) a phosphorous content ranging from
0.06 weight percent to 11 weight percent;
(q) a calcium content ranging from 0.04
weight percent to 9 weight percent;
(r) a zinc content ranging from 0.02
weight percent to 4.5 weight percent;
(s) a cellulose content ranging from
26 weight percent to 70 weight percent;
(t) a lignin content ranging from 4
weight percent to 33 weight percent;
(u) a hemicellulose content ranging
from 4 weight percent to 28 weight percent;
(v) a fat content ranging from 6 weigh
t percent to 33 weight percent;
(w) a fiber content ranging from 6
weight percent to 70 weight percent; and
(x) a protein content ranging from
6 weight percent to 33 weight percent;
wherein:
the *Cannabis Sativa* L. ssp *indica* content ranges from 20% to 60%;
the *Cannabis Sativa* L. ssp *sativa* content ranges from 25% to 65%;

FIG. 23'

FIG. 23' shows one non-limiting embodiment of a *cannabis* cloning assembly (CA). In embodiments, the *cannabis* cloning assembly (CA) includes a plurality of containers (TY1, TY2, TY3, $TY^N$, $Ty^{N+1}$) connected to at least one cloning enclosure (CHD). The cloning enclosure (CHD) when placed upon the plurality of containers (TY1, TY2, TY3, $TY^N$, $TY^{N+1}$) forms an interior (CHD-1). In embodiments, the cloning enclosure (CHD) does not let humidity, water vapor, carbon dioxide, or air to escape from within the interior (CHD-1). The cloning enclosure (CHD) is configured to contain humidity in the interior (CHD-1) above the plurality of containers (TY1, TY2, TY3, $TY^N$, $Ty^{N+1}$).

The *cannabis* cloning assembly (CA) is configured to asexually reproduce Beaufort Budman III (107, 207) that grow within in each growing assembly (100, 200). The present disclosure provides for a method to asexually clone a plurality of Beaufort Budman III (107, 207) plants, the method includes:
(a) providing:
(a0) a plurality of Beaufort Budman III (107, 207) plants;
(a1) a cutting tool (CT1);
(a2) a liquid, powder, or gel rooting solution (RS), the rooting solution includes one or more from the group consisting of water, carbohydrates, enzymes, vitamins, hormones, and microorganisms;
(a3) a growing medium (GM), the growing medium includes one or more from the group consisting of rockwool, perlite, amorphous volcanic glass, vermiculite, clay, clay pellets, LECA (lightweight expanded clay aggregate), coco-coir, fibrous coconut husks, soil, dirt, peat, peat moss, sand, soil, compost, manure, fir bark, foam, gel, oasis cubes, lime, gypsum, quartz, plastic, polyethylene, high-density polyethylene (HDPE), low-density polyethylene (LDPE), polyethylene terephthalate (PET), polyacrylonitrile, and polypropylene;
(a4) a plurality of containers (TY1, TY2, TY3, $TY^N$, $TY^{N+1}$) configured to accept the rooting solution (RS) and the growing medium (GM), the plurality of containers are configured to be positioned within a cloning enclosure (CHD);
(a5) the cloning enclosure (CHD) has an interior (CHD-1), the cloning enclosure (CHD) is configured to contain water vapor within the interior (CHD-1) to provide a humid environment for plants within the interior (CHD-1);
(b) introducing the rooting solution and the growing medium to the plurality of containers;
(c) using the cutting tool to sever the tips from a plurality of *Cannabis* plants to form a plurality of severed plants (107X, 207X);
(d) inserting the plurality of severed plants (107X, 207X) of step (c) into the plurality of containers;
(e) placing the plurality of containers within the interior of the cloning enclosure;
(f) illuminating the plants after step (e);
(g) growing the plants for 4 to 20 days or until roots are formed; and
(h) optionally venting the interior of the cloning enclosure;
wherein:
the carbohydrates are comprised of one or more from the group consisting of sugar, sucrose, molasses, and plant syrups;
the enzymes are comprised of one or more from the group consisting of amino acids, orotidine 5'-phosphate decarboxylase, OMP decarboxylase, glucanase, beta-glucanase, cellulase, xylanase, HYGROZYME®, CANNAZYME®, MICROZYME®, and SENSIZYME®;
the vitamins are comprised of one or more from the group consisting of vitamin B, vitamin C, vitamin D, and vitamin E;
the hormones are comprised of one or more from the group consisting of auxins, cytokinins gibberellins, abscic acid, brassinosteroids, salicylic acid, jasmonates, plant peptide hormones, polyamines, nitric oxide, strigolactones, and triacontanol;

the microorganisms are comprised of one or more from the group consisting of bacteria, diazotroph bacteria, diazotrop archaea, *Azotobacter vinelandii, Clostridium pasteurianu*, fungi, *Arbuscular mycorrhizal* fungi, mycorrhiza, *Glomus aggrefatum, Glomus etunicatum, Glomus intraradices, Rhizophagus irregularis*, and *Glomus mosseae.*

Thus, specific systems and methods of an Insect Production Superstructure System (IPSS) and/or a Farming Superstructure System (IPSS) have been disclosed. It should be apparent, however, to those skilled in the art that many more modifications besides those already described are possible without departing from the inventive concepts herein. The inventive subject matter, therefore, is not to be restricted except in the spirit of the disclosure.

Thus, the applicant(s) should be understood to have support to claim and make a statement of invention to at least: i) each of the process devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) each system, method, and element shown or described as now applied to any specific field or devices mentioned, x) methods and apparatuses substantially as described hereinbefore and with reference to any of the accompanying examples, xi) the various combinations and permutations of each of the elements disclosed, xii) each potentially dependent claim or concept as a dependency on each and every one of the independent claims or concepts presented, and xiii) all inventions described herein.

With regard to claims whether now or later presented for examination, it should be understood that for practical reasons and so as to avoid great expansion of the examination burden, the applicant may at any time present only initial claims or perhaps only initial claims with only initial dependencies. Support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible.

Finally, any claims set forth at any time are hereby incorporated by reference as part of this description of the inventive technology, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Although the foregoing text sets forth a detailed description of numerous different embodiments of the disclosure, it should be understood that the scope of the disclosure is defined by the words of the claims set forth at the end of this patent. The detailed description is to be construed as exemplary only and does not describe every possible embodiment of the disclosure because describing every possible embodiment would be impractical, if not impossible. Numerous alternative embodiments could be implemented, using either current technology or technology developed after the filing date of this patent, which would still fall within the scope of the claims defining the disclosure.

Thus, many modifications and variations may be made in the techniques and structures described and illustrated herein without departing from the spirit and scope of the present disclosure. Accordingly, it should be understood that the methods and apparatus described herein are illustrative only and are not limiting upon the scope of the disclosure.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, a limited number of the exemplary methods and materials are described herein. It must be noted that as used herein and in the appended claims, the singular forms "a", "an", and "the" include plural referents unless the context clearly dictates otherwise.

The invention claimed is:

1. A method to produce a *cannabis* oil nanoemulsion, the method includes:
   (a) emulsifying water and *cannabis* oil with a first emulsification system to produce a *cannabis* oil microemulsion comprising micro-sized *cannabis* oil droplets; and
   (b) after step (a), introducing the *cannabis* oil microemulsion to a second emulsification system to produce the *cannabis* oil nanoemulsion comprising a *cannabis* oil droplet size ranging from between 5 to 100 nanometers;
   wherein:
   the first emulsification system includes a rotor/stator; and
   the second emulsification system includes an ultrasonic homogenizer or a microfluidizer processor.

2. The method according to claim 1, wherein:
in step (b), the second emulsification system includes the ultrasonic homogenizer, the ultrasonic homogenizer includes a barbell ultrasonic horn, the barbell ultrasonic horn operates at a power level ranging from between 0.5 to 25 kw.

3. The method according to claim 1, wherein:
in step (b), the second emulsification system includes the ultrasonic homogenizer, the ultrasonic homogenizer operates at a power level ranging from between 0.5 to 25 kw.

4. The method according to claim 1, wherein:
in step (a), the *cannabis* oil includes distilled *cannabis* oil.

5. The method according to claim 1, comprising:
providing an emulsifier and/or a surfactant; and
in step (a), emulsifying the emulsifier and/or the surfactant with the water and the *cannabis* oil to produce the *cannabis* oil microemulsion; and/or
in step (b), emulsifying the emulsifier and/or the surfactant with the *cannabis* oil microemulsion to produce the *cannabis* oil nanoemulsion.

6. The method according to claim 1, comprising:
providing an acid; and
in step (a), emulsifying the acid with the water and the *cannabis* oil to produce the *cannabis* oil microemulsion; and/or
in step (b), emulsifying the acid with the *cannabis* oil microemulsion to produce the *cannabis* oil nanoemulsion.

7. The method according to claim 1, comprising:
(c) after step (b), spray drying the *cannabis* oil nanoemulsion.

8. The method according to claim 1, wherein:
in step (a) and/or in step (b), the *cannabis* oil microemulsion and/or the *cannabis* oil nanoemulsion are produced under inert gas conditions.

9. The method according to claim 1, comprising:
(i) providing a source of water;
(ii) after step (i), introducing the water to an adsorbent to produce a first treated water;
(iii) after step (ii), introducing the first treated water to a membrane and/or an ultraviolet unit to produce a second treated water; and
in step (a), the water includes the second treated water, and emulsifying the second treated water and the *cannabis* oil with the first emulsification system.

10. The method according to claim 1, wherein:
in step (b), the *cannabis* oil nanoemulsion includes a beverage, and the beverage includes a serving size ranging from 5 fluid ounces to 16 fluid ounces, and a calorie content of 0 to 200 calories per serving.

11. The method according to claim 1, wherein:
in step (b), the *cannabis* oil nanoemulsion includes one or more selected from the group consisting of basil, bergamot, black pepper, cacao, *cassia*, cedarwood, cinnamon, citronella, clary sage, clove, coffee, cypress, *eucalyptus*, evening primrose, fennel, fir needle, frankincense, *gardenia*, geranium, ginger, grapefruit, helichrysum, hops, hyssop, jasmine, juniper berry, lavender, lemon, lemongrass, mandarin, marjoram, *melaleuca*, myrrh, neroli, orange, oregano, palo santo, patchouli, peppermint, pine, powdered fruit material, roman chamomile, rose, rosemary, sandalwood, spikenard, sugar, tea tree, thyme, turmeric, vetiver, wintergreen, yeast, ylang ylang, and combinations thereof.

12. The method according to claim 1, wherein:
in step (b), the *cannabis* oil nanoemulsion includes one or more selected from the group consisting of ayahuasca, activated charcoal, capsaicin, carnitine, carnosine, cranberry, creatine, curcumin, *echinacea*, fish oil, garlic, ginger, ginkgo, *ginseng*, gluconic acid, glucosamine, green tea, hoodia, inositol, iowaska, lactic acid, lutein, magnesium, malate, melatonin, metformin, 3,4-methylenedioxymethamphetamine, milk thistle, n-acetylcysteine, niacin, niacinamide, nicotinamide riboside, omega-3 fatty acid, oxaloacetate, psilocybin, pyruvate, resveratrol, *rhodiola*, saw palmetto, theaflavins, turmeric, valerian, vitamin B3, vitamin C, zinc, and combinations thereof.

13. The method according to claim 1, wherein:

in step (b), the *cannabis* oil nanoemulsion includes a sweetener including one or more sweeteners selected from the group consisting of aspartame, acesulfame potassium, saccharin, sucralose, neotame, erythritol, *stevia, stevia* leaf extract, and combinations thereof.

14. The method according to claim 1, wherein:

in step (a), the *cannabis* oil includes carbon dioxide extracted *cannabis* oil, ethanol extracted *cannabis* oil, chromatography purified *cannabis* oil, and/or simulated moving bed extracted *cannabis* oil; and in step (a), the *cannabis* oil includes a cannabinoid, the cannabinoid includes cannabidiol (CBD) and/or tetrahydrocannabinol (THC).

15. A method to produce a *cannabis* oil nanoemulsion, the method includes:

(a) emulsifying water and *cannabis* oil with a first emulsification system to produce a *cannabis* oil microemulsion comprising micro-sized *cannabis* oil droplets; and (b) after step (a), introducing the *cannabis* oil microemulsion to a second emulsification system to produce the *cannabis* oil nanoemulsion;

wherein:

the first emulsification system includes a rotor/stator; and the second emulsification system includes a microfluidizer processor configured to operate at a pressure ranging from between 10,000 to 40,000 pounds per square inch.

16. A method to produce a *cannabis* oil nanoemulsion, the method includes:

(a) emulsifying water and *cannabis* oil with a first emulsification system to produce a *cannabis* oil microemulsion comprising micro-sized *cannabis* oil droplets; and (b) after step (a), introducing the *cannabis* oil microemulsion to a second emulsification system to produce the *cannabis* oil nanoemulsion;

wherein:

the first emulsification system includes a rotor/stator; and the second emulsification system includes an ultrasonic homogenizer.

17. The method according to claim 16, wherein:

in step (b), the *cannabis* oil nanoemulsion includes a beverage, and the beverage includes a serving size ranging from 5 fluid ounces to 16 fluid ounces, and a calorie content of 0 to 200 calories per serving.

18. The method according to claim 16, comprising:

(c) after step (b), spray drying the *cannabis* oil nanoemulsion.

19. The method according to claim 16, wherein:

in step (b), the ultrasonic homogenizer is configured to operate at a power level ranging from between 2 to 40 kw.

20. The method according to claim 16, wherein:

the *cannabis* oil nanoemulsion includes anti-inflammatory and/or pain management properties.

21. The method according to claim 16, wherein:

the *cannabis* oil nanoemulsion includes a biologically active organic compound with four rings.

22. The method according to claim 16, wherein:

the *cannabis* oil nanoemulsion includes a microorganism.

23. The method according to claim 16, wherein:

the *cannabis* oil nanoemulsion includes an enzyme.

24. The method according to claim 16, wherein:

the *cannabis* oil nanoemulsion includes a fungi.

25. The method according to claim 16, wherein:

the *cannabis* oil nanoemulsion includes a terpene.

26. The method according to claim 16, wherein:

the *cannabis* oil nanoemulsion includes an acid.

27. The method according to claim 16, wherein:

the *cannabis* oil nanoemulsion includes a surfactant.

28. The method according to claim 16, wherein:

the *cannabis* oil nanoemulsion includes aspirin.

29. The method according to claim 16, wherein:

the *cannabis* oil nanoemulsion includes psilocybin.

30. The method according to claim 16, wherein:

the *cannabis* oil nanoemulsion includes melatonin.

31. The method according to claim 16, wherein:

the *cannabis* oil nanoemulsion includes green tea.

32. The method according to claim 16, wherein:

the *cannabis* oil nanoemulsion includes capsaicin.

33. The method according to claim 16, wherein:

the *cannabis* oil nanoemulsion includes curcumin and black pepper.

34. The method according to claim 16, wherein:

the *cannabis* oil nanoemulsion includes one or more selected from the group consisting of malt, grain, barley, hops, and combinations thereof.

35. The method according to claim 16, wherein:

the *cannabis* oil nanoemulsion includes yeast.

36. The method according to claim 16, wherein:

the *cannabis* oil nanoemulsion includes ethanol.

37. The method according to claim 16, wherein:

the *cannabis* oil nanoemulsion includes no ethanol.

38. The method according to claim 16, wherein:

the *cannabis* oil nanoemulsion includes carbon dioxide.

39. The method according to claim 16, wherein:

the *cannabis* oil nanoemulsion includes lactic acid.

40. The method according to claim 16, wherein:

the *cannabis* oil nanoemulsion includes one or more selected from the group consisting of a nootropic drug, amphetamine, ayahuasca, activated charcoal, basil, beta carotene, bromelain, carnitine, carnosine, cranberry, creatine, cyanocobalamin, *echinacea*, fish oil, garlic, ginger, ginkgo, *ginseng*, gluconic acid, glucosamine, hoodia, inositol, iowaska, insect lipids, insects, lutein, malate, metformin, 3,4-methylenedioxymethamphetamine, milk thistle, n-acetylcysteine, niacin, niacinamide, nicotinamide riboside, omega-3 fatty acid, oxaloacetate, pyruvate, resveratrol, *rhodiola*, saw palmetto, sodium citrate, theaflavins, turmeric, white tea extract, and combinations thereof.

41. The method according to claim 16, wherein:

the *cannabis* oil nanoemulsion includes an electrolyte, the electrolyte comprises one or more selected from the group consisting of sodium, potassium, magnesium, calcium, and combinations thereof.

42. The method according to claim 16, wherein:

the *cannabis* oil nanoemulsion includes a sugar alcohol.

43. The method according to claim 16, wherein:

the *cannabis* oil nanoemulsion includes a sweetener including one or more sweeteners selected from the group consisting of aspartame, acesulfame potassium, erythritol, honey, neotame, saccharin, sucralose, sugar, *stevia, stevia* leaf extract, and combinations thereof.

44. The method according to claim 16, comprising:

(c) after step (b), introducing the *cannabis* oil nanoemulsion to a rotary die encapsulation system to produce a softgel, wherein the softgel includes a shell that encapsulates the *cannabis* oil nanoemulsion.

45. The method according to claim 44, wherein:
the shell includes one or more materials selected from the group consisting of gelatin, glycerin, sorbitol, and combinations thereof.

46. The method according to claim 44, wherein:
the softgel comprises a mass ranging from between 0.5 to 1.0 grams.

47. The method according to claim 44, wherein:
the softgel comprises a cannabidiol (CBD) and/or tetrahydrocannabinol (THC) concentration ranging from 20 to 500 milligrams.

48. The method according to claim 44, wherein:
the softgel comprises a length and a width;
wherein:
the length ranges from between 0.125 inches to 1.000 inch; and
the width ranges from between 0.125 inches to 0.313 inches.

49. The method according to claim 44, comprising:
(d) after step (c), washing the softgel and optionally drying the softgel.

50. The method according to claim 16, comprising:
(c) after step (b), producing a gel and/or a cream from the *cannabis* oil nanoemulsion.

51. The method according to claim 16, comprising:
(c) after step (b), mixing the *cannabis* oil nanoemulsion with one or more materials selected from the group consisting of agar, agave, alginin, arrowroot, carrageenan, collagen, cornstarch, egg whites, finely ground seeds, furcellaran, gelatin, guar gum, katakuri starch, locust bean gum, pectin, potato starch, *psyllium* husks, sago, tapioca, vegetable gums, xanthan gum, and combinations thereof.

52. The method according to claim 16, comprising:
(c) after step (b), mixing the *cannabis* oil nanoemulsion with an alcohol.

53. The method according to claim 16, comprising:
(c) after step (b), producing a foodstuff from the *cannabis* oil nanoemulsion, the foodstuff includes one or more foodstuffs selected from the group consisting of ada, bagels, baked goods, biscuits, bitterballen, bonda, breads, cakes, candies, cereals, chips, chocolate bars, chocolate, coffee, cokodok, confectionery, cookies, cooking batter, corn starch mixtures, crackers, crêpes, croissants, croquettes, croutons, dolma, dough, doughnuts, energy bars, flapjacks, french fries, frozen custard, frozen desserts, frying cakes, fudge, gelatin mixes, granola bars, gulha, hardtack, ice cream, khandvi, khanom buang, krumpets, meze, mixed flours, muffins, multi-grain snacks, nachos, nian gao, noodles, nougat, onion rings, pakora, pancakes, panforte, pastas, pastries, pie crust, pita chips, pizza, poffertjes, pretzels, pudding, rice krispie treats, sesame sticks, smoothies, specialty milk, tele-bhaja, tempura, toffee, tortillas, totopo, turkish delights, waffles, and combinations thereof.

54. A method to produce a foodstuff including a *cannabis* oil nanoemulsion and/or a spray-dried water-soluble cannabinoid powder, the method includes:
(a) emulsifying water and *cannabis* oil with a first emulsification system to produce a *cannabis* oil microemulsion comprising micro-sized *cannabis* oil droplets, the first emulsification system includes a rotor/stator;
(b) after step (a), introducing the *cannabis* oil microemulsion to a second emulsification system to produce the *cannabis* oil nanoemulsion and optionally spray drying the *cannabis* oil nanoemulsion to produce the spray-dried water-soluble cannabinoid powder, the second emulsification system includes an ultrasonic homogenizer or a microfluidizer processor; and
(c) after step (b), producing a foodstuff from the *cannabis* oil nanoemulsion and/or the spray-dried water-soluble cannabinoid powder, the foodstuff includes one or more foodstuffs selected from the group consisting of ada, bagels, baked goods, biscuits, bitterballen, bonda, breads, cakes, candies, cereals, chips, chocolate bars, chocolate, coffee, cokodok, confectionery, cookies, cooking batter, corn starch mixtures, crackers, crêpes, croissants, croquettes, croutons, dolma, dough, doughnuts, energy bars, flapjacks, french fries, frozen custard, frozen desserts, frying cakes, fudge, gelatin mixes, granola bars, gulha, hardtack, ice cream, khandvi, khanom buang, krumpets, meze, mixed flours, muffins, multi-grain snacks, nachos, nian gao, noodles, nougat, onion rings, pakora, pancakes, panforte, pastas, pastries, pie crust, pita chips, pizza, poffertjes, pretzels, pudding, rice krispie treats, sesame sticks, smoothies, specialty milk, tele-bhaja, tempura, toffee, tortillas, totopo, turkish delights, waffles, and combinations thereof.

55. The method according to claim 54, wherein:
the water includes adsorbent treated water and/or ultraviolet unit treated water and/or membrane treated water.

56. The method according to claim 54, wherein:
in step (b), the second emulsification system includes the ultrasonic homogenizer, the ultrasonic homogenizer includes a barbell ultrasonic horn, the barbell ultrasonic horn operates at a power level ranging from between 0.5 to 25 kw.

57. The method according to claim 54, wherein:
in step (a), the *cannabis* oil includes carbon dioxide extracted *cannabis* oil, ethanol extracted *cannabis* oil, chromatography purified *cannabis* oil, and/or simulated moving bed extracted *cannabis* oil; and
in step (a), the *cannabis* oil includes a cannabinoid, the cannabinoid includes cannabidiol (CBD) and/or tetrahydrocannabinol (THC).

* * * * *